US007868037B2

(12) United States Patent
Karp et al.

(10) Patent No.: US 7,868,037 B2
(45) **Date of Patent: *Jan. 11, 2011**

(54) METHODS FOR TREATING HEPATITIS C

(75) Inventors: Gary Mitchell Karp, Princeton Junction, NJ (US); Peter Seongwoo Hwang, Edison, NJ (US); James Jan Takasugi, Trenton, NJ (US); Hongyu Ren, Dayton, NJ (US); Richard Gerald Wilde, Somerville, NJ (US); Anthony Allan Turpoff, Edison, NJ (US); Alexander Arefolov, Piscataway, NJ (US); Guangming Chen, Bridgewater, NJ (US); Jeffrey Allen Campbell, Glen Gardner, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 957 days.

This patent is subject to a terminal disclaimer.

(21) Appl. No.: 11/331,180

(22) Filed: Jan. 13, 2006

(65) Prior Publication Data

US 2006/0189606 A1 Aug. 24, 2006

Related U.S. Application Data

(63) Continuation-in-part of application No. 11/180,961, filed on Jul. 14, 2005.

(60) Provisional application No. 60/587,487, filed on Jul. 14, 2004, provisional application No. 60/634,979, filed on Dec. 13, 2004, provisional application No. 60/645,586, filed on Jan. 24, 2005, provisional application No. 60/665,349, filed on Mar. 28, 2005, provisional application No. 60/675,440, filed on Apr. 28, 2005.

(51) Int. Cl.
*C07D 209/10* (2006.01)
*A61K 31/404* (2006.01)

(52) U.S. Cl. .................................... 514/415; 548/491

(58) Field of Classification Search ................ 548/491; 514/415

See application file for complete search history.

(56) References Cited

U.S. PATENT DOCUMENTS

| | | | |
|---|---|---|---|
| 4,788,206 | A | 11/1988 | Guthrie et al. |
| 4,874,756 | A | 10/1989 | Mertens et al. |
| 5,072,003 | A | 12/1991 | Behrend et al. |
| 5,190,942 | A | 3/1993 | Poss |
| 5,215,980 | A | 6/1993 | Jones |
| 5,217,996 | A | 6/1993 | Ksander |
| 5,354,759 | A | 10/1994 | Oku et al. |
| 5,369,120 | A | 11/1994 | Woodruff |
| 5,413,999 | A | 5/1995 | Vacca et al. |
| 5,474,994 | A | 12/1995 | Leonardi et al. |
| 5,527,819 | A | 6/1996 | Williams et al. |
| 5,559,127 | A | 9/1996 | Hartman et al. |
| 5,605,896 | A | 2/1997 | Leonardi et al. |
| 5,633,388 | A | 5/1997 | Diana et al. |
| 5,639,906 | A | 6/1997 | London et al. |
| 5,681,954 | A | 10/1997 | Yamamoto et al. |
| 5,693,643 | A | 12/1997 | Gilbert et al. |
| 5,714,496 | A | 2/1998 | Brown et al. |
| 5,880,137 | A | 3/1999 | Miller et al. |
| 5,922,898 | A | 7/1999 | Miller et al. |
| 5,958,086 | A | 9/1999 | Adam et al. |
| 5,977,090 | A | 11/1999 | Slusher et al. |
| 5,985,910 | A | 11/1999 | Miller et al. |
| 6,030,785 | A | 2/2000 | Katze et al. |
| 6,057,093 | A | 5/2000 | Han et al. |
| 6,124,311 | A | 9/2000 | Chandrasekhar et al. |
| 6,132,966 | A | 10/2000 | Draper |
| 6,194,599 | B1 | 2/2001 | Miller et al. |
| 6,221,902 | B1 | 4/2001 | Malamas et al. |
| 6,326,392 | B1 | 12/2001 | Gast et al. |
| 6,335,445 | B1 | 1/2002 | Chabrier de Lassauniere et al. |
| 6,358,992 | B1 | 3/2002 | Pamukcu et al. |
| 6,376,529 | B1 | 4/2002 | Tang et al. |
| 6,380,166 | B1 | 4/2002 | Miller et al. |
| 6,384,022 | B1 | 5/2002 | Jackson et al. |
| 6,555,555 | B1 | 4/2003 | Konishi et al. |
| 6,589,570 | B1 | 7/2003 | Thyagarajan |
| 6,589,954 | B1 | 7/2003 | Mavunkel et al. |
| 6,685,931 | B1 | 2/2004 | Grint et al. |
| 6,690,975 | B2 | 2/2004 | Yamamoto et al. |
| 6,974,870 | B2 | 12/2005 | Cywin et al. |
| 2002/0055651 | A1 | 5/2002 | Moran et al. |
| 2002/0091116 | A1 | 7/2002 | Zhu et al. |

(Continued)

FOREIGN PATENT DOCUMENTS

CA 2099060 12/1993

(Continued)

OTHER PUBLICATIONS

Ames et al. Journal of the Chemical Society (1959), 3388-3400.*

(Continued)

*Primary Examiner*—Kahsay T Habte
(74) *Attorney, Agent, or Firm*—Hoffman & Baron, LLP

(57) ABSTRACT

The present invention provides compounds, pharmaceutical compositions, and methods of using such compounds or compositions for treating infection by a virus, or for affecting viral IRES activity.

31 Claims, 1 Drawing Sheet

U.S. PATENT DOCUMENTS

| | | | |
|---|---|---|---|
| 2002/0099054 | A1 | 7/2002 | Connor et al. |
| 2002/0099080 | A1 | 7/2002 | Gagliardi et al. |
| 2002/0103210 | A1 | 8/2002 | Furuya et al. |
| 2002/0143022 | A1 | 10/2002 | Pamukeu et al. |
| 2002/0169101 | A1 | 11/2002 | Gonzalez et al. |
| 2002/0169107 | A1 | 11/2002 | Rajagopalan et al. |
| 2003/0004119 | A1 | 1/2003 | Ganguly et al. |
| 2003/0050320 | A1 | 3/2003 | Hashimoto et al. |
| 2003/0078420 | A1 | 4/2003 | Chabrier de Lassauniere et al. |
| 2003/0096825 | A1 | 5/2003 | Wang et al. |
| 2003/0176433 | A1 | 9/2003 | Beaulieu et al. |
| 2003/0176697 | A1 | 9/2003 | Overman et al. |
| 2003/0199689 | A1 | 10/2003 | Nazare et al. |
| 2003/0220377 | A1 | 11/2003 | Chesworth |
| 2003/0232866 | A1 | 12/2003 | Watterson et al. |
| 2003/0236391 | A1 | 12/2003 | Klunk et al. |
| 2004/0044059 | A1 | 3/2004 | Pinney et al. |
| 2004/0059131 | A1 | 3/2004 | Dell et al. |
| 2004/0067996 | A1 | 4/2004 | Sheppeck |
| 2004/0180945 | A1 | 9/2004 | Artico et al. |
| 2004/0186125 | A1 | 9/2004 | Poupart et al. |
| 2005/0026969 | A1 | 2/2005 | Cheng et al. |
| 2005/0075242 | A1 | 4/2005 | Holtcamp et al. |
| 2005/0075384 | A1 | 4/2005 | Sheppeck et al. |
| 2005/0085529 | A1 | 4/2005 | Brown et al. |
| 2005/0113283 | A1 | 5/2005 | Solow-Cordero et al. |
| 2005/0119318 | A1 | 6/2005 | Hudyma et al. |
| 2005/0123560 | A1 | 6/2005 | Sinnott |
| 2005/0227291 | A1 | 10/2005 | Kinsella |

FOREIGN PATENT DOCUMENTS

| | | | |
|---|---|---|---|
| CN | 1333206 | A | 1/2002 |
| DE | 25 26 317 | A1 | 1/1976 |
| DE | 29 09 779 | | 9/1980 |
| DE | 258014 | | 6/1988 |
| DE | 258015 | | 6/1988 |
| DE | 258016 | | 6/1988 |
| DE | 37 06 427 | A1 | 9/1988 |
| DE | 41 39 851 | A1 | 6/1992 |
| DE | 41 29 603 | A1 | 3/1993 |
| DE | 44 37 262 | A1 | 4/1995 |
| DE | 44 37 265 | A1 | 4/1995 |
| DE | 196 48 793 | A1 | 5/1998 |
| DE | 198 38 705 | A1 | 3/2000 |
| DE | 199 46 289 | A1 | 3/2001 |
| EP | 0 196 096 | A2 | 10/1986 |
| EP | 0 290 153 | A1 | 11/1988 |
| EP | 0 318 902 | A2 | 6/1989 |
| EP | 0 387 201 | A1 | 9/1990 |
| EP | 0 406 734 | A2 | 1/1991 |
| EP | 0 414 386 | A1 | 2/1991 |
| EP | 0 425 434 | A2 | 5/1991 |
| EP | 0 427 225 | A1 | 5/1991 |
| EP | 0 430 186 | A1 | 6/1991 |
| EP | 0 436 199 | A1 | 7/1991 |
| EP | 0 471 372 | A1 | 2/1992 |
| EP | 0 480 204 | A1 | 4/1992 |
| EP | 0 488 532 | | 6/1992 |
| EP | 0 497 659 | | 8/1992 |
| EP | 0 527 458 | A1 | 2/1993 |
| EP | 0 527 704 | A2 | 2/1993 |
| EP | 0 528 762 | A1 | 2/1993 |
| EP | 0 530 149 | | 3/1993 |
| EP | 0 548 798 | A1 | 6/1993 |
| EP | 0 553 682 | A1 | 8/1993 |
| EP | 0 556 949 | | 8/1993 |
| EP | 0 558 245 | A1 | 9/1993 |
| EP | 0 502 424 | B1 | 1/1994 |
| EP | 0 586 331 | A2 | 3/1994 |
| EP | 0 617 968 | A1 | 10/1994 |
| EP | 0 622 356 | A1 | 11/1994 |
| EP | 0 624 584 | A1 | 11/1994 |
| EP | 0 628 559 | | 12/1994 |
| EP | 0 630 895 | A1 | 12/1994 |
| EP | 0 639 573 | | 2/1995 |
| EP | 0 657 508 | A1 | 6/1995 |
| EP | 0 697 172 | | 2/1996 |
| EP | 0 708 091 | | 4/1996 |
| EP | 0 714 955 | A1 | 6/1996 |
| EP | 0 716 855 | A2 | 6/1996 |
| EP | 0 719 837 | A2 | 7/1996 |
| EP | 0 802 183 | | 10/1997 |
| EP | 0 802 184 | | 10/1997 |
| EP | 0 826 743 | A2 | 3/1998 |
| EP | 1 118 323 | | 7/2001 |
| EP | 1 120 114 | | 8/2001 |
| EP | 1 125 582 | | 8/2001 |
| EP | 1 149 579 | | 10/2001 |
| EP | 1 177 787 | | 2/2002 |
| EP | 1 192 945 | | 4/2002 |
| EP | 1 199 069 | | 4/2002 |
| EP | 1 226 823 | | 7/2002 |
| EP | 1 314 733 | A1 | 5/2003 |
| EP | 1 457 485 | A1 | 9/2004 |
| EP | 1 532 980 | | 5/2005 |
| EP | 1 574 502 | A1 | 9/2005 |
| FR | 2 854 159 | | 10/2004 |
| FR | 2865208 | | 7/2005 |
| GB | 2 282 808 | A | 4/1995 |
| GB | 2 292 149 | A | 2/1996 |
| JP | 57-085055 | A2 | 5/1982 |
| JP | 01273040 | | 10/1989 |
| JP | 3-32801 | | 2/1991 |
| JP | 3-43744 | | 2/1991 |
| JP | 4-319959 | | 11/1992 |
| JP | 5-58997 | | 3/1993 |
| JP | 5-339565 | | 12/1993 |
| JP | 06-23601 | | 8/1994 |
| JP | 6-306077 | | 11/1994 |
| JP | 8-157461 | | 6/1996 |
| JP | 8-244353 | | 9/1996 |
| JP | 9-20083 | | 1/1997 |
| JP | 9-169729 | | 6/1997 |
| JP | 9-258399 | | 10/1997 |
| JP | 10-45512 | | 2/1998 |
| JP | 11-302177 | | 11/1999 |
| JP | 2000-63354 | | 2/2000 |
| JP | 2001-55332 | | 2/2001 |
| JP | 2001-64166 | | 3/2001 |
| JP | 2001-64205 | | 3/2001 |
| JP | 2001-151751 | | 6/2001 |
| JP | 2001-206845 | | 7/2001 |
| JP | 2001-242165 | | 9/2001 |
| JP | 3246259 | | 11/2001 |
| JP | 2002-3368 | | 1/2002 |
| JP | 2002105081 | | 4/2002 |
| JP | 2003-300875 | | 10/2003 |
| JP | 2004-61583 | | 2/2004 |
| JP | 2004-327313 | | 11/2004 |
| JP | 2005-2346 | | 1/2005 |
| JP | 2005-82701 | | 3/2005 |
| JP | 2005-194198 | | 7/2005 |
| JP | 2005-225872 | | 8/2005 |
| KR | 93-12108 | | 12/1993 |
| WO | WO 92/15579 | | 9/1992 |
| WO | 93/14758 | | 8/1993 |
| WO | WO 93/18030 | | 9/1993 |
| WO | WO 93/18765 | | 9/1993 |
| WO | WO 93/18766 | | 9/1993 |
| WO | WO 93/19067 | | 9/1993 |
| WO | WO 94/04153 | | 3/1994 |
| WO | WO 94/04535 | | 3/1994 |
| WO | WO 94/08583 | | 4/1994 |

| | | | |
|---|---|---|---|
| WO | WO 94/08962 | | 4/1994 |
| WO | WO 94/11378 | | 5/1994 |
| WO | WO 94/14435 | | 7/1994 |
| WO | WO 94/14438 | | 7/1994 |
| WO | WO 94/14763 | | 7/1994 |
| WO | WO 94/14771 | | 7/1994 |
| WO | WO 94/26746 | | 11/1994 |
| WO | WO 95/02583 | | 1/1995 |
| WO | WO 95/07910 | | 3/1995 |
| WO | WO 95/14003 | | 5/1995 |
| WO | WO 95/32710 | | 12/1995 |
| WO | WO 95/33720 | | 12/1995 |
| WO | WO 96/10012 | | 4/1996 |
| WO | WO 96/16054 | | 5/1996 |
| WO | WO 96/26207 | | 8/1996 |
| WO | WO 96/32379 | | 10/1996 |
| WO | WO 96/40650 | | 12/1996 |
| WO | WO 96/41800 | | 12/1996 |
| WO | WO 97/14419 | | 4/1997 |
| WO | WO 97/45410 | | 4/1997 |
| WO | WO 98/13044 | | 4/1998 |
| WO | WO 98/22457 | | 5/1998 |
| WO | WO 98/25883 | | 6/1998 |
| WO | WO 98/48797 | | 11/1998 |
| WO | WO 99/06836 | | 2/1999 |
| WO | WO 99/11634 | | 3/1999 |
| WO | WO 99/13714 | | 3/1999 |
| WO | WO 99/18096 | | 4/1999 |
| WO | WO 99/23072 | | 5/1999 |
| WO | WO 99/24027 | | 5/1999 |
| WO | WO 99/26946 | | 6/1999 |
| WO | WO 99/33849 | | 7/1999 |
| WO | WO 99/43651 | | 9/1999 |
| WO | WO 99/50237 | | 10/1999 |
| WO | WO 99/58520 | | 11/1999 |
| WO | WO 99/59581 | | 11/1999 |
| WO | WO 99/59969 | | 11/1999 |
| WO | WO 99/61426 | | 12/1999 |
| WO | WO 99/64035 | | 12/1999 |
| WO | WO 99/64415 | | 12/1999 |
| WO | WO 00/15645 | | 3/2000 |
| WO | WO 00/28991 | | 5/2000 |
| WO | WO 00/29384 | | 5/2000 |
| WO | WO 00/35886 | | 6/2000 |
| WO | WO 00/43393 | | 7/2000 |
| WO | WO 00/61586 | | 10/2000 |
| WO | WO 00/73269 | A2 | 12/2000 |
| WO | WO 01/19798 | A2 | 3/2001 |
| WO | WO 01/19839 | | 3/2001 |
| WO | WO 01/21589 | A2 | 3/2001 |
| WO | WO 01/21609 | | 3/2001 |
| WO | WO 01/23353 | | 4/2001 |
| WO | WO 01/23390 | A2 | 4/2001 |
| WO | WO 01/44182 | | 6/2001 |
| WO | WO 01/47883 | A1 | 7/2001 |
| WO | WO 01/55111 | A1 | 8/2001 |
| WO | WO 01/55136 | | 8/2001 |
| WO | WO 01/55137 | | 8/2001 |
| WO | WO 01/55138 | | 8/2001 |
| WO | WO 01/55139 | | 8/2001 |
| WO | WO 01/55144 | | 8/2001 |
| WO | WO 01/58859 | A1 | 8/2001 |
| WO | WO 01/64678 | A2 | 9/2001 |
| WO | WO 01/68585 | A1 | 9/2001 |
| WO | WO 01/74773 | A2 | 10/2001 |
| WO | WO 01/83451 | A1 | 11/2001 |
| WO | WO 01/85687 | A1 | 11/2001 |
| WO | WO 01/90105 | | 11/2001 |
| WO | WO 02/00651 | A2 | 1/2002 |
| WO | WO 02/03975 | | 1/2002 |
| WO | WO 02/03976 | | 1/2002 |
| WO | WO 02/03977 | | 1/2002 |
| WO | WO 02/03986 | | 1/2002 |

| | | | |
|---|---|---|---|
| WO | WO 02/03987 | | 1/2002 |
| WO | WO 02/03988 | | 1/2002 |
| WO | WO 02/03989 | | 1/2002 |
| WO | WO 02/03990 | | 1/2002 |
| WO | WO 02/03991 | | 1/2002 |
| WO | WO 02/03992 | | 1/2002 |
| WO | WO 02/04418 | | 1/2002 |
| WO | WO 02/06226 | A1 | 1/2002 |
| WO | WO 02/13802 | | 2/2002 |
| WO | WO 02/16333 | A2 | 2/2002 |
| WO | WO 02/16353 | | 2/2002 |
| WO | WO 02/26696 | A1 | 4/2002 |
| WO | WO 02/26703 | A1 | 4/2002 |
| WO | WO 02/30358 | | 4/2002 |
| WO | WO 02/30879 | A2 | 4/2002 |
| WO | WO 02/36203 | A2 | 5/2002 |
| WO | WO 02/36562 | | 5/2002 |
| WO | WO 02/36580 | A2 | 5/2002 |
| WO | WO 02/42292 | | 5/2002 |
| WO | WO 02/48099 | A1 | 6/2002 |
| WO | WO 02/051805 | A1 | 7/2002 |
| WO | WO 02/053534 | A1 | 7/2002 |
| WO | WO 02/055496 | A1 | 7/2002 |
| WO | WO 02/059088 | | 8/2002 |
| WO | WO 02/059120 | | 8/2002 |
| WO | WO 02/060374 | A2 | 8/2002 |
| WO | WO 02/060447 | A1 | 8/2002 |
| WO | WO 02/066477 | A2 | 8/2002 |
| WO | WO 02/070462 | A1 | 9/2002 |
| WO | WO 02/070469 | A2 | 9/2002 |
| WO | WO 02/070510 | A2 | 9/2002 |
| WO | WO 02/072549 | | 9/2002 |
| WO | WO 02/074742 | | 9/2002 |
| WO | WO 02/076926 | | 10/2002 |
| WO | WO 02/083134 | A1 | 10/2002 |
| WO | WO 02/053545 | A1 | 11/2002 |
| WO | WO 02/053565 | A1 | 11/2002 |
| WO | WO 02/089811 | | 11/2002 |
| WO | WO 02/096426 | A1 | 12/2002 |
| WO | WO 02/098424 | | 12/2002 |
| WO | WO 03/000254 | A1 | 1/2003 |
| WO | WO 03/000690 | A1 | 1/2003 |
| WO | WO 03/004458 | A1 | 1/2003 |
| WO | WO 03/005025 | A1 | 1/2003 |
| WO | WO 03/006447 | A2 | 1/2003 |
| WO | 03/010140 | A2 | 2/2003 |
| WO | WO 03/010140 | A2 | 2/2003 |
| WO | WO 03/010141 | A2 | 2/2003 |
| WO | WO 03/022214 | A2 | 3/2003 |
| WO | WO 03/048101 | A1 | 6/2003 |
| WO | WO 03/053359 | A2 | 7/2003 |
| WO | WO 03/053368 | A2 | 7/2003 |
| WO | WO 03/053938 | A1 | 7/2003 |
| WO | WO 03/053941 | A2 | 7/2003 |
| WO | WO 03/055447 | A2 | 7/2003 |
| WO | WO 03/059269 | A2 | 7/2003 |
| WO | WO 03/062392 | A2 | 7/2003 |
| WO | WO 03/064539 | A1 | 8/2003 |
| WO | WO 03/066629 | A2 | 8/2003 |
| WO | WO 03/074047 | A1 | 9/2003 |
| WO | WO 03/082265 | | 10/2003 |
| WO | WO 03/087092 | | 10/2003 |
| WO | WO 03/091211 | | 11/2003 |
| WO | WO 03/097036 | A1 | 11/2003 |
| WO | 2005/058315 | | 12/2003 |
| WO | WO 03/099276 | A1 | 12/2003 |
| WO | WO 2004/003103 | A1 | 1/2004 |
| WO | WO 2004/012736 | A1 | 2/2004 |
| WO | WO 2004/013135 | | 2/2004 |
| WO | WO 2004/014912 | | 2/2004 |
| WO | WO 2004/022057 | A1 | 3/2004 |
| WO | WO 2004/024060 | A2 | 3/2004 |
| WO | WO 2004/024655 | A2 | 3/2004 |

| | | | |
|---|---|---|---|
| WO | WO 2004/024896 | A2 | 3/2004 |
| WO | 2004/035571 | A1 | 4/2004 |
| WO | WO 2004/030630 | | 4/2004 |
| WO | WO 2004/035047 | A1 | 4/2004 |
| WO | WO 2004/035522 | A1 | 4/2004 |
| WO | WO 2004/035525 | A1 | 4/2004 |
| WO | WO 2004/035571 | | 4/2004 |
| WO | WO 2004/037788 | | 5/2004 |
| WO | WO 2004/037791 | A1 | 5/2004 |
| WO | WO 2004/041256 | | 5/2004 |
| WO | WO 2004/041781 | A1 | 5/2004 |
| WO | WO 2004/050035 | A2 | 6/2004 |
| WO | 2004/065367 | A1 | 8/2004 |
| WO | WO 2004/064759 | | 8/2004 |
| WO | WO 2004/064925 | | 8/2004 |
| WO | WO 2004/065367 | | 8/2004 |
| WO | WO 2004/074447 | | 9/2004 |
| WO | WO 2004/082638 | | 9/2004 |
| WO | WO 2004/083195 | A1 | 9/2004 |
| WO | WO 2004/087714 | A1 | 10/2004 |
| WO | WO 2004/093871 | | 11/2004 |
| WO | WO 2004/093912 | A1 | 11/2004 |
| WO | WO 2004/094409 | | 11/2004 |
| WO | WO 2004/096210 | | 11/2004 |
| WO | WO 2004/099168 | A2 | 11/2004 |
| WO | WO 2004/099170 | A2 | 11/2004 |
| WO | WO 2004/099171 | A2 | 11/2004 |
| WO | WO 2004/099192 | A2 | 11/2004 |
| WO | WO 2004/099239 | A1 | 11/2004 |
| WO | WO 2004/111056 | A2 | 12/2004 |
| WO | WO 2005/003086 | A2 | 1/2005 |
| WO | WO 2005/003131 | A1 | 1/2005 |
| WO | WO 2005/009389 | | 2/2005 |
| WO | WO 2005/013950 | A2 | 2/2005 |
| WO | WO 2005/013976 | | 2/2005 |
| WO | WO 2005/013977 | | 2/2005 |
| WO | WO 2005/014000 | | 2/2005 |
| WO | WO 2005/014045 | | 2/2005 |
| WO | WO 2005/014543 | A1 | 2/2005 |
| WO | WO 2005/016862 | A1 | 2/2005 |
| WO | WO 2005/018531 | | 3/2005 |
| WO | WO 2005/020899 | A2 | 3/2005 |
| WO | WO 2005/020921 | A1 | 3/2005 |
| WO | WO 2005/021505 | | 3/2005 |
| WO | WO 2005/028502 | | 3/2005 |
| WO | 2005/034941 | A1 | 4/2005 |
| WO | WO 2005/034941 | | 4/2005 |
| WO | WO 2005/034943 | | 4/2005 |
| WO | WO 2005/039489 | A2 | 5/2005 |
| WO | WO 2005/042018 | | 5/2005 |
| WO | WO 2005/055940 | A2 | 6/2005 |
| WO | WO 2005/061519 | A1 | 7/2005 |
| WO | WO 2005/062676 | A1 | 7/2005 |
| WO | WO 2005/066180 | A1 | 7/2005 |
| WO | WO 2005/072132 | A2 | 8/2005 |
| WO | WO 2005/076861 | A2 | 8/2005 |
| WO | WO 2005/077122 | A2 | 8/2005 |
| WO | WO 2005/077969 | | 8/2005 |
| WO | WO 2005/080335 | | 9/2005 |
| WO | WO 2005/080388 | A1 | 9/2005 |
| WO | WO 2005/082895 | A1 | 9/2005 |
| WO | WO 2005/082905 | A1 | 9/2005 |
| WO | WO 2005/086754 | A2 | 9/2005 |
| WO | WO 2005/090282 | | 9/2005 |
| WO | WO 2005/092855 | | 10/2005 |
| WO | WO 2005/107747 | | 11/2005 |
| WO | WO 2005/112519 | | 11/2005 |
| WO | WO 2005/113529 | | 12/2005 |
| WO | 2006/019831 | | 2/2006 |
| WO | 2006/019831 | A1 | 2/2006 |
| WO | WO 2006/024699 | | 3/2006 |
| WO | WO 2006/041874 | | 4/2006 |
| WO | WO 2006/049013 | | 5/2006 |
| WO | WO 2006/050236 | | 5/2006 |
| WO | WO 2006/057354 | | 6/2006 |
| WO | WO 2006/083458 | | 8/2006 |

OTHER PUBLICATIONS

Al-Omran, STN Accession No. 2000:825367 Document No. 134:131488; Abstract of the Journal of Heterocyclic Chemistry, 37(5):1219-1223 (2000).

Boehm et al., STN Accession No. 1993:756686 Document No. 118:233974; Abstract of Pharmazie, 47(12):897-901 (1992).

Dyachenko et al., STN Accession No. 1996:756686 Document No. 126:74777; Abstract of Khimiya Geterotsiklicheskikh Soedinenii, 9:1232-1234 (1996).

Elgemeie et al., STN Accession No. 1994:54466 Document No. 120:54466; Abstract of Journal of Chemical Research, Synopses, 7:256-257 (1993).

Frolova et al., STN Accession No. 1996:396582 Document No. 125:167833; Abstract of Izvestiya Akademii Nauk, Seriya Khimicheskaya, 4:938-942 (1996).

Frolova et al., STN Accession No. 1997:73192 Document No. 126:131360; Abstract of Izvestiya Akademii Nauk, Seriya Khimicheskaya, 11:2719-2721 (1996).

International Search Report in PCT/US2007/000996 mailed Sep. 19, 2007.

Leistner et al., STN Accession No. 1992:235578 Document No. 116:235578; Abstract of Pharmazie, 47(1):11-14 (1992).

Paronikyan et al., STN Accession No. 1998:173599 Document No. 128:243969, Abstract of Khimiko-Farmatsevticheskii Zhurnal, 31(10):34-36 (1997).

Partial International Search Report in PCT/US2007/000996 mailed Jul. 16, 2007.

Quintela et al., STN Accession No. 1999:643470 Document No. 132:22945; Abstract of Journal of Medicinal Chemistry, 42(22):4720-4724 (1999).

Sharanin et al., STN Accession No. 1985:113330 Document No. 102:113330, Abstract of Zhumal Organicheskoi Khimii, 20(9):2002-2011 (1984).

Vieweg et al., STN Acession No. 1993:449330, Document No. 119:49330, Abstract of Pharmazie, 48(1):26-30 (1993).

Ali et al., "Human La Antigen is Required for the Hepatitis C Virus Internal Ribosome Entry Site-mediated Translation", *J Biol Chem*, 275(36):27531-27540 (2000).

Ali et al., "Interaction of Polypyrimidine Tract-Binding Protein with the 5' Noncoding Region of the Hepatitis C Virus RNA Genome and its Functional Requirement in Internal Initiation of Translation", *J Virol*, 69(10):6367-6375 (1995).

Ali et al., "The La Antigen Binds 5' Noncoding Region of the Hepatitis C Virus RNA in the Context of the Initiator AUG Codon and Stimulates Internal Ribosome Entry Site-Mediated Translation", *Proc Nat! Acad Sci USA*, 94:2249-2254 (1997).

Anwar et al., "Demonstration of Functional Requirement of Polypyrimidine Tract-binding Protein by SELEX RNA during Hepatitis C Virus Internal Ribosome Entry Site-mediated Translation Initiation", *J Biol Chem*, 275(44):34231-34235 (2000).

Beales et al., "The Internal Ribosome Entry Site (IRES) of Hepatitis C Virus Visualized by Electron Microscopy", *RNA*, 7:661-670 (2001).

Belsham et al., "A Region of the 5' Noncoding Region of Foot-and-Mouth Disease Virus RNA Directs Efficient Internal Initiation of Protein Synthesis within Cells: Involvement with the Role of L Protease in Translational Control", *J Virol*, 64(11):5389-5395 (1990).

Belsham et al., "Translation Initiation on Picornavirus RNA", p. 869-900, Cold Spring Harbor Laboratory Press, New York (2000).

Blight et al., "Efficient Initiation of HCV RNA Replication in Cell Culture", *Science*, 290:1972-1974 (2000).

Blight et al., "Highly Permissive Cell Lines for Subgenomic and Genomic Hepatitis C Virus RNA Replication", *J Virol*, 76(24):13001-13014 (2002).

Boni et al., "Hepatitis C Virus Core Protein Acts as a *trans*-Modulating Factor on Internal Translation Initiation of the Viral RNA", *J Biol Chem*, 280(18):17737-17748 (2005).

Borovjagin et al., "Pyrimidine Tract Binding Protein Strongly Stimulates in vitro Encephalomyocarditis Virus RNA Translation at the Level of Preinitiation Complex Formation" *FEBS Lett*, 351:299-302 (1994).
Brown et al., "Secondary Structure of the 5' Nontranslated Regions of Hepatitis C Virus and Pestivirus Genomic RNAs", *Nucleic Acids Res*, 20(19):5041-5045 (1992).
Buck et al., "The Human Immunodeficiency Virus Type 1 *gag* Gene Encodes an Internal Ribosome Entry Site", *J Virol*, 75(1):181-191 (2001).
Bukh et al. "Sequence Analysis of the 5' Noncoding Region of Hepatitis C Virus", *Proc Natl Acad Sci USA*, 89:4942-4946 (1992).
Bukh et al., "Sequence Analysis of the Core Gene of 14 Hepatitis C Virus Genotypes", *Proc Natl Acad Sci USA*, . 91:8239-8243 (1994).
Buratti et al., "Functional Analysis of the Interaction Between HCV 5'UTR and Putative Subunits of Eukaryotic Translation Initiation Factor eIF3", *Nucleic Acids Res*, 26(13):3179-3187 (1998).
Chappell et al., "A Mutation in the c-*myc*-IRES Leads to Enhanced Internal Ribosome Entry in Multiple Myeloma: A Novel Mechanism of Oncogene De-Regulation", *Oncogene*, 19:4437-4440 (2000).
Chung et al., "Hepatitis C Virus Replication is Directly Inhibited by IFN-α in a Full-Length Binary Expression System", *Proc Natl Acad Sci USA*, 98(17):9847-9852 (2001).
Coldwell et al., "Initiation of Apaf-1 Translation by Internal Ribosome Entry", *Oncogene*, 19:899-905 (2000).
Créancier et al., "Fibroblast Growth Factor 2 Internal Ribosome Entry Site (IRES) Activity Ex Vivo and in Transgenic Mice Reveals a Stringent Tissue-specific Regulation", *J Cell Biol*, 150(1):275-281 (2000).
Das et al., "Inhibition of Internal Entry Site (IRES)-Mediated Translation by a Small Yeast RNA: a Novel Strategy to Block Hepatitis C Virus Protein Synthesis" *Front Biosci*, (3)d1241-1252 (1998).
Dever, "Gene-Specific Regulation by General Translation Factors", *Cell*, 108:545-556 (2002).
Dumas et al., "A Promoter Activity is Present in the DNA Sequence Corresponding to the Hepatitis C Virus 5' UTR", *Nucleic Acids Res*, 31(4): 1275-1281 (2003).
Fukushi et al., "Complete 5' Noncoding Region is Necessary for the Efficient Internal Initiation of Hepatitis C Virus RNAa", *Biochem Biophys. Res Commun.*, 199(2):425-432 (1994).
Fukushi et al., "The Sequence Element of the Internal Ribosome Entry Site and a 25-Kilodalton Cellular Protein Contribute to Efficient Internal Initiation of Translation of Hepatitis C Virus RNA", *J Virol*, 71(2):1662-1666 (1997).
Fukushi et al., "Specific Interaction of a 25-Kilodalton Cellular Protein, a 40S Ribosomal Subunit Protein, with the Internal Ribosome Entry Site of Hepatitis C Virus Genome", *Virus Genes*, 19(2):153-161 (1999).
Fukushi et al., "Ribosomal Protein S5 Interacts with the Internal Ribosomal Entry Site of Hepatitis C Virus",*J Biol Chem*, 276(24):20824-20826 (2001).
Funkhouser et al., "Hepatitis A Virus Translation is Rate-Limiting for Virus Replication in MRC-5 Cells", *Virology*, 254:268-278 (1999).
Glass et al., "Identification of the Hepatitis A Virus Internal Ribosome Entry Site: In vivo and in vitro Analysis of Bicistronic RNAs Containing the HAV 5' Noncoding Region", *Virology*, 193:842-852 (1993).
Gordon et al., "A Phase II, 12-Week Study of ISIS 14803, an Antisense Inhibitor of HCV for the Treatment of Chronic Hepatitis C" AASLD Abst., 795, *Hepatology*, 36:362A (2002).
Gosert et al., "Transient Expression of Cellular Polypyrimidine-Tract Binding Protein Stimulates Cap-Independent Translation Directed by Both Picomaviral and Flaviviral Internal Ribosome Entry Sites In Vivo", *Mol Cell Biol*, 20(5):1583-1595 (2000).
Gray et al., "Control of Translation Initiation in Animals", *Annu Rev Cell Dev Biol*, 14:399-458 (1998).
Griffiths et al., "An Unusual Internal Ribosome Entry Site in the Herpes Simplex Virus Thymidine Kinase Gene", *Proc Natl Acad Sci USA*, 102(27):9667-72 (2005).
Guo et al., "Effect of Alpha Interferon on the Hepatitis C Virus Replicon", *J Virol*, 75(18):8516-8523 (2001).
Hahm et al., "Heterogeneous Nuclear Ribonucleoprotein L Interacts with the 3' Border of the Internal Ribosomal Entry Site of Hepatitis C Virus", *J Virol*, 72(11):8782-8788 (1998).
Haller et al., "Attenuation Stem-Loop Lesions in the 5' Noncoding Region of Poliovirus RNA: Neuronal Cell-Specific Translation Defects", *J Virol*, 70(3):1467-1474 (1996).
He et al., "The Regulation of Hepatitis C Virus (HCV) Internal Ribosome-Entry Site-Mediated Translation by HCV Replicons and Nonstructural Proteins", *J Gen Virol*, 84:535-543 (2003).
Hellen et al., "Translation of Hepatitis C Virus RNA", *J Viral Hepat*, 6:79-87 (1999).
Hellen et al., "A Cytoplasmic 57-kDa Protein that is Required for Translation of Picornavirus RNA by Internal Ribosomal Entry is Identical to the Nuclear Pyrimidine Tract-Binding Protein", *Proc Natl Acad Sci USA*, 90:7642-7646 (1993).
Hendrix et al., "Direct Observation of Aminoglycoside-RNA Interactions by Surface Plasmon Resonance" *J Amer Chem Soc*, 119(16):3641-8 (1997).
Holcik et al., "Functional Characterization of the X-Linked Inhibitor of Apoptosis (XIAP) Internal Ribosome Entry Site Element: Role of La Autoantigen in XIAP Translation", *Mol Cell Biol*, 20(13):4648-4657 (2000).
Holcik et al., "A new Internal-Ribosome-Entry-Site Motif Potentiates XIAP-Mediated Cytoprotection", *Nat Cell Biol*, 1:190-192 (1999).
Honda et al., "A Phylogenetically Conserved Stem-Loop Structure at the 5' Border of the Internal Ribosome Entry Site of Hepatitis C Virus is Required for Cap-Independent Viral Translation", *J Virol*, 73(2):1165-1174 (1999).
Honda et al., "Stability of a Stem-Loop Involving the Initiator AUG Controls the Efficiency of Internal Initiation of Translation on Hepatitis C Virus RNA", *RNA*, 2:955-968 (1996).
Honda et al., "Structural Requirements for Initiation of Translation by Internal Ribosome Entry within Genome-Length Hepatitis C Virus RNA", *Virology*, 222:31-42 (1996).
Honda et al., "Natural Variation in Translational Activities of the 5' Nontranslated RNAs of Hepatitis C Virus Genotypes 1a and 1b: Evidence for a Long-Range RNA-RNA Interaction Outside of the Internal Ribosomal Entry Site", *J Virol*, 73(6):4941-4951 (1999).
Huez et al., "New Vascular Endothelial Growth Factor Isoform Generated by Internal Ribosome Entry Site-Driven CUG Translation Initiation", *Mol Endocrinol.*, 15(12):2197-2210 (2001).
Huez et al., "Two Independent Internal Ribosome Entry Sites Are Involved in Translation Initiation of Vascular Endothelial Growwth Factor mRNA", *Mol cell Biol*, 18(11):6178-6190 (1998).
Ikeda et al., "Selectable Subgenomic and Genome-Length Dicistronic RNAs Derived from an Infectious Molecular Clone of the HCV-N. Strain of Hepatitis C Virus Replicate Efficiently in Cultured Huh7 Cells" *J Virol*, 76(6):2997-3006 (2002).
International Search Report for International Application No. PCT/US2005/024881, mailed Feb. 3, 2006.
Irvine et al., "MDCK (Madin-Darby Canine Kidney) Cells: A Tool for Membrane Permeability Screening", *J Pharm Sci*, 88(1):28-33 (1999).
Isoyama et al., "Lower Concentration of La Protein Required for Internal Ribosome Entry on Hepatitis C Virus RNA than on Poliovirus RNA", *J Gen Virol*, 80(9):2319-2327 (1999).
Ito et al., "An Internal Polypyrimidine-Tract-Binding Protein-Binding Site in the Hepatitis C Virus RNA Attenuates Translation, Which is Relieved by the 3'-Untranslated Sequence", *Virology* 254:288-296 (1999).
Jang et al., "A Segment of the 5' Nontranslated Region of Encephalomyocarditis Virus RNA Directs Internal Entry of Ribosomes during in Vitro Translation", *J Virol*, 62(8):2636-2643 (1988).
Jubin et al., "Hepatitis C Virus Internal Ribosome Entry Site (IRES) Stem Loop IIId Contains a Phylogenetically Conserved GGG Triplet Essential for Translation and IRES Folding", *J Virol*, 74(22):10430-10437 (2000).
Kalliampakou et al., "Mutational Analysis of the Apical Region of Domain II of the HCV IRES", *FEBS Lett*, 511:79-84 (2002).

Kaminski et al., "Direct Evidence that Polypyrimidine Tract Binding Protein (PTB) is Essential for Internal Initiation of Translation of Encephalomyocarditis Virus RNA", *RNA*, 1:924-938 (1995).

Kamoshita et al., "Genetic Analysis of Internal Ribosomal Entry Site on Hepatitis C Virus RNA: Implication for Involvement of the Highly Ordered Structure and Cell Type-Specific Transacting Factors", *Virology*, 233:9-18 (1997).

Kato et al., "Hepatitis C Virus NS4A and NS4B Proteins Suppress Translation In Vivo", *J Med Virol*, 66:187-199 (2002).

Kieft et al., "The Hepatitis C Virus Internal Ribosome Entry Site Adopts an Ion-dependent Tertiary Fold", *J Mol Biol*, 292:513-529 (1999).

Kieft et al., "Mechanism of Ribosome Recruitment by Hepatitis C IRES RNA", *RNA*, 7:194-206 (2001).

Klinck et al., "A Potential RNA Drug Target in the Hepatitis C Virus Internal Ribosomal Entry Site", *RNA*, 6:1423-1431 (2000).

Kolupaeva et al., "An Enzymatic Footprinting Analysis of the Interaction of 40S Ribosomal Subunits with the Internal Ribosomal Entry Site of Hepatitis C Virus", *J Virol*, 74(14):6242-6250 (2000).

Kolupaeva et al., "Structural Analysis of the Interaction of the Pyrimidine Tract-Binding Protein with the Internal Ribosomal Entry Site of Encephalomyocarditis Virus and Foot-and-Mouth Disease Virus RNAs", *RNA*, 2:1199-1212 (1996).

Kolupaeva et al., "Translation Eukaryotic Initiation Factor 4G Recognizes a Specific Structural Element within the Internal Ribosome Entry Site of Encephalomyocarditis Virus RNA", *J Biol Chem*, 273(29):18599-18604 (1998).

Kozak, "Initiation of Translation in Prokaryotes and Eukaryotes", *Gene*, 234:187-208 (1999).

Krüger et al., "Involvement of Proteasome α-Subunit PSMA7 in Hepatitis C Virus Internal Ribosome Entry Site-Mediated Translation", *Mol Cell Biol*, 21(24): 8357-8364 (2001).

La Monica et al., "Differences in Replication of Attenuated and Neurovirulent Polioviruses in Human Neuroblastoma Cell Line SH-SY5Y", *J Virol*, 63(5):2357-2360 (1989).

Le et al., "Unusual Folding Regions and Ribosome Landing Pad within Hepatitis C Virus and Pestivirus RNAs", *Gene*, 154:137-143 (1995).

Lerat et al., "Cell Type-Specific Enhancement of Hepatitis C Virus Internal Ribosome Entry Site-Directed Translation due to 5' Nontranslated Region Substitutions Selected during Passage of Virus in Lymphoblastoid Cells", *J Virol*, 74(15):7024-7031 (2000).

Li et al., "A Heterocyclic Inhibitor of the Rev-RRE Complex Binds to RRE as a Dimer", *Biochemistry*, 40:1150-1158 (2001).

Li et al., "Amino Acids 1-20 of the Hepatitis C Virus (HCV) Core Protein Specifically Inhibit HCV IRES-Dependent Translation in HepG2 Cells, and Inhibit Both HCV IRES- and Cap-Dependent Translation in HuH7 and CV-1 Cells", *J Gen Virol*, 84:815-825 (2003).

Lipinski, "Drug-Like Properties and the Causes of Poor Solubility and Poor Permeability", *J Pharm Tox Meth*, 44:235-249 (2000).

Llinás-Brunet, "NS3 Serine Protease Inhibitors as Potential Antiviral Agents for the Treatment of Hepatitis C Virus Infections", The 3rd Internatl Antiviral & Vaccine Discovery & Development Summit, Princeton, NJ (Mar. 13-14, 2002).

Lohmann et al., "Mutations in Hepatitis C Virus RNAs Conferring Cell Culture Adaptation", *J Virol*, 75(3):1437-1449 (2001).

Lohmann et al., "Replication of Subgenomic Hepatitis C Virus RNAs in a Hepatoma Cell Line", *Science*, 285:110-113 (1999).

Lopez de Quinto et al., "IRES Interaction with Translation Initiation Factors: Functional Characterization of Novel RNA Contacts with eIF3, eIF4B, and eIF4GII", *RNA*, 7:1213-1226 (2001).

Lopez de Quinto et al., "Interaction of the eIF4G Initiation Factor with the Aphthovirus IRES is Essential for Internal Translation Initiation In Vivo", *RNA*, 6:1380-1392 (2000).

Lu et al., "Poliovirus Chimeras Replicating Under the Translational Control of Genetic Elements of Hepatitis C Virus Reveal Unusual Properties of the Internal Ribosomal Entry Site of Hepatitis C Virus", *Proc Natl Acad Sci USA*, 93:1412-1417 (1996).

Lukaysky et al., "Structures of Two RNA Domains Essential for Hepatitis C Virus Internal Ribosome Entry Site Function", *Nat Struct Bio*, 7(12):1105-1110 (2000).

Lyons et al., "Hepatitis C Virus Internal Ribosome Entry Site RNA Contains a Tertiary Structural Element in a Functional Domain of Stem-Loop II", *Nucleic Acids Res*, 29(12):2535-2541 (2001).

Lukavsky et al., "Structure of HCV IRES Domain II Determined by NMR", *Nat Struct Biol*, 10(12):1033-1038 (2003).

Macejak et al., "Inhibition of Hepatitis C Virus (HCV)-RNA-Dependent Translation and Replication of a Chimeric HCV Poliovirus Using Synthetic Stabilized Ribozymes", *Hepatology*, 31:769-76 (2000).

Macejak et al., "Enhanced Antiviral Effect in Cell Culture of Type 1 Interferon and Ribozymes Targeting HCV RNA", *J Viral Hepatitis*, 8:400-405 (2001).

Macejak et al., "Internal Initiation of Translation Mediated by the 5' Leader of a Cellular mRNA", *Nature*, 353:90-94 (1991).

Major et al., "Hepatitis C Viruses.", p. 1127-1161. In D. Knipe and P. Howley (eds.), Fields Virology, vol. 1, $4^{th}$ Ed. Lippincott Williams and Wilkins, Philadelphia, PA (2001).

Manns et al., "Peginterferon alfa-2b Plus Ribavirin Compared with Interferon Alfa-2b Plus Ribavirin for Initial Treatment of Chronic Hepatitis C: A Randomised Trial", *The Lancet*, 358:958-965 (2001).

Martinez-Salas et al., "Functional Interactions in Internal Translation Initiation Directed by Viral and Cellular IRES Elements", *J Gen Virol*, 82:973-984 (2001).

Mazur et al., "A Thermodynamic and Structural Analysis of DNA Minor-groove Complex Formation", *J Mol Biol*, 300:321-337 (2000).

McHutchison et al., "Combination Therapy With Interferon Plus Ribavirin for the Initial Treatment of Chronic Hepatitis C", *Semin Liver Dis*, 19 Suppl 1:57-65 (1999).

McHutchison et al., "Hepatic HCV RNA Before and After Treatment With Interferon Alone or Combined With Ribavirin", *Hepatology*, 35(3):688-693 (2002).

Meerovitch et al., "A Cellular Protein that Binds to the 5'-Noncoding Region of Poliovirus RNA: Implications for Internal Translation Initiation", *Genes Dev*, 3:1026-1034 (1989).

Meerovitch et al., "La Autoantigen Enhances and Corrects Aberrant Translation of Poliovirus RNA in Reticulocyte Lysate", *J Virol*, 67(7): 3798-3807 (1993).

Mercer et al., "Hepatitis C Virus Replication in Mice with Chimeric Human Livers", *Nature Medicine*, 7(8):927-933 (2001).

Michel et al., "Eukaryotic Initiation Factor 4G-Poly(A) Binding Protein Interaction Is Required for Poly(A) Tail-Mediated Stimulation of Picornavirus Internal Ribosome Entry Segment-Driven Translation but Not for X-Mediated Stimulation of Hepatitis C Virus Translation", *Mol Cell Biol*, 21(13): 4097-4109 (2001).

Mitchell et al., "Protein Factor Requirements of the Apaf-1 Internal Ribosome Entry Segment: Roles of Polypyrimidine Tract Binding Protein and Upstream of N-ras", *Mol Cell Biol*, 21(10):3364-3374 (2001).

Moriguchi, et al., "Simple Method of Calculating Octanol/Water Partition Coefficient", *Chem Pharm Bull*, 40(1):127-130 (1992).

Nanbru et al., "Alternative Translation of the Proto-oncogene c-*myc* by an Internal Ribosome Entry Site", *J Biol Chem*, 272(51):32061-32066 (1997).

Niepmann et al., "Functional Involvement of Polypyrimidine Tract-Binding Protein in Translation Initiation Complexes with the Internal Ribosome Entry Site of Foot-and-Mouth Disease Virus", *J Virol*, 71(11):8330-8339 (1997).

Odreman-Macchioli et al., "Mutational Analysis of the Different Bulge Regions of Hepatitis C Virus Domain II and Their Influence on Internal Ribosome Entry Site Translational Ability", *J Biol Chem*, 276(45):41648-41655 (2001).

Odreman-Macchioli et al., "Influence of Correct Secondary and Tertiary RNA Folding on the Binding of Cellular Factors to the HCV IRES", *Nucleic Acids Res*, 28(4):875-885 (2000).

Ohlmann et al., "An Internal Ribosome Entry Segment Promotes Translation of the Simian Immunodeficiency Virus Genomic RNA", *J Biol Chem*, 275(16):11899-11906 (2000).

Otto et al., "The Pathway of HCV IRES-Mediated Translation Initiation", *Cell*, 119:369-380 (2004).

Pain, "Initiation of Protein Synthesis in Eukaryotic Cells", *Eur J Biochem*, 236:747-771 (1996).

Pelletier et al., "Internal Initiation of Translation of Eukaryotic mRNA Directed by a Sequence Derived from Poliovirus RNA", *Nature*, 334:320-325 (1988).
Pelletier et al., "Internal Binding of Eucaryotic Ribosomes on Poliovirus RNA: Translation in HeLa Cell Extracts", *J Virol*, 63(1):441-444 (1989).
Pestova et al., "Eukaryotic Ribosomes Require Initiation Factors 1 and 1A to Locate Initiation Codons", *Nature* 394:854-859 (1998).
Pestova et al., "A Prokaryotic-Like Mode of Cytoplasmic Eukaryotic Ribosome Binding to the Initiation Codon During Internal Translation Initiation of Hepatitis C and Classical Swine Fever Virus RNAs", *Genes Dev*, 12: 67-83 (1998).
Pestova et al., "Functional Dissection of Eukaryotic Initiation Factor 4F: the 4A Subunit and the Central Domain of the 4G Subunit Are Sufficient to Mediate Internal Entry of 43S Preinitiation Complexes", *Mol Cell Biol*, 16(12):6870-6878 (1996).
Peytou et al., "Synthesis and Antiviral Activity of Ethidium-Arginine Conjugates Directed Against the TAR RNA of HIV-1", *J Med Chem*, 42(20):4042-53 (1999).
Pietschmann et al., "Persistent and Transient Replication of Full-Length Hepatitis C Virus Genomes in Cell Culture", *J Virol*, 76(8):4008-4021 (2002).
Pietschmann et al., "Characterization of Cell Lines Carrying Self-Replicating Hepatitis C Virus RNAs", *J Virol*, 75(3):1252-1264 (2001).
Poole et al., "Pestivirus Translation Initiation Occurs by Internal Ribosome Entry", *Virology*, 206:750-754 (1995).
Pringle, "Virus Taxonomy—1999. The Universal System of Virus Taxonomy, Updated to Include the New Proposals Ratified by the International Committee on Taxonomy of Viruses During 1998", *Arch Virol*, 144(2):421-429 (1999).
Psaridi et al., "Mutational Analysis of a Conserved Tetraloop in the 5' Untranslated Region of Hepatitis C Virus Identifies a Novel RNA Element Essential for the Internal Ribosome Entry Site Function", *FEBS Lett*, 453:49-53 (1999).
Reynolds et al., "Internal Initiation of Translation of Hepatitis C Virus RNA: The Ribosome Entry Site is at the Authentic Initiation Codon", *RNA*, 2:867-878 (1996).
Reynolds et al., "Unique Features of Internal Initiation of Hepatitis C Virus RNA Translation", *EMBO J*, 14(23):6010-6020 (1995).
Rijnbrand et al., "Almost the Entire 5' Non-Translated Region of Hepatitis C Virus is Required for Cap-Independent Translation", *FEBS Lett*, 365:115-119 (1995).
Rijnbrand et al., "Internal Ribosome Entry Site-Mediated Translation in Hepatitis C Virus Replication", *Curr Top Microbiol Immunol*, 242:85-116 (2000).
Rijnbrand et al., "The Influence of Downstream Protein-Coding Sequence on Internal Ribosome Entry on Hepatitis C Virus and Other Flavivirus RNAs", *RNA*, 7:585-597 (2001).
Rijnbrand et al., "The Influence of AUG Codons in the Hepatitis C Virus 5' Nontranslated Region on Translation and Mapping of the Translation Initiation Window", *Virology*, 226:47-56 (1996).
Sachs et al., "Starting at the Beginning, Middle, and End: Translation Initiation in Eukaryotes", *Cell*, 89:831-838 (1997).
Saito et al., "Hepatitis C Virus Infection is Associated with the Development of Hepatocellular Carcinoma", *Proc Nail Acad Sci USA*, 87:6547-6549 (1990).
Schultz et al., "Mutations within the 5' Nontranslated RNA of Cell Culture-Adapted Hepatitis A Virus Which Enhance Cap-Independent Translation in Cultured African Green Monkey Kidney Cells", *J Virol*, 70(2):1041-1049 (1996).
Shimazaki et al., "Inhibition of Internal Ribosomal Entry Site-Directed Translation of HCV by Recombinant IFN-α Correlates With a Reduced La Protein", *Hepatology*, 35(1):199-208 (2002).
Simmonds, "Variability of Hepatitis C Virus", *Hepatology*, 21(2):570-583 (1995).
Sinha Roy et al., "Direct Interaction of a Vancomycin Derivative with Bacterial Enzymes Involved in Cell Wall Biosynthesis", *Chem Biol*, 8:1095-1106 (2001).
Sizova et al., "Specific Interaction of Eukaryotic Translation Initiation Factor 3 with the 5' Nontranslated Regions of Hepatitis C Virus and Classical Swine Fever Virus RNAs", *J Virol*, 72(6):4775-4782 (1998).
Smith, "Design of Drugs Through a Consideration of Drug Metabolism and Pharmacokinetics", *Eur J Drug Metab Pharm*, 3:193-199 (1994).
Smith et al., "Variation of the Hepatitis C Virus 5' Non-Coding Region: Implications for Secondary Structure, Virus Detection and Typing", *J Gen Virol*, 76(7):1749-1761 (1995).
Sonenberg et al., "Translational Control of Gene Expression", Cold Spring Harbor. Cold Spring Harbor Laboratory Press, New York (2000).
Spahn et al., "Hepatitis C Virus IRES RNA-Induced Changes in the Conformation of the 40s Ribosomal Subunit", *Science*, 291:1959-1962 (2001).
Spatzenegger et al., "Clinical Importance of Hepatic Cytochrome P450 in Drug Metabolism", *Drug Metab Rev* 27(3):397-417 (1995).
Subkhankulova et al., "Internal Ribosome Entry Segment-Mediated Initiation of c-Myc Protein Synthesis Following Genotoxic Stress", *Biochem J*, 359:183-192 (2001).
Tang et al., "Alterations to Both the Primary and Predicted Secondary Structure of Stem-Loop IIIc of the Hepatitis C Virus 1b 5' Untranslated Region (5'UTR) Lead to Mutants Severely Defective in Translation Which Cannot Be Complemented in *trans* by the Wild-Type 5'UTR Sequence", *J Virol*, 73(3):2359-2364 (1999).
Thiel et al., "Internal Ribosome Entry in the Coding Region of Murine Hepatitis Virus mRNA 5", *J Gen Virol.*, 75(11):3041-3046 (1994).
Tsukiyama-Kohara et al., "Internal Ribosome Entry Site within Hepatitis C Virus RNA", *J Virol*, 66(3):1476-1483 (1992).
Vagner et al., "Alternative Translation of Human Fibroblast Growth Factor 2 mRNA Occurs by Internal Entry of Ribosomes", *Mol Cell Biol*, 15(1):35-44 (1995).
Varaklioti et al., "Mutational Analysis of Two Unstructured Domains of the 5' Untranslated Region of HCV RNA", *Biochem Biophys. Res Commun.*, 253:678-685 (1998).
Wang et al., "An RNA Pseudolcnot is an Essential Structural Element of the Internal Ribosome Entry Site Located Within the Hepatitis C Virus 5' Noncoding Region", *RNA*, 1:526-537 (1995).
Wang et al., "Translation of Human Hepatitis C Virus RNA in Cultured Cells is Mediated by an Internal Ribosome-Binding Mechanism", *J Virol*, 67(6):3338-3344 (1993).
Wang et al., "A Conserved Helical Element is Essential for Internal Initiation of Translation of Hepatitis C Virus RNA", *J Virol*, 68(11):7301-7307 (1994).
Wang et al., "Screening poly(dA/dT)$^-$ cDNAs for Gene Identification", *PNAS USA*, 97(8):4162-7 (2000).
Wang et al., "Core Protein-Coding Sequence, but Not Core Protein, Modulates the Efficiency of Cap-Independent Translation Directed by the Internal Ribosome Entry Site of Hepatitis C Virus", *J Virol*, 74(23):11347-11358 (2000).
Wimmer et al., "Genetics of Poliovirus", *Annu Rev Genet*, 27:353-436 (1993).
Wong et al., "Cost-Effectiveness of 24 or 48 Weeks of Interferon α-2b Alone or With Ribavirin as Initial Treatment of Chronic Hepatitis C", *Am J Gastroenterol*, 95(6):1524-1530 (2000).
Zhao et al., "Genetic Analysis of a Poliovirus/Hepatitis C Virus Chimera: New Structure for Domain II of the Internal Ribosomal Entry Site of Hepatitis C Virus", *J Virol*, 75(8):3719-3730 (2001).
Zhao et al., "Poliovirus/Hepatitis C Virus (Internal Ribosomal Entry Site-Core) Chimeric Viruses: Improved Growth Properties through Modification of a Proteolytic Cleavage Site and Requirement for Core RNA Sequences but Not for Core-Related Polypeptides", *J Virol*, 73(2):1546-1554 (1999).
Patent Abstracts of Japan of Publication No. 08183260 Published Jul. 16, 1996.
Ahlquist et al., "Host Factors in Positive-Strand RNA Virus Genome Replication", *Journal of Virology*, 77(15):8181-8186 (2003).
Almerico et al., "Glycosidopyrroles Part 3. Effect of the Benzocondesnation on Acyclic Derivatives: 1-(2- hydroxyethoxy) Methylindoles as Potential Antiviral Agents", *Il Farmaco*, 53:409-414 (1998).
Almerico et al., "Glycosidopyrroles. part 4. 1-β-D-ribofuranosyl-pyrroles and Indoles as Potential Antiviral agents", *ARKIVOC*, 1(4):486-496 (2000).

Attaby et al., "Synthesis and Antimicrobial Evaluation of Several New Pyridine, Thienopyridine and Pyridothienopyrazole Derivatives", *Phosphorus, Sulfur and Silicon*, 149:49-64 (1999).

Cacchi et al., "2-Aryl and 2-Heteroaryl Indoles from 1-Alicynes and o-lodotrifluoroacetanilide through a Domino Copper-Catalyzed Coupling-Cyclization Process", *Organic Letters*, 5(21):3843-3846 (2003).

Carson et al., "The Synthesis and Properties of 2-p-Dimthylaminopheny1-1,3,3-trimethyl-3H-indolium Salts", *Journal of the Chemical Society*, 5819-5825 (1965).

Chikvaidze et al., "Synthesis and Antimicrobial Activity of New Derivatives of 2-Phenylindone", *Pharmaceutical Chemistry Journal*, 28(10):751-755 (1994).

Danilova et al., "Synthesis and Transformations of Aminoethyl Derivatives of Cyclic β-Diketones", *Zhurnal Obshchei Khimii*, 1(9):1708-9 (1965).

Dhar et al., "3-Cyanoindole-Based Inhibitors of Inosine Monophosphate Dehydrogenase: Synthesis and Initial Structure-Activity Relationships", *Bioorganic & Medicinal Chemistry Letters*, 13:3557-3560 (2003).

Font et al., "indoles and Pyridazino[4,5-*b*]indoles as Nonnucleoside Analog Inhibitors of HIV-1 Reverse Transcriptase", *Eur J Med Chem*, 30:963-971 (1995).

Germain Sanit-Ruf et al., "Analogues Méso-Hétérocycliques du dihydro-9,10 anthracéne. XII—Sur quelques Indoes Dérivés de la Dibenzo-p-Dioxine", *Notes*, 1069-1071 (1975).

International Search Report issued in Application No. PCT/US2005/024882.

Patent Abstracts of Japan of vol. 2003, No. 12 J1.

Patent Abstracts of Japan of JP 01273040 A published Oct. 31, 1989.

Patent Abstracts of Japan of JP 06236010 A published Aug. 23, 1994.

Patent Abstracts of Japan of JP 09169729 A published Jun. 30, 1997.

Perola et al., "Successful Virtual Screening of a Chemical Database for Farnesyltransferase Inhibitor Leads", *J. Med. Chem.*, 43:401-408 (2000).

Terent'ev et al., "Synthesis of Derivatives of 5-Methoxyinodle", *Doklady Akademii Nauk SSSR*, 114:560-563 (1957).

Wang et al., "Alpha Interferon Induces Distinct Translational Control Programs to Suppress Hepatitis C Virus RNA Replication", *Journal of Virology*, 77(7):3898-3912 (2003).

* cited by examiner

METHODS FOR TREATING HEPATITIS C

CROSS REFERENCES TO RELATED APPLICATIONS

This application is a continuation-in-part of U.S. application Ser. No. 11/180,961, filed Jul. 14, 2005, (having corresponding International Application No. PCT/US2005/024881, filed Jul. 14, 2005) which claims the benefit of U.S. Provisional Application No. 60/587,487, filed Jul. 14, 2004, U.S. Provisional Application No. 60/634,979, filed Dec. 13, 2004, U.S. Provisional Application No. 60/645,586, filed Jan. 24, 2005, U.S. Provisional Application No. 60/665,349, filed Mar. 28, 2005, and U.S. Provisional Application No. 60/675,440, filed Apr. 28, 2005, the entire contents of which applications are incorporated herein by reference.

GOVERNMENT SUPPORT

The present invention was made with U.S. Government support under DHHS Grant No. 5R44 AI054029-03. The U.S. Government has certain rights in the invention.

FIELD OF THE INVENTION

The present invention provides compounds, pharmaceutical compositions, and methods of using such compounds or compositions for treating infection by a virus, or for affecting viral IRES activity.

BACKGROUND OF THE INVENTION

An estimated 170 million people worldwide are reported to be infected with hepatitis C virus (HCV), the causative agent of hepatitis C. Seventy to eighty percent of HCV infections lead to chronic liver infection, which in turn may result in severe liver disease, including liver fibrosis, cirrhosis, and hepatocellular carcinoma (115).

HCV constitutes the *Hepacivirus* genus of the family Flaviviridae (106), and contains a positive-stranded 9.6 kb RNA genome. The features of the HCV genome include a 5'-untranslated region (UTR) that encodes an internal ribosome entry site (IRES) that directs the translation of a single long open reading frame (ORF) encoding a polyprotein of 3,010 amino acids. The HCV ORF is followed by a 3'-UTR of variable length, depending on the HCV variant, that encodes the sequences required for the initiation of antigenomic strand synthesis (79).

The HCV IRES and 3'-UTR both encode regions of RNA structures that are required for genome translation and replication. The HCV polyprotein is posttranslationally processed into at least 10 mature viral proteins, including the structural proteins core (putative nucleocapsid), E1 and E2 and the nonstructural (NS) proteins NS2 to NS5B.

Three distinct elements have been shown to be involved in HCV IRES-mediated translation: (1) integrity of the global structure of HCV IRES, (2) the 3'-terminal region of the HCV genome; and (3) trans-acting cellular factors that interact with the HCV IRES element and assist in translation initiation (35).

The initiation of protein synthesis in eukaryotic cells predominantly follows the 5' cap-dependent, first AUG rule (61). However, an increasing number of viral (6, 12, 28, 31a, 50, 95, 97, 98, 105, 128) and cellular mRNAs (18, 39, 45, 78, 91, 130) have been shown to use an IRES element to direct translation initiation. In 1992, an IRES element was reported in the 5' UTR of the HCV RNA genome (129), indicating that synthesis of the viral protein is initiated in a cap-independent fashion.

A bicistronic expression system can be used to define and evaluate the function of IRES elements. This test system harbors two different reporter genes in which the 5'-proximal reporter gene is expressed by a cap dependent translation mechanism while the second reporter is expressed only if an upstream sequence inserted in the intergenic space contains an IRES sequence element. Using this system, a putative IRES in the HCV 5' UTR was unambiguously demonstrated to function as an IRES involved in translational control of viral proteins (133). In vitro translation, RNA transfection, and mutagenesis studies provided further evidence that the HCV 5' UTR contains an IRES element (23, 41, 42, 108, 129, 132, 133, 134). Both in vitro and cell-based studies demonstrated that the HCV IRES guides cellular translation initiation factors to an internal site of the viral RNA (56, 58, 120), thus functionally demonstrating the HCV IRES activity. Taken together, these results demonstrate that the HCV 5'-UTR contains an IRES element that plays an active and crucial role in the mechanism of internal initiation for HCV protein translation.

The IRES is one of the most conserved regions of the HCV genome, reflecting its essential nature for viral replication and protein synthesis (13, 118, 122). Although both 5' and 3' sequences of the IRES appear to play a role in the control of initiation of translation (42, 109, 110, 113, 136), the minimal sequence requirement for HCV IRES function has been mapped to a region between nucleotides 44-354 (40).

Biochemical probing and computer modeling indicate that the HCV IRES and its 5' sequence is folded into a distinct structure that consists of four major domains and a pseudoknot (11, 42, 122). Domain I contains a small stem-loop structure that does not appear to be a functional part of the IRES element while domains II, III, and IV contain the HCV IRES activity (43, 111). The relationships between secondary and tertiary structures of the HCV IRES and their function have recently been established (5, 55, 56, 99, 124). Both domains II and III consist of multiple stems, loops, and bulges and are important for IRES activity (23, 40, 51, 52, 54, 56, 64, 74, 75, 93, 107, 108, 110, 124, 127, 131, 139, 141, 142). Domain II can induce conformational changes on the ribosome that have been implicated in the decoding process (124). Domain III has the highest degree of structural conservation among the different HCV strains. It comprises the core of the flavivirus IRES and has 6 subdomains (40). Various studies have shown that subdomain IIId forms complex secondary/tertiary structures and is critical for initiation activity (55, 56, 57, 124, 129). Domain IV has one stem-loop that spans the initiation codon and is specific for the HCV IRES (41, 122), but the precise role of domain IV in IRES activity remains controversial (41, 112).

The role of the HCV IRES is to position the translational machinery near an internal initiator codon in the viral mRNA. The translation initiation mechanism of the HCV and other viral IRES differs significantly from that of 5'-cap-dependent translation initiation (7, 21, 31, 35, 61, 71, 72, 81, 88, 96, 114, 123). Most cellular capped mRNAs utilize a number of initiation factors (eIFs) that are required for the translation initiation process. The initial steps of the process require proteins that interact with the 5' cap structure and recruit the 40S ribosomal subunit to the cap-proximal region of mRNA. This complex then scans 3' of the cap, until reaching an AUG codon at which translation will initiate (21, 114). However, in the case of HCV, the IRES functionally replaces the 5' cap structure, allowing the 40S ribosomal subunit and eIF3 to bind directly to the RNA. Subdomain IIId of the HCV IRES harbors the binding site for the 40S ribosomal subunit and the only initiation factors required for translation initiation are eIF2, eIF3, and eIF4E (15, 58, 94, 100, 120, 124).

The polypyrimidine track-binding protein (PTB) and La autoantigen are noncanonical translation initiation factors that bind to and enhance HCV IRES activity (1, 2, 3, 4, 5, 30, 48, 49, 53). PTB, a 57-kDa protein involved in RNA splicing, is also necessary for efficient IRES-mediated translation initiation of picornavirus mRNA, and some cellular mRNAs (10, 11, 36, 53, 59, 89, 92). The La autoantigen, a 52 kDa double-stranded RNA unwinding protein, also increases the activity of poliovirus and cellular IRES (38, 85, 86). Other cellular factors involved in HCV IRES-mediated translation initiation include proteasome α-subunit PSMA7 (62), ribosomal protein S5 (26), ribosomal protein S9 (24, 25, 100), and hnRNPL (33). However, the role of these RNA-binding proteins in HCV IRES-mediated initiation of translation is unclear. Recently, it was reported that the activity of interferon (IFN) α against HCV replication might target HCV IRES-mediated translation initiation by causing a reduction of La protein levels (117) Some HCV proteins, such as NS5A, core and NS4A/4B, also reported to be involved in the HCV IRES function (143-146). Thus, an inhibitor that blocks interaction between the IRES and the noncanonical factors might efficiently inhibit HCV replication and lack cytotoxicity.

Currently, only interferon (IFN) α and the nucleoside analogue ribavirin, in combination, are marketed for the treatment of HCV infection. However, these two agents are immunomodulators and have limited efficacy, relatively high toxicity, and high cost (80, 83, 84, 138). Although the treatment outcome is variable among the six major HCV genotypes, only about one-half of all treated patients respond to therapy, suggesting that the virus encodes protein products that may directly or indirectly attenuate the antiviral action of IFN. IFNs are naturally produced in response to virus infection, and cellular exposure to IFN leads to the induced expression of a variety of IFN-stimulated genes (ISGs), many of which have an antiviral function. ISG action can limit virus replication at multiple points within the replicative cycle.

There remains a need for an alternative means of treating patients afflicted with HCV. Specifically, a need exists for novel antiviral drugs, for example, that have no cross-resistance with existing treatment modalities, and which demonstrate synergy with other anti-HCV agents.

All documents referred to herein are incorporated by reference into the present application as though fully set forth herein.

SUMMARY OF THE INVENTION

The present invention provides compounds, pharmaceutical compositions, and methods of using such compounds or compositions for treating infection by a virus, or for affecting viral IRES activity.

DETAILED DESCRIPTION OF THE INVENTION

A. Compounds of the Invention

Figure 1:
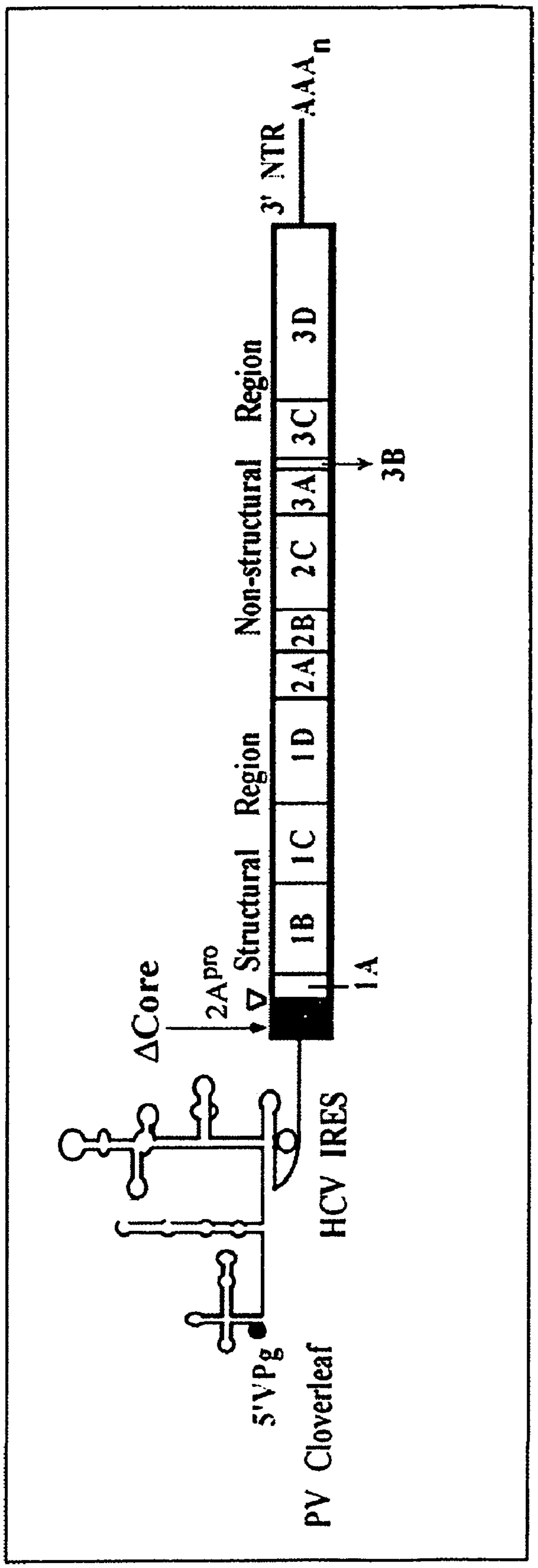
FIG. 1 illustrates the HCV-PV chimera construct. The cloverleaf-like RNA structure of PV, an essential cis-acting replication signal ending with the genome-linked protein VPg, is located at the 5' end of the genome. The solid (HCV) and open (PV) boxes depict open reading frames encoding viral polypeptides. The position of the HCV core fragment (the first 123 amino acids) gene is denoted by Δ Core. Overall, the HCV-specific sequence in the HCV-PV spans from nucleotides 18 to 710 (139).

One aspect of the invention relates to a compound of formula I

I

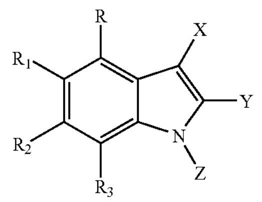

wherein:

X is:
- hydrogen;
- a nitro group;
- a cyano group;
- a —$COR_a$ group, where $R_a$ is:
  - a $C_1$ to $C_6$ alkyl,
  - a $C_6$ to $C_8$ aryl optionally substituted with an alkoxy or a halogen, or
  - a dialkyl-amino;
- a —$COOR_x$ group, where $R_x$ is a $C_1$ to $C_6$ alkyl;
- a formyl group;
- a $C_6$ to $C_8$ aryl optionally substituted with an alkoxy; or
- a 5 or 6-membered heteroaryl optionally substituted with:
  - a $C_1$ to $C_6$ alkyl,
  - a $C_6$ to $C_8$ aryl optionally substituted with an alkoxy or one or more halogen(s), or
  - a 5 to 6 membered heteroaryl;

Y is:
- a hydrogen;
- a haloalkyl;
- a halogen;
- an amino optionally substituted with one or more $C_1$ to $C_6$ alkyl(s);
- a benzofuran;
- a benzothiophene;
- a dibenzofuran;
- a dibenzothiophene;
- a benzothiazole;
- a naphthalene;
- an indole, optionally substituted on the nitrogen with a $C_1$ to $C_6$ alkyl;

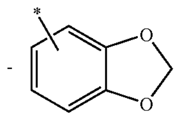

;

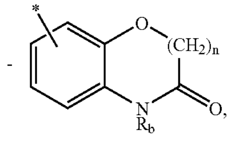

, where $R_b$ is a hydrogen or a $C_1$ to $C_6$ alkyl, and n is 0 or 1;

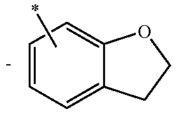

;

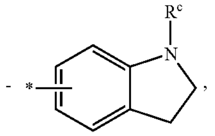

, where $R_c$ is a hydrogen, a —$CONHR_x$, where $R_x$ is as defined above, or an —$SO_2R_x$, where $R_x$ is as defined above; or

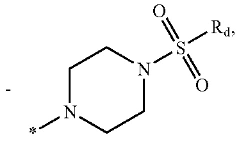

where $R_d$ is a $C_1$ to $C_6$ alkyl or a $C_6$ to $C_8$ aryl;

a —$NHCOR_e$ group, where $R_e$ is:
  a $C_1$ to $C_6$ alkyl;
  a $C_6$ to $C_8$ aryl optionally substituted with:
    a $C_1$ to $C_6$ alkyl,
    an alkoxy,
    a cyano group,
    a nitro group, or
    a halogen;
a —$NHCOOR_x$ group, where $R_x$ is as defined above;
a —$CH_2O$—$R_f$ group, where $R_f$ is a $C_6$ to $C_8$ aryl;
a —$NR_gR_h$ group, where $R_g$ is hydrogen or a $C_1$ to $C_6$ alkyl and $R_h$ is hydrogen or a $C_6$ to $C_8$ aryl optionally substituted with an alkoxy;
a $C_1$ to $C_6$ alkyl;
a 5 or 6 membered heteroaryl, optionally substituted with:
  a $C_1$ to $C_6$ alkyl, optionally substituted with a $C_6$ to $C_8$ aryl,
  a $C_6$ to $C_8$ aryl, optionally substituted with —$COOR_x$, where $R_x$ is as defined above, or
  an amino group;
a 5 or 6 membered heterocycle optionally substituted with:
  a —$COOR_x$ group, where $R_x$ is as defined above, or
  a —$NHCOOR_x$ group, where $R_x$ is as defined above;
a $C_6$ to $C_8$ aryl, optionally substituted with one or more of the following:
  an alkoxy, optionally substituted with:
    an alkoxy,
    a hydroxy,
    one or more halogen(s),
    a 5 or 6 membered heterocycle, optionally substituted with:
      a $C_1$ to $C_6$ alkyl, or
      a hydroxy,
    an amino group optionally substituted with one or more $C_1$ to $C_6$ alkyl(s),
    a —$NR_iSO_2R_x$ group, where $R_x$ is as defined above and $R_i$ is:
      a hydrogen,
      a $C_1$ to $C_6$ alkyl,
      a —$COR_x$ group, where $R_x$ is as defined above, a haloalkyl, or
      a haloalkoxy,
    a —$NR_jCOR_k$ group, where $R_k$ is:
      a $C_1$ to $C_6$ alkyl,
      a hydrogen, or
      an amino optionally substituted with one or more $C_1$ to $C_6$ alkyl(s),
    and $R_j$ is:
      a hydrogen,
      a $C_1$ to $C_6$ alkyl,
      a —$COR_x$ group, where $R_x$ is as defined above,
      a haloalkyl, or
      a haloalkoxy,
    a —$N{=}N^+{=}N^-$ group, or
    a —$COR_l$, where $R_l$ is a 5 or 6 membered heterocycle optionally substituted with a hydroxy,
  an amino optionally substituted with one or more $C_1$ to $C_6$ alkyl(s),
  a nitro group,
  a $C_1$ to $C_6$ alkyl group, optionally substituted with:
    a —$NHSO_2R_x$ group, where $R_x$ is as defined above, or
    a —$NR_xSO_2R_x$ group, where $R_x$ is as defined above,
  a haloalkoxy,
  a halogen,
  a hydroxy,
  a —$COOR_x$ group, where $R_x$ is as defined above,
  a —$COR_m$ group, where $R_m$ is:
    an amino optionally substituted with one or more $C_1$ to $C_6$ alkyl(s), where the one or more $C_1$ to $C_6$ alkyl(s) is/are optionally substituted with:
      a hydroxy
      a 5 or 6 membered heterocycle,
      an amino optionally substituted with one or more $C_1$ to $C_6$ alkyl(s),
      an alkoxy,
    a 3 to 7 membered heterocycle, optionally substituted with a $C_1$ to $C_6$ alkyl, optionally substituted with a dialkyl-amino,
    a —$NHR_n$ group, where $R_n$ is:
      a —$CH_2CONH_2$, or
      a $C_6$ to $C_8$ aryl optionally substituted with:
        an alkyl,
        one or more halogen(s),
        a nitro group, or
        one or more alkoxy(s),
  a —$NR_oCOR_p$ group, where $R_p$ is:
    a $C_1$ to $C_6$ alkyl optionally substituted with:
      a halogen,
      an alkoxy, or
      a $C_6$ to $C_8$ aryl,
    a 5 or 6 membered heterocycle,
    a $C_6$ to $C_8$ aryl, optionally substituted with a halogen,
    a 5 or 6 membered heteroaryl optionally substituted with one or more $C_1$ to $C_6$ alkyl(s),
    a hydrogen,

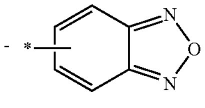

or

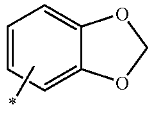

, and where $R_o$ is:
  a hydrogen,
  a $C_1$ to $C_6$ alkyl,
  a —$COR_x$ group, where $R_x$ is as defined above, a haloalkyl, or
a haloalkoxy,
a —$NR_qCONR_qR_r$ group, where $R_q$ is:
a hydrogen,
a $C_1$ to $C_6$ alkyl,
a haloalkyl,
a haloalkoxy, or
a —$COR_x$ group, where $R_x$ is as defined above,
and where $R_r$ is:
a $C_6$ to $C_8$ aryl optionally substituted with:

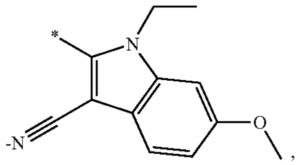

a $C_1$ to $C_6$ alkyl,
a haloalkyl,
a —$OR_s$ group, where $R_s$ is a $C_6$ to $C_8$ aryl, or
a —$COOR_x$ group, where $R_x$ is as defined above,
a $C_1$ to $C_6$ alkyl optionally substituted with one or more of the following:
a halogen,
an alkylene,
a $C_6$ to $C_8$ aryl, and/or
a —$COOR_x$ group, where $R_x$ is as defined above,
a —$COOR_x$ group, where $R_x$ is as defined above,
a —$NR_tCOOR_u$ group, where $R_u$ is:
a $C_1$ to $C_{12}$ alkyl, optionally substituted with:
a $C_6$ to $C_8$ aryl optionally substituted with a $C_1$ to $C_6$ alkyl or an alkoxy,
an alkylene,
an alkoxy,
an alkyne,
a halogen, or
a 5 or 6 membered heterocycle,
a $C_6$ to $C_8$ aryl, optionally substituted with:
an alkoxy,
a halogen, or
a $C_1$ to $C_6$ alkyl, or
a 5 or 6 membered heterocycle,
and $R_t$ is:
a hydrogen,
a $C_1$ to $C_6$ alkyl,
a —$COR_x$ group, where $R_x$ is as defined above,
a haloalkyl, or
a haloalkoxy,
a —$NR_vSO_2R_w$ group, where $R_v$ is:
a hydrogen,
a —$COR_x$, where $R_x$ is as defined above, or
a $C_1$ to $C_6$ alkyl, optionally substituted with:
a halogen,
a —$COR_x$ group, where $R_x$ is as defined above,
a —$OCOR_x$ group, where $R_x$ is as defined above,
a hydroxy, or
an alkoxy,
and where $R_w$ is:
a $C_1$ to $C_6$ alkyl optionally substituted with:
a halogen,
a haloalkyl,
a $C_6$ to $C_8$ aryl, or
a 5 or 6 membered heterocycle,
a $C_2$ to $C_6$ alkylene, an alkyl- or dialkyl-amino optionally substituted with a halogen,
a 5 or 6 membered heterocycle, or
a 5 or 6 membered heteroaryl optionally substituted with:
a $C_1$ to $C_6$ alkyl,
a 5 or 6 membered heterocycle, or

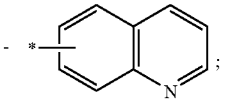
;

-a 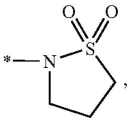

-a 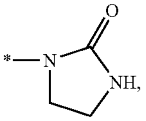

-a 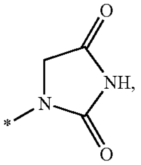

-a 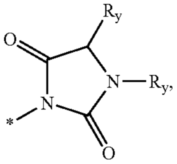

optionally substituted with a $C_1$ to $C_6$ alkyl, where $R_y$ is a $C_1$ to $C_6$ alkyl or hydrogen, -a 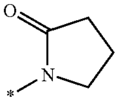
, -a 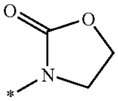
, -a 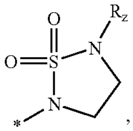
, where $R_z$ is hydrogen or a $C_1$ to $C_6$ alkyl, optionally substituted with a $C_6$ to $C_8$ aryl,
a —$SR_x$ group, where $R_x$ is as defined above,
a —$SO_2R_{aa}$ group, where $R_{aa}$ is:
a $C_1$ to $C_6$ alkyl,
an amino group,
an alkyl- or dialkyl-amino group optionally substituted with a hydroxy or a —$COOR_x$ group, where $R_x$ is as defined above,
a 5 or 6 membered heteroaryl,
a $C_6$ to $C_8$ aryl, and/or
a —$NHR_{bb}$ group, where $R_{bb}$ is:

- 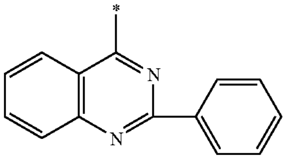 ,

- 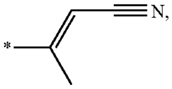

a —C(═S)$NH_2$ group, or
a —$PO(OR_x)_2$ group, where $R_x$ is as defined above;
a 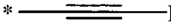 $R_{cc}$ group, where $R_{cc}$ is:
a naphthalene,
a 5 or 6 membered heteroaryl, -a 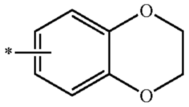 , a $C_6$ to $C_8$ aryl, optionally substituted with one or more of the following:
an alkoxy,
a hydroxy,
a halogen,
a $C_1$ to $C_6$ alkyl, optionally substituted with a cyano group,
an amino optionally substituted with one or more $C_1$ to $C_6$ alkyls,
a —$NHPOR_xR_x$, where $R_x$ is as defined above,
a —$NR_{ee}CONR_{ff}R_{ff}$ group, where $R_{ee}$ is a hydrogen or a $C_1$ to $C_6$ alkyl, optionally substituted with a halogen, and $R_{ff}$ is:
a hydrogen,
a haloalkyl,
a haloalkoxy,
a $C_1$ to $C_6$ alkyl, or
a —$COR_x$, where $R_x$ is as defined above,
a —$NR_{gg}COR_{hh}$ group, where $R_{hh}$ is:
a hydrogen,
a $C_1$ to $C_6$ alkyl optionally substituted with:
an alkoxy,
a halogen, or
an amino optionally substituted with one or more $C_1$ to $C_6$ alkyls,
an amino optionally substituted with one or more $C_1$ to $C_6$ alkyls, where the alkyls are optionally substituted with a halogen,
a 5 or 6 membered heterocycle,
a 5 or 6 membered heteroaryl,
and $R_{gg}$ is:
a hydrogen,
a $C_1$ to $C_6$ alkyl,
a haloalkyl,
a haloalkoxy, or
a —$COR_x$ group, where $R_x$ is as defined above,
a haloalkyl,
5 or 6 membered heterocycle groups,
an amino optionally substituted with one or more $C_1$ to $C_6$ alkyls, and/or
a —$NR_{ii}SO_2R_x$ group, where $R_x$ is as defined above, and $R_{ii}$ is:
a hydrogen,
a $C_1$ to $C_6$ alkyl,
a haloalkyl,
a haloalkoxy,
a —$COR_x$ group, where $R_x$ is as defined above;

Z is:
a hydrogen;
a $C_1$ to $C_6$ alkyl optionally substituted with:
an alkoxy,
one or more halogen(s), or
a $C_6$ to $C_8$ aryl;
a $C_2$ to $C_6$ alkylene;
a $C_6$ to $C_8$ aryl optionally substituted with an alkoxy or one or more $C_1$ to $C_6$ alkyl(s);
a —$COOR_x$ group, where $R_x$ is as defined above; or

- 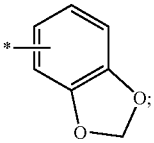

R is a hydrogen, a halogen or an alkoxy;
$R_1$ is:
a hydrogen;
a hydroxy;
a halogen;
a haloalkyl;
a nitro group;
a 5 or 6 membered heteroaryl;
a 5 or 6 membered heterocycle;
an alkoxy optionally substituted with:
one or more halogen(s),
a $C_6$ to $C_8$ aryl, or
a 5 or 6 membered heterocycle;
a $C_6$ to $C_8$ aryl optionally substituted with an alkoxy;
a —$COR_x$ group, where $R_x$ is as defined above;
a $C_1$ to $C_6$ alkyl optionally substituted with a dialkyl-amino or a 5 or 6 membered heterocycle; or $R_1$ joins together with $R_2$ to form:

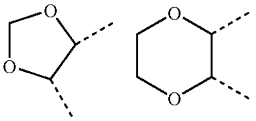 ;

$R_2$ is:
a nitro group;
a hydrogen;
a halogen;
a hydroxy group;
a $C_1$ to $C_6$ alkyl group, optionally substituted with one or more halogen(s);
an amino group;
an alkoxy group optionally substituted with:
one or more halogen(s),
an —$OCOR_x$ group, where $R_x$ is as defined above,
a dialkyl-amino optionally substituted with an alkoxy,
a 5 or 6 membered heterocycle group optionally substituted with a $C_1$ to $C_6$ alkyl, a 5 or 6 membered heteroaryl group, or
a $C_6$ to $C_8$ aryl group;
a —$COOR_x$ group, where $R_x$ is as defined above;
a haloalkyl;
an amide group optionally substituted with:
a hydroxy group, or
a $C_6$ to $C_8$ aryl;
a 5 or 6 membered heteroaryl;
a —$OCOR_x$ group, where $R_x$ is as defined above;
a —$NHCOR_{jj}$ group, where $R_{jj}$ is:
an alkoxy, or
an amino optionally substituted with one or more $C_1$ to $C_6$ alkyl(s);
a —$OR_{kk}$ group, where $R_{kk}$ is a 5 to 6 membered heteroaryl;
a —$NHSO_2R_x$ group, where $R_x$ is as defined above; or $R_2$ joins together with $R_1$ to form:

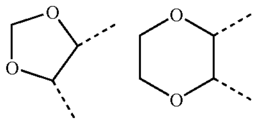
;

$R_3$ is:
a hydrogen; or
—$CH_2OCOR_x$, and $R_x$ is as defined above;

or a pharmaceutically acceptable salt thereof.

In some embodiments of formula I,

X is:
a nitro group;
a cyano group;
a —$COR_a$ group, where $R_a$ is:
a $C_1$ to $C_6$ alkyl,
a $C_6$ to $C_8$ aryl optionally substituted with an alkoxy or a halogen, or
a dialkyl-amino;
a —$COOR_x$ group, where $R_x$ is a $C_1$ to $C_6$ alkyl;
a formyl group;
a $C_6$ to $C_8$ aryl optionally substituted with an alkoxy; or
a 5 or 6-membered heteroaryl optionally substituted with:
a $C_1$ to $C_6$ alkyl,
a $C_6$ to $C_8$ aryl optionally substituted with an alkoxy or one or more halogen(s), or
a 5 to 6 membered heteroaryl;

Y is:
a haloalkyl;
a halogen;
an amino optionally substituted with one or more $C_1$ to $C_6$ alkyl(s);
a benzofuran;
a benzothiophene;
a dibenzofuran;
a dibenzothiophene;
a benzothiazole;
a naphthalene;
an indole, optionally substituted on the nitrogen with a $C_1$ to $C_6$ alkyl;

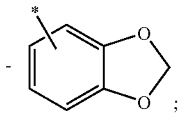
;

-continued

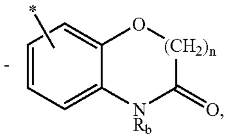

where $R_b$ is a hydrogen or a $C_1$ to $C_6$ alkyl, and n is 0 or 1;

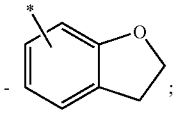
;

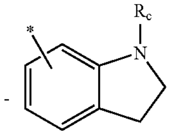
, where $R_c$ is a hydrogen, a —$CONHR_x$, where $R_x$ is as defined above, or an —$SO_2R_x$, where $R_x$ is as defined above; or

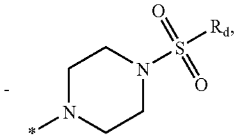

where $R_d$ is a $C_1$ to $C_6$ alkyl or a $C_6$ to $C_8$ aryl;
a —$NHCOR_e$ group, where $R_e$ is:
a $C_1$ to $C_6$ alkyl;
a $C_6$ to $C_8$ aryl optionally substituted with:
a $C_1$ to $C_6$ alkyl,
an alkoxy,
a cyano group,
a nitro group, or
a halogen;
a —$NHCOOR_x$ group, where $R_x$ is as defined above;
a —$CH_2O$—$R_f$ group, where $R_f$ is a $C_6$ to $C_8$ aryl;
a —$NR_gR_h$ group, where $R_g$ is a $C_1$ to $C_6$ alkyl or a hydrogen and $R_h$ is a $C_6$ to $C_8$ aryl optionally substituted with an alkoxy;
a $C_1$ to $C_6$ alkyl;
a 5 or 6 membered heteroaryl, optionally substituted with:
a $C_1$ to $C_6$ alkyl, optionally substituted with a $C_6$ to $C_8$ aryl,
a $C_6$ to $C_8$ aryl, optionally substituted with —$COOR_x$, where $R_x$ is as defined above, or
an amino group;
a 5 or 6 membered heterocycle optionally substituted with:
a —$COOR_x$ group, where $R_x$ is as defined above, or
a —$NHCOOR_x$ group, where $R_x$ is as defined above;
a $C_6$ to $C_8$ aryl, optionally substituted with one or more of the following:
an alkoxy, optionally substituted with:
an alkoxy,
a hydroxy,
one or more halogen(s), a 5 or 6 membered heterocycle, optionally substituted with:
a $C_1$ to $C_6$ alkyl, or
a hydroxy,
an amino group optionally substituted with one or more $C_1$ to $C_6$ alkyl(s),
a —$NR_iSO_2R_x$ group, where $R_x$ is as defined above and $R_i$ is:
a hydrogen,
a $C_1$ to $C_6$ alkyl,
a —$COR_x$ group, where $R_x$ is as defined above,
a haloalkyl, or
a haloalkoxy,
a —$NR_jCOR_k$ group, where $R_k$ is:
a $C_1$ to $C_6$ alkyl,
a hydrogen, or
an amino optionally substituted with one or more $C_1$ to $C_6$ alkyl(s),
and $R_j$ is:
a hydrogen,
a $C_1$ to $C_6$ alkyl,
a —$COR_x$ group, where $R_x$ is as defined above,
a haloalkyl, or
a haloalkoxy,
a —N═N$^+$═N$^-$ group, or
a —$COR_l$, where $R_l$ is a 5 or 6 membered heterocycle optionally substituted with a hydroxy,
an amino optionally substituted with one or more $C_1$ to $C_6$ alkyl(s),
a $C_1$ to $C_6$ alkyl group, optionally substituted with:
a —$NHSO_2R_x$ group, where $R_x$ is as defined above, or
a —$NR_xSO_2R_x$ group, where $R_x$ is as defined above,
a haloalkoxy,
a halogen,
a hydroxy,
a —$COOR_x$ group, where $R_x$ is as defined above,
a —$COR_m$ group, where $R_m$ is:
an amino optionally substituted with one or more $C_1$ to $C_6$ alkyl(s), where the one or more $C_1$ to $C_6$ alkyl(s) is/are optionally substituted with:
a hydroxy
a 5 or 6 membered heterocycle,
an amino optionally substituted with one or more $C_1$ to $C_6$ alkyl(s),
an alkoxy,
a 3 to 7 membered heterocycle, optionally substituted with a $C_1$ to $C_6$ alkyl, optionally substituted with a dialkyl-amino,
a —$NHR_n$ group, where $R_n$ is:
a —$CH_2CONH_2$, or
a $C_6$ to $C_8$ aryl optionally substituted with:
an alkyl,
one or more halogen(s),
a nitro group, or
one or more alkoxy(s),
a —$NR_oCOR_p$ group, where $R_p$ is:
a $C_1$ to $C_6$ alkyl optionally substituted with:
a halogen,
an alkoxy, or
a $C_6$ to $C_8$ aryl,
a 5 or 6 membered heterocycle,
a $C_6$ to $C_8$ aryl, optionally substituted with a halogen,
a 5 or 6 membered heteroaryl optionally substituted with one or more $C_1$ to $C_6$ alkyl(s),
a hydrogen,

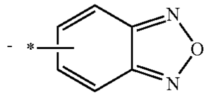 or 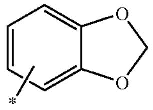, and where $R_o$ is:
a hydrogen,
a $C_1$ to $C_6$ alkyl,
a —$COR_x$ group, where $R_x$ is as defined above,
a haloalkyl, or
a haloalkoxy,
a —$NR_qCONR_qR_r$ group, where $R_q$ is:
a hydrogen,
a $C_1$ to $C_6$ alkyl,
a haloalkyl,
a haloalkoxy, or
a —$COR_x$ group, where $R_x$ is as defined above,
and where $R_r$ is:
a $C_6$ to $C_8$ aryl optionally substituted with:

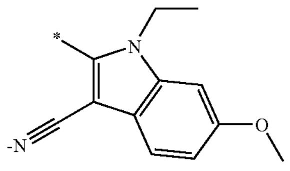, a $C_1$ to $C_6$ alkyl,
a haloalkyl,
a —$OR_s$ group, where $R_s$ is a $C_6$ to $C_8$ aryl, or
a —$COOR_x$ group, where $R_x$ is as defined above,
a $C_1$ to $C_6$ alkyl optionally substituted with one or more of the following:
a halogen,
an alkylene,
a $C_6$ to $C_8$ aryl, and/or
a —$COOR_x$ group, where $R_x$ is as defined above,
a —$COOR_x$ group, where $R_x$ is as defined above,
a —$NR_tCOOR_u$ group, where $R_u$ is:
a $C_1$ to $C_{12}$ alkyl, optionally substituted with:
a $C_6$ to $C_8$ aryl optionally substituted with a $C_1$ to $C_6$ alkyl or an alkoxy,
an alkylene,
an alkoxy,
an alkyne,
a halogen, or
a 5 or 6 membered heterocycle,
a $C_6$ to $C_8$ aryl, optionally substituted with:
an alkoxy,
a halogen, or
a $C_1$ to $C_6$ alkyl, or
a 5 or 6 membered heterocycle,
and $R_t$ is:
a hydrogen,
a $C_1$ to $C_6$ alkyl,
a —$COR_x$ group, where $R_x$ is as defined above,
a haloalkyl, or
a haloalkoxy,
a —$NR_vSO_2R_w$ group, where $R_v$ is:
a hydrogen,
a —$COR_x$, where $R_x$ is as defined above, or
a $C_1$ to $C_6$ alkyl, optionally substituted with:

a halogen,
a —$COR_x$ group, where $R_x$ is as defined above,
a —$OCOR_x$ group, where $R_x$ is as defined above,
a hydroxy, or
an alkoxy, and where $R_w$ is:
a $C_1$ to $C_6$ alkyl optionally substituted with:
a halogen,
a haloalkyl,
a $C_6$ to $C_8$ aryl, or
a 5 or 6 membered heterocycle,
a $C_2$ to $C_6$ alkylene,
an alkyl- or dialkyl-amino optionally substituted with a halogen,
a 5 or 6 membered heterocycle, or
a 5 or 6 membered heteroaryl optionally substituted with:
a $C_1$ to $C_6$ alkyl,
a 5 or 6 membered heterocycle, or

- 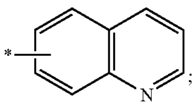 ;

-a 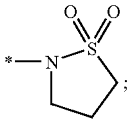 ;

-a 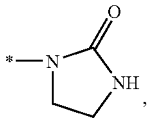 ,

-a 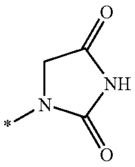 ,

-a 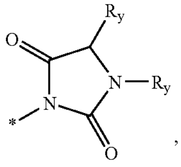 , optionally substituted with a $C_1$ to $C_6$ alkyl, where $R_y$ is a $C_1$ to $C_6$ alkyl or hydrogen, -a 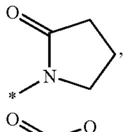 , -a 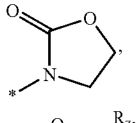 , -a 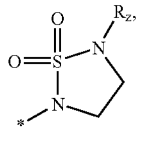

where $R_z$ is hydrogen or a $C_1$ to $C_6$ alkyl, optionally substituted with a $C_6$ to $C_8$ aryl,
a —$SR_x$ group, where $R_x$ is as defined above,
a —$SO_2R_{aa}$ group, where $R_{aa}$ is:
a $C_1$ to $C_6$ alkyl,
an amino group,
an alkyl- or dialkyl-amino group optionally substituted with a hydroxy or a —$COOR_x$ group, where $R_x$ is as defined above,
a 5 or 6 membered heteroaryl,
a $C_6$ to $C_8$ aryl, and/or
a —$NHR_{bb}$ group, where $R_{bb}$ is:

- 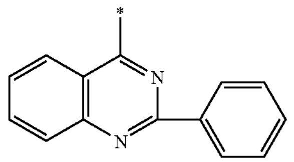 ,

- 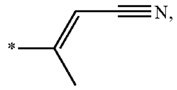

a —C(═S)$NH_2$ group, or
a —$PO(OR_x)_2$ group, where $R_x$ is as defined above;

a *—≡—$R_{cc}$ group, where $R_{cc}$ is:
a naphthalene,
a 5 or 6 membered heteroaryl, -a 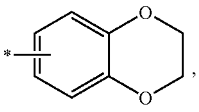 , a $C_6$ to $C_8$ aryl, optionally substituted with one or more of the following:
an alkoxy,
a hydroxy,
a halogen,
a $C_1$ to $C_6$ alkyl, optionally substituted with a cyano group,
an amino optionally substituted with one or more $C_1$ to $C_6$ alkyl(s),
a —$NHPOR_xR_x$, where $R_x$ is as defined above,
a —$NR_{ee}CONR_{ff}R_{ff}$ group, where $R_{ee}$ is a hydrogen or a $C_1$ to $C_6$ alkyl, optionally substituted with a halogen, and $R_{ff}$ is:
a hydrogen,
a haloalkyl,
a haloalkoxy,
a $C_1$ to $C_6$ alkyl, or
a —$COR_x$, where $R_x$ is as defined above,
a —$NR_{gg}COR_{hh}$ group, where $R_{hh}$ is:
a hydrogen,
a $C_1$ to $C_6$ alkyl optionally substituted with:
an alkoxy,
a halogen, or
an amino optionally substituted with one or more $C_1$ to $C_6$ alkyl(s),
an amino optionally substituted with one or more $C_1$ to $C_6$ alkyl(s), where the one or more $C_1$ to $C_6$ alkyl(s) is/are optionally substituted with a halogen, a 5 or 6 membered heterocycle,
a 5 or 6 membered heteroaryl,
and $R_{gg}$ is:
a hydrogen,
a $C_1$ to $C_6$ alkyl,
a haloalkyl,
a haloalkoxy, or
a —$COR_x$ group, where $R_x$ is as defined above,
a haloalkyl,
5 or 6 membered heterocycle groups,
an amino optionally substituted with one or more $C_1$ to $C_6$ alkyl(s), and/or
a —$NR_{ii}SO_2R_x$ group, where $R_x$ is as defined above, and $R_{ii}$ is:
a hydrogen,
a $C_1$ to $C_6$ alkyl,
a haloalkyl,
a haloalkoxy,
a —$COR_x$ group, where $R_x$ is as defined above;

Z is:
a $C_1$ to $C_6$ alkyl optionally substituted with:
an alkoxy,
one or more halogen(s), or
a $C_6$ to $C_8$ aryl;
a $C_2$ to $C_6$ alkylene;
a $C_6$ to $C_8$ aryl optionally substituted with an alkoxy or one or more $C_1$ to $C_6$ alkyl(s);
a —$COOR_x$ group, where $R_x$ is as defined above; or

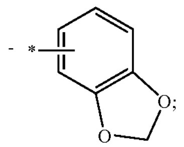

R is a hydrogen, a halogen or an alkoxy;

$R_1$ is:
a hydrogen;
a hydroxy;
a halogen;
a haloalkyl;
a nitro group;
a 5 or 6 membered heteroaryl;
a 5 or 6 membered heterocycle;
an alkoxy optionally substituted with:
one or more halogen(s),
a $C_6$ to $C_8$ aryl, or
a 5 or 6 membered heterocycle;
a $C_6$ to $C_8$ aryl optionally substituted with an alkoxy;
a —$COR_x$ group, where $R_x$ is as defined above;
a $C_1$ to $C_6$ alkyl optionally substituted with a dialkyl-amino or a 5 or 6 membered heterocycle; or $R_1$ joins together with $R_2$ to form:

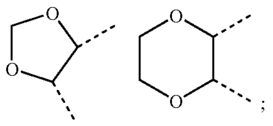

$R_2$ is:
a nitro group;
a hydrogen;
a halogen;
a hydroxy group;
a $C_1$ to $C_6$ alkyl group, optionally substituted with one or more halogen(s);
an amino group;
an alkoxy group optionally substituted with:
one or more halogen(s),
an —$OCOR_x$ group, where $R_x$ is as defined above,
a dialkyl-amino optionally substituted with an alkoxy,
a 5 or 6 membered heterocycle group optionally substituted with a $C_1$ to $C_6$ alkyl,
a 5 or 6 membered heteroaryl group, or
a $C_6$ to $C_8$ aryl group;
a —$COOR_x$ group, where $R_x$ is as defined above;
a haloalkyl;
an amide group optionally substituted with:
a hydroxy group, or
a $C_6$ to $C_8$ aryl;
a 5 or 6 membered heteroaryl;
a —$OCOR_x$ group, where $R_x$ is as defined above;
a —$NHCOR_{jj}$ group, where $R_{jj}$ is:
an alkoxy, or
an amino optionally substituted with one or more $C_1$ to $C_6$ alkyl(s);
a —$OR_{kk}$ group, where $R_{kk}$ is a 5 to 6 membered heteroaryl;
a —$NHSO_2R_x$ group, where $R_x$ is as defined above; or $R_2$ joins together with $R_1$ to form:

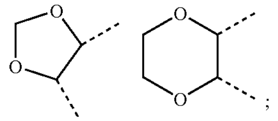

and $R_3$ is:
a hydrogen; or
—$CH_2OCOR_x$, and $R_x$ is as defined above;

provided that when X is phenyl substituted with alkoxy, Y is phenyl, R is hydrogen, $R_1$ is a halogen, $R_2$ is hydrogen, and $R_3$ is hydrogen, and provided that when X is phenyl, hydroxyphenyl or pyridyl, Y is alkyl, R is hydrogen, $R_1$ is hydrogen or hydroxy, $R_2$ is hydrogen or hydroxy, and $R_3$ is hydrogen, then Z is:
a $C_1$ to $C_6$ alkyl substituted with:
an alkoxy,
one or more halogen(s), or
a $C_6$ to $C_8$ aryl;
a $C_2$ to $C_6$ alkylene;
a $C_6$ to $C_8$ aryl optionally substituted with an alkoxy or one or more $C_1$ to $C_6$ alkyl(s);
a —$COOR_x$ group, where $R_x$ is as defined above; or

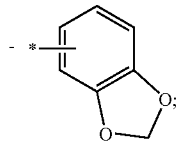

or or a pharmaceutically acceptable salt thereof.

In some embodiments, X is a nitro group or a cyano group. In other embodiments, X is a cyano group.

In some embodiments, Y is a $C_6$ to $C_8$ aryl, optionally substituted with one or more of the following:

an amino optionally substituted with one or more $C_1$ to $C_6$ alkyl(s), a $C_1$ to $C_6$ alkyl group, optionally substituted with a —$NHSO_2R_x$ group, a —$NR_oCOR_p$ group, where $R_p$ is:

a $C_1$ to $C_6$ alkyl optionally substituted with:

a halogen, or a $C_6$ to $C_8$ aryl, or a 5 or 6 membered heterocycle, and where $R_o$ is a hydrogen, a —$NR_qCONR_qR_r$ group, where $R_q$ is:

a hydrogen, or a $C_1$ to $C_6$ alkyl, and where $R_r$ is a $C_1$ to $C_6$ alkyl optionally substituted with one or more of the following:

a halogen, an alkylene, or a $C_6$ to $C_8$ aryl, a —$NR_tCOOR_u$ group, where $R_u$ is:

a $C_1$ to $C_{12}$ alkyl, optionally substituted with:

a $C_6$ to $C_8$ aryl optionally substituted with a $C_1$ to $C_6$ alkyl or an alkoxy, an alkylene, an alkoxy, an alkyne, a halogen, or a 5 or 6 membered heterocycle, a $C_6$ to $C_8$ aryl, optionally substituted with an alkoxy, a 5 or 6 membered heterocycle, and where $R_t$ is:

a hydrogen, or a $C_1$ to $C_6$ alkyl, a —$NR_vSO_2R_w$ group, where $R_v$ is a hydrogen, and where $R_w$ is a $C_1$ to $C_6$ alkyl optionally substituted with a halogen;

-a 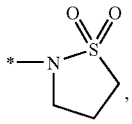 ,

-a 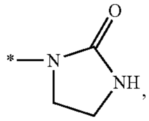 ,

-a 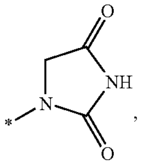 ,

-a 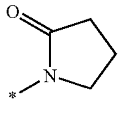 ,

-continued

-a 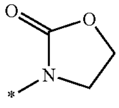 ,

-a 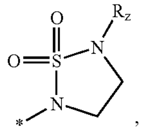 , where $R_z$ is a $C_1$ to $C_6$ alkyl, and/or a —$NHR_{bb}$ group, where $R_{bb}$ is a —$PO(OR_x)_2$ group.

In further embodiments, Y is a $C_6$ to $C_8$ aryl substituted with:

a —$NR_qCONR_qR_r$ group, a —$NR_tCOOR_u$ group, a —$NR_vSO_2R_w$ group, or a —$NHR_{bb}$ group, where $R_{bb}$ is -a —$PO(OR_x)_2$ group.

The $C_6$ to $C_8$ aryl may be substituted at the para, meta and/or ortho position(s). In some embodiments, the $C_6$ to $C_8$ aryl is phenyl. In other embodiments, the $C_6$ to $C_8$ aryl is phenyl substituted at the para position.

In some embodiments, Y is phenyl substituted with a —$NR_qCONR_qR_r$ group at the para position. In other embodiments, Y is phenyl substituted with a —$NR_tCOOR_u$ group at the para position. In yet other embodiments, Y is phenyl substituted with a —$NR_vSO_2R_w$ group at the para position. In yet other embodiments, Y is phenyl substituted with a —$NHPO(OR_x)_2$ group at the para position.

In some embodiments, Z is:

a $C_1$ to $C_6$ alkyl optionally substituted with an alkoxy, or one or more halogen(s), or a $C_2$ to $C_6$ alkylene.

In other embodiments, Z is a $C_1$ to $C_6$ alkyl. In yet other embodiments, Z is a a $C_2$ to $C_5$ alkyl. In yet other embodiments, Z is cyclobutyl, cyclopropyl, cyclopropylmethyl, ethyl or cyclopentyl.

In some embodiments, R is hydrogen.

In some embodiments, $R_1$ is:

a hydrogen;

an alkoxy group optionally substituted with:

one or more halogen(s), a $C_6$ to $C_8$ aryl group, or a 5 or 6 membered heterocycle; or $R_1$ joins together with $R_2$ to form:

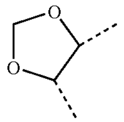 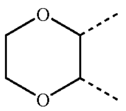 .

In some embodiments, $R_2$ is:

a hydrogen;

a halogen;

a hydroxy group;

a $C_1$ to $C_6$ alkyl group, optionally substituted with one or more halogen(s);

an amino group;

an alkoxy group optionally substituted with:

one or more halogen(s), an —$OCOR_x$ group, where $R_x$ is as defined above, a dialkyl-amino optionally substituted with an alkoxy,
a 5 or 6 membered heterocycle group optionally substituted with a $C_1$ to $C_6$ alkyl,
a 5 or 6 membered heteroaryl group, or
a $C_6$ to $C_8$ aryl group;
a —$COOR_x$ group; or
$R_2$ joins together with $R_1$ to form:

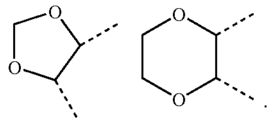

In other embodiments, at least one of $R_1$ and $R_2$ is a hydroxy group or an alkoxy group optionally substituted with:
one or more halogen(s),
a $C_6$ to $C_8$ aryl group, or
a 5 or 6 membered heterocycle group; or
$R_2$ is a —$OCOR_x$ group, a —$OR_{kk}$ group, or an alkoxy group substituted with:
an —$OCOR_x$ group,
a dialkyl-amino optionally substituted with an alkoxy,
a 5 or 6 membered heterocycle group substituted with a $C_1$ to $C_6$ alkyl; or
a 5 or 6 membered heteroaryl group.

In yet other embodiments, $R_2$ is a —$OR_{kk}$ group or an alkoxy group optionally substituted with:
a dialkyl-amino optionally substituted with an alkoxy,
a 5 or 6 membered heterocycle group optionally substituted with a $C_1$ to $C_6$ alkyl; or
a 5 or 6 membered heteroaryl group.

In yet further embodiments, $R_2$ is a $C_1$ to $C_6$ alkoxy group optionally substituted with:
a 5 or 6 membered heterocycle group optionally substituted with a $C_1$ to $C_6$ alkyl; or
a 5 or 6 membered heteroaryl group.

In some embodiments, $R_3$ is a hydrogen.

In some embodiments,
X is a cyano group;
Y is a $C_6$ to $C_8$ aryl substituted with:
a —$NR_qCONR_qR_r$ group,
a —$NR_tCOOR_u$ group,
a —$NR_vSO_2R_w$ group, or
a —$NHPO(OR_x)_2$ group;
Z is:
a $C_1$ to $C_6$ alkyl optionally substituted with
an alkoxy, or
one or more halogen(s), or
a $C_2$ to $C_6$ alkylene;
R is hydrogen;
at least one of $R_1$ and $R_2$ is a hydroxy group or an alkoxy group optionally substituted with:
one or more halogen(s),
a $C_6$ to $C_8$ aryl group, or
a 5 or 6 membered heterocycle group; or
$R_2$ is a —$OCOR_x$ group, a —$OR_{kk}$ group, or an alkoxy group substituted with:
an —$OCOR_x$ group,
a dialkyl-amino optionally substituted with an alkoxy,
a 5 or 6 membered heterocycle group substituted with a $C_1$ to $C_6$ alkyl; or
a 5 or 6 membered heteroaryl group; and
$R_3$ is hydrogen.

In some embodiments, Y is a phenyl substituted with a —$NR_tCOOR_u$ group. In further embodiments, $R_t$ is a hydrogen, and $R_u$ is:
a $C_1$ to $C_{12}$ alkyl, optionally substituted with one or more groups independently selected from the following:
a $C_6$ to $C_8$ aryl optionally substituted with halogen,
an alcoxy group optionally substituted with one or more alkoxy groups,
an amino optionally substituted with one or more $C_1$ to $C_6$ alkyl,
halogen, or
a 5 or 6 membered heteroaryl,
a $C_2$ to $C_6$ alkylene,
a $C_6$ to $C_8$ aryl, optionally substituted with halogen.

In yet further embodiments, $R_u$ is a $C_1$ to $C_6$ alkyl.

In some embodiments, Y is a phenyl substituted with a —$NR_qCONR_qR_r$ group. In further embodiments, $R_q$ is a hydrogen and $R_r$ is:
a $C_1$ to $C_6$ alkyl optionally substituted with one or more of the following:
a hydroxy,
an alkoxy,
a 5 or 6 membered heterocycle,
a 5 or 6 membered heteroaryl, or
a $C_6$ to $C_8$ aryl optionally substituted with a halogen,
a $C_2$ to $C_6$ alkylene group,
a $C_1$ to $C_6$ alkoxy group,
a 5 or 6 membered heterocycle group.

In yet further embodiments, $R_r$ is a a $C_1$ to $C_6$ alkyl.

In some embodiments, Y is phenyl substituted with a —$NR_vSO_2R_w$ group. In further embodiments, $R_v$ is a hydrogen, and where $R_w$ is -a $C_1$ to $C_6$ alkyl.

In some embodiments, Y is phenyl substituted with a —$NHPO(OR_x)_2$ group.

In some embodiments,
Y is a phenyl substituted at the para position with:
a —$NR_qCONNR_qR_r$ group,
a —$NR_tCOOR_u$ group,
a —$NR_vSO_2R_w$ group, or
a —$NHPO(OR_x)_2$ group;
Z is a $C_1$ to $C_6$ alkyl; and
$R_2$ is an alkoxy group optionally substituted with:
a 5- or 6 membered heterocycle group optionally substituted with a $C_1$ to $C_6$ alkyl; or
a 5- or 6 membered heteroaryl group.

In another preferred embodiment, a compound or a composition of the present invention includes a compound of Formula I, wherein the compound of Formula I is not Compound I

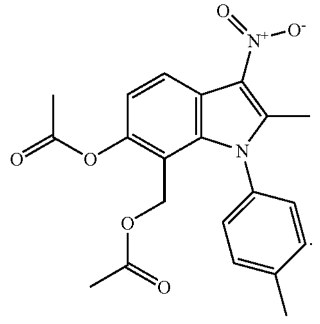

As used herein, the term "alkyl" generally refers to saturated hydrocarbyl radicals of straight or branched configuration, including methyl, ethyl, n-propyl, isopropyl, n-butyl, isobutyl, sec-butyl, tert-butyl, n-pentyl, n-hexyl, n-heptyl, octyl, n-octyl, and the like. In some embodiments, alkyl substituents may be $C_1$ to $C_{12}$, or $C_1$ to $C_8$ or $C_1$ to $C_6$ alkyl groups.

As used herein, "alkylene" generally refers to linear, branched or cyclic alkene radicals having one or more carbon-carbon double bonds, such as $C_2$ to $C_6$ alkylene groups including 3-propenyl.

As used herein, "aryl" refers to a carbocyclic aromatic ring structure. Included in the scope of aryl groups are aromatic rings having from five to twenty carbon atoms. Aryl ring structures include compounds having one or more ring structures, such as mono-, bi-, or tricyclic compounds. Examples of aryl groups that include phenyl, tolyl, anthracenyl, fluorenyl, indenyl, azulenyl, phenanthrenyl (i.e., phenanthrene), and napthyl (i.e., napthalene) ring structures. In certain embodiments, the aryl group may be optionally substituted.

As used herein, "heteroaryl" refers to cyclic aromatic ring structures in which one or more atoms in the ring, the heteroatom(s), is an element other than carbon. Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, the heteroaryl groups may be selected from heteroaryl groups that contain two or more heteroatoms, three or more heteroatoms, or four or more heteroatoms. Heteroaryl ring structures may be selected from those that contain five or more atoms, six or more atoms, or eight or more atoms. Examples of heteroaryl ring structures include: acridine, benzimidazole, benzoxazole, benzodioxole, benzofuran, 1,3-diazine, 1,2-diazine, 1,2-diazole, 1,4-diazanaphthalene, furan, furazan, imidazole, indole, isoxazole, isoquinoline, isothiazole, oxazole, purine, pyridazine, pyrazole, pyridine, pyrazine, pyrimidine, pyrrole, quinoline, quinoxaline, thiazole, thiophene, 1,3,5-triazine, 1,2,4-triazine, 1,2,3-triazine, tetrazole and quinazoline.

As used herein, "heterocycle" refers to cyclic ring structures in which one or more atoms in the ring, the heteroatom(s), is an element other than carbon. Heteroatoms are typically O, S or N atoms. Included within the scope of heterocycle, and independently selectable, are O, N, and S heterocycle ring structures. The ring structure may include compounds having one or more ring structures, such as mono-, bi-, or tricyclic compounds. Example of heterocyclo groups include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl or tetrahydrothiopyranyl and the like. In certain embodiments, the heterocycle may optionally be substituted.

As used herein, "alkoxy" generally refers to a group with the structure —O—R, where R is an alkyl group as defined above.

For the purposes of this invention, halo substituents may be independently selected from the halogens such as fluorine, chlorine, bromine, iodine, and astatine. A haloalkyl is an alkyl group, as defined above, substituted with one or more halogens. A haloalkoxy is an alkoxy group, as defined above, substituted with one or more halogens.

For the purposes of this invention, where one or more functionalities encompassing X, Y, Z, R, $R_1$, $R_2$, and $R_3$, are incorporated into a molecule of formula I, each functionality appearing at any location within the disclosed compound may be independently selected, and as appropriate, independently substituted. Further, where a more generic substituent is set forth for any position in the molecules of the present invention, it is understood that the generic substituent may be replaced with more specific substituents, and the resulting molecules are within the scope of the molecules of the present invention.

By "substituted" or "optionally substituted" it is meant that the particular substituent may be substituted with a chemical group known to one of skill in the art to be appropriate for the referred-to substituent, unless a chemical group is specifically mentioned.

Nonlimiting examples of X substituents include the following, where the * indicates the bond of attachment of the scaffold molecule:

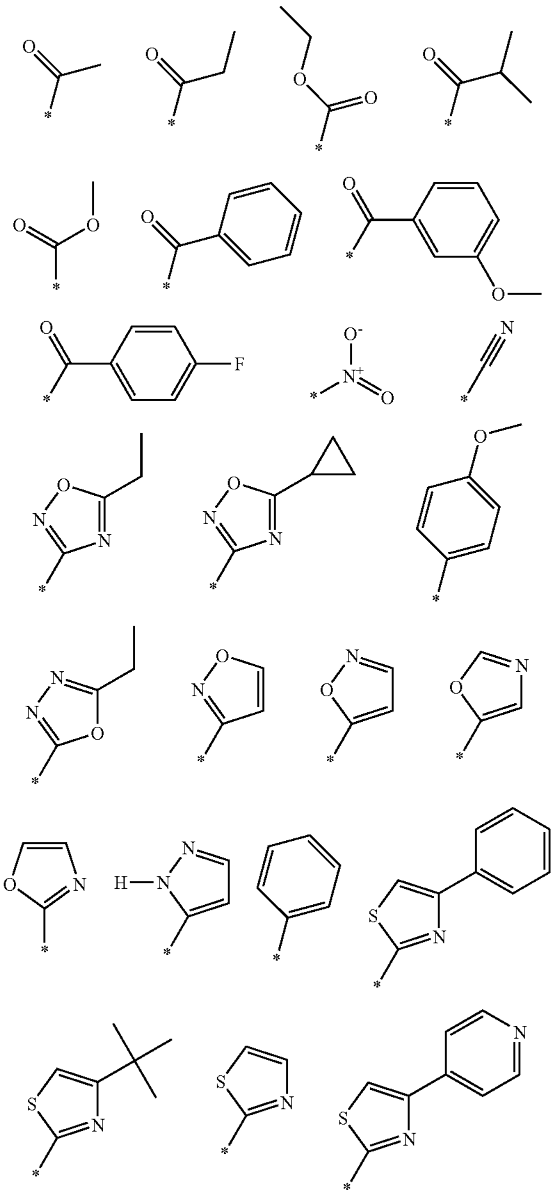

-continued
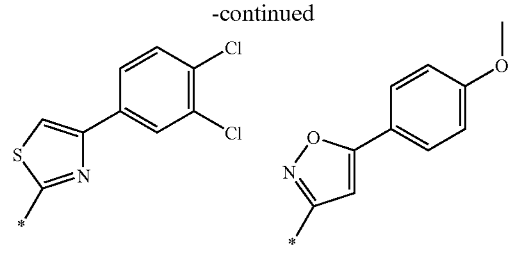
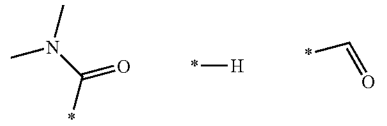
In some embodiments, the X substituent is hydrogen; a cyano group; or a —$COR_a$ group, where $R_a$ is a $C_1$ to $C_6$ alkyl, or a dialkyl-amino.
In other embodiments, the X substituent is selected from the following:
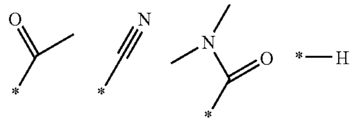
In yet other embodiments, the X substituent is selected from the following:
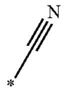
Nonlimiting examples of Y substituents include the following:
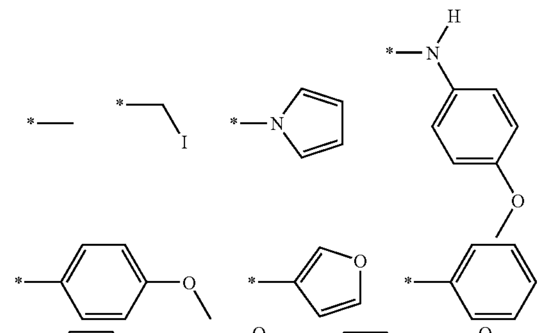
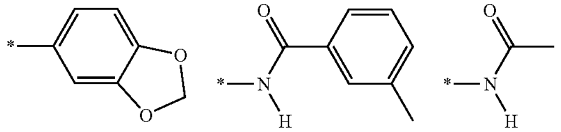
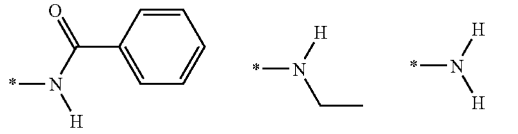
-continued
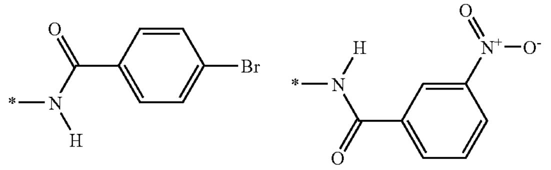
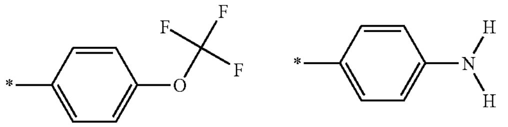
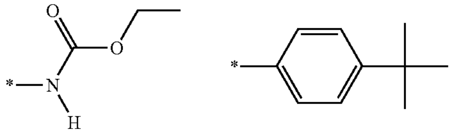
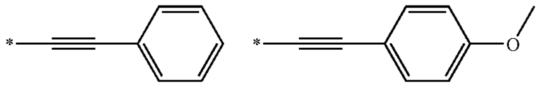
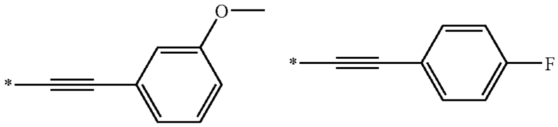
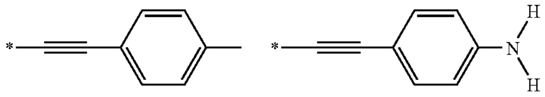
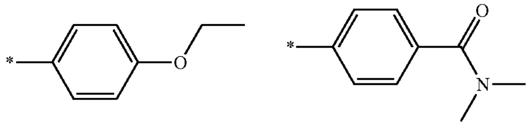
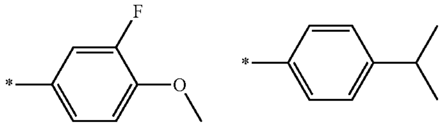
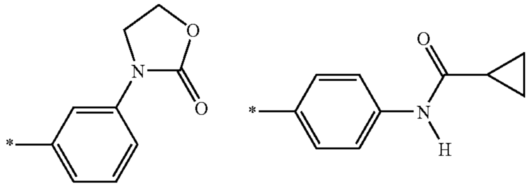
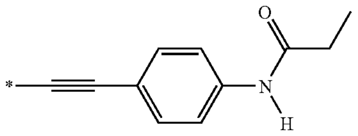
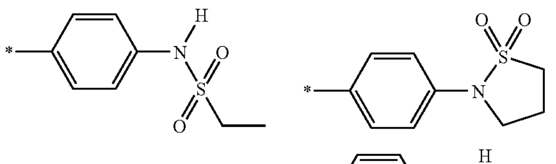
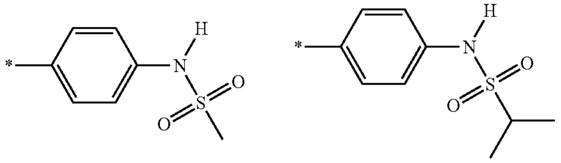

-continued
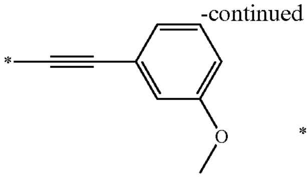
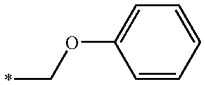
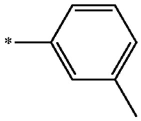
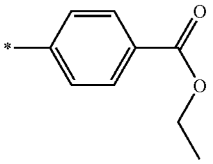
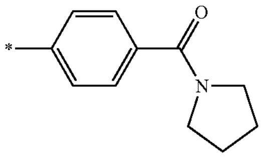
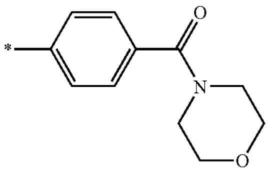
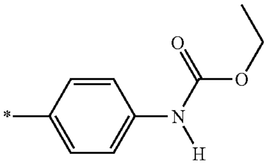
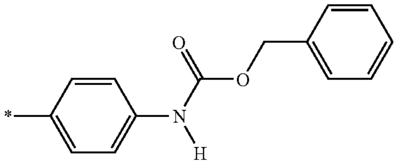
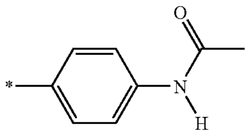
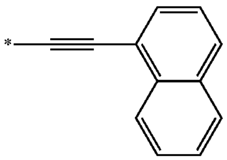
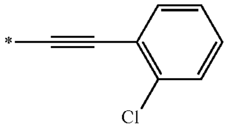
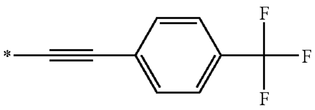
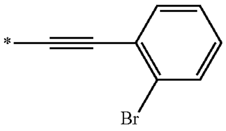
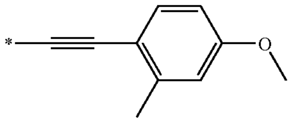
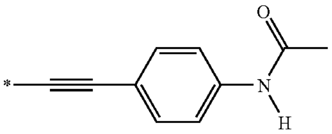
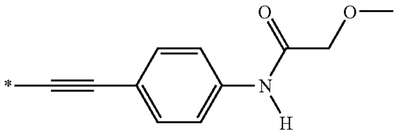
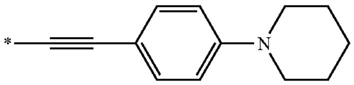
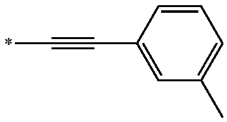
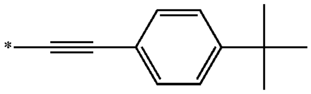
-continued
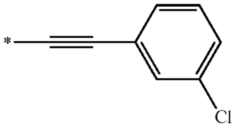
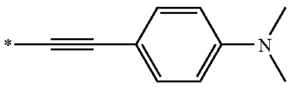
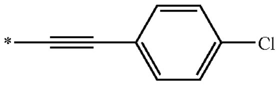
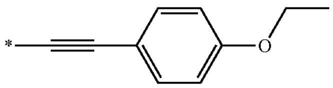
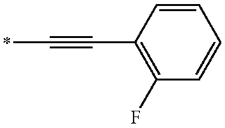
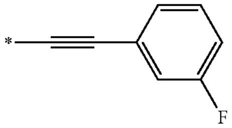
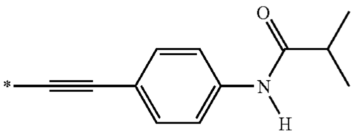
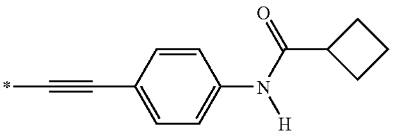
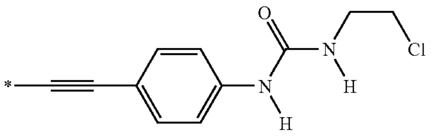
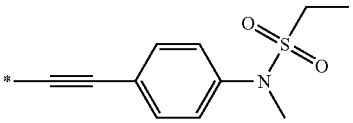
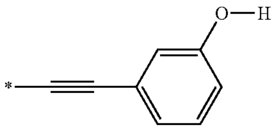
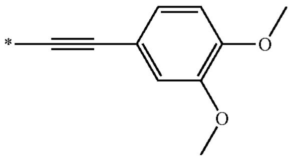
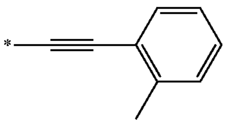
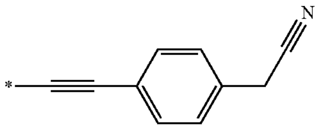
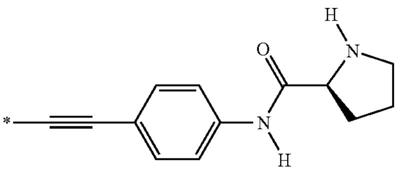
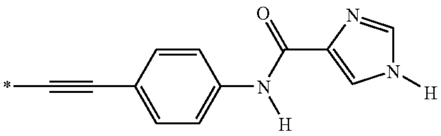

-continued
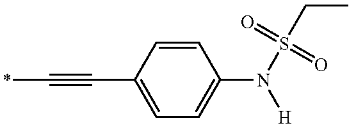
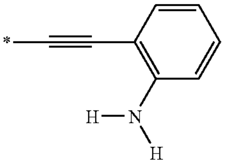
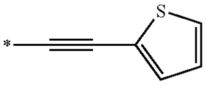
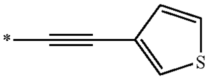
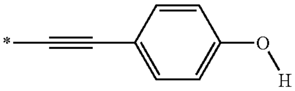
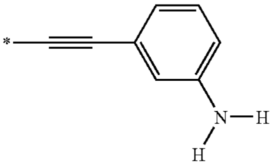
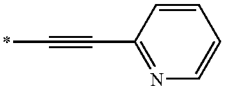
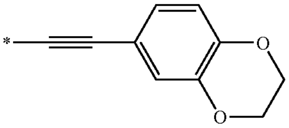
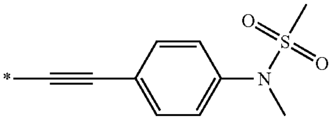
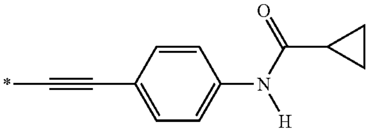
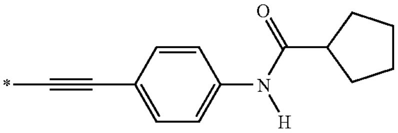
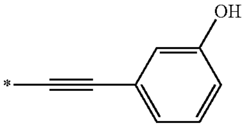
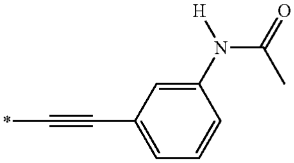
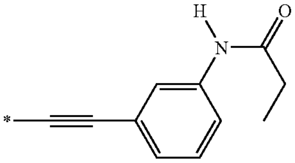
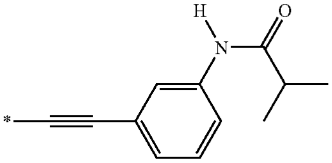
-continued
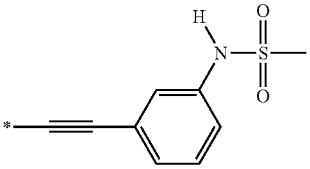
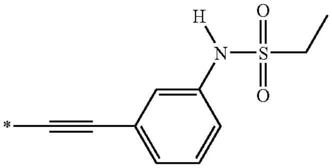
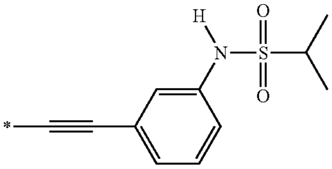
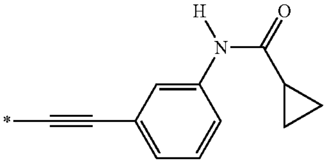
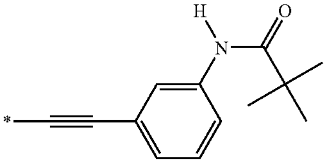
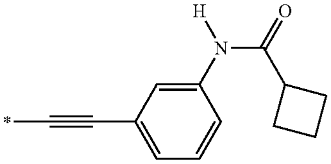
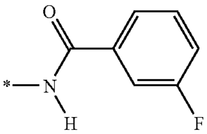
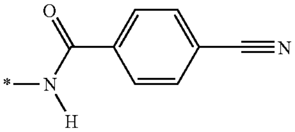
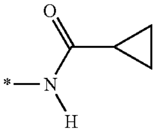
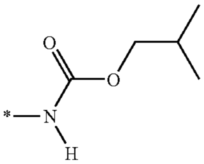
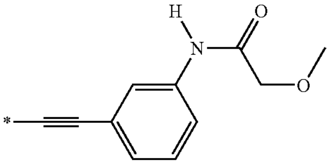
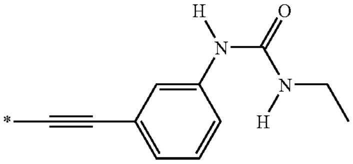
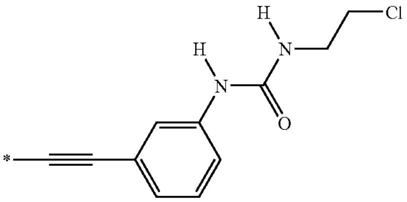

-continued
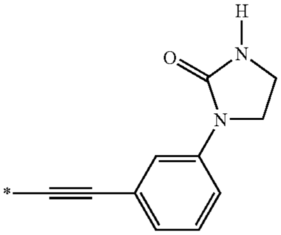
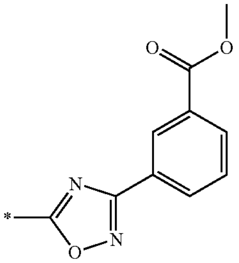
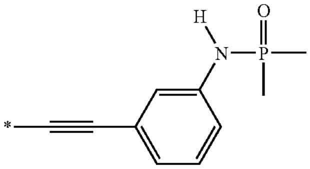
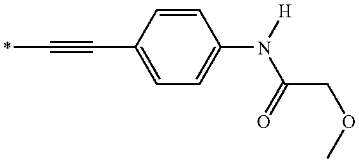
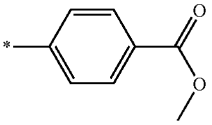
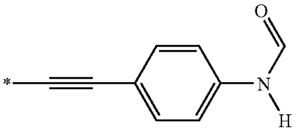
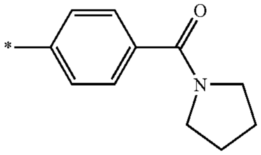
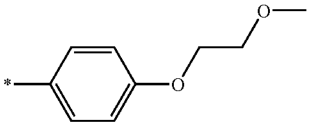
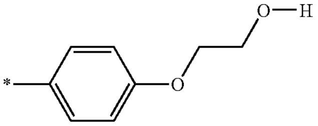
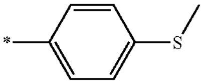
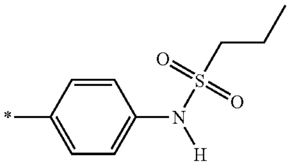
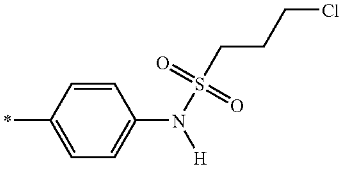
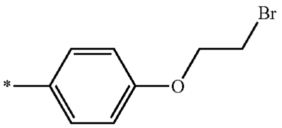
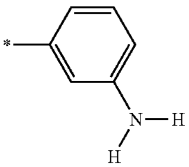
-continued
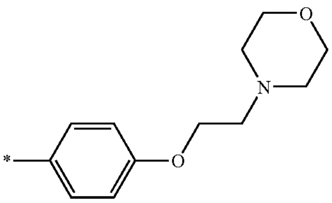
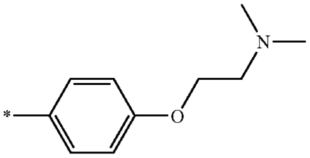
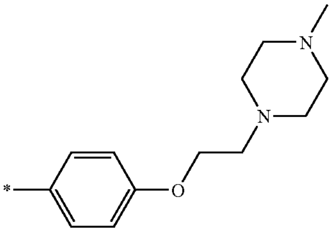
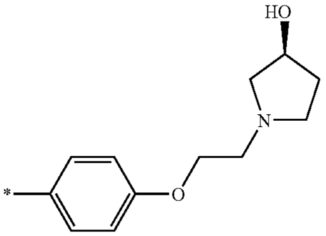
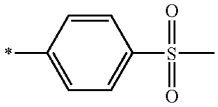
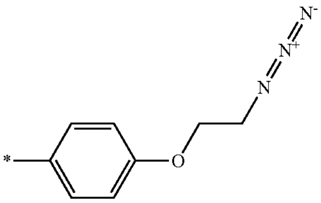
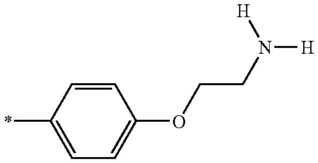
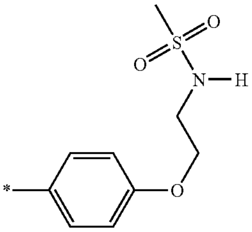
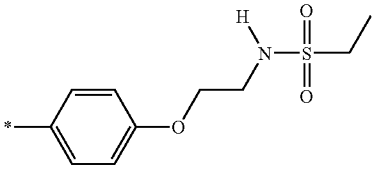

-continued
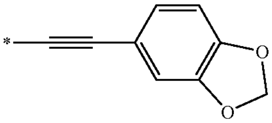
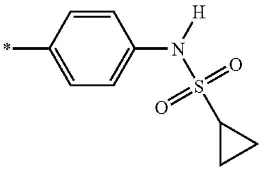
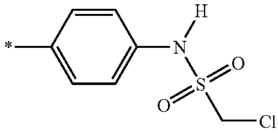
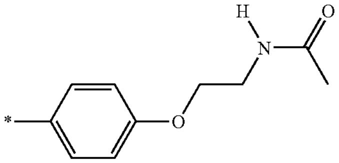
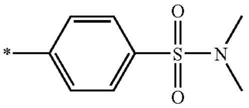
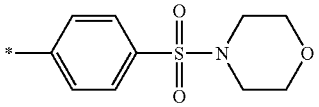
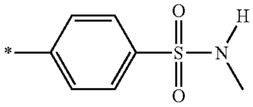
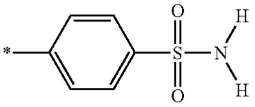
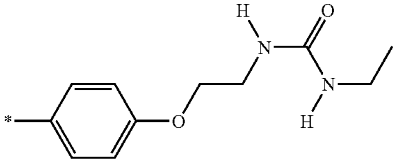
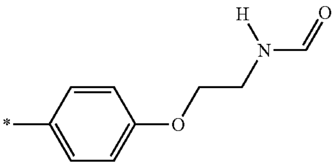
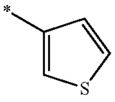
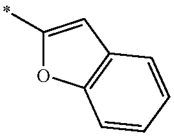
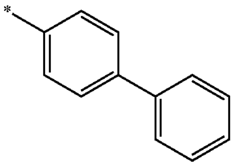
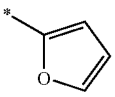
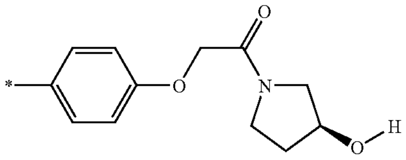
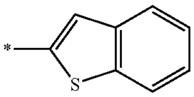
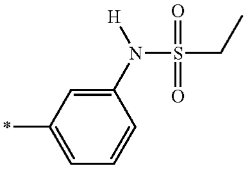
-continued
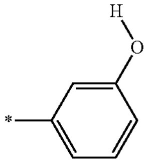
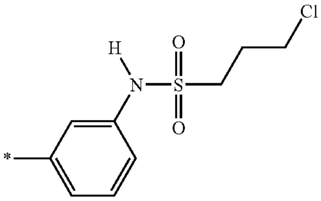
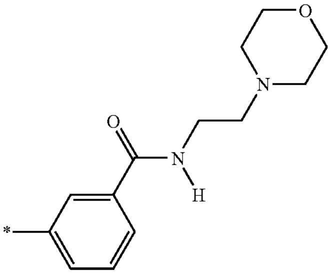
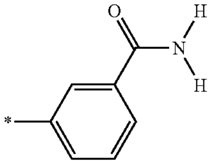
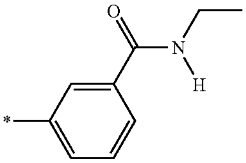
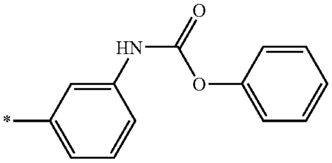
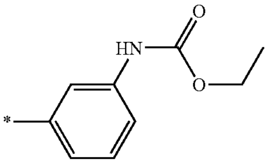
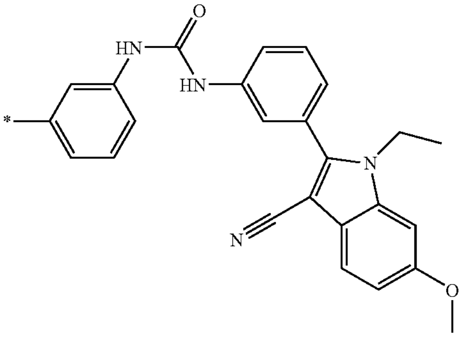
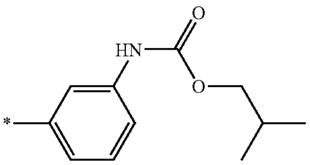
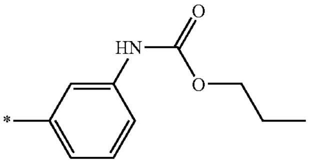

-continued
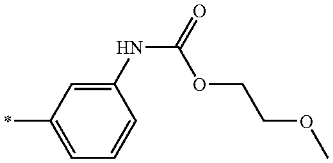
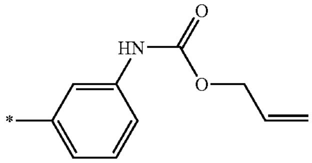
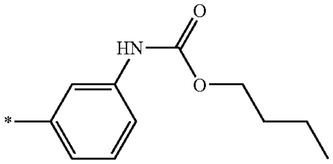
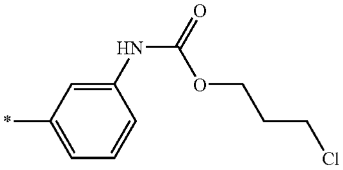
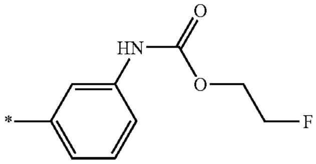
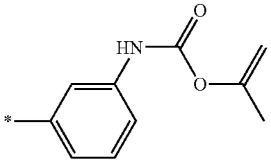
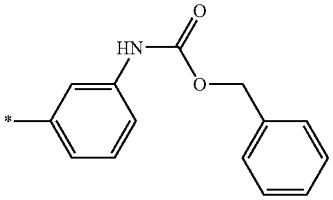
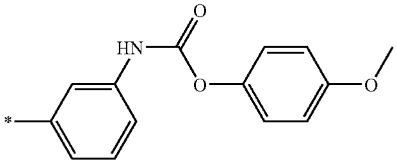
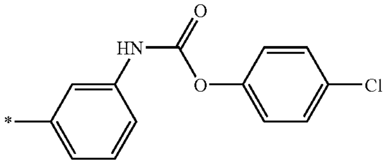
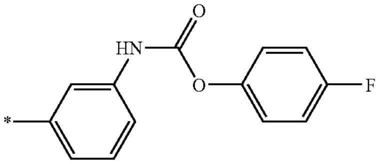
-continued
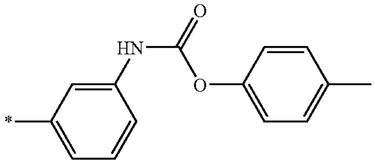
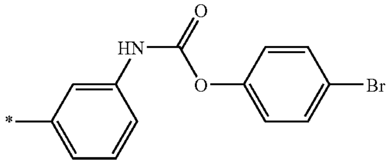
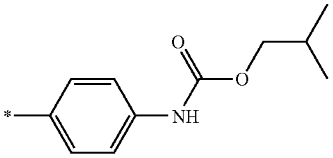
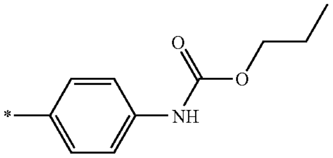
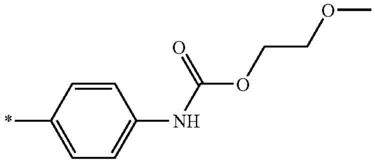
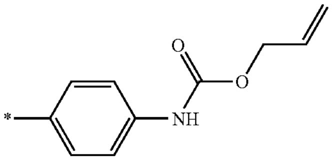
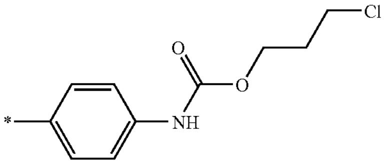
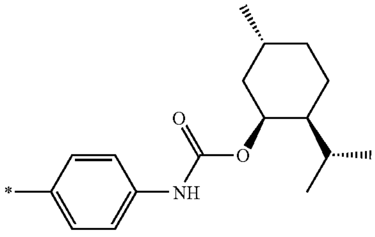
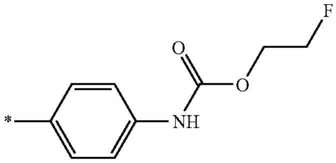

-continued
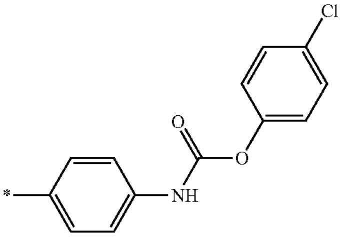
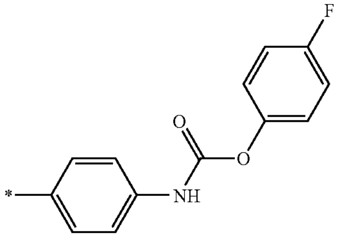
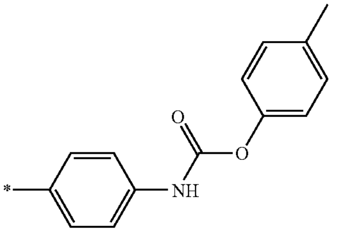
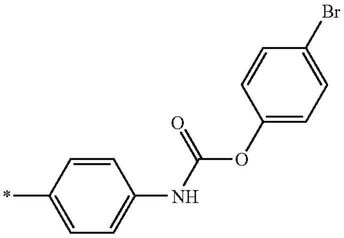
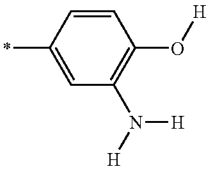
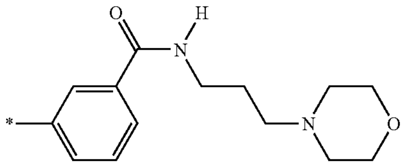
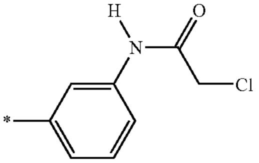
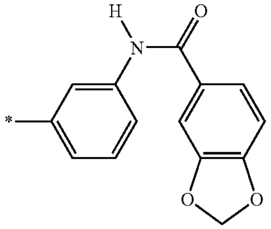
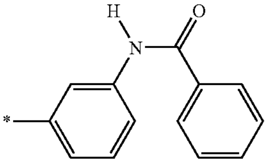
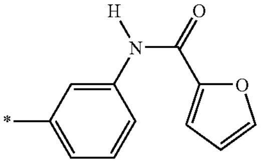
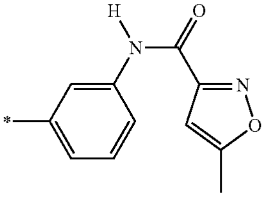
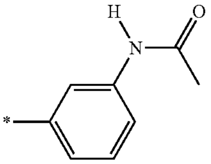
-continued
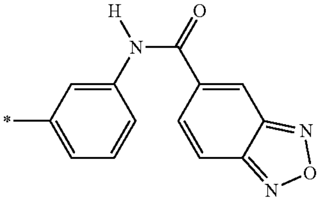
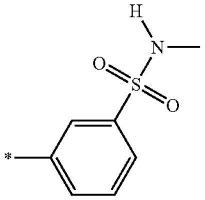
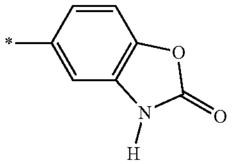
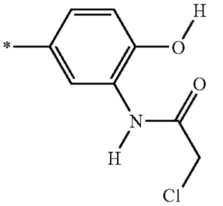
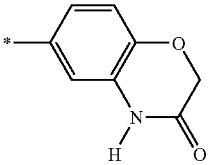
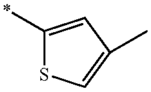
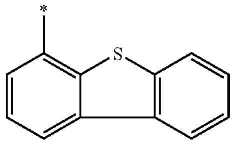
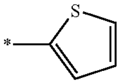
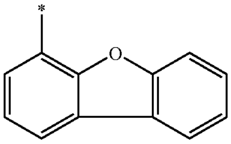
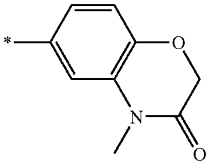
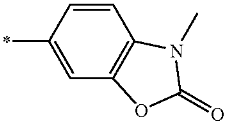
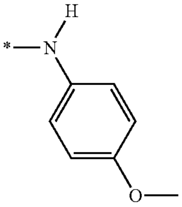
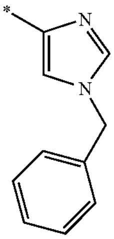
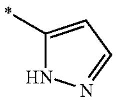
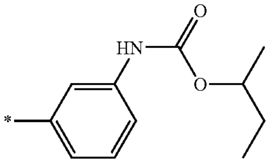
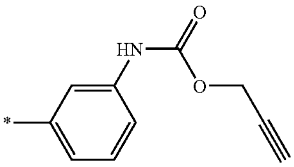
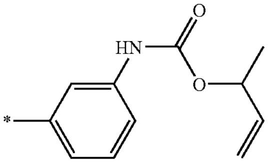
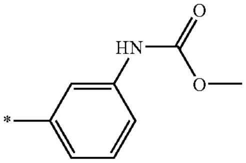

-continued
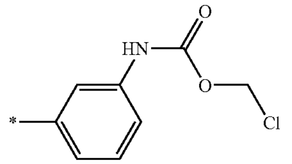
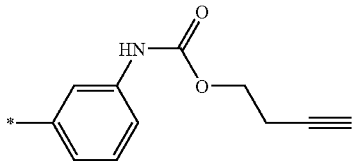
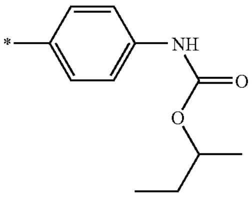
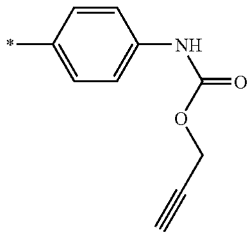
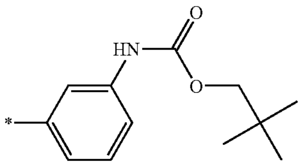
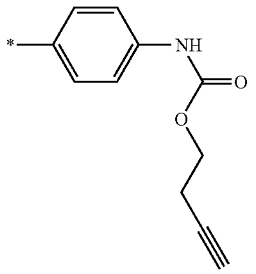
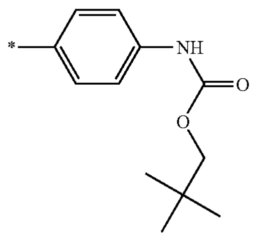
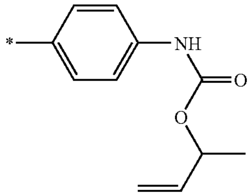
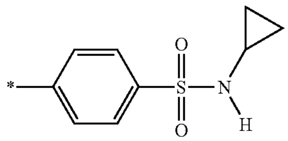
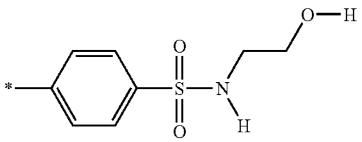
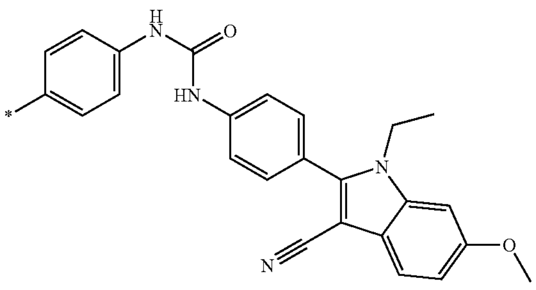
-continued
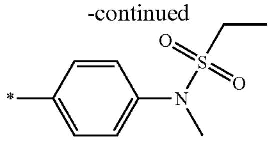
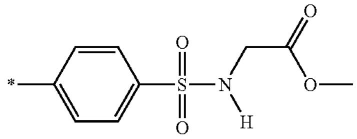
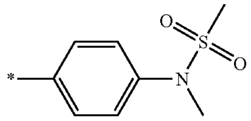
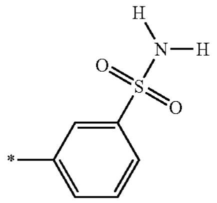
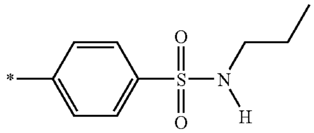
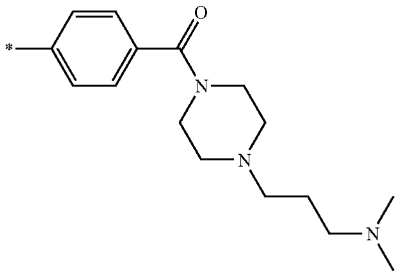
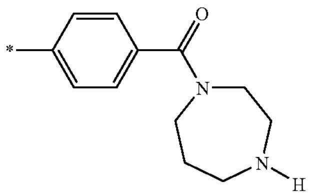
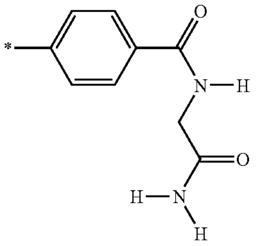
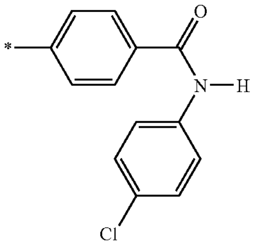
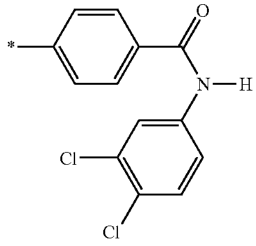
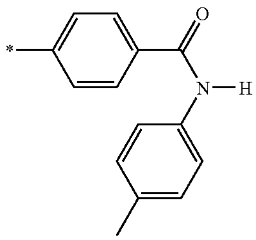
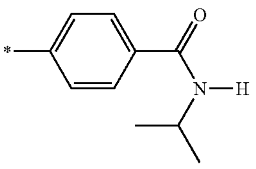
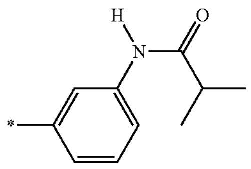

-continued
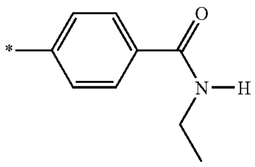
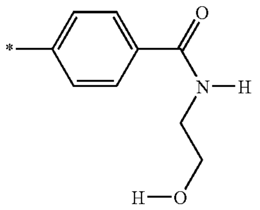
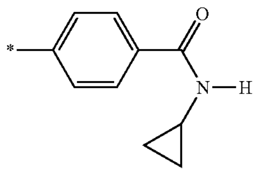
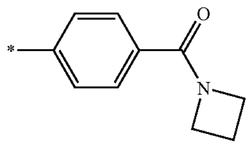
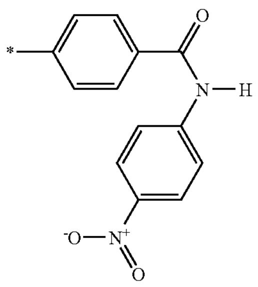
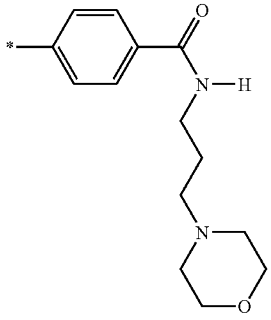
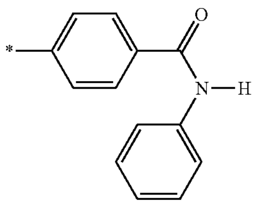
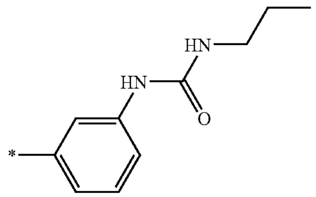
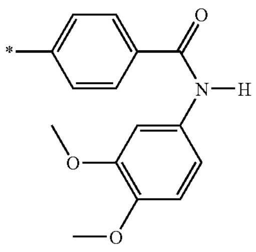
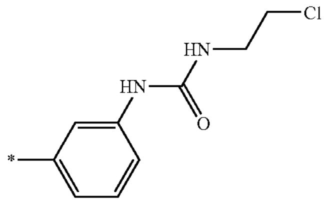
-continued
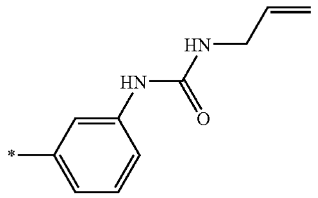
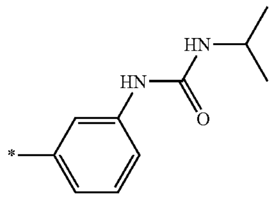
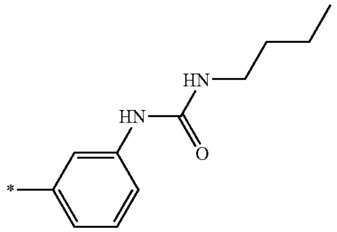
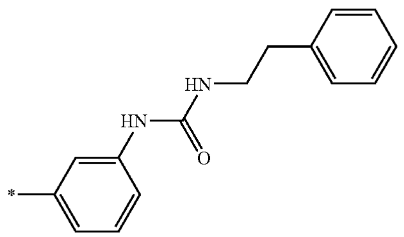
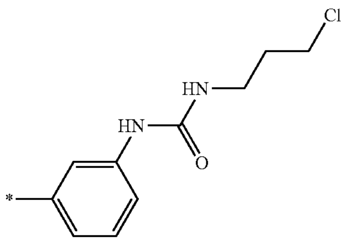
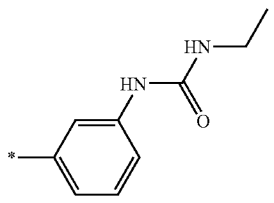
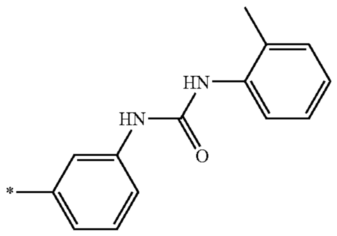

-continued
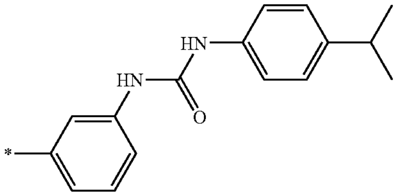
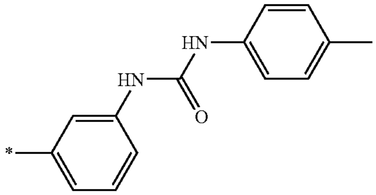
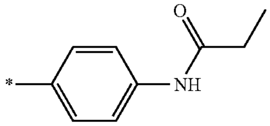
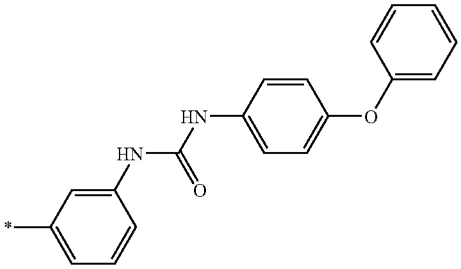
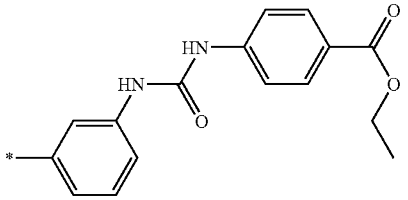
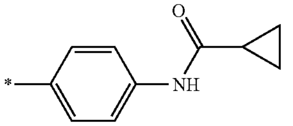
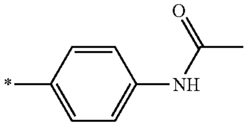
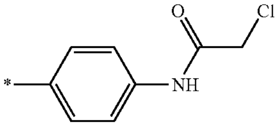
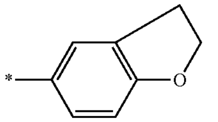
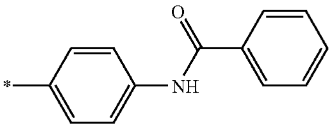
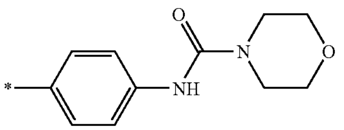
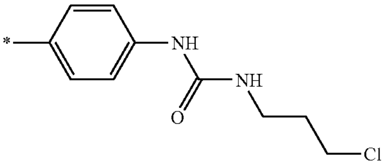
-continued
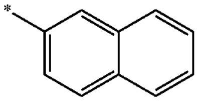
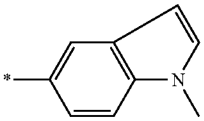
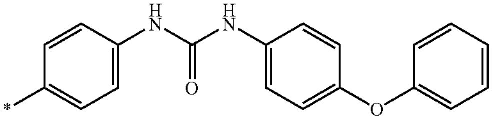
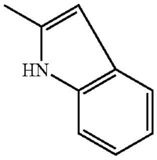
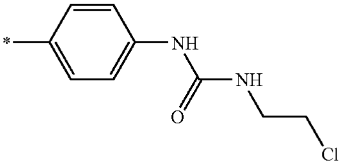
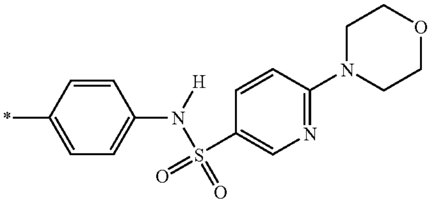
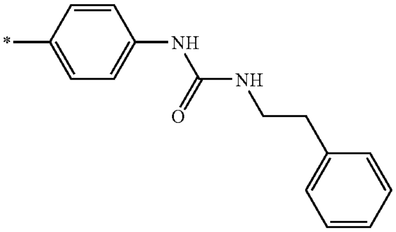
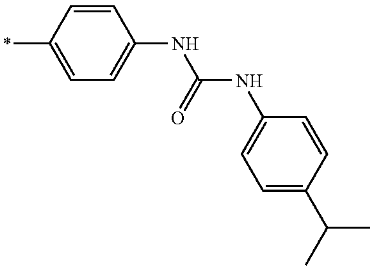
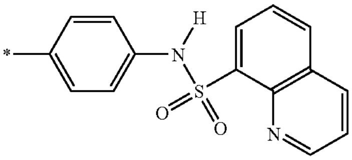
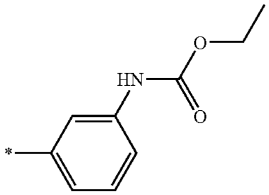
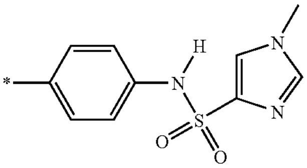

-continued
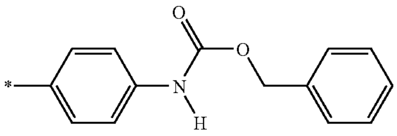
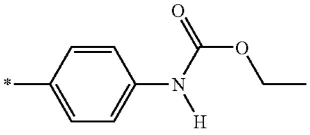
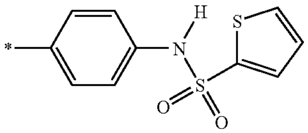
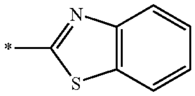
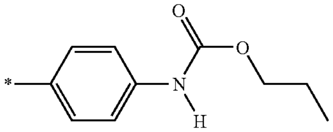
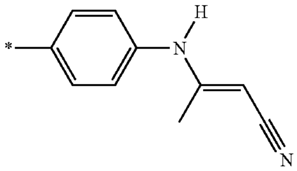
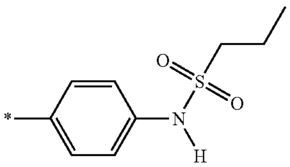
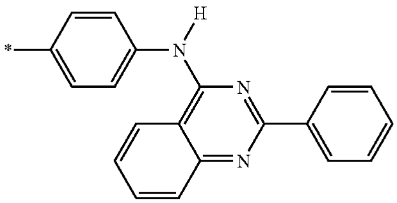
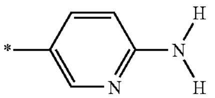
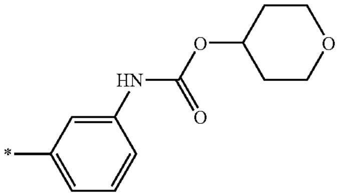
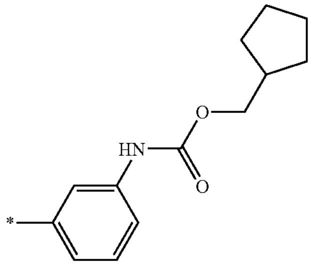
-continued
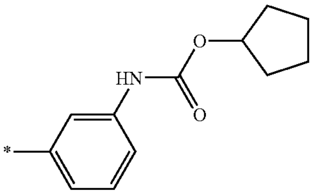
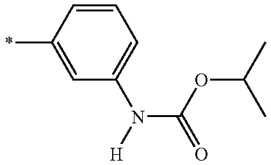
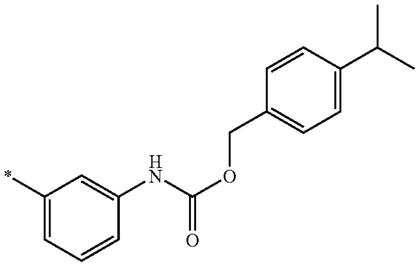
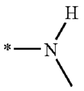
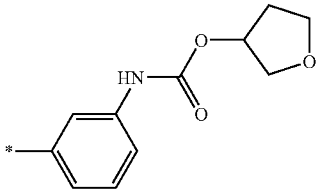
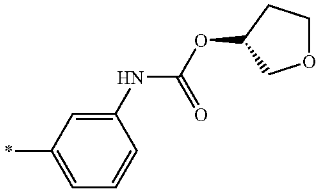
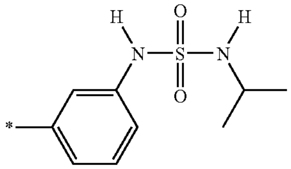
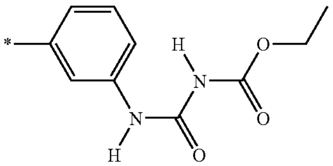
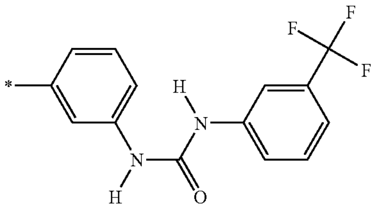

-continued
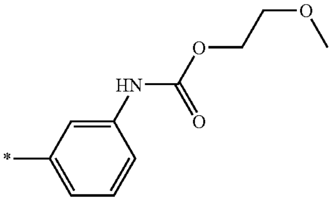
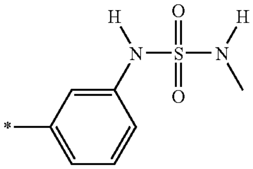
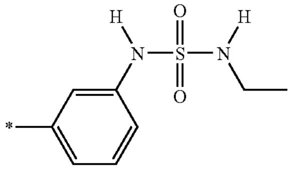
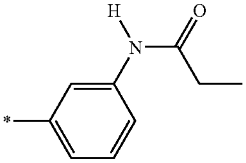
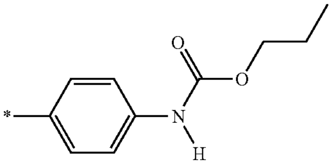
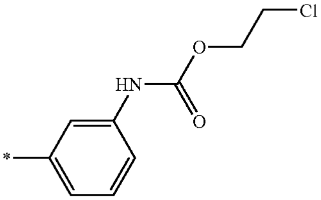
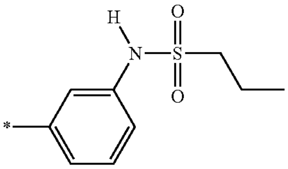
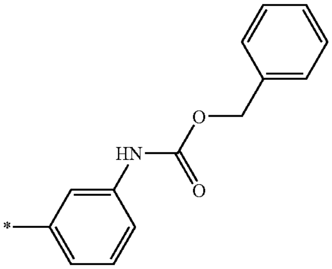
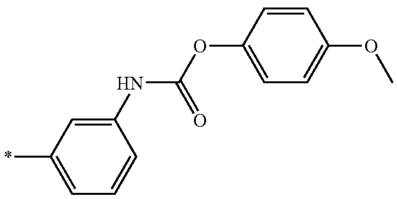
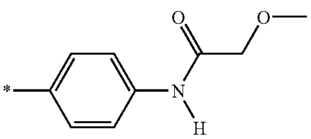
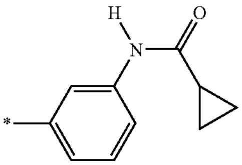
-continued
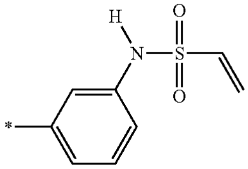
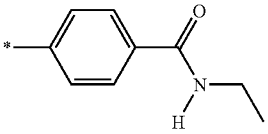
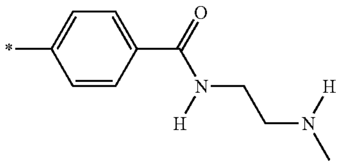
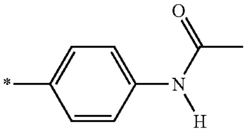
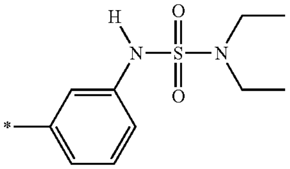
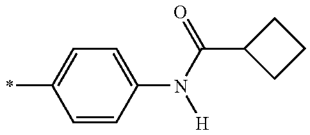
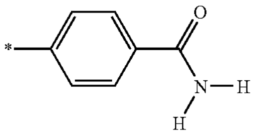
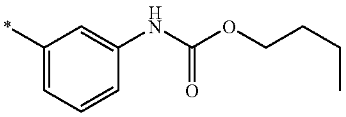
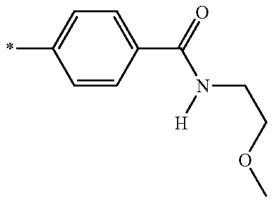
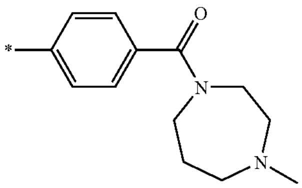
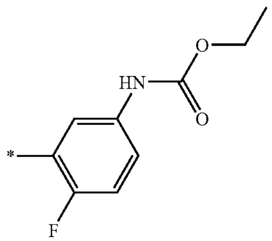
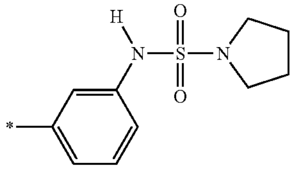
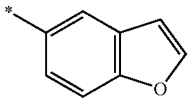

-continued
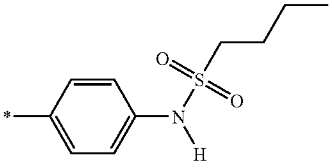
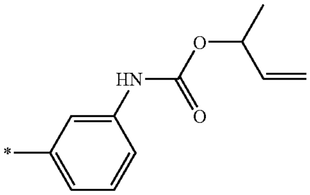
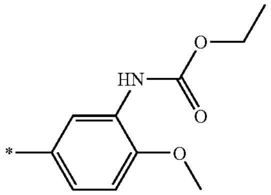
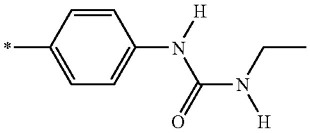
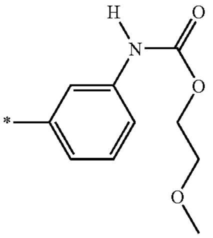
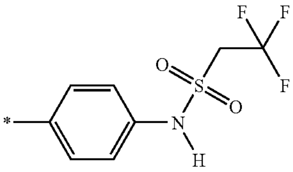
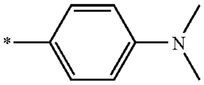
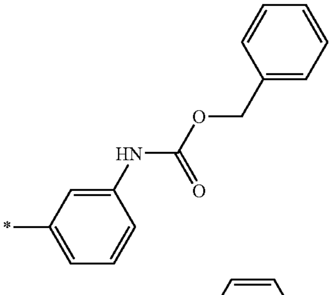
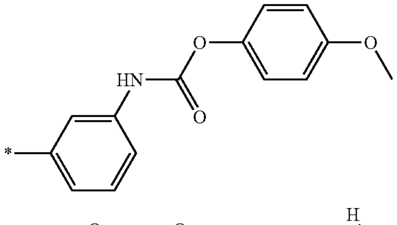
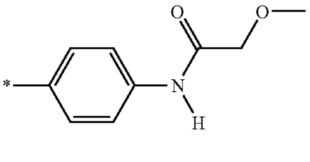
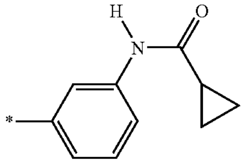
-continued
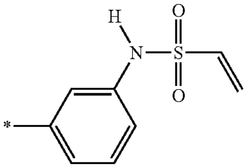
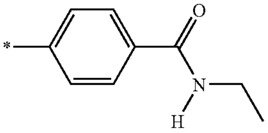
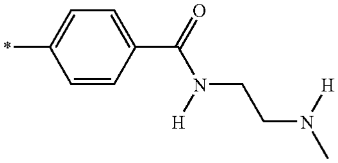
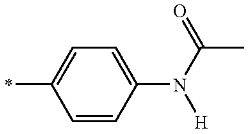
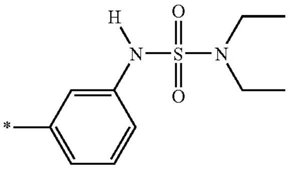
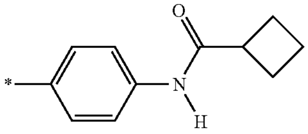
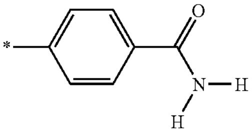
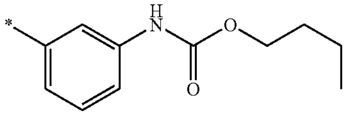
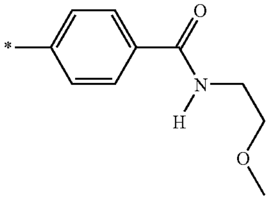
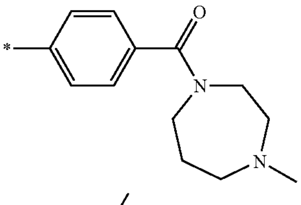
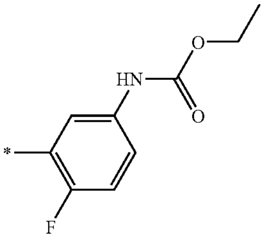
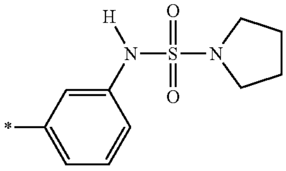
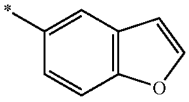
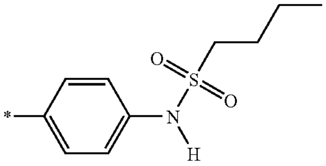

-continued
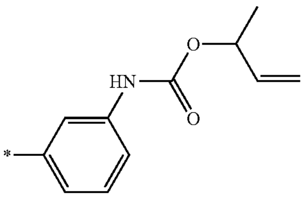
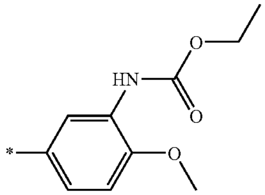
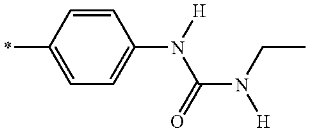
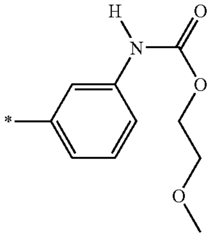
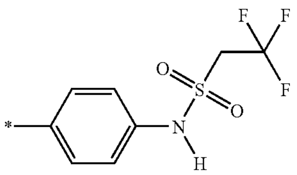
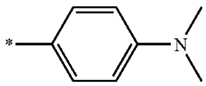
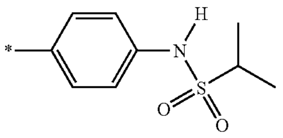
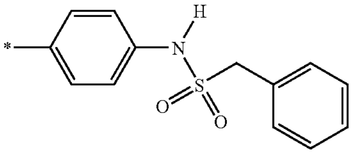
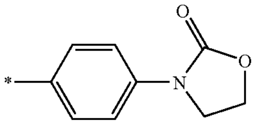
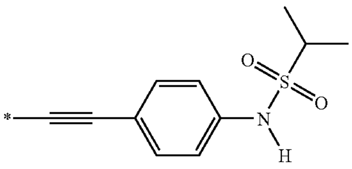
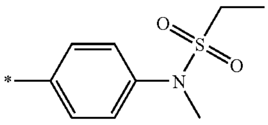
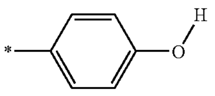
-continued
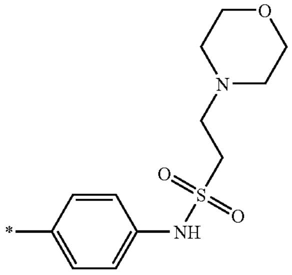
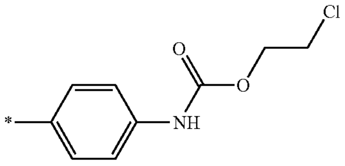
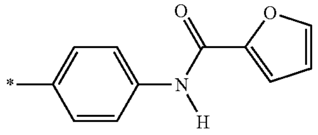
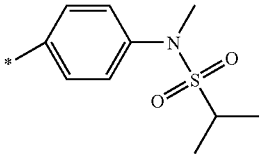
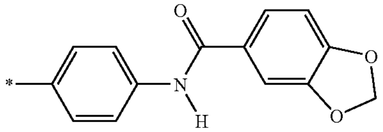
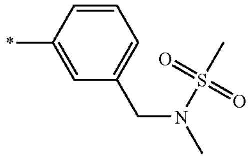
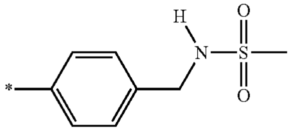
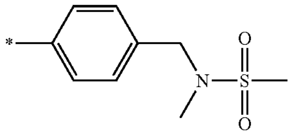
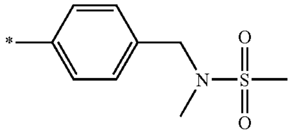
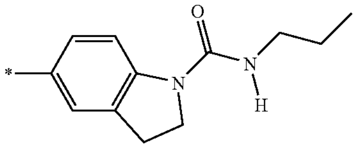
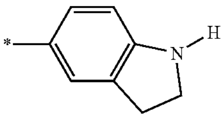
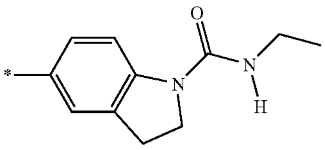

-continued
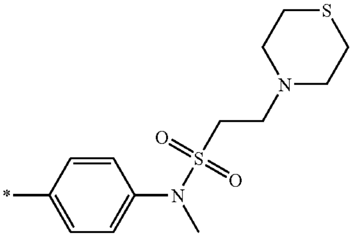
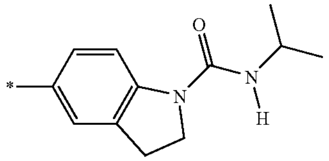
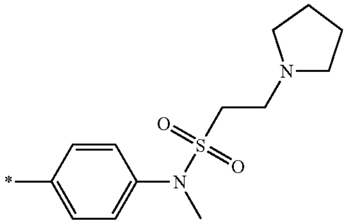
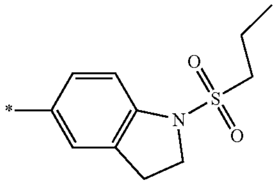
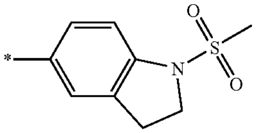
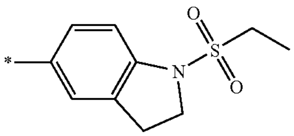
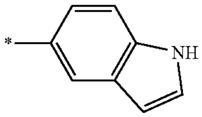
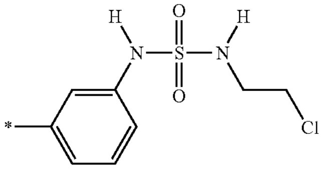
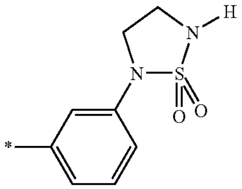
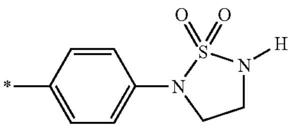
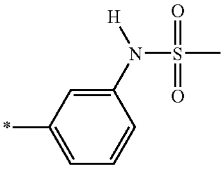
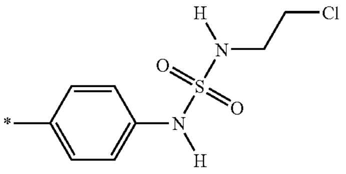
-continued
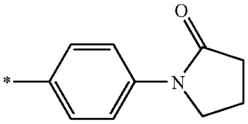
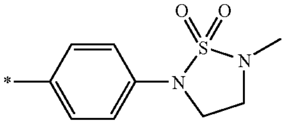
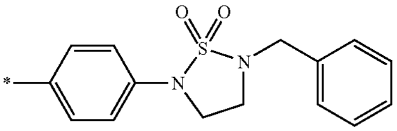
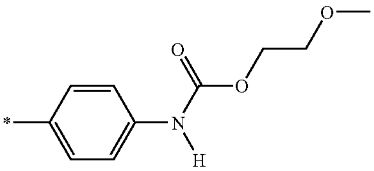
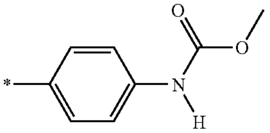
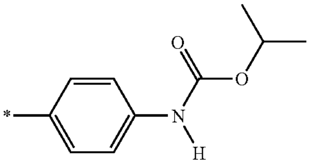
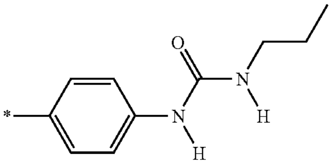
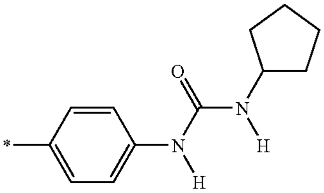
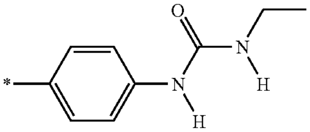
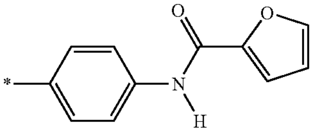
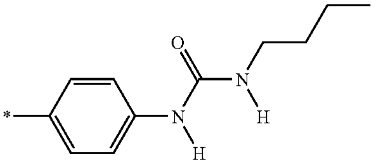
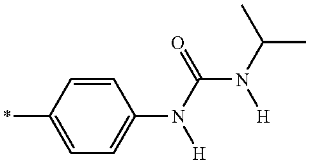

-continued
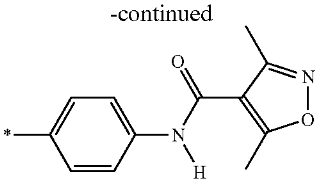
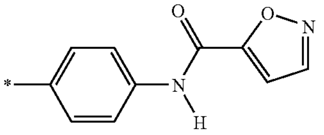
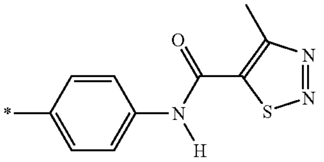
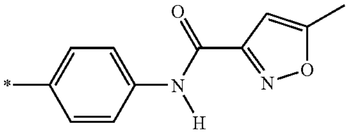
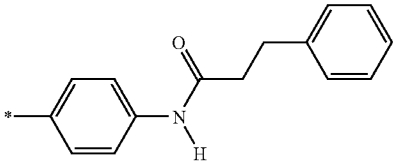
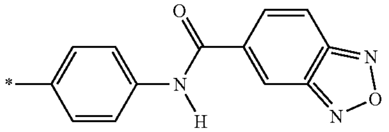
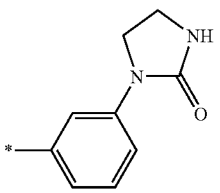
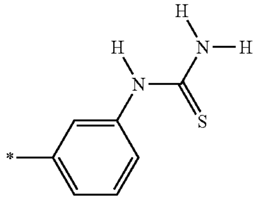
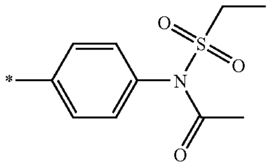
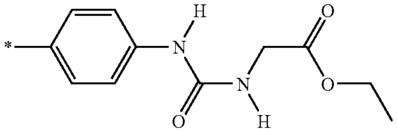
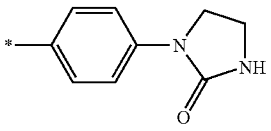
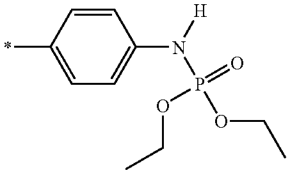
-continued
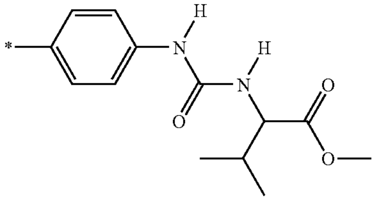
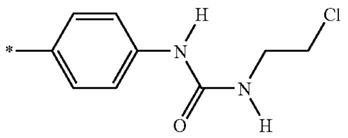
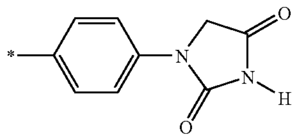
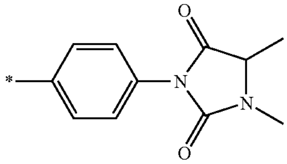
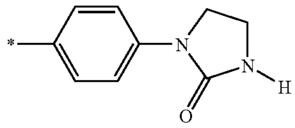
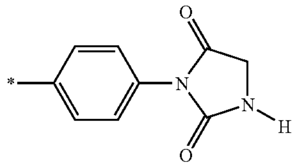
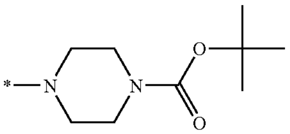
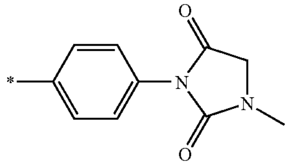
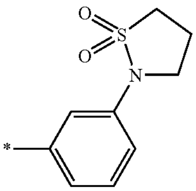
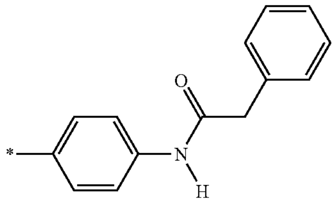
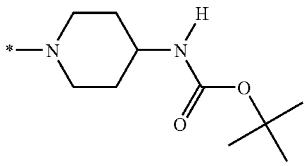

-continued
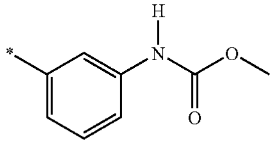
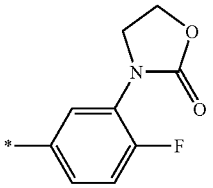
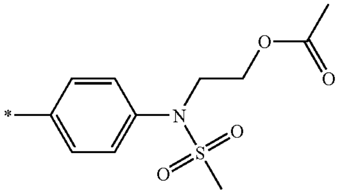
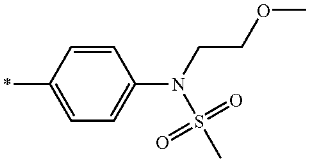
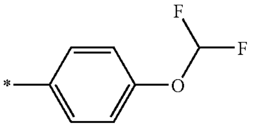
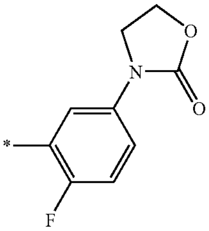
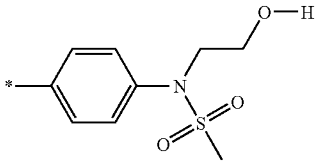
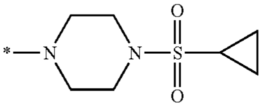
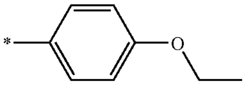
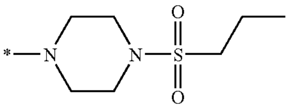
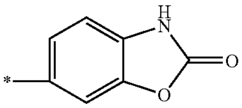
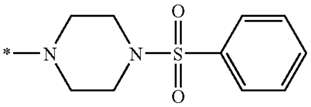
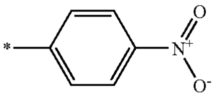
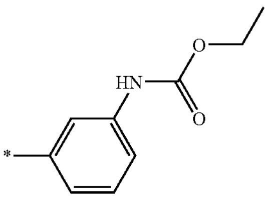
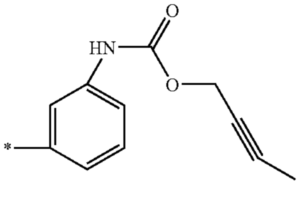
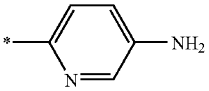
-continued
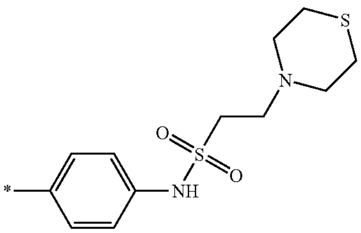
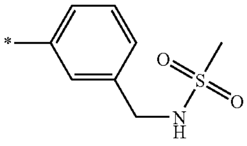
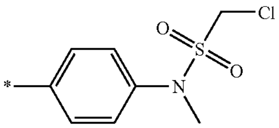
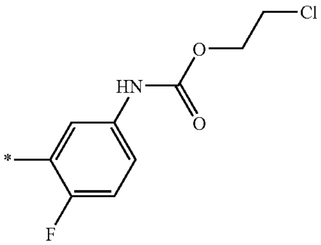
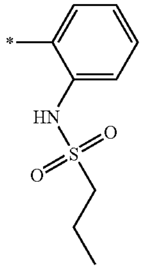
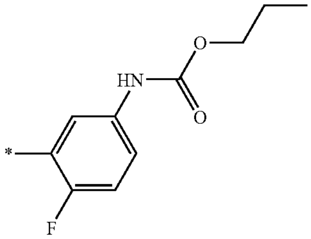
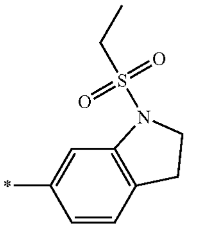
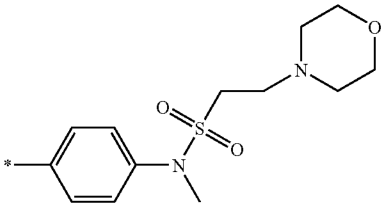
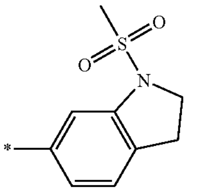
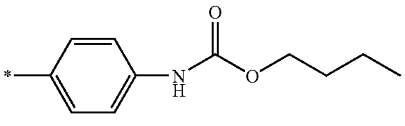

-continued
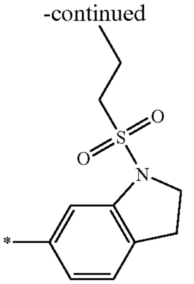
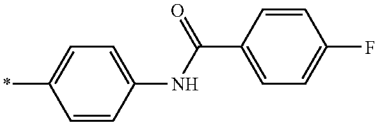
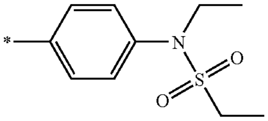
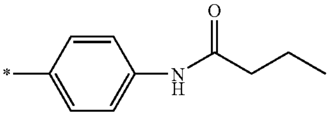
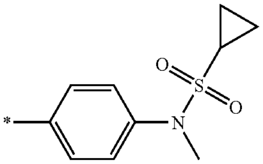
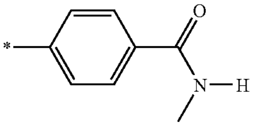
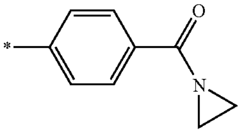
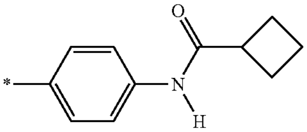
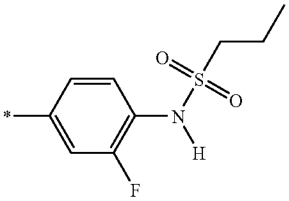
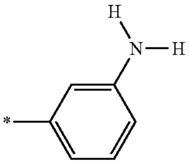
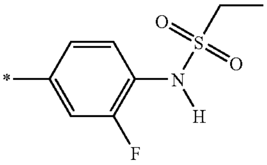
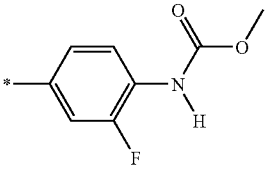
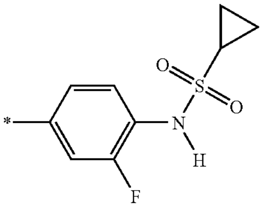
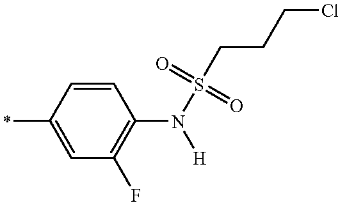
-continued
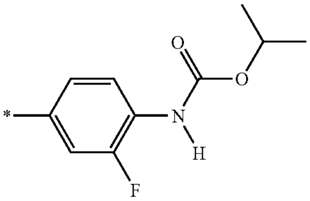
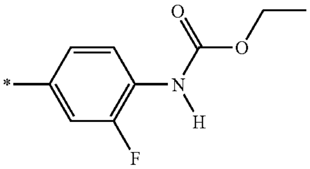
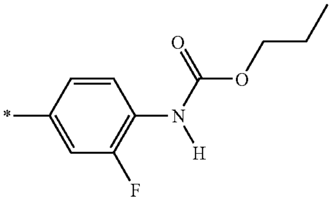
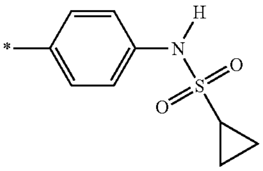
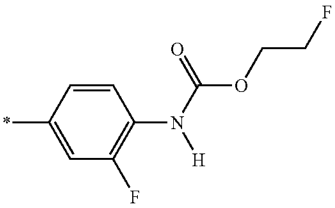
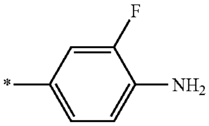
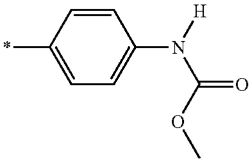
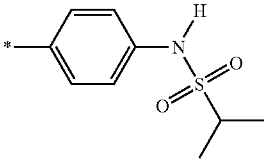
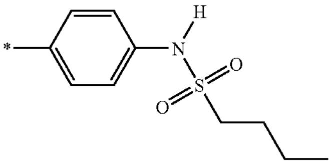
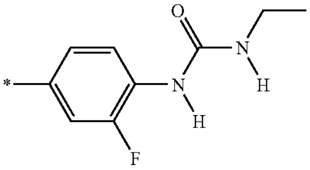
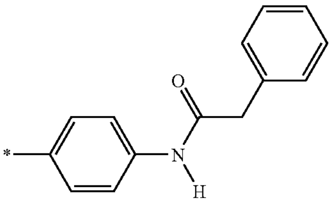

-continued
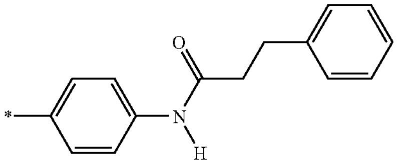
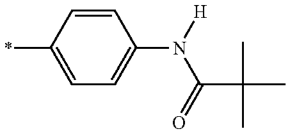
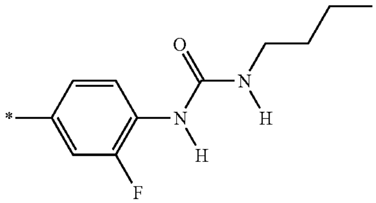
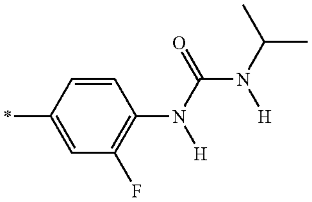
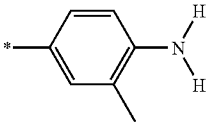
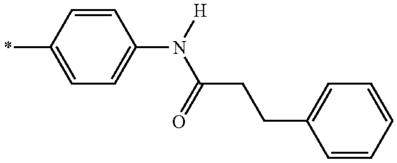
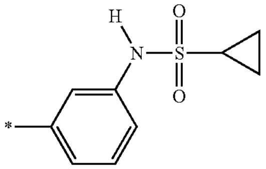
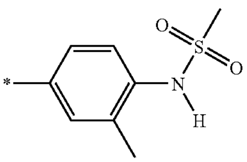
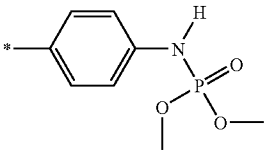
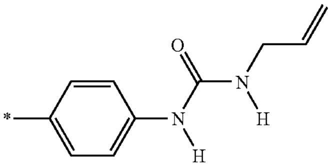
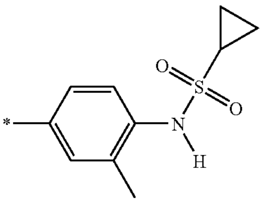
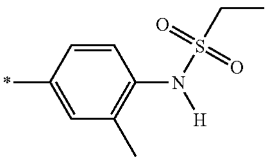
-continued
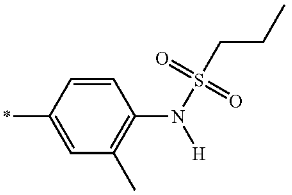
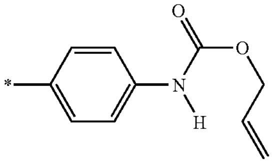
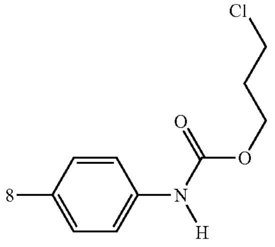
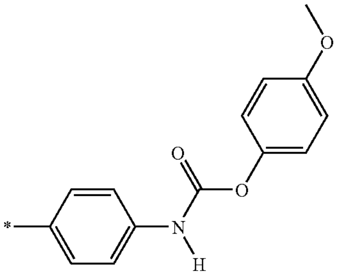
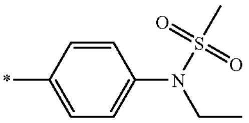
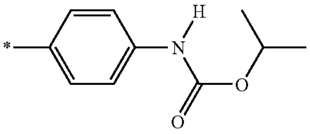
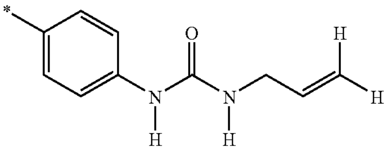
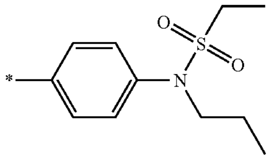
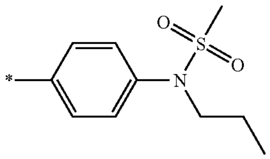
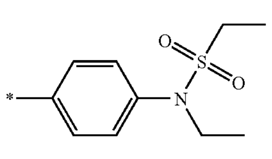
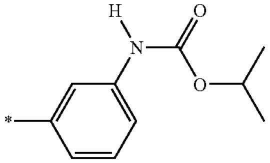
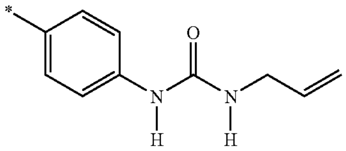

-continued
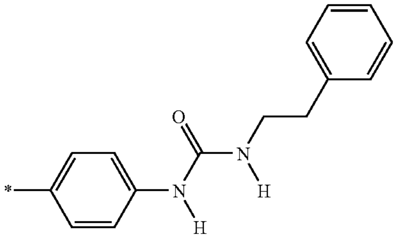
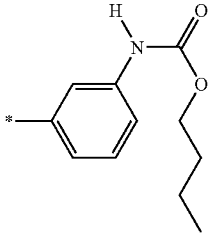
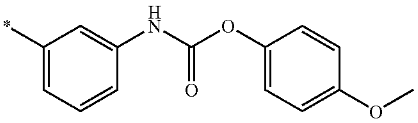
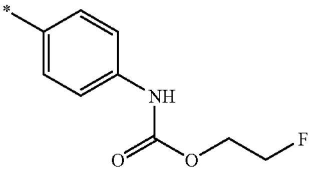
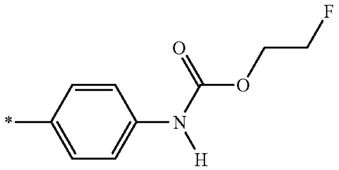
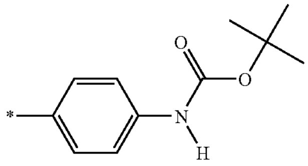
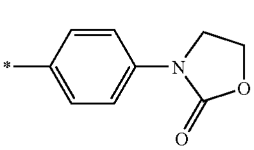
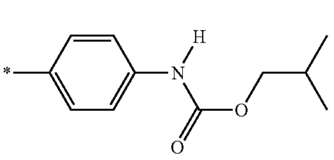
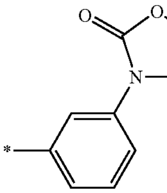
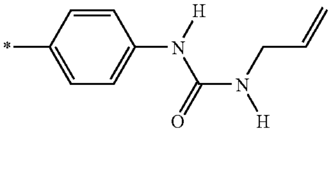
-continued
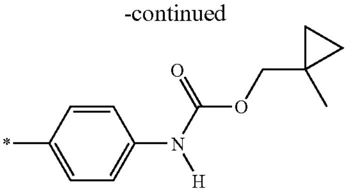
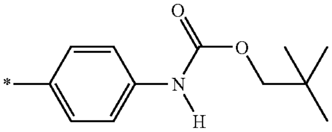
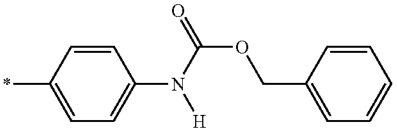
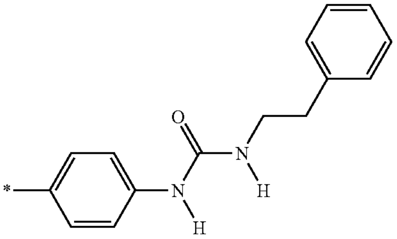
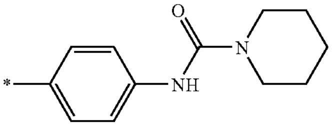
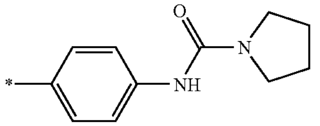
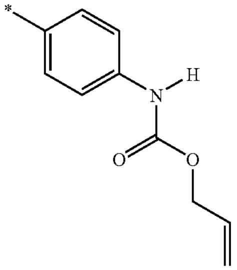
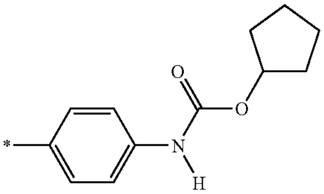
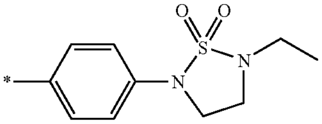
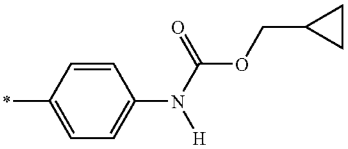
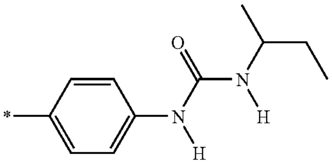

-continued
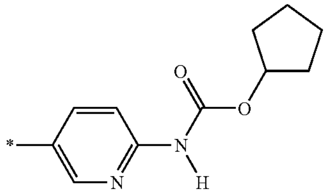
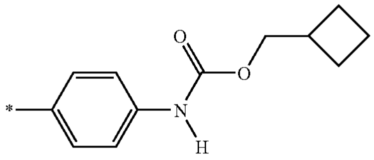
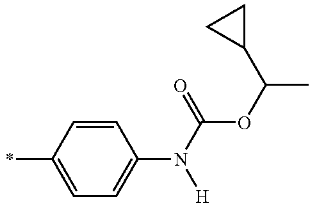
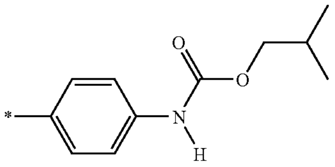
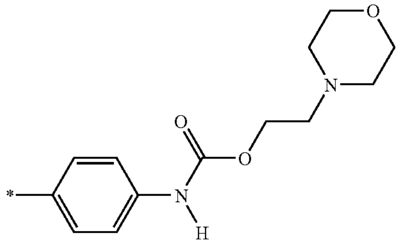
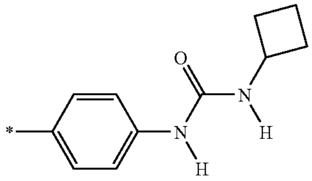
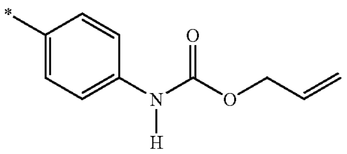
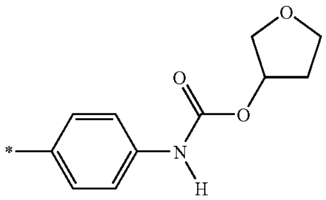
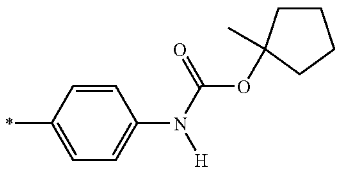
-continued
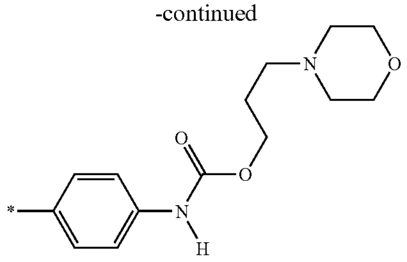
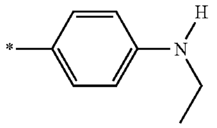
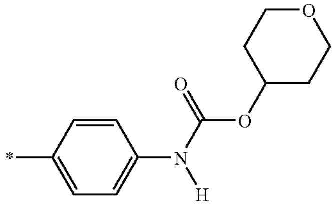
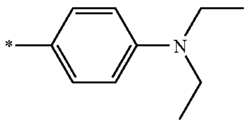
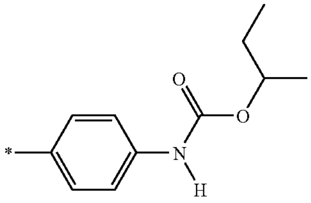
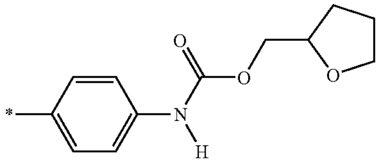
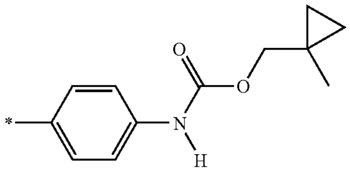
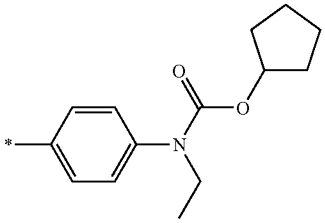
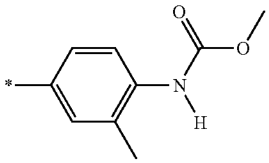
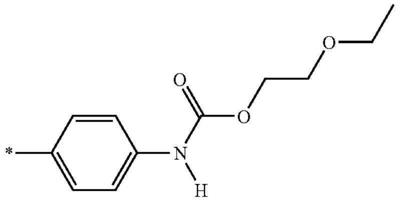

-continued
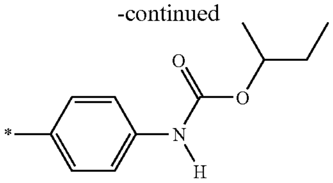
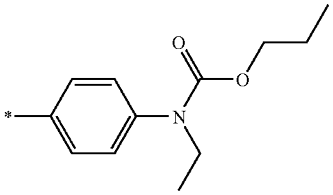
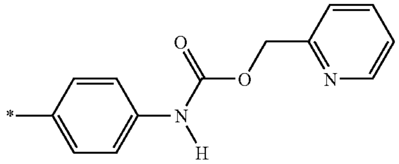
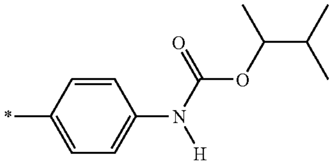
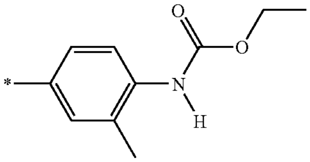
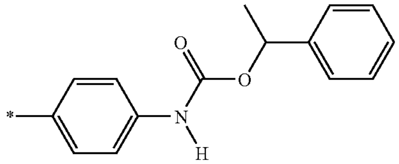
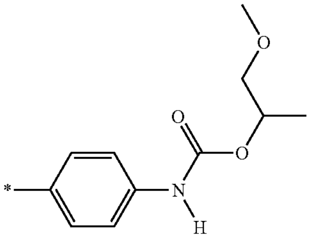
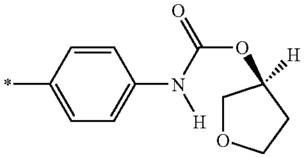
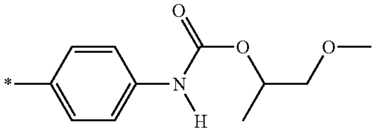
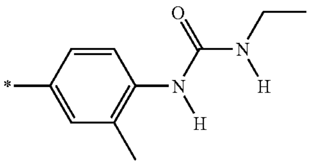
-continued
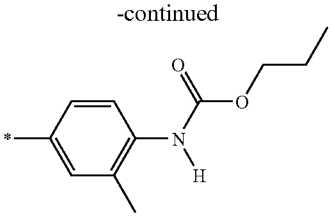
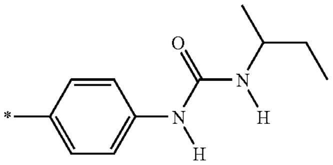
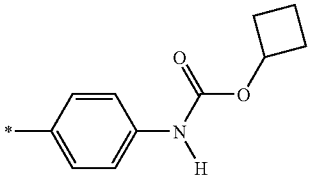
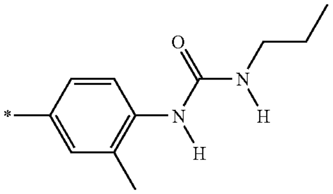
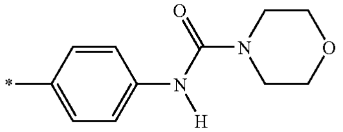
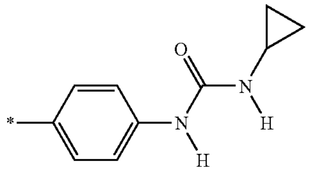
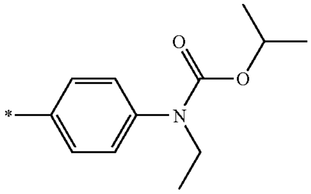
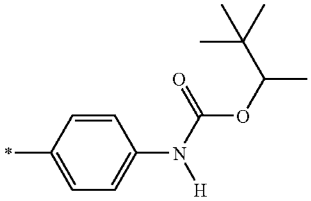
In some embodiments, the Y substituent is selected from the following:
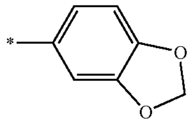
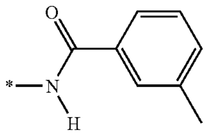

-continued
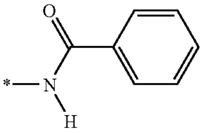
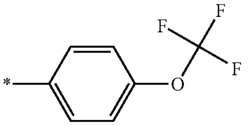
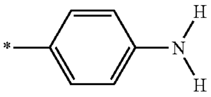
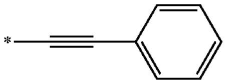
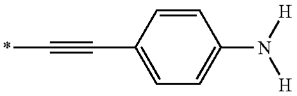
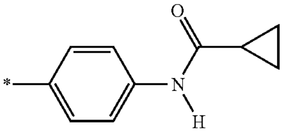
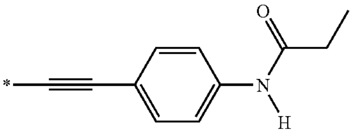
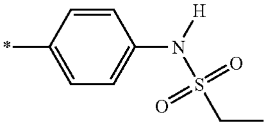
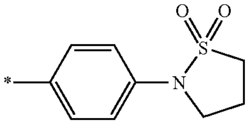
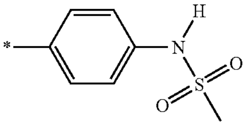
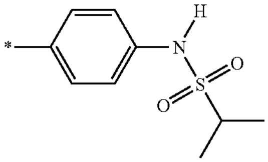
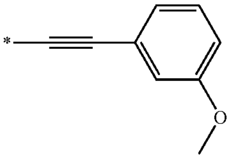
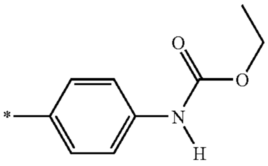
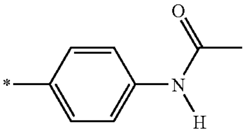
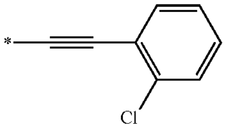
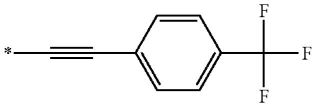
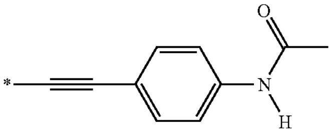
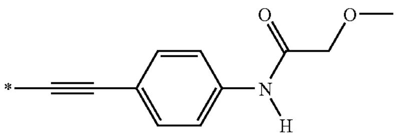
-continued
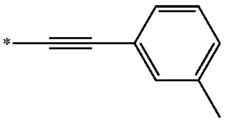
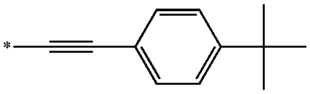
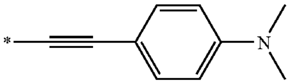
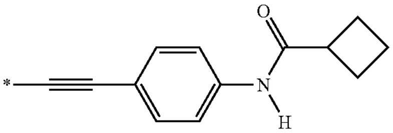
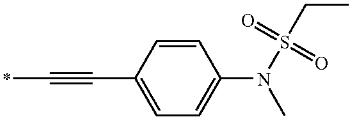
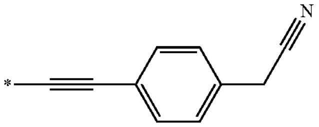
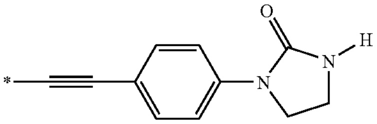
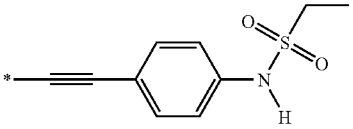
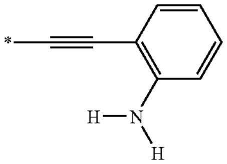
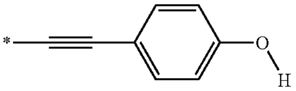
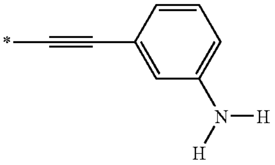
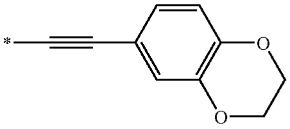
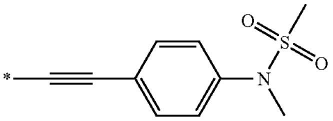
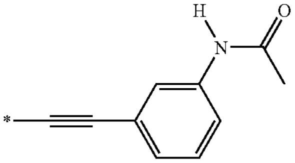

-continued
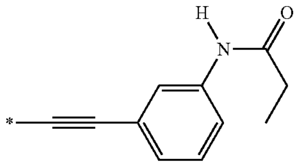
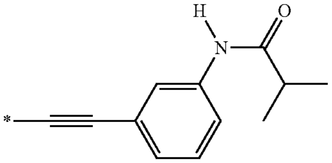
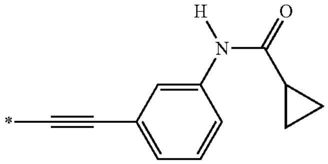
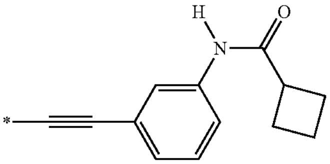
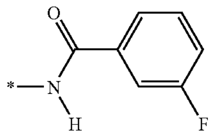
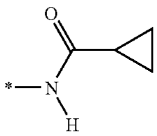
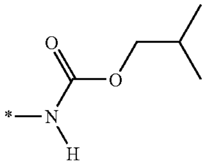
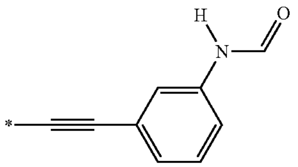
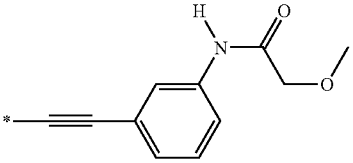
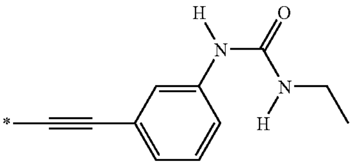
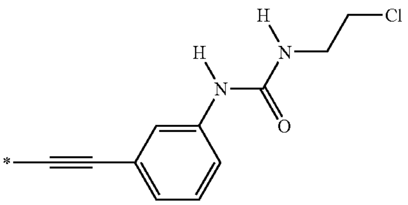
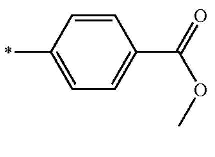
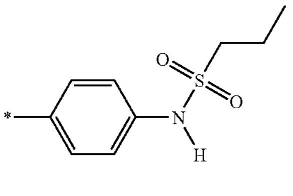
-continued
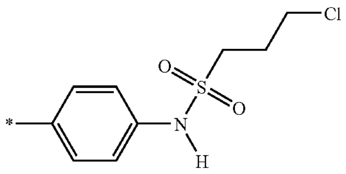
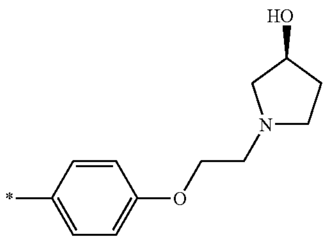
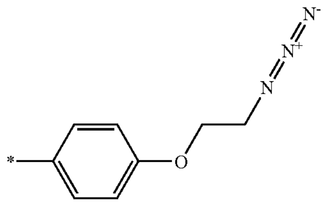
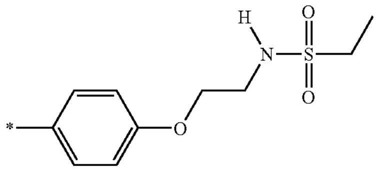
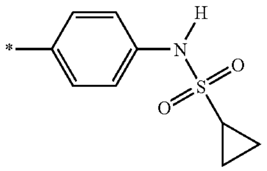
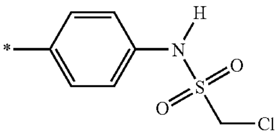
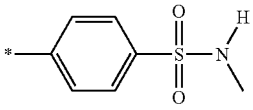
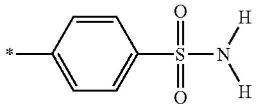
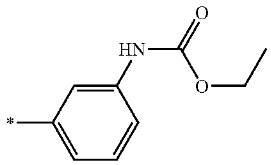
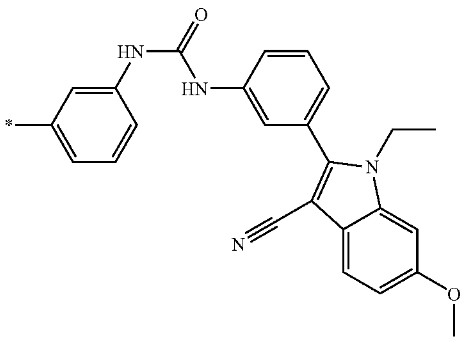

-continued
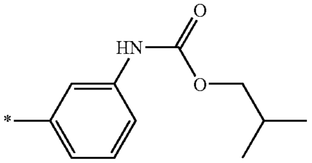
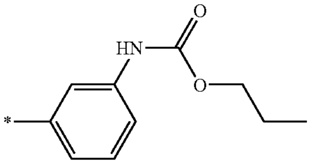
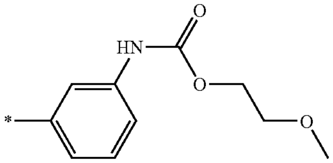
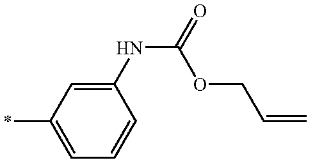
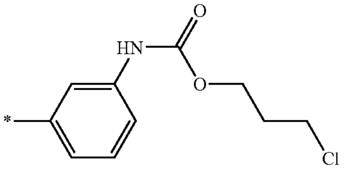
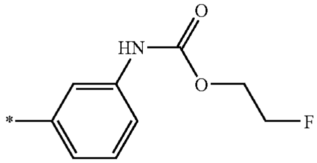
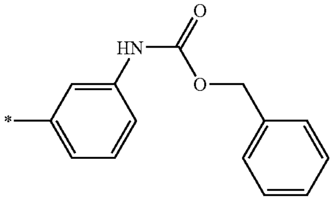
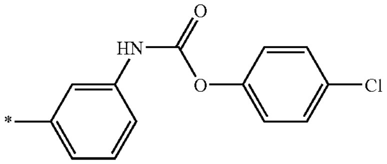
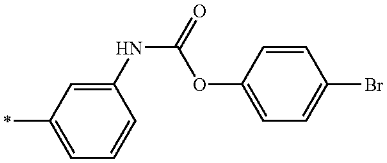
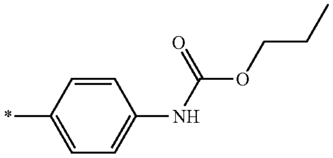
-continued
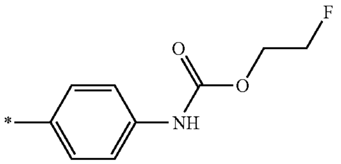
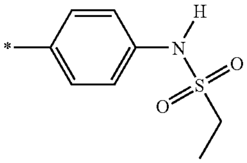
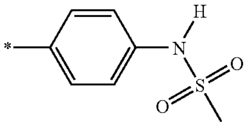
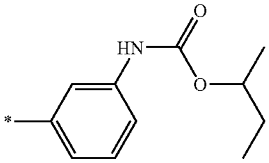
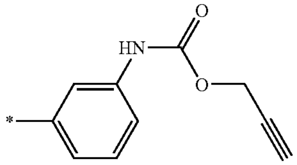
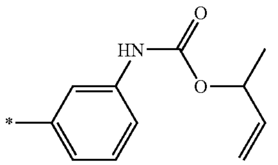
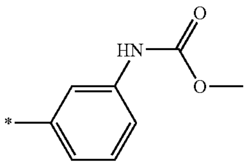
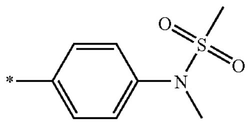
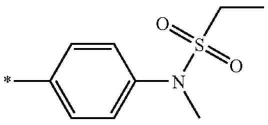
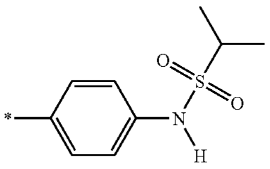
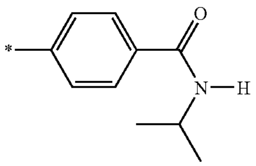
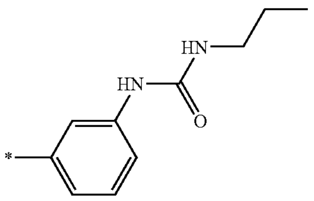

-continued
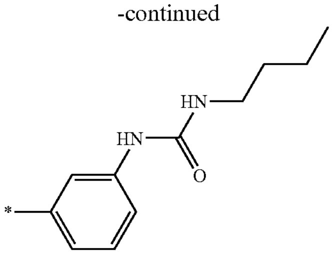
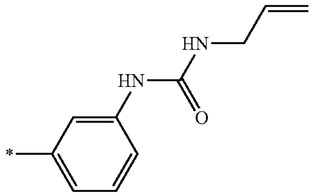
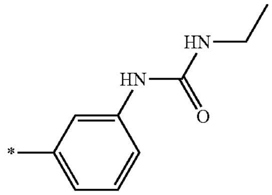
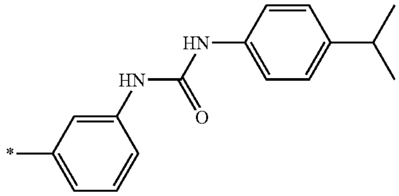
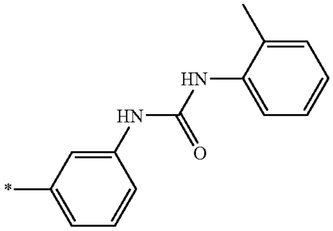
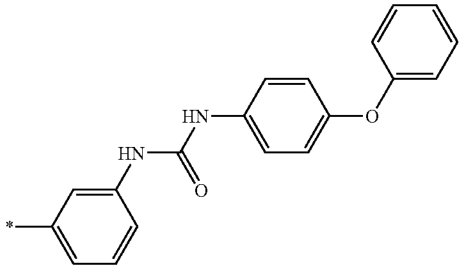
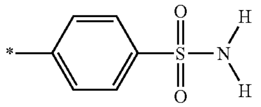
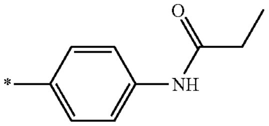
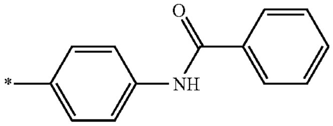
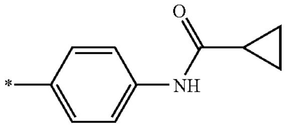
-continued
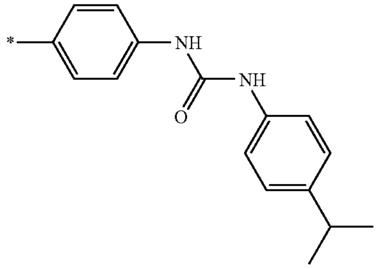
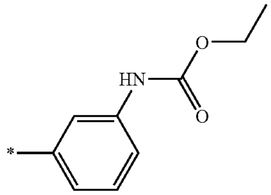
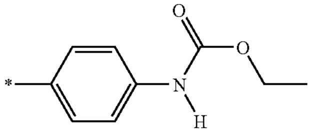
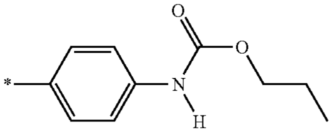
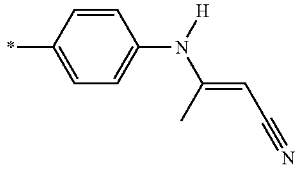
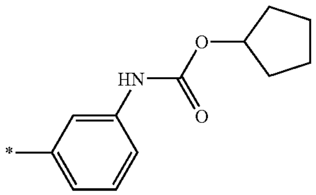
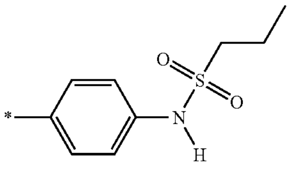
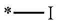
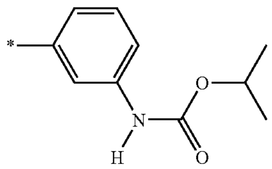
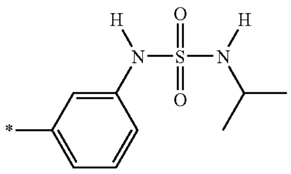

-continued
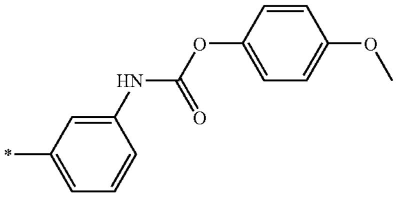
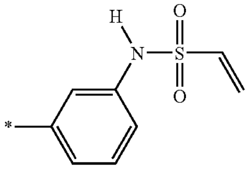
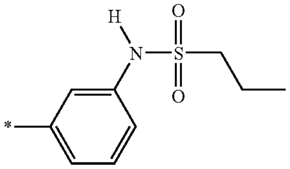
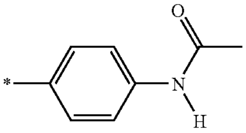
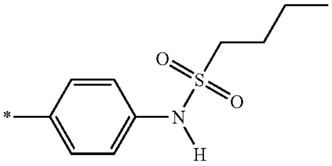
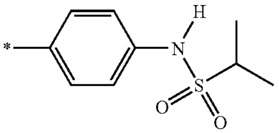
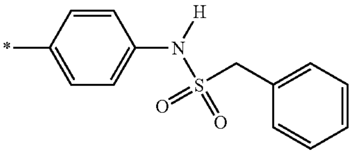
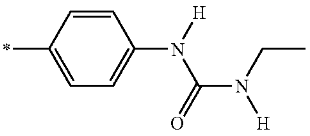
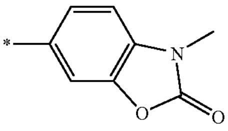
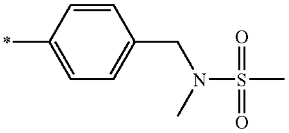
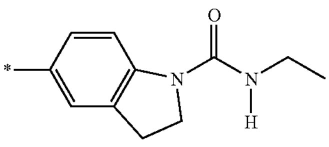
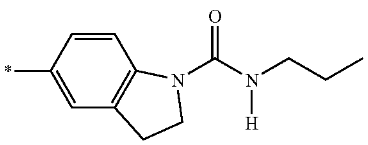
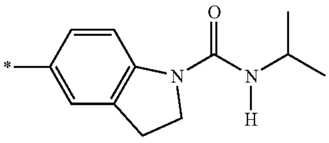
-continued
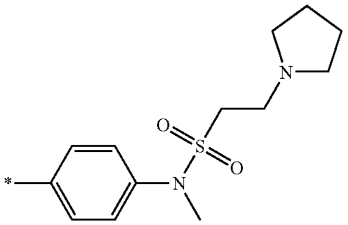
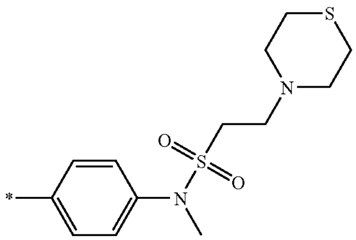
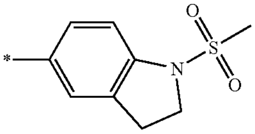
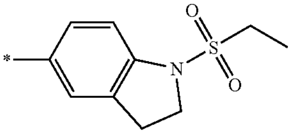
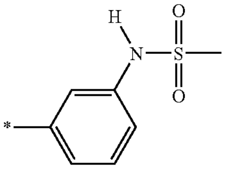
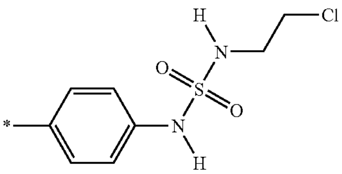
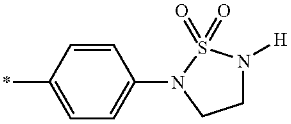
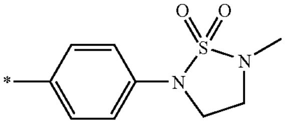
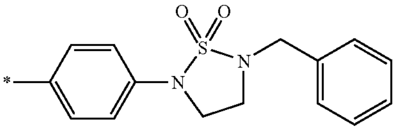
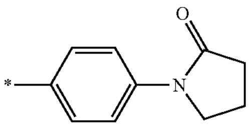
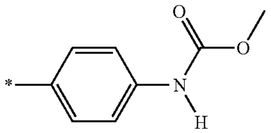
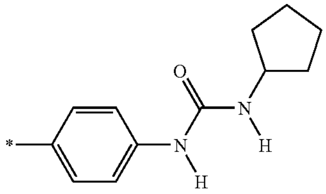

-continued
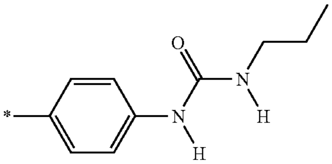
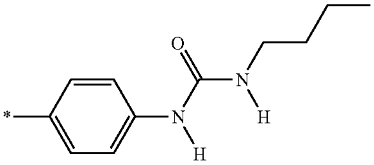
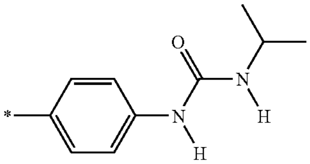
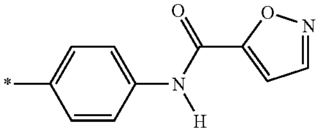
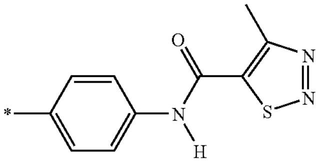
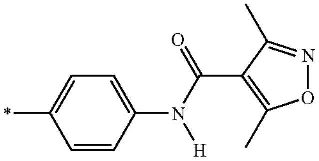
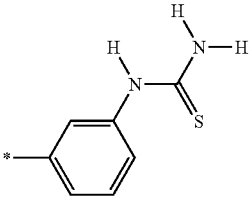
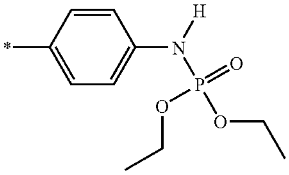
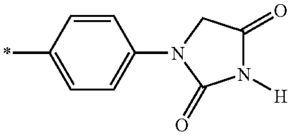
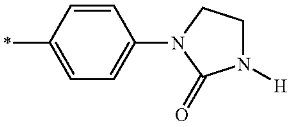
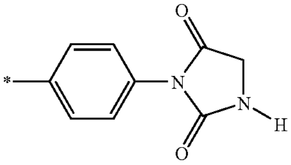
-continued
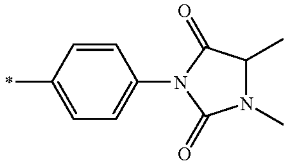
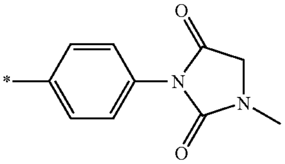
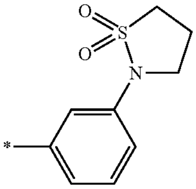
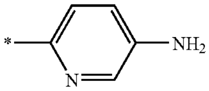
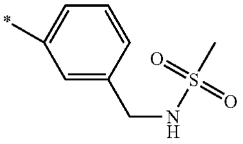
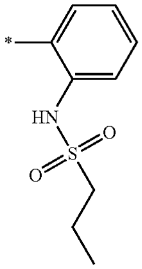
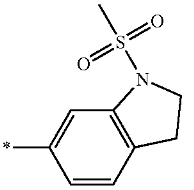
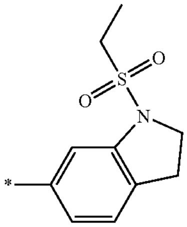
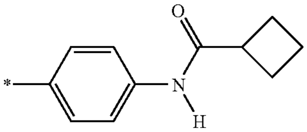
*—H
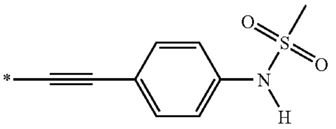
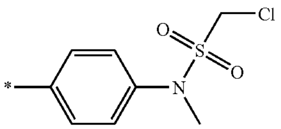
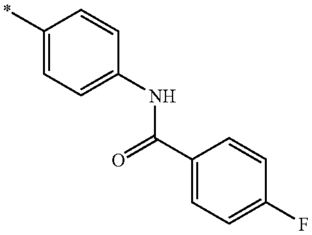

-continued
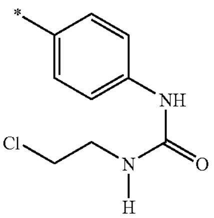
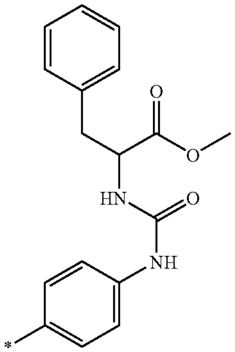
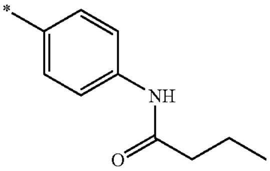
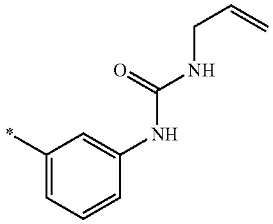
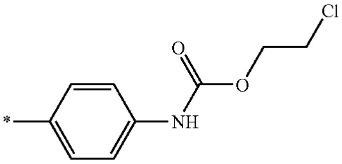
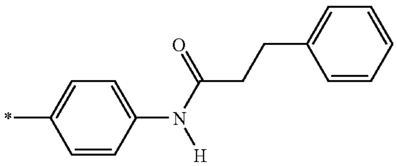
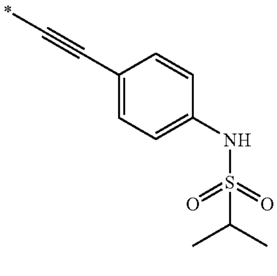
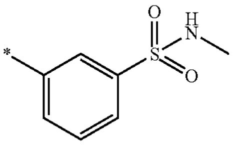
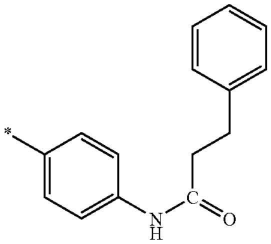
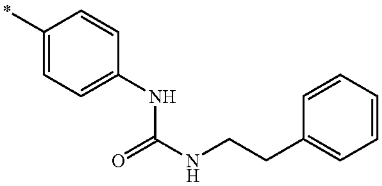
-continued
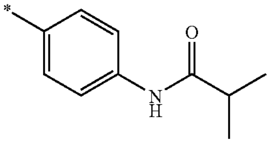
In other embodiments, the Y substituent is selected from the following:
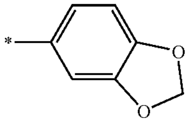
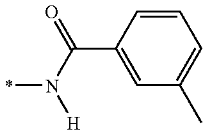
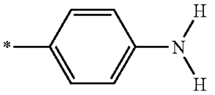
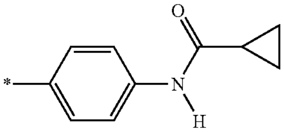
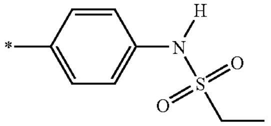
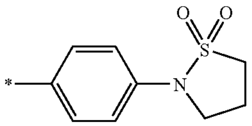
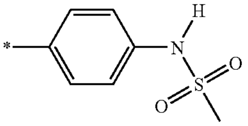
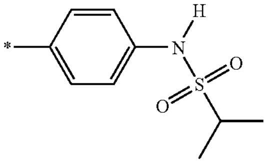
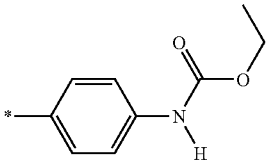
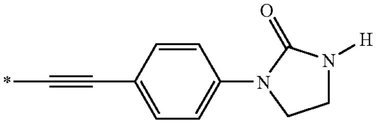
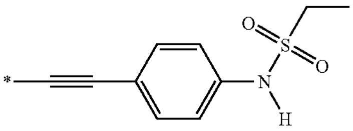
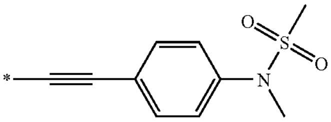
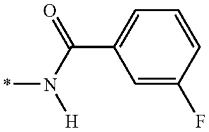
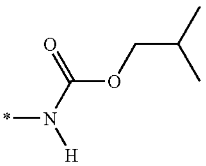
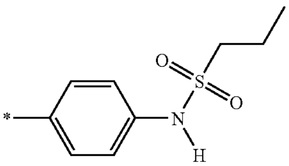

-continued
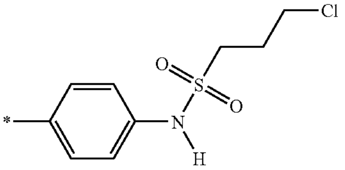
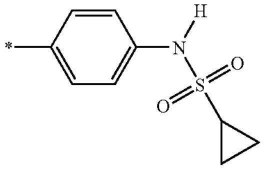
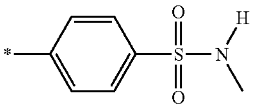
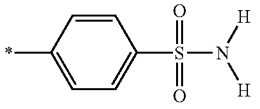
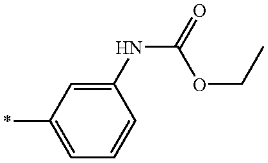
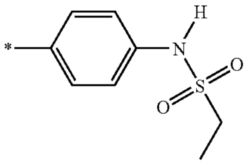
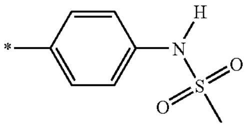
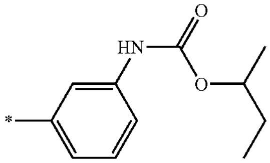
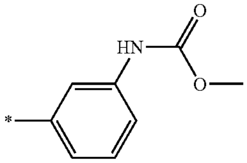
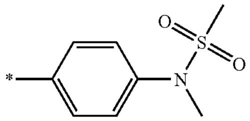
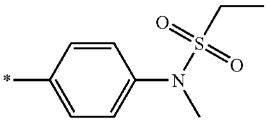
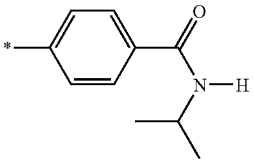
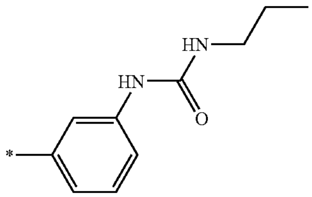
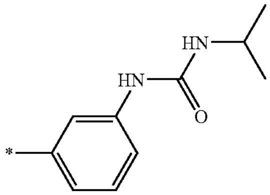
-continued
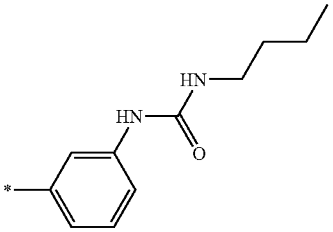
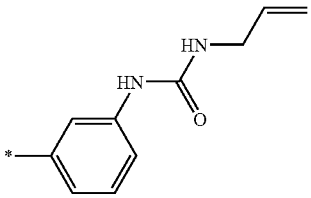
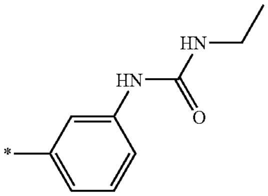
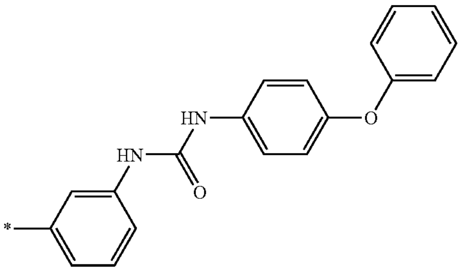
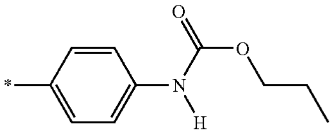
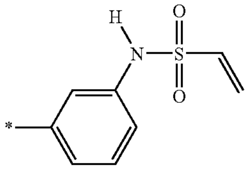
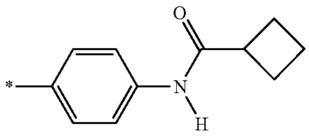
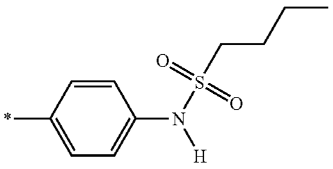
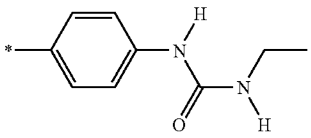
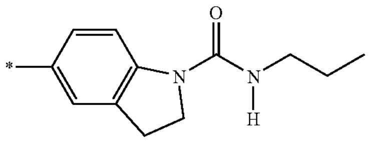

-continued
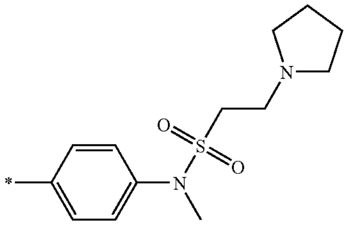
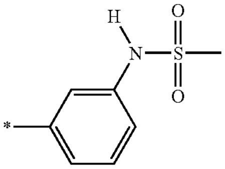
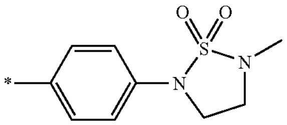
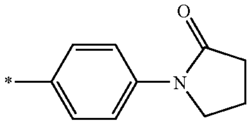
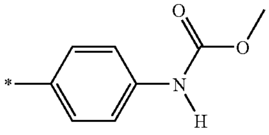
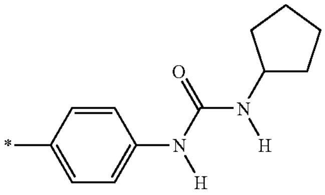
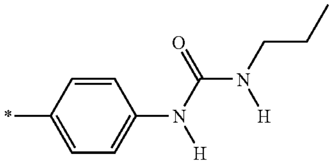
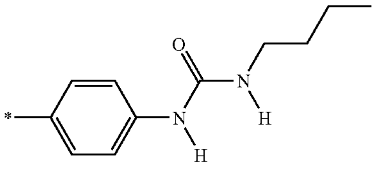
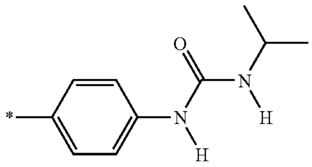
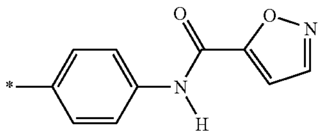
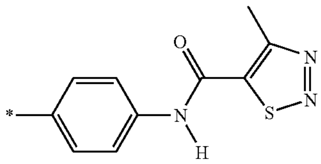
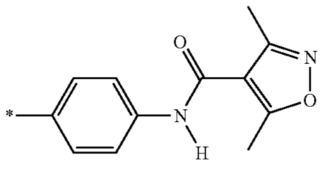
-continued
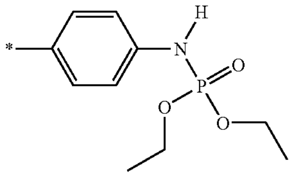
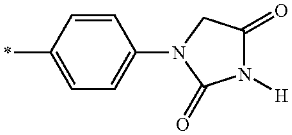
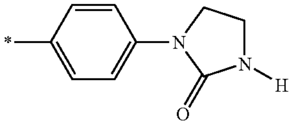
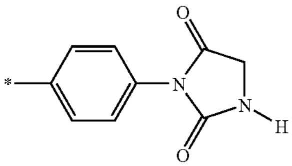
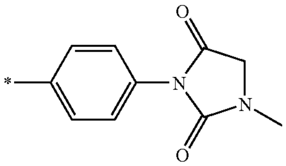
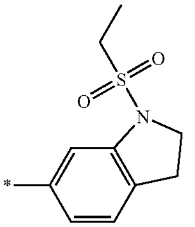
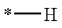
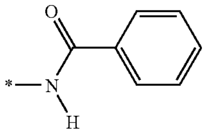
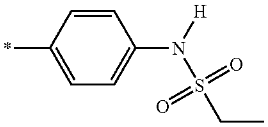
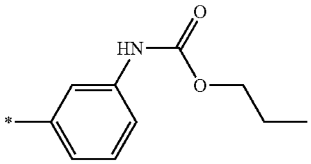
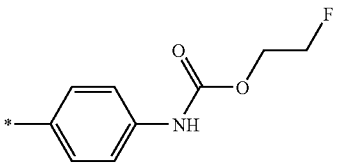
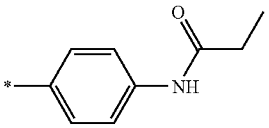
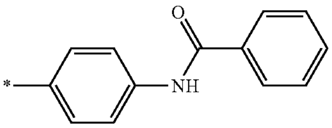
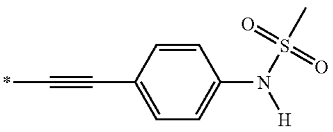

-continued
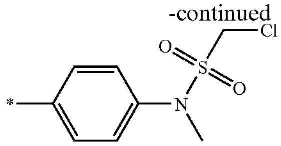
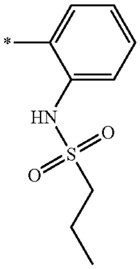
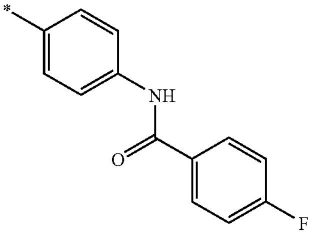
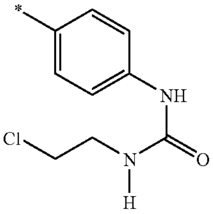
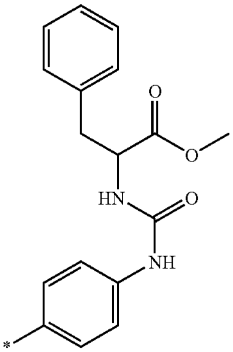
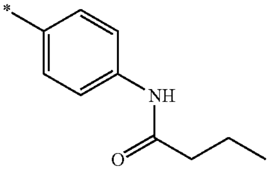
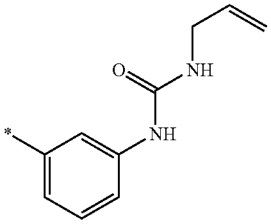
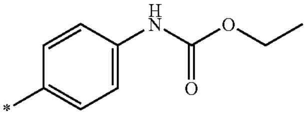
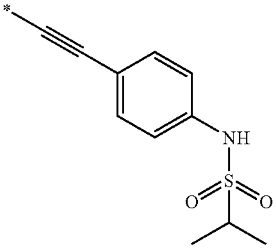
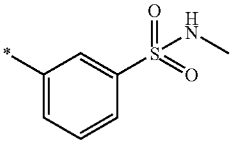
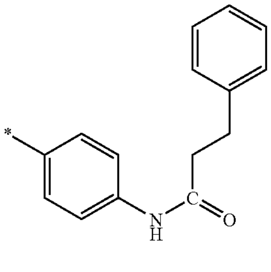
-continued
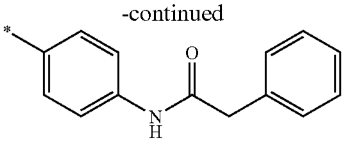
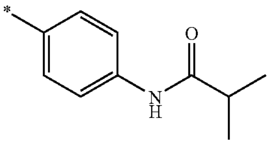
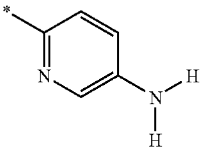
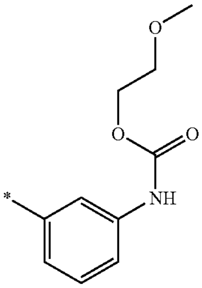
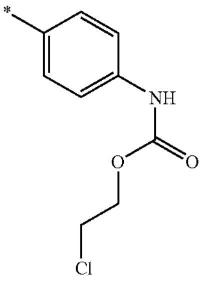
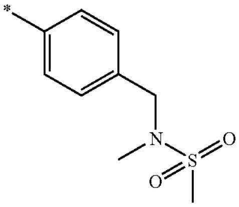
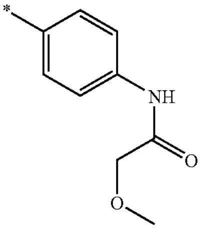
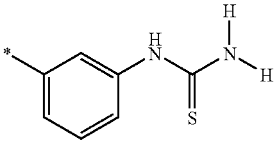
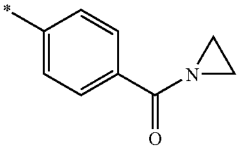
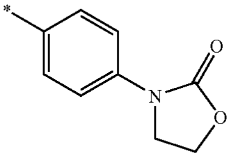
Nonlimiting examples of Z substituents include the following:
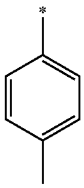
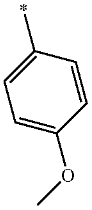
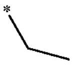
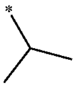
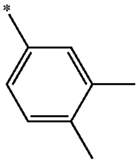
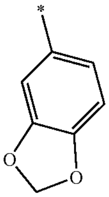
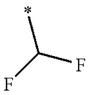
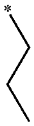
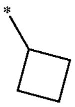
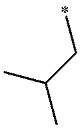
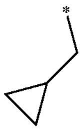

-continued

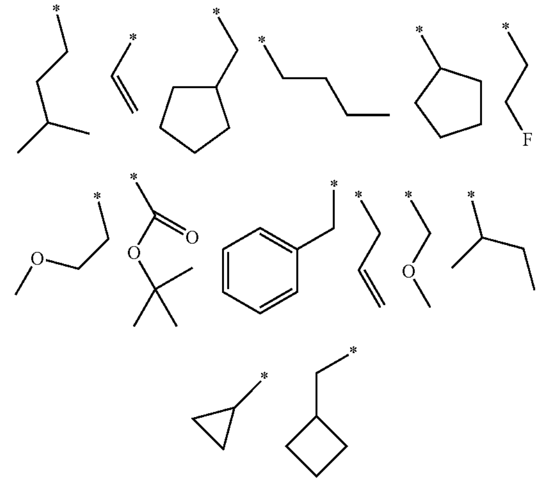

In some embodiments, the Z substituent is a hydrogen; a $C_1$ to $C_6$ alkyl optionally substituted with an alkoxy, one or more halogens, or a $C_6$ to $C_8$ aryl; a $C_2$ to $C_6$ alkylene; or a $C_6$ to $C_8$ aryl optionally substituted with an alkoxy.

In other embodiments, the Z substituent is selected from the following:

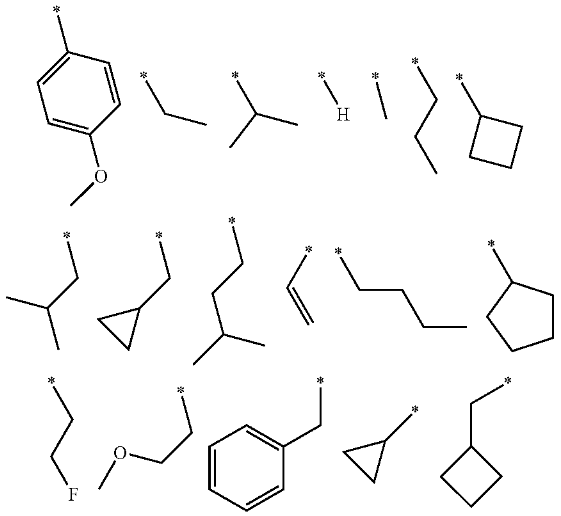

In yet other embodiments, the Z substituent is a hydrogen; a $C_1$ to $C_6$ alkyl optionally substituted with: -a $C_6$ to $C_8$ aryl; -a $C_2$ to $C_6$ alkylene; and -a $C_6$ to $C_8$ aryl optionally substituted with an alkoxy.

In yet further embodiments, the Z substituent is selected from the following:

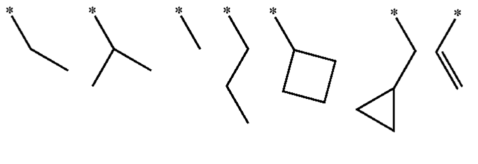

-continued

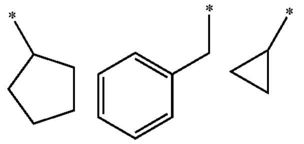

Nonlimiting examples of R substituents include the following:

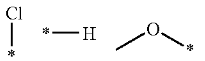

In some embodiments, the R substituent is the following:

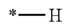

Nonlimiting examples of $R_1$ substituents include the following:

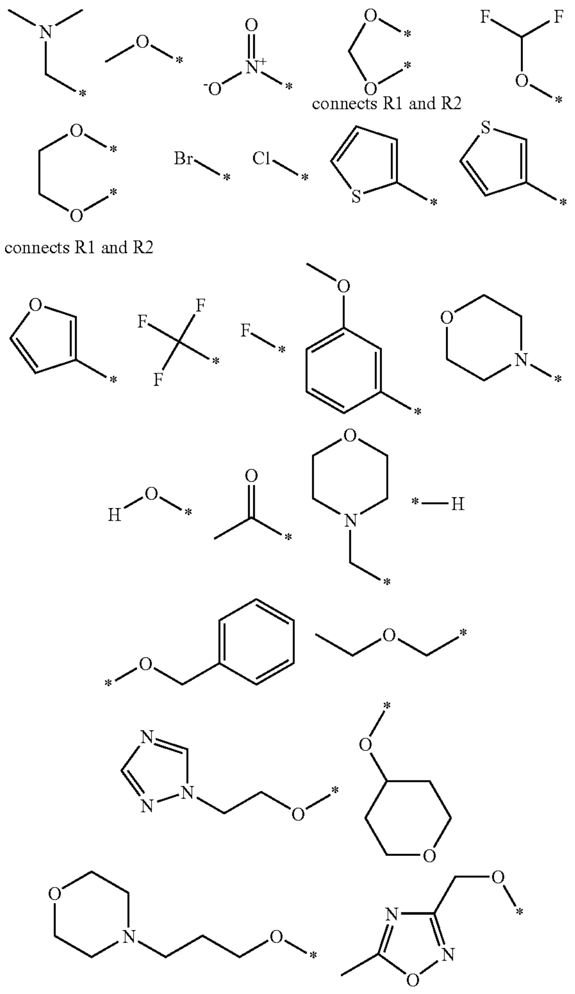

connects R1 and R2 connects R1 and R2

-continued

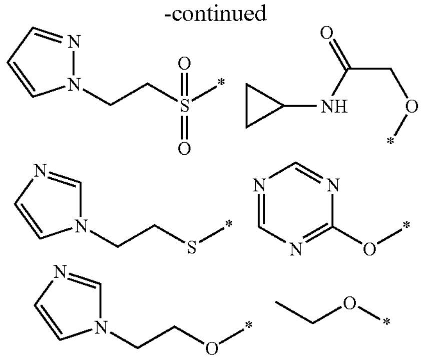

In some embodiments, the $R_1$ substituent is a hydrogen; a halogen; a nitro group; a 5 or 6 membered heterocycle; an alkoxy optionally substituted with a $C_6$ to $C_8$ aryl; or a $C_6$ to $C_8$ aryl optionally substituted with an alkoxy.

In other embodiments, the $R_1$ substituent is selected from the following:

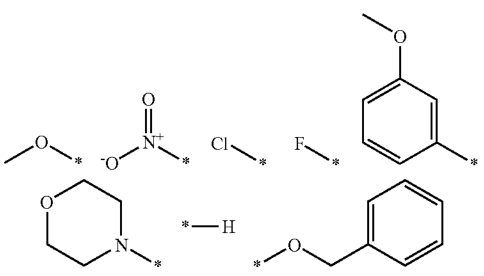

In yet other embodiments, the $R_1$ substituent is selected from the following:

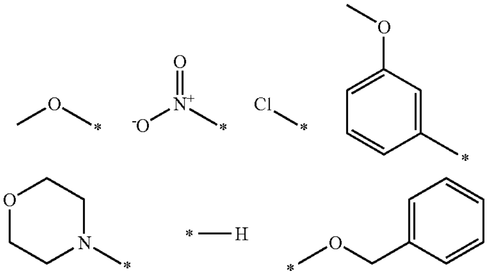

Nonlimiting examples of $R_2$ substituents include the following:

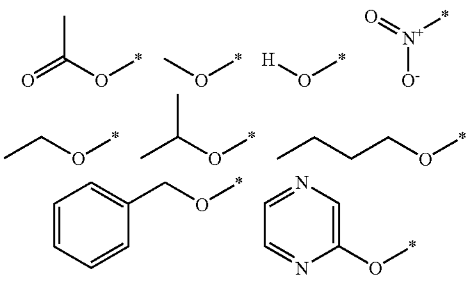

-continued

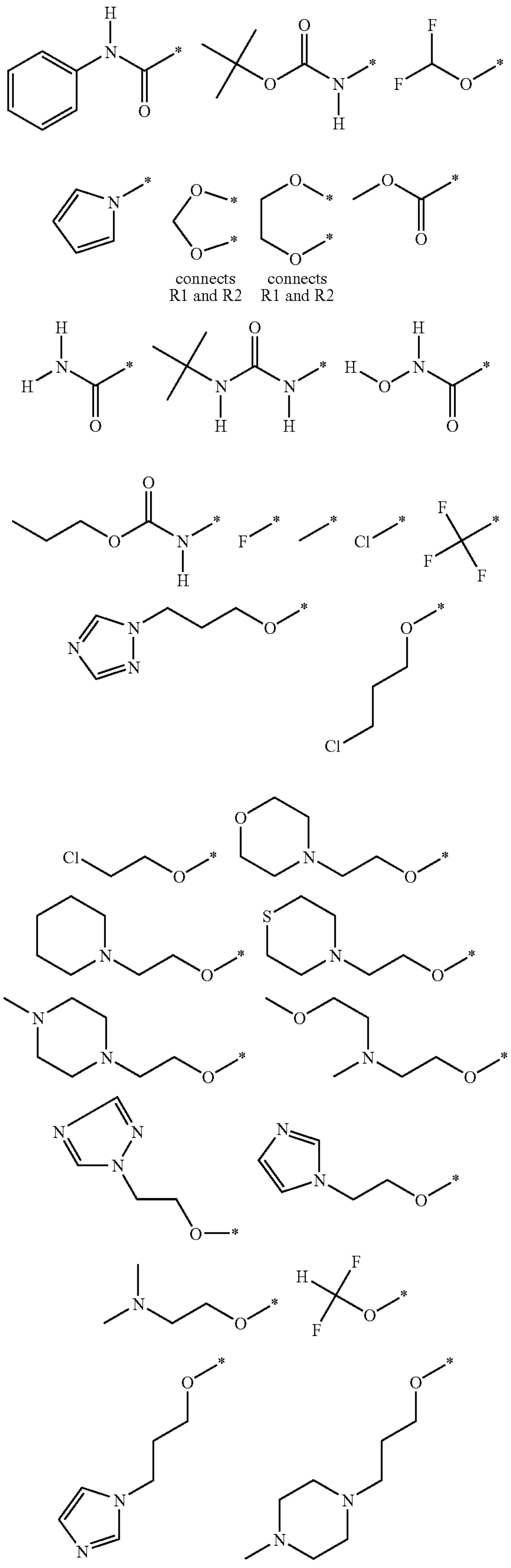

-continued
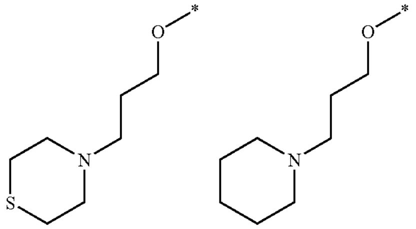
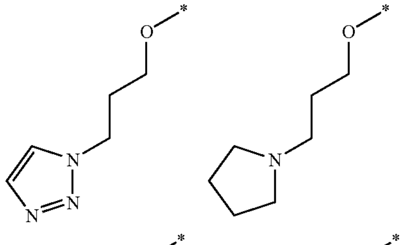
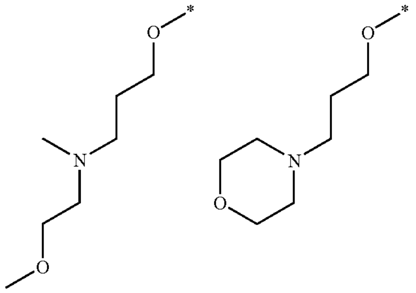
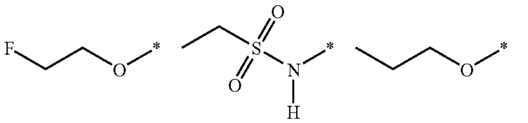
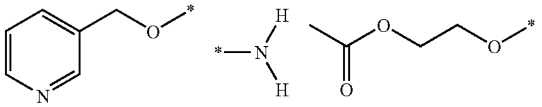
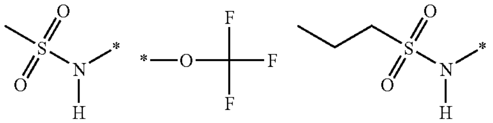
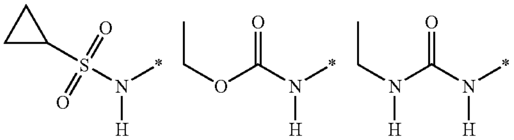
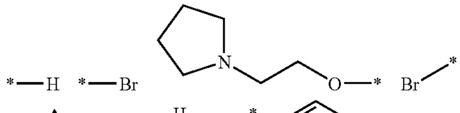
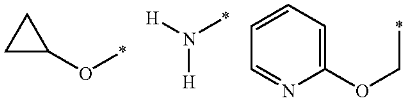
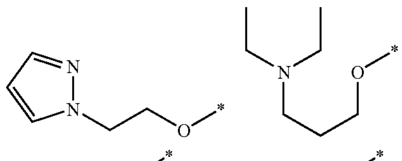
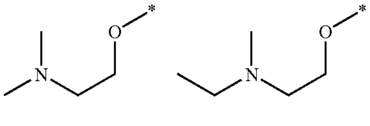
-continued
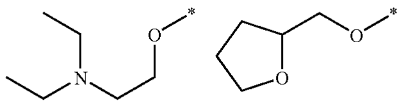
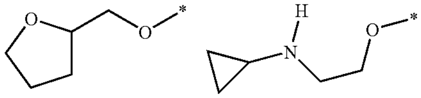
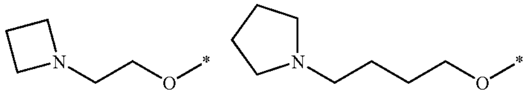
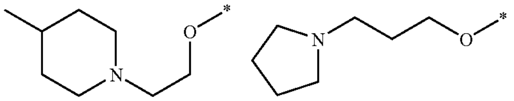
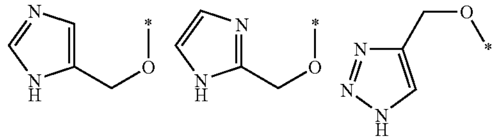
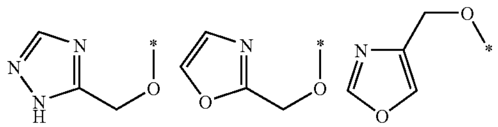
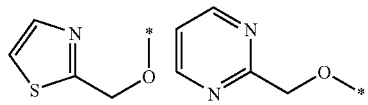
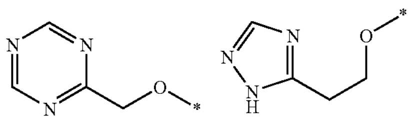
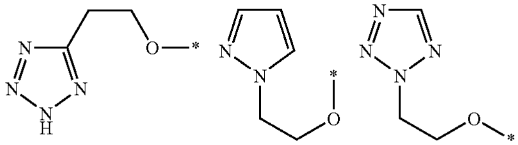
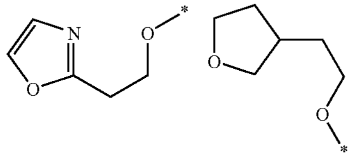
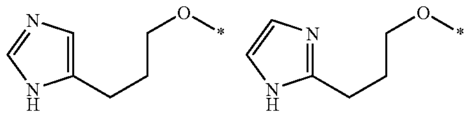
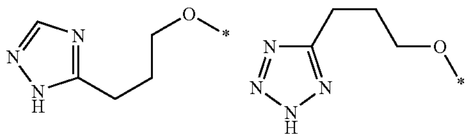
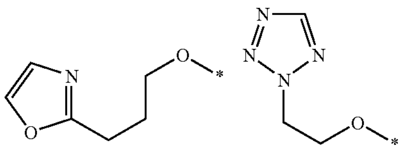

-continued

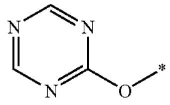

In some embodiments, the $R_2$ substituent is a nitro group; a hydrogen; a halogen; a hydroxy group; a $C_1$ to $C_6$ alkyl group, optionally substituted with one or more halogen(s); an alkoxy group optionally substituted with one or more halogen(s), a —$OCOR_x$ group, where $R_x$ is as defined above, -a dialkylamino optionally substituted with an alkoxy, -a 5 or 6 membered heterocycle group optionally substituted with a $C_1$ to $C_6$ alkyl, or -a 5 or 6 membered heteroaryl group; -an amide group; or a —$NHSO_2R_x$ group, where $R_x$ is as defined above.

In other embodiments, the $R_2$ substituent is selected from the following:

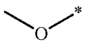 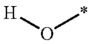 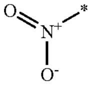 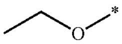 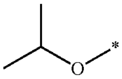

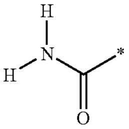 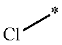 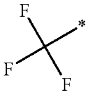

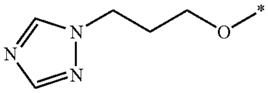 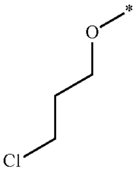

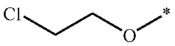 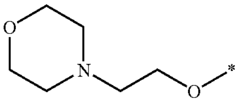

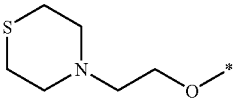 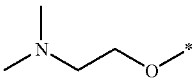

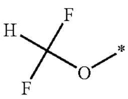 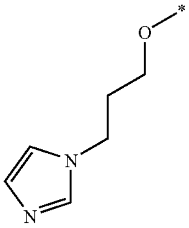

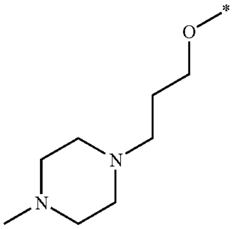 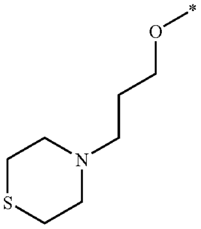

-continued

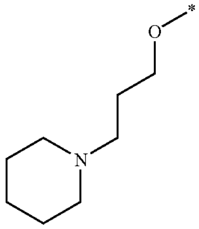 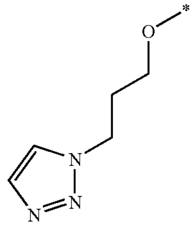

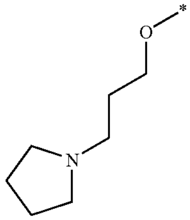 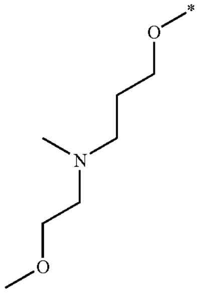

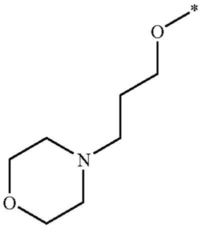 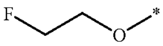 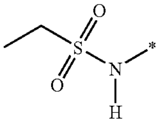

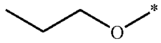 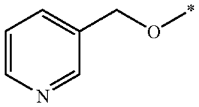

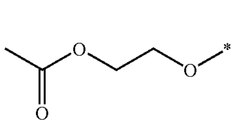 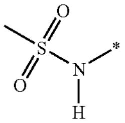 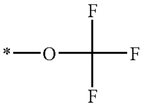

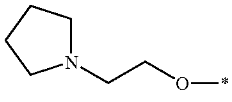 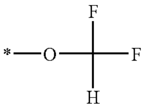

In yet other embodiments, the $R_2$ substituent is a hydrogen; a $C_1$ to $C_6$ alkyl group, optionally substituted with one or more halogens; or an alkoxy group optionally substituted with one or more halogens, a 5 or 6 membered heterocycle group optionally substituted with a $C_1$ to $C_6$ alkyl, or a 5 or 6 membered heteroaryl group.

In yet further embodiments, the $R_2$ substituent is selected from the following:

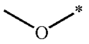 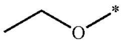 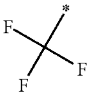 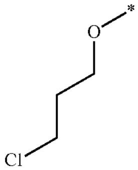

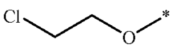 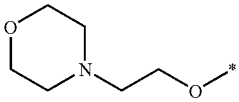

-continued
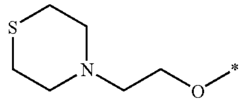
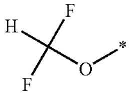
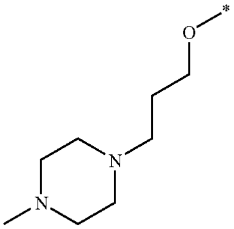
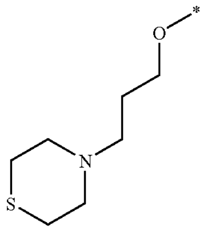
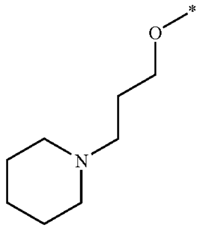
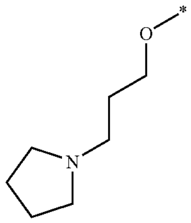
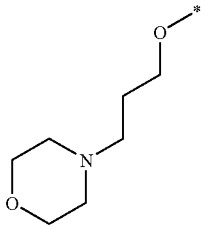
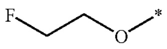
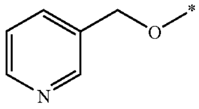
-continued
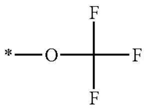
*—H
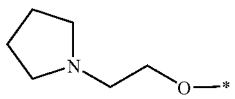
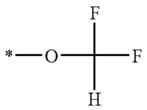
Nonlimiting examples of $R_3$ substituents include the following:
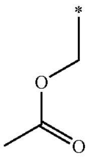
*—H
In some embodiments, the $R_3$ substituent is the following:
*—H
Nonlimiting examples of compounds of formula I include the following:
1
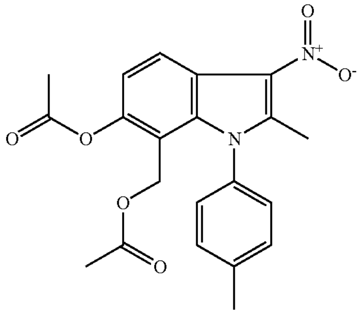
2
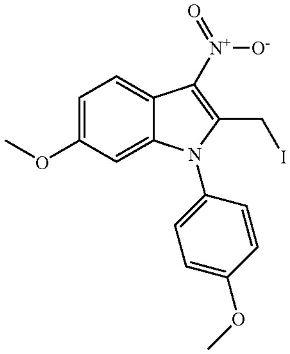
3
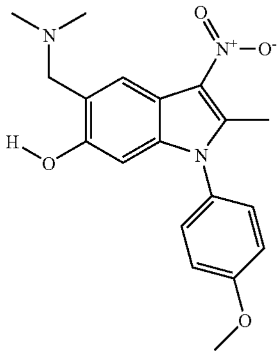
4
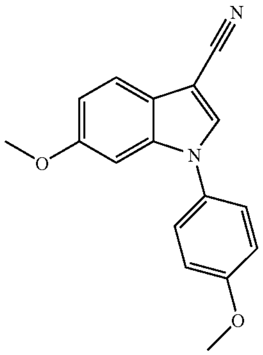

-continued
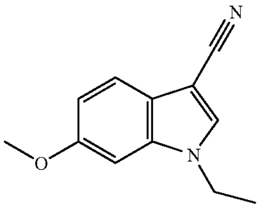
5
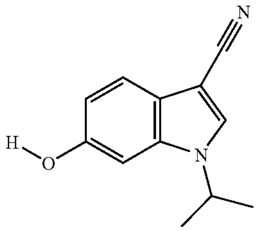
6
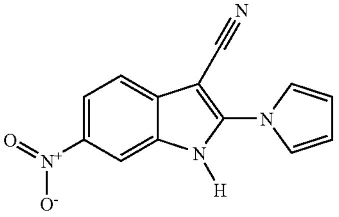
7
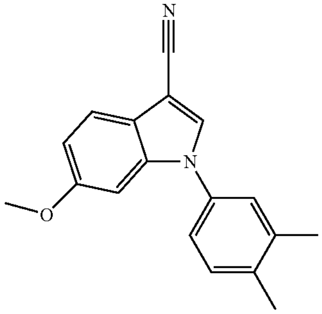
8
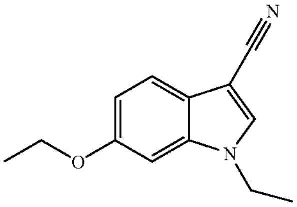
9
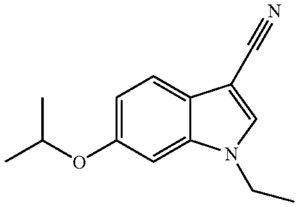
10
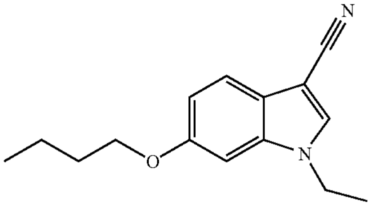
11
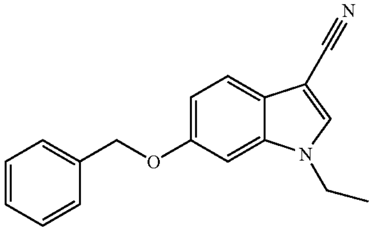
12
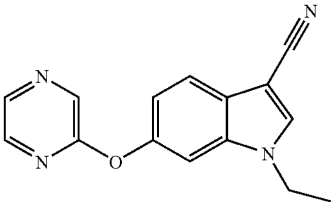
13
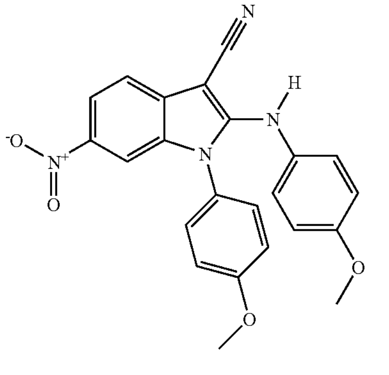
14
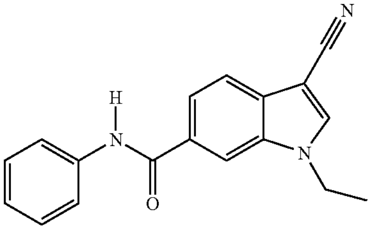
15
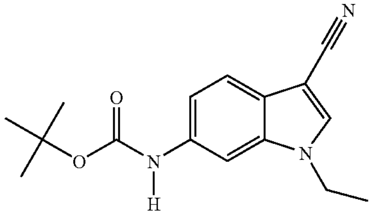
16

-continued
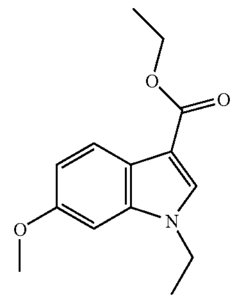
17
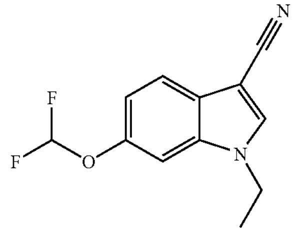
18
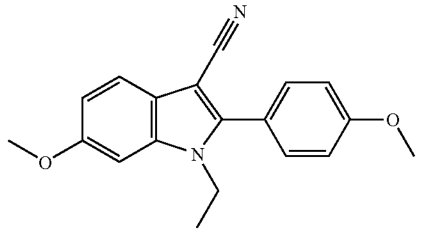
19
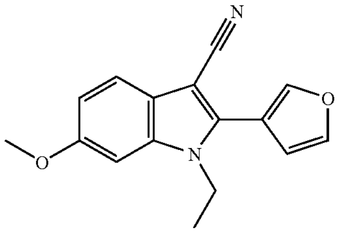
20
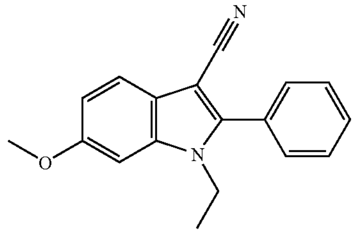
21
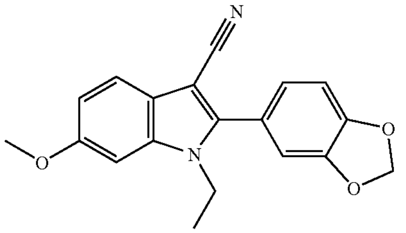
22
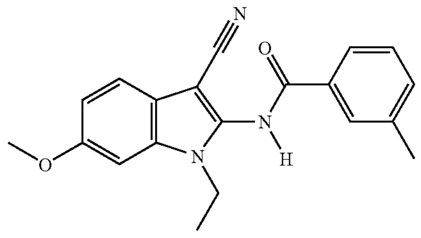
23
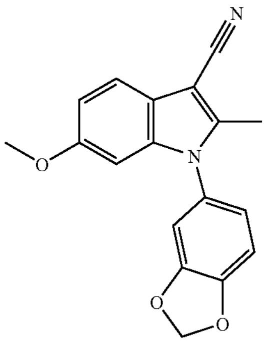
24
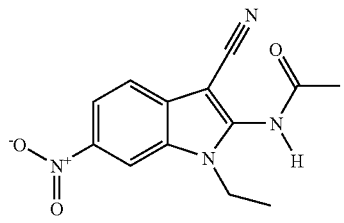
25
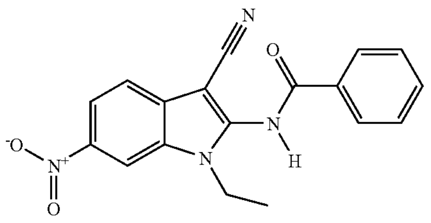
26
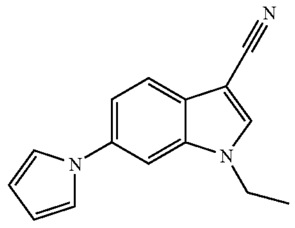
27
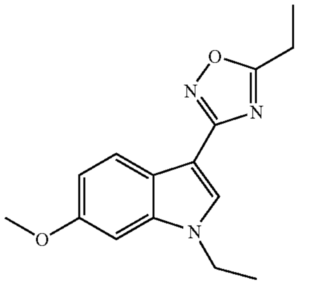
28

-continued
29
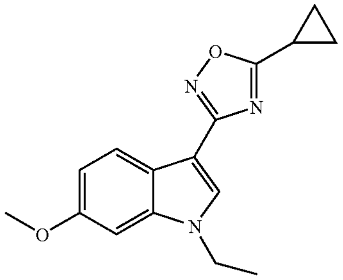
30
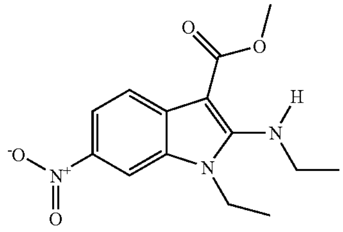
31
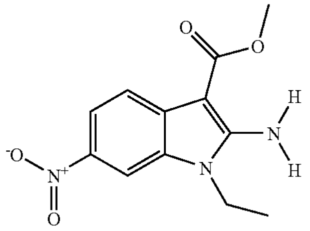
32
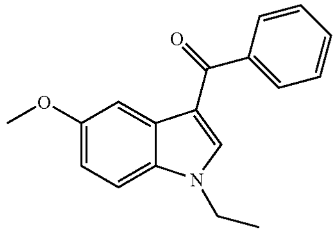
33
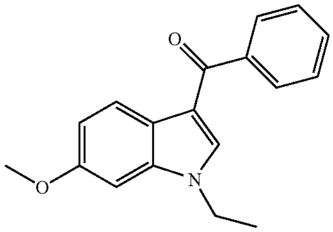
34
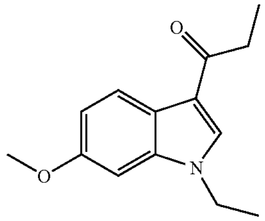
35
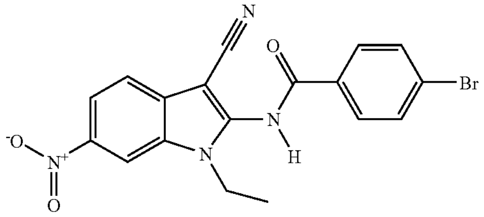
36
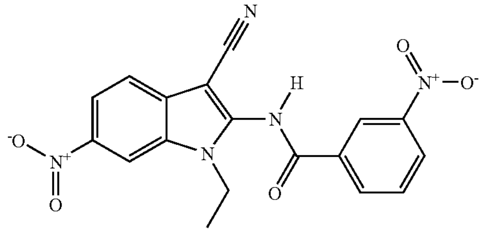
37
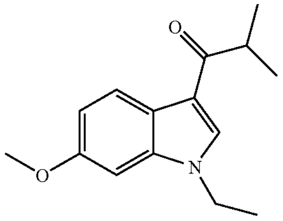
38
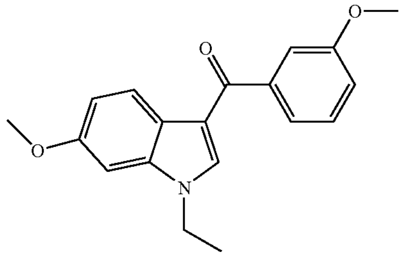
39
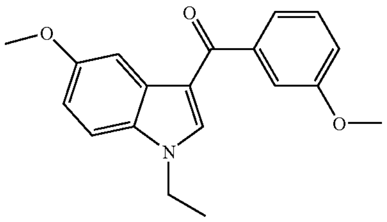
40
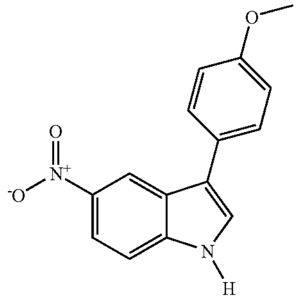

-continued
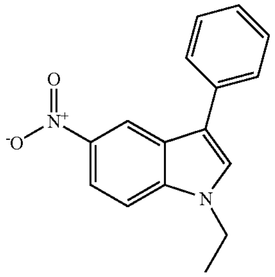
41
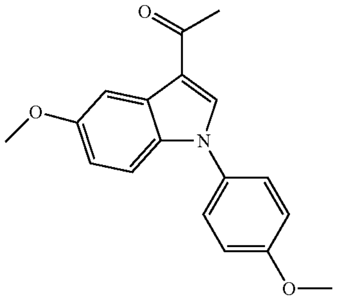
42
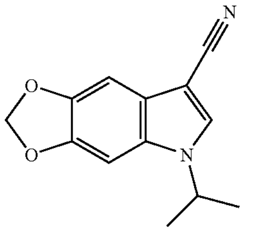
43
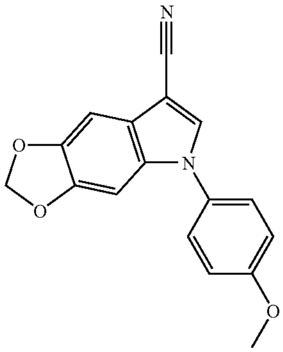
44
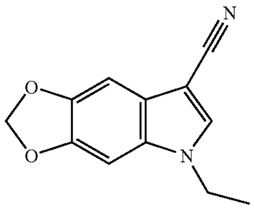
45
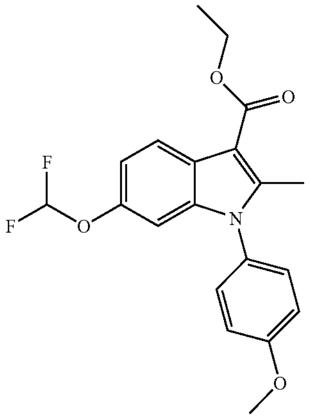
46
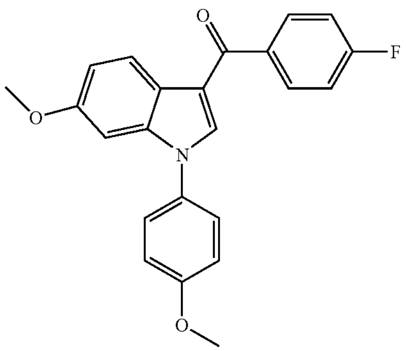
47
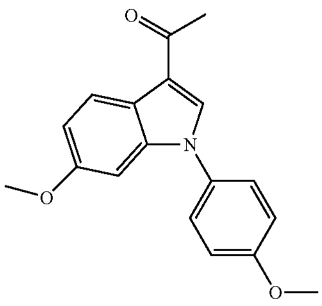
48

-continued
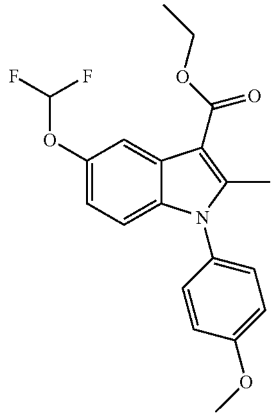
49
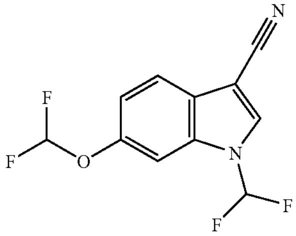
50
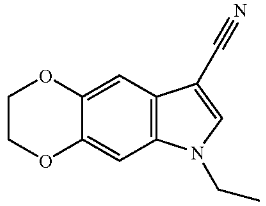
51
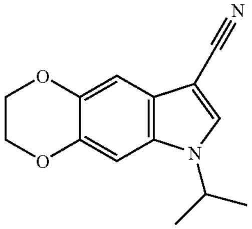
52
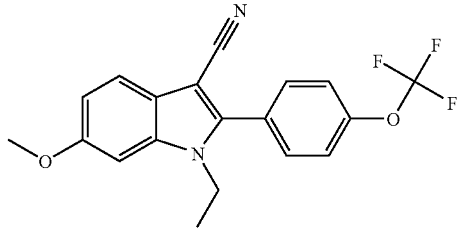
53
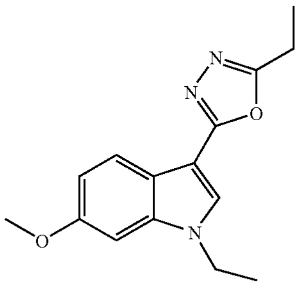
54
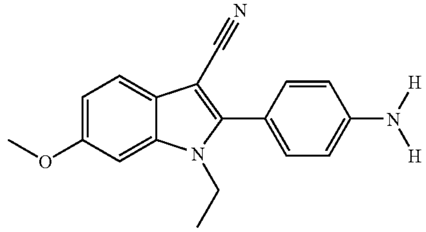
55
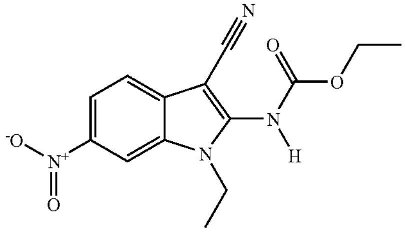
56
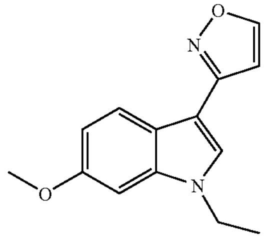
57
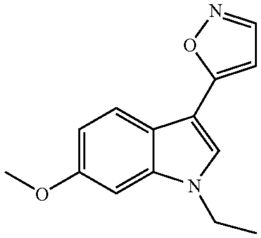
58

-continued
59
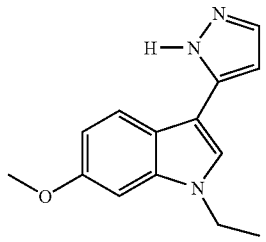
60
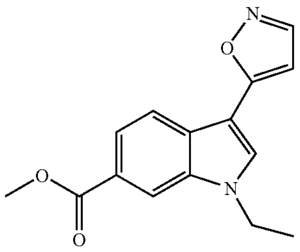
61
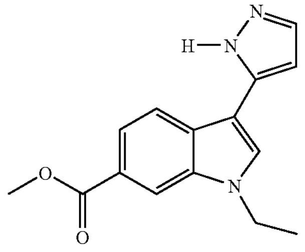
62
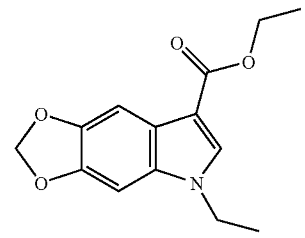
63
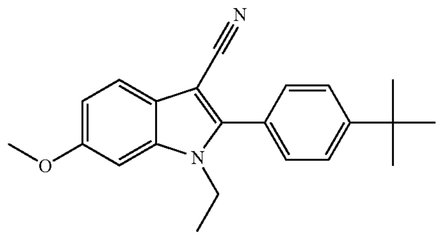
64
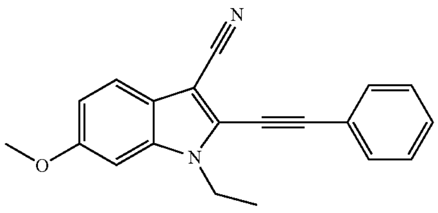
65
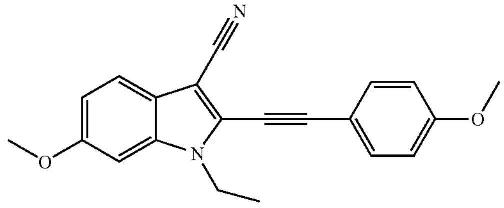
66
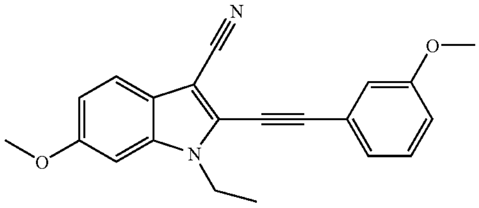
67
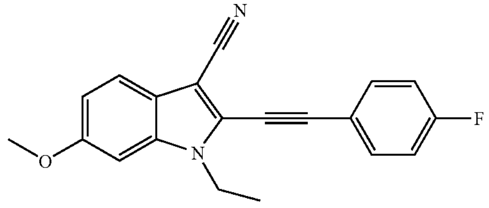
68
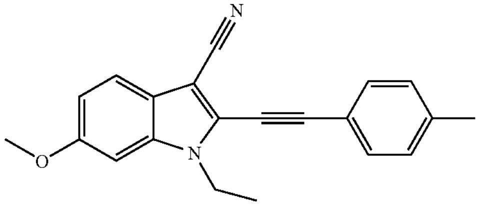
69
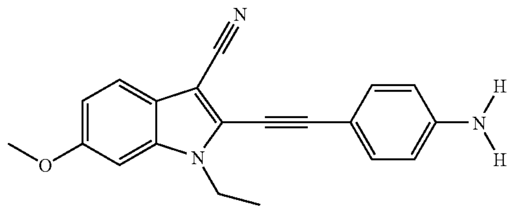
70
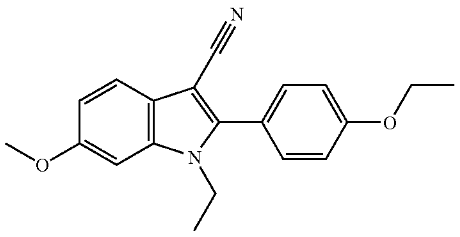

-continued
71
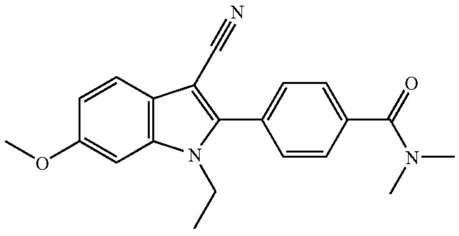
72
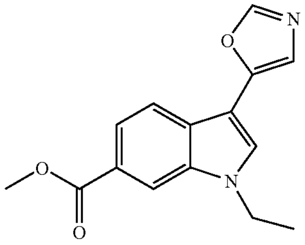
73
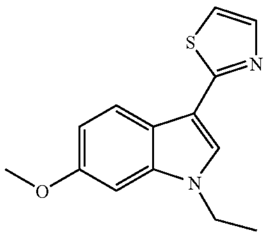
74
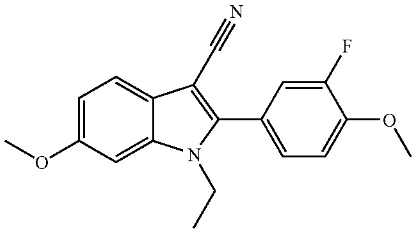
75
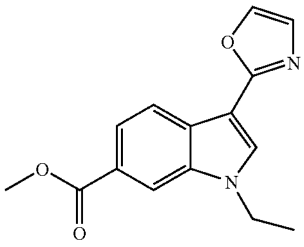
76
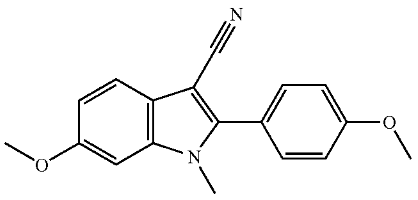
77
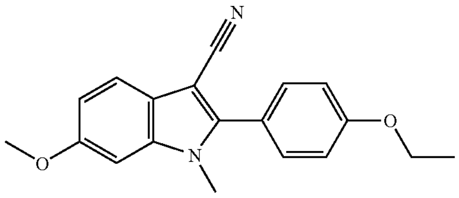
78
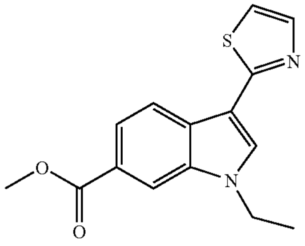
79
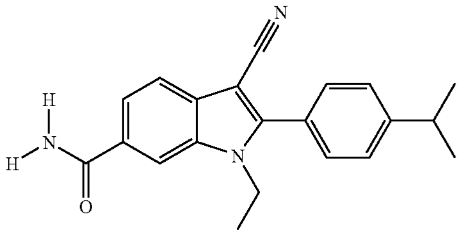
80
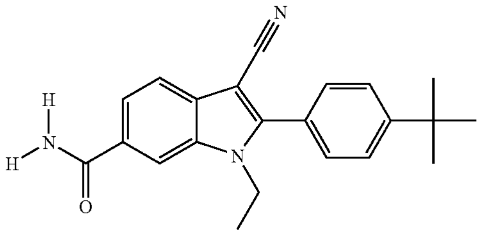
81
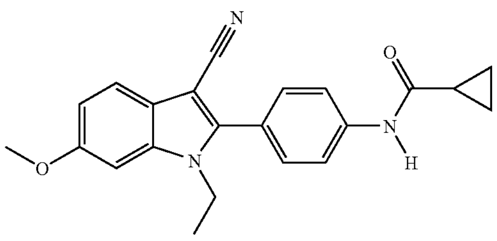
82
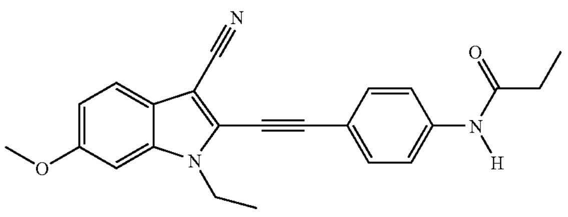

-continued
83
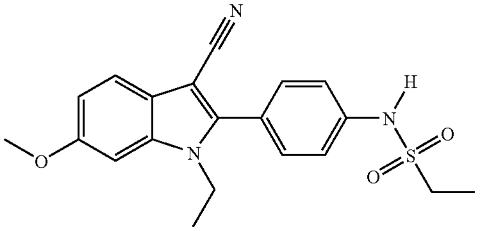
84
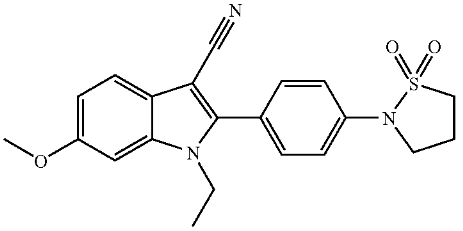
85
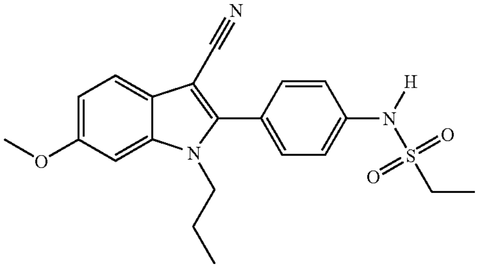
86
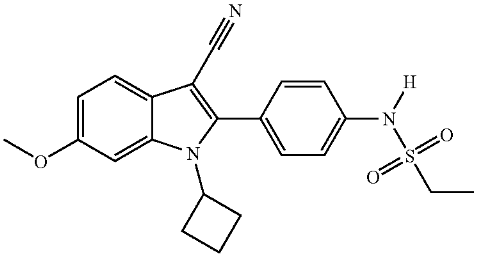
87
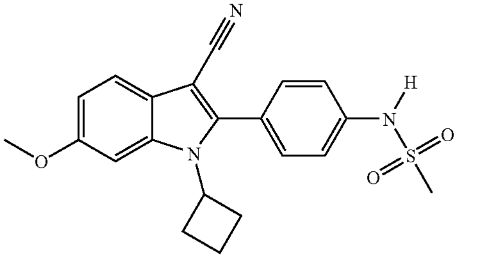
88
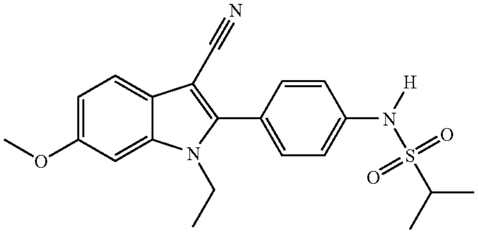
89
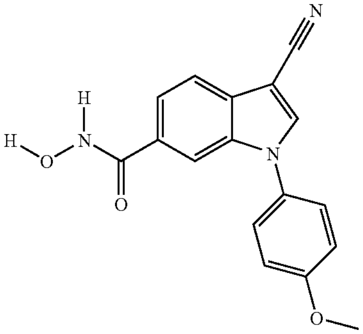
90
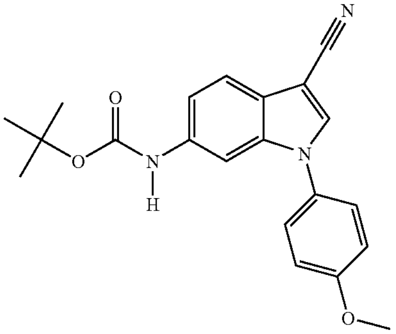
91
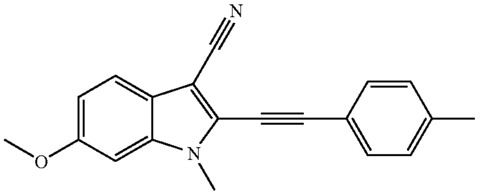
92
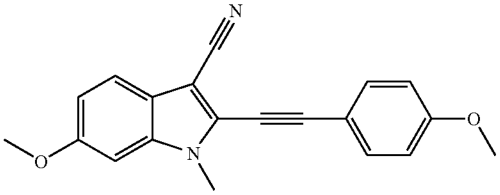
93
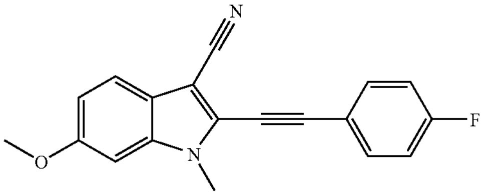
94
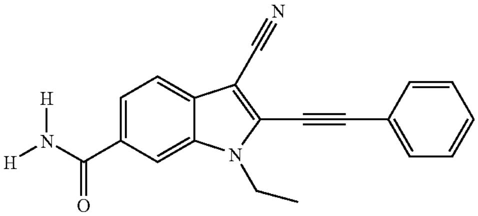

-continued
95
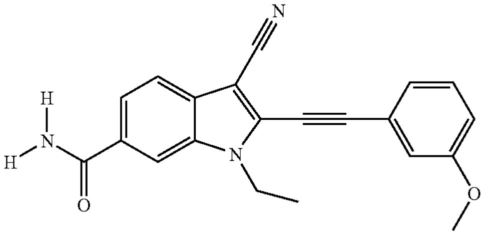
96
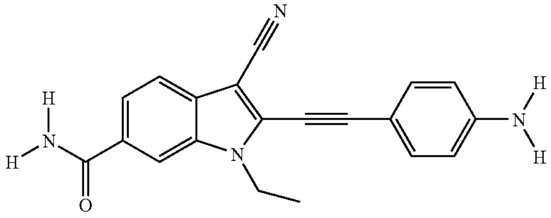
97
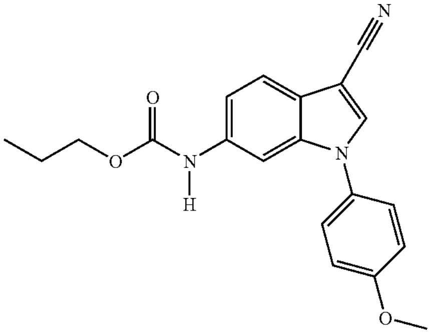
98
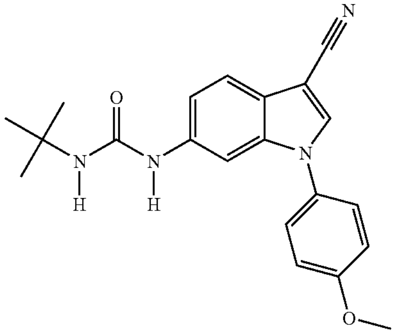
99
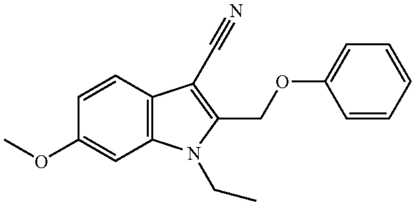
100
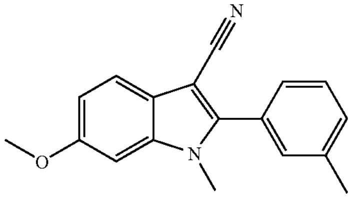
101
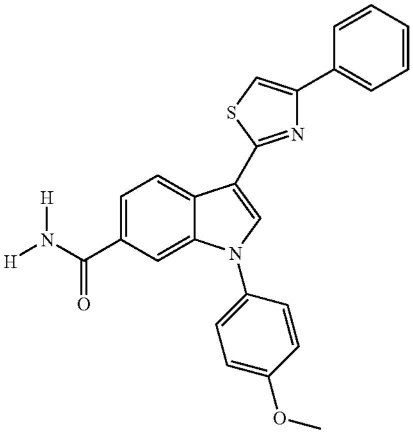
102
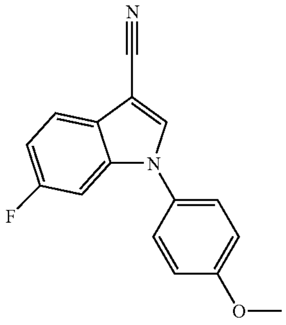
103
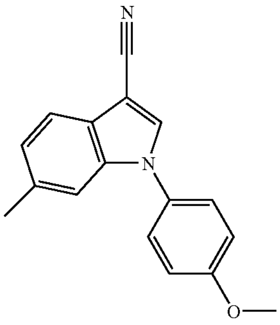
104
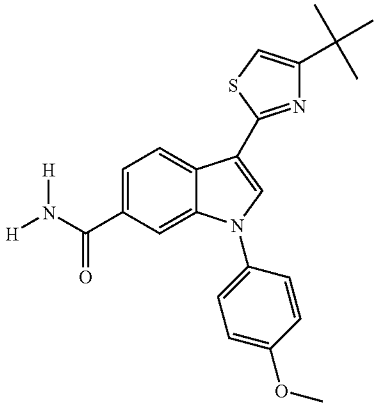

-continued
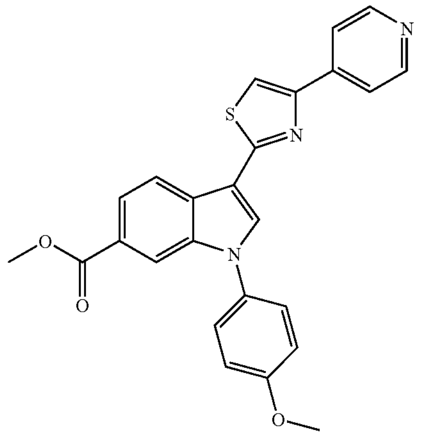
105
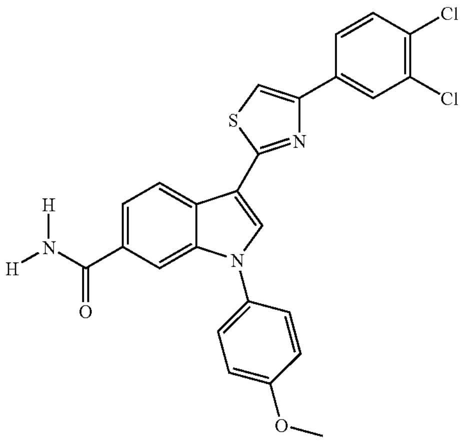
106
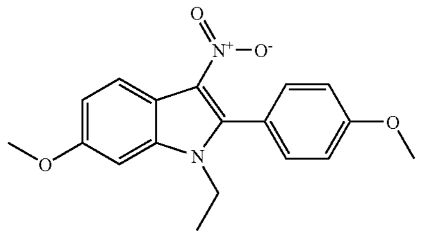
107
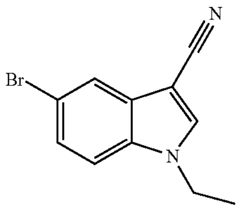
108
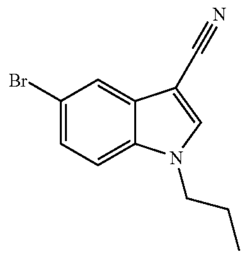
109
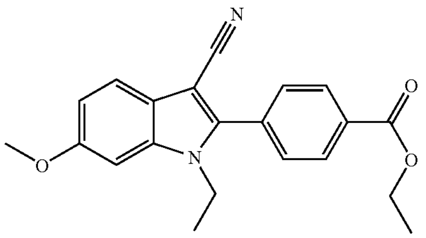
110
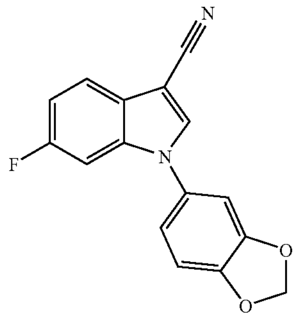
111
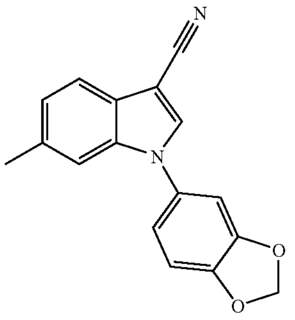
112
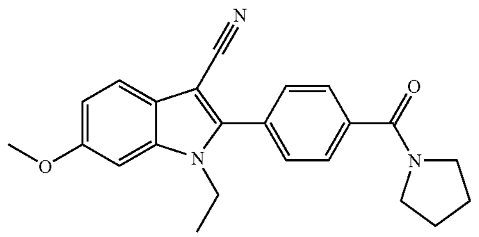
113
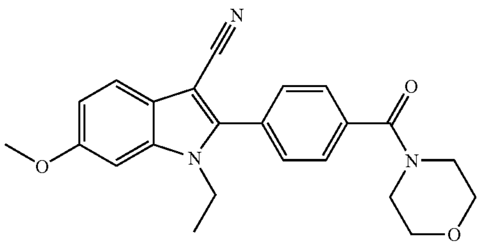
114

-continued
115
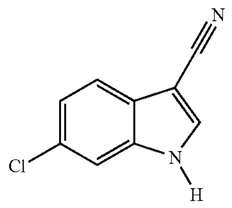
116
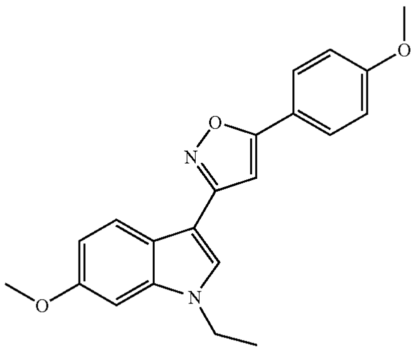
117
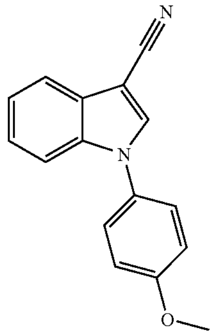
118
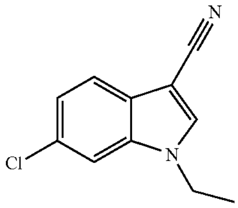
119
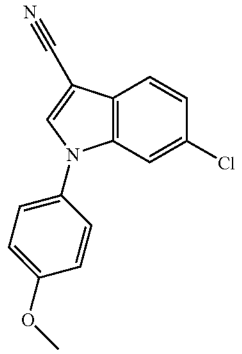
120
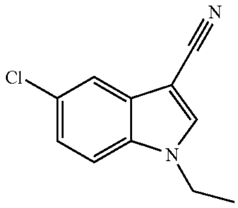
121
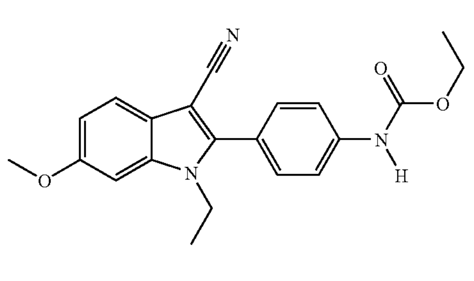
122
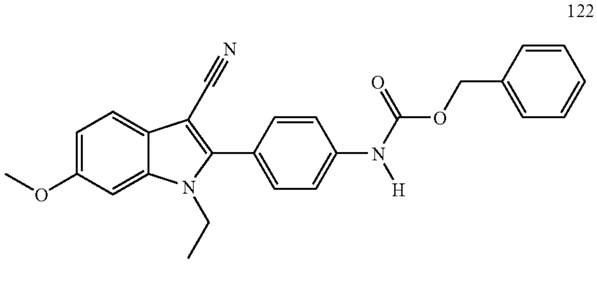

-continued
123
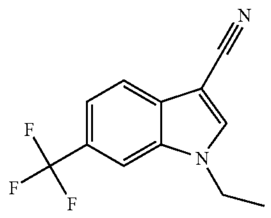
124
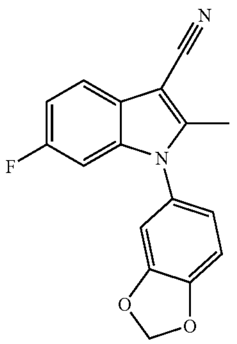
125
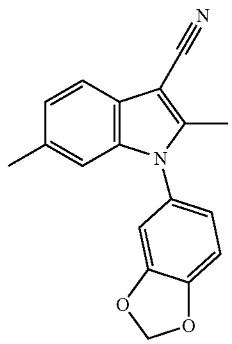
126
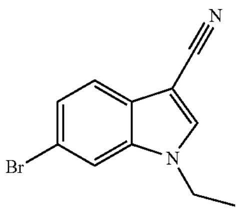
127
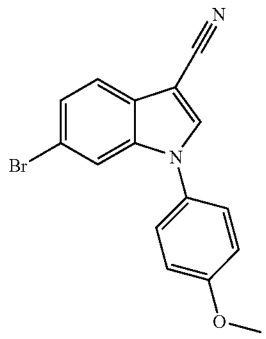
128
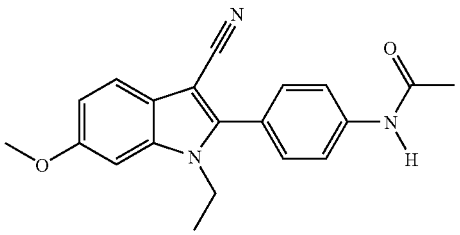
129
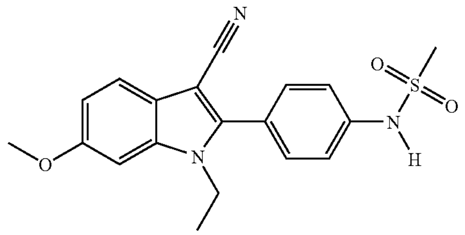
130
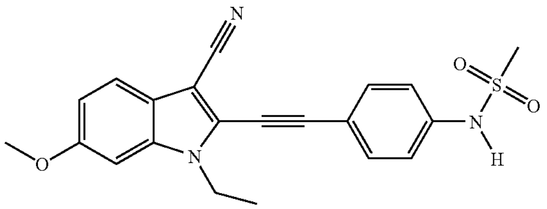
131
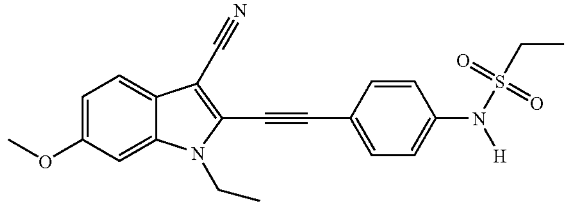
132
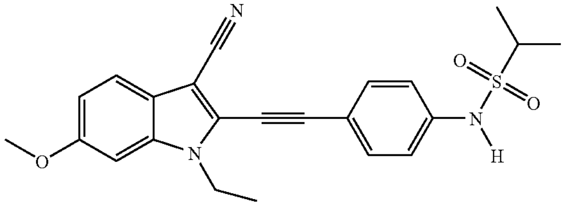

-continued
133
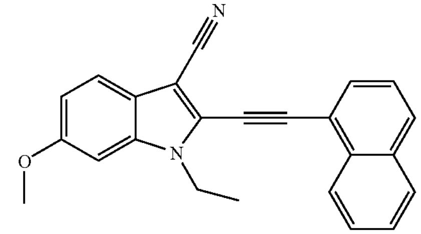
134
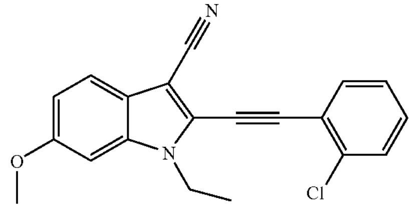
135
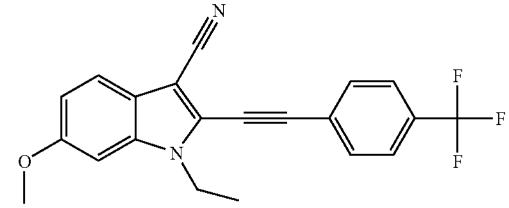
136
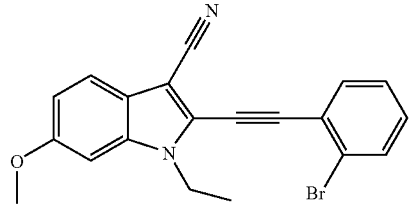
137
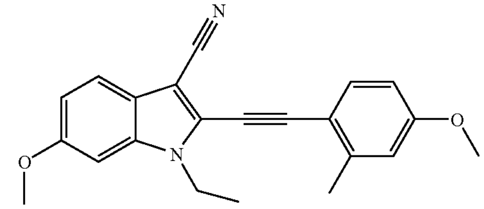
138
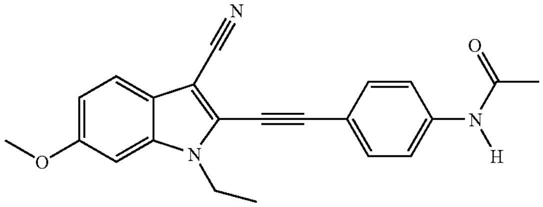
139
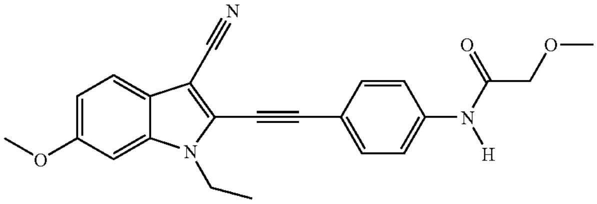
140
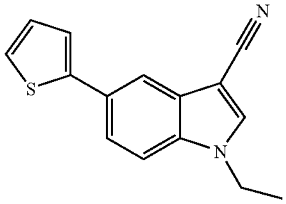
141
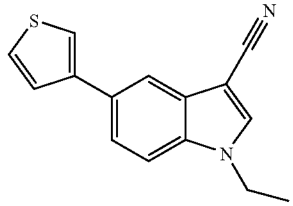
142
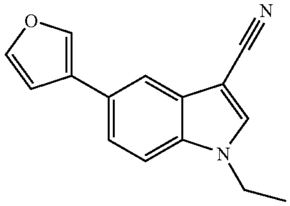
143
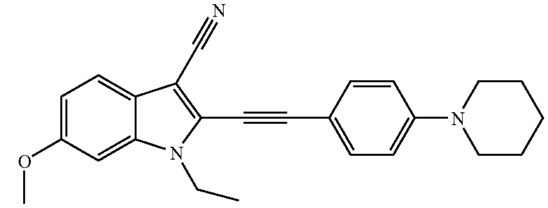
144
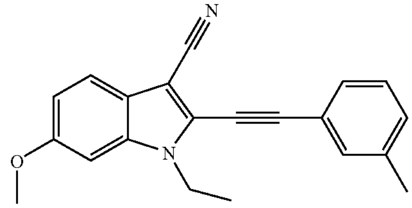
145
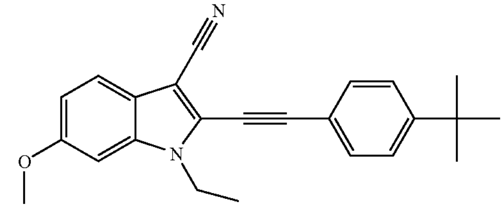
146
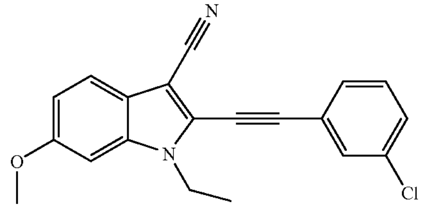

-continued
147
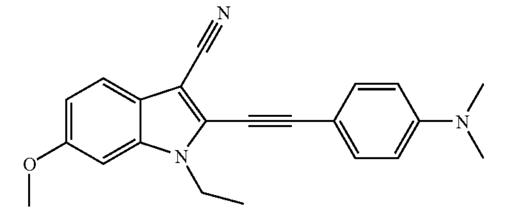
148
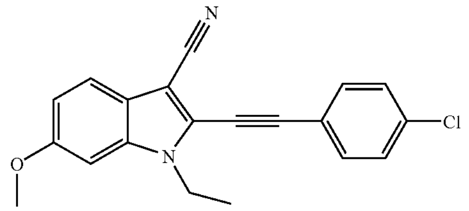
149
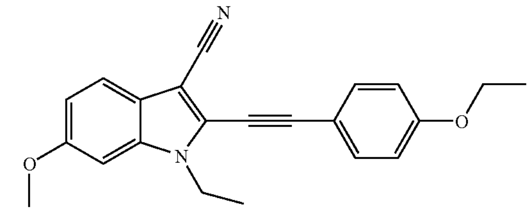
150
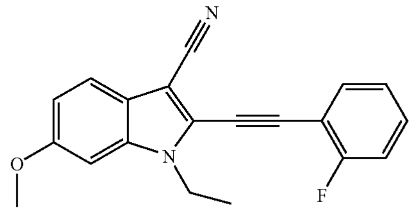
151
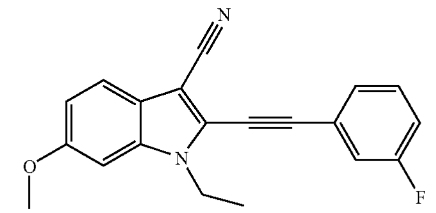
152
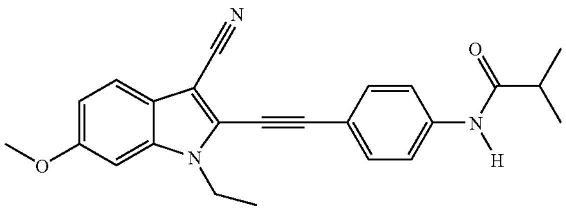
153
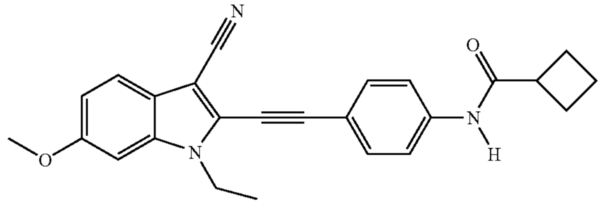
154
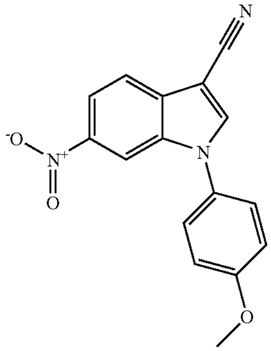
155
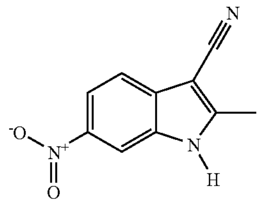
156
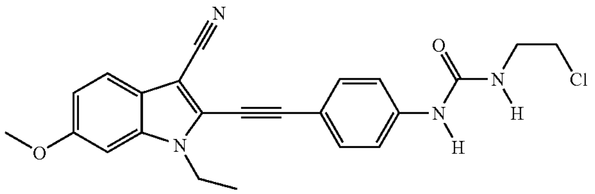
157
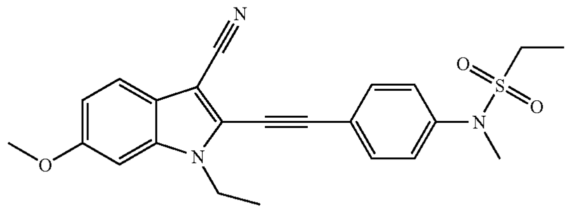
158
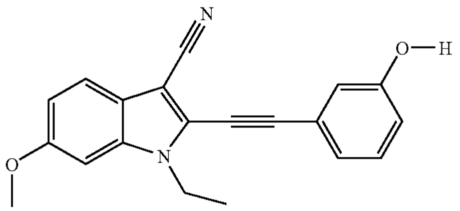

-continued
159
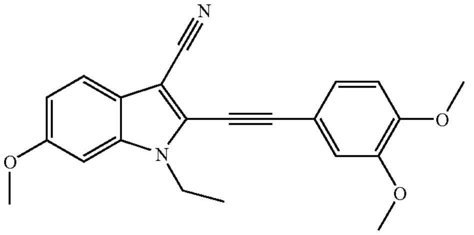
160
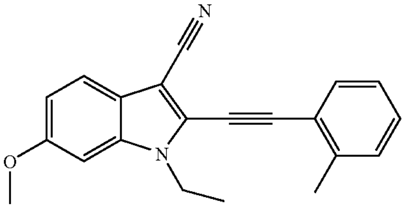
161
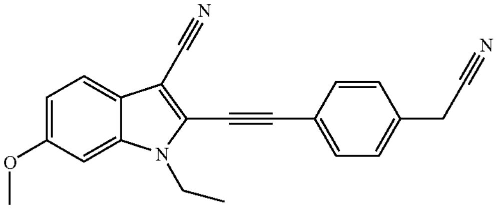
162
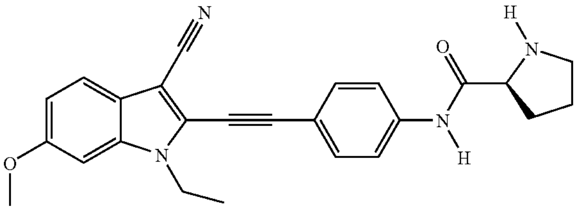
163
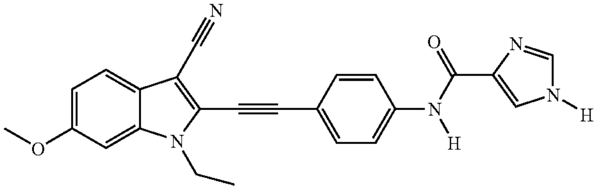
164
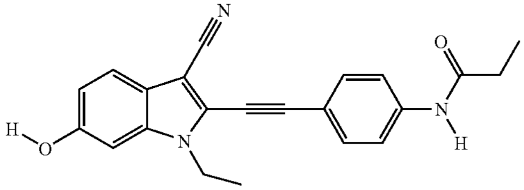
165
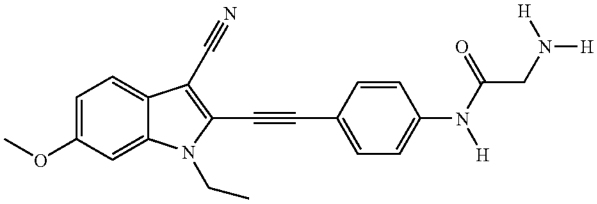
166
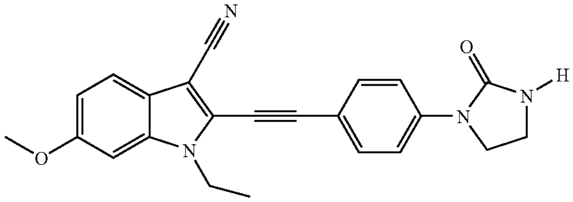
167
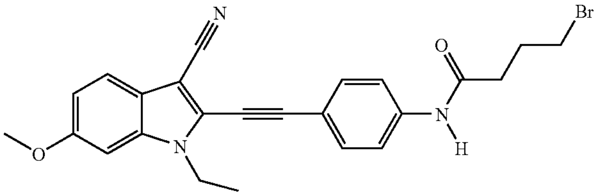
168
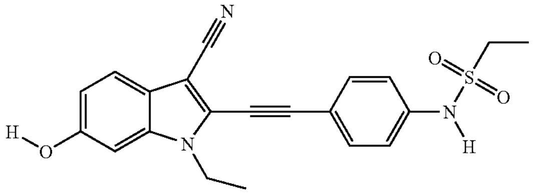
169
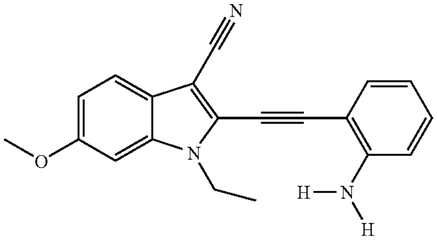
170
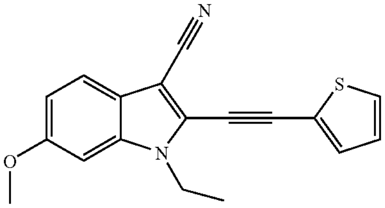
171
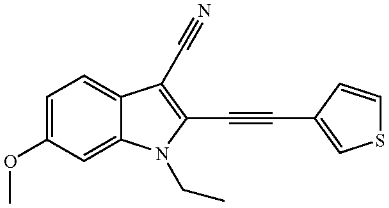
172
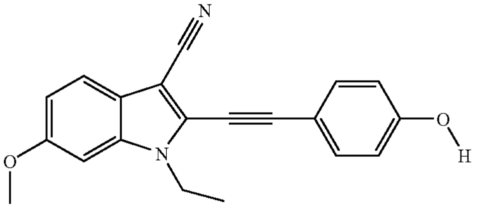

-continued
173
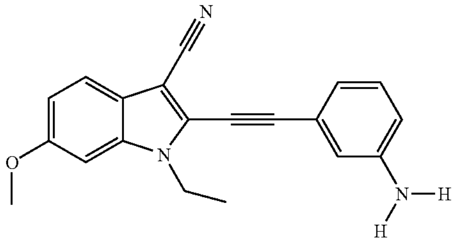
174
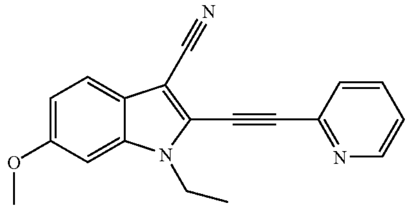
175
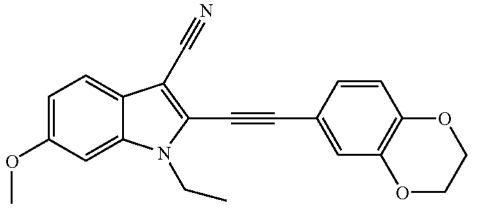
176
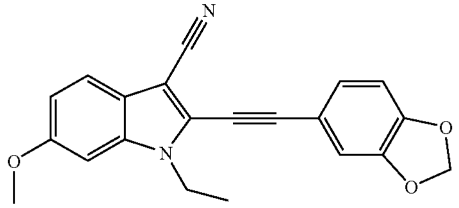
177
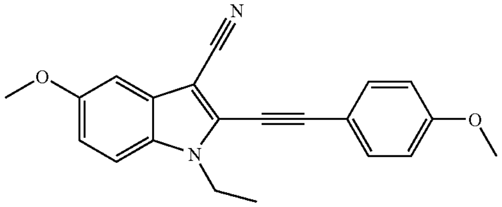
178
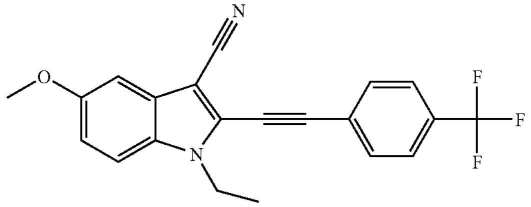
179
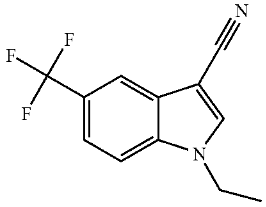
180
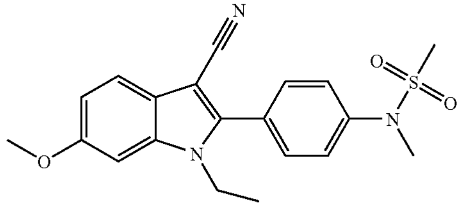
181
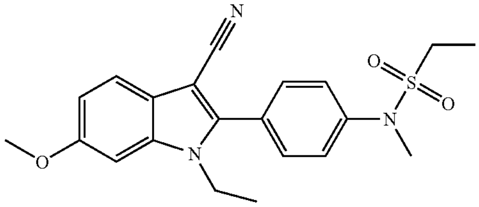
182
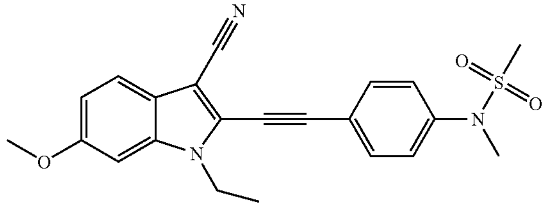
183
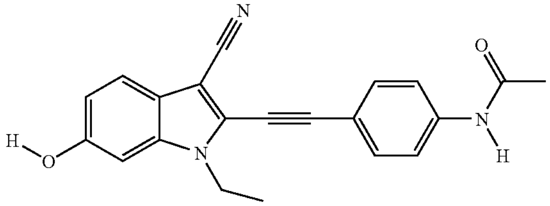
184
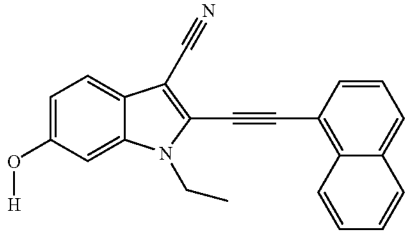
185
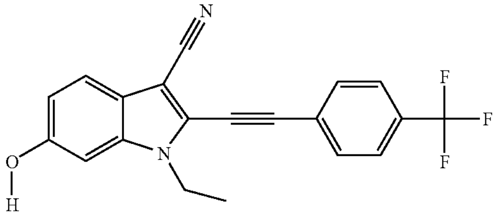
186
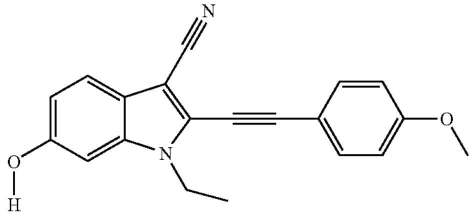

-continued
187
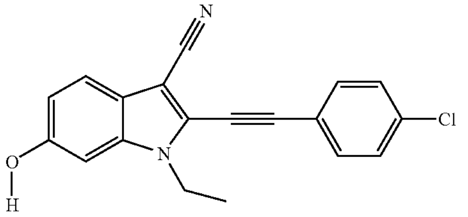
188
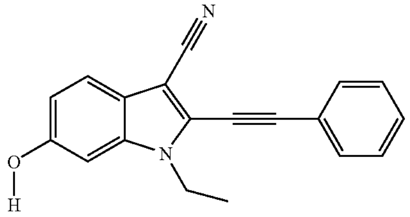
189
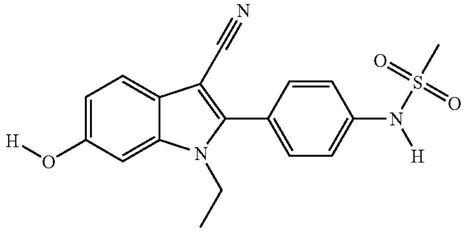
190
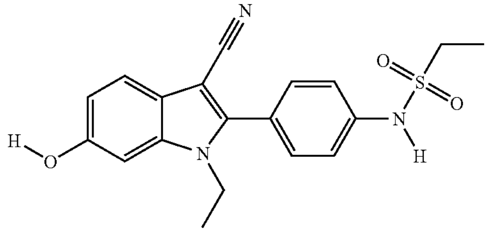
191
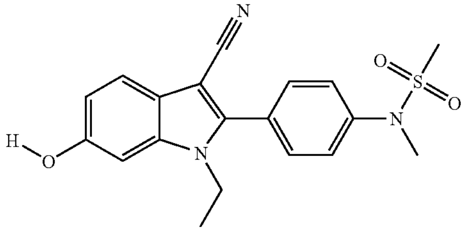
192
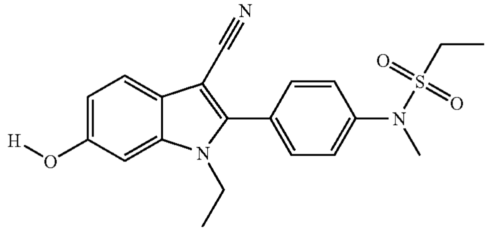
193
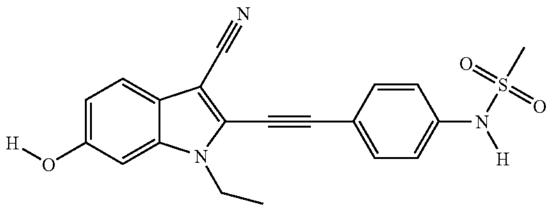
194
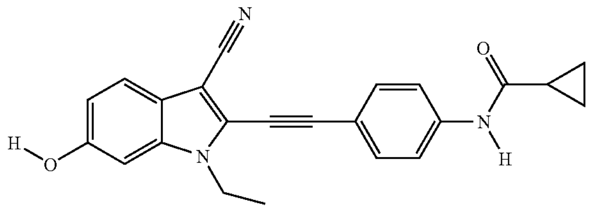
195
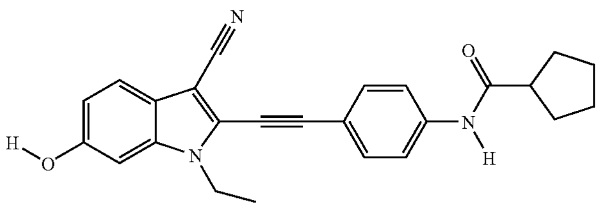
196
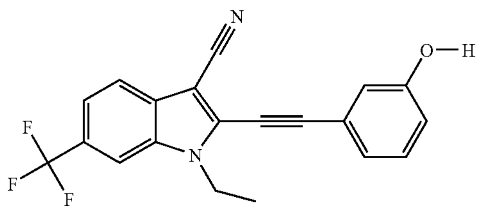
197
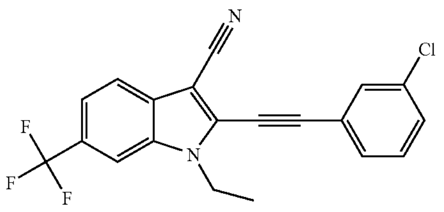
198
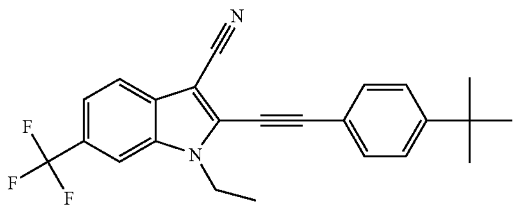
199
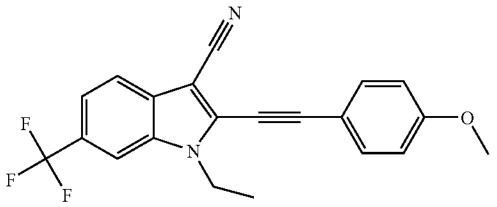
200
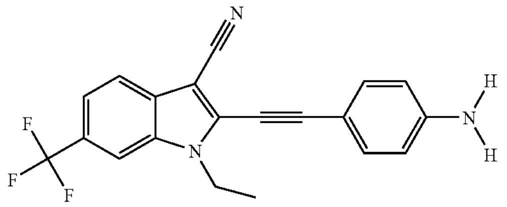

-continued
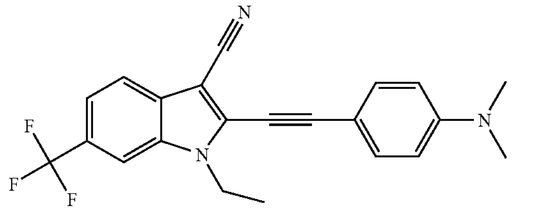
201
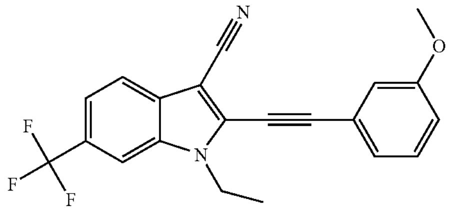
202
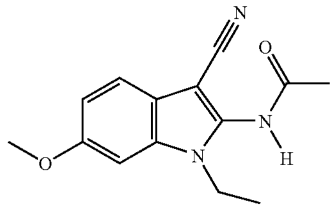
203
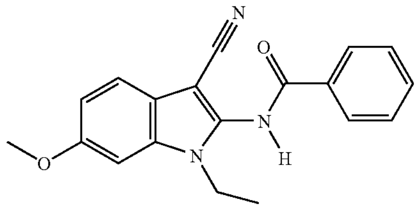
204
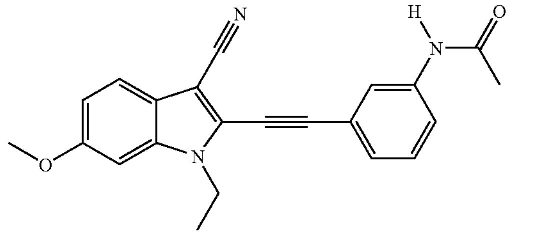
205
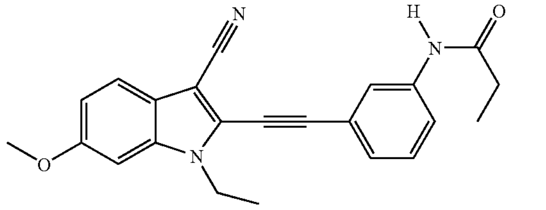
206
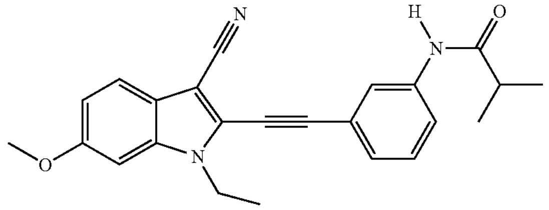
207
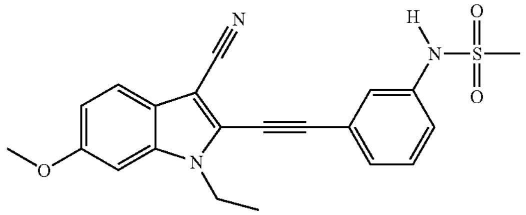
208
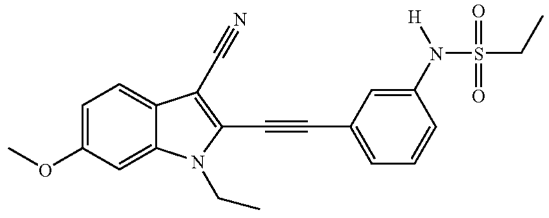
209
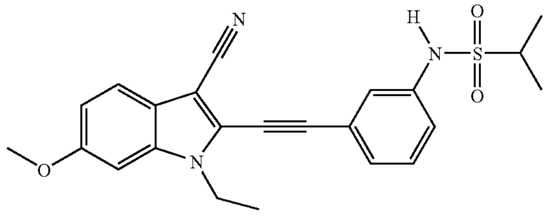
210
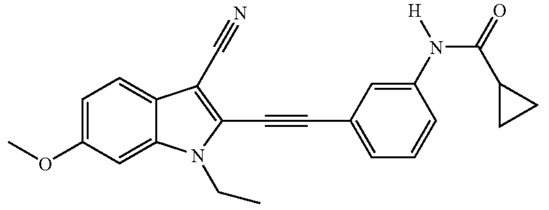
211
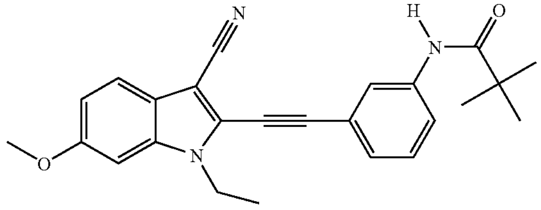
212
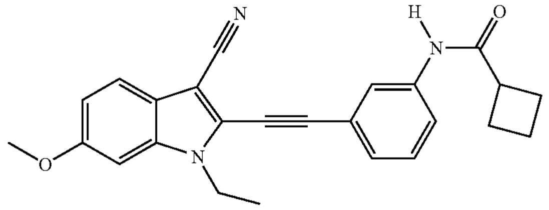
213
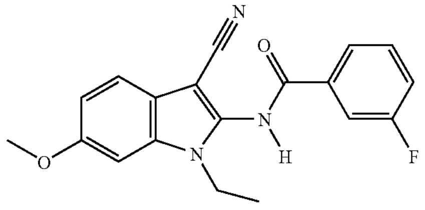
214

-continued
215
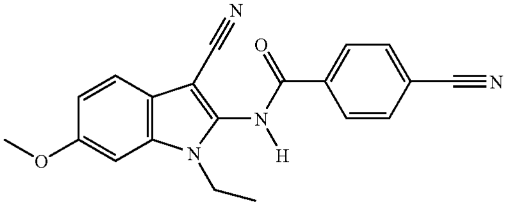
216
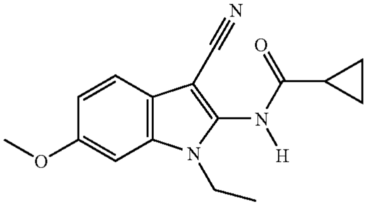
217
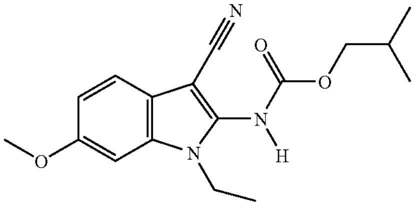
218
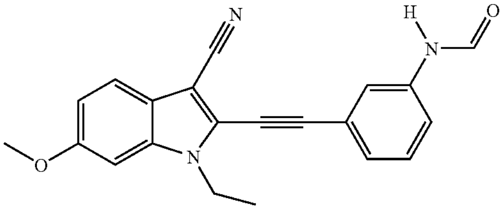
219
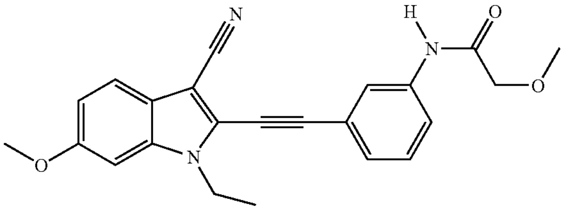
220
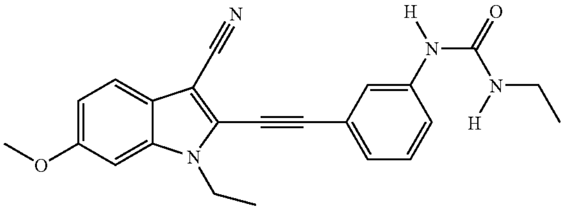
221
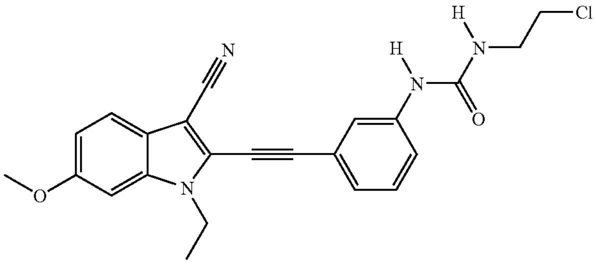
222
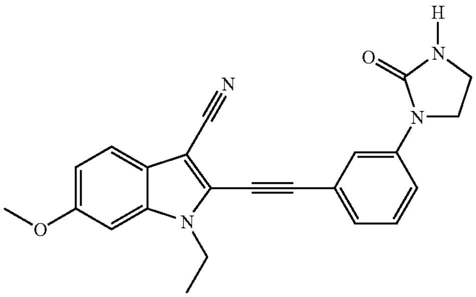
223
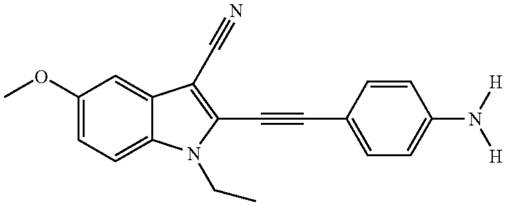
224
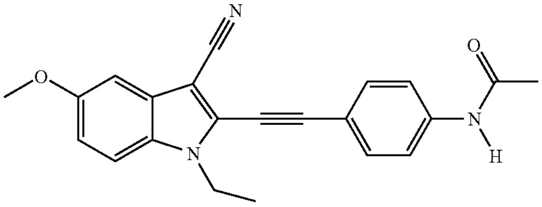
225
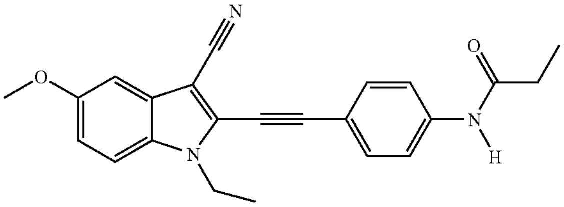
226
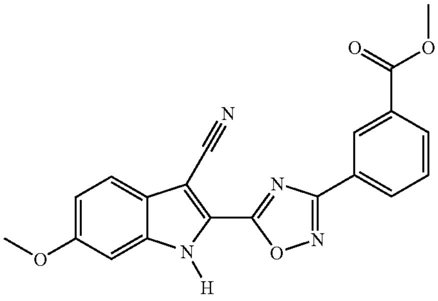

-continued
227
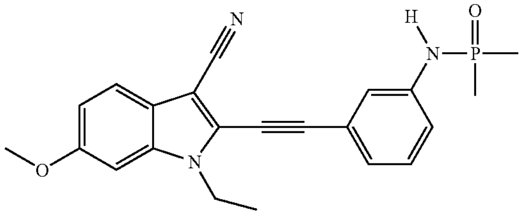
228
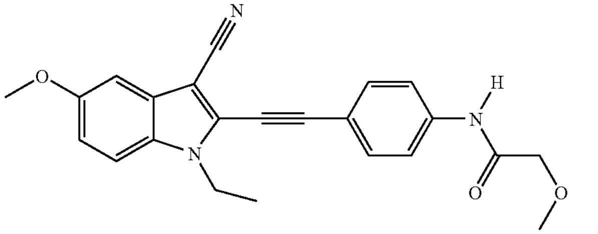
229
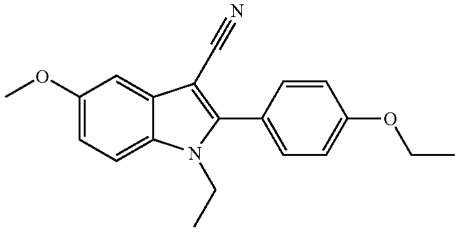
230
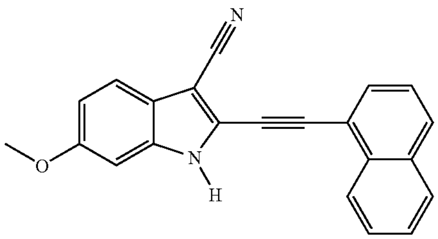
231
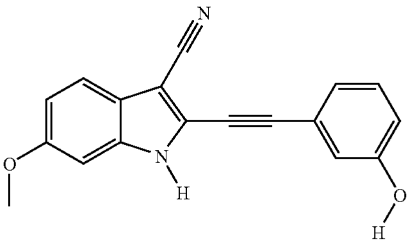
232
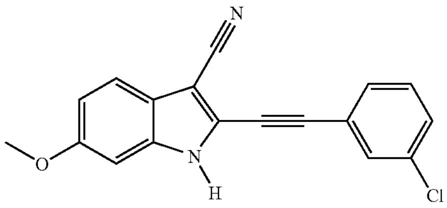
233
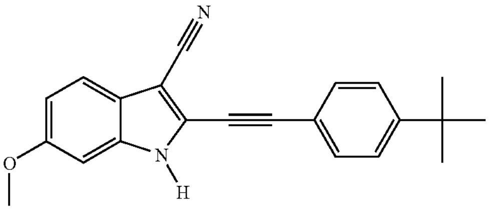
234
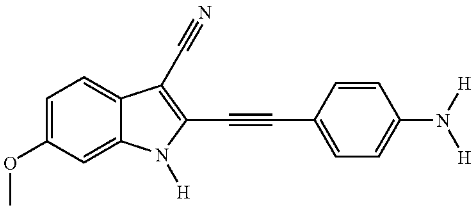
235
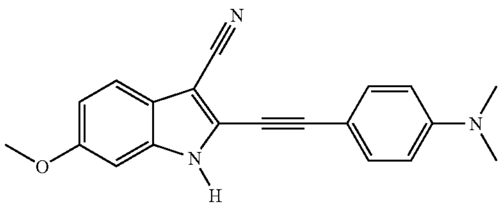
236
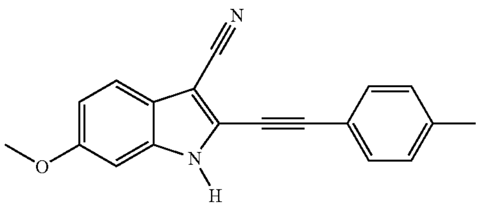
237
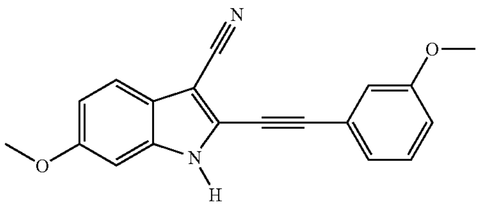
238
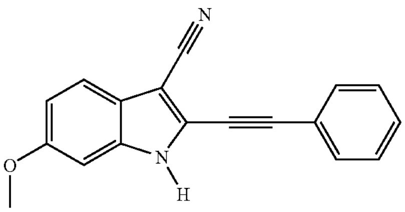

-continued
239
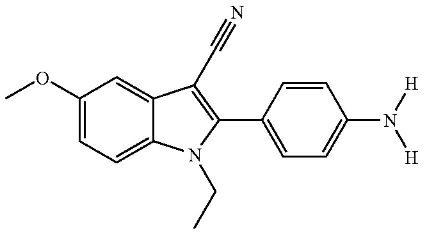
240
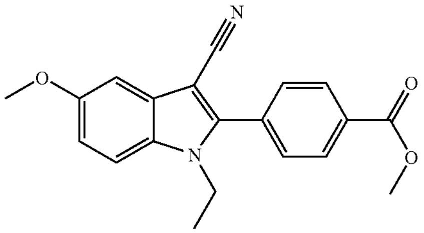
241
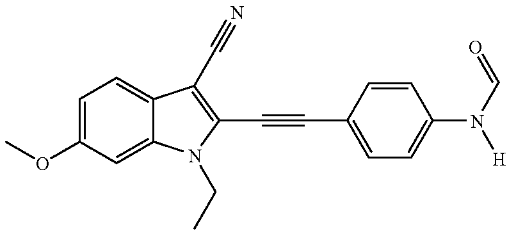
242
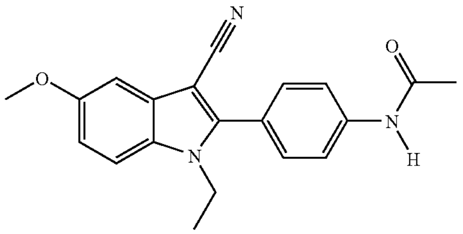
243
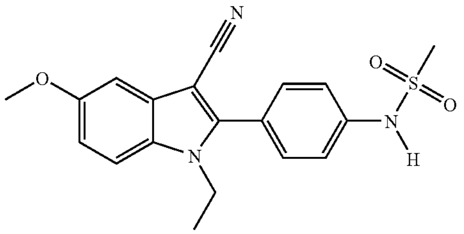
244
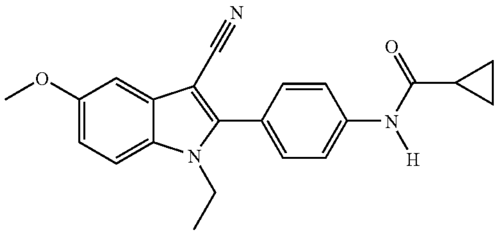
245
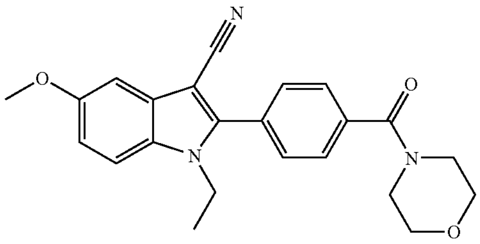
246
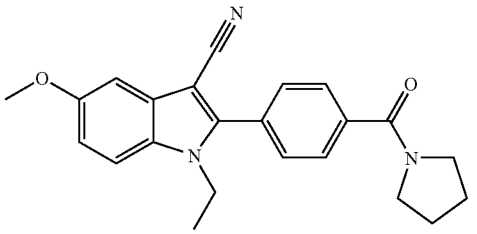
247
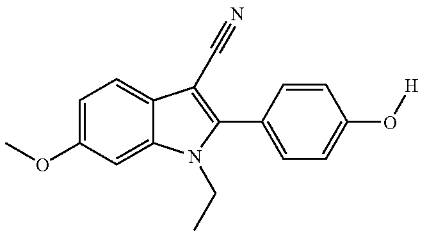
248
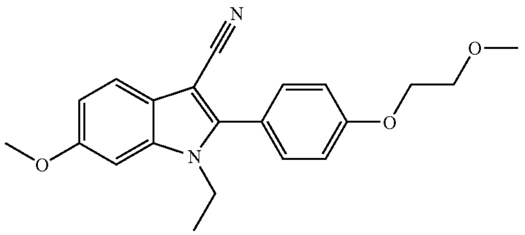
249
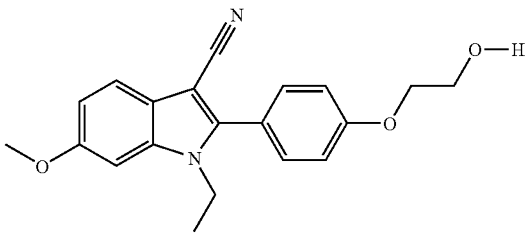
250
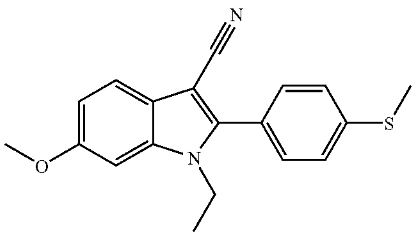

-continued
251
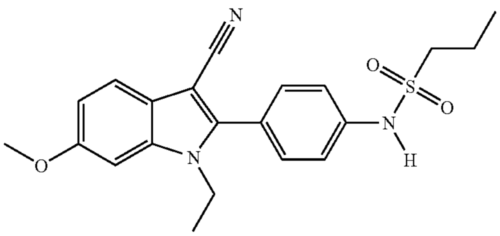
252
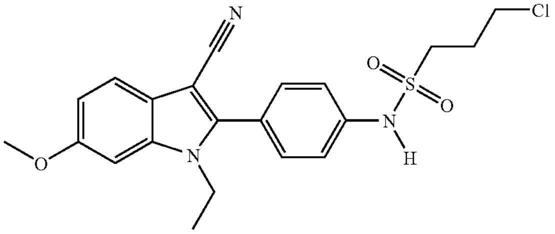
253
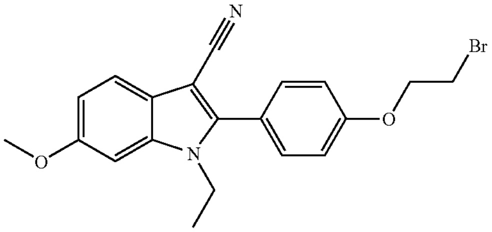
254
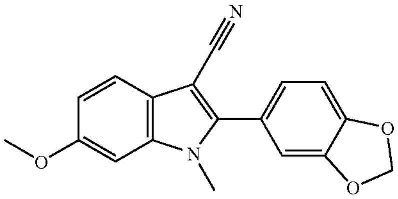
255
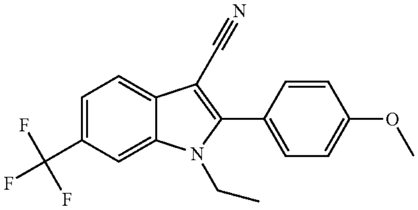
256
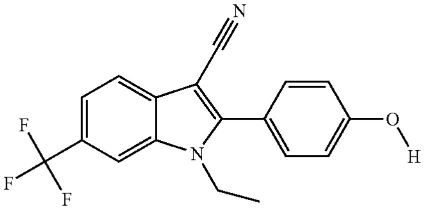
257
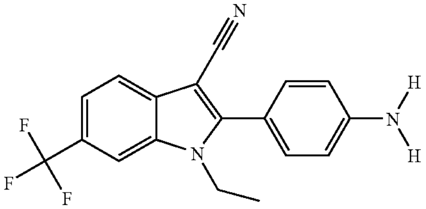
258
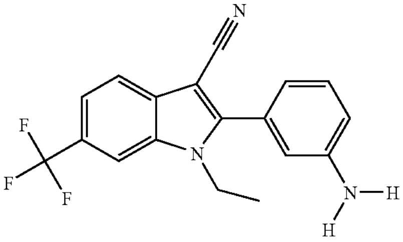
259
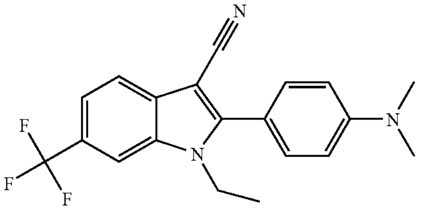
260
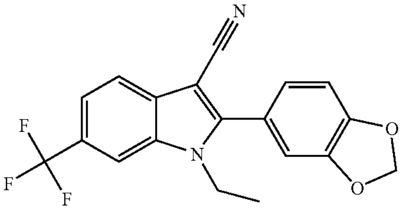
261
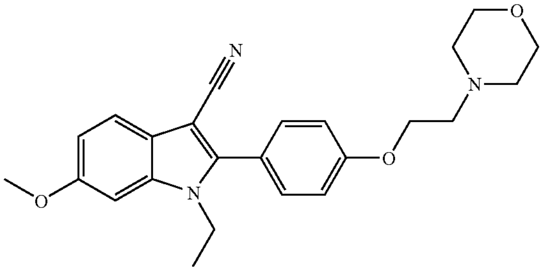
262
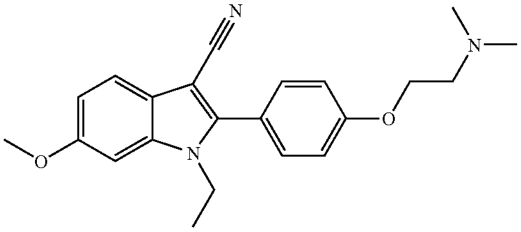

-continued
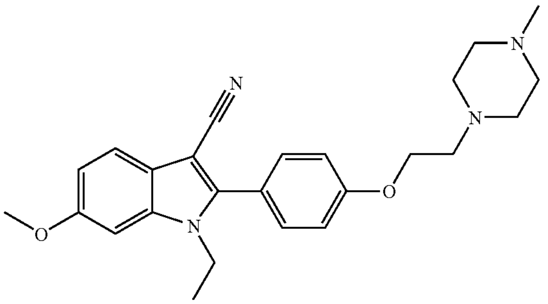
263
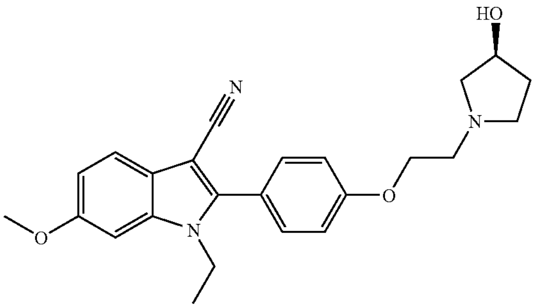
264
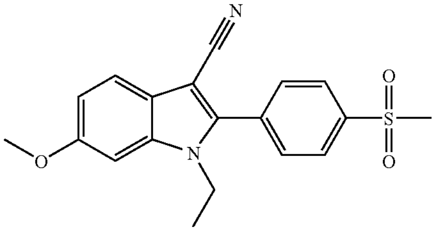
265
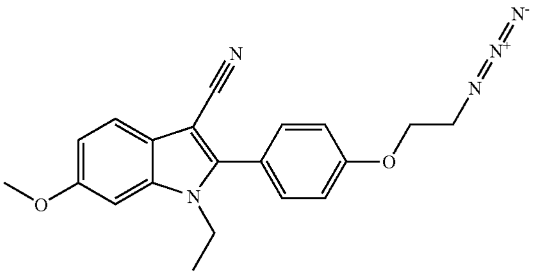
266
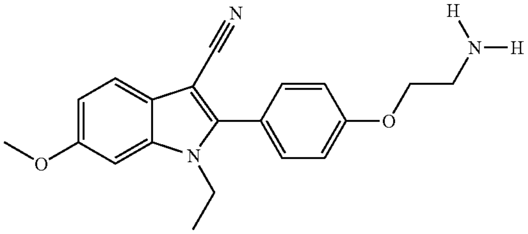
267
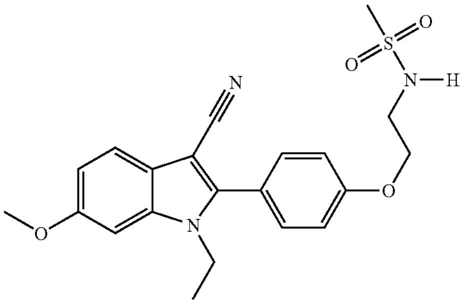
268
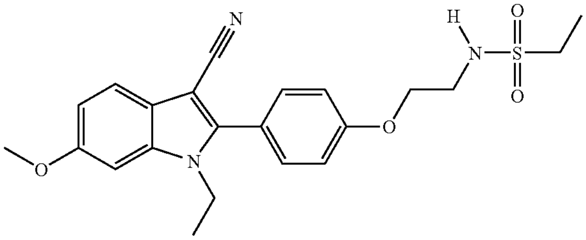
269
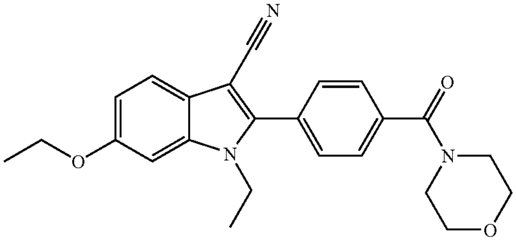
270
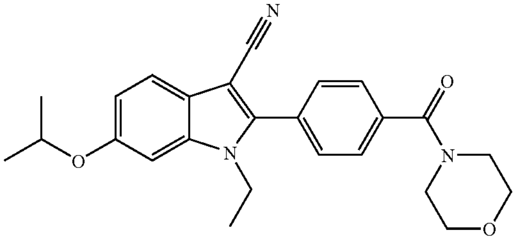
271
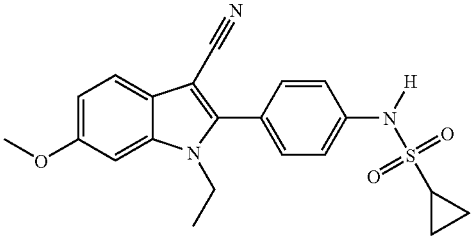
272

-continued
273
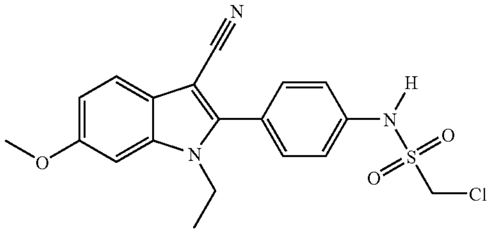
274
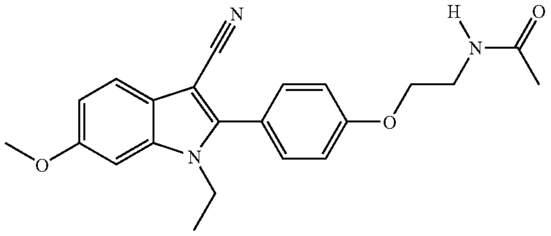
275
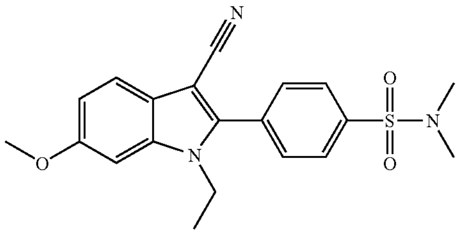
276
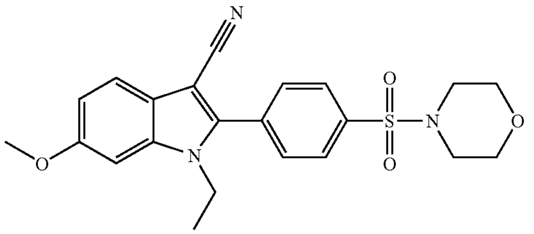
277
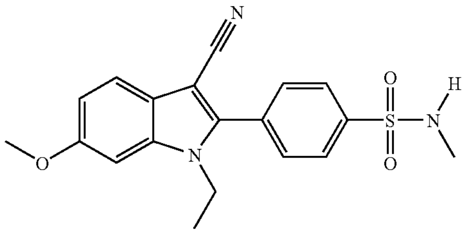
278
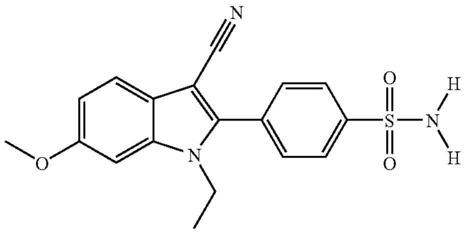
279
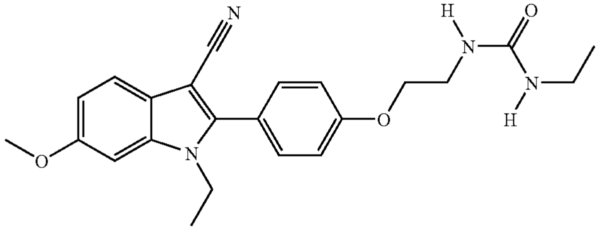
280
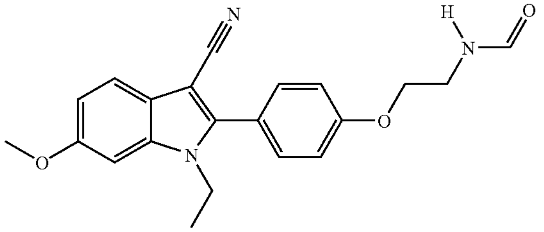
281
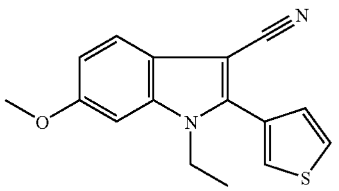
282
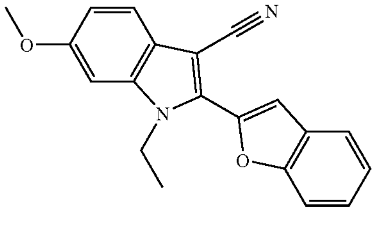
283
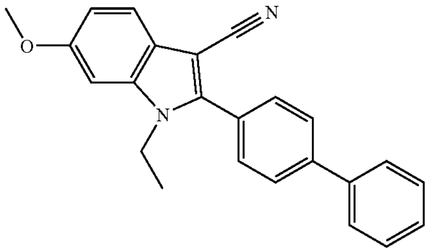
284
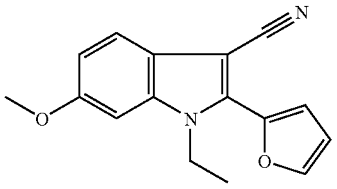

-continued
285
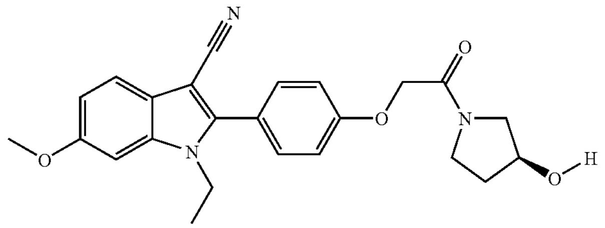
286
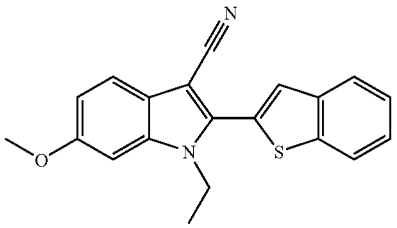
287
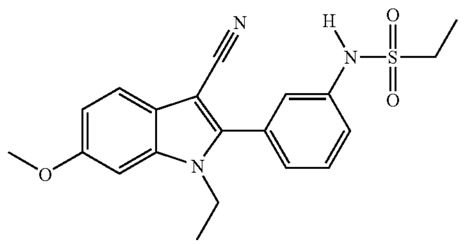
288
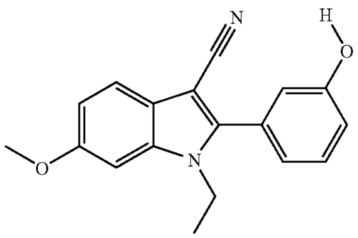
289
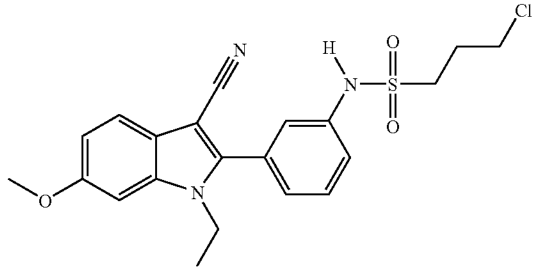
290
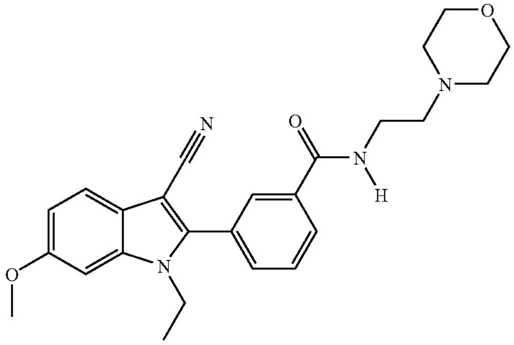
291
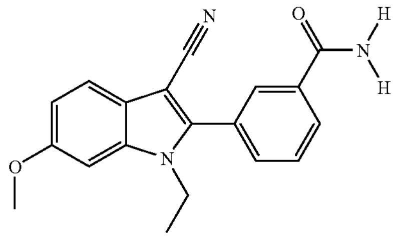
292
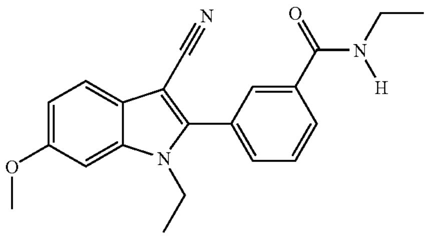
293
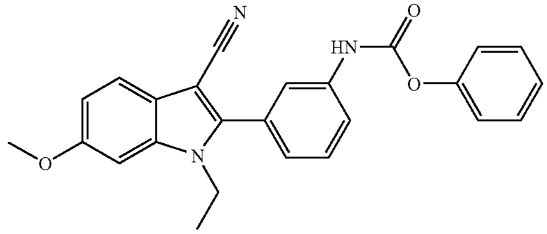
294
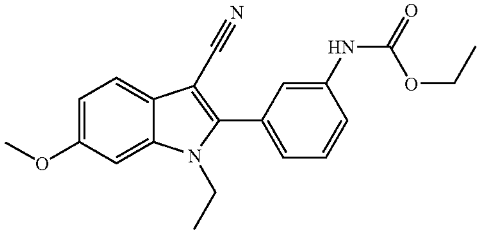

-continued
295
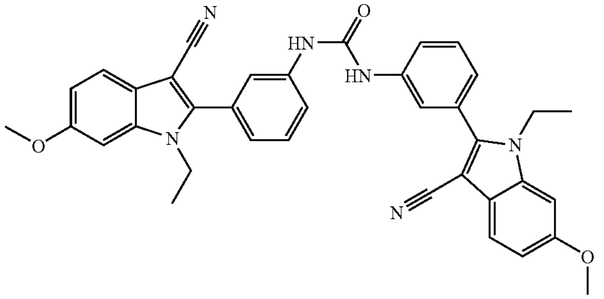
296
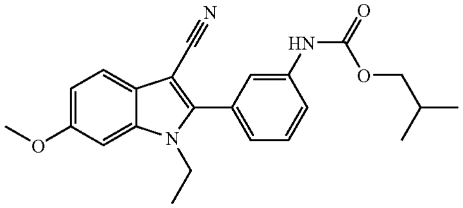
297
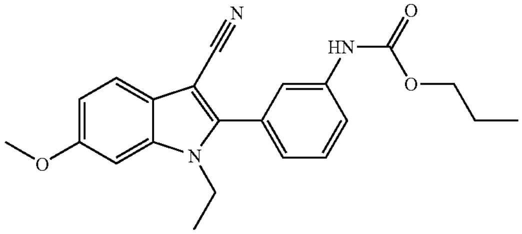
298
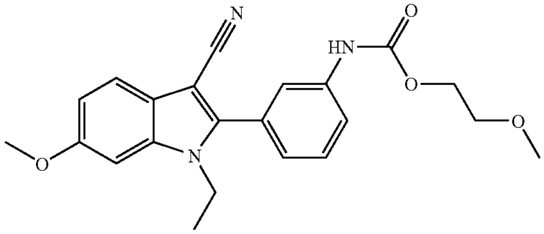
299
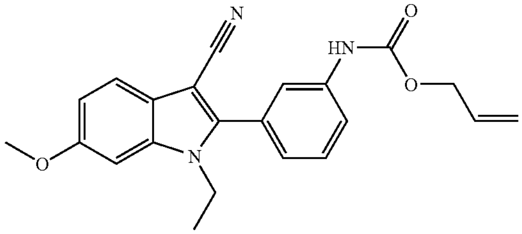
300
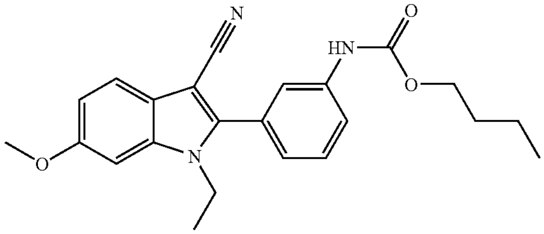
301
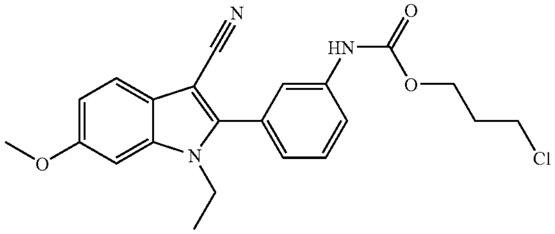
302
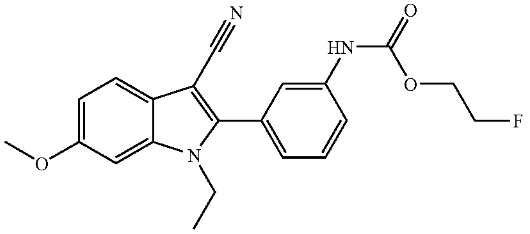
303
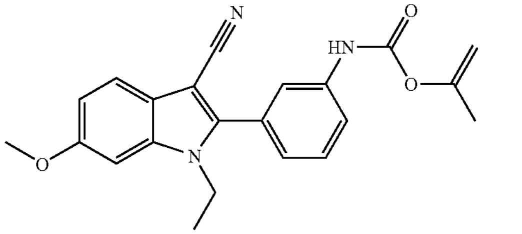
304
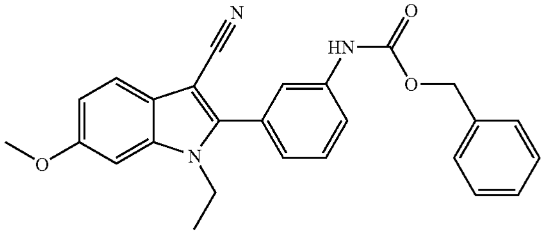
305
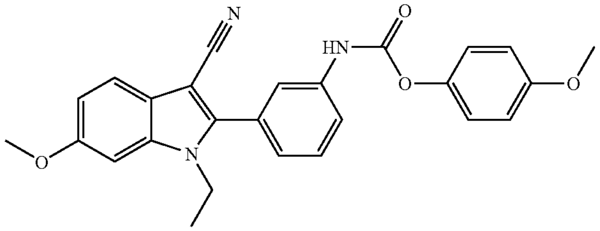
306
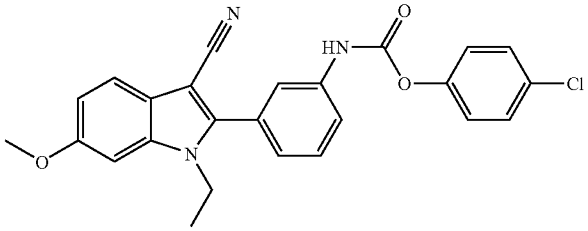

-continued
307
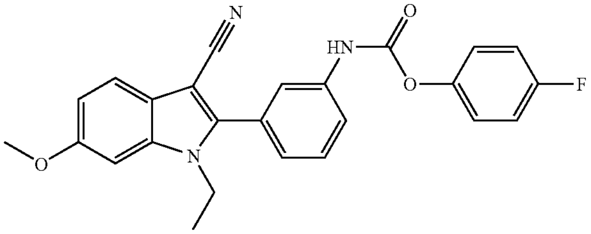
308
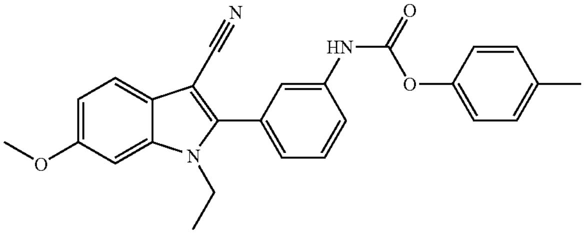
309
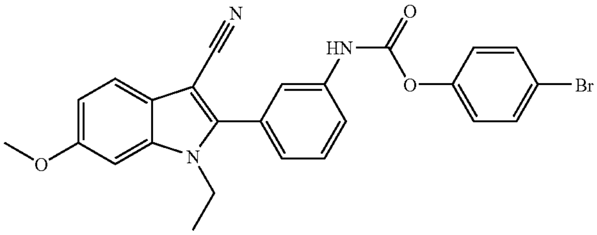
310
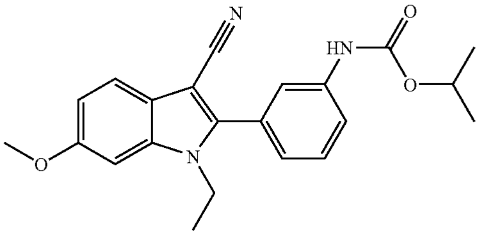
311
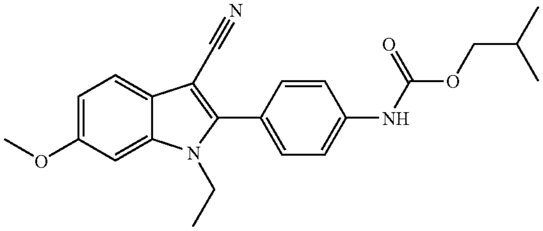
312
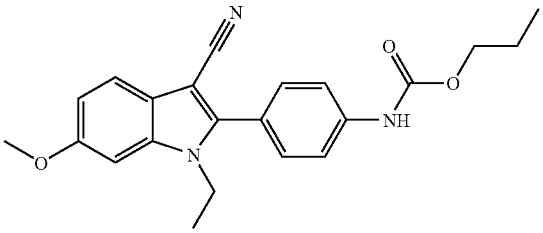
313
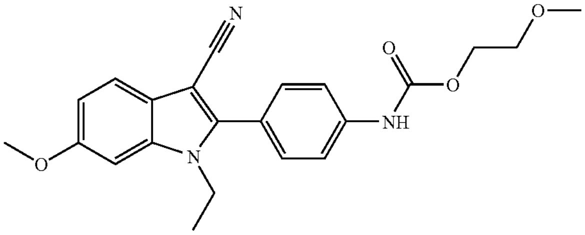
314
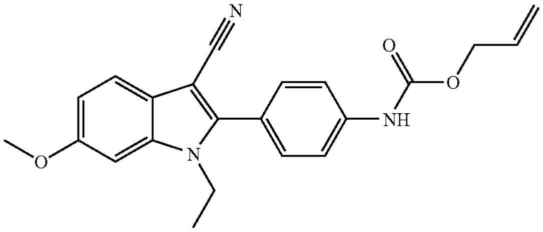
315
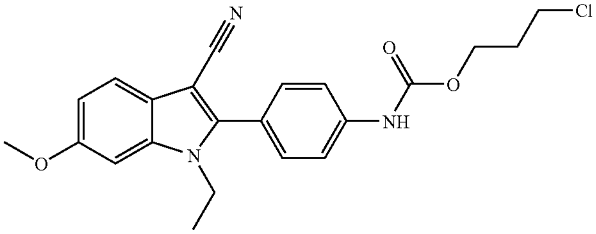
316
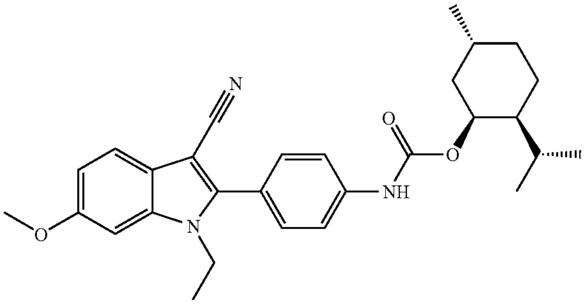

-continued
317
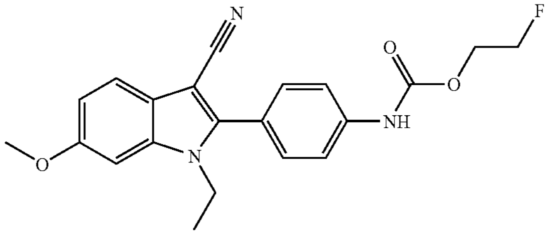
318
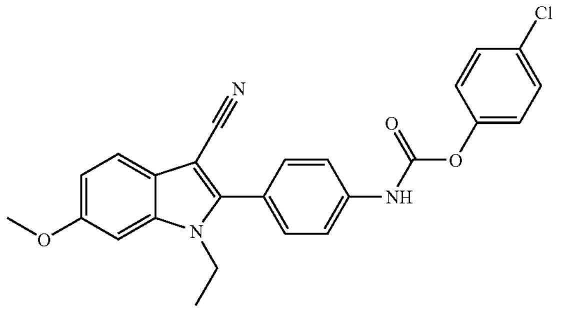
319
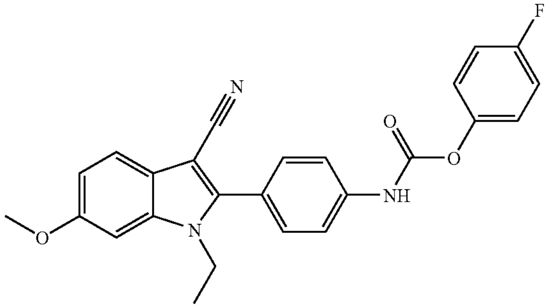
320
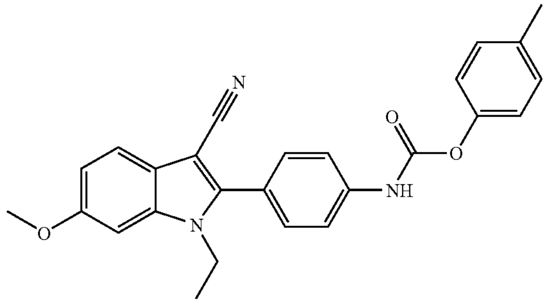
321
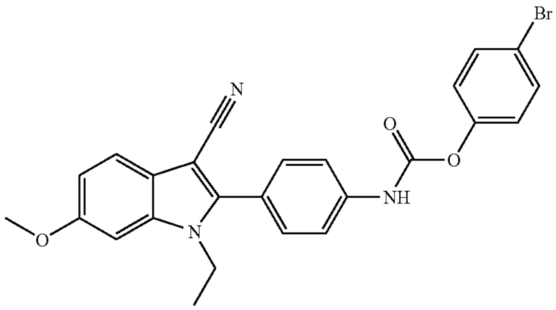
322
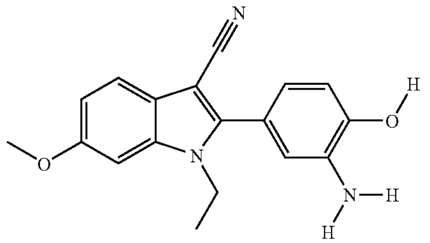
323
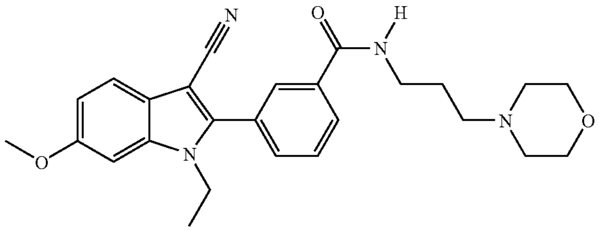
324
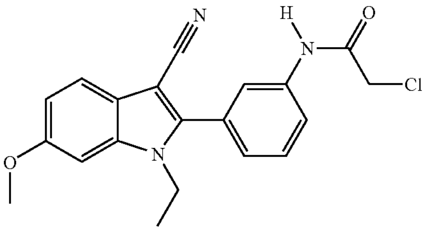
325
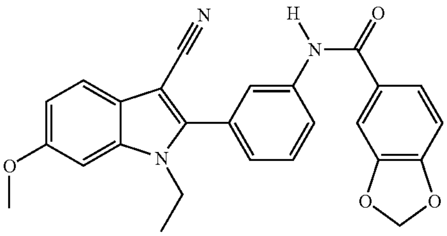
326
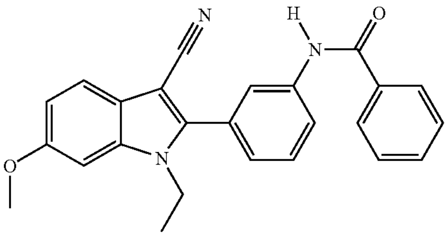

-continued
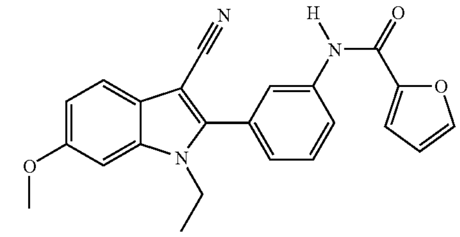
327
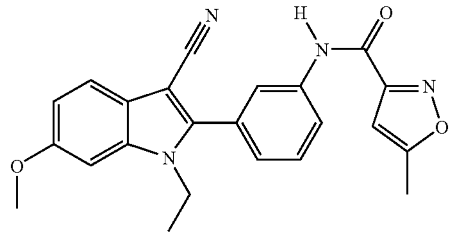
328
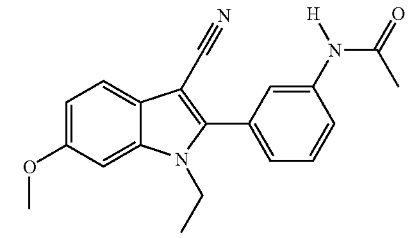
329
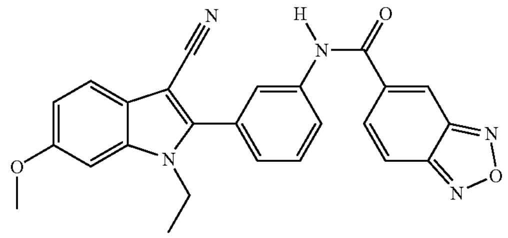
330
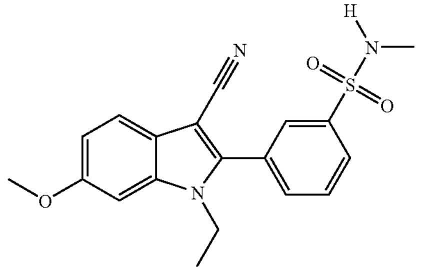
331
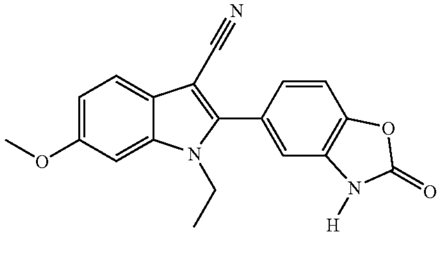
332
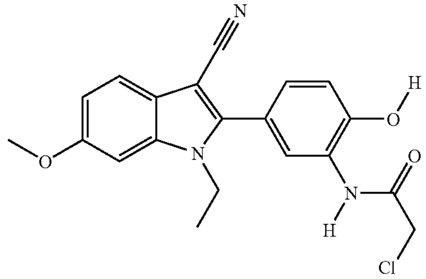
333
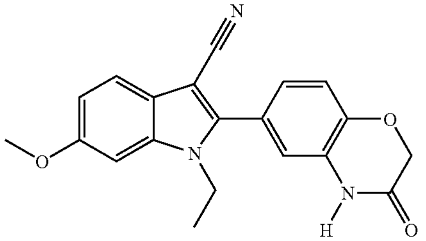
334
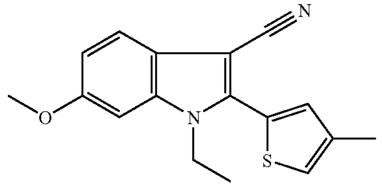
335
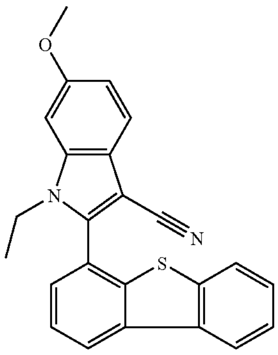
336

-continued
337
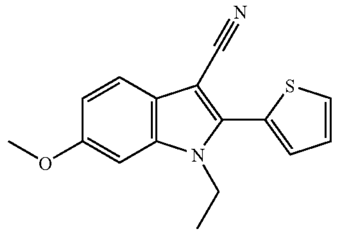
338
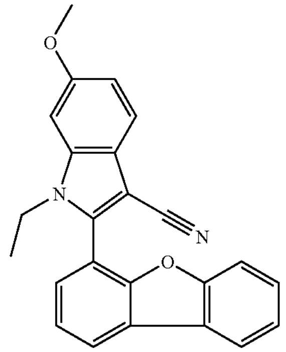
339
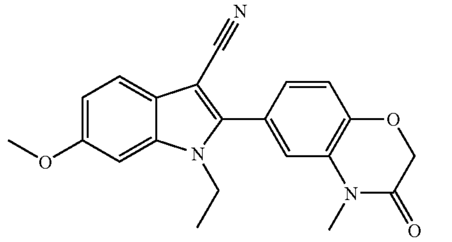
340
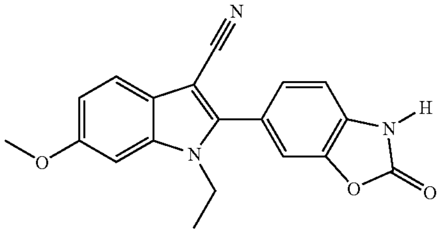
341
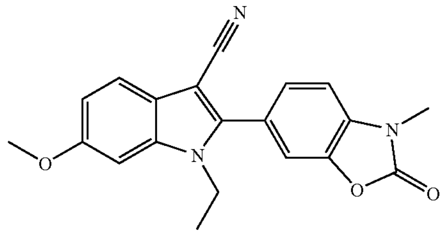
342
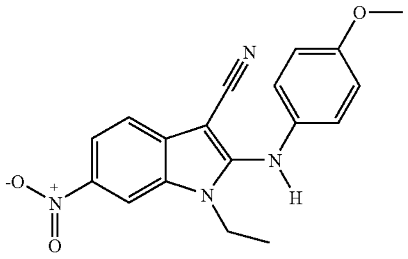
343
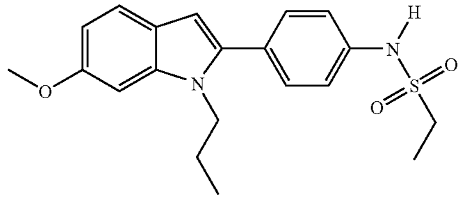
344
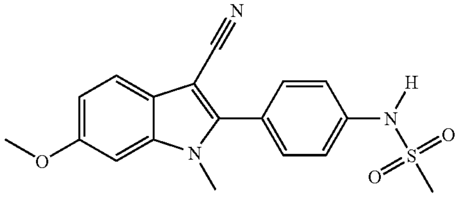
345
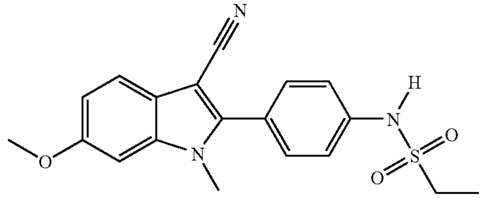
346
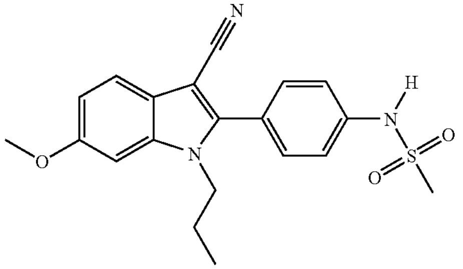

-continued
347
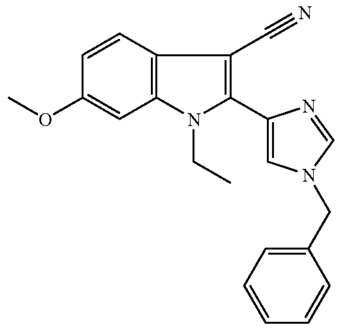
348
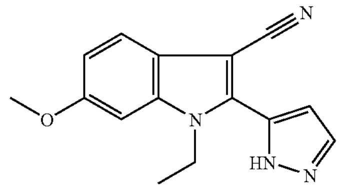
349
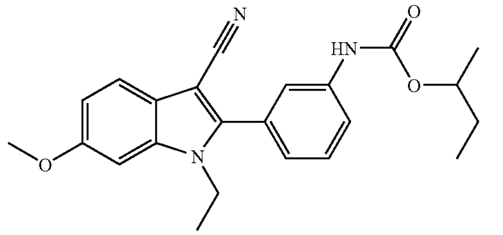
350
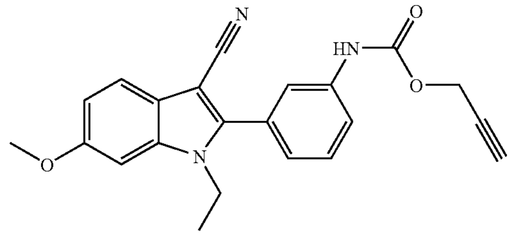
351
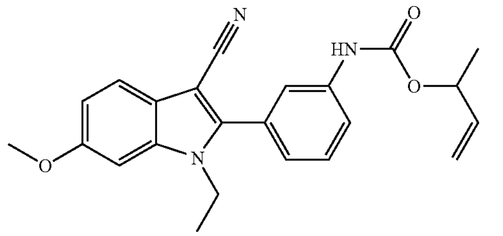
352
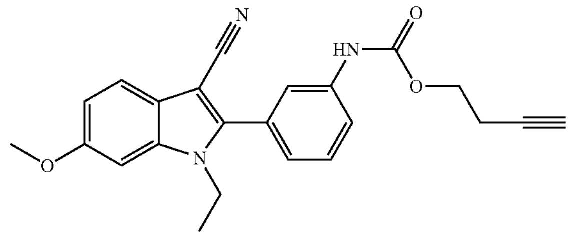
353
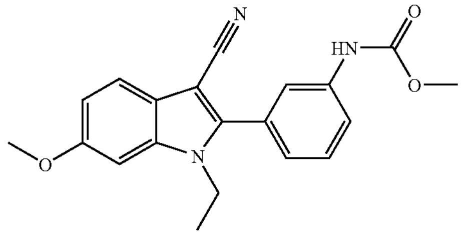
354
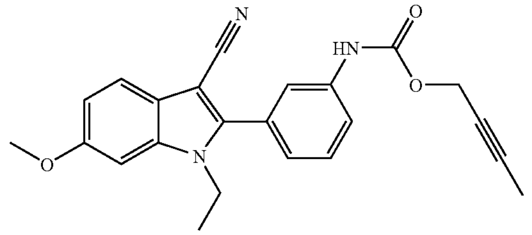
355
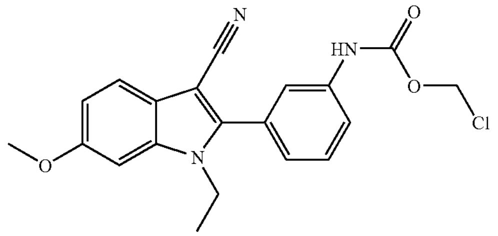
356
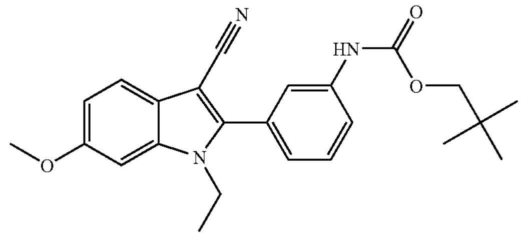
357
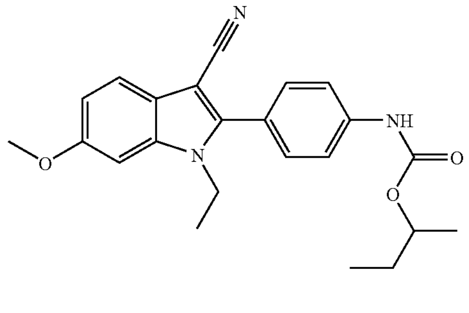
358
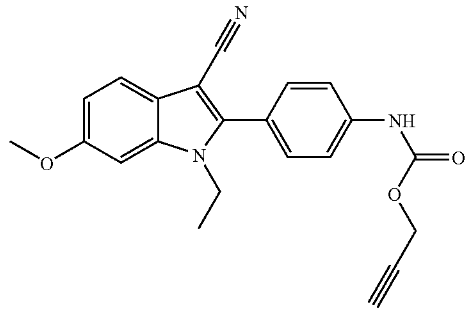

-continued
359
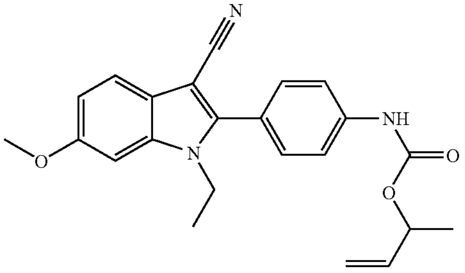
360
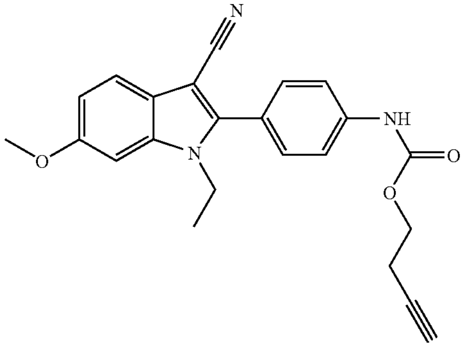
361
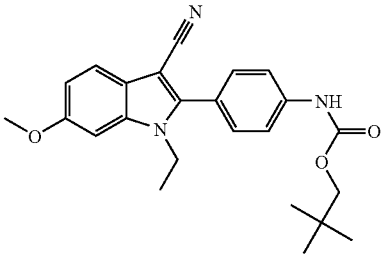
362
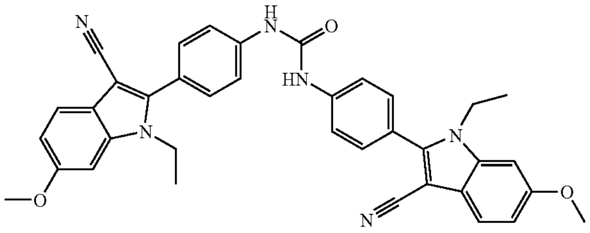
363
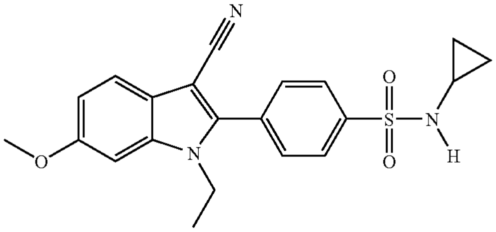
364
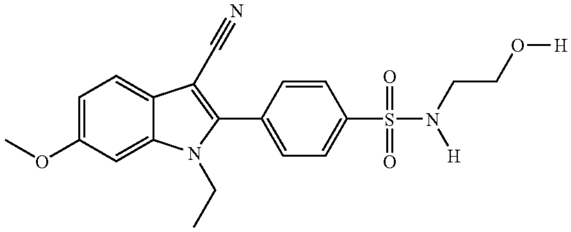
365
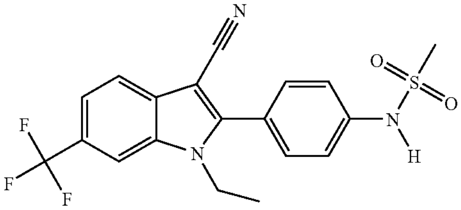
366
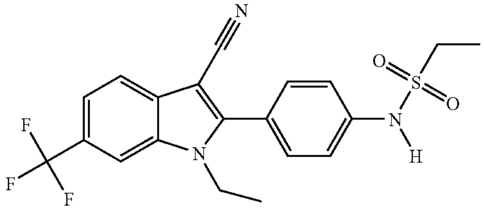
367
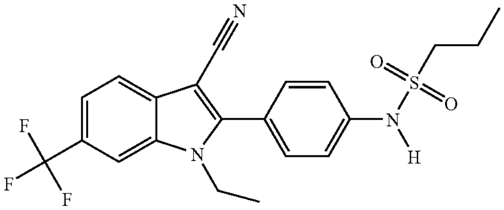
368
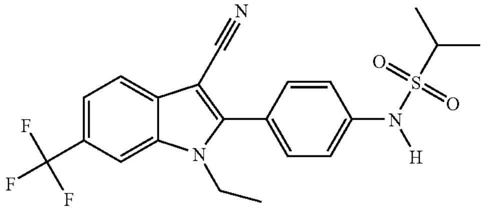
369
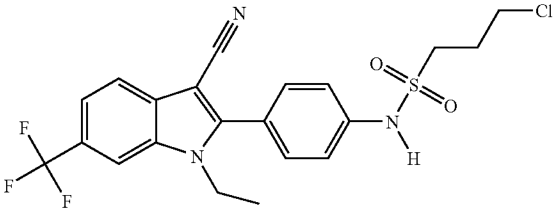
370
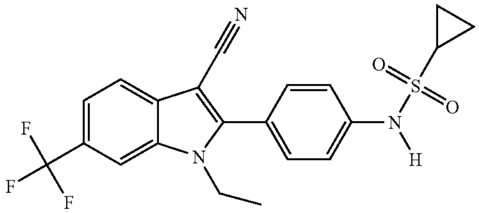

-continued
371
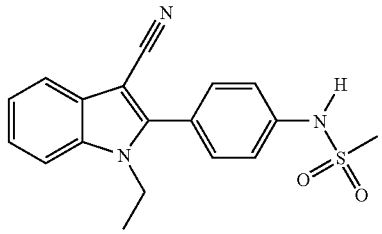
372
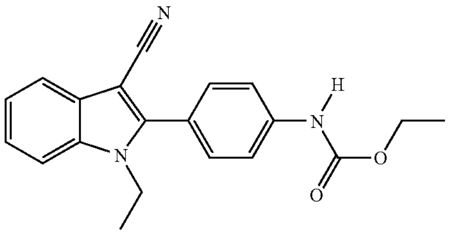
373
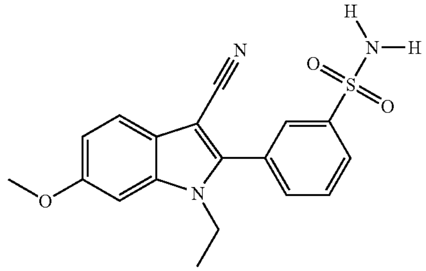
374
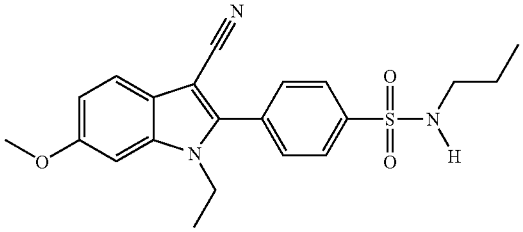
375
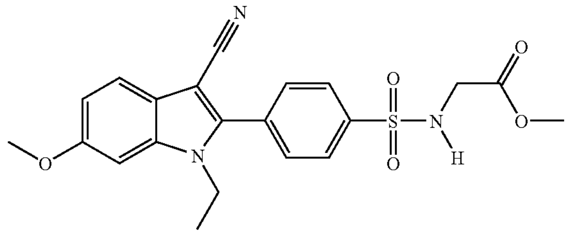
376
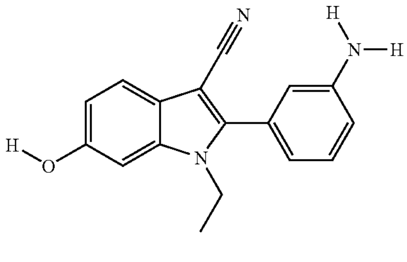
377
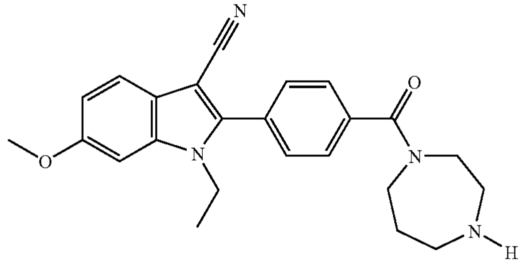
378
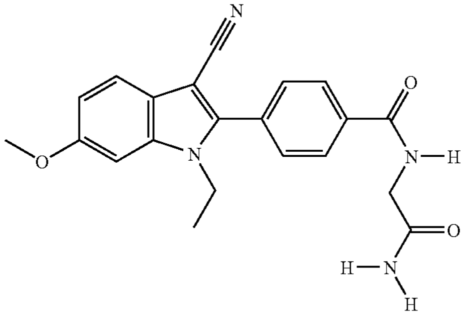
379
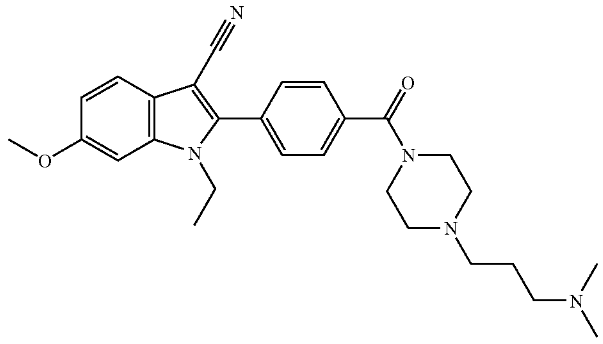
380
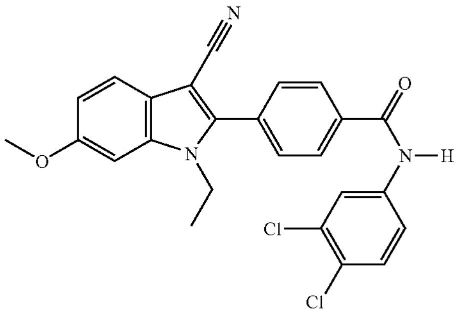

-continued
381
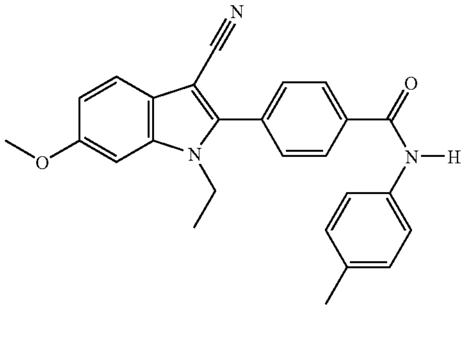
382
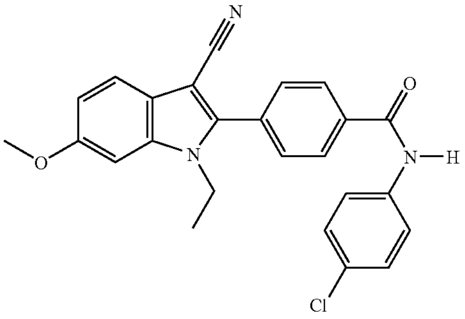
383
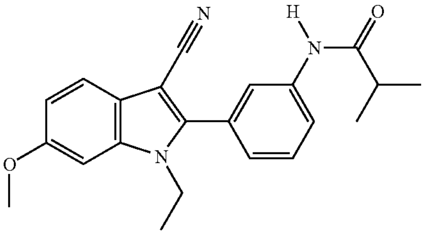
384
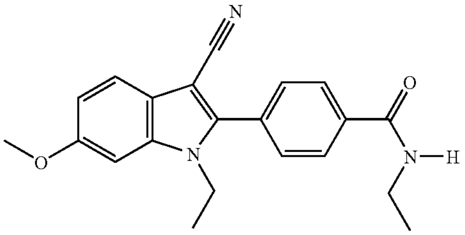
385
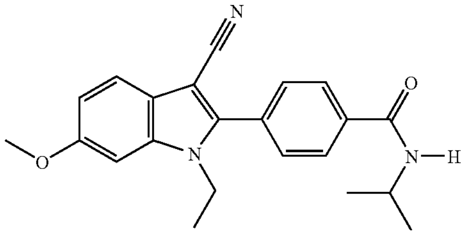
386
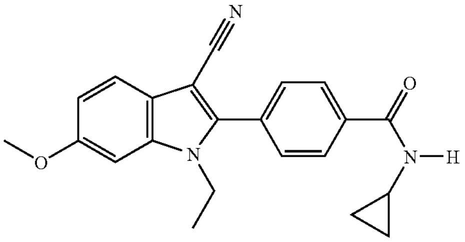
387
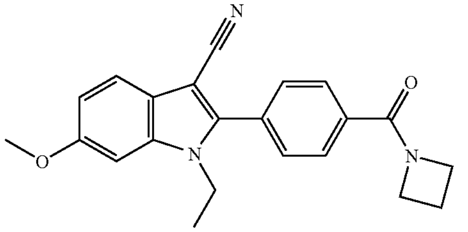
388
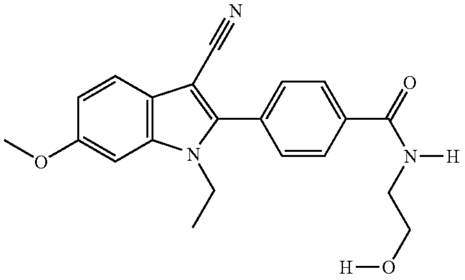
389
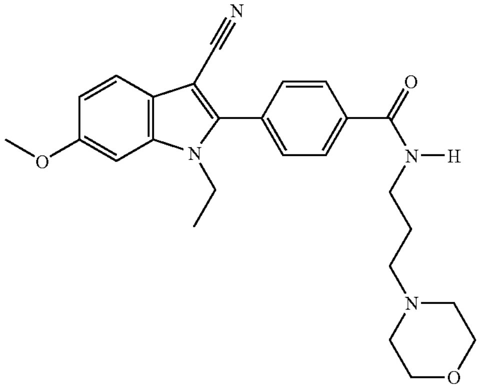
390
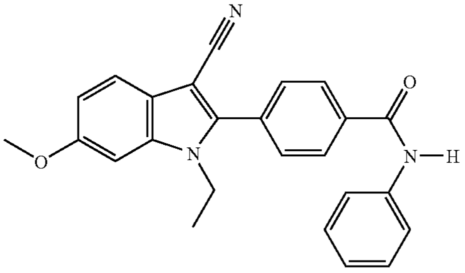

-continued
391
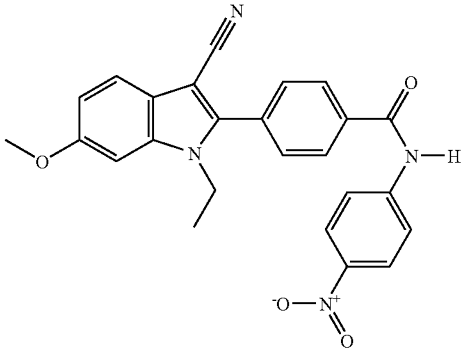
392
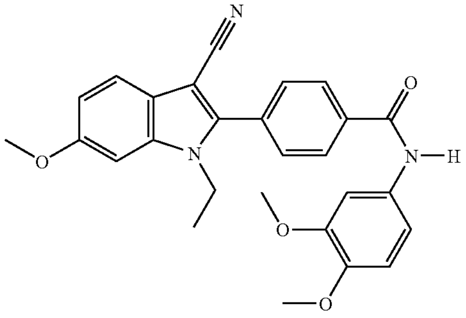
393
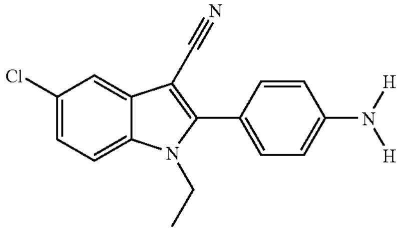
394
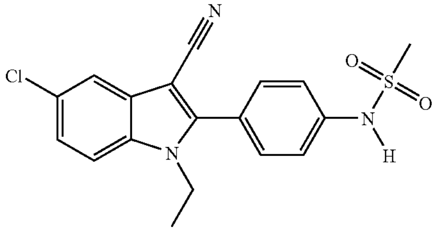
395
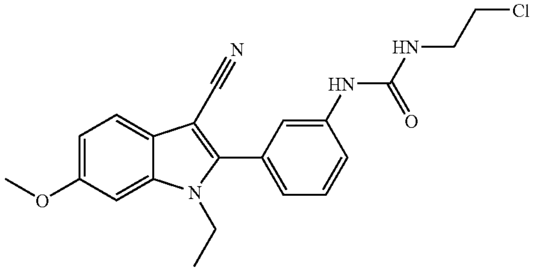
396
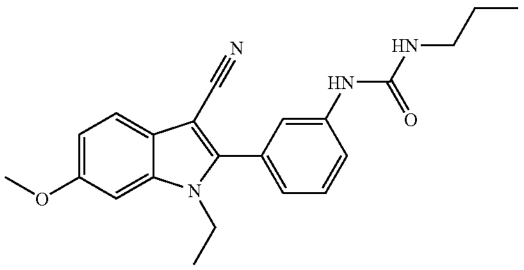
397
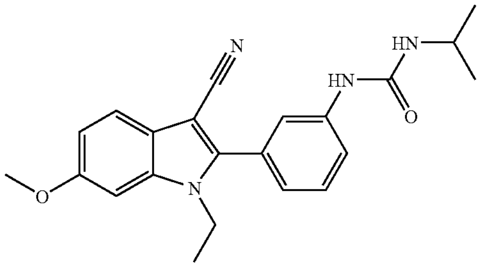
398
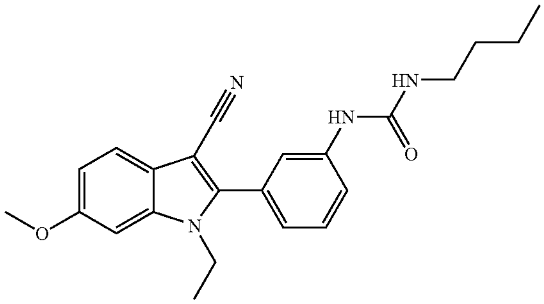
399
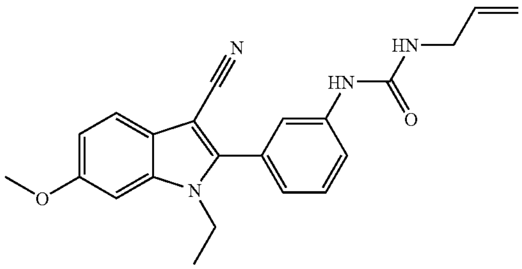
400
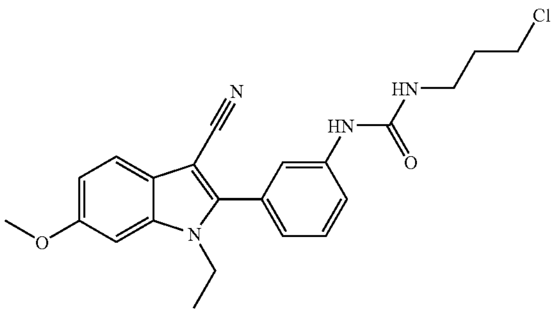

-continued
401
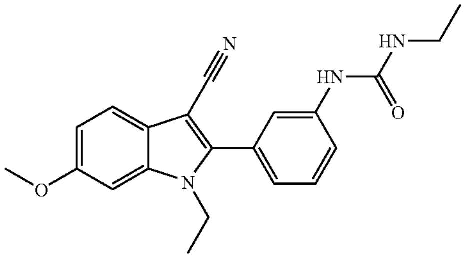
402
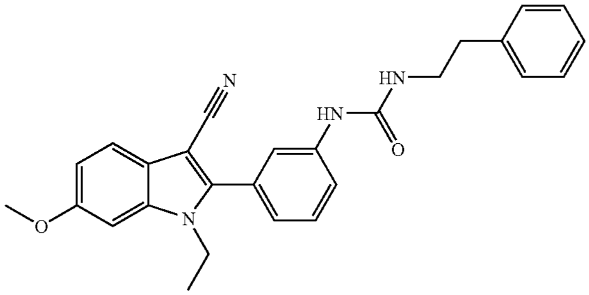
403
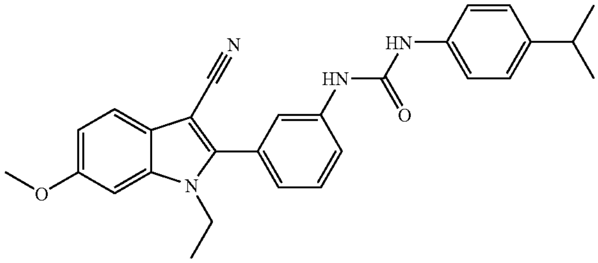
404
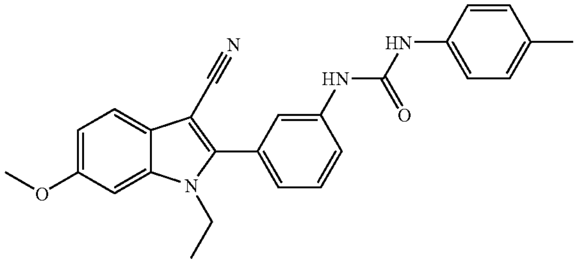
405
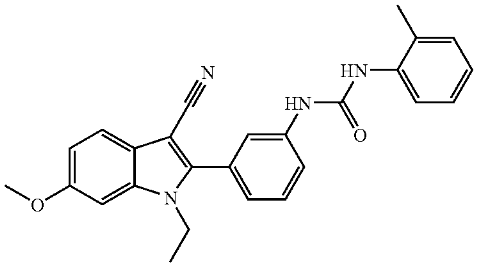
406
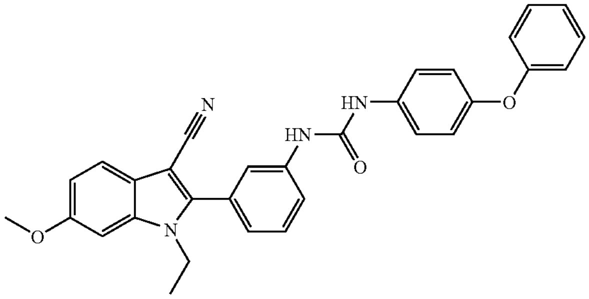
407
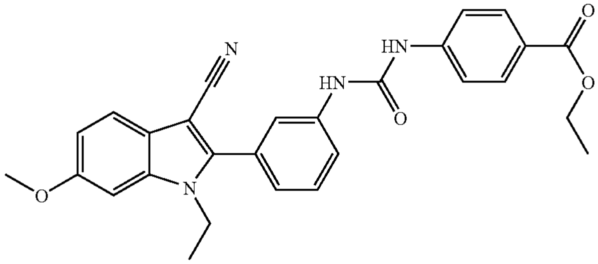
408
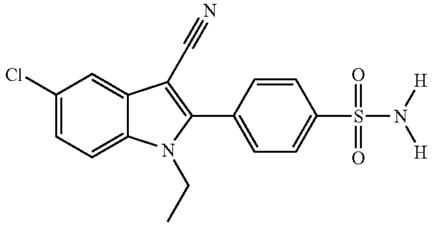
409
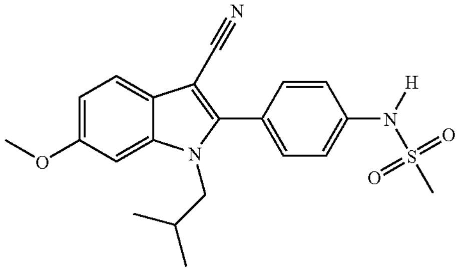
410
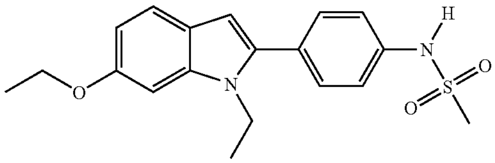

-continued
411
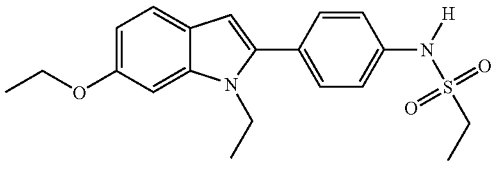
412
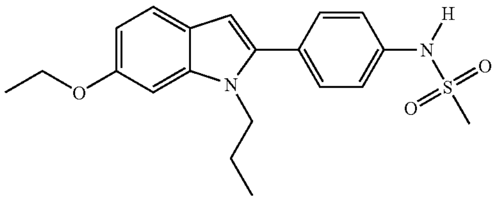
413
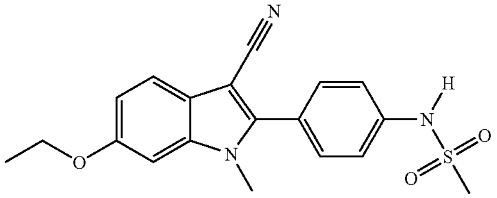
414
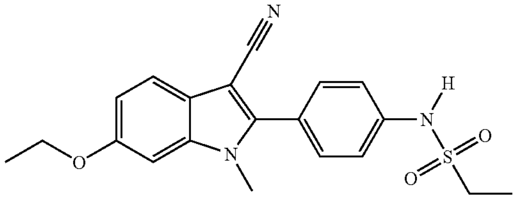
415
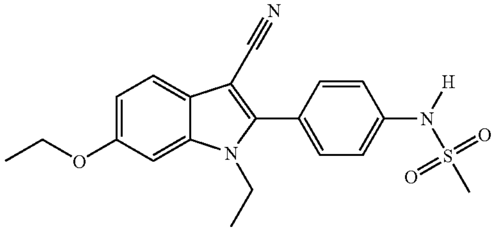
416
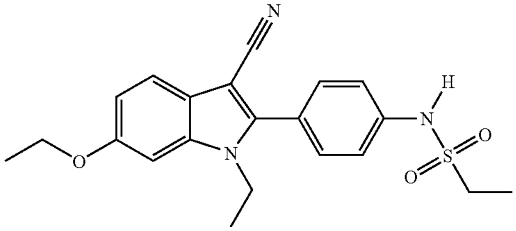
417
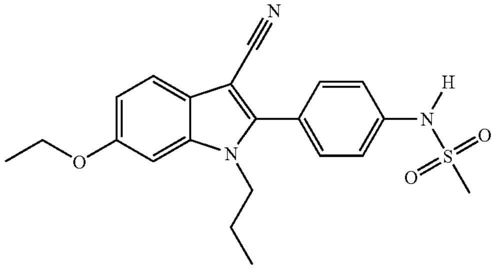
418
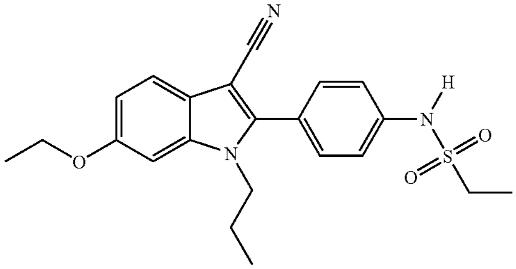
419
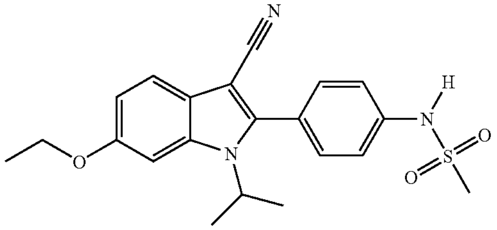
420
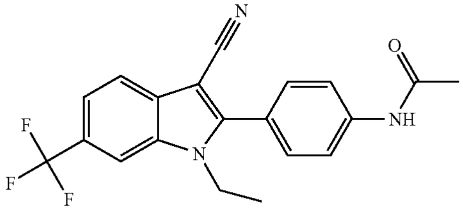
421
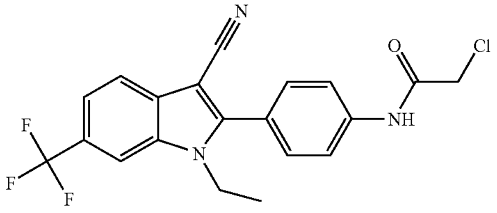
422
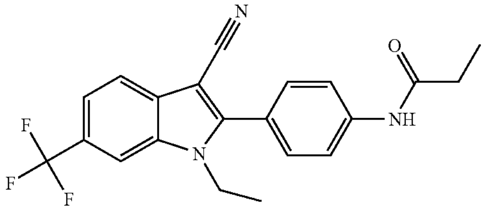
423
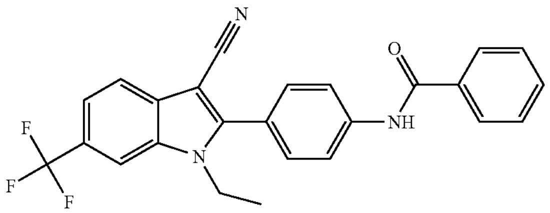
424
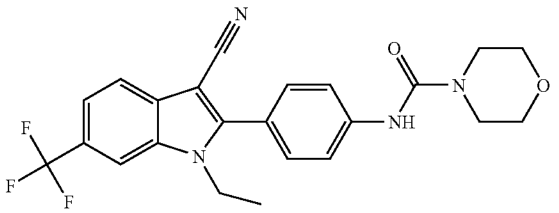

-continued
425
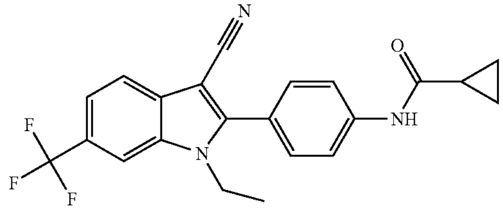
426
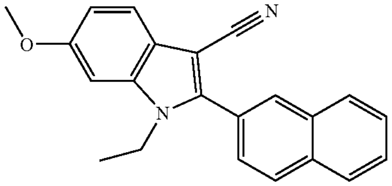
427
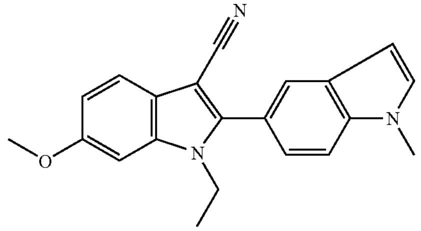
428
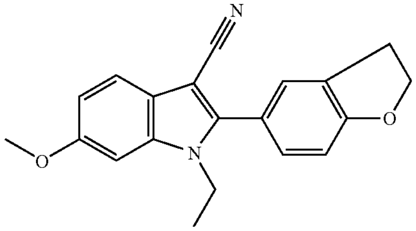
429
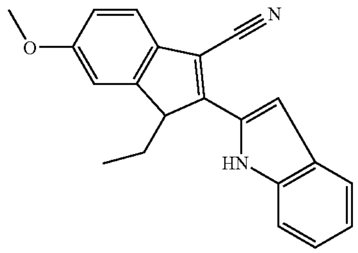
430
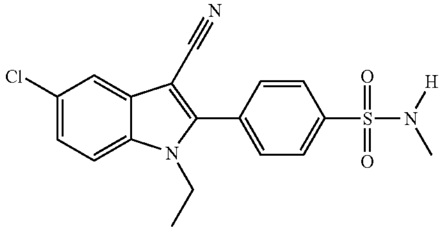
431
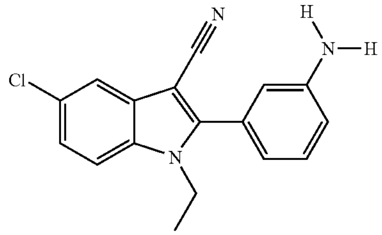
432
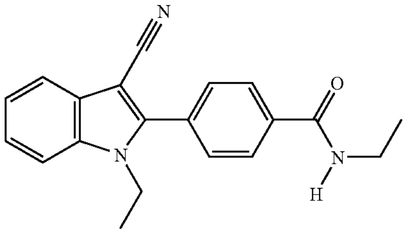
433
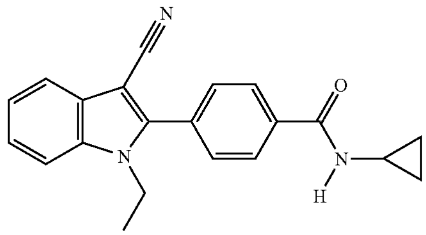
434
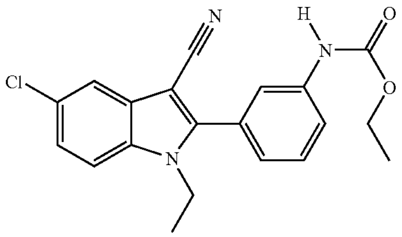
435
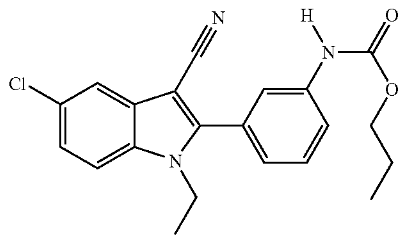
436
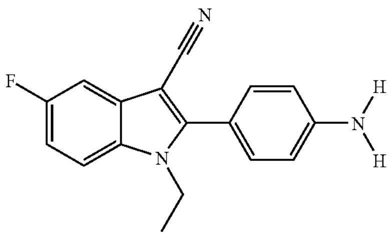

-continued
437
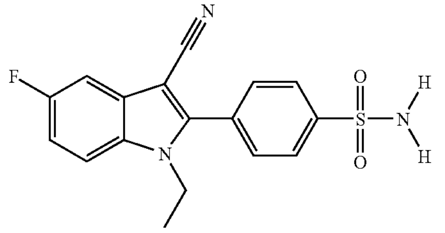
438
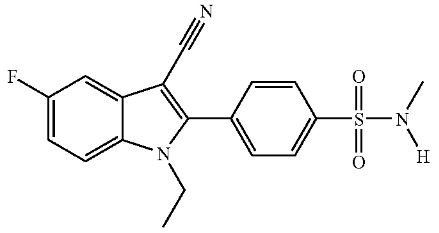
439
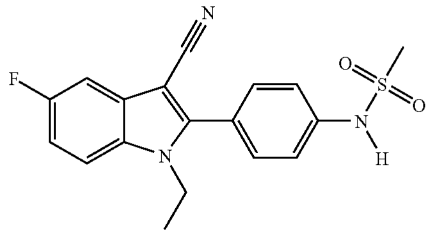
440
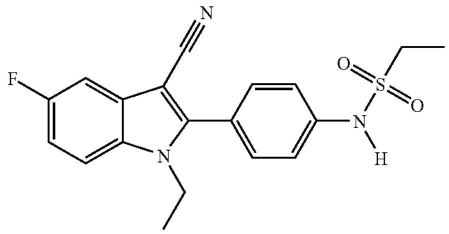
441
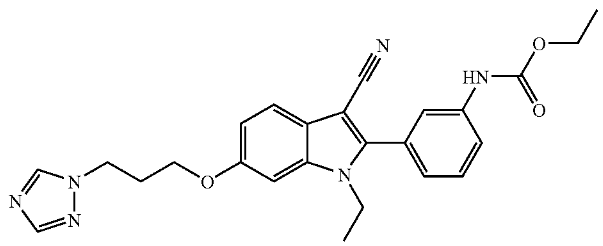
442
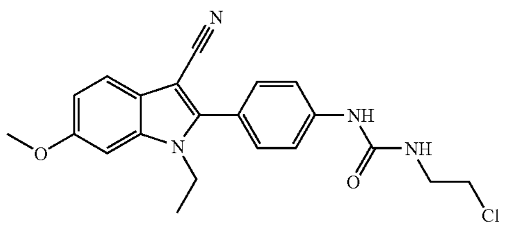
443
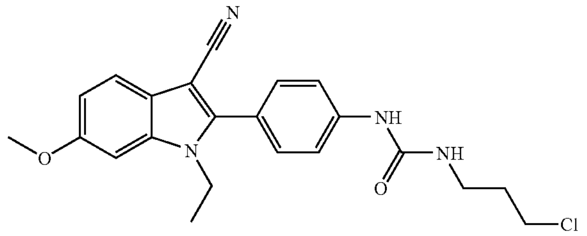
444
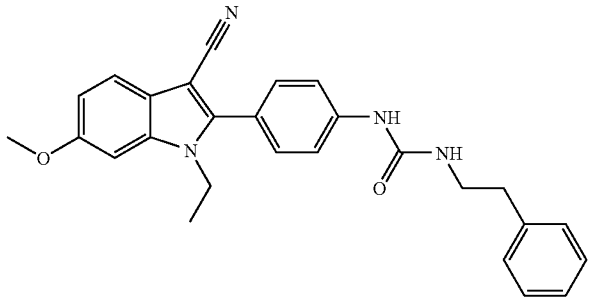
445
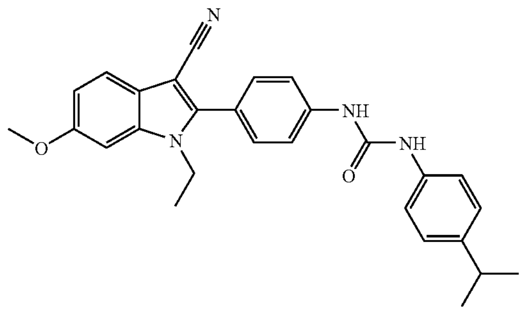
446
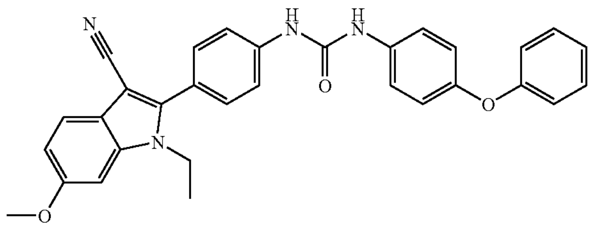

-continued
447
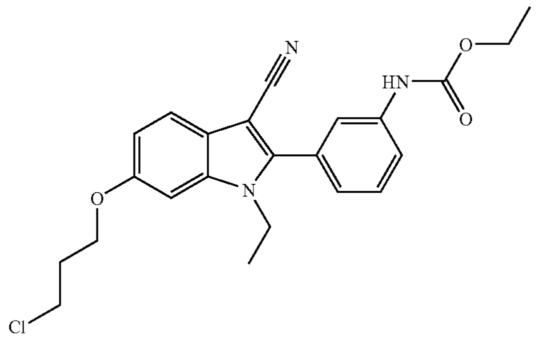
448
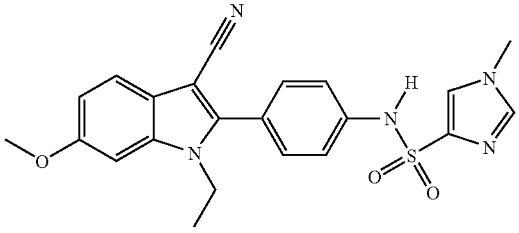
449
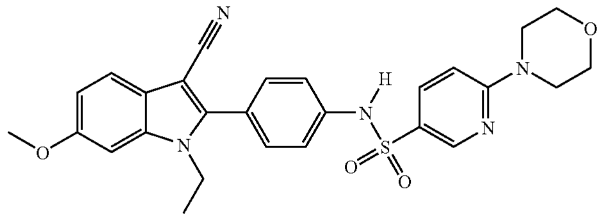
450
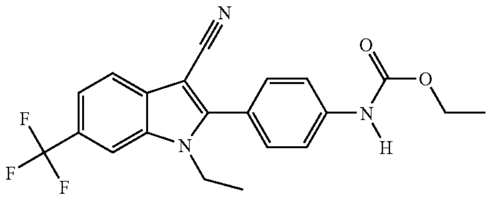
451
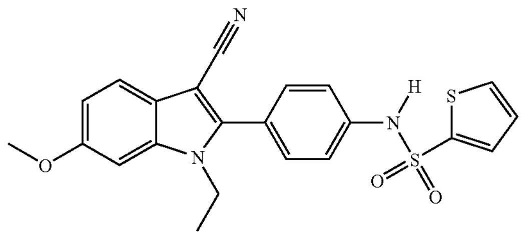
452
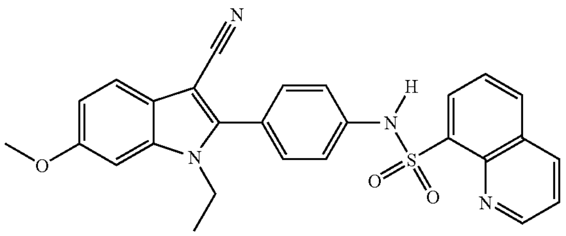
453
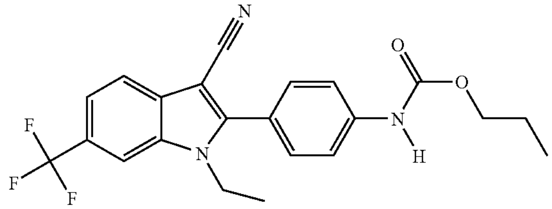
454
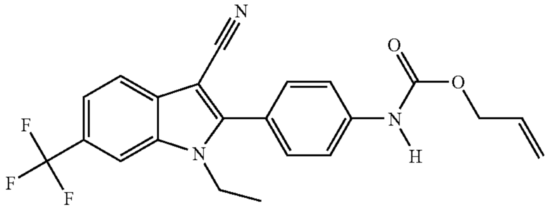
455
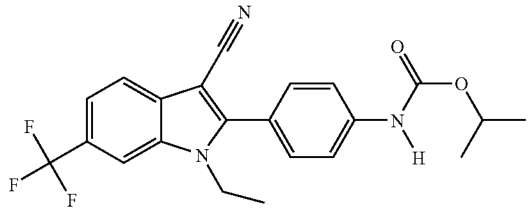
456
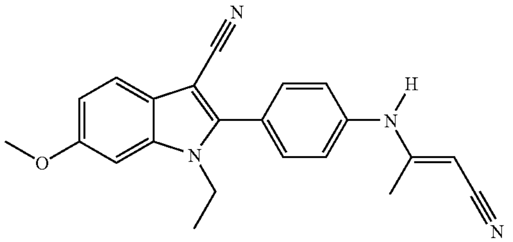
457
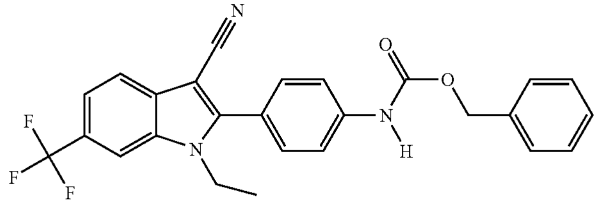
458
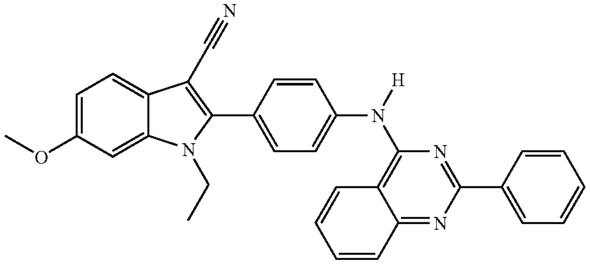

-continued
459
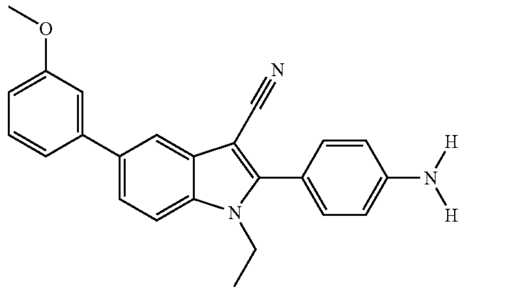
460
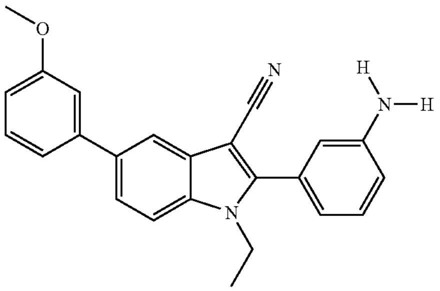
461
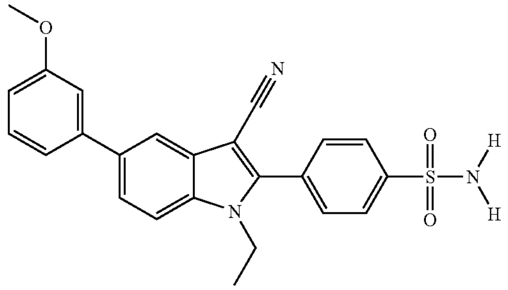
462
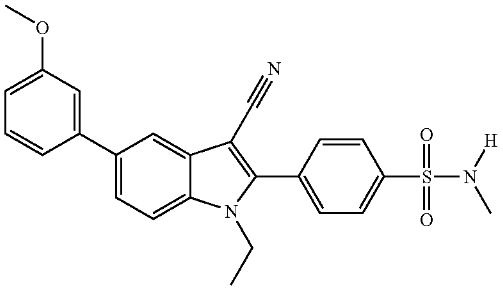
463
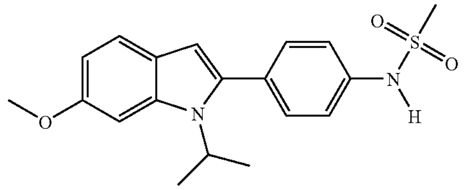
464
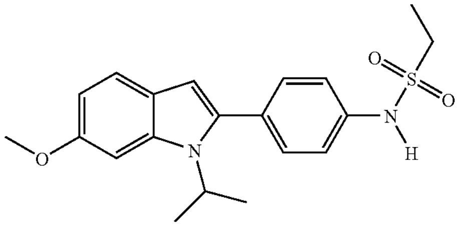
465
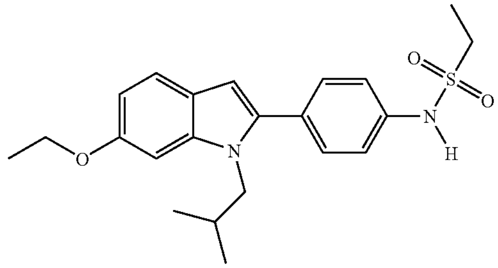
466
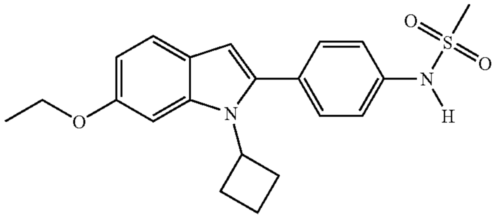
467
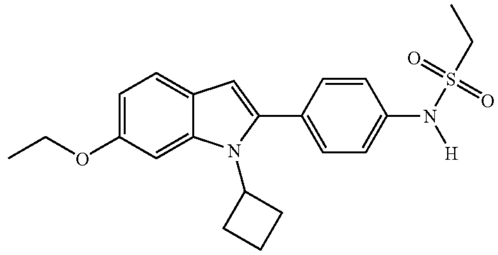
468
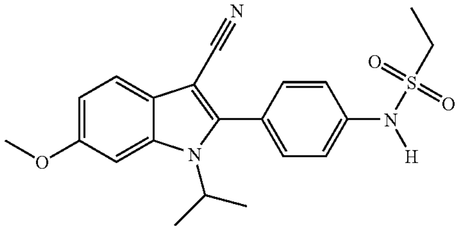
469
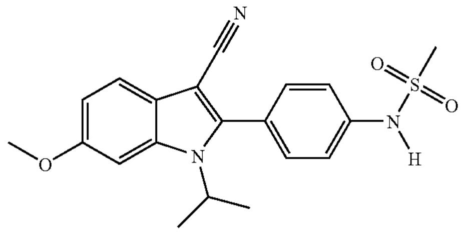
470
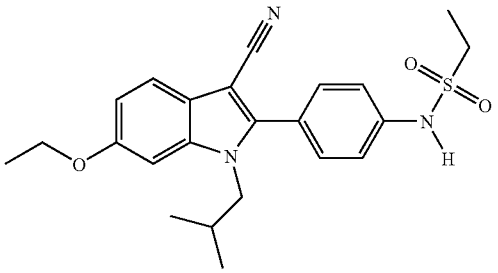

-continued
471
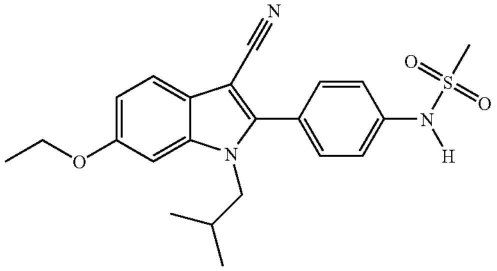
472
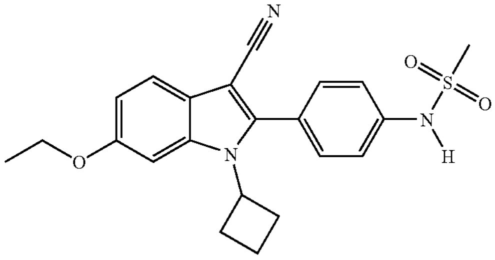
473
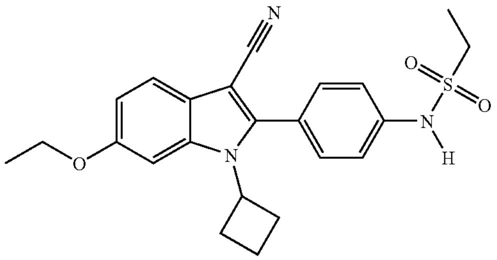
474
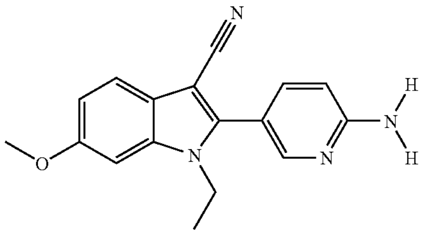
475
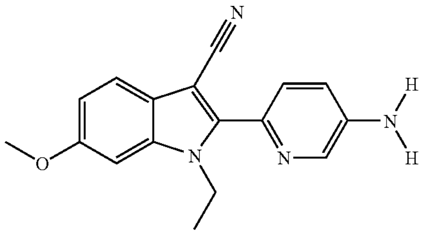
476
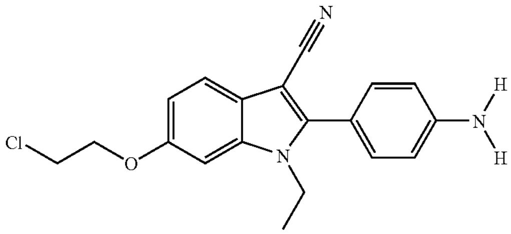
477
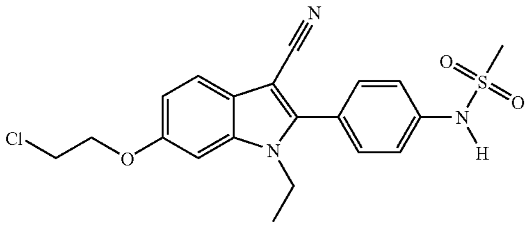
478
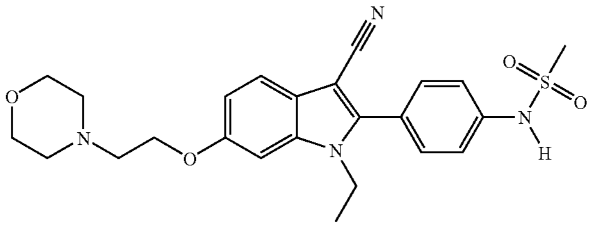
479
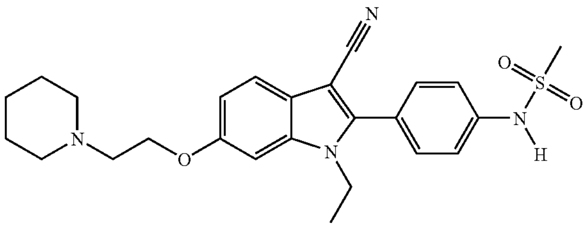
480
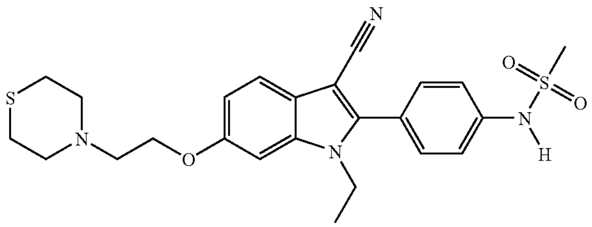
481
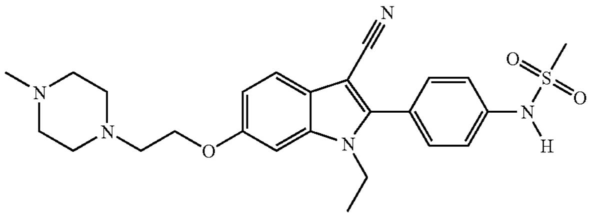
482
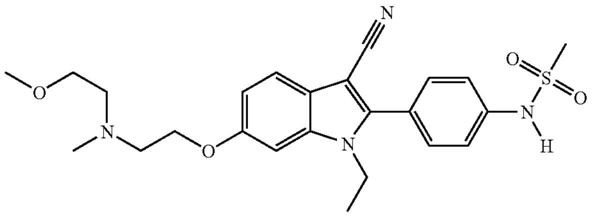

-continued
483
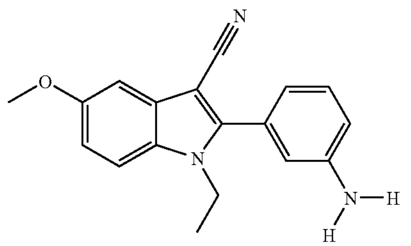
484
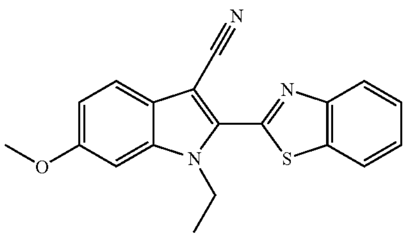
485
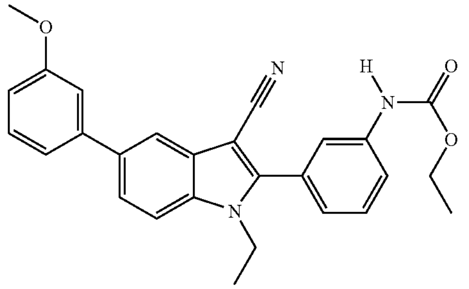
486
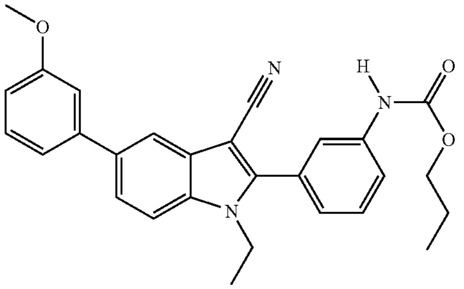
487
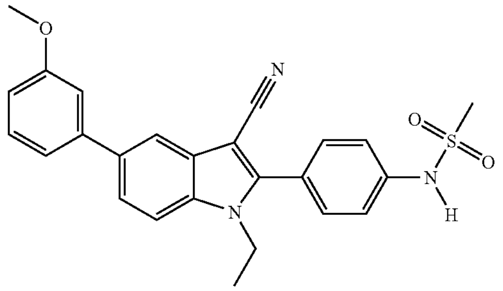
488
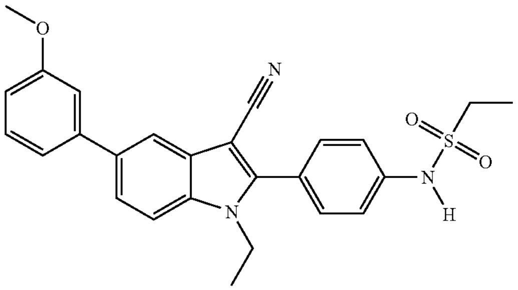
489
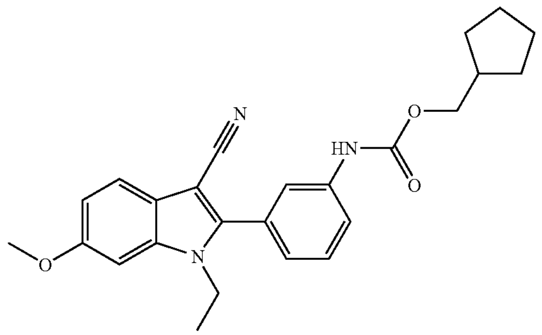
490
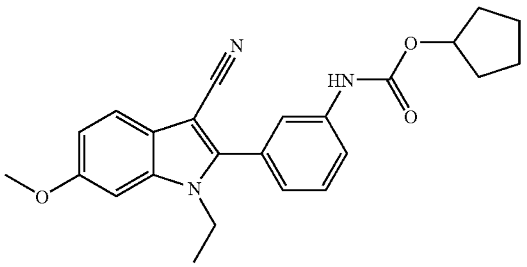
491
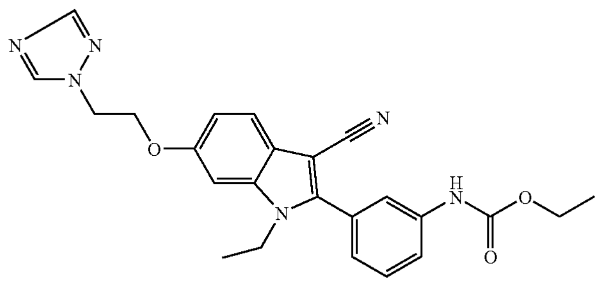
492
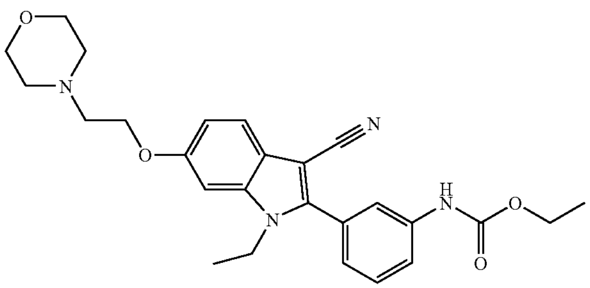

-continued
493
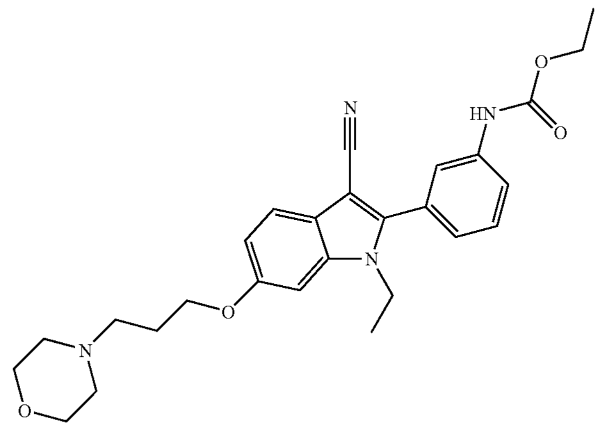
494
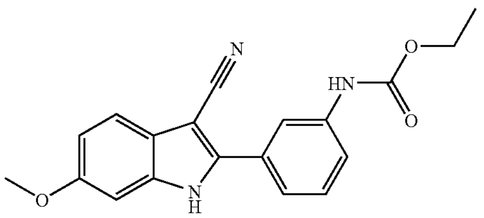
495
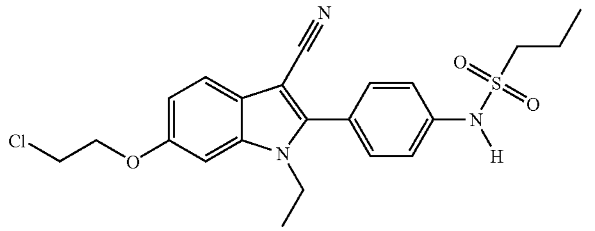
496
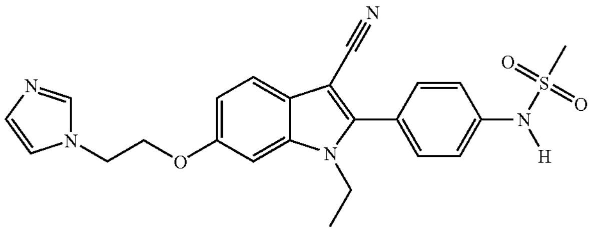
497
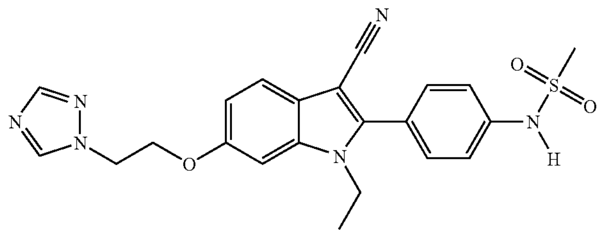
498
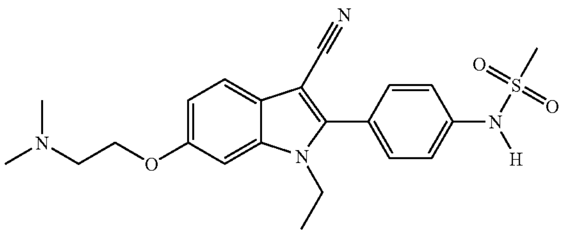
499
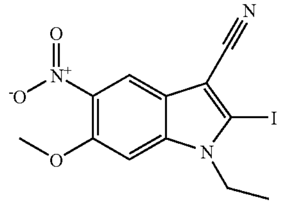
500
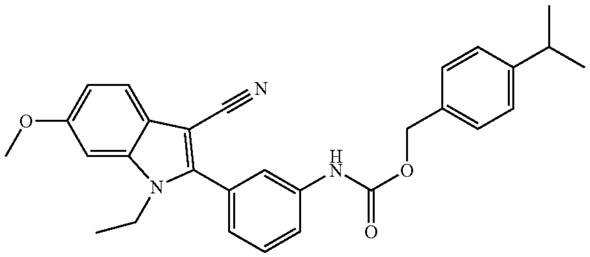
501
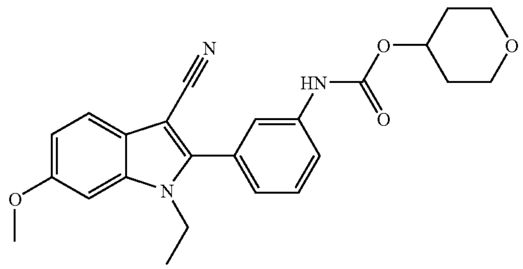
502
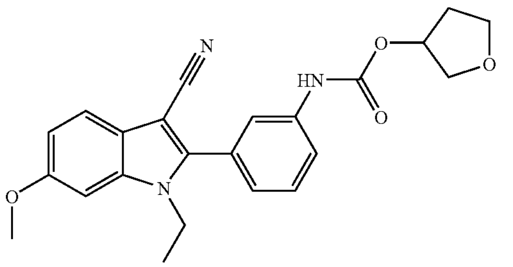

-continued
503
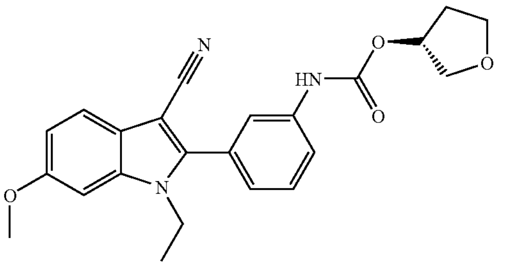
504
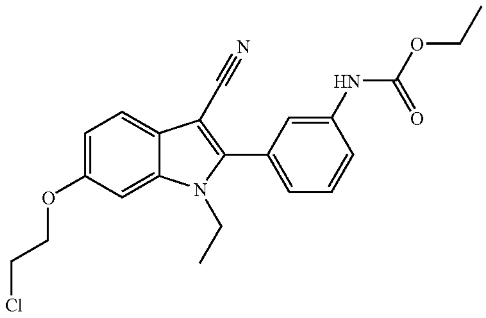
505
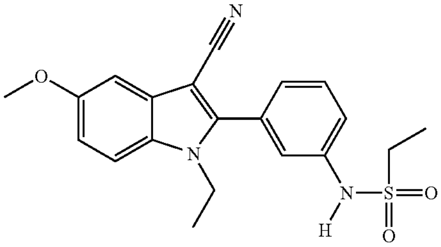
506
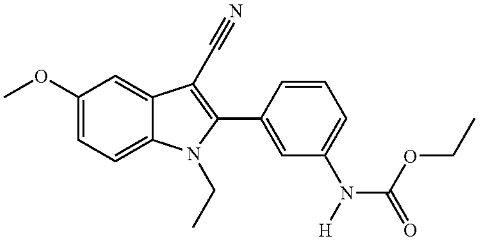
507
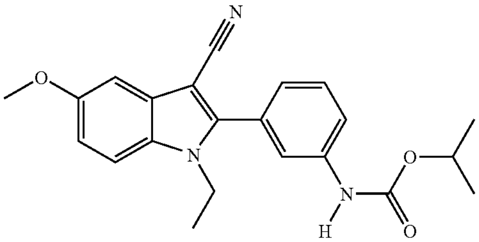
508
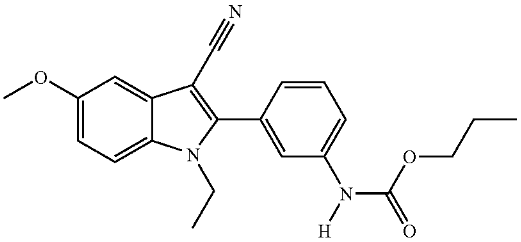
509
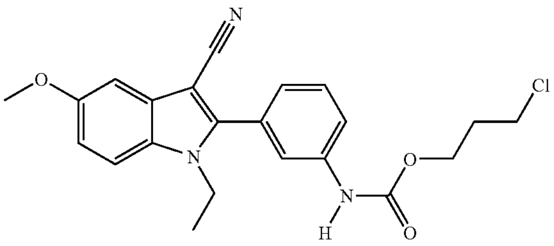
510
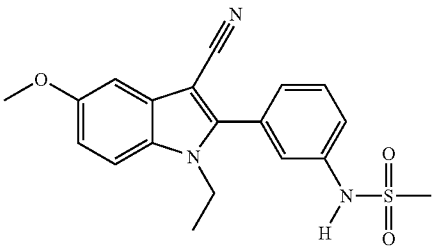
511
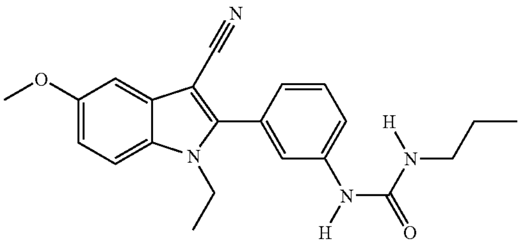
512
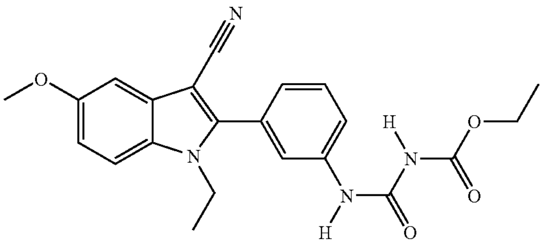
513
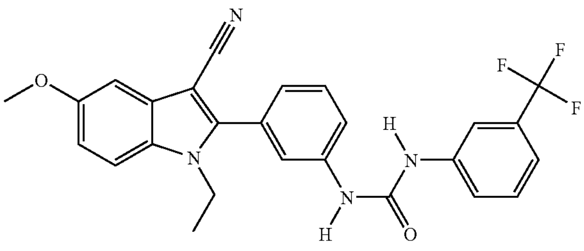
514
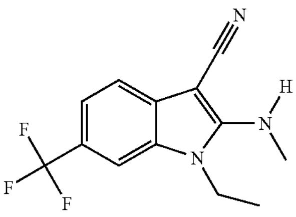

-continued
515
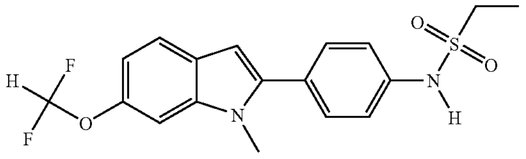
516
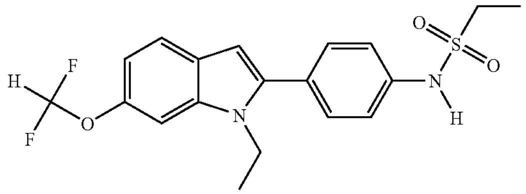
517
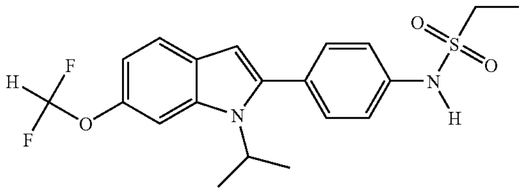
518
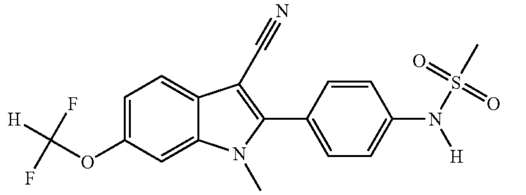
519
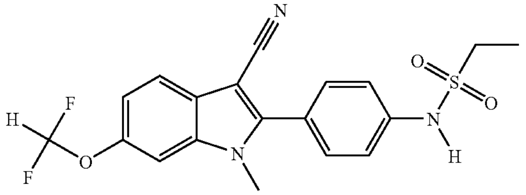
520
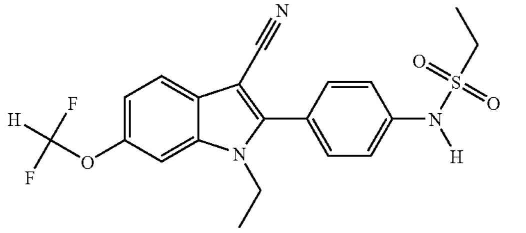
521
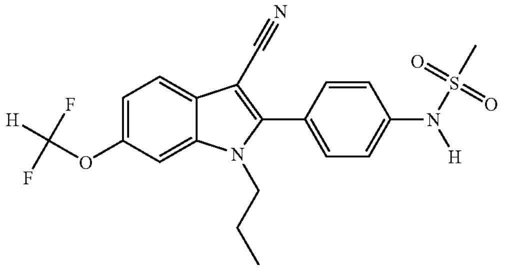
522
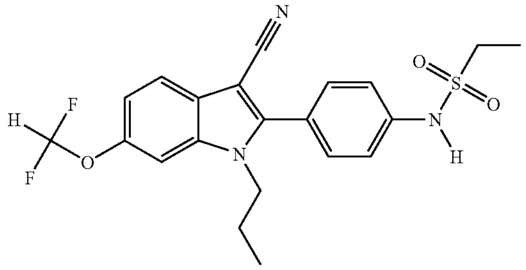
523
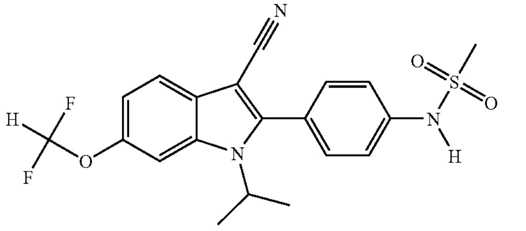
524
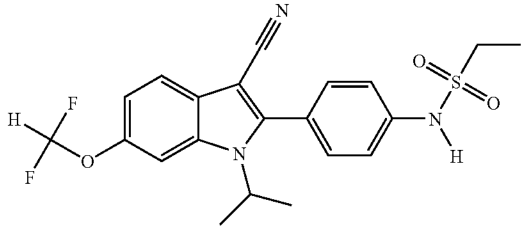
525
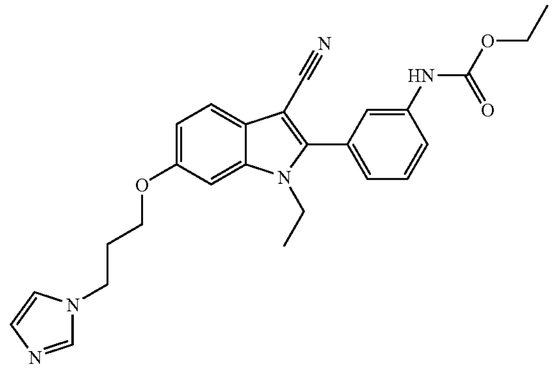
526
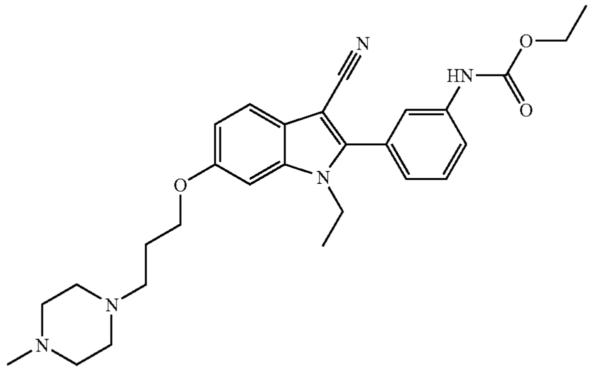

-continued
527
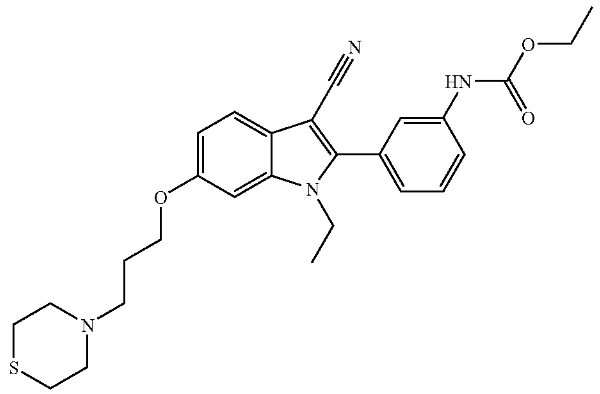
528
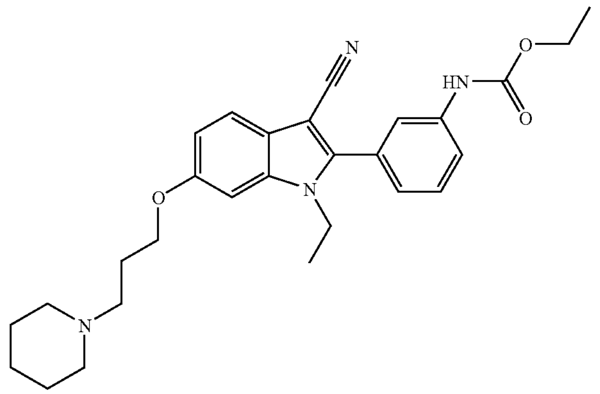
529
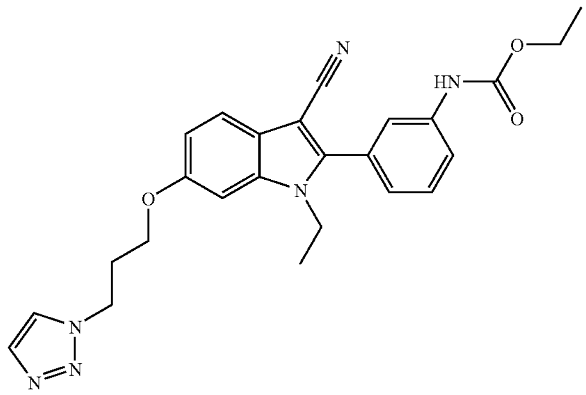
530
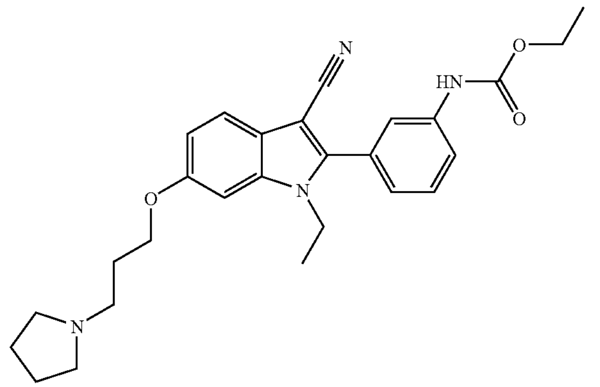
531
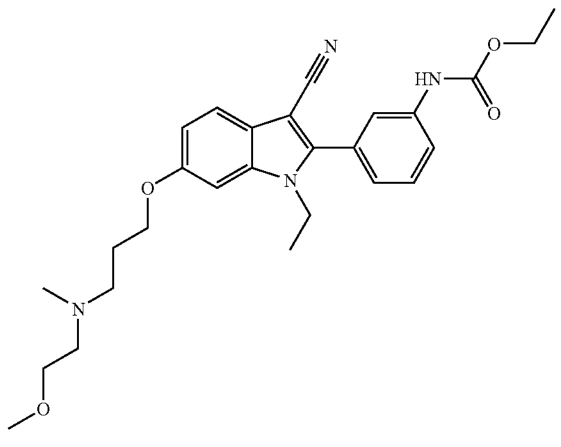
532
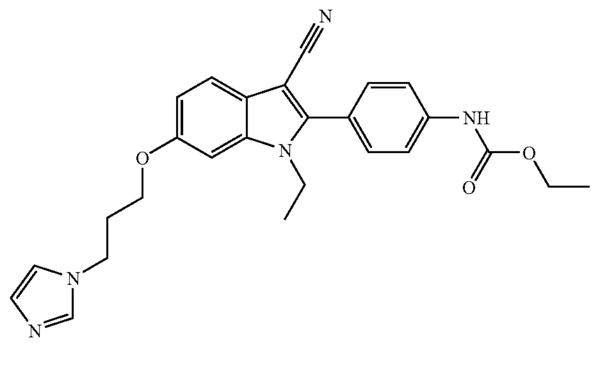
533
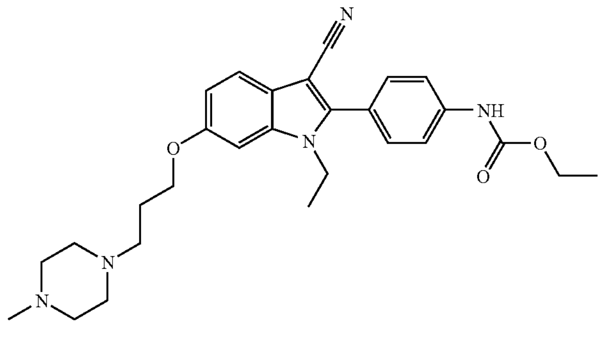
534
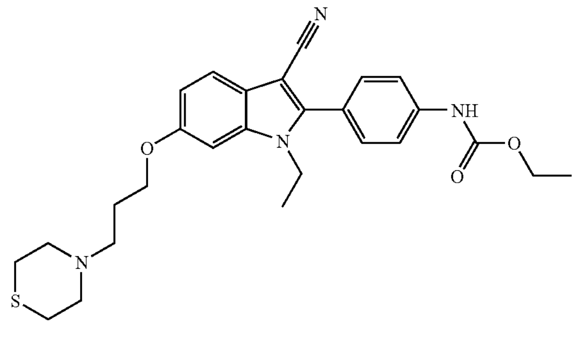

-continued
535
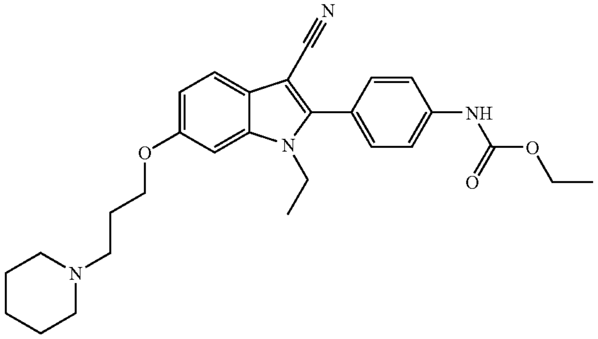
536
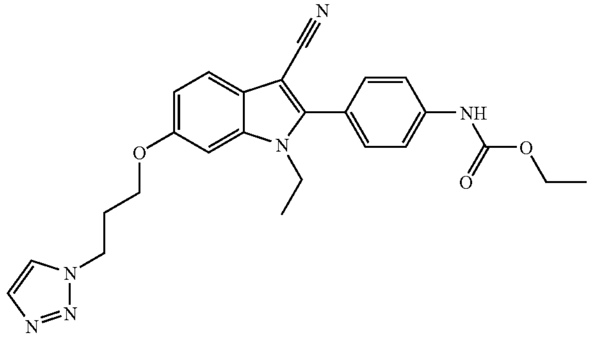
537
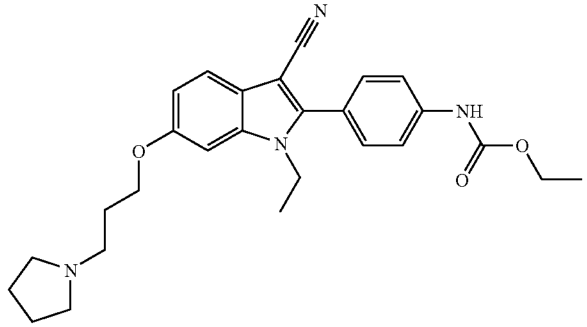
538
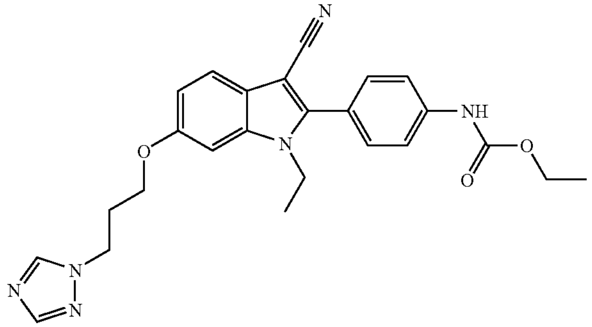
539
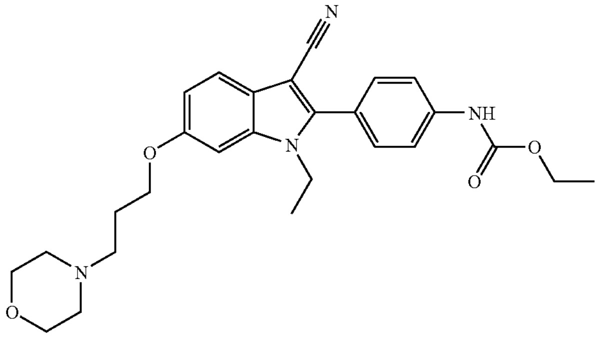
540
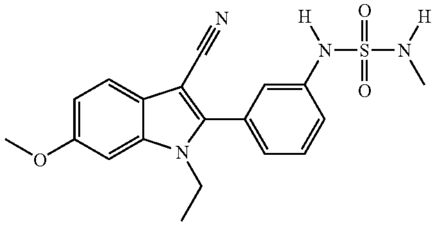
541
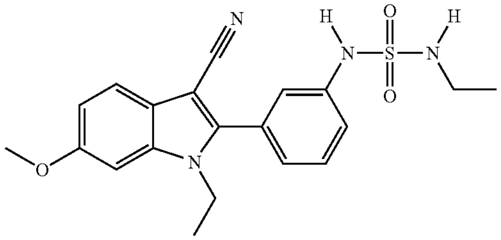
542
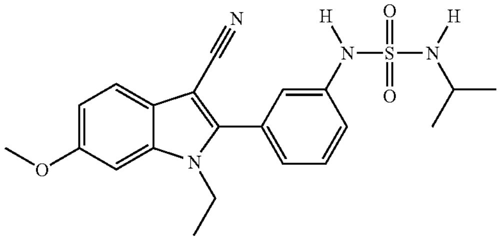
543
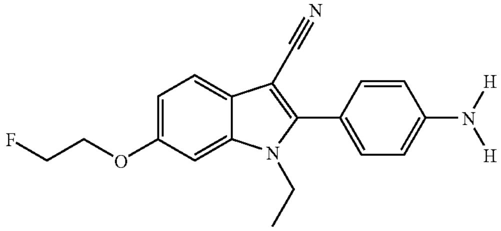
544
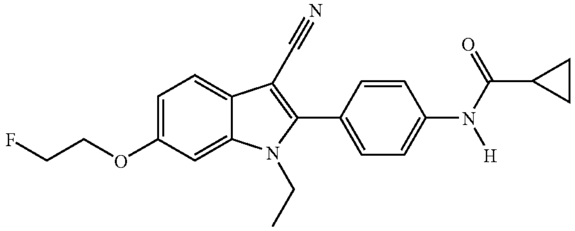

-continued
545
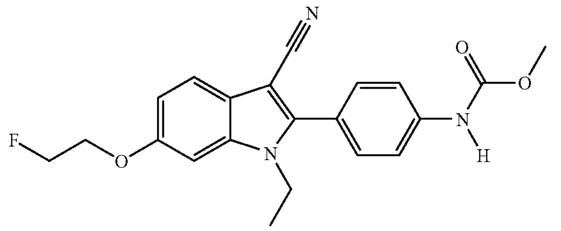
546
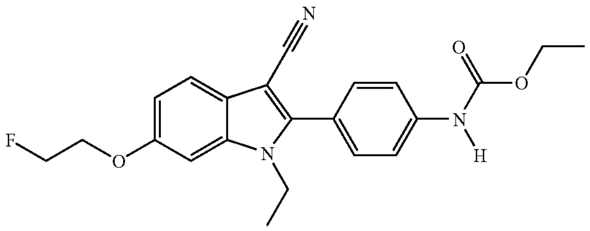
547
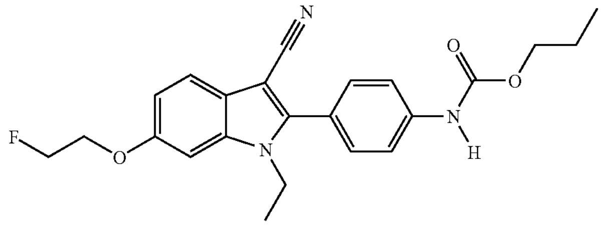
548
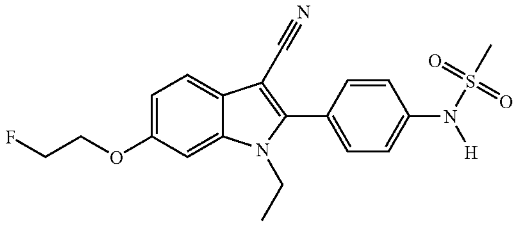
549
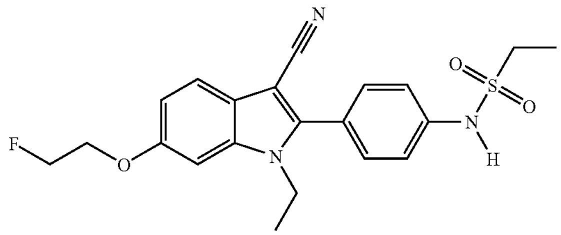
550
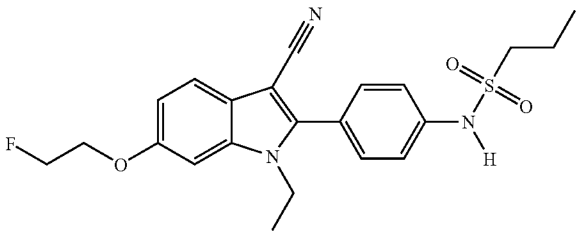
551
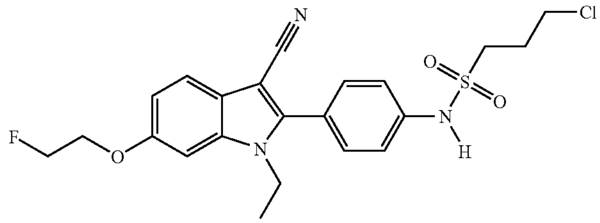
552
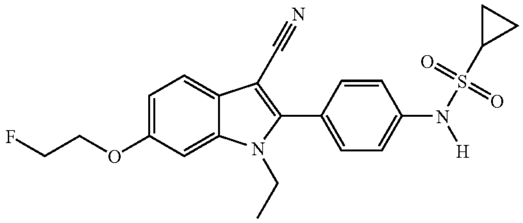
553
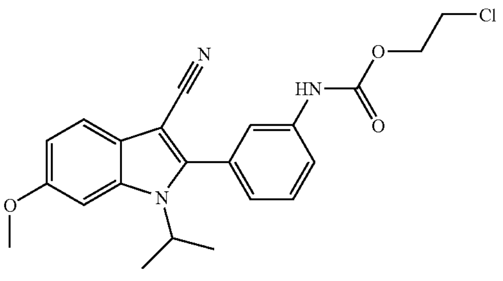
554
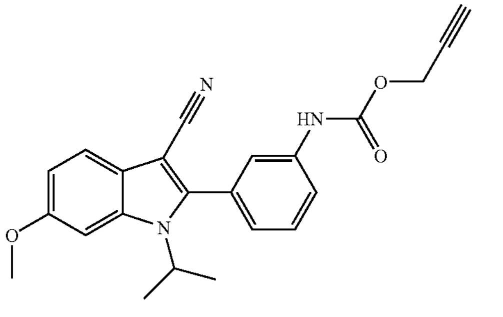

-continued
555
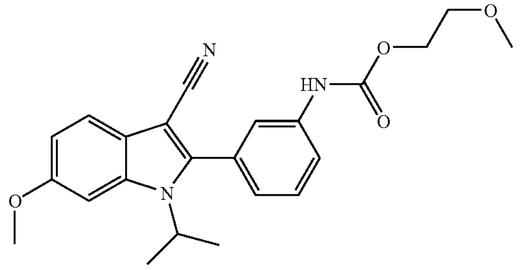
556
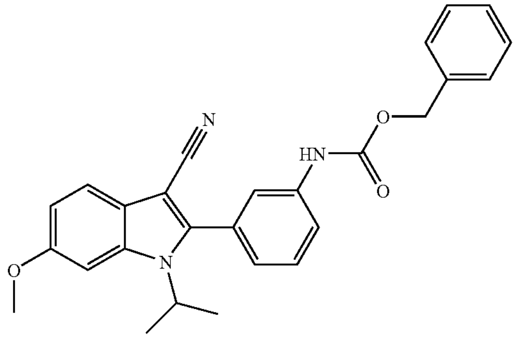
557
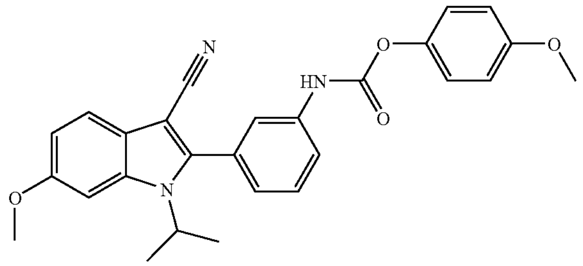
558
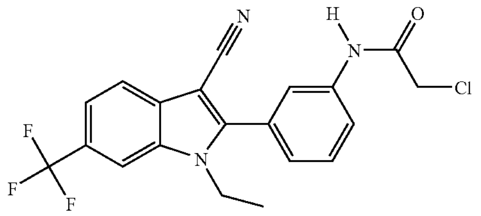
559
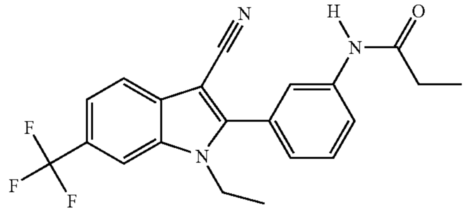
560
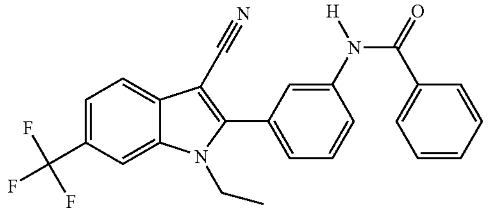
561
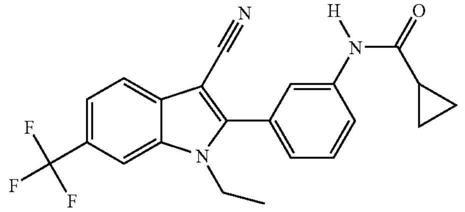
562
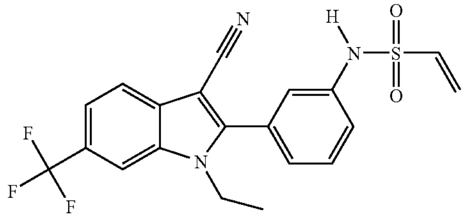
563
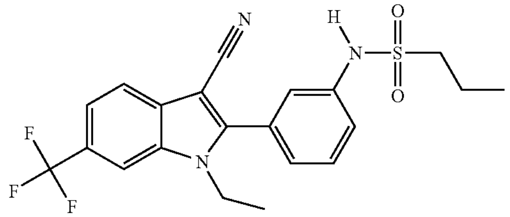
564
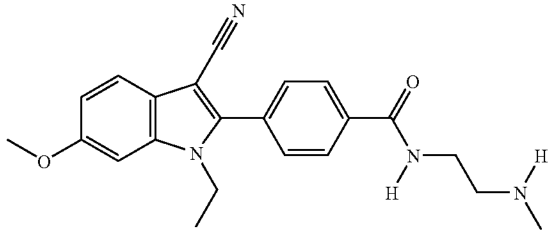
565
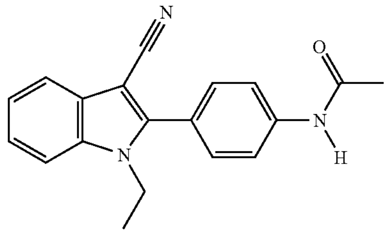
566
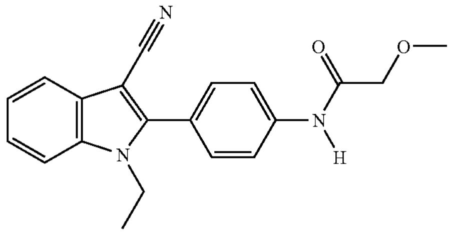

-continued
567
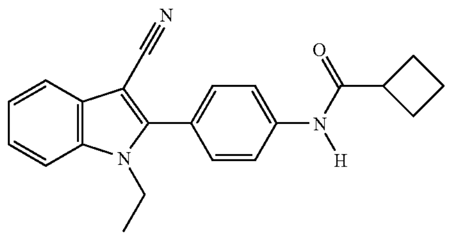
568
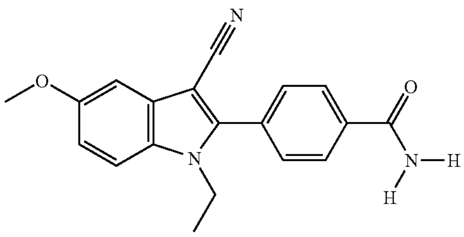
569
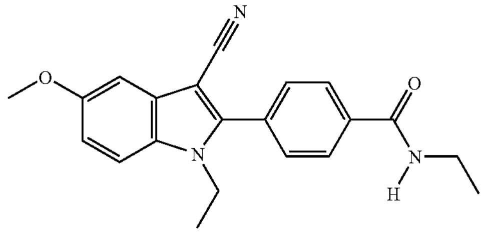
570
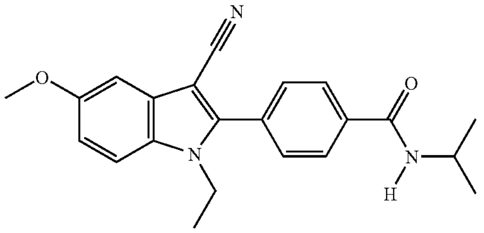
571
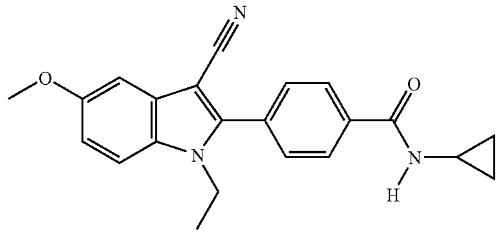
572
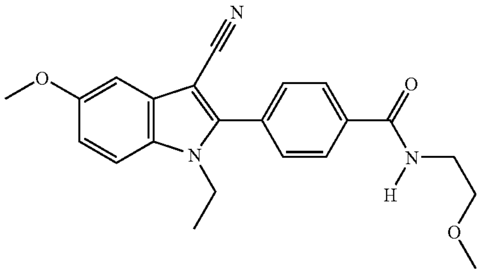
573
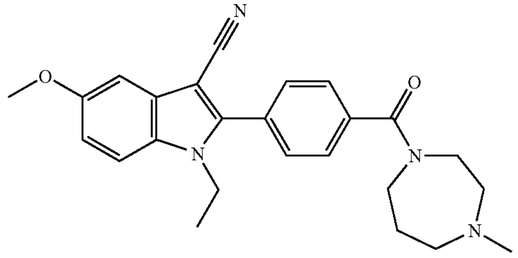
574
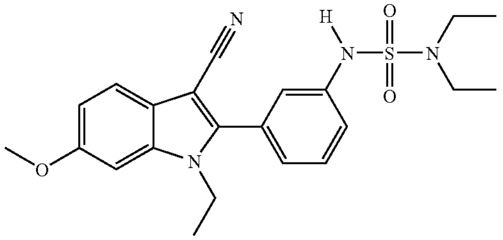
575
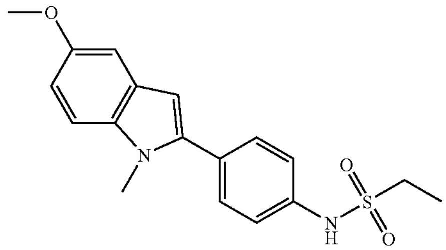
576
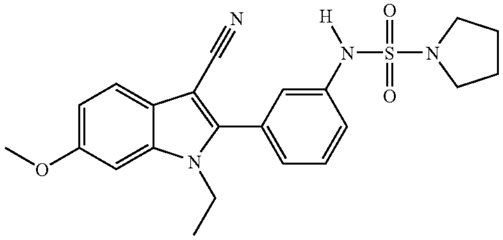
577
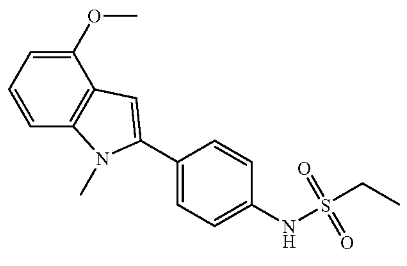
578
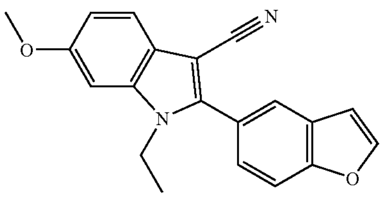

-continued
579
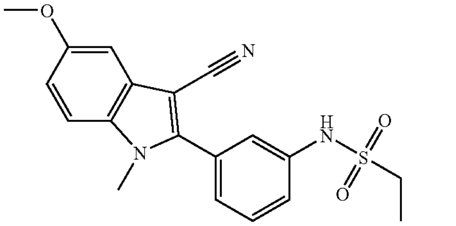
580
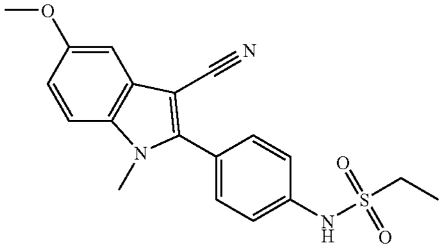
581
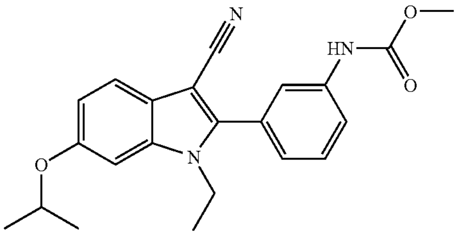
582
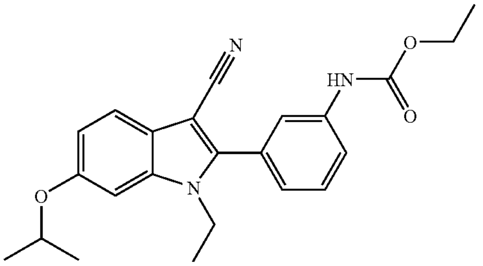
583
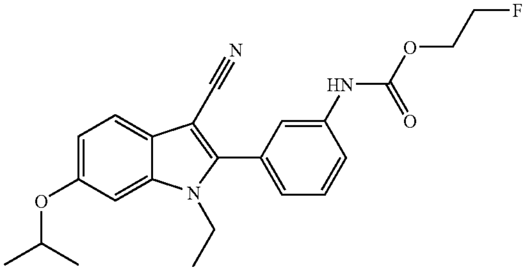
584
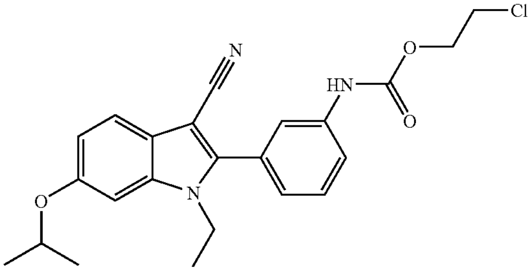
585
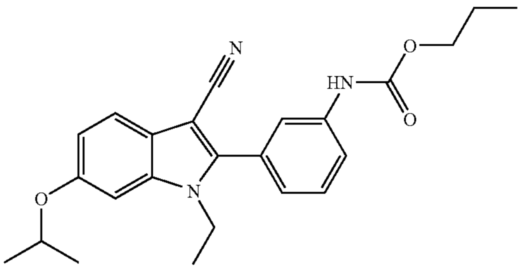
586
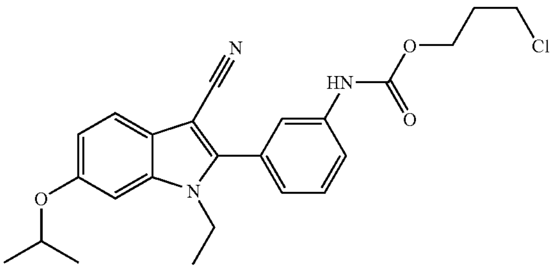
587
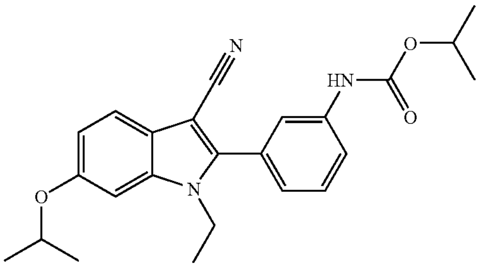
588
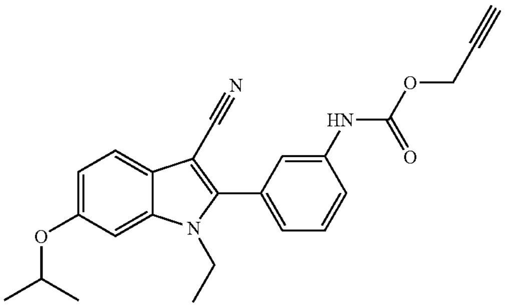

-continued
589
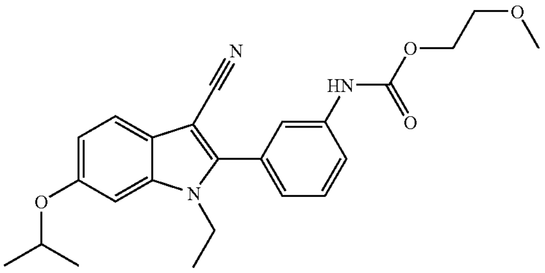
590
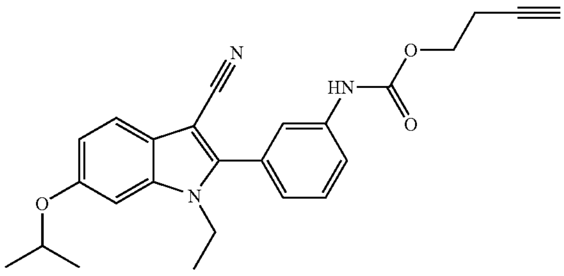
591
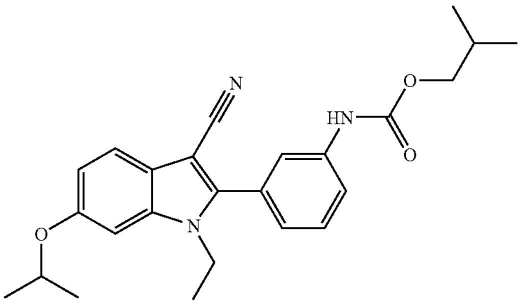
592
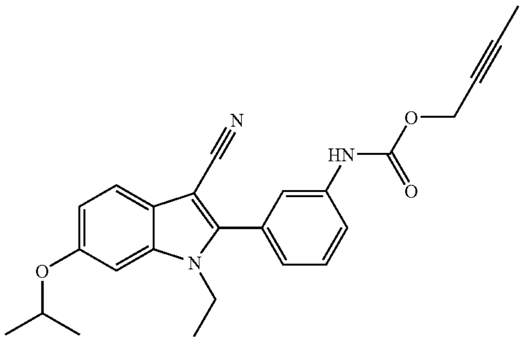
593
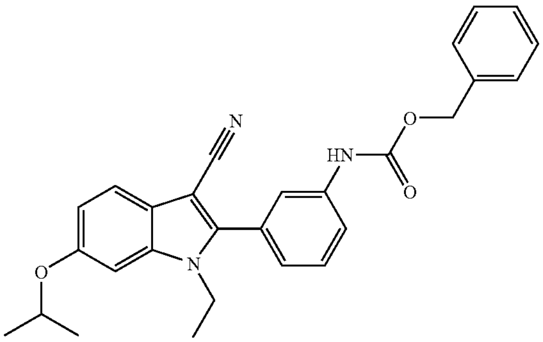
594
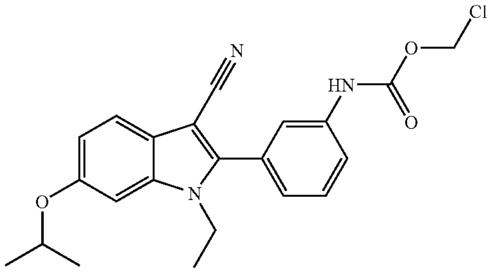
595
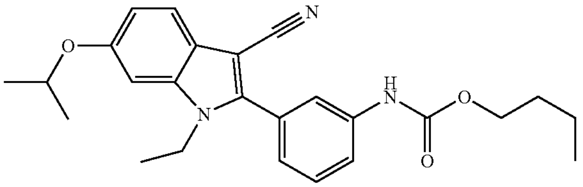
596
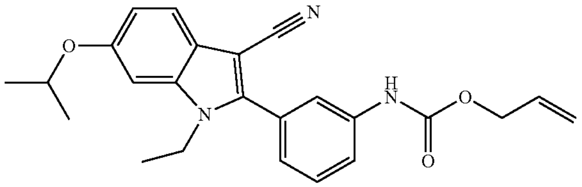
597
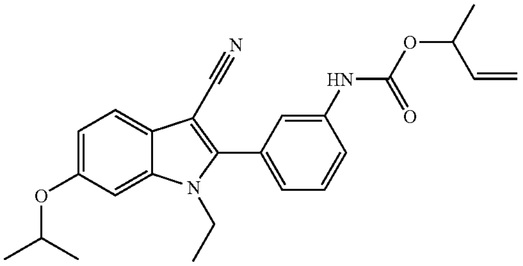
598
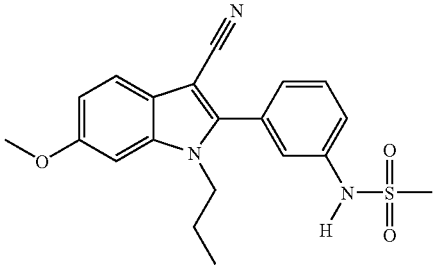

-continued
599
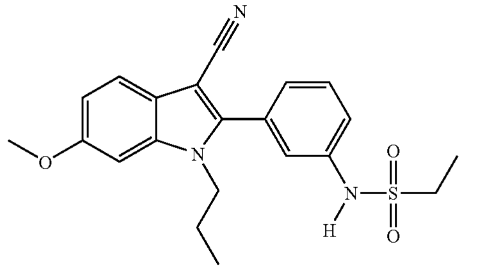
600
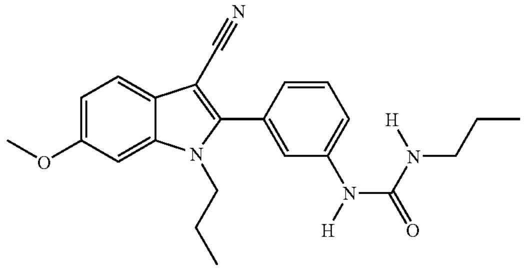
601
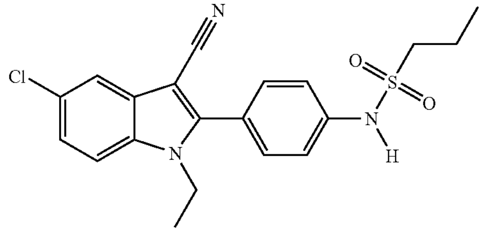
602
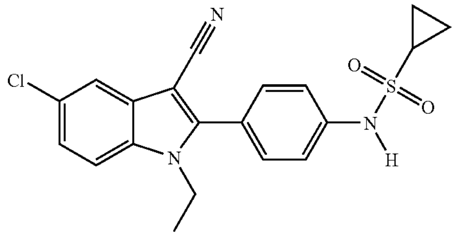
603
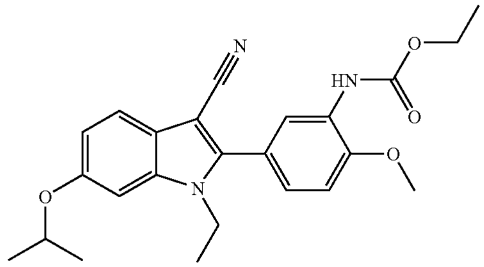
604
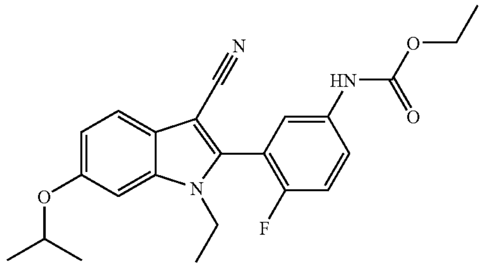
605
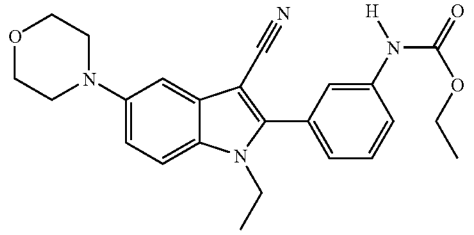
606
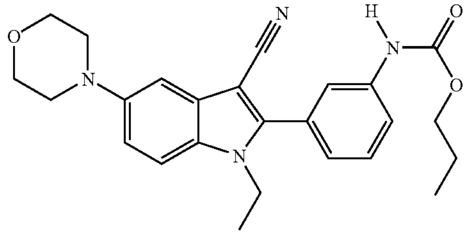
607
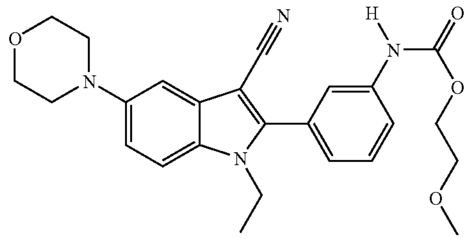
608
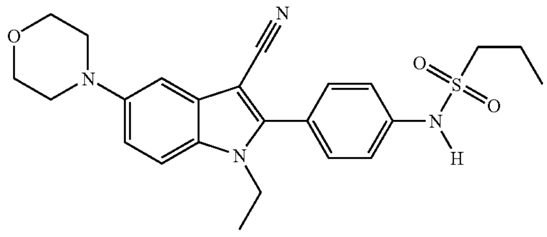
609
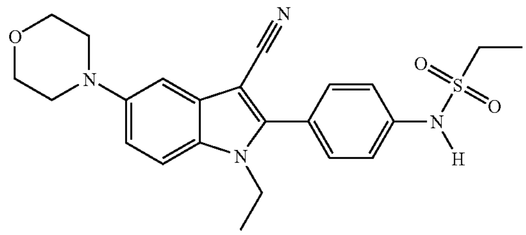
610
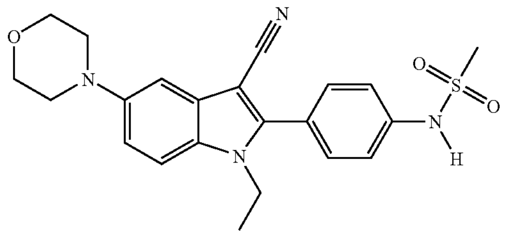

-continued
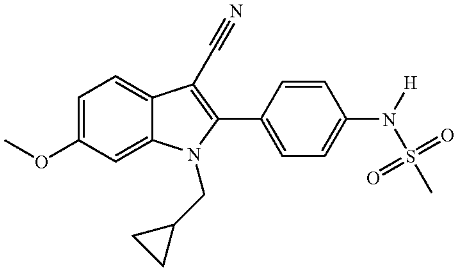
611
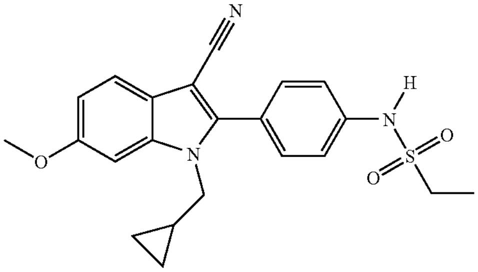
612
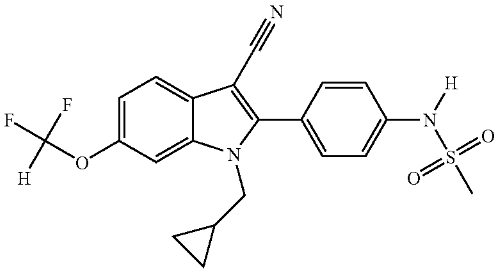
613
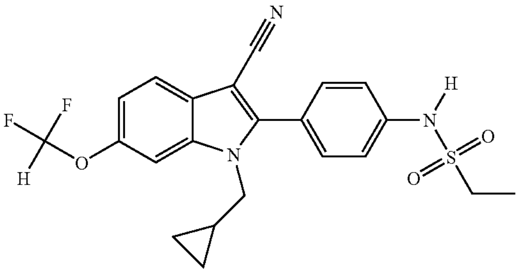
614
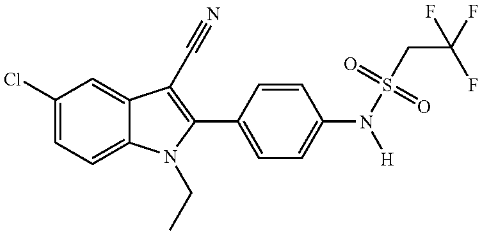
615
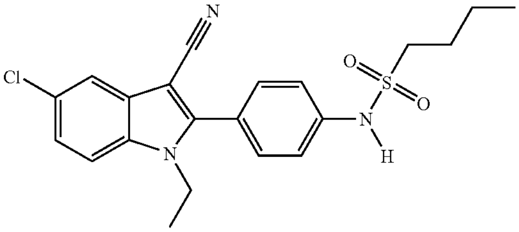
616
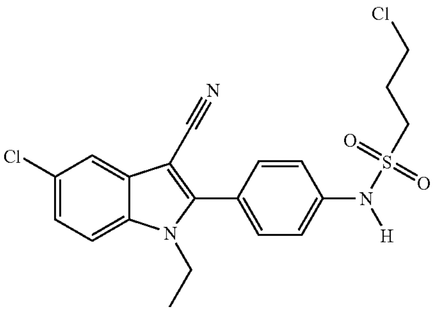
617
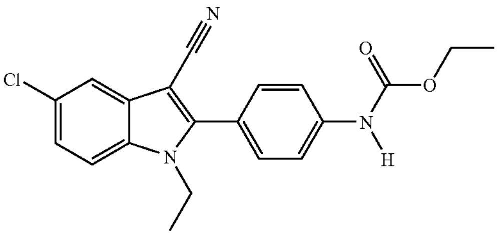
618
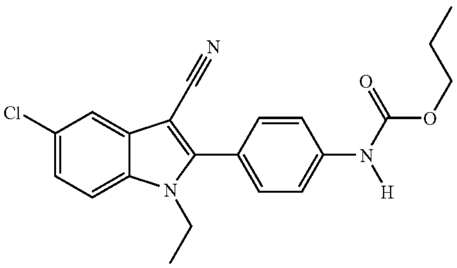
619
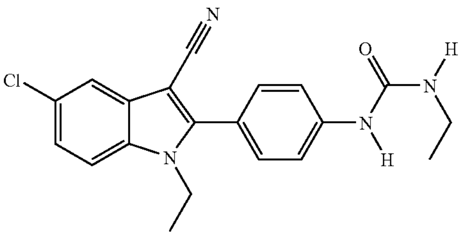
620

-continued
621
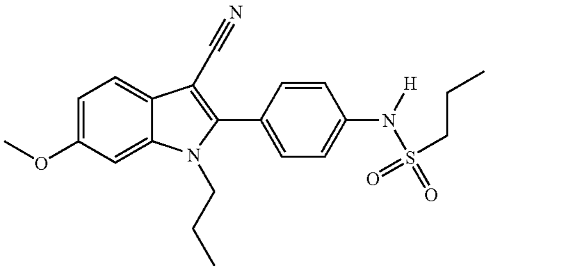
622
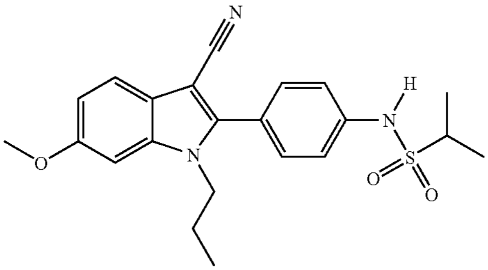
623
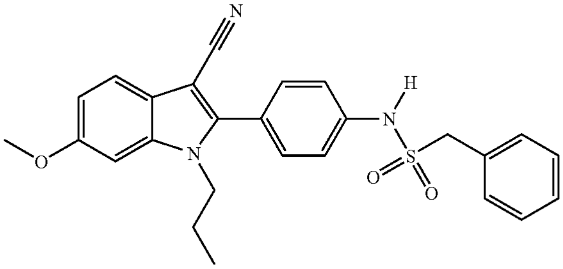
624
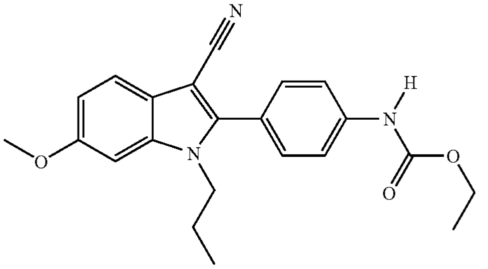
625
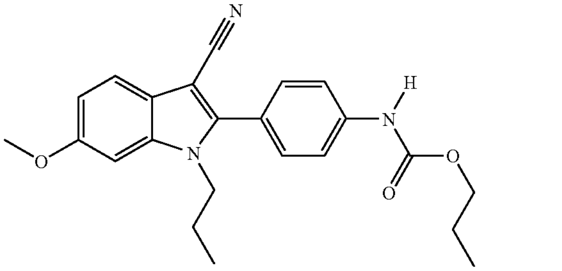
626
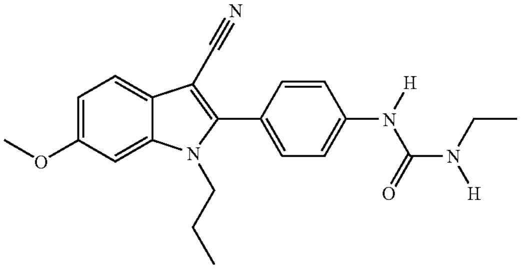
627
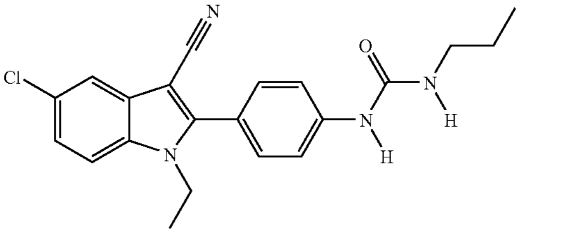
628
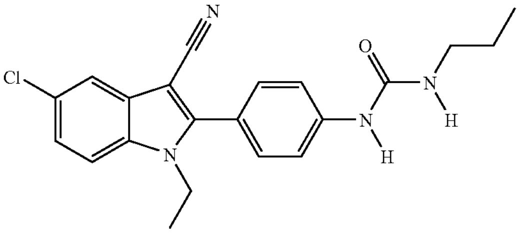
629
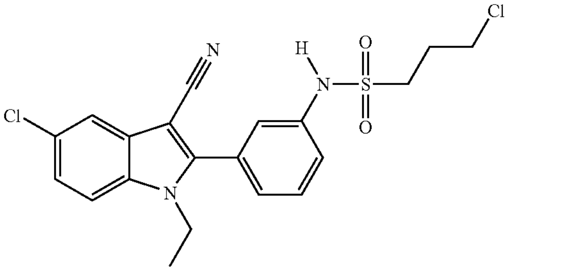
630
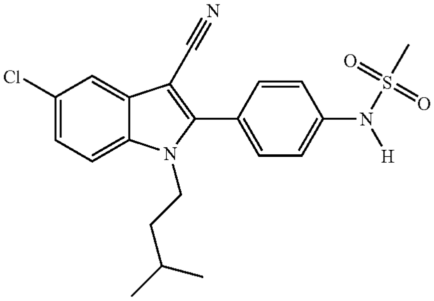

-continued
631
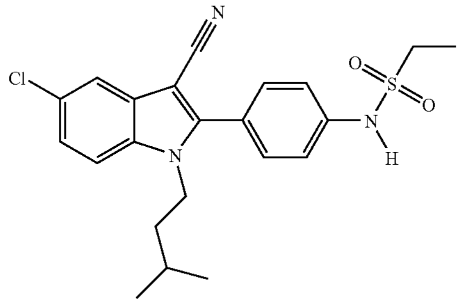
632
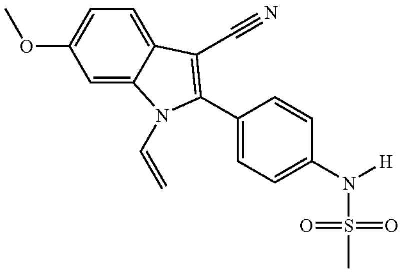
633
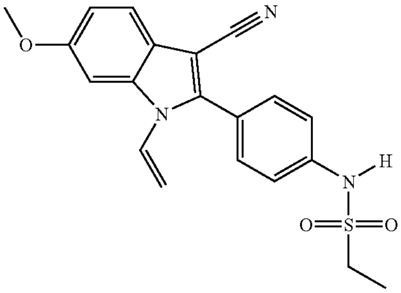
634
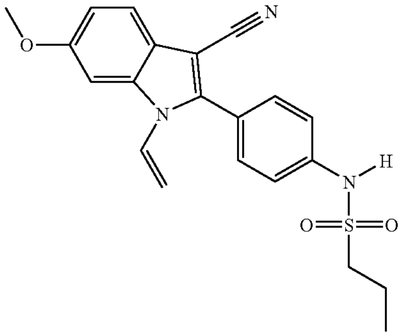
635
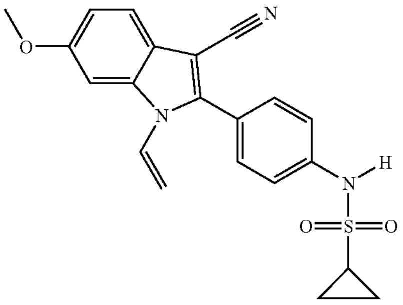
636
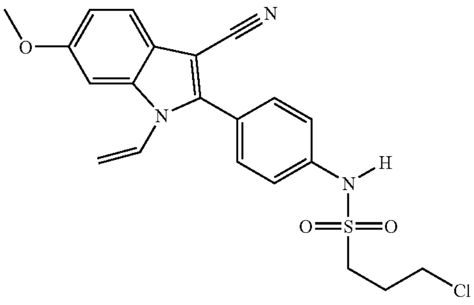
637
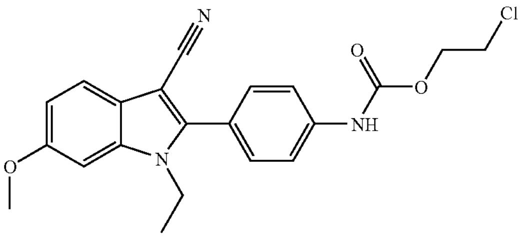
638
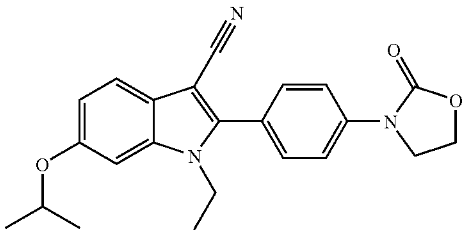
639
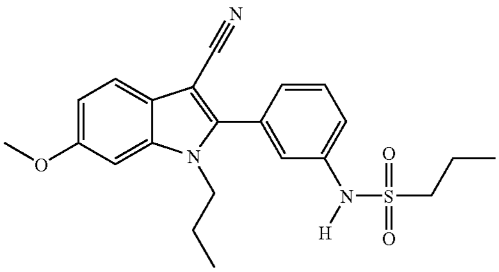
640
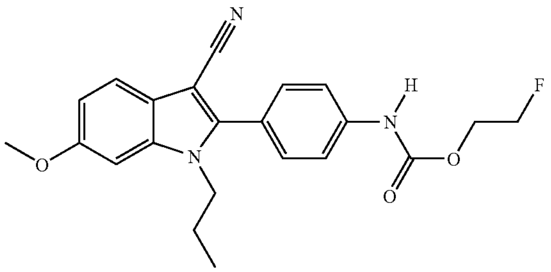

-continued
641
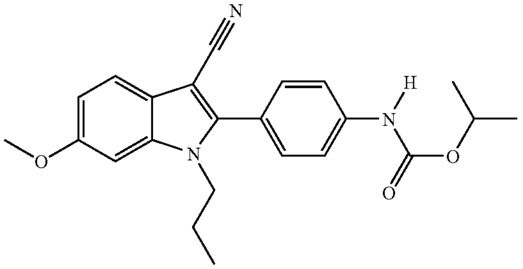
642
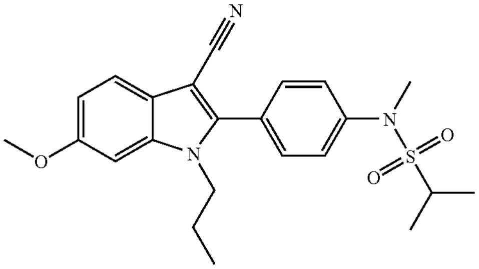
643
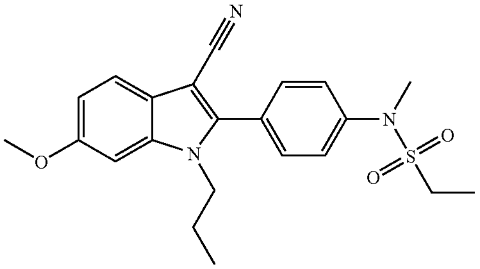
644
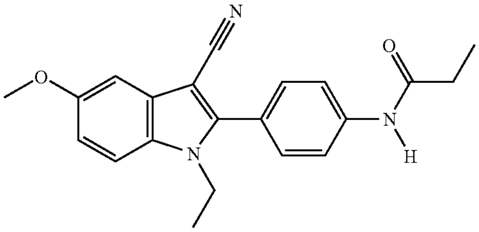
645
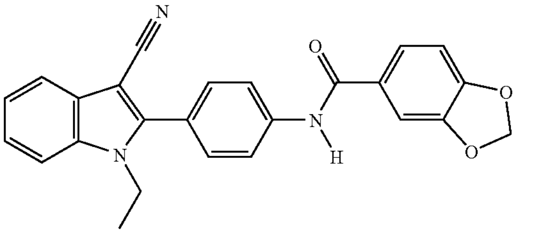
646
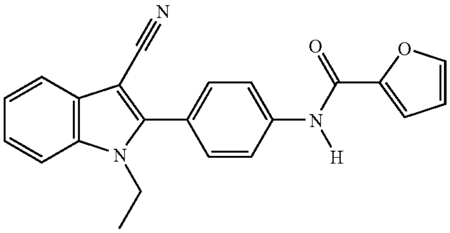
647
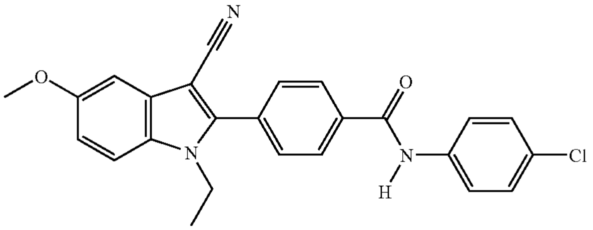
648
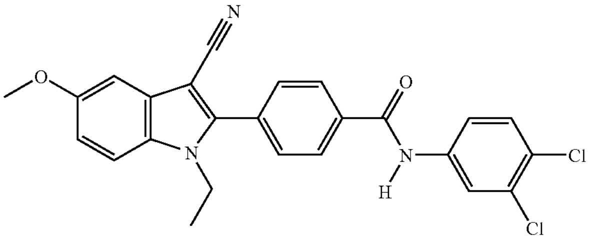
649
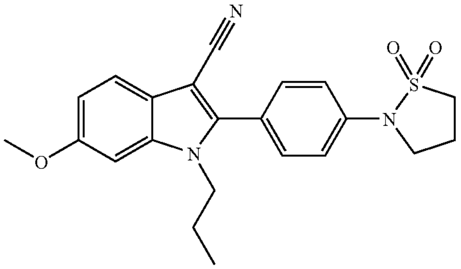
650
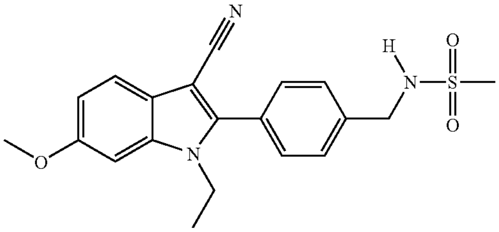
651
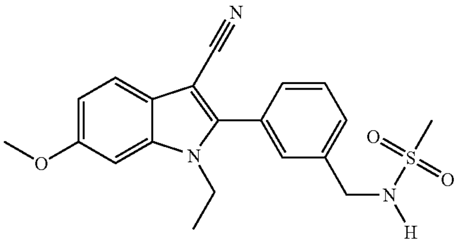
652
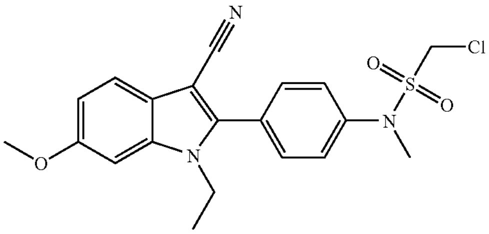

-continued
653
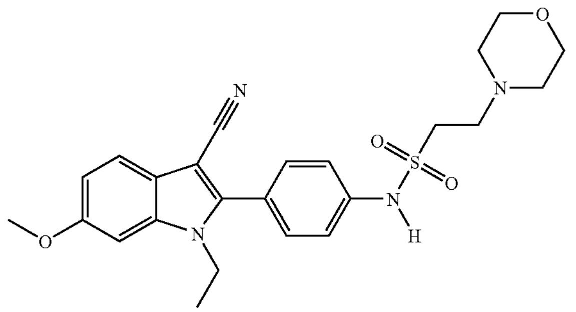
654
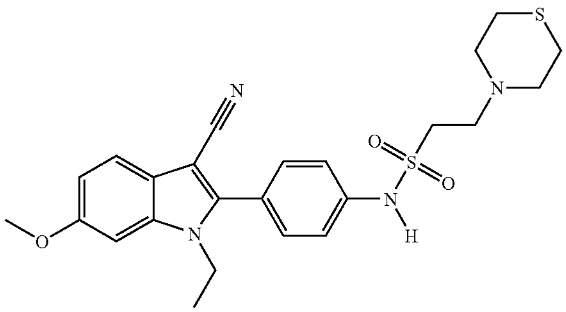
655
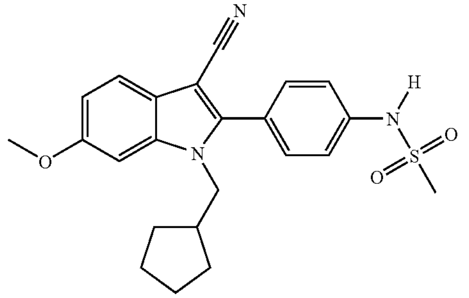
656
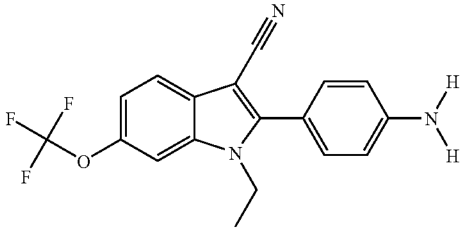
657
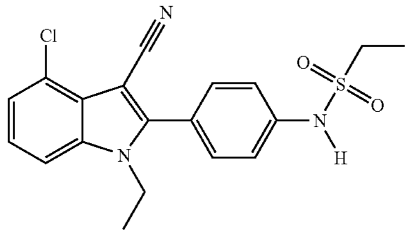
658
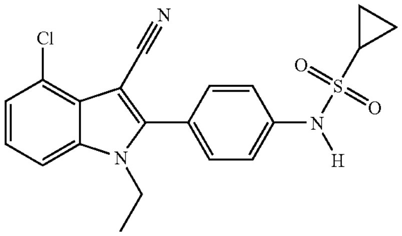
659
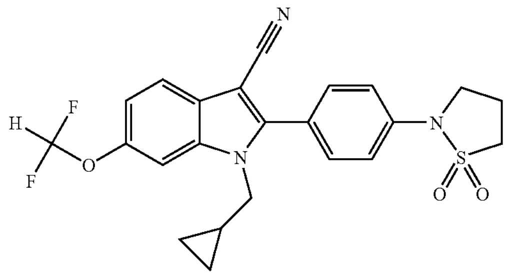
660
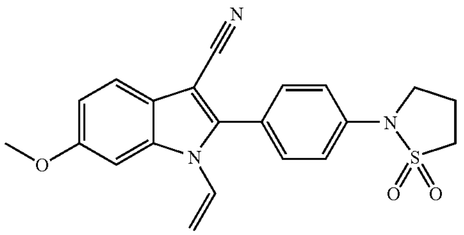
661
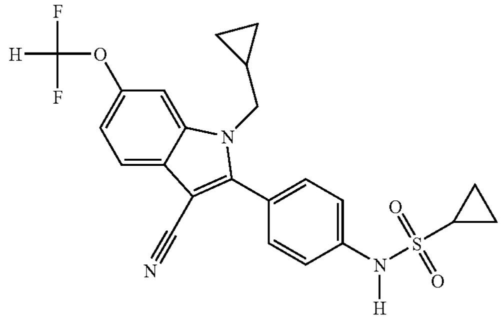
662
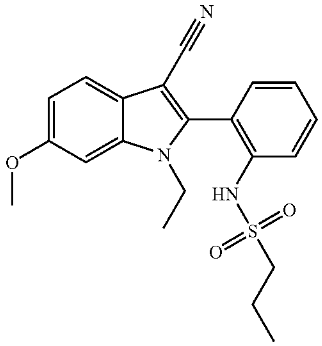

-continued
663
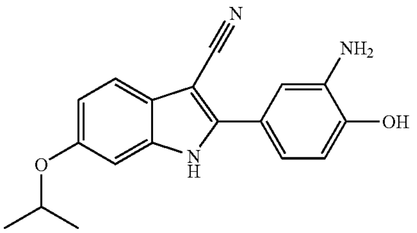
664
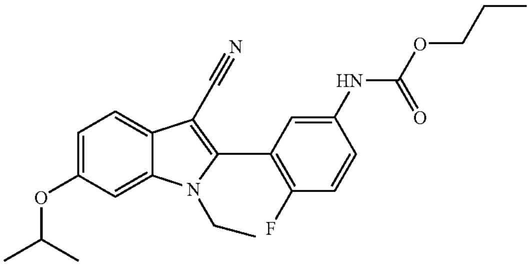
665
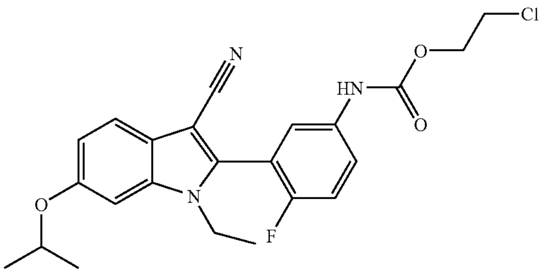
666
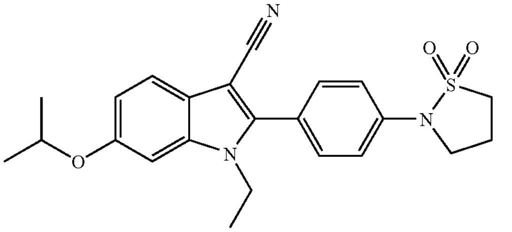
667
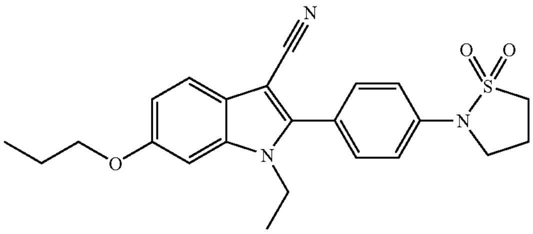
668
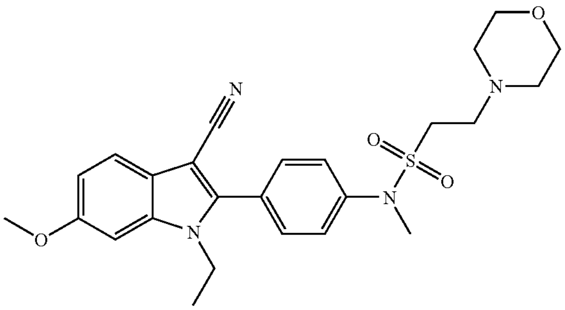
669
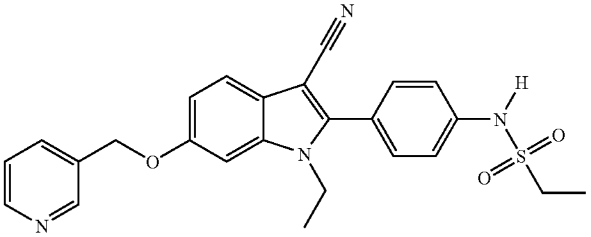
670
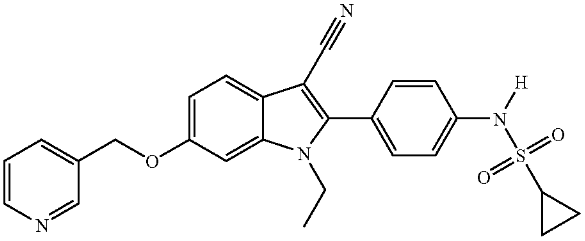
671
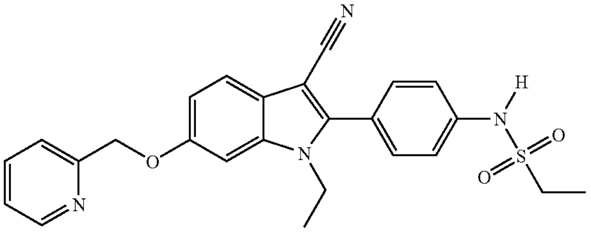
672
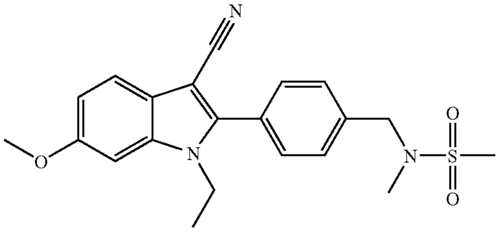

-continued
673
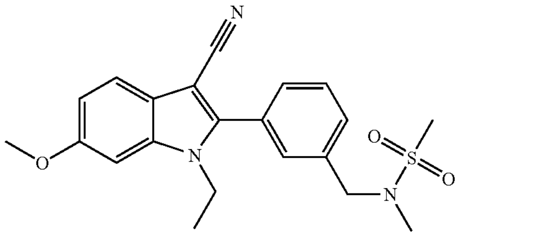
674
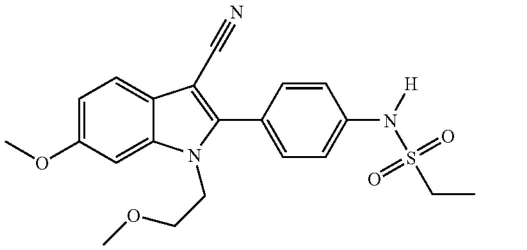
675
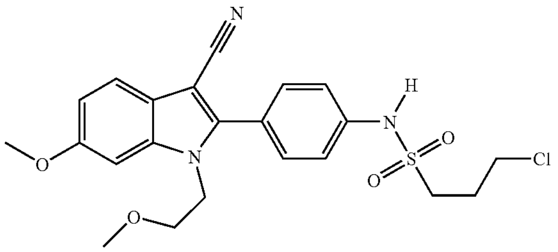
676
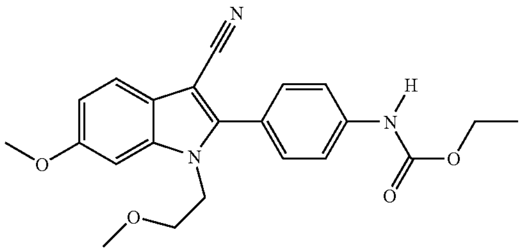
677
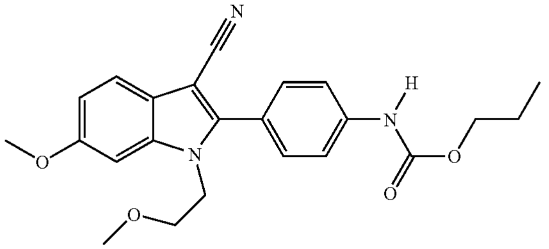
678
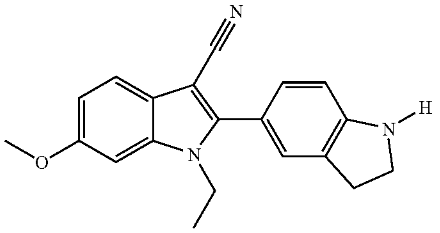
679
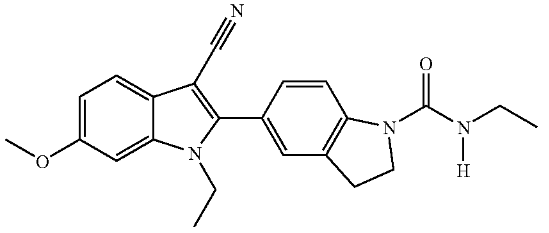
680
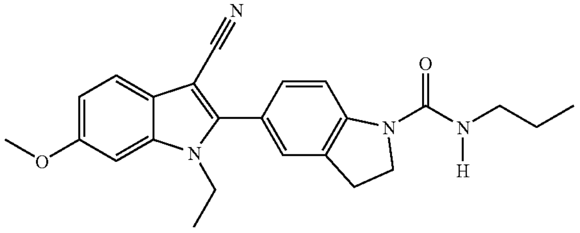
681
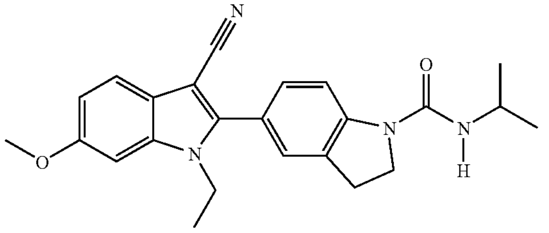
682
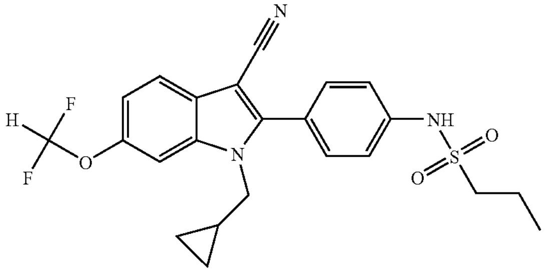
683
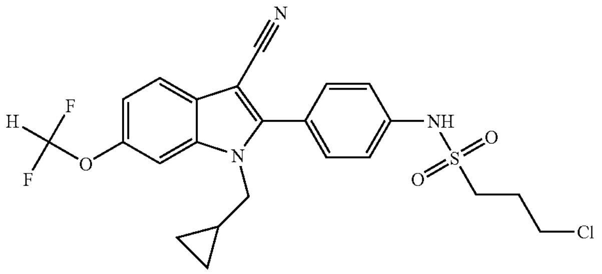
684
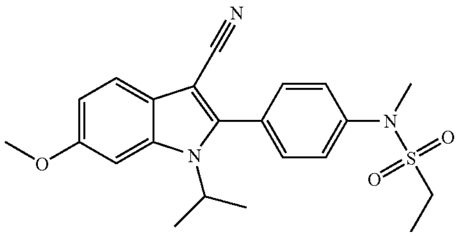

-continued
685
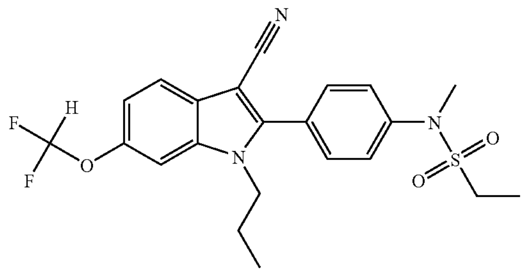
686
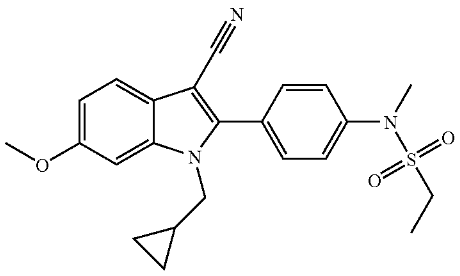
687
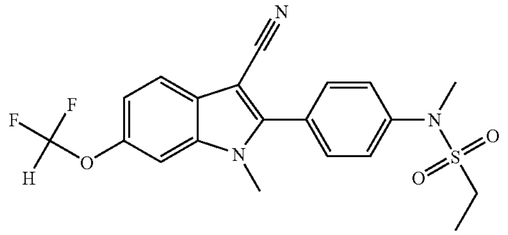
688
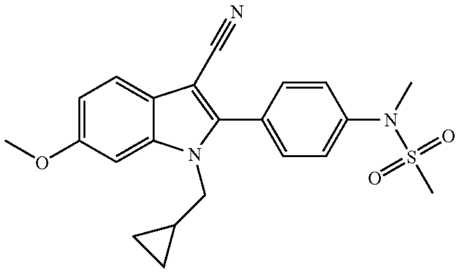
689
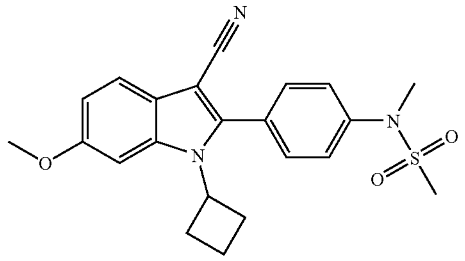
690
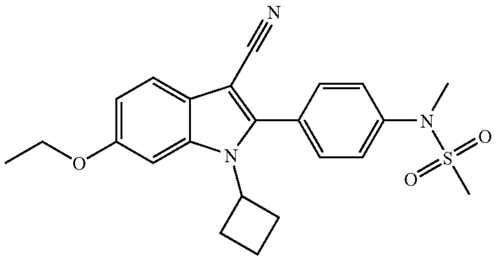
691
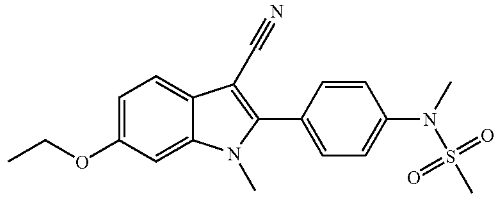
692
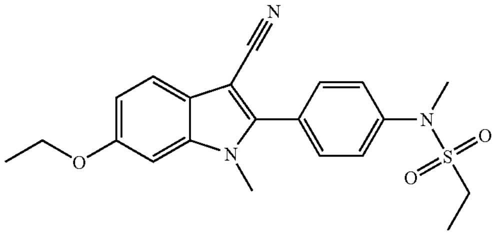
693
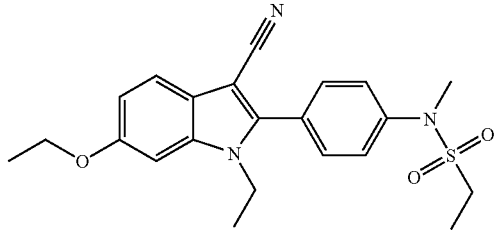
694
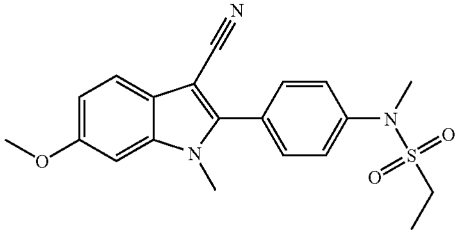
695
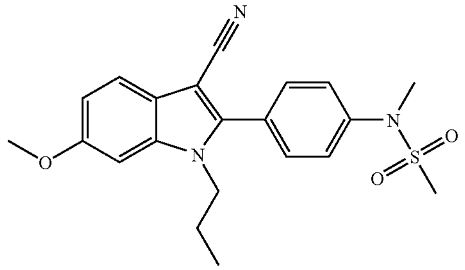
696
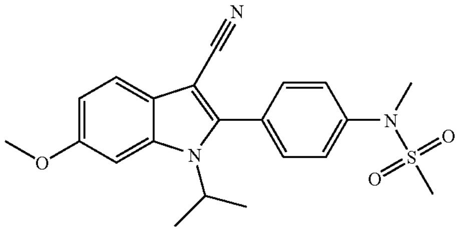

-continued
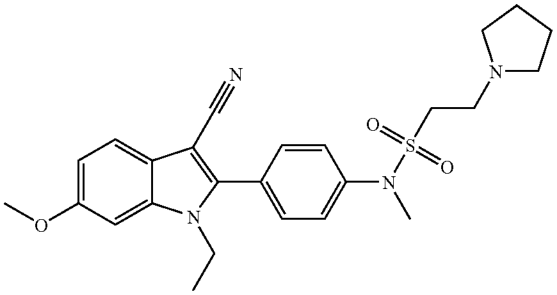
697
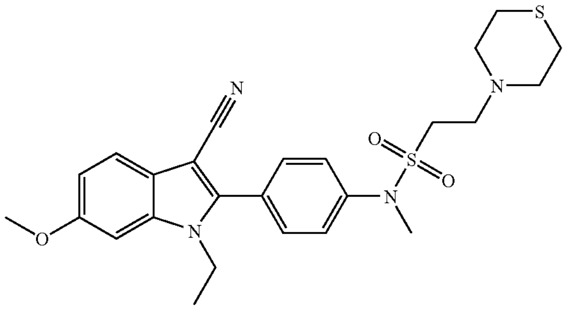
698
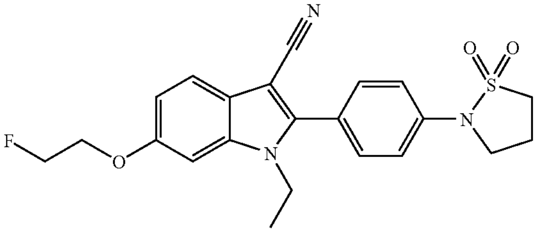
699
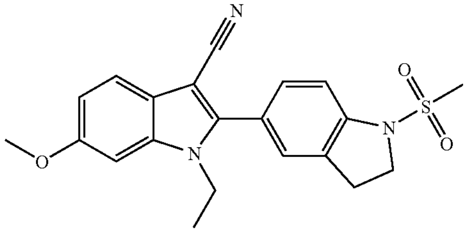
701
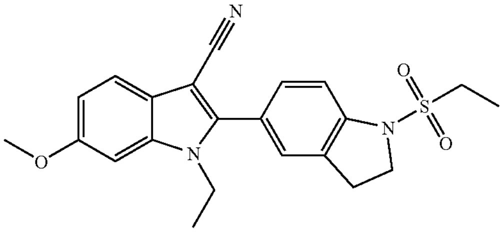
702
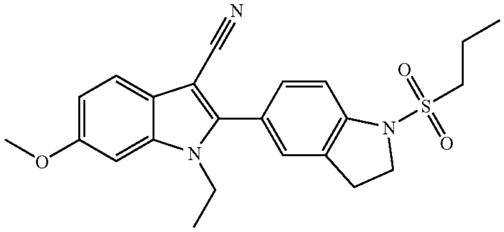
703
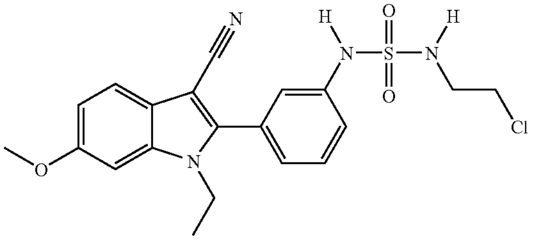
704
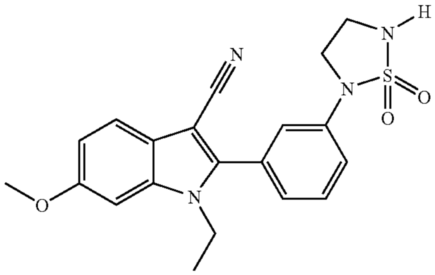
705
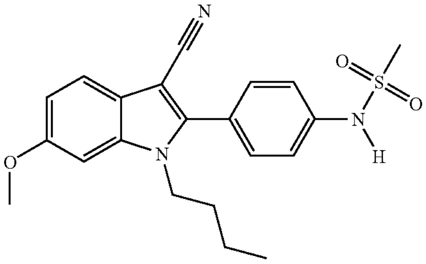
706
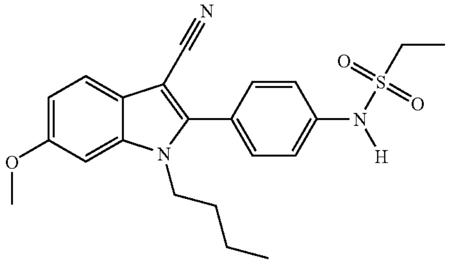
707
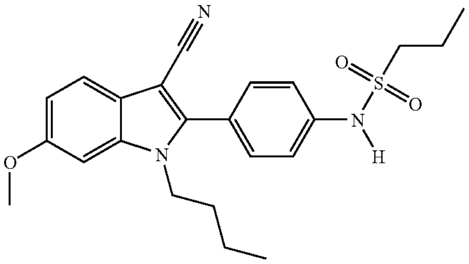
708
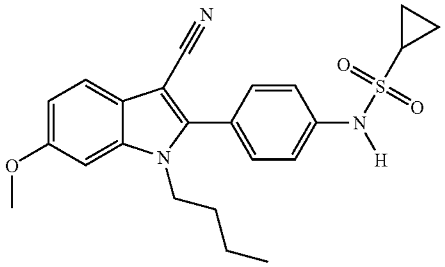
709

-continued
710
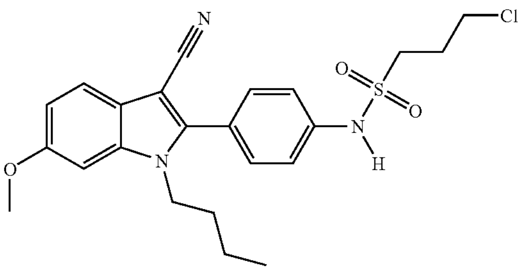
711
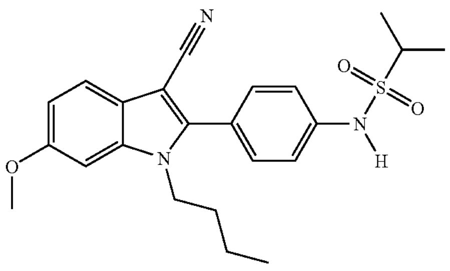
712
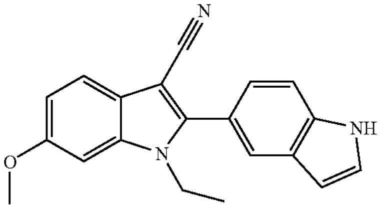
713
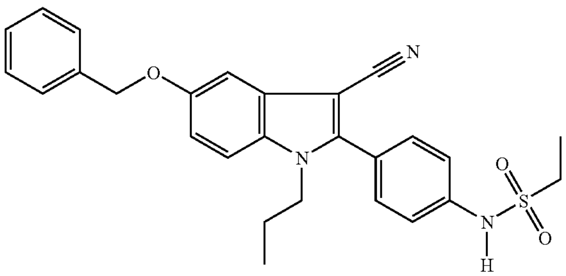
714
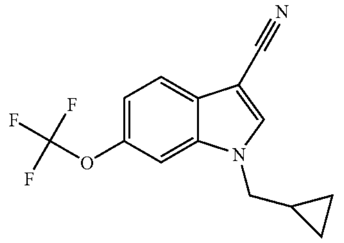
715
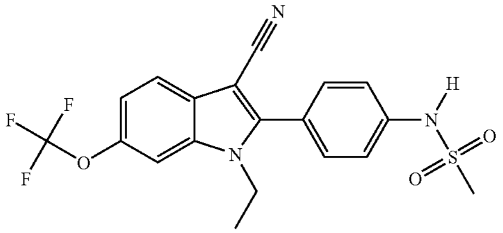
716
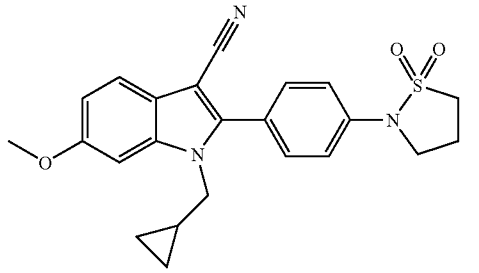
717
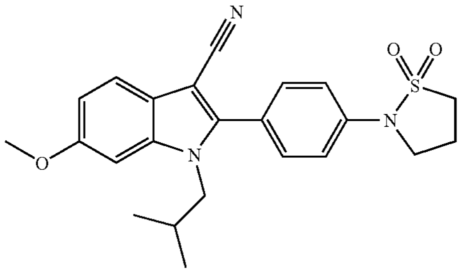
718
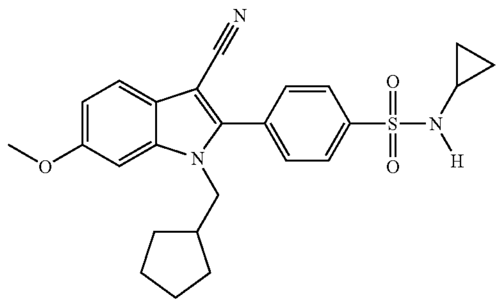
719
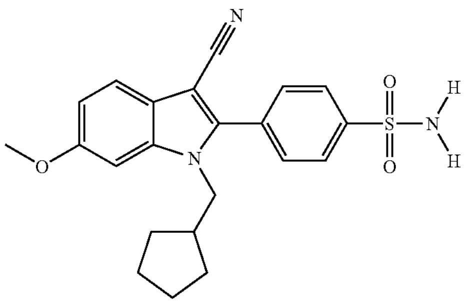

-continued
720
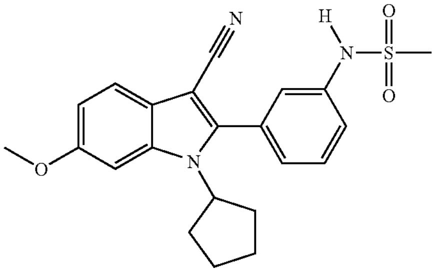
721
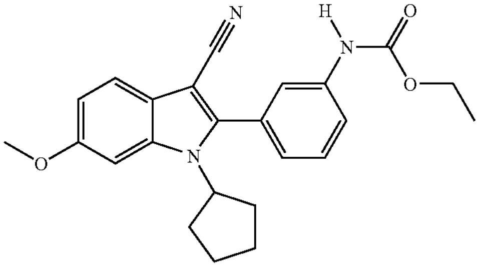
722
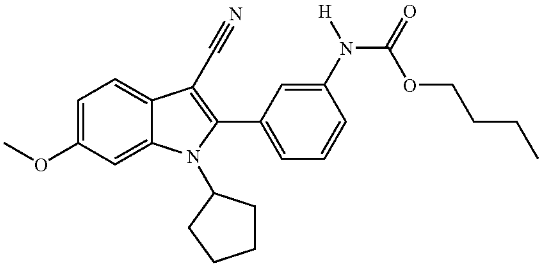
723
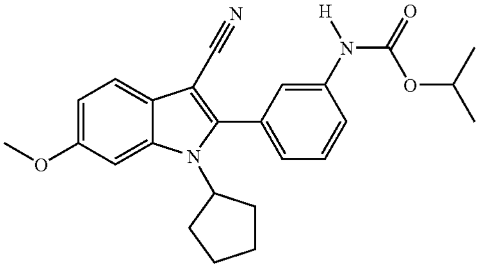
724
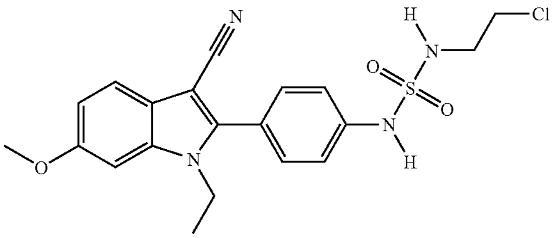
725
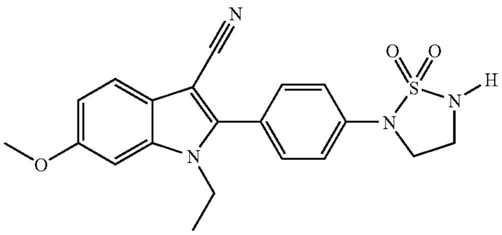
726
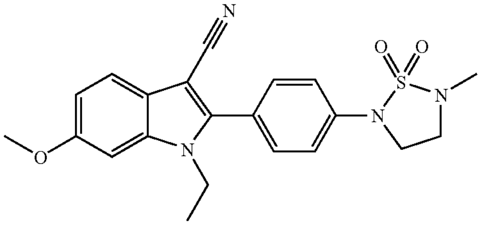
727
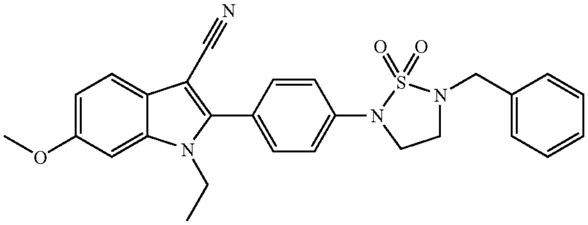
728
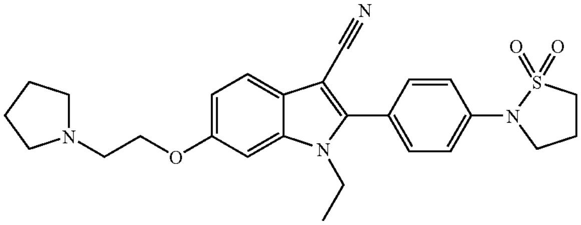
729
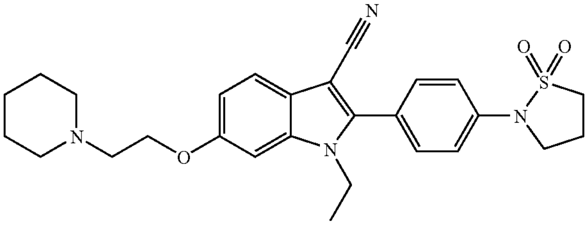
730
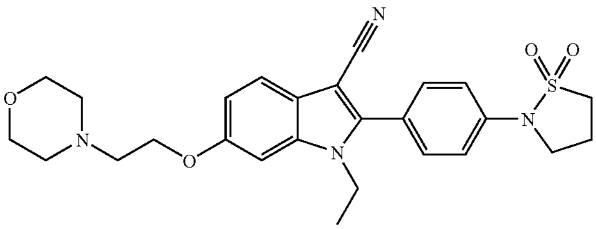
731
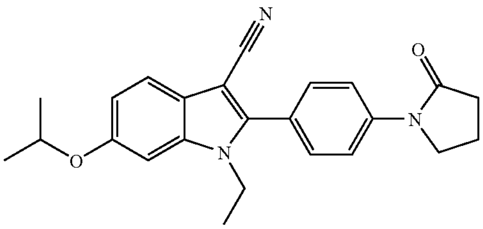

-continued
732
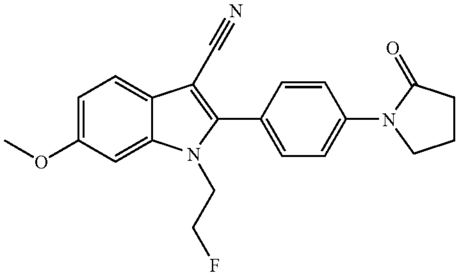
733
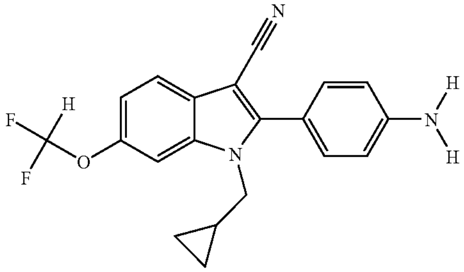
734
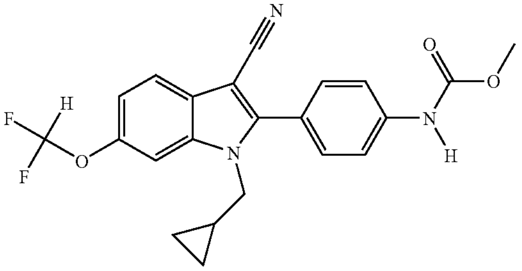
735
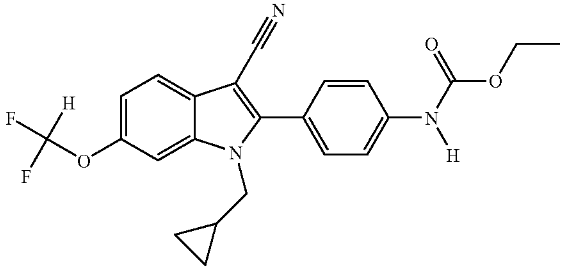
736
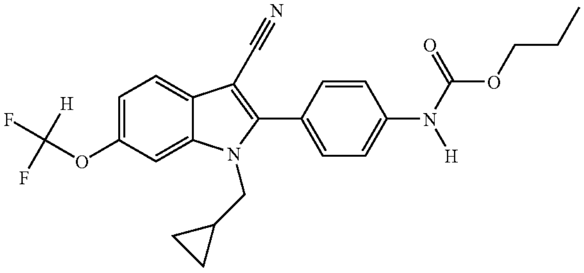
737
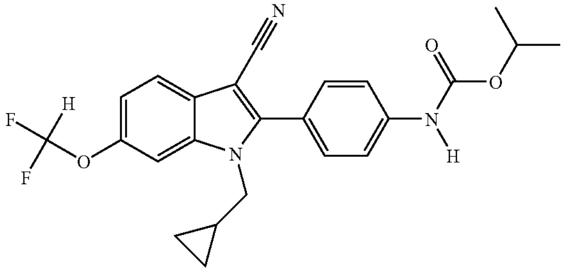
738
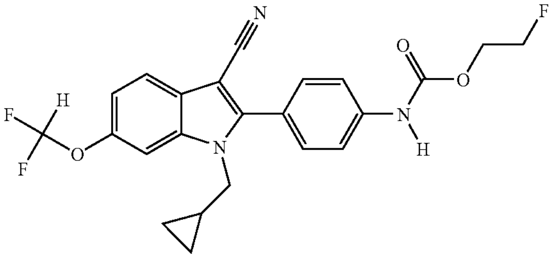
739
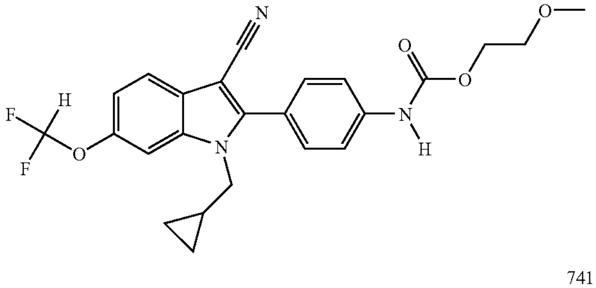
740
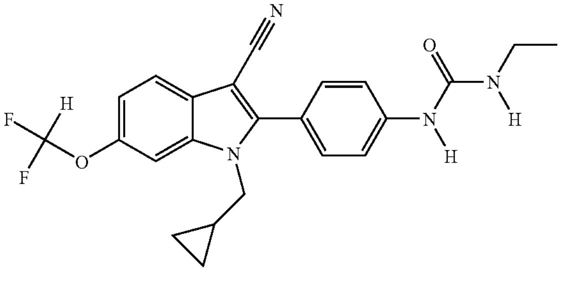
741
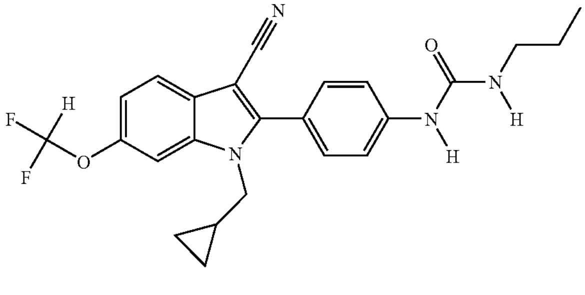

-continued
742
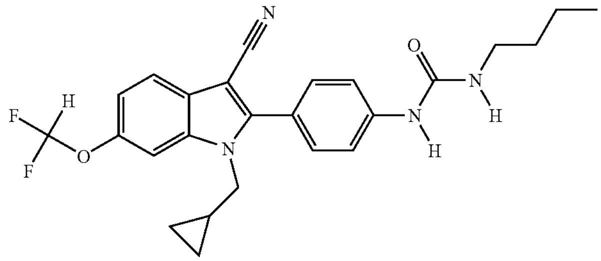
743
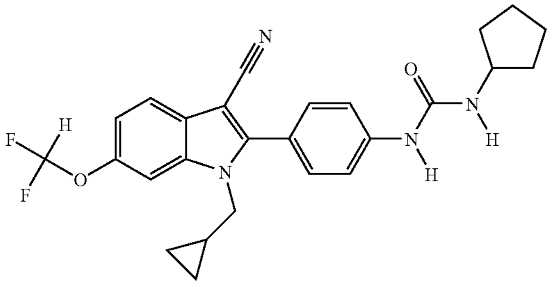
744
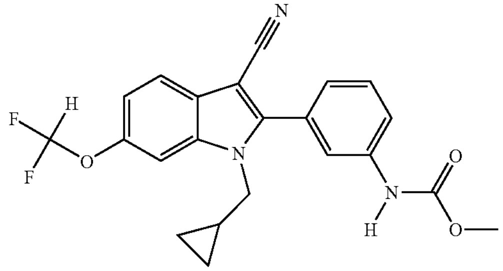
745
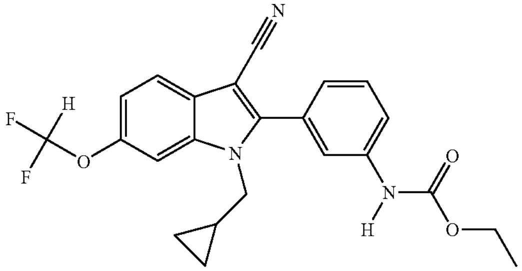
746
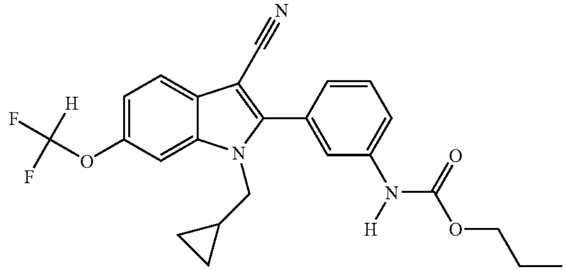
747
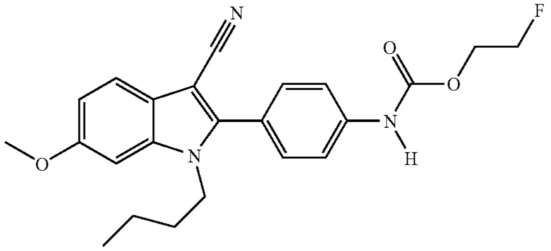
748
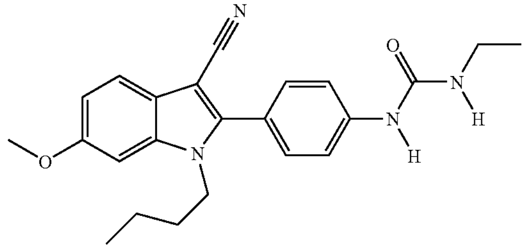
749
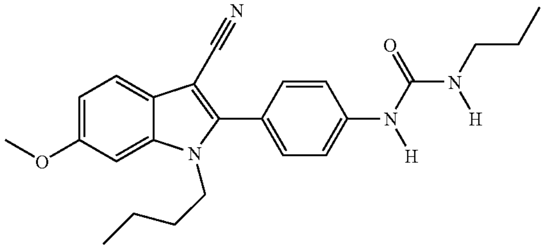
750
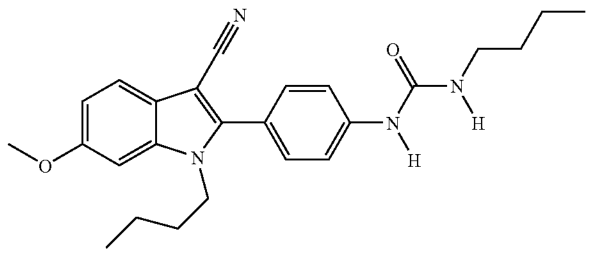
751
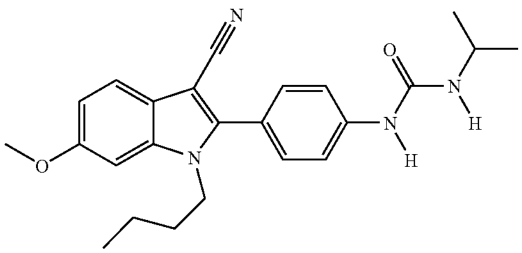

-continued
752
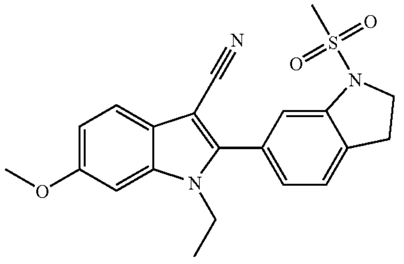
753
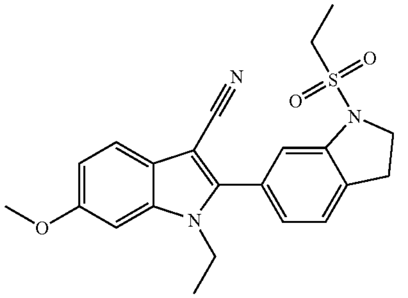
754
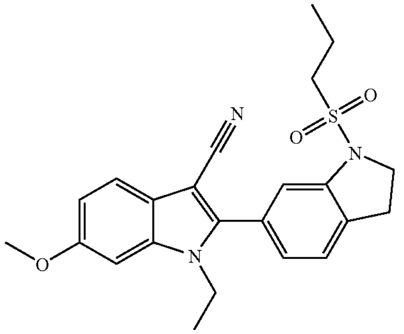
755
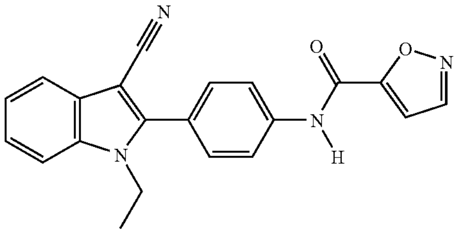
756
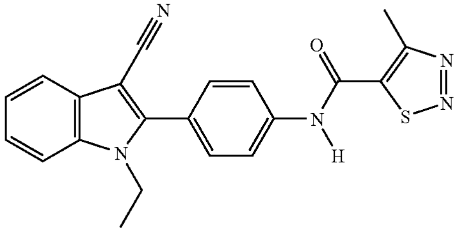
757
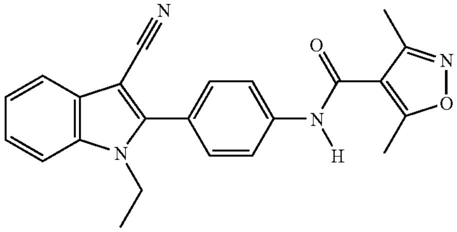
758
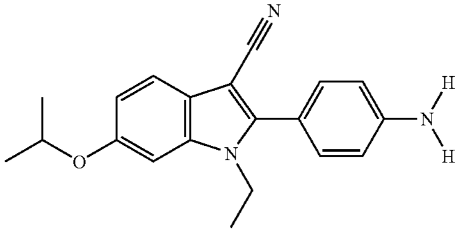
759
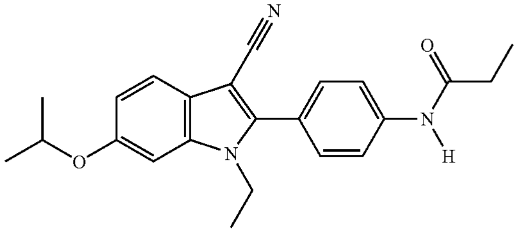
760
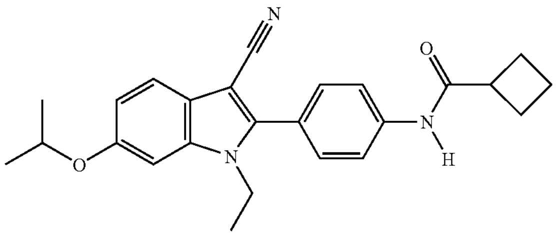
761
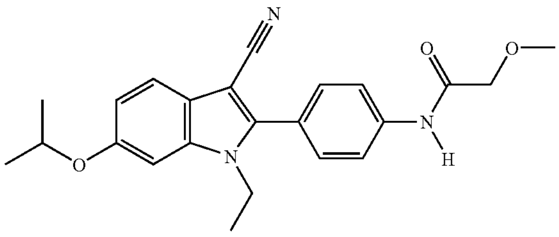
762
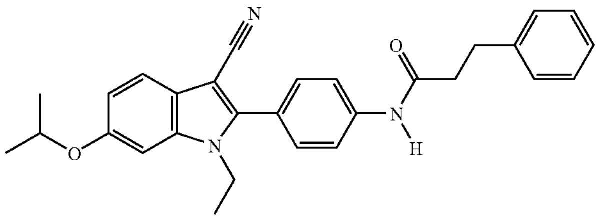
763
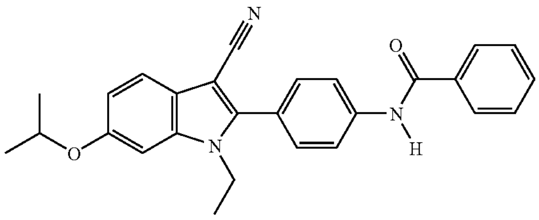

-continued
764
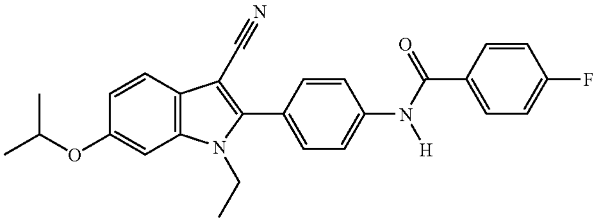
765
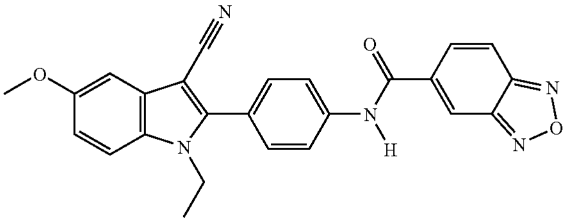
766
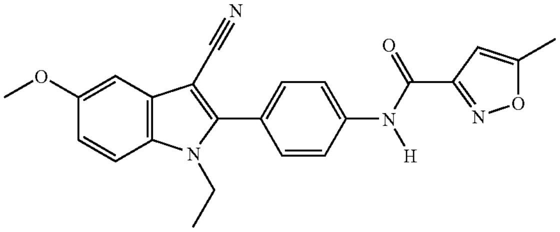
767
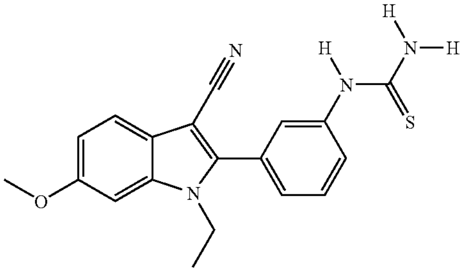
768
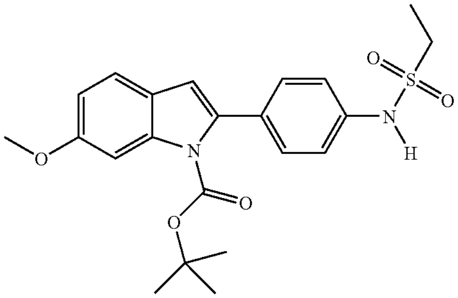
769
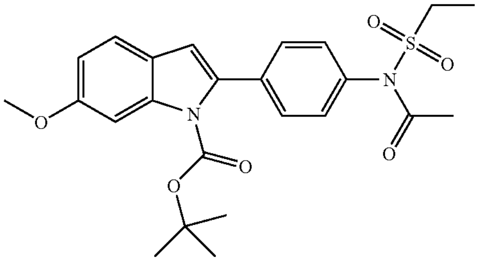
770
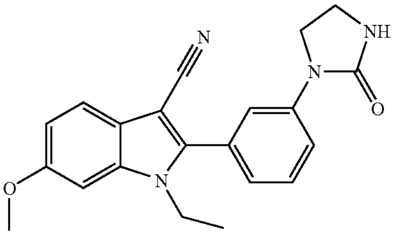
771
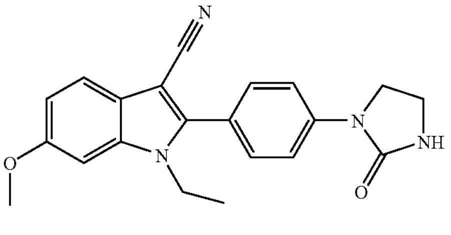
772
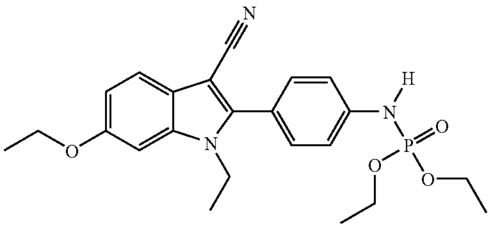
773
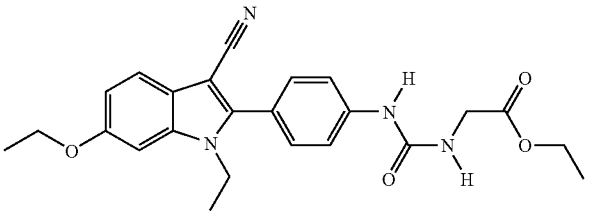
774
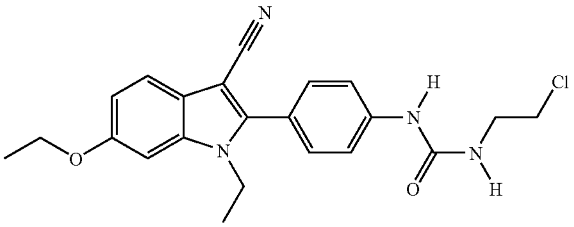
775
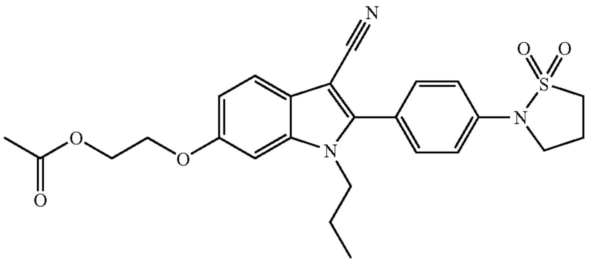

-continued
776
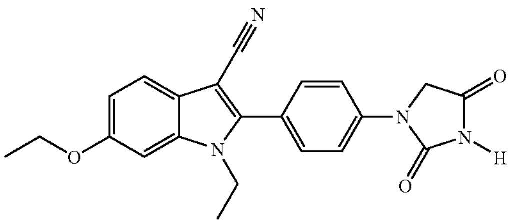
777
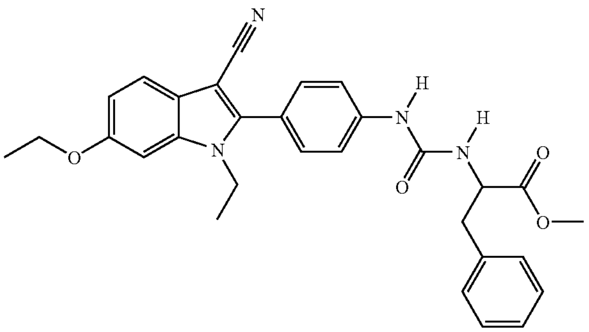
778
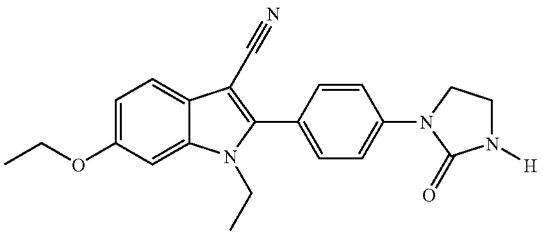
779
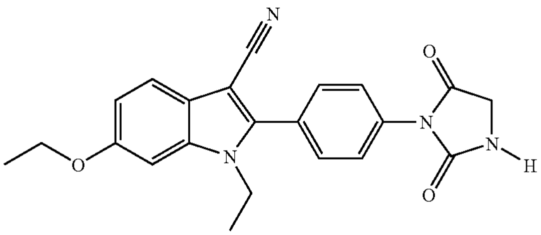
780
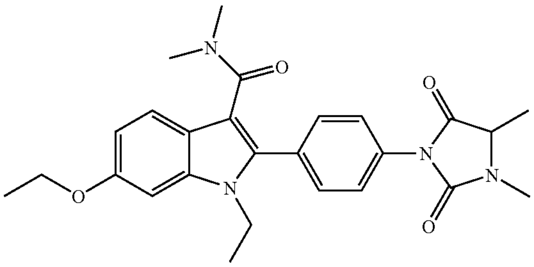
781
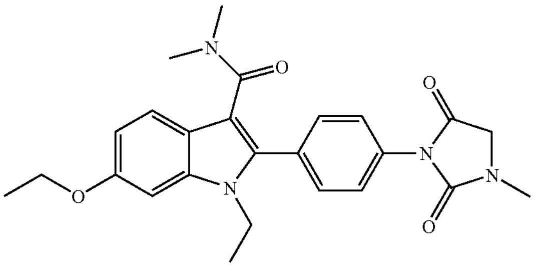
782
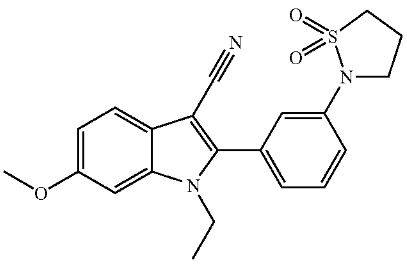
783
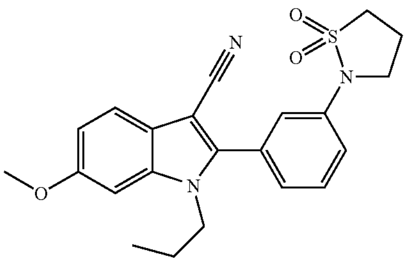
784
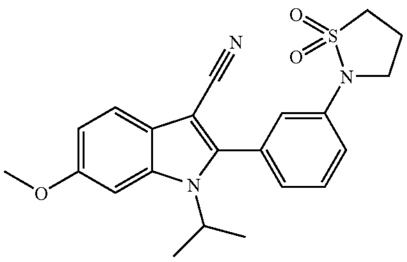
785
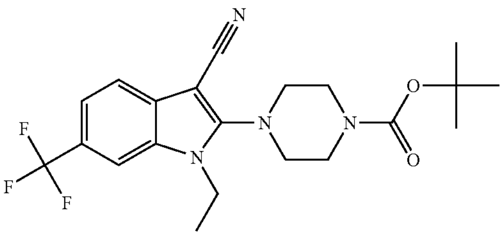

-continued
786
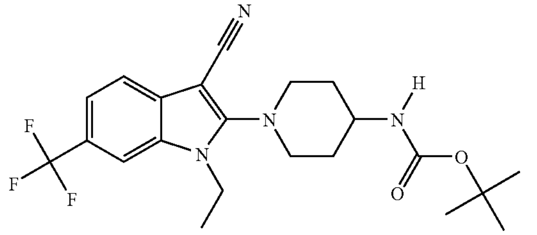
787
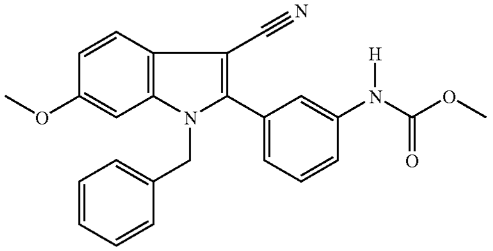
788
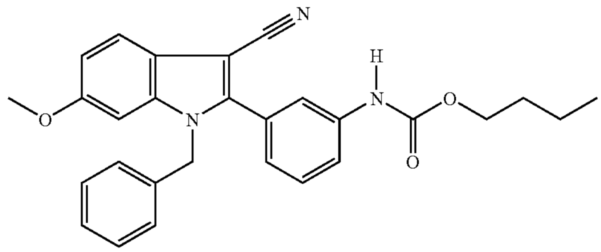
789
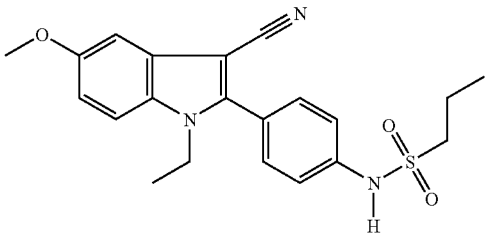
790
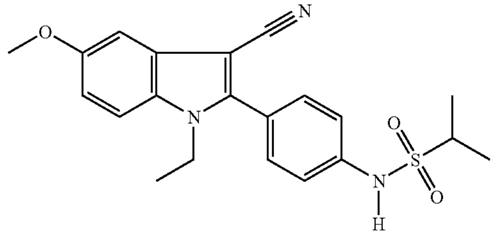
791
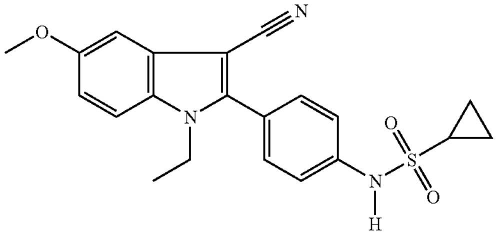
792
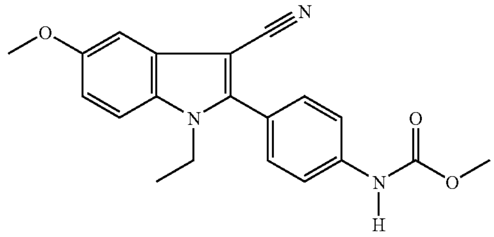
793
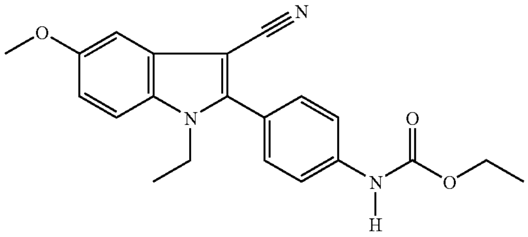
794
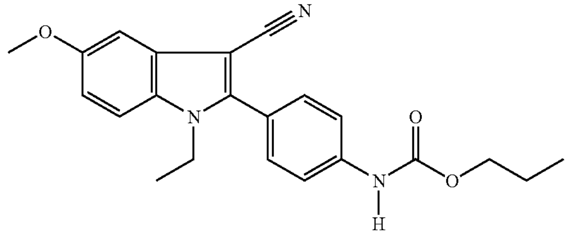
795
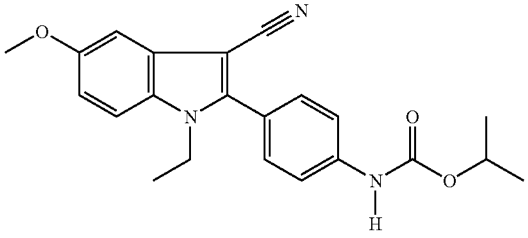
796
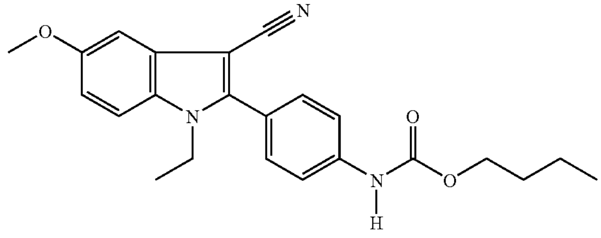
797
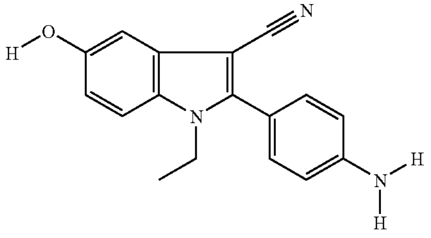

-continued
798
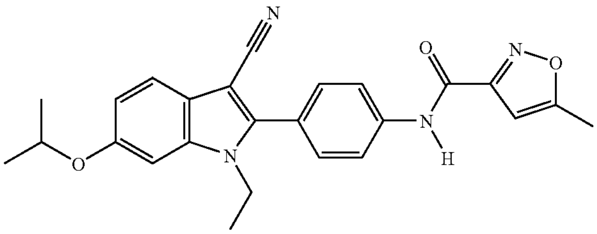
799
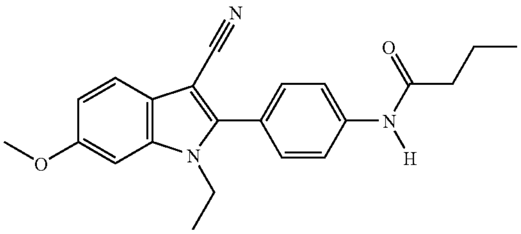
801
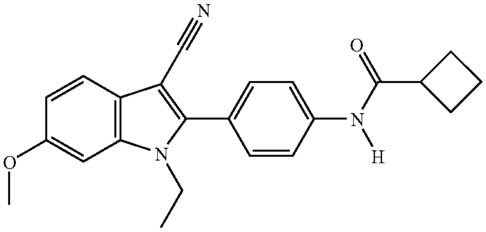
802
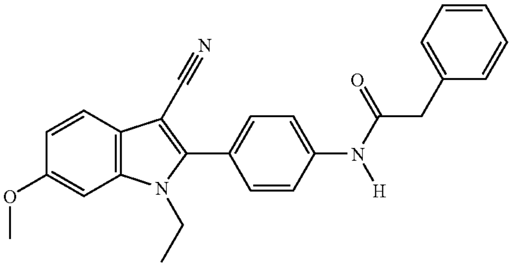
803
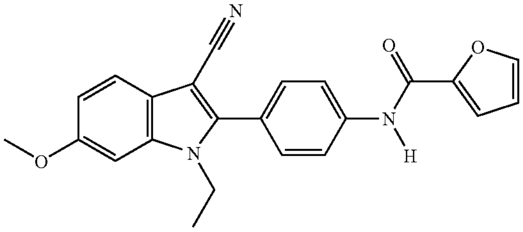
804
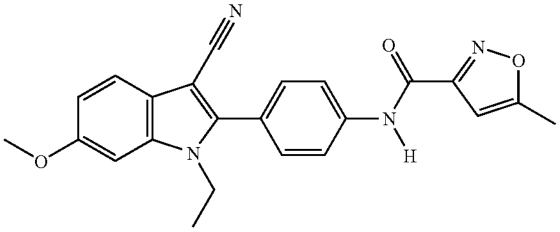
805
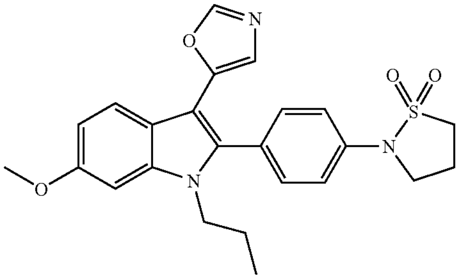
806
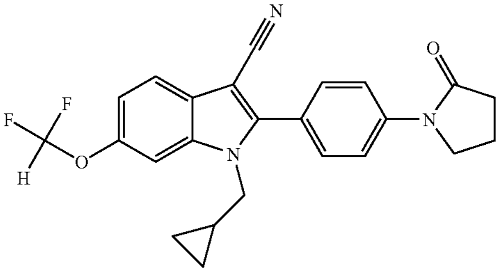
807
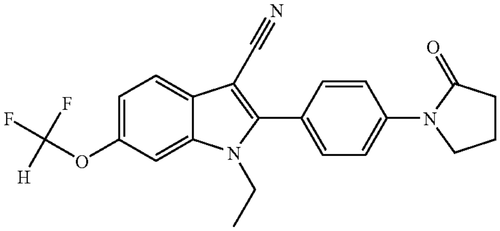
808
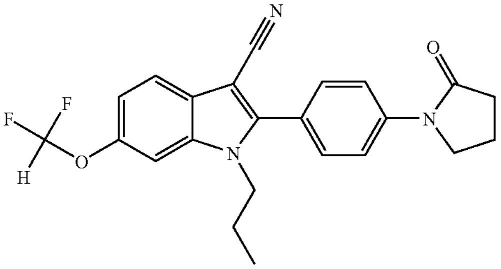
809
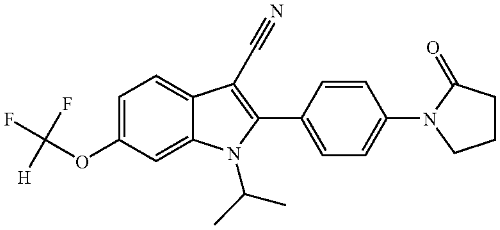
810
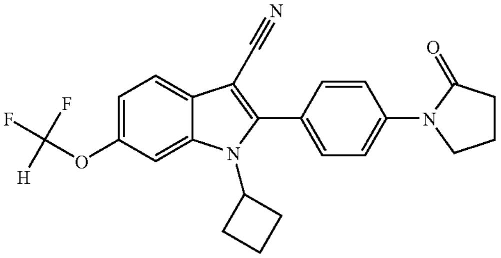

-continued
811
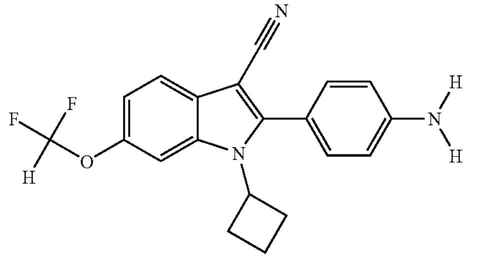
812
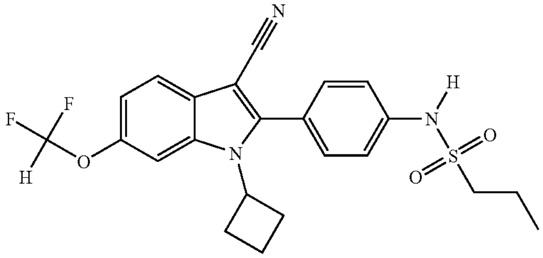
813
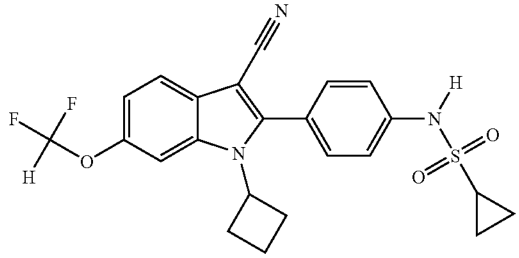
814
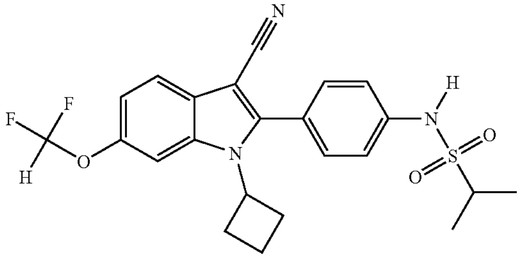
815
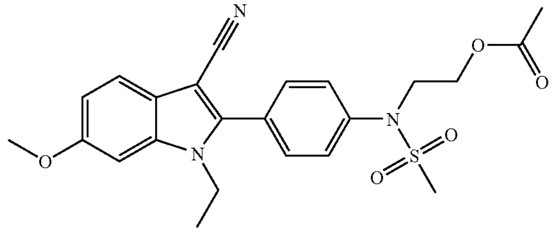
816
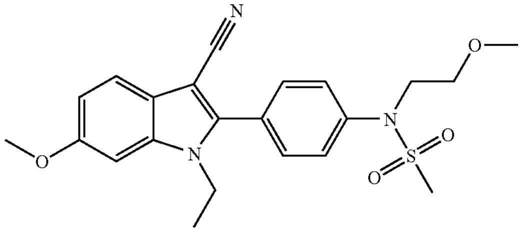
817
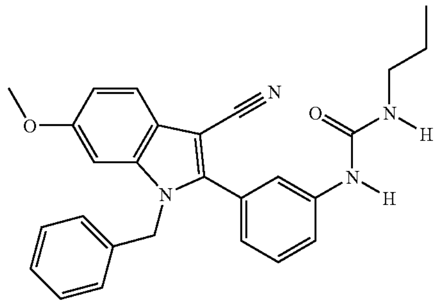
818
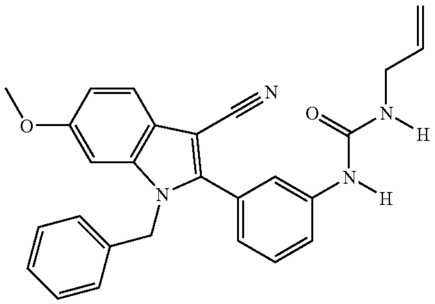
819
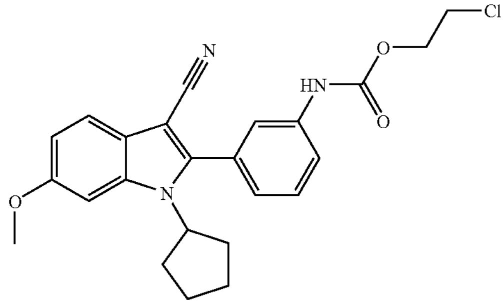
820
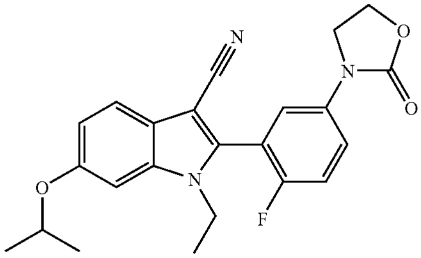

-continued
821
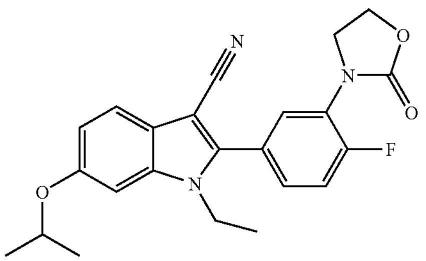
822
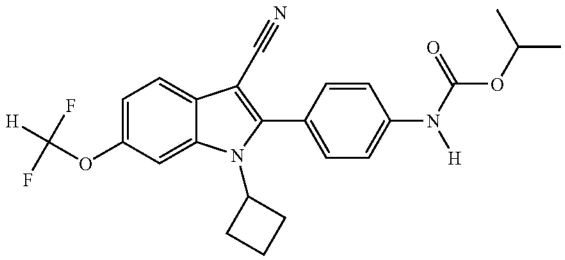
823
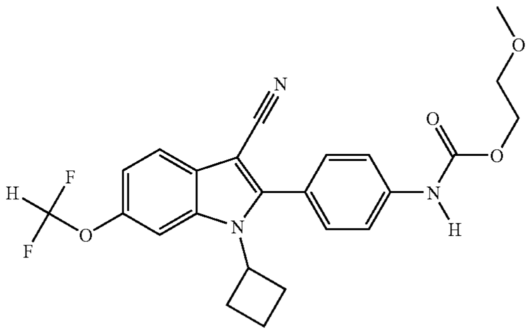
824
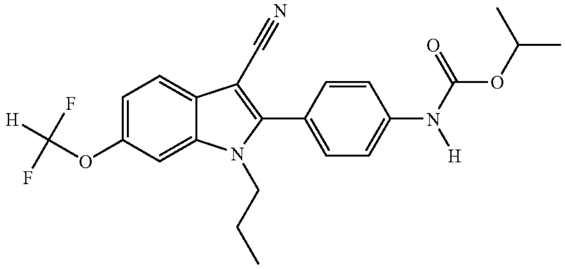
825
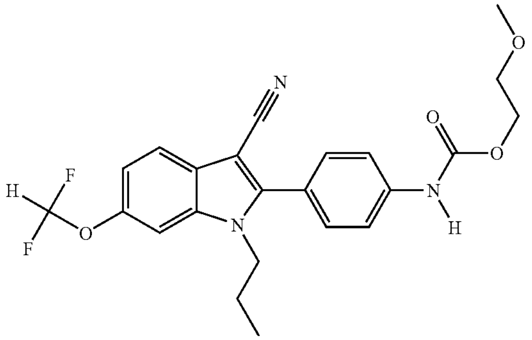
826
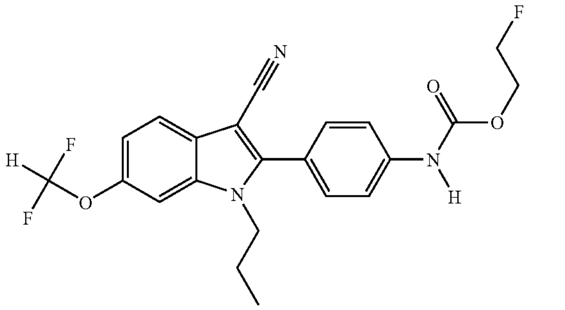
827
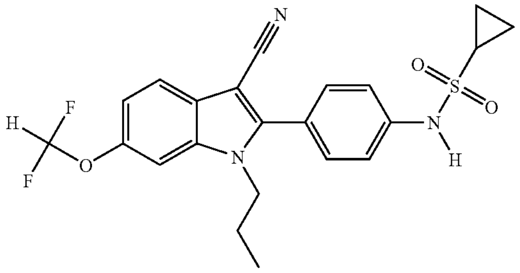
828
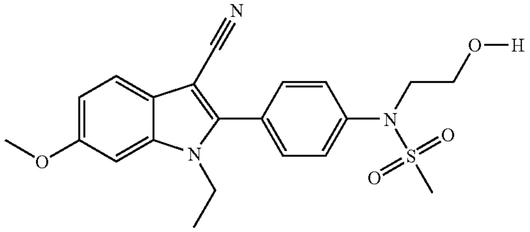
829
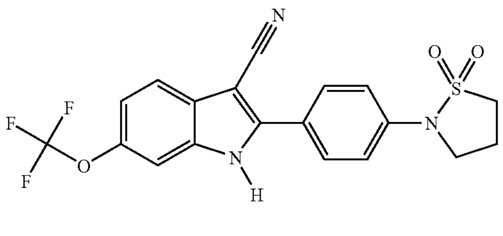
830
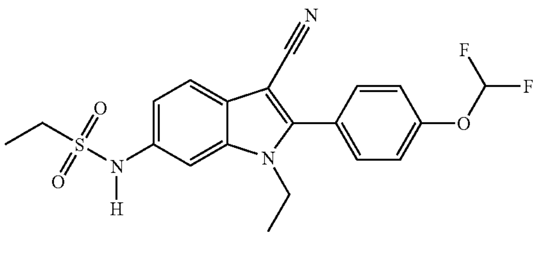

-continued
831
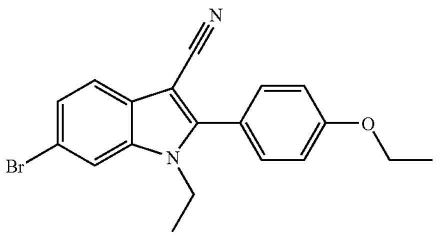
832
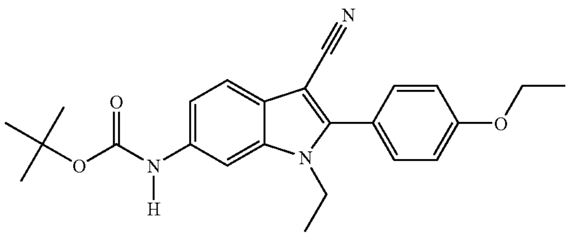
833
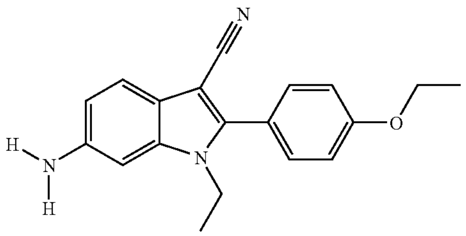
834
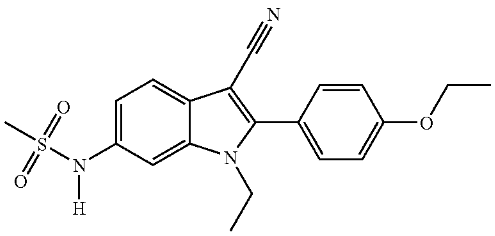
835
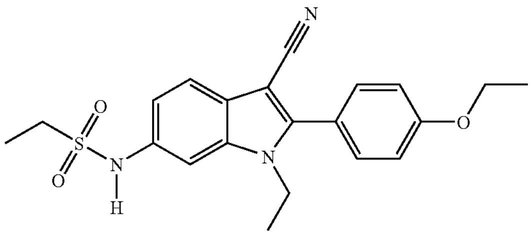
836
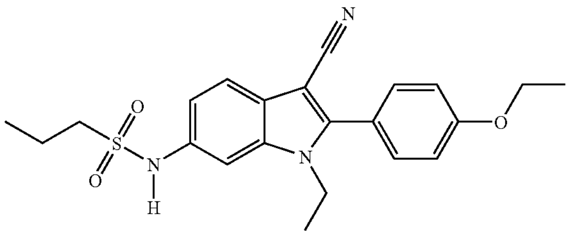
837
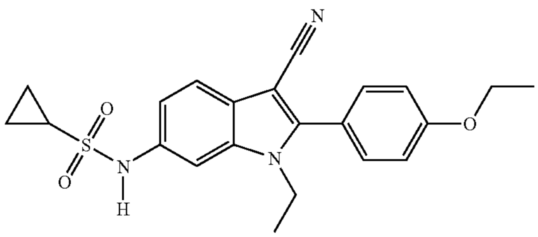
838
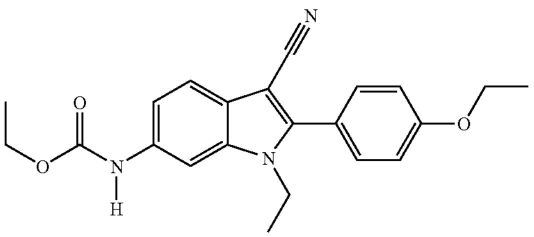
839
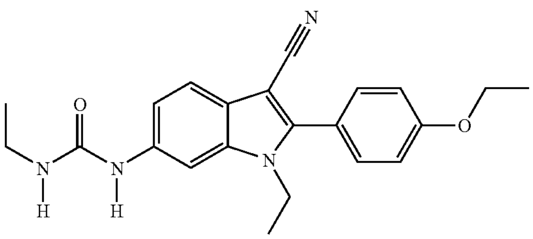
840
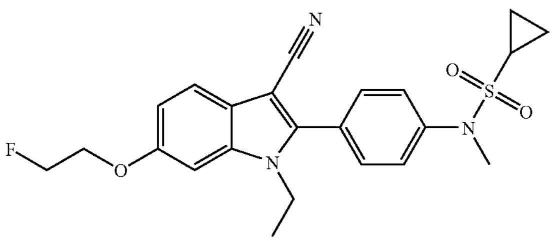
841
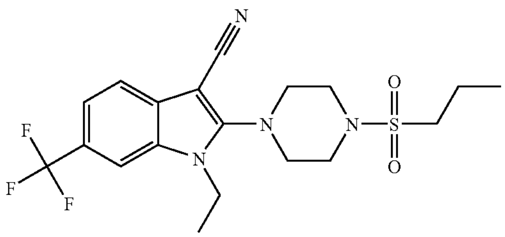
842
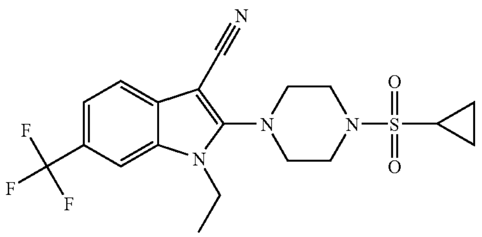

-continued
843
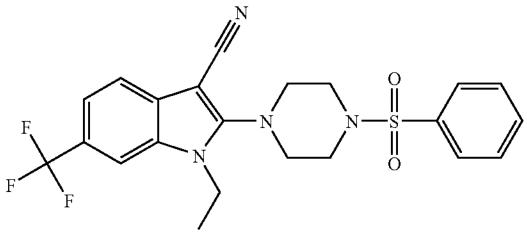
844
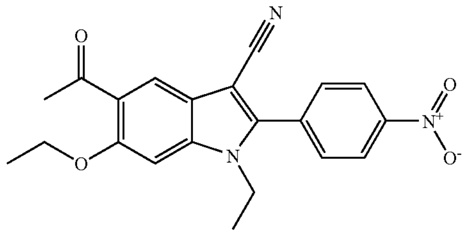
845
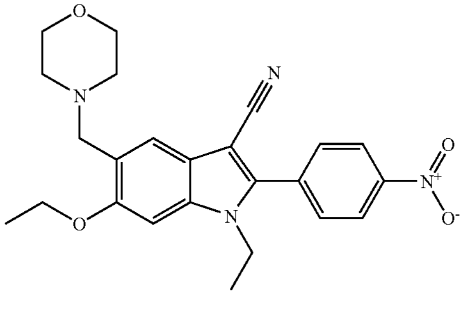
846
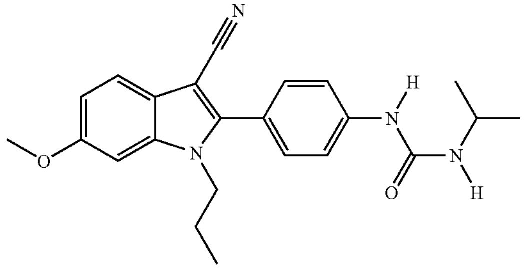
847
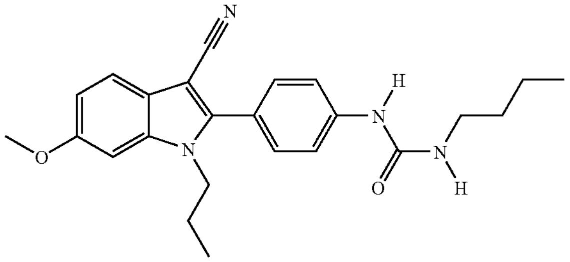
848
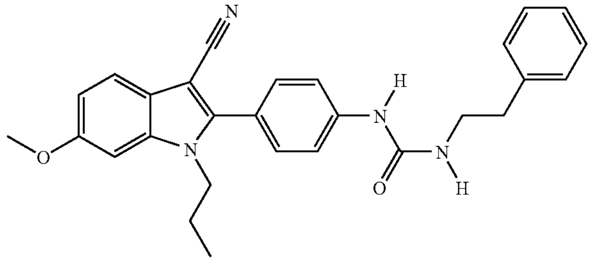
849
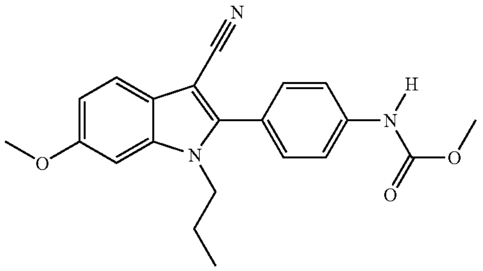
850
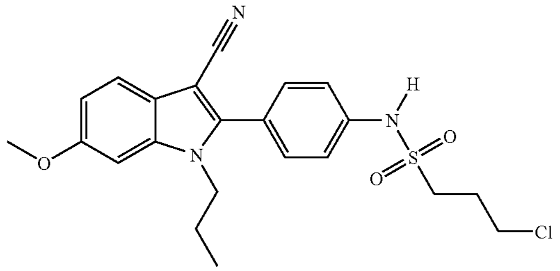
851
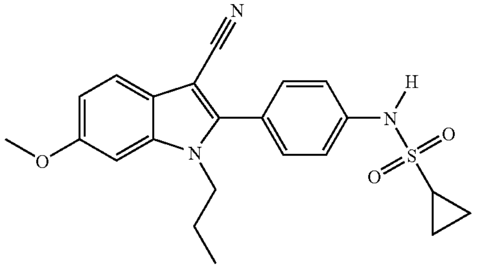
852
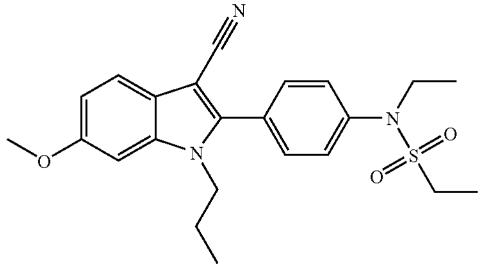
853
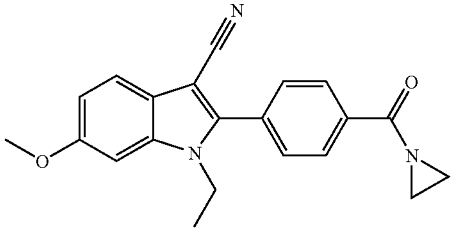
854
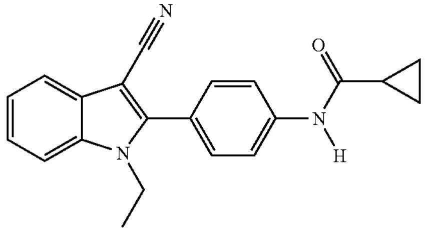

-continued
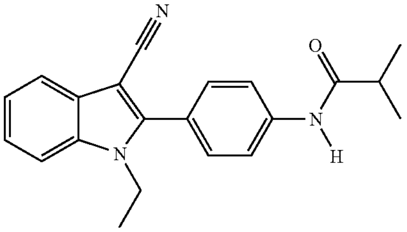
855
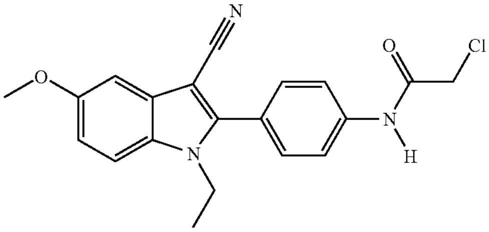
856
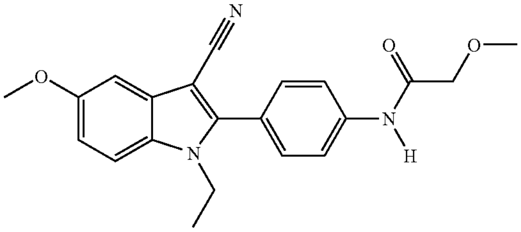
857
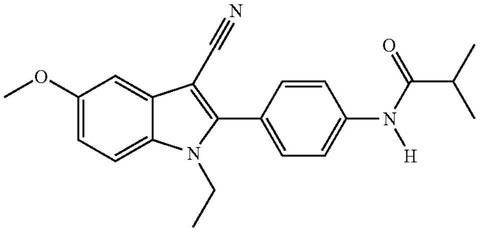
858
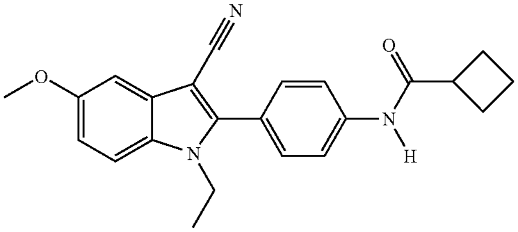
859
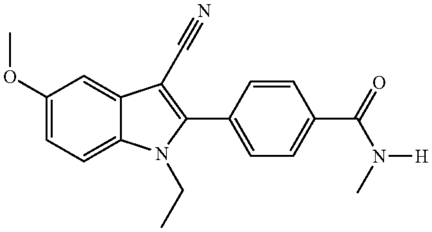
860
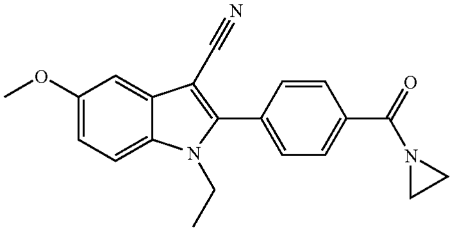
861
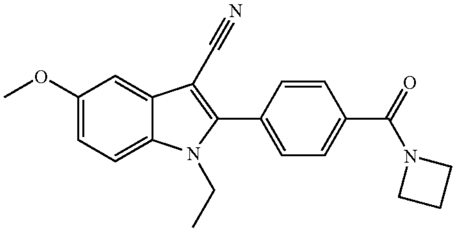
862
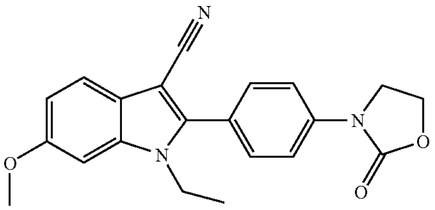
863
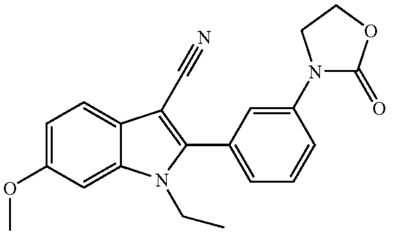
864
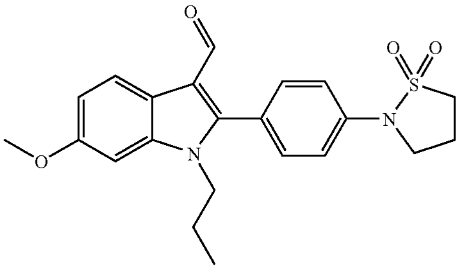
865
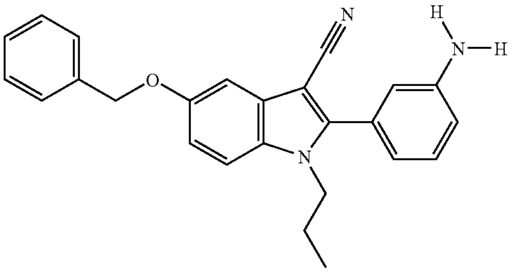
866

-continued
867
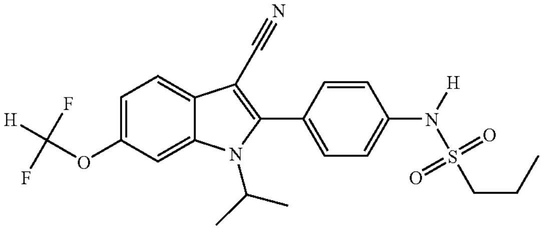
868
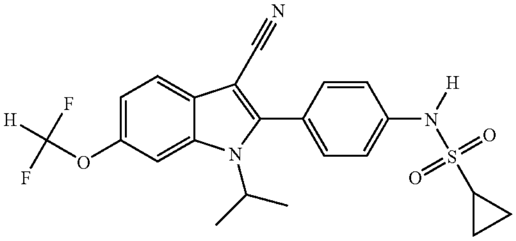
869
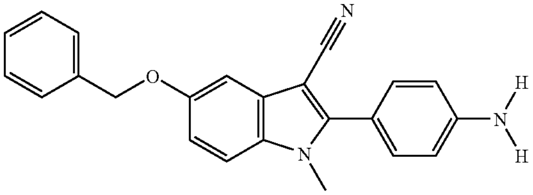
870
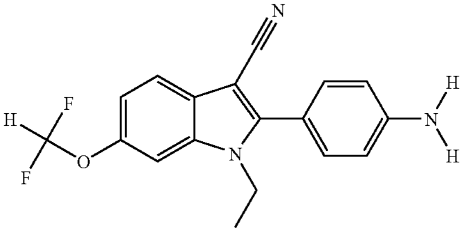
871
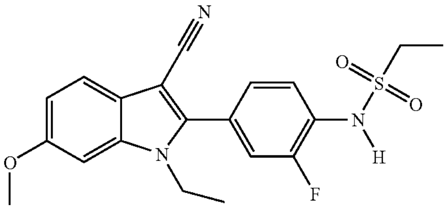
872
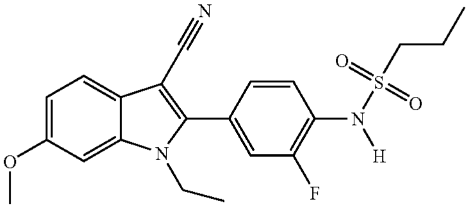
873
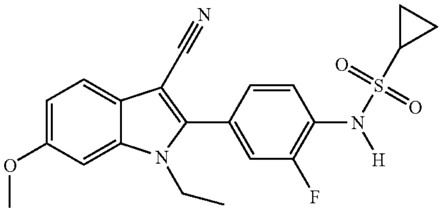
874
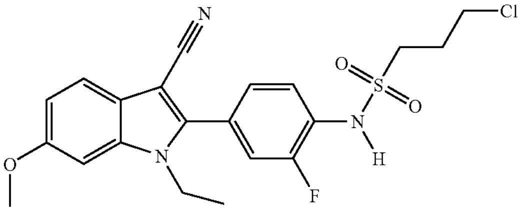
875
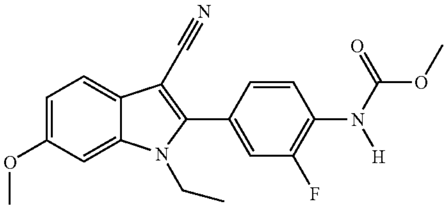
876
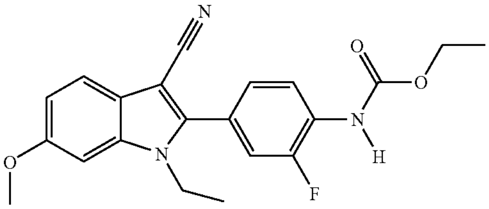
877
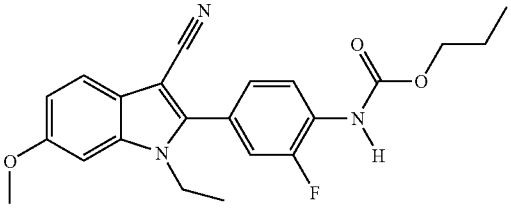
878
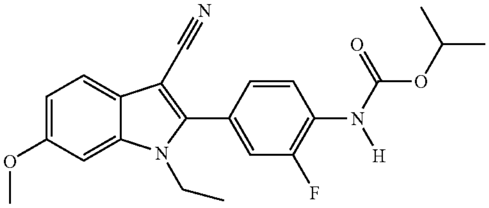
879
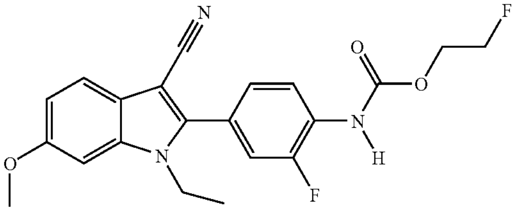
880
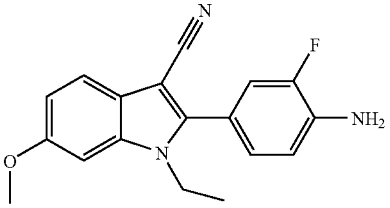

-continued
881
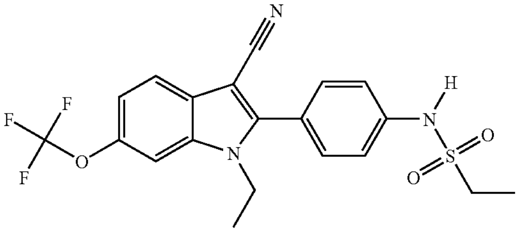
882
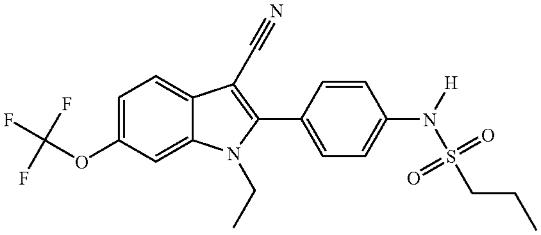
883
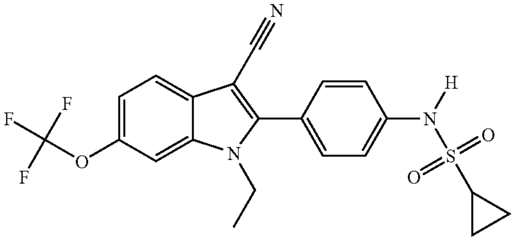
884
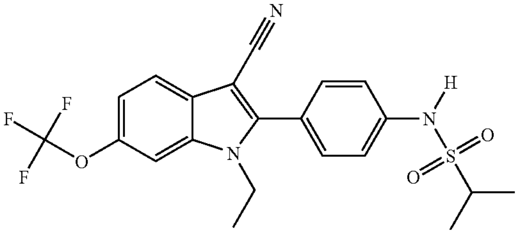
885
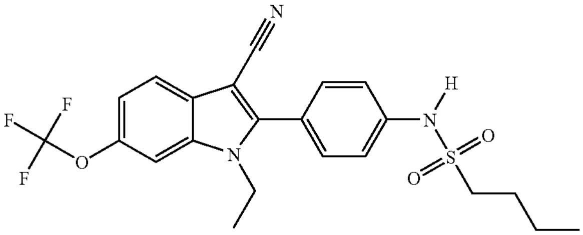
886
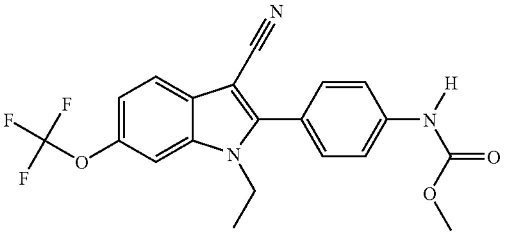
887
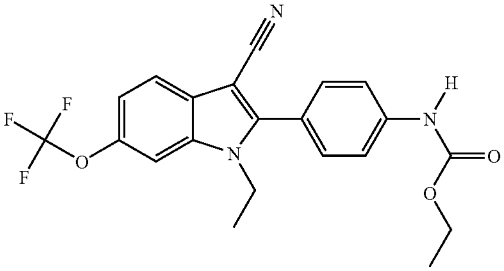
888
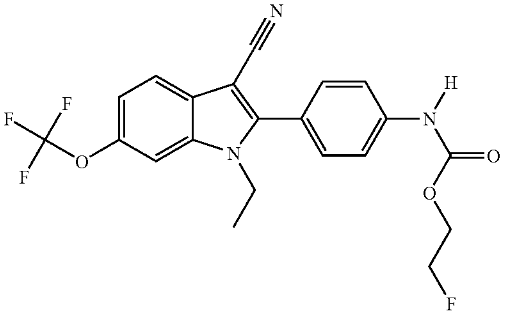
889
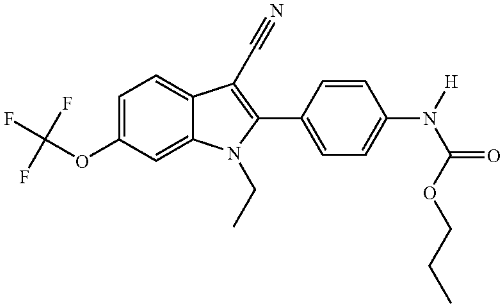
890
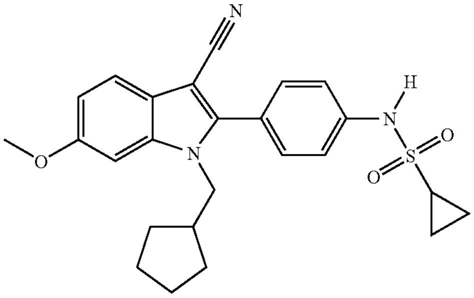

-continued
891
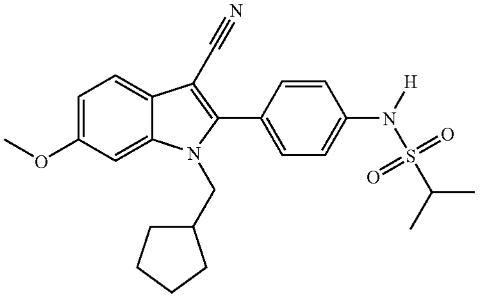
892
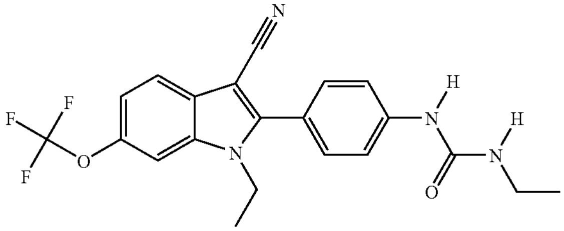
893
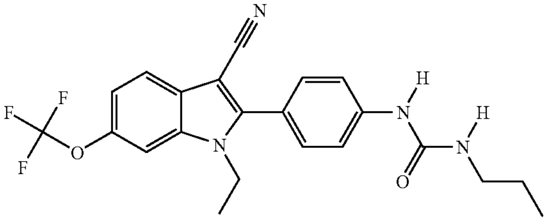
894
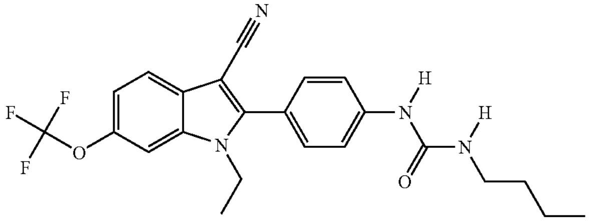
895
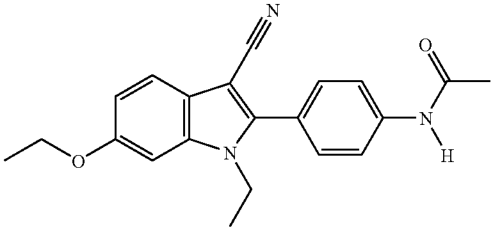
896
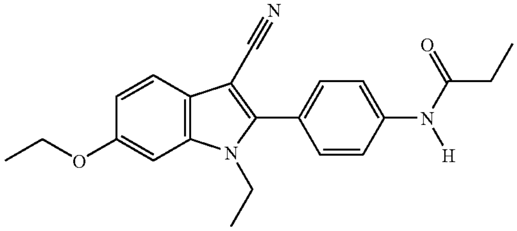
897
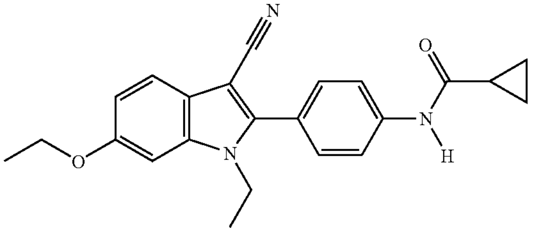
898
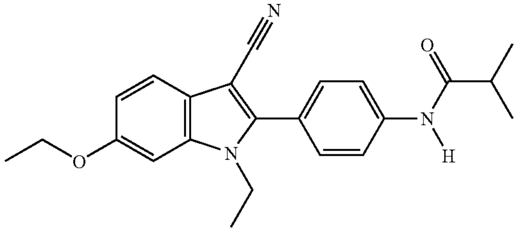
899
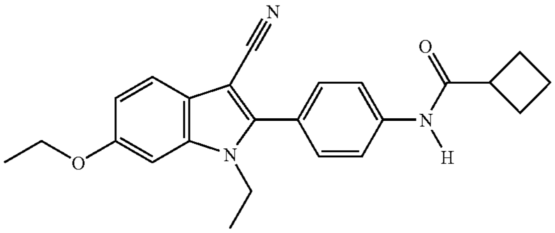
900
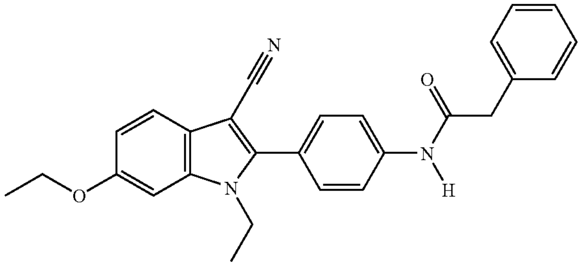
901
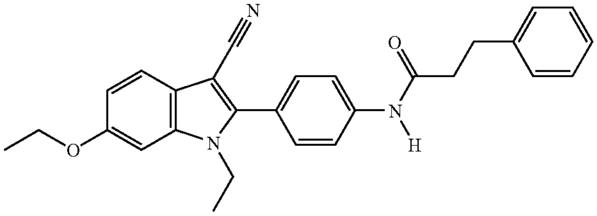
902
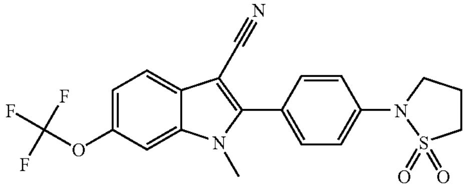

-continued
903
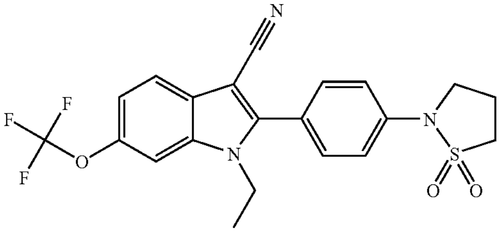
904
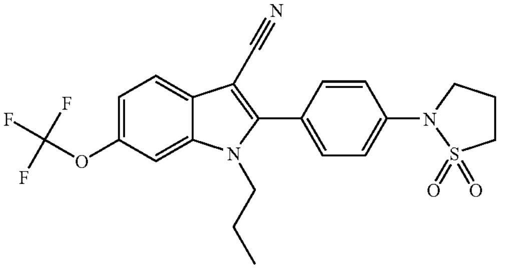
905
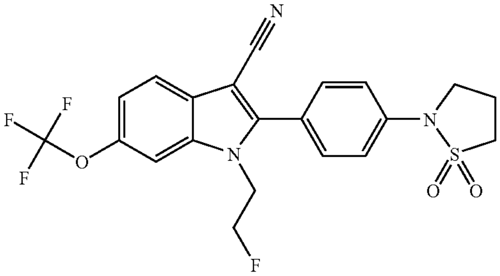
906
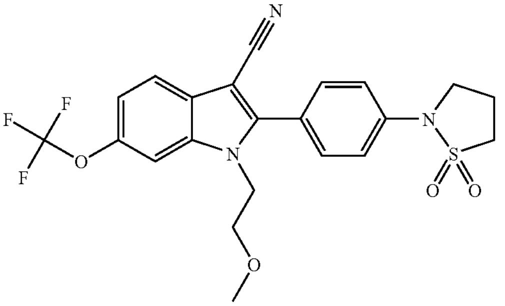
907
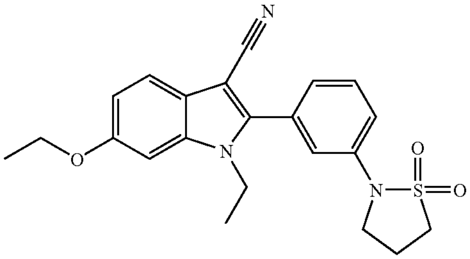
908
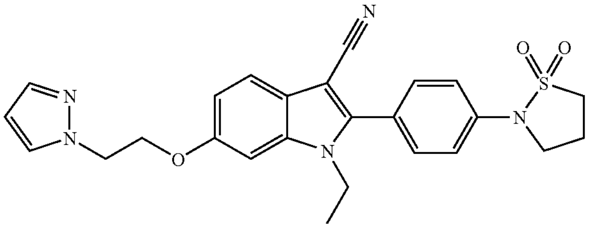
909
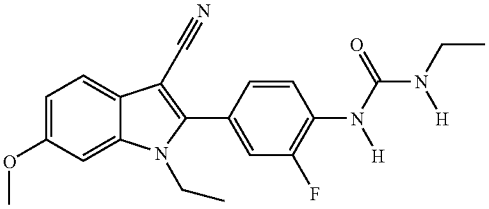
910
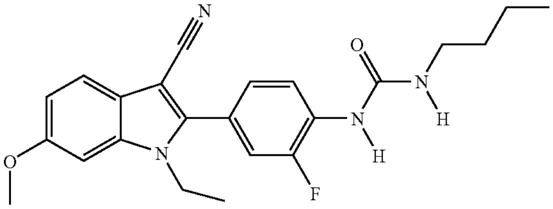
911
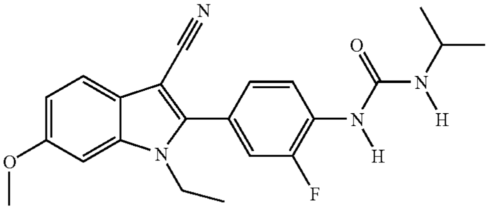
912
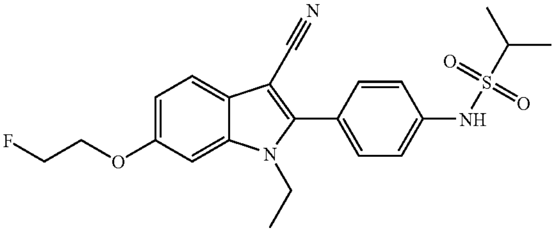
913
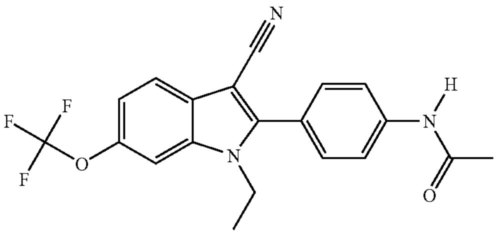
914
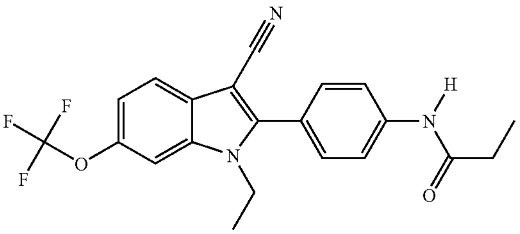

-continued
915
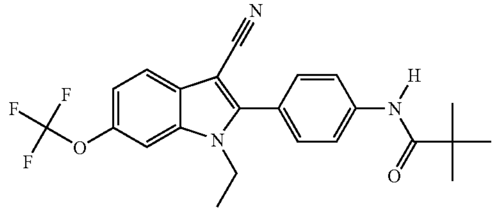
916
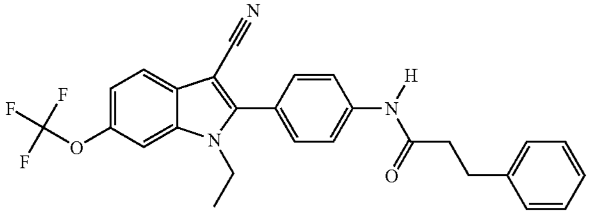
917
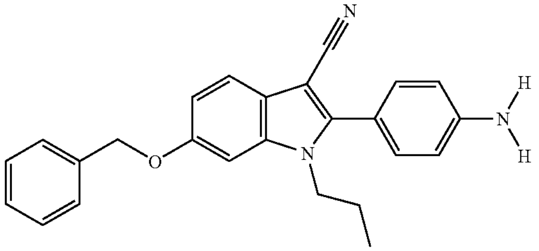
918
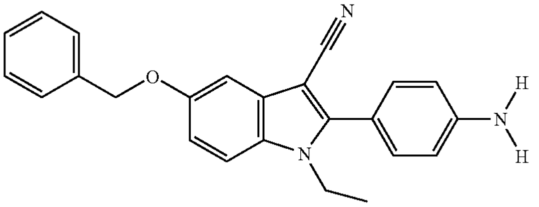
919
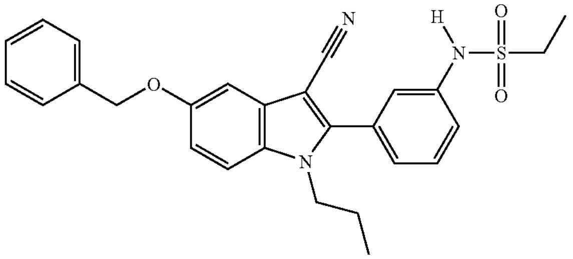
920
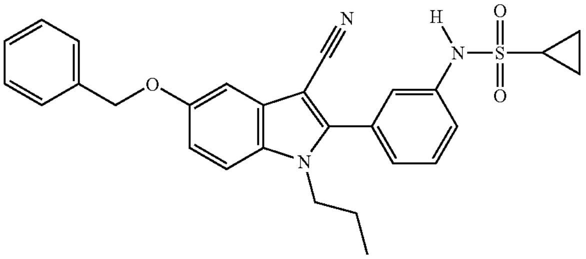
921
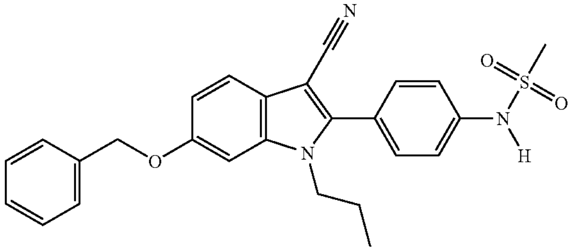
922
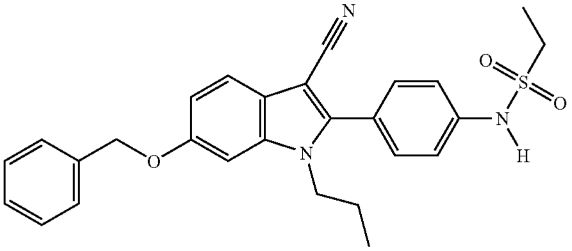
923
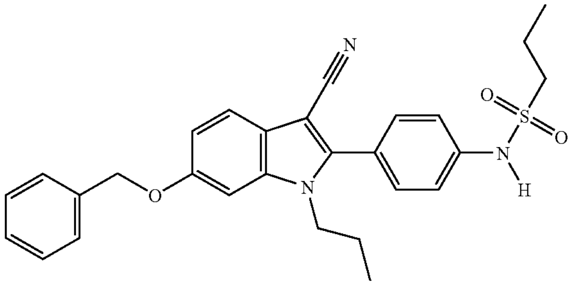
924
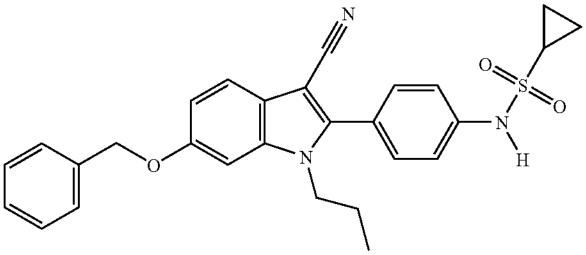
925
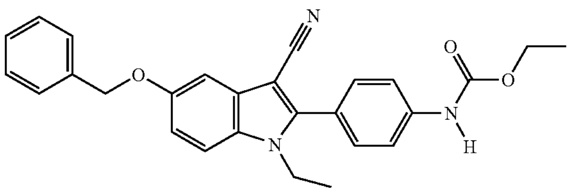
926
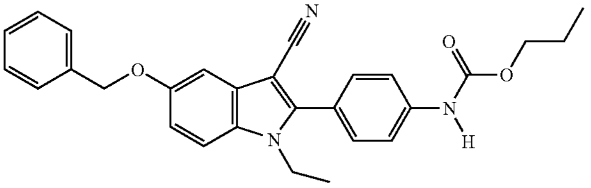

-continued
927
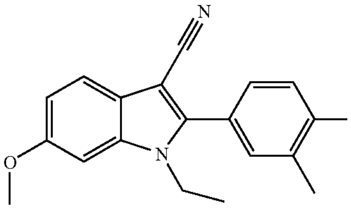
928
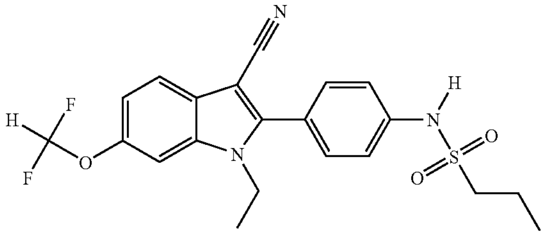
929
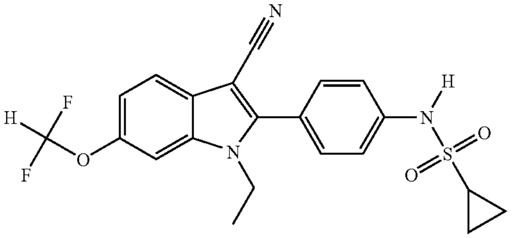
930
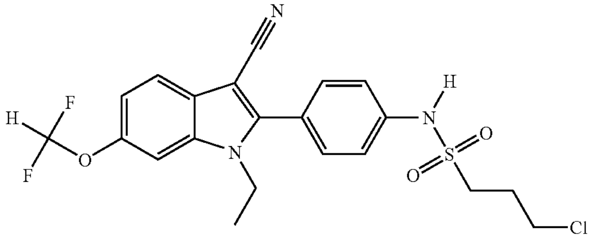
931
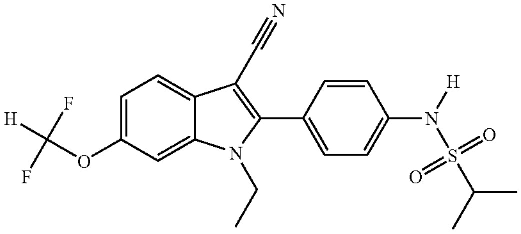
932
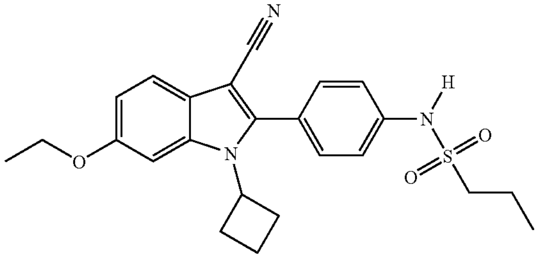
933
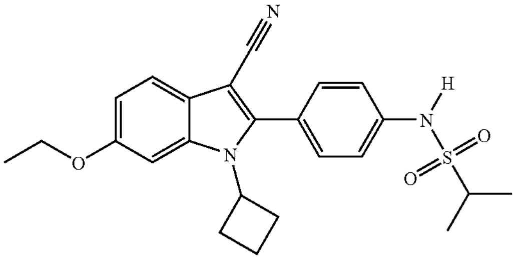
934
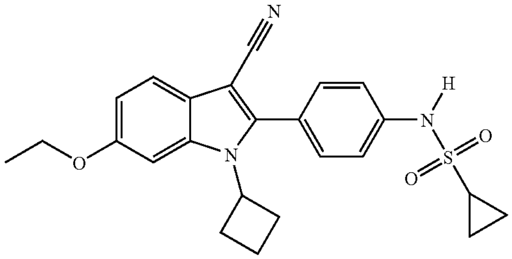
935
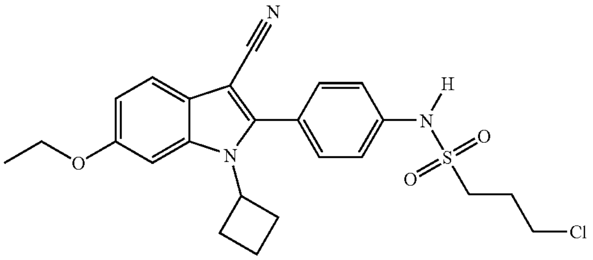
936
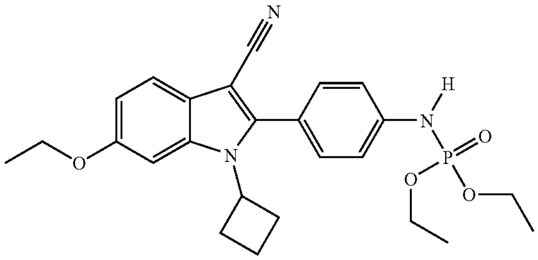
937
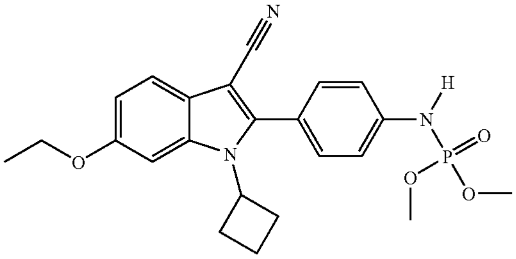
938
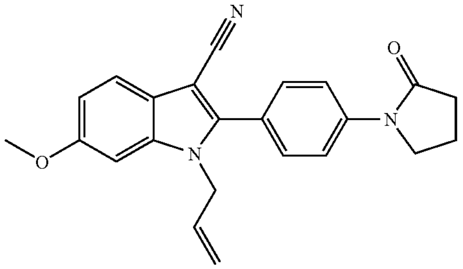

-continued
939
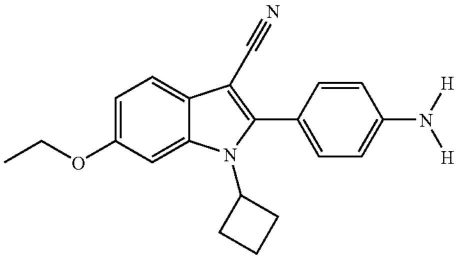
940
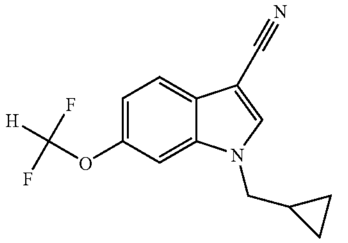
941
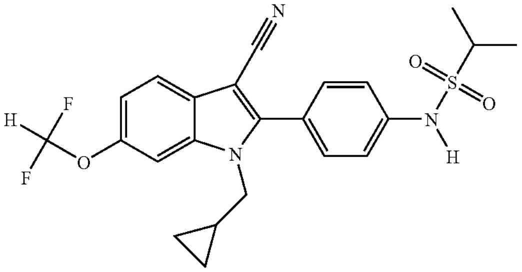
942
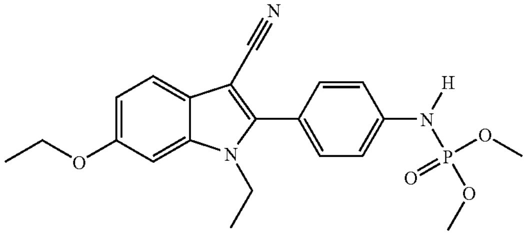
943
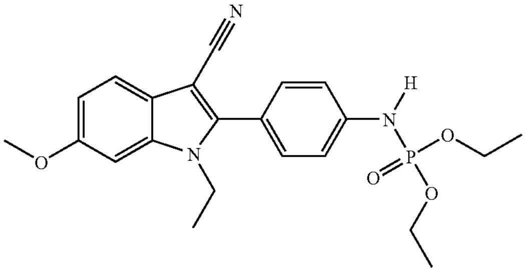
944
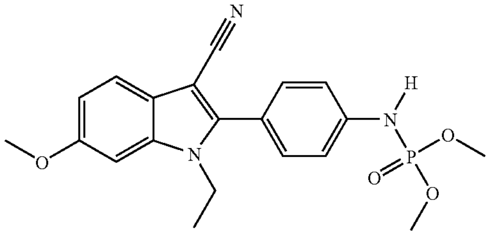
945
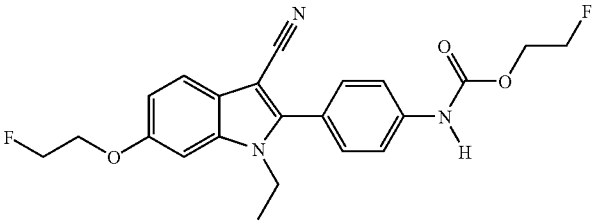
946
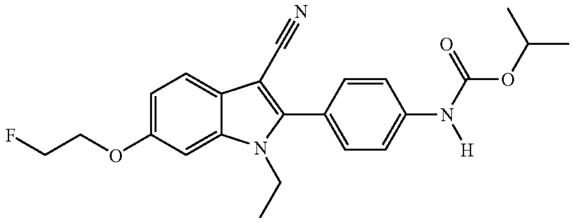
947
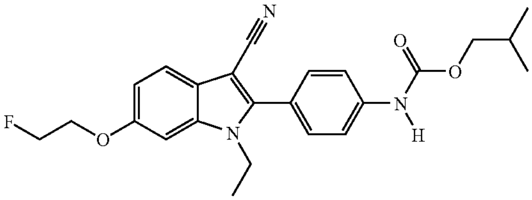
948
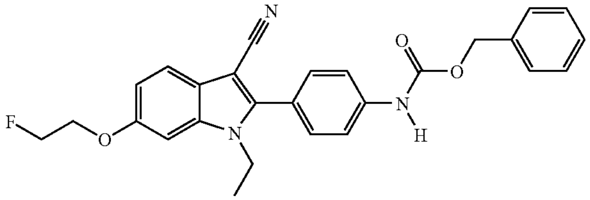
949
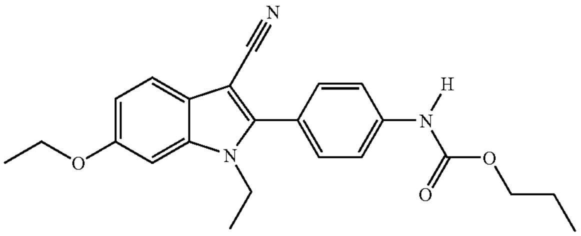
950
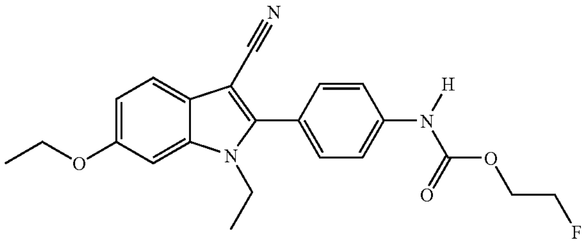

-continued
951
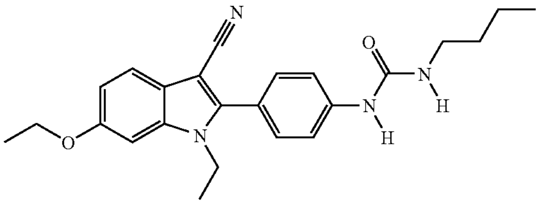
952
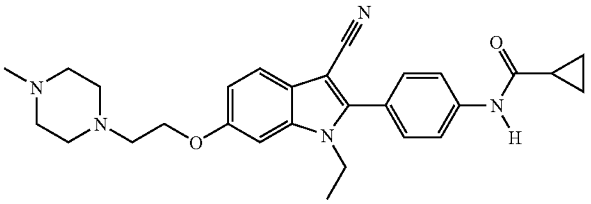
953
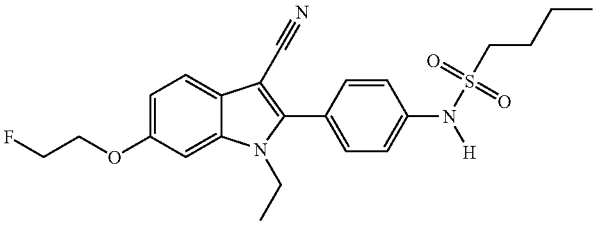
954
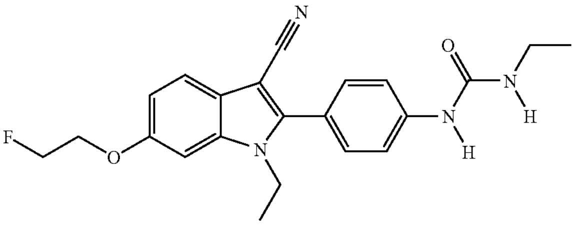
955
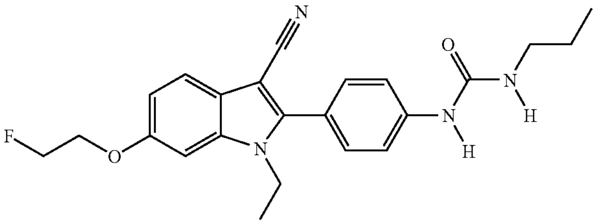
956
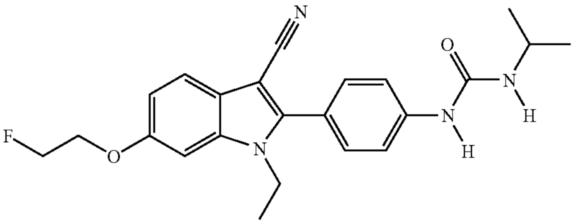
957
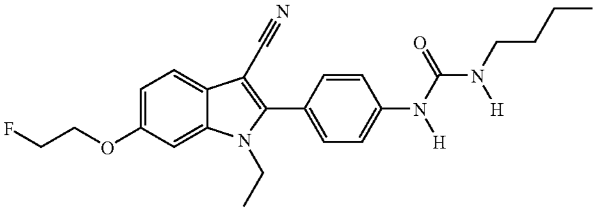
958
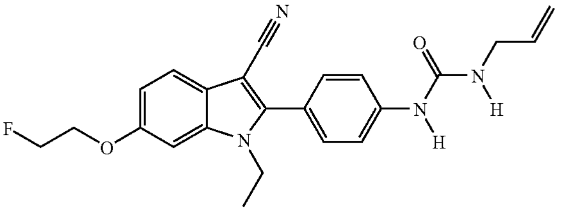
959
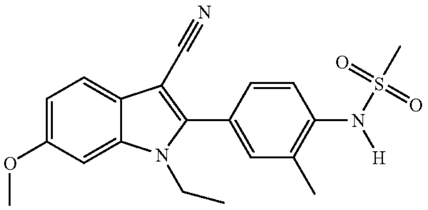
960
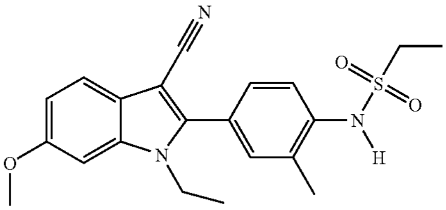
961
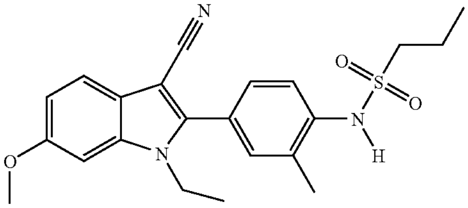
962
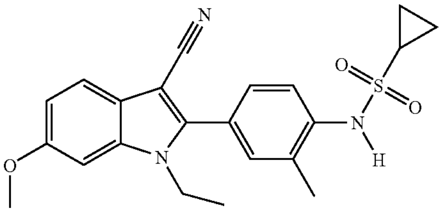
963
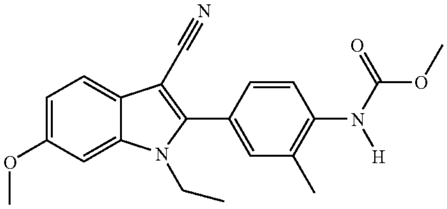
964
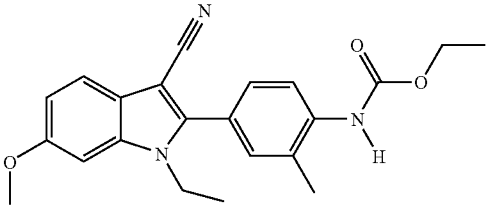

-continued
965
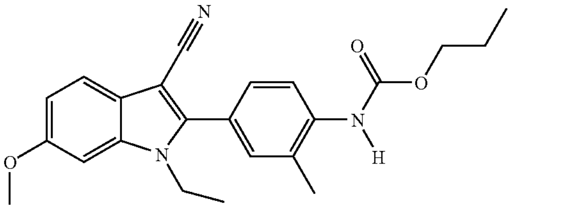
966
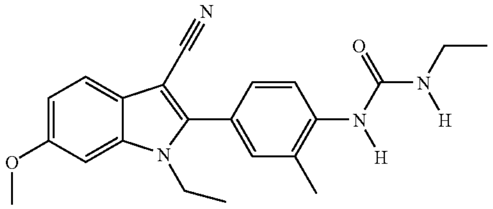
967
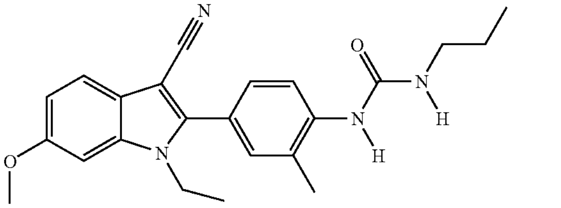
968
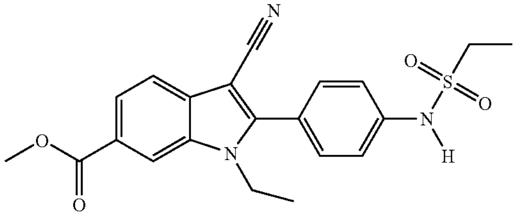
969
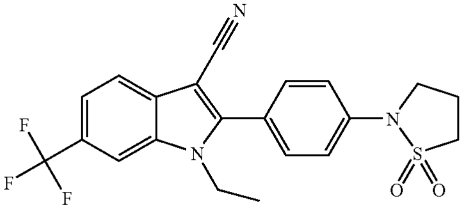
970
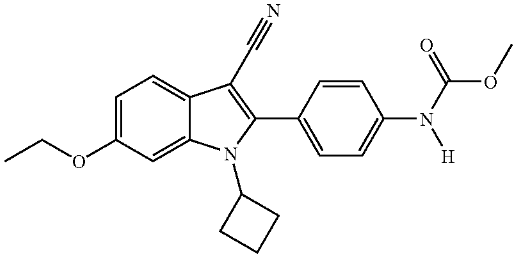
971
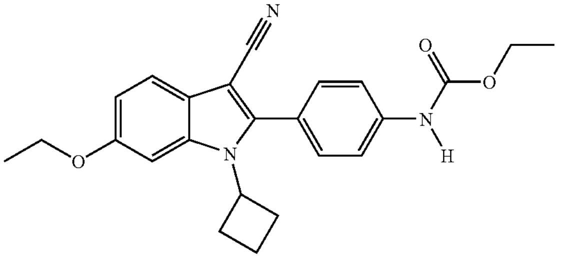
972
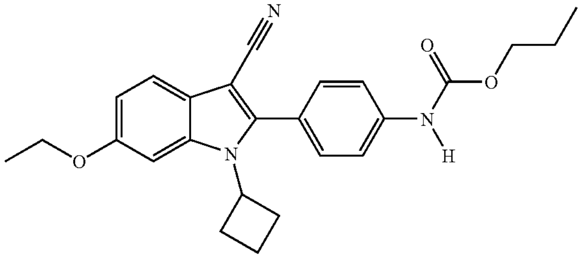
973
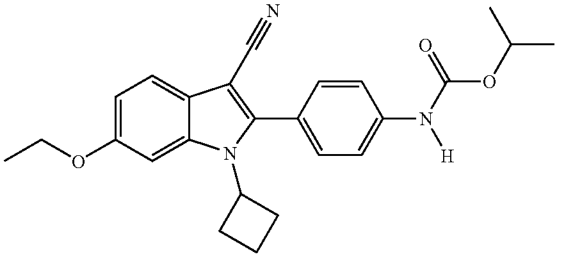
974
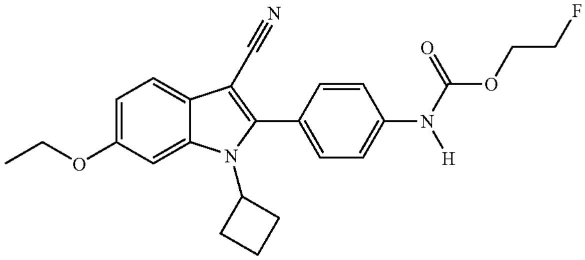
975
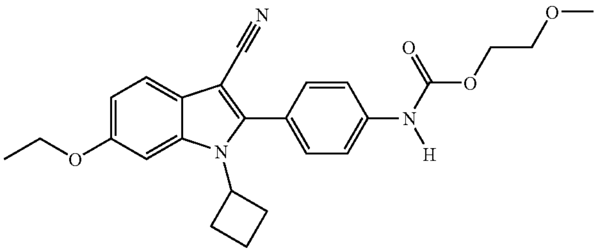
976
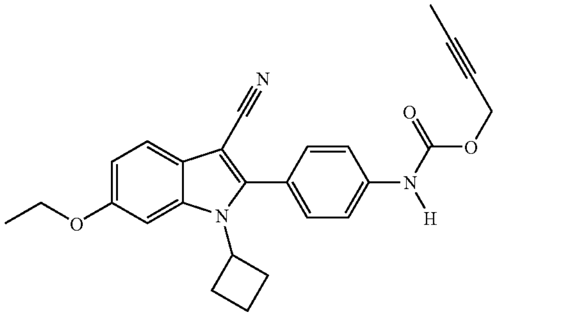

-continued
977
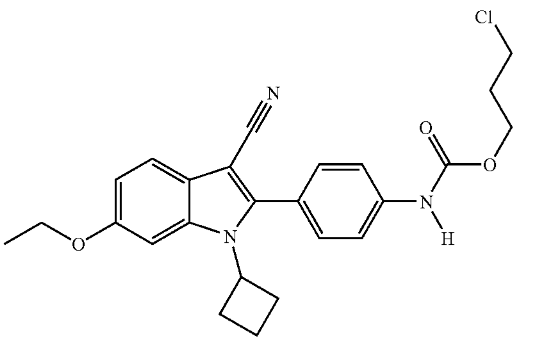
978
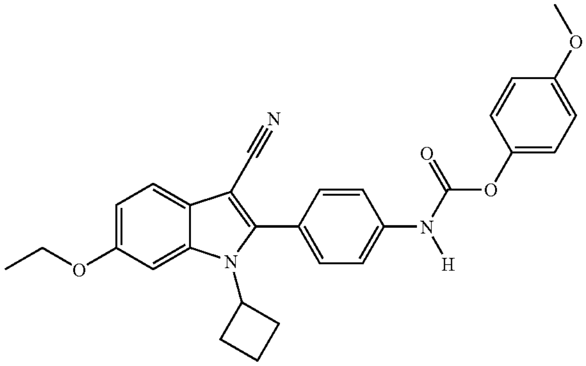
979
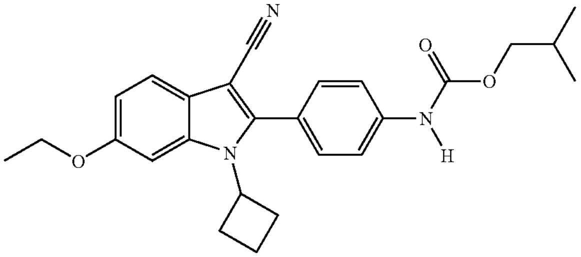
980
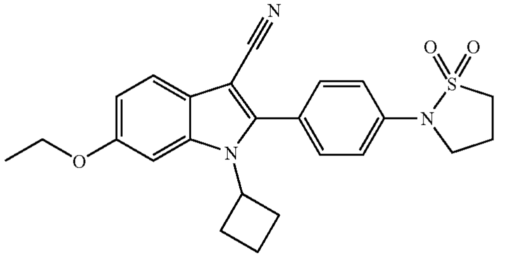
981
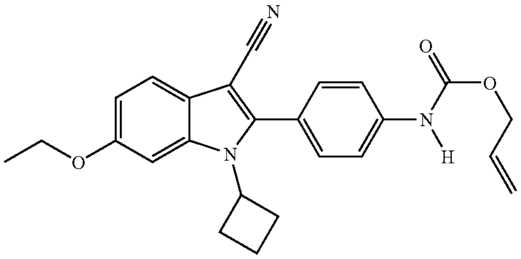
982
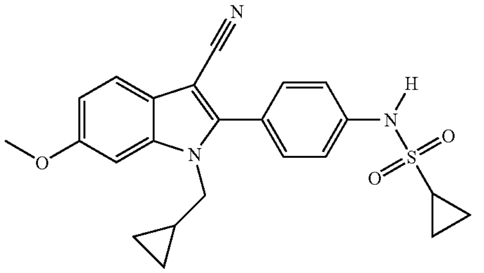
983
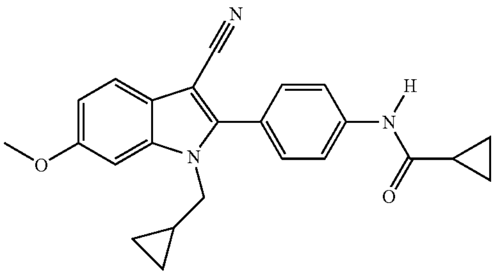
984
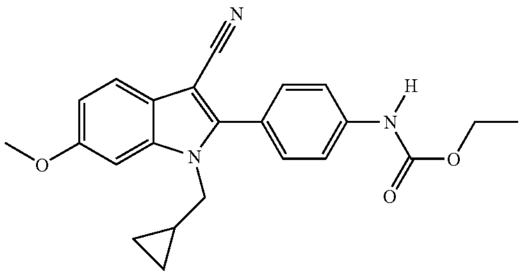
985
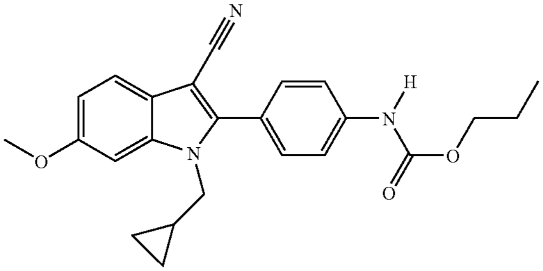
986
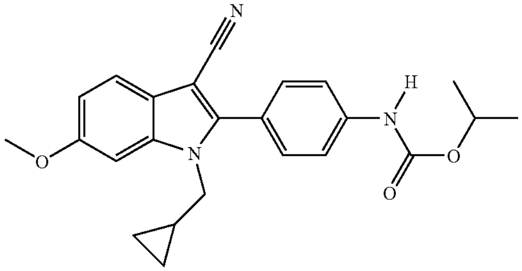

-continued
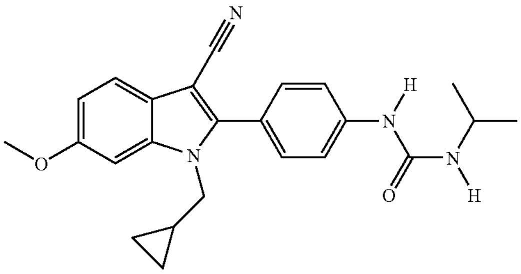
987
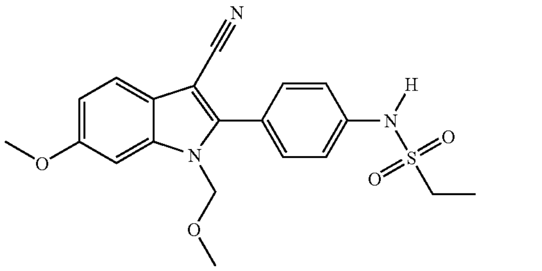
988
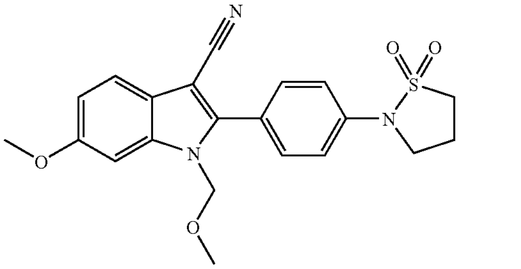
989
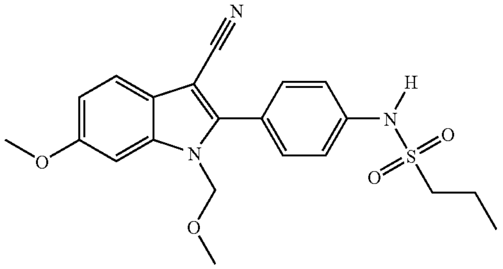
990
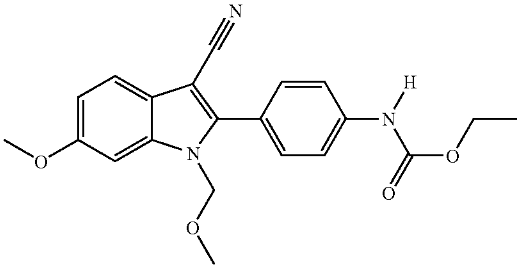
991
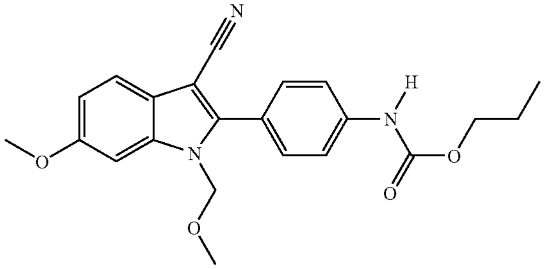
992
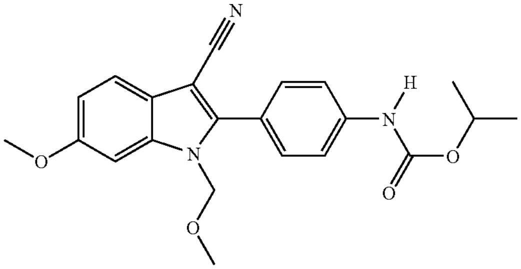
993
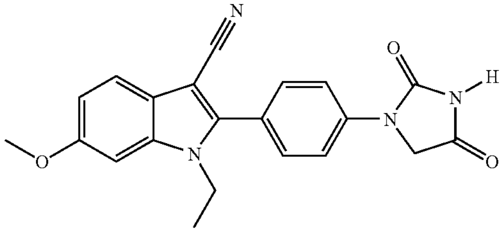
994
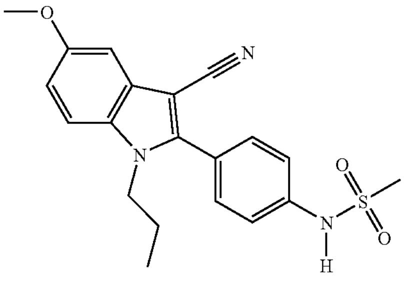
995
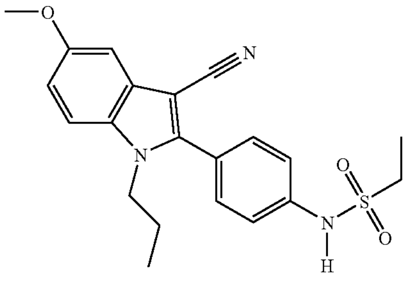
996

-continued
997
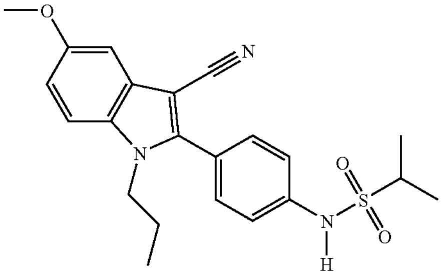
998
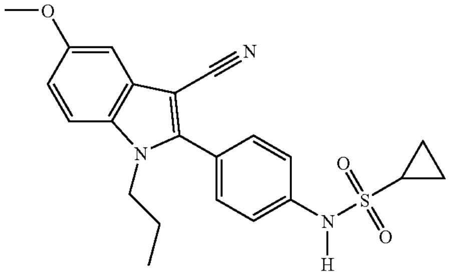
999
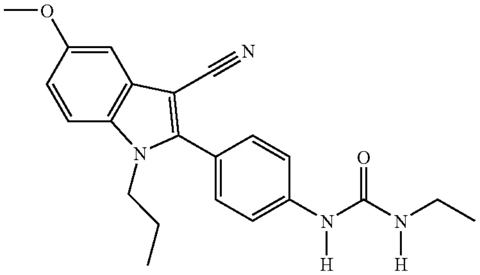
1000
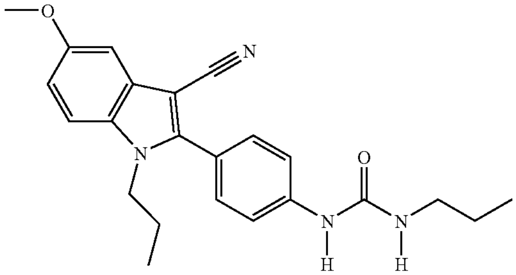
1001
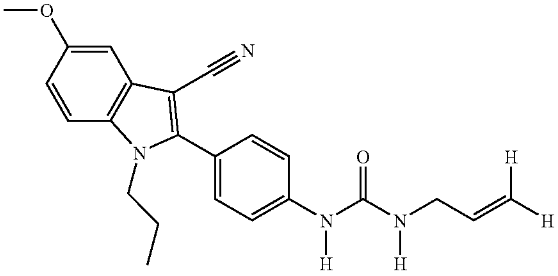
1002
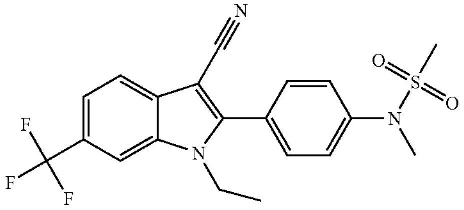
1003
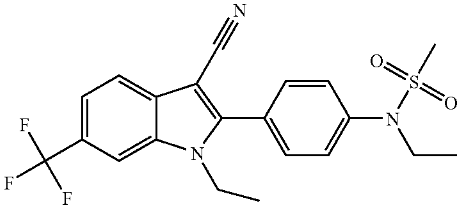
1004
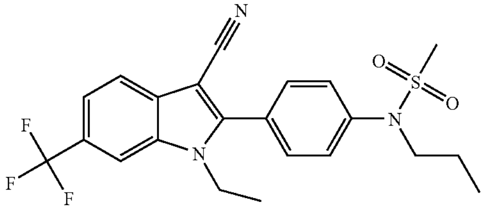
1005
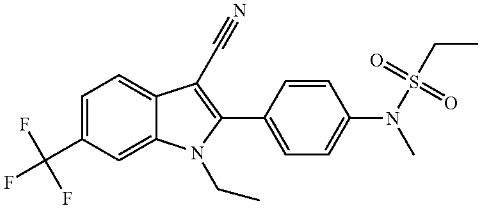
1006
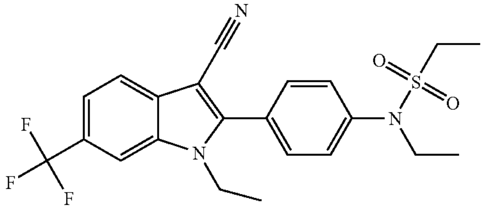
1007
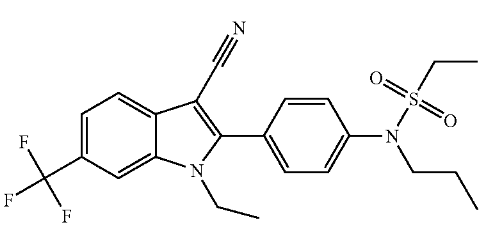
1008
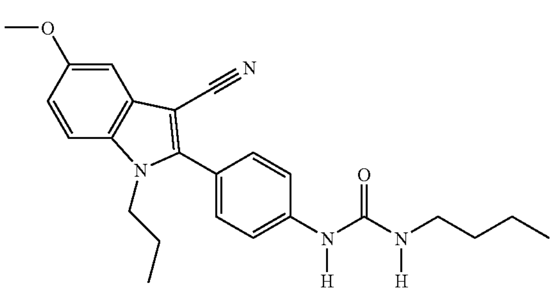

-continued
1009
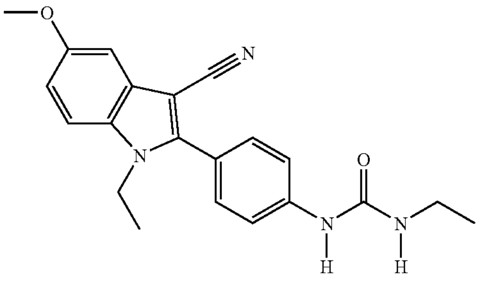
1010
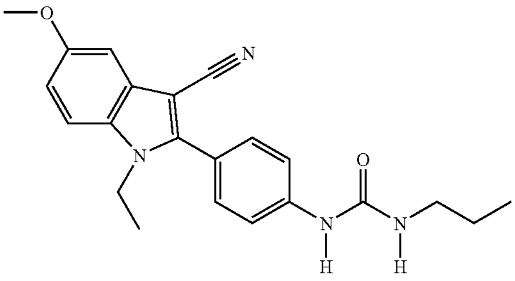
1011
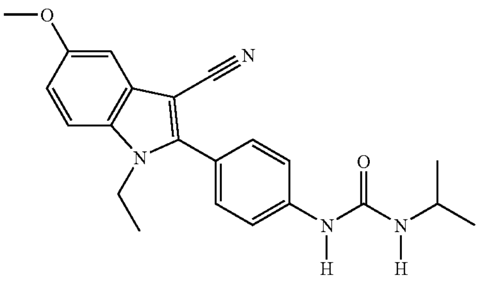
1012
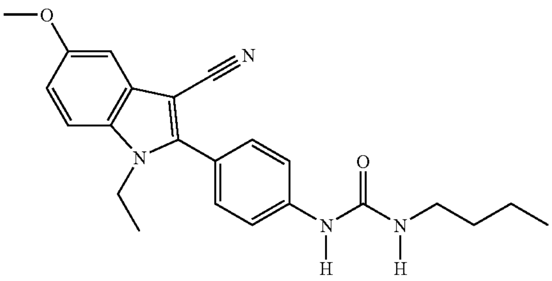
1013
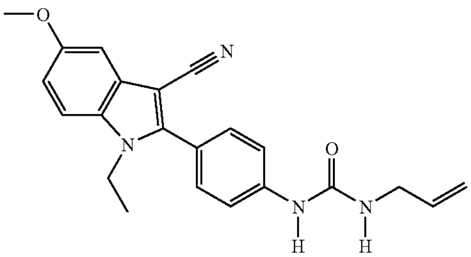
1014
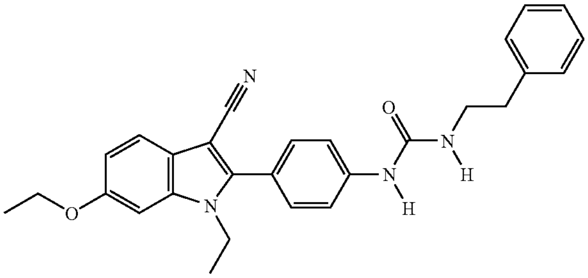
1015
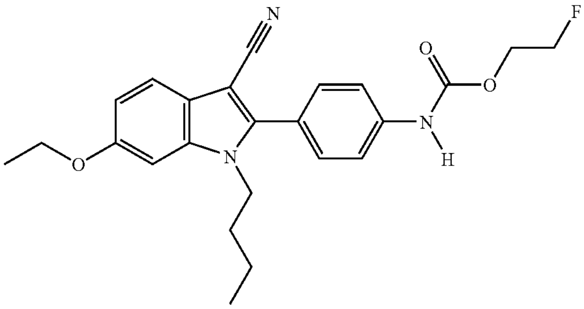
1016
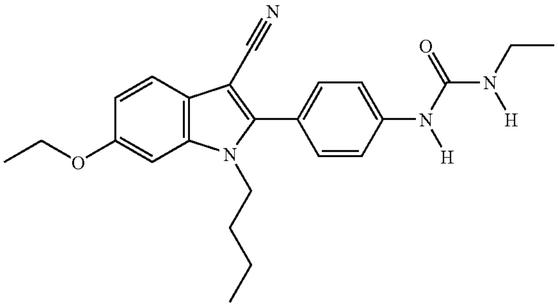
1017
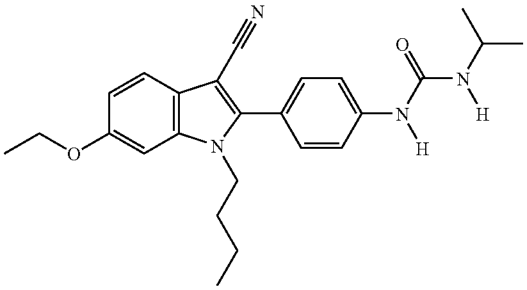
1018
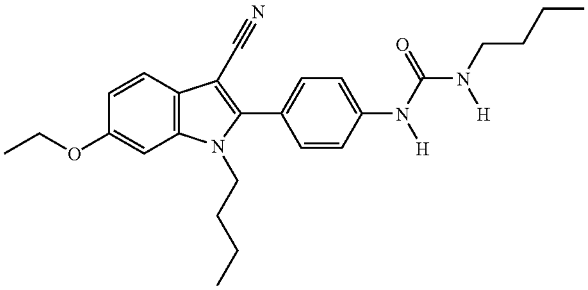

-continued
1019
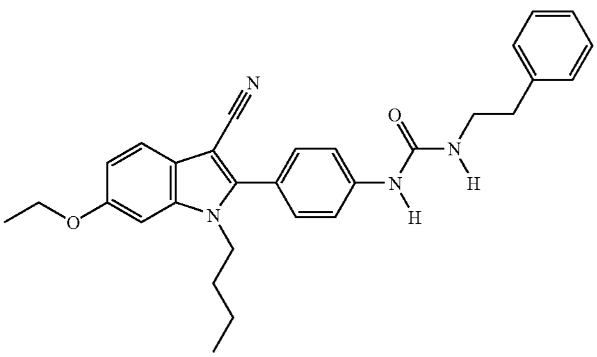
1020
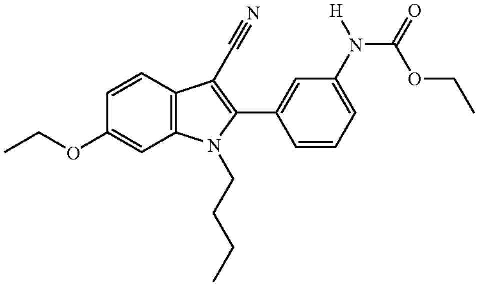
1021
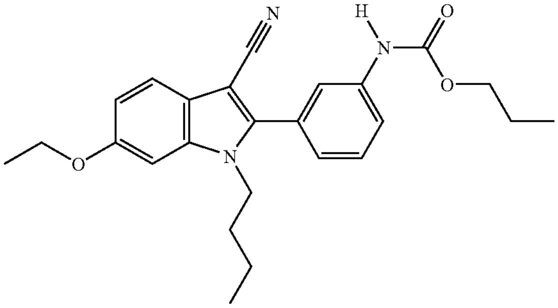
1022
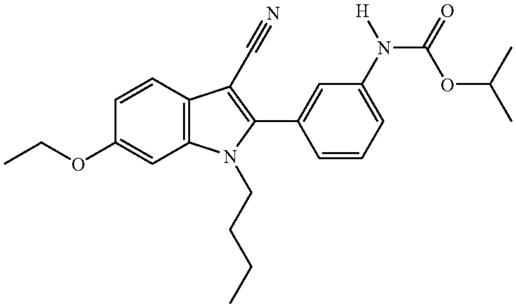
1023
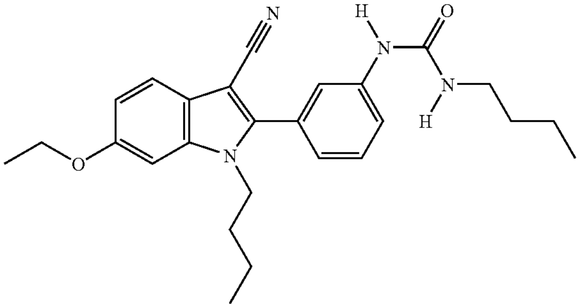
1024
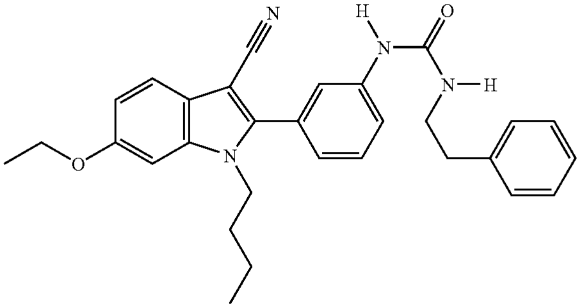
1025
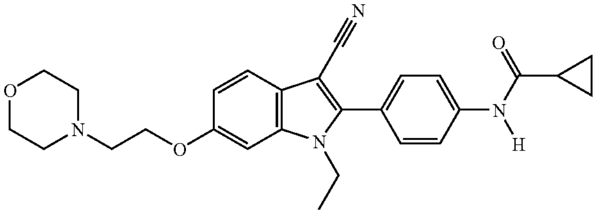
1026
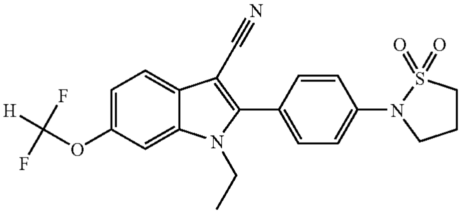
1027
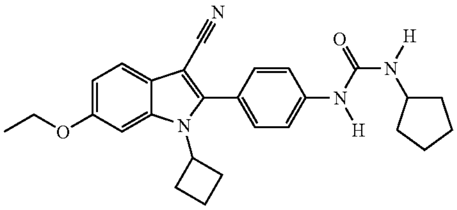
1028
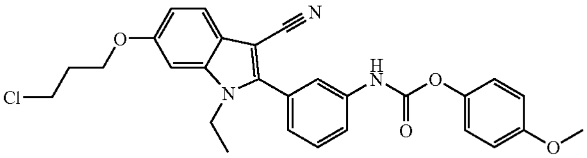

-continued
1029
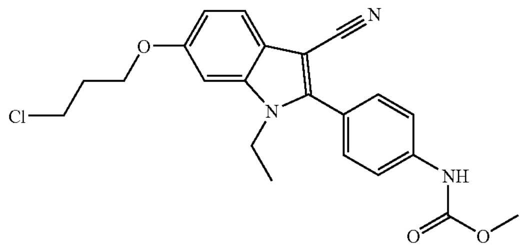
1030
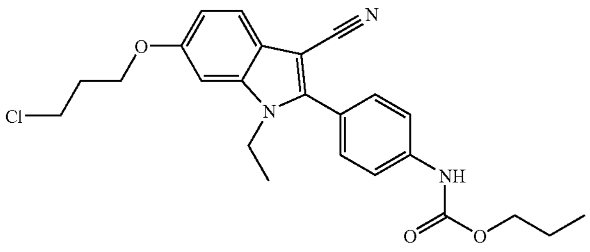
1031
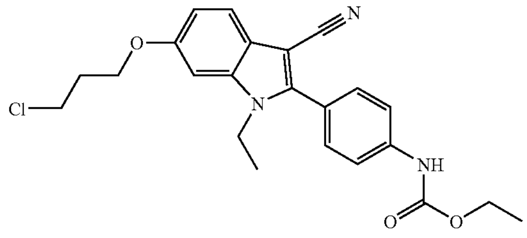
1032
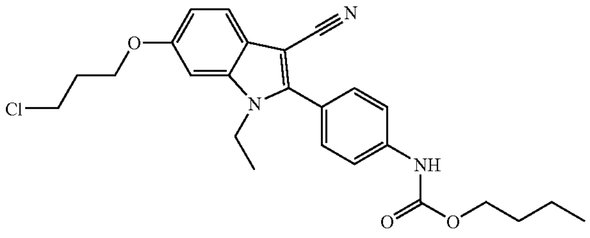
1033
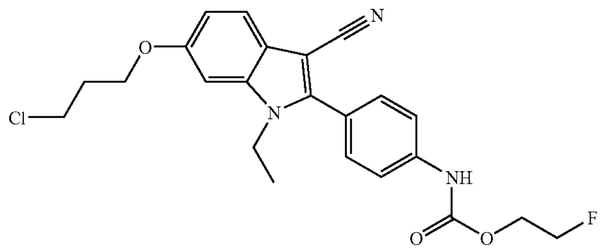
1034
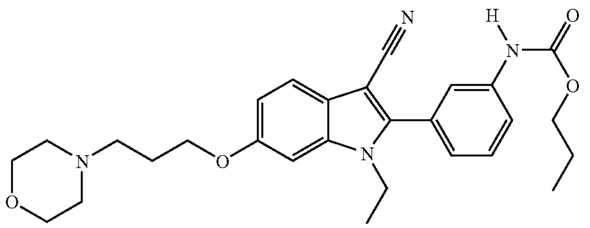
1035
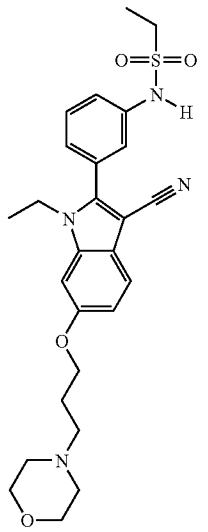
1036
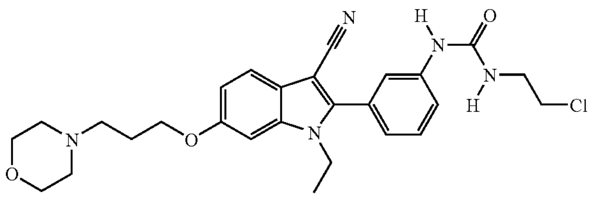

-continued
1037
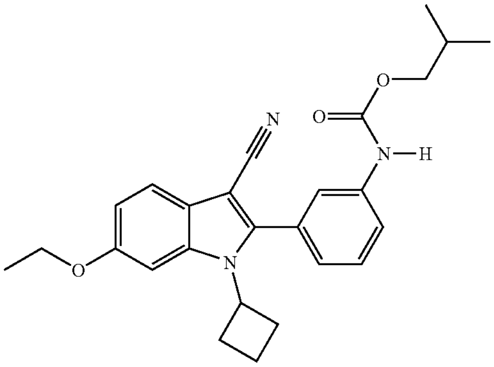
1038
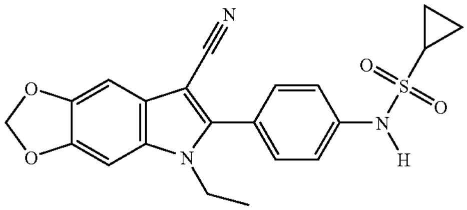
1039
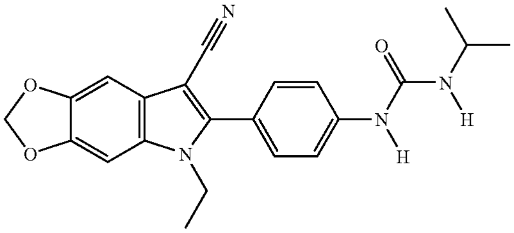
1040
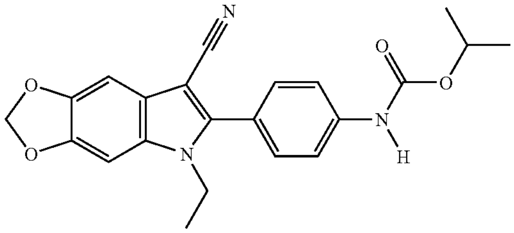
1041
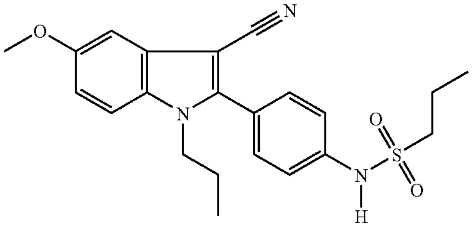
1042
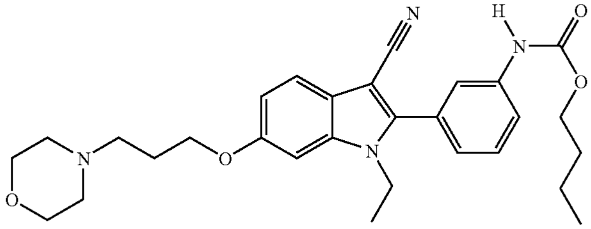
1043
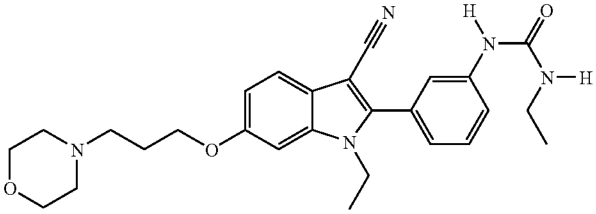
1044
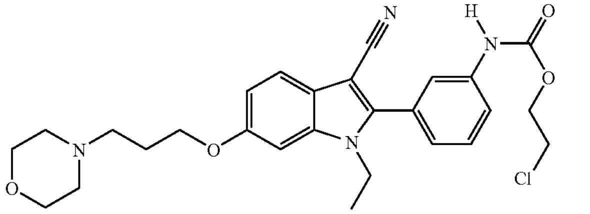
1045
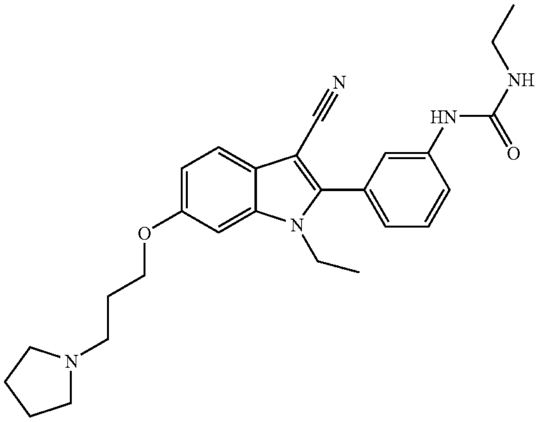
1046
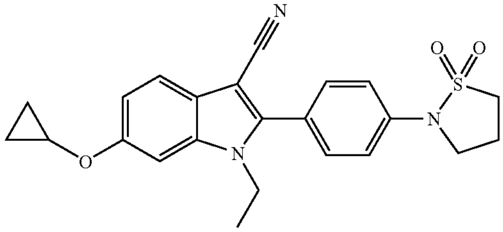

-continued
1047
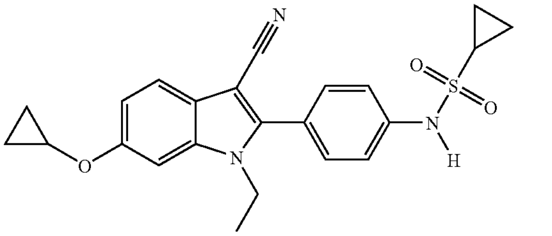
1048
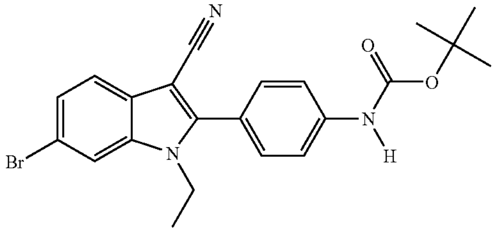
1049
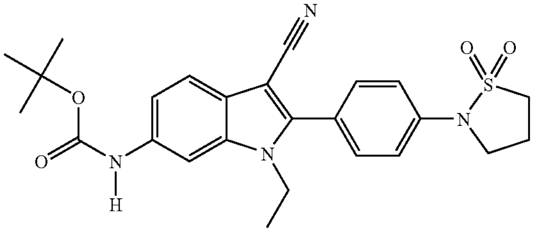
1050
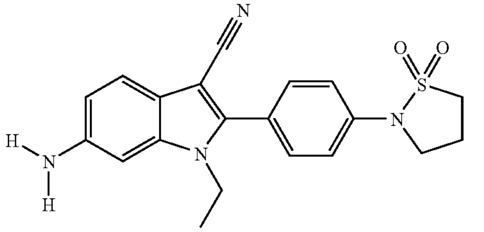
1051
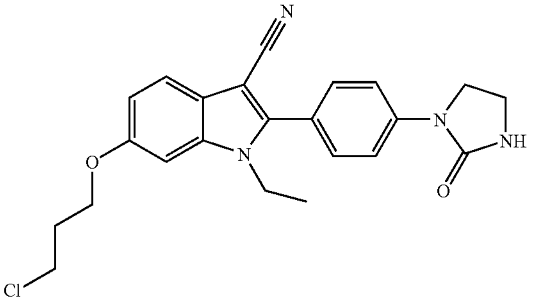
1052
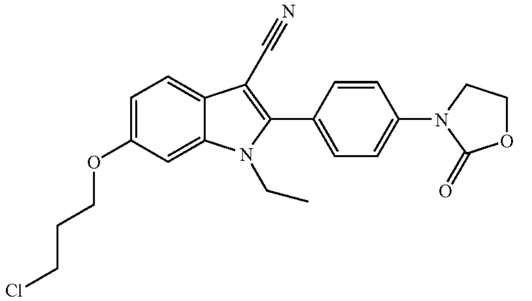
1053
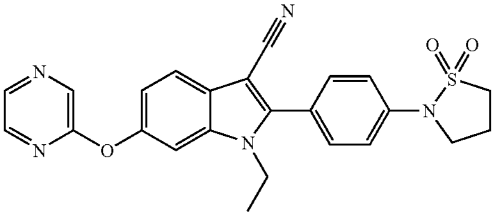
1054
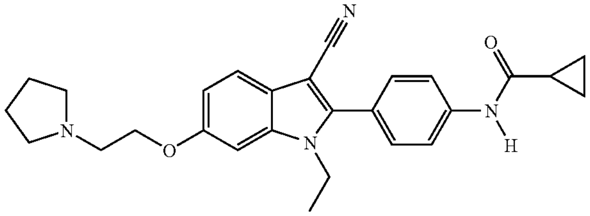
1055
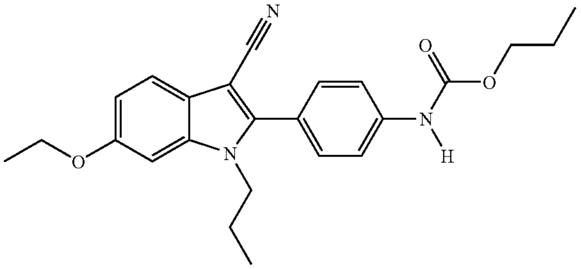
1056
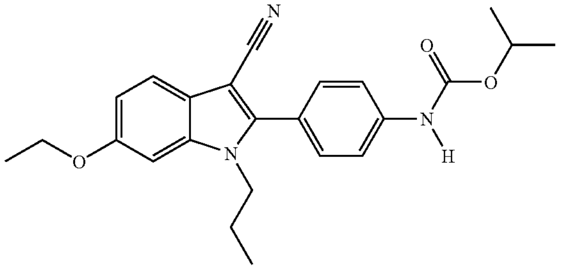
1057
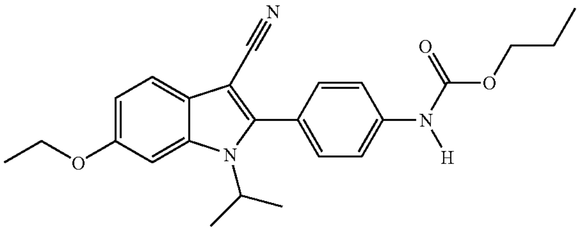
1058
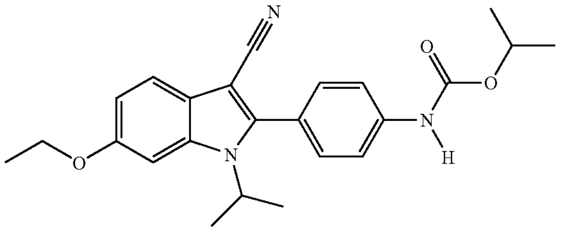

-continued
1059
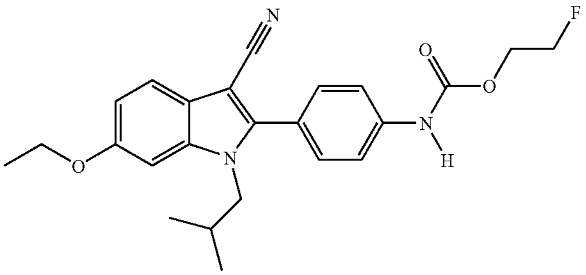
1060
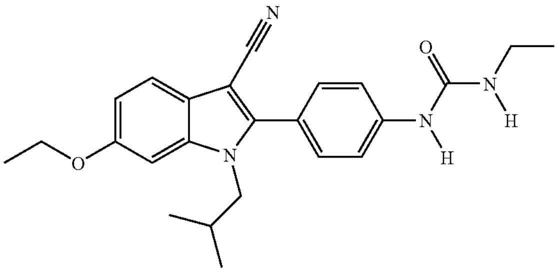
1061
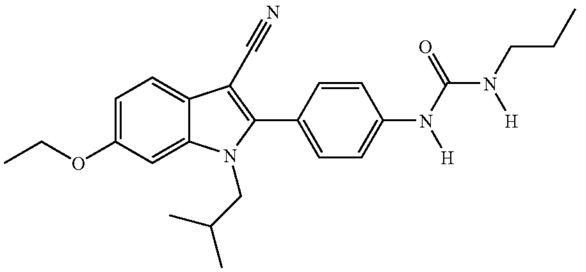
1062
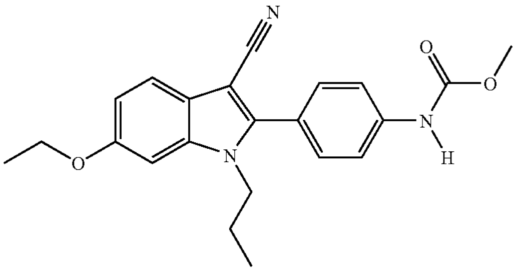
1063
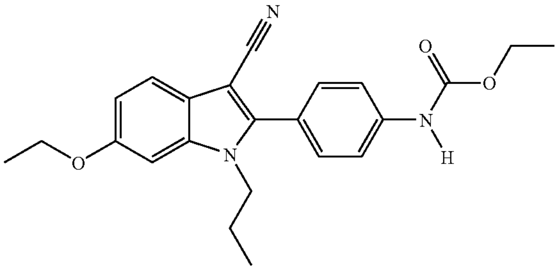
1064
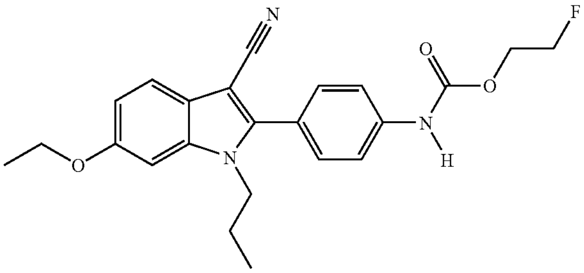
1065
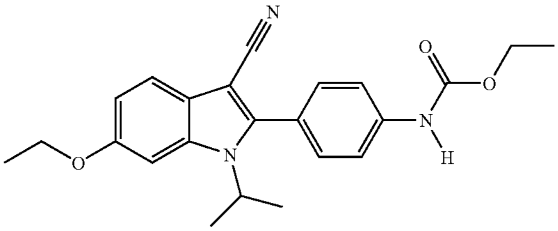
1066
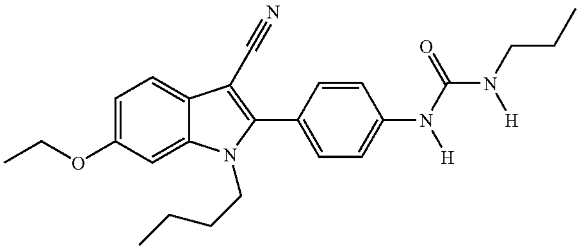
1067
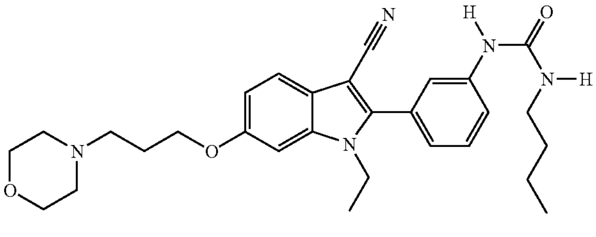
1068
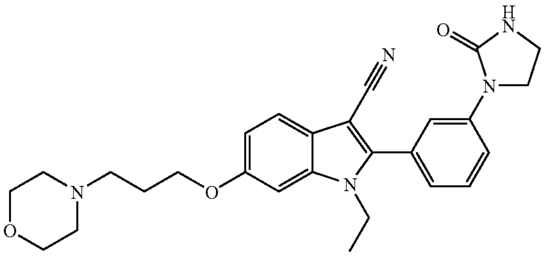

-continued
1069
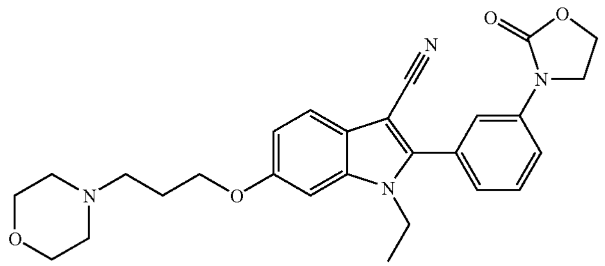
1070
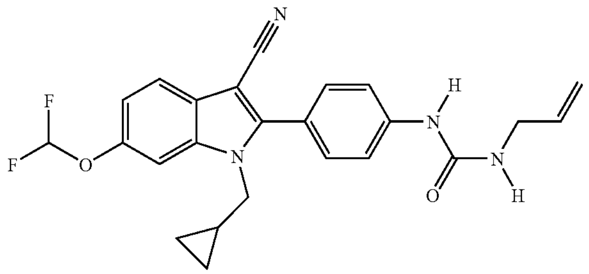
1071
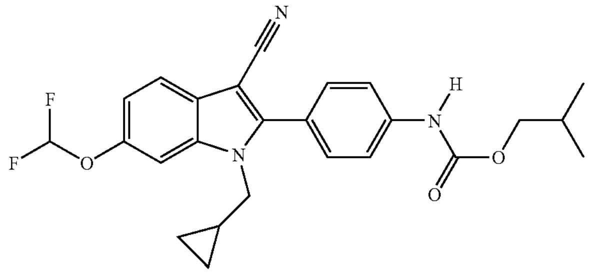
1072
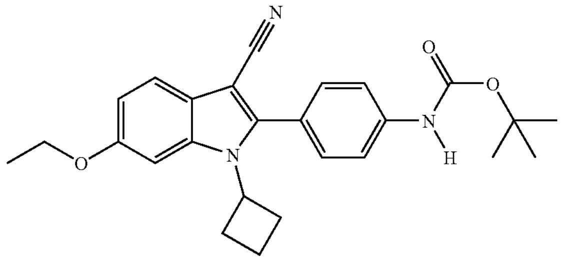
1073
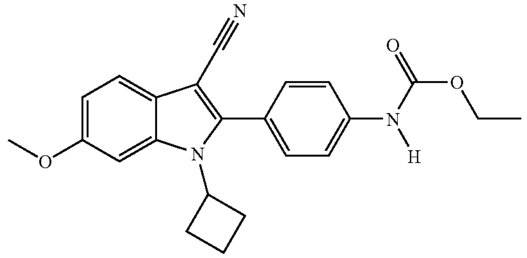
1074
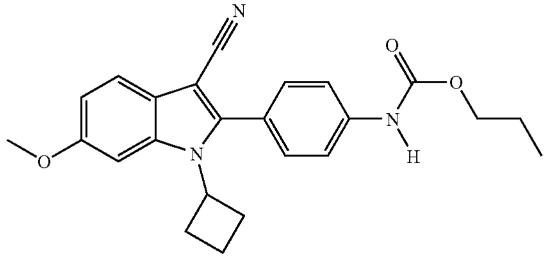
1075
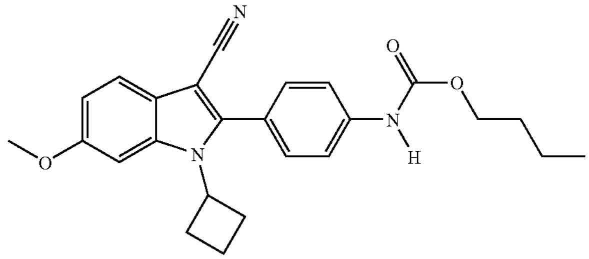
1076
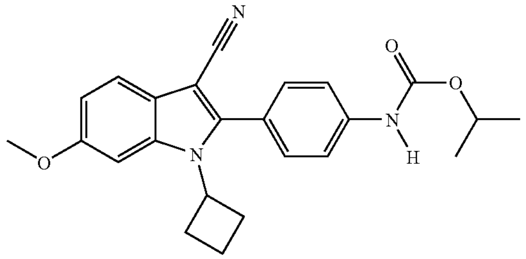
1077
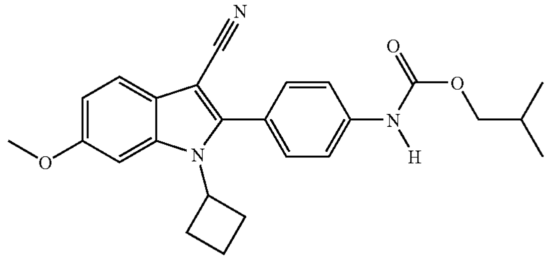
1078
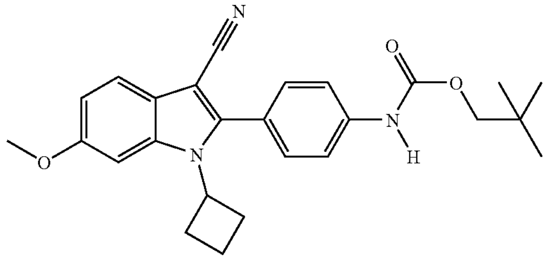

-continued
1079
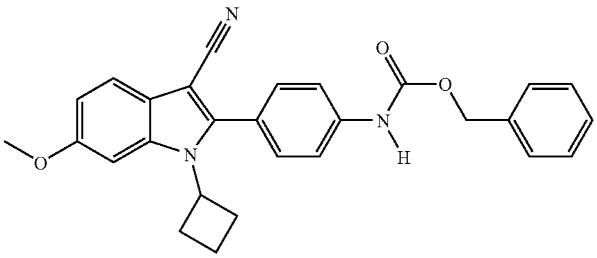
1080
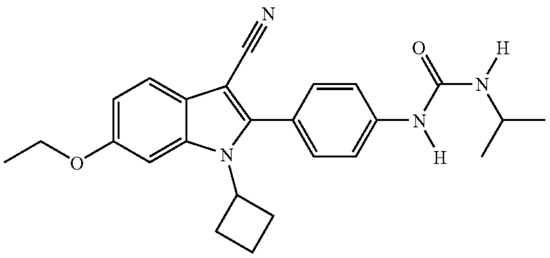
1081
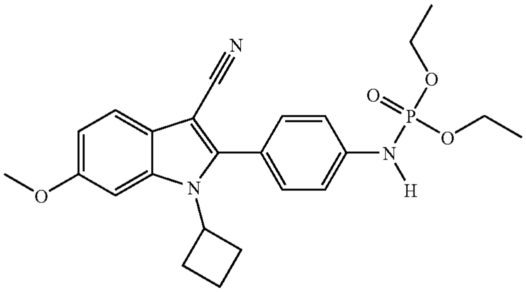
1082
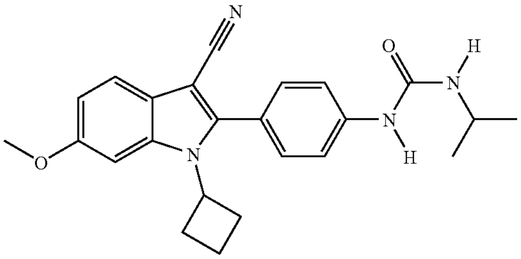
1083
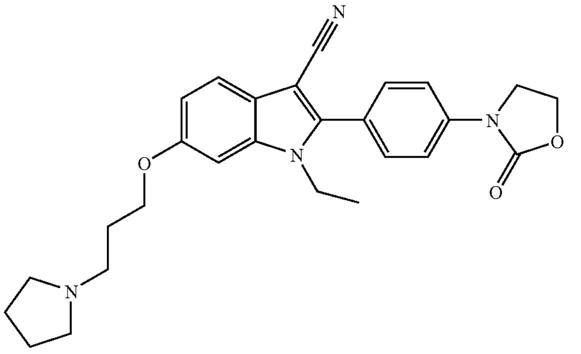
1084
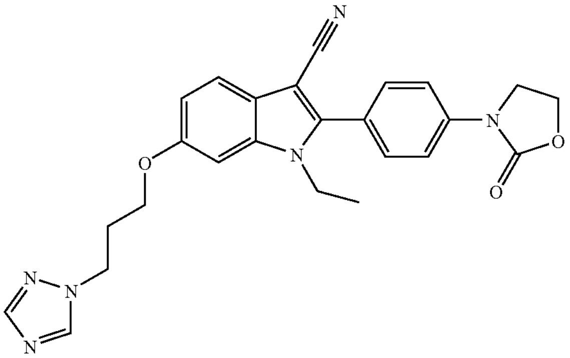
1085
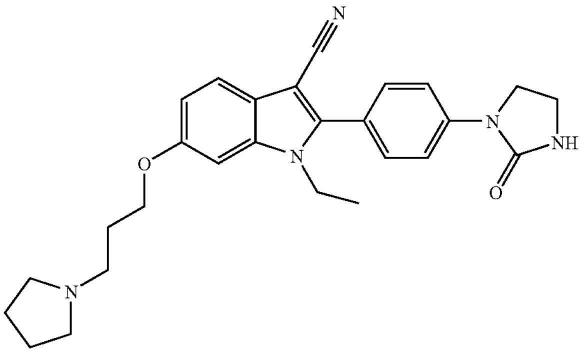
1086
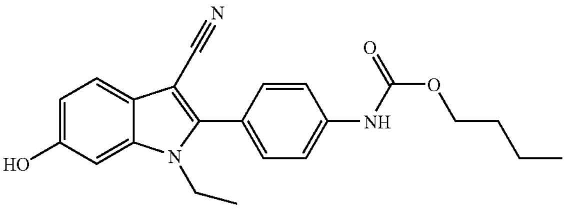
1087
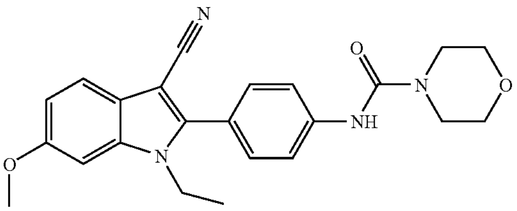
1088
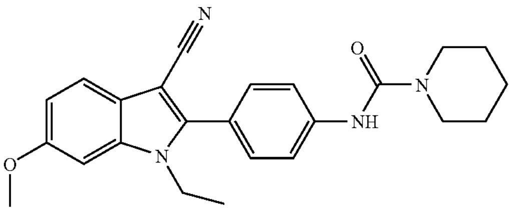

-continued
1089
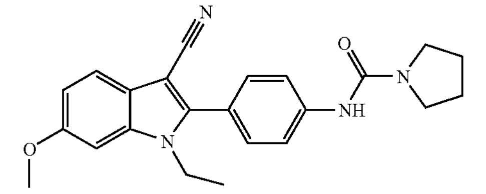
1090
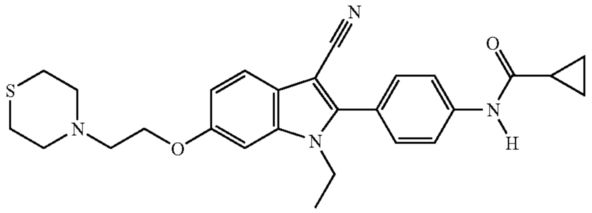
1091
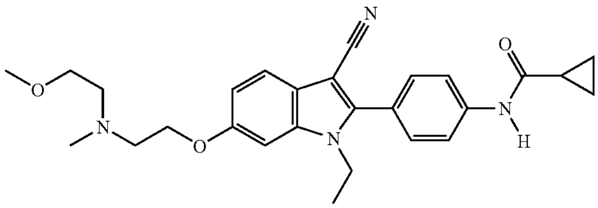
1092
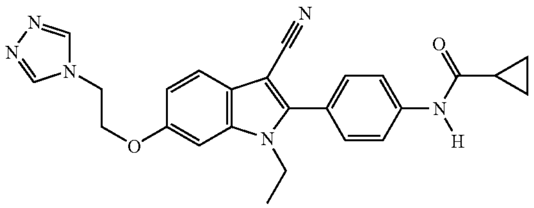
1093
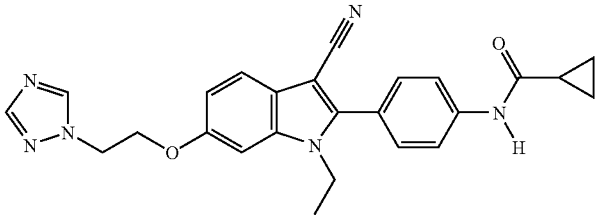
1094
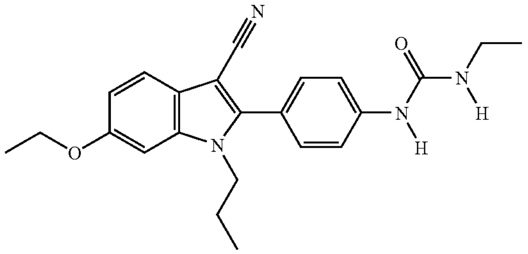
1095
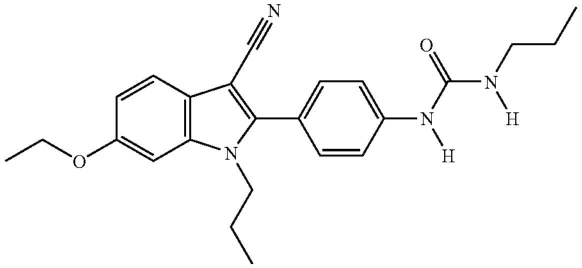
1096
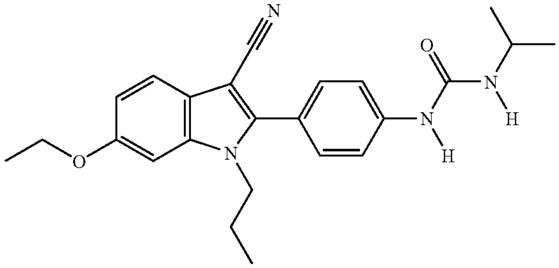
1097
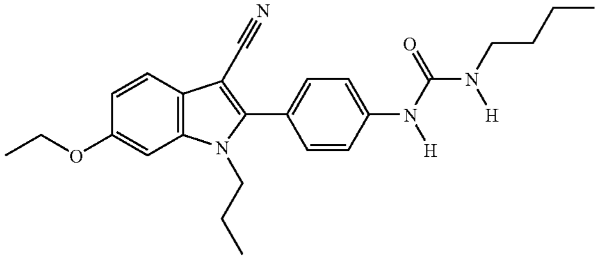
1098
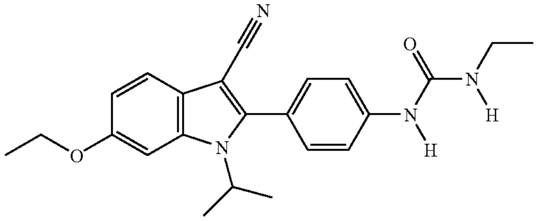
1099
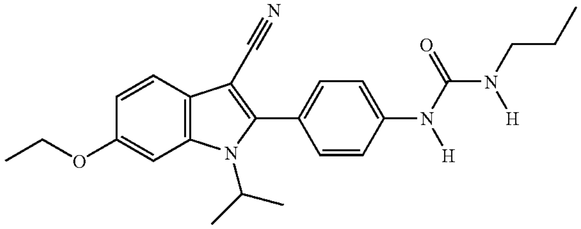
1100
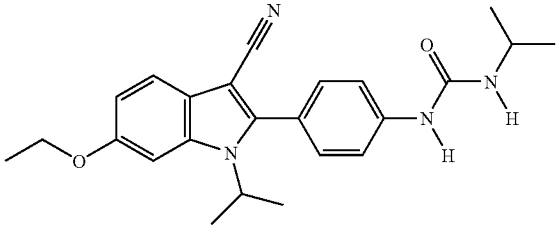

-continued
1101
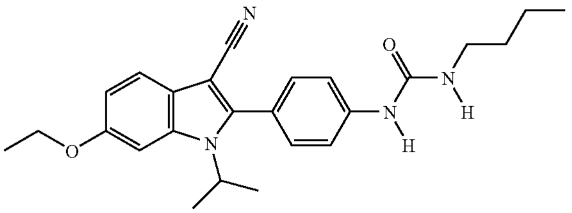
1102
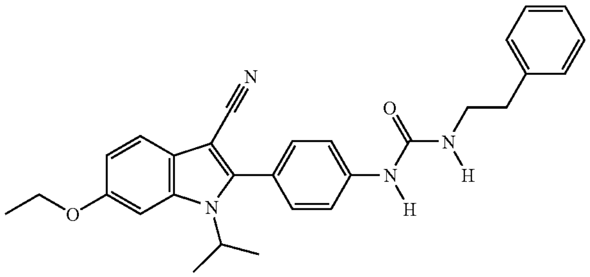
1103
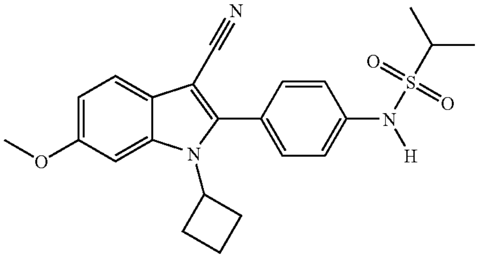
1104
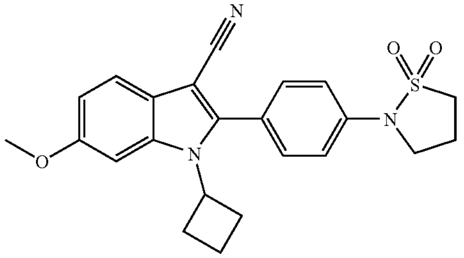
1105
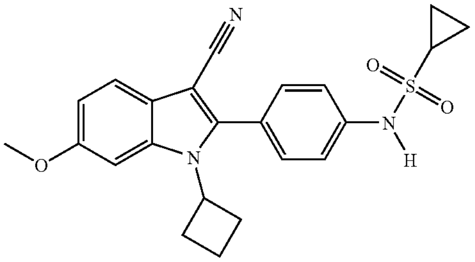
1106
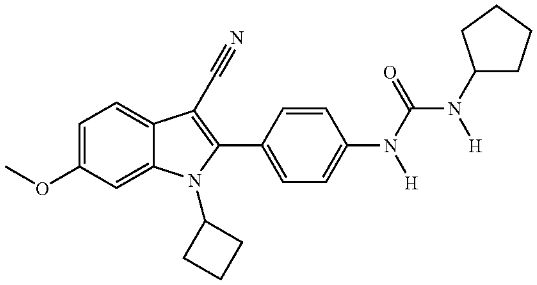
1107
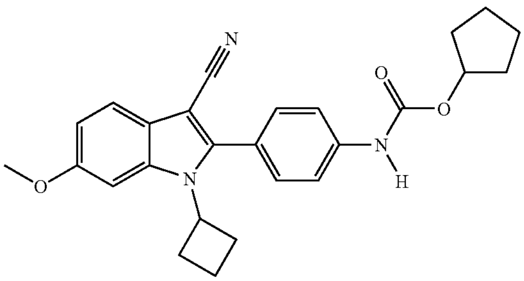
1108
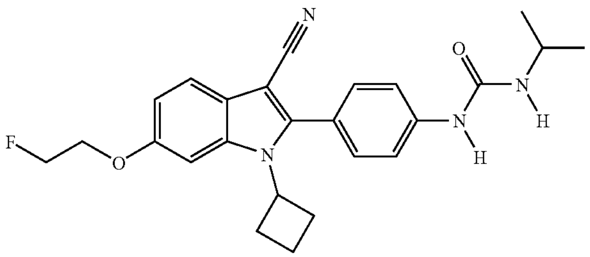
1109
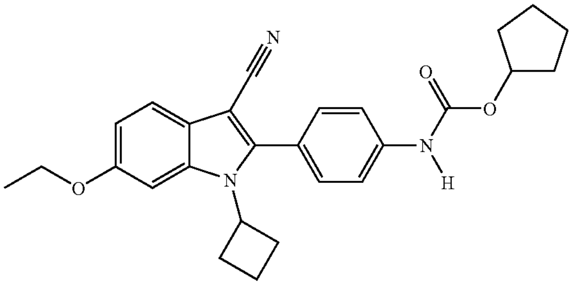
1110
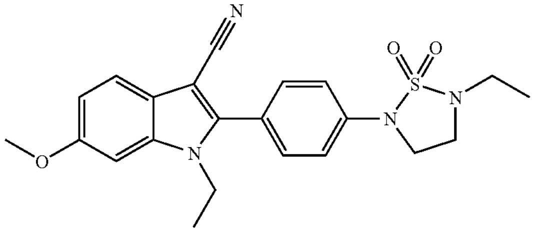

-continued
1111
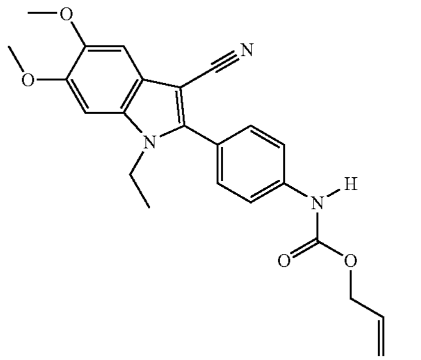
1112
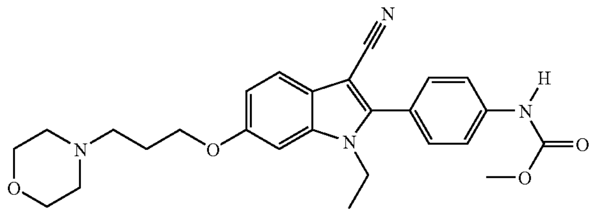
1113
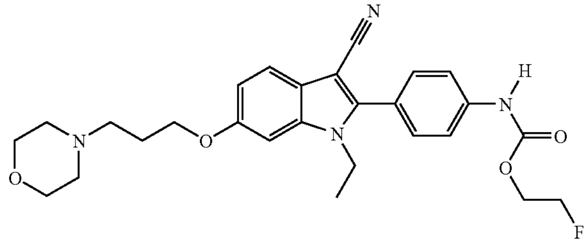
1114
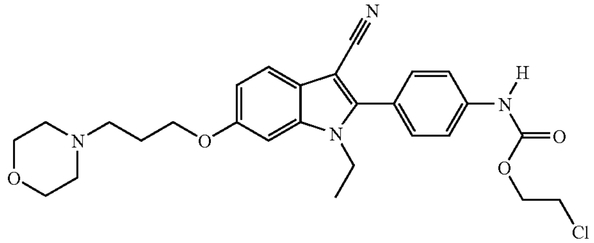
1115
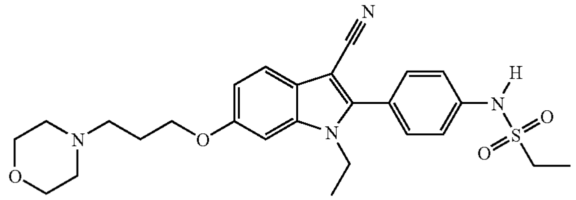
1116
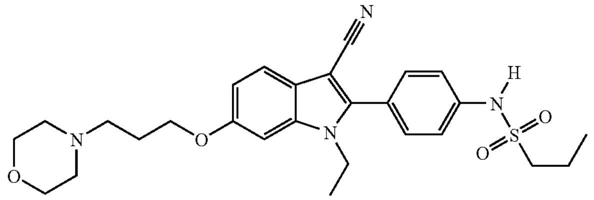
1117
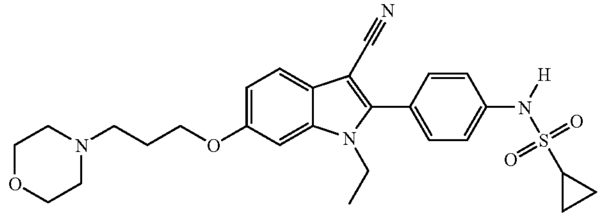
1118
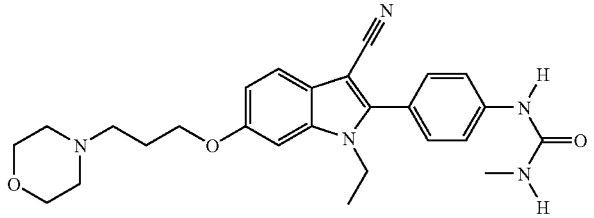
1119
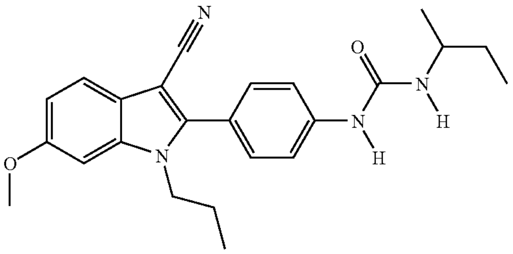
1120
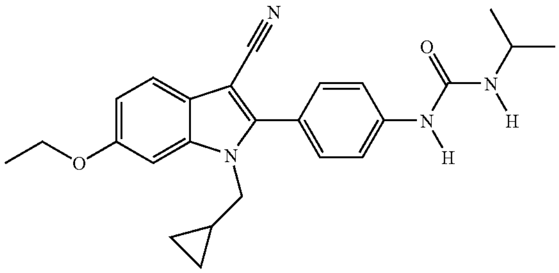

-continued
1121
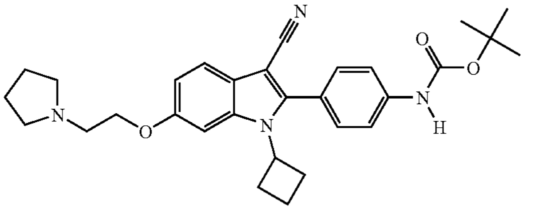
1122
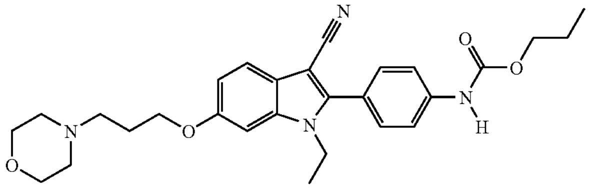
1123
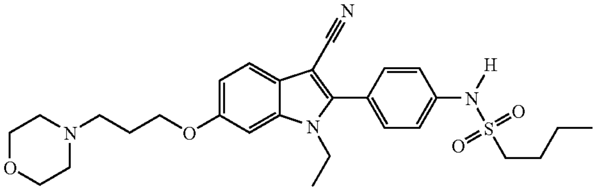
1124
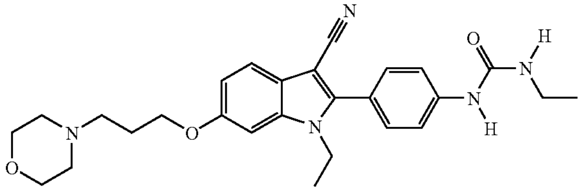
1125
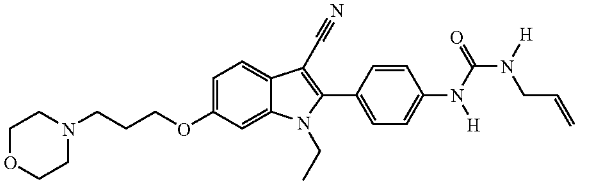
1126
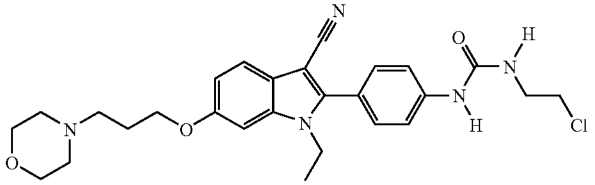
1127
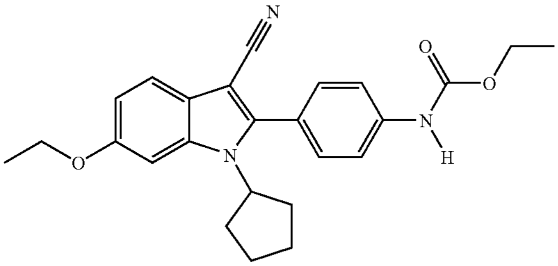
1128
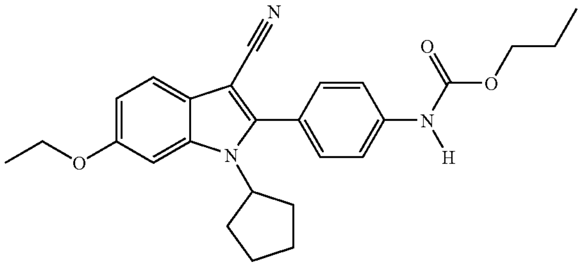
1129
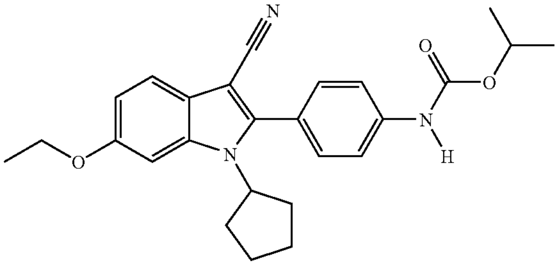
1130
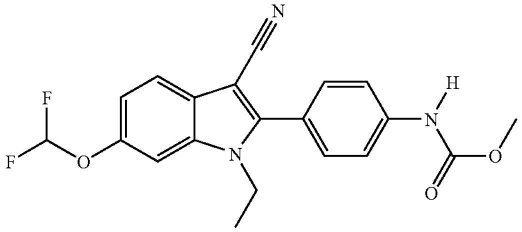
1131
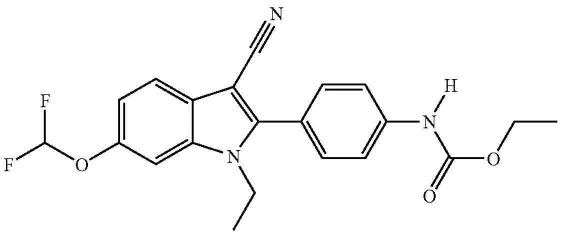
1132
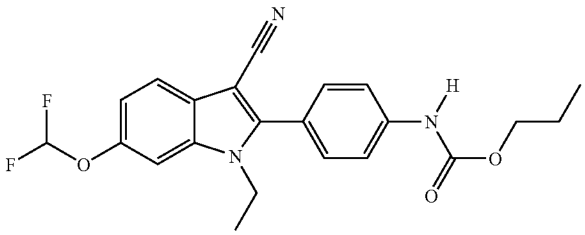

-continued
1133
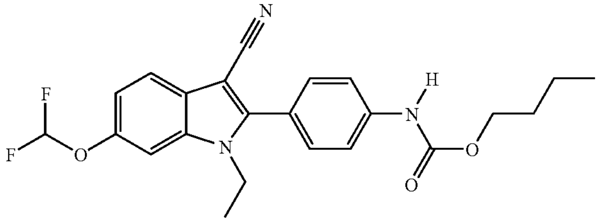
1134
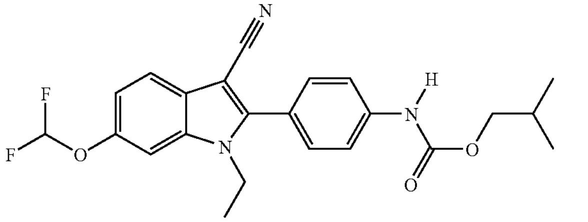
1135
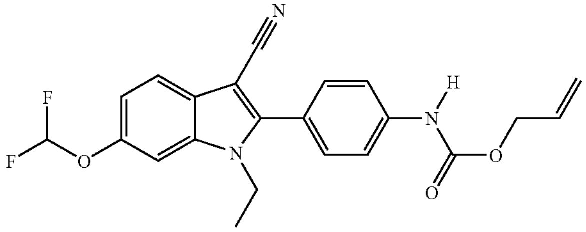
1136
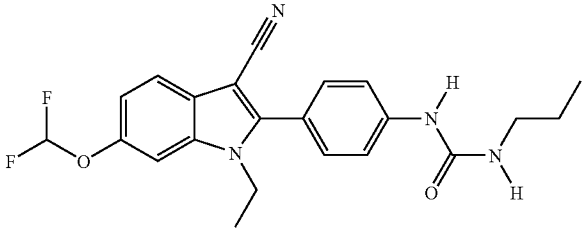
1137
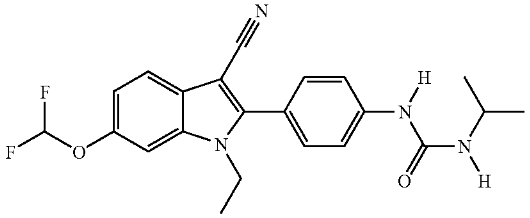
1138
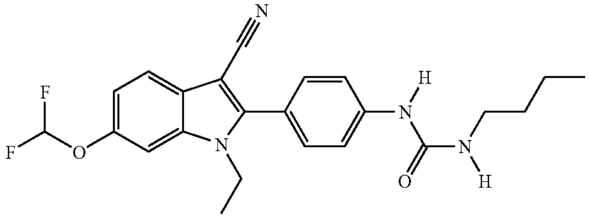
1139
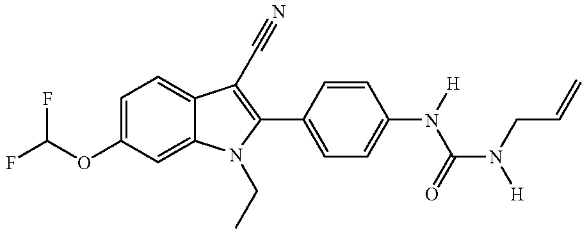
1140
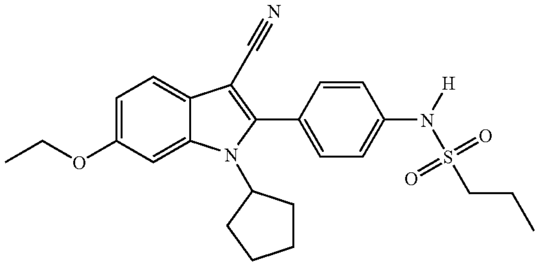
1141
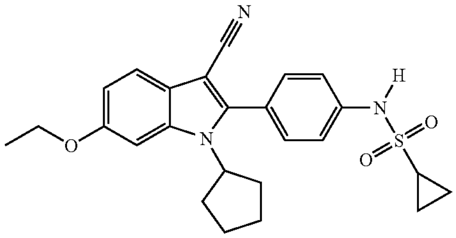
1142
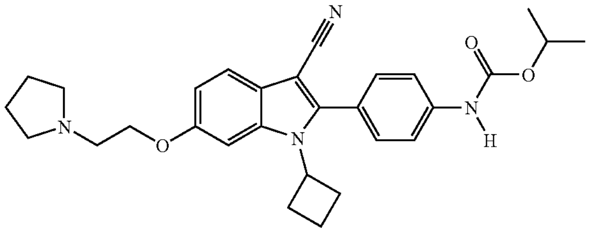
1143
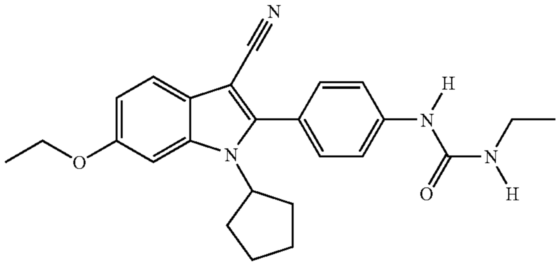
1144
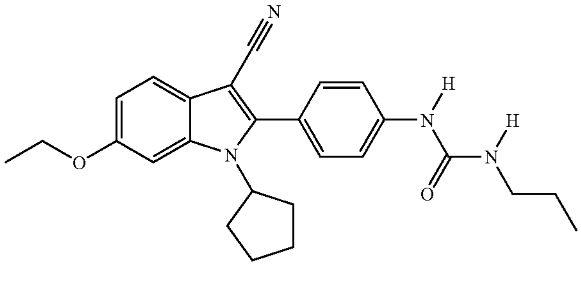

-continued
1145
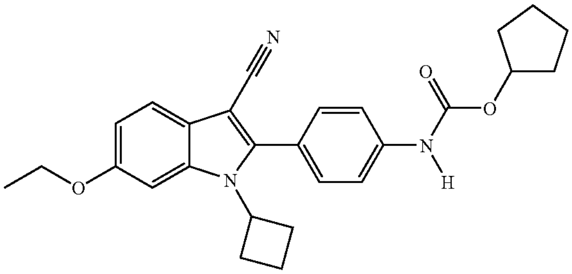
1146
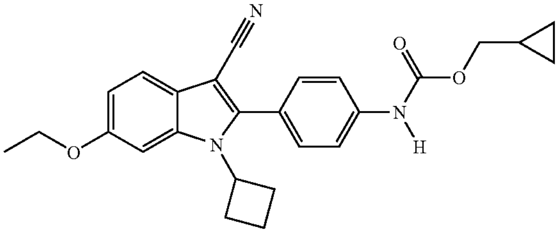
1147
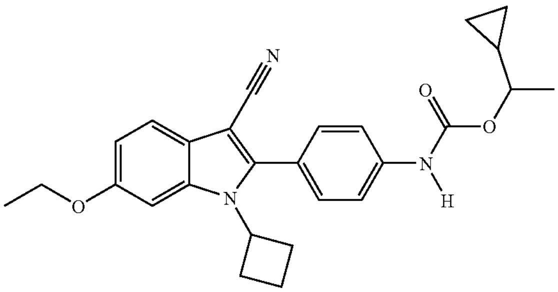
1148
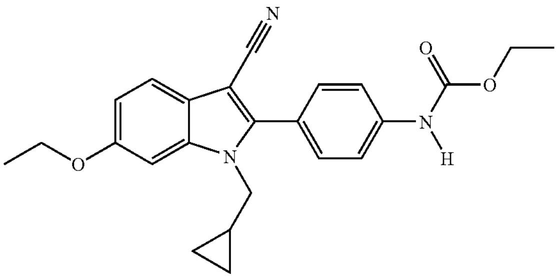
1149
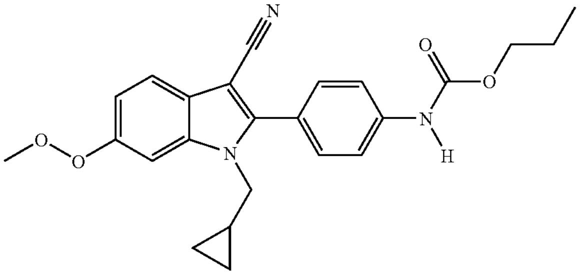
1150
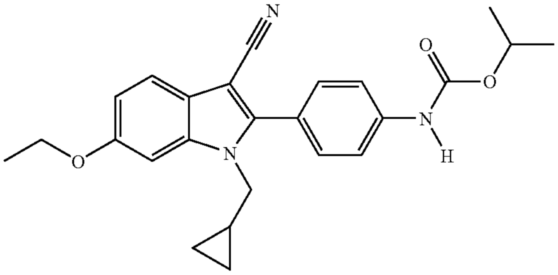
1151
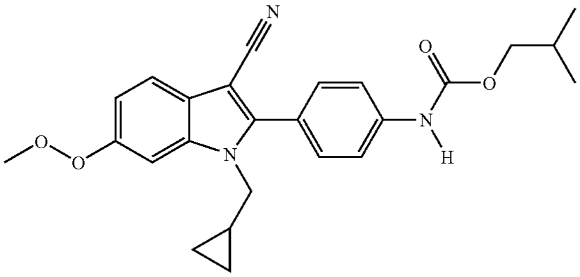
1152
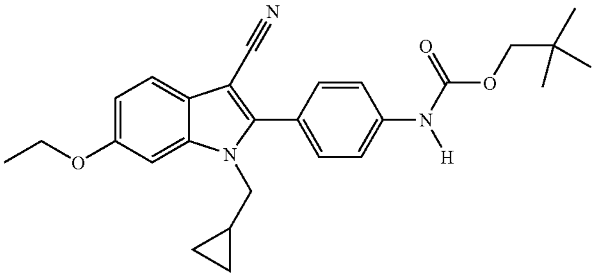
1153
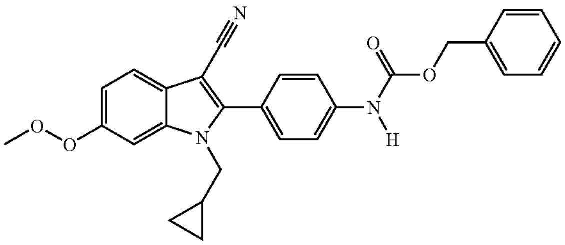
1154
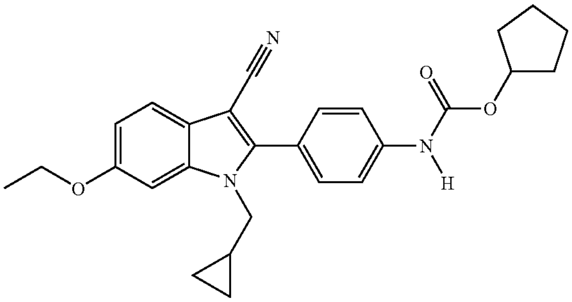

-continued
1155
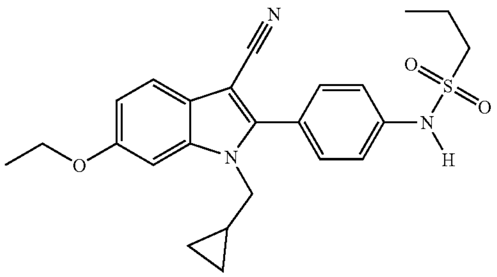
1156
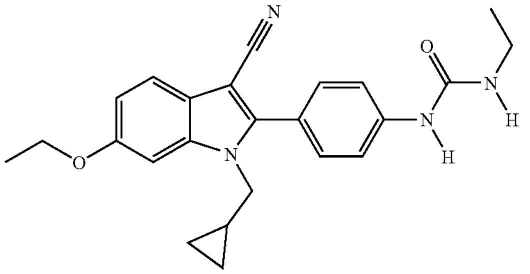
1157
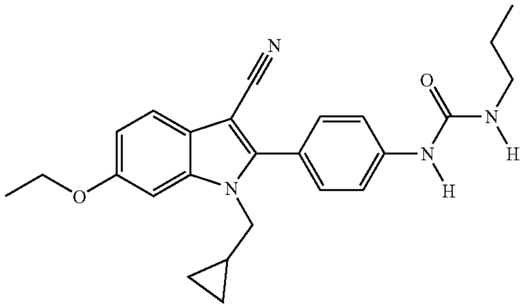
1158
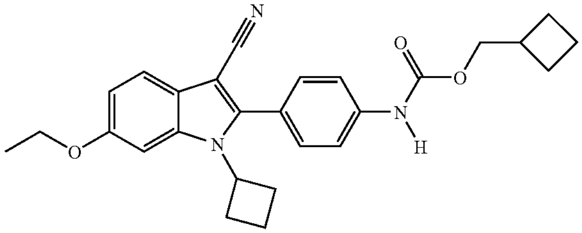
1159
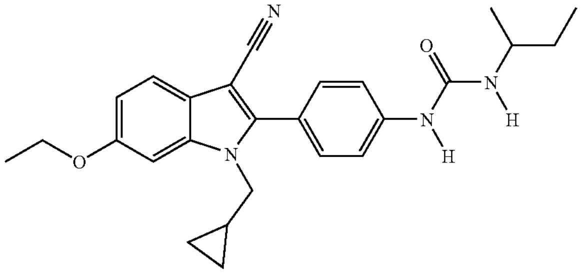
1160
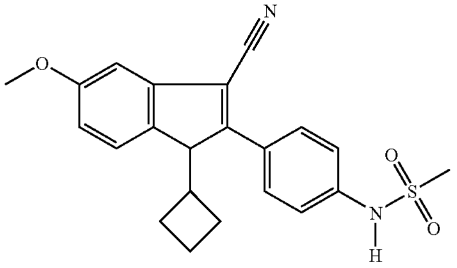
1161
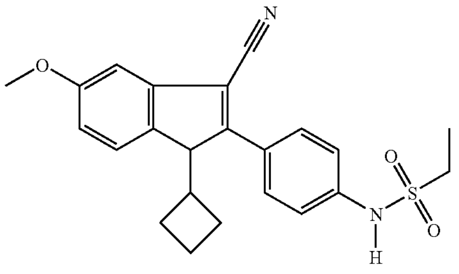
1162
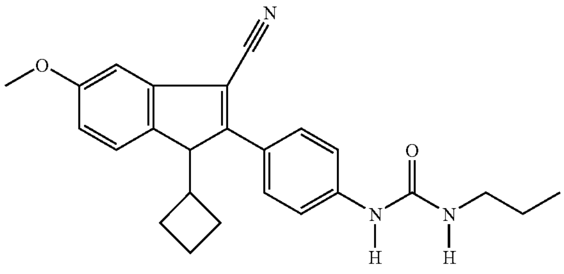
1163
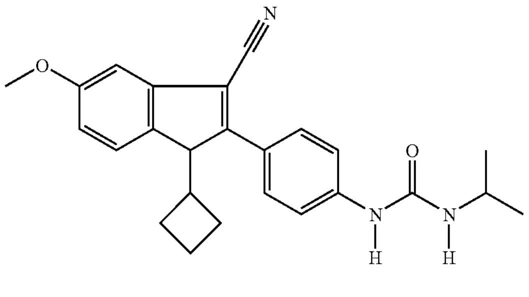
1164
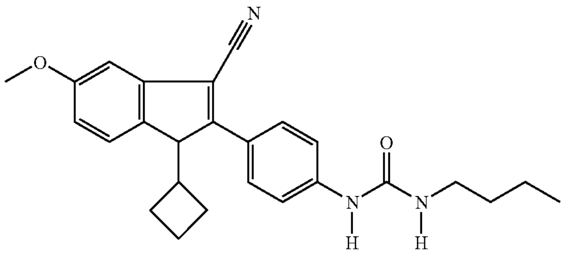

-continued
1165
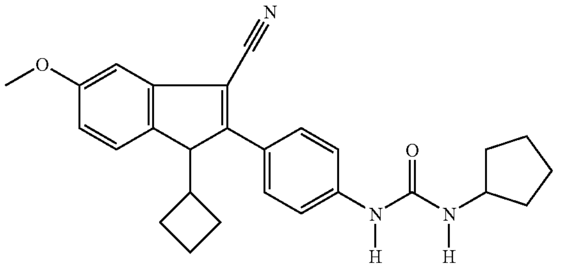
1166
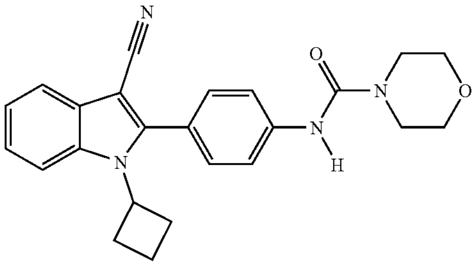
1167
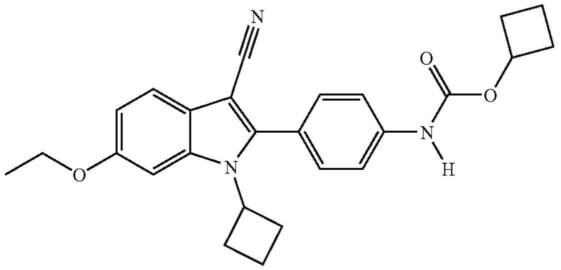
1168
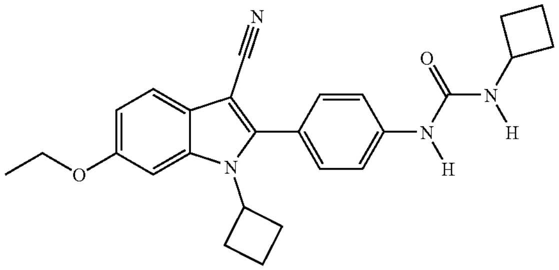
1169
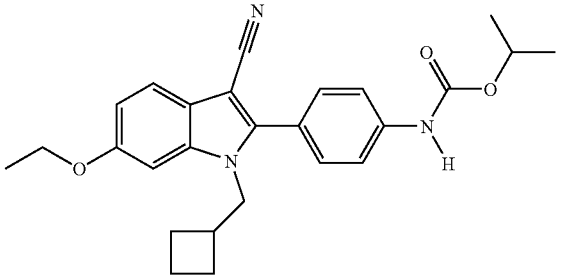
1170
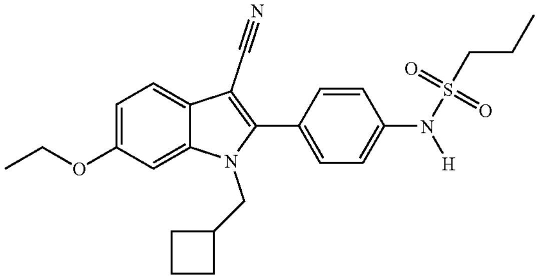
1171
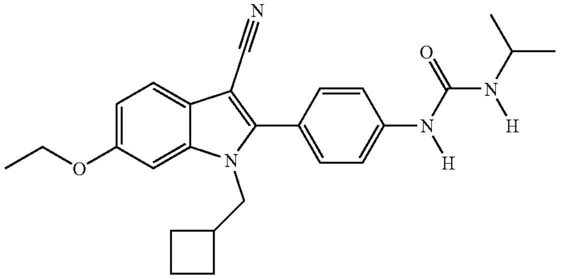
1172
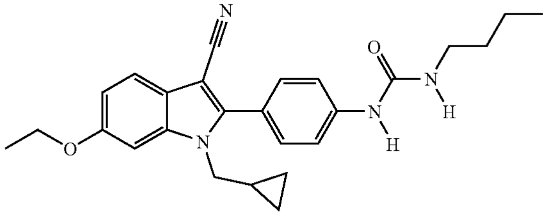
1173
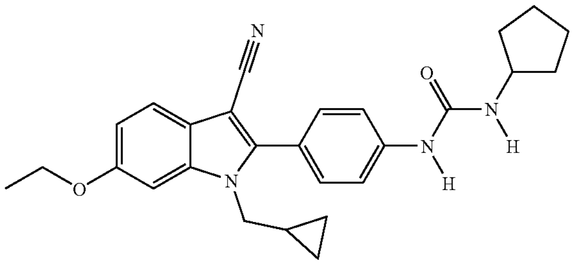
1174
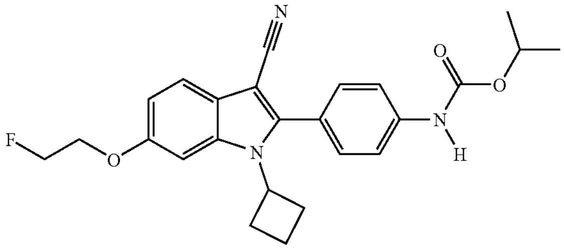

-continued
1175
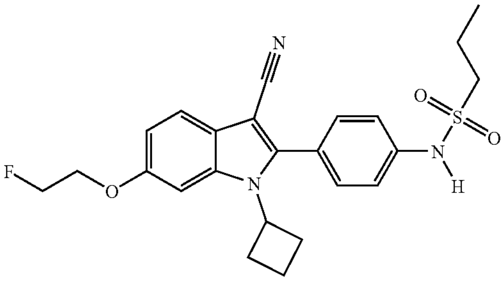
1176
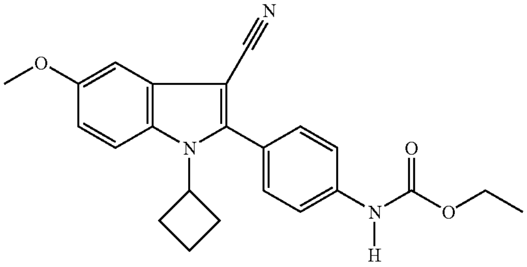
1177
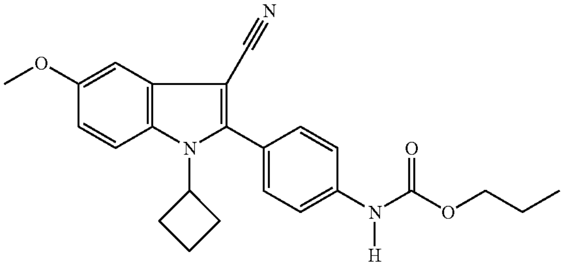
1178
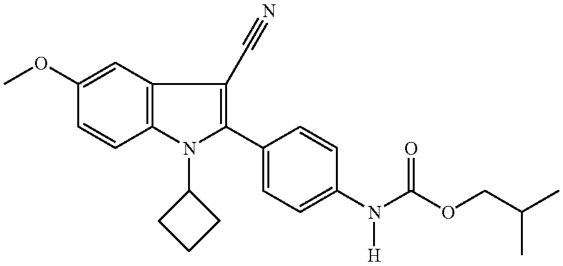
1179
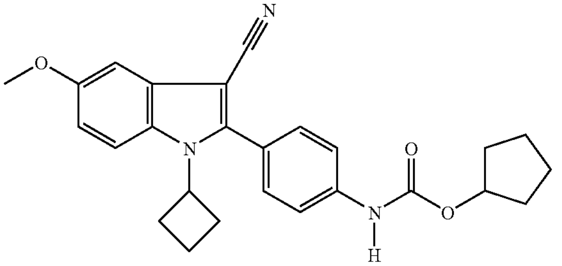
1180
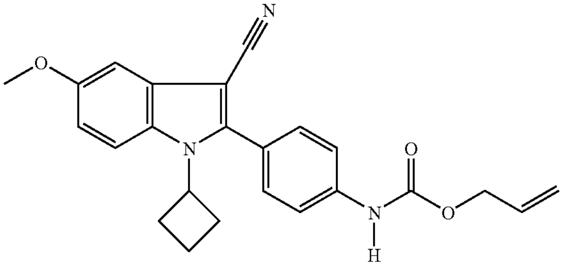
1181
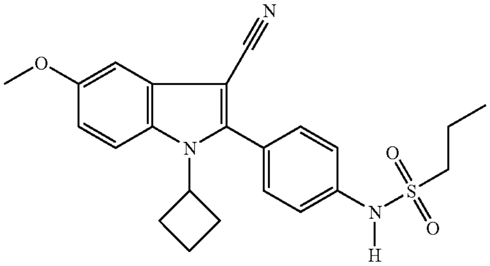
1182
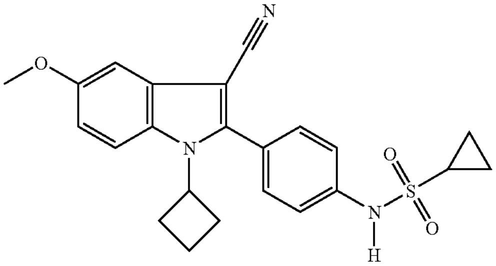
1183
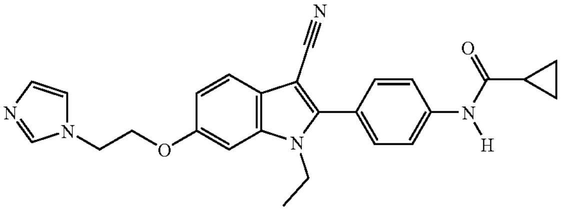
1184
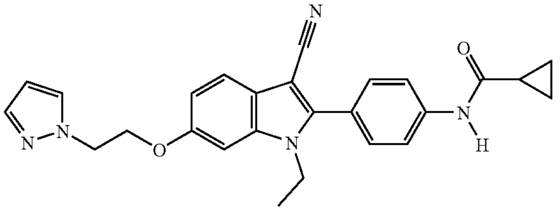
1185
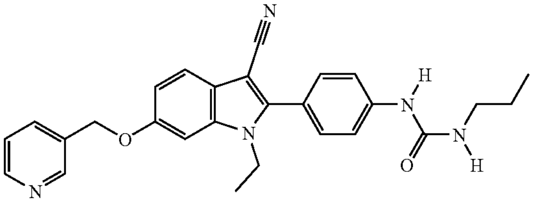
1186
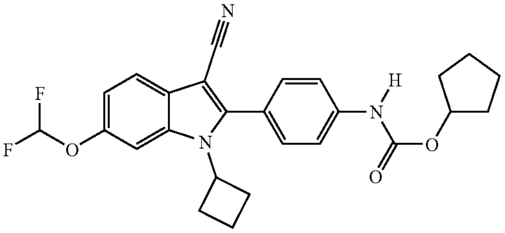

-continued
1187
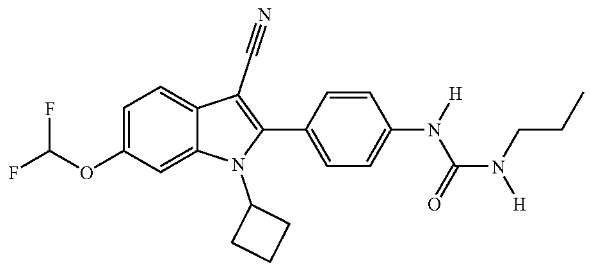
1188
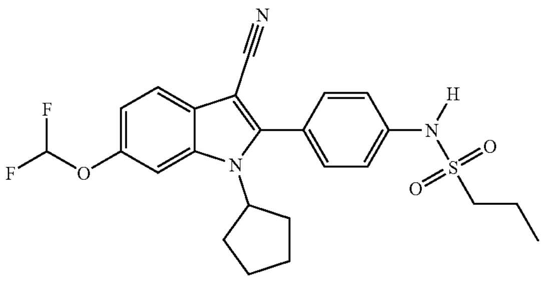
1189
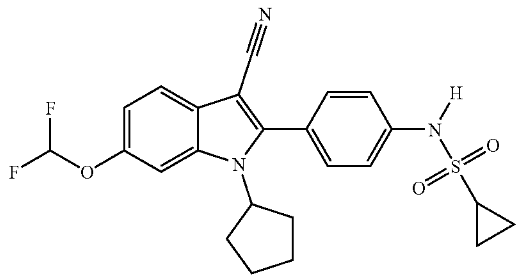
1190
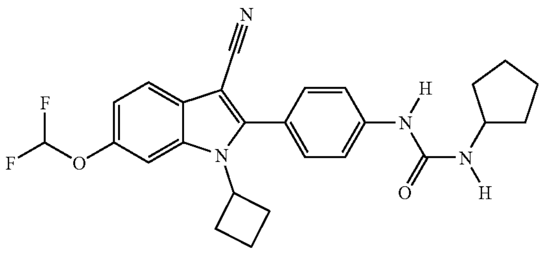
1191
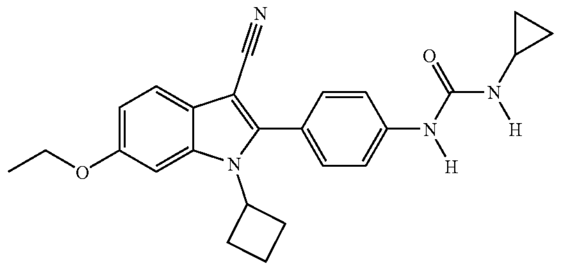
1192
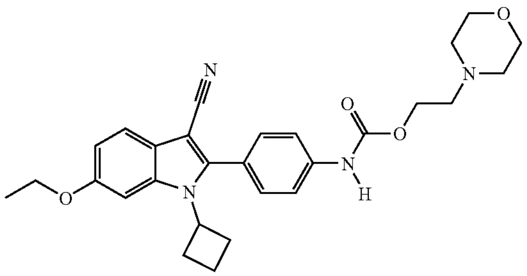
1193
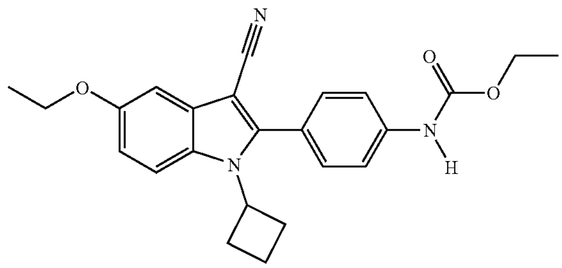
1194
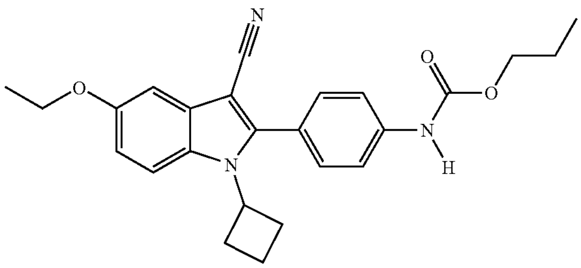
1195
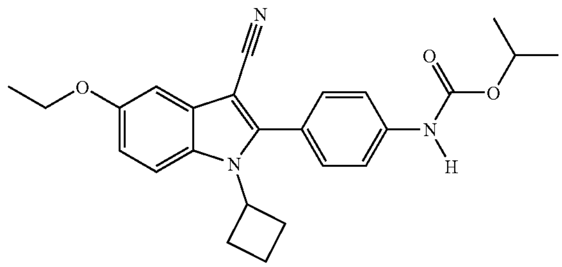
1196
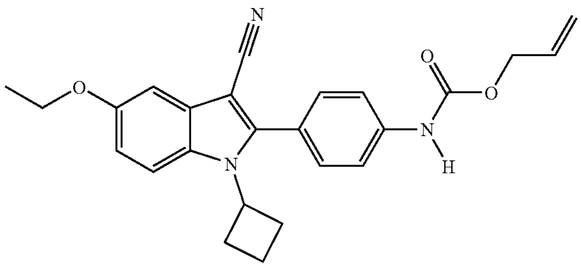

-continued
1197
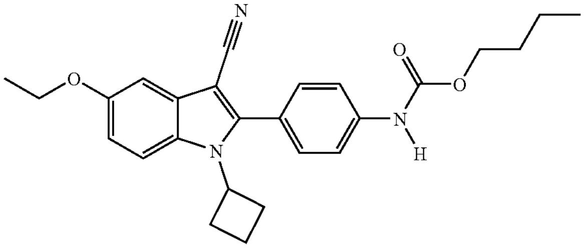
1198
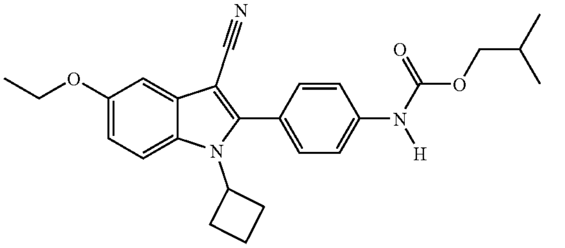
1199
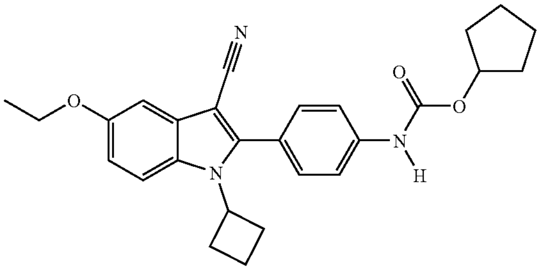
1200
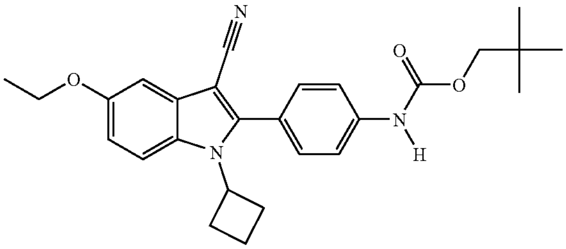
1201
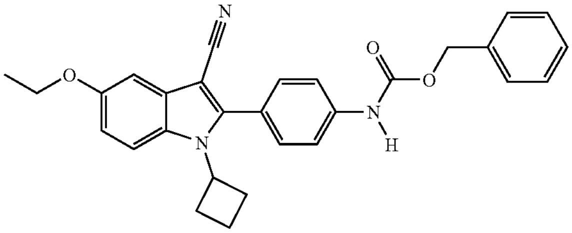
1202
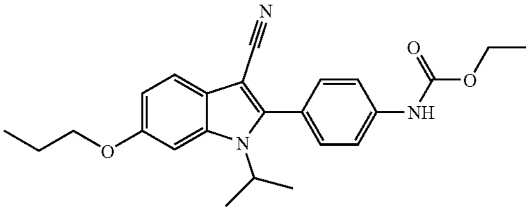
1203
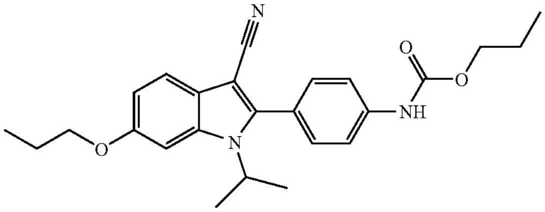
1204
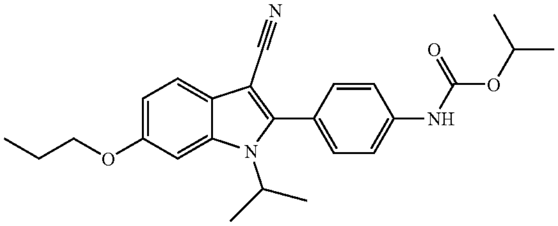
1205
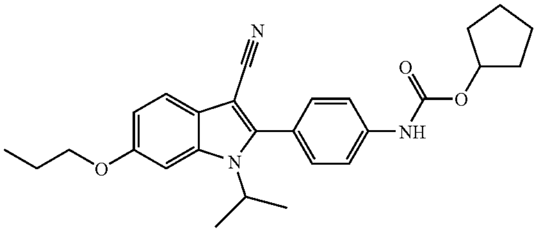
1206
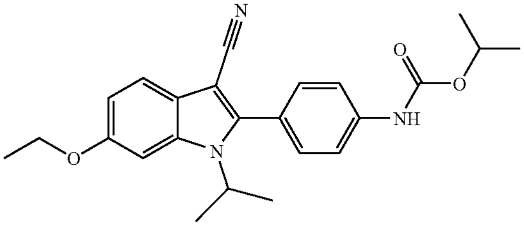
1207
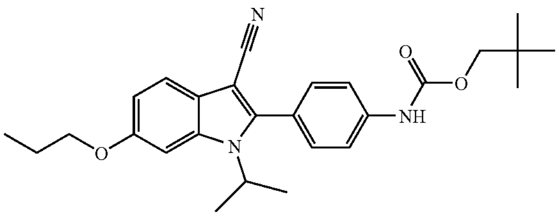
1208
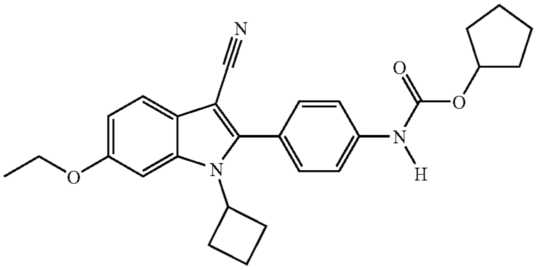

-continued
1209
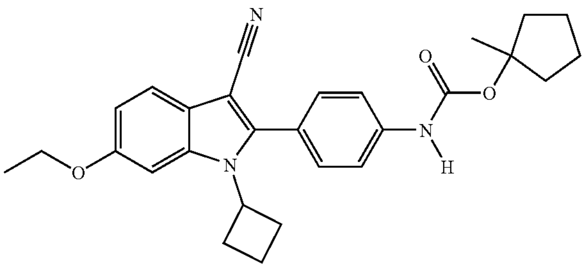
1210
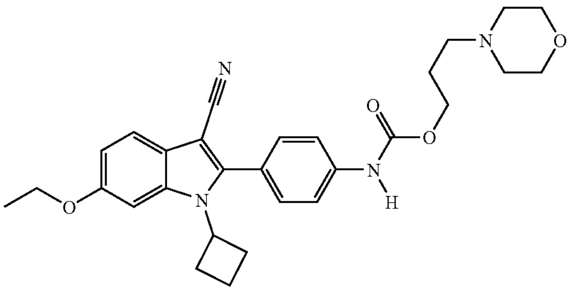
1211
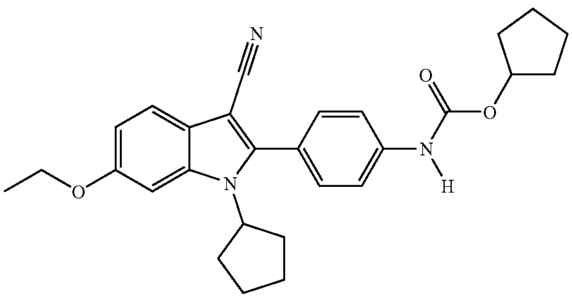
1212
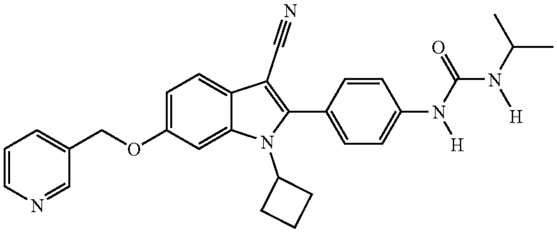
1213
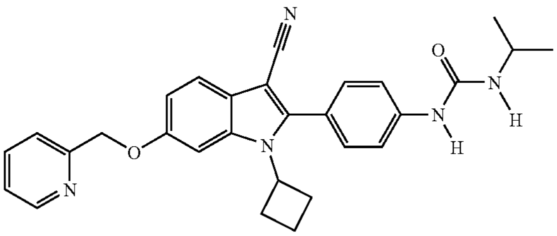
1214
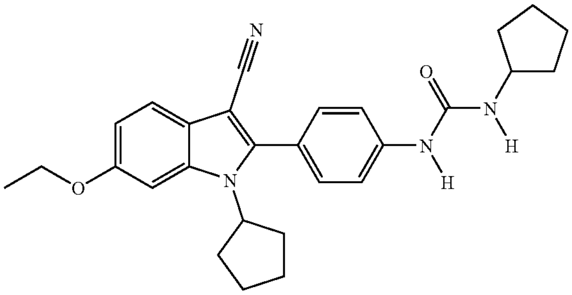
1215
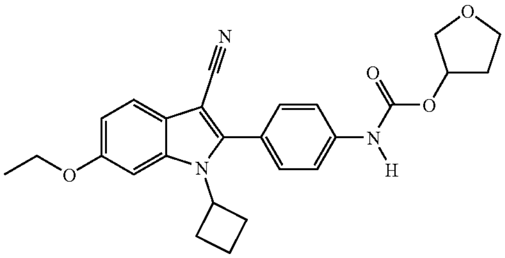
1216
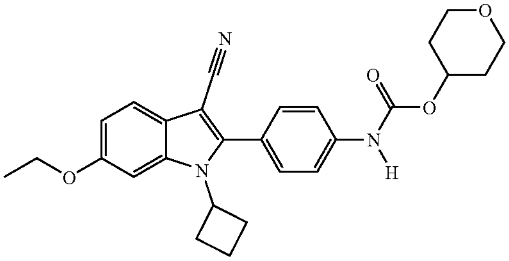
1217
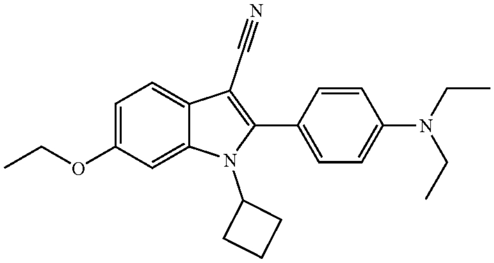
1218
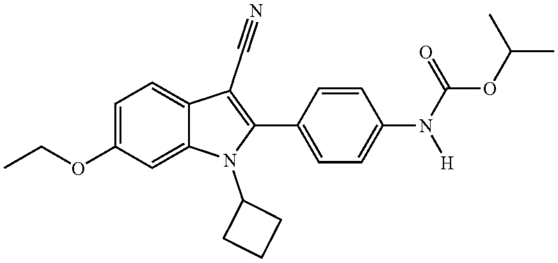

-continued
1219
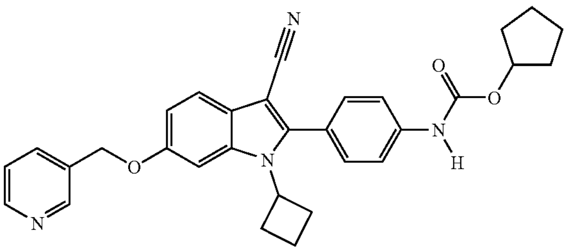
1220
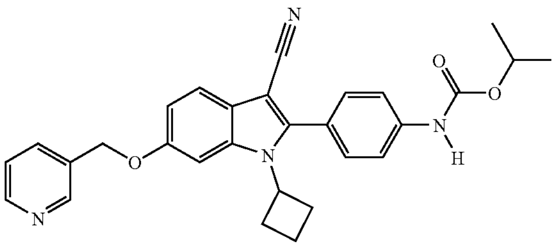
1221
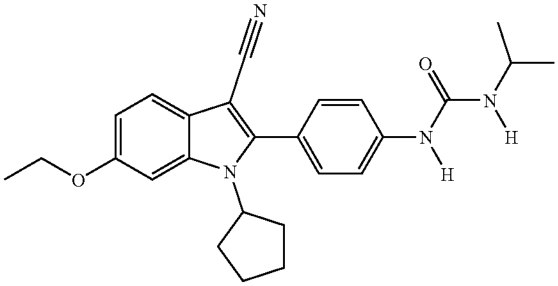
1222
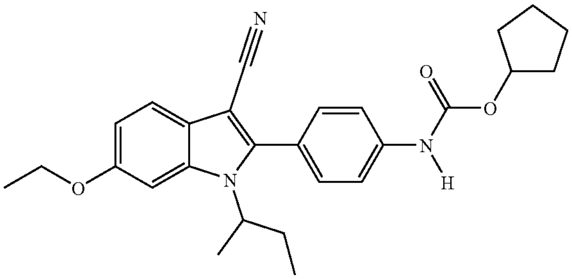
1223
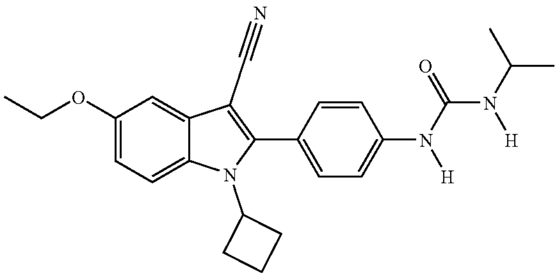
1224
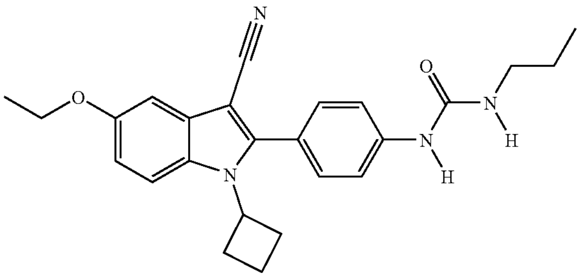
1225
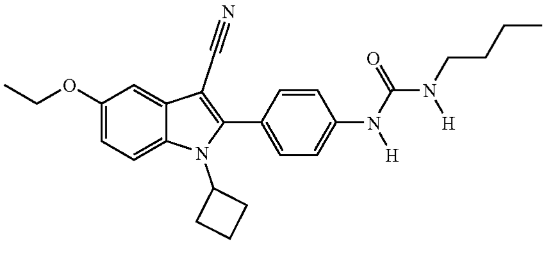
1226
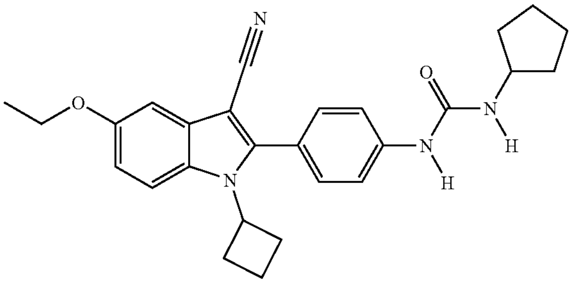
1227
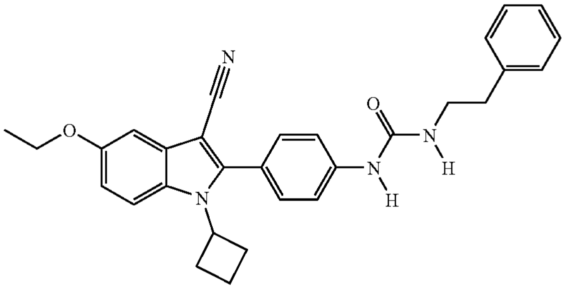
1228
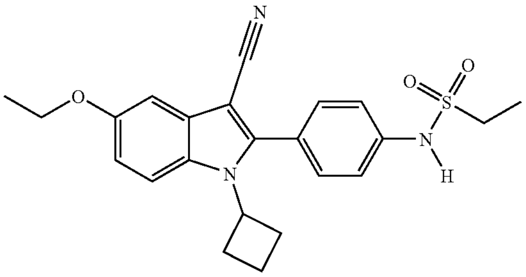

-continued
1229
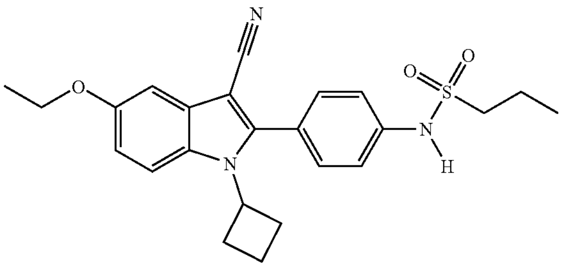
1230
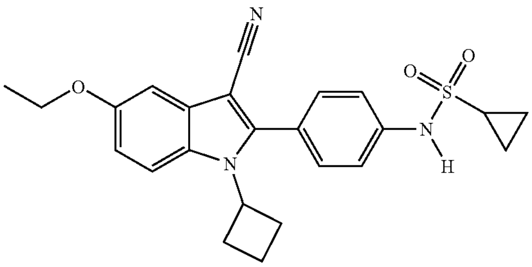
1231
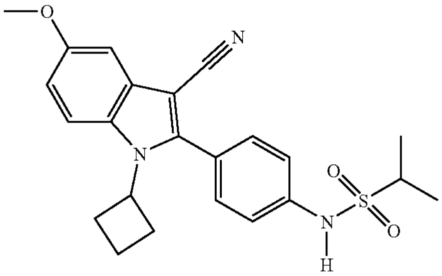
1232
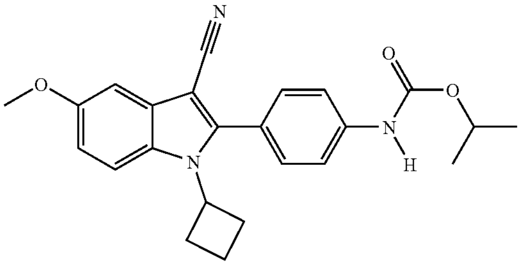
1233
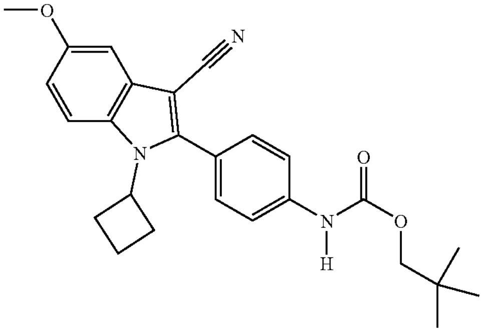
1234
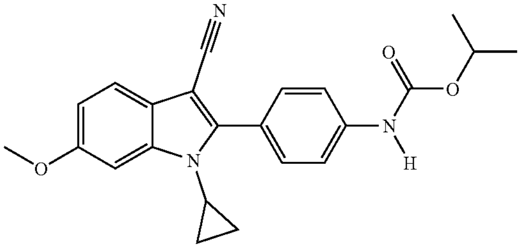
1235
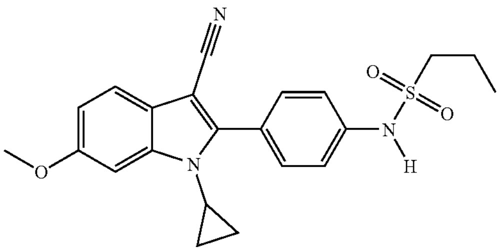
1236
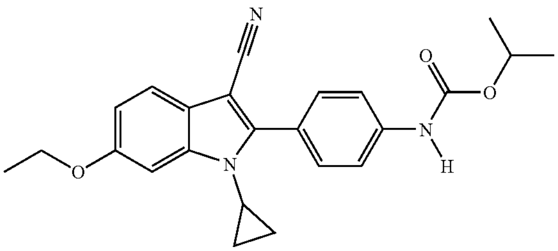
1237
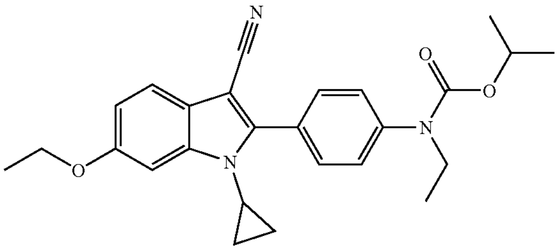
1238
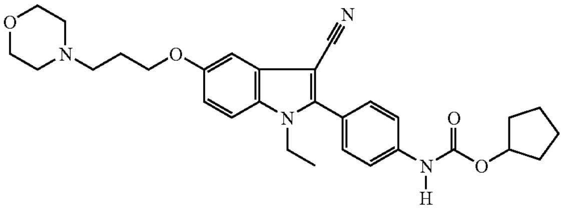

-continued
1239
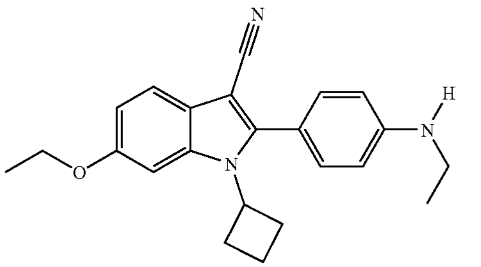
1240
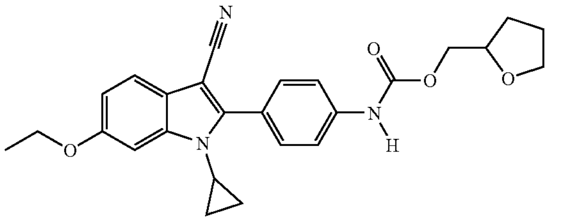
1241
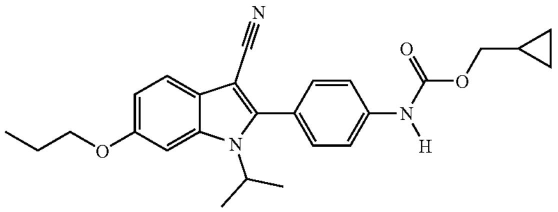
1242
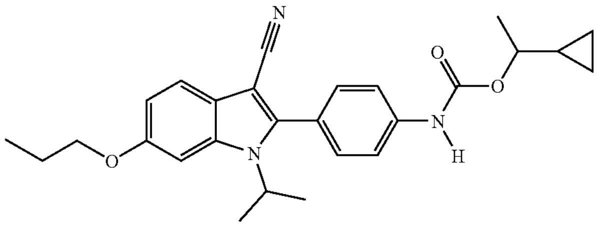
1243
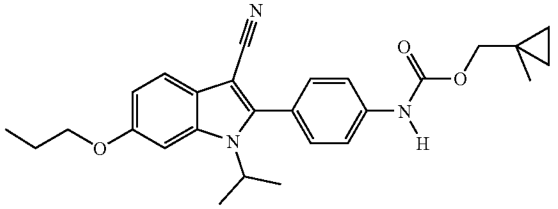
1244
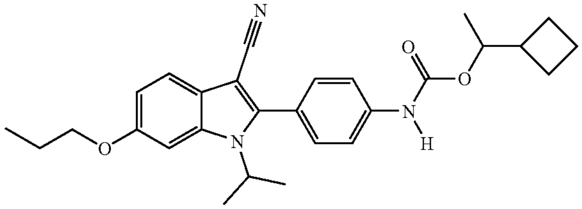
1245
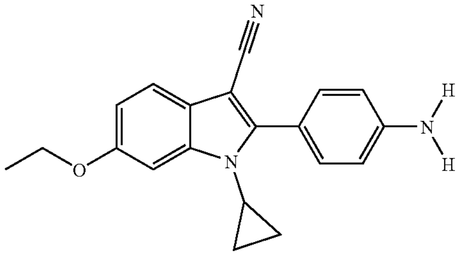
1246
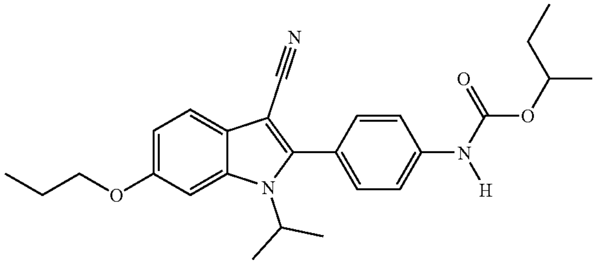
1247
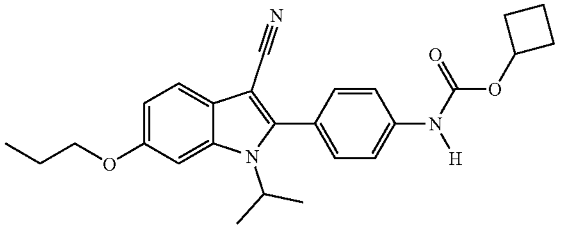
1248
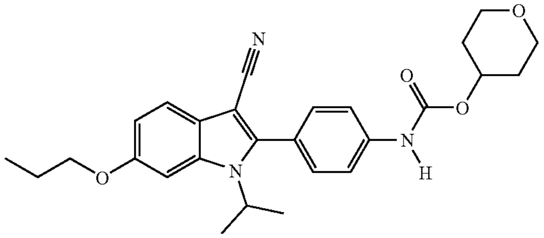
1249
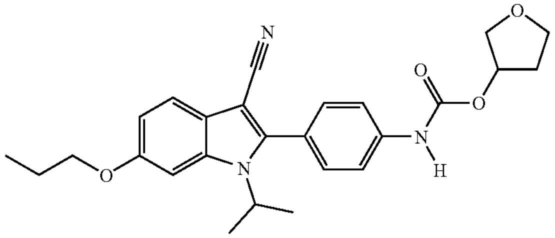
1250
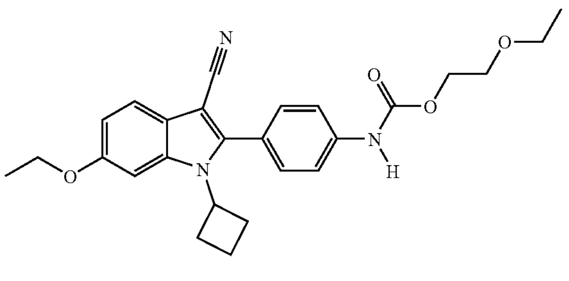

-continued
1251
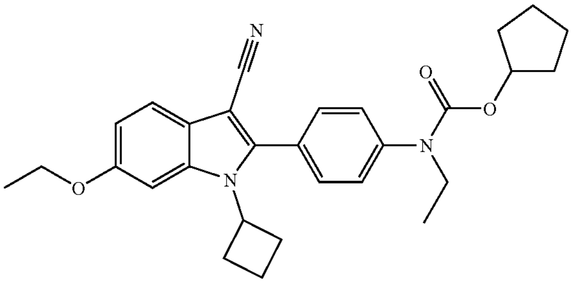
1252
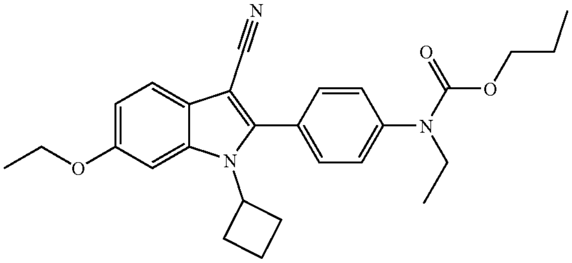
1253
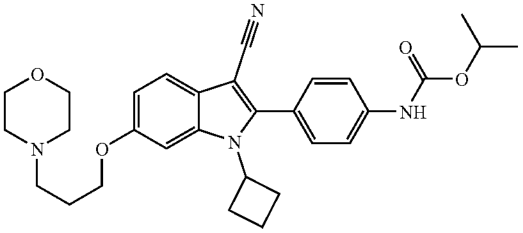
1254
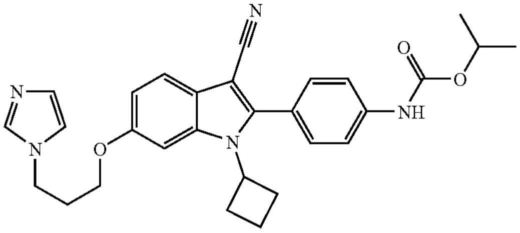
1255
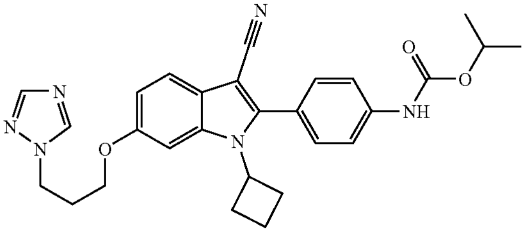
1256
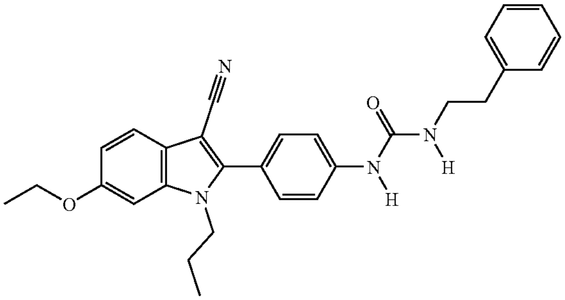
1257
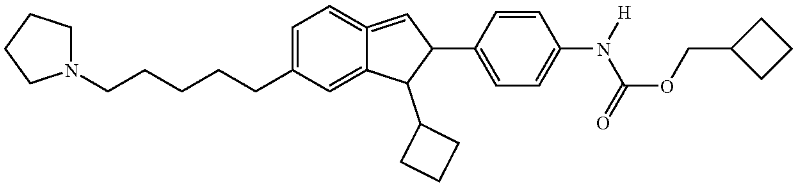
1258
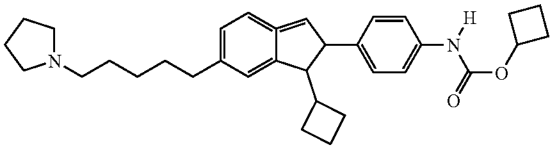
1259
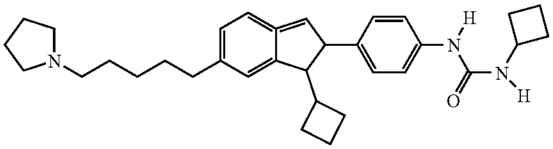
1260
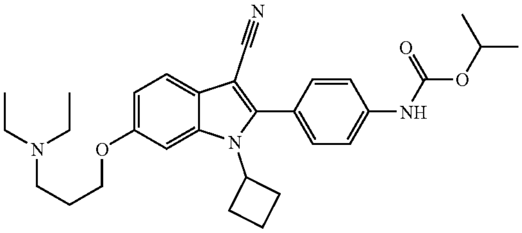
1261
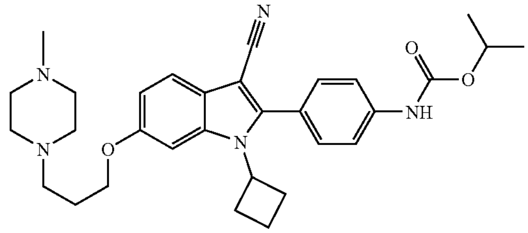

-continued
1262
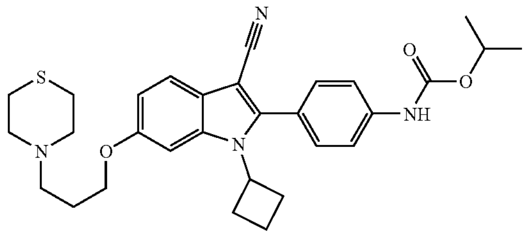
1263
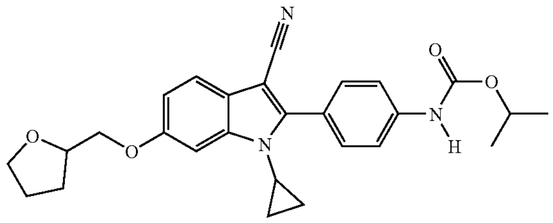
1264
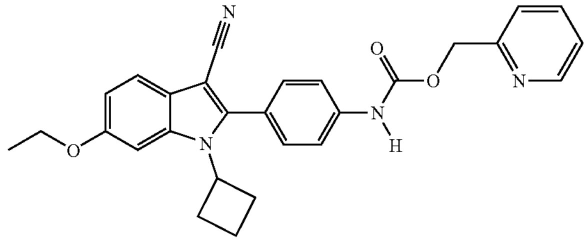
1265
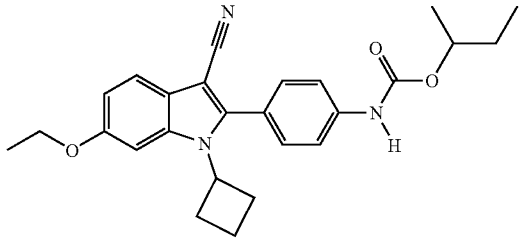
1266
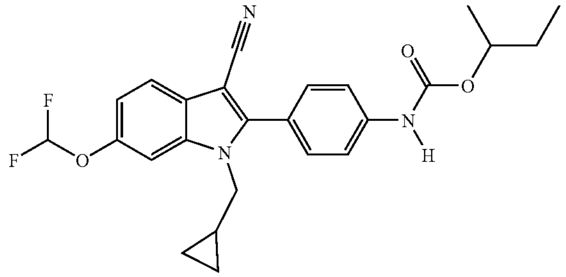
1267
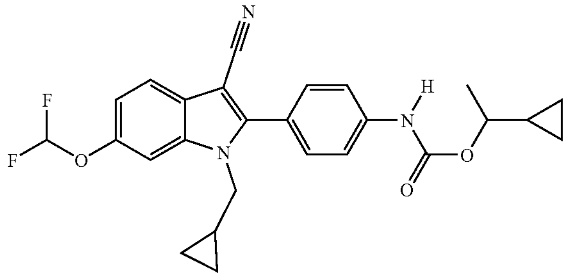
1268
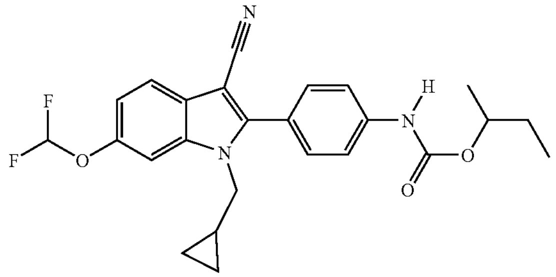
1269
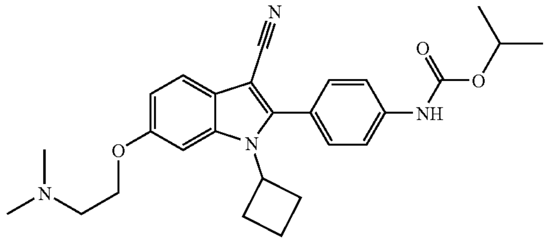
1270
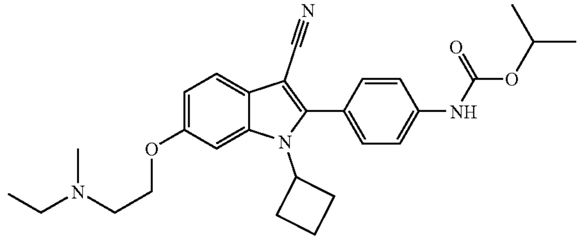
1271
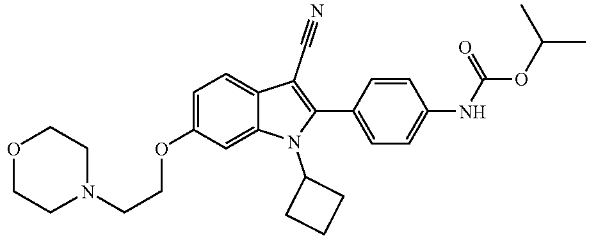

-continued
1272
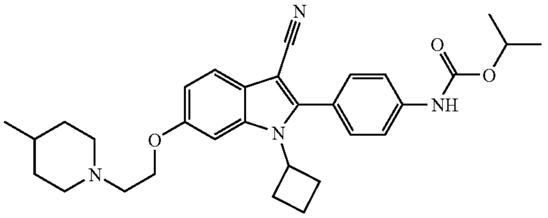
1273
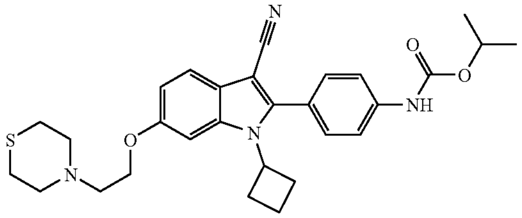
1274
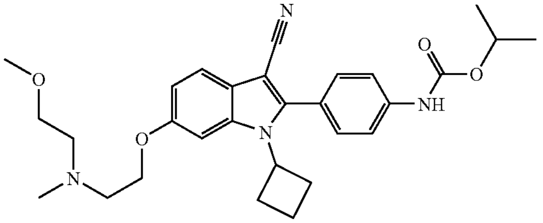
1275
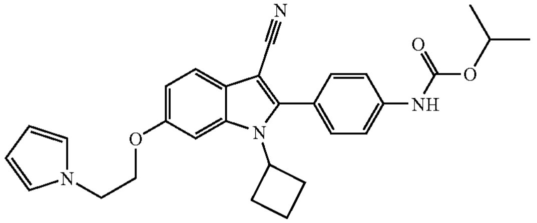
1276
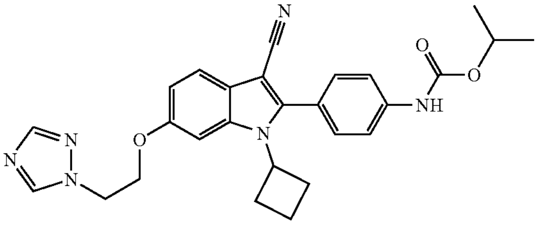
1277
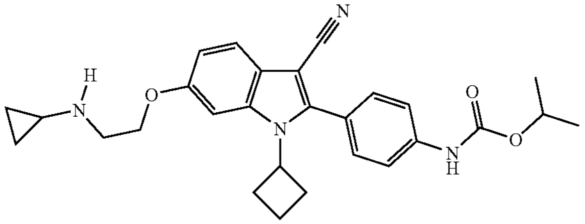
1278
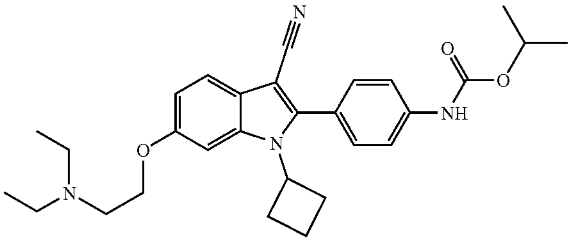
1279
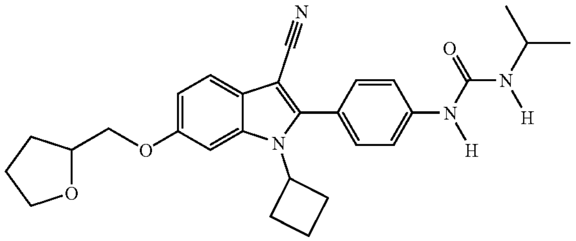
1280
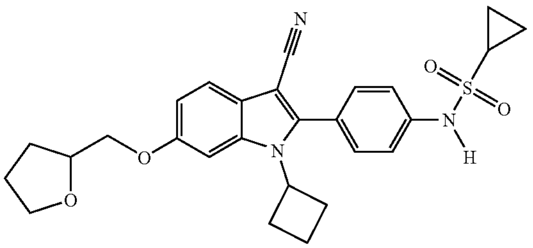
1281
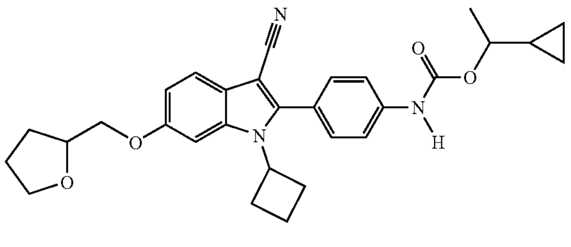
1282
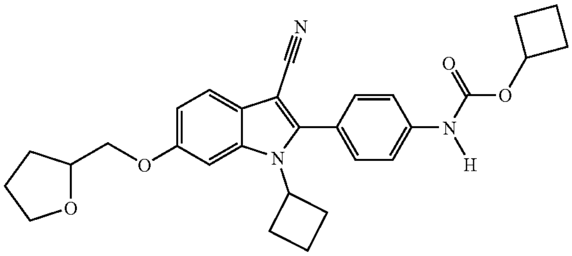
1283
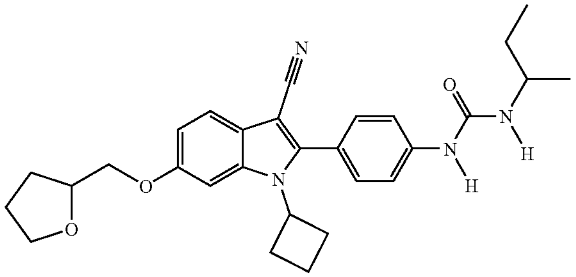

-continued
1284
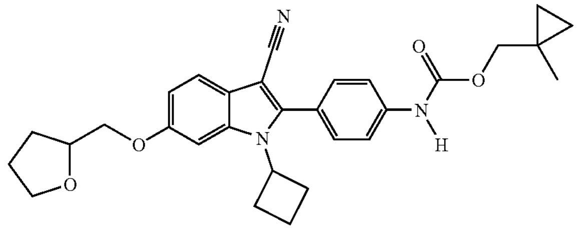
1285
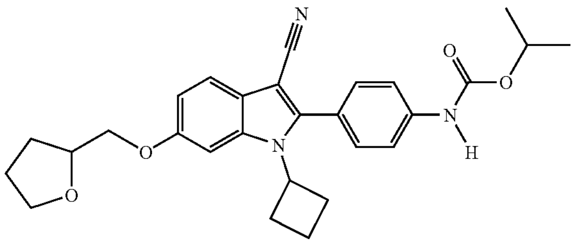
1286
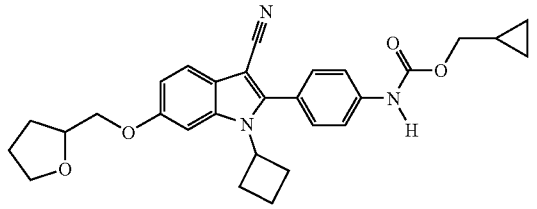
1287
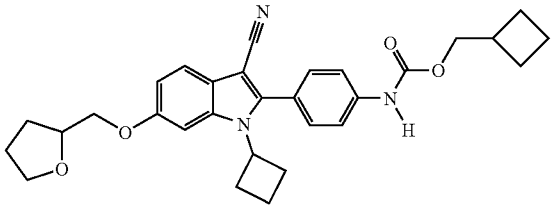
1288
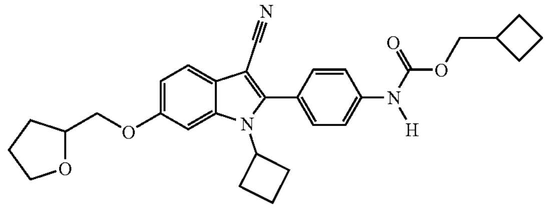
1289
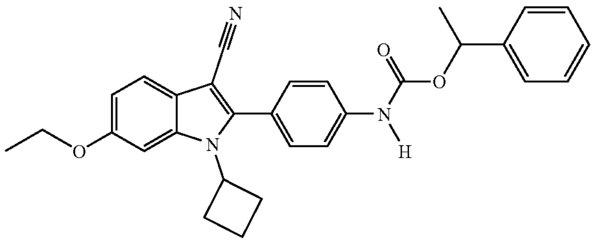
1290
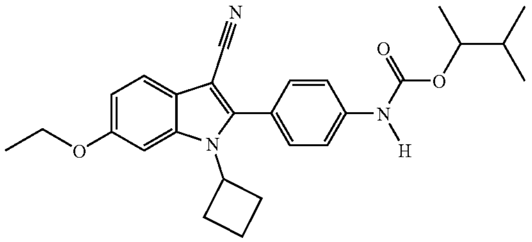
1291
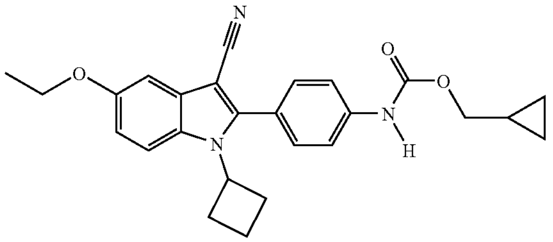
1292
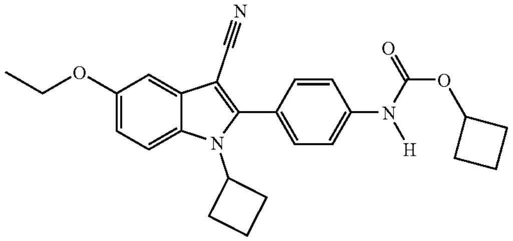
1293
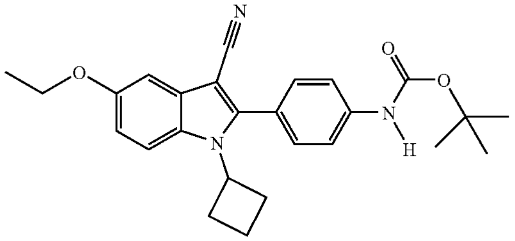
1294
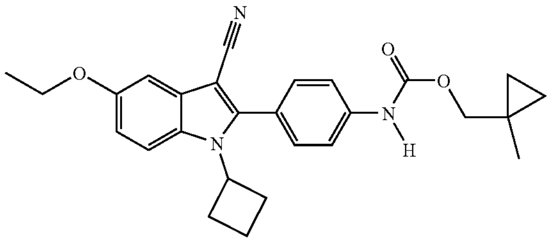
1295
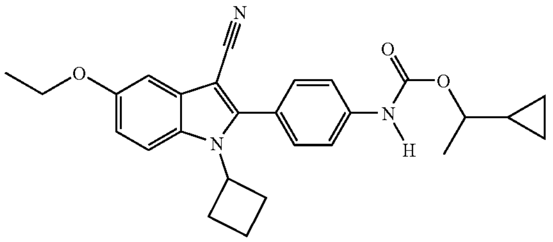

-continued
1296
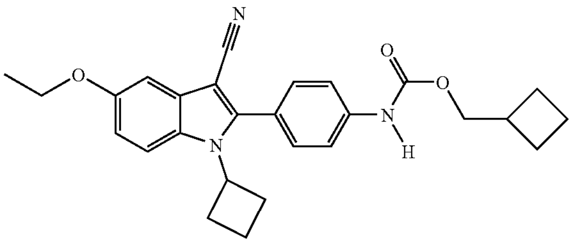
1297
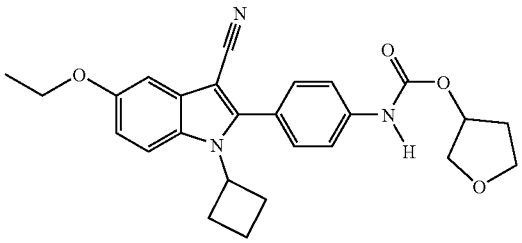
1298
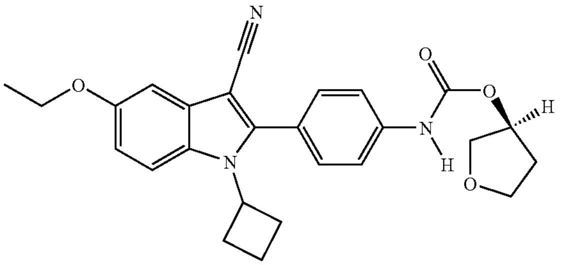
1299
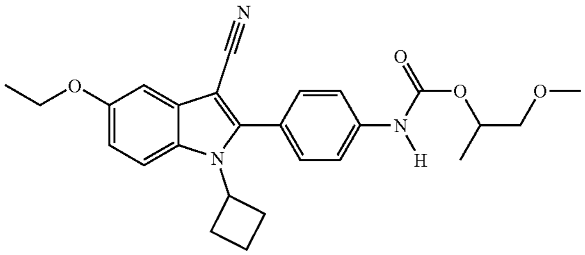
1300
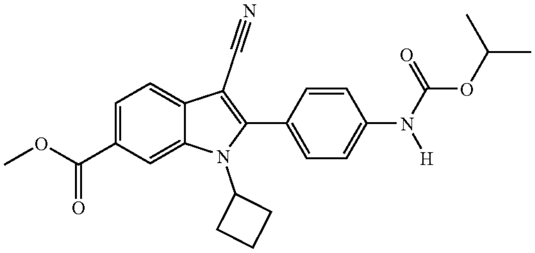
1301
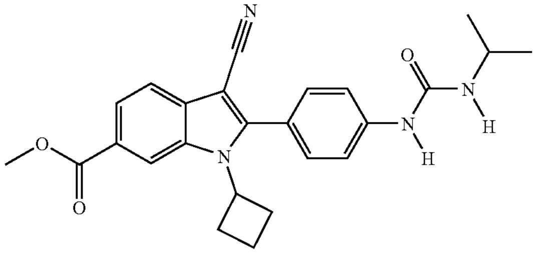
1302
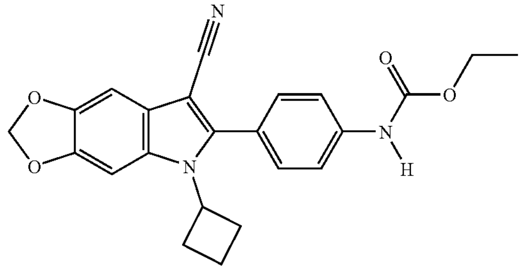
1303
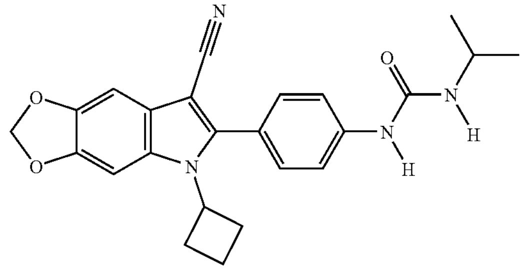
1304
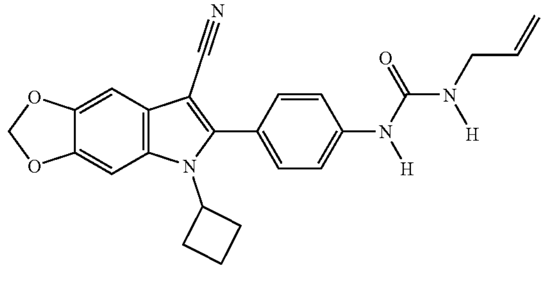
1305
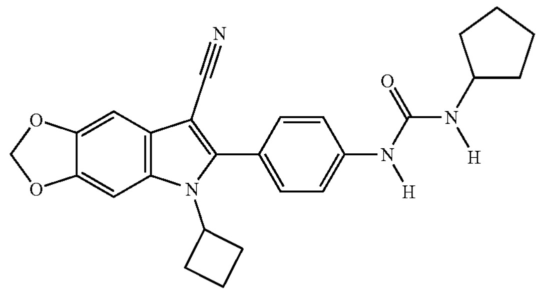
1306
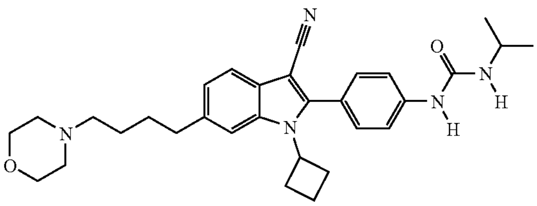
1307
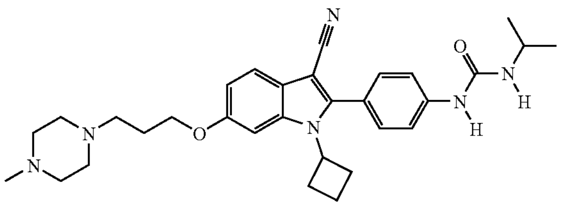

-continued
1308
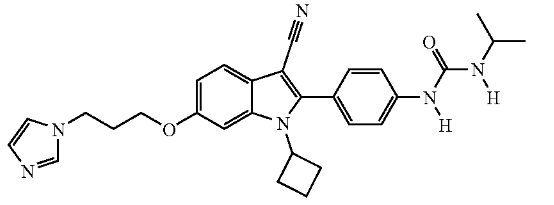
1309
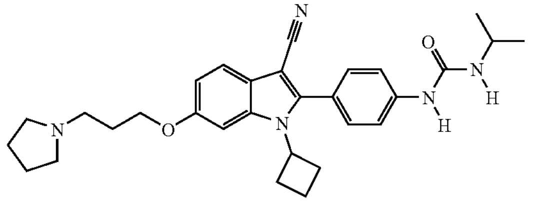
1310
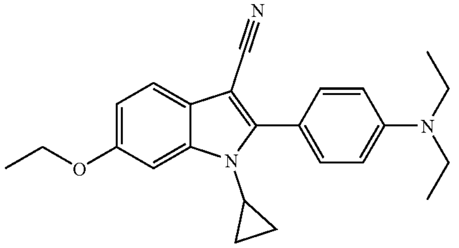
1311
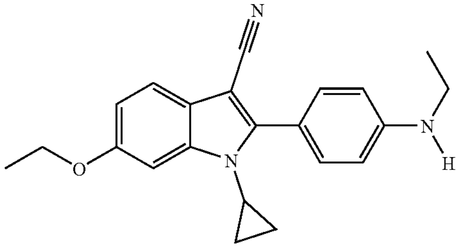
1312
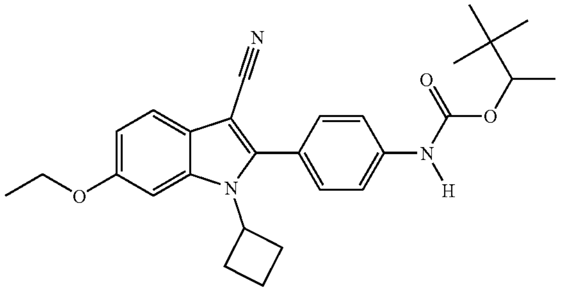
1313
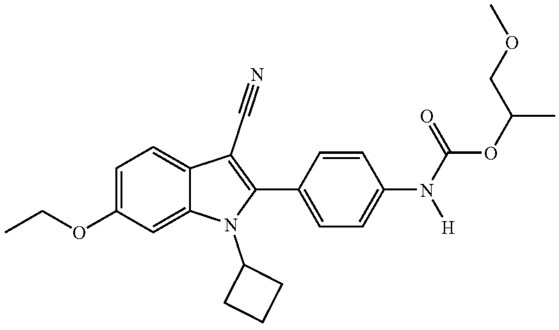
1314
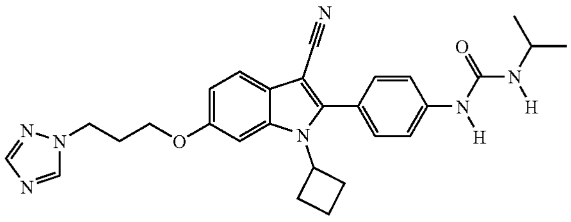
1315
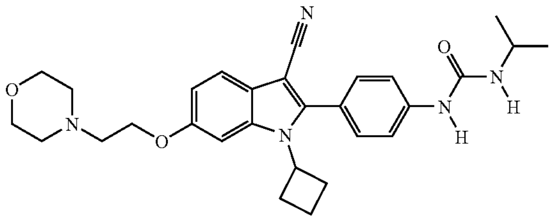
1316
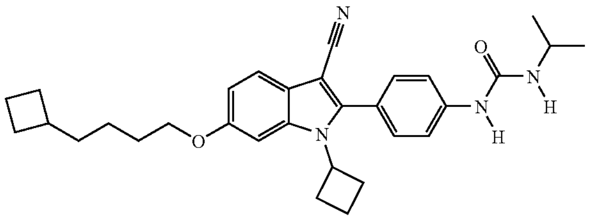
1317
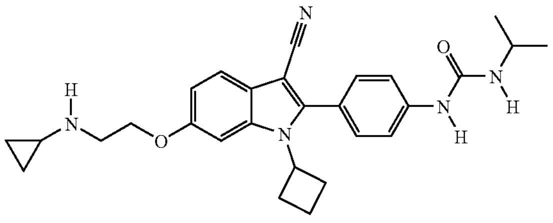
1318
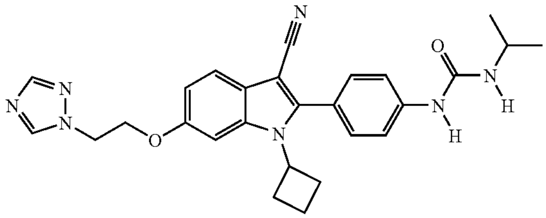
1319
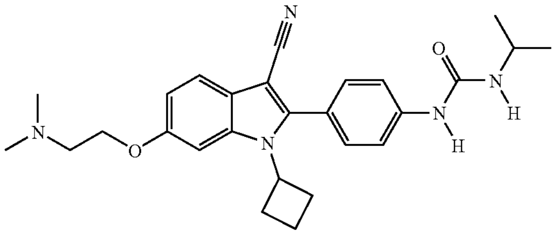

-continued
1320
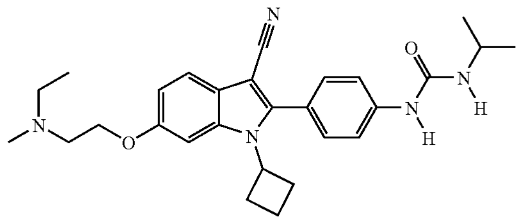
1321
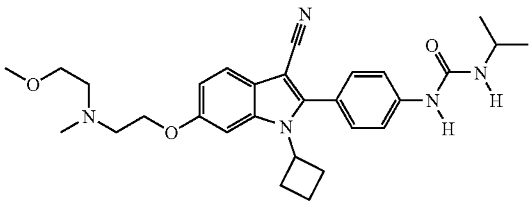
1322
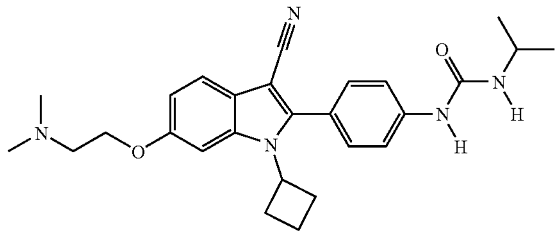
1323
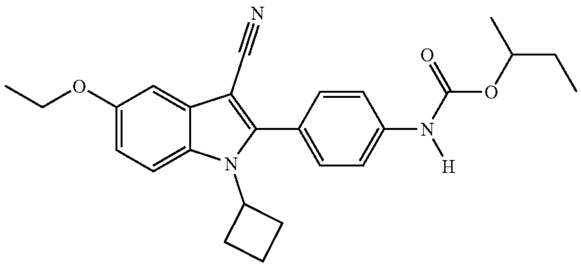
1324
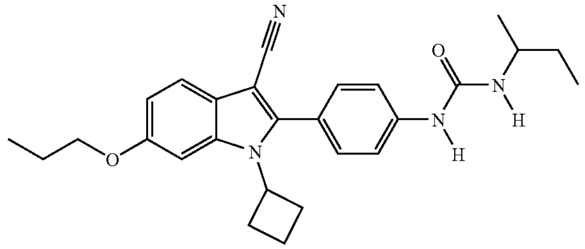
1325
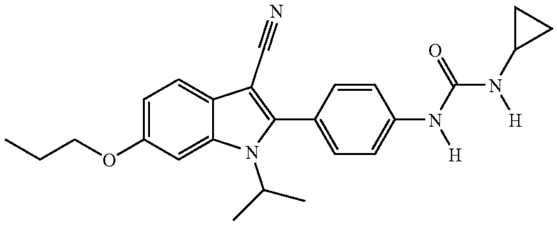
1326
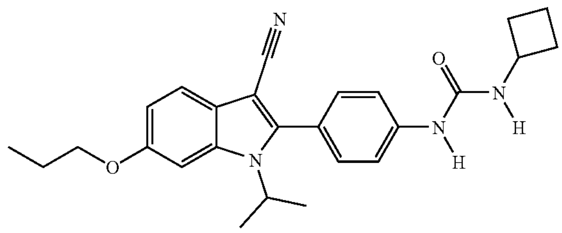
1327
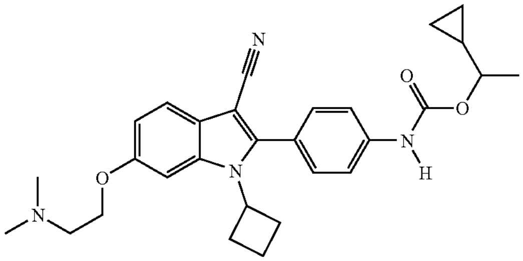
1328
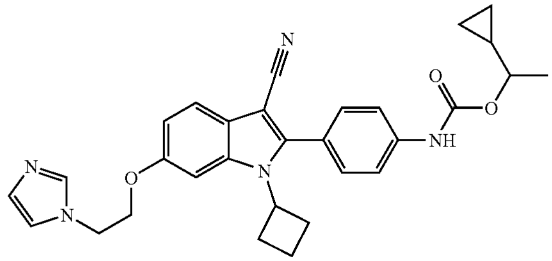
1329
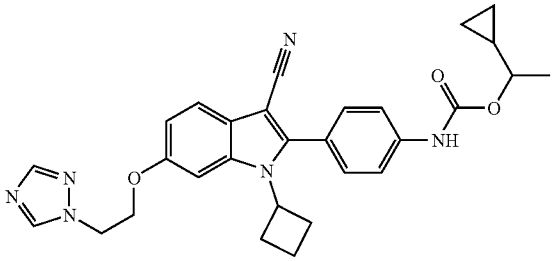

-continued
1484
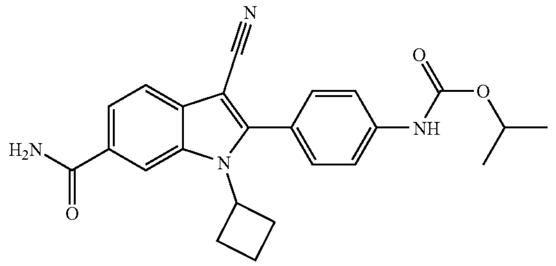
1491
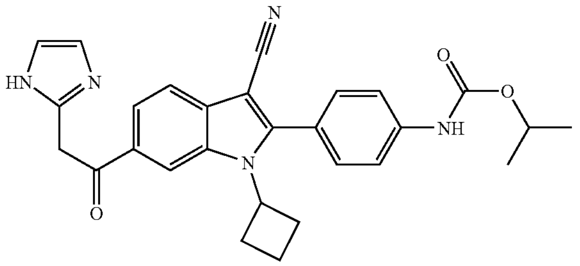
1492
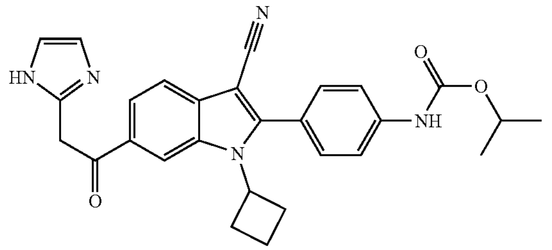
1493
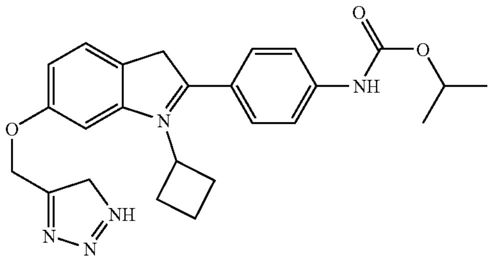
1494
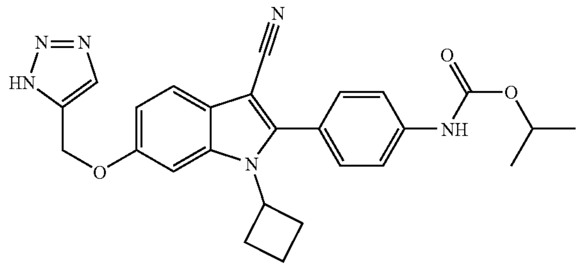
1495
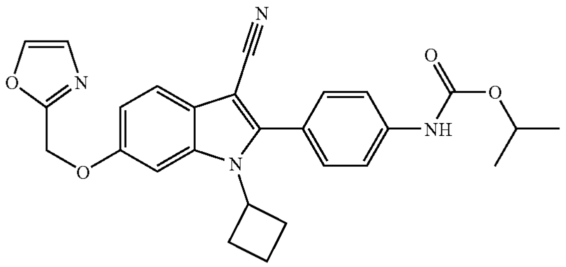
1496
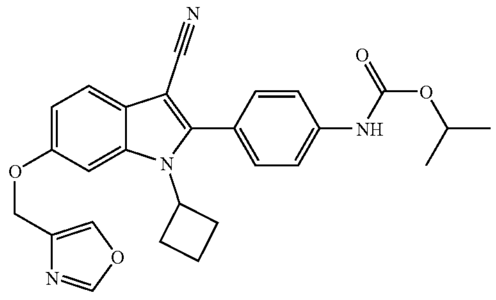
1497
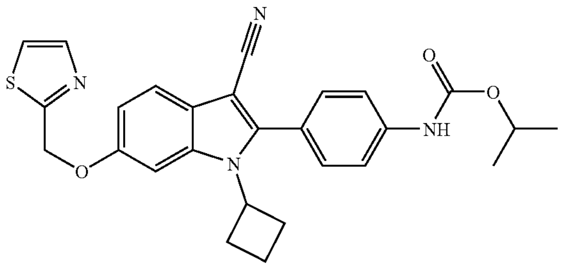
1506
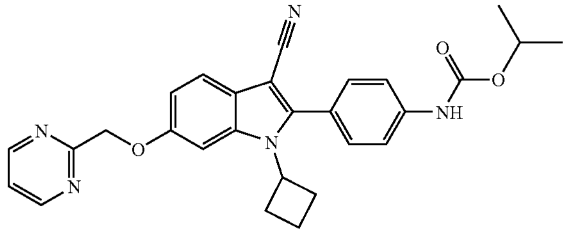
1507
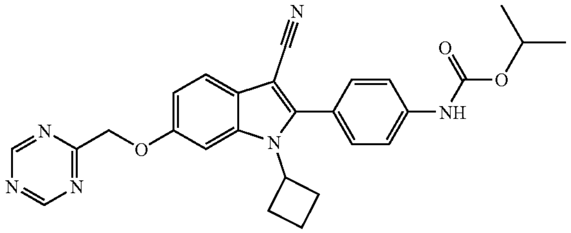

-continued
1510
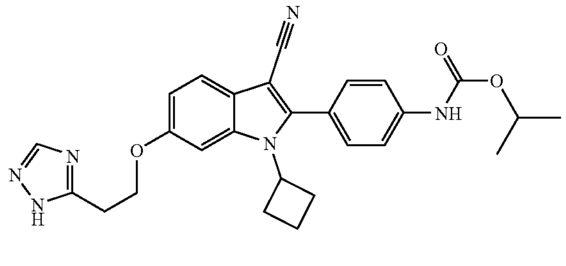
1511
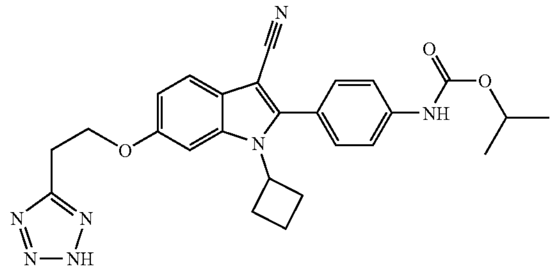
1512
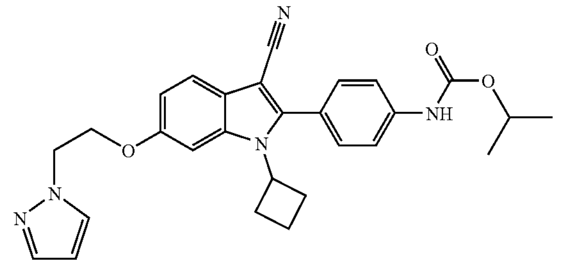
1513
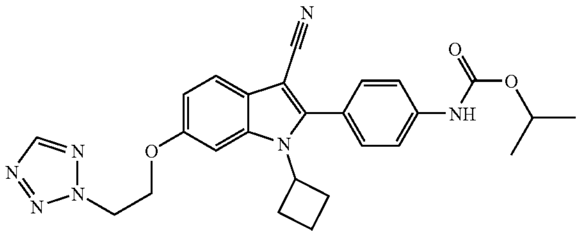
1514
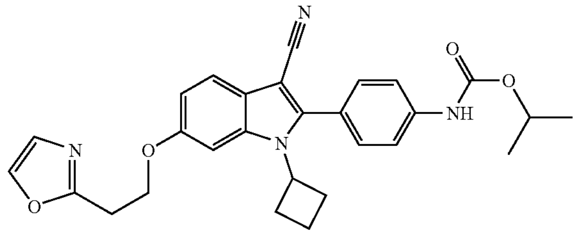
1517
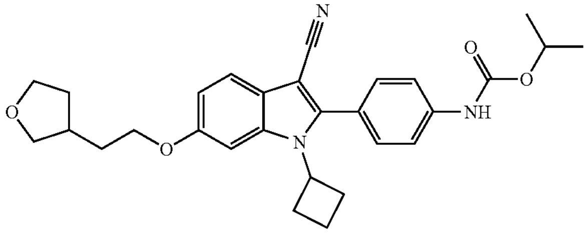
1518
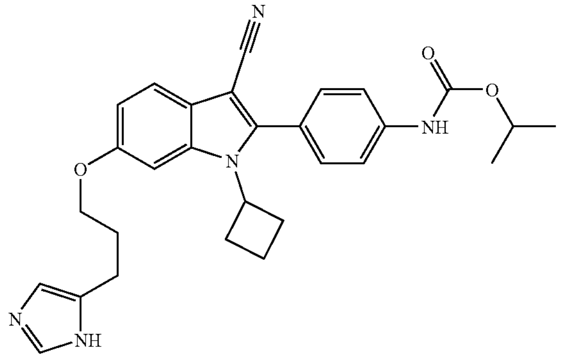
1519
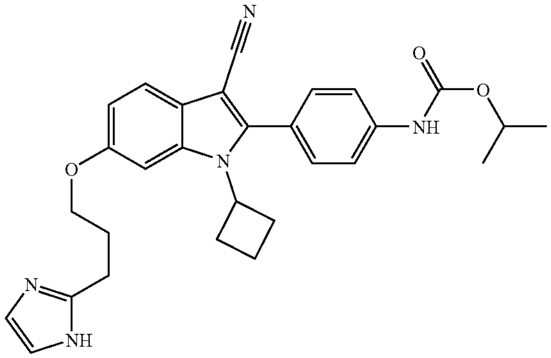
1520
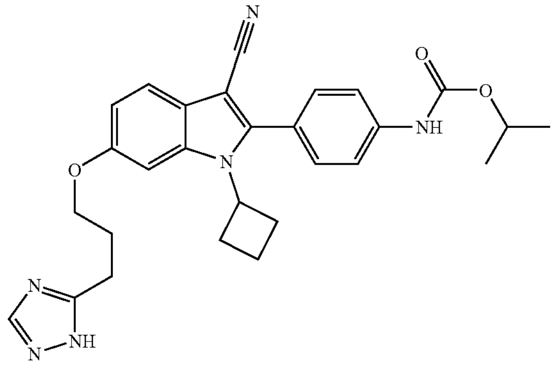
1521
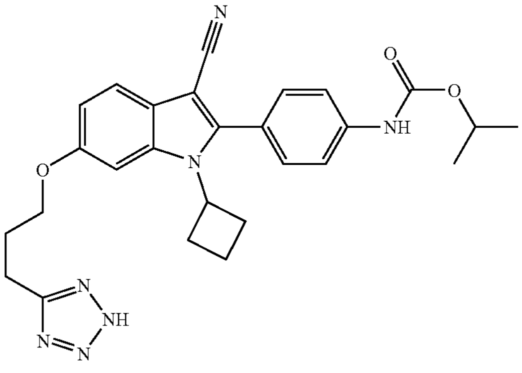

-continued
1522
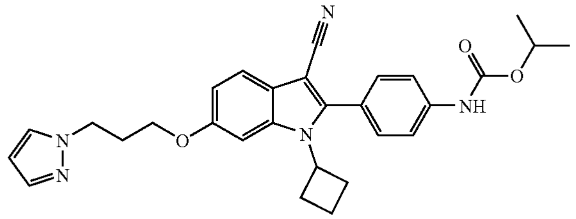
1523
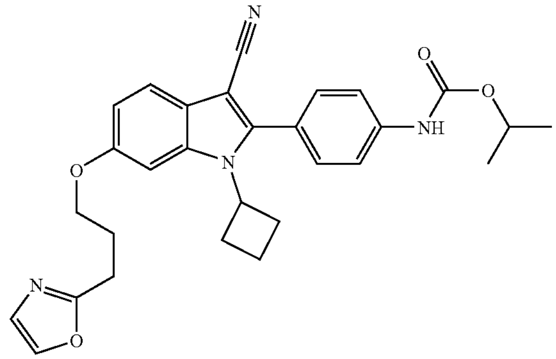
1540
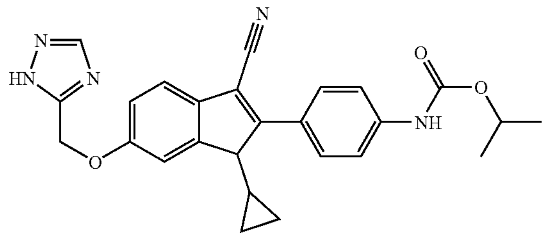
1541
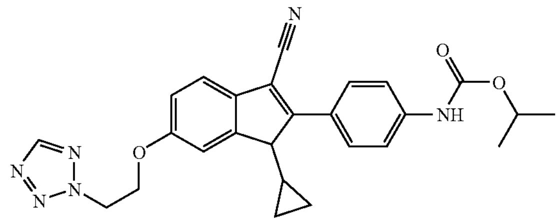
1542
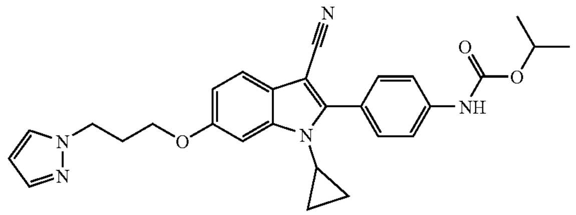
1556
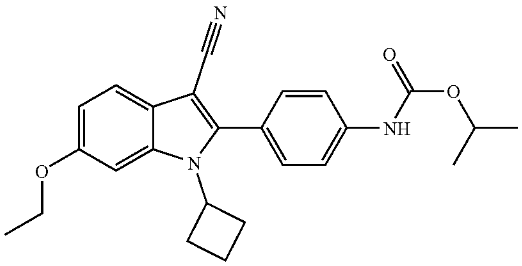
1574
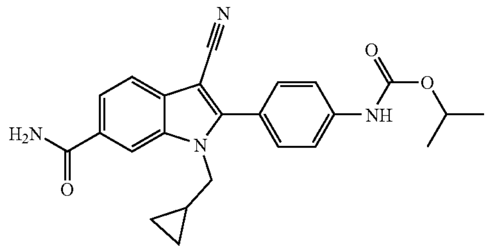
1581
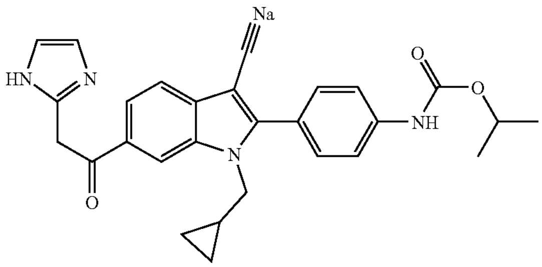
1582
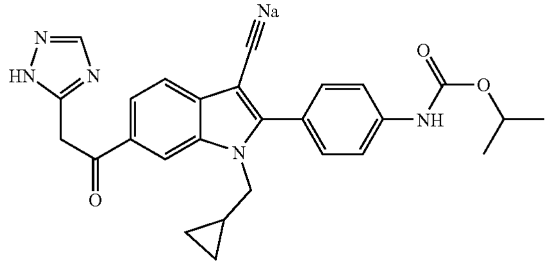
1583
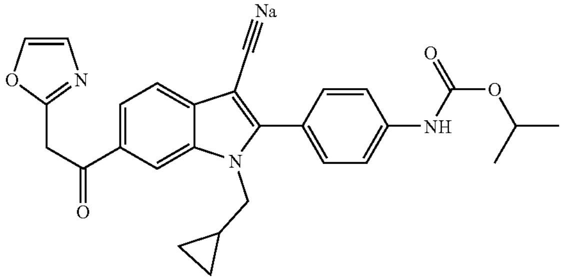

-continued
1584
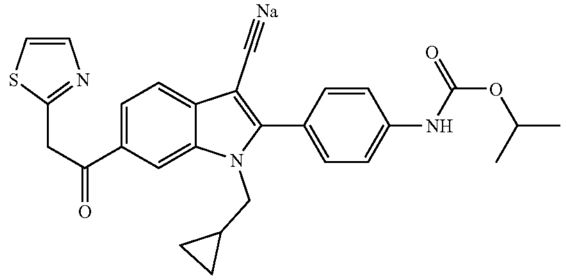
1590
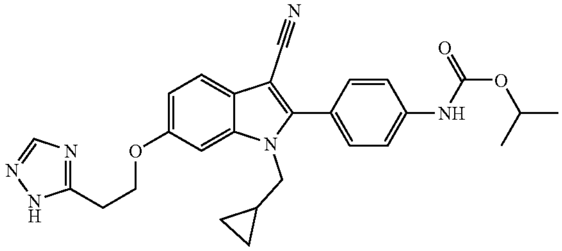
1591
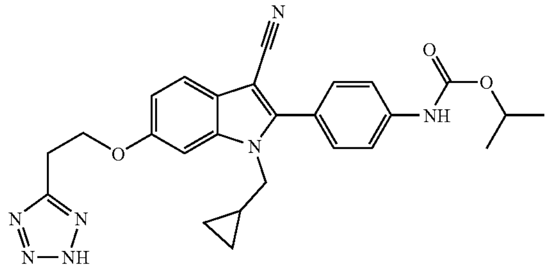
1592
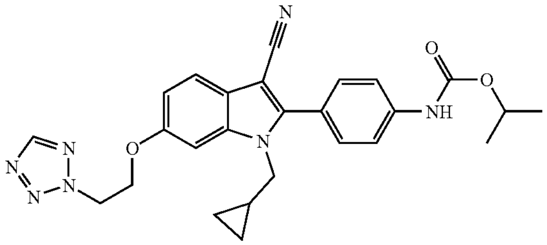
1593
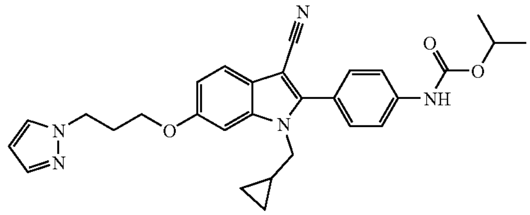
1610
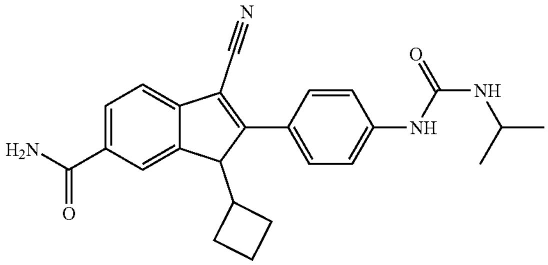
1617
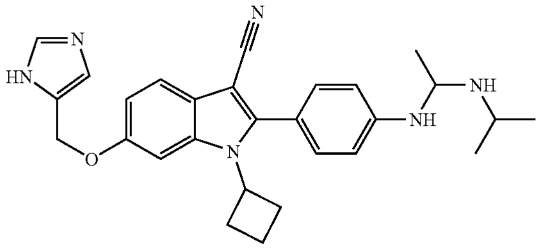
1618
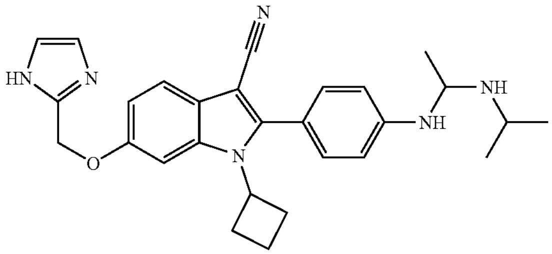
1619
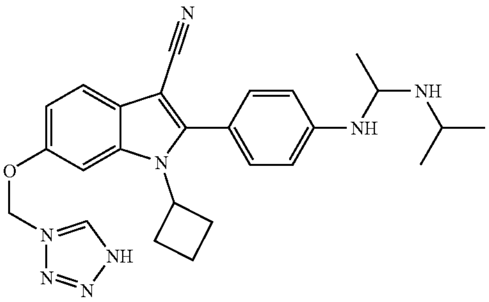
1620
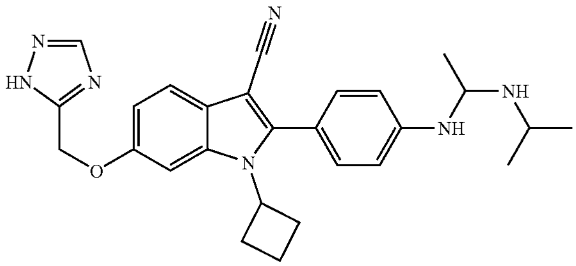

-continued
1621
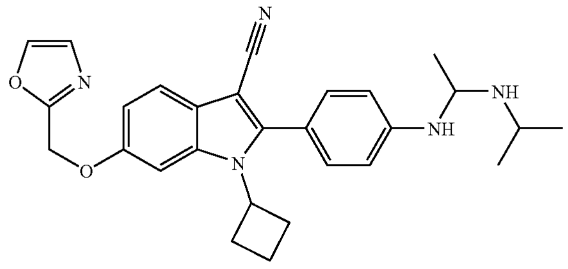
1622
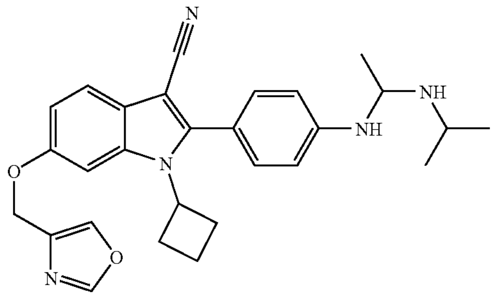
1623
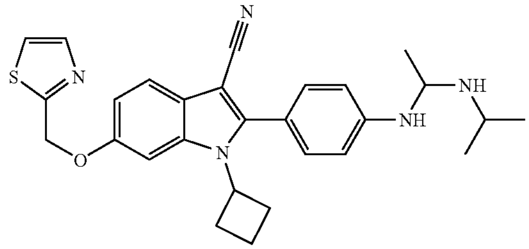
1632
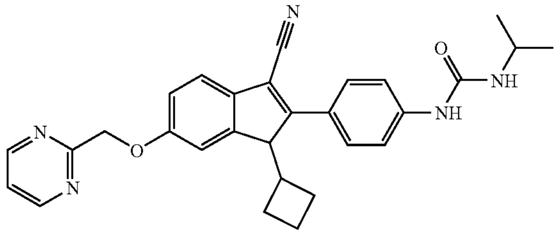
1633
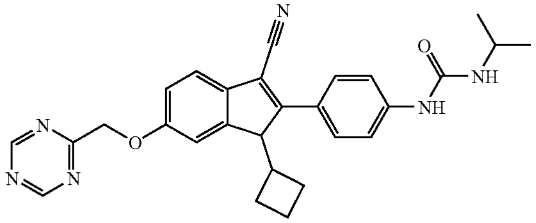
1636
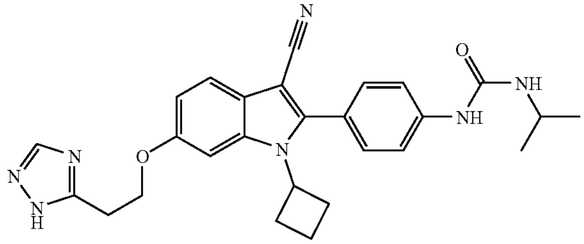
1637
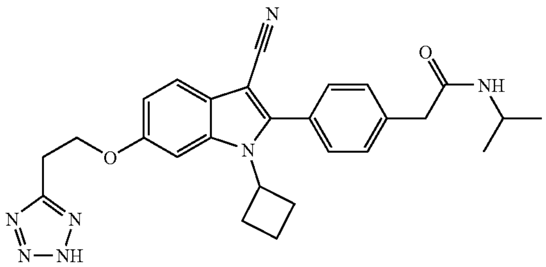
1638
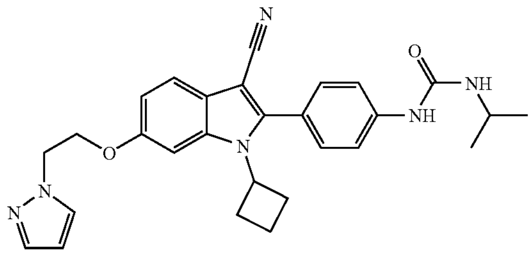
1639
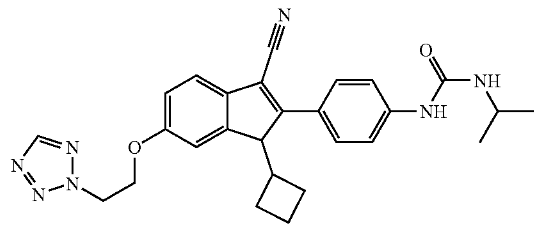
1640
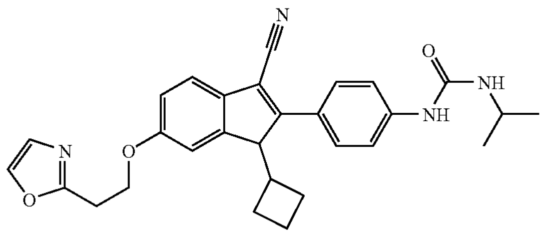

-continued
1643
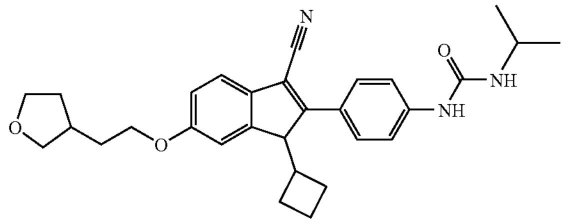
1644
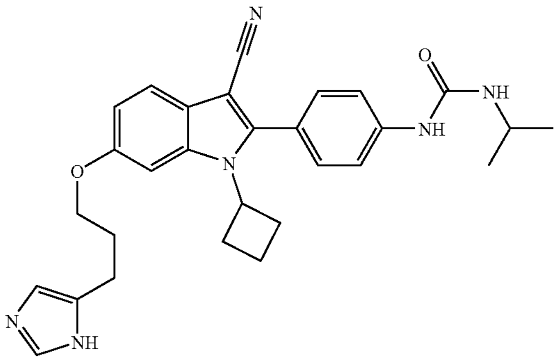
1645
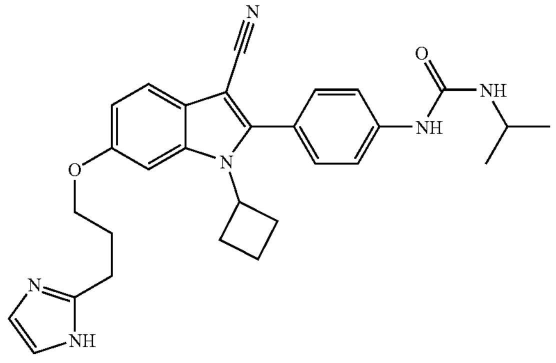
1646
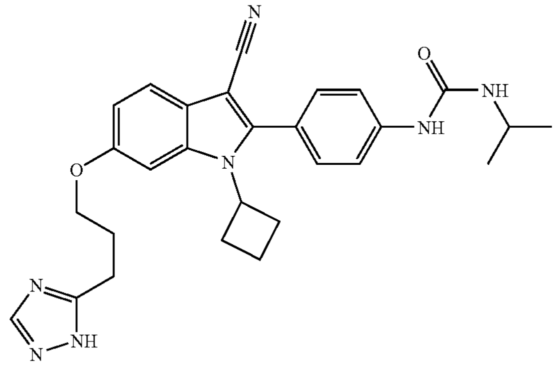
1647
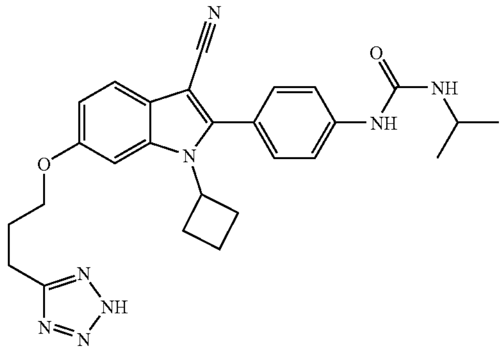
1648
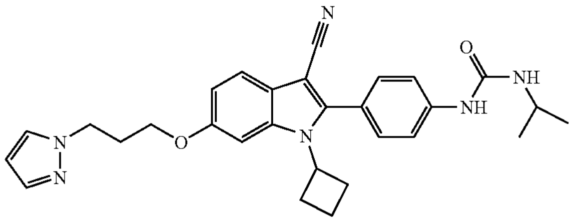
1649
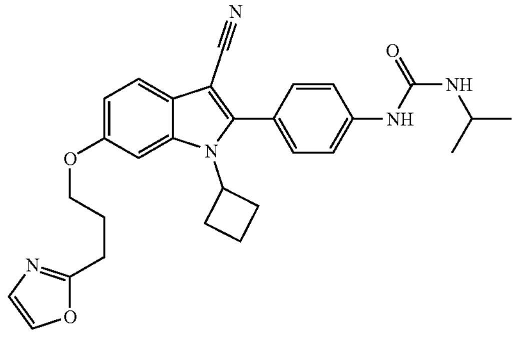
1667
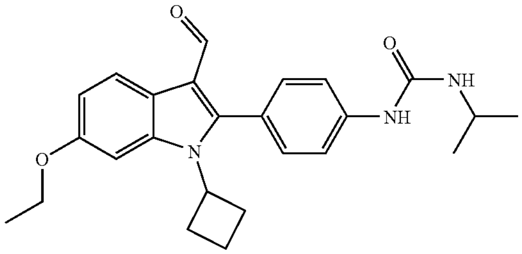

-continued
1687
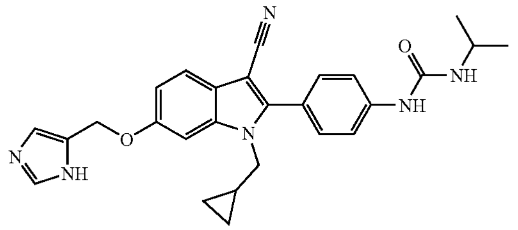
1688
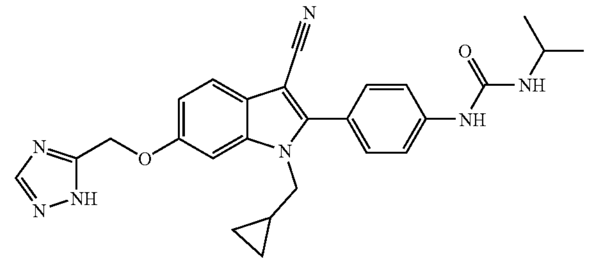
1689
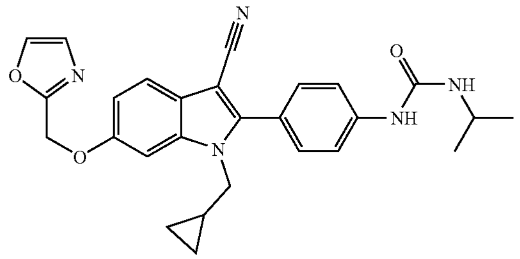
1690
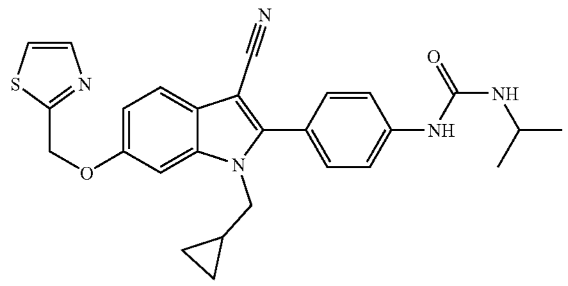
1695
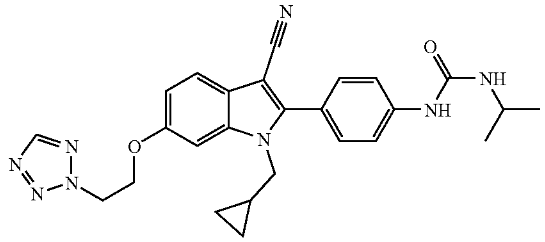
1702
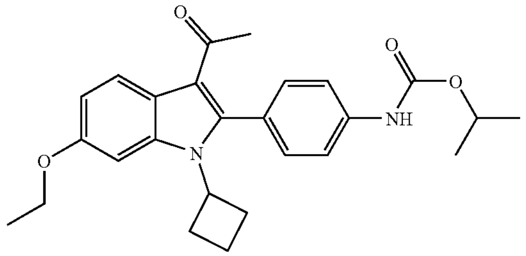
1720
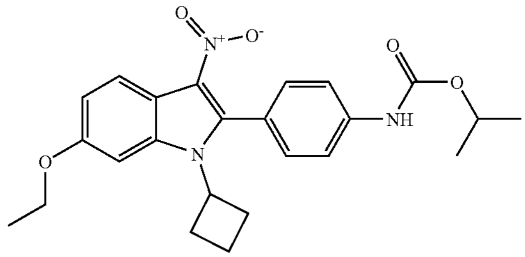
1726
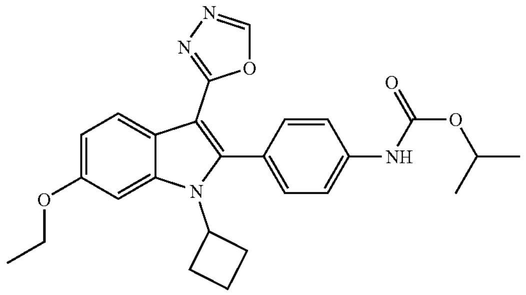
1728
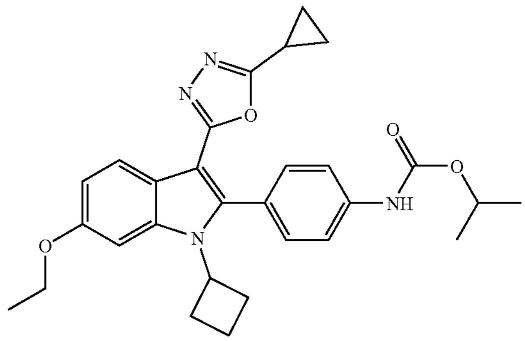
1730
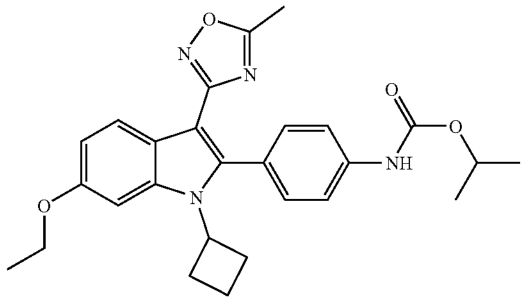

-continued
1732
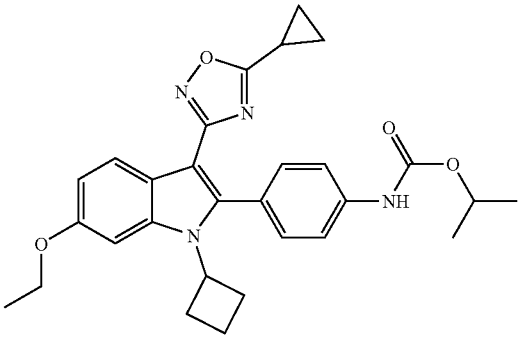
1734
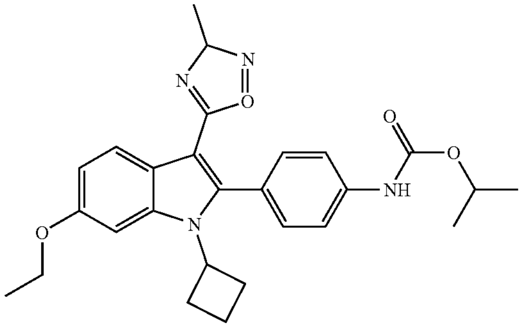
1736
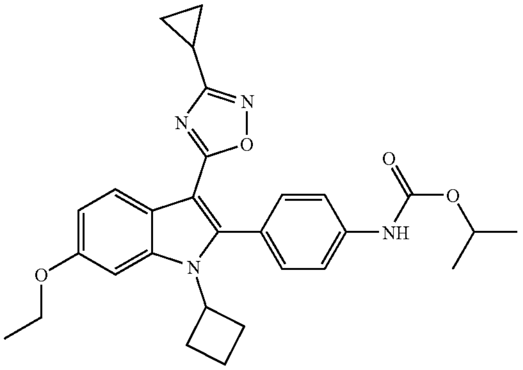
1738
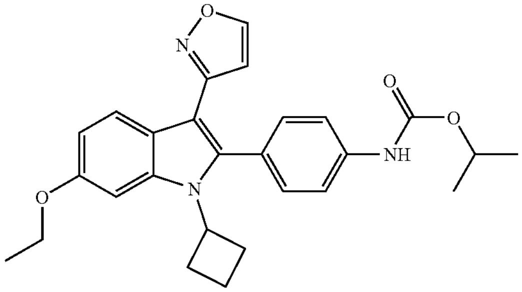
1740
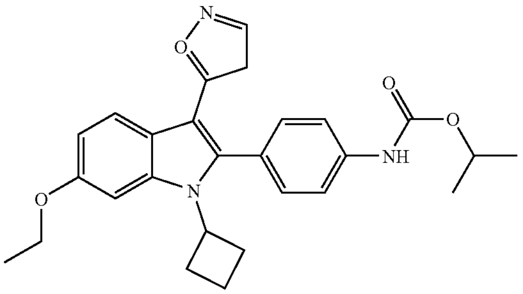
1749
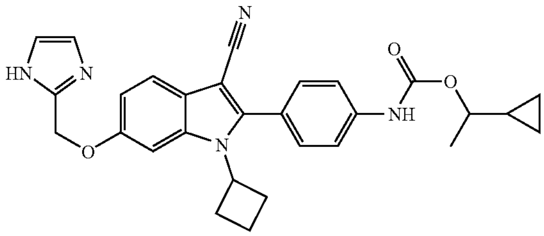
1750
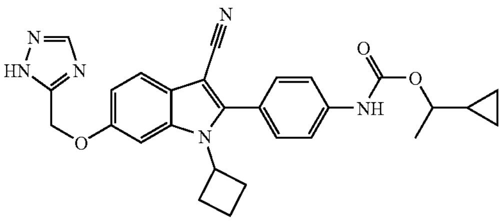
1751
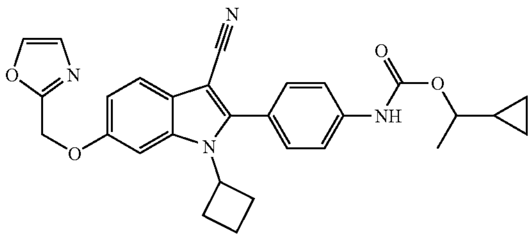
1752
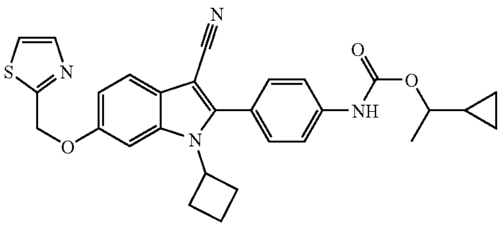
1759
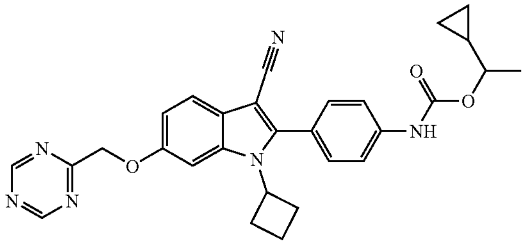

-continued
1761
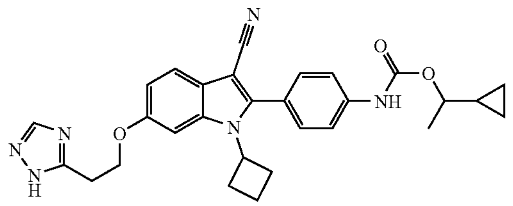
1762
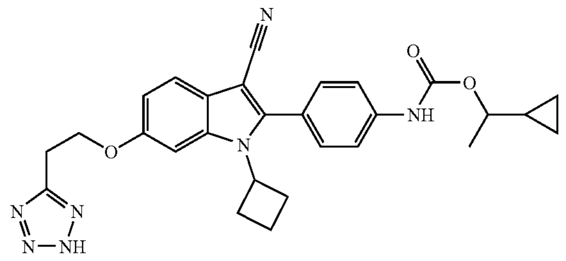
1763
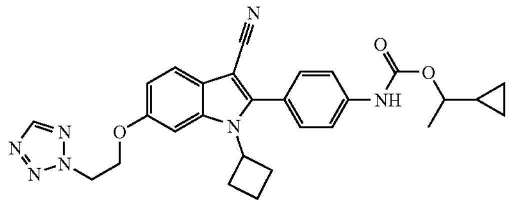
1765
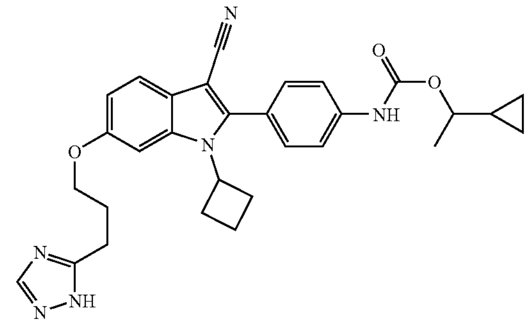
1766
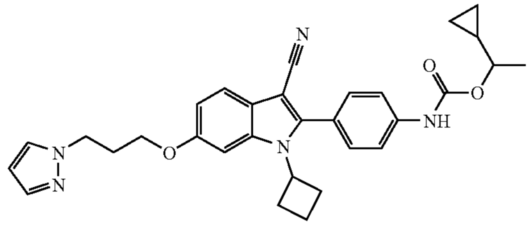
1771
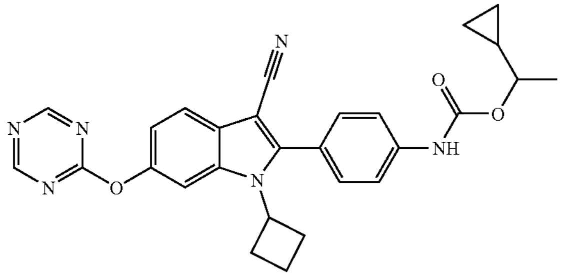
1778
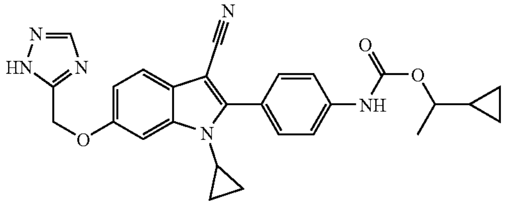
1783
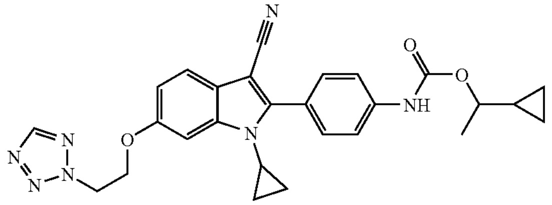
1784
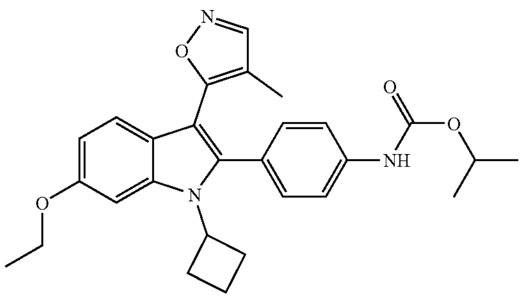
1785
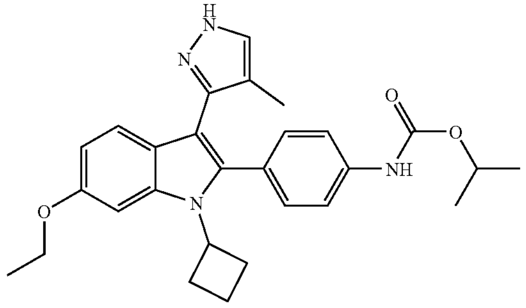

-continued
1787
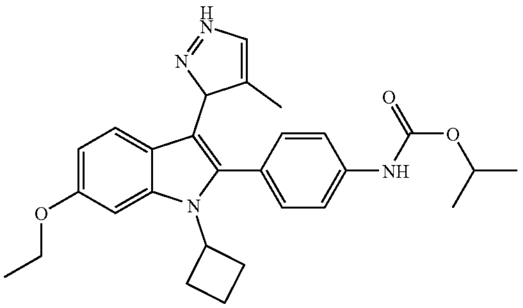
1789
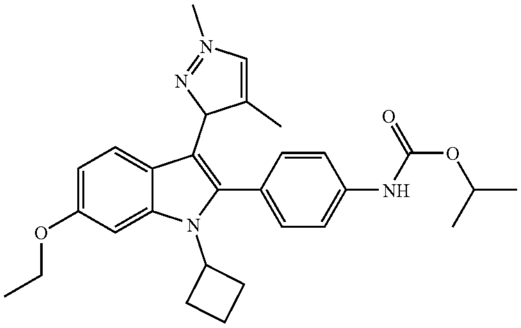
1791
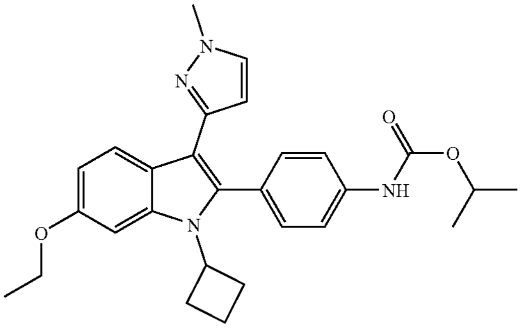
1793
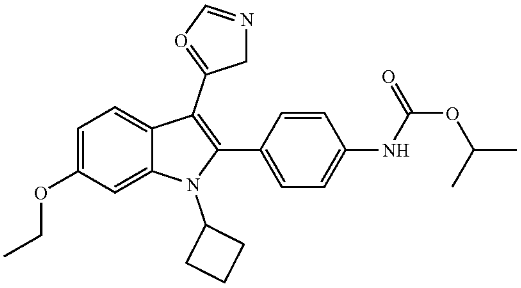
1795
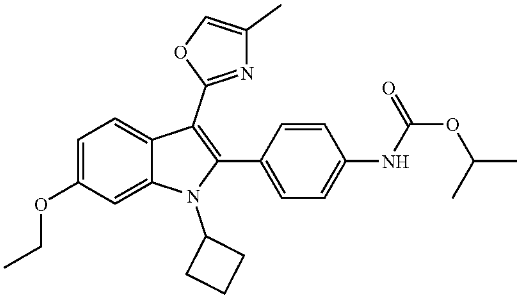
1799
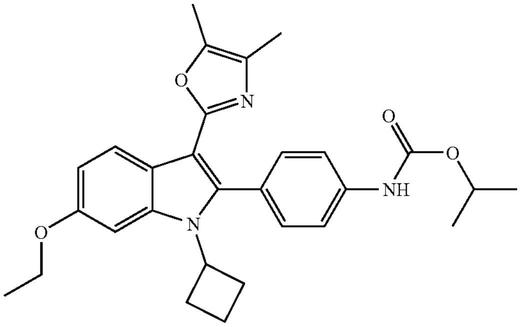
1801
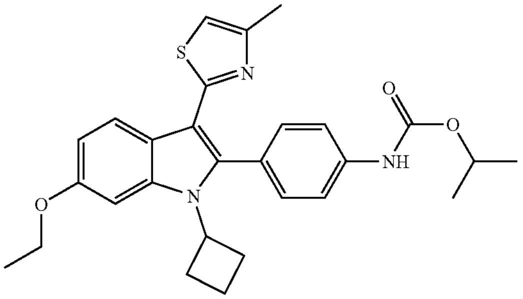
1803
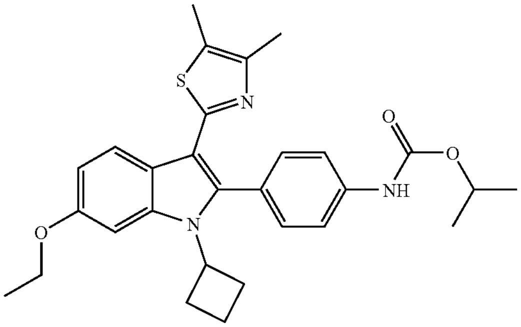
1807
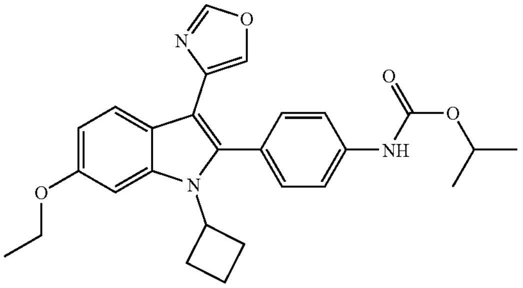
1809
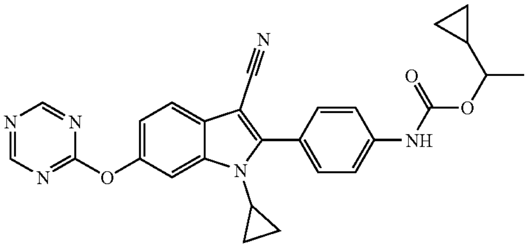

-continued
1812
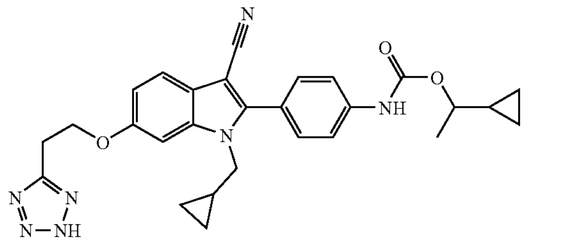
1813
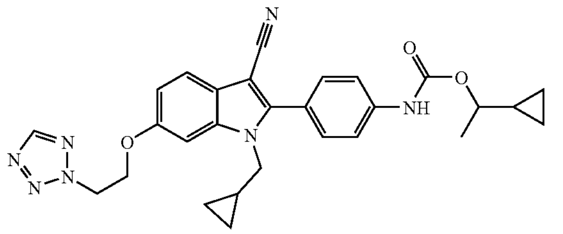
1816
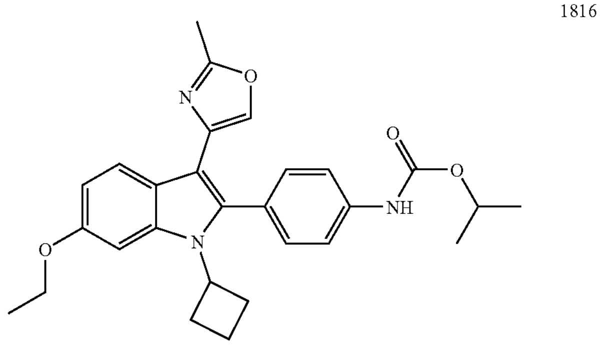
1818
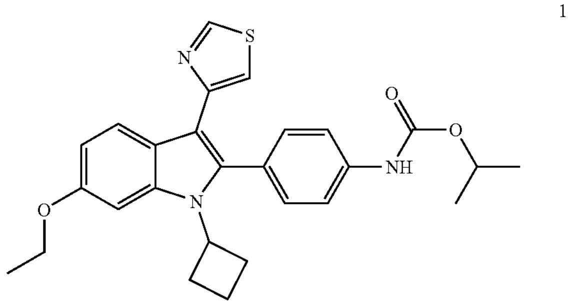
1820
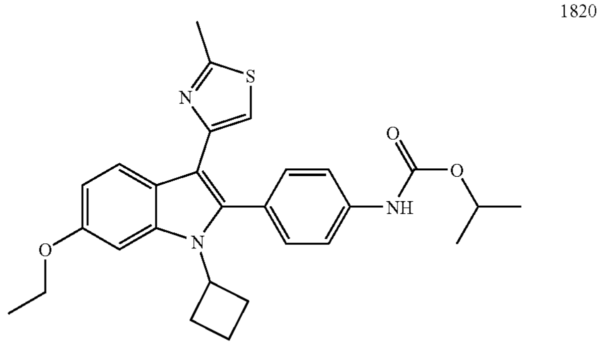
1830
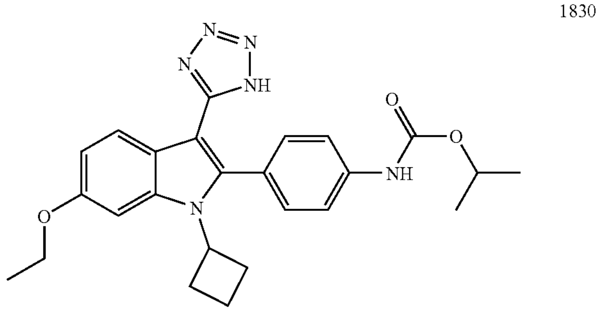
1832
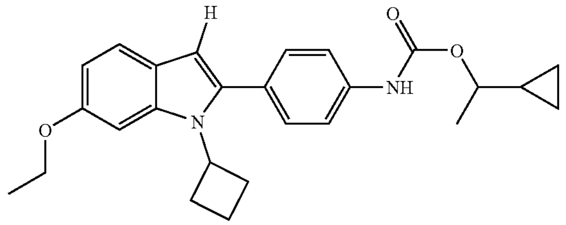
1856
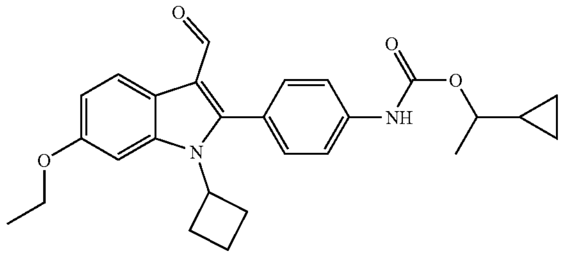
1862
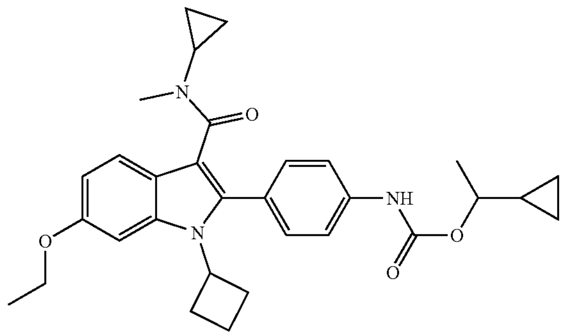
1872
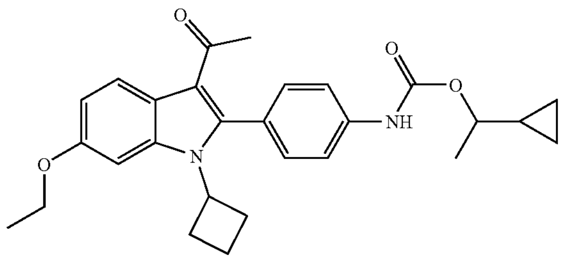

-continued
1885
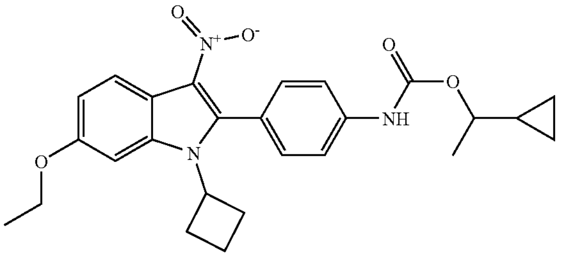
1891
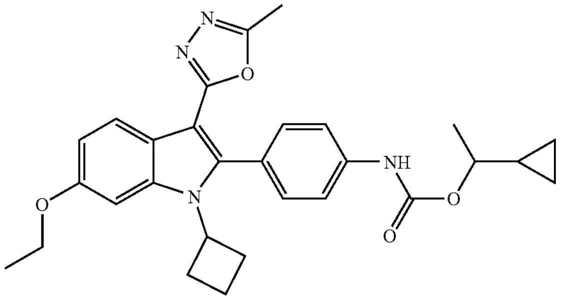
1893
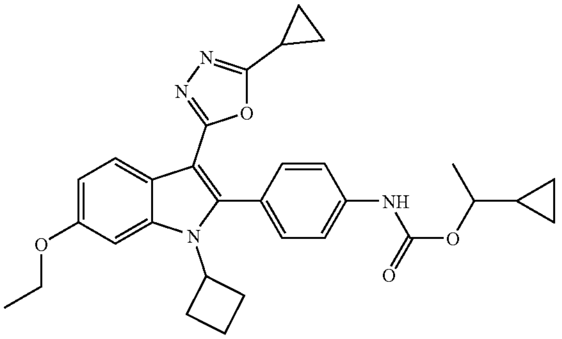
1895
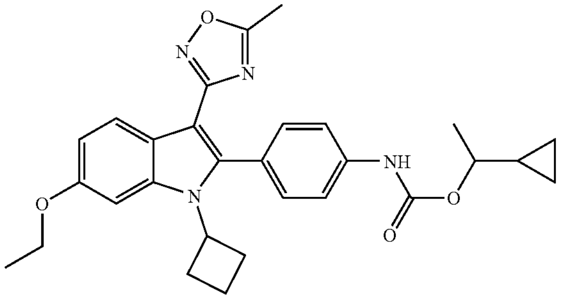
1897
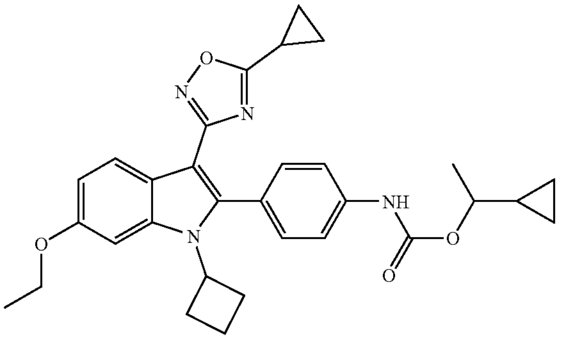
1899
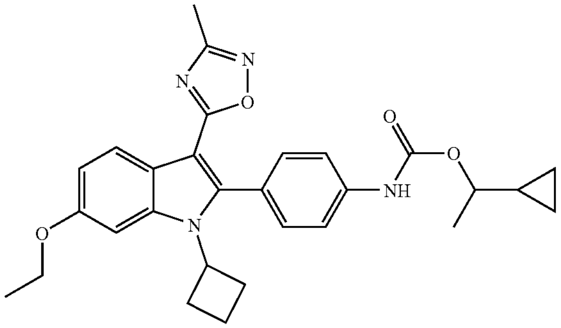
1901
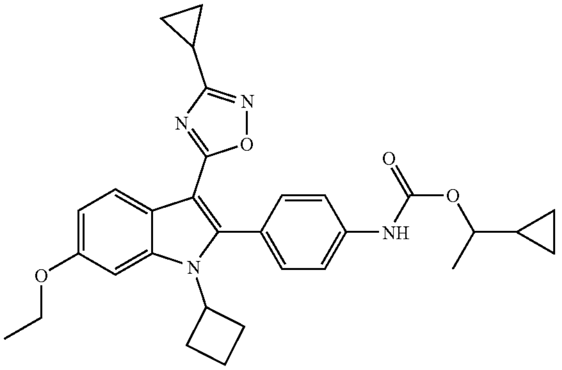
1903
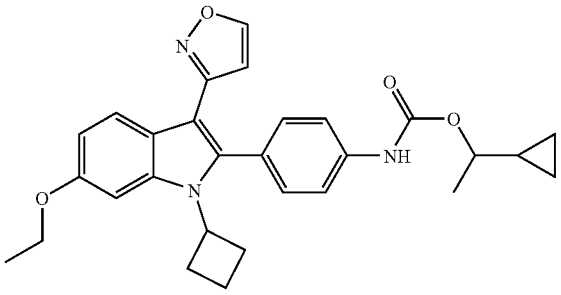

-continued
1905
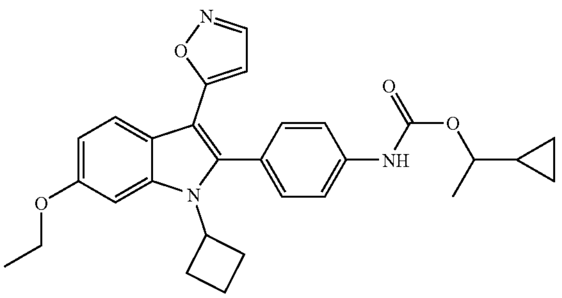
1907
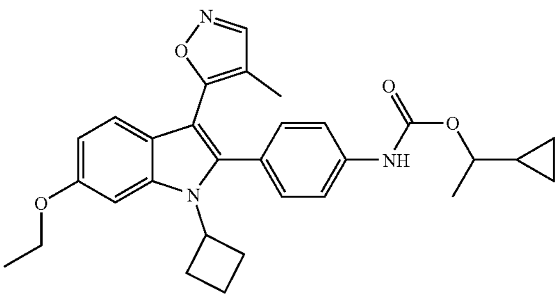
1909
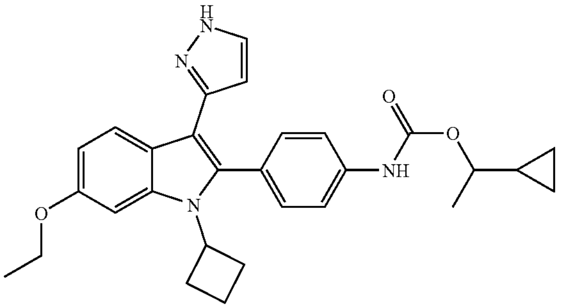
1911
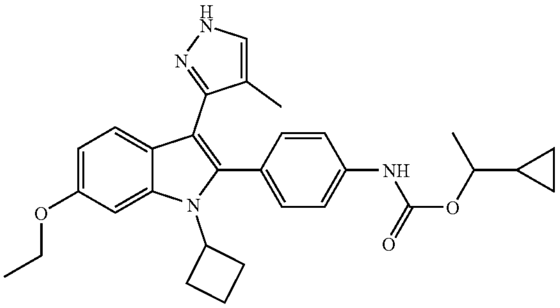
1913
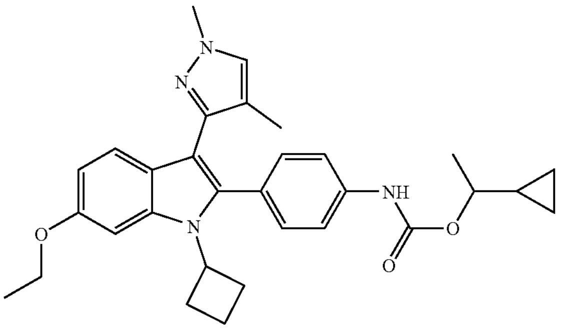
1915
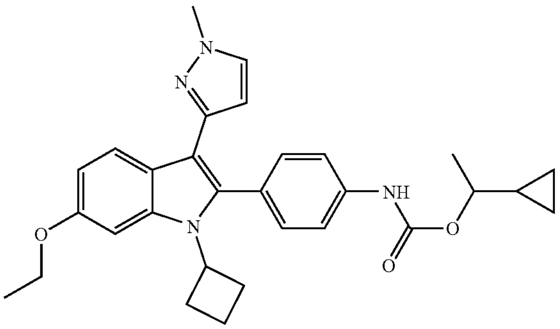
1925
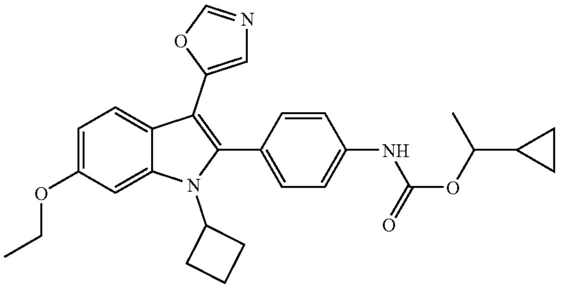
1927
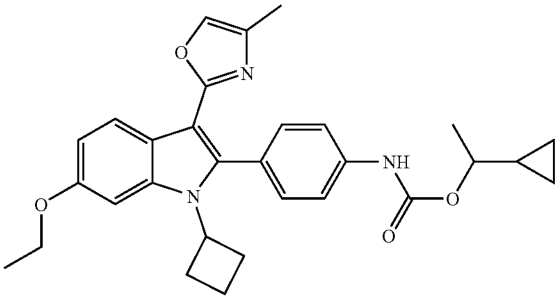

-continued
1929
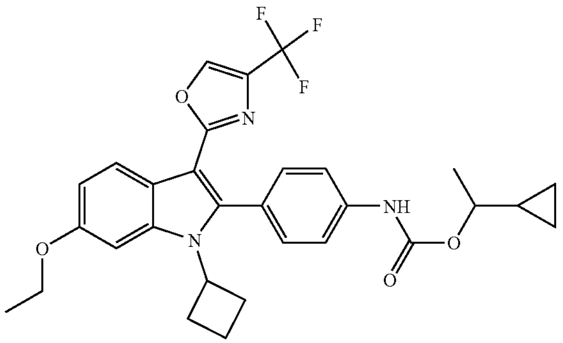
1931
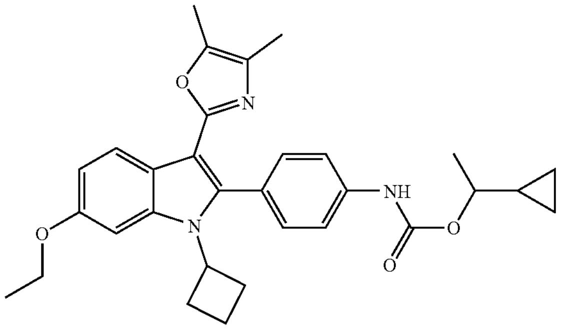
1933
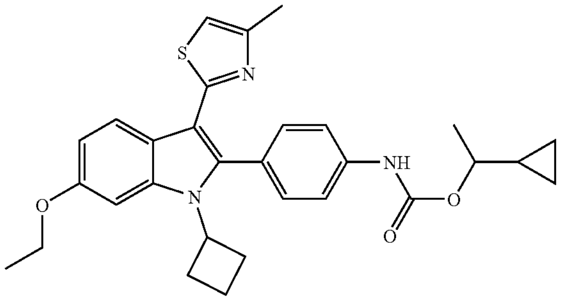
1935
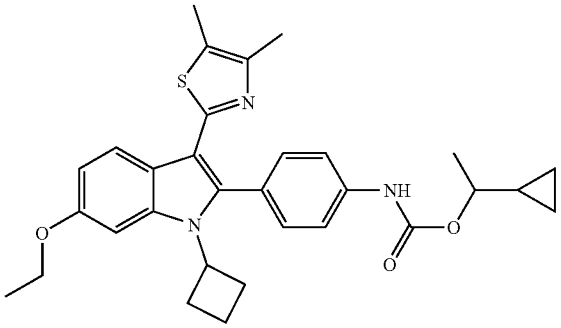
1939
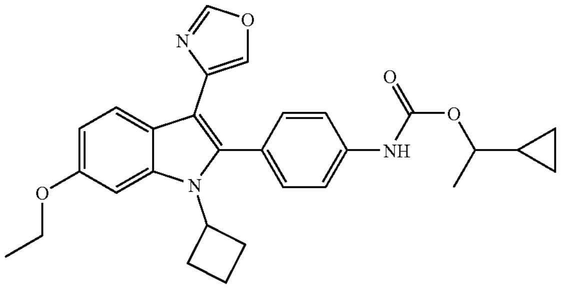
1941
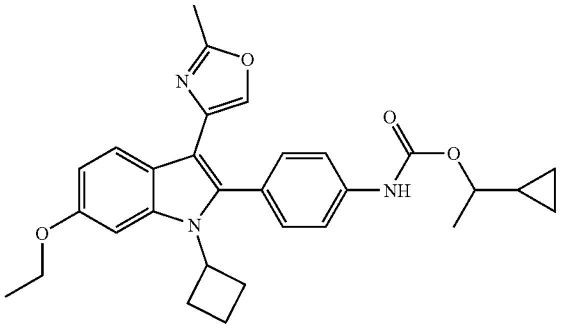
1943
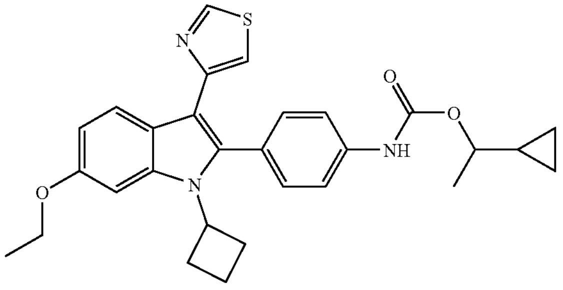
1945
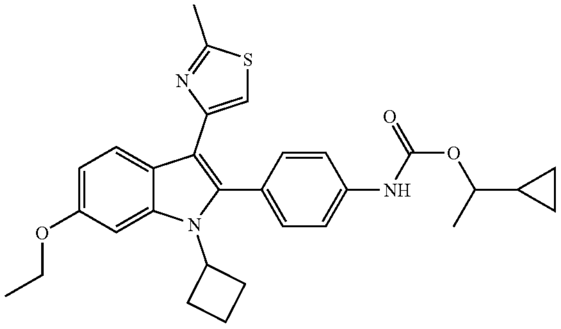

-continued
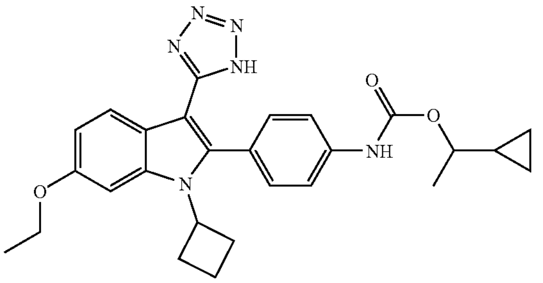
1955
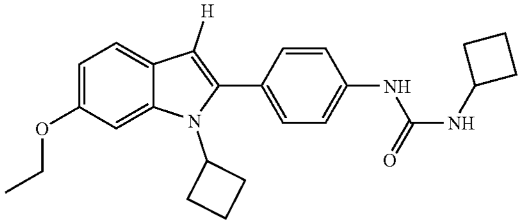
1957
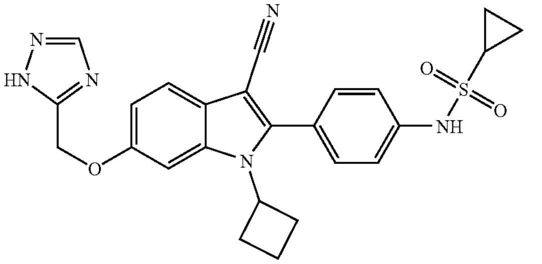
1967
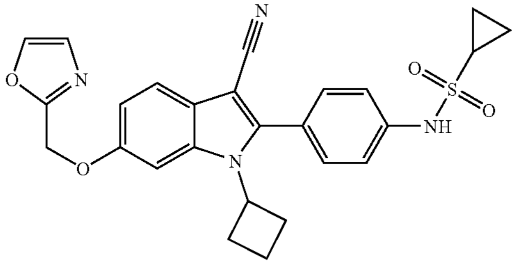
1968
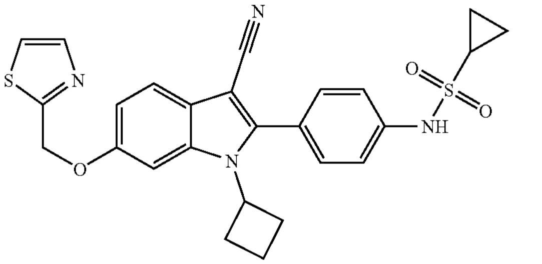
1969
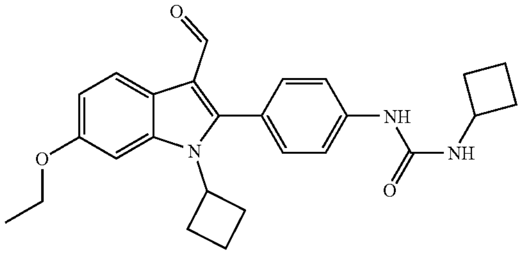
1994
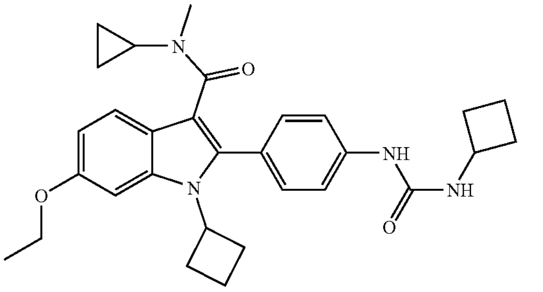
2000
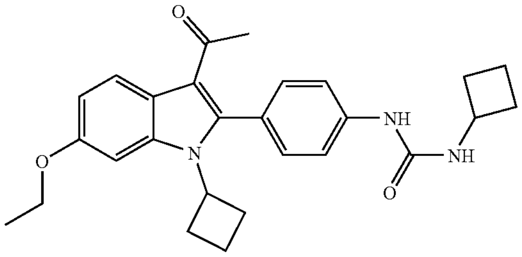
2002
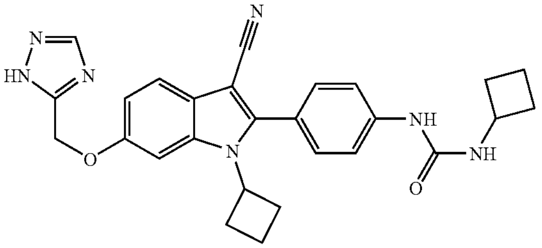
2015
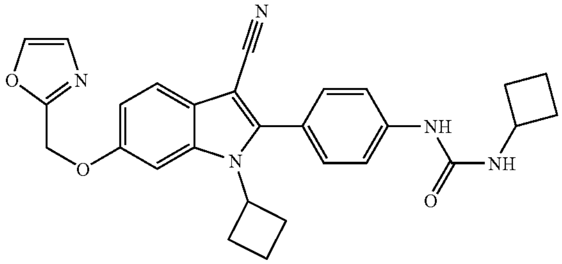
2016

-continued
2017
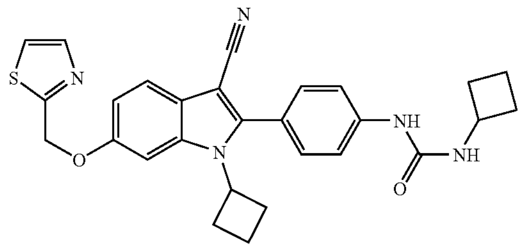
2022
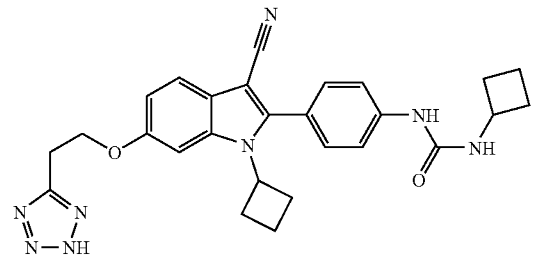
2023
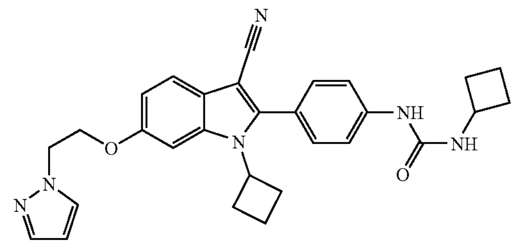
2024
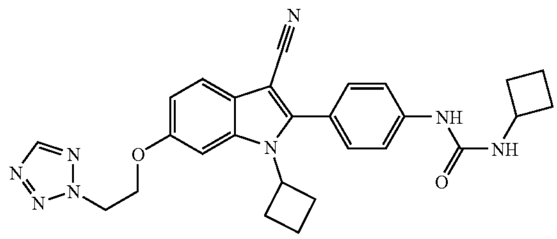
2034
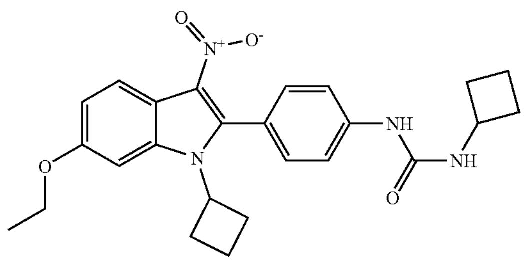
2040
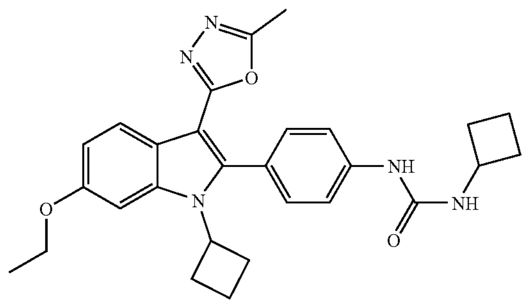
2042
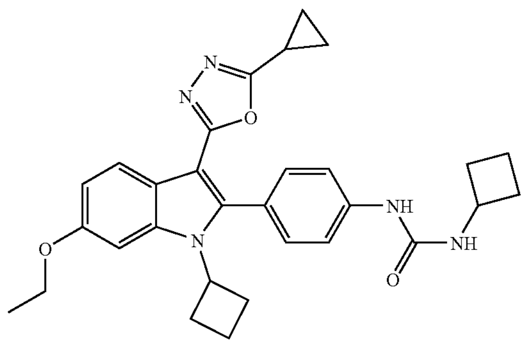
2044
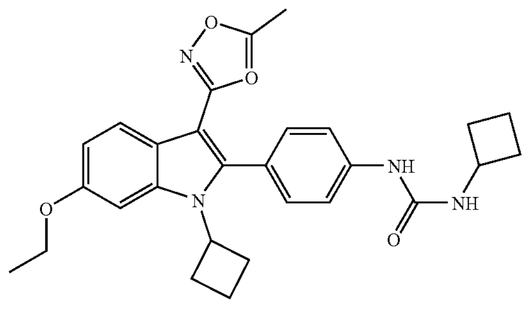
2046
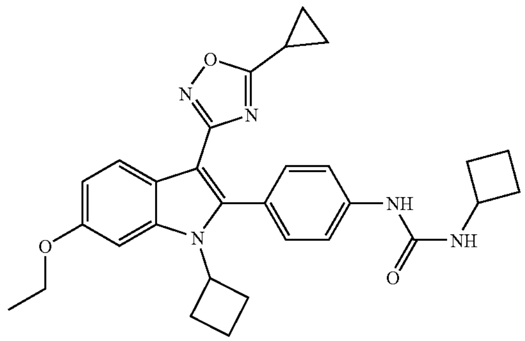
2048
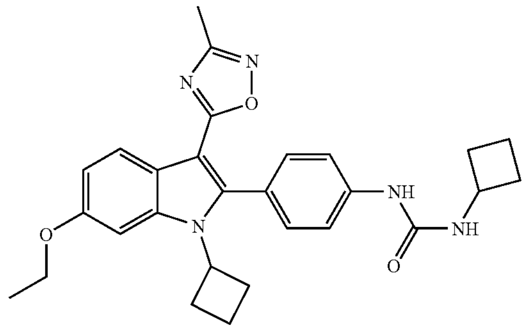

-continued
2050
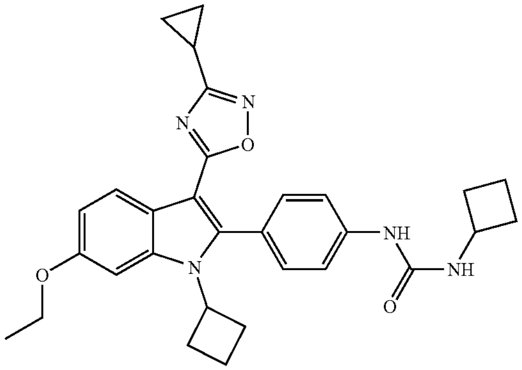
2056
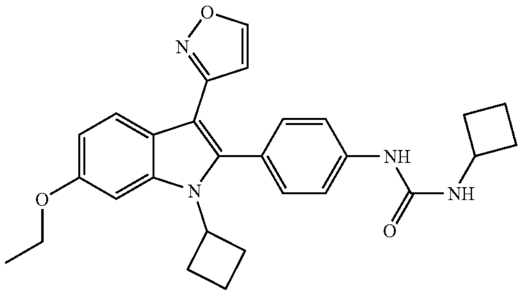
2058
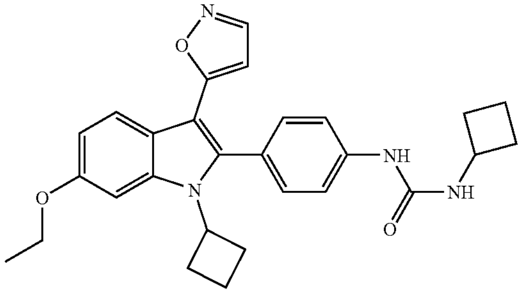
2060
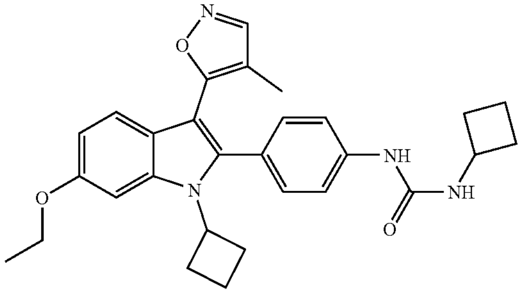
2062
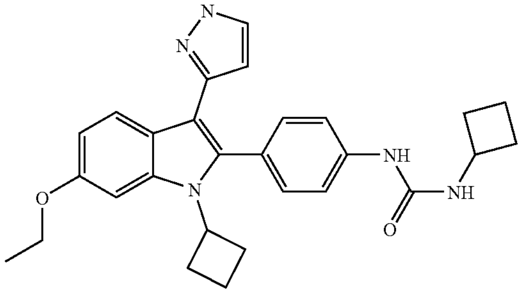
2068
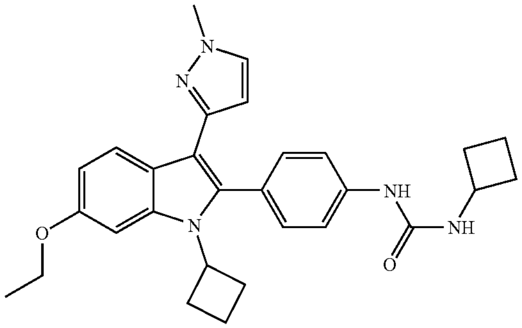
2070
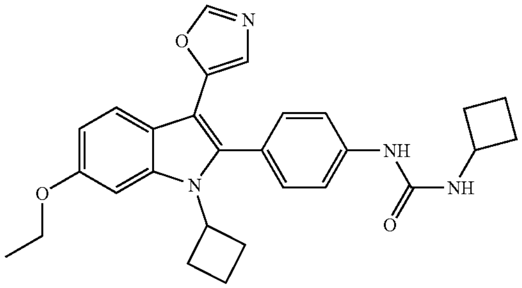
2072
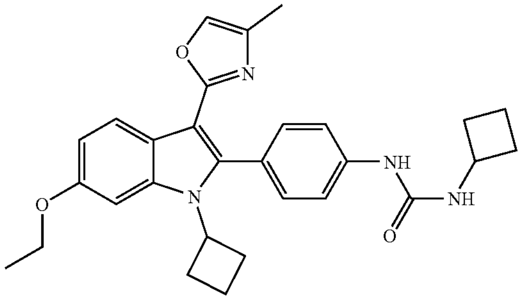
2076
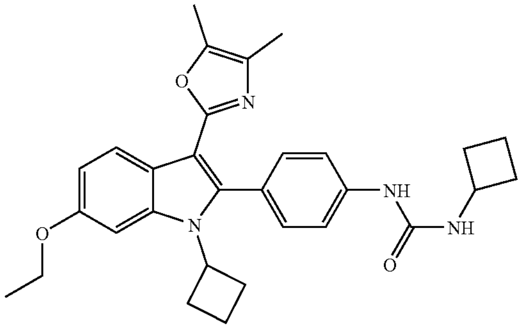
2078
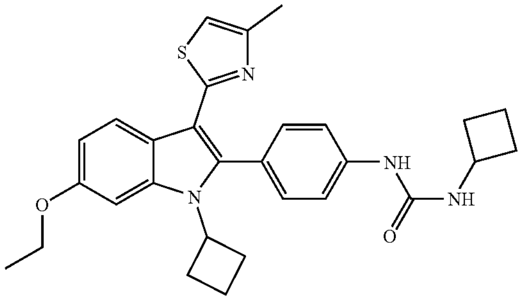

-continued

2080

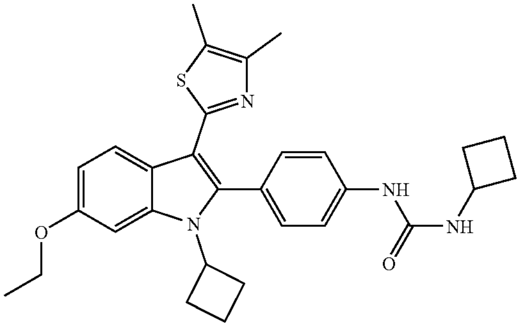

2084

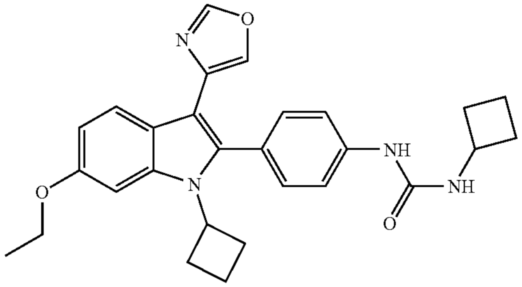

2086

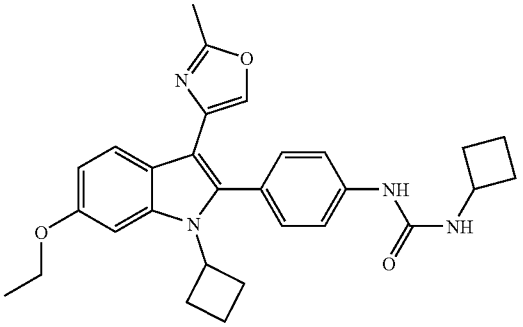

2088

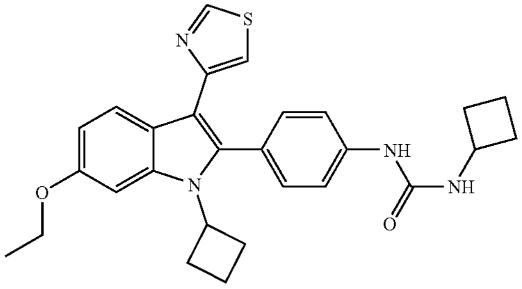

2090

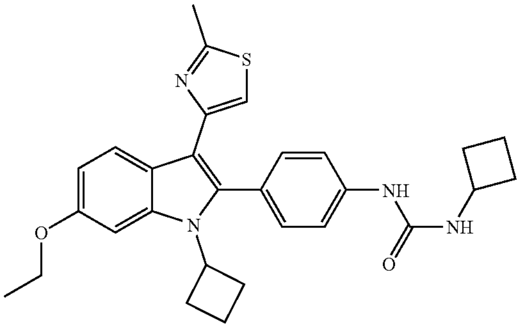

2105

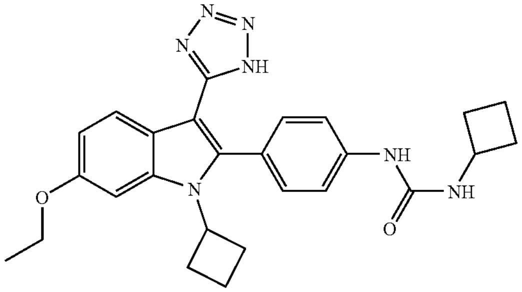

2127

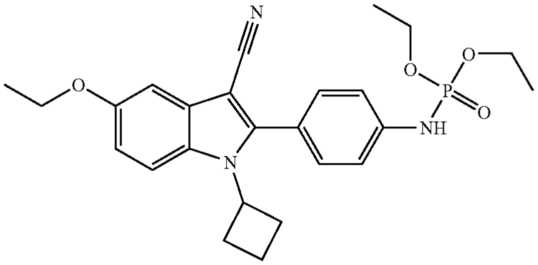

In some embodiments, the compound is selected from Compounds 866 to 2127. In other embodiments, the compound is selected from Compounds 866 to 1329.

B. Preparation of Compounds of the Invention

The compounds of the invention can be obtained via standard, well-known synthetic methodology. Many of the indole starting materials can be prepared using the routes described below or by those skilled in the art.

Compounds of formula I, represented by structure II can be prepared by the methodology depicted in Scheme A below:

An α-nitroketone derivative A2 can be derived from treatment of the anion of nitromethane, obtained from the treatment of nitromethane with a base, such as, e.g., sodium or potassium t-butoxide or sodium hydride, with an activated carboxylic acid derivative, e.g., the acyl imidazolide A1. Reaction of the α-nitroketone A2 with amine derivative A3 can afford the nitro enamine A4 by mixing the components A3 and A4 and heating in a suitable solvent such as an alcohol or an aprotic solvent. Treatment of the nitro enamine A4 with quinone A5 in a polar protic solvent such as acetic acid at or near ambient temperature gives the compound of formula II.

Scheme A

I.

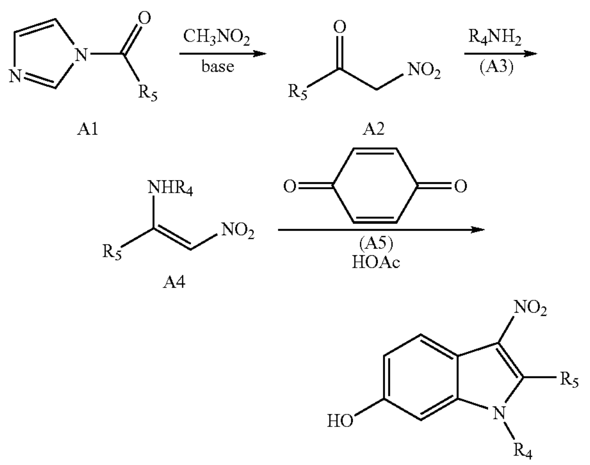

II

Compounds of formula I, represented by structure III can be prepared as shown in Scheme B below:

Treatment of B1 with a reactive alkyl or aryl group containing a leaving group L in a suitable solvent, with or without heat in the presence of a base, such an inorganic base, e.g., sodium or potassium carbonate or an organic base, e.g., triethylamine, can afford the compound of structure III. Examples of leaving groups include but are not limited to halogens (e.g., chlorine, bromine or iodine) or alkyl or arylsulfonates.

Scheme B

II.

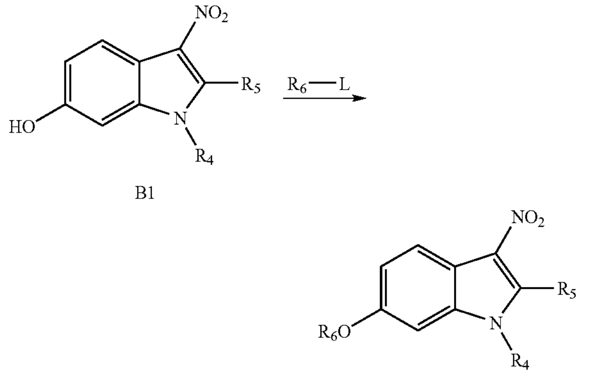

III

Compounds of formula I, represented by structure IV can be prepared as shown in Scheme C below:

Compounds of structure IV can be obtained by nitrating an indole of structure C1, to give the 3-nitroindole C2. The nitration can be carried out by treatment of C1 with a nitrating agent, such as nitric acid or sodium nitrite in a solvent such as acetic acid, acetic anhydride, sulfuric acid or in a mixed solvent system containing an organic solvent such as dichloromethane. The reaction can be carried out a temperature of −30° C. to +50° C. Treatment of C2 with a reactive functional group $R_9$ containing a suitable leaving group L (C3) can give compounds of structure IV. Reactive functional groups can consist of but are not limited to alkyl and aralkyl. L can represent a halide, particularly chloro, bromo or iodo or an alkylsulfonate. The reaction between C2 and C3 can be carried out in a suitable solvent in the presence of an inorganic base such as potassium carbonate or sodium hydride or an organic base such as a trialkylamine. Alternatively, the group $R_9$ can represent an aryl or heteroaryl group and L can represent a halide, particularly chloro, bromo or iodo. The reaction can be carried out in a polar or nonpolar solvent at a temperature from ambient to 200° C. in the presence of a copper catalyst, e.g., CuI, a base such as $Cs_2CO_3$ or $K_3PO_4$, and optionally an amine ligand such as 1,2-bis(methylamino) ethane or 1,2-cyclohexanediamine.

An alternative pathway is to convert C1 into C4 in similar fashion as described above and then carry out the nitration reaction to afford compounds of structure IV.

Scheme C

III.

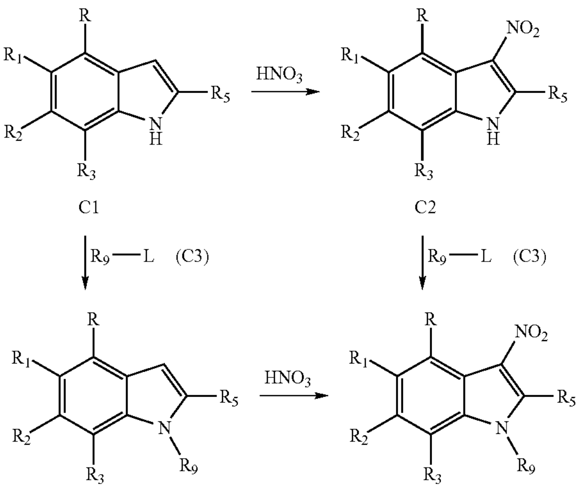

IV

Compounds of formula I, represented by structure V can be prepared as shown in Scheme D.

Treatment of β-ketoesters of structure D1 with amines D2 gives the amino crotonate derivatives D3 by heating in a suitable solvent such as an alcohol or an aprotic solvent. Reaction between D3 and quinone D4 in a polar protic solvent, such as acetic acid gives compounds of structure V.

Scheme D

IV.

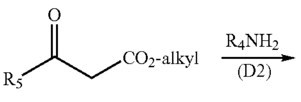

D1

-continued

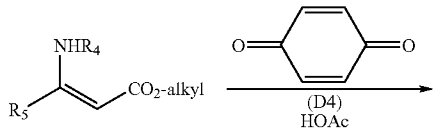

D3

V.

with coupling reagents such as EDCI or DCC with or without HOBt in the presence of the amine E3, or alternatively the acid can be activated as the acid chloride by treatment of the acid with, e.g., thionyl chloride or oxalyl chloride or as the acyl imidazolide, obtained by treatment of the acid with carbonyl diimidazole, followed by treatment of the amine E3. Compounds E4 can be converted to compounds of structure VI by treatment of E4 with a reactive functional group $R_9$ containing a suitable leaving group L (E5) as described previously. Alternatively, compounds of type E1 can be converted to compounds of structure E6 by treatment with E5. Indole-3-carboxylic esters E6 can then be converted to indole-3-carboxylic acids E7 by the methods described above. Conversion of E7 to compounds of structure VI can be carried out by the activation and reaction with an amine E3 as described above.

Scheme E

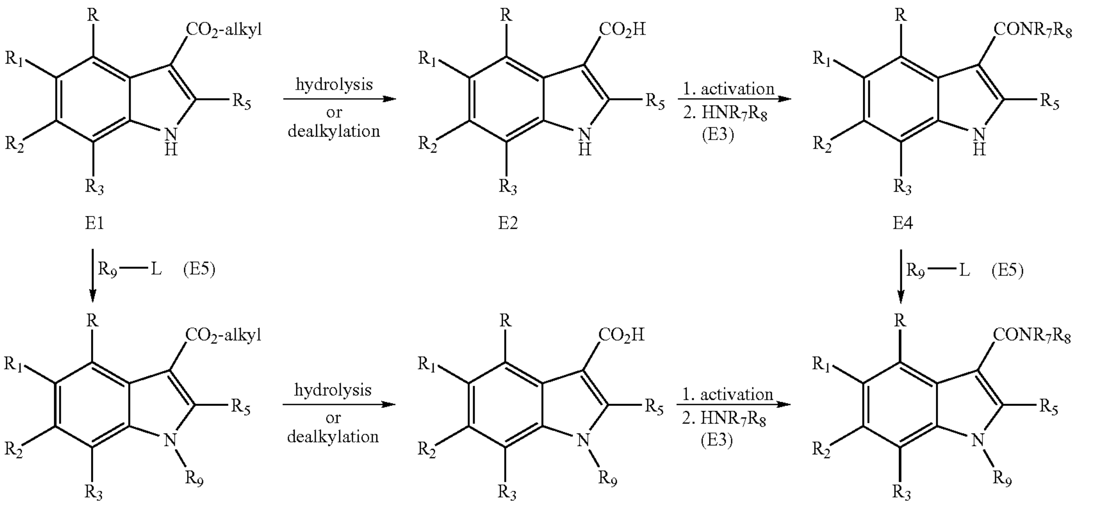

E1 E2 E4 E6 E7 VI

-continued

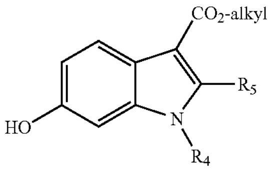

V

Compounds of the present invention, represented by structure VI compounds can be prepared by the chemistry described in scheme E below.

Indole-3-carboxylic esters E1 can be converted to indole-3-carboxylic acids E2 by treatment of compounds of structure E1 with, for example, either acid or base in aqueous or mixed aqueous-organic solvents at ambient or elevated temperature or by treatment with nucleophilic agents, for example, boron tribromide or trimethylsilyl iodide, in a suitable solvent. Compounds of type E2 can then be activated and treated with amines of type E3 to give compounds E4. Activation of the carboxylic acid can be carried out, for example, by any of the standard methods. For example, the acid E2 can be activated Compounds of the present invention, represented by structure VII compounds can be prepared by the chemistry described in scheme F below.

Indoles F1 can be formylated with reagents such as phosphorous oxychloride in the presence of DMF to give the indole-3-carboxaldehydes F2. Conversion to compounds of structure VII can be accomplished by treatment of F2 with compounds F3 as described previously. Alternatively, compounds of type F1 can first be converted to F4 and then be formylated to compounds of structure VII.

Scheme F

VI

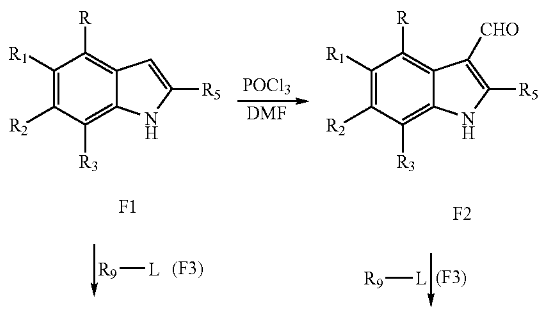

F1 F2

-continued

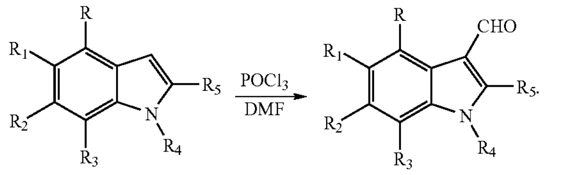

F4

VII

Compounds of formula G, represented by structure VIII can be prepared as shown in Scheme G.

Indole-3-carboxaldehydes of structure GI can be converted to the indole-3-carboxylic acid derivatives by oxidation with reagents such as potassium permanganate under aqueous conditions.

Scheme G

VII

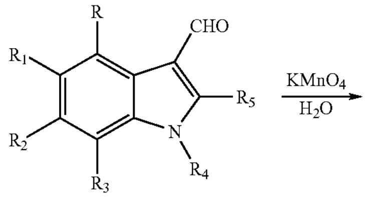

G1

-continued

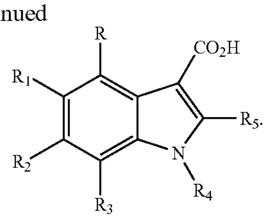

VIII

Compounds of formula H, represented by structure IX can be prepared as shown in Scheme H.

Indole-3-carboxaldehydes of structure H1 can be converted to the indole-3-carbonitrile derivatives H2 by a variety of methods. Treatment of H1 with a nitroalkane, e.g., nitropropane, in the presence of an amine source, e.g., ammonium hydrogen phosphate gives the indole-3-carbonitrile H2 derivative. An alternative pathway to compound H2 is via the intermediate H3. Conversion of H1 to the oxime derivative H3 can be followed by dehydration, e.g., treatment of the oxime with acetic anhydride and a base, or reaction of the oxime with thionyl chloride to give H2. The compound H2 can then be reacted with a reactive functional group $R_9$ containing a suitable leaving group L (H4) as described previously to afford compounds of structure IX.

Alternatively, H1 can be reacted with a reactive functional group $R_9$ containing a suitable leaving group L (H4) to give the intermediate H5, which can be reacted with a nitroalkane as above to give the indole-3-carbonitrile IX compound. Compound IX can also be obtained by conversion to the oxime H6 followed by a dehydration reaction as described above.

Scheme H

VIII

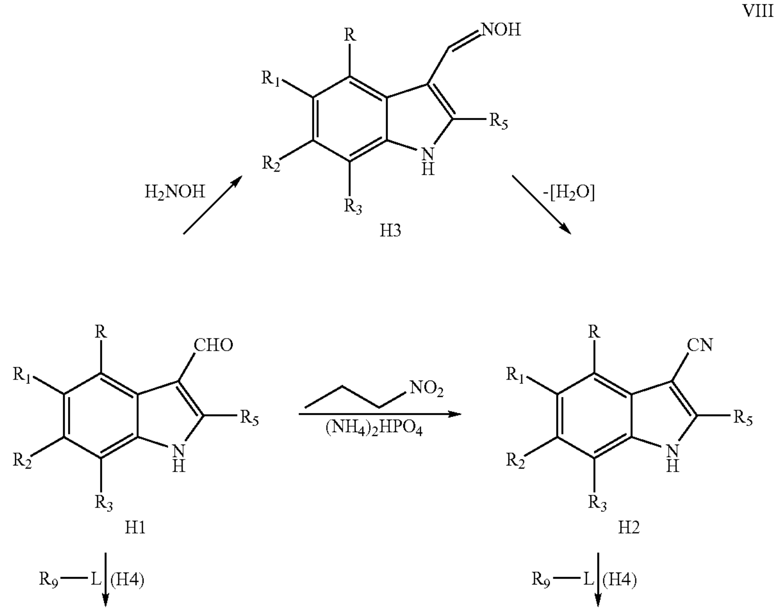

H3

H1

H2

-continued

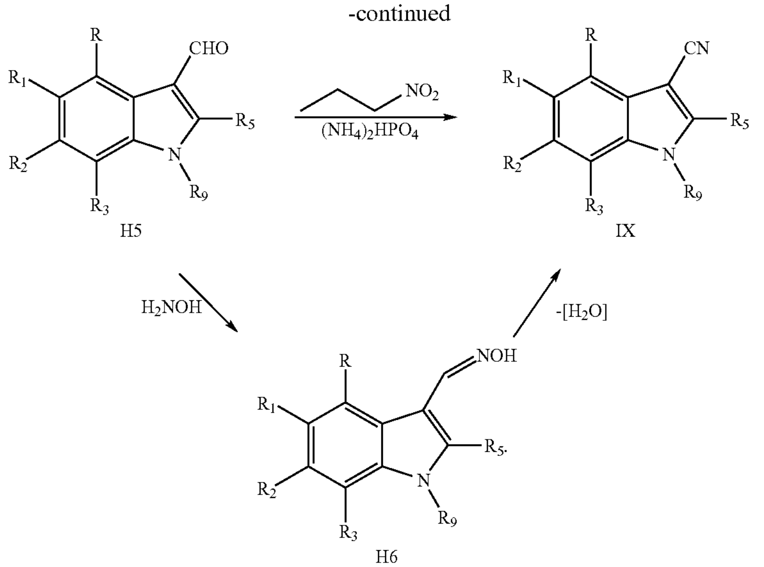

H5 IX H6

Compounds of the present invention, represented by structure X can also be prepared as described in scheme I below.

Indoles I1 can be cyanated with an appropriate cyanating agent, e.g., chlorosulfonyl isocyanate (I2) or a dialkyl phosphoryl isocyanate in a suitable solvent or solvent mixture, e.g. DMF, $CH_3CN$ or dioxane, to afford compounds of structure I3. The compound I3 can then be reacted with a reactive functional group $R_9$ containing a suitable leaving group L (14) as described previously afford the compound X.

Alternatively, compound I1 can be reacted with a reactive functional group $R_9$ containing a suitable leaving group L to give compounds of structure I5 that can then be cyanated as above to give compounds of formula X.

Scheme I

IX

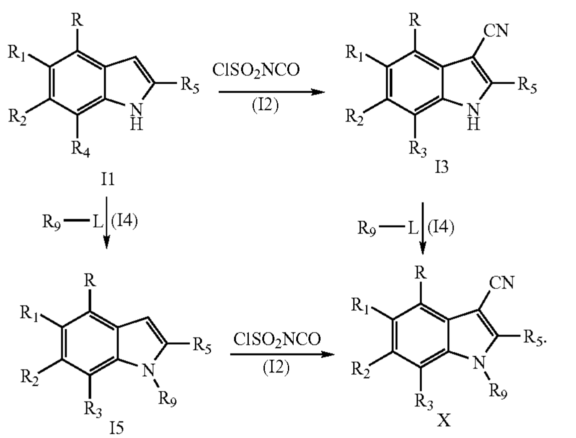

I1 I3 I5 X

Compounds of formula J, represented by structure XI can be prepared as shown in Scheme J.

Amino crotonates J1 can be reacted with amines J2 to give J3. Reaction of J3 with quinone in the presence of a polar, protic solvent, e.g., acetic acid, gives the compound of structure XI.

Scheme J

X

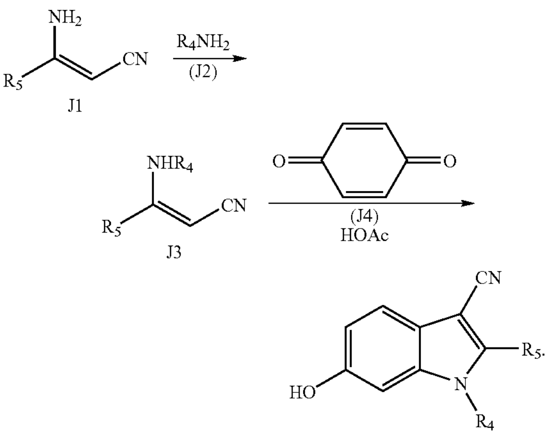

J1 J3 XI

Compounds of the present invention, represented by structure XII and XIII can be prepared as described in scheme K below.

Aldehydes of structure K1 can be reacted with an alkyl azidoacetate K2 by heating the components together in a suitable organic solvent, e.g., a protic or non-protic solvent, in the presence of an organic or inorganic base, to give the α-azidoacrylate K3. Heating K3 in the presence of a suitable non-reactive organic solvent, e.g., toluene or xylenes can give the 2-alkoxycarbonylindoles K4. Reduction of the ester functionality with a suitable reducing reagent, for example, lithium aluminum hydride, in a suitable solvent, e.g., ether or THF can give the intermediate K5. Reaction of K5 with a reactive functional group $R_9$ containing a suitable leaving group L (K6) as described previously affords the compound K7. Cyanation of K7 with a cyanating agent, e.g., chlorosulfonyl isocyanate as described previously can give compound XII. Alternatively, cyanation of K5 with chlorosulfonyl isocyanate gives K8, which can be reacted with a reactive functional group $R_9$ containing a suitable leaving group L (K6) as described previously, affords, the compound XII.

An alternative use of intermediate K4 is exemplified below. Hydrolysis of the 2-alkoxycarbonyl group of the indole K4 either under acidic or basic conditions followed by decarboxylation can give the intermediate K9. Decarboxylation can be carried out thermally, i.e., heating in an appropriate solvent, e.g., toluene, xylenes, or quinoline. Alternatively, a source of copper can be added, for example, copper bronze, to facilitate decarboxylation. Reaction of K9 with a reactive functional group $R_9$ containing a suitable leaving group L (K6) as described above can afford the compounds K10. Cyanation of K10 with a cyanating agent, e.g., chlorosulfonyl isocyanate as described previously can give compound XIII. Alternatively, cyanation of K9 with chlorosulfonyl isocyanate gives K11, which can be reacted with a reactive functional group $R_9$ containing a suitable leaving group L (K6) as described previously, affords the compound XIII.

Scheme K

XI

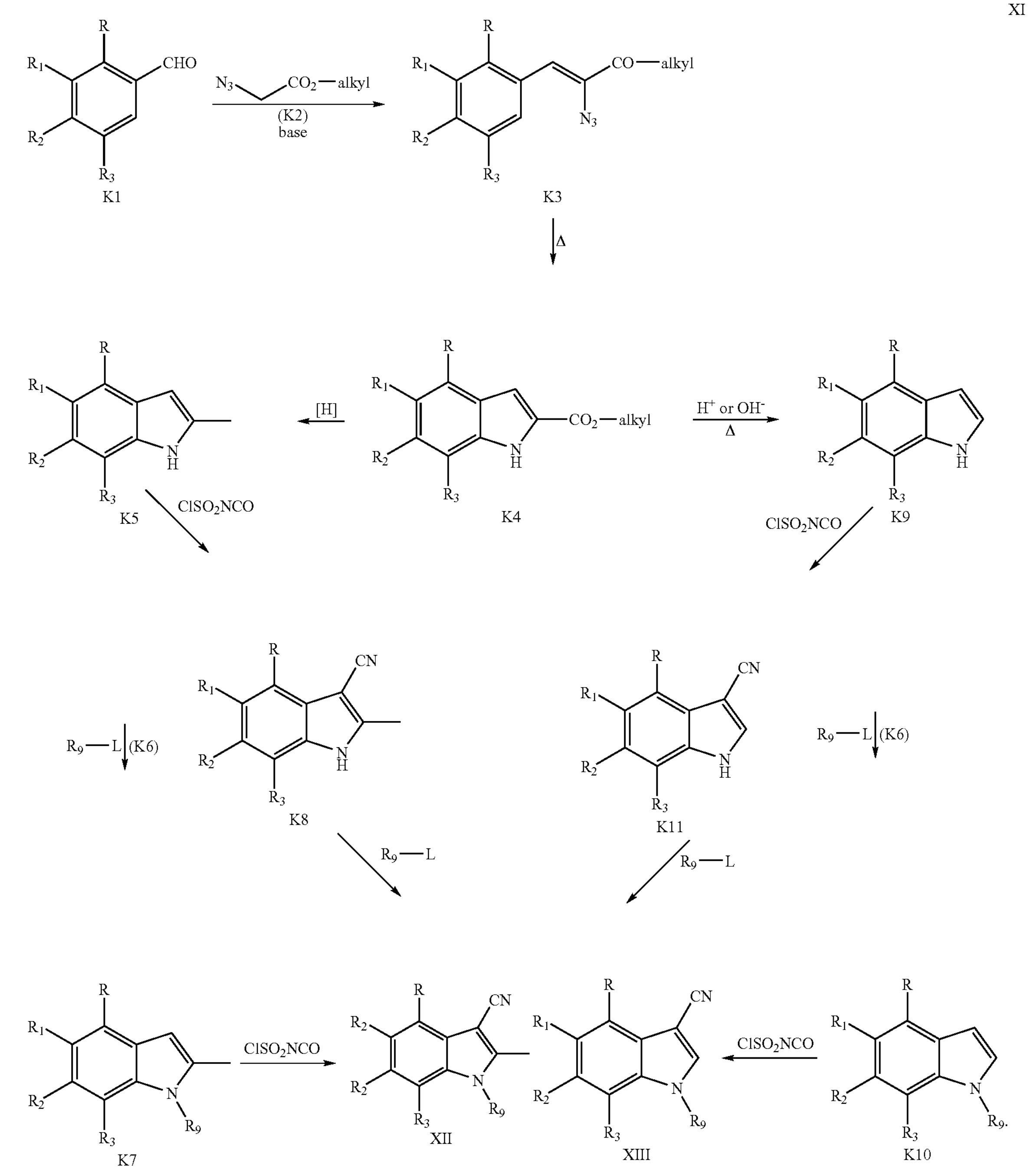

Compounds of formula L, represented by structure XIV can be prepared as shown in Scheme L.

Compounds of formula L1 can be halogenated on the 2-methyl group to give 2-bromomethyl or chloromethyl indoles L2. The halogenation reaction can be conducted with reagents, e.g., N-bromo- or chlorosuccinimide. The reaction can be conducted in a suitable solvent, such as chloroform, carbon tetrachloride, or THF and carried out in a range between ambient temperature and 80° C. Optionally, a radical initiator may be added, e.g., benzoyl peroxide or AIBN. The compound L2 can then be reacted with a nucleophile $R_5$—W (L3) to give compounds of structure XIV. The reaction can be conducted in a suitable solvent, e.g., THF, $CH_2Cl_2$ or DMF, within a temperature range of 0° C. to 120° C. A base, e.g., an inorganic base, such as potassium carbonate or an organic base, such as a trialkylamine can be used to remove the acid formed in the reaction. The group W can refer to an N, O or S atom.

Scheme L

XII

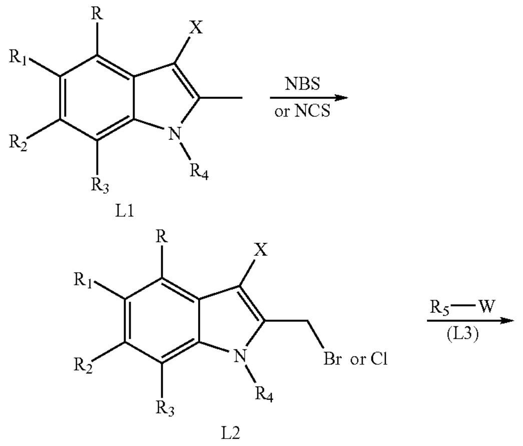

-continued

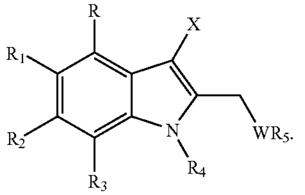

XIV

Compounds of the present invention, represented by structure XV can be prepared as described in scheme M below.

Anilines of structure M1 can be diazotized and the resulting diazonium salt can be reduced to give the phenyl hydrazine compound M2. Reaction between the hydrazine M2 and a ketone M3 under acidic conditions can give the indole compound M4. The conditions for the cyclization reaction can be carried out under typical conditions utilized by one skilled in the art, for example, acidic conditions, utilizing acids such as a Bronstead acid, e.g., acetic acid, hydrochloric acid or polyphosphoric acid or a Lewis acid, e.g., zinc chloride. The reaction can be carried out in the presence of a co-solvent, e.g., $CH_2Cl_2$ or THF typically within a temperature range of 0° C. to 120° C. Reaction of M4 with a reactive functional group $R_9$ containing a suitable leaving group L (M5) as described previously, can afford compounds M6. Cyanation of the indole M6 with a cyanating agent such as chlorosulfonyl isocyanate can give the compound of structure XV.

Alternatively, the indoles M4 can be cyanated to give compounds of structure M7. Reaction of M7 with a reactive functional group $R_9$ containing a suitable leaving group L (M5) as described above can give compounds of structure XV.

Scheme M

XIII

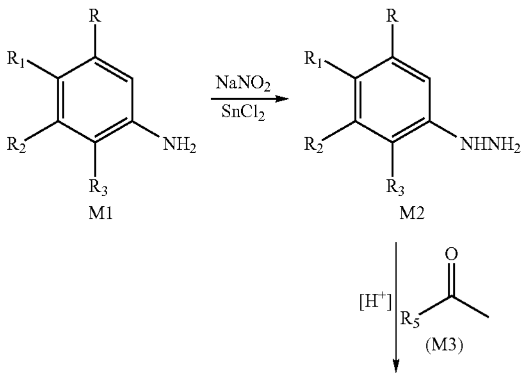

-continued

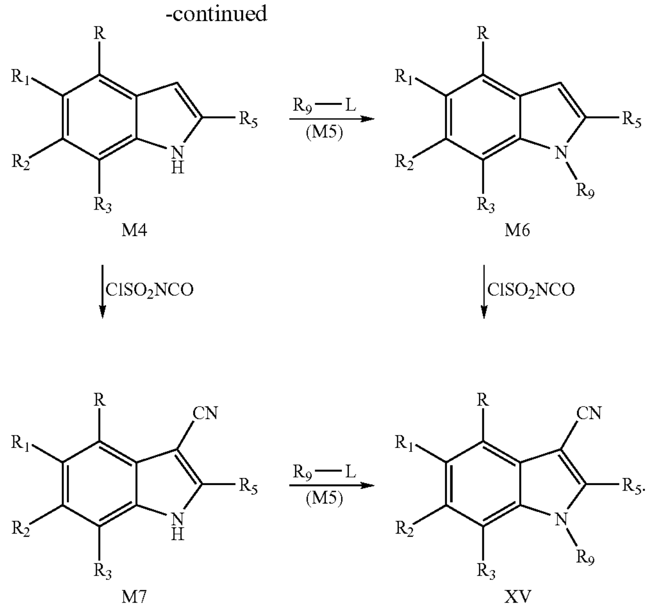

M4 M6 M7 XV

Compounds of formula I, represented by structure XVI can be prepared as shown in Scheme N.

Compounds of formula N1 can be reacted with a dialkylformamide dialkyl acetal, N2, e.g., dimethylformamide dimethyl acetal, optionally in the presence of a suitable solvent, e.g., DMF or dioxane, at a temperature range from ambient to 150° C. to give the compound of structure N3. Reduction of the nitro group of compounds of type N3 under standard conditions can give the indole compounds of structure N4. The reduction can be carried out via hydrogenation, using a sub-stoichiometric amount of a hydrogenation catalyst, e.g., platinum or palladium, in the presence of a hydrogen source in a protic or aprotic solvent. The reduction can be carried out in a temperature range of ambient to 80° C. Alternatively, the reduction can be carried out via chemical reduction, e.g., in the presence of stoichiometric amounts of Fe or Sn compounds in a suitable solvent at a temperature range of ambient to 100° C. The compound N4 can then be reacted with a reactive functional group $R_9$ containing a suitable leaving group L (N5) as described previously to afford compounds of structure N6. Cyanation of N6 with a cyanating agent such as chlorosulfonyl isocyanate in a suitable solvent can give the compounds of structure XVI.

Alternatively, compounds of structure N4 can be cyanated to give compounds of structure N7. Reaction of N7 with a reactive functional group $R_9$ containing a suitable leaving group L (N5) as described above can give compounds of structure XVI.

Scheme N

XIV

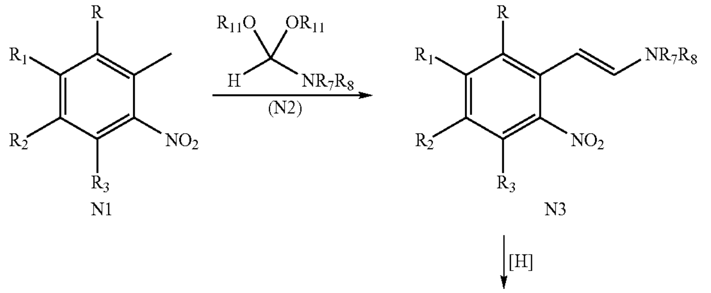

N1 N3

-continued

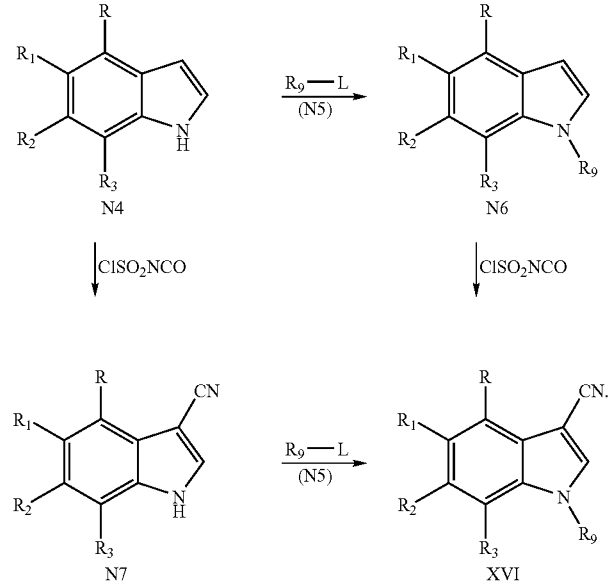

N4 N6 N7 XVI

Compounds of formula I, represented by structure XVII can be prepared as shown in Scheme O.

Compounds of structure O1 can be converted to 2-iodo- or bromoindoles O2. Typically, a strong base, such as n-butyllithium or s-butyllithium or lithium diisopropylamide or lithium or potassium hexamethyldisilazide is employed, with formation of the 2-indolyl anion generated in a suitable unreactive solvent, e.g., ether or THF, or solvent mixtures containing them. The reaction is typically carried out in the range of −78° C. to ambient temperature. The 2-indolyl anion can then be quenched with an electrophilic source of halogen, including but not limited to iodine, bromine or N-bromosuccinimide to give compounds of structure O2. Reaction of 2-iodo- or bromoindoles O2 with a boronic acid (commonly referred to as a Suzuki reaction) or trialkyl stannane (commonly referred to as a Stille reaction) can give the compounds of structure XVII. The coupling reactions are carried out by methods known to those skilled in the art and include conducting the reaction in the presence of a catalyst, such as tetrakis(triphenylphosphine)palladium (0), bis (triphenylphosphine)palladium (II) dichloride or palladium acetate with added phosphine ligand. The reactions are carried out in a suitable solvent, e.g., DMF, toluene, dimethoxy ethane or dioxane at a temperature range of ambient to 150° C. For the Suzuki reaction, a base is usually added. The base can be in aqueous solution, e.g., aqueous sodium carbonate or sodium bicarbonate, or the base can be employed under anhydrous conditions, e.g., cesium or potassium fluoride. For the Stille reaction a copper co-catalyst, e.g., copper iodide, can be added.

Alternatively, indoles O1 can be converted to the indole-2-boronic acid or indole-2-trialkylstannane derivatives O3 by reacting the 2-indolyl anion described above with a trialkylborate or chlorotrialkyl stannane derivative, respectively. Compounds of type O3 can be reacted with aryl and heteroaryl bromides and iodides under similar conditions to those described above to form compounds of structure XVII.

Scheme O

XV

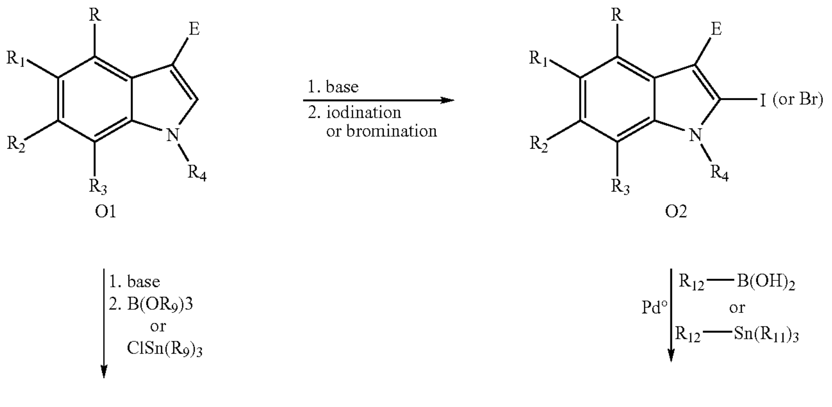

O1 O2

-continued

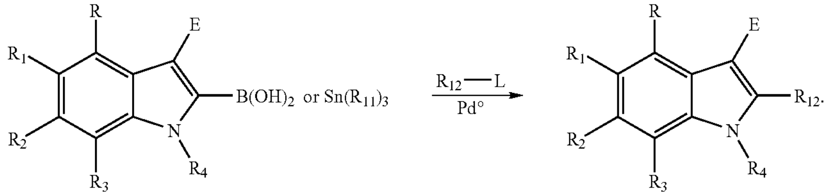

O3 XVII

Compounds of formula I, represented by structure XVIII can be prepared as shown in Scheme P.

Compounds of structure P1 can be converted to compounds P3 by treatment of P1 with an aryl or heteroaryl halide (P2) in the presence of organometallic catalysis. Such catalyst combinations can include palladium catalysts, e.g., palladium acetate and a source of copper, e.g., copper iodide. The reaction can be carried out in the presence of a base, e.g., cesium carbonate. The reaction can be carried out within a temperature range of ambient temperature to 150° C. Cyanation of the indole P3 with a cyanating agent such as chlorosulfonyl isocyanate can give the compound of structure XVIII.

Scheme P

XVI

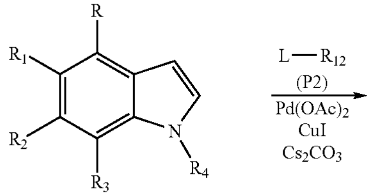

P1

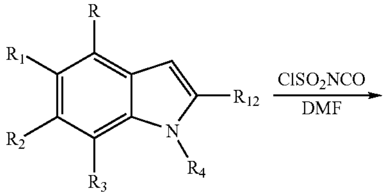

P3

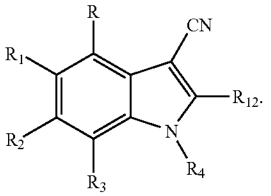

XVIII

Compounds of the present invention, represented by structure XIX can be prepared as described in scheme Q below.

Compounds of structure XIX can be prepared by protecting an indole compound of structure Q1 as e.g., the N-Boc derivative Q2. Alternatively, other protecting groups that can be utilized but not limited to include, e.g., benzyl, alkyl or aryl sulfonyl, or trialkyl silyl. Treatment of Q2 with a strong base, e.g., lithium diisopropyl amide in an aprotic solvent, e.g., THF followed by quenching with a trialkylborate derivative can give the indolyl-2-boronic acid Q3. Reaction with an aryl or heteroaryl halide Q4 in the presence of palladium catalysis, e.g., tetrakis(triphenylphosphine) palladium (0), bis(triphenylphosphine)palladium (II) dichloride or palladium acetate with added phosphine ligand, can give the compound Q5. Removal of the protecting group can give Q6. Reaction with Q6 with a reactive functional group $R_9$ containing a suitable leaving group L as described above can give compounds of structure Q7. Cyanation of compound Q7 can give the compounds of structure XIX.

Scheme Q

XVII

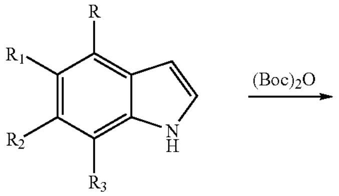

Q1

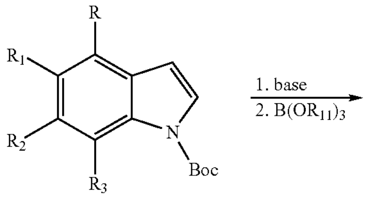

(Q2)

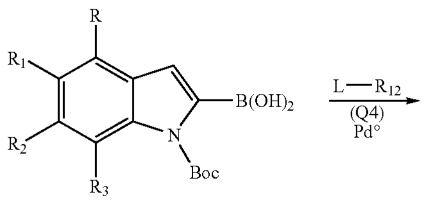

Q3

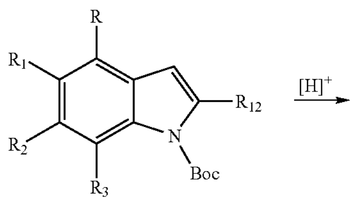

Q5

-continued

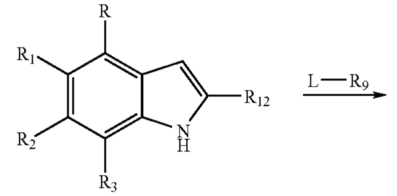

Q6

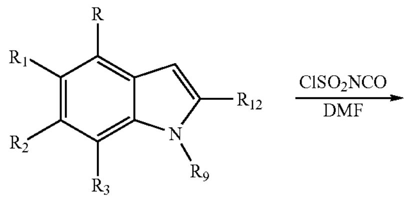

Q7

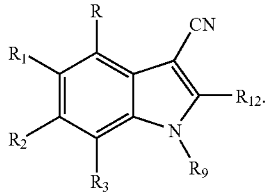

XIX

Compounds of formula I, represented by structure XX can be prepared as shown in Scheme R.

Compounds of structure R2 can be prepared by protecting an indole compound of structure R1 as e.g., the N-Boc derivative R2 as above. Compounds of structure R2 can be converted to 2-iodo- or bromoindoles R3. Typically, a strong base, such as n-butyllithium or s-butyllithium or lithium diisopropylamide or lithium or potassium hexamethyldisilazide is employed, with formation of the 2-indolyl anion generated in a suitable unreactive solvent, e.g., ether or THF, or solvent mixtures containing them. The reaction is typically carried out in the range of −78° C. to ambient temperature. The 2-indolyl anion can then be quenched with an electrophilic source of halogen, including but not limited to iodine, bromine or N-bromosuccinimide to give compounds of structure R3. After removal of the protecting group, compounds of R4 can be reacted with aryl or heteroaryl boronic acids or esters (R5) (commonly referred to as a Suzuki reaction) to give compounds of structure R6. The coupling reactions are carried out by methods known to those skilled in the art and include conducting the reaction in the presence of a catalyst, such as tetrakis (triphenylphosphine)palladium (0), bis(triphenylphosphine)palladium (II) dichloride or palladium acetate with added phosphine ligand. Reaction of R6 with a reactive functional group $R_9$ containing a suitable leaving group L as described above can give compounds of structure XX.

Scheme R

XVIII

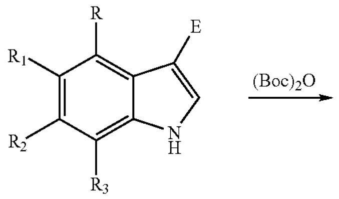

R1

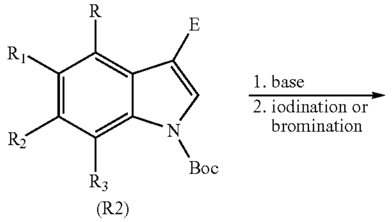

(R2)

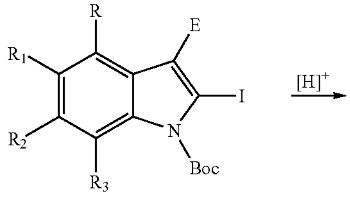

R3

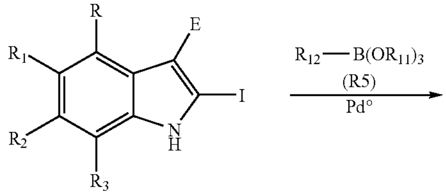

R4

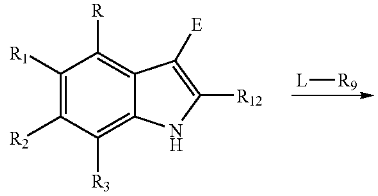

R6

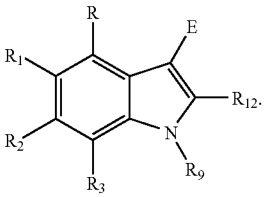

XX

Compounds of the present invention, represented by structure XXI can be prepared as described in scheme S below.

2-iodo- or bromoindoles of structure SI can be reacted with alkenes in the presence of a palladium catalyst (commonly referred to as the Heck reaction) to give compounds of type XXI. The coupling reactions can be carried out by methods known to those skilled in the art. The choice of catalyst and solvents are similar to those described previously.

Scheme S

XIX

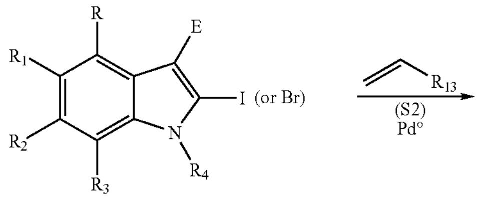

S1

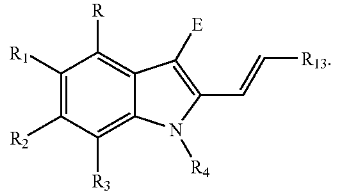

XXI

Compounds of formula I, represented by structure XXII can be prepared as shown in Scheme T.

-continued

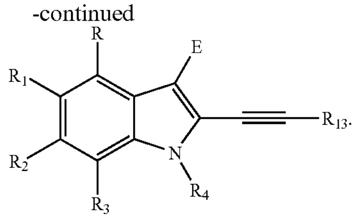

XXII

Compounds of formula I, represented by structure XXIII can be prepared as shown in Scheme U.

Compounds of structure XXIII can be obtained from the reduction of compounds XXI and XXII. Conditions for the reduction can include, but are not limited to catalytic reduction, e.g., hydrogenation over a source of platinum or palladium in a suitable solvent, e.g., $CH_2Cl_2$, ether, THF, methanol or solvent combinations.

Scheme U

XXI

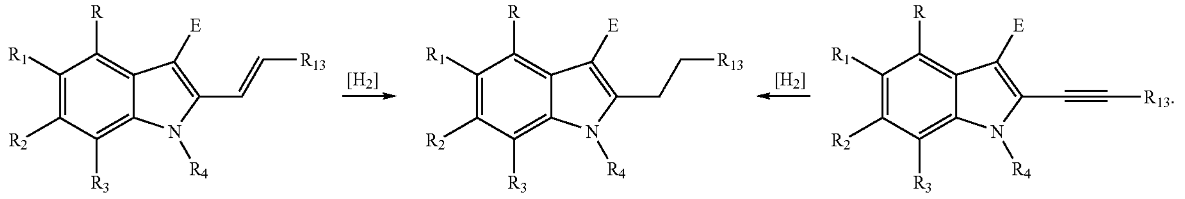

XXI XXIII XXII

2-Iodo- or 2-bromoindoles of structure T1 can be reacted with acetylenes in the presence of a palladium catalyst (commonly referred to as the Sonagashira reaction) to give compounds of type XXII. The coupling reactions can be carried out by methods known to those skilled in the art. A typical set of reaction conditions includes reacting the indoles of structure T1 with an acetylene compound T2 in the presence of a source of palladium, a copper co-catalyst and an amine source. The reaction is carried out in a suitably unreactive solvent and conducted within a temperature range from ambient to 150° C.

Scheme T

XX

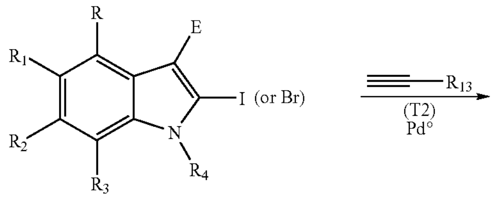

T1

Compounds of the present invention, represented by structure XXIV can be prepared as described in scheme V below.

Indoles of structure V1 can be reacted with a suitable base, such as lithium diisopropylamide or potassium hexamethyldisilazide to generate the 2-indolyl anion in a suitable unreactive solvent, e.g., ether or THF, or solvent mixtures containing them. The reaction is typically carried out in the range of −78° C. to ambient temperature. The 2-indolyl anion can then be quenched with a source of zinc halide, e.g., zinc halide metal or solutions containing them to give organozinc compounds of structure V2. Reaction of V2 with an arylhalide (V3) in the presence of a palladium catalyst (commonly referred to as the Negishi reaction) gives compounds of structure XXIV. Alternatively, 2-iodo or bromoindoles of structure V4, prepared from compounds V1 as described previously, can be reacted with organozinc compounds of structure V5 in the presence of a suitable palladium catalyst to give compounds of structure XXIV. The organozinc compound V5 can be derived from, e.g., an alkyl or alkenyl halide after treatment with activated zinc or an aryl or heteroaryl lithium or magnesium compound after treatment with zinc halide. Furthermore, the reactions of V2 or V4 can be carried out in the presence of a palladium source, e.g., as tetrakis(triphenylphosphine)palladium (0) or bis(triphenylphosphine)palladium (II) dichloride in a suitable solvent and at a temperature range from ambient to 150° C.

Scheme V

XXII

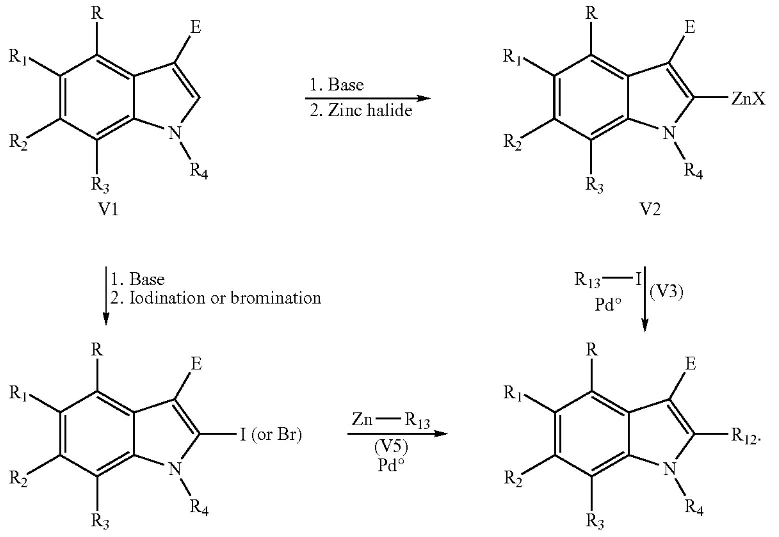

V1 V2 V4 XXIV

Compounds of formula I, represented by structure XXV-XXVIII can be prepared as shown in Scheme W.

2-Iodo- or bromoindoles of structure W1 can be reacted with acetylenes of structure W2 in the presence of a palladium catalyst (commonly referred to as the Sonagashira reaction) to give compounds of type XXV. The coupling reactions can be carried out by methods known to those skilled in the art. A typical set of reaction conditions includes reacting the indoles of structure W1 with an acetylene compound W2 in the presence of a source of palladium, an optional copper co-catalyst and an amine source. The reaction is carried out in a suitably unreactive solvent and conducted within a temperature range from ambient to 150° C. Reaction with XXV with a reactive functional group $R_9$ containing a suitable leaving group L as described above can give compounds of structure XXVI.

2-iodo- or bromoindoles of structure W1 can also be reacted with alkenes in the presence of a palladium catalyst (commonly referred to as the Heck reaction) to give compounds of type XXVII. The coupling reactions can be carried out by methods known to those skilled in the art. The choice of catalyst and solvents are similar to those described previously. Reaction with XXVII with a reactive functional group $R_9$ containing a suitable leaving group L as described above can give compounds of structure XXVIII.

Scheme W
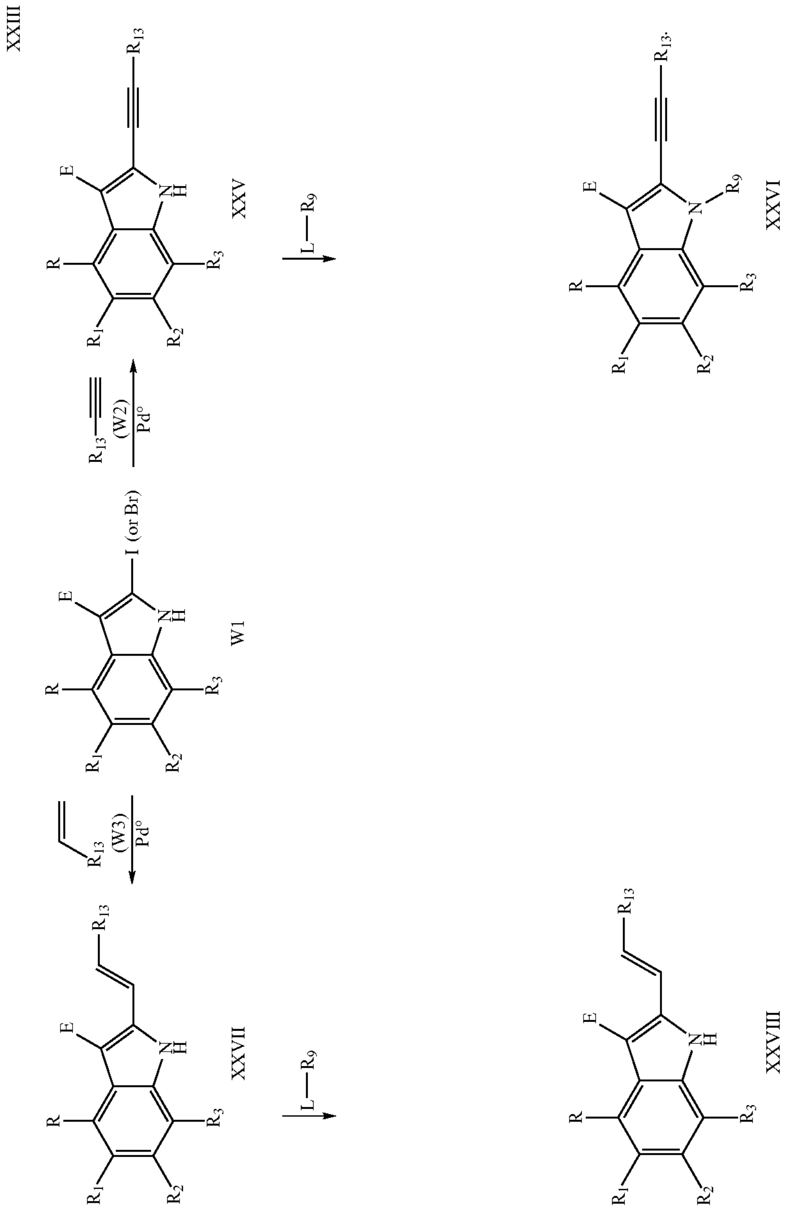
W1 XXIII XXV XXVI XXVII XXVIII

Compounds of formula I, represented by structure XXIX can be prepared as shown in Scheme X.

Indoles of structure X1 and be acylated with acyl halides of structure X2 to give compounds of structure XXIX. The reaction can be promoted with a Lewis acid. The choice of Lewis acid can be chosen from, but is not limited to aluminum chloride, ferric chloride, stannic chloride or diethyl aluminum. The reaction is typically carried out in a suitable non-reactive solvent including $CH_2Cl_2$, carbon disulfide or dichloroethane and is typically conducted within a temperature range of −20° C. to 80° C.

Scheme X

XXIV

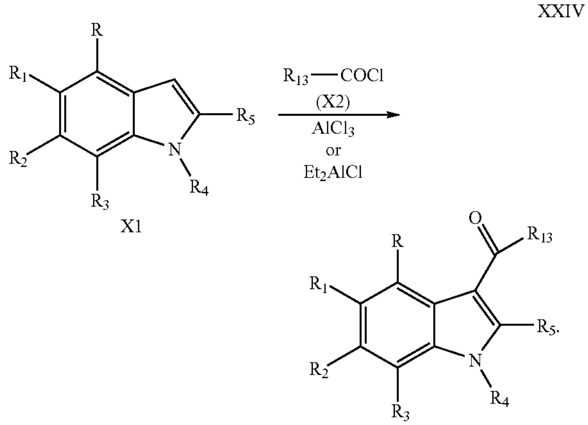

X1

XXIX

Compounds of formula I, represented by structure XXX can be prepared as shown in Scheme Y.

3-Cyanoindoles of structure Y1 can be converted to tetrazoles of structure Y2 by treatment with, e.g., sodium azide. Heating a mixture of Y2 and the reagent Y3 can give the 3-(1,2,4-oxadiazolyl)indole compound XXX. The reagent Y3 can be, e.g., an acyl halide or an acid derivative activated with a reagent such as dicyclohexyl carbodiimide or diisopropyl carbodiimide. The reaction can be carried out in a variety of solvents, including e.g., toluene, dioxane, pyridine and dichloroethane and can be carried out by heating Y2 and Y3 at a temperature range of 30° to 130° C.

Scheme Y

XXV

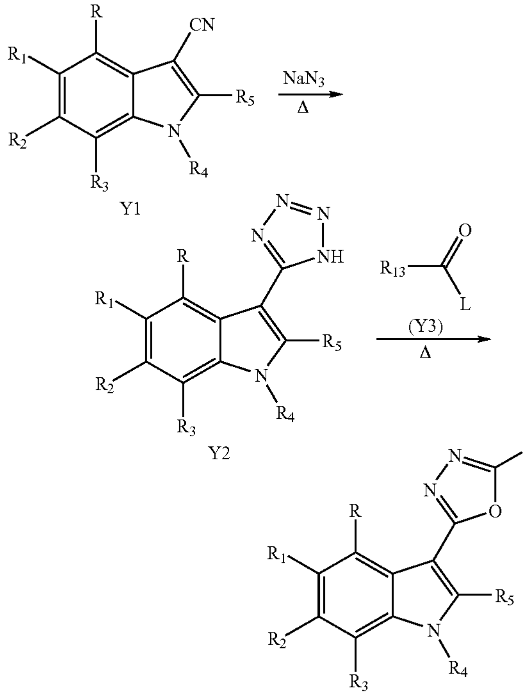

Y1

Y2

XXX

Compounds of formula I, represented by structure XXXI can be prepared as shown in Scheme Z.

3-Cyanoindoles of structure Z1 can be treated with hydroxyamine to give hydroxyamidine compounds of formula Z2. Reaction of hydroxyamidines of structure Z2 with compounds of structure Z3 can give O-acylhydroxyamidines Z4. Compounds Z3 can represent, for example, acyl halides or carboxylic acids activated with a reagent such as dicyclohexyl carbodiimide or diisopropyl carbodiimide. Heating compounds of structure Z4 in a non-reactive organic solvent, e.g., toluene, dichloroethane or dioxane in a temperature range of 30° C. to 150° C. can give compounds of structure XXXI.

Scheme Z

XXVI

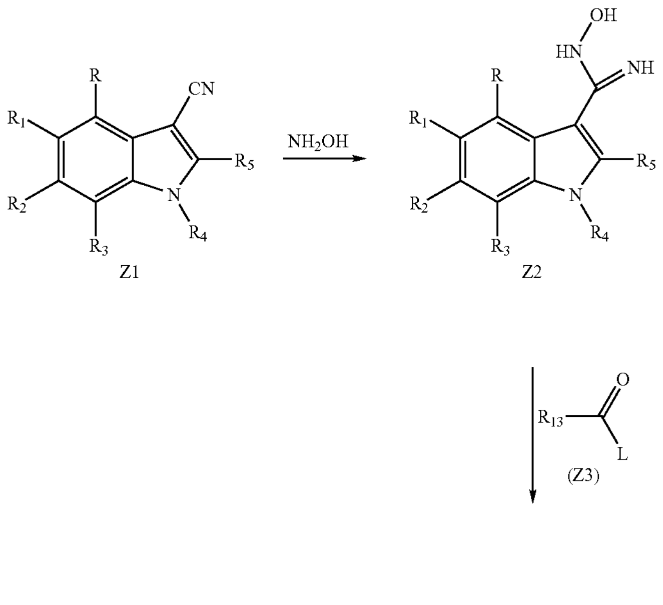

Z1

Z2

-continued

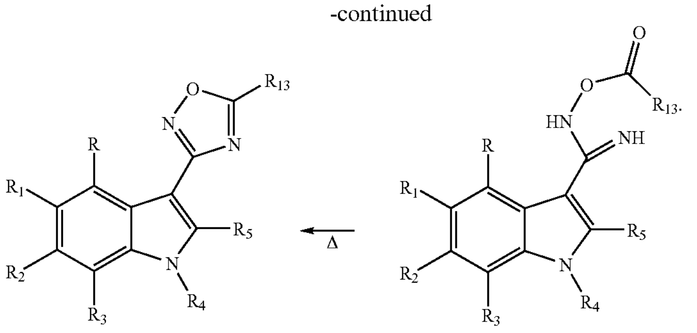

XXXI Z4

Compounds of the present invention, represented by structure XXXII can be prepared as described in scheme AA below.

Ketoindoles of type AA1 can be converted to oximes of structure AA2 by heating the ketoindoles with hydroxyamine (free base or acid salt) in a suitable solvent. Bis-deprotonation of compounds of type AA2 with a strong organic base (e.g., n-butyllityium or sec-butyllithium or tert-butyllithium) followed by reaction with DMF can give compounds of formula XXXII.

Scheme AA

XXVII

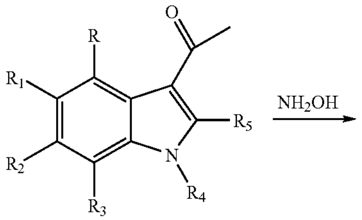

AA1

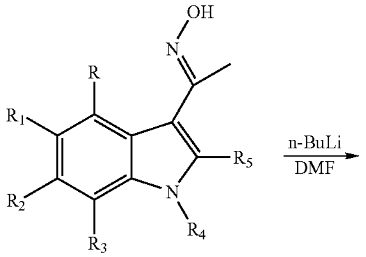

AA2

-continued

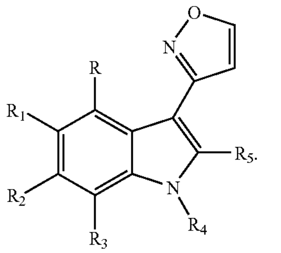

XXXII

Compounds of formula I, represented by structure XXXIII can be prepared as shown in Scheme AB.

3-Ketoindoles of structure AB1 can be homologated to vinylogous amides of structure AB3 by reaction with dialkyl amide dialkyl acetals AB2. The dialkyl amides can include e.g., lower alkyl amides such as formamide, acetamide and propionamide. Examples would include dimethlformamide dimethyl acetal and dimethyl acetamide dimethyl acetal. The reaction can be conducted by reacting AB1 and AB2 with or without additional solvent at a temperature from ambient to 150° C. Treatment of AB3 with hydroxyamine (free base or acid salt) in a suitable solvent can give compounds of structure XXXIII. The reaction is typically conducted within a temperature range from ambient to 120° C.

Scheme AB

XXVIII

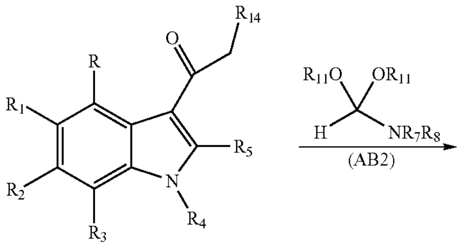

AB1

-continued

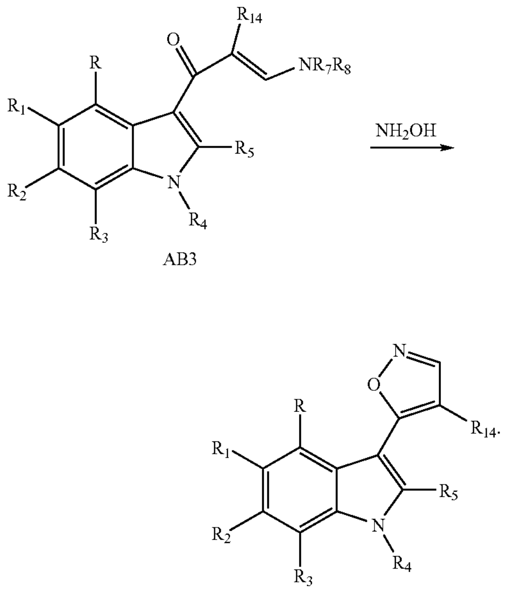

AB3

XXXIII

Compounds of formula I, represented by structure XXXIV can be prepared as shown in Scheme AC.

Vinylogous amides of structure AC1 (as prepared above) can be treated with hydrazines AC2 in a suitable organic solvent (DMF, alcohol or acetic acid) at temperatures ranging from ambient temperature to 150° C. to give compounds of structure XXXIV.

Scheme AC

XXIX

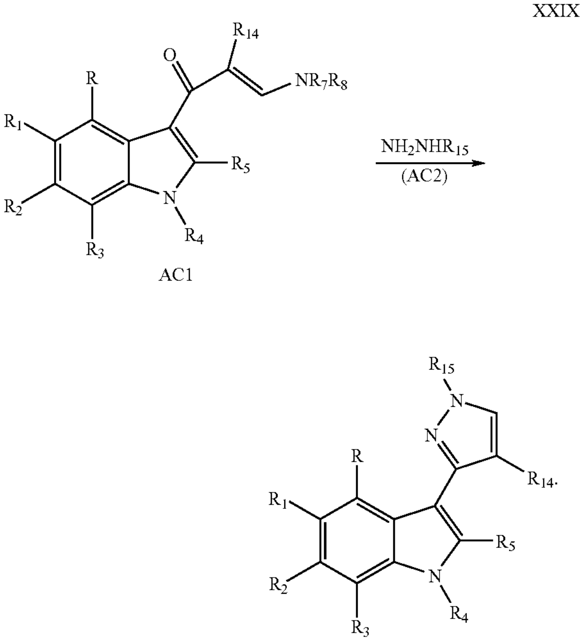

AC1

XXXIV

Compounds of the present invention, represented by structure XXXV can be prepared as described in scheme AD below.

Indole-3-carboxaldehydes of structure AD1 (as prepared in Scheme F) can be reacted with p-(toluenesulfonyl)methyl isocyanate (TOSMIC) in the presence of a base to give compounds of structure XXXV. Bases can include potassium carbonate or 1,8-diazabicyclo[5.4.0]undec-7-ene and the reaction can be carried out in a suitable organic solvent from ambient temperature to 150° C.

Scheme AD

XXX

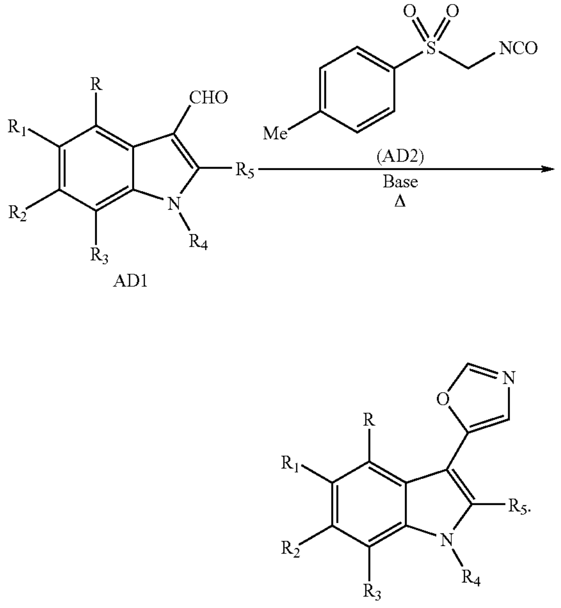

AD1

XXXV

Compounds of formula I, represented by structures XXXVI and XXXVII can be prepared as shown in Scheme AE.

3-Indolecarboxylic acids of structure AE1 (from Scheme E) can be converted to amides of structure AE2. Compounds of structure AE2 can be activated by any of the standard methods. For example, the acid AE1 can be activated with coupling reagents such as EDCI or DCC with or without HOBt in the presence of ammonia. Alternatively, the acid can be activated as the acid chloride or as the acyl imidazolide as described previously, followed by treatment of ammonia.

The indole-3-carboxamides of structure AE2 can be reacted with substituted aldehydes or ketones (AE3) containing a suitable leaving group L, in a suitable solvent at temperatures above ambient and up to 200° C. The reaction can be performed with or without added base to afford oxazoles of structure XXXVI.

The indole-3-carboxamides of structure AE2 can also be converted to thioamides of structure AE4 by treating the primary amides with Lawesson's reagent or phosphorous pentasulfide at or above ambient temperature in a suitable organic solvent. The resulting thioamides AE4 can be reacted with substituted aldehydes or ketones containing a suitable leaving group L (AE3), in a suitable solvent at temperatures above ambient and up to 150° C. The reaction can be performed with or without added base to afford thiazoles of structure XXXVII.

Scheme AE

XXXI

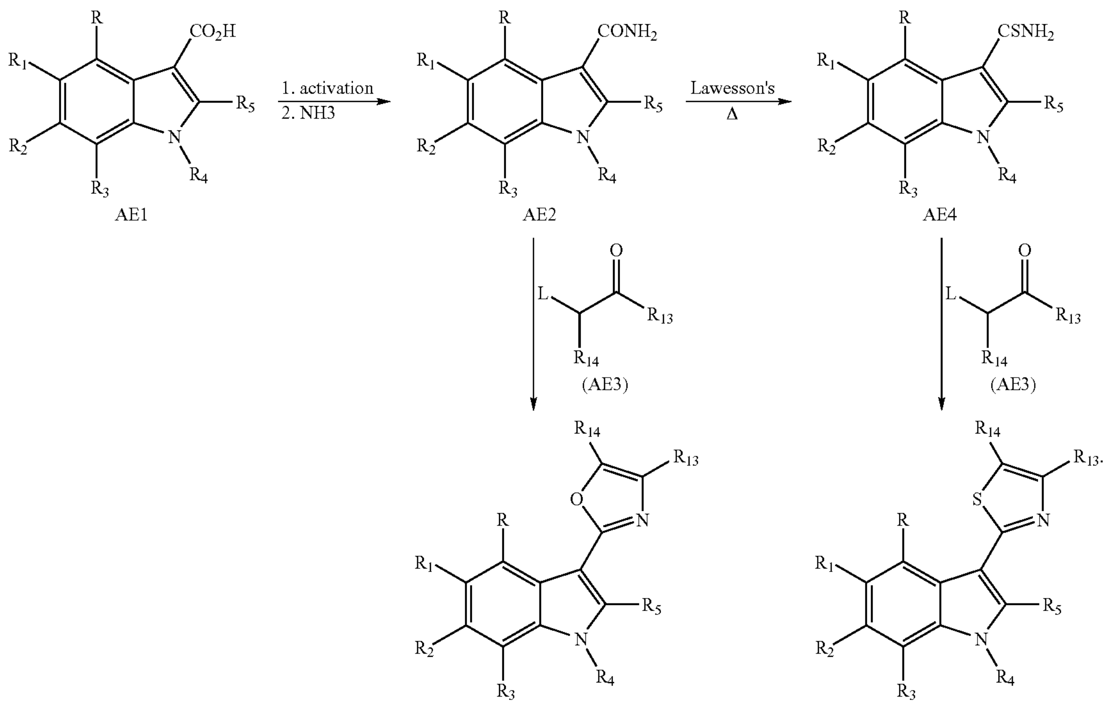

AE1 AE2 AE4 XXXVI XXXVII

Compounds of the present invention, represented by structure XXXVIII and XXXIX can be prepared as described in scheme AF below.

3-Ketoindoles of structure AF1 can be halogenated (e.g., brominated) to give compounds of structure AF3. Suitable brominating agents can include but are not limited to phenyltrimethylammonium tribromide (AF2), N-bromosuccinimide or bromine and can be carried out in a variety of organic solvents.

Treatment of compounds AF3 with amides of type AF4 in a suitable solvent at temperatures above ambient and up to 200° C. with or without added base can give oxazoles of structure XXXVIII.

Treatment of compounds AF3 with thioamides of type AF5 in a suitable solvent at temperatures above ambient and up to 150° C. with or without added base can give thiazoles of structure XXXIX.

Scheme AF

XXXII

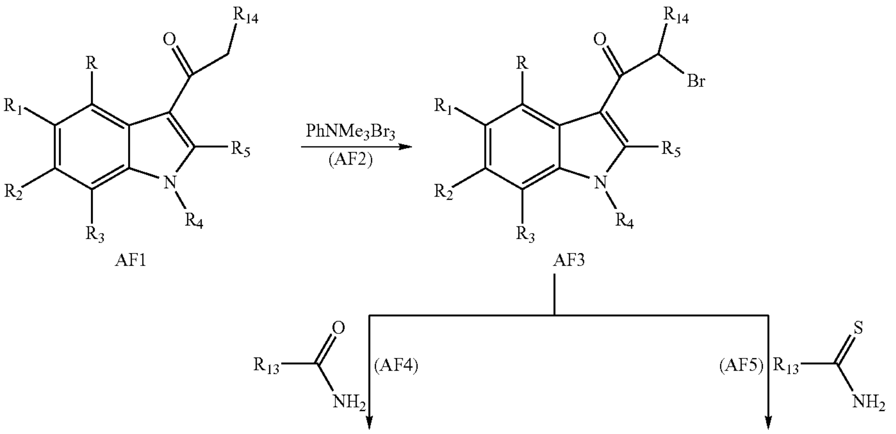

AF1 AF3

-continued

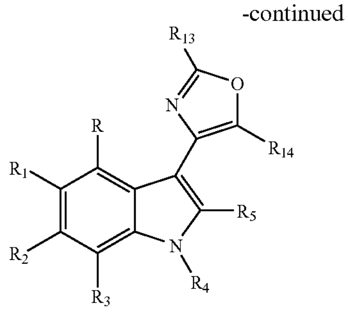

XXXVIII

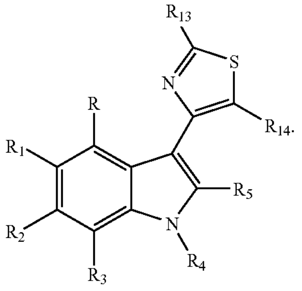

XXXIX

Compounds of formula I, represented by structure XL can be prepared as shown in Scheme AG.

Indoles of structure AG1 can be brominated or iodinated to give compounds of structure AG2. Brominating agents may include but are not limited to bromine or N-bromosuccinimide and iodinating reagents may include iodine monochloride or bis-trifluoroacetoxy iodobenzene. Reaction of 3-iodo- or bromoindoles AG2 with a boronic acid AG3 (commonly referred to as a Suzuki reaction) can give the compounds of structure XL. The coupling reactions are carried out by methods known to those skilled in the art and include conducting the reaction in the presence of a catalyst, such as tetrakis (triphenylphosphine)palladium (0), bis(triphenylphosphine) palladium (II) dichloride or palladium acetate with added phosphine ligand. The reactions are carried out in a suitable solvent, e.g., DMF, toluene, dimethoxy ethane or dioxane at a temperature range of ambient to 150° C. and typically in the presence of a base e.g., aqueous sodium carbonate or sodium bicarbonate, or the base can be employed under anhydrous conditions, e.g., cesium or potassium fluoride Alternatively, indole AG2 can be converted to the indole-3-boronic acid derivative AG5 by reacting the 3-haloindole . AG2 with a strong organic base (alkyllithium or Grignard reagent) and reacting the resultant anion with a trialkylborate reagent AG4. Compounds of type AG5 can be reacted with aryl and heteroaryl bromides and iodides under similar conditions to those described above to form compounds of structure XL.

Scheme AG

XXXIII

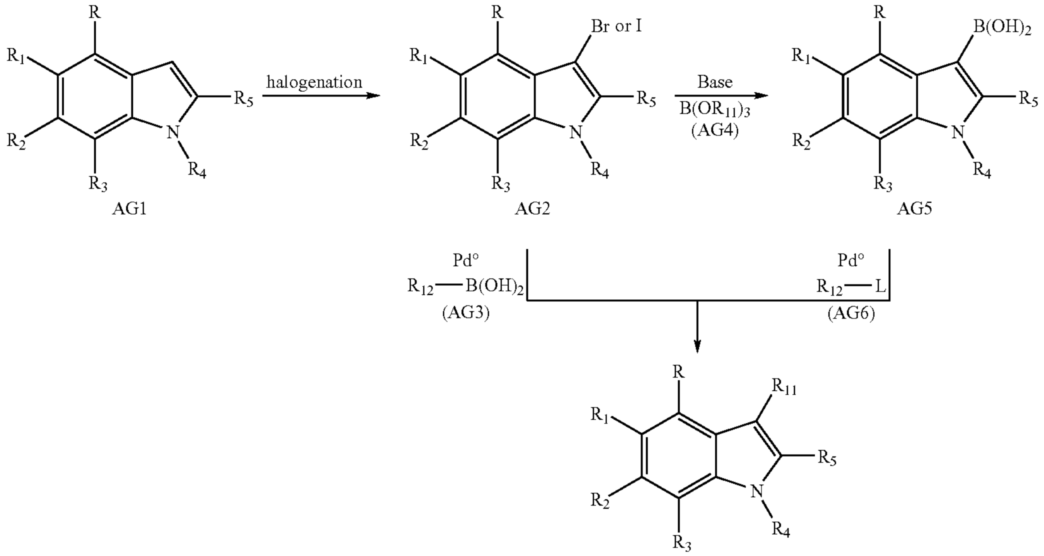

AG1 AG2 AG5 XL

Compounds of the present invention, represented by structure XLI can be prepared as described in scheme AH below.

3-iodo- or bromoindoles of structure AH1 can be reacted with alkenes AH2 in the presence of a palladium catalyst (commonly referred to as the Heck reaction) to give compounds of type XLI. The coupling reactions can be carried out by methods known to those skilled in the art. The choice of catalyst and solvents are similar to those described in Scheme AG.

Scheme AH

XXXIV

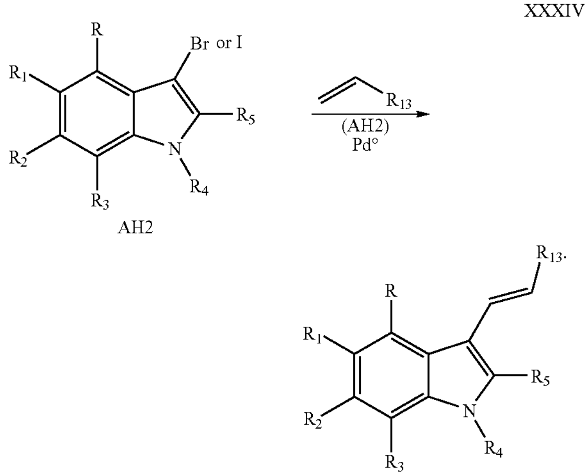

AH2

XLI

Compounds of formula I, represented by structure XLII can be prepared as shown in Scheme AI.

3-Iodo- or bromoindoles of structure AI1 can be reacted with acetylenes AI2 in the presence of a palladium catalyst (commonly referred to as the Sonagashira reaction) to give compounds of type XLII. The coupling reactions can be carried out by methods known to those skilled in the art. A typical set of reaction conditions includes reacting the indole of structure AI1 with an acetylene compound AI2 in the presence of a source of palladium, a copper co-catalyst and an amine source and carrying out the reaction at a temperature range of ambient to 150° C.

Scheme AI

XXXV

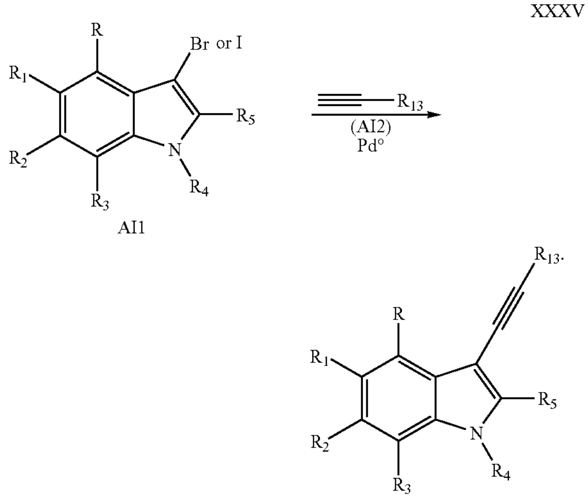

AI1

XLII

Compounds of the present invention, represented by structure XLIII and XLIV can be prepared as described in scheme AJ below.

Nitroanilines of structure AJ1 can be converted to indoles of structure XLIII by condensation and cyclization with nitriles of structure AJ2. The reaction can be carried out in a suitable organic solvent, e.g., DMF or dioxane. Treatment of compounds of structure XLIII with a base followed by reaction with a reactive functional group $R_9$ containing a suitable leaving group L can give the compounds of formula XLIV.

Scheme AJ

XXXVI

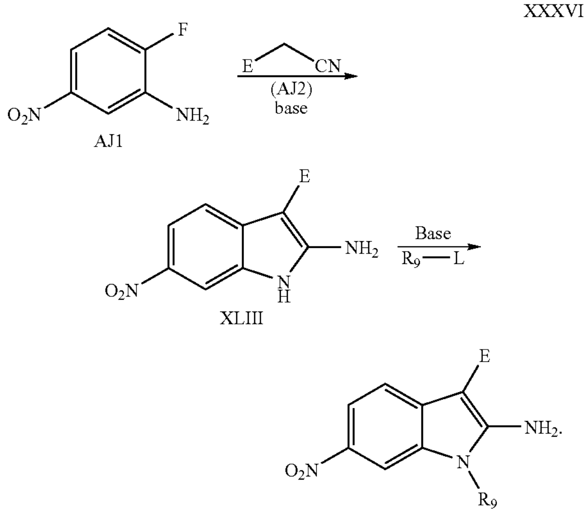

AJ1

XLIII

XLIV

Compounds of formula I, represented by structure XLV-XLVIII can be prepared as shown in Scheme AK.

2-aminoindoles of structure XLV can be alkylated with a reactive functional group $R_{15}$ containing a suitable leaving group L in the presence of a base, e.g., sodium hydride or potassium carbonate in a suitable organic solvent to give compounds of structure XLVI. A second alkylation utilizing a reactive functional group $R'_{15}$ containing a suitable leaving group L similarly can give compounds of structure XLVII.

Acylation of compounds of structure XLV with acyl chlorides of structure AK1 can give compounds of structure XLVIII. The reaction is typically carried out in the presence of an organic base, e.g., a trialkylamine or an inorganic base, e.g., potassium carbonate in a suitable organic solvent.

Scheme AK

XXXVII

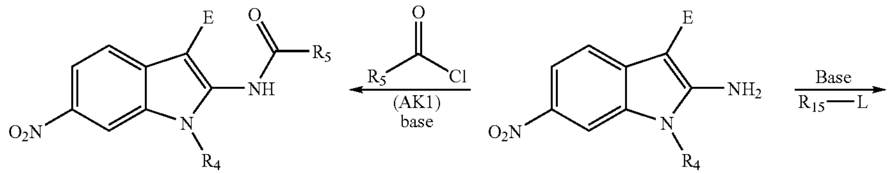

XLVIII XLV

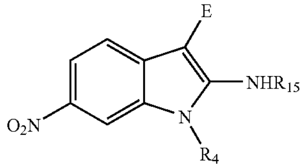

XLVI

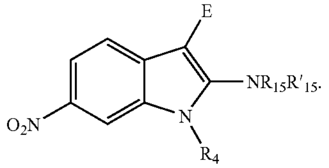

XLVII

Compounds of the present invention, represented by structure XLIX can be prepared as described in scheme AL below.

Indole-3-carboxylic acids of structure AL1 can be activated to give compounds of structure AL2. Compounds of structure AL2 can represent, for example, acyl halides or carboxylic acids activated with a reagent such as dicyclohexyl carbodiimide or diisopropyl carbodiimide. Reaction of compounds of structure AL2 with hydroxyamidines of structure AL3 can give O-acylhydroxyamidines AL4. Hydroxyamidines may be obtained commercially or by treatment of nitrile compounds with hydroxyamine. Heating compounds of structure AL4 in a non-reactive organic solvent, e.g., toluene, dichloroethane or dioxane in a temperature range of 30° C. to 150° C. can give compounds of structure XLIX.

Scheme AL

XXXVIII

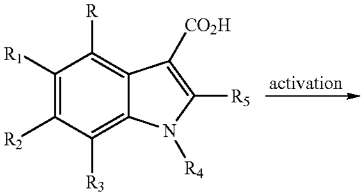

AL1

-continued

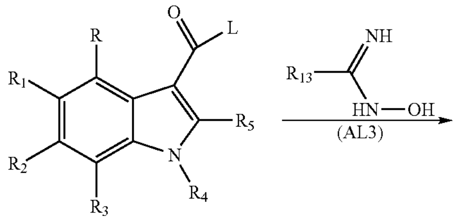

AL2

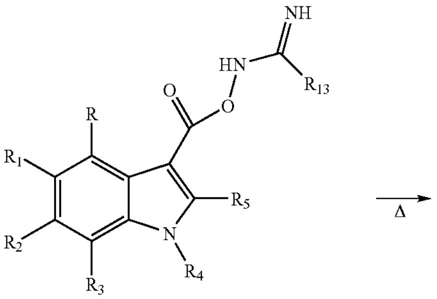

AL4

-continued

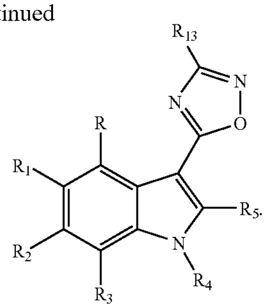

XLIX

C. Methods of the Invention

Another aspect of the invention relates to a method for treating Hepatitis C viral (HCV) infection in a subject in need thereof, comprising administering to the subject an effective amount of one or more compound(s) of formula I or one or more pharmaceutically acceptable salt(s) thereof, or a pharmaceutical composition comprising an effective amount of one of more compound(s) of formula I or one or more pharmaceutically acceptable salt(s) thereof, as described above.

As used herein, the term "treating" refers to: (i) preventing a disease, disorder or condition from occurring in a subject that may be predisposed to the disease, disorder and/or condition but has not yet been diagnosed as having it; (ii) inhibiting a disease, disorder or condition, i.e., arresting its development; and/or (iii) relieving a disease, disorder or condition, i.e., causing regression of the disease, disorder and/or condition.

As used herein, the term "subject" refers to an animal or any living organism having sensation and the power of voluntary movement, and which requires for its existence oxygen and organic food. Nonlimiting examples include members of the human, equine, porcine, bovine, murine, canine and feline species. In some embodiments, the subject is a mammal or a warm-blooded vertebrate animal. In other embodiments, the subject is a human. As used herein, the term "patient" may be used interchangeably with "human".

Without being limited to any particular theory, it is believed that the compounds of the present invention inhibit IRES-mediated initation, elongation and termination, i.e., translation. Thus, another aspect of the invention relates to a method for treating an infection by a virus in a subject in need thereof, wherein the virus contains an internal ribosome entry site (IRES), comprising administering to the subject an effective amount of one or more compound(s) of formula I or one or more pharmaceutically acceptable salt(s) thereof, or a pharmaceutical composition comprising an effective amount of one of more compound(s) of formula I or one or more pharmaceutically acceptable salt(s) thereof, as described above. Nonlimiting examples of such virus include viruses of the picornavirus genus, such as poliovirus, hepatitis A virus and rhinovirus; viruses of the coronaviridae genus, such as SARS; viruses of the arbovirus genus; viruses of the flavivirus genus, such as yellow fever, dengue, and West Nile virus; herpesviruses, such as herpes simplex virus and Kaposi's sarcoma-associated herpesvirus, and other viruses with a similar mode of replication; and HIV and other viruses with a similar mode of translation. In some embodiments, the IRES is essential for protein translation and/or replication.

Yet another aspect of the invention relates to a method for inhibiting HCV IRES-mediated initiation, translation and/or replication in a subject in need thereof, comprising administering to the subject an effective amount of one or more compound(s) of formula I or one or more pharmaceutically acceptable salt(s) thereof, or a pharmaceutical composition comprising an effective amount of one of more compound(s) of formula I or one or more pharmaceutically acceptable salt(s) thereof, as described above.

Some methods of the present invention comprise administering one or more compound(s) of formula I, or a pharmaceutical composition comprising one or more compound(s) of formula I wherein:

X is:

- a nitro group;
- a cyano group;
- a —$COR_a$ group, where $R_a$ is:
  - a $C_1$ to $C_6$ alkyl,
  - a $C_6$ to $C_8$ aryl optionally substituted with an alkoxy or a halogen, or
  - a dialkyl-amino;
- a —$COOR_x$ group, where $R_x$ is a $C_1$ to $C_6$ alkyl;
- a formyl group;
- a $C_6$ to $C_8$ aryl optionally substituted with an alkoxy; or
- a 5 or 6-membered heteroaryl optionally substituted with:
  - a $C_1$ to $C_6$ alkyl,
  - a $C_6$ to $C_8$ aryl optionally substituted with an alkoxy or one or more halogen(s), or
  - a 5 to 6 membered heteroaryl;

Y is:

- a haloalkyl;
- a halogen;
- an amino optionally substituted with one or more $C_1$ to $C_6$ alkyl(s);
- a benzofuran;
- a benzothiophene;
- a dibenzofuran;
- a dibenzothiophene;
- a benzothiazole;
- a naphthalene;
- an indole, optionally substituted on the nitrogen with a $C_1$ to $C_6$ alkyl;

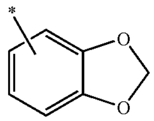 ; 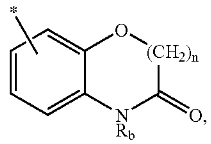

where $R_b$ is a hydrogen or a $C_1$ to $C_6$ alkyl, and n is 0 or 1;

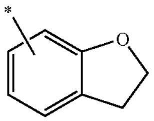 ; 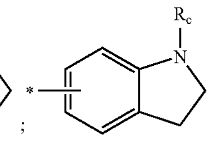 , where $R_c$ is a hydrogen, a —$CONHR_x$, where $R_x$ is as defined above, or an —$SO_2R_x$, where $R_x$ is as defined above; or

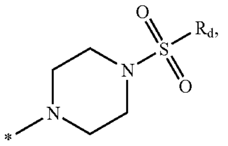

where $R_d$ is a $C_1$ to $C_6$ alkyl or a $C_6$ to $C_8$ aryl;
a —NHCOR$_e$ group, where $R_e$ is:
a $C_1$ to $C_6$ alkyl;
a $C_6$ to $C_8$ aryl optionally substituted with:
a $C_1$ to $C_6$ alkyl,
an alkoxy,
a cyano group,
a nitro group, or
a halogen;
a —NHCOOR$_x$ group, where $R_x$ is as defined above;
a —$CH_2O$—$R_f$ group, where $R_f$ is a $C_6$ to $C_8$ aryl;
a —NR$_g$R$_h$ group, where $R_g$ is a $C_1$ to $C_6$ alkyl or a hydrogen and $R_h$ is a $C_6$ to $C_8$ aryl optionally substituted with an alkoxy;
a $C_1$ to $C_6$ alkyl;
a 5 or 6 membered heteroaryl, optionally substituted with:
a $C_1$ to $C_6$ alkyl, optionally substituted with a $C_6$ to $C_8$ aryl,
a $C_6$ to $C_8$ aryl, optionally substituted with —COOR$_x$, where $R_x$ is as defined above, or
an amino group;
a 5 or 6 membered heterocycle optionally substituted with:
a —COOR$_x$ group, where $R_x$ is as defined above, or
a —NHCOOR$_x$ group, where $R_x$ is as defined above;
a $C_6$ to $C_8$ aryl, optionally substituted with one or more of the following:
an alkoxy, optionally substituted with:
an alkoxy,
a hydroxy,
one or more halogen(s),
a 5 or 6 membered heterocycle, optionally substituted with:
a $C_1$ to $C_6$ alkyl, or
a hydroxy,
an amino group optionally substituted with one or more $C_1$ to $C_6$ alkyl(s),
a —NR$_i$SO$_2$R$_x$ group, where $R_x$ is as defined above and $R_i$ is:
a hydrogen,
a $C_1$ to $C_6$ alkyl,
a —COR$_x$ group, where $R_x$ is as defined above,
a haloalkyl, or
a haloalkoxy,
a —NR$_j$COR$_k$ group, where $R_k$ is:
a $C_1$ to $C_6$ alkyl,
a hydrogen, or
an amino optionally substituted with one or more $C_1$ to $C_6$ alkyl(s),
and $R_j$ is:
a hydrogen,
a $C_1$ to $C_6$ alkyl,
a —COR$_x$ group, where $R_x$ is as defined above,
a haloalkyl, or
a haloalkoxy,
a —N═N$^+$═N$^-$ group, or
a —COR$_l$, where $R_1$ is a 5 or 6 membered heterocycle optionally substituted with a hydroxy,
an amino optionally substituted with one or more $C_1$ to $C_6$ alkyl(s),
a nitro group,
a $C_1$ to $C_6$ alkyl group, optionally substituted with:
a —NHSO$_2$R$_x$ group, where $R_x$ is as defined above, or
a —NR$_x$SO$_2$R$_x$ group, where $R_x$ is as defined above,
a haloalkoxy,
a halogen,
a hydroxy,
a —COOR$_x$ group, where $R_x$ is as defined above,
a —COR$_m$ group, where $R_m$ is:
an amino optionally substituted with one or more $C_1$ to $C_6$ alkyl(s), where the one or more $C_1$ to $C_6$ alkyl(s) is/are optionally substituted with:
a hydroxy
a 5 or 6 membered heterocycle,
an amino optionally substituted with one or more $C_1$ to $C_6$ alkyls, and/or
an alkoxy,
a 3 to 7 membered heterocycle, optionally substituted with a $C_1$ to $C_6$ alkyl, optionally substituted with a dialkyl-amino,
a —NHR$_n$ group, where $R_n$ is:
a —$CH_2CONH_2$, or
a $C_6$ to $C_8$ aryl optionally substituted with:
an alkyl,
one or more halogen(s),
a nitro group, or
one or more alkoxy(s),
a —NR$_o$COR$_p$ group, where $R_p$ is:
a $C_1$ to $C_6$ alkyl optionally substituted with:
a halogen,
an alkoxy, or
a $C_6$ to $C_8$ aryl,
a 5 or 6 membered heterocycle,
a $C_6$ to $C_8$ aryl, optionally substituted with a halogen,
a 5 or 6 membered heteroaryl optionally substituted with one or more $C_1$ to $C_6$ alkyl(s),
a hydrogen,

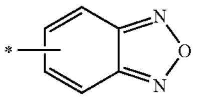
or
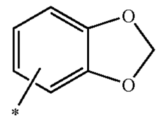
, and where $R_o$ is:
a hydrogen,
a $C_1$ to $C_6$ alkyl,
a —COR$_x$ group, where $R_x$ is as defined above,
a haloalkyl, or
a haloalkoxy,
a —NR$_q$CONR$_q$R$_r$ group, where $R_q$ is:
a hydrogen,
a $C_1$ to $C_6$ alkyl,
a haloalkyl,
a haloalkoxy, or
a —COR$_x$ group, where $R_x$ is as defined above,
and where $R_r$ is:

a $C_6$ to $C_8$ aryl optionally substituted with:

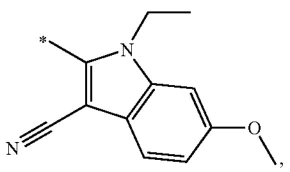

a $C_1$ to $C_6$ alkyl,
a haloalkyl,
a —$OR_s$ group, where $R_s$ is a $C_6$ to $C_8$ aryl, or
a —$COOR_x$ group, where $R_x$ is as defined above,
a $C_1$ to $C_6$ alkyl optionally substituted with one or more of the following:
a halogen,
an alkylene,
a $C_6$ to $C_8$ aryl, and/or
a —$COOR_x$ group, where $R_x$ is as defined above,
a —$COOR_x$ group, where $R_x$ is as defined above,
a —$NR_tCOOR_u$ group, where $R_u$ is:
a $C_1$ to $C_{12}$ alkyl, optionally substituted with:
a $C_6$ to $C_8$ aryl optionally substituted with a $C_1$ to $C_6$ alkyl or an alkoxy,
an alkylene,
an alkoxy,
an alkyne,
a halogen, or
a 5 or 6 membered heterocycle,
a $C_6$ to $C_8$ aryl, optionally substituted with:
an alkoxy,
a halogen, or
a $C_1$ to $C_6$ alkyl, or
a 5 or 6 membered heterocycle,
and $R_t$ is:
a hydrogen,
a $C_1$ to $C_6$ alkyl,
a —$COR_x$ group, where $R_x$ is as defined above,
a haloalkyl, or
a haloalkoxy,
a —$NR_vSO_2R_w$ group, where $R_v$ is:
a hydrogen,
a —$COR_x$, where $R_x$ is as defined above, or
a $C_1$ to $C_6$ alkyl, optionally substituted with:
a halogen,
a —$COR_x$ group, where $R_x$ is as defined above,
a —$OCOR_x$ group, where $R_x$ is as defined above,
a hydroxy, or
an alkoxy,
and where $R_w$ is:
a $C_1$ to $C_6$ alkyl optionally substituted with:
a halogen,
a haloalkyl,
a $C_6$ to $C_8$ aryl, or
a 5 or 6 membered heterocycle,
a $C_2$ to $C_6$ alkylene,
an alkyl- or dialkyl-amino optionally substituted with a halogen,
a 5 or 6 membered heterocycle, or
a 5 or 6 membered heteroaryl optionally substituted with:
a $C_1$ to $C_6$ alkyl,
a 5 or 6 membered heterocycle, or

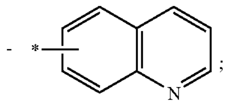

-a 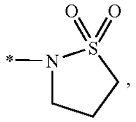

-a 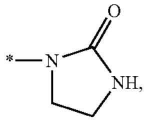

-a 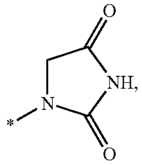

-a 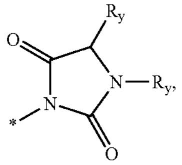

optionally substituted with a $C_1$ to $C_6$ alkyl, where $R_y$ is a $C_1$ to $C_6$ alkyl or hydrogen, a 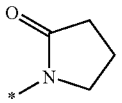, a 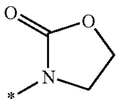, a 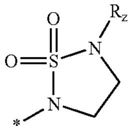, where $R_z$ is hydrogen or a $C_1$ to $C_6$ alkyl, optionally substituted with a $C_6$ to $C_8$ aryl,
a —$SR_x$ group, where $R_x$ is as defined above,
a —$SO_2R_{aa}$ group, where $R_{aa}$ is:
a $C_1$ to $C_6$ alkyl,
an amino group,
an alkyl- or dialkyl-amino group optionally substituted with a hydroxy or a —$COOR_x$ group, where $R_x$ is as defined above,
a 5 or 6 membered heteroaryl,
a $C_6$ to $C_8$ aryl, and/or
a —$NHR_{bb}$ group, where $R_{bb}$ is:

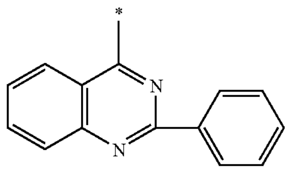, 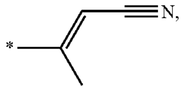

a —$C(=S)NH_2$ group, or
a —$PO(OR_x)_2$ group, where $R_x$ is as defined above;
a 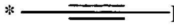$R_{cc}$ group, where $R_{cc}$ is:
a naphthalene,
a 5 or 6 membered heteroaryl, -a 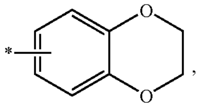

a $C_6$ to $C_8$ aryl, optionally substituted with one or more of the following:
an alkoxy,
a hydroxy,
a halogen,
a $C_1$ to $C_6$ alkyl, optionally substituted with a cyano group,
an amino optionally substituted with one or more $C_1$ to $C_6$ alkyl(s),
a —NHPOR$_x$R$_x$, where R$_x$ is as defined above,
a —NR$_{ee}$CONR$_{ff}$R$_{ff}$ group, where R$_{ee}$ is a hydrogen or a $C_1$ to $C_6$ alkyl, optionally substituted with a halogen, and R$_{ff}$ is:
a hydrogen,
a haloalkyl,
a haloalkoxy,
a $C_1$ to $C_6$ alkyl, or
a —COR$_x$, where R$_x$ is as defined above,
a —NR$_{gg}$COR$_{hh}$ group, where R$_{hh}$ is:
a hydrogen,
a $C_1$ to $C_6$ alkyl optionally substituted with:
an alkoxy,
a halogen, or
an amino optionally substituted with one or more $C_1$ to $C_6$ alkyl(s),
an amino optionally substituted with one or more $C_1$ to $C_6$ alkyl(s), where the alkyls are optionally substituted with a halogen,
a 5 or 6 membered heterocycle,
a 5 or 6 membered heteroaryl,
and R$_{gg}$ is:
a hydrogen,
a $C_1$ to $C_6$ alkyl,
a haloalkyl,
a haloalkoxy, or
a —COR$_x$ group, where R$_x$ is as defined above,
a haloalkyl,
5 or 6 membered heterocycle groups,
an amino optionally substituted with one or more $C_1$ to $C_6$ alkyl(s), and/or
a —NR$_{ii}$SO$_2$R$_x$ group, where R$_x$ is as defined above, and R$_{ii}$ is:
a hydrogen,
a $C_1$ to $C_6$ alkyl,
a haloalkyl,
a haloalkoxy,
a —COR$_x$ group, where R$_x$ is as defined above;

Z is:
a $C_1$ to $C_6$ alkyl optionally substituted with:
an alkoxy,
one or more halogen(s), or
a $C_6$ to $C_8$ aryl;
a $C_2$ to $C_6$ alkylene;
a $C_6$ to $C_8$ aryl optionally substituted with an alkoxy or one or more $C_1$ to $C_6$ alkyl(s);
a —COOR$_x$ group, where R$_x$ is as defined above; or

- 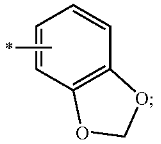

R is a hydrogen, a halogen or an alkoxy;

R$_1$ is:
a hydrogen;
a hydroxy;
a halogen;
a haloalkyl;
a nitro group;
a 5 or 6 membered heteroaryl;
a 5 or 6 membered heterocycle;
an alkoxy optionally substituted with:
one or more halogen(s),
a $C_6$ to $C_8$ aryl, or
a 5 or 6 membered heterocycle;
a $C_6$ to $C_8$ aryl optionally substituted with an alkoxy;
a —COR$_x$ group, where R$_x$ is as defined above;
a $C_1$ to $C_6$ alkyl optionally substituted with a dialkyl-amino or a 5 or 6 membered heterocycle; or R$_1$ joins together with R$_2$ to form:

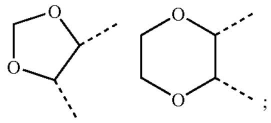

R$_2$ is:
a nitro group;
a hydrogen;
a halogen;
a hydroxy group;
a $C_1$ to $C_6$ alkyl group, optionally substituted with one or more halogen(s);
an amino group;
an alkoxy group optionally substituted with:
one or more halogen(s),
an —OCOR$_x$ group, where R$_x$ is as defined above,
a dialkyl-amino optionally substituted with an alkoxy,
a 5 or 6 membered heterocycle group optionally substituted with a $C_1$ to $C_6$ alkyl,
a 5 or 6 membered heteroaryl group, or
a $C_6$ to $C_8$ aryl group;
a —COOR$_x$ group, where R$_x$ is as defined above;
a haloalkyl;
an amide group optionally substituted with:
a hydroxy group, or
a $C_6$ to $C_8$ aryl;
a 5 or 6 membered heteroaryl;
a —OCOR$_x$ group, where R$_x$ is as defined above;
a —NHCOR$_{jj}$ group, where R$_{jj}$ is:
an alkoxy, or
an amino optionally substituted with one or more $C_1$ to $C_6$ alkyl(s);
a —OR$_{kk}$ group, where R$_{kk}$ is a 5 to 6 membered heteroaryl;
a —NHSO$_2$R$_x$ group, where R$_x$ is as defined above; or $R_2$ joins together with $R_1$ to form:

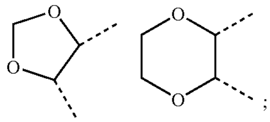

$R_3$ is:

a hydrogen; or

—$CH_2OCOR_x$, and $R_x$ is as defined above.

As used herein, the term "effective amount" refers to the amount required to produce a desired effect. For example, the effective amount may be the amount required to treat a Hepatitis C viral (HCV) infection, the amount required to treat an infection by a virus which comprises an internal ribosome entry site (IRES), the amount required to inhibit HCV IRES-mediated initiation and/or translation, or the amount required to inhibit viral replication or infectivity, in a subject or, more specifically, in a human. In some instances, the desired effect can be determined by analyzing (1) the presence of HCV-RNA; (2) the presence of anti-HCV antibodies; (3) the level of serum alanine amino transferase (ALT) and aspartate aminotransferase (AST) (ALT and AST are elevated in patients chronically infected with HCV); and/or (4) hepatocellular damage. The effective amount for a subject will depend upon farious factors, including the subject's body weight, size and health. Effective amounts for a given patient can be determined by routine experimentation that is within the skill and judgment of the clinician.

For any compound, the effective amount can be estimated initially either in cell culture assays or in relevant animal models, such as chimpanzees, marmosets and tamarins. The animal model may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. In some embodiments, the effective amount is such that a large therapeutic index is achieved. In further embodiments, the dosage is within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 0.1 μg/ml to approximately 100 μg/mL, from approximately 1 μg/mL to approximately 50 μg/mL, from approximately 5 μg/mL to approximately 50 μg/mL, or from approximately 10 μg/mL to approximately 25 μg/mL. To achieve such plasma concentrations, the compounds of the invention may be administered at doses that vary from 0.1 μg to 100,000 mg, depending upon the route of administration. Guidance as to particular dosages and methods of delivery is provided in the literature and is generally available to practitioners in the art. In general, the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject. Dosage and administration may be adjusted to provide sufficient levels of the active agent(s) or to maintain the desired effect. Factors which may be taken into account include the severity of the disease state, general health of the subject, ethinicity, age, weight, and gender of the subject, diet, time and frequency of administration, drug combination(s), reaction sensitivities, experience with other HCV therapies, and tolerance/response to therapy. Long-acting pharmaceutical compositions may be administered every 3 to 4 days, every week, or once every two weeks depending on half-life and clearance rate of the particular formulation.

The compounds and compositions of the present invention may be administered to the subject via any drug delivery route known in the art. Nonlimiting examples include oral, ocular, rectal, buccal, topical, nasal, ophthalmic, subcutaneous, intramuscular, intraveneous (bolus and infusion), intracerebral, transdermal, and pulmonary routes of administration.

D. Metabolites of the Compounds of the Invention

Also falling within the scope of the present invention are the in vivo metabolic products of the compounds described herein. Such products may result, for example, from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

E. Pharmaceutical Compositions of the Invention

Yet another aspect of the invention relates to a pharmaceutical composition comprising: (i) an effective amount of one or more compound(s) of formula I or one or more pharmaceutically acceptable salt(s) thereof, as described above; and (ii) one or more pharmaceutically acceptable excipient(s).

In some embodiments, the pharmaceutical composition comprises one or more compound(s) of formula I wherein:

X is:

a nitro group;

a cyano group;

a —$COR_a$ group, where $R_a$ is:

a $C_1$ to $C_6$ alkyl, a $C_6$ to $C_8$ aryl optionally substituted with an alkoxy or a halogen, or a dialkyl-amino;

a —$COOR_x$ group, where $R_x$ is a $C_1$ to $C_6$ alkyl;

a formyl group;

a $C_6$ to $C_8$ aryl optionally substituted with an alkoxy; or a 5 or 6-membered heteroaryl optionally substituted with:

a $C_1$ to $C_6$ alkyl, a $C_6$ to $C_8$ aryl optionally substituted with an alkoxy or one or more halogen(s), or a 5 to 6 membered heteroaryl;

Y is:

a haloalkyl;

a halogen;

an amino optionally substituted with one or more $C_1$ to $C_6$ alkyl(s);

a benzofuran;

a benzothiophene;

a dibenzofuran;

a dibenzothiophene;

a benzothiazole;

a naphthalene;

an indole, optionally substituted on the nitrogen with a $C_1$ to $C_6$ alkyl;

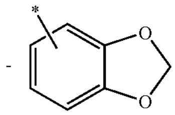
;

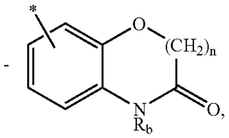

where $R_b$ is a hydrogen or a $C_1$ to $C_6$ alkyl, and n is 0 or 1;

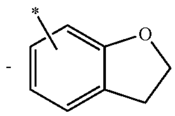
;

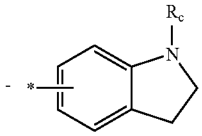
, where $R_c$ is a hydrogen, a —$CONHR_x$, where $R_x$ is as defined above, or an —$SO_2R_x$, where $R_x$ is as defined above; or

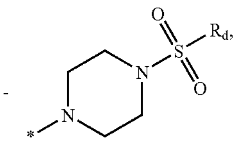

where $R_d$ is a $C_1$ to $C_6$ alkyl or a $C_6$ to $C_8$ aryl;

a —$NHCOR_e$ group, where $R_e$ is:

a $C_1$ to $C_6$ alkyl;

a $C_6$ to $C_8$ aryl optionally substituted with:

a $C_1$ to $C_6$ alkyl, an alkoxy, a cyano group, a nitro group, or a halogen;

a —$NHCOOR_x$ group, where $R_x$ is as defined above;

a —$CH_2O$—$R_f$ group, where $R_f$ is a $C_6$ to $C_8$ aryl;

a —$NR_gR_h$ group, where $R_g$ is a $C_1$ to $C_6$ alkyl or a hydrogen and $R_h$ is a $C_6$ to $C_8$ aryl optionally substituted with an alkoxy;

a $C_1$ to $C_6$ alkyl;

a 5 or 6 membered heteroaryl, optionally substituted with:

a $C_1$ to $C_6$ alkyl, optionally substituted with a $C_6$ to $C_8$ aryl, a $C_6$ to $C_8$ aryl, optionally substituted with —$COOR_x$, where $R_x$ is as defined above, or an amino group;

a 5 or 6 membered heterocycle optionally substituted with:

a —$COOR_x$ group, where $R_x$ is as defined above, or a —$NHCOOR_x$ group, where $R_x$ is as defined above;

a $C_6$ to $C_8$ aryl, optionally substituted with one or more of the following:

an alkoxy, optionally substituted with:

an alkoxy, a hydroxy, one or more halogen(s), a 5 or 6 membered heterocycle, optionally substituted with:

a $C_1$ to $C_6$ alkyl, or a hydroxy, an amino group optionally substituted with one or more $C_1$ to $C_6$ alkyl(s), a —$NR_iSO_2R_x$ group, where $R_x$ is as defined above and $R_i$ is:

a hydrogen, a $C_1$ to $C_6$ alkyl, a —$COR_x$ group, where $R_x$ is as defined above, a haloalkyl, or a haloalkoxy, a —$NR_jCOR_k$ group, where $R_k$ is:

a $C_1$ to $C_6$ alkyl, a hydrogen, or an amino optionally substituted with one or more $C_1$ to $C_6$ alkyl(s), and $R_j$ is:

a hydrogen, a $C_1$ to $C_6$ alkyl, a —$COR_x$ group, where $R_x$ is as defined above, a haloalkyl, or a haloalkoxy, a —$N{=}N^+{=}N^-$ group, or a —$COR_l$, where $R_l$ is a 5 or 6 membered heterocycle optionally substituted with a hydroxy, an amino optionally substituted with one or more $C_1$ to $C_6$ alkyl(s), a nitro group, a $C_1$ to $C_6$ alkyl group, optionally substituted with:

a —$NHSO_2R_x$ group, where $R_x$ is as defined above, or a —$NR_xSO_2R_x$ group, where $R_x$ is as defined above, a haloalkoxy, a halogen, a hydroxy, a —$COOR_x$ group, where $R_x$ is as defined above, a —$COR_m$ group, where $R_m$ is:

an amino optionally substituted with one or more $C_1$ to $C_6$ alkyl(s), where the $C_1$ to $C_6$ alkyls are optionally substituted with:

a hydroxy a 5 or 6 membered heterocycle, an amino optionally substituted with one or more $C_1$ to $C_6$ alkyl(s),
an alkoxy,
a 3 to 7 membered heterocycle, optionally substituted with a $C_1$ to $C_6$ alkyl, optionally substituted with a dialkyl-amino,
a —$NHR_n$ group, where $R_n$ is:
a —$CH_2CONH_2$, or
a $C_6$ to $C_8$ aryl optionally substituted with:
an alkyl,
one or more halogen(s),
a nitro group, or
one or more alkoxy(s),
a —$NR_oCOR_p$ group, where $R_p$ is:
a $C_1$ to $C_6$ alkyl optionally substituted with:
a halogen,
an alkoxy, or
a $C_6$ to $C_8$ aryl,
a 5 or 6 membered heterocycle,
a $C_6$ to $C_8$ aryl, optionally substituted with a halogen,
a 5 or 6 membered heteroaryl optionally substituted with one or more $C_1$ to $C_6$ alkyl(s),
a hydrogen,

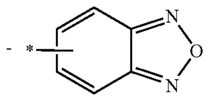
or
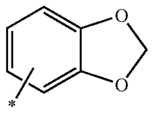
, and where $R_o$ is:
a hydrogen,
a $C_1$ to $C_6$ alkyl,
a —$COR_x$ group, where $R_x$ is as defined above,
a haloalkyl, or
a haloalkoxy,
a —$NR_qCONR_qR_r$ group, where $R_q$ is:
a hydrogen,
a $C_1$ to $C_6$ alkyl,
a haloalkyl,
a haloalkoxy, or
a —$COR_x$ group, where $R_x$ is as defined above,
and where $R_r$ is:
a $C_6$ to $C_8$ aryl optionally substituted with:

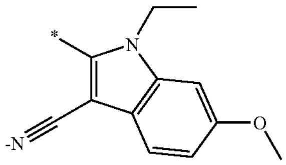
, a $C_1$ to $C_6$ alkyl,
a haloalkyl,
a —$OR_s$ group, where $R_s$ is a $C_6$ to $C_8$ aryl, or
a —$COOR_x$ group, where $R_x$ is as defined above,
a $C_1$ to $C_6$ alkyl optionally substituted with one or more of the following:
a halogen,
an alkylene,
a $C_6$ to $C_8$ aryl, and/or
a —$COOR_x$ group, where $R_x$ is as defined above,
a —$COOR_x$ group, where $R_x$ is as defined above, a —$NR_tCOOR_u$ group, where $R_u$ is:
a $C_1$ to $C_{12}$ alkyl, optionally substituted with:
a $C_6$ to $C_8$ aryl optionally substituted with a $C_1$ to $C_6$ alkyl or an alkoxy,
an alkylene,
an alkoxy,
an alkyne,
a halogen, or
a 5 or 6 membered heterocycle,
a $C_6$ to $C_8$ aryl, optionally substituted with:
an alkoxy,
a halogen, or
a $C_1$ to $C_6$ alkyl, or
a 5 or 6 membered heterocycle,
and $R_t$ is:
a hydrogen,
a $C_1$ to $C_6$ alkyl,
a —$COR_x$ group, where $R_x$ is as defined above,
a haloalkyl, or
a haloalkoxy,
a —$NR_vSO_2R_w$ group, where $R_v$ is:
a hydrogen,
a —$COR_x$, where $R_x$ is as defined above, or
a $C_1$ to $C_6$ alkyl, optionally substituted with:
a halogen,
a —$COR_x$ group, where $R_x$ is as defined above,
a —$OCOR_x$ group, where $R_x$ is as defined above,
a hydroxy, or
an alkoxy,
and where $R_w$ is:
a $C_1$ to $C_6$ alkyl optionally substituted with:
a halogen,
a haloalkyl,
a $C_6$ to $C_8$ aryl, or
a 5 or 6 membered heterocycle,
a $C_2$ to $C_6$ alkylene,
an alkyl- or dialkyl-amino optionally substituted with a halogen,
a 5 or 6 membered heterocycle, or
a 5 or 6 membered heteroaryl optionally substituted with:
a $C_1$ to $C_6$ alkyl,
a 5 or 6 membered heterocycle, or

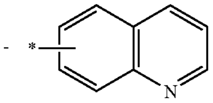
;

-a
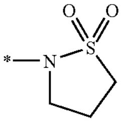
,

-a
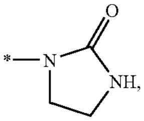
,

-a
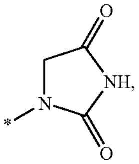

-continued

-a
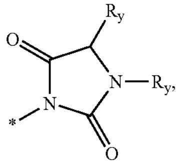

optionally substituted with a $C_1$ to $C_6$ alkyl, where $R_y$ is a $C_1$ to $C_6$ alkyl or hydrogen, -a
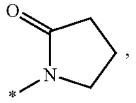

-a
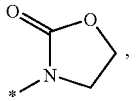

-a
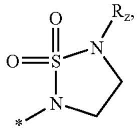

where $R_z$ is hydrogen or a $C_1$ to $C_6$ alkyl, optionally substituted with a $C_6$ to $C_8$ aryl, a —$SR_x$ group, where $R_x$ is as defined above, a —$SO_2R_{aa}$ group, where $R_{aa}$ is:

a $C_1$ to $C_6$ alkyl, an amino group, an alkyl- or dialkyl-amino group optionally substituted with a hydroxy or a —$COOR_x$ group, where $R_x$ is as defined above, a 5 or 6 membered heteroaryl, a $C_6$ to $C_8$ aryl, and/or a —$NHR_{bb}$ group, where $R_{bb}$ is:

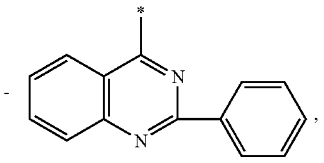

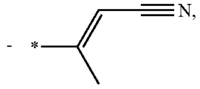

a —C(═S)$NH_2$ group, or a —$PO(OR_x)_2$ group, where $R_x$ is as defined above;

a 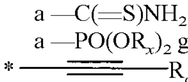 $R_{cc}$ group, where $R_{cc}$ is:

a naphthalene, a 5 or 6 membered heteroaryl,

-a
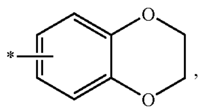

a $C_6$ to $C_8$ aryl, optionally substituted with one or more of the following:

an alkoxy, a hydroxy, a halogen, a $C_1$ to $C_6$ alkyl, optionally substituted with a cyano group, an amino optionally substituted with one or more $C_1$ to $C_6$ alkyl(s), a —$NHPOR_xR_x$, where $R_x$ is as defined above, a —$NR_{ee}CONR_{ff}R_{ff}$ group, where $R_{ee}$ is a hydrogen or a $C_1$ to $C_6$ alkyl, optionally substituted with a halogen, and $R_{ff}$ is:

a hydrogen, a haloalkyl, a haloalkoxy, a $C_1$ to $C_6$ alkyl, or a —$COR_x$, where $R_x$ is as defined above, a —$NR_{gg}COR_{hh}$ group, where $R_{hh}$ is:

a hydrogen, a $C_1$ to $C_6$ alkyl optionally substituted with:

an alkoxy, a halogen, or an amino optionally substituted with one or more $C_1$ to $C_6$ alkyl(s), an amino optionally substituted with one or more $C_1$ to $C_6$ alkyl(s), where the alkyls are optionally substituted with a halogen, a 5 or 6 membered heterocycle, a 5 or 6 membered heteroaryl, and $R_{gg}$ is:

a hydrogen, a $C_1$ to $C_6$ alkyl, a haloalkyl, a haloalkoxy, or a —$COR_x$ group, where $R_x$ is as defined above, a haloalkyl, 5 or 6 membered heterocycle groups, an amino optionally substituted with one or more $C_1$ to $C_6$ alkyl(s), and/or a —$NR_{ii}SO_2R_x$ group, where $R_x$ is as defined above, and $R_{ii}$ is:

a hydrogen, a $C_1$ to $C_6$ alkyl, a haloalkyl, a haloalkoxy, a —$COR_x$ group, where $R_x$ is as defined above;

Z is:

a $C_1$ to $C_6$ alkyl optionally substituted with:

an alkoxy, one or more halogen(s), or a $C_6$ to $C_8$ aryl;

a $C_2$ to $C_6$ alkylene;

a $C_6$ to $C_8$ aryl optionally substituted with an alkoxy or one or more $C_1$ to $C_6$ alkyl(s);

a —$COOR_x$ group, where $R_x$ is as defined above; or

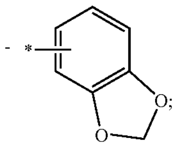

R is a hydrogen, a halogen or an alkoxy;

$R_1$ is:

a hydrogen;
a hydroxy;
a halogen;
a haloalkyl;
a nitro group;
a 5 or 6 membered heteroaryl;
a 5 or 6 membered heterocycle;
an alkoxy optionally substituted with:
one or more halogen(s),
a $C_6$ to $C_8$ aryl, or
a 5 or 6 membered heterocycle;
a $C_6$ to $C_8$ aryl optionally substituted with an alkoxy;
a —$COR_x$ group, where $R_x$ is as defined above;
a $C_1$ to $C_6$ alkyl optionally substituted with a dialkyl-amino or a 5 or 6 membered heterocycle; or $R_1$ joins together with $R_2$ to form:

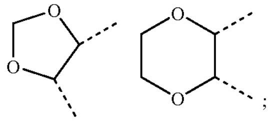

$R_2$ is:

a nitro group;
a hydrogen;
a halogen;
a hydroxy group;
a $C_1$ to $C_6$ alkyl group, optionally substituted with one or more halogen(s);
an amino group;
an alkoxy group optionally substituted with:
one or more halogen(s),
an —$OCOR_x$ group, where $R_x$ is as defined above,
a dialkyl-amino optionally substituted with an alkoxy,
a 5 or 6 membered heterocycle group optionally substituted with a $C_1$ to $C_6$ alkyl,
a 5 or 6 membered heteroaryl group, or
a $C_6$ to $C_8$ aryl group;
a —$COOR_x$ group, where $R_x$ is as defined above;
a haloalkyl;
an amide group optionally substituted with:
a hydroxy group, or
a $C_6$ to $C_8$ aryl;
a 5 or 6 membered heteroaryl;
a —$OCOR_x$ group, where $R_x$ is as defined above;
a —$NHCOR_{jj}$ group, where $R_{jj}$ is:
an alkoxy, or
an amino optionally substituted with one or more $C_1$ to $C_6$ alkyl(s);
a —$OR_{kk}$ group, where $R_{kk}$ is a 5 to 6 membered heteroaryl;
a —$NHSO_2R_x$ group, where $R_x$ is as defined above; or $R_2$ joins together with $R_1$ to form:

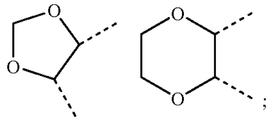

$R_3$ is:

a hydrogen; or
—$CH_2OCOR_x$, and $R_x$ is as defined above;

provided that when X is phenyl, hydroxyphenyl or pyridyl, Y is alkyl, R is hydrogen, $R_1$ is hydrogen or hydroxy, $R_2$ is hydrogen or hydroxy, and $R_3$ is hydrogen, then Z is:

a $C_1$ to $C_6$ alkyl substituted with:
an alkoxy,
one or more halogen(s), or
a $C_6$ to $C_8$ aryl;
a $C_2$ to $C_6$ alkylene;
a $C_6$ to $C_8$ aryl optionally substituted with an alkoxy or one or more $C_1$ to $C_6$ alkyl(s);
a —$COOR_x$ group, where $R_x$ is as defined above; or

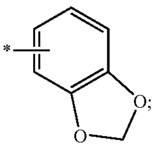

or one or more pharmaceutically acceptable salt(s) thereof.

The pharmaceutical composition may be formulated to achieve a physiologically compatible pH, ranging from a pH of about 3 to a pH of about 11. In some embodiments, the pharmaceutical composition is formulated to achieve a pH of about 3 to a pH of about 7. In other embodiments, the pharmaceutical composition is formulated to achieve a pH of about 5 to a pH of about 8.

The pharmaceutical composition may comprise a combination of compounds of the present invention, or may include a second active ingredient useful in the treatment of viral infections, such as anti-viral agents that include, but are not limited to: pegylated interferon, including by way of non-limiting example pegylated α-interferon; un-pegylated interferon, including by way of non-limiting example, un-pegylated α-interferon; ribavirin or prodrugs or derivatives thereof; protease inhibitors; polyermase inhibitors; p7 inhibitors; entry inhibitors, including fusion inhibitors such as Fuzeon™ (Trimeris); helicase inhibitors; a Toll-like receptor agonist, a caspase inhibitor, anti-fibrotics; drugs that target IMPDH (inosine monophosphate dehydrogenase inhibitors), such as Merimepadib™ (Vertex Pharmaceuticals Inc.); synthetic thymosin alpha 1 (ZADAXIN™, SciClone Pharmaceuticals Inc.); a glycosidase inhibitor; a glucosidase inhibitor; therapeutic viral vaccines, such as those produced by Chiron and Immunogenics; and immunomodulators, such as histamine, antibodies against HCV, such as XTL-6865 and XTL-002 (XTL Biopharmaceuticals), antisense RNA, ribozymes, RNAi, and anti-HCV agents with unknown mechanism of action.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exists a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. Suitable formulations for oral administration include solids, liquid solutions, emulsions and suspensions, while suitable inhaleable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In other embodiments, pharmaceutical compositions of the invention may be formulated as suspensions comprising one or more compound(s) of the present invention in admixture with at least one pharmaceutically acceptable excipient suitable for the manufacture of a suspension. In yet other embodiments, pharmaceutical compositions of the invention may be formulated as dispersible powders and granules suitable for preparation of a suspension by the addition of one or more excipient(s).

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds of the invention may be substantially insoluble in water and sparingly soluble in most pharmaceutically acceptable protic solvents and vegetable oils, but generally soluble in medium-chain fatty acids (e.g., caprylic and capric acids) or triglycerides and in propylene glycol esters of medium-chain fatty acids. Thus, contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compound of the invention is formulated for oral administration in a lipid-based composition suitable for low solubility compounds. Lipid-based formulations can generally enhance the oral bioavailability of such compounds. As such, pharmaceutical compositions of the invention may comprise a effective amount of one or more compound(s) of the invention, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polyoxyl 40 hydrogenated castor oil.

In alternative embodiments, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In some embodiments, the pharmaceutical composition further comprises about 0.11% to about 20% hydroxypropyl-β-cyclodextrin, about 1% to about 15% hydroxypropyl-β-cyclodextrin, or about 2.5% to about 10% hydroxypropyl-β-cyclodextrin. The amount of solubility enhancer employed may depend on the amount of the compound of the present invention in the composition.

F. Combination Therapy

It is also possible to combine any compound of the present invention with one or more other active ingredients useful in the treatment of HCV infection, including compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the viral inhibiting activity of the compounds of the invention. Such active ingredients include anti-HCV agents. Anti-HCV agents include agents that target the virus as well as agents that have an immunomodulatory effect. For example, anti-HCV agents include, but are not limited to, interferon, including, for example without limitation, IFN-α, ribavirin or prodrugs or derivatives thereof; protease inhibitors, polymerase inhibitors, helicase inhibitors, a Toll-like receptor agonist, a caspase inhibitor and a glycosidase inhibitor, antibodies against HCV, such as XTL-6865 and XTL-002 (XTL Biopharmaceuticals), anti sense RNA, ribozymes, RNAi, and anti-HCV agents with unknown mechanism of action. Furthermore, the compounds of the invention may also be administered in combination with other compounds that affect IRES activity.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

It will be apparent to those skilled in the art that specific embodiments of the present invention may be directed to one, some or all of the above-indicated aspects as well as other aspects, and may encompass one, some or all of the above- and below-indicated embodiments, as well as other embodiments.

Other than in the working examples, or where otherwise indicated, all numbers expressing quantities of ingredients, reaction conditions, and so forth used in the specification and claims are to be understood as being modified by the term "about". Accordingly, unless indicated to the contrary, such numbers are approximations that may vary depending upon the-desired properties sought to be obtained by the present invention. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the invention are approximations, the numerical values set forth in the working examples are reported as precisely as possible. Any numerical value, however, inherently contains certain errors necessarily resulting from the standard deviation found in their respective testing measurements.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

Preparation of Compounds of the Invention

Example 1A

Preparation of 1-ethyl-6-methoxy-1H-indole-3-carbonitrile (Compound 5)

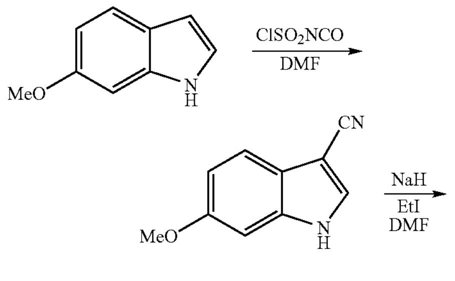

-continued

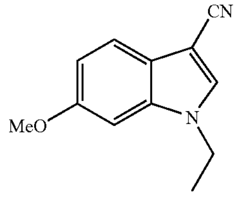

Step A: A solution of 6-methoxyindole (10.0 g, 68.0 mmol) in DMF (120 mL) is cooled to 0° C. and treated with chlorosulfonyl isocyanate (7.72 mL, 88.4 mmol). After the addition, the reaction mixture is stirred at this temperature for 1 h. The dark solution is poured into ice water (600 mL) and the light brown solid is collected by filtration, washed with additional $H_2O$ and dried to afford 9.9 g (85%) of 6-methoxy-1H-indole-3-carbonitrile as a light brown solid.

Step B: To a solution of 6-methoxy-1H-indole-3-carbonitrile (9.9 g, 57.6 mmol) in DMF (150 mL) is added NaH (60% dispersion in mineral oil, 3.45 g, 86.3 mmol). The reaction mixture is stirred for 15 min and then ethyl iodide (5.53 mL, 69.1 mmol) is added and the mixture is stirred at room temperature overnight. The reaction mixture is then diluted with $H_2O$ and extracted with EtOAc (2×). The organic phases are washed with $H_2O$ (3×) and saturated NaCl and then dried and concentrated to a semi-solid. The crude product is purified via column chromatography on silica gel (200 g) using $CH_2Cl_2$/hexanes (50-100%) as eluent to yield 6-methoxy-1-ethyl-1H-indole-3-carbonitrile as a tan solid.

Utilizing steps A and B above and substituting different indoles and alkyl halides gives the following compounds: Compounds 43, 45, 51, 52, 108, 109, 115, 118, 120, 123, 126, 179 and 714.

Example 1B

Preparation of 6-ethoxy-1-ethyl-1H-indole-3-carbonitrile (Compound 9)

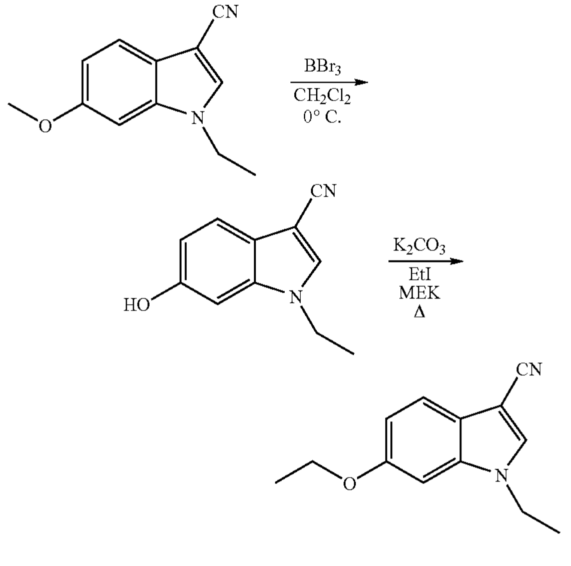

Step A: To a solution of 1-ethyl-6-methoxy-1H-indole-3-carbonitrile (2.85 g, 14.2 mmol), prepared by example 1A, step B, in $CH_2Cl_2$ (40 mL) is added a 1M solution of $BBr_3$ in $CH_2Cl_2$ (28.5 mL, 28.5 mmol) at 0° C. The mixture is allowed to warm to room temperature and kept for 2.5 h. The dark reaction mixture is then poured onto ice and sufficient 1M NaOH is added until the pH is 8-9. The product is extracted with $CH_2Cl_2$ (3×) and the combined organic phases are washed with saturated $NaHCO_3$, $H_2O$ and saturated NaCl. After drying over $MgSO_4$, the solution is concentrated and the product is purified by chromatography (EtOAc/$CH_2Cl_2$, 0-10%) to afford 2.15 g (82%) of 6-hydoxy-1-ethyl-1H-indole-3-carbonitrile as a yellow solid.

Step B: To a solution 6-hydoxy-1-ethyl-1H-indole-3-carbonitrile (80 mg, 0.43 mmol) in 5 mL of methyl ethyl ketone is added anhydrous $K_2CO_3$ (71 mg, 0.52 mmol) and iodoethane (0.05 mL, 0.60 mmol). After stirring overnight at reflux, the reaction mixture is cooled, diluted with $H_2O$ and extracted with EtOAc (3×). The combined organic phases are dried and concentrated. Flash chromatography ($CH_2Cl_2$) gives 94 mg (100%) of 6-ethoxy-1-ethyl-1H-indole-3-carbonitrile as a white wax.

In similar fashion, following steps A and B, above, the following compounds are also prepared: Compounds 6, 10, 11, 12 and 24

Example 1C

Preparation of 5-(4-methoxyphenyl)-5H-[1,3]dioxolo[4,5-f]indole-7-carbonitrile (Compound 44)

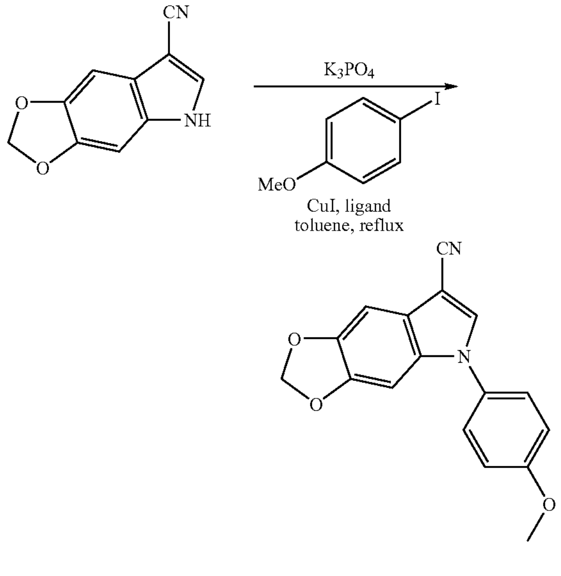

A mixture of p-iodoanisole (85 mg, 0.36 mmol), anhydrous $K_3PO_4$ (102 mg, 0.48 mmol), CuI (4.6 mg, 0.024 mmol) and N,N'-Dimethyl cyclohexane-1,2-diamine (14 mg, 0.096 mmol) is added to 5H-[1,3]dioxolo[4,5-f]indole-7-carbonitrile (45 mg, 0.24 mmol), prepared as described by the method of example 1A, step A, in anhydrous toluene (0.4 mL). After heating at reflux for 24 h, the solvent is evaporated under vacuum. The residue is dissolved with $CH_2Cl_2$ (5 mL) and the mixture is filtered. The filtrate is concentrated to afford crude product, which is purified by silica gel chromatography using EtOAc/petroleum ether (1:4) as eluent to yield 5-(4-methoxyphenyl)-5H-[1,3]dioxolo[4,5-f]indole-7-carbonitrile.

Utilizing the procedure above and substituting different aryl iodides gives the following compounds: Compounds 4, 8, 102, 103, 111, 112, 117, 119, 124, 125, 127, 154.

Example 1D

Preparation of 1-ethyl-6-(pyrazin-2-yloxy)-1H-indole-3-carbonitrile (Compound 13)

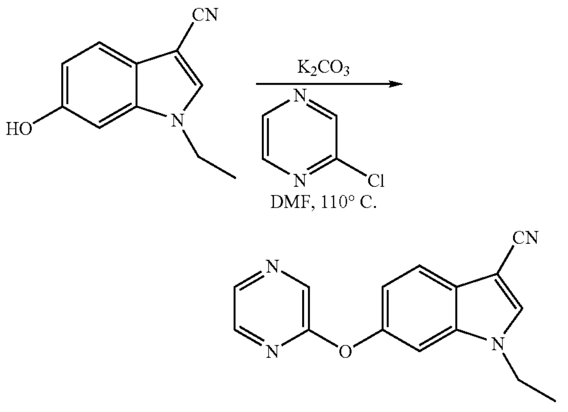

To a solution of 1-ethyl-6-hydroxy-1H-indole-3-carbonitrile (60 mg, 0.32 mmol) prepared as described in example 1A, step A, in DMF (5 mL) is added $K_2CO_3$ (55 mg, 0.40 mmol) and 2-chloropyridazine (45 mg, 0.40 mmol). The mixture is heated at 110° C. for 18 h. After cooling to room temperature, the reaction mixture is diluted with $H_2O$ and extracted with EtOAc (3×). The combined organic phases are washed with $H_2O$ and saturated NaCl, dried and concentrated. The product is isolated by chromatography (EtOAc/$CH_2Cl_2$, 1-3%) over silica gel to afford 76 mg (96%) of the title compound, 1-ethyl-6-(pyrazin-2-yloxy)-1H-indole-3-carbonitrile, as an off-white solid.

Example 1E

Preparation of 3-cyano-1-ethyl-1H-indole-6-carboxylic acid phenylamide (Compound 15)

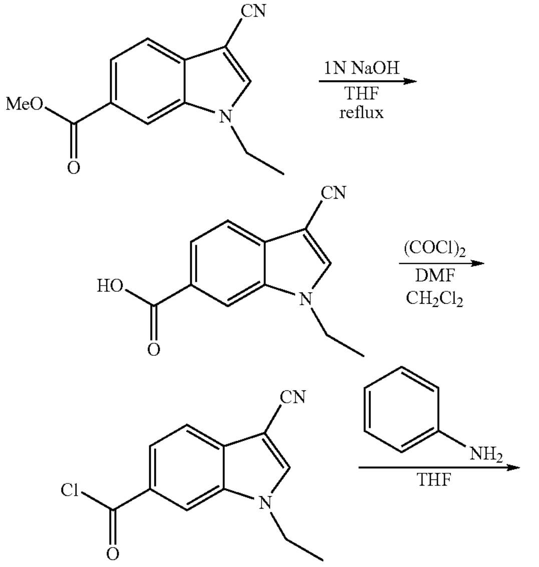

-continued

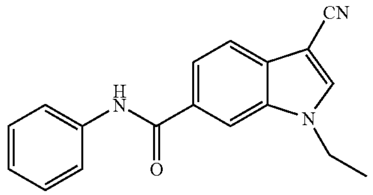

Step A: A solution of methyl 3-cyano-1-ethyl-1H-indole-6-carboxylate (1.60 g, 7.02 mmol), prepared by the method described in example 1A from methyl 1H-indole-6-carboxylate, in THF (35 mL) is treated with 1N NaOH (7.7 mL, 7.7 mmol) and heated at reflux for 2.5 h. After cooling to room temperature, most of the THF is removed and the solution is diluted with $H_2O$ and extracted with ether (2×). The ether extracts are discarded. The aqueous phase is then acidified with 6N HCl to pH 2 and then extracted with EtOAc (3×). The EtOAc layers are combined, washed with saturated NaCl and then dried and concentrated to afford 1.43 g (95%) of 3-cyano-1-ethyl-1H-indole-6-carboxylic acid as a white solid.

Step B: A suspension of 3-cyano-1-ethyl-1H-indole-6-carboxylic acid (0.42 g, 1.96 mmol) in $CH_2Cl_2$ (15 mL) is cooled to 0° C. The suspension is treated with DMF (2 drops) and then oxalyl chloride (0.34 mL, 3.92 mmol) is added via syringe during 2 minutes after which the ice bath is removed and the reaction mixture is allowed to warm to ambient temperature during 1.5 h during which time the reaction becomes a yellow solution. The solution is then concentrated in vacuo to afford 0.46 g (quantitative yield) of 3-cyano-1-ethyl-1H-indole-6-carbonyl chloride as a yellow solid.

Step C: A suspension of 3-cyano-1-ethyl-1H-indole-6-carbonyl chloride (70 mg, 0.30 mmol) in THF (5 mL) is cooled to 0° C. and treated with aniline (0.08 mL, 0.90 mmol). After the addition, the reaction is warmed to ambient temperature and after stirring for an additional 16 hours, the reaction mixture is diluted with $H_2O$ and extracted with EtOAc (2×). The combined organic phases are washed with saturated NaCl and then dried and concentrated to afford the product. Chromatography (EtOAc/$CH_2Cl_2$, 2/98) over silica gel gives 44 mg (51%) of 3-cyano-1-ethyl-1H-indole-6-carboxylic acid phenylamide.

Utilizing essentially the procedure above gives the following compound: Compound 89.

Example 1F

Preparation of t-butyl(3-cyano-1-ethyl-1H-indol-6-yl)-carbamate (Compound 16)

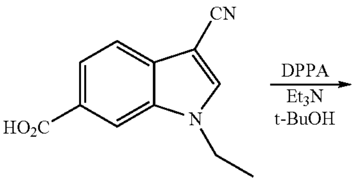

-continued

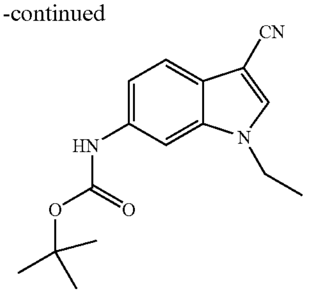

A solution of 3-cyano-1-ethyl-1H-indole-6-carboxylic acid (0.60 g, 2.80 mmol) from Example 1E, step A, in t-butanol (20 mL) is treated with $Et_3N$ (0.46 mL, 3.36 mmol) and diphenylphosphoryl azide (0.73 mL, 3.36 mmol) and then heated at reflux for 4 h. After cooling to room temperature, most of the t-butanol is removed in vacuo to give an oil, which is then dissolved in EtOAc. After washing with $H_2O$, the organic phase is back-extracted with EtOAc and the organic layers are combined and washed sequentially with additional $H_2O$, saturated $NaHCO_3$ and saturated NaCl. The organic phase is dried, concentrated and the resulting crude product is purified by chromatography over silica gel using EtOAc/$CH_2Cl_2$ (0-1%) to afford 0.52 g (65%) of t-butyl(3-cyano-1-ethyl-1H-indol-6-yl)-carbamate as a white solid.

The following compound is made in similar fashion: Compound 90.

Example 1Ga

Preparation of 2-(4-aminophenyl)-1-ethyl-6-methoxy-1H-indole-3-carbonitrile via Suzuki Route (Compound 55)

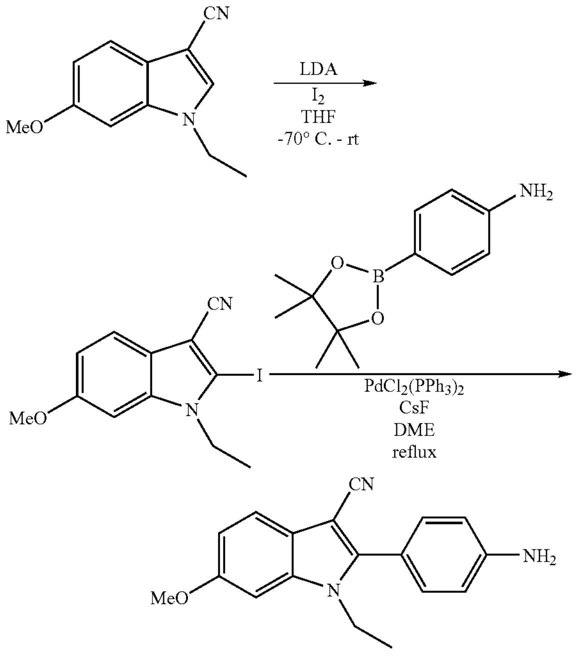

Step A: A 2M solution of lithium diisopropyl amide in THF/hexanes (Acros) (3.9 mL, 7.8 mmol) is diluted with THF (5 mL) in a flame-dried flask. After cooling the reaction to −30° C., a solution of 1-ethyl-6-methoxy-1H-indole-3-carbonitrile (1.30 g, 6.5 mmol) in THF (10 mL) is added dropwise during 10 min, maintaining the temperature at −30° C. After stirring for an additional 30 min at this temperature, a solution of iodine (2.31 g, 9.1 mmol) in THF (5 mL) is added during 10 min. After the addition, the reaction is warmed to ambient temperature during 1 h. The reaction is then diluted with ice-$H_2O$ and extracted with EtOAc (2×). The combined organic phases are washed with 1M sodium thiosulfate and saturated NaCl and then concentrated to a brown solid. Chromatography ($CH_2Cl_2$/hexanes, 1/1) over silica gel gives 1.31 g (62%) of 1-ethyl-2-iodo-6-methoxy-1H-indole-3-carbonitrile as an off-white solid.

Step B: A mixture of 1-ethyl-2-iodo-6-methoxy-1H-indole-3-carbonitrile (1.25 g, 3.83 mmol), 4-(4,4,5,5-tetramethyl)-1,3-2-dioxaboralanyl-2-yl-aniline (0.96 g, 4.90 mmol), CsF (1.46 g, 9.58 mmol) and $Pd(PPh_3)_2Cl_2$ (110 mg, 0.15 mmol) in DME (20 mL) is added to a flask and alternatively evacuated and flushed with $N_2$. The reaction is then heated at reflux for 24 h and then cooled to room temperature. The reaction mixture is diluted with $H_2O$ and extracted with EtOAc (2×). The combined organic phases are washed with $H_2O$ and saturated NaCl and then dried over $MgSO_4$ and concentrated. The crude reaction mix is purified by flash chromatography on silica gel using EtOAc/$CH_2Cl_2$ (5/95) as eluent to afford 765 mg (69%) of 2-(4-aminophenyl)-1-ethyl-6-methoxy-1H-indole-3-carbonitrile as a yellow solid.

Utilizing essentially the same procedure described above and substituting different boronic acids gives the following compounds: Compounds 19, 20, 21, 22, 53, 63, 70, 71, 74, 76, 77, 79, 80, 100, 110, 229, 239, 240, 247, 250, 254, 255, 256, 257, 258, 259, 260, 281, 282, 283, 284, 286, 335, 336, 337, 338, 339, 347, 348, 426, 427, 428, 429, 476, 543, 578, 758.

Example 1Gb

Preparation of 2-(4-aminophenyl)-1-butyl-6-methoxy-1H-indole-3-carbonitrile via Alternative Suzuki Route

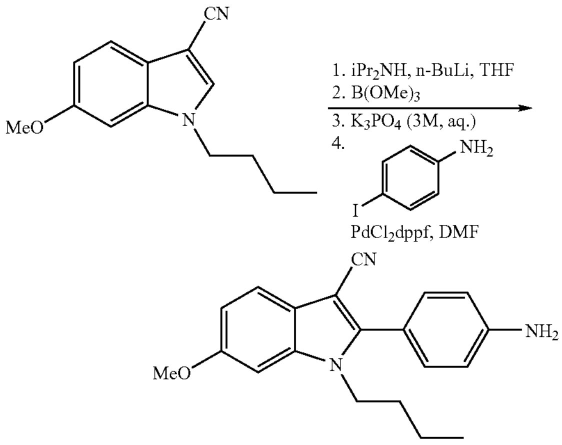

To a solution of $(i-Pr)_2NH$ (1.35 mL, 9.65 mmol) in THF (30 mL) cooled to −78° C. is added n-BuLi (3.7 mL, 2.5M in hexanes, 9.21 mmol) in one portion. The acetone/dry ice bath is exchanged for ice/water bath and the solution is stirred further for 40 min. The solution is cooled to −78° C. and solution of 1-butyl-6-methoxy-1H-indole-3-carbonitrile, prepared as in example 1A (2.0 g, 8.77 mmol) in THF (10 mL) is added dropwise. This solution is stirred for 15 min at −78° C., following by 20 min at −20° C. Trimethyl borate (1.0 mL, 8.77 mmol) is added, the reaction mixture is stirred for 15 min at −20° C. after which the cooling bath is removed and this solution is stirred further at room temperature for 1 h. A solution of $K_3PO_4$ is added (11.7 mL, 3M aqueous solution, 35.1 mmol) followed by a solution of 4-iodoaniline (2.5 g, 11.40 mmol) and $PdCl_2$dppf catalyst (640 mg, 0.88 mmol) in DMF (40 mL, plus a 5 mL rinse). The reaction mixture is stirred overnight (ca. 18 h) and then water (80 mL) is added and the product is extracted with EtOAc (3×50 mL). The combined organic fractions are dried over $MgSO_4$, filtered and concentrated under reduced pressure. The crude product is purified via flush chromatography on silica gel (5-60% EtOAc/Hexanes as eluant) to afford the desired 2-(4-aminophenyl)-1-butyl-6-methoxy-1H-indole-3-carbonitrile as a tan solid (2.4 g, 86% yield).

The following compounds are prepared in similar fashion utilizing other indole and aryl and hereroaryl bromides and iodides: Compounds 656, 659, 660, 661, 682, 683, 712, 731, 732, 733, 806, 807, 808, 809, 810, 811, 812, 813, 814, 827.

Example 1Gc

Preparation of 2-(4-aminophenyl)-6-methoxy-1-propyl-1H-indole-3-carbonitrile via Negishi Route

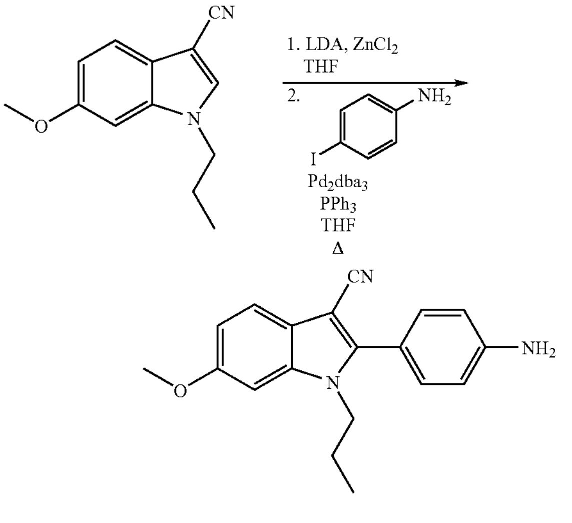

A nitrogen-purged flask fitted with a septum and a nitrogen needle is charged with dry THF (all additions performed by syringe) (20 mL). Diisopropylamine (Aldrich Sure-Seal, 2.00 mL, 14.3 mmol) is added, and the solution is cooled to 0° C. n-Butyllithium (8.50 mL of 1.6 M solution in hexane, 13.6 mmol) is added slowly. The flask is allowed to warm to room temperature briefly, and then is cooled to −78° C. A concentrated THF solution of 6-methoxy-1-propyl-1H-indole-3-carbonitrile (2.77 g, 12.9 mmol; prepared analogously to compound 5 of Example 1A) is added slowly, and the resulting solution is maintained at −78° C. for 30 min. The flask is then transferred to a water-ice bath and allowed to come to 0° C. for about 15 minutes. The solution is once again cooled to −78° C., and $ZnCl_2$ (0.5 M solution in THF, 27.0 mL, 13.5 mmol) is slowly added. A precipitate is observed at this point, which may be the bis(indole)zinc compound, but the solution becomes homogeneous when the entire volume of zinc chloride solution is added. After about 10 minutes, the solution is allowed to come to room temperature, and a THF solution (5 mL) of 4-iodoaniline (3.47 g, 15.8 mmol) and triphenylphosphine (338 mg, 1.29 mmol) is added. The septum is removed, and solid $Pd_2(dba)_3$ (295 mg, 0.322 mmol) is added. A reflux condenser is fitted to the flask, and the solution is degassed by three successive cycles of vacuum pumping/$N_2$ purging. The solution is then heated to reflux overnight. After cooling to room temperature, the solution is poured into 4 volumes of water, and 4 volumes of ethyl acetate are added. The resulting mixture is vigorously stirred for 30 minutes, then filtered through celite (with ethyl acetate washing) to remove solid Zn- and Pd-containing material. The phases are separated, and the aqueous phase is extracted with more ethyl acetate. The organic phases are washed in sequence with saturated brine, combined, dried over anhydrous sodium sulfate, filtered and evaporated. A solid precipitate forms at this point, which is sufficiently pure product and is collected by trituration with ether and filtration. The remaining material is purified by column chromatography (eluting 1:2 ethyl acetate-hexane on silica gel 60). Total yield of the product, 2-(4-amino-phenyl)-6-methoxy-1-propyl-1H-indole-3-carbonitrile, is 2.75 g (8.99 mmol, 70%).

The following compounds are made using essentially the same procedure and substituting other aryl or heteroaryl iodides or bromides: Compounds 393, 408, 430, 431, 436, 437, 438, 459, 460, 461, 462, 483, 484, 632, 633, 634, 635, 636, 650, 651.

Example 1Gd

Preparation of 1-ethyl-2-(3-hydroxyphenyl)-6-methoxy-1H-indole-3-carbonitrile (Compound 288)

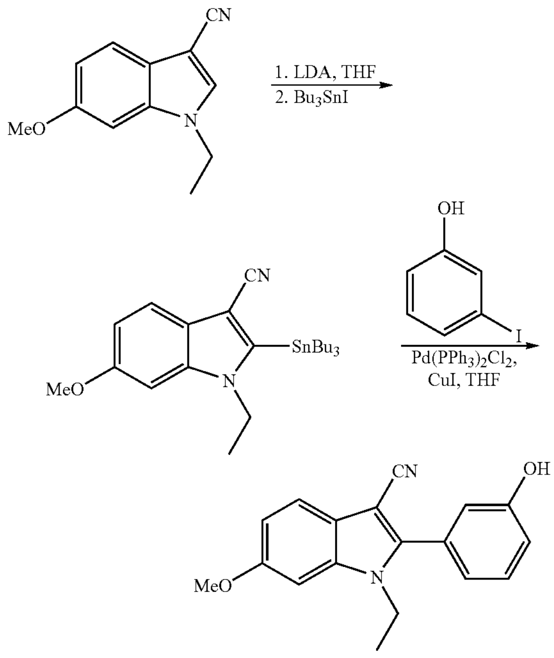

Step A: A solution of THF (60 mL) and diisopropylamine (5.5 mL, 39 mmol) is cooled to −78° C. n-Butyllithium (14.5 mL, 2.5M in hexanes, 36.2 mmol) is added dropwise over 5 minutes. The LDA mixture is stirred at −78° C. for 10 minutes, and then at 0° C. for 20 minutes. The solution is re-cooled to −78° C. 1-ethyl-6-methoxy-1H-indole-3-carbonitrile (5.0 g, 25 mmol), prepared as in example 1A, is taken up in THF (30 mL) and added dropwise to the LDA mixture over 15 minutes. The reaction is stirred at −78° C. for 10 minutes, and at 0° C. for 30 minutes. Once again, the reaction mixture is cooled to −78° C. Tributyltin iodide (10 mL, 35 mmol) is added dropwise. This is stirred at −78° C. for 15 minutes, and then at 0° C. for 30 minutes. The reaction mixture is absorbed onto silica gel and concentrated. Purification by chromatography ($CH_2Cl_2$) yields 1-ethyl-6-methoxy-2-tributylstannanyl-1H-indole-3-carbonitrile (12.05 g, 98%).

Step B: 1-Ethyl-6-methoxy-2-tributylstannanyl-1H-indole-3-carbonitrile (1.0 g, 2.05 mmol), prepared in step A, is combined with 3-iodophenol (474 mg, 2.15 mmol), $Pd(PPh_3)_2Cl_2$ (67 mg, 0.102 mmol), CuI (75 mg, 0.39 mmol) and THF (4.0 mL). This mixture is heated at 65° C. overnight. The reaction mixture is diluted in EtOAc, and is filtered through celite. The filtrate is concentrated and the residue is purified by silica gel chromatography (4:1, $CH_2Cl_2$/EtOAc) to yield crude product. Ether trituration yields 1-ethyl-2-(3-hydroxy-phenyl)-6-methoxy-1H-indole-3-carbonitrile (430 mg, 72%) as a yellow-white solid.

The following compounds are prepared similarly as above, using other commercially available iodides and bromides, or using iodides derived from a one step amidation of p-iodophenylsulfonyl chloride: Compounds 275, 276, 277, 278, 331, 363, 364, 373, 374, 375, 474, 475, 678.

Example 1Ge

Preparation of ethanesulfonic acid [4-(3-cyano-6-difluoromethoxy-1-ethyl-1H-indol-2-yl)-phenyl]-amide via Heck Route (Compound 519)

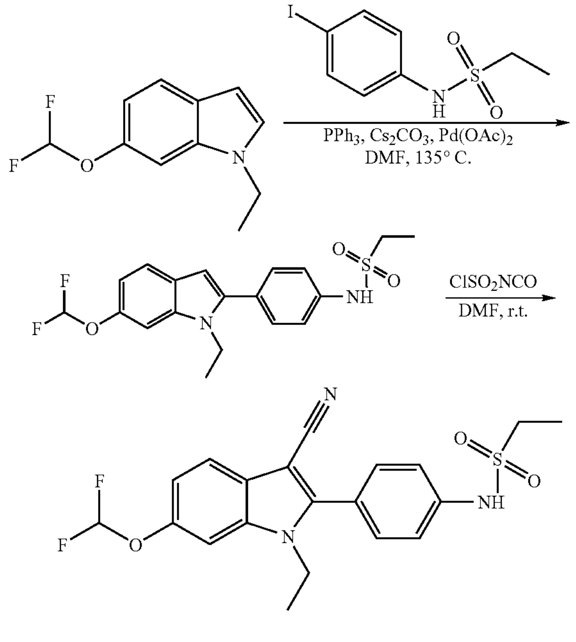

Step A: A solution of 6-difluoromethoxy-1-ethyl-1H-indole (402.8 mg, 2.04 mmol), ethanesulfonic acid (4-iodo-phenyl)-amide (712.1 mg, 2.29 mmol), cesium carbonate (733.2 mg, 3.82 mmol), triphenylphosphine (33.1 mg, 0.13 mmol) and palladium acetate (5.7 mg, 0.025 mmol) in DMF (5 ml) is heated to 135° C. for 48 h. The reaction mixture is diluted with water and extracted with EtOAc (2×10 mL). The combined organic phases are washed with brine, dried over $MgSO_4$, and then concentrated. The residue is purified via column chromatogrphy on silica gel (25 g) using EtOAc/Hexanes (10-20%) as eluent to afford 298.2 mg (37.1% yield) of ethanesulfonic acid [4-(6-difluoromethoxy-1-ethyl-1H-iodo-2-yl)-phenyl]-amide, compound 516, as a light brown solid.

Step B: Following the procedure 1A, step A, ethanesulfonic acid [4-(6-difluoromethoxy-1-ethyl-1H-iodo-2-yl)-phenyl]-amide is converted to ethanesulfonic acid [4-(3-cyano-6-difluoromethoxy-1-ethyl-1H-indol-2-yl)-phenyl]-amide, compound 519.

Following steps A and B above, the following compounds are prepared in similar fashion: Compounds 343, 344, 345, 346, 409, 410, 411, 412, 413, 414, 415, 416, 417, 418, 419, 463, 464, 465, 466, 467, 468, 469, 470, 471, 472, 473, 515, 517, 518, 520, 521, 522, 523, 524, 575, 577, 579, 580, 611, 612, 613, 614

Example 1H

Preparation of 1-ethyl-2-(4-fluorophenylethynyl)-6-methoxy-1H-indole-3-carbonitrile (Compound 67)

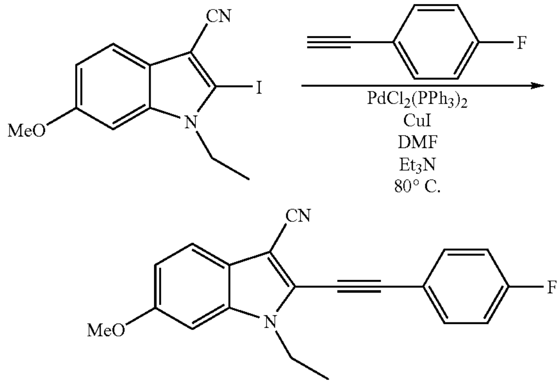

A mixture of 1-ethyl-2-iodo-6-methoxy-1H-indole-3-carbonitrile (150 mg, 0.46 mmol), prepared as described in example 1Ga, step A, 4-fluorophenylacetylene (80 mg, 0.0.69 mmol), bis(triphenylphosphine)palladium (II) dichloride (6 mg, 0.009 mmol) and CuI (4 mg, 0.018 mmol) is added to a sealable tube and alternately evacuated and flushed with $N_2$. To the tube is then added DMF (4 mL) and $Et_3N$ (0.25 mL, 1.84 mmol) and the reaction is heated at 80° C. for 20 h and then cooled to room temperature. The reaction mixture is diluted with $H_2O$ and extracted with EtOAc (2×). The combined organic phases are washed with $H_2O$ (3×) and saturated NaCl and then dried over MgSO4 and concentrated. The crude reaction mix is absorbed on silica gel (0.6 g) and chromatographed over silica gel using EtOAc/hexanes (10-20%) as eluent to afford 120 mg (82%) of 1-ethyl-2-(4-fluorophenylethynyl)-6-methoxy-1H-indole-3-carbonitrile as a yellow solid.

Utilizing essentially the same procedure described above and substituting different acetylene derivatives gives the following compounds: Compounds 64, 65, 66, 68, 69, 91, 92, 93, 94, 95, 96, 133, 134, 135, 136, 137, 143, 144, 145, 146, 147, 148, 149, 150, 151, 158, 159, 160, 161, 169, 170, 171, 172, 173, 174, 175, 176, 177, 178, 184, 185, 186, 187, 188, 196, 197, 198, 199, 200, 201, 202, 223, 230, 231, 232, 233, 234, 235, 236, 237, 238.

Example 1I

Preparation of 1-ethyl-3-(5-ethyl-[1,2,4]oxadiazol-3-yl)-6-methoxy-1H-indole (Compound 28)

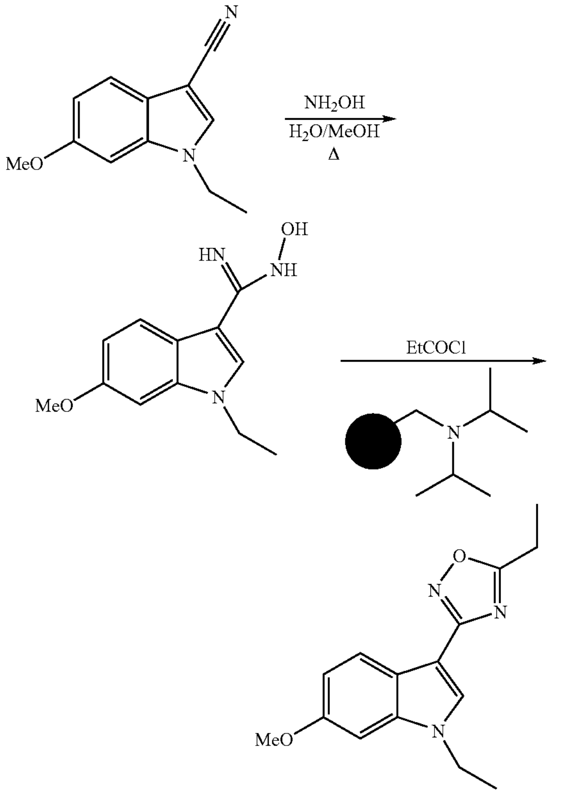

Step A: A solution of 1-ethyl-6-methoxy-1H-indole-3-carbonitrile (1.00 g, 5.00 mmol) in MeOH (10 mL) is treated with a 50% aqueous solution of hydroxyamine (0.38 mL, 6.25 mmol) and heated at reflux for 18 h. After cooling to room temperature, the heterogeneous mixture is filtered to afford 525 mg of desired product as a tan solid. The filtrate is concentrated to an oil, which is then dissolved in $CH_2Cl_2$ and chromatographed over silica gel using EtOAc/$CH_2Cl_2$ (15-50%) to afford an additional 295 mg of product as a tan solid. Total yield of 1-ethyl-N-hydroxy-6-methoxy-1H-indole-3-carboxamidine is 820 mg (70%).

Step B: The N-hydroxycarboxamidine above (50 mg, 0.21 mmol), polystyrene-diisopropylethylamine 165 mg, 3.90 mmol/g loading) and propionyl chloride (0.03 mL, 0.32 mmol) in $CH_2Cl_2$ (10 mL) are placed in a tube and rotated for 22 h at room temperature. After this time, trisamine resin (77 mg, 2.71 mmol/g loading) is then added and the tube rotated for an additional 30 min at room temperature. Solids are filtered and then the filtrate is concentrated and diluted with toluene (5 mL) and heated at 110° C. overnight. The crude reaction mixture is concentrated and purified by chromatography (EtOAc/$CH_2Cl_2$, 2/98) to afford 27 mg (46%) of 1-ethyl-3-(5-ethyl-[1,2,4]oxadiazol-3-yl)-6-methoxy-1H-indole as a white solid.

The following compound is prepared utilizing the above procedure with substitution of the appropriate acyl halide: Compound 29.

Example 1J

Preparation of 1-ethyl-6-methoxy-3-(5-ethyl-[1,3,4]oxadiazol-2-yl)-1H-indole (Compound 54)

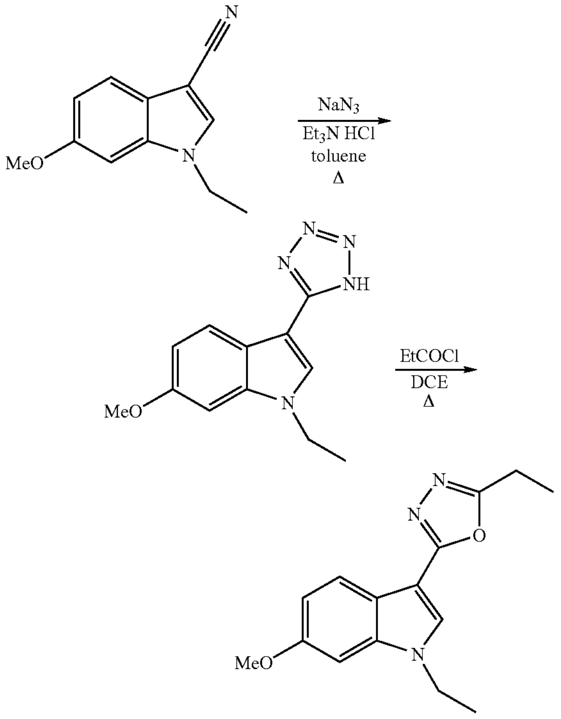

Step A: A mixture of 1-ethyl-6-methoxy-1H-indole-3-carbonitrile (1.00 g, 5.00 mmol) in toluene (30 mL) is treated with triethylamine hydrochloride (1.03 g, 7.50 mmol) and sodium azide (0.49 g, 7.50 mmol) and is heated at reflux for 16 h. After cooling to room temperature, the reaction mixture is diluted with saturated $NaHCO_3$ and extracted with EtOAc. The organic layer is then washed with additional $NaHCO_3$ (2×). The combined aqueous phases are acidified to pH 2 with 6N HCl. The resultant thick precipitate is extracted with hot EtOAc (3×) and the combined organic phases are washed with saturated NaCl and dried and concentrated to give 0.55 g (45%) of 1-ethyl-6-methoxy-3-(1H-tetrazol-5-yl)-1H-indole as a yellow solid.

Step B: A suspension of the tetrazole above (50 mg, 0.21 mmol) and propionyl chloride (0.03 mL, 0.31 mmol) in dichloroethane (5 mL) is heated at reflux for 21 h. After cooling the reaction mixture to room temperature, polystyrene trisamine resin (70 mg, 3.4 meq/g) is added and the reaction is rotated for 4 h at room temperature. After filtering off the resin, and removal of the solvent, the crude product is absorbed on silica gel and the product is isolated by silica gel chromatography (EtOAc/$CH_2Cl_2$, 5-10%) to afford 30 mg (53%) of 1-ethyl-6-methoxy-3-(5-ethyl-[1,3,4]oxadiazol-2-yl)-1H-indole as a tan solid.

Example 1K

Preparation of ethyl 5-difluoromethoxy-1-(4-methoxyphenyl)-2-methyl-1H-indole-3-carboxylate (Compound 49)

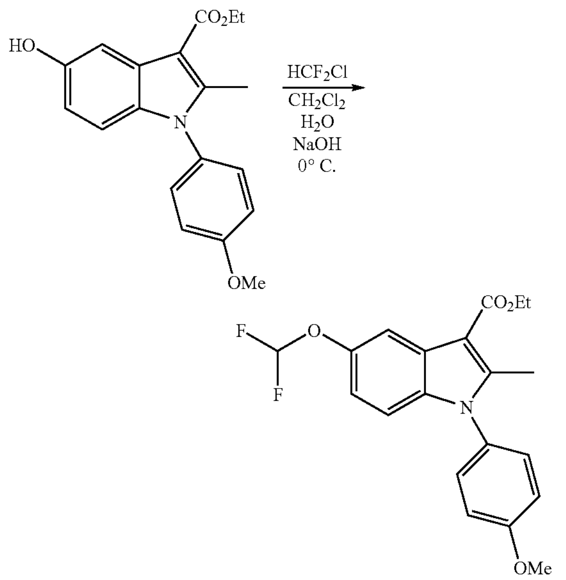

Freon-22 ($HCF_2Cl$) gas is bubbled into a solution of ethyl 5-hydroxy-1-(4-methoxyphenyl)-2-methyl-1H-indole-3-carboxylate (250 mg, 0.77 mmol) in $CH_2Cl_2$ (5 mL) at 0° C. containing a small amount of tetrabutylammonium bromide as a phase transfer catalyst. A 50% solution of NaOH is added dropwise at 0° C. After the addition, the mixture is stirred at 0° C. for 2 h. After the addition of $H_2O$, the organic phase is separated and washed with brine and dried over $Na_2SO_4$. The solvent is then concentrated and the residue is purified by column chromatography over silica gel using EtOAc/petroleum ether (1/2) as eluent to yield the desired product in 40% yield.

The following compounds are prepared utilizing the above procedure with substitution of the appropriate hydroxyindole: Compounds 18, 46, and 50.

Example 1L

Preparation of 1-[5-methoxy-1-(4-methoxyphenyl)-1-H-indol-3-yl]-ethanone (Compound 42)

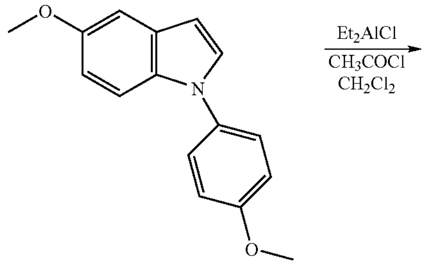

-continued

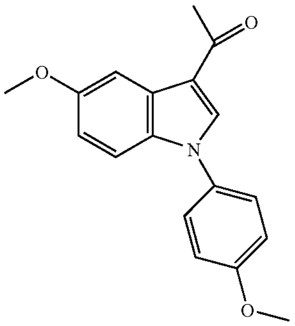

5-Methoxy-1-(4-methoxyphenyl)-1-H-indole (50 mg, 0.2 mmol), prepared by the method of example 1C, is dissolved in 1 mL of $CH_2Cl_2$ at 0° C. $Et_2AlCl$ (300 μL, 1M in hexanes, 0.3 mmol) is then added. After stirring at 0° C. for 30 min, a solution of acetyl chloride (22 mL, 0.3 mmol) in 1 mL of $CH_2Cl_2$ is added dropwise. This is stirred at 0° C. for a further 90 min. The reaction mixture is quenched with $H_2O$ and is extracted with $CH_2Cl_2$ and concentrated in vacuo. Purification by column chromatography on silica gel EtOAc/$CH_2Cl_2$ (5/95) yields the title compound as a white solid (42 mg, 71%).

Utilizing essentially the same procedure described above and substituting different acyl chlorides, the following compounds are prepared: Compounds 32, 33, 34, 37, 38, 39, 47, 48.

Example 1M

Preparation of 1-ethyl-3-isoxazol-3-yl-6-methoxy-1-H-indole (Compound 57)

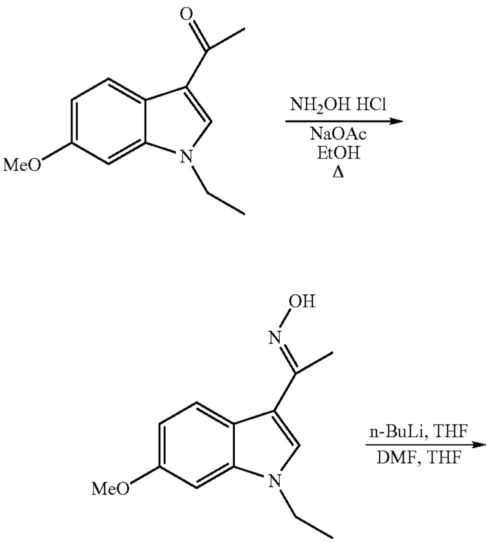

-continued

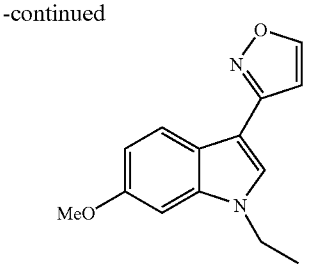

Step A: A mixture of 1-(1-ethyl-6-methoxy-1-H-indole-3-yl)ethanone (200 mg, 0.92 mmol), prepared from 1-ethyl-6-methoxy-1H-indole by the procedure described in example 1L, hydroxyamine hydrochloride (128 mg, 1.84 mmol), NaOAc (151 mg, 1.84 mmol) and EtOH (7 mL) is heated at 85° C. for 4 h. The reaction mixture is then partitioned between $H_2O$ and EtOAc. The organic phase is dried and concentrated in vacuo. Purification by column chromatography using EtOAc/$CH_2Cl_2$ (1/9) yields 1-(1-ethyl-6-methoxy-1-H-indole-3-yl)ethanone oxime as a white solid (189 mg, 92%).

Step B: 1-(1-Ethyl-6-methoxy-1-H-indole-3-yl)ethanone oxime (100 mg, 0.43 mmol) is dissolved in THF (900 μL) at 0° C. n-BuLi (450 μL, 2.5 M in hexanes, 1.12 mol) is added dropwise, resulting in instant precipitation of solids. DMF (70 μL, 0.9 mol) in 260 μL of THF is then added dropwise. This is stirred at 0° C. for 1 h, then at room temperature for 1 h. The reaction mixture is pipetted into a mixture containing 1 mL of $H_2O$, 1 mL of THF, and 100 mL of concentrated $H_2SO_4$. This mixture is heated at 75° C. for 1 h and then is partitioned between $H_2O$ and EtOAc. The organic phase is dried and concentrated. Purification by column chromatography ($CH_2Cl_2$) yields 1-ethyl-3-isoxazol-3-yl-6-methoxy-1-H-indole product as a white solid (13 mg, 12%).

Example 1N

Preparation of 1-ethyl-3-isoxazol-5-yl-6-methoxy-1H-indole (Compound 58)

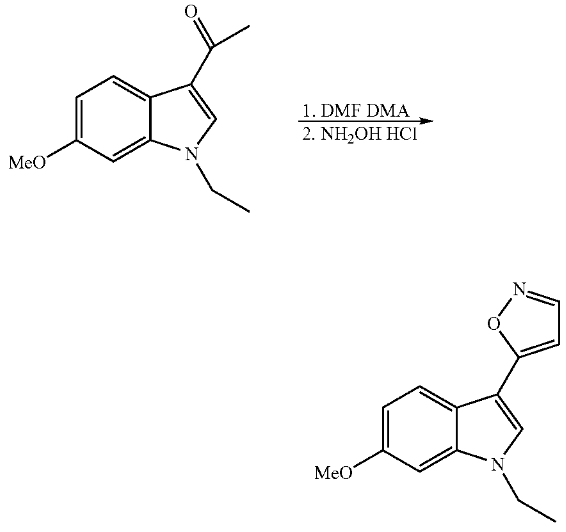

1-(1-Ethyl-6-methoxy-1H-indol-3-yl)ethanone (100 mg, 0.46 mmol), prepared from 1-ethyl-6-methoxy-1H-indole by the procedure described in example 1L, is heated with 1.5 mL of dimethylformamide dimethylacetal and 100 μL of pyrrolidine at 110° C. overnight. The dimethylformamide dimethylacetal is then concentrated in vacuo. The residue is redissolved in 1.25 mL of EtOH and 250 μL of $H_2O$, and is treated with hydroxyamine hydrochloride (66 mg, 0.95 mmol) and heated at 80° C. for 2 h. Partitioning between $H_2O$ and EtOAc and drying and concentration of the organic phase followed by purification by silica gel chromatography (EtOAc/$CH_2Cl_2$, 5/95) gives 1-ethyl-3-isoxazol-5-yl-6-methoxy-1H-indole as a white solid (72 mg, 66%).

Utilizing essentially the same procedure described above, the following compound is prepared: Compound 60.

Example 1O

Preparation of 1-ethyl-6-methoxy-3-(2H-pyrazol-3-yl)-1H-indole (Compound 59)

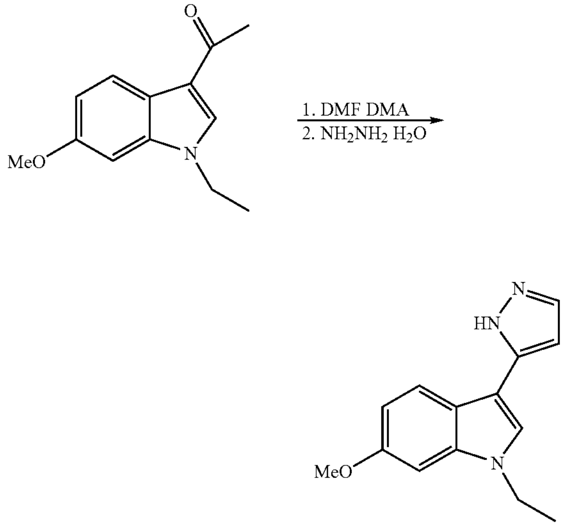

1-(1-Ethyl-6-methoxy-1H-indol-3-yl)-ethanone (100 mg, 0.46 mmol), prepared from 1-ethyl-6-methoxy-1H-indole by the procedure described in example 1L, is heated with 1.5 mL of dimethylformamide dimethyl acetal and 100 μL pyrrolidine at 110° C. overnight. The DMF dimethyl acetal is removed in vacuo. The residue is redissolved in 3 mL of acetic acid, hydrazine hydrate (70 μL, 1.38 mmol) is added, and the mixture is heated to 100° C. for 2 h. The acetic acid is removed in vacuo, and the residue is partitioned between EtOAc and saturated $NaHCO_3$. The organic phase is dried and concentrated and the product purified by silica gel chromatography (EtOAc/Hex, 1/1) to give 59 mg of 1-ethyl-6-methoxy-3-(2H-pyrazol-3-yl)-1H-indole (54%) as a colorless semisolid. Trituration in $Et_2O$ gives a white crystalline powder.

The following compound is prepared utilizing the above procedure: Compound 61.

Example 1P

Preparation of methyl 1-ethyl-3-oxazol-5-yl-1H-indole-6-carboxylate (Compound 72)

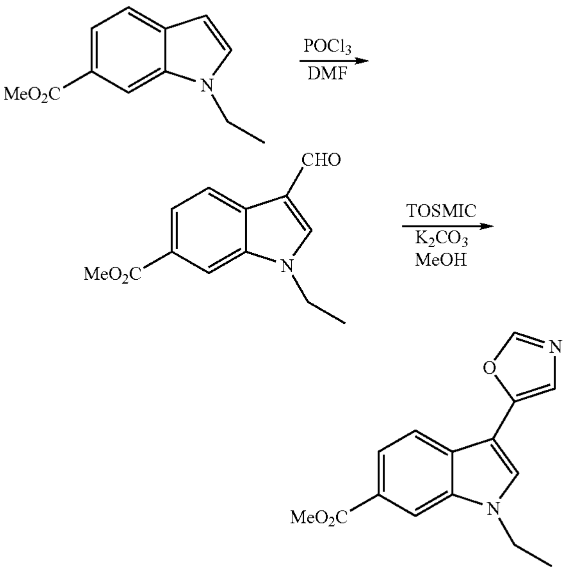

Step A: 1-Ethyl-1H-indole-6-carboxylic acid methyl ester (900 mg, 4.45 mmol) is dissolved in DMF (3.3 mL). This is added dropwise to an ice-cold solution of $POCl_3$ (430 μL, 4.5 mmol) in DMF (1.5 mL). The reaction mixture is stirred at room temperature for 90 minutes. The reaction mixture is then treated with 6N NaOH (3.5 ml). The mixture is then partitioned between $H_2O$ and ethyl acetate. Purification by silica gel chromatography (5-10% EtOAc/$CH_2Cl_2$) yields 1-ethyl-3-formyl-1H-indole-6-carboxylic acid methyl ester (985 mg, 96%) as a white solid.

Step B: 1-Ethyl-3-formyl-1H-indole-6-carboxylic acid methyl ester (100 mg, 0.42 mmol), TOSMIC (100 mg, 0.52 mmol), $K_2CO_3$ (178 mg, 1.29 mmol), and MeOH (800 μL) are heated at 80° C. overnight. The reaction mixture is then partitioned between $H_2O$ and ether. After drying and concentrating the organic phase, the product is purified by silica gel chromatography (EtOAc/$CH_2Cl_2$, 10/90) to give methyl 1-ethyl-3-oxazol-5-yl-1H-indole-6-carboxylate (26 mg, 23%) as an off-white solid.

Example 1Q

Preparation of methyl 1-ethyl-3-oxazol-2-yl-1H-indole-6-carboxylate (Compound 75)

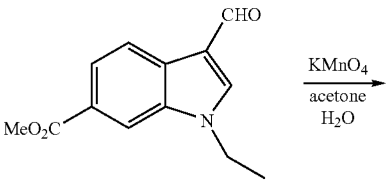

-continued

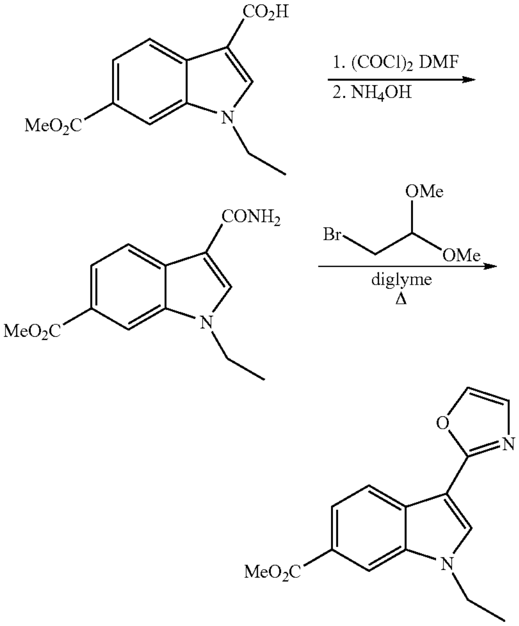

Step A: 1-Ethyl-3-formyl-1H-indole-6-carboxylic acid methyl ester (800 mg, 3.5 mmol), prepared as shown in example 1P, step A, is dissolved in acetone (98 mL). A solution of $KMnO_4$ (655 mg, 4.15 mmol) in $H_2O$ (31 mL) is added. The reaction mixture is stirred at room temperature for 90 minutes. Another addition of $KMnO_4$ (108 mg) in $H_2O$ (6 mL), followed by stirring for another 45 minutes is required to drive the reaction to completion. The reaction mixture is then quenched with 10% $H_2O_2$ (1.5 mL). The mixture is filtered through celite. The filtrate is stripped down under vacuum to roughly ⅓ of the volume. The residue is acidified with 6N HCl, and is extracted into ethyl acetate. The solids isolated from the ethyl acetate layer are triturated with acetone to yield 1-ethyl-1H-indole-3,6-dicarboxylic acid 6-methyl ester (696 mg, 79%) as a light orange solid.

Step B: 1-Ethyl-1H-indole-3,6-dicarboxylic acid 6-methyl ester (600 mg, 2.43 mmol) is suspended in a solution of $CH_2Cl_2$ (27 ml) and DMF (20 μL). Oxalyl chloride (470 μL, 5.38 mmol) is added, and the reaction mixture is stirred for 1 hour at room temperature. This mixture is then slowly poured into a rapidly stirring solution of concentrated $NH_4OH$ (10 mL). This is then partitioned in $H_2O$ and EtOAc. The residue from the ethyl acetate layer is triturated with acetone to yield 6-methoxycarbonyl-1-ethyl-1H-indole-3-carboxamide (511 mg, 85%) as a white solid.

Step C: A mixture of 150 mg (0.61 mmol) of 6-methoxycarbonyl-1-ethyl-1H-indole-3-carboxamide in diglyme (3.6 mL), and bromoacetaldehyde dimethyl acetal (430 μL, 3.7 mmol) is heated at 125° C. for 2 h. The reaction mixture is cooled and partitioned in $H_2O$ and EtOAc. The organic phase is dried and concentrated and the product is purified by silica gel chromatography (EtOAc/$CH_2Cl_2$ 5-10%). The product containing fractions are combined and concentrated and the solid is triturated with hexanes to yield methyl 1-ethyl-3-oxazol-2-yl-1H-indole-6-carboxylate (75 mg, 46%) as a yellow solid.

Example 1R

Preparation of 1-ethyl-6-methoxy-3-thiazol-2-yl-1H-indole (Compound 73)

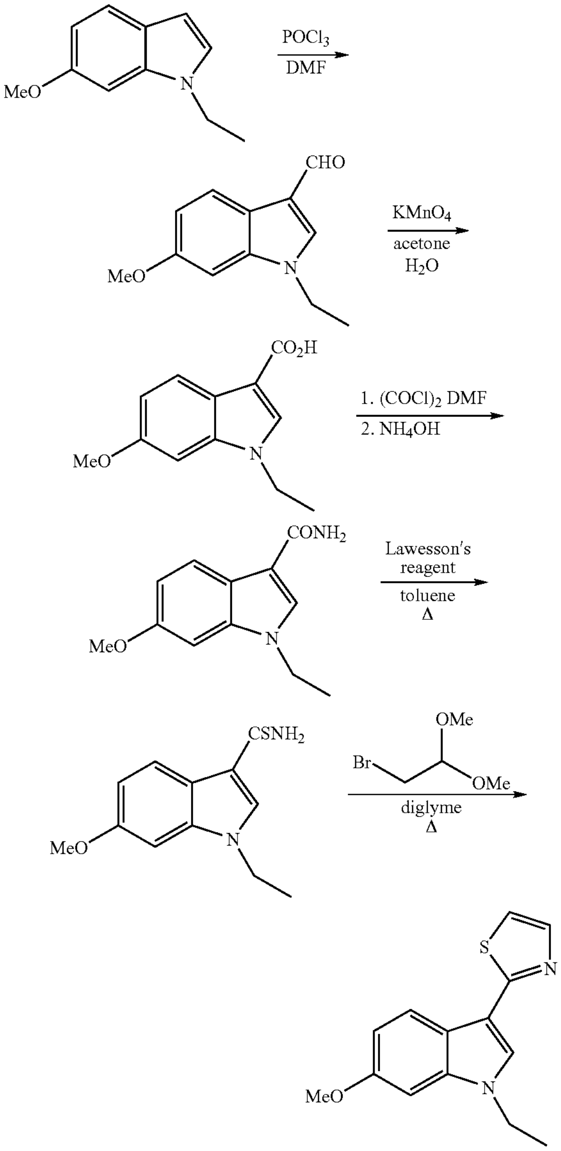

Step A: 1-Ethyl-6-methoxy-1H-indole (900 mg, 5.14 mmol) is dissolved in DMF (1.5 mL). This is added dropwise to an ice-cold solution of $POCl_3$ (500 μL, 5.2 mmol) in DMF (1.75 ml). After stirring at room temperature for 90 minutes, the reaction mixture is re-cooled in an ice bath and is slowly quenched with 6N NaOH (4 mL). The reaction mixture is partitioned between EtOAc and $H_2O$. Purification by silica gel chromatography ($EtOAc/CH_2Cl_2$, 5/95) yields 1-ethyl-6-methoxy-1H-indole-3-carbaldehyde (849 mg, 81%) as a yellow solid.

Step B: 1-Ethyl-6-methoxy-1H-indole-3-carbaldehyde (600 mg, 2.95 mmol) is dissolved in acetone (85 mL). A solution of $KMnO_4$ (450 mg, 2.85 mmol) in $H_2O$ (28 mL) is added. This is stirred at room temperature for 5 hours. Another solution of $KMnO_4$ (450 mg, 2.85 mmol) in $H_2O$ (25 mL) is then added. After stirring for another hour at room temperature, the reaction is complete. The reaction mixture is quenched with 10% $H_2O_2$ (1.5 mL), and is then filtered through celite. The filtrate is stripped down under vacuum to roughly ⅓ of the volume. The residue is acidified with 6N HCl, and is extracted into ethyl acetate. Purification by silica gel column (hexanes/acetone/acetic acid, 70/30/1) yields crude product. Trituration with ether yields pure 1-ethyl-6-methoxy-1H-indole-3-carboxylic acid (365 mg, 56%) as a yellow solid.

Step C: 1-Ethyl-6-methoxy-1H-indole-3-carboxylic acid (250 mg, 1.14 mmol) is suspended in a solution of $CH_2Cl_2$ (12.5 mL) and DMF (10 μL). Oxalyl chloride (230 μL, 2.64 mmol) is added, and the reaction mixture is stirred for 1 hour at room temperature. This mixture is then slowly poured into a rapidly stirring solution of concentrated $NH_4OH$ (5 mL). This is then partitioned in $H_2O$ and EtOAc. The residue from the ethyl acetate layer is triturated with acetone to yield 1-ethyl-6-methoxy-1H-indole-3-carboxamide (134 mg, 54%) as a white solid.

Step D: 1-Ethyl-6-methoxy-1H-indole-3-carboxamide (120 mg, 0.55 mmol), Lawesson's reagent (240 mg, 0.6 mmol), and toluene (2 mL) are heated at 90° C. for 90 min. The reaction mixture is concentrated and purified by silica gel chromatography ($EtOAc/CH_2Cl_2$, 1/9) to yield 1-ethyl-6-methoxy-1H-indole-3-thiocarboxamide as a yellow solid (92 mg, 71%).

Step E: 1-Ethyl-6-methoxy-1H-indole-3-thiocarboxamide (83 mg, 0.36 mmol), glyme (3.6 mL) and bromoacetaldehyde dimethyl acetal (220 μL, 1.86 mmol) are heated at 80° C. for 16 h. More bromoacetaldehyde dimethyl acetal (250 μL) is added. This is heated at 80° C. for 2 h. Addition of 250 μL more bromoacetaldehyde dimethyl acetal is followed by heating for another 2 hours. The reaction mixture is cooled to room temperature, absorbed onto silica and purified by silica gel chromatography (hexanes/EtOAc, 7/3) to afford 1-ethyl-6-methoxy-3-thiazol-2-yl-1H-indole as a brown oil (44 mg, 47%).

The following compounds are prepared following the procedure described above: Compounds 78, 101, 104, 105 and 106.

Example 1S

Preparation of 1-ethyl-6-methoxy-2-phenoxymethyl-1H-indole-3-carbonitrile (Compound 99)

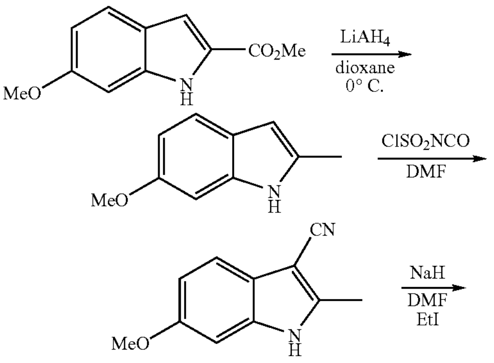

-continued

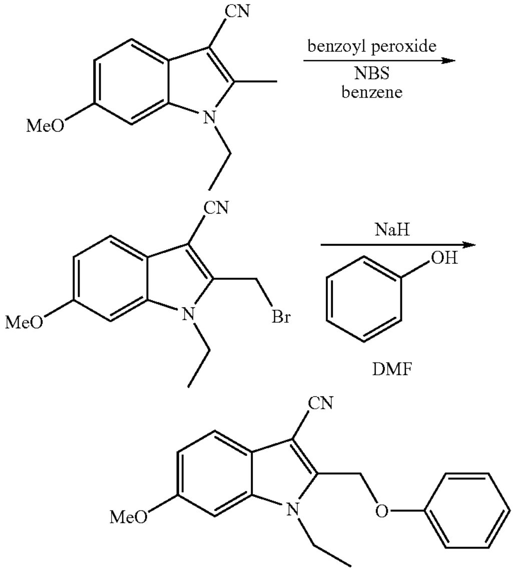

Step A: To a suspension of $LiAlH_4$ (7.6 g, 0.2 mol) in dioxane (100 mL) is added dropwise a solution of methyl 6-methoxy-1H-indole-2-carboxylate (8.2 g, 0.04 mol) in dioxane (50 mL) at 0° C. After the addition, the mixture is stirred at room temperature for 1 h and then heated at reflux for 5 h. After cooling to 0° C., the reaction is quenched by water (dropwise) and then 15% aqueous NaOH. After stirring at room temperature for 1 h, the mixture is filtered through Celite. The solid is washed with a large amount of EtOAc. The solvent is washed with brine, dried over $Na_2SO_4$ and evaporated under vacuum. The residue is purified by flash column chromatography on silica gel using EtOAc/petroleum ether (1/5) as eluent to yield 61% of 6-methoxy-2-methyl-1H-indole.

Step B: To a solution of 6-methoxy-2-methyl-1H-indole (3.9 g, 24 mmol) in acetonitrile (200 mL) and DMF (20 mL) is added dropwise a solution of $ClSO_2NCO$ (4 mL, 1.3 eq.) in acetonitrile (31 mL) at 0° C. After the addition, the mixture is stirred at room temperature for 3 h. Then it is poured into ice water and saturated $NaHCO_3$ is added to it until it becomes basic. The aqueous phase is extracted with $CH_2Cl_2$ and then evaporated. The residue is purified with flash column chromatography on silica gel using EtOAc/petroleum ether (1/5) as eluent to yield 81% of 6-methoxy-2-methyl-1H-indole-3-carbonitrile.

Step C: To a suspension of NaH (0.6 g, 2 eq.) in DMF (7 mL) is added a solution of 6-methoxy-2-methyl-1H-indole-3-carbonitrile (1.3 g, 7.0 mmol) in DMF (8 mL) followed by ethyl iodide (1.2 mL, 2 eq.) at 0° C. After stirring for 1 h, the mixture is poured into ice water and then extracted with $CH_2Cl_2$. The organic layer is washed with brine and dried with $Na_2SO_4$. The solvent is evaporated under vacuum and purified with flash column chromatography on silica gel using EtOAc/petroleum ether (1/5) as eluent to yield 92% of 1-ethyl-6-methoxy-2-methyl-1H-indole-3-carbonitrile.

Step D: To a solution of 1-ethyl-6-methoxy-2-methyl-1H-indole-3-carbonitrile (1.38 g, 6.45 mmol) in benzene (130 mL) is added benzoyl peroxide (226 mg) and NBS (1.21 g, 1.05 eq.). Then the mixture is heated to reflux for 3 h. After cooling and filtering, the filtrate is concentrated under vacuum. The crude 2-bromomethyl-1-ethyl-6-methoxy-1H-indole-3-carbonitrile (1.6 g, 86%) is used without further purification.

Step E: To a solution of NaH (44 mg, 4 eq.) in DMF (0.5 mL) is added 2-bromomethyl-1-ethyl-6-methoxy-1H-indole-3-carbonitrile (80 mg, 0.274 mmol) and phenol (2 eq.). After stirring for 20 h, the mixture is poured into ice water and extracted with $CH_2Cl_2$. The organic layer is washed with brine and dried with $Na_2SO_4$. The solvent is evaporated under vacuum and purified with flash column chromatography on silica gel using EtOAc/petroleum ether (1/5) as eluent to yield 1-ethyl-6-methoxy-2-phenoxymethyl-1H-indole-3-carbonitrile, compound 99.

Example 1T

Preparation of 6-nitro-2-pyrrol-1-yl-1H-indole-3-carbonitrile (Compound 7)

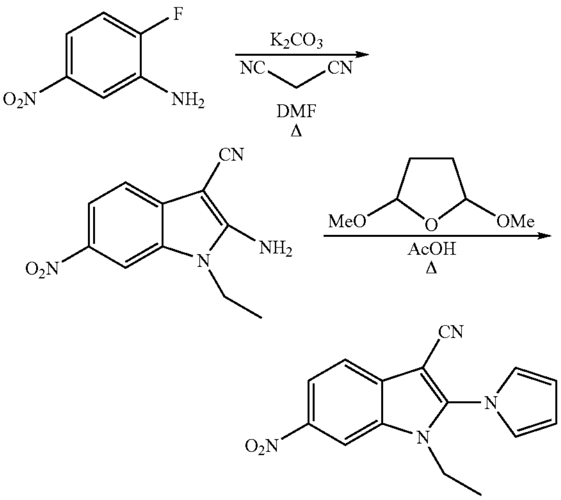

Step A: A solution of 2-fluoro-5-nitroaniline (11.7 g, 74.9 mmol) in dimethylformamide (120 mL) is treated with malononitrile (5.28 g, 80.0 mmol) and potassium carbonate (11.05 g, 80.0 mmol) (Modification of *Chem. Heterocyclic Cpd. Engl. Trans.*, 9, 37 (2001)). The resulting heterogeneous mixture is heated to gentle reflux for 3 h, then cooled and poured into water (500 mL). The resulting precipitate is collected by filtration and taken up into ethyl acetate (300 mL). This solution is dried over $Na_2SO_4$, filtered and partially evaporated to give a precipitate, which is collected by filtration. Further evaporation and filtration give a second crop. The two crops are combined and dried under vacuum to give 2-amino-1-ethyl-6-nitro-1H-indole-3-carbonitrile (7.90 g, 52%) as an orange powder.

Step B: A solution of 2-amino-6-nitro-1H-indole-3-carbonitrile (362 mg, 1.79 mmol) in acetic acid (5 mL) is treated with 2,5-dimethoxytetrahydrofuran (0.30 mL, 2.27 mmol), and the solution is heated to reflux for 14 h. After cooling to ambient temperature, the solution is poured into water (100 mL), and solid sodium bicarbonate is added until $CO_2$ evolution ceased. The mixture is extracted with EtOAc (2×100 mL), and the extracts are washed with saturated brine, combined, dried over $MgSO_4$, filtered and concentrated. The residual material is separated by silica gel chromatography (EtOAc/hexanes, 1/4) to afford 6-nitro-2-pyrrol-1-yl-1H-indole-3-carbonitrile, compound 5, as a yellow solid (232 mg, 51%).

Example 1U

Preparation of N-(3-cyano-1-ethyl-6-nitro-1H-indol-2-yl)acetamide (Compound 25)

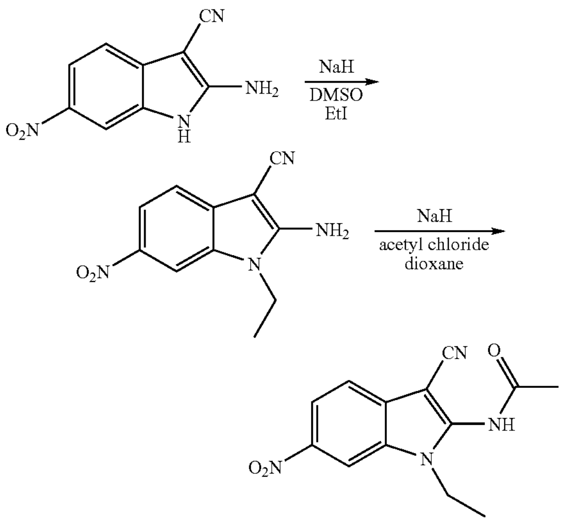

Step A: Sodium hydride (42 mg, 1.05 mmol, 60% w/w suspension in mineral oil) is washed with hexane and taken up in dimethylsulfoxide (1 mL). A solution of 2-amino-6-nitro-1H-indole-3-carbonitrile (prepared in procedure 1T) in dimethylsulfoxide (1 mL) is added by syringe, and the resulting mixture is stirred for 20 min. Then, iodoethane (77 μL, 0.96 mmol) is added by syringe, and the mixture is stirred for 14 h. The reaction is then poured into EtOAc (50 mL), and this solution is washed with water (3×50 mL) and saturated brine (40 mL). The aqueous phases are back-extracted with EtOAc, and the organic extracts are combined, dried over $Na_2SO_4$, filtered and evaporated. The residual material is separated by column chromatography over silica gel (EtOAc/hexanes, 1/1) to afford first a small amount of a dialkylated analog, then the desired compound, 2-amino-1-ethyl-6-nitro-1H-indole-3-carbonitrile (114 mg, 52%), and finally unreacted starting material. The desired product is isolated as an orange powder.

Step B: Sodium hydride (44 mg, 1.10 mmol, 60% w/w in mineral oil) is washed with hexanes and suspended in 1,4-dioxane (3 mL). A solution of 2-amino-1-ethyl-6-nitro-1H-indole-3-carbonitrile (120 mg, 0.521 mmol), prepared in step B, above, in dioxane (2 mL) is added, and the resulting mixture is allowed to stir for 30 min. Then, acetyl chloride (45 μL, 0.63 mmol) is added by syringe, and the solution is stirred for an additional 12 h. The reaction is partitioned between water and EtOAc (20 mL each), and the organic phase is washed with brine. The aqueous phases are back-extracted in sequence with ethyl acetate, and the organic extracts are combined, dried over $MgSO_4$, filtered and evaporated. The resulting solid is triturated with $Et_2O$, collected by filtration and dried under vacuum to afford N-(3-cyano-1-ethyl-6-nitro-1H-indol-2-yl)-acetamide (100 mg, 71%), compound 25, as an off-white powder.

Using this procedure and substituting the appropriate acid chlorides or chloroformates gives the following compounds: Compounds 23, 26, 35, 36, 203, 204, 214, 215, 216.

Example 1V

Preparation of N-ethyl-3-phenyl-5-nitroindole (Compound 41)

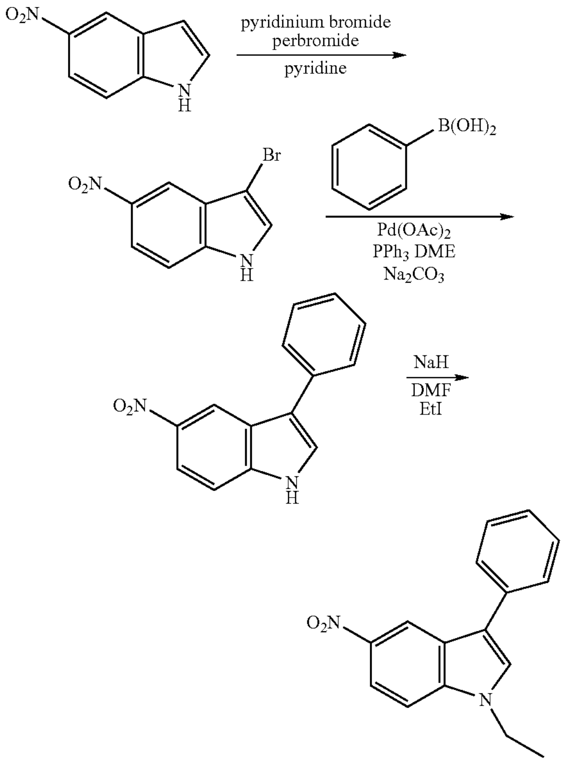

Step A: To a solution of 5-nitroindole (5.00 g, 30.8 mmol) in pyridine (200 mL) at −4° C. is added a solution of pyridinium bromide perbromide (10.99 g, 34.3 mmol) in pyridine (200 mL) dropwise under nitrogen with stirring. After complete addition, the reaction mixture is stirred for 5 min at 0° C. The reaction mixture is diluted in 0° C. water (200 mL) and extracted with 200 mL of $Et_2O$. The organic layer is washed with 6 M HCl (300 mL), 5% $NaHCO_3$ (300 mL), and brine (300 mL). The organic phase is dried over $MgSO_4$ and solvent is removed to give 3-bromo-5-nitroindole as a yellow powder, 80% pure with 20% 5-nitroindole (6.80 g, 74% yield).

Step B: A solution of 3-bromo-5-nitroindole from above (625 mg, 2.1 mmol), phenylboronic acid (381 mg, 3.13 mmol), triphenylphosphine (109.3 mg, 0.417 mmol) in dimethoxyethane (4.16 mL) is degassed. To this mixture 2N sodium carbonate (6.25 mL) is added, and the reaction mixture is degassed again. To the reaction is added palladium (II) acetate (23.4 mg, 0.104 mmol), and the reaction is refluxed under dry nitrogen with stirring for 8 hours. The reaction mixture is then diluted with 1 M HCl (100 mL), and extracted with ethyl acetate (100 mL). The organic phase is washed with water (100 mL), and brine (100 mL). The organic phase is dried over $MgSO_4$ and concentrated in vacuo. The crude product is purified by chromatography over silica gel (EtOAc/hexanes, 10/90) to afford 3-phenyl-5-nitroindole as an orange powder (45 mg, 9% yield).

Step C: To a mixture of 60% NaH in mineral oil (8.7 mg, 0.630 mmol) and DMF (1.0 mL) is added dropwise a solution of 3-phenyl-5-nitroindole (40.0 mg, 2.1 mmol) in DMF (0.75 mL). The reaction mixture is stirred for 20 min at 0° C. under $N_2$. Ethyl iodide (14.8 μL, 0.185 mmol) is added dropwise and the reaction mixture is stirred for an additional 3 hours. The reaction mixture is diluted with water (250 mL), and extracted with EtOAc (30 mL). The organic phase is washed with water (250 mL) and is then dried over $MgSO_4$ and the solvent is removed in vacuo. The desired N-ethyl-3-phenyl-5-nitroindole is obtained as a yellow powder (40.0 mg, 89.5% yield).

In similar fashion the following compound is prepared: Compound 40.

Example 1W

Preparation of [3-Cyano-1-(4-methoxyphenyl)-1H-indol-6-yl]-carbamic acid propyl ester (Compound 97)

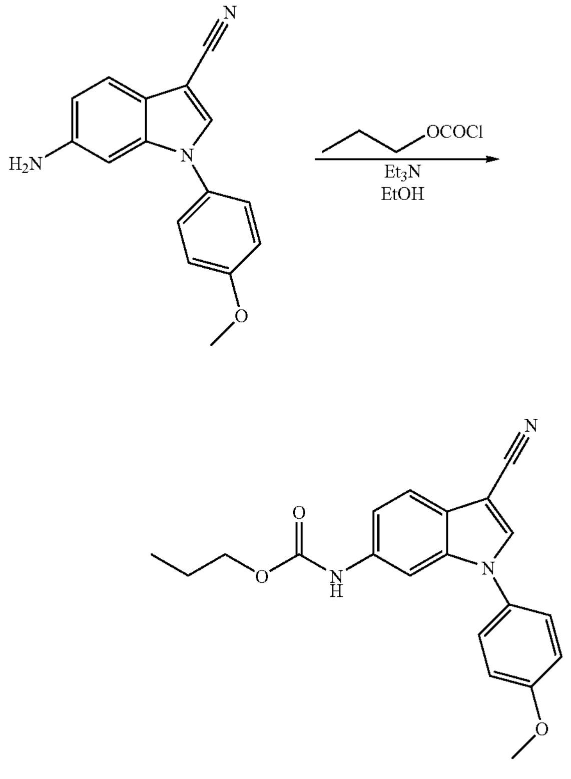

6-Amino-1-(4-methoxyphenyl)-1H-indole-3-carbonitrile (30 mg, 0.12 mmol), is suspended in EtOH (300 μL). Propyl chloroformate (168 μL, 1.5 mmol) is added, and this mixture is stirred at room temperature overnight. The addition of triethylamine (300 μL), followed by another hour of stirring at room temperature, completes the reaction. This reaction mixture is loaded directly onto a silica column, and is eluted with $CH_2Cl_2$. Another silica column (3/2, ether/hexanes) is needed to fully purify the product, [3-cyano-1-(4-methoxy-phenyl)-1H-indol-6-yl]-carbamic acid propyl ester (19 mg, 45%), as a white solid.

Example 1X

Preparation of N-[4-(3-cyano-1-ethyl-6-methoxy-1H-indol-2-ylethynyl)-phenyl]-methanesulfonamide (Compound 130)

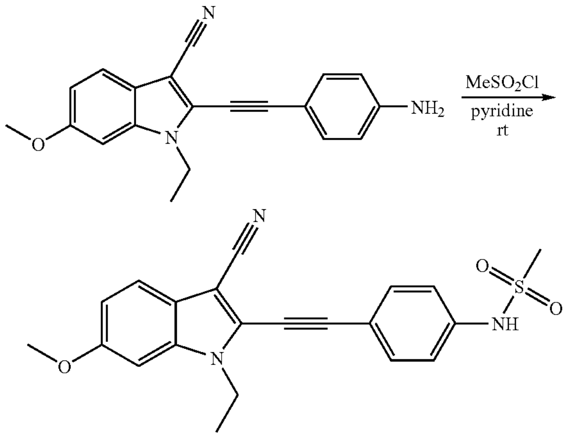

2-(4-Aminophenylethynyl)-1-ethyl-6-methoxy-1H-indole-3-carbonitrile (50 mg, 0.16 mmol), prepared as described by the method of Example 1H, is dissolved in pyridine (550 μL) at room temperature. Methanesulfonyl chloride (17 μL, 0.21 mmol) is added dropwise. This is stirred overnight at room temperature. The reaction mixture is then diluted in ethyl acetate and is washed with aqueous HCl, followed by brine. The organic layer is dried and concentrated. Purification by silica gel chromatography (9/1, $CH_2Cl_2$/EtOAc) yields N-[4-(3-cyano-1-ethyl-6-methoxy-1H-indol-2-ylethynyl)-phenyl]-methanesulfonamide (58 mg, 92%) as an off-white solid.

The following compounds are made using the procedure shown above, by substituting the appropriate aminophenyl-ethynyl indoles and sulfonyl chlorides: Compounds 131, 132, 208, 209, and 210.

Example 1Y

Preparation of N-[4-(3-Cyano-1-ethyl-6-methoxy-1H-indol-2-yl)-phenyl]-methanesulfonamide (Compound 129)

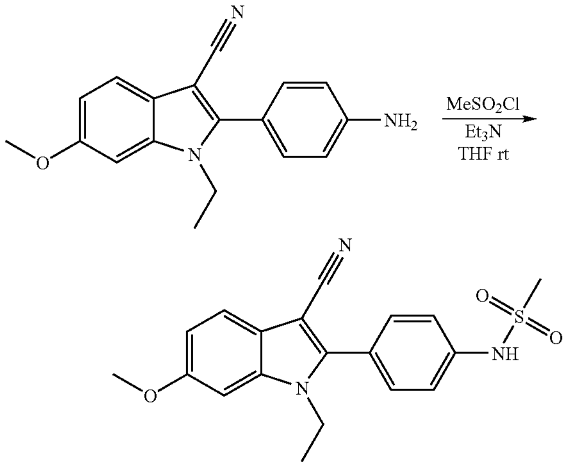

A solution of 2-(4-aminophenyl)-1-ethyl-6-methoxy-1H-indole-3-carbonitrile (70 mg, 0.24 mmol), prepared as described in Example 1Ga, step B in THF (3 mL) is cooled to 0° C. and treated with triethylamine (0.04 mL, 0.31 mmol) and methanesulfonylchloride (0.02 mL, 0.29 mmol) and stirred, warming to room temperature overnight. The reaction mixture is then diluted with $H_2O$ and extracted with ethyl acetate (3×). The organic phase is washed with $H_2O$ and saturated NaCl, dried and concentrated and purified by flash chromatography using EtOAc/hexanes (30-50%) to afford 60 mg (68%) of N-[4-(3-Cyano-1-ethyl-6-methoxy-1H-indol-2-yl)-phenyl]-methanesulfonamide as a tan solid.

Using essentially the same procedure as above and substituting the appropriate aminophenylindole and sulfonyl chloride or carrying out the reaction in pyridine as both base and solvent gives the following compounds: Compounds 83, 85, 86, 87, 88, 243, 251, 252, 272, 273, 287, 289, 365, 366, 367, 368, 369, 370, 371, 394, 439, 440, 448, 449, 451, 452, 477, 487, 488, 495, 505, 510, 548, 549, 550, 551, 552, 562, 563, 598, 599, 601, 602, 608, 609, 610, 615, 616, 617, 621, 622, 623, 629, 630, 631, 639, 655, 657, 658, 662, 669, 670, 671, 674, 675, 701, 702, 703, 706, 707, 708, 709, 710, 711, 713, 715, 720, 789, 790, 791, 850, 851, 867, 868, 890, 891, 912, 919, 920, 921, 922, 923, 924, 932, 933, 934, 935, 941, 953, 968, 982, 988, 990, 995, 996, 997, 998, 1035, 1038, 1041, 1103, 1105, 1115, 1116, 1117, 1123, 1140, 1141, 1155, 1160, 1161, 1170, 1175, 1181, 1182, 1188, 1189, 1228, 1229, 1230, 1231, 1280.

Example 1Za

Preparation of N-[4-(3-cyano-1-ethyl-6-methoxy-1H-indol-2-ylethynyl)-phenyl]-acetamide (Compound 138)

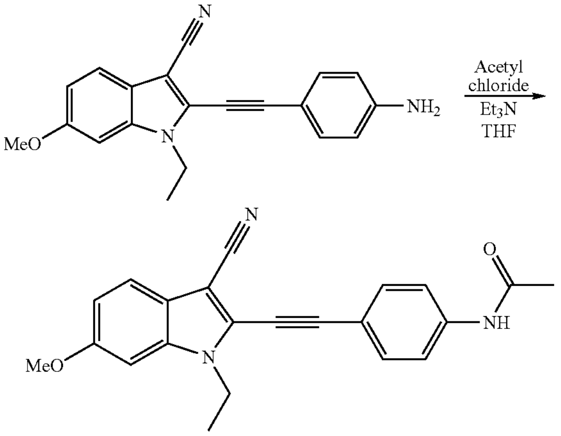

2-(4-Aminophenylethynyl)-1-ethyl-6-methoxy-1H-indole-3-carbonitrile (95 mg, 0.29 mmol), prepared as described in Example 1H, is dissolved in THF (1.4 mL). Triethylamine (84 μL, 0.6 mmol) is added, followed by dropwise addition of acetyl chloride (44 μL, 0.5 mmol). This is stirred at room temperature for 1 h. The reaction mixture is partitioned between $H_2O$ and EtOAc. The organic layer is dried and concentrated. Purification by silica chromatography (9/1, $CH_2Cl_2$/EtOAc) yields N-[4-(3-cyano-1-ethyl-6-methoxy-1H-indol-2-ylethynyl)-phenyl]-acetamide (103 mg, 96%) as a yellow solid.

The following compounds are prepared by the procedure shown above, substituting the appropriate aminophenylethynyl indoles and acid chlorides: Compounds 82, 139, 152, 153, 162, 163, 165, 167, 205, 206, 207, 211, 212, 213, 219, 224, 225, 228.

Example 1Zb

Preparation of N-[4-(3-cyano-1-ethyl-6-methoxy-1H-indol-2-ylethynyl)-phenyl]-formamide (Compound 241)

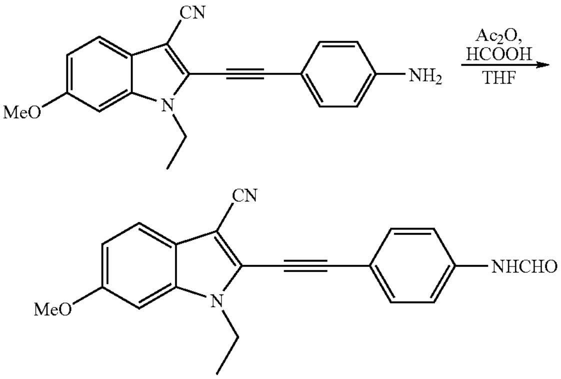

Acetic anhydride (2.5 mL) and 98% formic acid (1.0 mL) are heated at 65° C. for 1 hour. This is cooled to 0° C. 2-(4-Aminophenylethynyl)-1-ethyl-6-methoxy-1H-indole-3-carbonitrile (100 mg, 0.32 mmol), prepared as in example 1H, is taken up in THF (1.2 mL) and added to the formic acetic anhydride mixture. This is stirred at 0° C. for 30 minutes. The reaction mixture is then partitioned between $H_2O$ and EtOAc. The EtOAc layer is washed with saturated $NaHCO_3$, followed by saturated brine. The organic layer is dried and concentrated. Purification by silica gel chromatography (4/1, $CH_2Cl_2$/EtOAc) yields of N-[4-(3-cyano-1-ethyl-6-methoxy-1H-indol-2-ylethynyl)-phenyl]-formamide (105 mg, 96%) as a yellow solid.

The following compound is prepared similarly as described above: Compound 218.

Example 1AA

Preparation of N-[4-(3-Cyano-1-ethyl-6-methoxy-1H-indol-2-yl)-phenyl]-acetamide (Compound 128)

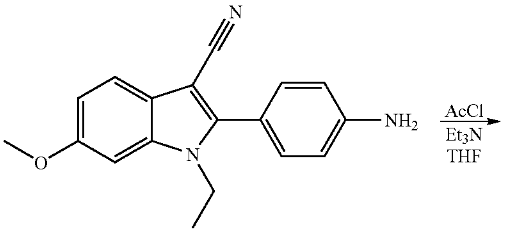

-continued

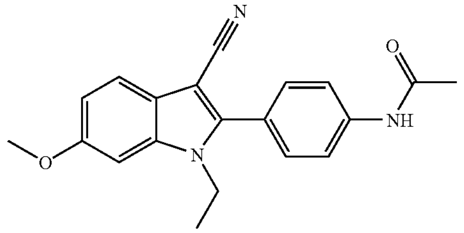

A solution of 2-(4-aminophenyl)-1-ethyl-6-methoxy-1H-indole-3-carbonitrile (70 mg, 0.24 mmol), prepared as described in Example 1Ga, step B in THF (3 mL) is cooled to 0° C. and treated with triethylamine (0.04 mL, 0.31 mmol) and acetyl chloride (0.02 mL, 0.29 mmol) and stirred, warming to room temperature overnight. The reaction mixture is then diluted with $H_2O$ and extracted with ethyl acetate (3×). The organic phase is washed with $H_2O$ and saturated NaCl, dried and concentrated and purified by flash chromatography using EtOAc/hexanes (30-50%) to afford 57 mg (71%) of N-[4-(3-cyano-1-ethyl-6-methoxy-1H-indol-2-yl)-phenyl] acetamide as a tan solid.

Using essentially the same procedure as above and substituting appropriate aminophenyl indoles and the acid chlorides, the following compounds are prepared: Compounds 81, 242, 244, 324, 325, 326, 327, 328, 329, 330, 383, 420, 421, 422, 423, 424, 425, 544, 558, 559, 560, 561, 565, 566 567, 644, 645, 646, 755, 756, 757, 759, 760, 761, 762, 763, 764, 765, 766, 798, 799, 801, 802, 803, 804, 854, 855, 856, 857, 858, 859, 895, 896, 897, 898, 899, 900, 901, 913, 914, 915, 916, 983.

Example 1AB

Preparation of 1-[3-(3-cyano-1-ethyl-6-methoxy-1H-indol-2-ylethynyl)phenyl]-3-ethyl urea (Compound 220)

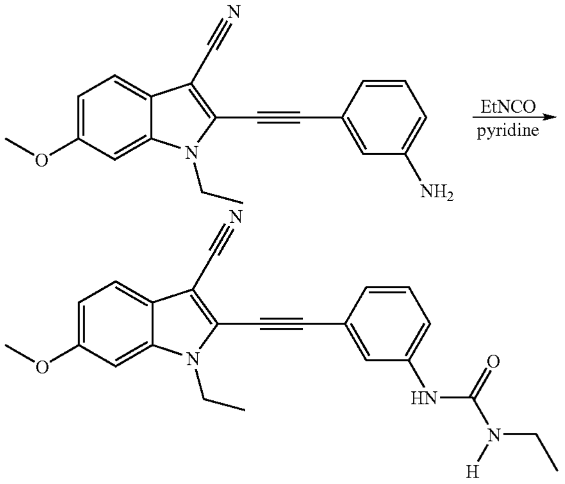

2-(3-Aminophenylethynyl)-1-ethyl-6-methoxy-1H-indole-3-carbonitrile (100 mg, 0.32 mmol), prepared as described in Example 1H, is dissolved in pyridine (670 μL). Ethyl isocyanate (62 μL, 0.75 mmol) is added. The reaction mixture is then heated at 100° C. for 2 h. The mixture is then diluted in EtOAc, and is washed with aqueous HCl, followed by brine. The organic layer is dried and concentrated. Purification by silica chromatography (4/1, $CH_2Cl_2$/EtOAc), followed by trituration with hexanes/acetone (1/1), yields 1-[3-(3-cyano-1-ethyl-6-methoxy-1H-indol-2-ylethynyl)-phenyl]-3-ethyl urea (44 mg, 36%) as a white solid.

Example 1AC

Preparation of 1-(2-chloroethyl)-3-[4-(3-cyano-1-ethyl-6-methoxy-1H-indol-2-ylethynyl)-phenyl]urea (Compound 156)

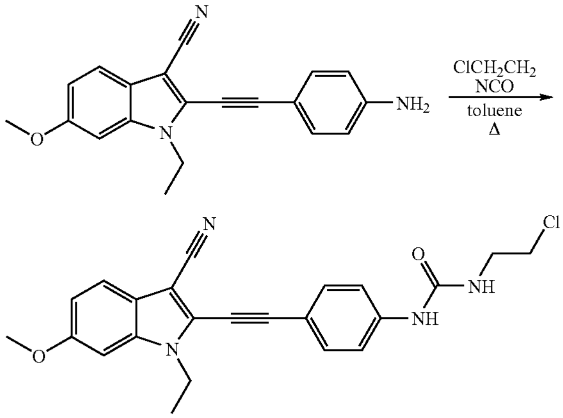

2-(4-Aminophenylethynyl)-1-ethyl-6-methoxy-1H-indole-3-carbonitrile (100 mg, 0.32 mmol), prepared as described in Example 1H, is suspended in toluene (600 μL). 2-Chloroethyl isocyanate (32 μL, 0.37 mmol) is added, and the mixture is heated at 100° C. for 5 h. The reaction mixture is then cooled, diluted in acetone, and absorbed onto silica. Purification by column chromatography (5-10% EtOAc in $CH_2Cl_2$) yields 1-(2-chloro-ethyl)-3-[4-(3-cyano-1-ethyl-6-methoxy-1H-indol-2-ylethynyl)-phenyl]urea (73 mg, 54%) as a yellow solid.

The following compound is prepared using the procedure above: Compound 221.

Example 1AD

Preparation of Ethanesulfonic acid [4-(3-cyano-1-ethyl-6-methoxy-1H-indol-2-ylethynyl)-phenyl]methyl amide (Compound 157)

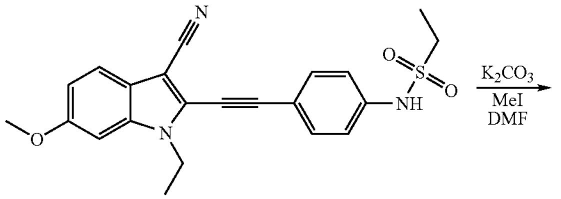

-continued

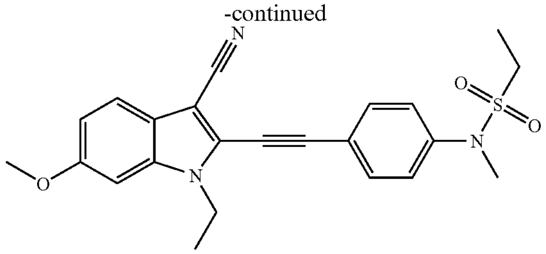

N-[4-(3-cyano-1-ethyl-6-methoxy-1H-indol-2-ylethynyl)phenyl]ethanesulfonamide (70 mg, 0.17 mmol), prepared as in Example 1X, is combined with $K_2CO_3$ (49 mg, 0.35 mmol), and DMF (1.0 mL). Iodomethane (16 μL, 0.26 mmol) is added, and the mixture is stirred at room temperature for 1 hour. The reaction mixture is then diluted in EtOAc, and is washed with $H_2O$ and then brine. The organic layer is dried and concentrated. Purification by silica chromatography (95/5, $CH_2Cl_2$/EtOAc) yields a light tan solid. Trituration gives ethanesulfonic acid [4-(3-cyano-1-ethyl-6-methoxy-1H-indol-2-ylethynyl)-phenyl]methyl amide (61 mg, 85%) as an orange-white solid.

The following compounds are prepared using the procedure above, substituting the appropriate sulfonamide: Compound 182, 652, 840.

Example 1AE

Preparation of 1-ethyl-5-methoxy-2-[4-(morpholine-4-carbonyl)-phenyl]-1H-indole-3-carbonitrile (Compound 245)

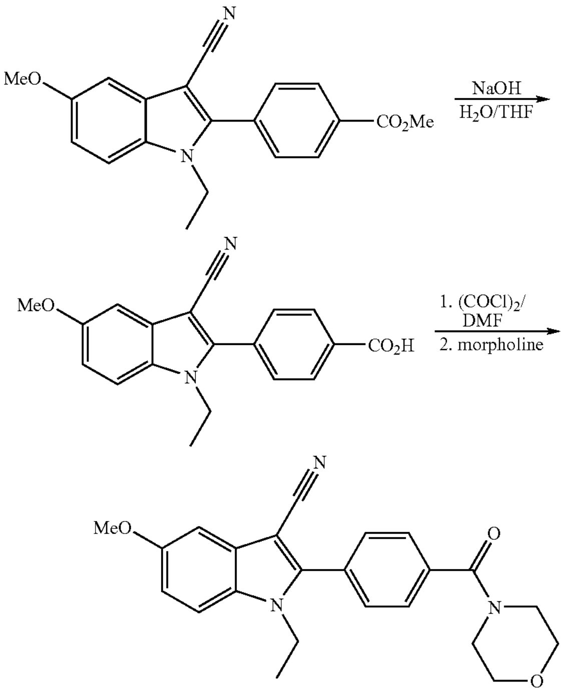

Step A: Methyl 4-(3-cyano-1-ethyl-5-methoxy-1H-indol-2-yl)-benzoate (350 mg, 1.05 mmol), prepared as described in Example 1Ga step B, is combined with NaOH (40 mg, 1 mmol), $H_2O$ (0.8 mL), and THF (3.4 mL) and is heated at 80° C. for 1 hour. The reaction mixture is diluted in $H_2O$ and is then ether-washed. The aqueous layer is acidified with aqueous HCl, and is extracted into EtOAc. The organic layer is dried and concentrated to yield 4-(3-cyano-1-ethyl-6-methoxy-1H-indol-2-yl)-benzoic acid (311 mg, 92%) as a pure white solid.

Step B: 4-(3-cyano-1-ethyl-6-methoxy-1H-indol-2-yl)-benzoic acid (50 mg, 0.16 mmol) is suspended in $CH_2Cl_2$ (2.2 mL) and catalytic DMF (2 μL). Oxalyl chloride (22 μL, 0.25 mmol) is added. The reaction mixture is stirred at room temperature for 1 hour, at which time full dissolution occurred. This reaction mixture is pipetted dropwise into a vigorously stirring solution of morpholine (1.0 mL) in $CH_2Cl_2$ (5 ml). After addition is complete, the reaction mixture is washed with aqueous HCl solution. The organic layer is dried and concentrated. Purification by silica column (1:1 $CH_2Cl_2$/EtOAc) yields 1-ethyl-6-methoxy-2-[4-(morpholine-4-carbonyl)-phenyl]-1H-indole-3-carbonitrile (56 mg, 90%) as a white solid.

The following compounds are prepared similarly as described above: Compounds 113, 114, 246, 270, 271 290, 291, 292, 323, 377, 378, 379, 380, 381, 382, 384, 385, 386, 387, 388, 389, 390, 391, 392, 432, 433, 564, 568, 569, 570, 571, 572, 573, 647, 648, 853, 860, 861, 862.

Example 1AF

Preparation of cyclopropanecarboxylic acid [4-(3-cyano-1-ethyl-6-hydroxy-1H-indol-2-ylethynyl)-phenyl]amide (Compound 194)

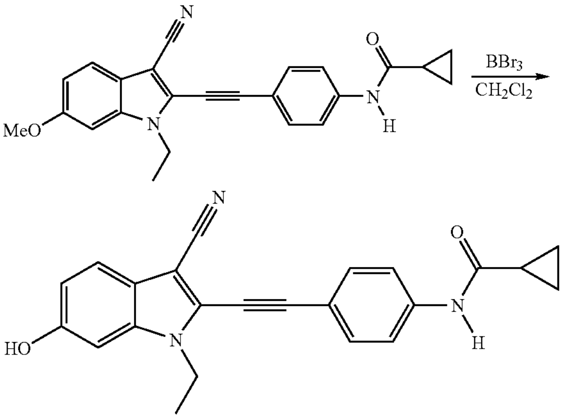

Cyclopropanecarboxylic acid [4-(3-cyano-1-ethyl-6-methoxy-1H-indol-2-ylethynyl)-phenyl]-amide (60 mg, 0.16 mmol), prepared as described in Example 1Za, is stirred in $BBr_3$ (800 μL, 1M in $CH_2Cl_2$, 0.8 mmol) at room temperature for 1 hour. The reaction mixture is quenched with $H_2O$, and is extracted with $CH_2Cl_2$. The organic layer is dried and concentrated. Purification by silica chromatography (EtOAC) gives impure product. This crude product is triturated with 1/1 hexanes/acetone to yield cyclopropanecarboxylic acid [4-(3-cyano-1-ethyl-6-hydroxy-1H-indol-2-ylethynyl)-phenyl]-amide (32 mg, 54%) as an off-white solid.

The following compounds are prepared using the procedure above, substituting the appropriate sulfonamides (from Example 1X) or amides (from Example 1Z): Compounds 164, 168, 183, 193, 195.

Example 1AG

Preparation of 1-ethyl-6-methoxy-2-[4-(2-oxo-imidazolidin-1-yl)-phenylethynyl]-1H-indole-3-carbonitrile (Compound 166)

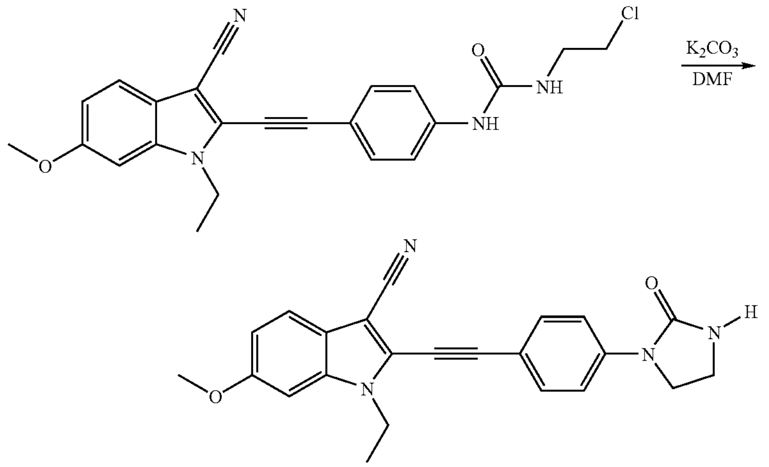

1-(2-Chloroethyl)-3-[4-(3-cyano-1-ethyl-6-methoxy-1H-indol-2-ylethynyl)-phenyl]urea (55 mg, 0.13 mmol), prepared as in Example 1AC, is combined with $K_2CO_3$ (50 mg, 0.36 mmol) and DMF (550 μL). This mixture is stirred at room temperature for 3 hours. The reaction mixture is diluted in EtOAc, and is washed with $H_2O$, and then with brine. The organic layer is dried and concentrated. Purification by silica chromatography (10-50%, EtOAc/$CH_2Cl_2$) yields 1-ethyl-6-methoxy-2-[4-(2-oxo-imidazolidin-1-yl)-phenylethynyl]-1H-indole-3-carbonitrile (47 mg, 94%) as a white solid.

The following compound is prepared using the above procedure, substituting the appropriate urea: Compound 222.

Example 1AH

Preparation of N-[4-(3-cyano-1-ethyl-6-methoxy-1H-indol-2-ylethynyl)-phenyl]-dimethylphosphinic amide (Compound 227)

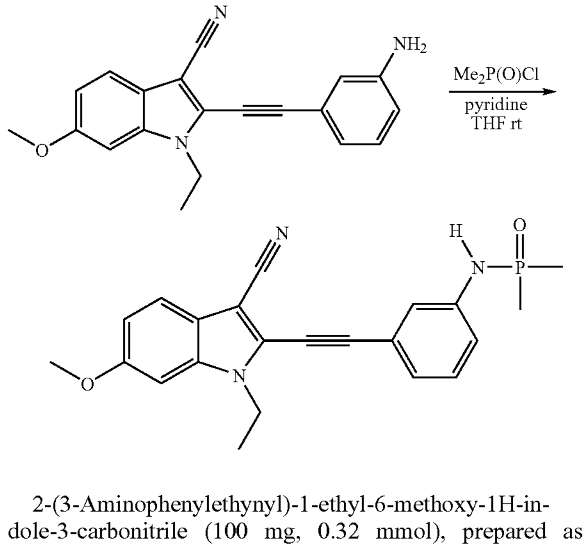

2-(3-Aminophenylethynyl)-1-ethyl-6-methoxy-1H-indole-3-carbonitrile (100 mg, 0.32 mmol), prepared as described in Example 1H, is dissolved in pyridine (300 μL) at 0° C. Dimethylphosphinic chloride (60 mg, 0.53 mmol) in THF (300 μL) is added. The reaction is stirred at room temperature for 2 hours. The reaction mixture is diluted in EtOAc, and is washed with aqueous HCl followed by brine. The organic layer is dried and concentrated. Purification by silica chromatography (acetone) yields N-[4-(3-cyano-1-ethyl-6-methoxy-1H-indol-2-ylethynyl)-phenyl]-dimethylphosphinic amide (65 mg, 52%), compound 227, as a pure white solid. The silica column is then flushed with 9/1 $CH_2Cl_2$/MeOH to yield 9 mg of N-[4-(3-cyano-1-ethyl-6-methoxy-1H-indol-2-ylethynyl)-phenyl]-bis-(dimethylphosphinic) amide as a by-product.

Example 1AI

Preparation of 1-ethyl-6-methoxy-3-[5-(4-methoxyphenyl)-isoxazol-3-yl]-1H-indole (Compound 116)

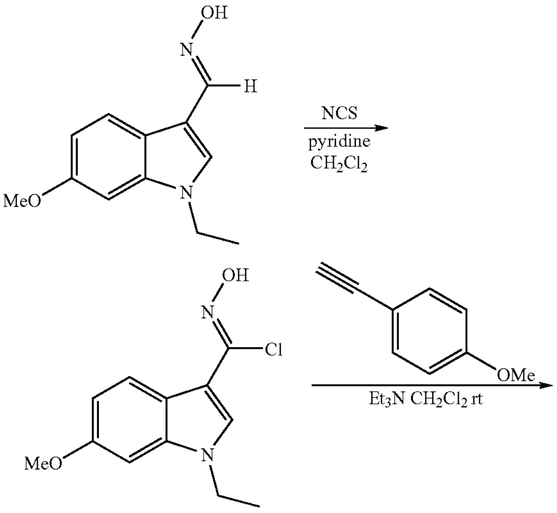

-continued

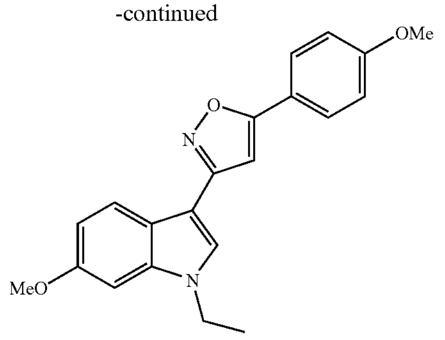

Step A: A mixture of 1-ethyl-6-methoxy-1H-indole-3-carbaldehyde oxime (0.20 g, 0.92 mmol), prepared from the aldehyde precursor in example 1R, in dichloroethane (3 mL) is treated with N-chlorosuccinimide (0.12 g, 0.92 mmol) and pyridine (0.04 mL, 0.46 mmol) and stirred at room temperature for 1 h. The reaction mixture is then poured into $H_2O$ and acidified with 1N HCl until the pH is 2. The mixture is extracted with EtOAc and the organic phases are washed with $H_2O$ and saturated NaCl and dried and concentrated to a mixture of chlorooximes, which are used in the next step without further purification.

Step B: The mixture of chlorooximes prepared above is dissolved in $CH_2Cl_2$ (5 mL) and to this is added 4-methoxyphenylacetylene (0.24 g, 1.84 mmol) and triethylamine (0.25 mL, 1.84 mmol) at 0° C. and the reaction is then stirred overnight warming to room temperature. The reaction is then diluted with $H_2O$ and extracted with EtOAc (3×). The organic phases are washed with $H_2O$ and saturated NaCl and dried and concentrated. Chromatography over silica gel (EtOAc/hexanes, 10-20%) gives 76 mg (24%) of 1-ethyl-6-methoxy-3-[5-(4-methoxy-phenyl)-isoxazol-3-yl]-1H-indole as a tan solid.

Example 1AJ

Preparation of [4-(3-cyano-1-ethyl-6-methoxy-1H-indol-2-yl)-phenyl]-carbamic acid ethyl ester (Compound 121)

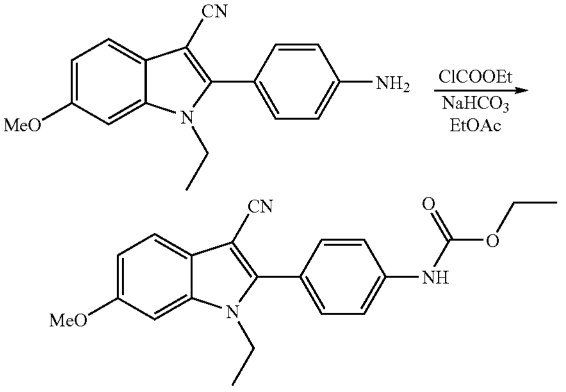

A biphasic mixture of 2-(4-amino-phenyl)-1-ethyl-6-methoxy-1H-indole-3-carbonitrile (70 mg, 0.24 mmol), prepared as described in example 1Ga step B, and ethyl chloroformate (0.03 mL, 0.29 mmol) in EtOAc (3 mL) and saturated $NaHCO_3$ (3 mL) is prepared at 0° C. and then allowed to warm to room temperature and stirred for 24 h. The reaction is then diluted with $H_2O$ and extracted with EtOAc (2×). The organic phases are washed with $H_2O$ and saturated NaCl and then dried and concentrated. Flash chromatography (EtOAc/hexanes 20-40%) gives 48 mg (55%) of [4-(3-cyano-1-ethyl-6-methoxy-1H-indol-2-yl)-phenyl]-carbamic acid ethyl ester as an off-white solid.

The following compounds are prepared in similar fashion: Compound 122, 293, 294, 296, 297, 298, 299, 300, 301, 302, 303, 304, 305, 306, 307, 308, 309, 310, 311, 312, 313, 314, 315, 316, 317, 318, 319, 320, 321, 349, 350, 351, 352, 353, 354, 355, 356, 357, 358, 359, 360, 361, 372, 434, 435, 450, 453, 454, 455, 457, 485, 486, 489, 490, 500, 501, 502, 503, 506, 507, 508, 509, 545, 546, 547, 553, 554, 555, 556, 557, 581, 582, 583, 584, 585, 585, 586, 587, 588, 589, 590, 591, 592, 593, 594, 595, 596, 597, 603, 604, 605, 606, 607, 618, 619, 624, 625, 637, 640, 641, 664, 665, 676, 677, 721, 722, 723, 734, 735, 736, 737, 738, 739, 744, 745, 746, 747, 787, 788, 792, 793, 794, 795, 796, 797, 819, 822, 823, 824, 825, 826, 849, 925, 926, 945, 946, 947, 948, 949, 950, 951, 970, 971, 972, 973, 974, 975, 976, 977, 978, 979, 981, 984, 985, 986, 991, 992, 993, 1015, 1020, 1021, 1022, 1029, 1030, 1031, 1032, 1033, 1034, 1037, 1040, 1042, 1044, 1055, 1056, 1057, 1058, 1059, 1062, 1063, 1064, 1065. 1071, 1073, 1074, 1075, 1077, 1078, 10791107, 1109, 1111, 1112, 1113, 1114, 1122, 1127, 1128, 1129, 1145, 1148, 1149, 1150, 1151, 1152, 1153, 1154, 1169, 1174, 1176, 1177, 1178, 1179, 1180, 1186, 1193, 1194, 1195, 1196, 1197, 1198, 1199, 1200, 1201, 1202, 1203, 1204, 1205, 1206, 1207, 1211, 1222, 1232, 1233, 1300, 1302.

Example 1AK

Preparation of 1-ethyl-5-thiophen-3-yl-1H-indole-3-carbonitrile (Compound 141)

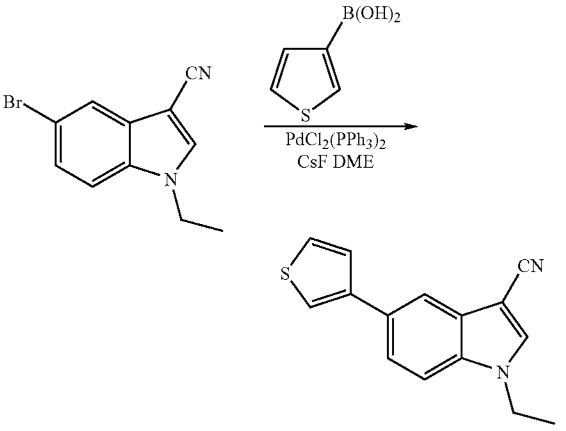

A tube is charged with a mixture of 5-bromo-1-ethyl-1H-indole-3-carbonitrile (100 mg, 0.40 mmol), thiophene-3-boronic acid (72 mg, 0.56 mmol), $PdCl_2(PPh_3)_2$ (11 mg, 0.016 mmol) and CsF (152 mg, 1 mmol) and then alternately evacuated and filled with nitrogen (3×) and diluted with dimethoxyethane (3 mL) and then heated to 90° C. for 19 h. After cooling, the crude reaction mixture is diluted with saturated $NaHCO_3$ and extracted with EtOAc (2×). The combined organic phases are washed with saturated NaCl and dried and concentrated. Flash chromatography over silica gel ($CH_2Cl_2$/hexanes, 40/60) gives 25 mg (25%) of 1-ethyl-5-thiophen-3-yl-1H-indole-3-carbonitrile as a white solid.

The following compounds are prepared in similar fashion: Compounds 140 and 142.

Example 1AL

Preparation of N-[4-(3-cyano-1-ethyl-6-methoxy-1H-indol-2-yl)-phenyl]-N-methyl methanesulfonamide (Compound 180)

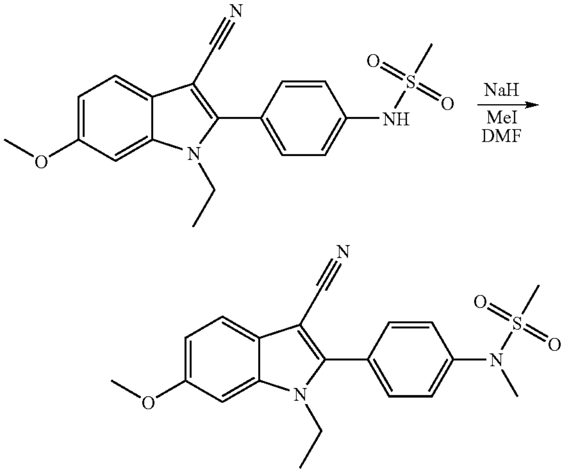

A solution of N-[4-(3-cyano-1-ethyl-6-methoxy-1H-indol-2-yl)-phenyl]methanesulfonamide (130 mg, 0.35 mmol), prepared as in Example 1Y, in DMF (10 mL) is treated with NaH (21 mg, 0.53 mmol), and stirred at room temperature for 10 min. Iodomethane (0.03 mL, 0.53 mmol) is added, and the mixture is stirred at room temperature for 18 h. The reaction mixture is then diluted with $H_2O$, and extracted with EtOAc (2×). The organic phases are washed with $H_2O$ and saturated NaCl and then dried and concentrated. Purification by flash chromatography over silica gel (EtOAc/$CH_2Cl_2$, 0-1%) gives 60 mg (45%) of N-[4-(3-cyano-1-ethyl-6-methoxy-1H-indol-2-yl)-phenyl]-N-methyl methanesulfonamide as a white solid.

In similar fashion the following compounds are prepared: Compounds 181, 642, 643, 672, 673, 816, 852, 1002, 1003, 1004, 1005, 1006, 1007.

Example 1AM

Preparation of N-[4-(3-cyano-1-ethyl-6-hydroxy-1H-indol-2-yl)-phenyl]-methanesulfonamide (Compound 189)

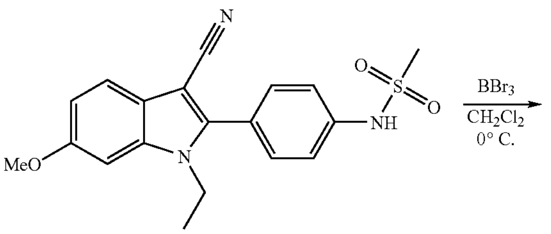

-continued

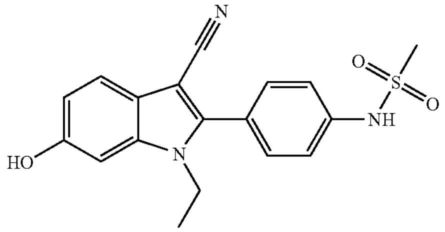

A solution of N-[4-(3-cyano-1-ethyl-6-methoxy-1H-indol-2-yl)-phenyl]methanesulfonamide (85 mg, 0.23 mmol) in $CH_2Cl_2$ (2 mL) is cooled to −5° C. A solution of boron tribromide (1.15 mL, 1.15 mmol, 1M solution in $CH_2Cl_2$) is added and the reaction mixture is allowed to warm to 10° C. over 4 h. The reaction mixture is poured into $H_2O$ and extracted with EtOAc (3×). The combined organic phases are washed with $H_2O$ and saturated NaCl and dried and concentrated. Chromatography over silica gel (EtOAc/$CH_2Cl_2$, 5-10%) gives 18 mg (22%) of N-[4-(3-cyano-1-ethyl-6-hydroxy-1H-indol-2-yl)-phenyl]methanesulfonamide as a tan solid.

The following compounds are made similarly: Compounds 190, 191, 192.

Example 1AN

Preparation of methyl 3-[5-(3-cyano-6-methoxy-1H-indol-2-yl)-[1,2,4]oxadiazol-3-yl]benzoate (Compound 226)

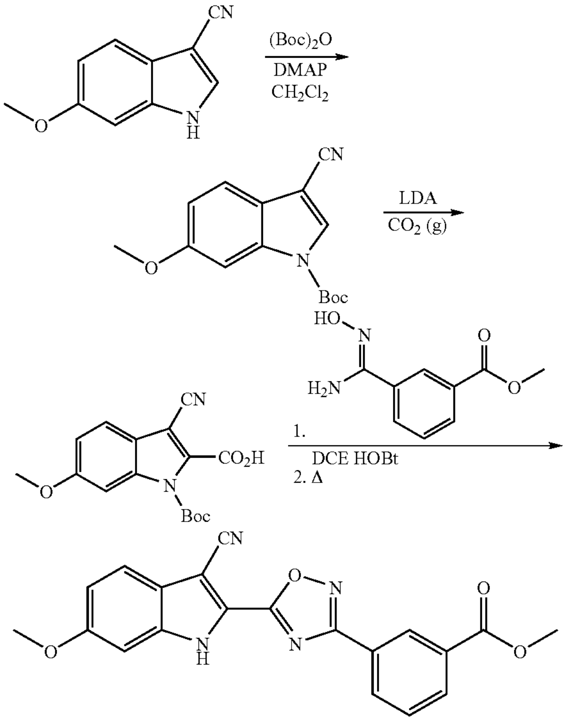

Step A: To a mixture of 6-methoxy-1H-indole-3-carbonitrile (5.88 g, 40 mmol), prepared as described in the previous examples, and $(Boc)_2O$ (9.59 g, 44.0 mmol) in DCM (50 mL)

is added DMAP (0.10 g, 0.8 mmol). The mixture is stirred at room temperature for 48 h, then treated with water (30 mL) and dried over anhydrous $Na_2SO_4$. The crude product is chromatographed over silica gel (hexanes/EtOAc, 7/1) to furnish the desired intermediate, 3-cyano-6-methoxyindole-1-carboxylic acid tert-butyl ester (8.48 g, 86%).

Step B: The above intermediate (2.72 g, 10.0 mmol) is dissolved in anhydrous THF (20 mL), and cooled at −78° C., followed by the addition of LDA (1.5 M monoTHF in cyclohexane, 10.0 mL, 15 mmol). After stirring for 45 min, $CO_2$ gas is introduced for 2 h. The mixture is then brought to room temperature and the solvent is removed in vacuo, and the residue is treated with water and acidified to pH=2 with 6 N HCl. The precipitate is collected and washed with water and dried to provide the acid intermediate, 3-cyano-6-methoxyindole-1,2-dicarboxylic acid 1-tert-butyl ester (2.40 g, 73%).

Step C: To a solution of 3-cyano-6-methoxyindole-1,2-dicarboxylic acid 1-tert-butyl ester (474 mg, 1.5 mmol) prepared above, and HOBt (200 mg, 1.5 mmol) in DCE/DMF (10 mL/1 mL), is added DCC (310 mg, 1.5 mmol), followed by 3-(N-hydroxycarbamimidoyl)benzoic acid methyl ester (291 mg, 1.5 mmol). The mixture is stirred at room temperature for 2 h and filtered. The filtrate is collected and the solvent is replaced with chlorobenzene, followed by the heating at 150° C. for 48 h. After cooling to room temperature, the solvent is removed in vacuo and the residue is chromatographed (silica gel, $CH_2Cl_2$/EtOAc, 8/2) to furnish the intermediate, 3-cyano-6-methoxy-2-[3-(3-methoxycarbonylphenyl)-[1,2,4]oxadiazol-5-yl]-indole-1-carboxylic acid tert-butyl ester, which is treated with 50% TFA in DCM (10.0 mL) at room temperature for 1 h. After removal of the volatiles in vacuo, the residue is suspended in water and neutralized with $K_2CO_3$ to provide the desired product, methyl 3-[5-(3-cyano-6-methoxy-1H-indol-2-yl-)[1,2,4]oxadiazol-3-yl]benzoate, compound 226 (350 mg, 62%).

Example 1AO

Preparation of 1-ethyl-2-(4-methanesulfonylphenyl)-6-methoxy-1H-indole-3-carbonitrile (Compound 265)

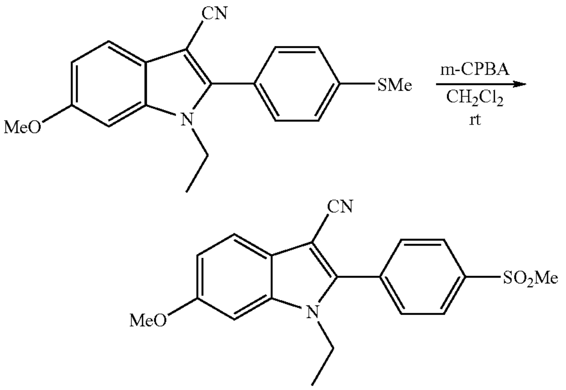

A solution of 1-ethyl-6-methoxy-2-(4-methylsulfanylphenyl)-1H-indole-3-carbonitrile (0.12 g, 0.37 mmol) in $CH_2Cl_2$ (5 mL) is treated with m-chloroperbenzoic acid (Aldrich, <77%, 0.26 g,) in one portion and the reaction is stirred for 10 h at room temperature. The reaction is then diluted with $H_2O$ and saturated $NaHCO_3$ and extracted twice with EtOAc. The organic phases are washed with $NaHCO_3$ (2×) and saturated NaCl and dried and concentrated to a dark semi-solid. The crude product is purified by flash chromatography (EtOAc/$CH_2Cl_2$, 0-3%) through a 5 gram silica cartridge topped with 1 gram of basic alumina to give 72 mg (55%) of 1-ethyl-6-methoxy-2-(4-methylsulfanylphenyl)-1H-indole-3-carbonitrile as an off-white solid.

Example 1AP

Preparation of N-{4-[3-cyano-1-ethyl-6-(2-morpholin-4-yl-ethoxy)-1H-indol-2-yl]-phenyl}methanesulfonamide (Compound 478)

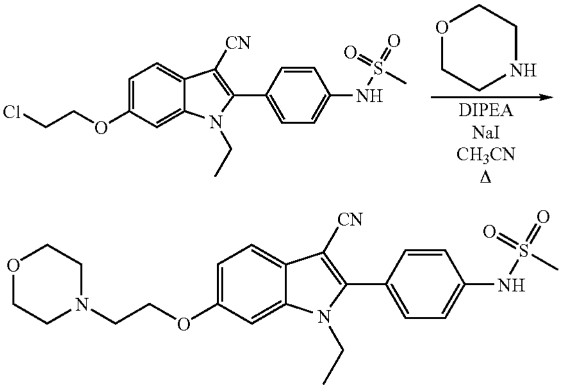

A solution of N-{4-[6-(2-chloroethoxy)-3-cyano-1-ethyl-1H-indol-2-yl]-phenyl}methanesulfonamide (90 mg, 0.21 mmol), morpholine (0.06 mL, 0.65 mmol), NaI (32 mg, 0.21 mmol) and diisopropyl ethylamine (0.06 mL, 0.32 mmol) in $CH_3CN$ (2 mL) is heated in a sealed tube at 100° C. for 25 h. The reaction mixture is cooled to room temperature, diluted with $H_2O$ and extracted with EtOAc (3×). The combined organic phases are washed with saturated NaCl, dried and concentrated. The crude solid is triturated with EtOAc and filtered to give 41 mg (41%) of N-{4-[3-cyano-1-ethyl-6-(2-morpholin-4-yl-ethoxy)-1H-indol-2-yl]-phenyl}methanesulfonamide as a tan solid.

The following compounds are made similarly: Compounds 479, 480, 481, 482, 496, 497 and 498.

Example 1AQ

Preparation of 2-morpholin-4-yl-ethanesulfonic acid [4-(3-cyano-1-ethyl-6-methoxy-1H-indol-2-yl)-phenyl]amide (Compound 653)

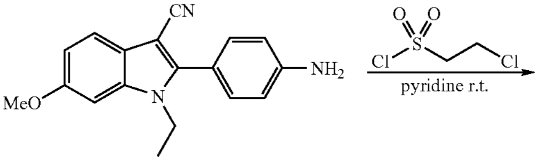

-continued

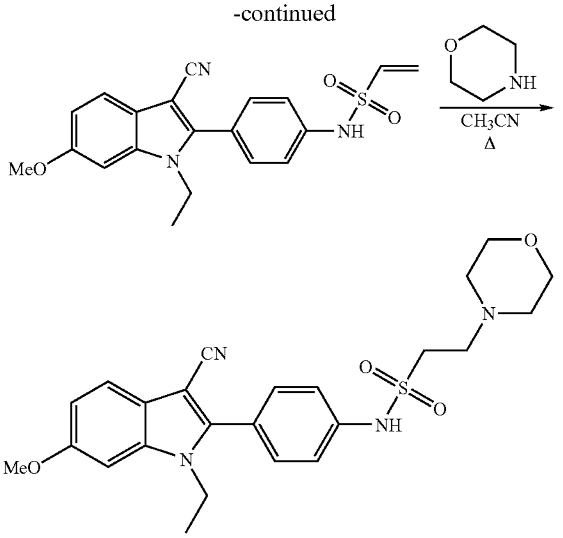

Step A: A solution of 2-(4-aminophenyl)-1-ethyl-6-methoxy-1H-indole-3-carbonitrile, prepared by example 1Ga step B, (0.82 mg, 2.82 mmol), in pyridine (10 mL) is treated dropwise with chloroethyl sulfonylchloride (0.38 mL, 3.66 mmol) at room temperature. After stirring for 4 h, the reaction mixture is quenched with ice-water and enough 6N HCl is added until the pH is lowered to 2. The suspension is extracted with hot EtOAc (3×). The organic phases are then washed sequentially with 1N HCl, $H_2O$ and saturated NaCl and dried and concentrated to give ethenesulfonic acid [4-(3-cyano-1-ethyl-6-methoxy-1H-indol-2-yl)-phenyl]amide as a pale orange solid which is used directly in the next step without further purification.

Step B: A suspension of ethenesulfonic acid [4-(3-cyano-1-ethyl-6-methoxy-1H-indol-2-yl)-phenyl]amide, prepared above, (70 mg, 0.18 mmol), morpholine (0.05 mL, 0.55 mmol) in $CH_3CN$ (1.5 mL) is heated at reflux for 1.5 h. After cooling to room temperature, the reaction is concentrated and the residue is purified by flash chromatography (acetone/EtOAc, 2/98) over silica gel to afford 89 mg (100%) of 2-morpholin-4-yl-ethanesulfonic acid [4-(3-cyano-1-ethyl-6-methoxy-1H-indol-2-yl)-phenyl]amide as a tan foam.

The following compound is made similarly: Compound 654.

Example 1AR

Preparation of 2-morpholin-4-yl-ethanesulfonic acid [4-(3-cyano-1-ethyl-6-methoxy-1H-indol-2-yl)-phenyl]methyl amide (Compound 668)

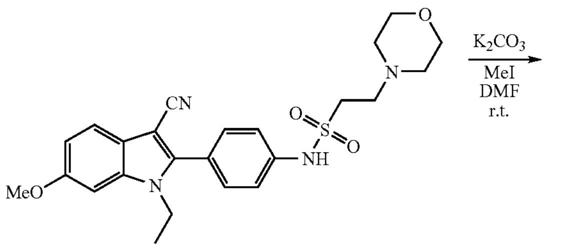

-continued

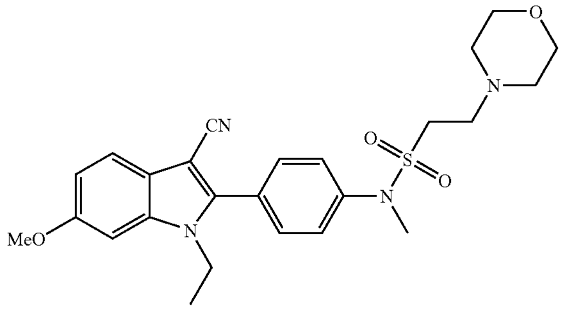

A solution of 2-morpholin-4-yl-ethanesulfonic acid [4-(3-cyano-1-ethyl-6-methoxy-1H-indol-2-yl)-phenyl]amide, prepared in example 1AQ (60 mg, 0.13 mmol) in DMF (3 mL) is treated with $K_2CO_3$ (35 mg, 0.26 mmol) and methyl iodide (0.02 mL, 0.26 mmol). After stirring at room temperature for 1.5 h, the reaction mixture is diluted with $H_2O$ and extracted with EtOAc (2×). The organic phases are then washed with $H_2O$ (3×) and saturated NaCl, and then dried and concentrated to afford a residue. Flash chromatography over silica gel (acetone/EtOAc, 0-2%) gives 31 mg (50%) of 2-morpholin-4-yl-ethanesulfonic acid [4-(3-cyano-1-ethyl-6-methoxy-1H-indol-2-yl)-phenyl]methyl amide as an off white solid.

The following compounds are made similarly: Compounds 684, 685, 686, 687, 688, 689, 690, 691, 692, 693, 694, 695, 696, 697, 698.

Example 1AS

Preparation of 2-[4-(1,1-dioxo-1×6-isothiazolidin-2-yl)phenyl]-1-ethyl-6-methoxy-1H-indole-3-carbonitrile (Compound 84)

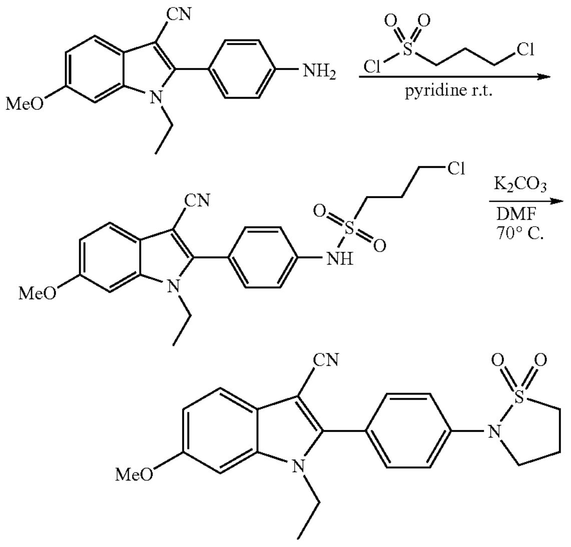

Step A: A solution of 2-(4-aminophenyl)-1-ethyl-6-methoxy-1H-indole-3-carbonitrile, prepared by example 1Ga step B, (2.78 g, 9.55 mmol) in pyridine (40 mL) is treated dropwise with 3-chloropropanesulfonyl chloride (1.45 mL, 11.9 mmol) and the reaction is stirred for 4 h at room temperature. The reaction is diluted with water and enough 6N HCl to lower the pH to 2. The reaction mixture is extracted with EtOAc (3×) and the combined organic layers are washed sequentially with 1N HCl, water and saturated NaCl and then dried and concentrated to give 3.9 g (95%), of 3-chloropropane-1-sulfonic acid [4-(3-cyano-1-ethyl-6-methoxy-1H-indol-2-yl)-phenyl]amide as a brown foam which is used directly in the next step.

Step B: A solution of 3-chloropropane-1-sulfonic acid [4-(3-cyano-1-ethyl-6-methoxy-1H-indol-2-yl)-phenyl]amide, prepared above (3.65 g, 2.33 mmol) in DMF (100 mL) is treated with $K_2CO_3$ and heated at 70° C. for 2 h. After cooling to room temperature, the reaction mixture is diluted with $H_2O$ and extracted 3× with hot EtOAc. The hot organic layers are washed with warm $H_2O$ (3×) and saturated NaCl and dried and concentrated to a solid. Trituration ($CH_2Cl_2$/hexanes) gives 2.27 g (68%) of 2-[4-(1,1-dioxo-1λ$^6$-isothiazolidin-2-yl)phenyl]-1-ethyl-6-methoxy-1H-indole-3-carbonitrile as a light brown solid.

The following compounds are made in similar fashion: Compound 649, 775, 809, 969, 980.

Example 1AT

Preparation of 2-[4-(1,1-dioxo-1λ$^6$-isothiazolidin-2-yl)phenyl]-1-ethyl-6-methoxy-1H-indole-3-carbonitrile (Compound 666)

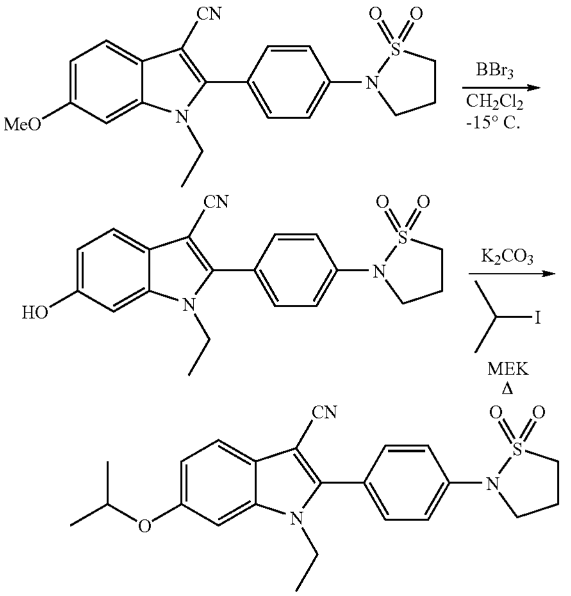

Step A: Following the procedure in example 1B step A, 2-[4-(1,1-dioxo-1λ$^6$-isothiazolidin-2-yl)phenyl]-1-ethyl-6-methoxy-1H-indole-3-carbonitrile is treated with 1M $BBr_3$ solution in $CH_2Cl_2$ at −15° C. for 1.5 h and then poured into ice-water and filtered and dried to afford 2-[4-(1,1-dioxo-1λ$^6$-isothiazolidin-2-yl)phenyl]-1-ethyl-6-hydroxy-1H-indole-3-carbonitrile in nearly quantitative yield.

Step B: Following the procedure in example 1B step B, 2-[4-(1,1-dioxo-1λ$^6$-isothiazolidin-2-yl)phenyl]-1-ethyl-6-hydroxy-1H-indole-3-carbonitrile, $K_2CO_3$, 2-iodopropane and methyl ethyl ketone are heated at reflux to give, after flash chromatography (EtOAc/$CH_2Cl_2$, 0-2%), 61% of 2-[4-(1,1-dioxo-1λ$^6$-isothiazolidin-2-yl)phenyl]-1-ethyl-6-isopropoxy-1H-indole-3-carbonitrile as an off-white solid.

The following compounds are made similarly: Compounds 667, 699.

Example 1AU

Preparation of 2-[4-(1,1-dioxo-1λ$^6$-isothiazolidin-2-yl)-phenyl]-1-ethyl-6-(2-morpholin-4-yl-ethoxy)-1H-indole-3-carbonitrile (Compound 729)

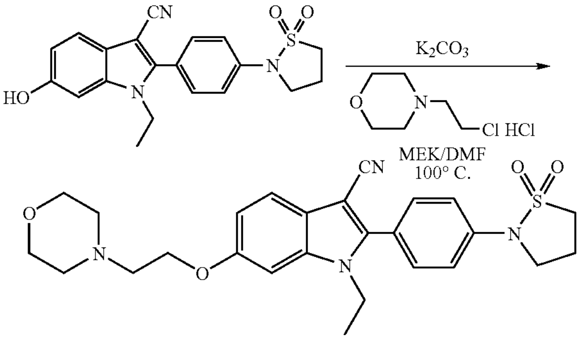

A mixture of 2-[4-(1,1-dioxo-1)$_6$-isothiazolidin-2-yl)phenyl]-1-ethyl-6-hydroxy-1H-indole-3-carbonitrile, prepared in example 1AT above (70 mg, 0.25 mmol), $K_2CO_3$ (75 mg, 0.51 mmol), sodium iodide (27 mg, 0.18 mmol), 4-(2-chloroethyl)morpholine hydrochloride (42 mg, 0.25 mmol) in methyl ethyl ketone (3 mL) is heated in a sealed tube at 100° C. After 13 hours, DMF (3 mL) is added and the reaction is heated for an additional 6 h. After this time, an additional 42 mg of 4-(2-chloroethyl)morpholine hydrochloride and 135 mg of $K_2CO_3$ is added and the reaction is heated for an additional 6 h to complete the reaction. The reaction mixture is cooled to room temperature, diluted with water, and extracted with EtOAc (3×). The combined organic phases are washed with water (2×) and saturated NaCl and dried and concentrated. Pure 2-[4-(1,1-dioxo-1,6-isothiazolidin-2-yl)-phenyl]-1-ethyl-6-(2-morpholin-4-yl-ethoxy)-1H-indole-3-carbonitrile is obtained by flash chromatography (MeOH/$CH_2Cl_2$, 0-6%) to give 29 mg (34%) of a tan solid.

The following compounds are made similarly: Compounds 728 and 730.

Example 1AV

Preparation of 2-[4-(2,5-dioxo-imidazolidin-1-yl)-phenyl]-6-ethoxy-1-ethyl-1H-indole-3-carbonitrile (Compound 779)

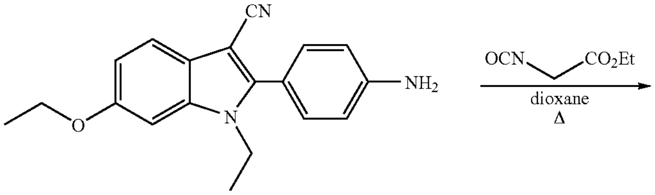

-continued

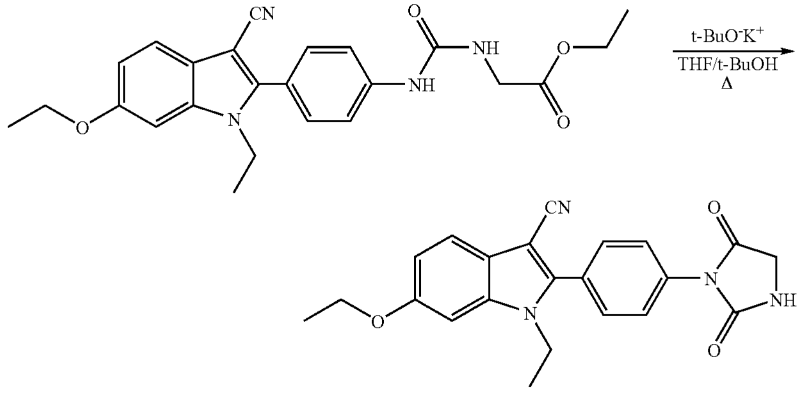

Step A: A solution of 2-(4-aminophenyl)-6-ethoxy-1-ethyl-1H-indole-3-carbonitrile (585 mg, 1.92 mmol) in 10 mL of 1,4-dioxane is treated with ethyl isocyanatoacetate (0.25 mL, 2.12 mmol), and the resulting solution is heated to reflux overnight. The solution is allowed to cool, and the solvent is removed by rotary evaporation. The residual material is triturated with ether, and the resulting precipitate is collected by filtration and dried under vacuum to afford compound 773 (587 mg, 1.35 mmol, 70%).

A similar procedure is used to prepare methyl 2-{3-[4-(3-cyano-6-ethoxy-1-ethyl-1H-indol-2-yl)-phenyl]-ureido}-3-phenyl-propionate (compound 777).

Step B: A solution of ethyl {3-[4-(3-cyano-6-ethoxy-1-ethyl-1H-indol-2-yl)-phenyl]-ureido}-acetate (compound 773, 101 mg, 0.232 mmol) in THF (10 mL) is treated with a solution of potassium tert-butoxide in tert-butanol (0.30 mL, 1.0 M, 0.30 mmol), and the resulting mixture is allowed to stir overnight. The reaction mixture is partitioned between water and ethyl acetate (50 mL each), and the organic phase is washed with saturated brine. The aqueous phases are extracted with more ethyl acetate, and the extracts are combined, dried over anhydrous magnesium sulfate, filtered and evaporated. The residual material is separated by column chromatography (eluting 2/1 ethyl acetate/hexane on silica gel 60) to afford 2-[4-(2,5-dioxo-imidazolidin-1-yl)-phenyl]-6-ethoxy-1-ethyl-1H-indole-3-carbonitrile, compound 779, which is purified further by trituration with ether, collection by filtration and drying under high vacuum (76 mg, 0.196 mmol, 84%).

Example 1AW

Preparation of 2-[4-(2,4-dioxo-imidazolidin-1-yl) phenyl]-6-ethoxy-1-ethyl-1H-indole-3-carbonitrile (Compound 776)

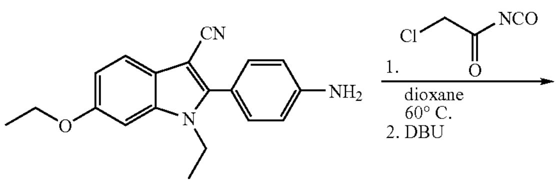

-continued

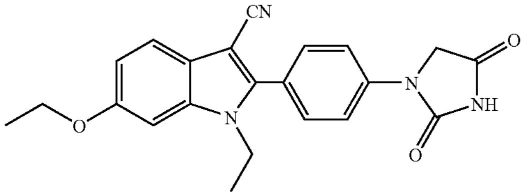

A solution of 2-(4-aminophenyl)-6-ethoxy-1-ethyl-1H-indole-3-carbonitrile (319 mg, 1.04 mmol) in 1,4-dioxane (3 mL) is treated with chloroacetyl isocyanate (0.10 mL, 1.17 mmol), and the resulting solution is warmed to 60° C. overnight. The solution is cooled, and DBU (0.20 mL, 1.31 mmol) is added. This mixture is stirred at ambient temperature overnight, and then is partitioned between water and ethyl acetate (50 mL each). The organic layer is washed with saturated brine, and then dried over anhydrous magnesium sulfate, filtered and evaporated. The residual material is triturated with ether, and the resulting solid is collected by filtration and dried under high vacuum to afford the title product (319 mg, 0.821 mmol, 79%).

Example 1AX

Preparation of N,N-Dimethyl-2-[4-(3,4-dimethyl-2,5-dioxo-imidazolidin-1-yl)-phenyl]-6-ethoxy-1-ethyl-1H-indole-3-carboxamide (Compound 780) and N,N-Dimethyl-6-ethoxy-1-ethyl-2-[4-(3-methyl-2,5-dioxo-imidazolidin-1-yl)-phenyl]-1H-indole-3-carboxamide (Compound 781)

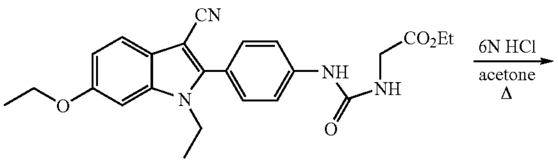

-continued

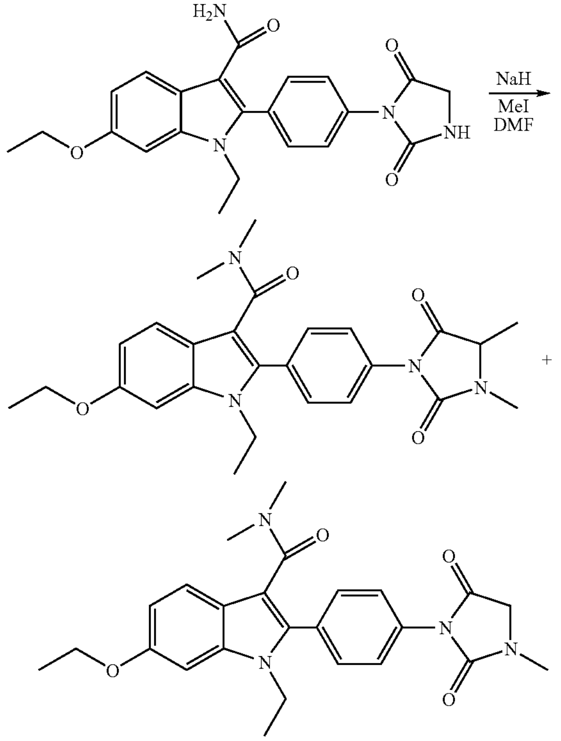

Step A. A solution of ethyl {3-[4-(3-cyano-6-ethoxy-1-ethyl-1H-indol-2-yl)-phenyl]-ureido}acetate (compound 773, 325 mg, 0.748 mmol), prepared in procedure 1AV, step A, in acetone (5 mL) is treated with HCl (3 mL, 6 N), and the resulting solution is heated to reflux overnight. The reaction mixture is cooled, and the resulting precipitate is collected by filtration, washed with ether and dried under high vacuum to afford the product, 6-ethoxy-1-ethyl-2-[4-(2,5-dioxo-imidazolidin-1-yl)-phenyl]-1H-indole-3-carboxamide (264 mg, 0.650 mmol, 87%).

Step B. Sodium hydride dispersion in mineral oil (75 mg) is washed with a small portion of hexane, and the hexane layer is decanted off. A solution of 6-ethoxy-1-ethyl-2-[4-(2,5-dioxo-imidazolidin-1-yl)-phenyl]-1H-indole-3-carboxamide (190 mg, 0.468 mmol) in dimethylformamide (2 mL) is added, and the mixture is stirred for 1 hour. Then, methyl iodide (0.10 mL, 1.61 mmol) is added by syringe. The resulting mixture is allowed to stir at ambient temperature overnight and then is poured into 50 mL of ethyl acetate. The organic phase is washed with water (3×50 mL) and saturated brine (20 mL), then dried over anhydrous magnesium sulfate, filtered and evaporated. The residual material is separated by column chromatogaphy (1/1 ethyl acetate/hexane, eluting on silica gel 60) to afford the title products, compounds 780 and 781.

Example 1AY

Preparation of N-[4-(3-cyano-1-ethyl-6-methoxy-1H-indol-2-yl)-phenyl]-N-(2-hydroxyethyl)-methanesulfonamide (Compound 828)

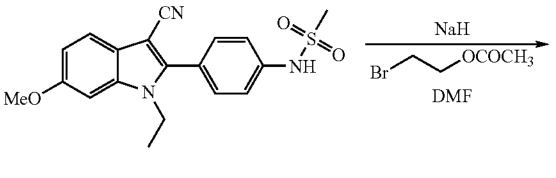

-continued

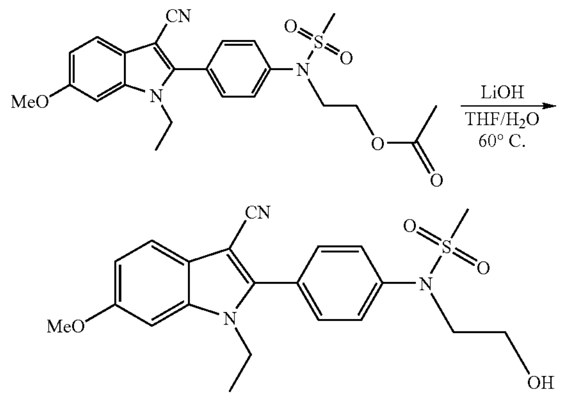

Step A: Sodium hydride dispersion in mineral oil (108 mg) is washed with a small portion of hexane, and the hexane layer is decanted off. A solution of N-[4-(3-cyano-1-ethyl-6-methoxy-1H-indol-2-yl)-phenyl]methanesulfonamide (compound 129, 500 mg, 1.35 mmol) in DMF (5 mL) is slowly added. After gas evolution is complete, 2-bromoethyl acetate (0.30 mL, 2.64 mmol) and sodium iodide (20 mg) are added. The mixture is stirred at ambient temperature overnight, and then is poured into 50 mL of ethyl acetate. This is washed with water (3×50 mL) and saturated brine (20 mL), then dried over anhydrous magnesium sulfate, filtered and evaporated. The residual material is separated by column chromatogaphy (1/1 ethyl acetate/hexane, eluting on silica gel 60) to afford compound 815 (364 mg, 0.799 mmol, 59%).

Step B: A mixture of N-(2-acetoxyethyl)-N-[4-(3-cyano-1-ethyl-6-methoxy-1H-indol-2-yl)-phenyl]methanesulfonamide (compound 815, 164 mg, 0.360 mmol) and lithium hydroxide hydrate (45 mg, 1.07 mmol) in 5 mL THF/1 mL water is warmed to 60° C. overnight. The mixture is cooled and poured into ethyl acetate (50 mL). This is washed with water (50 mL) and brine (20 mL), dried over anhydrous magnesium sulfate, filtered and evaporated to afford a solid. The solid is triturated with ether, collected by filtration and dried under high vacuum to afford N-[4-(3-cyano-1-ethyl-6-methoxy-1H-indol-2-yl)-phenyl]-N-(2-hydroxyethyl)methanesulfonamide, compound 828 (137 mg, 0.331 mmol, 92%).

Example 1 AZ

Preparation of 1-ethyl-6-methoxy-2-[4-(2-methoxyethoxy)-phenyl]-1H-indole-3-carbonitrile (Compound 248)

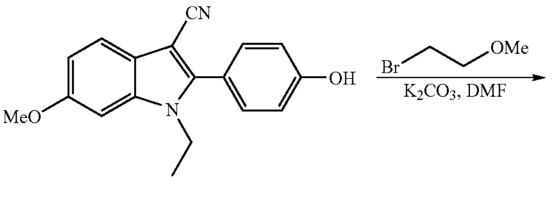

-continued

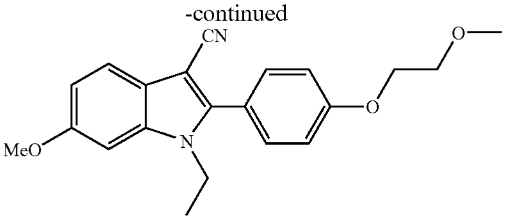

1-Ethyl-2-(4-hydroxy-phenyl)-6-methoxy-1H-indole-3-carbonitrile (40 mg, 0.14 mmol), prepared as in example 1Ga step B, is combined with $K_2CO_3$ (77 mg, 0.56 mmol), bromoethyl methyl ether (26 μL, 0.28 mmol), and DMF (450 μL). This is stirred at room temperature for 1 hour, and then at 75° C. for 3 hours. The reaction mixture is then partitioned between $H_2O$ and EtOAc. The organic layer is dried and concentrated. Purification by silica gel chromatography ($CH_2Cl_2$, 0-5% EtOAc) yields 1-ethyl-6-methoxy-2-[4-(2-methoxyethoxy)-phenyl]-1H-indole-3-carbonitrile (44 mg, 90%) as a white solid.

The following compound is prepared similarly as above: Compound 249.

Example 1BA

Preparation of 1-ethyl-6-methoxy-2-[4-(2-morpholin-4-yl-ethoxy)-phenyl]-1H-indole-3-carbonitrile (Compound 261)

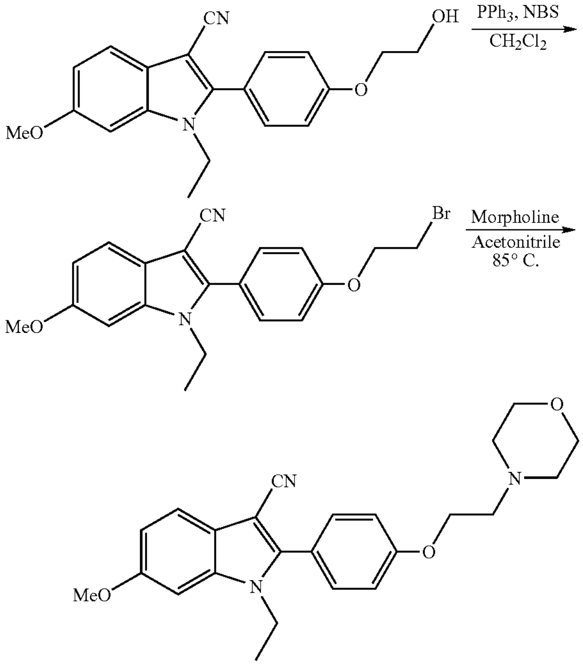

Step A: 1-Ethyl-6-methoxy-2-[4-(2-hydroxyethoxy)-phenyl]-1H-indole-3-carbonitrile (450 mg, 1.34 mmol), prepared as in example 1AZ, is combined with $PPh_3$ (878 mg, 3.35 mmol) in $CH_2Cl_2$ (32 mL) at 0° C. N-bromosuccinimide (600 mg, 3.37 mmol) is added in one portion. The reaction mixture is stirred at room temperature for 30 minutes. The reaction mixture is washed with aqueous $NaHCO_3$. The organic layer is dried and concentrated, and purified by silica gel chromatography ($CH_2Cl_2$) to yield 2-[4-(2-bromoethoxy)-phenyl]-1-ethyl-6-methoxy-1H-indole-3-carbonitrile (506 mg, 95%), compound 253 as a white solid.

Step B: 2-[4-(2-bromoethoxy)-phenyl]-1-ethyl-6-methoxy-1H-indole-3-carbonitrile (40 mg, 0.1 mmol), prepared as in step A above, is combined with morpholine (50 μL, 0.58 mmol) and acetonitrile (1.0 mL). This is heated at 85° C. for 2 h. The reaction mixture is then partitioned between $CH_2Cl_2$ and $H_2O$. The organic layer is dried and concentrated. Purification by silica gel chromatography (6/4, acetone/hexanes) yields 1-ethyl-6-methoxy-2-[4-(2-morpholin-4-yl-ethoxy)-phenyl]-1H-indole-3-carbonitrile (39 mg, 96%) as a white solid.

The following compounds are prepared similarly as above, using different amines: Compounds 262, 263, 264.

Example 1BB

Preparation of N-{2-[4-(3-cyano-1-ethyl-6-methoxy-1H-indol-2-yl)-phenoxy]-ethyl}methanesulfonamide (Compound 268)

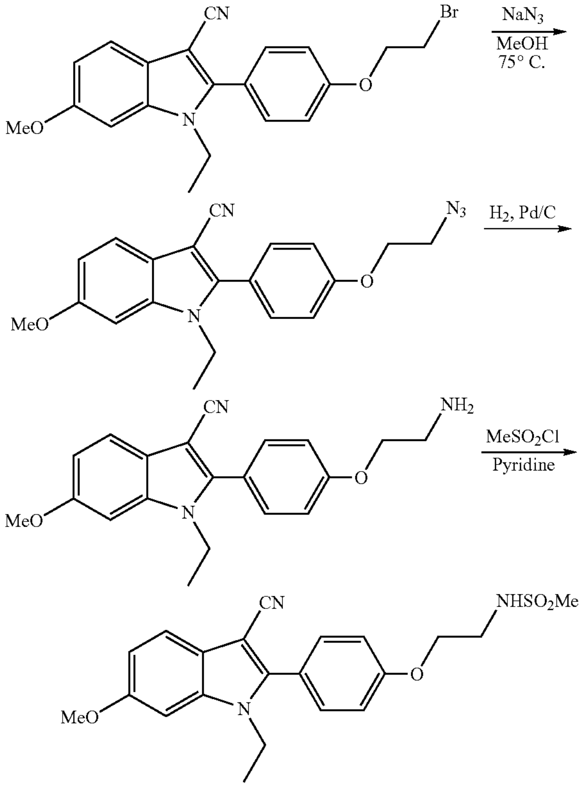

Step A: 2-[4-(2-Bromoethoxy)phenyl]-1-ethyl-6-methoxy-1H-indole-3-carbonitrile (258 mg, 0.65 mmol), prepared in example 1BA, step A, is combined with $NaN_3$ (144 mg, 2.2 mmol), and MeOH (3.2 mL). This is heated overnight at 75° C. The reaction mixture is then partitioned between $CH_2Cl_2$ and $H_2O$. The organic layer is dried and concentrated. Purification by silica gel chromatography ($CH_2Cl_2$) yields 2-[4-(2-azidoethoxy)phenyl]-1-ethyl-6-methoxy-1H-indole-3-carbonitrile (187 mg, 80%), compound 266 as a white solid.

Step B: 2-[4-(2-Azidoethoxy)phenyl]-1-ethyl-6-methoxy-1H-indole-3-carbonitrile (410 mg, 1.14 mmol), prepared as in step A, above, is suspended in a solution of MeOH (20 mL)

and concentrated HCl (500 μL). Pd/C (150 mg, 10%) is added, and this mixture is hydrogenated at 30 p.s.i. for 1 h. This is filtered and the filtrate is concentrated. The filtrate residue is partitioned between EtOAc and 0.5N NaOH. The organic layer is dried and concentrated. Purification by silica gel chromatography (10-30%, $MeOH/CH_2Cl_2$) yields 2-[4-(2-aminoethoxy)phenyl]-1-ethyl-6-methoxy-1H-indole-3-carbonitrile (298 mg, 78%), compound 267, as a white solid.

Step C: 2-[4-(2-Aminoethoxy)phenyl]-1-ethyl-6-methoxy-1H-indole-3-carbonitrile (30 mg, 0.09 mmol), prepared in step B, above, is dissolved in pyridine (300 μL). Methanesulfonyl chloride (8 μL, 0.1 mmol) is added. This is stirred at room temperature for 45 minutes. More methansulfonyl chloride (4 μL, 0.05 mmol) is added. Stirring continues for another hour. The reaction mixture is partitioned between EtOAc and aqueous HCl. The organic layer is dried and concentrated. Purification by silica gel chromatography (1/1 $CH_2Cl_2$/EtOAc) yields N-{2-[4-(3-cyano-1-ethyl-6-methoxy-1H-indol-2-yl)phenoxy]ethyl}methanesulfonamide, compound 268 (32 mg, 86%) as a white solid.

The following compound is prepared similarly as above: Compound 269.

Example 1BC

Preparation of N-{2-[4-(3-cyano-1-ethyl-6-methoxy-1H-indol-2-yl)-phenoxy]-ethyl}acetamide (Compound 274)

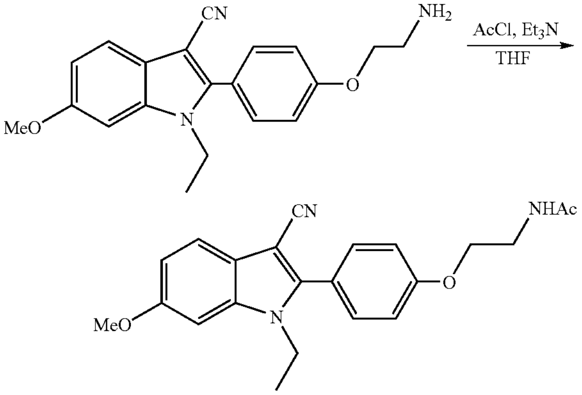

2-[4-(2-Aminoethoxy)phenyl]-1-ethyl-6-methoxy-1H-indole-3-carbonitrile (30 mg, 0.09 mmol), prepared as in example 1BB, step B, is dissolved in THF (400 μL), and $Et_3N$ (24 μL, 0.17 mmol). Acetyl chloride (10 μL, 0.14 mmol) is added, and the reaction mixture is stirred at room temperature for 2 h. The reaction mixture is partitioned between EtOAc and $H_2O$. The organic layer is dried and concentrated. Purification by silica gel chromatography (EtOAc) yields N-{2-[4-(3-cyano-1-ethyl-6-methoxy-1H-indol-2-yl)phenoxy]ethyl}acetamide (33 mg, 97%) as a white solid.

Example 1BD

Preparation of 1-{2-[4-(3-cyano-1-ethyl-6-methoxy-1H-indol-2-yl)-phenoxy]ethyl}-3-ethyl-urea (Compound 279)

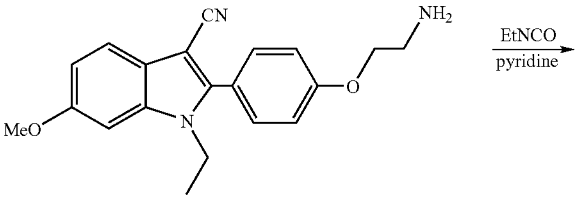

-continued

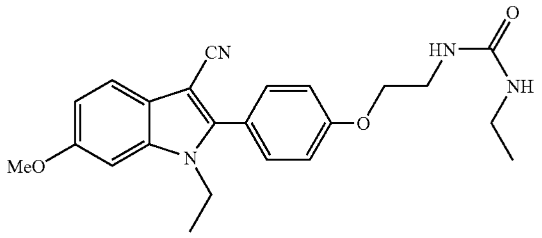

2-[4-(2-Aminoethoxy)phenyl]-1-ethyl-6-methoxy-1H-indole-3-carbonitrile (30 mg, 0.09 mmol), prepared as in example 1BB, is combined with ethyl isocyanate (18 μL, 0.21 mmol) and pyridine (300 μL). This mixture is stirred at room temperature for 90 minutes, and is then partitioned between EtOAc and aqueous HCl. The organic layer is dried and concentrated. Purification by silica gel chromatography (EtOAc) yields 1-{2-[4-(3-cyano-1-ethyl-6-methoxy-1H-indol-2-yl)-phenoxy]-ethyl}-3-ethyl-urea (34 mg, 93%) as a white solid.

Example 1BE

Preparation of N-{2-[4-(3-cyano-1-ethyl-6-methoxy-1H-indol-2-yl)-phenoxy]ethyl}formamide (Compound 280)

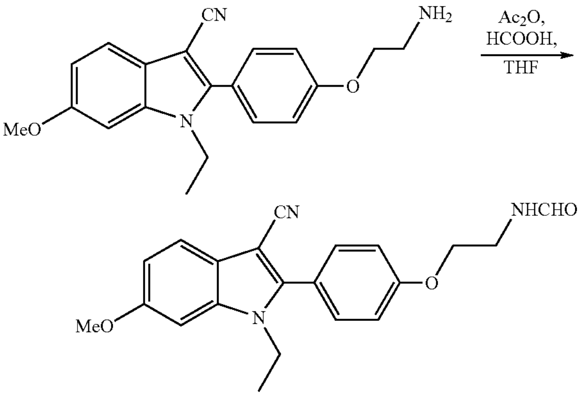

Acetic anhydride (700 μL) and 98% formic acid (280 μL) are heated at 65° C. for 1 h. This is cooled to 0° C. 2-[4-(2-Aminoethoxy)phenyl]-1-ethyl-6-methoxy-1H-indole-3-carbonitrile (30 mg, 0.09 mmol), prepared as in example 1BB, is taken up in THF (400 μL), and added to the mixed anhydride. This is stirred at 0° C. for 45 minutes. The mixture is then portioned between EtOAc and aqueous $NaHCO_3$. The organic layer is dried and concentrated. Purification by silica gel chromatography (4/1, $CH_2Cl_2$/acetone) yields N-{2-[4-(3-cyano-1-ethyl-6-methoxy-1H-indol-2-yl)phenoxy]-ethyl}formamide (28 mg, 86%) as a white solid.

Example 1BF

Preparation of 1-ethyl-2-{4-[2-(3-hydroxypyrrolidin-1-yl)-2-oxo-ethoxy]phenyl}-6-methoxy-1H-indole-3-carbonitrile (Compound 285)

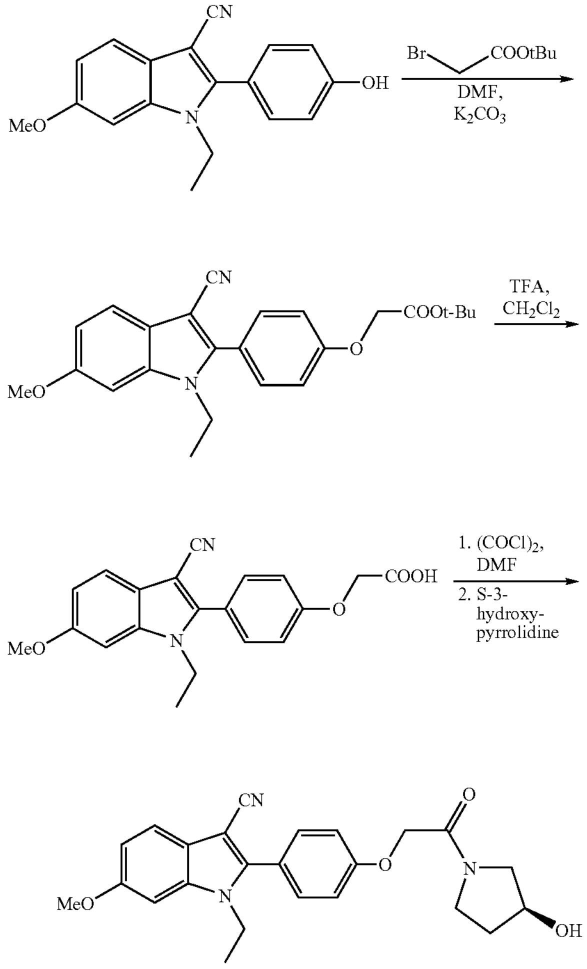

Step A: 1-Ethyl-2-(4-hydroxyphenyl)-6-methoxy-1H-indole-3-carbonitrile (559 mg, 1.91 mmol), is used to prepare [4-(3-cyano-1-ethyl-6-methoxy-1H-indol-2-yl)-phenoxy]-acetic acid tert-butyl ester (780 mg, 100%) utilizing essentially the same procedure as example 1AZ.

Step B: [4-(3-Cyano-1-ethyl-6-methoxy-1H-indol-2-yl)-phenoxy]-acetic acid tert-butyl ester (745 mg, 1.83 mmol) is stirred in 20% TFA in $CH_2Cl_2$ at room temperature for 3 hours. This is concentrated and the residue is partitioned between $H_2O$ and EtOAc. The organic layer is dried and concentrated. The residue is triturated with $CH_2Cl_2$ to yield [4-(3-cyano-1-ethyl-6-methoxy-1H-indol-2-yl)-phenoxy]-acetic acid (634 mg, 99%) as a white solid.

Step C: [4-(3-Cyano-1-ethyl-6-methoxy-1H-indol-2-yl)-phenoxy]-acetic acid (40 mg, 0.12 mmol) is suspended in $CH_2Cl_2$ (1.65 mmol) and DMF (2 μL). Oxalyl chloride (17 μL, 0.19 mmol) is added. This is stirred at room temperature for 30 minutes. The resulting solution is then pipetted into a stirring solution of S-3-hydroxypyrrolidine (150 μL) and $CH_2Cl_2$ (3.0 mL). The mixture is washed with aqueous HCl. The organic layer is dried and concentrated. Purification by silica gel chromatography (3/2 $CH_2Cl_2$/acetone) yields 1-ethyl-2-{4-[2-(3-hydroxy-pyrrolidin-1-yl)-2-oxo-ethoxy]-phenyl}-6-methoxy-1H-indole-3-carbonitrile (40 mg, 79%), compound 285 as a white solid.

Example 1BG

Preparation of 1-ethyl-6-methoxy-2-(2-oxo-2,3-dihydro-benzooxazol-5-yl)-1H-indole-3-carbonitrile (Compound 332)

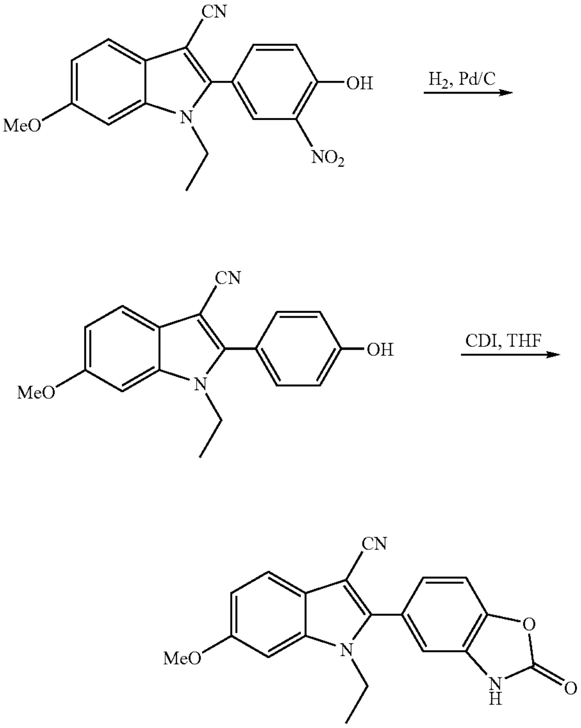

Step A: 1-Ethyl-2-(4-hydroxy-3-nitrophenyl)-6-methoxy-1H-indole-3-carbonitrile (369 mg, 1.1 mmol), prepared as in example 1Gd, is combined with EtOAc (20 mL) and Pd/C (150 mg, 10%). This mixture is hydrogenated at 30 p.s.i. for 1 h. This is filtered through celite. The filtrate is concentrated and triturated with ether to yield 2-(3-amino-4-hydroxyphenyl)-1-ethyl-6-methoxy-1H-indole-3-carbonitrile (307 mg, 91%), compound 322, as a white solid.

Step B: 2-(3-Amino-4-hydroxyphenyl)-1-ethyl-6-methoxy-1H-indole-3-carbonitrile (100 mg, 0.33 mmol), prepared as in step A, is combined with CDI (83 mg, 0.51 mmol), and THF (1.1 mL). This is heated at 65° C. for 1 hour. The reaction mixture is partitioned between EtOAc and aqueous HCl. The organic layer is dried and concentrated. Purification by silica gel chromatography (9/1, $CH_2Cl_2$/EtOAc) yields 1-ethyl-6-methoxy-2-(2-oxo-2,3-dihydro-benzooxazol-5-yl)-1H-indole-3-carbonitrile (89 mg, 81%) as a white solid.

Example 1BH

Preparation of 1-ethyl-6-methoxy-2-(3-oxo-3,4-dihydro-2H-benzo[1,4]oxazin-6-yl)-1H-indole-3-carbonitrile (Compound 334)

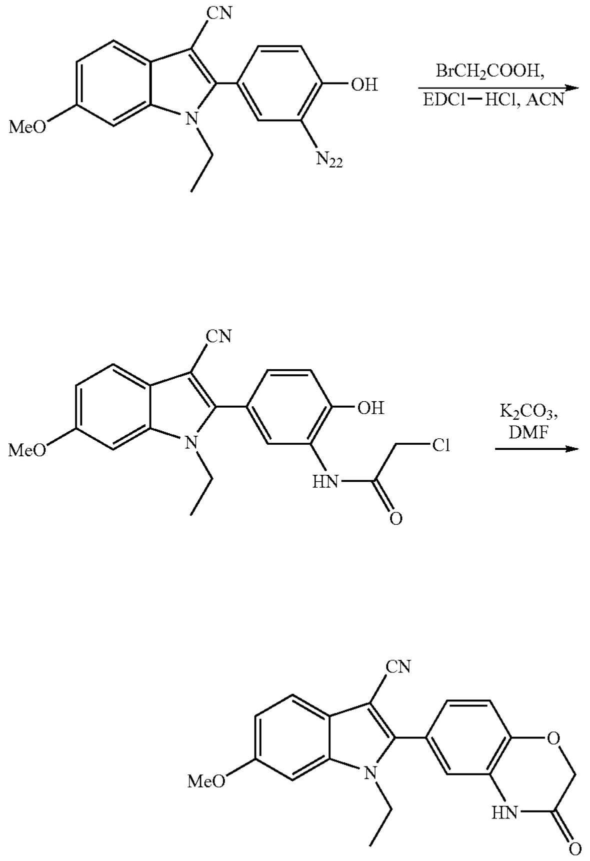

Step A: Bromoacetic acid (52 mg, 0.37 mmol) is combined with EDCI hydrochloride (62 mg, 0.4 mmol) and acetonitrile (900 μL) to form a homogeneous solution. 2-(3-Amino-4-hydroxyphenyl)-1-ethyl-6-methoxy-1H-indole-3-carbonitrile (100 mg, 0.33 mmol), prepared as in example 1BG, step B, is added to the solution. A thick paste soon forms. Another 1.1 mL of acetonitrile is added and the mixture is then stirred at room temperature for 2 hours. The reaction mixture is then partitioned between $H_2O$ and EtOAc. The organic layer is dried and concentrated. Purification by silica gel chromatography (4/1, $CH_2Cl_2$/EtOAc) yields 2-chloro-N-[5-(3-cyano-1-ethyl-6-methoxy-1H-indol-2-yl)-2-hydroxyphenyl]acetamide (82 mg, 60%), compound 333, as a white solid.

Step B: 2-Chloro-N-[5-(3-cyano-1-ethyl-6-methoxy-1H-indol-2-yl)-2-hydroxy-phenyl]acetamide (57 mg, 0.13 mmol), prepared in step A, is combined with $K_2CO_3$ (55 mg, 0.4 mmol), and DMF (400 μL). This is heated at 80° C. for 1 hour. The reaction mixture is then partitioned between $H_2O$ and EtOAc. The organic layer is dried and concentrated. Purification by silica gel chromatography (9/1, $CH_2Cl_2$/EtOAc) yields 1-ethyl-6-methoxy-2-(3-oxo-3,4-dihydro-2H-benzo[1,4]oxazin-6-yl)-1H-indole-3-carbonitrile (45 mg, 90%) as a white solid.

Example 1BI

Preparation of 1-ethyl-6-methoxy-2-(2-oxo-2,3-dihydro-benzooxazol-6-yl)-1H-indole-3-carbonitrile (Compound 340)

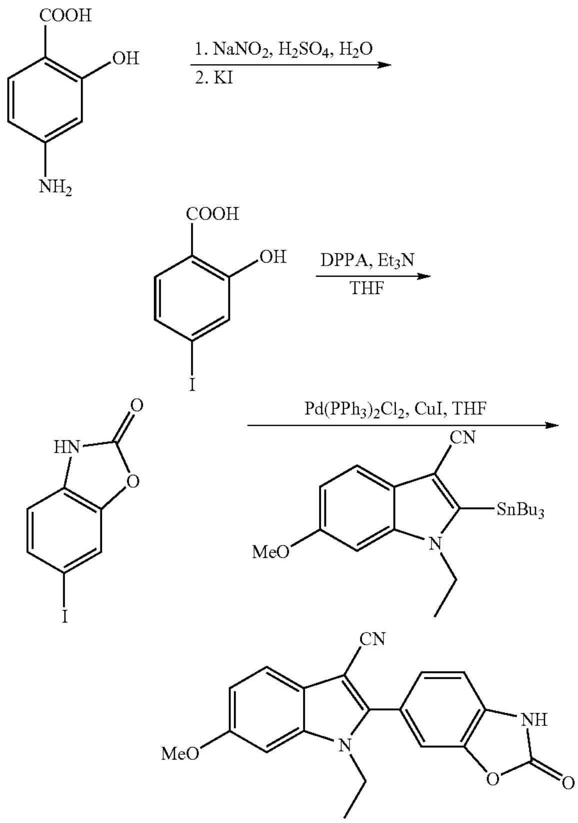

Step A: 4-Aminosalicylic acid (4.0 g, 26 mmol) is suspended in $H_2SO_4$ (26 mL, 2.7M) at −5° C. Sodium nitrite (1.8 g, 26.1 mmol) in $H_2O$ (6.5 mL) is cooled to ice bath temperature and is added dropwise to the aminosalicylic acid mixture over 5 minutes. The resulting suspension is stirred at −5° C. for 15 minutes. A solution of KI (6.8 g, 41 mmol) in $H_2SO_4$ (13 mL, 1M) is added dropwise to the diazonium salt, with considerable evolution of $N_2$. The reaction mixture is heated at 70° C. for 20 minutes. The reaction mixture is then partitioned between $H_2O$ and EtOAc. The organic layer is dried and concentrated. Purification by silica gel chromatography (7/3, hexanes/acetone, 1% acetic acid) yields 4-iodosalicylic acid (5.33 g, 85-90% pure).

Step B: Crude 4-Iodosalicylic acid (1.0 g, 3.8 mmol) is dissolved in THF (28 mL) and $Et_3N$ (1.15 mL, 8.2 mmol). DPPA (1.7 mL, 7.8 mmol) is added. This is heated at 70° C. overnight. The reaction mixture is then partitioned between $H_2O$ and EtOAc. The organic layer is dried and concentrated. Purification by silica gel chromatography (9/1, $CH_2Cl_2$/EtOAc) yields 472 mg crude intermediate. Trituration with ether yields 6-iodo-3H-benzooxazol-2-one (369 mg, 37%) as a white solid.

Step C: 6-Iodo-3H-benzooxazol-2-one (118 mg, 0.45 mmol) is used to prepare 1-ethyl-6-methoxy-2-(2-oxo-2,3-dihydro-benzooxazol-6-yl)-1H-indole-3-carbonitrile, compound 340 (75 mg, 55%), utilizing essentially the same procedure as in example 1Gd.

Example 1BJ

Preparation of 1-ethyl-6-methoxy-2-(4-methyl-3-oxo-3,4, -dihydro-2H-benzo[1,4]oxazin-6-yl)-1H-indole-3-carbonitrile (Compound 339)

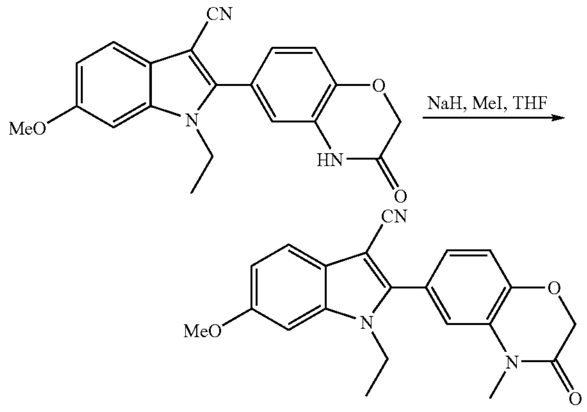

1-Ethyl-6-methoxy-2-(3-oxo-3,4-dihydro-2H-benzo[1,4]oxazin-6-yl)-1H-indole-3-carbonitrile (20 mg, 0.058 mmol), prepared as in example 1BH, is combined with NaH (14 mg, 60% suspension in oil, 0.35 mmol). THF (300 μL) is added. This is stirred at room temperature for 5 minutes. A solution of methyl iodide (4.4 μL) in THF (100 μL) is added. This is stirred at room temperature for 1 hour. The reaction mixture is partitioned between EtOAc and aqueous HCl. The organic layer is dried and concentrated. Purification by silica gel chromatography (9/1, $CH_2Cl_2$/EtOAc) yields 1-ethyl-6-methoxy-2-(4-methyl-3-oxo-3,4,-dihydro-2H-benzo[1,4]oxazin-6-yl)-1H-indole-3-carbonitrile (16 mg, 76%) as a white solid.

The following compound is prepared similarly: Compound 341.

Example 1BK

Preparation of 1-ethyl-2-iodo-6-methoxy-5-nitro-1H-indole-3-carbonitrile (Compound 499)

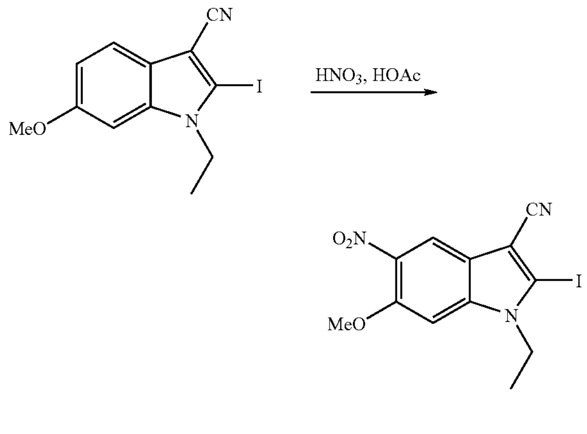

1-Ethyl-2-iodo-6-methoxy-1H-indole-3-carbonitrile (50 mg, 0.15 mmol), prepared as in example 1Ga, Step A, is suspended in acetic acid (620 μL) at 0° C. Nitric acid (4.25M in AcOH) is added. This is stirred at room temperature for 2 hours. The reaction mixture is then partitioned between $CH_2Cl_2$ and $H_2O$. The organic layer is washed with aqueous $NaHCO_3$, and then is dried and concentrated. Purification by silica gel chromatography (6/4, $CH_2Cl_2$/hexanes), followed by ether trituration, yields 1-ethyl-2-iodo-6-methoxy-5-nitro-1H-indole-3-carbonitrile (16 mg, 29%) as a yellow solid.

Example 1BL

Preparation of 1'-ethanesulfonyl-1-ethyl-6-methoxy-2',3'-dihydro-1H,1H'-[2,6']biindolyl-3-carbonitrile (Compound 753)

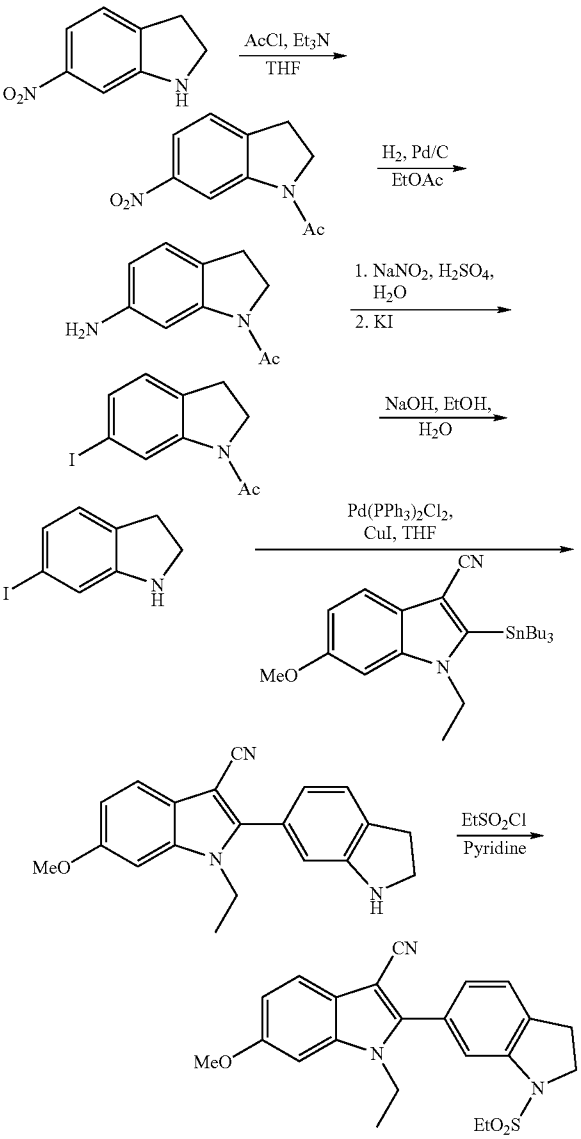

Step A: 6-Nitroindoline (3.0 g, 18.3 mmol) is dissolved in THF (45 mL) and $Et_3N$ (3.4 mL, 24.4 mmol) at 0° C. Acetyl chloride (1.5 mL, 21 mmol) is added dropwise. The mixture is stirred at room temperature for 30 minutes. The mixture is partitioned between EtOAc and aqueous HCl. The organic layer is dried and concentrated to yield 1-acetyl-6-nitroindoline (3.8 g, 100%) as a yellow solid.

Step B: 1-Acetyl-6-nitroindoline (3.8 g, 18.3 mmol) is suspended in EtOAc (200 mL). Pd/C (650 mg, 10%) is added, and the mixture is hydrogenated at 40-55 p.si.i. for 2 hours. The mixture is then filtered through celite. The filtrate is concentrated, and the residue is triturated with ether to yield 1-acetyl-6-aminoindoline (3.18 g, 99%) as an orange solid.

Step C: 1-Acetyl-6-aminoindoline (1.5 g, 8.5 mmol) is used to prepare 1-acetyl-6-iodoindoline (1.06 g, 43%), utilizing essentially the same procedure in example 1BI, Step A.

Step D: 1-Acetyl-6-iodoindoline (1.06 g, 3.7 mmol), NaOH (1.16 g, 29 mmol), EtOH (8 mL), and $H_2O$ (6 mL) are heated at 90° C. overnight. The reaction mixture is then partitioned between $H_2O$ and EtOAc. The organic layer is extracted into aqueous HCl. The aqueous layer is in turn basified with NaOH, and is extracted with EtOAc. The organic layer is dried and concentrated. Hexane trituration yields 6-iodoindoline (577 mg, 64%) as a brown solid.

Step E: 1-Iodoindoline (600 mg, 2.45 mmol) is used to prepare 1-ethyl-6-methoxy-2',3'-dihydro-1H,1H'-[2,6']biindolyl-3-carbonitrile (535 mg, 67%), utilizing essentially the same procedure as in example 1Gd, Step B.

Step F: 1-Ethyl-6-methoxy-2',3'-dihydro-1H,1H'-[2,6']biindolyl-3-carbonitrile (30 mg, 0.095 mmol) is used to prepare 1'-Ethanesulfonyl-1-Ethyl-6-methoxy-2',3'-dihydro-1H,1H'-[2,6']biindolyl-3-carbonitrile (24 mg, 62%), utilizing the procedure in example 1Y.

The following compounds are prepared similarly as above: Compounds 752 and 754.

Example 1BM

Preparation of 5-acetyl-1-ethyl-6-methoxy-2-(4-nitro-phenyl)-1H-indole-3-carbonitrile (Compound 844)

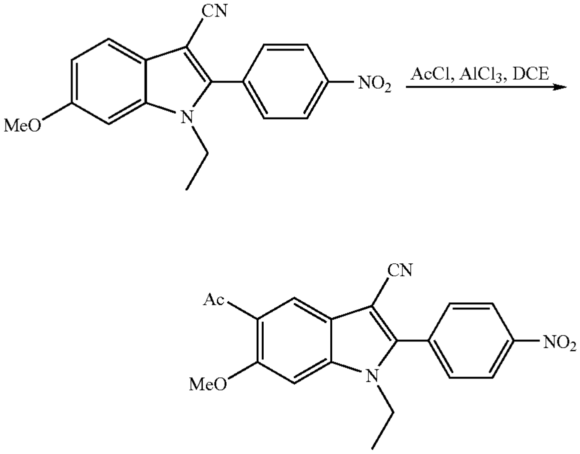

1-Ethyl-6-methoxy-2-(4-nitrophenyl)-1H-indole-3-carbonitrile (100 mg, 0.3 mmol), prepared by the method of example 1Gc is suspended in 1,2-dichloroethane (500 μL) at 0° C. Acetyl chloride (50 μL, 0.69 mmol) is added, followed by $AlCl_3$ (55 mg, 0.4 mmol) in one portion. This is stirred at 0° C. for 1 hour, at room temperature for 4 hours, and at 45° C. overnight. The reaction mixture is then partitioned between $CH_2Cl_2$ and $H_2O$. The organic layer is dried and concentrated. Purification by silica gel chromatography (195:5 $CH_2Cl_2$/EtOAc) yields 5-acetyl-1-ethyl-6-methoxy-2-(4-nitro-phenyl)-1H-indole-3-carbonitrile (33 mg, 29%) as an orange solid.

Example 1BN

Preparation of 1-ethyl-6-methoxy-5-morpholin-4-ylmethyl-2-(4-nitro-phenyl)-1H-indole-3-carbonitrile (Compound 845)

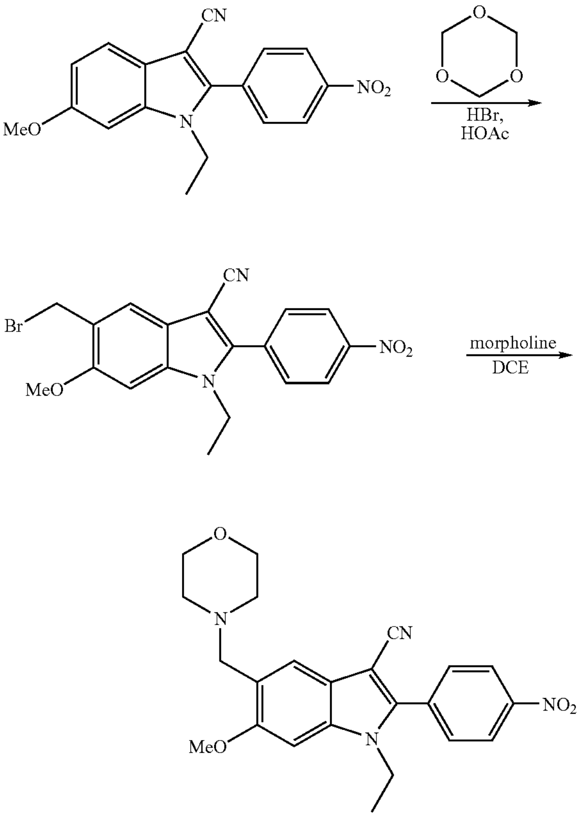

Step A: 1-Ethyl-6-methoxy-2-(4-nitrophenyl)-1H-indole-3-carbonitrile (100 mg, 0.3 mmol), prepared by the method of example 1Gc, is combined with 1,3,5-trioxane (64 mg, 0.71 mmol) and acetic acid (2.0 mL). 33% HBr in acetic acid (2.0 mL) is added. This is stirred at room temperature for 4 hours. The reaction mixture is then partitioned between $CH_2Cl_2$ and $H_2O$. The organic layer is washed with aqueous $NaHCO_3$, and is subsequently dried and concentrated. The crude material is carried through to the next step.

Step B: Crude 6-bromomethyl-1-ethyl-6-methoxy-2-(4-nitro-phenyl)-1H-indole-3-carbonitrile (0.3 mmol) is heated with morpholine (150 μL, 1.75 mmol) and DCE (1.0 mL) at 90° C. overnight. The reaction mixture is then partitioned between $H_2O$ and EtOAc. The organic layer is dried and concentrated. Purification by silica gel chromatography (50-100%, EtOAc/$CH_2Cl_2$), followed by trituration with 1/1 hexane/acetone yields 1-ethyl-6-methoxy-5-morpholin-4-ylmethyl-2-(4-nitrophenyl)-1H-indole-3-carbonitrile (57 mg, 44% overall yield) as a yellow solid.

Example 1BO

2-[4-(1,1-dioxidoisothiazolidin-2-yl)phenyl]-1-cyclopropylmethyl-6-methoxy-1H-indole-3-carbonitrile (Compound 716)

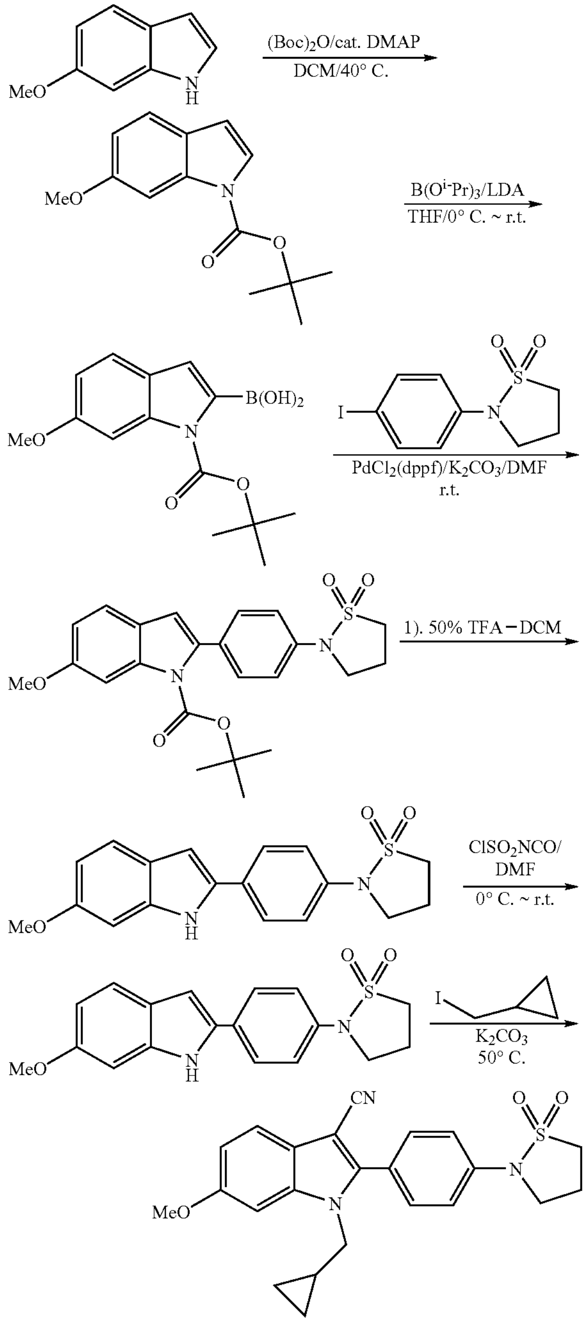

Step A: To a solution of 6-methoxyindole (5.88 g, 40.0 mmol) and di-tert-butyl dicarbonate (9.59 g, 44.0 mmol) in DCM (50 mL) is added, at 40° C. while stirring, DMAP (0.10 g). After stirring overnight, the mixture is washed sequentially with 0.1 N HCl, water and brine and dried over anhydrous $Na_2SO_4$. The solvent is evaporated and the residue is chromatographed (silica gel, EtOAc/hexanes, 1/7) to provide tert-butyl 6-methoxy-1H-indole-1-carboxylate (8.48 g, 86%).

Step B: The above Boc-indole (3.08 g, 12.5 mmol) and isopropylborate (4.83 mL, 21.9 mmol) are dissolved in anhydrous THF (20 mL) and the solution is cooled at 0° C. While stirring, LDA (12.5 mL, 1.5 M mono-THF complex in cyclohexane, 18.7 mmol) is added dropwise. The mixture is stirred at 0° C. for 15 min and then room temperature for 0.5 h, followed by the addition of HCl (6 N, 3.0 mL, 18 mmol) in an ice-water bath. The organic solvent is removed in vacuo and the residue is suspended in $H_2O$ (100 mL) and acidified with HCl (6 N) to pH 4-5. The precipitate is collected via filtration and washed with water and hexanes and dried in air to provide 1-Boc-6-mehoxyindole-2-boronic acid (3.38 g, 93%).

Step C: To a solution of 4-iodoanilline (3.18 g, 14.5 mmol) in pyridine (15 mL) at 0° C., is added 3-chloropropanesulfonyl chloride (2.3 mL, 18.9 mmol). After the addition, the mixture is stirred for 2 h at room temperature, and poured into ice-water (200 mL). The organic is separated and the aqueous layer is extracted with DCM (2×50 mL). The combined organics are washed with HCl (2 N, 2×15 mL), water (2×50 mL) and brine (20 mL) consecutively and dried over anhydrous $Na_2SO_4$. The solvent is then evaporated and the residue is chromatographed to furnish 3-chloro-N-(4-iodophenyl) propane-1-sulfonamide (4.68 g, 90%). The chlorosulfonamide obtained (3.47 g, 9.6 mmol) is then treated with $K_2CO_3$ (3.33 g, 24.1 mmol) in DMF (50 mL) at 50° C. for 2 h. The mixture is poured into ice-water (300 mL) and the precipitate is collected and dried in air to provide essentially pure 2-(4-iodophenyl)isothiazolidine-1,1-dioxide (3.11 g, 100%).

Step D: To a mixture of 1-Boc-6-mehoxyindole-2-boronic acid prepared in step B above (0.36 g, 1.25 mmol), 2-(4-iodophenyl)isothiazolidine-1,1-dioxide (0.32 g, 1.0 mmol) and $PdCl_2$(dppf) (0.037 g, 0.05 mmol) in DMF (4.0 mL), is added aqueous $K_2CO_3$ solution (1.5 mL, 2.0 M, 3.0 mmol). The mixture is stirred at room temperature overnight and then poured into ice-water (100 mL). The precipitate is collected and washed with water and purified by flash column chromatography (silica gel, DCM/EtOAc, 9/1) to furnish 1-Boc-2-[4-(1,1-dioxidoisothiazolidin-2-yl)phenyl]-6-methoxy-1H-indole (0.43 g, 98%).

The following compound is made similarly: Compound 768

Step D: 1-Boc-2-[4-(1,1-dioxidoisothiazolidin-2-yl)phenyl]-6-methoxy-1H-indole (1.63 g, 3.7 mmol) is treated with TFA (25 mL) in DCM (25 mL) at room temperature for 4 h. After the removal of the volatiles, the residue is carefully stirred with saturated $NaHCO_3$ for 0.5 h. The precipitate is collected via filtration and washed with water thoroughly and dried to provide essentially pure 1-H-2-[4-(1,1-dioxidoisothiazolidin-2-yl)phenyl]-6-methoxyindole (1.17 g, 92%).

Step E: At 0° C., 1-H-2-[4-(1,1-dioxidoisothiazolidin-2-yl)phenyl]-6-methoxyindole (0.95 g, 2.8 mmol) is dissolved in DMF (10 mL) and treated with chlorosulfonyl isocyanate (0.36 mL, 4.2 mmol). The mixture is then stirred at room temperature overnight and poured into ice-water (150 mL) then stirred for 0.5 h. The precipitate is collected via filtration and washed thoroughly with water and dried in air to furnish 1-H-2-[4-(1,1-dioxidoisothiazolidin-2-yl)phenyl]-6-methoxyindole-3-carbonitrile (0.89 g, 87%).

The following compound is prepared in the same fashion as described above: Compound 829

Step F: To a solution of 1-H-2-[4-(1,1-dioxidoisothiazolidin-2-yl)phenyl]-6-methoxyindole-3-carbonitrile (73 mg, 0.2 mmol) and $K_2CO_3$ (69 mg, 0.5 mmol) in DMF (3.0 mL) is added cyclopropylmethyl iodide (0.029 mL, 0.3 mmol). The mixture is stirred at 50° C. overnight and poured into ice-water (10 mL). The precipitate is collected via filtration, washed with water and purified by column chromatography to provide 2-[4-(1,1-dioxidoisothiazolidin-2-yl)phenyl]-6-methoxy-1-cyclopropylmethylindole-3-carbonitrile, compound 716 (73 mg, 87%).

The following compounds are prepared in the same fashion as described above: Compounds 717, 718, 719, 782, 783, 784.

Example 1BP

Preparation of 2-[4-(1,1'-dioxo-1λ$^6$-isothiazolidin-2-yl)-6-methoxy-3-oxazol-5-yl-1-propyl-1H-indole (Compound 805)

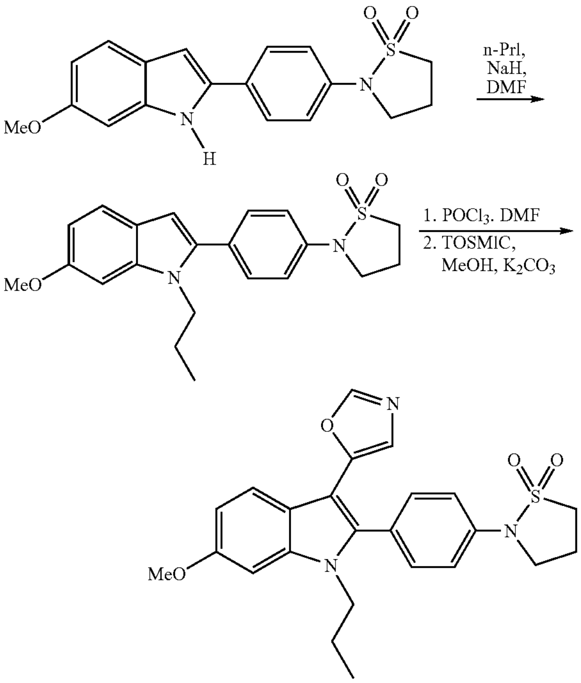

Step A: 2-[4-(1,1'-Dioxo-1λ$^6$-isothiazolidin-2-yl)-6-methoxy-indole (900 mg, 2.62 mmol), prepared in example 1BO, step D is used to prepare 2-[4-(1,1'-dioxo-1λ$^6$-isothiazolidin-2-yl)-6-methoxy-1-propyl-1H-indole (608 mg, 60%), utilizing essentially the same procedure as example 1A, Step B.

Step B: 2-[4-(1,1'-Dioxo-1λ$^6$-isothiazolidin-2-yl)-6-methoxy-1-propyl-1H-indole (50 mg, 0.13 mmol) is used to prepare 2-[4-(1,1'-dioxo-1λ$^6$-isothiazolidin-2-yl)-6-methoxy-3-oxazol-5-yl-1-propyl-1H-indole (9 mg, 15% overall yield) according to the protocol in example 1P.

Example BQ

Preparation of 2-[4-(cyclopropylsulfonyl)piperazin-1-yl]-1-ethyl-6-(trifluoromethyl)-1H-indole-3-carbonitrile (Compound 842)

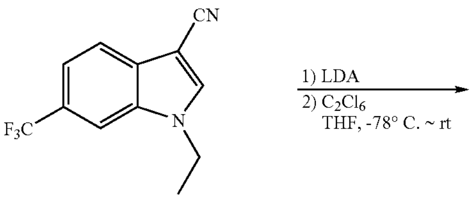

-continued

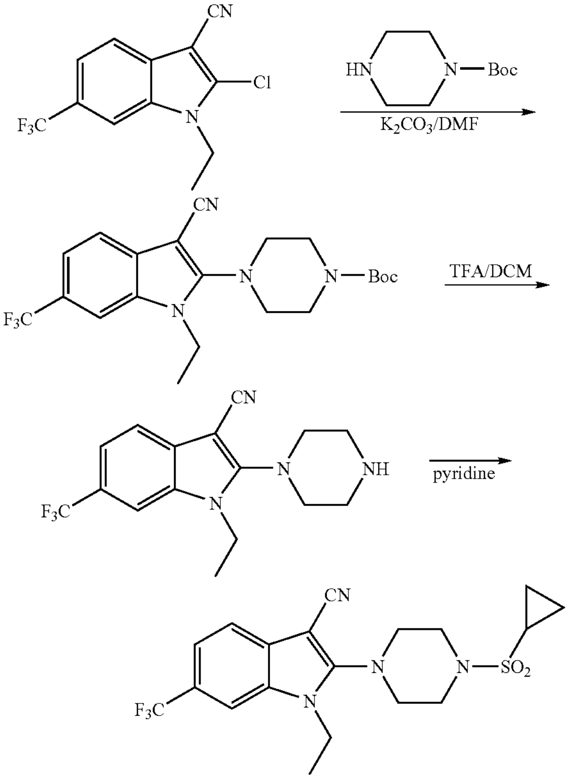

Step A: To a solution of 1-ethyl-6-trifluoromethylindole-3-carbonitrile (2.54 g, 10.0 mmol), prepared by the method of procedure 1A, in anhydrous THF (20.0 mL), at −78° C. is added LDA (8.3 mL, 1.5 M mono-THF in cyclohexane, 12.5 mmol) dropwise. The mixture is continued for 0.5 h after the addition, followed by the addition of hexachloroethane and the mixture is then brought to room temperature slowly and stirred for 0.5 h. The solvent is then evaporated and the residue is treated with water. The organics are extracted with dichloromethane, washed with water and brine and dried over anhydrous $Na_2SO_4$. The crude product obtained after the removal of the solvent is chromatographed (silica gel, dichloromethane/hexanes, 3/2) to provide 2-chloro-1-ethyl-6-(trifluoromethyl)-1H-indole-3-carbonitrile (1.75 g, 64%).

Step B: The chloroindole obtained above (0.27 g, 1.0 mmol), $K_2CO_3$ (0.35 g, 2.5 mmol) and N-Boc-piperazine (0.28 g, 1.5 mmol) are stirred at 70° C. in DMF (5.0 mL) for 3 days and then poured into water (50 mL). The precipitate is collected via filtration and washed with water. Chromatography of this crude product (silica gel, dichloromethane/ethyl acetate, 9/1) provides 4-(3-cyano-1-ethyl-6-trifluoromethyl-1H-indol-2-yl)-piperazine-1-carboxylic acid tert-butyl ester, compound 785 (0.30 g, 71%).

The following compounds are prepared in the same fashion as described above, by using other amines: Compounds 514, 785, 786.

Step C: 4-(3-cyano-1-ethyl-6-trifluoromethyl-1H-indol-2-yl)-piperazine-1-carboxylic acid tert-butyl ester (0.26 g, 6.1 mmol) is treated with TFA (5 mL) in dichloromethane (5 mL) for 1 h at room temperature. After the removal of the volatiles, the residue is treated with saturated $NaHCO_3$ and the precipitate is collected via filtration, washed with water thoroughly and dried in air to furnish essentially pure 1-ethyl-2-piperazin-1-yl-6-(trifluoromethyl)-1H-indole-3-carbonitrile (0.20 g, 100%).

Step D: To a solution of 1-ethyl-2-piperazin-1-yl-6-(trifluoromethyl)-1H-indole-3-carbonitrile (32 mg, 0.1 mmol), pyridine (0.1 mL) in dichloromethaene (1.0 mL) is added cyclopropanesulfonyl chloride (28 mg, 0.2 mmol) and the mixture is stirred at room temperature overnight. This is then diluted with dichloromethane (5 mL), washed with HCl (2 N, 2×2 mL), water (2×5 mL) and brine (5 mL) and chromatographed over silica gel (dichloromethane/ethyl acetate, 9/1) to provide 2-[4-(cyclopropylsulfonyl)piperazin-1-yl]-1-ethyl-6-(trifluoromethyl)-1H-indole-3-carbonitrile, compound 842 (30 mg, 70%).

The following compounds are prepared in the same fashion as described above, using corresponding sulfonyl chlorides: Compounds 841, 843.

Example 1BR

Ethanesulfonic acid [3-cyano-2-(4-ethoxyphenyl)-1-ethyl-1H-indol-6-yl]-amide (Compound 835)

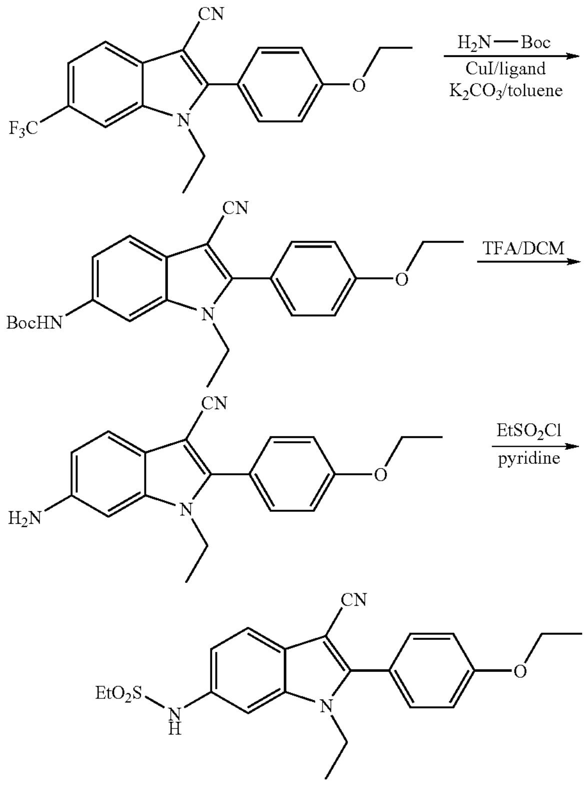

Step A: 6-Bromo-2-(4-ethoxyphenyl)-1-ethyl-1H-indole-3-carbonitrile (0.74 g, 2.0 mmol), compound 831, prepared from 6-bromoindole as described in example 1Gb, is mixed with $K_2CO_3$ (0.55 g, 4.0 mmol), CuI (0.02 g, 0.1 mmol), tert-butyl carbamate (0.35 g, 3.0 mmol), N,N'-dimethylcyclohexane-1,2-diamine ligand (0.028 g, 0.2 mmol) and anhydrous toluene (5.0 mL) in a sealed tube. The reaction system is flushed with nitrogen and then stirred at 110° C. overnight. After cooling, the solvent is replaced with dichloromethane and chromatographed (silica gel, dichloromethane) to provide [3-cyano-2-(4-ethoxy-phenyl)-1-ethyl-1H-indol-6-yl]-carbamic acid tert-butyl ester (0.68 g, 84%), compound 832.

Step B: Compound 832 prepared in step A above (0.63 g, 1.56 mmol) is treated with TFA/DCM (7.5 mL/7.5 mL) at room temperature for 2 h, and the volatiles are removed in vacuum. The residue is treated with saturated $NaHCO_3$ and the precipitate is collected via filtration and washed thoroughly with water, dried in air to provide 6-amino-2-(4-ethoxyphenyl)-1-ethyl-1H-indole-3-carbonitrile (0.45 g, 96%), compound 833.

Step C: The above amine (31 mg, 0.1 mmol) is treated with ethanesulfonyl chloride (19 mg, 0.15 mmol) in pyridine (1.0 mL) at room temperature overnight to provide, after purification using column chromatography, ethanesulfonic acid [3-cyano-2-(4-ethoxy-phenyl)-1-ethyl-1H-indol-6-yl]-amide (83%), compound 835.

The following compounds are prepared in the same fashion as described above: Compounds 830, 834, 836 and 837.

Example 1BS

Preparation of [3-cyano-2-(4-ethoxyphenyl)-1-ethyl-1H-indol-6-yl]-carbamic acid ethyl ester (Compound 838)

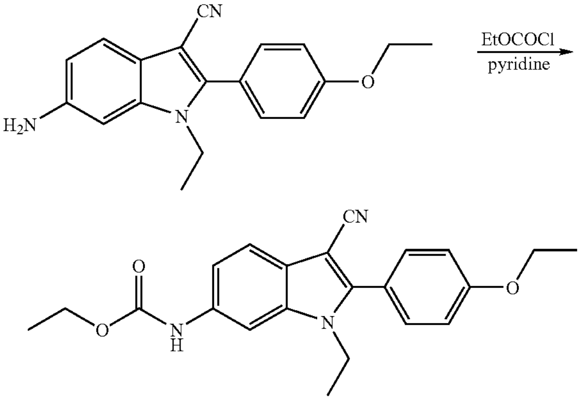

6-Amino-2-(4-ethoxyphenyl)-1-ethyl-1H-indole-3-carbonitrile (31 mg, 0.1 mmol), compound 833, prepared in example 1BR, step B is treated with ethyl chloroformate (16 mg, 0.15 mmol) in pyridine (1.0 mL) at room temperature overnight to furnish, after purification using column chromatography [3-cyano-2-(4-ethoxyphenyl)-1-ethyl-1H-indol-6-yl]-carbamic acid ethyl ester (30 mg, 79%).

Example 1BT

Preparation of 1-[3-cyano-2-(4-ethoxyphenyl)-1-ethyl-1H-indol-6-yl]-3-ethyl-urea (Compound 839)

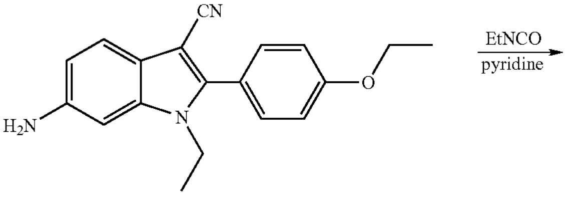

-continued

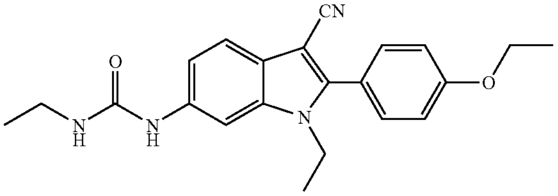

6-Amino-2-(4-ethoxyphenyl)-1-ethyl-1H-indole-3-carbonitrile (31 mg, 0.1 mmol) is treated with ethyl isocyanate (14 mg, 0.2 mmol) in dichloromethane (1.0 mL) at 40° C. overnight. The precipitate is collected via filtration, washed with dichloromethane an dried in air to furnish, 1-[3-cyano-2-(4-ethoxy-phenyl)-1-ethyl-1H-indol-6-yl]-3-ethyl-urea (36 mg, 95%).

Example 1BU

Preparation of 1-(2-chloroethyl)-3-[4-(3-cyano-1-ethyl-6-methoxy-1H-indol-2-yl)-phenyl]-urea (Compound 442)

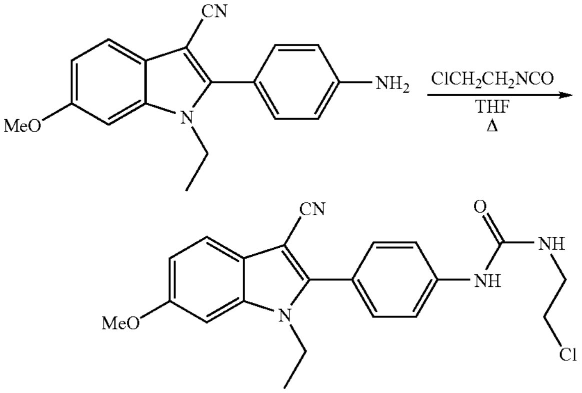

To a solution of 2-(4-aminophenyl)-1-ethyl-6-methoxy-1H-indole-3-carbonitrile (50 mg, 0.172 mmol) in THF (2 mL) is added 2-chloroethyl isocyanate (22 uL, 0.258 mmol) at room temperature. After stirring overnight at reflux, the reaction mixture is concentrated in vacuo and the residue is diluted with ethyl acetate. The resulting semi-solid is triturated with hexane and the precipitate collected is collected by filtration and washed well with 50% ethyl acetate in hexane and dried in vacuo to afford (62 mg, 91%) of 1-(2-chloroethyl)-3-[4-(3-cyano-1-ethyl-6-methoxy-1H-indol-2-yl)-phenyl]-urea.

Utilizing essentially the same procedure, the following compounds are prepared: Compounds 295, 362, 395, 396, 397, 398, 399, 400, 401, 402, 403, 404, 405, 406, 407, 443, 444, 445, 446, 511, 512, 513, 600, 620, 626, 627, 628, 679, 680, 681, 740, 741, 742, 743, 748, 749, 750, 751, 774, 817, 818, 846, 847, 848, 954, 955, 956, 957, 958, 987, 999, 1000, 1001, 1008, 1009, 1010, 1011, 1012, 1013, 1014, 1016, 1017, 1018, 1019, 1023, 1024, 1027, 1036, 1039, 1043, 1045, 1060, 1061, 1066, 1067, 1070, 1080, 1092, 1094, 1095, 1096, 1097, 1098, 1099, 1100, 1101, 1102, 1106, 1108, 1118, 1120, 1124, 1125, 1126, 1136, 1137, 1138, 1139, 1143, 1144, 1156, 1157, 1162, 1163, 1164, 1165, 1171, 1172, 1173, 1197, 1190, 1214, 1221, 1223, 1224, 1225, 1225, 1227, 1256, 1279, 1301, 1303, 1304, 1305,

Example 1BV

Preparation of 1-ethyl-6-methoxy-2-[4-(2-oxo-imidazolidin-1-yl)-phenyl]-1H-indole-3-carbonitrile (Compound 771)

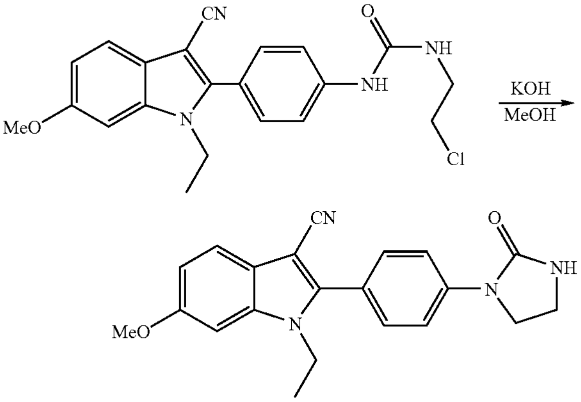

To a solution of 1-(2-chloroethyl)-3-[4-(3-cyano-1-ethyl-6-methoxy-1H-indol-2-yl)-phenyl]-urea (100 mg, 0.252 mmol) in MeOH (10 mL) is added aqueous 1M KOH (504 uL) and then stirred at 49° C. for 24 h. The solvents are removed under reduced pressure. The residue is diluted with ethyl acetate and then washed with water. The organic layer is dried over anhydrous $MgSO_4$, filtered and concentrated under reduced pressure. The residue is diluted with ethyl acetate and then triturated with hexane and the precipitate collected by filtration and washed well with 50% ethyl acetate in hexane and dried in vacuo to afford 1-ethyl-6-methoxy-2-[4-(2-oxo-imidazolidin-1-yl)-phenyl]-1H-indole-3-carbonitrile (56 mg, 62%).

Using essentially the same procedure, the following compounds are prepared: Compounds 770, 778

Example 1BW

Preparation of 1-ethyl-6-isopropoxy-2-[4-(2-oxo-oxazolidin-3-yl)-phenyl]-1H-indole-3-carbonitrile (Compound 638)

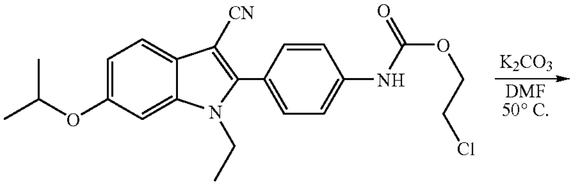

-continued

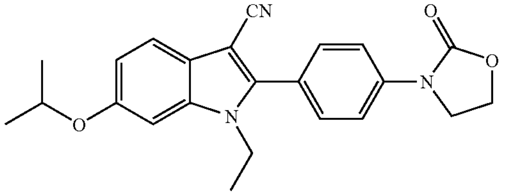

To a solution of [4-(3-cyano-1-ethyl-6-isopropoxy-1H-indol-2-yl)-phenyl]-carbamic acid 2-chloro-ethyl ester (30 mg, 0.07 mmol) in DMF (1 mL) is added aqueous $K_2CO_3$ (10 mg) and then stirred at 50° C. for 18 h. The reaction mixture is poured into cold water and the precipitate collected by filtration and washed with hexane and dried in vacuo to afford the title compound (21 mg, 81%).

The following compounds are made in similar fashion: Compounds 820, 821, 863, 864.

Example 1BX

Preparation of {3-[3-cyano-1-ethyl-6-(3-pyrrolidin-1-yl-propoxy)-1H-indol-2-yl]-phenyl}-carbamic acid ethyl ester (Compound 530)

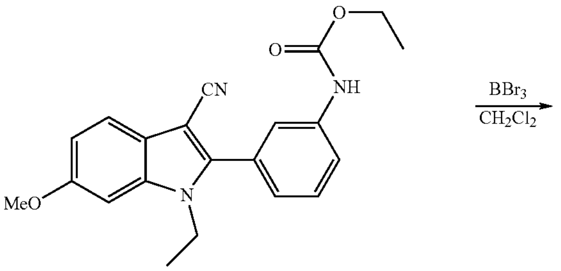

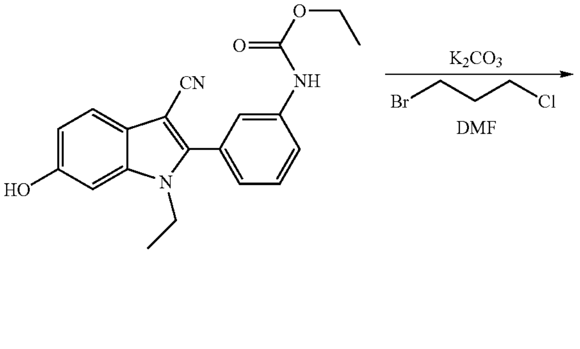

-continued

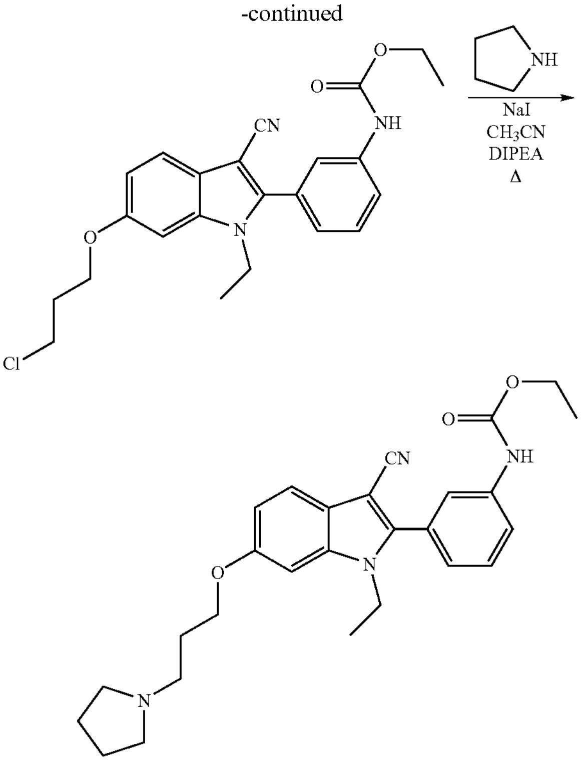

Step A: To a solution of [3-(3-cyano-1-ethyl-6-methoxy-1H-indol-2-yl)-phenyl]-carbamic acid ethyl ester (1.65 g, 4.37 mmol) in DCM (20 mL) is added 1M $BBr_3$ in DCM (13.12 mL) over a period of 20 min. The reaction mixture is stirred further 1 h at room temperature and then the solvents are removed under reduced pressure. The residue is dissolved in MeOH and then poured into cold water. The precipitate is collected by filtration and washed with hexane and dried in vacuo to afford [3-(3-cyano-1-ethyl-6-hydroxy-1H-indol-2-yl)-phenyl]-carbamic acid ethyl ester (1.5 g, 98%).

Step B: To a solution of [3-(3-cyano-1-ethyl-6-hydroxy-1H-indol-2-yl)-phenyl]-carbamic acid ethyl ester (1.2 g, 2.91 mmol) in DMF (10 mL) is added $K_2CO_3$ (538 mg, 3.9 mmol) and 3-bromo-1-chloropropane (383 uL, 3.9 mmol) and the reaction is stirred for overnight at 50° C. The reaction mixture is then poured into cold water and the precipitate is collected by filtration and washed with hexane and dried in vacuo to afford 1.1 g, 89% of the desired product.

Step C: To a solution of {3-[3-cyano-1-ethyl-6-(3-pyrrolidin-1-yl-propoxy)-1H-indol-2-yl]-phenyl}-carbamic acid ethyl ester (50 mg, 0.12 mmol) in $CH_3CN$ (2 mL) is added DIPEA (31 uL, 0.18 mmol), sodium iodide (20 mg, 0.132 mmol) and pyrrolidine (30 uL, 0.36 mmol). The resulting mixture is stirred at reflux temperature for overnight. The solvent is evaporated and the residue is diluted with ethyl acetate and then triturated with hexane and the precipitate collected by filtration and washed well with 50% ethyl acetate in hexane and dried in vacuo to afford 1-ethyl-6-isopropoxy-2-[4-(2-oxo-oxazolidin-3-yl)-phenyl]-1H-indole-3-carbonitrile, compound 638 (46 mg, 85%).

The following compounds are made in similar fashion following steps A-C, above: Compounds 441, 447, 491, 492, 493, 504, 525, 526, 527, 528, 529, 531, 532, 533, 534, 535, 536, 537, 538, 539.

Example 1BY

Preparation of [3-(3-cyano-1-ethyl-6-methoxy-1H-indol-2-yl)-phenyl]-thiourea (Compound 767)

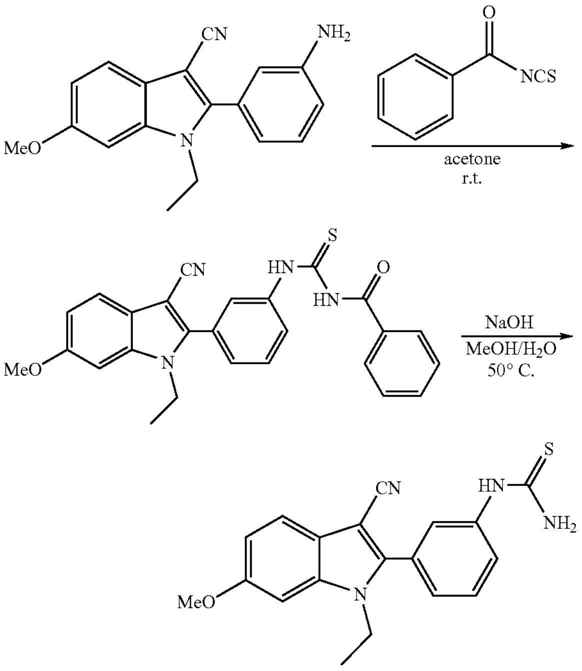

Step A: The starting material 2-(3-amino-phenyl)-1-ethyl-6-methoxy-1H-indole-3-carbonitrile (187 mg, 0.642 mmol) is dissolved in anhydrous acetone (3.0 mL). Benzoyl isothiocyanate (107 mg, 0.656 mmol) is added to the solution at room temperature and the mixture is stirred for 17 h during which time a precipitate forms. The precipitate is filtered, washed with acetone and dried to give 264 mg of 1-benzoyl-3-[3-(3-cyano-1-ethyl-6-methoxy-1H-indol-2-yl)-phenyl]-thiourea (90% yield) as a light yellow solid.

Step B: A suspension of 1-benzoyl-3-[3-(3-cyano-1-ethyl-6-methoxy-1H-indol-2-yl)-phenyl]-thiourea (241 mg, 0.530 mmol) in methyl alcohol (2.0 ml) and water (0.5 mL) is stirred at room temperature as sodium hydroxide (31 mg, 0.78 mmol) is added. The reaction mixture is heated to 50° C. for 17 h. The reaction mixture is concentrated to remove methyl alcohol. Water is added to the mixture and the solid is filtered, washed with water and dried to give 179 mg of [3-(3-cyano-1-ethyl-6-methoxy-1H-indol-2-yl)-phenyl]-thiourea, compound 767 (96% yield) as a white solid.

Example 1BZ

Preparation of 1-ethyl-6-methoxy-2-[4-(2-phenylquinazolin-4-ylamino)-phenyl]-1H-indole-3-carbonitrile (Compound 458)

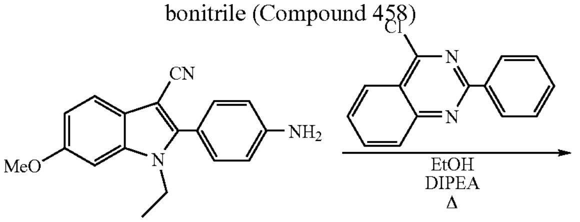

-continued

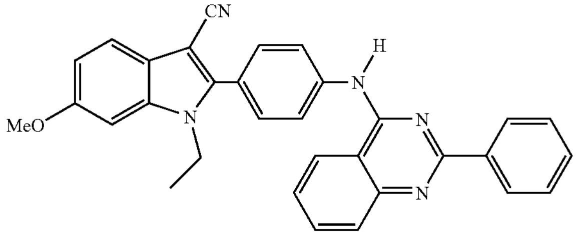

A solution of 2-(4-aminophenyl)-1-ethyl-6-methoxy-1H-indole-3-carbonitrile (100 mg, 0.343 mmol), 4-chloro-2-phenyl-quinazoline (83 mg, 0.34 mmol) and diisopropylethylamine (0.10 mL, 0.57 mmol) in absolute ethanol (3 mL) is heated to reflux overnight. The solution is cooled and evaporated, and the residue taken up in ethyl acetate (50 mL). This is washed with water and saturated brine (50 mL each), then dried over anhydrous sodium sulfate, filtered and evaporated. The resulting solid is triturated with ether, collected by filtration and dried under vacuum to afford 1-ethyl-6-methoxy-2-[4-(2-phenylquinazolin-4-ylamino)-phenyl]-1H-indole-3-carbonitrile (139 mg, 0.280 mmol, 82%).

Example 1CA

Preparation of diethyl[4-(3-cyano-6-ethoxy-1-ethyl-1H-indol-2-yl)-phenyl]-phosphoramidate (Compound 772)

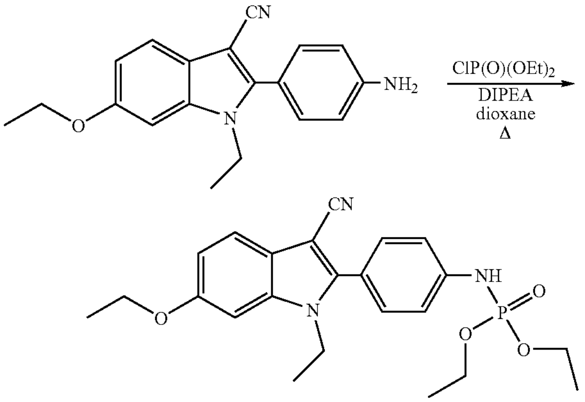

A solution of 2-(4-aminophenyl)-6-ethoxy-1-ethyl-1H-indole-3-carbonitrile (148 mg, 0.484 mmol), diethyl chlorophosphate (0.086 mL, 0.58 mmol) and diisopropylethylamine (0.10 mL, 0.57 mmol) in 1,4-dioxane (5 mL) is stirred at ambient temperature for 12 hours, then heated to 80° C. for an additional 24 hours. The solution is cooled and poured into 50 mL of ethyl acetate. This is washed with water and saturated brine (50 mL each), then dried over anhydrous magnesium sulfate, filtered and evaporated. The residual material is separated by flash chromatography (eluting 2/1 ethyl acetate/hexane on silica gel 60) to afford diethyl[4-(3-cyano-6-ethoxy-1-ethyl-1H-indol-2-yl)-phenyl]-phosphoramidate (108 mg, 0.245 mmol, 51%) as a white powder after evaporation.

The following examples are made in similar fashion: Compounds 936, 937, 942, 943, 944, 1081.

Example 1CB

Preparation of 1-ethyl-6-methoxy-2-[4-(5-methyl-1,1-dioxo-1λ$^6$-[1,2,5]thiadiazolidin-2-yl)-phenyl]-1H-indole-3-carbonitrile (Compound 726)

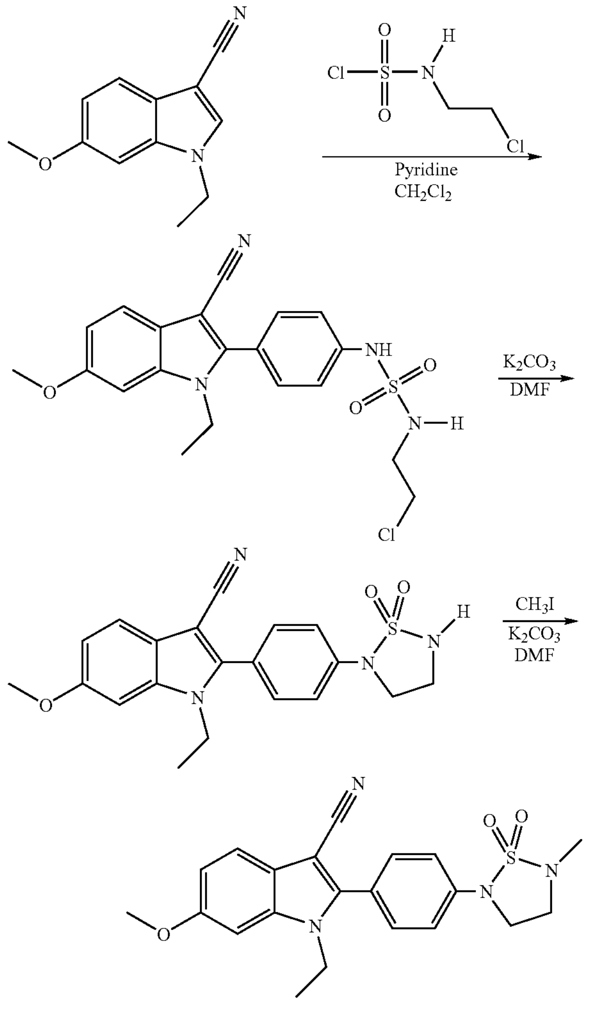

Step A: To a solution of 2-(4-aminophenyl)-1-ethyl-6-methoxy-1H-indole-3-carbonitrile (202 mg, 0.693 mmol) in pyridine (2.0 mL) is added the N-β-(chloroethylamino)sulfonyl chloride (222 mg, 1.39 mmol). The mixture is stirred at room temperature for 17 h then water (12.0 mL) is added and the mixture is extracted with ethyl acetate (3×2 mL). The extract is washed with 10% aqueous HCl (2×2 mL), water (2×2 mL), dried over $MgSO_4$, filtered and concentrated on a rotary evaporator. The crude product is purified by flash chromatography (0-5%, ethyl acetate/methylene chloride) to give 217 mg of N-(2-chloro-ethyl)-N'-[4-(3-cyano-1-ethyl-6-methoxy-1H-indol-2-yl)phenyl]sulfamide, compound 724, as a tan solid (75% yield).

In similar fashion the following compounds are prepared: Compounds 540, 541, 542, 574, 576, 704.

Step B: To a solution of N-(2-chloro-ethyl)-N'-[4-(3-cyano-1-ethyl-6-methoxy-1H-indol-2-yl)phenyl]sulfamide (100 mg, 0.241 mmol) in anhydrous DMF (1.25 mL), is added potassium carbonate (71.0 mg, 0.514 mmol). The mixture is stirred at room temperature for 17 h, then diluted with water (7.5 mL). The reaction mixture is extracted with ethyl acetate (3×2 mL) and the extract is washed with water (2×2 mL), dried over $MgSO_4$ and concentrated to give 2-[4-(1,1-dioxo-1λ$^6$-[1,2,5]thiadiazolidin-2-yl)phenyl]-1-ethyl-6-methoxy-1H-indole-3-carbonitrile, compound 725, as a white solid (84 mg, 88% yield).

In similar fashion the following compound is prepared: Compound 705.

Step C: To a solution of 2-[4-(1,1-dioxo-1λ$^6$-[1,2,5]thiadiazolidin-2-yl)phenyl]-1-ethyl-6-methoxy-1H-indole-3-carbonitrile (34 mg, 0.086 mmol) in anhydrous DMF (1.0 mL) is added potassium carbonate (25 mg, 0.18 mmol) and iodomethane (20.4 mg, 0.144 mmol). The mixture is stirred at room temperature for 2 h and then diluted with water (6.0 mL) to give a precipitate. The precipitate is filtered, washed with water and dried to give I-ethyl-6-methoxy-2-[4-(5-methyl-1,1-dioxo-1λ$^6$-[1,2,5]thiadiazolidin-2-yl)-phenyl]-1H-indole-3-carbonitrile, compound 726, as a white solid (35 mg, 98% yield).

In similar fashion the following compounds are prepared: Compounds 727, 1110.

Example 1CC

Preparation of [4-(3-cyano-1-ethyl-6-methoxy-1H-indol-2-yl)-2-fluorophenyl]-carbamic acid propyl ester (Compound 877)

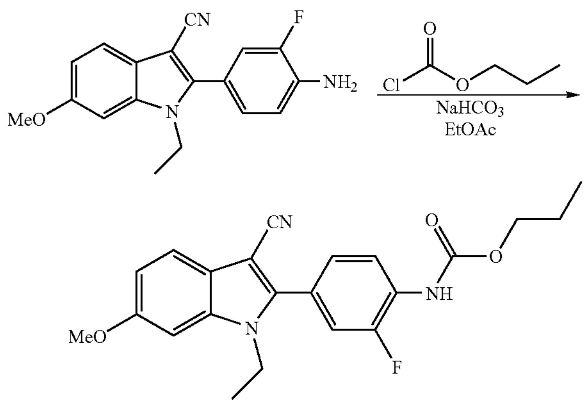

A biphasic mixture of 2-(4-amino-3-fluorophenyl)-1-ethyl-6-methoxy-1H-indole-3-carbonitrile (74 mg, 0.24 mmol), prepared as described in example 1Gb, and propyl chloroformate (0.033 mL, 0.29 mmol) in EtOAc (3 mL) and saturated $NaHCO_3$ (3 mL) is prepared at 0° C. and then allowed to warm to room temperature and stirred for 24 h. The reaction is then diluted with $H_2O$ and extracted with EtOAc (2×). The organic phases are washed with $H_2O$ and saturated NaCl and then dried and concentrated. Flash chromatography (EtOAc/hexanes 10-40%) gives 60 mg (63%) of [4-(3-cyano-1-ethyl-6-methoxy-1H-indol-2-yl)-2-fluorophenyl]-carbamic acid propyl ester as an off-white solid.

The following compounds are prepared in a similar fashion: Compounds 875, 876, 878, 879. By utilizing 2-(4-amino-3-methylphenyl)-1-ethyl-6-methoxy-1H-indole-3-carbonitrile the following compounds are prepared: Compounds: 963, 964, 965.

Utilizing the same starting material and procedures described in examples 1Y, the following compounds are prepared: Compounds 871, 872, 873, 874. In similar fashion, utilizing 2-(4-amino-3-methylphenyl)-1-ethyl-6-methoxy-1H-indole-3-carbonitrile, the following compounds are prepared: Compounds 959, 960, 961, 962.

Utilizing the same starting material and procedures described in examples 1BU, the following compounds are prepared: 909, 910, 911. In a similar fashion, utilizing 2-(4-amino-3-methylphenyl)-1-ethyl-6-methoxy-1H-indole-3-carbonitrile, the following compounds are prepared: Compound: 966, 967.

Example CD

Preparation of cyclopropanecarboxylic acid {4-[3-cyano-1-ethyl-6-(2-imidazol-1-yl-ethoxy)-1H-indol-2-yl]-phenyl}-amide (Compound 1183)

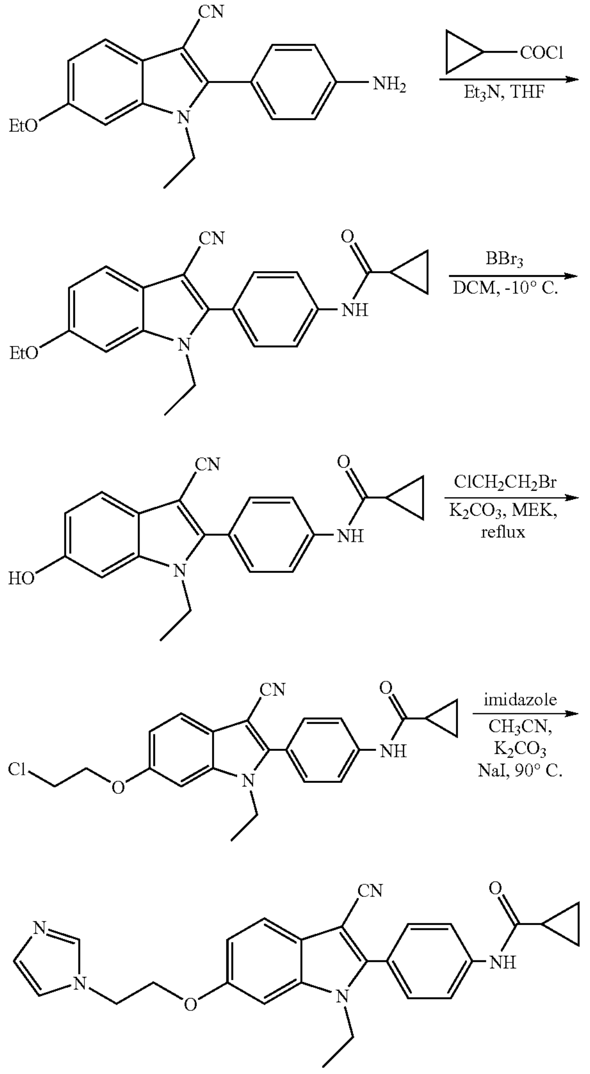

Step A: To a solution of compound 2-(4-aminophenyl)-6-ethoxy-1-ethyl-1H-indole-3-carbonitrile (3.66 g, 12 mmol), prepared as described in example 1Gb, in 20 mL of THF is added $Et_3N$ (3.37 ml) and cyclopropanecarbonyl chloride (1.6 mL, 18 mmol). The mixture is stirred for 3 h at room temperature. Then water and ethyl acetate are added to the reaction mixture. The organic layer is separated, washed with brine (2×), dried over anhydrous $Na_2SO_4$, filtered and concentrated. The residue is recrystallized with ethyl acetate and hexane to yield 99% of cyclopropanecarboxylic acid [4-(3-cyano-6-ethoxy-1-ethyl-1H-indol-2-yl)-phenyl]-amide.

Step B: To a solution of cyclopropanecarboxylic acid [4-(3-cyano-6-ethoxy-1-ethyl-1H-indol-2-yl)-phenyl]-amide (4.4 g, 11.8 mmol) in 60 mL of DCM is added $BBr_3$ (6.65 mL, 70 mmol) at −10° C. After the addition, the mixture is stirred for 3 h at 0° C. Then aqueous $NaHCO_3$ is added to the mixture carefully until it became basic. The crude solid is collected by filtration to give 91% of cyclopropanecarboxylic acid [4-(3-cyano-1-ethyl-6-hydroxy-1H-indol-2-yl)-phenyl]-amide and is used for the next step without further purification.

Step C: To a solution of cyclopropanecarboxylic acid [4-(3-cyano-1-ethyl-6-hydroxy-1H-indol-2-yl)-phenyl]-amide (4 g, 11.6 mmol) in 15 mL of MEK is added $K_2CO_3$ (8 g, 58 mmol) and 1-bromo-2-chloro-ethane (6.7 mL, 70 mmol). Then the mixture is heated at reflux overnight. After it is cooled to room temperature, water and ethyl acetate are added. The organic layer is separated, washed with brine (2×), dried over anhydrous $Na_2SO_4$, filtered and concentrated to yield 81% of the crude cyclopropanecarboxylic acid {4-[6-(2-chloroethoxy)-3-cyano-1-ethyl-1H-indol-2-yl]-phenyl}-amide.

Step D: To a solution of cyclopropanecarboxylic acid {4-[6-(2-chloroethoxy)-3-cyano-1-ethyl-1H-indol-2-yl]-phenyl}-amide (102 mg, 0.25 mmol) in 1.5 mL of acetonitrile are added NaI (46 mg, 0.275 mmol), $K_2CO_3$ (138 mg, 1 mmol) and imidazole (51 mg, 0.75 mmol) in a sealed tube. Then the mixture is heated to 90° C. and stirred overnight. After it is cooled to room temperature, water and ethyl acetate are added. The organic layer is separated, washed with brine (2×), dried over anhydrous $Na_2SO_4$, filtered and concentrated. The crude compound is purified by preparative HPLC to give 71% of cyclopropanecarboxylic acid {4-[3-cyano-1-ethyl-6-(2-imidazol-1-yl-ethoxy)-1H-indol-2-yl]-phenyl}-amide.

Using the same procedure and substituting the appropriate nucleophilic reagents gives the following compounds: Compounds 952, 1025, 1054, 1090, 1091, 1092, 1093, 1184.

Example CE

Preparation of ethanesulfonic acid [4-(3-cyano-1-ethyl-6-trifluoromethoxyindol-2-yl)phenyl]amide (Compound 881)

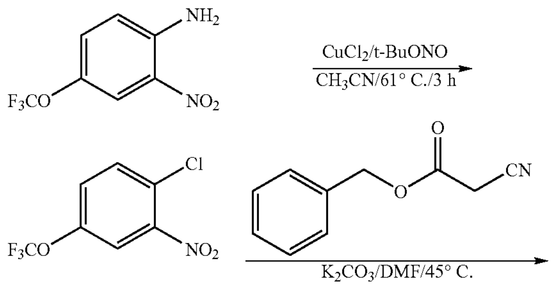

-continued

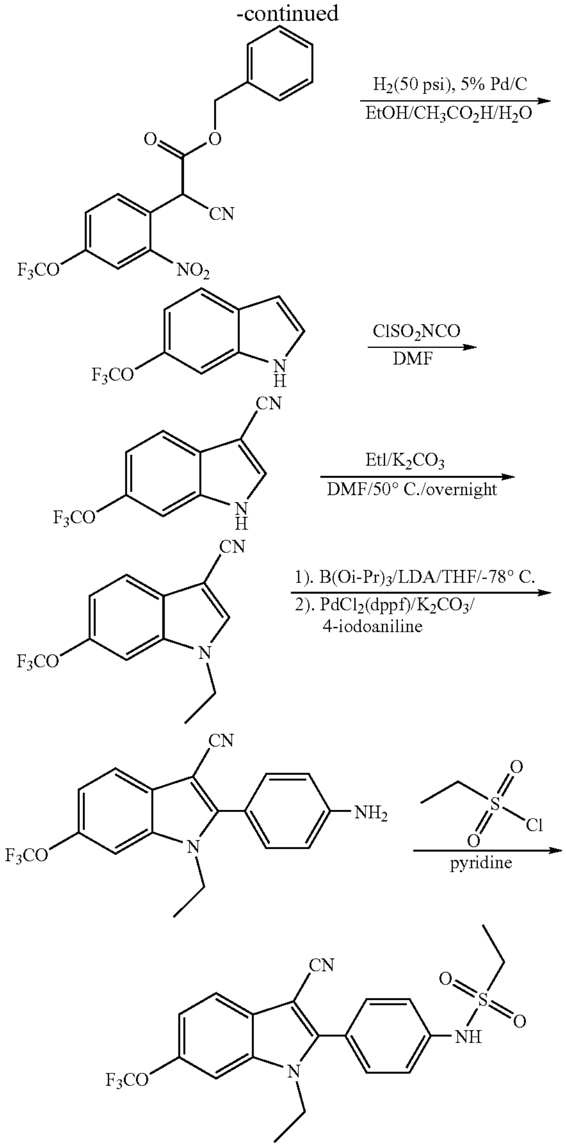

Step A: To a suspension of t-BuONO (8.01 mL, 67.5 mmol) and $CuCl_2$ (7.26 g, 54 mmol) in acetonitrile (50 mL), at 61° C. with gentle stirring, is added 2-nitro-4-trifluoromethoxyaniline (10.0 g, 45.0 mmol) portionwise. The mixture is stirred at this temperature for 2 h after the addition. The solvent is removed on a rotorvap and the residue is treated with HCl (6 N, 200 mL), and extracted with dichloromethane (3×100 mL). The extracts are combined, dried over anhydrous $Na_2SO_4$, and passed through a short silica gel pad. The solvent is removed and the residue is added to a suspension of benzyl cyanoacetate (7.88 g, 45 mmol) and $K_2CO_3$ (12.42 g, 90 mmol) in DMF (100 mL). This mixture is then stirred at 45° C. overnight and poured into ice-water (700 mL), and extracted with dichloromethane (3×100 mL). The organics are dried over anhydrous $Na_2SO_4$ and again passed through a short silica gel pad, eluting with ethyl acetate. The solvent is then replaced with EtOH (160 mL), acetic acid (16 mL) and water (16 mL), and the reaction mixture is hydrogenated over 5% Pd/C (2.80 g) at 50 psi overnight. The mixture is filtered over Celite and the volatiles are removed in vacuo. The residue is dissolved in dichloromethane (200 mL), washed with $Na_2CO_3$ (2 M, 2×50 mL), water (2×50 mL), brine (50 mL) and dried over anhydrous $Na_2SO_4$. The crude product, obtained after the removal of the solvent, is chromatographed (silica gel, DCM/Hexanes, 1/1) to provide 6-trifluoromethoxyindole (5.70 g, 63% based on 2-nitro-4-trifluoromethoxyaniline).

Step B: To a solution of 6-trifluoromethoxyindole (2.68 g, 13.3 mmol) in dry DMF (10 mL) at 0° C., is added chlorosulfonylisocyanate (2.35 g, 1.44 mL, 16.6 mmol). The mixture is then brought to room temperature slowly and stirred for 1 h. The mixture is poured into ice (100 mL) and stirred for 1 h. The precipitate is collected by filtration and washed thoroughly with water and dried in vacuo, which is then dissolved in DMF (15 mL). To the solution is added $K_2CO_3$ and EtI (2.59 g, 1.34 mL, 16.6 mmol), and the mixture is stirred at 50° C. overnight. It is then poured into ice-water (200 mL). The precipitate is collected by filtration and washed with water, dried in air and purified by chromatography (silica gel, DCM) to furnish 1-ethyl-6-trifluoromethoxyindole-3-carbonitrile (2.90 g, 86%).

Step C: To a solution of the intermediate (2.03 g, 8.0 mmol) obtained above, triisopropylborate (2.16 g, 2.65 mL, 12.0 mmol) in dry THF (15 mL) at −78° C. is added LDA (6.7 mL, 1.5 M, 10.0 mmol). The mixture is stirred at −78° C. for 15 min after the addition, then slowly brought to room temperature and stirred for 30 min. It is then cooled at −78° C. and followed by the addition of 4-iodoaniline (2.10 g, 9.6 mmol), $PdCl_2$(dppf) (0.29 g, 0.4 mmol), DMF (30 mL) and $K_2CO_3$ (12.0 mL, 2.0 M, 24.0 mmol). The mixture is brought to room temperature slowly and stirred overnight and poured into ice-water (400 mL). The precipitate is collected and washed with water, chromatographed (silica gel, EtOAc/DCM, 0.5/9.5) to furnish 2-(4-aminophenyl)-1-ethyl-6-trifluoromethoxyindole-3-carbonitrile (1.99 g, 72%).

Step D: To a solution of the compound obtained in step C (31 mg, 0.1 mmol) in dry pyridine (1.0 mL) is added ethanesulfonyl chloride (14 μL, 0.15 mmol). The mixture is stirred at room temperature overnight and diluted with water (5 mL). The organic is extracted with DCM (5 mL) and washed with HCl (2N, 2×3 mL), water (2×4 mL) and brine (3 mL) and chromatographed (silica gel, EtOAc/DCM, 0.5/9.5) to provide the product, ethanesulfonic acid [4-(3-cyano-1-ethyl-6-trifluoromethoxyindol-2-yl)phenyl]amide (33 mg, 83%).

Compounds 882, 883, 884, 885, 886, 887, 888, 889 are prepared utilizing the above route using either the appropriate alkylsulfonyl chlorides (procedure 1Y) or chloroformates (procedure 1AJ).

Example 1CF

Preparation of 2-[4-(1,1-dioxidoisothiazolidin-2-yl)phenyl]-1-ethyl-6-(trifluoromethoxy)indole-3-carbonitrile (Compound 903)

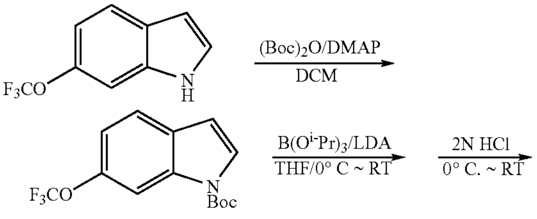

-continued

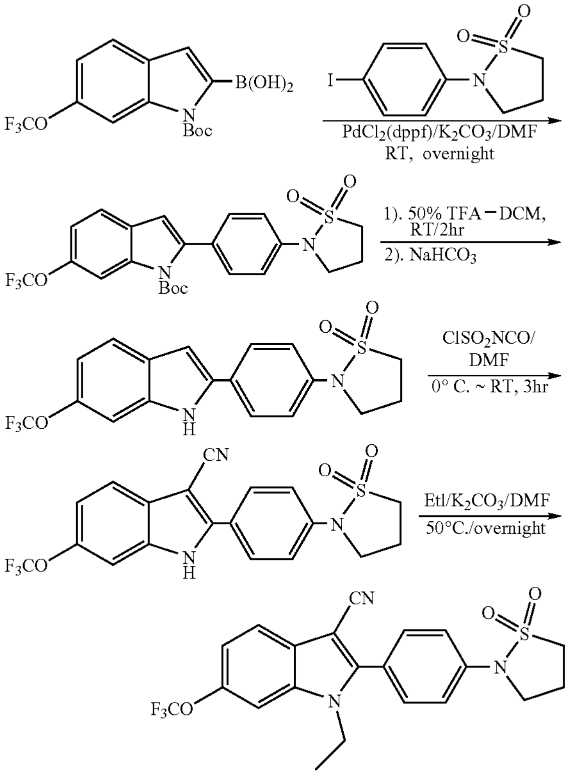

Step A: To a solution of 6-trifluoromethoxyindole (3.01 g, 15.0 mmol) and di-tert-butyl dicarbonate (3.59 g, 16.5 mmol) in DCM (30 mL) at 40° C. is added DMAP (0.04 g) while stirring. After stirring overnight, the mixture is washed sequentially with 0.1 N HCl, water and brine and dried over anhydrous $Na_2SO_4$. The solvent is evaporated and the residue is chromatographed (silica gel, EtOAc/Hexanes, 1/9) to provide tert-butyl 6-trifluoromethoxy-1H-indole-1-carboxylate.

Step B: The above Boc-indole and triisopropylborate (4.73 g, 5.8 mL, 26.3 mmol) are dissolved in anhydrous THF (20 mL) and the solution is cooled to 0° C. While stirring, LDA (15.0 mL, 1.5 M mono-THF complex in cyclohexane, 22.5 mmol) is added dropwise. The mixture is stirred at 0° C. for 15 min and then room temperature for 0.5 h, followed by the addition of HCl (6 N, 3.75 mL, 22.5 mmol) in an ice-water bath. The organic solvent is removed in vacuo and the residue is suspended in $H_2O$ (100 mL) and acidified with HCl (6 N) to pH 4-5. The precipitate is collected via filtration and washed with water and hexanes and dried in air to provide 1-Boc-6-trifluoromehoxyindole-2-boronic acid (2.56 g, 49%).

Step C: To a mixture of 1-Boc-6-trifluoromehoxyindole-2-boronic acid prepared above (0.74 g, 2.1 mmol), 2-(4-iodophenyl)isothiazolidine-1,1-dioxide (0.76 g, 2.4 mmol), and $PdCl_2$(dppf) (0.08 g, 0.1 mmol) in DMF (6.0 mL), is added $K_2CO_3$ solution (3.2 mL, 2.0 M, 6.4 mmol). The mixture is stirred at room temperature overnight and then poured into ice-water (100 mL). The precipitate is collected and washed with water and purified by flash column chromatography (silica gel, DCM/EtOAc, 9/1) to furnish 1-Boc-2-[4-(1,1-dioxidoisothiazolidin-2-yl)phenyl]-6-methoxyindole, which is treated with 50% TFA in DCM (15 mL) at room temperature for 1 h. After the removal of the volatiles, the residue is carefully stirred with saturated $NaHCO_3$ for 0.5 h. The precipitate is collected via filtration and washed thoroughly with water and dried to provide essentially pure 1-H-2-[4-(1,1-dioxidoisothiazolidin-2-yl)phenyl]-6-trifluoromethoxyindole.

Step D: At 0° C., a solution of the intermediate obtained above in dry DMF (10 mL) is treated with chlorosulfonyl isocyanate (0.38 g, 0.23 mL, 2.68 mmol). The mixture is then stirred at room temperature overnight and poured into ice-water (150 mL) then stirred for 0.5 h. The precipitate is collected via filtration and washed thoroughly with water and dried in air to furnish 1-H-2-[4-(1,1-dioxidoisothiazolidin-2-yl)phenyl]-6-trifluoromethoxyindole-3-carbonitrile (0.81 g, 90%).

Step E: To a solution of 1-H-2-[4-(1,1-dioxidoisothiazolidin-2-yl)phenyl]-6-trifluoromethoxyindole-3-carbonitrile (63 mg, 0.15 mmol) and $K_2CO_3$ (62 mg, 0.45 mmol) in DMF (2.0 mL) is added ethyl iodide (36 μL, 0.45 mmol). The mixture is stirred at 50° C. overnight and poured into ice-water (10 mL). The precipitate is collected via filtration, washed with water and purified by column chromatography to provide 2-[4-(1,1-dioxidoisothiazolidin-2-yl)phenyl]-6-trifluoromethoxy-1-ethylindole-3-carbonitrile (59 mg, 88%).

The following compounds are prepared in the same fashion as described above: Compounds 902, 904, 905, 906.

Example 1CG

Preparation of [4-(3-cyano-1-cyclopropyl-6-methoxyindol-2-yl)phenyl]carbamic acid isopropyl ester (Compound 1234)

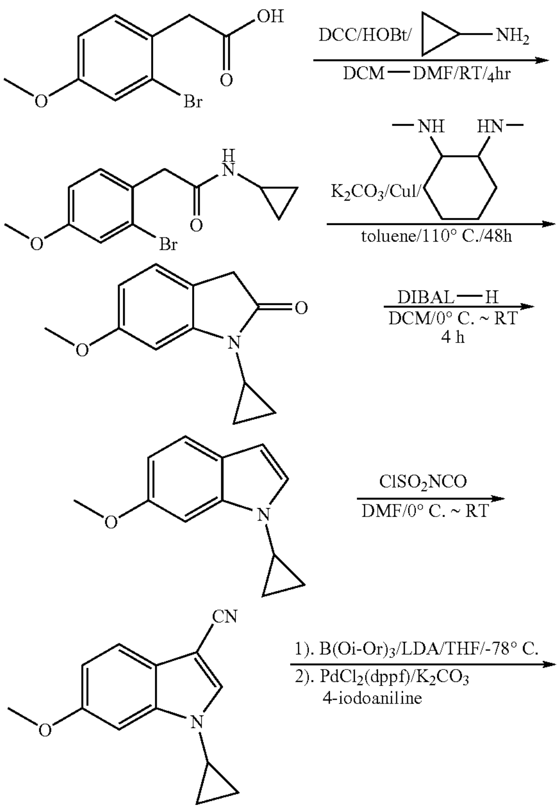

-continued

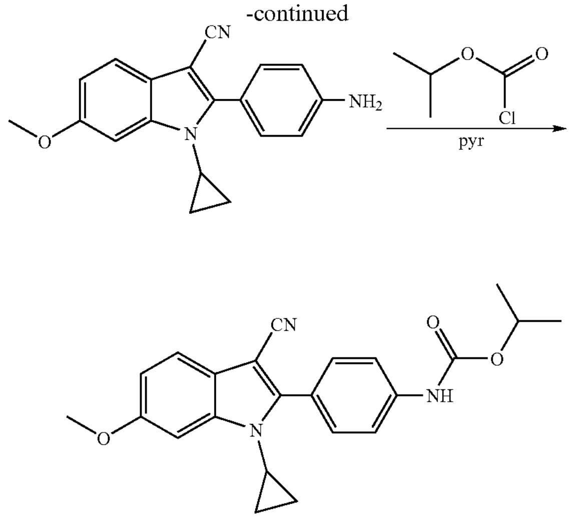

Step A: To a suspension of 2-bromo-4-methoxyphenylacetic acid (24.5 g, 100 mmol) in DCM (100 mL), while stirring, is added DMF (~10 mL) until all the solid disappears, which is followed by the addition of DCC (22.66 g, 110 mmol) and HOBt (14.85 g, 110 mmol). After stirring at RT for 10 min, cyclopropylamine (8.55 g, 10.4 mL, 150 mmol) is added to the mixture, and the resulting mixture is stirred at room temperature for 4 h. The solid is filtered and washed thoroughly with DCM (300 mL). The filtrate is cooled to −10° C. and gently stirred for 1 h and filtered again to remove additional urea by-product. The filtrate is passed through a silica gel pad and eluted with DCM/EtOAc, 8/2). After the removal of the solvent, the cyclopropyl amide intermediate is obtained as white solid (28.34 g, 100%).

Step B: A mixture of above amide (14.2 g, 50.0 mmol), $K_2CO_3$ (13.8 g, 100 mmol), CuI (0.74 g, 5.0 mmol) and N,N'-dimethylcyclohexanediamine (1.42 g, 1.57 mL, 10.0 mmol) in toluene (150 mL) is stirred at 110° C. under $N_2$ atmosphere for 48 h. After cooling to room temperature, the mixture is filtered over Celite and washed thoroughly with DCM. The filtrate is evaporated under reduced pressure to dryness and the residue is chromatographed (DCM/EtOAc, 9.5/0.5) to provide the product, 1-cyclopropyl-6-methoxyoxindole as pale yellow solid (4.30 g, 42%).

Step C: To a solution of the oxindole obtained above (5.0 g, 24.6 mmol) in dry DCM (25 mL), at 0° C., is added DIBAL-H (1.0 M in DCM, 35.0 mL, 35.0 mmol). After the addition, the mixture is stirred at room temperature for 4 h and re-cooled to 0° C., followed by the addition of HCl (2 N) dropwise. The DCM layer is washed with HCl (2 N, 10 mL) water and brine and dried over anhydrous $Na_2SO_4$. The crude product obtained after the removal of the solvent is chromatographed (hexanes/EtOAc, 9.5/0.5) to provide the 1-cyclopropyl-6-methoxyindole as a colorless oil (4.52 g, 98%).

Step D: To a solution of 1-cyclopropyl-6-methoxylindole (3.29 g, 17.6 mmol) in dry DMF (30 mL), at 0° C., is added chlorosulfonyl isocyanate (3.11 g, 1.91 mL, 22.0 mmol). After the addition, the mixture is stirred at room temperature for 2 h, followed by aqueous work-up. Chromatography (silica gel, hexanes/EtOAc, 9/1) furnishes 3-cyano-1-cyclopropyl-6-methoxyindole (3.05 g, 82%).

Step E: To a solution of the intermediate (2.65 g, 12.5 mmol) obtained above and triisopropyl borate (3.38 g, 4.14 mL, 18.8 mmol) in dry THF (18 mL) at −78° C. is added LDA (10 mL, 1.5 M, 15.0 mmol). The mixture is stirred at −78° C. for 15 min after the addition, then slowly brought to room temperature and stirred for 30 min. It is then cooled at −78° C. and followed by the addition of 4-iodoaniline (3.29 g, 15.0 mmol), $PdCl_2$(dppf) (0.46 g, 0.6 mmol), DMF (40 mL) and $K_2CO_3$ (18.8 mL, 2.0 M, 37.6 mmol). The mixture is brought to room temperature slowly and stirred overnight and then poured into ice-water (400 mL). The precipitate is collected and washed with water, and after drying, is chromatographed (silica gel, EtOAc/DCM, 0.5/9.5) to furnish 2-(4-aminophenyl)-1-cyclopropyl-6-methoxyindole-3-carbonitrile (2.84 g, 75%).

Step F: To a solution of the compound obtained in step E (61 mg, 0.2 mmol) in dry pyridine (2.0 mL) is added isopropylchloroformate (0.3 mL, 1.0 M, 0.3 mmol) in toluene. The mixture is stirred at room temperature overnight and diluted with water (10 mL). The organic layer is extracted with DCM (10 mL) and washed with HCl (2N, 2×3 mL), water (2×4 mL) and brine (3 mL) and chromatographed (silica gel, EtOAc/DCM, 0.5/9.5) to provide the product, [4-(3-cyano-1-cyclopropyl-6-methoxyindol-2-yl)phenyl]carbamic acid isopropyl ester (66 mg, 85%).

Compounds 1235 and 1236 are prepared by utilizing the above chemistry.

Example 1CH

Preparation of 1-allyl-6-methoxy-2-[4-(2-oxopyrrolidin-1-yl)-phenyl]-1H-indole-3-carbonitrile (Compound 938)

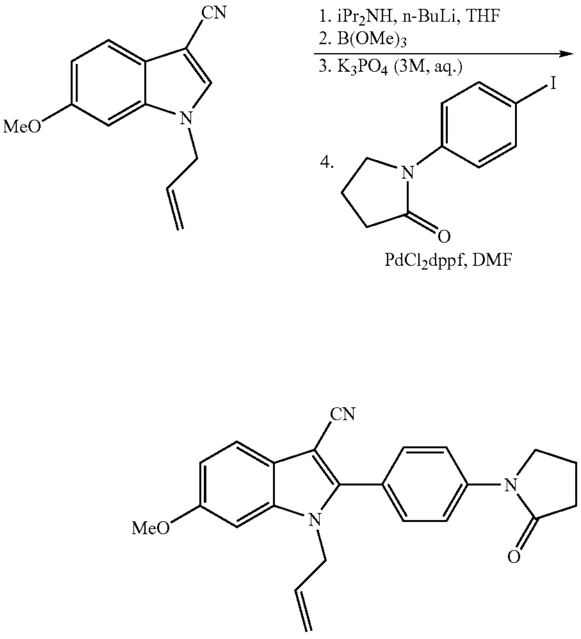

Utilizing the procedure described in Example 1Gb, substituting 1-allyl-6-methoxy-1H-indole-3-carbonitrile (92.3 mg, 0.43 mmol) and 1-(4-iodophenyl)-pyrrolidin-2-one gives 99.0 mg (61.3% yield) of compounds 938.

Example 1CI

Preparation of 6-cyclopropoxy-2-[4-(1,1-dioxo-1λ⁶-isothiazolidin-2-yl)-phenyl]-1-ethyl-1H-indole-3-carbonitrile (Compound 1046)

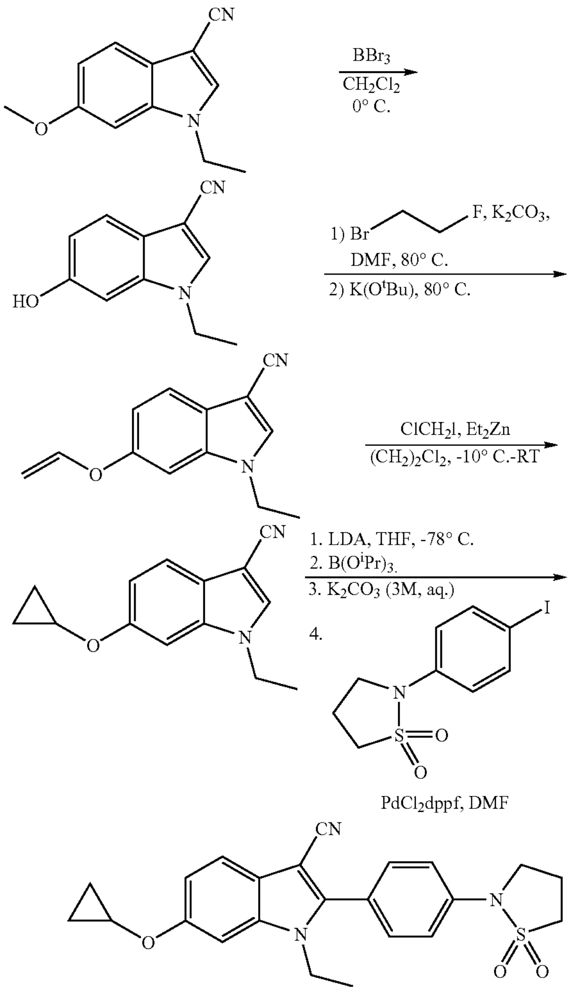

Step A: Utilizing the procedure described in Example 1B (Step A) gives 6-hydoxy-1-ethyl-1H-indole-3-carbonitrile.

Step B: To a solution of 6-hydoxy-1-ethyl-1H-indole-3-carbonitrile (503.9 mg, 2.70 mmol) in 5 mL of DMF is added anhydrous $K_2CO_3$ (1.12 g, 8.12 mmol) and 1-bromo 2-fluoroethane (413.7 mg, 3.29 mmol). The resulting mixture is stirred at 80° C. until complete consumption of the starting material as determined by TLC. The reaction mixture is cooled, potassium tert-butoxide (1M solution in THF, 5.5 ml, 5.43 mmol) is added, and stirring continued at 80° C. overnight. The mixture is partitioned between EtOAc (30 mL) and 1N HCl (20 mL). The organic phase is washed with saturated $NaHCO_3$, saturated NaCl and dried and concentrated. The product is isolated by chromatography (EtOAc/hexanes, 10-25%) over silica gel to afford 430.2 mg (74.9%) 1-ethyl-6-vinyloxy-1H-indole-3-carbonitrile as a white solid.

Step C: Via a syringe, diethyl zinc is added to a mixture of 1-ethyl-6-vinyloxy-1H-indole-3-carbonitrile (288.1 mg, 1.36 mmol), chloroiodomethane (268.9 mg, 1.53 mmol) and 5 ml of 1,2-dichloroethane over a period of 10 min, maintaining the temperature at −10° C. The mixture is warmed to 20-25° C. for 20 min., and then cooled back to 0° C. Saturated $NH_4Cl$ (15 mL), concentrated ammonium hydroxide (15 mL), and ethyl acetate (15 mL) are added in sequence at this temperature, and stirred for 10 min. After the phases are separated, the aqueous phase is back-extracted with ethyl acetate (10 mL). The combined organic phases are washed with saturated $NH_4Cl$ (10 mL), dried over $MgSO_4$ and then the solution is concentrated and the product is purified by chromatography, eluting with 15-30% ethyl acetate/hexanes to afford 140.5 mg (45.7% yield) of 6-cyclopropoxy-1-ethyl-1H-indole-3-carbonitrile as a yellow solid.

Step D: Utilizing the same procedure described in Example 1Gb substituting 4-iodoaniline with 2-(4-iodo-phenyl)-isothiazolidine 1,1-dioxide gives the title compound.

In similar fashion, following steps A to D, above, compound 1047 is also prepared.

Example CJ

Propane-1-sulfonic acid [4-(3-cyano-6-difluoromethoxy-1-ethyl-1H-indoel-2-yl)-phenyl]-amide (Compound 928)

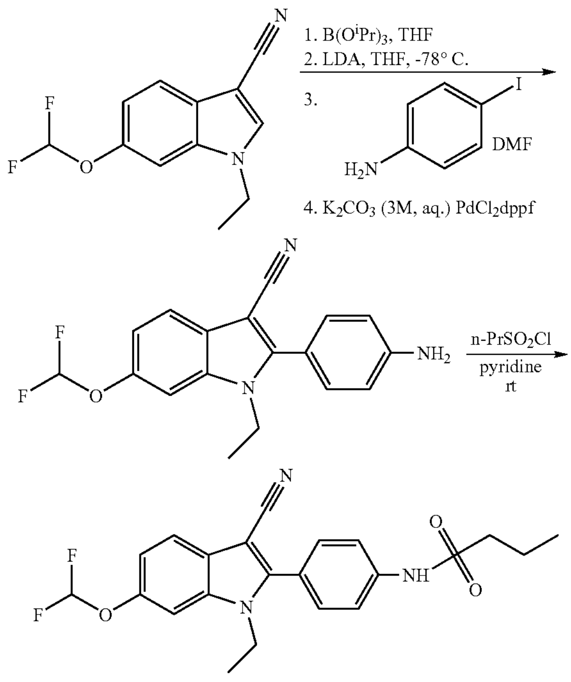

Step A: A solution of 6-difluoromethoxy-1-ethyl-1H-indole-3-carbonitrile (316.3 mg, 1.34 mmol) and triisopropyl borate (402.9 mg, 2.14 mmol) in THF (15 mL) is cooled to −78° C. and treated with LDA (1.5 M mono-THF in cyclohexane, 1.07 mL, 1.61 mmol). After the addition, the acetone/dry ice bath is exchanged for an ice water bath and the solution is stirred further for 30 min. The solution is cooled to −78° C. and a solution of 4-iodoaniline (299.5 mg, 1.37 mmol) in DMF (8 mL), $K_2CO_3$ (2M, 2.01 mL, 6.02 mmol) and $PdCl_2dppf$ (51.3 mg, 0.07 mmol) are added in sequence. The mixture is degassed by three successive cycles of vacuum pumping/$N_2$ purging and is stirred overnight (ca. 16 h.). The reaction mixture is poured into 4 volumes of water, and 4 volumes of ethyl acetate are added. The phases are separated, and the aqueous phase is extracted with more ethyl acetate. The organic phases are washed by water, saturated NaCl and then dried over anhydrous $MgSO_4$, filtered and evaporated. The remaining material is purified by column chromatography, eluting with 5-15% ethyl acetate/hexanes on silica gel to yield 304.5 mg (70%) of the aniline intermediate as a white solid.

Step B: Utilizing the same procedure described in Example 1Y and substituting n-propylsulfonyl chloride gives the title compound.

The following compounds are made using essentially the same procedure and substituting other sulfonyl chlorides: Compounds 929, 930, 931.

Example 1CK

[4-(3-cyano-6-difluoromethoxy-1-ethyl-1H-indol-2-yl)-phenyl]-carbamic acid methyl ester (Compound 1130)

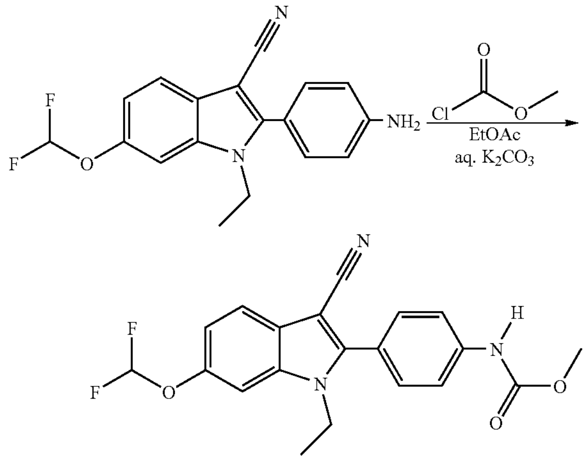

A solution of 2-(4-aminophenyl)-6-difluoromethoxy-1-ethyl-1H-indole-3-carbonitrile (200 mg, 0.611 mmol) and methyl chloroformate (95 μL, 1.23 mmol) in ethyl acetate (2 mL) is treated with 2 M aqueous potassium carbonate solution (0.370 mL, 0.74 mmol), and the resulting mixture is stirred vigorously overnight. Saturated brine solution (1 mL) is added, and the mixture is stirred for 10 minutes. The organic layer is removed, dried over anhydrous magnesium sulfate, filtered and evaporated. The resulting solid is triturated with 1/1 ether-hexane, collected by filtration and dried under vacuum to afford the title product as a white solid.

Similarly prepared from appropriate reagents are: Compounds 1131, 1132, 1133, 1134, 1135.

Example 1CL

1-[4-(3-cyano-6-difluoromethoxy-1-ethyl-1H-indol-2-yl)-phenyl]-3-propyl-urea (Compound 893)

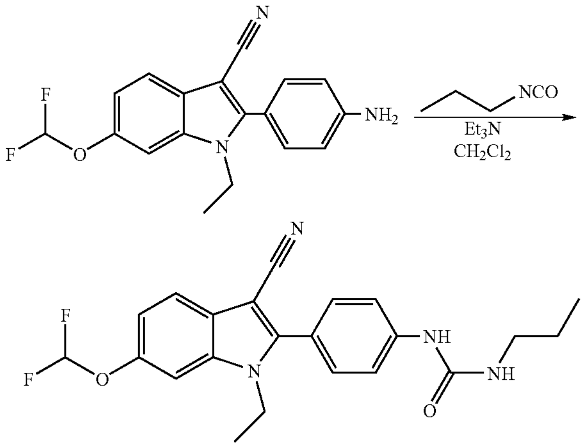

A solution of 2-(4-aminophenyl)-6-difluoromethoxy-1-ethyl-1H-indole-3-carbonitrile (200 mg, 0.611 mmol) in 1,2-dichloroethane (2 mL) is treated with n-propylisocyanate (115 mL, 1.23 mmol) and triethylamine (170 mL, 1.22 mmol). The resulting solution is stirred at ambient temperature for 12 hours, and then concentrated. The residual material is separated by silica gel chromatography (1/2 ethyl acetate-hexane) to afford the title product as a solid.

Similarly prepared from appropriate reagents are: Compounds 892, 894.

Example 1CM

Preparation of morpholine-4-carboxylic acid [4-(3-cyano-1-cyclobutyl-6-ethoxy-1H-indol-2-yl)-phenyl]-amide (Compound 1166)

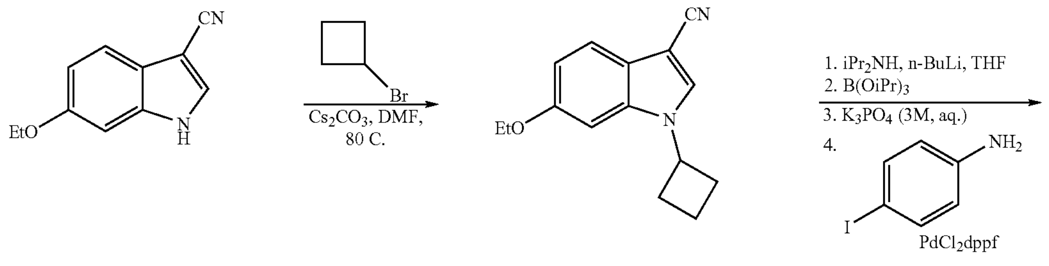

-continued

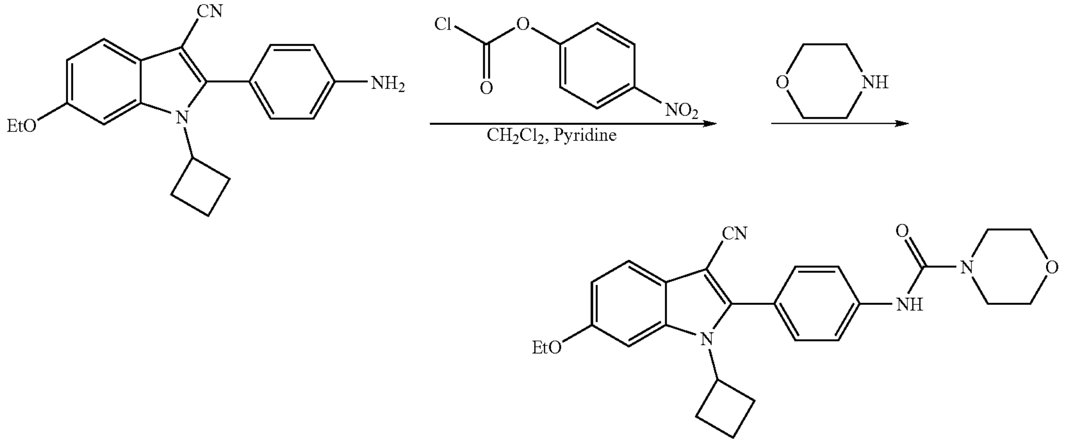

Step A: 6-Ethoxy-1H-indole-3-carbonitrile (2.8 g, 15 mmol), prepared as shown in example 1A, step A, is combined with $Cs_2CO_3$ (11.6 g, 35.6 mmol), DMF (21 mL), and cyclobutyl bromide (1.73 mL, 17.9 mmol) in a capped tube. The reaction mixture is heated at 80° C. for 8 h. This is then quenched with $H_2O$ (200 mL) and is extracted with EtOAc. The EtOAc layer is backwashed with $H_2O$, and then with brine. The organic phase is dried and concentrated. Purification by silica gel chromatography (hexanes/$CH_2Cl_2$, 50-100%) yields 1-cyclobutyl-6-ethoxy-1H-indole-3-carbonitrile (3.00 g, 83%) as a white solid.

Step B: Following essentially the procedure in example 1Gb, 1-cyclobutyl-6-ethoxy-1H-indole-3-carbonitrile (3.0 g, 12.4 mmol) is converted via Suzuki coupling to yield 2-(4-aminophenyl)-1-cyclobutyl-6-ethoxy-1H-indole-3-carbonitrile (2.60 g, 68%) as an off-white solid.

Step C: 2-(4-aminophenyl)-1-cyclobutyl-6-ethoxy-1H-indole-3-carbonitrile (40 mg, 0.12 mmol), 4-nitrophenyl chloroformate (60 mg, 0.30 mmol), $CH_2Cl_2$ (400 μL), and pyridine (25 μL, 0.31 mmol) are stirred at room temperature for 1 hour. Morpholine (60 μL, 0.70 mmol) is added. After stirring at room temperature for an additional 30 minutes, the reaction mixture is diluted in $CH_2Cl_2$ and is washed with dilute aqueous NaOH to remove the yellow nitrophenol byproduct. The organic layer is dried and concentrated. Purification by silica gel chromatography ($CH_2Cl_2$/EtOAc, 7/3) yields morpholine-4-carboxylic acid [4-(3-cyano-1-cyclobutyl-6-ethoxy-1H-indol-2-yl)-phenyl]-amide (53 mg, 100%) as a white solid.

The following compounds are prepared in a similar fashion, using the appropriate amine in the final step: compounds 1087, 1088, 1089, 1119, 1159, 1168, 1191, 1266, 1288, 1324, 1325, 1326.

Example 1CN

Preparation of rac-[4-(3-cyano-1-cyclobutyl-6-ethoxy-1H-indol-2-yl)-phenyl]-carbamic acid 1-cyclopropyl-ethyl ester (Compound 1147)

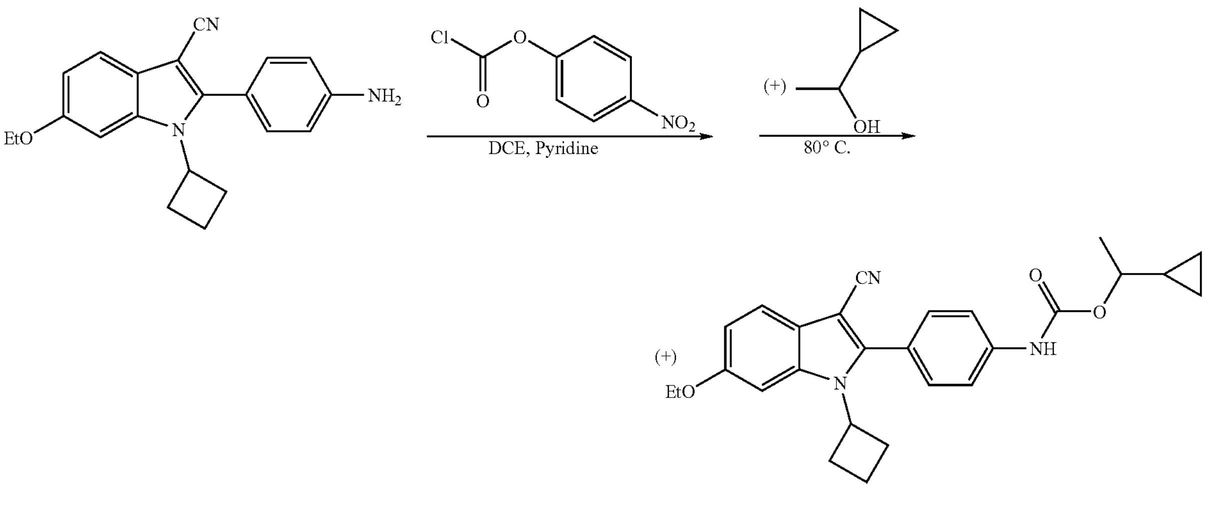

2-(4-Aminophenyl)-1-cyclobutyl-6-ethoxy-1H-indole-3-carbonitrile (50 mg, 0.15 mmol), prepared as in example 1CM, step B, is combined with 4-nitrophenyl chloroformate (76 mg, 0.38 mmol), DCE (0.5 mL), and pyridine (30 μL, 0.37 mmol). This suspension is stirred at room temperature for 1 h. Rac-cyclopropyl methyl carbinol (100 μL, 0.98 mmol) is added. This mixture is heated at 75° C. overnight. The reaction mixture is then diluted in $CH_2Cl_2$ and is washed with dilute aqueous NaOH to remove the yellow nitrophenol byproduct. The organic layer is dried and concentrated. Purification by silica gel chromatography ($CH_2Cl_2$) yields rac-[4-(3-cyano-1-cyclobutyl-6-ethoxy-1H-indol-2-yl)-phenyl]-carbamic acid 1-cyclopropyl-ethyl ester (40 mg, 60%) as a white solid.

The following compounds are prepared in a similar fashion, using the appropriate alcohols: Compounds 1146, 1158, 1167, 1192, 1208, 1209, 1210, 1215, 1216, 1240, 1241, 1242, 1243, 1244, 1246, 1247, 1248, 1249, 1250, 1264, 1265, 1267, 1268, 1281, 1282, 1283, 1286, 1287, 1289, 1290, 1291, 1292, 1294, 1295, 1296, 1297, 1298, 1299, 1312, 1313.

Example 1CO

Preparation of 1-cyclobutyl-6-ethoxy-2-(4-ethylaminophenyl)-1H-indole-3-carbonitrile (Compound 1239)

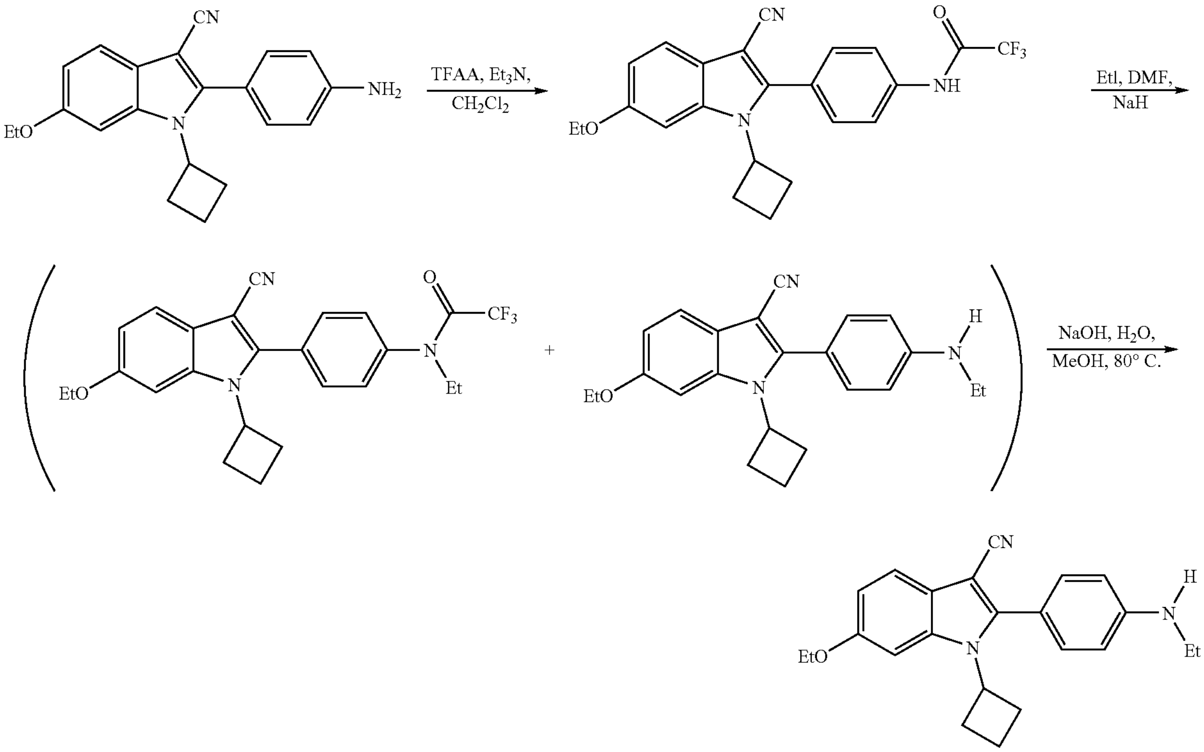

Step A: 2-(4-Aminophenyl)-1-cyclobutyl-6-ethoxy-1H-indole-3-carbonitrile (600 mg, 1.81 mmol), prepared as in example 1CM, step B, is suspended in $CH_2Cl_2$ (18 mL), and $Et_3N$ (390 μL, 2.7 mmol). Trifluoroacetic anhydride (310 μL, 2.2 mmol) is added dropwise. The reaction mixture is stirred at room temperature for 30 minutes, after which time dissolution is complete. The reaction mixture is then washed with saturated $NaHCO_3$ solution. The organic layer is dried and concentrated to yield N-[4-(3-cyano-1-cyclobutyl-6-ethoxy-1H-indol-2-yl)-phenyl]-2,2,2-trifluoro-acetamide (802 mg, 100%) as a yellow solid.

Step B: N-[4-(3-Cyano-1-cyclobutyl-6-ethoxy-1H-indol-2-yl)-phenyl]-2,2,2-trifluoro-acetamide (800 mg, 1.8 mmol) is dissolved in DMF (10 mL). NaH (140 mg, 60% oil suspension, 3.5 mmol) is added. This is stirred at room temperature for a few minutes, after which ethyl iodide (176 μL, 2.2 mmol) is added. This is stirred at room temperature overnight, and then at 75° C. for 6 h. Additional portions of NaH (200 mg, 5.0 mmol) and iodoethane (200 μL, 2.5 mmol) are necessary to push the reaction further. This is heated overnight at 75° C. Additional ethyl iodide (200 μL, 2.5 mmol) is added. This is heated for another 2 h. The reaction mixture is then diluted in $H_2O$ and is extracted into EtOAc. The EtOAc layer is dried and concentrated. Silica gel chromatography ($CH_2Cl_2$) yields 384 mg of an inseparable mixture of expected N-[4-(3-cyano-1-cyclobutyl-6-ethoxy-1H-indol-2-yl)-phenyl]-N-ethyl-2,2,2-trifluoro-acetamide and hydrolyzed 1-cyclobutyl-6-ethoxy-2-(4-ethylamino-phenyl)-1H-indole-3-carbonitrile.

Step C: The crude mixture from the previous step is dissolved in methanol (5 mL). 6N NaOH (1.0 mL, 6 mmol) is added, and the mixture is heated at 80° C. for 1 h. The reaction mixture is then diluted in $H_2O$ and is extracted into $CH_2Cl_2$. The organic layer is dried and concentrated. Purification by silica gel chromatography ($CH_2Cl_2$) yields pure 1-cyclobutyl-6-ethoxy-2-(4-ethylaminophenyl)-1H-indole-3-carbonitrile (343 mg, 53% over two steps) as a white solid.

1-Cyclobutyl-2-(4-diethylamino-phenyl)-6-ethoxy-1H-indole-3-carbonitrile (compound 1217, 77 mg, 11%) is isolated as a byproduct of the reaction described in example 1CO, step B.

Example 1CP

Preparation of [4-(3-cyano-1-cyclobutyl-6-ethoxy-1H-indol-2-yl)-phenyl]-ethyl-carbamic acid cyclopentyl ester (Compound 1251)

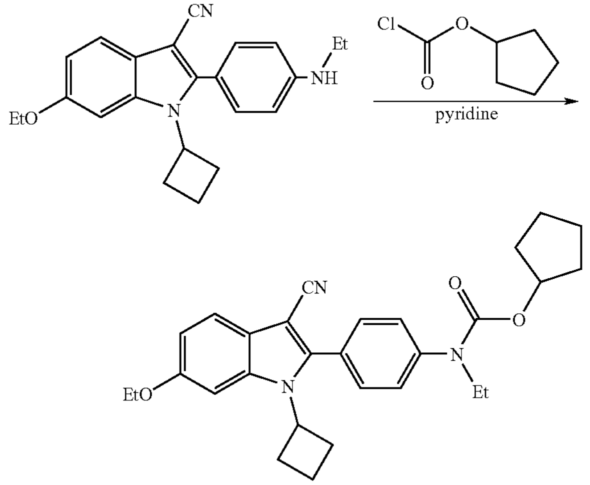

1-Cyclobutyl-6-ethoxy-2-(4-ethylaminophenyl)-1H-indole-3-carbonitrile (35 mg, 0.10 mmol), prepared as in example 1CO, step C, is dissolved in pyridine (300 μL). Cyclopentyl chloroformate (25 μL, 0.17 mmol) is added. The reaction mixture is stirred at room temperature for 2.5 h. More chloroformate (10 μL, 0.07 mmol) is added to drive the reaction to completion. After an additional 90 min of stirring, the reaction mixture is partitioned between aqueous HCl and EtOAc. The organic layer is dried and concentrated. Purification by silica gel chromatography yields [4-(3-cyano-1-cyclobutyl-6-ethoxy-1H-indol-2-yl)-phenyl]-ethyl-carbamic acid cyclopentyl ester (41 mg, 87%) as a white solid.

Compound 1252 is prepared similarly using the appropriate chloroformate.

Example 1CQ

Preparation of {4-[3-cyano-1-cyclobutyl-6-(3-[1,2,4]triazol-1-yl-propoxy)-1H-indol-2-yl]-phenyl}-carbamic acid isopropyl ester (Compound 1255)

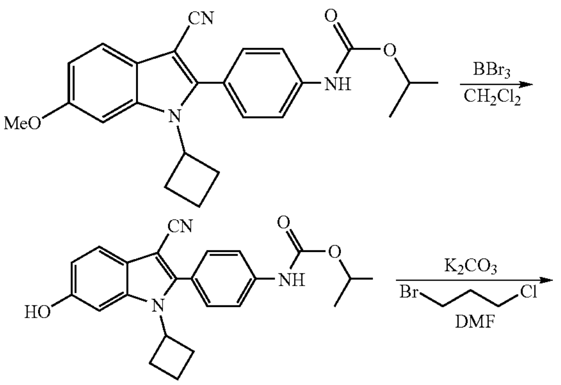

-continued

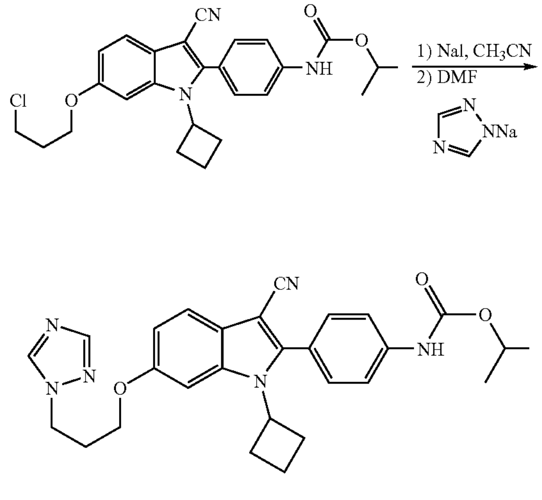

Step A: To a solution [4-(3-cyano-1-cyclobutyl-6-methoxy-1H-indol-2-yl)-phenyl]-carbamic acid isopropyl ester (950 mg, 2.35 mmol) in DCM (10 mL) is added $BBr_3$ (556 uL, 5.9 mmol) over a period of 20 min. The reaction mixture is stirred further for 1 h at room temperature and then water (1 mL) is added. The solvents are removed under reduced pressure. The residue is dissolved in MeOH and then poured into cold water. The precipitate is collected by filtration and washed with hexane and dried in vacuo to afford [4-(3-cyano-1-cyclobutyl-6-hydroxy-1H-indol-2-yl)-phenyl]-carbamic acid isopropyl ester (650 mg, 71%).

Step B: To a solution of [4-(3-cyano-1-cyclobutyl-6-hydroxy-1H-indol-2-yl)-phenyl]-carbamic acid isopropyl ester (340 mg, 0.87 mmol) in DMF (2 mL) is added $K_2CO_3$ (132 mg, 0.96 mmol) and 3-bromo-1-chloroproane (172 uL, 1.75 mmol) and the reaction is stirred for 5 h at 60° C. The reaction mixture is then poured into cold water and the precipitate is collected by filtration and washed with hexane and dried in vacuo to afford 370 mg (92%) of the desired product.

Step C: To a solution of {4-[6-(3-chloro-propoxy)-3-cyano-1-cyclobutyl-1H-indol-2-yl]-phenyl}-carbamic acid isopropyl ester (37 mg, 0.08 mmol) in $CH_3CN$ (1 mL) is added sodium iodide (71 mg, 0.48 mmol). The resulting mixture is stirred at reflux temperature overnight. The solvent is then evaporated and the residue is diluted with anhydrous DMF (1 mL) and then treated with the sodium salt of 1,2,4-triazole (0.16 mmol) at room temperature overnight. The solvent is removed under reduced pressure and the residue is diluted with ethyl acetate and then washed with water. The organic layer is concentrated and triturated with hexane and the precipitate is collected by filtration and washed well with 50% ethyl acetate in hexane and dried in vacuo to afford {4-[3-cyano-1-cyclobutyl-6-(3-[1,2,4]triazol-1-yl-propoxy)-1H-indol-2-yl]-phenyl}-carbamic acid isopropyl ester, compound 1255 (31 mg, 78%).

The following compounds are made in similar fashion following steps A-C, above: Compounds 1253, 1254, 1260, 1261, 1262.

Example 1CR

Preparation of {4-[3-cyano-1-cyclobutyl-6-(2-[1,2,4]triazol-1-yl-ethoxy)-1H-indol-2-yl]-phenyl}-carbamic acid isopropyl ester (Compound 1276)

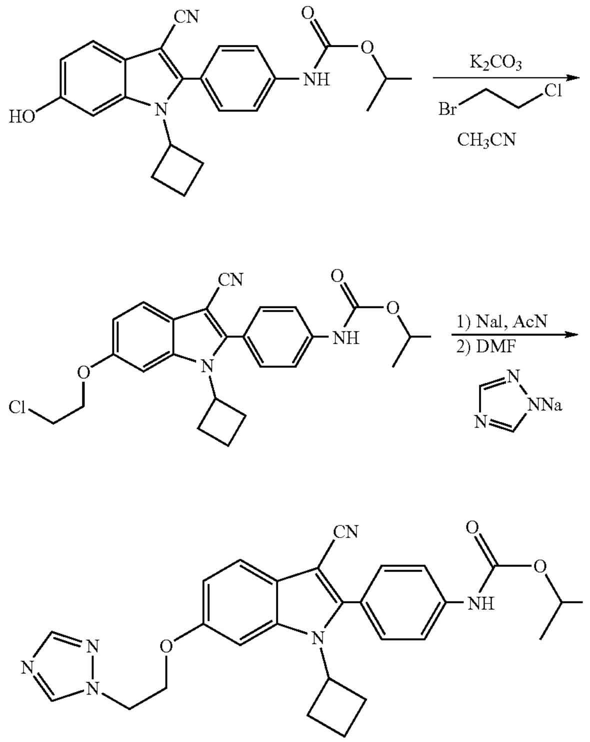

Step A: To a solution of [4-(3-cyano-1-cyclobutyl-6-hydroxy-1H-indol-2-yl)-phenyl]-carbamic acid isopropyl ester (390 mg, 1.0 mmol) in $CH_3CN$ (5 mL) is added $K_2CO_3$ (414 mg, 3.0 mmol) and 3-bromo-1-chloroetahne (250 uL, 3.0 mmol) and the reaction is stirred for 18 h at 80° C. The reaction mixture is then poured into cold water and the precipitate is collected by filtration and washed with hexane and dried in vacuo to afford 420 mg, 93% of the desired product.

Step B: To a solution of {4-[6-(3-chloroethoxy)-3-cyano-1-cyclobutyl-1H-indol-2-yl]-phenyl}-carbamic acid isopropyl ester (42 mg, 0.09 mmol) in $CH_3CN$ (1 mL) is added sodium iodide (56 mg, 0.37 mmol). The resulting mixture is stirred at reflux temperature overnight. The solvent is evaporated and the residue is diluted with anhydrous DMF (1 mL) and then treated with the sodium salt of 1,2,4-triazole (0.18 mmol) at room temperature for overnight. The solvent is removed under reduced pressure and the residue is diluted with ethyl acetate and then washed with water. The organic layer is concentrated and triturated with hexane. The precipitate is collected by filtration and washed well with 50% ethyl acetate in hexane and dried in vacuo to afford {4-[3-cyano-1-cyclobutyl-6-(3-[1,2,4]triazol-1-yl-ethoxy)-1H-indol-2-yl]-phenyl}-carbamic acid isopropyl ester, compound 1276 (28 mg, 64%).

The following compounds are made in similar fashion following steps A and B, above: Compounds 1269, 1270, 1271, 1272, 1273, 1274, 1275, 1276, 1277, 1278.

Example 1CS

Preparation of {4-[3-cyano-1-cyclobutyl-6-(2-[1,2,4]triazol-1-yl-ethoxy)-1H-indol-2-yl]-phenyl}-carbamic acid 1-cyclopropyl-ethyl ester (Compound 1329)

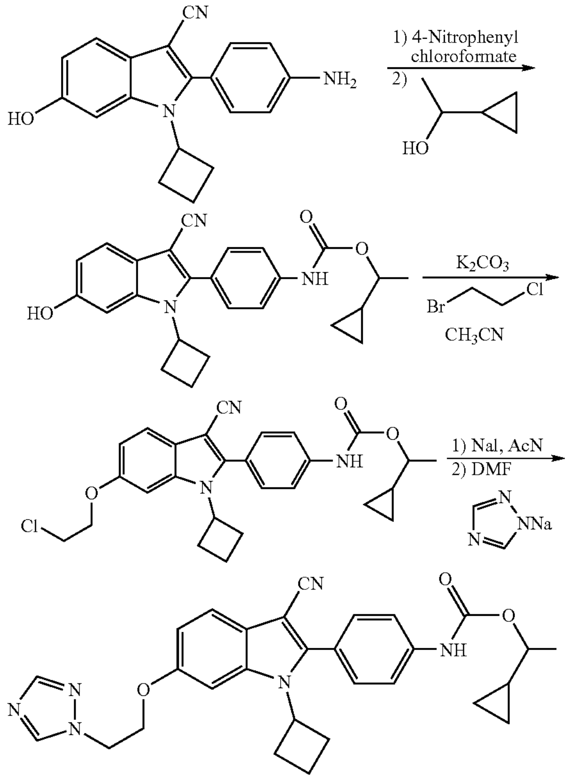

Step A: To a solution of 2-(4-aminophenyl)-1-cyclobutyl-6-hydroxy-1H-indole-3-carbonitrile (909 mg, 3 mmol) in pyridine (5 mL) is added 4-nitrophenyl chloroformate (6 mmol) at room temperature and then stirred for 2 h at room temperature. To the reaction is added cyclopropyl methyl carbinol and then stirred for 8 h at 80° C. The reaction mixture is diluted with 1N HCl and then extracted with ethyl acetate. The organic layer is concentrated and the residue is dissolved in EtOAc and triturated with hexane. The precipitate is collected by filtration and washed with hexane and dried in vacuo to afford [4-(3-cyano-1-cyclobutyl-6-hydroxy-1H-indol-2-yl)-phenyl]-carbamic acid 1-cyclopropyl-ethyl ester (996 mg, 80%).

Step B: To a solution of [4-(3-cyano-1-cyclobutyl-6-hydroxy-1H-indol-2-yl)-phenyl]-carbamic acid 1-cyclopropyl-ethyl ester (1.5 g, 3.61 mmol) in $CH_3CN$ (8 mL) is added $K_2CO_3$ (1.5 g, 10.8 mmol) and 2-bromo-1-chloroethane (895 uL, 10.8 mmol) and the reaction is stirred for 18 h at 80° C. The reaction mixture is then poured into cold water and the precipitate is collected by filtration and washed with hexane and dried in vacuo to afford 1.46 g, 84% of the desired product.

Step C: To a solution of {4-[6-(2-chloroethoxy)-3-cyano-1-cyclobutyl-1H-indol-2-yl]-phenyl}-carbamic acid 1-cyclopropyl-ethyl ester (1.46 g, 3.05 mmol) in $CH_3CN$ (10 mL) is added sodium iodide (1.84 g, 12.22 mmol). The resulting mixture is stirred at reflux temperature overnight. The solvent is evaporated and the residue is diluted with anhydrous DMF (20 mL) and then used without further purification. To 1 mL of the DMF solution containing the iodoethyl intermediate (0.153 mmol) is added the sodium salt of 1,2,4-triazole (0.31 mmol) and the reaction is stirred at room temperature overnight. The reaction mixture is diluted with 0.5 mL DMF and the desired product is purified by preparative LC to give {4-[3-cyano-1-cyclobutyl-6-(2-[1,2,4]triazol-1-yl-ethoxy)-1H-indol-2-yl]-phenyl}-carbamic acid 1-cyclopropyl-ethyl ester, compound 1329 (23 mg, 29%).

The following compounds are made in similar fashion following steps A-C, above: Compounds 1327, 1328.

Example 1CT

Preparation of 1-{4-[3-cyano-1-cyclobutyl-6-(3-[1,2,4]triazol-1-yl-propoxy)-1H-indol-2-yl]-phenyl}-3-isopropyl-urea (Compound 1314)

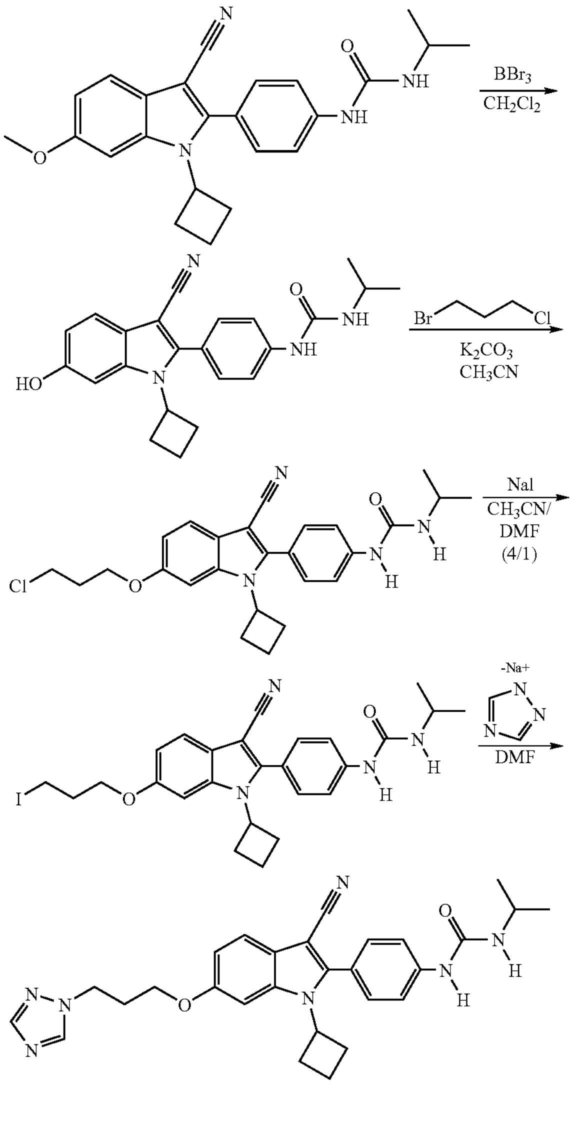

Step A: To a solution of 1-[4-(3-cyano-1-cyclobutyl-6-methoxy-1H-indol-2-yl)-phenyl]-3-isopropyl-urea (2.21 g, 5.49 mmol in $CH_2Cl_2$ (30 mL) is added a 1M solution of $BBr_3$ in $CH_2Cl_2$ (16.5 mL, 16.5 mmol) at 0° C. The mixture is allowed to warm to room temperature and kept for 1 h. The reaction mixture is then poured onto ice and aqeous 1M $NaHCO_3$ is added until the pH is 7-8. The product is extracted with 100 mL of ethyl acetate (3×) and the organic phases are washed with 100 mL of saturated NaCl. The organic phases are combined and dried over $MgSO_4$. Solvent is removed to recover 1.95 g (92%) of 1-[4-(3-cyano-1-cyclobutyl-6-hydroxy-1H-indol-2-yl)-phenyl]-3-isopropyl-urea, as a tan solid.

Step B: To a solution of 1-[4-(3-cyano-1-cyclobutyl-6-hydroxy-1H-indol-2-yl)-phenyl]-3-isopropyl-urea (750 mg, 1.93 mmol) in 10 mL of acetonitrile is added anhydrous $K_2CO_3$ (800 mg, 5.79 mmol) and 1-bromo-3-chloropropane (382 μL, 3.86 mmol). After stirring overnight at 80° C., the reaction mixture is cooled and solvent is removed. The reaction is re-suspended in 100 mL of ethyl acetate. The organic phase is washed with 200 mL of $H_2O$, and the aqueous phase is re-extracted 2× with 100 mL of ethyl acetate. The organic phases are combined, dried over $MgSO_4$ and the solvent is removed to afford 769 mg (86%) of 1-{4-[6-(3-chloropropoxy)-3-cyano-1-cyclobutyl-1H-indol-2-yl]-phenyl}-3-isopropyl-urea as a tan powder.

Step C: To a solution of 1-{4-[6-(3-chloropropoxy)-3-cyano-1-cyclobutyl-1H-indol-2-yl]-phenyl}-3-isopropyl-urea (400 mg, 0.860 mmol) in 8 mL of acetonitrile/DMF, (4/1) is added anhydrous NaI (258 mg, 1.72 mmol). After stirring overnight at 60° C., the reaction shows conversion to product by LCMS-UV. The reaction mixture is cooled, the solvent is removed and redissolved in DMF to 14.0 mL total volume.

Step D: To 1 mL of the DMF solution above, 1-{4-[3-cyano-1-cyclobutyl-6-(3-iodopropoxy)-1H-indol-2-yl]-phenyl}-3-isopropyl-urea (34 mg, 0.062 mmol) is added anhydrous 1,2,4-triazole, sodium salt (10.0 mg, 0.110 mmol). After stirring overnight at rt, the reaction mixture is filtered and purified by preparatory LC/UV purification. The solvent is removed to obtain 12.3 mg (40%) of 1-{4-[3-cyano-1-cyclobutyl-6-(3-[1,2,4]triazol-1-yl-propoxy)-1H-indol-2-yl]-phenyl}-3-isopropyl-urea (compound 1314), as a white powder.

The following compounds are prepared following the above procedure: Compounds 1306, 1307, 1308, 1309, 1315, 1316, 1317, 1318, 1319, 1320, 1321, 1323 and 1324.

Example 2

Screening of Low Molecular Weight Compounds Using a Cell-Based HCV IRES Monocistronic Translation Assay Chemical libraries are screened using a cell-based monocistronic HCV IRES-regulated translation assay designed to closely mimic natural HCV mRNA translation and then compound analogs are made based on hits in the chemical libraries and screened as well. A DNA construct is prepared, termed pHCVIRESmono, in which HCV IRES sequences (HCV 2b, nucleotides 18-347) are inserted between a promoter and the firefly luciferase (Fluc) reporter gene. A stably transfected HepG2 (hepatoblastoma) cell line (termed HepG mono-4) or a Huh7 cell line (termed Huhmono 7), or a Hela-cell line (termed Helamono), are established by transfection with the pHCVIRESmono DNA by selecting for resistance to hygromycin.

Example 3

Determination of Selectivity for HCV IRES-Regulated Translation Using the Cell-Based Cap-Dependent Translation Assays Since translation assays are used to screen HCV IRES inhibitors, the selected hits may specifically act on HCV IRES-driven translation or may modulate general protein synthesis in mammalian cells. The compounds that act on general translation will most likely have significant toxicity. To address this possibility, various cell-based cap-dependent translation assays are established for the further evaluation of all selected compounds. Plasmid DNAs containing 130 nucleotides of vector sequence 5' to Fluc are constructed. This construct is referred to herein as pLuc. A stable cell line is established in cap-dependent translation assays using 293T cells (a human embryonic kidney cell line). HepGmono-4 and pLuc are treated with compound for 20 hours and activity is determined by quantifying the Fluc signal. A five-fold selectivity between the HCV IRES and cap-dependent translation is considered to be desirable. For example, using these cell-based cap-dependent translation assays, Applicants identified compounds that showed $IC_{50}$ values that were at least 5-fold greater in the cap-dependent translation assays than in the HCV IRES translation assay. FIG. 1 shows an example of a hit that was selective against HCV IRES-regulated translation over cap-dependent pLuc translation. Importantly, the compound had the same level of activity in an HCV IRES monocistronic 293T cell line as in HepGmono-4 (data not shown). It is thus unlikely that the selectivity of the compounds between HepGmono-4 (HepG 2) and the cap-dependent translations (293T) is due to the different cell types used.

Additionally, western blotting assays are used to further demonstrate that the compounds selectively inhibit HCV IRES-driven translation. Both HepGmono-4 and pLuc cells are treated with the compounds as described above, following treatment with the test compounds for 20 hours, cells are collected and lysed in Laemmli buffer containing 0.5% SDS. Proteins are separated on a 10% SDS-PAGE, then transferred onto a nitrocellulose membrane, and blotted using antibodies against Fluc (RDI) and β-actin (Oncogene). For example, some of the compounds of the present invention were tested in this manner and as expected, the compounds that selectively inhibited HCV IRES-driven translation in assays using Fluc signal as an end point showed comparable reductions of the luciferase reporter protein levels in HepGmono-4 cells and were relatively inactive against pLuc in the Western blot (data not shown). Importantly, these compounds did not inhibit the expression of endogenous β-actin, the translation of which is cap-dependent in both cell lines. Consistently, compounds that did not show selectivity in the translation assays inhibited protein accumulation in both the HCV IRES and cap-dependent translation assays (data not shown). As expected, the general protein translation inhibitor puromycin also inhibited both the HCV IRES-driven and cap-dependent protein production (data not shown). Therefore, the Western blot results confirm that the compounds of the present invention selectively inhibit HCV IRES-driven translation.

Testing conditions for these cell lines are optimized and the effects of mRNA level on activity of the compounds are controlled by quantitating Fluc mRNA levels by RT real-time PCR. For example, some of the compounds of the present invention were tested in this manner, and no significant differences in Fluc mRNA levels were observed between the HepGmono-4, or the Helamono cells, or the Huhmono cells, and cap-dependent translation cell lines used (data not shown).

Example 4

Evaluation of the Selectivity for HCV IRES-Driven Translation Using Cellular IRES-Mediated Translation Assays A number of human mRNAs have been shown to harbor IRES elements (18, 19, 39, 44, 45, 91, 126, 130). Although the primary sequences and secondary structures of the HCV IRES are different from those of cellular IRES, an important test for selectivity is to determine whether the selected compounds are active against cellular IRES. The VEGF IRES has poor initiation activity in in vitro assays, but demonstrates substantial activity in cell-based translation assays (45). For example, some of the compounds of the present invention were tested and all of the compounds that had good selectivity with respect to cap-dependent translation exhibited at least 5-fold higher $IC_{50}$ values against the VEGF IRES than against the HCV IRES (data not shown). These data indicate that the selected compounds have selectivity against viral IRES. In addition to having different structures, the VEGF IRES also have different interactions with non-canonical cellular translation factors. These differences may contribute to the selectivity of the HCV IRES inhibitors that we have identified.

Example 5

Evaluation of Cytotoxicity

Effects on cell proliferation are a critical issue for any drug discovery effort. Therefore, a cell proliferation/cytotoxicity assay is used to eliminate any compounds that affect mammalian cell growth. The effects of the selected hits on cell proliferation are tested in human cell lines 293 T and Huh7 (a human hepatoblastoma cell line). Cells are grown in Dulbecco's modified Eagle's medium supplemented with 10% fetal bovine serum, L-glutamine, penicillin, and streptomycin. Cells in log phase are treated with test compounds for three days, with 250 μM being the highest concentration of test compound used. The effect of the compounds on cell proliferation is assessed by using the CellTiter 96 AQueous One Solution Cell Proliferation Assay (Promega, Madison, Wis.). Compounds that have at least 5-fold higher $CC_{50}$ values relative to $IC_{50}$ values in HepGmono-4 are considered to have a sufficient window between activity and cytotoxicity and, hence, are selected for further evaluation. For example, some of the compounds of the present invention were tested in this manner, and importantly, all compounds that had good selectivity with respect to cap-dependent translation also demonstrated a greater than 5-fold ratio of $CC_{50}$ to $IC_{50}$ values.

Example 6

Evaluation of the Efficacy of the Compounds in the HCV Replicon System

The lack of reliable and readily accessible cell-culture and small animal models permissive for HCV replication has limited the development of new anti-HCV agents. Self-replicating subgenomic HCV systems, termed HCV replicons, have been described and have been widely used to assess the efficacy of anti-HCV inhibitors (8, 9, 46, 70, 103, 104). Interferon (IFN) α and inhibitors of the HCV protease and polymerase have been reported to be active in the HCV replicon system (8, 17, 32, 68, 69, 117).

HCV replicons that include bicistronic and monocistronic systems are available and can be used for testing the HCV inhibitors. In the bicistronic replicons, the HCV IRES directs the expression of the selective marker (Neo and/or a Fluc reporter), and the EMCV IRES mediates the expression of viral non-structural proteins. In the monocistronic replicon, the HCV IRES directly mediates viral protein synthesis. The HCV IRES inhibitors are analyzed in the bicistronic replicon by quantitating the Fluc reporter signal. Replicon-containing cells are cultured with the compounds of the invention for 2 days or for 3 days. Interferon (IFN) α is used as a positive control. For example, the compounds of the present invention were tested in this manner, and the experiments showed that compounds that selectively inhibited HCV IRES-mediated translation inhibited Fluc expression in the bicistronic replicon.

In the following tables (Tables 1A and 1B),

*=replicon or HCV-PV $IC_{50}$>2 μM

**=replicon or HCV-PV $IC_{50}$ between 0.5 uM and 2 μM

***=replicon or HCV-PV $IC_{50}$<0.5 μM

Replicon $IC_{50}$ values are determined by firefly luciferase signal.

HCV-PV $IC_{50}$ values are determined by viral RNA reduction.

TABLE 1A

| Compound Number | Melting Point (° C.) | Mass Spec [M+H] | HCV-PV $IC_{50}$ μM | Replicon $IC_{50}$ μM | NMR Data |
|---|---|---|---|---|---|
| 1 | | | | * | |
| 2 | | 311.1 | | * | |
| 3 | | 356.0 | | * | |
| 4 | | 279.2 | | * | |
| 5 | 64-66 | 201.3 | | * | |
| 6 | | 201.1 | | * | |
| 7 | 304-305 | 251.1 | | ** | $^1$H NMR(300MHz, DMSO-$d_6$): δ 8.23(1H, d, J=2.1Hz), 8.08(1H, dd, J=8.8, 2.1Hz), 7.74(1H, d, J=8.8Hz), 7.55(2H, t, J=2.2Hz), 6.51(2H, t, J=2.2Hz). |
| 8 | | 277.3 | | ** | |
| 9 | 61-63 | 215.2 | | * | |
| 10 | 69-71 | 229.2 | | * | |
| 11 | 78-80 | 243.2 | | * | |
| 12 | 94-97 | 277.2 | | ** | |
| 13 | 161-164 | 265.3 | | * | |
| 14 | 206-207 | 415.2 | | * | $^1$H NMR(300MHz, $CDCl_3$): δ 8.09(1H, dd, J=8.8, 1.7Hz), 7.75(1H, d, J=1.7Hz), 7.49(1H, d, J=8.8Hz), 7.40(2H, d, J=8.8Hz), 7.22(2H, d, J=8.8Hz), 7.17(2H, d, J=8.8Hz), 6.93(2H, d, J=8.8Hz), 6.15(1H, s), 3.93(3H, s), 3.83(3H, s). |
| 15 | 225-226 | 290.3 | | * | |
| 16 | 175-177 | 286.3 | | * | |
| 17 | | 248.1 | | * | |
| 18 | | 237.3 | | * | |
| 19 | | 307.4 | | * | |
| 20 | 159-160 | 267.2 | | * | |
| 21 | 125 | 277.3 | | * | |
| 22 | 146-149 | 321.1 | | ** | |
| 23 | 234-235 | 334.2 | | *** | |
| 24 | 123-124 | 307.1 | | ** | |
| 25 | 291-293 | 271.2 | | * | $^1$H NMR(300MHz, DMSO-$d_6$): δ 10.81(1H, s), 8.63(1H, d, J=1.7Hz), 8.10(1H, dd, J=8.8, 1.7Hz), 7.76(1H, d, J=8.8Hz), 4.35(2H, q, J=7.0Hz), 2.22(3H, s), 1.26(3H, t, J=7.0Hz). |
| 26 | 287-288 | 335.3 | | ** | $^1$H NMR(300MHz, $CDCl_3$): δ 10.83(1H, s), 8.23(1H, s), 8.00(1H, d, J=8.8Hz), 7.92(2H, d, J=7.3Hz), 7.60(1H, d, J=8.5Hz), 7.53-7.43(1H, m), 7.41-7.30(2H, m), 4.12(2H, q, J=7.3Hz), 1.31(3H, t, J=7.3Hz). |
| 27 | 138-140 | 236.3 | | ** | |
| 28 | 68-70 | 272.2 | | ** | |
| 29 | oil | 284.3 | | * | |
| 30 | 114-116 | 292.2 | | * | $^1$H NMR(300MHz, DMSO-$d_6$): δ 8.19(1H, d, J=2.3Hz), 7.96(1H, dd, J=8.8, 2.3Hz), 7.69(1H, d, J=8.8Hz), 7.38(1H, t, J=7Hz), 4.32(2H, q, J=7.0Hz), 3.81(3H, s), 3.61(2H, pentet, J=7Hz), |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| | | | | | 1.29(3H, t, J=6.7Hz), 1.24(3H, t, J=7.0Hz). |
| 31 | 189-190 | 264.1 | | * | $^1$H NMR(300MHz, DMSO-$d_6$): δ 8.11(1H, d, J=2.0Hz), 7.94(1H, dd, J=8.5, 2.0Hz), 7.65(1H, d, J=8.5Hz), 7.54(2H, br s), 4.21(2H, q, J=7.0Hz), 3.79(3H, s), 1.20(3H, t, J=7.0Hz). |
| 32 | oil | 280.2 | | * | |
| 33 | 113-117 | 280.2 | | * | |
| 34 | 137-141 | 232.1 | | * | |
| 35 | 318-319 | 411.0, 413.0(M−H$^-$) | | * | $^1$H NMR(300MHz, DMSO-$d_6$): δ 11.29(1H, s), 8.71(1H, d, J=2.0Hz), 8.13(1H, dd, J=8.8, 2.0Hz), 7.98(2H, d, J=8.5Hz), 7.84(2H, d, J=8.5Hz), 7.83(1H, d, J=8.8Hz), 4.41(2H, q, J=7.0Hz), 1.28(3H, t, J=7.0Hz). |
| 36 | 273-274 | 380.1 | | * | $^1$H NMR(300MHz, DMSO-$d_6$): δ 11.58(1H, s), 8.87(1H, s), 8.72(1H, s), 8.53(1H, d, J=7.0Hz), 8.47(1H, d, J=7.0Hz), 8.14(1H, d, J=8.5Hz), 7.91(1H, t, J=8.2Hz), 7.86(1H, d, J=8.8Hz), 4.45(2H, q, J=7.0Hz), 1.30(3H, t, J=7.0Hz). |
| 37 | 56-60 | 246.2 | | * | |
| 38 | 96-100 | 310.1 | | * | |
| 39 | 94-98 | 310.1 | | * | |
| 40 | 176-180 | 269.1 | | * | |
| 41 | 155-175 | 267.1 | | * | |
| 42 | 138-143 | 296.1 | | * | |
| 43 | | 229.2 | | * | |
| 44 | | 293.2 | | * | |
| 45 | 130-131 | 215.5 | | * | |
| 46 | | 376.2 | | * | |
| 47 | 140-145 | 376.2 | | * | |
| 48 | 138-142 | 296.3 | | ** | |
| 49 | 89-90 | 376.3 | | * | |
| 50 | 91-92 | 259.3 | | * | |
| 51 | 95-96 | 229.4 | | * | |
| 52 | | 243.2 | | * | |
| 53 | 145-147 | 363.1 | | ** | |
| 54 | 99-101 | 272.3 | | * | |
| 55 | 183-185 | 292.2 | | * | |
| 56 | 223-224 | 301.2 | | ** | |
| 57 | 130-133 | 243.2 | | * | |
| 58 | 76-79 | 243.2 | | * | |
| 59 | 81-85 | 242.2 | | * | |
| 60 | 133-136 | 271.2 | | * | |
| 61 | 153-158 | 270.2 | | * | |
| 62 | | 262.0 | | * | |
| 63 | 188-192 | 333.4 | | * | |
| 64 | 108-113 | 301.3 | | * | |
| 65 | 130-132 | 331.3 | | ** | |
| 66 | 119-122 | 331.3 | | * | |
| 67 | 132-136 | 319.3 | | ** | |
| 68 | 140-147 | 315.3 | | ** | |
| 69 | 163-166 | 316.3 | | ** | |
| 70 | 142-141 | 321.2 | | * | |
| 71 | 199.4 | 348.2 | | * | |
| 72 | 144-149 | 271.3 | | * | |
| 73 | oil | 259.2 | | * | |
| 74 | 179-182 | 325.3 | | * | |
| 75 | 118-123 | 271.3 | | * | |
| 76 | 118-120 | 293.3 | | * | |
| 77 | 117-118 | 307.3 | | * | |
| 78 | 110-114 | 287.2 | | * | |
| 79 | 257-260 | 332.4 | | * | |
| 80 | 292-294 | 356.5 | | ** | |
| 81 | 209-211 | 360.5 | *** | *** | |
| 82 | 223-228 | 372.5 | *** | ** | |
| 83 | 221-223 | 384.4 | *** | *** | |
| 84 | 232-237 | 396.4 | *** | *** | |
| 85 | 163-165 | 398.3 | *** | *** | |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| 86 | 158-160 | 410.3 | | *** | |
| 87 | 187-189 | 396.3 | *** | *** | |
| 88 | 209-213 | 398.4 | *** | ** | |
| 89 | 148-155 | 308.3 | | ** | |
| 90 | 80-95 | 364.4 | | * | |
| 91 | 160-161 | 301.2 | | * | |
| 92 | 155-156 | 317.2 | | * | |
| 93 | 172.4-172.6 | 305.3 | | * | |
| 94 | 262-265 | 314.4 | | ** | |
| 95 | 248-251 | 344.4 | | ** | |
| 96 | 243-250 | 329.4 | | ** | |
| 97 | 164-167 | 350.4 | | * | |
| 98 | 180-185 | 363.2 | | * | |
| 99 | 123.4-123.8 | 307.0 | | * | |
| 100 | 128-129 | 277.2 | | * | |
| 101 | 204-209 | 426.6 | | ** | |
| 102 | 136.7-136.9 | 267.2 | | * | |
| 103 | 90-93 | 263.2 | | * | |
| 104 | 190-194 | 406.4 | | ** | |
| 105 | 204-206 | 442.4 | | * | |
| 106 | 230-243 | 494.4 | | * | |
| 107 | 157-158 | 327.1 | | * | |
| 108 | 94-96 | 249.2<br>251.2 | | * | |
| 109 | 54-56 | 263.2<br>265.2 | | * | |
| 110 | 128-130 | 349.3 | | ** | |
| 111 | 208.5 | 374.3 | | * | $^1$H NMR($CDCl_3$, 400MHz), δ=7.75-7.72(m, 2H), 7.13-7.10(m, 2H), 6.97-6.88(m, 3H), 6.11(s, 2H) |
| 112 | 173.1-173.5 | 277.3 | | ** | $^1$H NMR($CDCl_3$, 400MHz), δ=7.67(t, J=8.4Hz, 2H), 7.24(d, J=14.8Hz, 1H), 7.16(d, J=8.0Hz, 1H), 6.96-6.90(m, 3H), 6.10(s, 2H), 2.46(s, 3H) |
| 113 | 193-194 | 374.3 | | * | |
| 114 | 207-298 | 390.3 | | * | |
| 115 | 175-177 | 177.1 | | * | |
| 116 | 116-118 | 349.4 | | * | |
| 117 | 120-123 | 249.3 | | * | |
| 118 | 62-65 | 205.2 | | ** | |
| 119 | 126-128 | 283.2 | | ** | |
| 120 | 69-71 | 205.5 | | * | |
| 121 | 167-169 | 364.5 | | ** | |
| 122 | 163-169 | 426.5 | | * | |
| 123 | 113-117 | 239.4 | | * | |
| 124 | 212.2-212.3 | 295.3 | | * | $^1$H NMR($CDCl_3$, 400MHz), δ=7.61(dd, J=8.4Hz and 4.4Hz, 1H), 7.04-6.96(m, 2H), 6.77(m, 3H), 6.12(s, 2H), 2.42(s, 3H) |
| 125 | 151.2-151.7 | 291.3 | | ** | $^1$H NMR($CDCl_3$, 400MHz), δ=7.57(d, J=8.0Hz, 1H), 7.09(d, J=8.0Hz, 1H), 6.97(d, J=8.0Hz, 1H), 6.86(s, 1H), 6.79(dd, J=11.2Hz and 2.0Hz, 2H), 6.12(s, 2H), 2.42(s, 3H), 2.40(s, 3H) |
| 126 | 146-148 | 251.3 | | * | |
| 127 | 173-175 | 327.3 | | * | |
| 128 | 218-220 | 334.5 | | * | |
| 129 | 188-190 | 370.4 | | ** | |
| 130 | 227-233 | 394.5 | | *** | |
| 131 | 199-204 | 408.5 | | ** | |
| 132 | 209-212 | 422.5 | | ** | |
| 133 | 144-146 | 351.5 | | ** | |
| 134 | 155-157 | 335.4 | | ** | |
| 135 | 168-170 | 369.5 | | ** | |
| 136 | 159-161 | 381.4 | | ** | |
| 137 | 129-132 | 345.5 | | ** | |
| 138 | 235-239 | 358.5 | *** | ** | |
| 139 | 191-195 | 388.5 | *** | ** | |
| 140 | 83-96 | 253.3 | | * | |
| 141 | 145-146 | 253.4 | | * | |
| 142 | 103-105 | 237.4 | | * | |
| 143 | 168-171 | 384.5 | | * | |
| 144 | 97-100 | 315.4 | | ** | |
| 145 | 110-113 | 357.5 | | ** | |

TABLE 1A-continued

| Compound Number | Melting Point (° C.) | Mass Spec [M+H] | HCV-PV $IC_{50}$ µM | Replicon $IC_{50}$ µM | NMR Data |
|---|---|---|---|---|---|
| 146 | 169-172 | 335.3 | | ** | |
| 147 | 183-186 | 344.4 | | ** | |
| 148 | 155-157 | 335.4 | | ** | |
| 149 | 134-136 | 345.4 | | ** | |
| 150 | 141-143 | 319.4 | | ** | |
| 151 | 146-148 | 319.4 | | ** | |
| 152 | 207-211 | 386.5 | | * | |
| 153 | 225-228 | 398.5 | * | ** | |
| 154 | | 293.1 | | ** | $^1$H NMR(DMSO-$d_6$, 400MHz), δ=8.13(d, J=6.4Hz, 1H), 8.01(s, 2H), 7.84(s, 1H), 7.54(dd, J=12.4Hz and 3.6Hz, 1H), 7.15(d, J=8.8Hz, 2H), 3.83(s, 3H) |
| 155 | | | | ** | $^1$H NMR($CDCl_3$, 300MHz), δ=9.31(s, 1H), 8.32(s, 1H), 8.19-8.17(m, 1H), 7.75(s, 1H), 2.70(s, 3H) |
| 156 | 205-209 | 421.5 | | ** | |
| 157 | 149-153 | 422.5 | | ** | |
| 158 | 153-156 | 317.5 | | ** | |
| 159 | 147-150 | 361.3 | | ** | |
| 160 | 117-119 | 315.7 | | ** | |
| 161 | 174-176 | 340.3 | | ** | |
| 162 | 185-190 | 413.5 | | * | |
| 163 | 235-239 | 410.5 | | ** | |
| 164 | 273-280 | 358.5 | | ** | |
| 165 | 211-225 | 373.5 | | * | |
| 166 | 236-240 | 385.5 | | *** | |
| 167 | 196-200 | 464.5 | | ** | |
| 168 | 199-204 | 394.5 | | * | |
| 169 | 147-150 | 316.5 | | ** | |
| 170 | 148-151 | 307.4 | | ** | |
| 171 | 134-137 | 307.4 | | ** | |
| 172 | 221-223 | 317.4 | | ** | |
| 173 | 150-153 | 316.5 | | ** | |
| 174 | 139-142 | 302.4 | | ** | |
| 175 | 132-135 | 359.5 | | ** | |
| 176 | 162-164 | 343.5 | | ** | |
| 177 | 125-130 | 331.4 | | ** | |
| 178 | 119-123 | 369.4 | | * | |
| 179 | 79-80 | 239.4 | | ** | |
| 180 | 170-171 | 384.5 | ** | ** | |
| 181 | 177-178 | 398.5 | | ** | |
| 182 | 148-154 | 408.5 | | *** | |
| 183 | 276-284 | 344.5 | | ** | |
| 184 | 197-200 | 337.4 | | ** | |
| 185 | 157-160 | 355.4 | | ** | |
| 186 | 166-169 | 317.4 | | ** | |
| 187 | 187-191 | 321.4 | | ** | |
| 188 | 209-212 | 287.4 | | ** | |
| 189 | 252-253 | 356.4 | | * | |
| 190 | 234-236 | 370.4 | | ** | |
| 191 | 208-210 | 370.4 | ** | * | |
| 192 | 205-207 | 384.5 | | ** | |
| 193 | 228-232 | 378.5[M−H] | | ** | |
| 194 | 278-284 | 370.4 | | ** | |
| 195 | 271-275 | 398.4 | | ** | |
| 196 | 187-189 | 354.3 | | ** | |
| 197 | 147-149 | 373.6 | | * | |
| 198 | 163-165 | 395.7 | | * | |
| 199 | 156-158 | 369.2 | *** | * | |
| 200 | 187-189 | 354.4 | | ** | |
| 201 | 147-150 | 381.2 | | ** | |
| 202 | 137-139 | 369.4 | | ** | |
| 203 | | 257.9 | | ** | $^1$H NMR(DMSO-$d_6$, 300MHz) δ=10.34(s, 1H), 7.42(d, J=8.7Hz, 1H), 7.14(d, J=2.1Hz, 1H), 6.87(dd, J=8.7Hz and 2.1Hz, 1H), 4.08(q, J=7.2Hz, 2H), 3.80(s, 3H), 2.12(s, 3H), 1.21(t, J=7.2Hz, 3H) |
| 204 | | 320.1 | | *** | $^1$H(DMSO-$d_6$, 300MHz), δ=10.81(s, 1H), 8.02(t, J=7.2Hz, 2H), 7.67-7.47(m, 4H), 7.21(d, J=2.4Hz, 1H), 6.90(dd, J=8.4Hz and 2.1Hz, 1H), 4.12(q, J=6.9Hz, 2H), 3.83(s, 3H), 1.24(t, J=7.5Hz, 3H) |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| 205 | 181-184 | 358.4 | | ** | |
| 206 | 187-191 | 372.4 | | ** | |
| 207 | 179-183 | 386.4 | | ** | |
| 208 | 192-194 | 394.4 | | ** | |
| 209 | 180-183 | 408.4 | | ** | |
| 210 | 213-216 | 422.4 | | ** | |
| 211 | 186-191 | 384.4 | | ** | |
| 212 | 180-183 | 400.4 | | ** | |
| 213 | 165-168 | 398.4 | | ** | |
| 214 | 254.8-255.1 | 338.1 | | *** | $^1$H NMR(DMSO-$d_6$, 300MHz), δ=7.88(d, J=7.5Hz, 1H), 7.82(d, J=9.9Hz, 1H), 7.64(q, J=8.1Hz, 1H), 7.21(d, J=2.4Hz, 1H), 7.56-7.48(m, 2H), 7.21(d, J=2.1Hz, 1H), 6.91(dd, J=8.7Hz and 2.1Hz, 1H), 4.12(q, J=7.2Hz, 2H), 4.13(s, 3H), 1.23(t, J=6.9Hz, 3H) |
| 215 | 245-246 | 345.1 | | ** | $^1$H NMR(DMSO-$d_6$, 300MHz), δ=11.08(s, 1H), 8.16(d, J=8.4Hz, 2H), 8.07(d, J=7.8Hz, 2H), 7.49(d, J=8.4Hz, 1H), 7.21(d, J=2.1Hz, 1H), 6.91(dd, J=8.4Hz and 1.8Hz, 1H), 4.08(q, J=2.1Hz, 2H), 3.80(s, 3H), 1.25(t, J=7.2Hz, 3H) |
| 216 | 261 | 283.9 | | ** | $^1$H NMR(DMSO-$d_6$, 300MHz), δ=10.58(br, 1H), 7.42(d, J=8.7Hz, 1H), 7.15(d, J=2.1Hz, 1H), 6.86(dd, J=8.7Hz and 2.4Hz, 1H), 4.08(q, J=7.2Hz, 2H), 3.80(s, 3H), 2.04(br, 1H), 1.21(t, J=6.9Hz, 3H), 0.89-0.84(m, 5H) |
| 217 | 272-273 | 315.9 | | *** | $^1$H NMR(DMSO-$d_6$, 300MHz), δ=9.94(s, 1H), 7.43(d, J=8.7Hz, 1H), 7.15(d, J=2.1Hz, 1H), 6.87(dd, J=8.7Hz and 2.4Hz, 1H), 4.12(q, J=7.2Hz, 2H), 3.91(d, J=6.6Hz, 2H), 3.80(s, 3H), 1.89-1.92(m, 1H), 1.21(t, J=7.2Hz, 3H), 0.89(d, J=6.6Hz, 6H) |
| 218 | 174-177 | 344.3 | | ** | |
| 219 | 145-149 | 388.4 | | ** | |
| 220 | 219-223 | 387.7 | | ** | |
| 221 | 195-200 | 421.3 | | ** | |
| 222 | 216-219 | 385.4 | | ** | |
| 223 | 210-216 | 316.4 | | ** | |
| 224 | 245-249 | 358.3 | | ** | |
| 225 | 231-236 | 372.3 | | ** | |
| 226 | 294-295 | 375.9 | | * | $^1$H NMR($CDCl_3$, 300MHz)δ(ppm), 3.72(s, 3H), 3.80(s, 3H), 6.75-6.91(m, 2H), 7.42-7.56(m, 2H), 8.04(d, 1H), 8.23(d, 1H), 8.67(d, 1H). |
| 227 | 198-203 | 392.3 | | ** | |
| 228 | 195-198 | 388.3 | | * | |
| 229 | 142-147 | 321.3 | | * | |
| 230 | 218-220 | 323.4 | | * | |
| 231 | 201-203 | 289.3 | | * | |
| 232 | 190-193 | 307.3 | | * | |
| 233 | 232-234 | 329.4 | | ** | |
| 234 | 221-223 | 288.3 | | * | |
| 235 | 218-222 | 316.4 | | ** | |
| 236 | 145-147 | 287.3 | | * | |
| 237 | 146-148 | 303.3 | | * | |
| 238 | 189-191 | 273.3 | | * | |
| 239 | 212-218 | 292.3 | | * | |
| 240 | 164-167 | 335.3 | | * | |
| 241 | 184-188 | 344.3 | | * | |
| 242 | 242-248 | 334.3 | | * | |
| 243 | 194-198 | 370.3 | | *** | |
| 244 | 187-190 | 360.4 | | ** | |
| 245 | 192-195 | 390.4 | | * | |
| 246 | 160-164 | 374.4 | | * | |
| 247 | 212-217 | 293.3 | | * | |
| 248 | 117-121 | 351.4 | | ** | |
| 249 | 132-136 | 337.4 | | ** | |
| 250 | 160-162 | 323.3 | | * | |
| 251 | 186-187 | 398.4 | *** | ** | |

TABLE 1A-continued

| Compound Number | Melting Point (° C.) | Mass Spec [M+H] | HCV-PV $IC_{50}$ µM | Replicon $IC_{50}$ µM | NMR Data |
|---|---|---|---|---|---|
| 252 | 176-177 | 432.4 | | ** | |
| 253 | 121-125 | 399.2 | | ** | |
| 254 | 153-154 | 307.21 | | * | |
| 255 | 149-151 | 435.5 | | ** | |
| 256 | 230-232 | 331.3 | | * | |
| 257 | 174-176 | 330.3 | | * | |
| 258 | 146-148 | 330.3 | | * | |
| 259 | foam | 358.3 | | * | |
| 260 | 109-111 | 359.3 | | * | |
| 261 | 138-143 | 406.4 | | ** | |
| 262 | 117-121 | 365.4 | | ** | |
| 263 | 121-127 | 419.4 | | ** | |
| 264 | glass | 406.5 | | ** | |
| 265 | 204-206 | 355.3 | | * | |
| 266 | 96-99 | 362.4 | | ** | |
| 267 | 106-112 | 336.4 | | * | |
| 268 | 137-143 | 414.4 | | ** | |
| 269 | 153-158 | 428.4 | | ** | |
| 270 | 175-177 | 404.4 | | * | |
| 271 | 158-160 | 418.4 | | ** | |
| 272 | 173-176 | 396.4 | | ** | |
| 273 | 207-209 | 404.4 | | * | |
| 274 | 166-172 | 378.4 | | * | |
| 275 | 201-206 | 384.4 | | * | |
| 276 | 224-228 | 426.4 | | * | |
| 277 | 186-191 | 370.4 | | * | |
| 278 | 234-240 | 356.4 | | * | |
| 279 | 197-202 | 407.5 | | * | |
| 280 | 89-95 | 364.4 | | * | |
| 281 | 132-134 | 283.3 | | * | |
| 282 | 135-136 | 317.3 | | * | |
| 283 | 215-218 | 353.4 | | * | |
| 284 | 112-114 | 267.3 | | * | |
| 285 | 185-190 | 420.5 | | * | |
| 286 | 191-192 | 333.3 | | ** | $^1$H NMR(300MHz, $CDCl_3$): δ 7.92-7.88(2H, m), 7.67(1H, s), 7.66(1H, d, J=8.8Hz), 7.46-7.42(2H, m), 6.98(1H, dd, J=8.8, 2.3Hz), 6.88(1H, d, J=2.3Hz), 4.35(2H, q, J=7.3Hz), 3.92(3H, s), 1.46(3H, t, J=7.3Hz). |
| 287 | 175-177 | 384.4 | | * | |
| 288 | 194-199 | 293.3 | | * | |
| 289 | 173-175 | 432.2 | | * | |
| 290 | | 433.1 | | * | $^1$H NMR(CDCl3, 300MHz), δ 7.97-7.92(m, 2H), 7.70-7.62(m, 3H), 7.10(br, 1H), 6.98(dd, J=8.7Hz and 2.1Hz, 1H), 6.88(d, J=2.1Hz, 1H), 4.16(q, J=7.5Hz, 2H), 3.91(s, 3H), 3.77(t, J=4.2Hz, 4H), 3.62(q, J=5.4Hz, 2H), 2.68(t, J=5.7Hz, 2H), 2.59(br, 4H), 1.36(t, J=7.2Hz, 3H) |
| 291 | | 319.9 | | * | $^1$H NMR($CD_3OD$, 300MHz), δ 8.07(d, J=7.2Hz, 2H), 7.79-7.68(m, 2H), 7.54(d, J=8.7Hz, 1H), 7.12(d, J=2.1Hz, 1H), 6.97(dd, J=8.7Hz and 2.1Hz, 1H), 4.24(q, J=7.5Hz, 2H), 3.90(s, 3H), 1.26(t, J=7.2Hz, 3H) |
| 292 | 176-177 | 348.0 | | * | $^1$H NMR(CDCl3, 300MHz), δ 7.93-7.88(m, 2H), 7.69-7.60(m, 3H), 6.98(dd, J=8.7Hz and 2.1Hz, 1H), 6.88(d, J=2.1Hz, 1H), 6.17(br, 1H), 4.15(q, J=7.2Hz, 2H), 3.91(s, 3H), 3.53(m, 2H), 1.35(t, J=7.2Hz, 3H), 1.28(t, J=7.2Hz, 3H) |
| 293 | | 412.5 | | * | |
| 294 | | 364.4 | | *** | |
| 295 | | 609.4 | | ** | |
| 296 | | 392.4 | | ** | |
| 297 | | 378.4 | | ** | |
| 298 | | 394.4 | | ** | |
| 299 | | 376.4 | | ** | |
| 300 | | 392.4 | | ** | |
| 301 | | 412.4 | | ** | |
| 302 | | 382.4 | | ** | |

TABLE 1A-continued

| Compound Number | Melting Point (° C.) | Mass Spec [M+H] | HCV-PV $IC_{50}$ µM | Replicon $IC_{50}$ µM | NMR Data |
|---|---|---|---|---|---|
| 303 | | 374.2 | | * | |
| 304 | | 426.4 | | ** | |
| 305 | | 442.4 | | * | |
| 306 | | 446.4 | | ** | |
| 307 | | 430.4 | | ** | |
| 308 | | 424.3 | | * | |
| 309 | | 490.3 | | ** | |
| 310 | | 378.4 | | ** | |
| 311 | | 392.1 | | * | |
| 312 | | 378.1 | | * | |
| 313 | | 394.1 | | * | |
| 314 | | 376.1 | | * | |
| 315 | | 412.0 | | * | |
| 316 | | 474.1 | | * | |
| 317 | | 382.1 | | * | |
| 318 | | 446.1 | | * | |
| 319 | | 430.1 | | * | |
| 320 | | 426.1 | | * | |
| 321 | | 490.9 | | * | |
| 322 | 223-230 | 308.4 | | * | |
| 323 | 102.9-103.4 | 447.2 | | * | $^1$H NMR($CD_3OD$, 300MHz), δ 8.02-8.00(m, 2H), 7.78-7.68(m, 2H), 7.55(d, J=8.4Hz, 1H), 7.12(s, 1H), 6.97(dd, J=6.6Hz and 1.5Hz, 1H), 4.24(q, J=7.5Hz, 2H), 3.90(s, 3H), 3.68(t, J=4.2Hz, 4H), 3.52(q, J=5.4Hz, 2H), 2.50(t, J=6.9Hz, 6H), 1.86(br, 2H), 1.28(t, J=7.2Hz, 3H) |
| 324 | 165.3-165.7 | 368.1 | | * | $^1$H NMR(DMSO-$d_6$, 300MHz), δ 10.56(s, 1H), 7.85(s, 1H), 7.73(d, J=7.8Hz, 1H), 7.54(q, J=7.8Hz, 2H), 7.31(d, J=7.8Hz, 1H), 7.23(s, 1H), 6.92(d, J=8.7Hz, 1H), 4.27(s, 2H), 4.18(q, J=7.5Hz, 2H), 3.83(s, 3H) 1.20(t, J=7.2Hz, 3H) |
| 325 | | 462.1 | | * | $^1$H NMR(DMSO-$d_6$, 300MHz), δ 10.30(s, 1H), 8.02(s, 1H), 7.91(d, J=7.5Hz, 1H), 7.58-7.54(m, 4H), 7.51-7.49(m, 2H), 7.04(d, J=8.4Hz, 1H), 6.92(dd, J=8.7Hz and 1.8Hz, 1H), 6.11(s, 2H), 4.22(q, J=7.5Hz, 2H), 3.83(s, 3H), 1.21(t, J=6.9Hz, 3H) |
| 326 | 137-138 | 396.1 | | * | |
| 327 | 154-155 | 386.1 | | * | $^1$H NMR(DMSO-$d_6$, 300MHz), δ 10.45(s, 1H), 8.02(s, 1H), 7.95(d, J=8.1Hz, 2H), 7.55(q, J=7.8Hz, 2H), 7.33(q, J=3.6Hz, 2H), 7.25(s, 1H), 6.95(dd, J=3.6 and J=2.4Hz, 1H), 6.70(q, J=1.8Hz, 1H), 4.22(q, J=7.5Hz, 2H), 3.84(s, 3H), 1.22(t, J=6.9Hz, 3H) |
| 328 | 174-175 | 401.1 | | * | $^1$H NMR(CDCl3, 300MHz), δ 8.68(s, 1H), 8.00(s, 1H), 7.65(m, 2H), 7.55(t, J=8.4Hz, 1H), 7.40(d, J=7.2Hz, 1H), 6.95(dd, J=7.2 and 1.8Hz, 1H), 6.90(d, J=2.1, 1H), 6.54(s, 1H), 4.20(q, J=7.2Hz, 2H), 3.92(s, 3H), 2.53(s, 3H), 1.39(t, J=7.2Hz, 3H) |
| 329 | 175-176 | 334.0 | | * | $^1$H NMR(CDCl3, 300MHz), δ 7.79(s, 1H), 7.64(d, J=8.4Hz, 1H), 7.58(d, J=8.7Hz, 1H), 7.49(t, J=7.8Hz, 1H), 7.38(s, 1H), 7.30(d, J=4.5Hz, 1H), 6.99(d, J=2.1Hz, 1H), 6.92(d, J=2.1Hz, 1H) 4.19(q, J=6.9Hz, 2H), 3.91(s, 3H), 2.22(s, 3H), 1.39(t, J=7.2Hz, 3H) |
| 330 | 237-238 | 438.1 | | * | $^1$H NMR(DMSO-$d_6$, 300MHz), δ 10.90(s, 1H), 8.71(s, 1H), 8.18(d, J=9.9Hz, 1H), 8.06(s, 1H), 7.97(t, J=9.3Hz, 2H), 7.63(t, J=8.1Hz, 1H), 7.53(d, J=8.7, 1H), 7.39(d, J=8.4Hz, 1H), 7.27(d, J=1.8Hz, 1H), 6.94(dd, J=8.7Hz and 2.1Hz, 1H), 4.23(q, J=6.6Hz, 2H), 3.84(s, 3H), 1.23(t, J=7.2Hz, 3H) |
| 331 | 160-165 | 370.5 | | ** | |

TABLE 1A-continued

| Compound Number | Melting Point (° C.) | Mass Spec [M+H] | HCV-PV $IC_{50}$ µM | Replicon $IC_{50}$ µM | NMR Data |
|---|---|---|---|---|---|
| 332 | 239-145 | 334.5 | | * | |
| 333 | 237-240 | 384.5 | | ** | |
| 334 | 242-246 | 348.5 | | ** | |
| 335 | 87-88 | 297.5 | | ** | |
| 336 | 129-132 | 384.5 | | * | |
| 337 | 135-137 | 283.4 | | * | |
| 338 | 125-135 | 367.5[M−H] | | * | |
| 339 | 215-219 | 362.5 | | ** | |
| 340 | 243-248 | 334.2 | | * | |
| 341 | 227-230 | 348.3 | | ** | |
| 342 | 258-261 | 337.3 | | * | $^1$H NMR(300MHz, $CDCl_3$): δ 8.70(1H, s), 7.79(1H, d, J=1.8Hz), 7.73(1H, dd, J=8.5, 1.8Hz), 7.07(1H, d, J=8.5Hz), 6.95(2H, d, J=8.8Hz), 6.65(2H, d, J=8.8Hz), 3.97(2H, q, J=7.0Hz), 3.54(3H, s), 1.12(3H, t, J=7.0Hz). |
| 343 | 131-133 | 373.5 | | * | |
| 344 | 177-178 | 356.5 | | ** | |
| 345 | 191-192 | 370.5 | | ** | |
| 346 | 178-180 | 384.3 | | *** | |
| 347 | 146-148 | 357.3 | | * | |
| 348 | 126-128 | 267.2 | | * | |
| 349 | | 392.3 | | *** | |
| 350 | | 374.3 | | ** | |
| 351 | | 390.3 | | ** | |
| 352 | | 388.3 | | ** | |
| 353 | | 350.2 | | *** | |
| 354 | | 388.3 | | ** | |
| 355 | | 384.2 | | * | |
| 356 | | 404.3[M−H] | | * | |
| 357 | | 392.3 | | * | |
| 358 | | 374.3 | | * | |
| 359 | | 390.3 | | * | |
| 360 | | 388.3 | | * | |
| 361 | | 404.3 | | * | |
| 362 | | 609.5[M−H] | | ** | |
| 363 | 201-207 | 394.2[M−H] | | ** | |
| 364 | 183-188 | 398.2 | | ** | |
| 365 | oil | 408.2 | | *** | |
| 366 | 223-225 | 420.2 | | *** | |
| 367 | 225-227 | 434.2 | | ** | |
| 368 | 168-170 | 434.2 | | ** | |
| 369 | 174-177 | 470.2 | | ** | |
| 370 | 159-164 | 432.2 | | * | |
| 371 | 168-170 | 340.2 | | * | $^1$H NMR(300MHz, DMSO-$d_6$): δ 10.24(1H, s), 7.75-7.60(1H, m), 7.60(2H, d, J=8.8Hz), 7.45-7.25(3H, m), 7.41(2H, d, J=8.8Hz), 4.21(2H, q, J=7.0Hz), 3.13(3H, s), 1.22(3H, t, J=7.0Hz). |
| 372 | 211-212 | 334.3 | | ** | $^1$H NMR(300MHz, DMSO-$d_6$): δ 9.98(1H, s), 7.73-7.62(2H, m), 7.69(2H, d, J=8.4Hz), 7.54(2H, d, J=8.4Hz), 7.39-7.24(2H, m), 4.26-4.12(4H, m), 1.26(3H, t, J=7.0Hz), 1.20(3H, t, J=7.3Hz). |
| 373 | 222-228 | 354.2[M−H] | | * | |
| 374 | 180-186 | 396.2[M−H] | | * | |
| 375 | 161-166 | 425.6[M−H] | | * | |
| 376 | | 278.4 | | * | |
| 377 | 153-156 | 403.1 | | * | $^1$H NMR(DMSO-$d_6$, 300MHz), δ 7.66-7.51(m, 5H), 7.25(d, J=2.1Hz, 1H), 6.91(dd, J=8.7Hz and 2.4Hz, 1H), 4.20(q, J=7.5Hz, 2H), 3.83(s, 3H), 3.65-3.55(m, 2H), 2.73-2.68(m, 4H), 1.71-1.54(m, 4H), 1.18(t, J=7.2Hz, 3H). |
| 378 | | 376.7 | | * | $^1$H NMR(DMSO-$d_6$, 300MHz), δ 8.84(t, J=1.8Hz, 1H), 8.02(d, J=8.1Hz, 2H), 7.67(d, J=7.8Hz, 2H), 7.49(d, J=8.7Hz, 1H), 7.38(s, 1H), 7.22(s, 1H), 7.02(s, 1H), 6.89(d, J=7.2Hz, 1H), 4.17(q, J=6.9Hz, 2H), 3.80-3.77(m, 5H), 1.12(t, J=7.2Hz, 3H). |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| 379 | 228-232 | 474.2 | | ** | $^1$H NMR(DMSO-$d_6$, 300MHz), δ 7.72-7.67(m, 2H), 7.78-7.68(m, 2H), 7.55(d, J=8.4Hz, 1H), 7.12(s, 1H), 6.97(dd, J=6.6Hz and 1.5Hz, 1H), 4.20(q, J=7.5Hz, 2H), 3.83(s, 3H), 3.06(t, J=4.2Hz, 6H), 2.76-2.69(m, 6H), 2.50(s, 6H), 1.96(br, 2H), 1.18(t, J=7.2Hz, 3H). |
| 380 | | | | * | $^1$H NMR(DMSO-$d_6$, 300MHz), δ 10.67(s, 1H), 8.16(d, J=2.4Hz, 1H), 8.11(d, J=4.5Hz, 2H), 7.78(d, J=8.4Hz, 2H), 7.73(d, J=2.4Hz, 1H), 7.61(d, J=9.0Hz, 1H), 7.54(d, J=9.0Hz, 1H), 7.27(s, 1H), 6.94(d, J=8.7Hz, 1H), 4.28-4.26(m, 2H), 3.84(s, 3H), 1.17(t, J=7.2Hz, 3H). |
| 381 | 216-220 | 410.1 | | * | $^1$H NMR(DMSO-$d_6$, 300MHz), δ 10.34(s, 1H), 8.10(d, J=8.1Hz, 2H), 7.75(d, J=8.1Hz, 2H), 7.65(d, J=8.4Hz, 2H), 7.53(d, J=8.7Hz, 1H), 7.26(s, 1H), 7.14(d, J=8.1Hz, 2H), 6.94(dd, J=8.7Hz and 2.4Hz, 1H), 4.21(q, J=6.9Hz, 2H), 3.83(s, 3H), 2.25(s, 3H), 1.17(t, J=6.9Hz, 3H). |
| 382 | 236-238 | | | ** | $^1$H NMR(DMSO-$d_6$, 300MHz), δ 10.55(s, 1H), 8.10(d, J=7.8Hz, 2H), 7.83-7.76(m, 4H), 7.54(d, J=8.4Hz, 1H), 7.41(d, J=8.1Hz, 2H), 7.27(s, 1H), 6.93(dd, J=9.9Hz and 1.2Hz, 1H), 4.22(q, J=6.9Hz, 2H), 3.84(s, 3H), 1.17(t, J=7.2Hz, 3H). |
| 383 | 161.2-162.2 | 362.1 | | * | $^1$H NMR(CDCl3, 300MHz), δ 7.79(s, 1H), 7.65-7.59(m, 2H), 7.48(t, J=7.8Hz, 1H), 7.30(t, J=11.4Hz, 2H), 6.96(dd, J=8.7Hz and 2.1Hz, 1H), 6.88(d, J=2.1Hz, 1H), 4.18(q, J=7.2Hz, 2H), 3.91(s, 3H), 2.57-2.52(m, 1H), 1.36(t, J=7.2Hz, 3H) 1.28-1.23(m, 6H). |
| 384 | 199-201 | 348.0 | | * | $^1$H NMR(CDCl3, 300MHz), δ 7.93(d, J=8.4Hz, 2H), 7.67-7.61(m, 3H), 6.98(dd, J=8.7Hz and 2.1Hz, 1H), 6.88(d, J=2.1Hz, 1H), 6.14(br, 1H), 4.14(q, J=7.5Hz, 2H), 3.93(s, 3H), 3.57-3.53(m, 2H), 1.36-1.26(m, 6H). |
| 385 | 213-213.9 | 362.0 | | ** | $^1$H NMR(DMSO-$d_6$, 300MHz), δ 8.37(d, J=6.6Hz, 1H), 7.98(d, J=7.8Hz, 2H), 7.65(d, J=7.8Hz, 2H), 7.50(d, J=9.0Hz, 1H), 7.23(s, 1H), 6.90(d, J=7.8Hz, 1H), 4.19-4.16(m, 2H), 4.08-4.06(m, 1H), 3.80(s, 3H), 1.14-1.12(m, 9H). |
| 386 | 198-199 | 359.9 | | * | $^1$H NMR(DMSO-$d_6$, 300MHz), δ 8.59(d, J=4.2Hz, 1H), 7.97(d, J=8.1Hz, 2H), 7.67(d, J=8.1Hz, 2H), 7.52(d, J=8.7Hz, 1H), 7.25(d, J=2.1Hz, 1H), 6.92(dd, J=8.7Hz and 2.1Hz, 1H), 4.19(q, J=7.2Hz, 2H), 3.83(s, 3H), 2.90-2.80(m, 1H), 1.16(t, J=7.2Hz, 3H), 0.69(q, J=4.8Hz, 2H), 0.57(q, J=3.3Hz, 2H). |
| 387 | 189-189.5 | 360.1 | | * | $^1$H NMR(DMSO-$d_6$, 300MHz), δ 7.81(d, J=8.4Hz, 2H), 7.67(d, J=8.1Hz, 2H), 7.53(d, J=8.7Hz, 1H), 7.25(d, J=1.8Hz, 1H), 6.93(dd, J=8.7Hz and 2.1Hz, 1H), 4.35(t, J=6.8Hz, 2H), 4.18(q, J=7.2Hz, 2H), 4.06(t, J=6.8Hz, 2H), 3.83(s, 3H), 2.24(m, 2H), 1.16(t, J=7.2Hz, 3H). |
| 388 | 160.1-161.8 | 363.9 | | * | $^1$H NMR(DMSO-$d_6$, 300MHz), δ 8.60(t, J=2.1Hz, 1H), 8.02(d, J=8.4Hz, 2H), 7.68(d, J=8.1Hz, 2H), 7.53(d, J=9.0Hz, 1H), 7.25(s, 1H), 6.93(dd, J=6.9Hz and 1.8Hz, 1H), 4.72(t, J=5.4Hz, 1H), 4.19(q, J=7.2Hz, 2H), |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| | | | | | 3.83(s, 3H), 3.48(q, J=6.0Hz, 2H), 3.33(m, 2H), 1.15(t, J=7.2Hz, 3H). |
| 389 | 130-132 | 447.1 | | * | $^1$H NMR(CDCl3, 300MHz), δ 8.36(br, 1H), 8.12(d, J=7.2Hz, 2H), 7.67-7.59(m, 3H), 6.97(dd, J=9.3Hz and 1.8Hz, 1H), 6.89(s, 1H), 4.18(q, J=7.5Hz, 2H), 3.98(br, 2H), 3.84(s, 3H), 3.67(q, J=6.9Hz, 2H), 2.87(br, 4H), 2.17(s, 1H) 2.14(br, 1H), 2.09(s, 1H), 1.40(t, J=10.5Hz, 3H), 1.31(t, J=7.5Hz, 3H). |
| 390 | 236-236.8 | 396.1 | | * | $^1$H NMR(DMSO-$d_6$, 300MHz), δ 10.42(s, 1H), 8.12(d, J=8.4Hz, 2H), 7.79-7.75(m, 4H), 7.55(d, J=8.7Hz, 1H), 7.35(t, J=10.6Hz, 2H), 7.27(d, J=2.1Hz, 1H), 7.09(t, J=10.6Hz, 1H), 6.94(dd, J=8.7Hz and 2.1Hz, 1H), 4.23(m, 2H), 3.84(s, 3H), 1.18(t, J=6.9Hz, 3H). |
| 391 | 240-242 | | | ** | $^1$H NMR(DMSO-$d_6$, 300MHz), δ 10.55(s, 1H), 8.11(d, J=8.1Hz, 2H), 7.82(m, 4H), 7.55(d, J=8.7Hz, 1H), 7.41(d, J=9.0Hz, 2H), 7.27(d, J=1.8Hz, 1H), 6.94(dd, J=8.7Hz and 2.1Hz, 1H), 4.23(q, J=7.1Hz, 2H), 3.84(s, 3H), 1.78(t, J=7.1Hz, 3H). |
| 392 | 243-246 | 456.1 | | * | $^1$H NMR(DMSO-$d_6$, 300MHz), δ 10.27(s, 1H), 8.11(d, J=8.4Hz, 2H), 7.76(d, J=8.4Hz, 2H), 7.54(d, J=8.7Hz, 1H), 7.48(d, J=2.4Hz, 1H), 7.33(d, J=7.2Hz, 1H), 7.29(s, 1H), 6.96-6.91(m, 2H), 4.25(q, J=8.5Hz, 2H), 3.84(s, 3H), 3.73(s, 3H), 3.72(s, 3H), 1.18(t, J=7.2Hz, 3H). |
| 393 | 202-206 | 296.4 | | ** | |
| 394 | 192-195 | 372.3[M−H] | | *** | |
| 395 | | 397.4 | | ** | |
| 396 | | 377.2 | *** | *** | |
| 397 | | 377.5 | *** | *** | |
| 398 | | 391.5 | | *** | |
| 399 | | 375.5 | | *** | |
| 400 | | 411.3 | | ** | |
| 401 | | 363.3 | *** | *** | |
| 402 | | 439.5 | | ** | |
| 403 | | 453.5 | | ** | |
| 404 | | 425.5 | | * | |
| 405 | | 425.5 | | ** | |
| 406 | | 503.5 | | *** | |
| 407 | | 483.5 | | ** | |
| 408 | 231-235 | 358.1 | | ** | |
| 409 | 163-164 | 398.3 | | ** | |
| 410 | 139-141 | 359.2 | | ** | |
| 411 | 148-149 | 373.3 | | ** | |
| 412 | 143-144 | 373.3 | | * | |
| 413 | 184-185 | 370.4 | | *** | |
| 414 | 156-157 | 384.4 | | ** | |
| 415 | 163-165 | 384.4 | | *** | |
| 416 | 173-175 | 398.4 | | *** | |
| 417 | 199-201 | 398.4 | | *** | |
| 418 | 183-184 | 412.4 | | *** | |
| 419 | 213-215 | 398.4 | | ** | |
| 420 | 241-243 | 372.5 | | ** | |
| 421 | 214-216 | 406.3 | | * | |
| 422 | 259-261 | 386.5 | | ** | |
| 423 | 291-294 | 434.4 | | * | |
| 424 | 150-153 | 443.5 | | * | |
| 425 | 273-275 | 398.4 | | ** | |
| 426 | 178-180 | 327.2 | | ** | |
| 427 | 199-202 | 330.3 | | ** | |
| 428 | 144-146 | 319.2[M−H] | | * | |
| 429 | 200-206 | 314.3 | | ** | |
| 430 | 180-186 | 372.4[M−H] | | ** | |
| 431 | 167-173 | 296.4 | | * | |
| 432 | 160-162 | 318.1 | | * | $^1$H NMR(DMSO-$d_6$, 300MHz), δ 8.64(t, J=5.4Hz, 1H), 8.02(d, |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| | | | | | J=8.1Hz, 2H), 7.80-7.65(m, 4H), 7.40-7.28(m, 2H), 4.21(q, J=6.9Hz, 2H), 3.29(q, J=7.2Hz, 2H), 1.20-1.08(m, 6H). |
| 433 | 187-189 | 329.9 | | * | $^1$H NMR(DMSO-$d_{6F}$, 300MHz), δ 8.61(d, J=3.6Hz, 1H), 7.79(d, J=8.1Hz, 2H), 7.76-7.64(m, 4H), 7.40-7.27(m, 2H), 4.20(q, J=7.2Hz, 2H), 2.88-2.82(m, 1H), 1.17(t, J=7.2Hz, 3H), 0.69(q, J=7.2Hz, 2H), 0.56(q, J=7.8Hz, 2H). |
| 434 | 170-175 | 368.4 | | * | |
| 435 | 112-117 | 382.5 | | * | |
| 436 | 196-202 | 280.5 | | * | |
| 437 | 220-227 | 342.3[M−H] | | * | |
| 438 | 188-194 | 356.3[M−H] | | * | |
| 439 | 181-186 | 358.4 | | ** | |
| 440 | 177-181 | 370.3[M−H] | | ** | |
| 441 | | 459.5 | | ** | |
| 442 | | 397.5 | | * | |
| 443 | | 411.5 | | * | |
| 444 | | 439.5 | | * | |
| 445 | | 453.5 | | ** | |
| 446 | | 503.5 | | * | |
| 447 | | 426.5 | | *** | |
| 448 | 301-303 | 436.5 | | * | $^1$H NMR(300MHz, DMSO-$d_6$): δ 10.65(1H, s), 7.94(1H, s), 7.76(1H, s), 7.48(1H, d, J=8.5Hz), 7.45(2H, d, J=8.5Hz), 7.33(2H, d, J=8.5Hz), 7.21(1H, d, J=2.0Hz), 6.90(1H, dd, J=8.5, 2.0Hz), 4.13(2H, q, J=7.0Hz), 3.82(3H, s), 3.66(3H, s), 1.15(3H, t, J=7.0Hz). |
| 449 | 242-243 | 518.5 | | * | $^1$H NMR(300MHz, DMSO-$d_6$): δ 10.59(1H, s), 8.49(1H, d, J=2.3Hz), 7.81(1H, dd, J=9.1, 2.3Hz), 7.52-7.44(3H, m), 7.29(2H, d, J=8.5Hz), 7.21(1H, d, J=2.3Hz), 6.90(2H, d, J=8.8Hz), 4.12(2H, q, J=7.0Hz), 3.82(3H, s), 3.63-3.55(8H, m), 1.12(3H, t, J=7.0Hz). |
| 450 | 217-220 | 402.5 | | ** | |
| 451 | 179-182 | 438.4 | | * | $^1$H NMR(300MHz, DMSO-$d_6$): δ 10.87(1H, s), 7.94(1H, dt, J=5.0, 1.0Hz), 7.66(1H, dt, J=3.5, 1.2Hz), 7.55-7.48(3H, m), 7.33(2H, d, J=8.0Hz), 7.22(1H, d, J=1.8Hz), 7.14(1H, ddd, J=5.0, 3.8, 1.0Hz), 6.90(1H, dt, J=8.8, 1.0Hz), 4.13(2H, q, J=7.3Hz), 3.83(3H, s), 1.13(3H, t, J=7.3Hz). |
| 452 | 299-301 | 483.4 | | * | $^1$H NMR(300MHz, DMSO-$d_6$): δ 10.62(1H, s), 9.12(1H, dd, J=4.1, 1.7Hz), 8.53-8.45(2H, m), 8.29(1H, d, J=8.5Hz), 7.78-7.68(2H, m), 7.44(1H, d, J=8.8Hz), 7.36(2H, d, J=8.8Hz), 7.27(2H, d, J=8.8Hz), 7.16(1H, d, J=2.0Hz), 6.87(1H, dd, J=8.8, 2.0Hz), 4.04(2H, q, J=7.0Hz), 3.80(3H, s), 1.06(3H, t, J=7.0Hz). |
| 453 | 198-200 | 416.5 | | ** | |
| 454 | 180-182 | 412.4 | | * | $^1$H NMR(300MHz, $CDCl_3$): δ 7.44-7.11(4.8H, m), 6.97(1.2H, d, J=8.4Hz), 6.78-6.69(2H, m), 4.00-3.90(2H, m), 3.713(1.2H, s), 3.707(1.8H, s), 2.93(1H, v br), 2.12(1.8H, s), 2.09(1.2H, s), 1.17(1.2H, t, J=7.3Hz), 1.14(1.8H, t, J=7.3Hz). |
| 455 | 221-223 | 414.4 | | * | |
| 456 | 157-159 | 357.5 | | ** | |
| 457 | 156-158 | 464.5 | | ** | |
| 458 | 272-273 | 496.5 | | * | $^1$H NMR(300MHz, DMSO-$d_6$): δ 10.10(1H, s), 8.62(1H, d, J=8.2Hz), 8.49-8.45(2H, m), |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| | | | | | 8.27(2H, d, J=8.8Hz), 7.90(2H, d, J=3.8Hz), 7.72(2H, d, J=8.8Hz), 7.70-7.62(1H, m), 7.55-7.49(4H, m), 7.26(1H, d, J=2.0Hz), 6.94(1H, dd, J=8.8, 2.0Hz), 4.27(2H, q, J=7.0Hz), 3.85(3H, s), 1.24(3H, t, J=7.0Hz). |
| 459 | 158-163 | 368.5 | | ** | |
| 460 | oil | 368.3[M−H] | | ** | |
| 461 | 200-205 | 432.3 | | *** | |
| 462 | 135-140 | 444.2[M−H] | | *** | |
| 463 | 178-179 | 359.5 | | * | |
| 464 | 164-166 | 401.5 | | * | |
| 465 | 99-100 | 401.5 | | * | |
| 466 | 164-166 | 385.5 | | ** | |
| 467 | 169-170 | 399.5 | | ** | |
| 468 | 201-202 | 398.5 | ** | *** | |
| 469 | 243-245 | 384.5 | | ** | |
| 470 | 178-180 | 426.5 | | *** | |
| 471 | 154-156 | 412.2 | | *** | |
| 472 | 215-217 | 410.5 | | *** | |
| 473 | 189-191 | 424.5 | | *** | |
| 474 | 218-222 | 293.5 | | * | |
| 475 | 178-181 | 293.5 | | *** | |
| 476 | 175-178 | 340.4 | | ** | |
| 477 | 194-195 | 418.4 | | *** | |
| 478 | 172-175 | 469.5 | | *** | |
| 479 | 190-192 | 467.5 | | * | |
| 480 | 207-208 | 485.4 | | *** | |
| 481 | 209-211 | 482.5 | | * | |
| 482 | 128-130 | 471.5 | | ** | |
| 483 | 149-150 | 292.2 | | * | $^{1}$H NMR(300MHz, $CDCl_3$): δ 7.32-7.25(2H, m), 7.19(1H, d, J=2.4Hz), 6.97(1H, dd, J=8.9, 2.4Hz), 6.92-6.80(3H, m), 4.17(2H, q, J=7.3Hz), 3.89(3H, s), 3.80(2H, v br), 1.34(3H, t, J=7.3Hz). |
| 484 | 156-157 | 334.2 | | * | $^{1}$H NMR(300MHz, $CDCl_3$): δ 8.16(1H, d, J=8.5Hz), 8.00(1H, d, J=8.7Hz), 7.68(1H, d, J=8.8Hz), 7.60-7.50(2H, m), 7.25(1H, obscured), 7.10(1H, d, J=8.8Hz), 5.20(2H, q, J=7.3Hz), 4.02(3H, s), 1.55(3H, t, J=7.3Hz). |
| 485 | 128-133 | 440.2 | | * | |
| 486 | 116-123 | 454.2 | | ** | |
| 487 | 175-179 | 446.2 | | ** | |
| 488 | 158-164 | 460.2 | | *** | |
| 489 | | 418.5 | | ** | |
| 490 | | 404.5 | | ** | |
| 491 | | 445.2 | | * | |
| 492 | | 463.2 | | ** | |
| 493 | | 477.2 | | *** | |
| 494 | | 336.2 | | * | |
| 495 | 126-128 | 444.3 | | ** | |
| 496 | 236-239 | | | ** | |
| 497 | 235-239 | | | * | |
| 498 | 192-194 | 427.5 | | ** | |
| 499 | 235-250 | | | *** | |
| 500 | | 468.2 | | * | |
| 501 | | 420.2 | | * | |
| 502 | | 406.2 | | * | |
| 503 | | 406.2 | | * | |
| 504 | | 412.2 | | * | |
| 505 | 164-166 | 384.2 | | * | $^{1}$H NMR(300MHz, $CDCl_3$): δ 7.52(1H, t, J=7.9Hz), 7.47(1H, t, J=1.9Hz), 7.36-7.30(3H, m), 7.18(1H, d, J=2.3Hz), 7.00(1H, dd, J=8.9, 2.3Hz), 6.91(1H, br s), 4.18(2H, q, J=7.3Hz), 3.90(3H, s), 3.25(2H, q, J=7.3Hz), 1.43(3H, t, J=7.3Hz), 1.38(3H, t, J=7.3Hz) |
| 506 | 156-157 | 364.2 | | * | $^{1}$H NMR(300MHz, $CDCl_3$): δ 7.67(1H, s), 7.48-7.44(2H, m), 7.33(1H, d, J=9.0Hz), 7.26-7.23(1H, |

TABLE 1A-continued

| Compound Number | Melting Point (° C.) | Mass Spec [M+H] | HCV-PV $IC_{50}$ µM | Replicon $IC_{50}$ µM | NMR Data |
|---|---|---|---|---|---|
| | | | | | m), 7.19(1H, d, J=2.3Hz), 6.98(1H, dd, J=9.0, 2.3Hz), 6.79(1H, s), 4.24(2H, q, J=7.3Hz), 4.19(2H, q, J=7.3Hz), 1.36(3H, t, J=7.3Hz), 1.32(3H, t, J=7.3Hz). |
| 507 | 152-153 | 378.2 | | * | $^1$H NMR(300MHz, $CDCl_3$): δ 7.66(1H, s), 7.46(2H, d, J=5.0Hz), 7.33(1H, d, J=9.0Hz), 7.26-7.21(1H, m), 7.19(1H, d, J=2.3Hz), 6.98(1H, dd, J=9.0, 2.3Hz), 6.72(1H, s), 5.03(1H, hp, H=6.1Hz), 4.19(2H, q, J=7.3Hz), 3.89(3H, s), 1.36(3H, t, J=7.3Hz), 1.30(6H, d, J=6.1Hz). |
| 508 | glass | 378.2 | | * | $^1$H NMR(300MHz, $CDCl_3$): δ 7.67(1H, s), 7.48-7.45(2H, m), 7.33(1H, d, J=9.0Hz), 7.27-7.23(1H, m), 7.19(1H, d, J=2.3Hz), 6.98(1H, dd, J=9.0, 2.3Hz), 6.77(1H, s), 4.19(2H, q, J=7.0Hz), 4.14(2H, t, J=6.7Hz), 3.89(3H, s), 1.72(2H, m, J=7.0Hz), 1.37(3H, t, J=7.0Hz), 0.99(3H, t, J=6.5Hz). |
| 509 | 92-95 | 412.1 | | * | $^1$H NMR(300MHz, $CDCl_3$): δ 7.67(1H, s), 7.48-7.45(2H, m), 7.33(1H, d, J=8.8Hz), 7.27-7.24(1H, m), 7.19(1H, d, J=2.3Hz), 6.99(1H, dd, J=8.8, 2.3Hz), 6.83(1H, s), 4.35(2H, t, J=6.0Hz), 4.19(2H, q, J=7.3Hz), 3.89(3H, s), 3.66(2H, t, J=6.5Hz), 2.16(2H, p, J=6.1Hz), 1.37(3H, t, J=7.3Hz). |
| 510 | 210-211 | 368.3 | | ** | $^1$H NMR(300MHz, 9:1 $CDCl_3$-DMSO-$d_6$): δ 9.64(1H, s), 7.28-7.17(3H, m), 7.14(1H, d, J=9.0Hz), 7.04(1H, d, J=7.3Hz), 6.91(1H, d, J=2.0Hz), 6.75(1H, dd, J=9.0, 2.0Hz), 3.95(2H, q, J=7.3Hz), 3.66(3H, s), 2.81(3H, s), 1.15(3H, t, J=7.3Hz). |
| 511 | 146-148 | 377.3 | | * | $^1$H NMR(300MHz, $CDCl_3$): δ 7.34-7.27(2H, m), 7.19(1H, d, J=2.3Hz), 6.97(1H, dd, J=8.8, 2.3Hz), 6.88-6.79(3H, m), 4.17(2H, q, J=7.0Hz), 3.89(3H, s), 3.87(2H, v br), 1.34(3H, t, J=7.0Hz). |
| 512 | 67-69 | 407.2 | | * | $^1$H NMR(300MHz, $CDCl_3$): δ 10.06(1H, s), 7.86(1H, s), 7.56-7.47(2H, m), 7.36-7.30(3H, m), 7.19(1H, d, J=2.0Hz), 7.00-6.96(1H, m), 4.62(1H, br), 4.27(2H, q, J=7.0Hz), 4.18(2H, q, J=7.0Hz), 3.89(3H, s), 1.37(3H, t, J=7.0Hz), 1.33(3H, t, J=7.0Hz). |
| 513 | 210-211 | 479.2 | | * | $^1$H NMR(300MHz, 9:1 $CDCl_3$-DMSO-$d_6$): δ 8.44(2H, d, J=7.0Hz), 7.61(1H, s), 7.45(1H, s), 7.36-7.13(3H, m), 7.10(2H, d, J=8.8Hz), 6.93(1H, d, J=7.6Hz), 6.89(1H, d, J=7.9Hz), 6.85(1H, d, J=2.3Hz), 6.69(1H, dd, J=8.8, 2.3Hz), 3.94(2H, q, J=7.0Hz), 3.60(3H, s), 1.08(3H, t, J=7.0Hz). $^{19}$F NMR(300MHz, 9:1 $CDCl_3$-DMSO-$d_6$): δ– 63.02(3F, s). |
| 514 | 248-250 | 268.2 | | * | |
| 515 | 137-139 | 381.1 | | ** | |
| 516 | 155-156 | 395.3 | | ** | $^1$H NMR(300MHz, $CDCl_3$): δ 7.57(1H, d, J=8.5Hz), 7.45(2H, d, J=8.2Hz), 7.31(2H, d, J=8.2Hz), 7.25(1H, s), 6.95(1H, dd, J=9.1, 1.7Hz), 6.67(1H, s), 6.54(1H, t, J=74.8Hz), 6.48(1H, s), 4.15(2H, q), 3.23(2H, q), 1.45(3H, t, J=7.5Hz), 1.32(3H, t, J=7.2Hz). |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| 517 | 160-161 | 409.1 | | * | |
| 518 | 197-199 | 392.1 | | ** | |
| 519 | 174-175 | 406.1 | | *** | |
| 520 | 175-177 | 420.0 | | *** | $^1$H NMR(300MHz, $CDCl_3$): δ 7.73(1H, d, J=8.4Hz), 7.52(2H, d, J=8.2Hz), 7.39(2H, d, J=8.2Hz), 7.25(1H, s), 7.13(1H, dd, J=7.5, 2.4Hz), 6.96(1H, s), 6.56(1H, t, J=74.1Hz), 4.16(2H, q), 3.26(2H, q), 1.46(3H, t, J=7.5Hz), 1.32(3H, t, J=6.9Hz). |
| 521 | 184-186 | [NH−] 418.1 | | *** | |
| 522 | 187-188 | [NH−] 432.1 | | *** | |
| 523 | 190-192 | [NH−] 418.1 | | *** | |
| 524 | 186-188 | 434.2 | | *** | |
| 525 | | 458.2 | | ** | |
| 526 | | 490.3 | | *** | |
| 527 | | 493.3 | | ** | |
| 528 | | 475.3 | | ** | |
| 529 | | 459.2 | | ** | |
| 530 | | 461.3 | | *** | |
| 531 | | 479.5 | | ** | |
| 532 | | 458.2 | | ** | |
| 533 | | 490.3 | | ** | |
| 534 | | 493.3 | | *** | |
| 535 | | 475.3 | | *** | |
| 536 | | 459.2 | | ** | |
| 537 | | 461.3 | | *** | |
| 538 | | 459.2 | | ** | |
| 539 | | 477.3 | | *** | |
| 540 | 182-183 | 385.2 | | ** | |
| 541 | 149-151 | 399.2 | | * | |
| 542 | 186-188 | 413.2 | | ** | |
| 543 | 197-200 | 324.2 | | ** | |
| 544 | 263-265 | 392.2 | *** | *** | |
| 545 | 203-205 | 382.2 | ** | ** | |
| 546 | 208-210 | 396.2 | | *** | |
| 547 | 180-182 | 410.2 | | *** | |
| 548 | 171-174 | 402.1 | | ** | |
| 549 | 150-153 | 416.1 | | *** | |
| 550 | 183-185 | 430.0 | | ** | |
| 551 | 187-190 | 462.3 | | ** | |
| 552 | 185-188 | 428.1 | | *** | |
| 553 | | 412.2 | | * | |
| 554 | | 388.2 | | * | |
| 555 | | 408.2 | | * | |
| 556 | | 440.2 | | * | |
| 557 | | 454.3[M−H] | | ** | |
| 558 | 87-90 | 406.2 | | ** | |
| 559 | 92-94 | 386.2 | | * | |
| 560 | 207-210 | 434.2 | | * | |
| 561 | 182-185 | 398.2 | | * | |
| 562 | oil | 420.1 | | *** | |
| 563 | 210-212 | 436.1 | | ** | |
| 564 | 210-211 | 377.1 | | ** | $^1$H NMR(DMSO-$d_6$, 300MHz), δ 8.61(t, J=2.4Hz, 1H), 8.35(br, 2H), 8.04(d, J=8.4Hz, 2H), 7.73(d, J=8.4Hz, 2H), 7.52(d, J=8.7Hz, 2H), 7.26(d, J=2.4Hz, 1H), 6.94(dd, J=8.7Hz and 2.1Hz, 1H), 4.20(q, J=7.5Hz, 2H), 3.83(s, 3H), 3.55(q, J=6.0Hz, 2H), 3.09(br, 2H), 2.60-2.53(m, 3H), 1.15(t, J=7.2Hz, 3H). |
| 565 | 228-229 | 304.2 | | * | $^1$H NMR(DMSO-$d_6$, 300MHz), δ 10.23(s, 1H), 7.79(d, J=8.4Hz, 2H), 7.69(d, J=7.2Hz, 1H), 7.62(d, J=7.8Hz, 1H), 7.54(d, J=7.8Hz, 2H), 7.38-7.22(m, 2H), 4.20(q, J=7.2Hz, 2H), 2.07(s, 3H), 1.19(t, J=7.2Hz, 3H). |
| 566 | | 334.1 | | * | $^1$H NMR(CDCl3, 300MHz), δ 8.42(s, 1H), 7.80-7.76(m, 3H), 7.54(d, J=8.4Hz, 2H), 7.44(d, J=7.8Hz, 1H), |

TABLE 1A-continued

| Compound Number | Melting Point (° C.) | Mass Spec [M+H] | HCV-PV $IC_{50}$ µM | Replicon $IC_{50}$ µM | NMR Data |
|---|---|---|---|---|---|
| | | | | | 7.36-7.26(m, 2H), 4.20(q, J=7.2Hz, 2H), 4.07(s, 2H), 3.55(s, 3H), 1.36(t, J=7.2Hz, 3H). |
| 567 | 238.6-238.6 | 344.2 | | ** | $^1$H NMR(CDCl3, 300MHz), δ 7.78-7.73(m, 2H), 7.60(d, J=5.7Hz, 2H), 7.51(d, J=5.7Hz, 1H), 7.38-7.28(m, 2H), 4.20(q, J=6.8Hz, 2H), 3.26(br, 1H), 2.43(br, 2H), 2.27(br, 2H), 2.06-1.90(m, 2H), 1.36(t, J=6.9Hz, 3H). |
| 568 | 195-200 | 320.0 | | * | $^1$H NMR(CDCl3, 400MHz), δ 7.99(d, J=8.4Hz, 2H), 7.66(d, J=7.6Hz, 2H), 7.35(d, J=9.2Hz, 1H), 7.20(s, 1H), 7.01(d, J=9.0Hz, 1H), 6.15(br, 1H), 5.65(br, 1H), 4.17(q, J=6.8Hz, 2H), 3.90(s, 3H), 1.36(t, J=7.6Hz, 3H). |
| 569 | | 348.1 | | ** | $^1$H NMR(CDCl3, 400MHz), δ7.93(d, J=8.4Hz, 2H), 7.62(d, J=8.0Hz, 2H), 7.34(d, J=8.8Hz, 1H), 7.19(d, J=2.0Hz, 1H), 7.01(dd, J=8.8Hz and J=2.4Hz, 1H), 6.19(br, 1H), 4.16(q, J=7.2Hz, 2H), 3.90(s, 3H), 3.56-3.52(m, 2H), 1.38-1.23(m, 6H). |
| 570 | 220-222 | 362.1 | | ** | $^1$H NMR(CDCl3, 300MHz), δ 7.92(d, J=8.1Hz, 2H), 7.62(d, J=8.1Hz, 2H), 7.34(d, J=9.0Hz, 1H), 7.19(d, J=2.1Hz, 1H), 7.00(dd, J=9.0Hz and 2.4Hz, 1H), 6.02(d, J=7.8Hz, 1H), 4.35(m, 1H), 4.16(q, J=7.2Hz, 2H), 3.90(s, 3H), 1.36-1.26(m, 9H). |
| 571 | | 360.0 | | ** | $^1$H NMR(CDCl3, 400MHz), δ 7.91(d, J=8.0Hz, 2H), 7.61(d, J=8.0Hz, 2H), 7.34(d, J=8.8Hz, 1H), 7.19(d, J=2.0Hz, 1H), 7.01(dd, J=9.2Hz and 2.4Hz, 1H), 6.34(s, 1H), 4.15(q, J=7.2Hz, 2H), 3.90(s, 3H), 2.97-2.93(m, 1H), 1.34(t, J=7.2Hz, 3H), 0.66(q, J=7.2Hz, 2H), 0.07(t, J=2.1Hz, 2H). |
| 572 | 168-171 | 378.0 | | ** | $^1$H NMR(CDCl3, 300MHz), δ 7.96(d, J=8.4Hz, 2H), 7.63(d, J=8.4Hz, 2H), 7.34(d, J=8.7Hz, 1H), 7.19(d, J=2.1Hz, 1H), 7.02(dd, J=8.4Hz and 2.4Hz, 1H), 6.60(br, 1H), 4.16(q, J=6.6Hz, 2H), 3.90(s, 3H), 3.68(q, J=4.5Hz, 2H), 3.59(t, J=4.8Hz, 2H), 3.41(s, 3H), 1.35(t, J=6.9Hz, 3H). |
| 573 | | 417.2 | | * | $^1$H NMR(CDCl3, 400MHz), δ 7.59(s, 4H), 7.34(d, J=8.8Hz, 1H), 7.20(s, 1H), 7.01(d, J=8.4Hz, 1H), 4.15(q, J=6.4Hz, 2H), 3.90(s, 3H), 3.90-3.79(m, 2H), 3.60(br, 1H), 3.54(q, J=5.6Hz, 1H), 2.78(br, 1H), 2.69-2.67(m, 1H), 2.61(br, 2H), 2.41(d, J=18.4Hz, 3H), 2.04(br, 1H), 1.92(br, 1H), 1.34(t, J=6.8Hz, 3H). |
| 574 | 155-161 | 427.4 | | * | |
| 575 | 144-146 | 345.2 | | ** | |
| 576 | 141-142 | 425.4 | | * | |
| 577 | 171-173 | 345.4 | | ** | |
| 578 | 171-173 | 317.4 | | ** | |
| 579 | 178-179 | 368.5[M−H] | | ** | |
| 580 | 198-200 | 370.4 | | *** | |
| 581 | | 378.5 | | ** | |
| 582 | | 392.5 | | ** | |
| 583 | | 410.4 | | ** | |
| 584 | | 426.4 | | * | |
| 585 | | 406.5 | | ** | |
| 586 | | 440.4 | | ** | |
| 587 | | 406.5 | | ** | |
| 588 | | 402.5 | | * | |
| 589 | | 422.5 | | ** | |
| 590 | | 446.5 | | ** | |
| 591 | | 420.5 | | * | |
| 592 | | 416.4 | | * | |
| 593 | | 454.5 | | * | |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| 594 | | 412.4 | | * | |
| 595 | | 420.5 | | * | |
| 596 | | 404.4 | | ** | |
| 597 | | 418.5 | | * | |
| 598 | 169-170 | 382.5 | | * | $^1$H NMR(300MHz, $CDCl_3$): δ 7.64(1H, d, J=8.8Hz), 7.53(1H, t, J=7.9Hz), 7.46(1H, t, J=1.9Hz), 7.34-7.29(2H, m), 6.97(1H, dd, J=8.8, 2.3Hz), 6.95(1H, s), 6.86(1H, d, J=2.3Hz), 4.08(2H, t, J=7.6Hz), 3.91(3H, s), 3.13(3H, s), 1.75(2H, hx, J=6.6Hz), 0.80(3H, t, J=7.3Hz). |
| 599 | 163-164 | 398.4 | | * | $^1$H NMR(300MHz, $CDCl_3$): δ 7.64(1H, d, J=8.8Hz), 7.51(1H, dd, J=8.5, 7.3Hz), 7.44(1H, t, J=1.8Hz), 7.30(2H, dd, J=7.9, 2.0Hz), 6.97(1H, dd, J=8.8, 2.3Hz), 6.86(1H, d, J=2.3Hz), 6.85(1H, s), 4.08(2H, t, J=7.6Hz), 3.91(3H, s), 3.25(2H, q, J=7.3Hz), 1.75(2H, hx, J=7.6Hz), 1.42(3H, t, J=7.5Hz), 0.80(3H, t, J=7.4Hz). |
| 600 | 144-145 | 391.5 | | * | $^1$H NMR(300MHz, $CDCl_3$): δ 7.60(1H, d, J=8.8Hz), 7.57-7.54(1H, m), 7.35-7.31(2H, m), 7.13-7.09(1H, m), 6.94(1H, dd, J=8.8, 2.0Hz), 6.84(1H, d, J=2.0Hz), 4.07(2H, t, J=7.4Hz), 3.89(3H, s), 3.21(2H, t, J=7.0Hz), 1.68(2H, hx, J=7.3Hz), 1.53(2H, hx, J=7.3Hz), 0.91(3H, t, J=7.3Hz), 0.73(3H, t, J=7.4Hz). |
| 601 | 195-200 | 400.4[M−H] | | *** | |
| 602 | 179-184 | 398.4[M−H] | | *** | |
| 603 | | 422.4 | | * | |
| 604 | | 410.3 | | * | |
| 605 | 175-180 | 419.4 | | * | |
| 606 | 166-170 | 433.4 | | *** | |
| 607 | 189-194 | 449.5 | | *** | |
| 608 | 223-228 | 452.9 | | ** | |
| 609 | 230-234 | 439.4 | | ** | |
| 610 | 226-231 | 424.8 | | ** | |
| 611 | 126-128 | 396.4 | | ** | |
| 612 | 198-200 | 410.4 | | ** | |
| 613 | 116-117 | [NH−] 430.4 | | *** | |
| 614 | 176-177 | [NH−] 444.4 | | *** | |
| 615 | 220-225 | 440.3[M−H] | | * | |
| 616 | 143-149 | 414.4[M−H] | | *** | |
| 617 | 164-167 | 433.8[M−H] | | *** | |
| 618 | 205-211 | 368.4 | | *** | |
| 619 | 201-206 | 382.3 | | ** | |
| 620 | 215-223 | 367.4 | | ** | |
| 621 | 187-188 | 412.4 | | ** | $^1$H NMR(300MHz, $CDCl_3$): δ 7.64(1H, d, J=8.8Hz), 7.50(2H, d, J=8.5Hz), 7.36(2H, d, J=8.5Hz), 6.97(1H, dd, J=8.8, 2.3Hz), 6.86(1H, d, J=2.3Hz), 6.79(1H, s), 4.05(2H, t, J=7.6Hz), 3.91(3H, s), 3.23-3.17(2H, m), 1.93(2H, hx, J=7.3Hz), 1.73(2H, hx, J=7.6Hz), 1.09(3H, t, J=7.4Hz), 0.79(3H, t, J=7.4Hz). |
| 622 | 182-183 | 412.4 | | ** | $^1$H NMR(300MHz, $CDCl_3$): δ 7.63(1H, d, J=8.8Hz), 7.48(2H, d, J=8.5Hz), 7.38(2H, d, J=8.5Hz), 6.96(1H, dd, J=8.8, 2.3Hz), 6.86(1H, d, J=2.3Hz), 6.83(1H, s), 4.05(2H, t, J=7.6Hz), 3.90(3H, s), 3.43(1H, hp, J=6.6Hz), 1.73(2H, hx, J=7.6Hz), 1.46(6H, d, J=6.6Hz), 0.79(3H, t, J=7.5Hz). |
| 623 | 217-218 | 460.4 | | ** | $^1$H NMR(300MHz, $CDCl_3$): δ 7.65(1H, d, J=8.8Hz), 7.47(2H, d, J=8.5Hz), |

TABLE 1A-continued

| Compound Number | Melting Point (° C.) | Mass Spec [M+H] | HCV-PV $IC_{50}$ µM | Replicon $IC_{50}$ µM | NMR Data |
|---|---|---|---|---|---|
| | | | | | 7.40-7.28(5H, m), 7.25(2H, d, J=8.5Hz), 6.97(1H, dd, J=8.8, 2.3Hz), 6.86(1H, d, J=2.3Hz), 6.55(1H, s), 4.45(2H, s), 4.05(2H, t, J=7.6Hz), 3.91(3H, s), 1.74(2H, hx, J=7.3Hz), 0.80(3H, t, J=7.4Hz). |
| 624 | 187-188 | 378.5 | | ** | $^1$H NMR(300MHz, $CDCl_3$): δ 7.63(1H, d, J=8.5Hz), 7.57(2H, d, J=8.8Hz), 7.46(2H, d, J=8.8Hz), 6.95(1H, dd, J=8.8, 2.3Hz), 6.85(1H, d, J=2.3Hz), 6.79(1H, s), 4.26(2H, q, J=7.0Hz), 4.05(2H, t, J=7.5Hz), 3.90(3H, s), 1.72(2H, hx, J=7.6Hz), 1.34(3H, t, J=7.0Hz), 0.78(3H, t, J=7.4Hz). |
| 625 | 152-153 | 392.4 | | *** | $^1$H NMR(300MHz, $CDCl_3$): δ 7.63(1H, d, J=8.5Hz), 7.57(2H, d, J=8.5Hz), 7.46(2H, d, J=8.5Hz), 6.95(1H, dd, J=8.5, 2.3Hz), 6.85(1H, d, J=2.3Hz), 6.77(1H, s), 4.17(2H, t, J=6.7Hz), 4.05(2H, t, J=7.4Hz), 3.90(3H, s), 1.73(2H, hx, J=7.3Hz), 1.00(3H, t, J=7.4Hz), 0.78(3H, t, J=7.4Hz). |
| 626 | 193-194 | 377.5 | | ** | $^1$H NMR(300MHz, $CDCl_3$): δ 7.61(1H, d, J=8.5Hz), 7.52(2H, d, J=8.8Hz), 7.41(2H, d, J=8.8Hz), 7.30(1H, br), 6.96(1H, dd, J=8.8, 2.0Hz), 6.86(1H, d, J=2.0Hz), 4.05(2H, t, J=7.6Hz), 3.90(3H, s), 3.32(2H, q, J=7.3Hz), 1.71(2H, hx, J=7.3Hz), 1.19(3H, t, J=7.3Hz), 0.77(3H, t, J=7.3Hz). |
| 627 | 188-189 | 391.5 | | *** | $^1$H NMR(300MHz, $CDCl_3$): δ 7.61(1H, d, J=8.5Hz), 7.52(2H, d, J=8.8Hz), 7.41(2H, d, J=8.8Hz), 7.34(1H, br), 6.96(1H, dd, J=8.5, 2.0Hz), 6.86(1H, d, J=2.0Hz), 4.05(2H, t, J=7.4Hz), 3.90(3H, s), 3.24(2H, t, J=7.0Hz), 1.72(2H, hx, J=7.6Hz), 1.57(2H, hx, J=7.0Hz), 0.95(3H, t, J=7.3Hz), 0.77(3H, t, J=7.3Hz). |
| 628 | 221-226 | 381.4 | | ** | |
| 629 | 204-210 | 436.3 | | * | |
| 630 | 205-210 | 416.3 | | ** | |
| 631 | 177-182 | 428.5[M−H] | | ** | |
| 632 | 176-178 | 366.4[M−H] | | ** | |
| 633 | 159-161 | 380.5[M−H] | | ** | |
| 634 | 163-165 | 396.3 | | ** | |
| 635 | 200-201 | 392.5[M−H] | | *** | |
| 636 | 97-98 | 428.4[M−H] | | ** | |
| 637 | | 398.4 | | *** | |
| 638 | | 390.5 | | * | |
| 639 | 159-160 | 412.5 | | * | $^1$H NMR(300MHz, $CDCl_3$): δ 7.63(1H, d, J=8.8Hz), 7.50(1H, t, J=7.9Hz), 7.44(1H, t, J=1.8Hz), 7.33-7.28(2H, m), 7.18(1H, s), 6.96(1H, dd, J=8.8, 2.3Hz), 6.86(1H, d, J=2.3Hz), 4.08(2H, t, J=7.6Hz), 3.90(3H, s), 3.22-3.16(2H, m), 1.90(2H, hx, J=7.8Hz), 1.74(2H, hx, J=7.6Hz), 1.05(3H, t, J=7.4Hz), 0.79(3H, t, J=7.5Hz). |
| 640 | 197-198 | 396.5 | | ** | $^1$H NMR(300MHz, $CDCl_3$): δ 7.63(1H, d, J=8.8Hz), 7.58(2H, d, J=8.8Hz), 7.48(2H, d, J=8.8Hz), 6.95(1H, dd, J=8.8, 2.0Hz), 6.92(1H, s), 6.85(1H, d, J=2.0Hz), 4.62(2H, dt, J=74.3, 4.2Hz), 4.50(2H, dt, J=55.8, 4.2Hz), 4.05(2H, t, J=7.6Hz), 3.90(3H, s), 1.72(2H, hx, J=7.6Hz), 0.78(3H, t, J=7.4Hz). |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| | | | | | $^{19}F$ NMR(300MHz, $CDCl_3$): δ 5.11(1F, m). |
| 641 | 177-178 | 392.5 | | ** | $^1H$ NMR(300MHz, $CDCl_3$): δ 7.63(1H, d, J=8.8Hz), 7.57(2H, d, J=8.5Hz), 7.46(2H, d, J=8.5Hz), 6.95(1H, dd, J=8.5, 2.0Hz), 6.85(1H, d, J=2.0Hz), 6.72(1H, s), 5.05(1H, hp, J=7.1Hz), 4.05(2H, t, J=7.6Hz), 3.90(3H, s), 1.72(2H, hx, J=7.6Hz), 1.33(6H, d, J=7.1Hz), 0.78(3H, t, J=7.4Hz). |
| 642 | 152-153 | 426.5 | | ** | $^1H$ NMR(300MHz, $CDCl_3$): δ 7.66-7.57(3H, m), 7.53(2H, d, J=8.8Hz), 6.97(1H, dd, J=8.8, 2.0Hz), 6.86(1H, d, J=2.0Hz), 4.07(2H, t, J=7.4Hz), 3.91(3H, s), 3.46(3H, s), 3.40(1H, hp, J=7.0Hz), 1.74(2H, hx, J=7.3Hz), 1.40(6H, d, J=7.0Hz), 0.79(3H, t, J=7.4Hz). |
| 643 | 150-151 | 412.4 | | ** | $^1H$ NMR(300MHz, $CDCl_3$): δ 7.64(1H, d, J=8.8Hz), 7.58(2H, d, J=9.0Hz), 7.53(2H, d, J=9.0Hz), 6.97(1H, dd, J=8.8, 2.0Hz), 6.86(1H, d, J=2.0Hz), 4.07(2H, t, J=7.6Hz), 3.91(3H, s), 3.44(3H, s), 3.12(2H, q, J=7.6Hz), 1.75(2H, hx, J=7.6Hz), 1.41(3H, t, J=7.3Hz), 0.79(3H, t, J=7.5Hz). |
| 644 | | 348.2 | | * | $^1H$ NMR(DMSO-$d_6$, 300MHz), δ 10.12(s, 1H), 7.77(d, J=8.4Hz, 2H), 7.58(d, J=8.7Hz, 1H), 7.49(d, J=8.7Hz, 2H), 7.03(s, 1H), 6.92(d, J=8.4Hz, 1H), 4.13(q, J=6.9Hz, 2H), 3.77(s, 3H), 2.31(q, J=7.5Hz, 2H), 1.16(t, J=8.7Hz, 3H), 1.06(t, J=7.5Hz, 3H). |
| 645 | 242-244 | 410.2 | | * | $^1H$ NMR(DMSO-$d_6$, 300MHz), δ 10.33(s, 1H), 7.99(d, J=8.4Hz, 2H), 7.72(d, J=7.8Hz, 1H), 7.64-7.56(m, 4H), 7.51(d, J=1.8Hz, 1H), 7.36-7.07(m, 2H), 7.06(d, J=8.1Hz, 1H), 6.12(s, 2H), 4.22(q, J=7.2Hz, 2H), 1.21(t, J=7.2Hz, 3H). |
| 646 | | 356.2 | | ** | $^1H$ NMR(DMSO-$d_6$, 300MHz), δ 10.47(s, 1H), 8.01-7.96(m, 3H), 7.72(d, J=8.4Hz, 1H), 7.65-7.59(m, 3H), 7.38-7.29(m, 3H), 6.71(dd, J=3.9Hz and J=1.8Hz, 1H), 4.22(q, J=6.9Hz, 2H), 1.21(t, J=7.2Hz, 3H). |
| 647 | | 430.1 | | * | $^1H$ NMR(DMSO-$d_6$, 300MHz), δ 10.56(s, 1H), 8.12(d, J=8.4Hz, 2H), 7.84-7.76(m, 4H), 7.67(d, J=9.0Hz, 1H), 7.41(d, J=9.0Hz, 2H), 7.11(d, J=8.7Hz, 1H), 6.98(dd, J=8.7Hz and 2.1Hz, 1H), 4.22(q, J=7.2Hz, 2H), 3.82(s, 3H), 1.18(t, J=7.2Hz, 3H). |
| 648 | | 464.0 | | ** | $^1H$ NMR(DMSO-$d_6$, 300MHz), δ 10.69(s, 1H), 8.18-8.09(m, 3H), 7.82-7.72(m, 3H), 7.70-7.56(m, 2H), 7.11(d, J=2.1Hz, 1H), 6.96(dd, J=8.1Hz and 2.4Hz, 1H), 4.22(q, J=7.2Hz, 2H), 3.82(s, 3H), 1.19(t, J=7.2Hz, 3H). |
| 649 | 210-212 | 410.5 | | ** | $^1H$ NMR(300MHz, DMSO-$d_6$): δ 7.60(2H, d, J=8.8Hz), 7.50(1H, d, J=8.8Hz), 7.36(2H, d, J=8.8Hz), 7.25(1H, d, J=2.1Hz), 6.91(1H, dd, J=8.8, 2.1Hz), 4.15(2H, t, J=7.3Hz), 3.833(2H, t, J=6.4Hz), 3.831(3H, s), 3.57(2H, t, J=7.3Hz), 2.45-2.40(2H, m), 1.54(2H, hx, J=7.3Hz), 0.62(3H, t, J=7.3Hz). |
| 650 | 165-166 | 384.5 | | ** | $^1H$ NMR(300MHz, $CDCl_3$): δ 7.64(1H, d, J=8.8Hz), 7.54(4H, s), 6.96(1H, dd, J=8.8, 2.0Hz), 6.87(1H, d, J=2.0Hz), 4.84(1H, br t, J=6.1Hz), |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| | | | | | 4.41(2H, d, J=6.1Hz), 4.13(2H, q, J=7.3Hz), 3.90(3H, s), 2.97(3H, s), 1.33(3H, t, J=7.3Hz). |
| 651 | 146-147 | 384.5 | | ** | $^1$H NMR(300MHz, $CDCl_3$): δ 7.63(1H, d, J=8.8Hz), 7.56-7.45(4H, m), 6.96(1H, dd, J=8.8, 2.0Hz), 6.87(1H, d, J=2.0Hz), 4.89(1H, br t, J=5.9Hz), 4.42(2H, d, J=5.9Hz), 4.13(2H, t, J=7.0Hz), 3.91(3H, s), 2.94(3H, s), 1.34(3H, t, J=7.0Hz). |
| 652 | 191-194 | 418.5 | | *** | |
| 653 | foam | 469.5 | | * | |
| 654 | 197-201 | 485.5 | | * | |
| 655 | 184-187 | 424.2 | | * | |
| 656 | 159-161 | 346.2 | | * | |
| 657 | 196-198 | 388.2 | | * | |
| 658 | 203-205 | 400.5 | | * | |
| 659 | 175-177 | 458.4 | | ** | |
| 660 | 215-217 | 394.5 | | ** | |
| 661 | 156-158 | 458.5 | | *** | |
| 662 | | 398.4 | | *** | |
| 663 | | 308.3 | | * | |
| 664 | | 424.4 | | * | |
| 665 | | 444.5 | | * | |
| 666 | 207-209 | 424.4 | | *** | |
| 667 | 242-244 | 424.4 | | *** | |
| 668 | 171-174 | 483.0 | | ** | |
| 669 | 213-215 | 461.5 | | *** | $^1$H NMR(300MHz, 9:1 $CDCl_3$-DMSO-$d_6$): δ 9.73(1H, s), 8.76(1H, s), 8.54(1H, d, J=5.2Hz), 8.11(1H, d, J=7.9Hz), 7.58(1H, dd, J=7.9, 5.2Hz), 7.45(1H, d, J=9.3Hz), 7.28(4H, s), 6.88-6.82(2H, m), 5.15(2H, s), 3.97(2H, q, J=7.2Hz), 2.99(2H, q, J=7.3Hz), 1.21(3H, t, J=7.3Hz), 1.15(3H, t, J=7.2Hz). |
| 670 | 231-233 | 473.4 | | *** | $^1$H NMR(300MHz, 9:1 $CDCl_3$-DMSO-$d_6$): δ 9.59(1H, s), 8.87(1H, s), 8.60(1H, d, J=5.2Hz), 8.35(1H, d, J=7.6Hz), 7.80(1H, dd, J=7.6, 5.2Hz), 7.45(1H, d, J=8.5Hz), 7.32-7.23(4H, m), 6.88(1H, d, J=2.0Hz), 6.83(1H, dd, J=8.5, 2.0Hz), 5.21(2H, s), 3.97(2H, q, J=7.3Hz), 2.44-2.35(1H, m), 1.14(3H, t, J=7.3Hz), 1.07-0.99(2H, m), 0.84-0.78(2H, m). |
| 671 | 221-222 | 461.4 | | *** | $^1$H NMR(300MHz, 9:1 $CDCl_3$-DMSO-$d_6$): δ 9.72(1H, s), 8.56(1H, d, J=5.0Hz), 8.13(1H, br t, J=7Hz), 7.87(1H, d, J=7.6Hz), 7.53-7.50(1H, m), 7.41(1H, d, J=8.5Hz), 7.25(4H, s), 7.01(1H, d, J=2.0Hz), 6.86(1H, dd, J=8.5, 2.0Hz), 5.50(2H, s), 3.98(2H, q, J=7.3Hz), 2.97(2H, q, J=7.3Hz), 1.19(3H, t, J=7.3Hz), 1.11(3H, t, J=7.3Hz). |
| 672 | 165-166 | 415.5 | | *** | $^1$H NMR(300MHz, $CDCl_3$): δ 7.65(1H, d, J=8.8Hz), 7.55(4H, s), 6.97(1H, dd, J=8.8, 2.3Hz), 6.88(1H, d, J=2.3Hz), 4.41(2H, s), 4.14(2H, q, J=7.3Hz), 3.91(3H, s), 2.91(3H, s), 2.86(3H, s), 1.35(3H, t, J=7.3Hz). |
| 673 | 131-132 | 398.4 | | * | $^1$H NMR(300MHz, $CDCl_3$): δ 7.65(1H, d, J=8.8Hz), 7.57-7.48(4H, m), 6.97(1H, dd, J=8.8, 2.0Hz), 6.88(1H, d, J=2.0Hz), 4.42(2H, s), 4.15(2H, q, J=7.3Hz), 3.91(3H, s), 2.89(3H, s), 2.87(3H, s), 1.37(3H, t, J=7.3Hz). |
| 674 | 159-160 | 414.4 | | * | $^1$H NMR(300MHz, 9:1 $CDCl_3$-DMSO-$d_6$): δ 9.67(1H, s), 7.36(1H, |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| | | | | | d, J=8.8Hz), 7.31(2H, d, J=8.8Hz), 7.23(2H, d, J=8.8Hz), 6.76(1H, d, J=2.0Hz), 6.72(1H, dd, J=8.8, 2.0Hz), 4.05(2H, t, J=5.6Hz), 3.68(3H, s), 3.44(2H, t, J=5.6Hz), 3.00(3H, s), 2.95(2H, q, J=7.3Hz), 1.17(3H, t, J=7.3Hz). |
| 675 | | 460.4 | | ** | $^1$H NMR(300MHz, 9:1 $CDCl_3$-DMSO-$d_6$): δ 9.83(1H, s), 7.61-7.27(5H, m), 6.82-6.78(2H, m), 4.10(2H, t, J=5.6Hz), 3.74(3H, s), 3.56-3.47(4H, m), 3.16(2H, t, J=7.3Hz), 3.06(3H, s), 2.21-2.01(2H, m). |
| 676 | 174-175 | 394.4 | | ** | $^1$H NMR(300MHz, 9:1 $CDCl_3$-DMSO-$d_6$): δ 8.77(1H, s), 7.51(2H, d, J=8.5Hz), 7.41(1H, d, J=8.5Hz), 7.31(2H, d, J=8.5Hz), 6.80(1H, d, J=2.0Hz), 6.77(1H, dd, J=8.5, 2.0Hz), 4.12-4.04(4H, m), 3.72(3H, s), 3.46(2H, t, J=5.6Hz), 3.04(3H, s), 1.18(3H, t, J=7.2Hz). |
| 677 | 133-134 | 408.4 | | ** | $^1$H NMR(300MHz, $CDCl_3$): δ 7.64-7.51(5H, m), 6.98-6.94(2H, m), 6.78(1H, s), 4.25(2H, t, J=5.7Hz), 4.17(2H, t, J=6.7Hz), 3.90(3H, s), 3.63(2H, t, J=5.7Hz), 3.22(3H, s), 1.73(2H, hx, J=7.3Hz), 1.00(3H, t, J=7.4Hz). |
| 678 | 184-188 | 318.3 | | * | |
| 679 | 212-220 | 389.5 | | ** | |
| 680 | 163-168 | 403.3 | | *** | |
| 681 | 192-197 | 403.3 | | ** | |
| 682 | 194-195 | 460.4 | | ** | |
| 683 | 157-159 | 494.2 | | ** | |
| 684 | 175-176 | 412.5 | | * | |
| 685 | 140-141 | 448.4 | | ** | |
| 686 | 173-174 | 424.5 | | ** | |
| 687 | 124-125 | 420.4 | | *** | |
| 688 | 178-179 | 410.4 | | ** | |
| 689 | 204-205 | 409.5 | | ** | |
| 690 | 192-193 | 423.9 | | ** | |
| 691 | 203-205 | 383.8 | | ** | |
| 692 | 175-176 | 397.8 | | ** | |
| 693 | 163-164 | 411.8 | | *** | |
| 694 | 135-136 | 383.8 | | ** | |
| 695 | 159-160 | 397.8 | | ** | |
| 696 | 194-196 | 397.8 | | ** | |
| 697 | foam | 467.0 | | *** | |
| 698 | foam | 499.5 | | ** | |
| 699 | 255-258 | 427.8 | | *** | |
| 701 | 188-194 | 395.8 | | ** | |
| 702 | 147-150 | 409.8 | | ** | |
| 703 | 160-165 | 424.5 | | ** | |
| 704 | 169-170 | 433.4 | | * | |
| 705 | 199-201 | 397.4 | | * | |
| 706 | 151-153 | 396.4 | | *** | |
| 707 | 159-161 | 412.5 | | ** | |
| 708 | 175-177 | 426.5 | | ** | |
| 709 | 166-168 | 424.4 | | *** | |
| 710 | oil | 458.5 | | * | |
| 711 | oil | 424.5 | | * | |
| 712 | 259-261 | 316.5 | | * | |
| 713 | 199-202 | 474.5 | | ** | |
| 714 | 52-53 | 281.4 | | ** | |
| 715 | 174-175 | 424.1 | | *** | |
| 716 | 204-205 | 422.4 | | *** | $^1$H NMR($CDCl_3$, 300MHz)δ(ppm) 0.04-0.12(m, 2H), 0.41-0.50(m, 2H), 0.98-1.13(m, 1H), 2.54-2.67(m, 2H), 3.45(t, 2H), 3.87(t, 3H), 3.91(s, 2H), 3.99(d, 2H), 6.93-6.99(m, 2H), 7.36-7.43(m, 2H), 7.49-7.56(m, 2H), 7.61-7.66(m, 1H). |
| 717 | 205-207 | 424.5 | | ** | |
| 718 | 195-196 | 450.2 | | ** | |

TABLE 1A-continued

| Compound Number | Melting Point (° C.) | Mass Spec [M+H] | HCV-PV $IC_{50}$ µM | Replicon $IC_{50}$ µM | NMR Data |
|---|---|---|---|---|---|
| 719 | 192-193 | 410.2 | | * | |
| 720 | 172-178 | 410.5 | | ** | |
| 721 | 158-160 | 404.6 | | ** | |
| 722 | 160-162 | 432.6 | | ** | |
| 723 | 175-180 | 418.6 | | ** | |
| 724 | 168-170 | 416.4 | | ** | |
| 725 | 215-216 | 397.5 | | ** | |
| 726 | 221-222 | 411.4 | | ** | |
| 727 | 217-218 | 487.5 | | ** | |
| 728 | 197-199 | 479.5 | | *** | |
| 729 | 213-217 | 493.6 | | * | |
| 730 | 210-214 | 495.2 | | *** | |
| 731 | 173-174 | 388.5 | | *** | |
| 732 | 219-221 | 378.2 | | ** | |
| 733 | 146-148 | 354.5 | | * | |
| 734 | 167-169 | 412.5 | | ** | |
| 735 | 123-125 | 426.5 | | *** | |
| 736 | 125-126 | [NH−] 438.5 | | *** | |
| 737 | 153-155 | [NH−] 438.5 | | ** | |
| 738 | 149-151 | [NH−] 442.4 | | *** | |
| 739 | oil | 456.5 | | * | |
| 740 | 203-205 | 424.9 | | ** | |
| 741 | 194-196 | 438.9 | | *** | |
| 742 | 171-173 | [NH−] 451.5 | | ** | |
| 743 | 129-129 | 465.5 | | *** | |
| 744 | 92-93 | 412.5 | | *** | |
| 745 | oil | 426.5 | | *** | |
| 746 | oil | 440.5 | | * | |
| 747 | 136-137 | 410.5 | | *** | |
| 748 | 186-188 | 391.6 | | *** | |
| 749 | 176-178 | 405.6 | | *** | |
| 750 | 173-174 | 419.6 | | *** | |
| 751 | 159-162 | 405.6 | | ** | |
| 752 | 198-202 | 396.5 | | ** | |
| 753 | 157-161 | 409.9 | | *** | |
| 754 | 146-150 | 424.5 | | ** | |
| 755 | | 357.2 | | *** | $^1$H NMR(DMSO-$d_6$, 300MHz), δ 11.02(s, 1H), 8.83(d, J=1.8Hz, 1H), 8.01(d, J=8.4Hz, 2H), 7.71(d, J=7.2Hz, 1H), 7.66-7.63(m, 3H), 7.39-7.26(m, 3H), 4.22(q, J=7.5Hz, 2H), 1.20(t, J=6.9Hz, 3H). |
| 756 | | 388.0 | | *** | $^1$H NMR(CDCl3, 300MHz), δ 8.04(s, 1H), 7.83(d, J=8.4Hz, 2H), 7.77(d, J=7.5Hz, 1H), 7.60(d, J=8.7Hz, 2H), 7.46(d, J=7.2Hz, 1H), 7.42-7.31(m, 2H), 4.23(t, J=7.8Hz, 2H), 3.01(s, 3H), 1.38(t, J=7.2, 3H). |
| 757 | 218-225 | 358.2 | | *** | $^1$H NMR(CDCl3, 300MHz), δ 7.79-7.76(m, 3H), 7.58(d, J=8.4Hz, 2H), 7.46(d, J=7.5Hz, 2H), 7.39-7.32(m, 2H), 4.23(q, J=7.5Hz, 2H), 2.71(s, 3H), 2.54(s, 3H), 1.38(t, J=7.2Hz, 3H). |
| 758 | 149-153 | 320.2 | | *** | |
| 759 | | 376.2 | | *** | $^1$H NMR(DMSO-$d_6$, 300MHz)δ 10.14(s, 1H), 7.79(d, J=8.4Hz, 2H), 7.58-7.45(m, 3H), 7.22(d, J=1.5Hz, 1H), 6.88(dd, J=8.7Hz and 1.8Hz, 1H), 4.75-4.67(m, 1H), 4.15(q, J=6.9Hz, 2H), 2.34(q, J=7.6Hz, 2H), 1.27(d, J=6.0Hz, 6H), 1.16-1.07(m, 6H). |
| 760 | | 402.2 | | *** | $^1$H NMR(DMSO-$d_6$, 300MHz)δ 9.99(s, 1H), 7.80(d, J=8.7Hz, 2H), 7.51-7.45(m, 3H), 7.22(s, 1H), 6.87(dd, J=9.0Hz and 1.8Hz, 1H), 4.72-4.69(m, 1H), 4.15(q, J=6.6Hz, 2H), 2.23-1.80(m, 7H), 1.26(d, J=6.0Hz, 6H), 1.13(t, J=7.2Hz, 3H). |
| 761 | 169-173 | 392.1 | | *** | $^1$H NMR(DMSO-$d_6$, 300MHz)δ 10.06(s, 1H), 7.90(d, J=8.7Hz, 2H), |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| | | | | | 7.54-7.46(m, 3H), 7.22(d, J=1.5Hz, 1H), 6.88(dd, J=8.4Hz and 2.1Hz, 1H), 4.75-4.66(m, 1H), 4.15(q, J=7.2Hz, 2H), 4.03(s, 2H), 3.37(s, 3H), 1.26(d, J=6.0Hz, 6H), 1.16(t, J=7.2Hz, 3H). |
| 762 | 190-193 | 452.3 | | *** | $^1$H NMR(DMSO-$d_6$, 300MHz)δ 10.20(s, 1H), 7.78(d, J=8.7Hz, 2H), 7.52-7.45(m, 3H), 7.30-7.21(m, 5H), 7.18-7.14(m, 1H), 6.88(dd, J=8.4Hz and 2.1Hz, 1H), 4.73-4.69(m, 1H), 4.15(q, J=6.6Hz, 2H), 2.91(t, J-7.5Hz, 2H), 2.65(t, J=7.6Hz, 2H), 1.27(d, J=6.0Hz, 6H), 1.14(t, J=7.2Hz, 3H). |
| 763 | 209.2-209.7 | 424.3 | | *** | $^1$H NMR(DMSO-$d_6$, 300MHz)δ 10.54(s, 1H), 8.93-7.96(m, 4H), 7.62-7.49(m, 6H), 7.26(d, J=1.8Hz, 1H), 6.91(dd, J=8.7Hz and 2.1Hz, 1H), 4.76-4.72(m, 1H), 4.21(q, J=7.2Hz, 2H), 1.30(d, J=6.0Hz, 6H), 1.18(t, J=6.9Hz, 3H). |
| 764 | 213.5-231.7 | 442.2 | | *** | $^1$H NMR(DMSO-$d_6$, 300MHz)δ 10.52(s, 1H), 8.06-7.96(m, 4H), 7.58(d, J=8.4Hz, 2H), 7.49(d, J=8.4Hz, 1H), 7.37(t, J=8.7Hz, 2H), 7.24(s, 1H), 6.89(dd, J=9.0Hz and 1.5Hz, 1H), 4.72-4.66(m, 1H), 4.18(q, J=7.2Hz, 2H), 1.27(d, J=6.0Hz, 6H), 1.16(t, J=6.9Hz, 3H). |
| 765 | 288.5-288.9 | 438.2 | | ** | $^1$H NMR(DMSO-$d_6$, 300MHz)δ 10.91(s, 1H), 8.72(s, 1H), 8.20(d, J=9.3Hz, 1H), 8.03-7.98(m, 3H), 7.65-7.62(d, J=9.0Hz, 3H), 7.08(d, J=2.4Hz, 1H), 6.96(dd, J=8.7Hz and 2.4Hz, 1H), 4.20(q, J=6.8Hz, 2H), 3.81(s, 3H), 1.19(t, J=7.2Hz, 3H). |
| 766 | 192.8-193.1 | 440.1 | | ** | $^1$H NMR($CD_3OD$, 300MHz)δ 7.98(d, J=8.7Hz, 2H), 7.60(d, J=8.1Hz, 2H), 7.50(d, J=9.3Hz, 1H), 7.11(s, 1H), 6.99(d, J=6.6Hz, 1H), 6.60(s, 1H), 4.24(q, J=7.4Hz, 2H), 3.87(s, 3H), 2.54(s, 3H), 1.30(t, J=6.9Hz, 3H). |
| 767 | 204-205 | 350.9 | | *** | |
| 768 | 170-175 | 429.4[M−H] | | * | |
| 769 | 118-123 | 473.5 | | * | |
| 770 | | 361.5 | | * | |
| 771 | | 361.5 | | *** | |
| 772 | 211-212 | 442.4 | | *** | $^1$H NMR(300MHz, $CDCl_3$): δ 7.62(1H, d, J=8.5Hz), 7.42(2H, d, J=8.5Hz), 7.13(2H, d, J=8.5Hz), 6.95(1H, dd, J=8.5, 1.8Hz), 6.87(1H, d, J=1.8Hz), 5.67(1H, d, J=8.8Hz), 4.28-4.08(8H, m), 1.47(3H, t, J=6.9Hz), 1.37(6H, td, J=7.0, 0.6Hz), 1.34(3H, t, J=7.3Hz). |
| 773 | 191-193 | 434.9 | | ** | $^1$H NMR(300MHz, $CDCl_3$): δ 7.60(1H, d, J=8.8Hz), 7.52(2H, d, J=8.8Hz), 7.43(2H, d, J=8.8Hz), 6.94(1H, dd, J=8.8, 2.2Hz), 6.86(1H, d, J=2.2Hz), 4.24(2H, q, J=7.0Hz), 4.22-4.06(6H, m), 1.47(3H, t, J=7.0Hz), 1.34-1.25(6H, m). |
| 774 | 205-206 | 410.9 | | ** | $^1$H NMR(300MHz, $CDCl_3$): δ 7.63(1H, d, J=8.8Hz), 7.53(2H, d, J=9.0Hz), 7.46(2H, d, J=9.0Hz), 6.98(1H, br s), 6.96(1H, dd, J=8.8, 2.0Hz), 6.88(1H, d, J=2.0Hz), 4.17-4.09(4H, m), 3.71-3.61(4H, m), 1.48(3H, t, J=7.0Hz), 1.34(3H, t, J=7.1Hz). |
| 775 | | 482.1 | | ** | $^1$H NMR(300MHz, $CDCl_3$): δ 7.64(1H, d, J=8.5Hz), 7.52(2H, d, J=9.0Hz), 7.40(2H, d, J=9.0Hz), 6.97(1H, dd, J=8.5, 2.2Hz), 6.90(1H, d, J=2.2Hz), 4.48(2H, t, J=4.7Hz), |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| | | | | | 4.26(2H, t, J=4.7Hz), 4.05(2H, t, J=7.6Hz), 3.87(2H, t, J=6.6Hz), 3.45(2H, t, J=6.9Hz), 2.61(2H, p, J=7.3Hz), 2.13(3H, s), 1.72(2H, hx, J=7.3Hz), 0.79(3H, t, J=7.4Hz). |
| 776 | 257-258 | 389.5 | | *** | $^1$H NMR(300MHz, DMSO-$d_6$): δ 11.32(1H, s), 7.82(2H, d, J=8.8Hz), 7.61(2H, d, J=8.8Hz), 7.50(1H, d, J=8.8Hz), 7.24(1H, d, J=1.8Hz), 6.91(1H, dd, J=8.8, 1.8Hz), 4.52(2H, s), 4.18(2H, q, J=7.0Hz), 4.11(2H, q, J=7.0Hz), 1.36(3H, t, J=7.0Hz), 1.16(3H, t, J=7.0Hz). |
| 777 | 124-127 | 511.6 | | *** | $^1$H NMR(300MHz, $CDCl_3$): δ 7.58(1H, d, J=8.8Hz), 7.45(2H, d, J=8.8Hz), 7.39(2H, d, J=8.8Hz), 7.33(1H, br s), 7.31-7.15(5H, m), 6.94(1H, dd, J=8.8, 2.2Hz), 6.86(1H, d, J=2.2Hz), 4.84(1H, t, J=6.0Hz), 4.11(2H, q, J=7.0Hz), 4.08(2H, q, J=7.3Hz), 3.74(3H, s), 3.18(1H, dd, J=14.0, 5.6Hz), 3.07(1H, dd, J=14.0, 6.4Hz), 1.47(3H, t, J=7.0Hz), 1.30(3H, t, J=7.3Hz). |
| 778 | 225-227 | 375.5 | | *** | $^1$H NMR(300MHz, $CDCl_3$): δ 7.73(2H, d, J=8.8Hz), 7.62(1H, d, J=8.8Hz), 7.52(2H, d, J=8.8Hz), 6.95(1H, dd, J=8.8, 2.0Hz), 6.88(1H, d, J=2.0Hz), 4.13(2H, q, J=7.0Hz), 4.12(2H, q, J=7.0Hz), 4.04-3.99(2H, m), 3.67-3.62(2H, m), 1.47(3H, t, J=7.0Hz), 1.34(3H, t, J=7.0Hz). |
| 779 | 265-267 | 389.5 | | *** | $^1$H NMR(300MHz, DMSO-$d_6$): δ 8.42(1H, s), 7.72(2H, d, J=8.8Hz), 7.61(2H, d, J=8.8Hz), 7.53(1H, d, J=8.5Hz), 7.26(1H, d, J=2.0Hz), 6.93(1H, dd, J=8.5, 2.0Hz), 4.25-4.08(6H, m), 1.36(3H, t, J=7.0Hz), 1.19(3H, t, J=7.0Hz). |
| 780 | 219-220 | 463.6 | | ** | $^1$H NMR(300MHz, $CDCl_3$): δ 7.65(1H, d, J=8.8Hz), 7.58(2H, d, J=8.8Hz), 7.48(2H, d, J=8.8Hz), 6.97(1H, dd, J=8.8, 2.0Hz), 6.88(1H, d, J=2.0Hz), 4.18-4.08(5H, m), 3.09(3H, s), 3.00(3H, s), 2.94(3H, s), 1.53(3H, d), 1.47(3H, t, J=7.0Hz), 1.34(3H, t, J=7.0Hz). |
| 781 | 207-208 | 449.8 | | *** | $^1$H NMR(300MHz, $CDCl_3$): δ 7.64(2H, d, J=8.8Hz), 7.60(4H, s), 6.97(1H, d, J=8.8, 2.0Hz), 6.88(1H, d, J=2.0Hz), 4.12(2H, q, J=7.0Hz), 4.11(2H, q, J=7.0Hz), 3.36(3H, s), 3.23(2H, s), 3.14(3H, s), 2.88(3H, s), 1.48(3H, t, J=7.0Hz), 1.33(3H, t, J=7.0Hz). |
| 782 | 188-190 | 396.5 | | ** | |
| 783 | 201-202 | 410.5 | | * | |
| 784 | 245-246 | 410.5 | | ** | |
| 785 | 151-153 | 423.5 | | ** | $^1$H NMR($CDCl_3$, 300MHz)δ(ppm) 1.38(t, 3H), 3.30-3.37(m, 4H), 3.51-3.58(m, 4H), 4.06-4.18(q, 2H), 7.45(d, 1H), 7.54(s, 1H), 7.66(d, 1H). |
| 786 | 202-203 | 437.5 | | * | |
| 787 | 261-263 | 412.2 | | * | |
| 788 | 112-114 | 453.9 | | * | |
| 789 | 154-156 | 398.2 | | *** | |
| 790 | | 398.2 | | *** | |
| 791 | 149-152 | 396.5 | | *** | |
| 792 | 182-185 | 350.5 | | *** | |
| 793 | 154-155 | 364.5 | | *** | |
| 794 | 149-151 | 378.5 | | *** | |
| 795 | 183-185 | 378.5 | | *** | |

TABLE 1A-continued

| Compound Number | Melting Point (° C.) | Mass Spec [M+H] | HCV-PV $IC_{50}$ µM | Replicon $IC_{50}$ µM | NMR Data |
|---|---|---|---|---|---|
| 796 | 124-125 | 392.6 | | ** | |
| 797 | 209-212 | 277.9 | | ** | |
| 798 | 193.4-193.7 | 429.2 | | * | ($CD_3CN$, 400MHz)δ9.19(s, 1H), 7.95(d, J=7.6Hz, 2H), 7.61(d, J=8.0Hz, 2H), 7.56(d, J=8.8Hz, 1H), 7.10(s, 1H), 6.92(dd, J=8.8Hz and 0.8Hz, 1H), 6.56(s, 1H), 4.74-4.64(m, 1H), 4.18(q, J=7.2Hz, 2H), 2.51(s, 3H), 1.27(d, J=6.0Hz, 6H), 1.27(t, J=7.2Hz, 3H). |
| 799 | | 362.2 | | *** | $^1$H NMR(DMSO-$d_6$, 300MHz), δ 10.14(s, 1H), 7.79(d, J=8.4Hz, 2H), 7.52-7.50(m, 3H), 7.22(s, 1H), 6.91(d, J=8.7Hz, 1H), 4.17(q, J=7.5Hz, 2H), 3.82(s, 3H), 2.24(t, J=7.2Hz, 2H), 1.60(q, J=7.2Hz, 2H), 1.23(t, J=7.2Hz, 3H), 0.90(t, J=7.2Hz, 3H). |
| 801 | 199-219 | 374.2 | | *** | $^1$H NMR(CDCl3, 300Hz), 7.72(d, J=8.4Hz, 2H), 7.63(d, J=8.7Hz, 1H), 7.50(d, J=8.7Hz, 2H), 7.22(s, 1H), 6.91(dd, J=6.6Hz and 2.1Hz, 1H), 6.87(d, J=2.1Hz, 1H), 4.14(q, J=7.2Hz, 2H), 3.90(s, 3H), 3.24-3.18(m, 1H), 2.46-2.25(m, 4H), 2.06-1.97(m, 2H), 1.33(t, J=8.1Hz, 3H). |
| 802 | 196-198 | 410.2 | | ** | $^1$H NMR(DMSO-$d_6$, 300Hz), δ 10.45(s, 1H), 7.80(d, J=8.4Hz, 2H), 7.54-7.48(m, 3H), 7.33-7.21(m, 6H), 6.92(dd, J=6.6Hz and 2.1Hz, 1H),, 4.17(q, J=6.6Hz, 2H), 3.82(s, 3H), 3.67(s, 2H), 1.15(t, J=7.2Hz, 3H). |
| 803 | 216-217 | 386.1 | | * | $^1$H NMR(DMSO-$d_6$, 300Hz), δ 10.90(s, 1H), 8.71(s, 1H), 8.19(d, J=9.3Hz, 1H), 8.02-7.98(m, 3H), 7.63(d, J=8.7Hz, 2H), 7.51(d, J=8.7Hz, 1H), 7.24(d, J=2.1Hz, 1H), 6.92(dd, J=6.6Hz and 2.1Hz, 1H), 4.20(q, J=6.6Hz, 2H), 3.83(s, 3H), 1.16(t, J=6.6Hz, 3H). |
| 804 | 214-216 | 401.2 | | * | $^1$H NMR(DMSO-$d_6$, 300Hz), δ 10.92(s, 1H), 8.00(d, J=8.7Hz, 2H), 7.59(d, J=8.7Hz, 2H), 7.51(d, J=8.7Hz, 1H), 7.23(d, J=2.1Hz, 1H), 6.92(dd, J=6.6Hz and 2.1Hz, 1H), 6.69(s, 1H), 4.19(q, J=6.6Hz, 2H), 3.83(s, 3H), 2.49(s, 3H), 1.17(t, J=7.2Hz, 3H). |
| 805 | 217-222 | 452.5 | | * | |
| 806 | 157-159 | 422.5 | | ** | |
| 807 | 171-172 | 396.5 | | *** | |
| 808 | 195-197 | 410.5 | | ** | |
| 809 | 167-168 | 410.5 | | ** | |
| 810 | 209-211 | 422.5 | | ** | |
| 811 | 166-168 | 354.5 | | * | |
| 812 | 206-208 | 460.4 | | ** | |
| 813 | 176-177 | 458.4 | | *** | |
| 814 | 164-165 | [NH−]458.5 | | * | |
| 815 | 153-154 | 473.5 | | * | $^1$H NMR(300MHz, $CDCl_3$): δ 7.65(1H, d, J=8.8Hz), 7.61(2H, d, J=8.8Hz), 7.56(2H, d, J=8.8Hz), 6.98(1H, dd, J=8.8, 2.3Hz), 6.89(1H, d, J=2.3Hz), 4.24(2H, t, J=5.4Hz), 4.17(2H, q, J=7.3Hz), 4.02(2H, q, J=5.4Hz), 3.91(3H, s), 3.00(3H, s), 2.01(3H, s), 1.38(3H, t, J=7.3Hz). |
| 816 | 186-187 | 445.5 | | ** | $^1$H NMR(300MHz, $CDCl_3$): δ 7.66(1H, d, J=8.5Hz), 7.60(2H, d, J=8.8Hz), 7.55(2H, d, J=8.8Hz), 6.98(1H, dd, J=8.5, 2.0Hz), 6.89(1H, d, J=2.0Hz), 4.16(2H, q, J=7.3Hz), 3.93(2H, t, J=6.0Hz), 3.91(3H, s), 3.53(2H, t, J=6.0Hz), 3.38(3H, s), 3.07(3H, s), 1.38(3H, t, J=7.3Hz). |
| 817 | 188-190 | 439.2 | | * | |
| 818 | 158-159 | 437.0 | | *** | |

TABLE 1A-continued

| Compound Number | Melting Point (° C.) | Mass Spec [M+H] | HCV-PV $IC_{50}$ µM | Replicon $IC_{50}$ µM | NMR Data |
|---|---|---|---|---|---|
| 819 | | 438.9 | | * | |
| 820 | | 408.4 | | ** | |
| 821 | | 408.4 | | * | |
| 822 | 144-145 | 439.9 | | ** | |
| 823 | 93-94 | 456.2 | | * | |
| 824 | 169-170 | 428.2 | | * | |
| 825 | 109-110 | 444.2 | | * | |
| 826 | 160-161 | 432.1 | | ** | |
| 827 | 189-191 | 446.1 | | *** | |
| 828 | 198-200 | 431.2 | | ** | $^1$H NMR(300MHz, $CDCl_3$): δ 7.65(1H, d, J=8.8Hz), 7.62(2H, d, J=8.8Hz), 7.57(2H, d, J=8.8Hz), 6.98(1H, dd, J=8.8, 2.0Hz), 6.89(1H, d, J=2.0Hz), 4.17(2H, q, J=7.2Hz), 3.93(2H, t, J=5.3Hz), 3.91(3H, s), 3.77(2H, t, J=5.3Hz), 3.06(3H, s), 1.38(3H, t, J=7.2Hz). |
| 829 | 271-275 | 422.1 | | ** | |
| 830 | 178-179 | 420.1 | | ** | |
| 831 | 140-141 | 371.0 | | * | |
| 832 | 206-207 | 406.3 | | ** | $^1$H NMR($CDCl_3$, 300MHz)δ(ppm) 1.34(t, 3H), 1.47(t, 3H), 1.55(s, 9H), 4.04-4.25(m, 4H), 6.62(s, 1H), 6.86-6.92(m, 1H), 7.02-7.08(m, 2H), 7.43-7.49(m, 2H), 7.62(d, 1H), 7.95(d, 1H). |
| 833 | 183-185 | 306.3 | | ** | $^1$H NMR($CDCl_3$, 300MHz)δ(ppm) 1.21(t, 3H), 1.37(t, 3H), 3.84-4.09(m, 6H), 6.54-6.71(m, 2H), 6.85-7.01(m, 2H), 7.23-7.45(m, 3H). |
| 834 | 179-180 | 384.2 | | ** | |
| 835 | 178-179 | 398.2 | | ** | $^1$H NMR($CDCl_3$, 300MHz)δ(ppm), 1.32-1.52(m, 9H), 3.06-3.17(q, 2H), 4.07-4.24(m 4H), 6.55(s, 1H), 6.99-7.10(m, 3H), 7.42-7.50(m, 2H), 7.52-7.53(m, 1H), 7.69(d, 1H). |
| 836 | 167-169 | 412.2 | | * | |
| 837 | 144-145 | 410.2 | | * | |
| 838 | 193-194 | 378.1 | | ** | $^1$H NMR($CDCl_3$, 300MHz)δ(ppm), 1.31-1.39(m, 6H), 1.48(t, 3H), 4.07-4.31(m, 6H), 6.73(s, 1H), 6.88-6.95(m, 1H), 7.01-7.08(m, 2H), 7.42-7.53(m, 2H), 7.63(d, 1H), 7.99(s, 1H). |
| 839 | 249-250 | 377.3 | | * | $^1$H NMR($CDCl_3$, 300MHz)δ(ppm), 1.13(t, 3H), 1.32(t, 3H), 1.43(t, 3H), 3.20-3.32(m, 2H), 4.13-4.26(m, 4H), 5.77(t, 1H), 7.06-7.18(m, 3H), 7.48(d, 1H), 7.52-7.59(m, 2H), 8.02(s, 1H), 8.18(d, 1H). |
| 840 | 182-183 | 442.5 | | * | |
| 841 | 140-141 | 429.2 | | * | |
| 842 | 170-171 | 427.2 | | * | $^1$H NMR($CDCl_3$, 300MHz)δ(ppm) 1.04-1.13(m, 2H), 1.20-1.28(m, 2H), 1.44(t, 3H), 2.30-2.43(m, 1H) 3.44-3.61(m, 8H), 4.10-4.23(q, 2H), 7.49(d, 1H), 7.56(s, 1H), 7.72(d, 1H). |
| 843 | 143-146 | 463.1 | | * | |
| 844 | 220-227 | 378.1 | | * | |
| 845 | 210-215 | 435.0 | | * | |
| 846 | 201-202 | 391.5 | | ** | |
| 847 | 166-167 | 405.5 | | ** | |
| 848 | 193-194 | 453.5 | | ** | |
| 849 | 159-161 | 364.5 | | ** | |
| 850 | 179-180 | 446.4 | | ** | |
| 851 | 186-187 | 410.4 | | ** | |
| 852 | 171-172 | 426.4 | | ** | |
| 853 | 159-161 | 346.2 | | *** | |
| 854 | | 330.2 | | ** | |
| 855 | | 332.1 | | ** | |
| 856 | 202-202 | 368.1 | | * | |
| 857 | 192-192 | 364.2 | | ** | |
| 858 | | 362.2 | | *** | |
| 859 | 191-192 | 374.2 | | ** | |
| 860 | 242-244 | 334.1 | | ** | |
| 861 | | 346.2 | | ** | |

TABLE 1A-continued

| Compound Number | Melting Point (° C.) | Mass Spec [M+H] | HCV-PV $IC_{50}$ μM | Replicon $IC_{50}$ μM | NMR Data |
|---|---|---|---|---|---|
| 862 | | 360.1 | | * | |
| 863 | | 362.5 | | ** | |
| 864 | | 362.5 | | ** | |
| 865 | 187-192 | 412.9 | | * | |

TABLE 1B

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| 866 | 143-145 | 382.5 | ** | | |
| 867 | 198-200 | 448.26 | ** | | |
| 868 | 188-190 | 446.23 | *** | *** | |
| 869 | 205-206 | 354.3 | ** | | |
| 870 | | 328.28 | ** | | |
| 871 | 158-161 | 402.24 | * | | |
| 872 | 176-179 | 416.28 | * | | |
| 873 | 183-187 | 414.27 | * | | |
| 874 | 182-186 | 448.26 | ** | | |
| 875 | 136-140 | 368.15 | ** | | |
| 876 | | 382.18 | ** | | |
| 877 | | 396.19 | ** | | |
| 878 | | 396.19 | ** | | |
| 879 | | 400.14 | ** | | |
| 880 | | 310.26 | ** | | |
| 881 | 194-195 | 438.2 | *** | *** | |
| 882 | 181-183 | 452.3 | *** | | |
| 883 | 198-200 | 450.2 | *** | *** | |
| 884 | 195-196 | 452.3 | *** | *** | |
| 885 | 148-150 | 466.3 | *** | | |
| 886 | 173-175 | 404.2 | ** | | |
| 887 | 181-183 | 418.2 | ** | | |
| 888 | 187-189 | 436.3 | ** | | |
| 889 | 160-162 | 432.2 | ** | | |
| 890 | 158-160 | 450.3 | ** | | |
| 891 | 144-146 | 452.3 | ** | | |
| 892 | 225-226 | 417.2 | ** | | |
| 893 | 191-193 | 431.3 | ** | | |
| 894 | 180-182 | 445.3 | ** | | |
| 895 | 225-226.7 | 348.4 | ** | | $^1$H NMR(DMSO-$d_6$, 300MHz), δ 10.17(s, 1H), 7.73(d, J=7.2Hz, 2H), 7.48-7.43(m, 3H), 7.17(s, 1H), 6.61(d, J=7.5Hz, 1H), 4.13-4.05(m, 4H), 2.03(s, 3H), 1.31(t, J=6.6Hz, 3H), 1.12(t, J=7.5Hz, 3H). |
| 896 | 245.9-247 | 362.1 | ** | | $^1$H NMR(DMSO-$d_6$, 300MHz), δ 10.13(s, 1H), 7.77(d, J=8.7Hz, 2H), 7.51-7.45(m, 3H), 7.20(s, 1H), 6.88(dd, J=6.9Hz and 2.1Hz, 1H), 4.16-4.05(m, 4H), 2.34(q, J=7.5Hz, 2H), 1.33(t, J=6.9Hz, 3H), 1.19-1.04(m, 6H). |
| 897 | 254.4-256.3 | 374.1 | ** | | $^1$H NMR(DMSO-$d_6$, 300MHz), δ 10.45(s, 1H), 7.78(d, J=8.7Hz, 2H), 7.51-7.45(m, 3H), 7.20(d, J=1.8Hz 1H), 6.88(dd, J=6.6Hz and 2.1Hz, 1H), 4.16-4.05(m, 4H), 1.81-1.75(m, 1H), 1.34(t, J=6.9Hz, 3H), 1.14(t, J=6.9Hz, 3H), 0.81-0.79(m, 4H). |
| 898 | >300° C. decomposed | 374.5 | ** | | $^1$H NMR(DMSO-$d_6$, 300MHz), δ 10.09(s, 1H), 7.80(d, J=8.7Hz, 2H), 7.62-7.45(m, 3H), 7.20(d, J=1.5Hz, 1H), 6.88(dd, J=8.7Hz and 2.4Hz, 1H), 4.18-4.05(m, 4H), 2.62-2.56(m, 1H), 1.33(t, J=6.9Hz, 3H), 1.19-1.04(m, 9H). |
| 899 | 246.8-249.7 | 386.5 | ** | | $^1$H NMR(DMSO-$d_6$, 300MHz), δ 9.99(s, 1H), 7.80(d, J=8.4Hz, 2H), 7.51-7.45(m, 3H), 7.20(s, |

TABLE 1B-continued

| Compound Number | Melting Point (° C.) | Mass Spec [M + H] | Replicon $IC_{50}$ µM 2-day | Replicon $IC_{50}$ µM 3-day | NMR Data |
|---|---|---|---|---|---|
| | | | | | 1H), 6.89(dd, J=8.7Hz and 2.4Hz, 1H), 4.16-4.05(m, 4H), 2.25-2.02(m, 4H), 2.01-1.86(m, 1H), 1.84-1.76(m, 1H), 1.34(t, J=6.9Hz, 3H), 1.17(t, J=7.8Hz, 3H). |
| 900 | 185.7 | 422.4 | ** | | $^1$H NMR(DMSO-$d_6$, 300MHz), δ 10.44(s, 1H), 7.79(d, J=8.7Hz, 2H), 7.52-7.48(m, 3H), 7.32-7.19(m, 6H), 6.88(dd, J=8.7Hz and 2.1Hz, 1H), 4.16-4.05(m, 4H), 3.66(s, 2H), 1.35(t, J=7.2Hz, 3H), 1.14(t, J=7.2Hz, 3H). |
| 901 | 160.4 | 436.5 | ** | | $^1$H NMR(DMSO-$d_6$, 300MHz), δ 10.18(s, 1H), 7.76(d, J=8.7Hz, 2H), 7.52-7.45(m, 3H), 7.26-7.13(m, 6H), 6.89(dd, J=8.7Hz and 1.8Hz, 1H), 4.16-4.05(m, 4H), 2.92(t, J=2.7Hz, 2H), 2.68-2.62(m, 2H), 1.33(t, J=6.9Hz, 3H), 1.14(t, J=6.9Hz, 3H). |
| 902 | 233-235 | 436.1 | ** | | |
| 903 | 230-232 | 450.2 | *** | | |
| 904 | 193-195 | 464.1 | ** | | |
| 905 | 171-173 | 468.2 | *** | *** | |
| 906 | 246-247 | 480.1 | ** | | |
| 907 | 224-225 | 410.17 | ** | | $^1$H NMR(300MHz, $CDCl_3$): δ 7.63(1H, d, J=8.8Hz), 7.53(1H, td, J=7.7, 1.1Hz), 7.41-7.32(2H, m), 6.96(1H, dd, J=8.5, 2.0Hz), 6.89(1H, d, J=2.0Hz), 4.16(2H, q, J=7.0Hz), 4.12(2H, q, J=7.0Hz), 3.86(2H, t, J=6.6Hz), 3.42(2H, t, J=7.4Hz), 2.58(2H, p, J=7.0Hz), 1.48(3H, t, J=7.0Hz), 1.38(3H, t, J=7.0Hz). |
| 908 | 186-189 | 476.2 | ** | | |
| 909 | 180-182 | 381.24 | ** | | |
| 910 | 195-198 | 409.26 | ** | | |
| 911 | 228-230 | 395.24 | ** | | |
| 912 | 217-221 | 428.2 $[MH]^-$ | ** | | |
| 913 | 200-202 | 388.2 | ** | | |
| 914 | 212-214 | 402.2 | ** | | |
| 915 | 200-202 | 430.2 | ** | | |
| 916 | 183-185 | 478.2 | ** | | |
| 917 | 207-209 | 266.2 | ** | | |
| 918 | 219-221 | 277.4 | ** | | |
| 919 | 181-183 | 474.2 | ** | | |
| 920 | 182-183 | 453.3 | ** | | |
| 921 | 237-238 | 460.2 | ** | | |
| 922 | 246-248 | 474.2 | ** | | |
| 923 | 225-229 | 488.2 | ** | | |
| 924 | 221-223 | 486.2 | ** | | |
| 925 | 190-192 | 440.2 | ** | | |
| 926 | 195-196 | 454.3 | ** | | |
| 927 | 204-206 | 306.25 | ** | | |
| 928 | 206-208 | 432.14 (M−H+) | *** | *** | |
| 929 | 177-178 | 432.09 | *** | *** | |
| 930 | 183-184 | 468.02 | *** | *** | |
| 931 | 196-197 | 432.15 (M−H+) | *** | *** | |
| 932 | 184-185 | 438.22 | *** | *** | |
| 933 | 156-157 | 438.21 | ** | | |
| 934 | 192-193 | 436.15 | *** | *** | |
| 935 | 152-153 | 472.14 | *** | ** | |
| 936 | 191-192 | 468.23 | *** | *** | $^1$H NMR(300MHz, $CDCl_3$): δ 7.62(1H, d, J=9.1Hz), 7.38(2H, d, J=8.3Hz), 7.23(1H, d, J=2.3Hz), 7.12(2H, d, J=8.3Hz), 6.95(1H, dd, J=8.8, J=2.2Hz), 6.12(1H, d, J=9.0Hz), 4.93(1H, m), 4.20(6H, m), 2.85(2H, m), 2.35(2H, m), 1.96(2H, m), 1.48(3H, t, J=6.9Hz), 1.37(6H, t, J=6.3Hz) |
| 937 | 204-205 | 440.17 | *** | | |
| 938 | 147-148 | 372.21 | ** | | |
| 939 | 253-255 | 332.29 | ** | | |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| 940 | 58-59 | 263.20 | ** | | |
| 941 | | 460.19 | *** | *** | |
| 942 | 209-210 | 412.18 (M−H+) | ** | | $^1$H NMR(300MHz, DMSO-$d_6$): δ 8.48(1H, d, J=9.0Hz), 7.48(1H, d, J=8.8Hz), 7.46(2H, d, J=8.5Hz), 7.21(1H, obscurred), 7.20(2H, d, J=8.5Hz), 6.90(1H, dd, J=8.8, 2.2Hz), 4.16(2H, q, J=7.3Hz), 4.10(2H, q, J=7.0Hz), 3.69(6H, d, J=11.4Hz), 1.36(3H, t, J=7.0Hz), 1.18(3H, t, J=7.0Hz). |
| 943 | 219-220 | 428.25 | ** | | $^1$H NMR(300MHz, DMSO-$d_6$): δ 8.40(1H, d, J=9.0Hz), 7.49(1H, d, J=8.8Hz), 7.45(2H, d, J=8.5Hz), 7.23(1H, obscurred), 7.21(2H, d, J=8.5Hz), 6.91(1H, dd, J=8.8, 2.0Hz), 4.17(2H, q, J=7.0Hz), 4.13-3.97(4H, m), 3.84(3H, s), 1.24(6H, td, J=7.0, 0.6Hz), 1.15(3H, t, J=7.0Hz). |
| 944 | 223-224 | 400.20 | ** | | $^1$H NMR(300MHz, DMSO-$d_6$): δ 8.48(1H, d, J=9.0Hz), 7.49(1H, d, J=8.8Hz), 7.46(2H, d, J=8.5Hz), 7.22(1H, d, J=2.0Hz), 7.20(2H, d, J=8.5Hz), 6.91(1H, dd, J=8.8, 2.0Hz), 4.17(2H, q, J=7.0Hz), 3.84(3H, s), 3.68(6H, d, J=11.1Hz), 1.19(3H, t, J=7.0Hz). |
| 945 | 190-193 | 414.2 | ** | | |
| 946 | 163-172 | 410.2 | *** | *** | |
| 947 | 146-148 | 424.3 | *** | *** | |
| 948 | 166-167 | 458.2 | *** | *** | |
| 949 | decomposed >300 | 392.2 | ** | | $^1$H NMR(DMSO-$d_6$, 300MHz), δ 9.94(s, 1H), 7.66(d, J=8.7Hz, 2H), 7.51-7.45(m, 3H), 7.20(s, 1H), 6.88(d, J=8.7Hz, 1H), 4.16-4.02(m, 6H), 1.64-1.61(m, 2H), 1.34(t, J=6.9Hz, 3H), 1.15(t, J=6.9Hz, 3H), 0.92(t, J=7.5Hz, 3H). |
| 950 | decomposed >300 | 396.3 | ** | | $^1$H NMR(DMSO-$d_6$, 300MHz), δ 10.13(s, 1H), 7.67(d, J=8.4Hz, 2H), 7.52-7.46(m, 3H), 7.20(s, 1H), 6.89(d, J=8.7Hz, 1H), 4.73(br, 1H), 4.57(br, 1H), 4.40(br, 1H), 4.30(br, 1H), 4.16-4.05(m, 4H), 1.33(t, J=7.2Hz, 3H), 1.15(t, J=7.2Hz, 3H). |
| 951 | decomposed >300 | 405.1 | ** | | $^1$H NMR(CD3Cl, 300MHz), δ 7.62(d, J=8.4Hz, 1H), 7.52-7.42(m, 4H), 6.96(dd, J=1.8Hz and 8.4Hz, 1H), 6.88(d, J=1.8Hz, 1H), 6.71(s, 1H), 4.86-4.82(m, 1H), 4.12(q, J=6.9Hz, 4H), 3.29(q, J=6.3Hz, 2H), 1.52-1.31(m, 10H), 0.95(t, J=7.5Hz, 3H). |
| 952 | not detected | 472.3 | ** | | $^1$H NMR(CD3CN, 300MHz), δ 9.01(s, 1H), 7.79(d, J=8.7Hz, 2H), 7.58-7.49(m, 3H), 7.11(d, J=1.5Hz, 1H), 6.96(d, J=8.4Hz, 1H), 4.31(t, J=4.2Hz, 2H), 4.16(q, J=6.9Hz, 2H), 3.34-3.19(m, 10H), 2.77(s, 3H), 2.35-2.30(m, 1H), 1.25(t, J=6.9Hz, 3H), 0.92-0.82(m, 4H). |
| | 184-186 | 442.2 $[MH]^-$ | ** | | |
| 954 | 232-234 | 395.2 | ** | | |
| 955 | 203-206 | 409.2 | ** | *** | |
| 956 | 217-220 | 409.2 | *** | *** | |
| 957 | 192-195 | 423.3 | *** | *** | |
| 958 | 210-212 | 407.2 | ** | *** | |
| 959 | 169-171 | 384.19 | ** | | |
| 960 | 178-180 | 398.25 | ** | | |
| 961 | 174-177 | 412.24 | ** | | |
| 962 | 172-174 | 410.24 | ** | | |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| 963 | 203-206 | 364.24 | ** | | |
| 964 | 153-155 | 378.28 | ** | | |
| 965 | 156-157 | 392.27 | ** | | |
| 966 | 212-215 | 377.25 | ** | | |
| 967 | 218-221 | 391.27 | ** | | |
| 968 | 241-244 | 412.18 | *** | ** | |
| 969 | 264-266 | 434.15 | *** | *** | |
| 970 | 206-208 | 390.22 | *** | *** | |
| 971 | 213-215 | 404.27 | *** | *** | |
| 972 | 195-196 | 418.27 | *** | *** | |
| 973 | 190-192 | 418.27 | *** | *** | $^1$H NMR(300MHz, $CDCl_3$): δ 7.63(1H, d, J=8.5Hz), 7.54(2H, d, J=8.5Hz), 7.43(2H, d, J=8.5Hz), 7.21(1H, d, J=2.2Hz), 6.95(1H, dd, J=8.8, J=2.2Hz), 6.70(1H, s), 5.05(1H, m), 4.94(1H, m), 4.14(2H, q, 6.9Hz), 2.82(2H, m), 2.33(2H, m), 1.87(2H, m), 1.51(3H, t, J=4.6Hz), 1.33(6H, d, J=6.1Hz). |
| 974 | 215-217 | 422.22 | *** | *** | |
| 975 | 140-141 | 434.27 | ** | | |
| 976 | 158-159 | 428.25 | ** | | |
| 977 | 181-182 | 452.22 | *** | | |
| 978 | 185-186 | 482.28 | ** | | |
| 979 | 179-180 | 432.26 | *** | *** | |
| 980 | 236-238 | 436.24 | * | | |
| 981 | 201-203 | 416.26 | *** | *** | |
| 982 | 169-171 | 422.22 | * | | $^1$H NMR(300MHz, DMSO-$d_6$): δ 10.16(1H, br), 7.57(2H, d, J=8.5Hz), 7.52(1H, d, J=8.5Hz), 7.42(2H, d, J=8.5Hz), 7.33(1H, d, J=2.0Hz), 6.93(1H, dd, J=8.5, 2.0Hz), 4.13(2H, d, J=7.0Hz), 3.85(3H, s), 2.77(1H, p, J=6.3Hz), 0.98(6H, d, J=6.3Hz), 0.96-0.88(1H, m), 0.34-0.27(2H, m), 0.05-0.00(2H, m). |
| 983 | 217-219 | 386.22 | ** | | $^1$H NMR(300MHz, DMSO-$d_6$): δ 10.48(1H, s), 7.80(2H, d, J=8.8Hz), 7.53(2H, d, J=8.8Hz), 7.52(1H, d, J=8.6Hz), 7.32(1H, d, J=2.0Hz), 6.92(1H, dd, J=8.6, 2.0Hz), 4.13(2H, d, J=6.8Hz), 3.84(3H, s), 1.82(1H, p, J=6.0Hz), 0.99-0.90(1H, m), 0.89-0.75(4H, m), 0.33-0.27(2H, m), 0.05-0.00(2H, m). |
| 984 | 179-180 | 390.25 | ** | | $^1$H NMR(300MHz, DMSO-$d_6$): δ 9.95(1H, s), 7.67(2H, d, J=8.4Hz), 7.52(2H, d, J=8.4Hz), 7.51(1H, d, J=8.8Hz), 7.32(1H, d, J=2.3Hz), 6.91(1H, dd, J=8.8, 2.3Hz), 4.15(2H, q, J=7.0Hz), 4.12(2H, d, J=7.0Hz), 3.84(3H, s), 1.26(3H, t, J=7.0Hz), 1.00-0.90(1H, m), 0.33-0.25(2H, m), 0.05-0.00(2H, m). |
| 985 | 124-125 | 404.21 | ** | | $^1$H NMR(300MHz, DMSO-$d_6$): δ 9.96(1H, s), 7.67(2H, d, J=8.5Hz), 7.52(2H, d, J=8.5Hz), 7.50(1H, d, J=8.8Hz), 7.32(1H, d, J=2.0Hz), 6.92(1H, dd, J=8.8, 2.0Hz), 4.12(2H, d, J=6.7Hz), 4.07(2H, t, J=6.8Hz), 3.84(3H, s), 1.65(2H, hx, J=7.3Hz), 0.94(3H, t, J=7.3Hz), 0.93-0.89(1H, m), 0.33-0.26(2H, m), 0.05-0.00(2H, m). |
| 986 | 157-158 | 404.21 | ** | | $^1$H NMR(300MHz, DMSO-$d_6$): δ 9.90(1H, s), 7.67(2H, d, J=8.5Hz), 7.53-7.49(3H, m), 7.32(1H, d, J=2.0Hz), 6.92(1H, dd, J=8.8, 2.0Hz), 4.92(1H, hp, J=6.3Hz), 4.12(2H, d, J=6.7Hz), |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| | | | | | 3.84(3H, s), 1.27(6H, d, J=6.3Hz), 1.00-0.90(1H, m), 0.33-0.26(2H, m), 0.07-0.01(2H, m). |
| 987 | 183-184 | 403.26 | ** | | $^1$H NMR(300MHz, DMSO-$d_6$): δ 8.59(1H, s), 7.56(2H, d, J=8.5Hz), 7.47(1H, d, J=8.8Hz), 7.42(2H, d, J=8.5Hz), 7.29(1H, d, J=2.0Hz), 6.89(1H, dd, J=8.8, 2.0Hz), 6.11(1H, d, J=7.6Hz), 4.10(2H, d, J=7.0Hz), 3.82(3H, s), 3.75(1H, m, J=7.0Hz), 1.08(6H, d, J=6.5Hz), 0.97-0.88(1H, m), 0.31-0.25(2H, m), 0.04-0.02(2H, m). |
| 988 | 168-169 | 398.25 (M−H+) | ** | | $^1$H NMR(300MHz, DMSO-$d_6$): δ 10.22(1H, s), 7.63(2H, d, J=8.8Hz), 7.54(1H, d, J=8.5Hz), 7.39(2H, d, J=8.8Hz), 7.35(1H, d, J=2.0Hz), 6.96(1H, dd, J=8.8, 2.0Hz), 5.46(2H, s), 3.84(3H, s), 3.22(2H, q, J=7.3Hz), 3.17(3H, s), 1.23(3H, t, J=7.3Hz). |
| 989 | 195-196 | 380.18 (M−$CH_3O^-$) | ** | | $^1$H NMR(300MHz, DMSO-$d_6$): δ 7.68(2H, d, J=8.8Hz), 7.54(1H, d, J=8.5Hz), 7.38(2H, d, J=8.8Hz), 7.36(1H, d, J=2.2Hz), 6.97(1H, dd, J=8.5, 2.2Hz), 5.47(2H, s), 3.86-3.81(2H, m), 3.84(3H, s), 3.58(2H, t, J=7.3Hz), 3.17(3H, s), 2.47-2.41(2H, m). |
| 990 | 179-180 | 412.27 (M−H+) | ** | | $^1$H NMR(300MHz, DMSO-$d_6$): δ 10.22(1H, s), 7.63(2H, d, J=8.8Hz), 7.54(1H, d, J=8.5Hz), 7.38(2H, d, J=8.8Hz), 7.34(1H, d, J=2.0Hz), 6.96(1H, dd, J=8.5, 2.0Hz), 5.46(2H, s), 3.84(3H, s), 3.20(2H, t, J=7.6Hz), 3.16(3H, s), 1.72(2H, hx, J=7.6Hz), 0.96(3H, t, J=7.5Hz). |
| 991 | 179-180 | 348.17 (M−$CH_3O^-$) | ** | | $^1$H NMR(300MHz, DMSO-$d_6$): δ 9.97(1H, s), 7.67(2H, d, J=8.8Hz), 7.58(2H, d, J=8.8Hz), 7.53(1H, d, J=8.8Hz), 7.33(1H, d, J=2.0Hz), 6.96(1H, dd, J=8.8, 2.0Hz), 5.45(2H, s), 4.15(2H, q, J=7.0Hz), 3.83(3H, s), 3.16(3H, s), 1.26(3H, t, J=7.0Hz). |
| 992 | 155-157 | 362.23 (M−$CH_3O^-$) | ** | | $^1$H NMR(300MHz, DMSO-$d_6$): δ 9.67(1H, s), 7.68(2H, d, J=8.8Hz), 7.58(2H, d, J=8.8Hz), 7.53(1H, d, J=8.5Hz), 7.34(1H, d, J=2.0Hz), 6.96(1H, dd, J=8.5, 2.0Hz), 5.45(2H, s), 4.07(2H, t, J=6.7Hz), 3.84(3H, s), 3.31(3H, s), 1.65(2H, hx, J=7.0Hz), 0.94(3H, t, J=7.3Hz). |
| 993 | 146-148 | 392.29 (M−H+) | ** | | $^1$H NMR(300MHz, DMSO-$d_6$): δ 9.90(1H, s), 7.67(2H, d, J=8.6Hz), 7.57(2H, d, J=8.6Hz), 7.53(1H, d, J=8.8Hz), 7.33(1H, d, J=2.0Hz), 6.96(1H, dd, J=8.8, 2.0Hz), 5.45(2H, s), 4.92(1H, hp, J=6.3Hz), 3.83(3H, s), 3.15(3H, s), 1.26(6H, d, J=6.3Hz). |
| 994 | 266-267 | 375.22 | ** | | $^1$H NMR(300MHz, DMSO-$d_6$): δ 11.32(1H, s), 7.83(2H, d, J=8.8Hz), 7.62(2H, d, J=8.8Hz), 7.52(1H, d, J=8.5Hz), 7.25(1H, d, J=2.0Hz), 6.93(1H, dd, J=8.5, 2.0Hz), 4.52(2H, s), 4.20(2H, q, J=7.0Hz), 3.85(3H, s), 1.18(3H, t, J=7.0Hz). |
| 995 | 179-181 | 384.2 | ** | ** | |
| 996 | 200-201 | 398.2 | *** | ** | |
| 997 | 169-171 | 412.2 | ** | | |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| 998 | 166-167 | 410.2 | ** | | |
| 999 | 172-174 | 377.3 | ** | | |
| 1000 | 156-158 | 391.3 | ** | | |
| 1001 | 120-124 | 389.3 | ** | ** | |
| 1002 | 166-158 | 422.15 | ** | | |
| 1003 | 189-191 | 436.15 | ** | | |
| 1004 | 191-193 | 450.15 | ** | | |
| 1005 | 169-171 | 436.15 | ** | | |
| 1006 | 187-188 | 450.15 | *** | ** | |
| 1007 | 179-180 | 464.20 | *** | | |
| 1008 | 114-115 | 405.3 | ** | | |
| 1009 | 202-203 | 363.3 | ** | | |
| 1010 | 196-197 | 377.3 | ** | | |
| 1011 | 205-206 | 377.3 | ** | | |
| 1012 | 165-166 | 391.3 | ** | | |
| 1013 | 192-193 | 375.3 | ** | | |
| 1014 | 178.1-183.5 | 453.1 | *** | *** | $^1$H NMR(DMSO-$d_6$, 300MHz), δ 8.80(s, 1H), 7.58(d, J=6.3Hz, 2H), 7.48-7.42(m, 3H), 7.29(t, J=5.1Hz, 2H), 7.24-7.19(m, 4H), 6.89(d, J=6.6Hz, 1H), 6.22(br, 1H), 4.16-4.08(m, 4H), 3.35-3.33(m, 2H), 2.75(t, J=5.1Hz, 2H), 1.34(t, J=5.1Hz, 3H), 1.16(t, J=5.7Hz, 3H). |
| 1015 | 150.1-155.6 | 424.0 | ** | | $^1$H NMR($CD_3CN$, 300Hz), δ 8.06(s, 1H), 7.66(d, J=8.7Hz, 2H), 7.55-7.50(m, 3H), 7.04(d, J=1.8Hz, 1H), 6.91(dd, J=6.6Hz and 2.1Hz, 1H), 4.73(t, J=3.9Hz, 1H), 4.57(t, J=3.9Hz, 1H), 4.43(t, J=3.9Hz, 1H), 4.34(t, J=3.9Hz, 1H), 4.16-4.09(m, 4H), 1.65-1.61(m, 2H), 1.40(t, J=7.2Hz, 3H), 1.18-1.06(m, 2H), 0.74(t, J=7.2Hz, 3H). |
| 1016 | 204.2-209.7 | 405.2 | ** | | $^1$H NMR(DMSO-$d_6$, 300Hz), δ 8.74(s, 1H), 7.59(d, J=8.4Hz, 2H), 7.49-7.42(m, 3H), 7.20(s, 1H), 6.90(dd, J=8.4Hz and 2.4Hz, 1H), 6.22(t, J=5.7Hz, 1H), 4.17-4.09(m, 4H), 3.14-3.10(m, 2H), 1.52-1.50(m, 2H), 1.32(t, J=7.2Hz, 3H), 1.13-1.03(m, 5H), 0.68(t, J=6.9Hz, 3H). |
| 1017 | 181.3-187.8 | 419.2 | *** | *** | $^1$H NMR(DMSO-$d_6$, 300Hz), δ 8.67(s, 1H), 7.58(d, J=8.7Hz, 2H), 7.49-7.41(m, 3H), 7.20(s, 1H), 6.92(dd, J=8.7Hz and 2.4Hz, 1H), 6.16(d, J=7.2, 1H), 4.32-4.02(m, 4H), 3.80-3.70(m, 1H), 1.50-1.49(m, 2H), 1.35(t, J=6.6Hz, 3H) 1.11-1.00(m, 8H), 0.68(t, J=7.2Hz, 3H). |
| 1018 | 172.7-177.6 | 433.2 | *** | *** | $^1$H NMR(DMSO-$d_6$, 300Hz), δ 8.71(s, 1H), 7.59(d, J=8.1Hz, 2H), 7.49-7.41(m, 3H), 7.20(s, 1H), 6.90(dd, J=8.7Hz and 2.4Hz, 1H), 6.23(br, 1H), 4.17-4.09(m, 4H), 3.10-3.09(m, 2H) 1.50-1.30(m, 9H), 1.05-1.03(m, 2H), 0.88(t, J=6.6Hz, 3H), 0.69(t, J=7.2Hz, 3H). |
| 1019 | 153.7-160 | 481.2 | *** | *** | $^1$H NMR(DMSO-$d_6$, 300Hz), δ 8.80(s, 1H), 7.59(d, J=8.4Hz, 2H), 7.46-7.45(m, 3H), 7.31-7.20(m, 6H), 6.90(dd, J=8.7Hz and 2.4Hz, 1H), 6.25-6.24(m, 1H), 4.17-4.09(m, 4H), 3.37-3.31(m, 2H), 2.78-2.71(m, 2H), 1.53-1.51(m, 2H), 1.35(t, J=6.9Hz, 3H), 1.13-1.00(m, 2H), 0.67(t, J=7.2Hz, 3H). |
| 1020 | 135-141.7 | 406.0 | *** | ** | $^1$H NMR($CD_3CN$, 300Hz), δ 7.91(s, 1H), 7.68(d, J=8.7Hz, 2H), |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| | | | | | 7.55-7.49(m, 3H), 7.36(d, J=2.1Hz, 1H), 6.91(dd, J=6.3Hz and 2.4Hz, 1H), 4.36-4.02(m, 4H), 1.66-1.56(m, 2H), 1.40(t, J=7.2Hz, 3H), 1.31(t, J=7.2Hz, 3H), 1.22-1.07(m, 2H), 0.74(t, J=7.2Hz, 3H). |
| 1021 | 112.1-119.5 | 420.0 | *** | *** | $^1$H NMR($CD_3CN$, 300Hz), δ 7.94(s, 1H), 7.65(d, J=8.7Hz, 2H), 7.55-7.49(m, 3H), 7.37(d, J=2.1Hz, 1H), 6.91(dd, J=6.6Hz and 2.1Hz, 1H), 4.16-4.07(m, 4H), 1.72-1.56(m, 4H), 1.40(t, J=7.2Hz, 3H), 1.16-1.06(m, 2H), 0.98(t, J=7.2Hz, 3H), 0.76(t, J=7.2Hz, 3H). |
| 1022 | 104.3-109.7 | 420.0 | *** | * | $^1$H NMR(DMSO-$d_6$, 300Hz), δ 9.87(s, 1H), 7.67(d, J=8.7Hz, 2H), 7.51-7.47(m, 3H), 7.21(s, 1H), 6.90(dd, J=8.7Hz and 2.4Hz, 1H), 4.96-4.89(m, 1H), 4.16-4.06(m, 4H), 1.51-1.47(m, 2H), 1.35(t, J=6.9Hz, 3H), 1.21-1.27(m, 6H), 1.06-0.99(m, 2H), 0.67(t, J=7.2Hz, 3H). |
| 1023 | 152.7-161.3 | 433.2 | ** | | $^1$H NMR(DMSO-$d_6$, 300Hz), δ 8.71(s, 1H), 7.58(d, J=9.0Hz, 1H), 7.49-7.42(m, 3H), 7.20(d, J=1.8Hz, 1H), 6.89(dd, J=6.6Hz and 2.1Hz, 1H), 6.23(br, 1H), 4.17-4.09(m, 4H), 3.13-3.06(m, 2H), 1.53-1.28(m, 9H), 1.05-1.03(m, 2H), 0.89(t, J=7.2Hz, 3H), 0.68(t, J=7.2Hz, 3H). |
| 1024 | 160.2-167.8 | 481.2 | *** | *** | $^1$H NMR(DMSO-$d_6$, 300Hz), δ 8.80(s, 1H), 7.59(d, J=8.7Hz, 2H), 7.49-7.42(m, 3H), 7.33-7.20(m, 6H), 6.90(dd, J=6.9Hz and 2.1Hz, 1H), 6.23(br, 1H), 4.17-4.07(m, 4H), 3.39-3.34(m, 2H), 2.79-2.71(m, 2H), 1.52-1.49(m, 2H), 1.36(t, J=6.9Hz, 3H), 1.08-1.01(m, 2H), 0.68(t, J=7.2Hz, 3H). |
| 1025 | 133.3-141.8 | 459.2 | ** | | $^1$H NMR($CDCl_3$, 300MHz), δ 7.98(s, 1H), 7.71(d, J=7.8Hz, 2H), 7.61(d, J=8.4Hz, 1H), 7.41(d, J=7.8Hz, 2H), 6.91-6.88(m, 2H), 4.49(br, 2H), 4.12-4.02(m, 6H), 3.73-3.53(m, 4H), 3.09(br, 2H), 1.64(br, 1H), 1.28-1.26(m, 3H), 1.11(br, 2H), 0.89-0.87(m, 2H),. |
| 1026 | 220-222 | 432.16 | ** | *** | |
| 1027 | 138-140 | 443.31 | *** | *** | |
| 1028 | | | *** | *** | |
| 1029 | 188 | 412.8 | ** | | |
| 1030 | 173 | 440.2 | *** | | |
| 1031 | 195 | 426.2 | *** | | |
| 1032 | 145 | 424.2 | *** | | |
| 1033 | 181 | 444.2 | *** | | |
| 1034 | 154-155 | 491.3 | *** | | |
| 1035 | 173-175 | 497.3 | ** | | |
| 1036 | 230-235 | 510.3 | ** | | |
| 1037 | 155-156 | 430.25 (M−H+) | ** | | |
| 1038 | 236-238 | 410.2 | ** | | |
| 1039 | 243-248 | 391.3 | ** | | |
| 1040 | 215-217 | 392.2 | ** | ** | |
| 1041 | 164-166 | 412.2 | ** | *** | |
| 1042 | 135-138 | 505.4 | ** | | |
| 1043 | 165-166 | 476.3 | ** | | |
| 1044 | 167-168 | 511.3 | *** | | |
| 1045 | 117 | 460.3 | *** | | |
| 1046 | 232-234 | 422.21 | *** | *** | |
| 1047 | | 422.24 | *** | *** | |
| 1048 | 200-203 | 440.0 | ** | | |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| 1049 | 247-249 | 481.3 | *** | | |
| 1050 | 246-248 | 381.2 | ** | | |
| 1051 | 177 | 423.2 | ** | | |
| 1052 | 194 | 424.2 | ** | | |
| 1053 | 236-238 | 460.2 | ** | | |
| 1054 | 187.6-195.2 | 443.2 | ** | | $^1$H NMR(CDCl3, 300MHz), δ 7.91(br, 1H), 7.71(d, J=8.1Hz, 2H), 7.61(d, J=8.7Hz, 1H), 7.42(d, J=8.4Hz, 2H), 6.95-6.88(m, 2H), 4.44(br, 2H), 4.08(q, J=6.9Hz, 2H), 3.94-3.90(m, 2H), 3.62-3.56(m, 2H), 3.14(br, 1H), 2.90(br, 2H), 2.17-2.07(m, 4H), 1.28(t, J=7.2Hz, 3H), 1.15-1.11(m, 2H), 0.87-0.73(m, 2H). |
| 1055 | 148.1-153.2 | 406.0 | ** | *** | $^1$H NMR(DMSO-$d_6$, 300Hz), δ 9.94(s, 1H), 7.67(d, J=8.7Hz, 2H), 7.51-7.47(m, 3H), 7.23(d, J=2.4Hz, 1H), 6.90(dd, J=1.8Hz and 6.6Hz, 1H), 4.15-4.04(m, 6H), 1.68-1.52(m, 4H), 1.35(t, J=6.9Hz, 3H), 0.94(t, J=7.2Hz, 3H), 0.63(t, J=7.2Hz, 3H). |
| 1056 | 169-173.9 | 406.0 | *** | *** | $^1$H NMR(DMSO-$d_6$, 300Hz), δ 9.87(s, 1H), 7.67(d, J=8.7Hz, 2H), 7.51-7.47(m, 3H), 7.23(d, J=1.8Hz, 1H), 6.90(dd, J=2.1Hz and 6.6Hz, 1H), 4.94-4.90(m, 1H), 4.15-4.09(m, 4H), 1.54-1.52(m, 2H), 1.35(t, J=6.9Hz, 3H), 1.28-1.25(m, 6H), 0.63(t, J=7.2Hz, 3H). |
| 1057 | 184.5-193.9 | 406.0 | ** | | $^1$H NMR(DMSO-$d_6$, 300Hz), δ 9.41(s, 1H), 8.26(d, J=6.9Hz, 2H), 8.01-7.94(m, 3H), 7.70(d, J=2.1Hz, 1H), 7.41(dd, J=2.1Hz and 6.6Hz, 1H), 5.21-5.15(m, 1H), 4.64-4.53(m, 4H), 2.17-2.12(m, 2H), 2.07(d, J=6.9Hz, 6H), 1.86(t, J=6.9Hz, 3H), 1.41(t, J=7.5Hz, 3H). |
| 1058 | 160.1-166.5 | 406.0 | *** | *** | $^1$H NMR(DMSO-$d_6$, 300Hz), δ 9.87(s, 1H), 7.66(d, J=8.4Hz, 2H), 7.51-7.43(m, 3H), 7.20(d, J=2.1Hz, 1H), 6.92(dd, J=2.1Hz and 6.6Hz, 1H), 4.94-4.89(m, 1H), 4.57-4.53(m, 1H), 4.10(q, J=6.9Hz, 2H), 1.52(d, J=6.6Hz, 6H), 1.35(t, J=6.9Hz, 3H), 1.25(d, J=6.6Hz, 6H). |
| 1059 | 135-142.6 | 424.0 | ** | | $^1$H NMR($CD_3CN$, 300Hz), δ 8.07(s, 1H), 7.65(d, J=8.7Hz, 2H), 7.55-7.49(m, 2H), 7.04(d, J=1.8Hz, 1H), 6.91(dd, J=6.6Hz and 2.1Hz, 1H), 5.30(br, 1H), 4.16-4.09(m, 4H), 4.73(t, J=4.2Hz, 1H), 4.57(t, J=3.9Hz, 1H), 4.43(t, J=4.2Hz, 1H), 4.34(t, J=3.9Hz, 1H), 4.15-4.01(m, 4H), 1.40(t, J=6.9Hz, 3H), 0.87-0.85(m, 6H). |
| 1060 | 193.2-199.2 | 405.1 | ** | | $^1$H NMR($CD_3CN$, 300Hz), δ 7.65-7.51(m, 3H), 7.45-7.42(m, 2H), 7.36-7.31(m, 1H), 7.04(d, J=2.1Hz, 1H), 6.94-6.89(m, 1H), 5.25(br, 1H), 4.15-4.07(m, 4H), 3.20(br, 2H), 1.39(t, J=6Hz, 3H), 1.10(t, J=7.2Hz, 3H), 0.63(d, J=6.6Hz, 6H). |
| 1061 | 182.7-186.3 | 419.1 | ** | | $^1$H NMR($CD_3CN$, 300Hz), δ 7.66-7.53(m, 3H), 7.45-7.43(m, 2H), 7.38-7.33(m, 1H), 7.06-7.05(m, 1H), 6.94-6.91(m, 1H), 5.34(br, 1H), 4.15-4.02(m, 4H), 3.16-3.13(m, 2H), 1.55-1.50(m, 2H), |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| | | | | | 1.50-1.39(m, 3H), 0.98(t, J=7.2Hz, 3H), 0.63(d, J=6.6Hz, 6H). |
| 1062 | 156.7-162.2 | 378.0 | ** | | $^1$H NMR($CDCl_3$, 300MHz), δ 7.62(d, J=8.7Hz, 1H), 7.56(d, J=8.1Hz, 2H), 7.46(d, J=8.7Hz, 2H), 6.94(d, J=8.4Hz, 1H), 6.85(m, 2H), 4.11(q, J=6.9Hz, 2H), 4.03(t, J=7.8Hz, 2H), 3.82(s, 3H), 1.72(q, J=7.5Hz, 2H), 1.49(t, J=6.9Hz, 3H), 0.78(t, J=7.5Hz, 3H). |
| 1063 | 183.2-187.6 | 392.1 | ** | | $^1$H NMR($CDCl_3$, 300MHz), δ 7.62(d, J=8.4Hz, 1H), 7.56(d, J=7.8Hz, 2H), 7.45(d, J=8.1Hz, 2H), 6.94(d, J=8.4Hz, 1H), 6.86(s, 1H), 6.81(s, 1H), 4.26(q, J=6.9Hz, 2H), 4.11(q, J=6.9Hz, 2H), 4.03(t, J=7.8Hz, 2H), 1.72(q, J=7.5Hz, 2H), 1.49(t, J=6.9Hz, 3H), 1.34(t, J=7.2Hz, 3H), 0.77(t, J=7.5Hz, 3H). |
| 1064 | 103.2-107.7 | 410.0 | ** | | $^1$H NMR($CDCl_3$, 300MHz), δ 7.62(d, J=8.7Hz, 1H), 7.57(d, J=8.7Hz, 2H), 7.47(d, J=8.7Hz, 2H), 6.97(s, 1H), 6.95(dd, J=8.7Hz and 2.1Hz, 1H), 6.86(d, J=2.1Hz, 1H), 4.75(t, J=4.2Hz, 1H), 4.59(t, J=4.2Hz, 1H), 4.50(t, J=4.5Hz, 1H), 4.41(t, J=4.2Hz, 1H), 4.11(q, J=6.9Hz, 2H), 4.03(t, J=7.5Hz, 2H), 1.72(q, J=7.5Hz, 2H), 1.47(t, J=6.9Hz, 3H), 0.78(t, J=7.2Hz, 3H). |
| 1065 | 196.3-220.2 | 392.0 | ** | *** | $^1$H NMR($CDCl_3$, 400MHz), δ 7.63(d, J=8.8Hz, 1H), 7.56(d, J=8.4Hz, 2H), 7.42(d, J=8.4Hz, 2H), 7.10(s, 1H), 6.94(d, J=8.4Hz, 1H), 6.85(s, 1H), 4.68-4.61(m, 1H), 4.26(q, J=7.2Hz, 2H), 4.12(q, J=6.8Hz, 2H), 1.58(d, J=6.8Hz, 6H), 1.48(t, J=7.2Hz, 3H), 1.34(t, J=7.2Hz, 3H). |
| 1066 | 198.3-205.6 | 419.0 | ** | | $^1$H NMR($CD_3CN$, 300Hz), δ 7.61(d, J=8.7Hz, 2H), 7.53(d, J=8.7Hz, 1H), 7.44(d, J=8.7Hz, 2H), 7.38(s, 1H) 7.03(d, J=1.8Hz, 1H), 6.91(dd, J=6.6Hz and 2.1Hz, 1H), 5.30(br, 1H), 4.16-4.09(m, 4H), 3.18-3.11(m, 2H), 1.66-1.46(m, 4H), 1.40(t, J=6.9Hz, 3H), 1.16-1.06(m, 2H), 0.92(t, J=7.5Hz, 3H), 0.76(t, J=7.5Hz, 3H). |
| 1067 | 95-100 | 504.4 | ** | | |
| 1068 | 170-174 | 474.3 | ** | | |
| 1069 | 155-156 | 475.3 | ** | | |
| 1070 | 208-209 | 437.22 | ** | | $^1$H NMR(300MHz, DMSO-$d_6$): δ 8.86(1H, s), 7.67(1H, d, J=2.0Hz), 7.65(1H, d, J=8.5Hz), 7.61(2H, d, J=8.8Hz), 7.47(2H, d, J=8.8Hz), 7.25(1H, t, J=74.4Hz), 7.11(1H, dd, J=8.5, 2.0Hz), 6.40(1H, t, J=5.8Hz), 5.86(1H, ddt, J=17.1, 10.4, 5.1Hz), 5.15(1H, ddt, J=17.1, 1.8, 1.7Hz), 5.06(1H, ddt, J=10.4, 1.8, 1.7Hz), 4.12(2H, d, J=7.0Hz), 3.73(2H, narrow m), 0.93-0.84(1H, m), 0.32-0.23(2H, m), 0.05-0.00(2H m). $^{19}$F NMR(300MHz, DMSO-$d_6$): δ −82.03(2F, d, J=73.3Hz). |
| 1071 | 125-126 | 452.22 (M−H+) | ** | * | $^1$H NMR(300MHz, $CDCl_3$): δ 7.69(1H, d, J=8.2Hz), 7.56(2H, d, J=8.5Hz), 7.44(2H, d, J=8.5Hz), 7.24(1H, d, J=1.8Hz), |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| | | | | | 7.07(1H, dd, J=8.2, 1.8Hz), 6.80(1H, s), 6.52(1H, t, J=74.0Hz), 3.98(2H, d, J=7.0Hz), 3.96(2H, d, J=7Hz), 1.97(1H, m, J=6.7Hz), 1.03-0.94(1H, m), 0.95(6H, d, J=6.7Hz), 0.46-0.39(2H, m), 0.05-0.00(2H, m). $^{19}$F NMR(300MHz, $CDCl_3$): δ −80.76(2F, d, J=73.3Hz). |
| 1072 | 197-198 | 430.30 (M−H+) | *** | *** | |
| 1073 | 191-192 | 390.25 | ** | | |
| 1074 | 140-141 | 404.27 | ** | | |
| 1075 | 140-141 | 418.27 | ** | ** | |
| 1076 | 175-176 | 404.27 | *** | *** | |
| 1077 | 187-188 | 418.27 | *** | *** | |
| 1078 | 188-189 | 430.30 (M−H+) | *** | ** | |
| 1079 | 178-179 | 452.25 | *** | *** | |
| 1080 | 221-223 | 417.28 | *** | *** | $^{1}$H NMR(300MHz, $CDCl_3$): 7.61(1H, d, J=8.5Hz), 7.58(2H, d, J=8.3Hz), 7.37(2H, d, J=8.3Hz), 7.23(1H, d, J=1.0Hz), 6.96(1H, dd, J=8.8, J=1.7Hz), 4.90(1H, s), 4.15(2H, q, J=6.9), 4.01(1H, m), 2.82(2H, m), 2.33(2H, m), 1.81(2H, m), 1.48(3H, t, J=6.9Hz)), 1.21(6H, d, J=6.6Hz). |
| 1081 | 179-180 | 452.23 (M−H+) | ** | | |
| 1082 | 206-207 | 403.27 | ** | | |
| 1083 | 156 | 495.3 | *** | | |
| 1084 | 167 | 457.2 | ** | | |
| 1085 | 162 | 458.4 | *** | | |
| 1086 | 170 | 378.2 | *** | | |
| 1087 | 205 | 405.2 | ** | | |
| 1088 | 215 | 403.2 | ** | | |
| 1089 | 195 | 389.2 | ** | | |
| 1090 | 145.6-149.7 | 475.2 | ** | | $^{1}$H NMR($CD_3OD$, 300MHz), δ 7.80(d, J=8.7Hz, 2H), 7.58-7.49(m, 3H), 7.22(d, J=2.1Hz, 1H), 7.04(d, J=2.1Hz and 8.7Hz, 1H), 4.48(t, J=4.8Hz, 2H), 4.23(q, J=6.9Hz, 2H), 4.01-3.73(m, 6H), 3.02(br, 4H), 1.86-1.77(m, 1H), 1.28(t, J=7.2Hz, 3H), 1.00-0.87(m, 4H). |
| 1091 | 81.4-86.2 | 461.2 | ** | | $^{1}$H NMR($CD_3OD$, 300MHz), δ 7.78(d, J=8.4Hz, 2H), 7.55-7.47(m, 3H), 7.20(d, J=1.8Hz, 1H), 7.02(dd, J=1.8Hz and 8.4Hz, 1H), 4.46(t, J=4.8Hz, 2H), 4.21(q, J=6.6Hz, 2H), 3.81-3.64(m, 6H), 3.55(s, 3H), 3.03(s, 3H), 1.84-1.78(m, 1H), 1.26(t, J=7.2Hz, 3H), 0.99-0.86(m, 4H). |
| 1092 | 193.8-197.4 | 441.2 | ** | | $^{1}$H NMR($CD_3OD$, 300MHz), δ 9.03(s, 2H), 7.79(d, J=8.7Hz, 2H), 7.56-7.49(m, 3H), 7.14(d, J=1.8Hz, 1H), 6.99(dd, J=2.1Hz and 8.4Hz, 1H), 4.68(t, J=4.8Hz, 2H), 4.44(t, J=5.1Hz, 2H), 4.21(q, J=6.9Hz, 2H), 1.85-1.77(m, 1H), 1.27(t, J=6.9Hz, 3H), 1.01-0.93(m, 2H), 0.91-0.87(m, 2H). |
| 1093 | 130.7-134.3 | 441.2 | ** | | |
| 1094 | 205.3-208 | 391.0 | ** | | $^{1}$H NMR(DMSO-$d_6$, 300Hz), δ 8.74(s, 1H), 7.59(d, J=8.4Hz, 2H), 7.49-7.41(m, 3H), 7.22(s, 1H), 6.89(dd, J=1.8Hz and 6.9Hz, 1H), 6.22(t, J=5.4Hz, 1H), 4.15-4.06(m, 4H), 3.14-3.10(m, 2H), 1.58-1.51(m, 2H), 1.35(t, J=6.9Hz, 3H), 1.05(t, J=7.2Hz, 3H), 0.63(t, J=7.5Hz, 3H). |
| 1095 | 195.3-200.1 | 405.1 | *** | *** | $^{1}$H NMR(DMSO-$d_6$, 300Hz), δ 8.72(s, 1H), 7.59(d, J=8.7Hz, 2H), 7.49-7.41(m, 3H), 7.22(s, 1H), 6.89(dd, J=1.8Hz and 6.9Hz, |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| | | | | | 1H), 6.26(t, J=5.4Hz, 1H), 4.20-4.07(m, 4H), 3.09-3.03(m, 2H), 1.58-1.41(m, 4H), 1.35(t, J=6.9Hz, 3H), 0.87(t, J=6.9Hz, 3H), 0.64(t, J=7.2Hz, 3H). |
| 1096 | 192.1-196.2 | 405.1 | *** | *** | $^1$H NMR(DMSO-$d_6$, 300Hz), δ 8.60(s, 1H), 7.58(d, J=8.4Hz, 2H), 7.49-7.41(m, 3H), 7.22(s, 1H), 6.89(dd, J=2.1Hz and 6.6Hz, 1H), 6.12(d, J=7.5Hz, 1H), 4.15-4.06(m, 4H), 3.80-3.73(m, 1H), 1.58-1.50(m, 2H), 1.35(t, J=6.9Hz, 3H), 1.10(d, J=6.6Hz, 6H), 0.64(t, J=7.2Hz, 3H). |
| 1097 | 196.4-202.3 | 419.1 | *** | *** | $^1$H NMR(DMSO-$d_6$, 300Hz), δ 8.72(s, 1H), 7.59(d, J=8.4Hz, 2H), 7.49-7.41(m, 3H), 7.22(s, 1H), 6.89(dd, J=1.8Hz and 6.9Hz, 1H), 6.24(t, J=5.4Hz, 1H), 4.15-4.06(m, 4H), 3.12-3.06(m, 2H), 1.58-1.51(m, 2H), 1.44-1.21(m, 7H), 0.89(t, J=7.2Hz, 3H), 0.83(t, J=7.2Hz, 3H). |
| 1098 | 217.8-221.4 | 391.0 | ** | | $^1$H NMR(DMSO-$d_6$, 300Hz), δ 8.74(s, 1H), 7.59(d, J=8.7Hz, 2H), 7.49(d, J=8.7Hz, 1H), 7.38(d, J=8.4Hz, 2H), 7.20(d, J=2.1Hz, 1H), 6.92(dd, J=2.1Hz and 6.6Hz, 1H), 6.22(t, J=5.4Hz, 1H), 4.62-4.53(m, 1H), 4.11(q, J=6.9Hz, 2H), 3.16-3.07(m, 2H), 1.52(d, J=6.6Hz, 6H), 1.35(t, J=6.9Hz, 3H), 1.05(t, J=7.2Hz, 3H). |
| 1099 | 162.1-165.1 | 405.1 | ** | | $^1$H NMR(DMSO-$d_6$, 300Hz), δ 8.73(s, 1H), 7.59(d, J=8.4Hz, 2H), 7.49(d, J=8.1Hz, 1H), 7.38(d, J=8.7Hz, 2H), 7.20(d, J=2.1Hz, 1H), 6.92(dd, J=2.1Hz and 6.6Hz, 1H), 6.26(t, J=5.7Hz, 1H), 4.62-4.53(m, 1H), 4.11(q, J=6.9Hz, 2H), 3.09-3.02(m, 2H), 1.52(d, J=6.6Hz, 6H), 1.48-1.41(m, 2H), 1.35(t, J=6.9Hz, 3H), 0.87(t, J=7.2Hz, 3H). |
| 1100 | 228.6-231.4 | 405.1 | *** | | $^1$H NMR(DMSO-$d_6$, 300Hz), δ 8.60(s, 1H), 7.57(d, J=8.1Hz, 2H), 7.49(d, J=8.7Hz, 1H), 7.38(d, J=8.7Hz, 2H), 7.20(d, J=2.1Hz, 1H), 6.92(dd, J=2.1Hz and 6.6Hz, 1H), 6.11(d, J=7.8Hz, 1H), 4.62-4.52(m, 1H), 4.11(q, J=6.9Hz, 2H), 3.79-3.72(m, 1H), 1.53-1.51(m, 6H), 1.35(t, J=6.9Hz, 3H), 1.11-1.09(m, 6H). |
| 1101 | 157.2-160.5 | 419.1 | *** | | (DMSO, 300Hz), δ 8.72(s, 1H), 7.58(d, J=8.7Hz, 2H), 7.49(d, J=8.7Hz, 1H), 7.37(d, J=8.4Hz, 2H), 7.20(d, J=2.1Hz, 1H), 6.92(dd, J=2.1Hz and 6.6Hz, 1H), 6.23(t, J=5.7Hz, 1H), 4.62-4.55(m, 1H), 4.11(q, J=6.9Hz, 2H), 3.12-3.06(m, 2H), 1.52(d, J=6.6Hz, 6H), 1.47-1.21(m, 7H), 0.86(t, J=6.9Hz, 3H). |
| 1102 | 197.3-201.6 | 467.0 | *** | *** | $^1$H NMR($CD_3CN$, 300Hz), δ 7.58-7.46(m, 4H), 7.38(d, J=8.7Hz, 2H), 7.30-7.15(m, 5H), 7.15(s, 1H), 6.89(dd, J=2.1Hz and 6.6Hz, 1H), 5.31(br, 1H), 4.64-4.59(m, 1H), 4.09(q, J=6.9Hz, 2H), 3.44-3.42(m, 2H), 2.80(t, J=6.6Hz, 2H), 1.54(d, J=6.6Hz, 6H), 1.38(t, J=6.9Hz, 3H). |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| 1103 | 162-163 | 424.27 | ** | | |
| 1104 | 245-248 | 422.29 | ** | | |
| 1105 | 175-176 | 422.27 | ** | | |
| 1106 | 217-219 | 429.32 | *** | *** | |
| 1107 | 157-158 | 428.25 (M−H+) | *** | *** | |
| 1108 | 213-215 | 435.28 | *** | *** | |
| 1109 | 155-156 | 444.31 | *** | *** | |
| 1110 | 191-195 | 425.2 | ** | | |
| 1111 | 180-183 | 406.2 | ** | | |
| 1112 | 173-175 | 463.2 | ** | | |
| 1113 | 151.155 | 495.4 | ** | | |
| 1114 | 171-176 | 511.2 | *** | | |
| 1115 | 155-156 | 497.2 | ** | | |
| 1116 | 218-220 | 511.2 | ** | | |
| 1117 | 106-109 | 509.2 | ** | | |
| 1118 | 126-130 | 462.2 | ** | | |
| 1119 | 184-186 | 405.31 | ** | | |
| 1120 | 223-225 | 417.37 | *** | *** | $^1$H NMR(300MHz, $CDCl_3$): 7.61(1H, d, J=9.2Hz), 7.51(2H, d, J=8.5Hz), 7.43(2H, d, J=8.5Hz), 7.10(2H, m), 4.90(2H, m), 4.13(2H, q, J=6.9Hz), 3.97(2H, d, J=6.6Hz), 1.47(3H, t, J=7.0Hz), 1.20(6H, d, J=8.6Hz), 1.05(1H, m), 0.43(2H, m), 0.06(2H, m) |
| 1121 | 162-164 | 501.17 | *** | | |
| 1122 | 170-173 | 491.4 | *** | | |
| 1123 | 75-80 | 525.4 | *** | | |
| 1124 | 100-104 | 474.5 $[M-H]^-$ | *** | ** | |
| 1125 | 188-190 | 488.4 | *** | *** | |
| 1126 | 130-134 | 510.3 | ** | | |
| 1127 | 112-115 | 418.3 | *** | *** | |
| 1128 | 203-204 | 432.3 | *** | *** | |
| 1129 | 115-116 | 432.3 | *** | *** | |
| 1130 | 177-178 | 386.26 | ** | | $^1$H NMR(300MHz, DMSO-$d_6$): δ 10.02(1H, s), 7.69(2H, d, J=8.8Hz), 7.67(1H, d, J=8.5Hz), 7.61(1H, d, J=2.0Hz), 7.55(2H, d, J=8.8Hz), 7.28(1H, t, J=74.4Hz), 7.13(1H, dd, J=8.5, 2.0Hz), 4.20(2H, q, J=7.3Hz), 3.70(3H, s), 1.18(3H, t, J=7.3Hz). $^{19}$F NMR(300MHz, DMSO-$d_6$): δ −81.95(2F, d, J=73.3Hz). |
| 1131 | 174-175 | 400.26 | ** | | $^1$H NMR(300MHz, DMSO-$d_6$): δ 9.98(1H, s), 7.69(2H, d, J=8.8Hz), 7.67(1H, d, J=8.8Hz), 7.61(1H, d, J=2.0Hz), 7.54(2H, d, J=8.8Hz), 7.28(1H, t, J=74.4Hz), 7.13(1H, dd, J=8.8, 2.0Hz), 4.20(2H, q, J=7.0Hz), 4.15(2H, q, J=7.3Hz), 1.26(3H, t, J=7.0Hz), 1.18(3H, t, J=7.3Hz). $^{19}$F NMR(300MHz, DMSO-$d_6$): δ −81.95(2F, d, J=75.3Hz). |
| 1132 | 148-149 | 414.25 | ** | | $^1$H NMR(300MHz, DMSO-$d_6$): δ 9.99(1H, s), 7.70(2H, d, J=8.8Hz), 7.67(1H, d, J=8.5Hz), 7.61(1H, d, J=2.0Hz), 7.54(2H, d, J=8.8Hz), 7.28(1H, t, J=74.4Hz), 7.13(1H, dd, J=8.5, 2.0Hz), 4.20(2H, q, J=7.0Hz), 4.07(2H, t, J=6.7Hz), 1.65(2H, hx, J=7.6Hz), 1.18(3H, t, J=7.2Hz), 0.94(3H, t, J=7.5Hz). $^{19}$F NMR(300MHz, DMSO-$d_6$): δ −81.96(2F, d, J=73.3Hz). |
| 1133 | 139-140 | 428.25 | ** | | $^1$H NMR(300MHz, DMSO-$d_6$): δ 9.98(1H, s), 7.72-7.66(3H, m), 7.61(1H, d, J=2.0Hz), 7.54(2H, d, J=8.8Hz), 7.28(1H, t, J=74.4Hz), 7.13(1H, dd, J=8.8, 2.0Hz), 4.20(2H, q, J=7.3Hz), 4.11(2H, t, J=6.9hz), |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| | | | | | 1.66-1.56(2H, m), 1.45-1.35(2H, m), 1.18(3H, t, J=7.3Hz), 0.91(3H, t, J=7.3Hz). $^{19}$F NMR(300MHz, DMSO-$d_6$): δ −81.92(2F, d, J=73.3Hz). |
| 1134 | 142-143 | 426.30 (M−H+) | ** | | $^1$H NMR(300MHz, DMSO-$d_6$): δ 9.99(1H, s), 7.70(2H, d, J=8.8Hz), 7.67(1H, d, J=8.8Hz), 7.61(1H, d, J=2.0Hz), 7.54(2H, d, J=8.8Hz), 7.28(1H, t, J=74.4Hz), 7.13(1H, dd, J=8.8, 2.0Hz), 4.20(2H, q, J=7.0Hz), 3.90(2H, d, J=6.7Hz), 1.93(1H, m, J=6.7Hz), 1.18(3H, t, J=7.0Hz), 0.93(6H, d, J=6.7Hz). $^{19}$F NMR(300MHz, DMSO-$d_6$): δ −81.92(2F, d, J=73.3Hz). |
| 1135 | 144-145 | 412.24 | *** | | $^1$H NMR(300MHz, DMSO-$d_6$): δ 10.10(1H, s), 7.72-7.66(3H, m), 7.62(1H, d, J=2.0Hz), 7.55(2H, d, J=8.8Hz), 7.28(1H, t, J=74.4Hz), 7.13(1H, dd, J=8.5, 2.0Hz), 6.06-5.93(1H, m), 5.41-5.22(2H, m), 4.64(2H, dt, J=5.5, 1.3Hz), 4.20(2H, q, J=7.3Hz), 1.18(3H, t, J=7.3Hz). $^{19}$F NMR(300MHz, DMSO-$d_6$): δ −81.92(2F, d, J=73.3Hz). |
| 1136 | 172-174 | 413.25 | ** | | $^1$H NMR(300MHz, DMSO-$d_6$): δ 8.77(1H, s), 7.66(1H, d, J=8.8Hz), 7.62(2H, d, J=8.8Hz), 7.47(2H, d, J=8.8Hz), 7.46(1H, d, J=2.0Hz), 7.27(1H, t, J=74.4Hz), 7.13(1H, dd, J=8.8, 2.0Hz), 6.28(1H, t, J=5.7Hz), 4.20(2H, q, J=7.3Hz), 3.05(2H, q, J=6.2Hz), 1.44(2H, hx, J=6.7Hz), 1.19(3H, t, J=7.2Hz), 0.87(3H, t, J=7.5Hz). $^{19}$F NMR(300MHz, DMSO-$d_6$): δ −81.92(2F, d, J=73.3Hz). |
| 1137 | 180-182 | 413.26 | ** | | $^1$H NMR(300MHz, DMSO-$d_6$): δ 8.65(1H, s), 7.66(1H, d, J=8.8Hz), 7.61(1H, d, J=2.0Hz), 7.60(2H, d, J=8.8Hz), 7.47(2H, d, J=8.8Hz), 7.27(1H, t, J=74.4Hz), 7.13(1H, dd, J=8.8, 2.0Hz), 6.14(1H, d, J=7.6Hz), 4.20(2H, q, J=7.0Hz), 3.77(1H, m, J=7.3Hz), 1.18(3H, t, J=7.3Hz), 1.10(6H, d, J=6.5Hz). $^{19}$F NMR(300MHz, DMSO-$d_6$): δ −81.92(2F, d, J=73.3Hz). |
| 1138 | 146-149 | 427.27 | ** | | $^1$H NMR(300MHz, DMSO-$d_6$): δ 8.76(1H, s), 7.66(1H, d, J=8.8Hz), 7.62(2H, d, J=8.8Hz), 7.61(1H, d, J=2.0Hz), 7.47(2H, d, J=8.8Hz), 7.27(1H, t, J=74.4Hz), 7.13(1H, dd, J=8.8, 2.0Hz), 6.25(1H, t, J=5.7Hz), 4.21(2H, q, J=7.3Hz), 3.09(2H, q, J=5.8Hz), 1.47-1.25(4H, m), 1.18(3H, t, J=7.0Hz), 0.89(3H, t, J=7.0Hz). $^{19}$F NMR(300MHz, DMSO-$d_6$): δ −81.92(2F, d, J=73.3Hz). |
| 1139 | 179-180 | 411.27 | ** | | $^1$H NMR(300MHz, DMSO-$d_6$): δ 8.92(1H, s), 7.66(1H, d, J=8.8Hz), 7.63(2H, d, J=8.8Hz), 7.61(1H, d, J=2.0Hz), 7.48(2H, d, J=8.8Hz), 7.28(1H, t, J=74.4Hz), 7.13(1H, dd, J=8.8, 2.0Hz), 6.43(1H, t, J=5.8Hz), 5.95-5.80(1H, m), 5.22-5.07(2H, m), 4.21(2H, q, J=7.3Hz), 3.75(2H, t, J=6Hz), 1.19(3H, t, J=7.3Hz). |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| | | | | | $^{19}F$ NMR(300MHz, DMSO-$d_6$): δ −81.92(2F, d, J=73.3Hz). |
| 1140 | 198-202 | 450.2 $[M-H]^-$ | ** | | |
| 1141 | 156-160 | 448.2 $[M-H]^-$ | ** | | |
| 1142 | 110-111 | 487.41 | *** | *** | |
| 1143 | 215-218 | 417.5 | *** | *** | |
| 1144 | 207-210 | 429.5 | *** | *** | |
| 1145 | 205-208 | 445.2 | ** | | |
| 1146 | 187-191 | 430.32 | *** | *** | |
| 1147 | 154-158 | 444.25 | *** | *** | $^1H$ NMR(300MHz, $d_6$-acetone): δ 8.92(s, 1H), 7.82(d, 2H, J=8.7Hz), 7.62-7.49(m, 3H), 7.30(d, 1H, J=2.1Hz), 6.98(dd, 1H, J=8.7, 2.1Hz), 5.095(pentet, 1H, J=9.0Hz), 4.32(m, 1H), 4.17(q, 2H, J=6.9Hz), 2.7-2.8(m, 2H), 2.35-2.5(m, 2H), 1.8-2.0(m, 2H), 1.42(t, 3H, J=6.9Hz), 1.34(d, 3H, J=6.3Hz), 1.0-1.1(m, 1H), 0.6-0.8(m, 3H), 0.5-0.59(m, 1H) |
| 1148 | 193-195 | 402.24 (M−H+) | *** | *** | |
| 1149 | 158-159 | 416.37 (M−H+) | *** | *** | |
| 1150 | 173-175 | 416.32 (M−H+) | *** | *** | $^1H$ NMR(300MHz, $CDCl_3$): δ 7.62(1H, d, J=9.3Hz), 7.58(2H, d, J=8.8Hz), 7.46(2H, d, J=8.8Hz), 7.10(2H, m), 6.77(1H, s), 5.05(1H, m), 4.13(2H, q, J=7.2Hz), 3.97(2H, d, J=6.6Hz), 1.47(3H, t, J=6.9Hz), 1.32(6H, d, J=6.0Hz), 1.05(1H, m), 0.43(2H, m), 0.05(2H, m) |
| 1151 | 171-172 | 432.30 | *** | *** | |
| 1152 | 198-199 | 444.31 (M−H+) | *** | *** | |
| 1153 | 154-155 | 466.28 | *** | *** | |
| 1154 | 207-208 | 444.31 (M−H+) | *** | *** | |
| 1155 | 200-202 | 466.28 | ** | | |
| 1156 | 226-228 | 444.31 (M−H+) | *** | *** | |
| 1157 | 199-201 | 466.28 | *** | *** | |
| 1158 | 173-179 | 442.27 (ES−) | *** | *** | |
| 1159 | 206-208 | (Weak ionization) | *** | *** | |
| 1160 | 193-194 | 422.3 | *** | ** | |
| 1161 | 183-185 | 410.2 | *** | ** | |
| 1162 | 192-193 | 403.3 | ** | | |
| 1163 | 188-189 | 403.2 | ** | | |
| 1164 | 188-190 | 417.2 | *** | * | |
| 1165 | 190-192 | 429.3 | ** | ** | |
| 1166 | 260-266 | 445.25 | ** | | |
| 1167 | 208-212 | 430.25 | *** | *** | |
| 1168 | 218-221 | (Weak ionization) | *** | *** | $^1H$ NMR(300MHz, $d^6$-acetone): δ 8.08(s, 1H), 7.69(d, 2H, J=8.7Hz), 7.54(d, 1H, J=8.7Hz), 7.43(d, 2H, J=8.7Hz), 7.30(d, 1H, J=2.1Hz), 6.97(dd, 1H, J=8.7, 2.1Hz), 6.10(d, 1H, J=8.1Hz), 5.08(pentet, 1H, J=9.3Hz), 4.32(sextet, 1H, J=8.1Hz), 4.16(q, 2H, J=6.9Hz), 2.7-2.85(m, 2H), 2.35 2.5(m, 2H), 2.15-2.35(m, 2H), 1.8 2.0(m, 4H), 1.6-1.7(m 2H), 1.42(t, 3H, J=6.9Hz) |
| 1169 | 224-226 | 432.3 | *** | *** | |
| 1170 | 180-181 | 469.3 | ** | | |
| 1171 | 219-220 | 431.2 | *** | *** | |
| 1172 | 198-199 | 431.33 | *** | *** | |
| 1173 | 203-205 | 443.31 | *** | *** | |
| 1174 | 180-181 | 436.28 | *** | *** | |
| 1175 | 202-203 | 456.27 | *** | *** | |
| 1176 | 170-172 | 390.2 | ** | | |
| 1177 | 145-147 | 404.2 | *** | ** | |
| 1178 | 182-183 | 418.3 | *** | *** | |
| 1179 | 173-174 | 430.2 | ** | | |
| 1180 | 179-180 | 402.2 | ** | | |
| 1181 | 179-180 | 424.2 | ** | | |
| 1182 | 162-163 | 422.2 | *** | * | |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| 1183 | 202.3-205.9 | 440.3 | *** | | $^1H$ NMR(CD3CN, 300MHz), δ 8.86(s, 1H), 8.66(s, 1H), 7.80(d, J=8.7Hz, 2H), 7.58-7.49(m, 4H), 7.42(s, 1H), 7.09(d, J=2.1Hz, 1H), 6.95(dd, J=2.1Hz and 8.7Hz, 1H), 4.58(t, J=4.8Hz, 2H), 4.42(t, J=4.8Hz, 2H), 4.16(q, J=6.9Hz, 2H), 1.76-1.67(m, 1H), 1.25(t, J=7.2Hz, 3H), 0.95-0.89(m, 4H). |
| 1184 | 165.4-170.1 | 440.3 | ** | | $^1H$ NMR(CD3CN, 300MHz), δ 8.81(s, 1H), 7.79(d, J=8.7Hz, 2H), 7.70(d, J=2.1Hz, 1H), 7.54-7.49(m, 4H), 7.02(d, J=2.1Hz, 1H), 6.88(dd, J=2.1Hz and 8.7Hz, 1H), 6.30(t, J=1.8Hz, 1H), 4.57(t, J=4.8Hz, 2H), 4.44(t, J=5.1Hz, 2H), 4.13(q, J=7.2Hz, 2H), 1.73-1.68(m, 1H), 1.24(t, J=7.2Hz, 3H), 0.95-0.82(m, 4H). |
| 1185 | 211-213 | 454.30 | *** | | $^1H$ NMR(300MHz, DMSO-$d_6$): δ 8.76-8.70(2H, m), 8.53(1H, d, J=4.7Hz), 7.91(1H, d, J=7.9Hz), 7.60(2H, d, J=8.5Hz), 7.51(1H, d, J=8.5Hz), 7.46-7.38(8H, m), 7.00(1H, dd, J=8.5, 1.2Hz), 6.27(1H, t, J=5.6Hz), 5.25(2H, s), 4.18(2H, q, J=7.0Hz), 3.05(2H, q, J=6.4Hz), 1.44(2H, hx, J=7.3Hz), 1.17(3H, t, J=7.0Hz), 0.87(3H, t, J=7.4Hz). |
| 1186 | 150 | 464.34 (M−H+) | ** | | $^1H$ NMR(300MHz, DMSO-$d_6$): δ 9.90(1H, s), 7.67(1H, d, J=8.8Hz), 7.66(2H, d, J=8.8Hz), 7.58(1H, d, J=2.0Hz), 7.48(2H, d, J=8.8Hz), 7.29(1H, t, J=74.4Hz), 7.15(1H, dd, J=8.8, 2.0Hz), 5.13-5.08(1H, m), 4.99(1H, p, J=8.5Hz), 2.55-2.40(2H, m), 2.37-2.24(2H, m), 1.92-1.57(10H, m). $^{19}F$ NMR(300MHz, DMSO-$d_6$): δ −82.08(2F, d, J=73.3Hz). |
| 1187 | 198-199 | 439.29 | ** | | $^1H$ NMR(300MHz, DMSO-$d_6$): δ 8.76(1H, s), 7.67(1H, d, J=8.5Hz), 7.59(2H, d, J=8.8Hz), 7.58(1H, d, J=2.0Hz), 7.42(2H, d, J=8.8Hz), 7.29(1H, t, J=74.4Hz), 7.14(1H, dd, J=8.5, 2.0Hz), 6.28(1H, t, J=5.7Hz), 5.00(1H, p, J=8.6Hz), 3.05(2H, q, J=6.1Hz), 2.59-2.42(2H, m), 2.39-2.24(2H, m), 1.84-1.66(2H, m), 1.44(2H, hx, J=7.0Hz), 0.87(3H, t, J=7.4Hz). $^{19}F$ NMR(300MHz, DMSO-$d_6$): δ −82.05(2F, d, J=73.3Hz). |
| 1188 | 222-223 | 474.25 | ** | | $^1H$ NMR(300MHz, DMSO-$d_6$): δ 10.26(1H, s), 7.70(1H, d, J=8.8Hz), 7.54(2H, d, J=8.8Hz), 7.40(1H, d, J=2.0Hz), 7.39(2H, d, J=8.8Hz), 7.29(1H, t, J=74.4Hz), 7.16(1H, dd, J=8.8, 2.0Hz), 4.71(1H, p, J=9.1Hz), 3.24-3.19(2H, m), 2.22-1.60(10H, m), 0.97(3H, t, J=7.4Hz). $^{19}F$ NMR(300MHz, DMSO-$d_6$): δ −82.05(2F, d, J=73.3Hz). |
| 1189 | 183-158 | 472.24 | *** | *** | $^1H$ NMR(300MHz, DMSO-$d_6$): δ 10.24(1H, s), 7.70(1H, d, J=8.8Hz), 7.55(2H, d, J=8.8Hz), 7.44(2H, d, J=8.8Hz), 7.40(1H, d, J=2.0Hz), 7.30(1H, t, J=74.4Hz), 7.16(1H, dd, J=8.8, 2.0Hz), 4.71(1H, p, J=9.1Hz), 2.84-2.75(1H, m), 2.20-1.84(6H, |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| | | | | | m), 1.65-1.60(2H, m), 1.05-0.95(2H, m), 0.60-0.49(2H, m). $^{19}$F NMR(300MHz, DMSO-$d_6$): δ −82.05(2F, d, J=75.3Hz). |
| 1190 | 185-186 | 465.27 | ** | | $^{1}$H NMR(300MHz, DMSO-$d_6$): δ 8.60(1H, s), 7.67(1H, d, J=8.8Hz), 7.58(1H, d, J=1.9Hz), 7.57(2H, d, J=8.8Hz), 7.42(2H, d, J=8.8Hz), 7.29(1H, t, J=74.4Hz), 7.14(1H, dd, J=8.8, 1.9Hz), 6.30(1H, d, J=7.3Hz), 5.00(1H, p, J=8.6Hz), 3.94(1H, hx, J=6.7Hz), 2.60-2.40(2H, m), 2.38-2.23(2H, m), 1.90-1.34(10H, m). $^{19}$F NMR(300MHz, DMSO-$d_6$): δ −82.05(2F, d, J=75.3Hz). |
| 1191 | 216-219 | 415.31 | ** | | |
| 1192 | 159-162 | 489.37 | ** | | |
| 1193 | 213-214 | 404.3 | *** | | |
| 1194 | 196-197 | 418.3 | *** | *** | |
| 1195 | 114-115 | 418.3 | *** | *** | |
| 1196 | 124-125 | 416.3 | *** | *** | |
| 1197 | 118-119 | 432.3 | ** | *** | |
| 1198 | 181-182 | 432.3 | *** | *** | |
| 1199 | 187-188 | 444.3 | *** | *** | |
| 1200 | 188-189 | 446.3 | *** | *** | |
| 1201 | 182-183 | 466.3 | *** | *** | |
| 1202 | 195-197 | 406.3 | *** | *** | |
| 1203 | 184-187 | 420.3 | *** | *** | |
| 1204 | 168-169 | 420.3 | *** | *** | |
| 1205 | 155-157 | 445.3 | *** | *** | |
| 1206 | 178-180 | 434.3 | *** | *** | |
| 1207 | 204-205 | 448.3 | *** | *** | |
| 1208 | 186-190 | 444.30 | *** | *** | |
| 1209 | 189-192 | 456.30 (ES−) | *** | *** | |
| 1210 | 148-152 | 503.36 | *** | *** | |
| 1211 | 203-205 | 458.3 | *** | *** | |
| 1212 | 192-193 | 480.34 | *** | *** | |
| 1213 | 192-193 | 480.33 | *** | *** | |
| 1214 | 170-173 | 457.3 | *** | *** | |
| 1215 | 200-204 | 446.26 | *** | *** | |
| 1216 | 205-209 | 460.31 | ** | | |
| 1217 | 135-141 | 388.34 | ** | | |
| 1218 | 192-193 | 481.31 | *** | *** | |
| 1219 | 192-193 | 507.35 | *** | *** | |
| 1220 | 192-193 | 481.28 | *** | *** | |
| 1221 | 222-225 | 431.3 | *** | *** | |
| 1222 | 191-192 | 446.35 | ** | | |
| 1223 | 206-208 | 417.3 | *** | *** | |
| 1224 | 191-192 | 417.3 | ** | | |
| 1225 | 183-184 | 431.3 | ** | *** | |
| 1226 | 189-190 | 443.3 | *** | *** | |
| 1227 | 168-169 | 479.3 | *** | *** | |
| 1228 | 174-175 | 423.5 | ** | | |
| 1229 | 163-164 | 438.3 | ** | | |
| 1230 | 179-180 | 436.3 | ** | | |
| 1231 | 189-191 | 424.2 | ** | | |
| 1232 | 184-185 | 404.2 | *** | ** | |
| 1233 | 192-193 | 430.4 | *** | *** | |
| 1234 | 204-205 | 390.1 | ** | | |
| 1235 | 209-211 | 410.1 | ** | | |
| 1236 | 196-197 | 404.14 | *** | *** | |
| 1237 | 150-151 | 432.1 | ** | | |
| 1238 | 176-177 | 458.4 | ** | | |
| 1239 | 187-193 | 360.35 | *** | *** | |
| 1240 | 168-170 | 460.38 | *** | *** | |
| 1241 | 151-168 | 432.3 | *** | *** | |
| 1242 | 134-136 | 446.3 | *** | *** | |
| 1243 | 161-163 | 446.3 | *** | *** | |
| 1244 | 145-147 | 446.3 | *** | *** | |
| 1245 | 245-246 | 318.3 | ** | | |
| 1246 | 157-163 | 434.4 | *** | *** | |
| 1247 | 188-190 | 432.4 | *** | *** | |
| 1248 | 207-210 | 462.4 | *** | *** | |
| 1249 | 181-184 | 448.4 | *** | *** | |

TABLE 1B-continued

| Compound Number | Melting Point (° C.) | Mass Spec [M + H] | Replicon $IC_{50}$ μM 2-day | Replicon $IC_{50}$ μM 3-day | NMR Data |
|---|---|---|---|---|---|
| 1250 | 144-148 | 448.38 | *** | *** | |
| 1251 | 137-142 | (Weak ionization) | ** | ** | |
| 1252 | 131-134 | 446.37 | ** | | |
| 1253 | 224 | 517.3 | ** | | |
| 1254 | 189 | 498.6 | *** | *** | $^1$H NMR(300MHz, DMSO-$d_6$): δ 9.89(1H), 7.64(3H), 7.46(3H), 7.19(2H), 6.94(1H), 6.87(1H), 4.91(2H), 4.19(2H), 4.01(2H), 2.48(2H), 2.21(2H), 2.17(2H), 1.71(2H), 1.27(6H) |
| 1255 | 208 | 499.4 | *** | *** | $^1$H NMR(300MHz, DMSO-$d_6$): δ 9.91(1H), 8.53(1H), 7.97(1H), 7.65(2H), 7.46(3H), 7.19(1H), 6.92(1H), 4.95(2H), 4.39(2H), 4.06(2H), 2.48(2H), 2.67(4H), 1.72(2H), 1.24(6H). |
| 1256 | 188.4-191.3 | 467.1 | | *** | $^1$H NMR(($CD_3CN$, 300Hz), δ 7.60(d, J=9.0Hz, 2H), 7.53(d, J=8.7Hz, 1H), 7.47-7.23(m, 7H), 7.04(s, 1H), 6.91(dd, J=2.1Hz and 6.6Hz, 1H), 5.31-5.27(m, 1H), 4.16-4.07(m, 4H), 4.45(q, J=6.6Hz, 2H), 2.83(t, J=6.6Hz, 2H), 1.69-1.61(m, 2H), 1.41(t, J=6.9Hz, 3H), 0.71(t, J=7.5Hz, 3H). |
| 1257 | | 541.55 | | *** | |
| 1258 | | 527.55 | | *** | |
| 1259 | | 526.57 | | *** | |
| 1260 | 208 | 503.5 | | *** | |
| 1261 | 156 | 530.5 | | *** | |
| 1262 | 167 | 533.5 | | ** | |
| 1263 | 155-157 | 458.4 (ES−) | | *** | |
| 1264 | 177-180 | 467.40 | | *** | |
| 1265 | 164-167 | 432.37 | | *** | |
| 1266 | 175-176 | 453.34 | | ** | $^1$H NMR(300MHz, $CDCl_3$): δ 7.70(1H, d, J=8.8Hz), 7.55(2H, d, J=8.8Hz), 7.42(2H, d, J=8.8Hz), 7.29(1H, d, J=1.8Hz), 7.22(1H, br s), 7.13(1H, dd, J=8.8, 1.8Hz), 6.81(1H, t, J=74.4Hz), 4.02(2H, d, J=6.7Hz), 3.82(1H, hx, J=6.4Hz), 1.51(2H, p, J=7.1Hz), 1.17(3H, d, J=6.7Hz), 1.07-0.99(1H, m), 0.94(3H, t, J=7.4Hz), 0.48-0.41(2H, m), 0.09-0.04(2H, m). $^{19}$F NMR(300MHz, $CDCl_3$): δ −80.81(2F, d, J=73.3Hz). |
| 1267 | 139-140 | 466.06 | | ** | $^1$H NMR(300MHz, $CDCl_3$): δ 7.72(1H, d, J=8.8Hz), 7.59(2H, d, J=8.8Hz), 7.47(2H, d, J=8.8Hz), 7.28(1H, d, J=1.8Hz), 7.12(1H, dd, J=8.8, 1.8Hz), 6.79(1H, br s), 6.56(1H, t, J=74.4Hz), 4.35(1H, dq, J=8.6, 6.7Hz), 4.02(2H, d, J=6.7Hz), 1.39(3H, d, J=6.7Hz), 1.11-0.99(2H, m), 0.64-0.43(5H, m), 0.34-0.28(1H, m), 0.09-0.04(2H, m). $^{19}$F NMR(300MHz, $CDCl_3$): δ −80.75(2F, d, J=75.3Hz). |
| 1268 | 145-146 | 454.30 | | ** | $^1$H NMR(300MHz, $CDCl_3$): δ 7.73(1H, d, J=8.5Hz), 7.60(2H, d, J=8.8Hz), 7.47(2H, d, J=8.8Hz), 7.28(1H, d, J=1.8Hz), 7.12(1H, t, J=8.5, 1.8Hz), 6.76(1H, br s), 6.56(1H, t, J=74.4Hz), 4.89(1H, hx, J=6.4Hz), 4.02(2H, d, J=6.7Hz), 1.74-1.59(2H, m), 1.30(3H, d, J=6.1Hz), 1.11-1.00(1H, m), 0.97(3H, t, J=7.4Hz), 0.49-0.43(2H, m), 0.09-0.04(2H, m). $^{19}$F NMR(300MHz, $CDCl_3$): δ −80.75(2F, d, J=73.3Hz). |

TABLE 1B-continued

| Compound Number | Melting Point (° C.) | Mass Spec [M + H] | Replicon IC50 μM 2-day | Replicon IC50 μM 3-day | NMR Data |
|---|---|---|---|---|---|
| 1269 | 112 | 461.4 | | *** | |
| 1270 | 158 | 475.5 | | *** | |
| 1271 | 192 | 503.5 | | *** | |
| 1272 | 199 | 515.6 | | *** | |
| 1273 | 212 | 519.5 | | ** | |
| 1274 | 139 | 505.5 | | *** | |
| 1275 | 115 | 484.5 | | *** | |
| 1276 | 214 | 485.4 | | *** | |
| 1277 | 208 | 473.5 | | *** | |
| 1278 | 181 | 489.5 | | *** | |
| 1279 | 205-207 | 473.43 | | *** | |
| 1280 | 175-176 | 490.35 (M−H+) | | *** | |
| 1281 | 168-169 | 500.47 | | *** | |
| 1282 | 196-197 | 486.43 | | *** | |
| 1283 | 169-170 | 486.42 (M−H+) | | *** | |
| 1284 | 154-155 | 498.31 (M−H+) | | *** | |
| 1285 | 168-170 | 472.39 (M−H+) | | *** | |
| 1286 | 161-163 | 486.43 | | *** | |
| 1287 | 141-143 | 498.27(M−H+) | | *** | |
| 1288 | 211-213 | 485.42 | | *** | |
| 1289 | 178-185 | 478.32 (ES−) | | *** | |
| 1290 | 172-174 | 444.39 (ES−) | | *** | |
| 1291 | 177-178 | 430.4 | | *** | |
| 1292 | 202-203 | 430.4 | | *** | |
| 1293 | 193-194 | 430.4 | | *** | |
| 1294 | 155-157 | 444.4 | | *** | |
| 1295 | 174-175 | 444.4 | | *** | |
| 1296 | 170-171 | 444.4 | | ** | |
| 1297 | 163-165 | 446.4 | | ** | |
| 1298 | 178-180 | 446.4 | | ** | |
| 1299 | 150-152 | 448.4 | | ** | |
| 1300 | 201-203 | 432.31 | | *** | |
| 1301 | 216-218 | 431.37 | | *** | |
| 1302 | 226-227 | 417.4 | | ** | |
| 1303 | 215-216 | 417.3 | | ** | |
| 1304 | 209-211 | 415.3 | | ** | |
| 1305 | | 443.4 | | *** | |
| 1306 | 155-160 | 516.5 | | ** | |
| 1307 | 115-119 | 529.5 | | ** | |
| 1308 | 109-110 | 497.7 | | *** | |
| 1309 | 210-212 | 500.6 | | *** | |
| 1310 | 129-131 | 374.4 | | ** | |
| 1311 | 205-207 | 346.4 | | *** | |
| 1312 | 180-185 | 458.43 (ES−) | | *** | |
| 1313 | 155-160 | 448.07 | | *** | |
| 1314 | 88-90 | 498.5 | | *** | |
| 1315 | 125-130 | 502.5 | | ** | |
| 1316 | 110-112 | 472.5 | | *** | |
| 1317 | 122-125 | 472.5 | | *** | |
| 1318 | 130-134 | 484.5 | | *** | |
| 1319 | 108-113 | 460.5 | | *** | |
| 1320 | 98-101 | 474.5 | | *** | |
| 1321 | 83-87 | 504.6 | | ** | |
| 1322 | 112-115 | 483.5 | | *** | |
| 1323 | 148-150 | 432.4 | | *** | |
| 1324 | 227-229 | 433.4 | | *** | |
| 1325 | 195-198 | 417.4 | | *** | |
| 1326 | 246-248 | 431.4 | | ** | |
| 1327 | 93 | 487.5 | | *** | |
| 1328 | 162 | 510.5 | | *** | |
| 1329 | 98 | 511.4 | | *** | |

Example 7

Evaluation of the Activity of Compounds Using an HCV-Poliovirus Chimera

In a HCV-poliovirus (HCV-PV) chimera, the PV 5' UTR is replaced by the HCV 5' UTR and partial (the first 123 amino acids) core coding sequences (nucleotides 18 to 710 of HCV 1b) as shown in FIG. 1 (139, 140). As a consequence, the expression of poliovirus proteins is under regulation of the HCV IRES. Poliovirus is a picornavirus in which protein translation initiation is mediated by an IRES element located in the 5' UTR. At the 5' end of the HCV-PV chimeric genome, there is the cloverleaf-like RNA structure of PV, an essential cis-acting replication signal ending with the genome-linked protein VPg. Replication kinetics of the HCV-PV chimera matches that of the parental poliovirus (Mahoney) and can result in cytopathic effects (CPE) in cell culture. Heptazyme (29), a ribozyme that targets the HCV IRES, was shown to be active against the chimeric virus in cell culture (76, 77).

To evaluate compounds for activity against the chimeric virus, HeLa cells are seeded and incubated at 37° C. under 5% $CO_2$ for 24 hours. The cells are then infected with HCV-PV at a multiplicity of infection (MOI) at 0.1 for 30 min and then treated with compound for 1 day (treatment time will be optimized). The activity of compounds is determined by a change in cytopathic effect, plaque assay, and/or viral RNA production (see e.g., Tables 1A and 1B).

Example 8

Evaluation of the Activity of Compounds Against a Wild-Type Poliovirus (WT-PV) and the Poliovirus IRES Translation Assay (WT-PV Mono Luc)

A DNA construct is prepared, termed pPVIRESmono, in which PV IRES sequences are inserted (nucleotide number 1-742) between a promoter and the firefly luciferase (Fluc) reporter gene. A stably transfected 293 T cell line, is established by transfection with the pPVIRESmono DNA by selecting for resistance to hygromycin. As previously described, cells are treated with compounds for 20 hours, and activity is determined by quantifying the Fluc signal. Additionally, to evaluate compounds activity against wild-type poliovirus, Helacells are seeded and incubated at 37° C. under 5% $CO_2$ for 24 hours. Cells are then infected with wild-type poliovirus at a MOI at 0.1 for 30 minutes, and then treated with compound for one day. The activity of compounds is determined by changes in cytopathic effect, plaque assay, and RT-PCR using poliovirus IRES primers and probes (see e.g., Table 2).

Furthermore, if compounds are active against the poliovirus and other virus IRES, then the compounds may be useful for treating viral infection by any virus containing an IRES.

TABLE 2

| Compound No. | WT-PV CPE (100 μM)* | WT-PV CPE (10 μM)* | WT-PV CPE (1 μM)* | WTPV mono luc $IC_{50}$ (μM) |
|---|---|---|---|---|
| 4 | 3 | 2 | 1 | 0.8 |
| 5 | 3 | 2 | 1 | 9 |
| 9 | 3 | 2 | 2 | >100 |
| 10 | 3 | 2 | 2 | >100 |
| 19 | 3 | 2 | 1 | 15 |
| 24 | 3 | 2 | 2 | 1.5 |

Example 9

In Vitro Translation Assay

In vitro translation assays can be used to distinguish between the compounds that act on HCV IRES RNA or cellular translation factors. In exemplary assays, the mRNA that will direct translation is a transcribed runoff product from the T7 RNA polymerase promoter of the pHCVIRESmono plasmid DNA generated with Ambion RNA MegaTranscript kit (Ambion, Inc., Austin, Tex.). In vitro translation is performed using HeLa cell lysates using methods known to one of skill in the art. Preliminary results indicate that one or more of the compounds of the present invention has significantly higher activity against HCV IRES regulated translation after preincubating the compound with the HCV IRES RNA transcripts than after preincubating with HeLa cell lysate for 30 min at 37° C. or without preincubation (data not shown). This suggests that this compound may interact with the HCV IRES RNA in the in vitro translation assay. To demonstrate whether the compounds selectively act on the HCV IRES, pLuc is used together with cellular IRES mRNA transcripts as controls for in vitro translation.

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

REFERENCES

1. Ali, N., G. J. Pruijn, D. J. Kenan, J. D. Keene, and A. Siddiqui. 2000. Human La antigen is required for the hepatitis C virus internal ribosome entry site-mediated translation. J Biol Chem 275:27531-27540.
2. Ali, N. and A. Siddiqui. 1995. Interaction of polypyrimidine tract-binding protein with the 5' noncoding region of the hepatitis C virus RNA genome and its functional requirement in internal initiation of translation. J Virol 69:6367-6375.
3. Ali, N. and A. Siddiqui. 1997. The La antigen binds 5' noncoding region of the hepatitis C virus RNA in the context of the initiator AUG codon and stimulates internal ribosome entry site-mediated translation. Proc Natl Acad Sci USA 94:2249-2254.
4. Anwar, A., N. Ali, R. Tanveer, and A. Siddiqui. 2000. Demonstration of functional requirement of polypyrimidine tract-binding protein by SELEX RNA during hepatitis C virus internal ribosome entry site-mediated translation initiation. J Biol Chem 275:34231-34235.
5. Beales, L. P., D. J. Rowlands, and A. Holzenburg. 2001. The internal ribosome entry site (IRES) of hepatitis C virus visualized by electron microscopy. RNA 7:661-670.
6. Belsham, G. J. and J. K. Brangwyn. 1990. A region of the 5' noncoding region of foot-and-mouth disease virus RNA directs efficient internal initiation of protein synthesis within cells: involvement with the role of L protease in translational control. J Virol 64:5389-5395.
7. Belsham, G. J. and R. J. Jackson. 2000. Translation initiation on picornavirus RNA., p. 869-900. Cold Spring Harbor Laboratory Press, New York.
8. Blight, K. J., A. A. Kolykhalov, and C. M. Rice. 2000. Efficient initiation of HCV RNA replication in cell culture. Science 290:1972-1974.
9. Blight, K. J., J. A. McKeating, and C. M. Rice. 2002. Highly permissive cell lines for subgenomic and genomic hepatitis C virus RNA replication. J Virol 76:13001-13014.
10. Borvjagin, G., T. Pestova, and I. Shatsky. 1994. Pyrimidine tract binding protein strongly stimulates in vitro encephalomyocarditis virus RNA translation at the level of the preinitiation complex formation. FEBS Lett 351:291-302.
11. Brown, E. A., H. Zhang, L. H. Ping, and S. M. Lemon. 1992. Secondary structure of the 5' nontranslated regions of hepatitis C virus and pestivirus genomic RNAs. Nucleic Acids Res 20:5041-5045.
12. Buck C B, Shen X, Egan M A, Pierson T C, Walker C M, and Siliciano R F. 2001. The human immunodeficiency virus type 1 gag gene encodes an internal ribosome entry site. J Virol 75:181-191.

13. Bukh, J., R. H. Purcell, and R. H. Miller. 1992. Sequence analysis of the 5' noncoding region of hepatitis C virus. Proc Natl Acad Sci USA 89:4942-4946.

14. Bukh, J., R. H. Purcell, and R. H. Miller. 1994. Sequence analysis of the core gene of 14 hepatitis C virus genotypes. Proc Natl Acad Sci USA 91:8239-8243.

15. Buratti, E., S. Tisminetzky, M. Zotti, and F. E. Baralle. 1998. Functional analysis of the interaction between HCV 5'UTR and putative subunits of eukaryotic translation initiation factor eIF3. Nucleic Acids Res 26:3179-3187.

16. Chappell, S. A., J. P. LeQuesne, F. E. Paulin, M. L. deSchoolmeester, M. Stoneley, R. L. Soutar, S. H. Ralston, M. H. Helfrich, and A. E. Willis. 2000. A mutation in the c-myc-IRES leads to enhanced internal ribosome entry in multiple myeloma: a novel mechanism of oncogene de-regulation. Oncogene 19:4437-4440.

17. Chung, R. T., W. He, A. Saquib, A. M. Contreras, R. J. Xavier, A. Chawla, T. C. Wang, and E. V. Schmidt. 2001. Hepatitis C virus replication is directly inhibited by IFN-alpha in a full-length binary expression system. Proc Natl Acad Sci USA 98:9847-9852.

18. Coldwell, M. J., S. A. Mitchell, M. Stoneley, M. MacFarlane, and A. E. Willis. 2000. Initiation of Apaf-1 translation by internal ribosome entry. Oncogene 19:899-905.

19. Creancier, L., D. Morello, P. Mercier, and A. C. Prats. 2000. Fibroblast growth factor 2 internal ribosome entry site (IRES) activity ex vivo and in transgenic mice reveals a stringent tissue-specific regulation. J Cell Biol 150:275-281.

20. Das, S., M. Ott, A. Yamane, A. Venkatesan, S. Gupta, and A. Dasgupta. 1998. Inhibition of internal entry site (IRES)-mediated translation by a small yeast RNA: a novel strategy to block hepatitis C virus protein synthesis. Front Biosci 3:D1241-D1252.

21. Dever, T. E. 2002. Gene-specific regulation by general translation factors. Cell 108:545-556.

22. Dumas, E., C. Staedel, M. Colombat, S. Reigadas, S. Chabas, T. Astier-Gin, A. Cahour, S. Litvak, and M. Ventura. 2003. A promoter activity is present in the DNA sequence corresponding to the hepatitis C virus 5' UTR. Nucleic Acids Res 31:1275-1281.

23. Fukushi, S., K. Katayama, C. Kurihara, N. Ishiyama, F. B. Hoshino, T. Ando, and A. Oya. 1994. Complete 5' noncoding region is necessary for the efficient internal initiation of hepatitis C virus RNA. Biochem Biophys. Res Commun. 199:425-432.

24. Fukushi, S., C. Kurihara, N. Ishiyama, F. B. Hoshino, A. Oya, and K. Katayama. 1997. The sequence element of the internal ribosome entry site and a 25-kilodalton cellular protein contribute to efficient internal initiation of translation of hepatitis C virus RNA. J Virol 71:1662-1666.

25. Fukushi, S., M. Okada, T. Kageyama, F. B. Hoshino, and K. Katayama. 1999. Specific interaction of a 25-kilodalton cellular protein, a 40S ribosomal subunit protein, with the internal ribosome entry site of hepatitis C virus genome. Virus Genes 19:153-161.

26. Fukushi, S., M. Okada, J. Stahl, T. Kageyama, F. B. Hoshino, and K. Katayama. 2001. Ribosomal protein S5 interacts with the internal ribosomal entry site of hepatitis C virus. J Biol Chem 276:20824-20826.

27. Funkhouser, A. W., D. E. Schultz, S. M. Lemon, R. H. Purcell, and S. U. Emerson. 1999. Hepatitis A virus translation is rate-limiting for virus replication in MRC-5 cells. Virology 254:268-278.

28. Glass, M. J., X. Y. Jia, and D. F. Summers. 1993 Identification of the hepatitis A virus internal ribosome entry site: in vivo and in vitro analysis of bicistronic RNAs containing the HAV 5' noncoding region. Virology. 193:842-852.

29. Gordon S. C., B. R. Bacon, I. M. Jacobson, M. I. Shiffman, N. H. Afdhal, J. G. McHutchison, T. J. Kwoh, and F. A. Dorr. 2002. A Phase II, 12-week study of ISIS 14803, an antisense inhibitor of HCV for the treatment of chronic hepatitis C. AASLD Abst. 795. Hepatology 36:362A.

30. Gosert, R., K. H. Chang, R. Rijnbrand, M. Yi, D. V. Sangar, and S. M. Lemon. 2000. Transient expression of cellular polypyrimidine-tract binding protein stimulates cap-independent translation directed by both picornaviral and flaviviral internal ribosome entry sites In vivo. Mol Cell Biol 20:1583-1595.

31. Gray, N, and M. Wickens. 1998. Control of translation initiation in animals. Annu Rev Cell Dev Biol 14:399-458.

31a. Griffith, A., and D. M. Coen. 2005. An unusual internal ribosome entry site in the herpes simplex virus thymidine kinase gene. Proc Natl Acad Sci USA 102:9667-9672.

32. Guo, J. T., V. V. Bichko, and C. Seeger. 2001. Effect of alpha interferon on the hepatitis C virus replicon. J Virol 75:8516-8523.

33. Hahm, B., Y. K. Kim, J. H. Kim, T. Y. Kim, and S. K. Jang. 1998. Heterogeneous nuclear ribonucleoprotein L interacts with the 3' border of the internal ribosomal entry site of hepatitis C virus. J Virol 72:8782-8788.

34. Haller, A. A., S. R. Stewart, and B. L. Semler. 1996. Attenuation stem-loop lesions in the 5' noncoding region of poliovirus RNA: neuronal cell-specific translation defects. J Virol 70:1467-1474.

35. Hellen, C. U., and T. V. Pestova. 1999. Translation of hepatitis C virus RNA. J Viral Hepat 6:79-87.

36. Hellen, C. U., G. W. Witherell, M. Schmid, S. H. Shin, T. V. Pestova, A. Gil, and E. Wimmer. 1993. A cytoplasmic 57-kDa protein that is required for translation of picornavirus RNA by internal ribosomal entry is identical to the nuclear pyrimidine tract-binding protein. Proc Natl Acad Sci USA 90:4672-7646

37. Hendrix, M., E. S. Priestley, G. F. Joyce, and C. H. Wong. 1997. Direct observation of aminoglycoside-RNA interactions by surface plasmon resonance. Journal of the American Chemical Society 119:3641-3648.

38. Holcik, M. and R. G. Korneluk. 2000. Functional characterization of the X-linked inhibitor of apoptosis (XIAP) internal ribosome entry site element: role of La autoantigen in XIAP translation. Mol Cell Biol 20:4648-4657.

39. Holcik, M., C. Lefebvre, C. Yeh, T. Chow, and R. G. Korneluk. 1999. A new internal-ribosome-entry-site motif potentiates XIAP-mediated cytoprotection. Nat Cell Biol 1:190-192.

40. Honda, M., M. R. Beard, L. H. Ping, and S. M. Lemon. 1999. A phylogenetically conserved stem-loop structure at the 5' border of the internal ribosome entry site of hepatitis C virus is required for cap-independent viral translation. J. Virol 72:1165-1174.

41. Honda, M., E. A. Brown, and S. M. Lemon. 1996. Stability of a stem-loop involving the initiator AUG controls the efficiency of internal initiation of translation on hepatitis C virus RNA. RNA 2:955-968.

42. Honda, M., L. H. Ping, R. C. Rijnbrand, E. Amphlett, B. Clarke, D. Rowlands, and S. M. Lemon. 1996. Structural requirements for initiation of translation by internal ribosome entry within genome-length hepatitis C virus RNA. Virology 222:31-42.

43. Honda, M., R. Rijnbrand, G. Abell, D. Kim, and S. M. Lemon. 1999. Natural variation in translational activities of the 5' nontranslated RNAs of hepatitis C virus genotypes 1a and 1b: evidence for a long-range RNA-RNA interaction outside of the internal ribosomal entry site. J Virol 73:4941-4951.

44. Huez, I., S. Bornes, D. Bresson, L. Creancier, and H. Prats. 2001. New vascular endothelial growth factor isoform generated by internal ribosome entry site-driven CUG translation initiation. Mol Endocrinol. 15:2197-2210.

45. Huez, I., L. Creancier, S. Audigier, M. C. Gensac, A. C. Prats, and H. Prats. 1998. Two independent internal ribosome entry sites are involved in translation initiation of vascular endothelial growth factor mRNA. Mol Cell Biol 18:6178-6190

46. Ikeda, M., M. Yi, K. Li, and S. M. Lemon. 2002. Selectable subgenomic and genome-length dicistronic RNAs derived from an infectious molecular clone of the HCV-N strain of hepatitis C virus replicate efficiently in cultured Huh7 cells. J Virol 76:2997-3006.

47. Irvine, J. D., L. Takahashi, K. Lockhart, J. Cheong, J. W. Tolan, H. E. Selick, and J. R. Grove. 1999. MDCK (Madin-Darby canine kidney) cells: A tool for membrane permeability screening. J Pharm Sci 88:28-33.

48. Isoyama, T., N. Kamoshita, K. Yasui, A. Iwai, K. Shiroki, H. Toyoda, A. Yamada, Y. Takasaki, and A. Nomoto. 1999. Lower concentration of La protein required for internal ribosome entry on hepatitis C virus RNA than on poliovirus RNA. J Gen Virol 80 (Pt 9):2319-2327.

49. Ito, T. and M. M. Lai. 1999. An internal polypyrimidine-tract-binding protein-binding site in the hepatitis C virus RNA attenuates translation, which is relieved by the 3'-untranslated sequence. Virology 254:288-296.

50. Jang, S. K., H. G. Krausslich, M. J. Nicklin, G. M. Duke, A. C. Palmenberg, and E. Wimmer. 1988. A segment of the 5' nontranslated region of encephalomyocarditis virus RNA directs internal entry of ribosomes during in vitro translation. J Virol 62:2636-2643.

51. Jubin, R., N. E. Vantuno, J. S. Kieft, M. G. Murray, J. A. Doudna, J. Y. Lau, and B. M. Baroudy. 2000. Hepatitis C virus internal ribosome entry site (IRES) stem loop IIId contains a phylogenetically conserved GGG triplet essential for translation and IRES folding. J Virol 74:10430-10437.

52. Kalliampakou, K. I., L. Psaridi-Linardaki, and P. Mavromara. 2002. Mutational analysis of the apical region of domain II of the HCV IRES. FEBS Lett 511:79-84.

53. Kaminski, A., S. L. Hunt, J. G. Patton, and R. J. Jackson. 1995. Direct evidence that polypyrimidine tract binding protein (PTB) is essential for internal initiation of translation of encephalomyocarditis virus RNA.RNA 1:924-938

54. Kamoshita, N., K. Tsukiyama-Kohara, M. Kohara, and A. Nomoto. 1997. Genetic analysis of internal ribosomal entry site on hepatitis C virus RNA: implication for involvement of the highly ordered structure and cell type-specific transacting factors. Virology 233:9-18.

55. Kieft, J. S., K. Zhou, R. Jubin, M. G. Murray, J. Y. Lau, and J. A. Doudna. 1999. The hepatitis C virus internal ribosome entry site adopts an ion-dependent tertiary fold. J Mol Biol 292:513-529.

56. Kieft, J. S., K. Zhou, R. Jubin, M. G. Murray, J. Y. Lau, and J. A. Doudna. 2001. Mechanism of ribosome recruitment by hepatitis C IRES RNA. RNA 7:194-206.

57. Klinck, R., E. Westhof, S. Walker, M. Afshar, A. Collier, and F. Aboul-Ela. 2000. A potential RNA drug target in the hepatitis C virus internal ribosomal entry site. RNA 6:1423-1431.

58. Kolupaeva V G, Pestova T V, and Hellen C U T. 2000. An enzymatic foot-printing analysis of the interaction of 40S ribosomal subunits with the internal ribosomal entry site of hepatitis C virus. J Virol 74:6242-6250.

59. Kolupaeva, V. G., C. U. Hellen, and I. N. Shatsky. 1996. Structural analysis of the interaction of the pyrimidine tract-binding protein with the internal ribosomal entry site of encephalomyocarditis virus and foot-and-mouth disease virus RNAs. RNA 2:1199-1212.

60. Kolupaeva, V. G., T. V. Pestova, C. U. Hellen, and I. N. Shatsky. 1998. Translation eukaryotic initiation factor 4G recognizes a specific structural element within the internal ribosome entry site of encephalomyocarditis virus RNA. J Biol Chem 273:18599-18604.

61. Kozak, M. 1999. Initiation of translation in prokaryotes and eukaryotes. Gene 234:187-208.

62. Kruger, M., C. Beger, P. J. Welch, J. R. Barber, M. P. Manns, and F. Wong-Staal. 2001. Involvement of proteasome alpha-subunit PSMA7 in hepatitis C virus internal ribosome entry site-mediated translation. Mol Cell Biol 21: 8357-8364.

63. La Monica, N. and V. R. Racaniello. 1989. Differences in replication of attenuated and neurovirulent polioviruses in human neuroblastoma cell line SH-SY5Y. J Virol 63:2357-2360.

64. Le, S. Y., N. Sonenberg, and J. V. Maizel, Jr. 1995. Unusual folding regions and ribosome landing pad within hepatitis C virus and pestivirus RNAs. Gene 154:137-143.

65. Lerat, H., Y. K. Shimizu, and S. M. Lemon. 2000. Cell type-specific enhancement of hepatitis C virus internal ribosome entry site-directed translation due to 5' nontranslated region substitutions selected during passage of virus in lymphoblastoid cells. J Virol 74:7024-7031.

66. Li, K., T. M. Davis, C. Bailly, A. Kumar, D. W. Boykin, and W. D. Wilson. 2001. A heterocyclic inhibitor of the REV-RRE complex binds to RRE as a dimer. Biochemistry 40:1150-1158.

67. Lipinski, C. A. 2000. J. Pharm. Tox. Meth. 44:235-249.

68. Llinàs-Brunet, M. 2002. NS3 serine protease inhibitors as potential antiviral agents for the treatment of hepatitis C virus infections. The 3rd internatl antiviral & vaccine discovery and development summit. March 13-14. Princeton, N.J.

69. Lohmann, V., F. Korner, A. Dobierzewska, and R. Bartenschlager. 2001. Mutations in hepatitis C virus RNAs conferring cell culture adaptation. J Virol 75:1437-1449.

70. Lohmann, V., F. Korner, J. Koch, U. Herian, L. Theilmann, and R. Bartenschlager. 1999. Replication of subgenomic hepatitis C virus RNAs in a hepatoma cell line. Science 285:110-113.

71. Lopez, D. Q., E. Lafuente, and E. Martinez-Salas. 2001. IRES interaction with translation initiation factors: functional characterization of novel RNA contacts with eIF3, eIF4B, and eIF4GII. RNA 7:1213-1226.

72. Lopez, D. Q. and E. Martinez-Salas. 2000. Interaction of the eIF4G initiation factor with the aphthovirus IRES is essential for internal translation initiation in vivo. RNA 6:1380-1392.

73. Lu, H. H. and E. Wimmer. 1996. Poliovirus chimeras replicating under the translational control of genetic elements of hepatitis C virus reveal unusual properties of the internal ribosomal entry site of hepatitis C virus. Proc Natl Acad Sci USA 93:1412-1417.

74. Lukavsky, P. J., G. A. Otto, A. M. Lancaster, P. Sarnow, and J. D. Puglisi. 2000. Structures of two RNA domains essential for hepatitis C virus internal ribosome entry site function. Nat Struct Bio 7:1105-1110.

75. Lyons, A. J., J. R. Lytle, J. Gomez, and H. D. Robertson. 2001. Hepatitis C virus internal ribosome entry site RNA contains a tertiary structural element in a functional domain of stem-loop II. Nucleic Acids Res 29:2535-2546.

76. Macejak, D. G., K. L. Jensen, S. F. Jamison, K. Domenico, E. C. Roberts, N. Chaudhary, I. von_Carlowitz, L. Bellon, M. J. Tong, A. Conrad, P. A. Pavco, and L. M. Blatt. 2000. Inhibition of hepatitis C virus (HCV)-RNA-dependent translation and replication of a chimeric HCV poliovirus using synthetic stabilized ribozymes. Hepatology 31:769-776.
77. Macejak, D. G., K. L. Jensen, P. A. Pavco, K. M. Phipps, B. A. Heinz, J. M. Colacino, and L. M. Blatt. 2001. Enhanced antiviral effect in cell culture of type 1 interferon and ribozymes targeting HCV RNA. J Viral Hepatitis 8:400-405.
78. Macejak, D. G. and P. Sarnow. 1991. Internal initiation of translation mediated by the 5' leader of a cellular mRNA. Nature 353:90-94.
79. Major M. E., Rehermann B, and S. M. Feinstone. 2001. Hepatitis C viruses., p. 1127-1153. In D. Knipe and P. Howley (eds.), Fields Virology. Lippincott Williams and Wilkins, Philadelphia, Pa.
80. Manns M. P., McHutchison J. G., Gordon S. C., Rustgi V. K., Shiffman M., Reindollar R., Goodman Z. D., Koury K., Ling M., and Albrecht J. K. 2003. Peginterferon alfa-2b plus ribavirin compared with interferon alfa-2b plus ribavirin for initial treatment of chronic hepatitis C: a randomised trial. Lancet 358:958-965.
81. Martinez-Salas, E., R. Ramos, E. Lafuente, and d. Q. Lopez. 2001. Functional interactions in internal translation initiation directed by viral and cellular IRES elements. J Gen Virol 82:973-984.
82. Mazur, S., F. A. Tanious, D. Ding, A. Kumar, D. W. Boykin, I. J. Simpson, S. Neidle, and W. D. Wilson. 2000. A thermodynamic and structural analysis of DNA minor-groove complex formation. Journal of Molecular Biology 300:321-37.
83. McHutchison J. G. and Poynard T. 1999. Combination therapy with interferon plus ribavirin for the initial treatment of chronic hepatitis C. Semin. Liver Dis. 19 Suppl 1:57-65.
84. McHutchison, J. G., T. Poynard, R. Esteban-Mur, G. L. Davis, Z. D. Goodman, J. Harvey, M. H. Ling, J. J. Garaud, J. K. Albrecht, K. Patel, J. L. Dienstag, and T. Morgan. 2002. Hepatic HCV RNA before and after treatment with interferon alone or combined with ribavirin. Hepatology 35:688-693.
85. Meerovitch, K., J. Pelletier, and N. Sonenberg. 1989. A cellular protein that binds to the 5'-noncoding region of poliovirus RNA: implications for internal translation initiation. Genes Dev 3:1026-1034.
86. Meerovitch, K., Y. V. Svitkin, H. S. Lee, F. Lejbkowicz, D. J. Kenan, E. K. Chan, V. I. Agol, J. D. Keene, and N. Sonenberg. 1993. La autoantigen enhances and corrects aberrant translation of poliovirus RNA in reticulocyte lysate. J Virol 67: 3798-3807.
87. Mercer, D. F., D. E. Schiller, J. F. Elliott, D. N. Douglas, C. Hao, A. Rinfret, W. R. Addison, K. P. Fischer, T. A. Churchill, J. R. Lakey, D. L. Tyrrell, and N. M. Kneteman. 2001. Hepatitis C virus replication in mice with chimeric human livers. Nature Medicine 7:927-933.
88. Michel, Y. M., A. M. Borman, S. Paulous, and K. M. Kean. 2001. Eukaryotic initiation factor 4G-poly(A) binding protein interaction is required for poly(A) tail-mediated stimulation of picornavirus internal ribosome entry segment-driven translation but not for X-mediated stimulation of hepatitis C virus translation. Mol Cell Biol 21: 4097-4109.
89. Mitchell, S. A., E. C. Brown, M. J. Coldwell, R. J. Jackson, and A. E. Willis. 2001. Protein factor requirements of the Apaf-1 internal ribosome entry segment: roles of polypyrimidine tract binding protein and upstream of N-ras. Mol Cell Biol 21:3364-3374.
90. Moriguchi, et al. 1992. Chem Pharm Bull 40:127-130.
91. Nanbru, C., I. Lafon, S. Audigier, M. C. Gensac, S. Vagner, G. Huez, and A. C. Prats. 2003. Alternative translation of the proto-oncogene c-myc by an internal ribosome entry site. J Biol Chem 272:32061-32066.
92. Niepmann, M., A. Petersen, K. Meyer, and E. Beck. 1997. Functional involvement of polypyrimidine tract-binding protein in translation initiation complexes with the internal ribosome entry site of foot-and-mouth disease virus. J Virol 71:8330-8339.
93. Odreman-Macchioli, F., F. E. Baralle, and E. Buratti. 2001. Mutational analysis of the different bulge regions of hepatitis C virus domain II and their influence on internal ribosome entry site translational ability. J Biol Chem 276: 41648-41655.
94. Odreman-Macchioli, F. E., S. G. Tisminetzky, M. Zotti, F. E. Baralle, and E. Buratti. 2000. Influence of correct secondary and tertiary RNA folding on the binding of cellular factors to the HCV IRES. Nucleic Acids Res 28:875-885.
95. Ohlmann, T., M. Lopez-Lastra, and J. L. Darlix. 2000. An internal ribosome entry segment promotes translation of the simian immunodeficiency virus genomic RNA. J Biol Chem 275:11899-11906.
96. Pain V M. 1996. Initiation of protein synthesis in eukaryotic cells. Eur J Biochem 236:747-771.
97. Pelletier, J., and N. Sonenberg. 1988. Internal initiation of translation of eukaryotic mRNA directed by a sequence derived from poliovirus RNA. Nature 334:320-325.
98. Pelletier, J., and N. Sonenberg. 1989. Internal binding of eucaryotic ribosomes on poliovirus RNA: translation in HeLa cell extracts. J Virol 63:441-444.
99. Pestova, T. V., S. I. Borukhov, and C. U. Hellen. 1998. Eukaryotic ribosomes require initiation factors 1 and 1A to locate initiation codons. Nature 394:854-859.
100. Pestova, T. V., I. N. Shatsky, S. P. Fletcher, R. J. Jackson, and C. U. Hellen. 1998. A prokaryotic-like mode of cytoplasmic eukaryotic ribosome binding to the initiation codon during internal translation initiation of hepatitis C and classical swine fever virus RNAs. Genes Dev 12: 67-83.
101. Pestova, T. V., I. N. Shatsky, and C. U. Hellen. 1996. Functional dissection of eukaryotic initiation factor 4F: the 4A subunit and the central domain of the 4G subunit are sufficient to mediate internal entry of 43S preinitiation complexes. Mol Cell Biol 16:6870-6878.
102. Peytou, V., R. Condom, N. Patino, R. Guedj, A. M. Aubertin, N. Gelus, C. Bailly, R. Terreux, and D. Cabrol-Bass. 1999. Synthesis and antiviral activity of ethidium-arginine conjugates directed against the TAR RNA of HIV-1. Journal of Medicinal Chemistry 42:4042-4053.
103. Pietschmann, T., V. Lohmann, A. Kaul, N. Krieger, G. Rinck, G. Rutter, D. Strand, and R. Bartenschlager. 2002. Persistent and transient replication of full-length hepatitis C virus genomes in cell culture. J Virol 76:4008-4021.
104. Pietschmann, T., V. Lohmann, G. Rutter, K. Kurpanek, and R. Bartenschlager. 2001. Characterization of cell lines carrying self-replicating hepatitis C virus RNAs. J Virol 75:1252-1264.
105. Poole, T. L., C. Wang, R. A. Popp, L. N. Potgieter, A. Siddiqui, and M. S. Collett. 1995. Pestivirus translation initiation occurs by internal ribosome entry. Virology 206: 750-754.

106. Pringle, C. 1999. Virus taxonomy—1999. The universal system of virus taxonomy, updated to include the new proposals ratified by the International Committee on Taxonomy of Viruses during 1998. Arch Virol 144:421-429.
107. Psaridi, L., U. Georgopoulou, A. Varaklioti, and P. Mavromara. 1999. Mutational analysis of a conserved tetraloop in the 5' untranslated region of hepatitis C virus identifies a novel RNA element essential for the internal ribosome entry site function. FEBS Lett 453:49-53.
108. Reynolds, J. E., A. Kaminski, A. R. Carroll, B. E. Clarke, D. J. Rowlands, and R. J. Jackson. 1996. Internal initiation of translation of hepatitis C virus RNA: the ribosome entry site is at the authentic initiation codon. RNA 2:867-878.
109. Reynolds, J. E., A. Kaminski, H. J. Kettinen, K. Grace, B. E. Clarke, A. R. Carroll, D. J. Rowlands, and R. J. Jackson. 1995. Unique features of internal initiation of hepatitis C virus RNA translation. EMBO J 14: 6010-6020.
110. Rijnbrand R, Bredenbeek P, van der Straaten T, Whetter L, Inchauspe G, Lemon S, and Spaan W. 1995. Almost the entire 5' non-translated region of hepatitis C virus is required for cap-independent translation. FEBS Lett 365: 115-119.
111. Rijnbrand R. C. and Lemon S. M. 2000. Internal ribosome entry site-mediated translation in hepatitis C virus replication. Curr Top. Microbiol Immunol. 242:85-116.
112. Rijnbrand, R., P. J. Bredenbeek, P. C. Haasnoot, J. S. Kieft, W. J. Spaan, and S. M. Lemon. 2001. The influence of downstream protein-coding sequence on internal ribosome entry on hepatitis C virus and other flavivirus RNAs. RNA 7:585-597.
113. Rijnbrand, R. C., T. E. Abbink, P. C. Haasnoot, W. J. Spaan, and P. J. Bredenbeek. 1996. The influence of AUG codons in the hepatitis C virus 5' nontranslated region on translation and mapping of the translation initiation window. Virology 226:47-56.
114. Sachs, A. B., P. Sarnow, and M. W. Hentze. 1997. Starting at the beginning, middle, and end: translation initiation in eukaryotes. Cell 89:831-838.
115. Saito I, Miyamura T, Ohbayashi A, Harada H, Katayama T, Kikuchi S, Watanabe Y, Koi S, Onji M, Ohta Y, Choo Q, Houghton M, and Kuo G. 2003. Hepatitis C virus infection is associated with the development of hepatocellular carcinoma. Proc Natl Acad Sci U.S. A 87:6547-6549.
116. Schultz, D. E., M. Honda, L. E. Whetter, K. L. McKnight, and S. M. Lemon. 1996. Mutations within the 5' nontranslated RNA of cell culture-adapted hepatitis A virus which enhance cap-independent translation in cultured African green monkey kidney cells. J Virol 70:1041-1049.
117. Shimazaki, T., M. Honda, S. Kaneko, and K. Kobayashi. 2002. Inhibition of internal ribosomal entry site-directed translation of HCV by recombinant IFN-alpha correlates with a reduced La protein. Hepatology 35:199-208.
118. Simmonds, P. 2003. Variability of hepatitis C virus. Hepatology 21:570-583.
119. Sinha, R., P. Yang, S. Kodali, Y. Xiong, R. M. Kim, P. R. Griffin, H. R. Onishi, J. Kohler, L. L. Silver, and K. Chapman. 2001. Direct interaction of a vancomycin derivative with bacterial enzymes involved in cell wall biosynthesis. Chem Biol 8:1095-1106.
120. Sizova, D. V., V. G. Kolupaeva, T. V. Pestova, I. N. Shatsky, and C. U. Hellen. 1998. Specific interaction of eukaryotic translation initiation factor 3 with the 5' nontranslated regions of hepatitis C virus and classical swine fever virus RNAs. J Virol 72:4775-4782.
121. Smith. 1994. Eur J Drug Metab Pharm 3:193-199.
122. Smith, D. B., J. Mellor, L. M. Jarvis, F. Davidson, J. Kolberg, M. Urdea, P. L. Yap, and P. Simmonds. 1995. Variation of the hepatitis C virus 5' non-coding region: implications for secondary structure, virus detection and typing. The International HCV Collaborative Study Group. J Gen Virol 76 (Pt 7):1749-1761.
123. Sonenberg N., Mathews M. B., and Hershey J. W. B. 2000. Translational control of gene expression. Cold Spring Harbor. Cold Spring Harbor Laboratory Press, New York.
124. Spahn, C. M., J. S. Kieft, R. A. Grassucci, P. A. Penczek, K. Zhou, J. A. Doudna, and J. Frank. 2001. Hepatitis C virus IRES RNA-induced changes in the conformation of the 40s ribosomal subunit. Science 291:1959-1962.
125. Spatzenegger, M. and W. Jaeger. 1995. Clinical importance of hepatic cytochrome P450 in drug metabolism. Drug Metab Rev 27:397-417.
126. Subkhankulova, T., S. A. Mitchell, and A. E. Willis. 2001. Internal ribosome entry segment-mediated initiation of c-Myc protein synthesis following genotoxic stress. Biochem J 359:183-192.
127. Tang, S., A. J. Collier, and R. M. Elliott. 1999. Alterations to both the primary and predicted secondary structure of stem-loop IIIc of the hepatitis C virus 1b 5' untranslated region (5'UTR) lead to mutants severely defective in translation which cannot be complemented in trans by the wild-type 5'UTR sequence. J Virol 73:2359-2364.
128. Thiel, V. and S. G. Siddell. 1994. Internal ribosome entry in the coding region of murine hepatitis virus mRNA 5. J Gen Virol. 75 (Pt 11):3041-3046.
129. Tsukiyama-Kohara, K., N. Iizuka, M. Kohara, and A. Nomoto. 1992. Internal ribosome entry site within hepatitis C virus RNA. J Virol 66:1476-1483.
130. Vagner, S., M. C. Gensac, A. Maret, F. Bayard, F. Amalric, H. Prats, and A. C. Prats. 1995. Alternative translation of human fibroblast growth factor 2 mRNA occurs by internal entry of ribosomes. Mol Cell Biol 15:35-44.
131. Varaklioti A., Georgopoulou U., Kakkanas A., Psaridi L., Serwe M., Caselmann W. H., and Mavromara P. 1998. Mutational analysis of two unstructured domains of the 5, untranslated region of HCV RNA. Biochem Biophys. Res Commun. 253:678-685.
132. Wang, C., S. Y. Le, N. Ali, and A. Siddiqui. 1995. An RNA pseudoknot is an essential structural element of the internal ribosome entry site located within the hepatitis C virus 5' noncoding region. RNA 1:526-537.
133. Wang, C., P. Sarnow, and A. Siddiqui. 1993. Translation of human hepatitis C virus RNA in cultured cells is mediated by an internal ribosome-binding mechanism. J Virol 67:3338-3344.
134. Wang, C., P. Sarnow, and A. Siddiqui. 1994. A conserved helical element is essential for internal initiation of translation of hepatitis C virus RNA. J Virol 68:7301-7307.
135. Wang, S. M., S. C. Fears, L. Zhang, J. J. Chen, and J. D. Rowley. 2000. Screening poly(dA/dT)-cDNAs for gene identification. Proceedings of the National Academy of Sciences of the USA 97:4162-4167.
136. Wang, T. H., R. C. Rijnbrand, and S. M. Lemon. 2000. Core protein-coding sequence, but not core protein, modulates the efficiency of cap-independent translation directed by the internal ribosome entry site of hepatitis C virus. J Virol 74:11347-11358.
137. Wimmer, E., C. U. Hellen, and X. Cao. 1993. Genetics of poliovirus. Annu Rev Genet 27:353-436.
138. Wong, J. B., T. Poynard, M. H. Ling, J. K. Albrecht, and S. G. Pauker. 2000. Cost-effectiveness of 24 or 48 weeks of interferon alpha-2b alone or with ribavirin as initial treatment of chronic hepatitis C. International Hepatitis Interventional Therapy Group. Am. J Gastroenterol. 95:1524-1530.

139. Zhao, W. D., and E. Wimmer. 2001. Genetic analysis of a poliovirus/hepatitis C virus chimera: new structure for domain II of the internal ribosomal entry site of hepatitis C virus. J Virol 75:3719-3730.

140. Zhao, W. D., E. Wimmer, and F. C. Lahser. 1999. Poliovirus/Hepatitis C virus (internal ribosomal entry site-core) chimeric viruses: improved growth properties through modification of a proteolytic cleavage site and requirement for core RNA sequences but not for core-related polypeptides. Journal of Virology 73:1546-1554.

141. Lukavsky, P. J., I. Kim, G. A. Otto, and J. D. Puglisi. 2003. Structure of HCV IRES domain II determined by NMR. Nat Struct Biol 10:1033-1038.

142. Otto, G. A., and J. D. Puglisi. 2005. The pathway of HCV IRES-mediated translation initiation. Cell 119:369-380.

143. Boni, S., L. J. P. Layergne, S. Boulant, and A. Cahour. 2005. Hepatitis C virus core protein acts as a trans-modulating factor on internal translation initiation of the viral RNA. J Biol Chem 280:17737-17748.

144. He, Y., W. Yan, C. Coito, Y. Li, M. Gale, Jr., and M. G. Katze. 2003. The regulation of hepatitis C virus (HCV) internal ribosome-entry site-mediated translation by HCV replicons and nonstructural proteins. J Gen Virol 84:535-543.

145. Kato, J., N. Kato, H. Yoshida, S. K. Ono-Nita, Y. Shiratori, and M. Omata. 2002. Hepatitis C virus NS4A and NS4B proteins suppress translation in vivo. J Med Virol 66:187-199.

146. Li, D., S. T. Takyar, W. B. Lott, and E. J. Gowans. 2003. Amino acids 1-20 of the hepatitis C virus (HCV) core protein specifically inhibit HCV IRES dependent translation in HepG2 cells, and inhibit both HCV IRES- and cap-dependent translation in HuH7 and CV-1 cells. J Gen Virol 84:815-825.

All documents referred to herein are incorporated by reference into the present application as though fully set forth herein.

We claim:

1. A compound of formula I

I

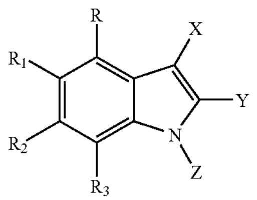

wherein:

X is:

a cyano group;

Y is:

a $C_6$ aryl, substituted with one or more of the following:

an alkoxy, optionally substituted with:

an alkoxy, a hydroxy, one or more halogen(s), a 5 or 6 membered heterocycle, optionally substituted with:

a $C_1$ to $C_6$ alkyl, or a hydroxy, an amino group optionally substituted with one or more $C_1$ to $C_6$ alkyl(s), a $-NR_iSO_2R_x$ group, where $R_x$ is a $C_1$ to $C_6$ alkyl and $R_i$ is:

a hydrogen, a $C_1$ to $C_6$ alkyl, a $-COR_x$ group, where $R_x$ is as defined above, a haloalkyl, or a haloalkoxy, a $-NR_jCOR_k$ group, where $R_k$ is:

a $C_1$ to $C_6$ alkyl, a hydrogen, or an amino optionally substituted with one or more $C_1$ to $C_6$ alkyl(s), and $R_j$ is:

a hydrogen, a $C_1$ to $C_6$ alkyl, a $-COR_x$ group, where $R_x$ is as defined above, a haloalkyl, or a haloalkoxy, a $-N{=}N^+{=}N^-$group, or a $-COR_1$, where $R_1$ is a 5 or 6 membered heterocycle optionally substituted with a hydroxy, an amino optionally substituted with one or more $C_1$ to $C_6$ alkyl(s), a $C_1$ to $C_6$ alkyl group, optionally substituted with:

a $-NHSO_2R_x$ group, where $R_x$ is as defined above, or a $-NR_xSO_2R_x$ group, where $R_x$ is as defined above, a haloalkoxy, a halogen, a hydroxy, a $-COOR_x$ group, where $R_x$ is as defined above, a $-COR_m$ group, where $R_m$ is:

an amino optionally substituted with one or more $C_1$ to $C_6$ alkyl(s), where the one or more $C_1$ to $C_6$ alkyl(s) is optionally substituted with:

a hydroxy a 5 or 6 membered heterocycle, an amino optionally substituted with one or more $C_1$ to $C_6$ alkyl(s), or an alkoxy, a 3 to 7 membered heterocycle, optionally substituted with a $C_1$ to $C_6$ alkyl, optionally substituted with a dialkyl-amino, or a $-NHR_n$ group, where $R_n$ is:

a $-CH_2CONH_2$, or a $C_6$ to $C_8$ aryl optionally substituted with:

an alkyl, one or more halogen(s), a nitro group, or one or more alkoxy(s), a $-NR_oCOR_p$ group, where $R_p$ is:

a $C_1$ to $C_6$ alkyl optionally substituted with:

a halogen, an alkoxy, or a $C_6$ to $C_8$ aryl, a 5 or 6 membered heterocycle, a $C_6$ to $C_8$ aryl, optionally substituted with a halogen, a 5 or 6 membered heteroaryl optionally substituted with one or more $C_1$ to $C_6$ alkyl(s), a hydrogen, a cyclopropyl, a cyclobutyl, a cyclopentyl, a cyclohexyl, a cyclopropylmethyl,

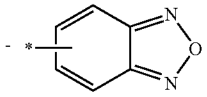 or 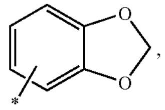

and where $R_o$ is:
a hydrogen,
a $C_1$ to $C_6$ alkyl,
a —$COR_x$ group, where $R_x$ is as defined above,
a haloalkyl, or
a haloalkoxy,
a —$NR_qCONR_qR_{r'}$ group, where $R_q$ is:
a hydrogen,
a $C_1$ to $C_6$ alkyl,
a haloalkyl,
a haloalkoxy, or
a —$COR_x$ group, where $R_x$ is as defined above, and where $R_{r'}$ is:
a $C_6$ to $C_8$ aryl optionally substituted with:

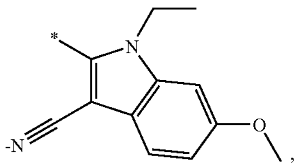

a $C_1$ to $C_6$ alkyl,
a haloalkyl,
a —$OR_s$ group, where $R_s$ is a $C_6$ to $C_8$ aryl, or
a —$COOR_x$ group, where $R_x$ is as defined above,
a $C_1$ to $C_6$ alkyl optionally substituted with one or more of the following:
a halogen,
an alkenyl,
a $C_6$ to $C_8$ aryl, or
a —$COOR_x$ group, where $R_x$ is as defined above,
a —$COOR_x$ group, where $R_x$ is as defined above,
a cyclopropyl,
a cyclobutyl,
a cyclopentyl,
a cyclohexyl, or
a cyclopropylmethyl,
a —$NR_tCOOR_u$ group, where $R_u$ is:
a $C_1$ to $C_{12}$ alkyl, optionally substituted with:
a $C_6$ to $C_8$ aryl optionally substituted with a $C_1$ to $C_6$ alkyl or an alkoxy,
an alkenyl,
an alkoxy,
an alkynyl,
a halogen, or
a 5 or 6 membered heterocycle,
a $C_6$ to $C_8$ aryl, optionally substituted with:
an alkoxy,
a halogen, or
a $C_1$ to $C_6$ alkyl,
a 5 or 6 membered heterocycle,
a cyclopropyl,
a cyclobutyl,
a cyclopentyl.,
a cyclohexyl,
a cyclopropylmethyl, a cyclopropylethyl,
a cyclobutylmethyl,
a (1-methylcyclopropyl)methyl, or
a 1-methylcyclopentyl,
and where $R_t$ is:
a hydrogen,
a $C_1$ to $C_6$ alkyl,
a —$COR_x$ group, where $R_x$ is as defined above,
a haloalkyl, or
a haloalkoxy,
a —$NR_vSO_2R_w$ group, where $R_v$ is:
a hydrogen,
a —$COR_x$, where $R_x$ is as defined above, or
a $C_1$ to $C_6$ alkyl, optionally substituted with:
a halogen,
a —$COR_x$ group, where $R_x$ is as defined above,
a —$OCOR_x$ group, where $R_x$ is as defined above,
a hydroxy, or
an alkoxy,
and where $R_w$ is:
a $C_1$ to $C_6$ alkyl optionally substituted with:
a halogen,
a haloalkyl,
a $C_6$ to $C_8$ aryl, or
a 5 or 6 membered heterocycle,
a $C_2$ to $C_6$ alkenyl,
a mono-alkyl-amino or dialkyl-amino optionally substituted on alkyl with a halogen,
a 5 or 6 membered heterocycle,
a 5 or 6 membered heteroaryl optionally substituted with:
a $C_1$ to $C_6$ alkyl,
a 5 or 6 membered heterocycle, or

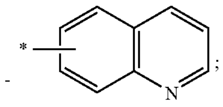

a cyclopropyl,
a cyclobutyl,
a cyclopentyl,
a cyclohexyl, or
a cyclopropylmethyl,

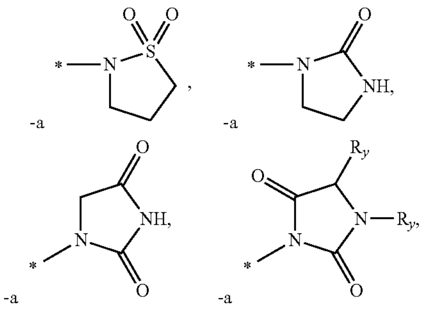

optionally substituted with a $C_1$ to $C_6$ alkyl, where $R_y$ is a $C_1$ to $C_6$ alkyl or hydrogen, -a 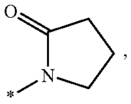 , -a 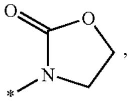 , -a 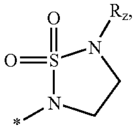

where $R_z$ is hydrogen or a $C_1$ to $C_6$ alkyl, optionally substituted with a $C_6$ to $C_8$ aryl, a —$SR_x$ group, where $R_x$ is as defined above, a —$SO_2R_{aa}$ group, where $R_{aa}$ is:

a $C_1$ to $C_6$ alkyl, an amino group, a mono-alkyl-amino or dialkyl-amino group optionally substituted on alkyl with a hydroxy or a —$COOR_x$ group, where $R_x$ is as defined above, a 5 or 6 membered heteroaryl, a $C_6$ to $C_8$ aryl, or a —$NHR_{bb}$ group, where $R_{bb}$ is:

- 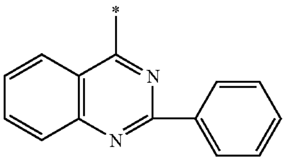 ,

- 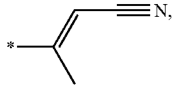

a —C(=S)$NH_2$ group, or a —$PO(OR_x)_2$ group, where $R_x$ is as defined above;

Z is:

a $C_1$ to $C_6$ alkyl optionally substituted with:

an alkoxy, one or more halogen(s), or a $C_6$ to $C_8$ aryl;

a $C_2$ to $C_6$ alkenyl;

a cyclopropyl;

a cyclobutyl;

a cyclopentyl;

a cyclohexyl;

a cyclopropylmethyl;

a cyclobutylmethyl; or a cyclopentylmethyl;

R is a hydrogen, a halogen or an alkoxy;

$R_1$ is:

a hydrogen;

a hydroxy;

a halogen;

a haloalkyl;

a nitro group;

a 5 or 6 membered heteroaryl;

a 5 or 6 membered heterocycle;

an alkoxy optionally substituted with:

one or more halogen(s), a $C_6$ to $C_8$ aryl, or a 5 or 6 membered heterocycle;

a $C_6$ to $C_8$ aryl optionally substituted with an alkoxy;

a —$COR_x$ group, where $R_x$ is as defined above; or a $C_1$ to $C_6$ alkyl optionally substituted with a dialkyl-amino or a 5 or 6 membered heterocycle;

$R_2$ is:

a nitro group;

a hydrogen;

a halogen;

a hydroxy group;

a $C_1$ to $C_6$ alkyl group, optionally substituted with one or more halogen(s);

an amino group;

an alkoxy group optionally substituted with:

one or more halogen(s), an —$OCOR_x$ group, where $R_x$ is as defined above, an amino substituted with:

(i) —a cyclopropyl, (ii) —a cyclobutyl, (iii) —a cyclopentyl, (iv) —a cyclohexyl, or (v) —a cyclopropylmethyl, a dialkyl-amino optionally substituted on alkyl with an alkoxy, a 5 or 6 membered heterocycle group optionally substituted with a $C_1$ to $C_6$ alkyl, a 5 or 6 membered heteroaryl group, or a $C_6$ to $C_8$ aryl group;

a —$COOR_x$ group, where $R_x$ is as defined above;

a haloalkyl;

an amide group optionally substituted with:

a hydroxy group, or a $C_6$ to $C_8$ aryl;

a 5 or 6 membered heteroaryl;

a —$OCOR_x$ group, where $R_x$ is as defined above;

a —$NHCOR_{jj}$ group, where $R_{jj}$ is:

an alkoxy, or an amino optionally substituted with one or more $C_1$ to $C_6$ alkyl(s);

a —$OR_{kk}$ group, where $R_{kk}$ is a 5 to 6 membered heteroaryl;

a —$NHSO_2R_x$ group, where $R_x$ is as defined above;

a cyclopropyl; —a cyclobutyl; —a cyclopentyl; —a cyclohexyl; —a cyclopropylmethyl; or a cyclopropoxy; and $R_3$ is:

a hydrogen; or

—$CH_2OCOR_x$, and $R_x$ is as defined above;

or a pharmaceutically acceptable salt thereof.

2. The compound of claim 1, wherein:

Y is a $C_6$ aryl, substituted with one or more of the following:

an amino optionally substituted with one or more $C_1$ to $C_6$ alkyl(s), a $C_1$ to $C_6$ alkyl group, optionally substituted with a —$NHSO_2R_x$ group, a —$NR_oCOR_p$ group, where $R_p$ is:

a $C_1$ to $C_6$ alkyl optionally substituted with:

a halogen, or a $C_6$ to $C_8$ aryl, a 5 or 6 membered heterocycle, a cyclopropyl, or a cyclobutyl, and where $R_o$ is a hydrogen, a —$NR_qCONR_{q'}R_{r'}$ group, where $R_q$ is:

a hydrogen, or a $C_1$ to $C_6$ alkyl, and where $R_{r'}$ is:

(a) a $C_1$ to $C_6$ alkyl optionally substituted with one or more of the following:

a halogen, an alkenyl, or a $C_6$ to $C_8$ aryl, (b) —a cyclopropyl, —a cyclobutyl, or —a cyclopentyl;

a —$NR_tCOOR_u$ group, where $R_u$ is:

a $C_1$ to $C_{12}$ alkyl, optionally substituted with:

a $C_6$ to $C_8$ aryl optionally substituted with a $C_1$ to $C_6$ alkyl or an alkoxy, an alkenyl, an alkoxy, an alkynyl, a halogen, or a 5 or 6 membered heterocycle, a $C_6$ to $C_8$ aryl, optionally substituted with an alkoxy, a 5 or 6 membered heterocycle, a cyclobutyl, a cyclopentyl, a cyclopropylmethyl, a cyclopropylethyl, a cyclobutylmethyl, a (1-methylcyclopropyl)methyl, or a 1-methylcyclopentyl, and where $R_t$ is:

a hydrogen, or a $C_1$ to $C_6$ alkyl, a —$NR_vSO_2R_w$ group, where $R_v$is a hydrogen, and where $R_w$ is:

(i) a $C_1$ to $C_6$ alkyl optionally substituted with a halogen; or (ii) a cyclopropyl;

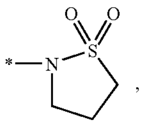

-a 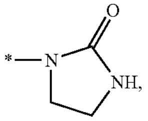

-a 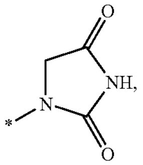

-a 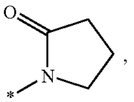

-a 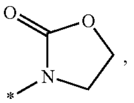

-a 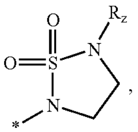

where $R_z$ is a $C_1$ to $C_6$ alkyl, or a —$NHR_{bb}$ group, where $R_{bb}$ is a —$PO(OR_x)_2$ group.

3. The compound of claim 2, wherein Y is a $C_6$ aryl substituted with:

a —$NR_qCONR_qR_r$ group, a —$NR_tCOOR_u$ group, a —$NR_vSO_2R_w$ group, or a —$NHR_{bb}$ group, where $R_{bb}$ is —a —$PO(OR_x)_2$ group.

4. The compound of claim 1, wherein Y is phenyl substituted at the para position.

5. The compound of claim 4, wherein Y is phenyl substituted with a —$NR_qCONR_qR_r$ group at the para position.

6. The compound of claim 4, wherein Y is phenyl substituted with a —$NR_tCOOR_u$ group at the para position.

7. The compound of claim 4, wherein Y is phenyl substituted with a —$NR_vSO_2R_w$ group at the para position.

8. The compound of claim 4, wherein Y is phenyl substituted with a —$NHPO(OR_x)_2$ group at the para position.

9. The compound of claim 1, wherein Z is a $C_1$ to $C_6$ alkyl; —cyclopropyl; —cyclobutyl; —cyclopentyl; —cyclohexyl; —cyclopropylmethyl; —cyclobutylmethyl; or -cyclopentylmethyl.

10. The compound of claim 9, wherein Z is a $C_2$ to $C_5$ alkyl; —cyclopropyl; —cyclobutyl; —cyclopentyl; —cyclopropylmethyl; or —cyclobutylmethyl.

11. The compound of claim 10, wherein Z is cyclobutyl, cyclopropyl, cyclopropylmethyl, ethyl or cyclopentyl.

12. The compound of claim 1, wherein R is hydrogen.

13. The compound of claim 1, wherein $R_1$ is:

a hydrogen; or an alkoxy group optionally substituted with:

one or more halogen(s), a $C_6$ to $C_8$ aryl group, or a 5 or 6 membered heterocycle.

14. The compound of claim 1, wherein $R_2$ is:

a hydrogen;

a halogen;

a hydroxy group;

a $C_1$ to $C_6$ alkyl group, optionally substituted with one or more halogen(s);

an amino group;

an alkoxy group optionally substituted with:

one or more halogen(s), an —$OCOR_x$ group, where $R_x$ is as defined above, an amino substituted with cyclopropyl, a dialkyl-amino optionally substituted on alkyl with an alkoxy, a 5 or 6 membered heterocycle group optionally substituted with a $C_1$ to $C_6$ alkyl, a 5 or 6 membered heteroaryl group, or a $C_6$ to $C_8$ aryl group;

a —$COOR_x$ group; or a cyclopropoxy.

15. The compound of claim 1, wherein:

$R_1$ is a hydroxy group or an alkoxy group optionally substituted with:

one or more halogen(s), a $C_6$ to $C_8$ aryl group, or a 5 or 6 membered heterocycle group; or $R_2$ is a —$OCOR_x$ group, a —$OR_{kk}$ group, or an alkoxy group substituted with:

an —$OCOR_x$ group, an amino substituted with cyclopropyl, a dialkyl-amino optionally substituted on alkyl with an alkoxy, a 5 or 6 membered heterocycle group substituted with a $C_1$ to $C_6$ alkyl;

a 5 or 6 membered heteroaryl group; or a cyclopropoxy.

16. The compound of claim 15, wherein $R_2$ is an alkoxy group optionally substituted with:

a 5 or 6 membered heterocycle group optionally substituted with a $C_1$ to $C_6$ alkyl; or a 5 or 6 membered heteroaryl group.

17. The compound of claim 16, wherein $R_2$ is a $C_1$ to $C_6$ alkoxy group optionally substituted with:

a 5 or 6 membered heterocycle group optionally substituted with a $C_1$ to $C_6$ alkyl; or a 5 or 6 membered heteroaryl group.

18. The compound of claim 1, wherein $R_3$ is a hydrogen.

19. The compound of claim 1, wherein:

Y is a $C_6$ aryl substituted with:

a —$NR_qCONR_qR_r$ group, a —$NR_tCOOR_u$ group, a —$NR_vSO_2R_w$ group, or a —$NHPO(OR_x)_2$ group;

R is hydrogen;

$R_1$ is a hydroxy group or an alkoxy group optionally substituted with:

one or more halogen(s), a $C_6$ to $C_8$ aryl group, or a 5 or 6 membered heterocycle group; or $R_2$ is a —$OCOR_x$ group, a —$OR_{kk}$ group, or an alkoxy group substituted with:

an —$OCOR_x$ group, an amino substituted with cyclopropyl, a dialkyl-amino optionally substituted on alkyl with an alkoxy, a 5 or 6 membered heterocycle group substituted with a $C_1$ to $C_6$ alkyl;

a 5 or 6 membered heteroaryl group; or a cyclopropoxy; and $R_3$ is hydrogen.

20. The compound of claim 19, wherein Y is a phenyl substituted with a —$NR_qCONR_qR_r$ group.

21. The compound of claim 20, wherein:

Z is a $C_1$ to $C_6$ alkyl; —a cyclopropyl; —a cyclobutyl; —a cyclopentyl; —a cyclohexyl; —a cyclopropylmethyl; —a cyclobutylmethyl; or —a cyclopentylmethyl; and $R_2$ is an alkoxy group optionally substituted with:

a 5 or 6 membered heterocycle group optionally substituted with a $C_1$ to $C_6$ alkyl; or a 5 or 6 membered heteroaryl group.

22. The compound of claim 19, wherein Y is a phenyl substituted with a —$NR_tCOOR_u$ group.

23. The compound of claim 22, wherein:

Z is a $C_1$ to $C_6$ alkyl; —a cyclopropyl; —a cyclobutyl; —a cyclopentyl; —a cyclohexyl; —a cyclopropylmethyl; —a cyclobutylmethyl; or —a cyclopentylmethyl; and $R_2$ is an alkoxy group optionally substituted with:

a 5 or 6 membered heterocycle group optionally substituted with a $C_1$ to $C_6$ alkyl; or a 5 or 6 membered heteroaryl group.

24. The compound of claim 19, wherein Y is a phenyl substituted with a —$NR_vSO_2R_w$ group.

25. The compound of claim 24, wherein:

Z is a $C_1$ to $C_6$ alkyl; —a cyclopropyl; —a cyclobutyl; —a cyclopentyl; —a cyclohexyl; —a cyclopropylmethyl; —a cyclobutylmethyl; or —a cyclopentylmethyl; and $R_2$ is an alkoxy group optionally substituted with:

a 5 or 6 membered heterocycle group optionally substituted with a $C_1$ to $C_6$ alkyl; or a 5 or 6 membered heteroaryl group.

26. The compound of claim 19, wherein Y is a phenyl substituted with a —$NHPO(OR_x)_2$ group.

27. The compound of claim 26, wherein:

Z is a $C_1$ to $C_6$ alkyl; —a cyclopropyl; —a cyclobutyl; —a cyclopentyl; —a cyclohexyl; —a cyclopropylmethyl; —a cyclobutylmethyl; or —a cyclopentylmethyl; and $R_2$ is an alkoxy group optionally substituted with:

a 5 or 6 membered heterocycle group optionally substituted with a $C_1$ to $C_6$ alkyl; or a 5 or 6 membered heteroaryl group.

28. A compound selected from:

866

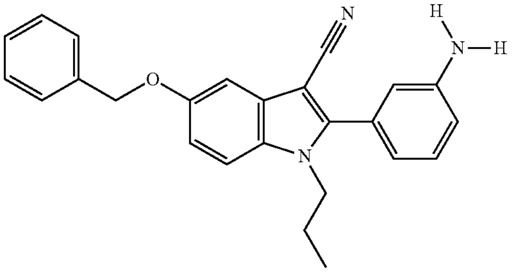

867

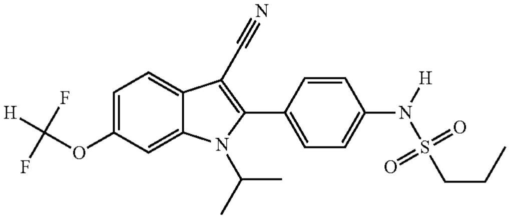

-continued
868
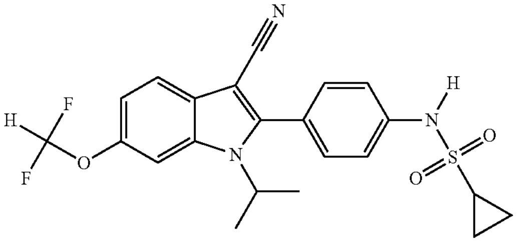
869
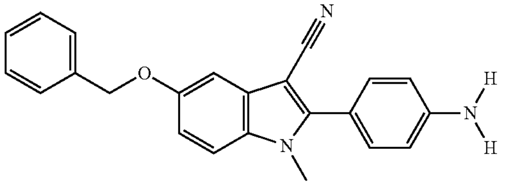
870
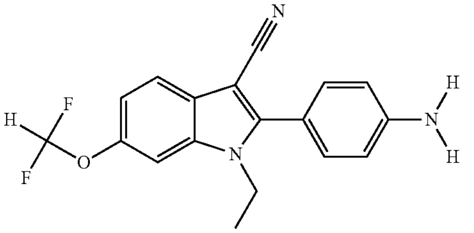
871
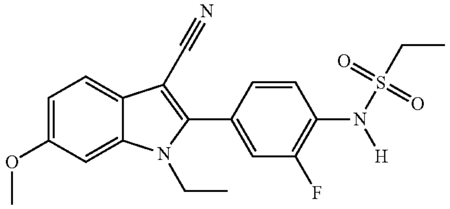
872
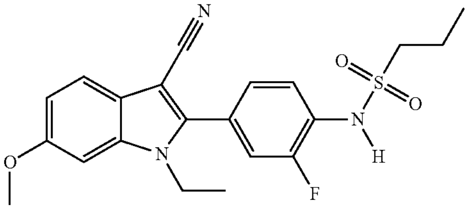
873
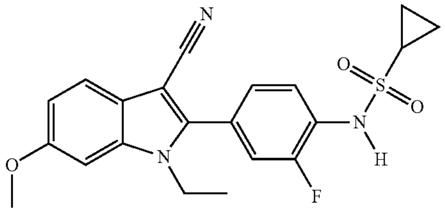
874
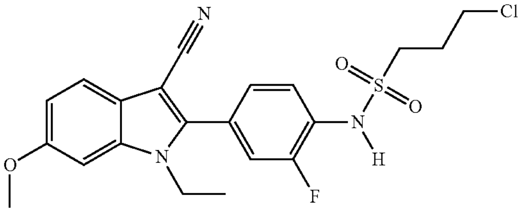
875
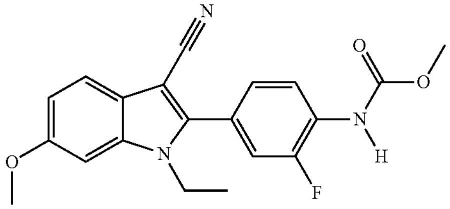
876
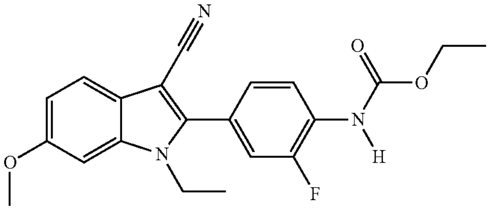
877
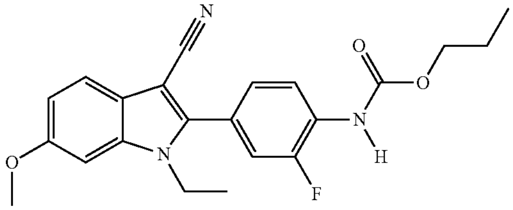
878
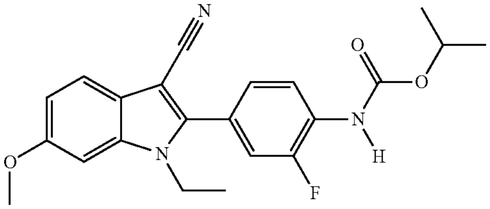
879
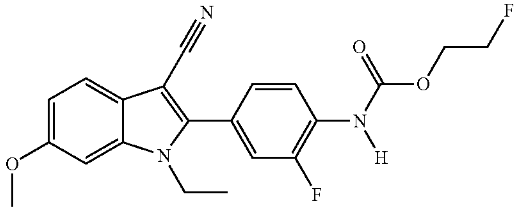
880
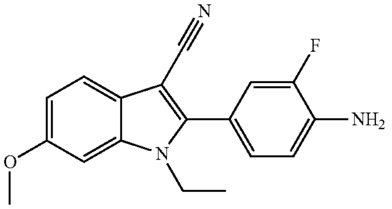
881
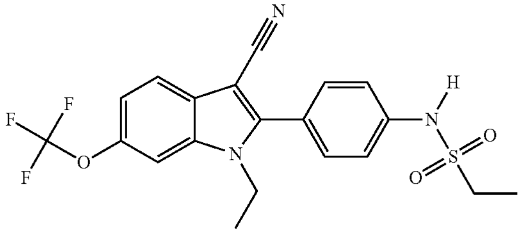

-continued
882
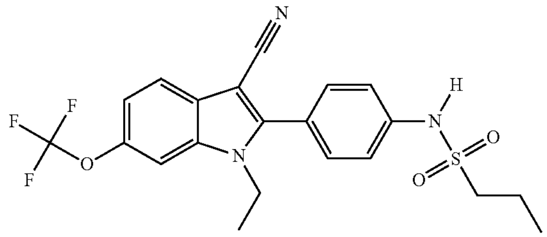
883
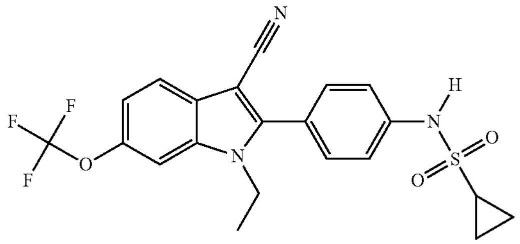
884
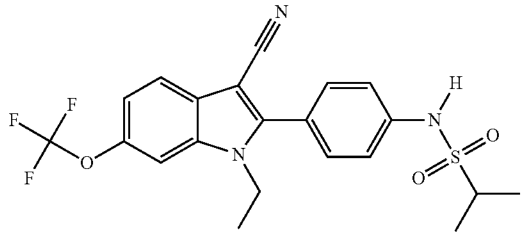
885
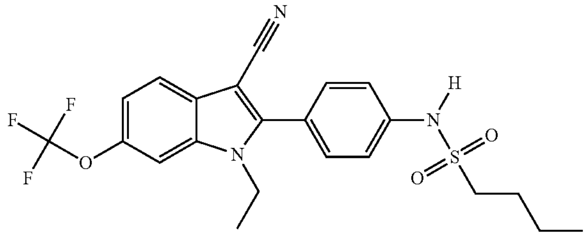
886
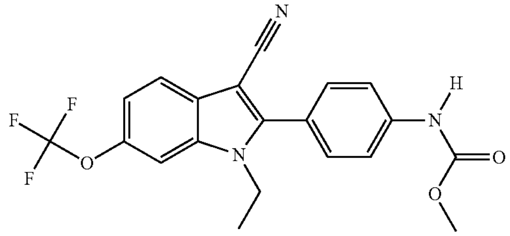
887
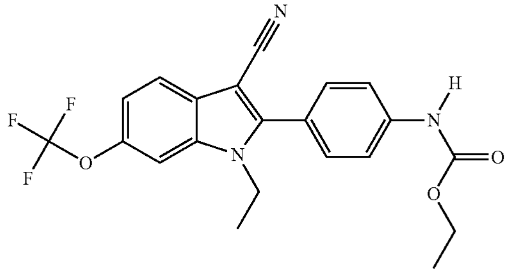
888
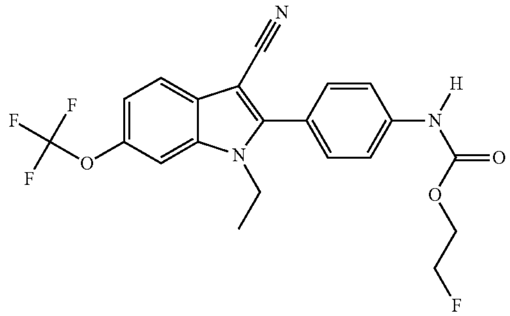
889
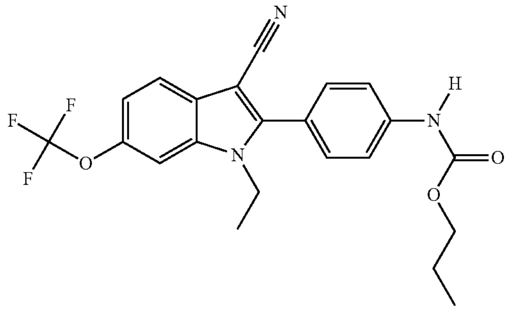
890
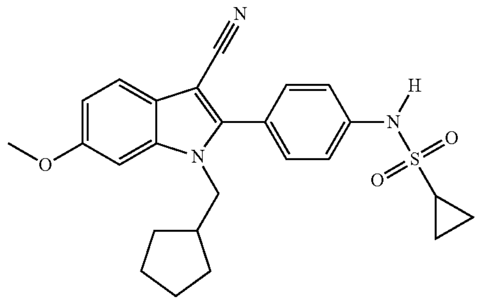
891
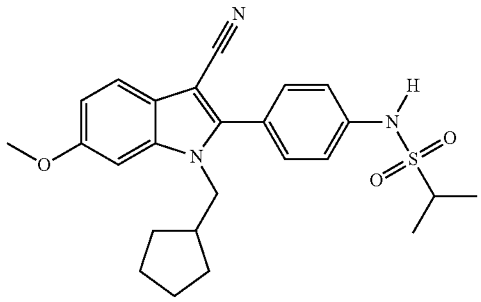

-continued
892
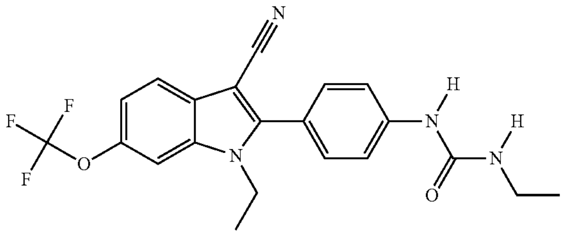
893
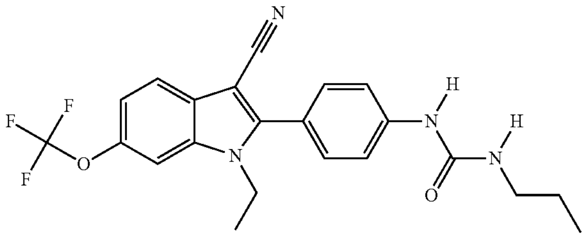
894
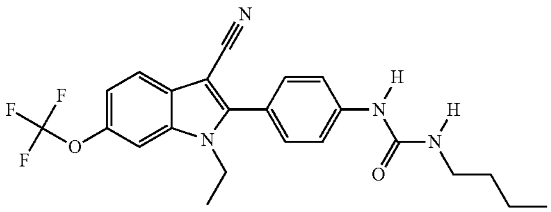
895
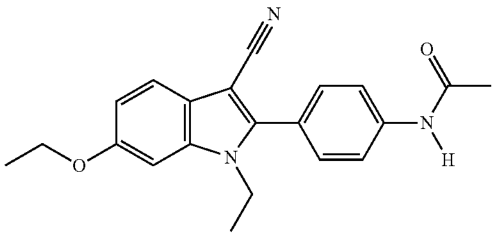
896
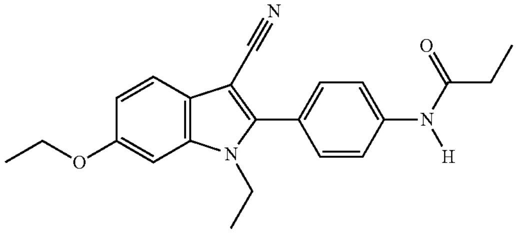
897
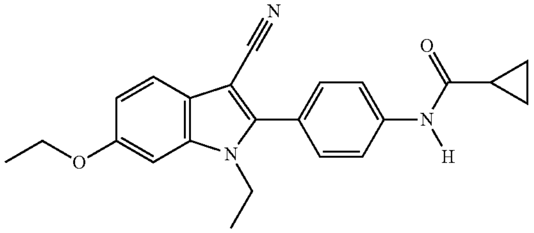
898
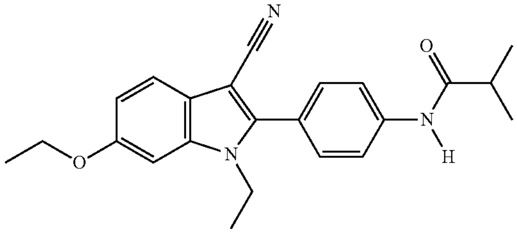
899
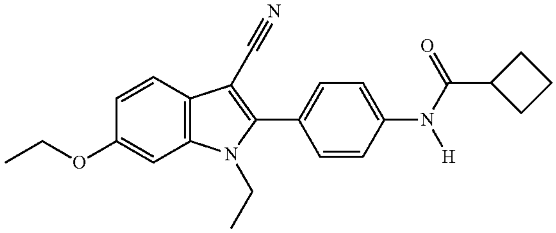
900
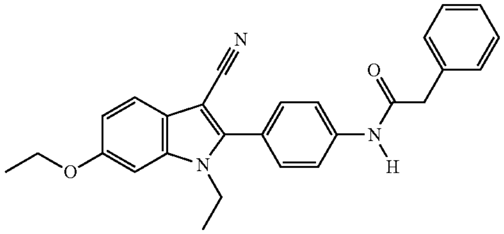
901
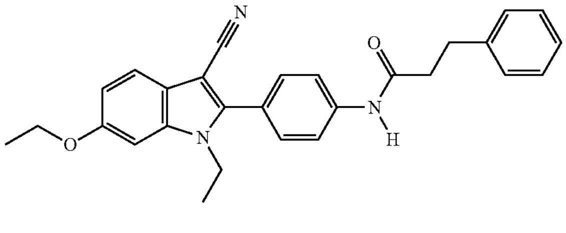
902
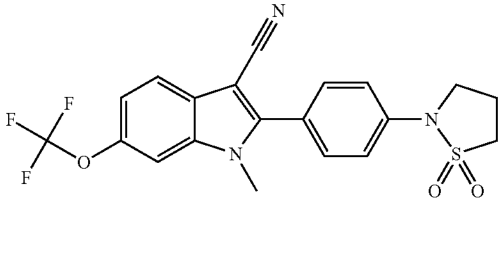
903
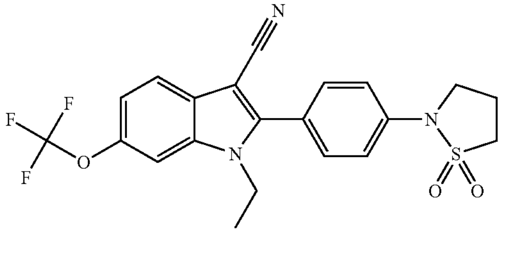

-continued
904
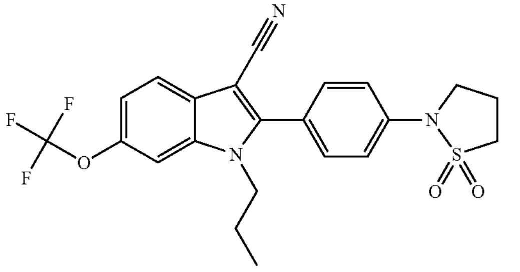
905
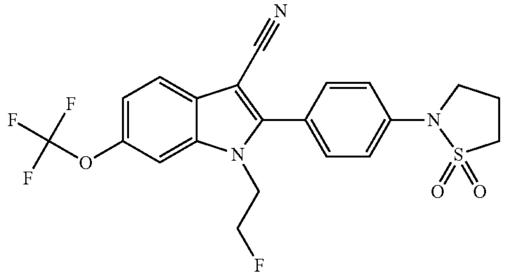
906
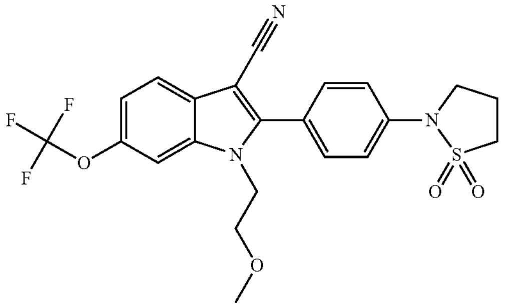
907
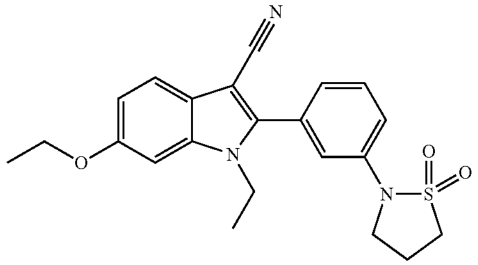
908
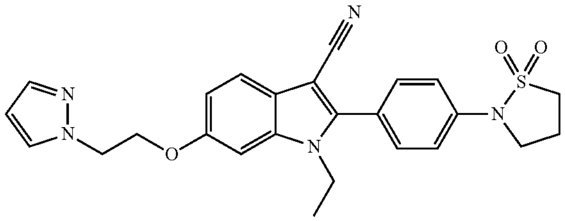
909
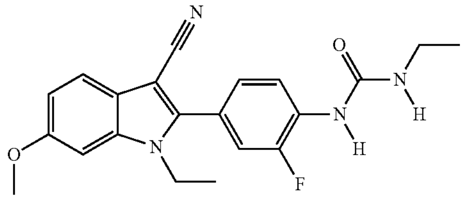
910
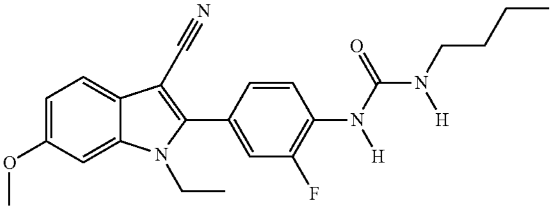
911
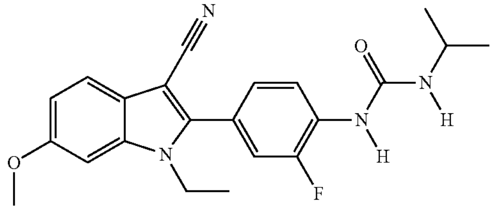
912
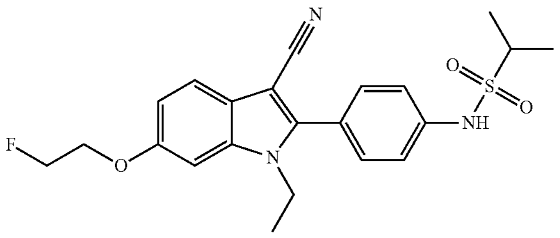
913
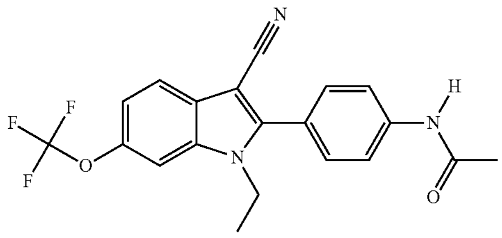
914
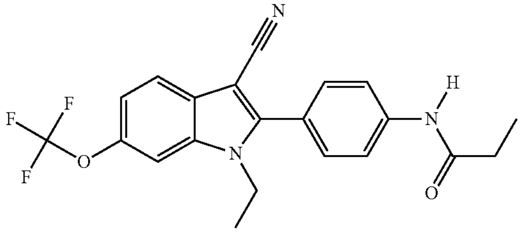
915
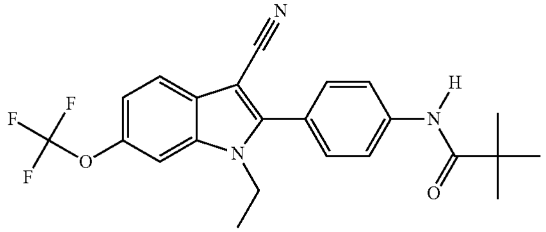

-continued
916
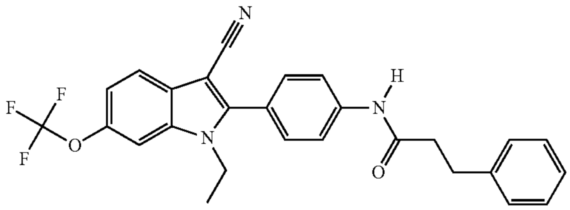
917
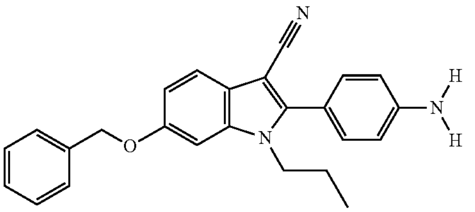
918
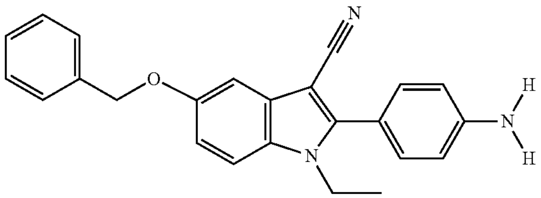
919
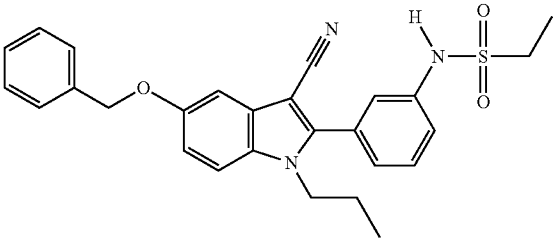
920
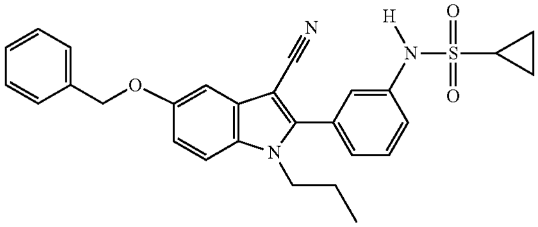
921
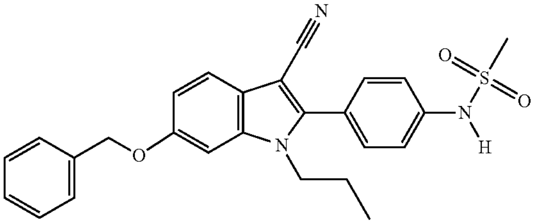
922
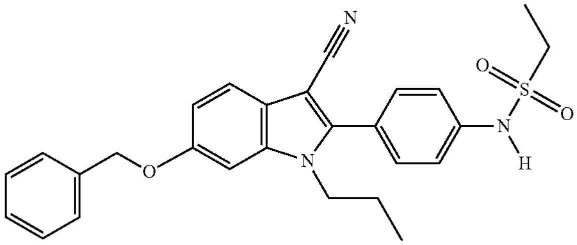
923
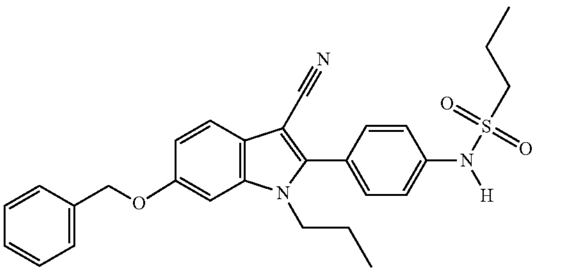
924
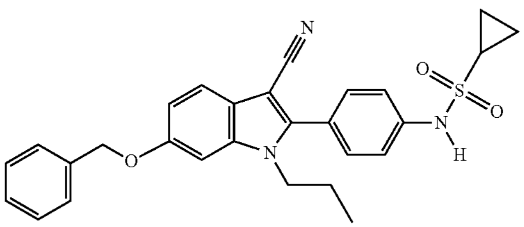
925
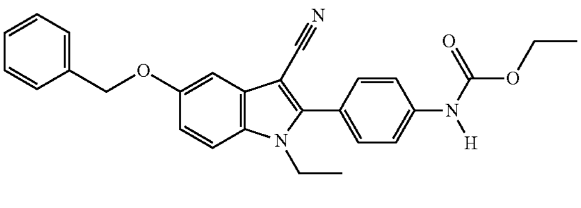
926
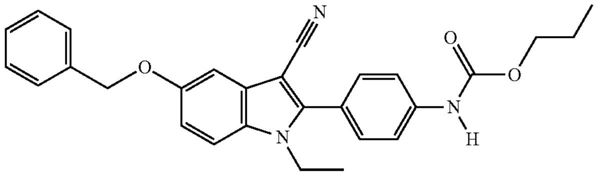
927
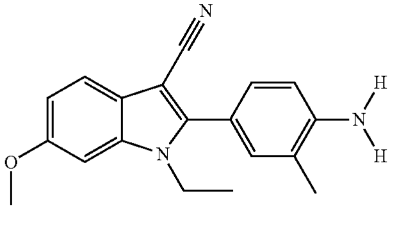

-continued
928
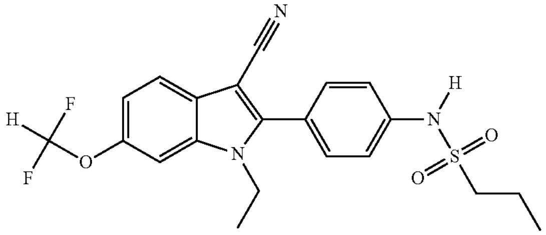
929
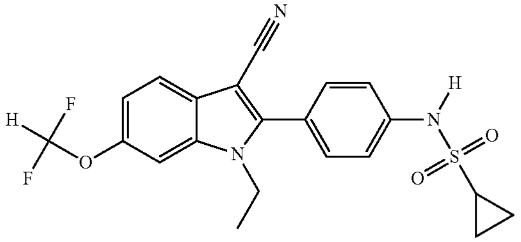
930
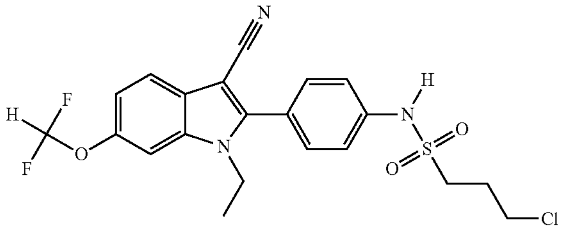
931
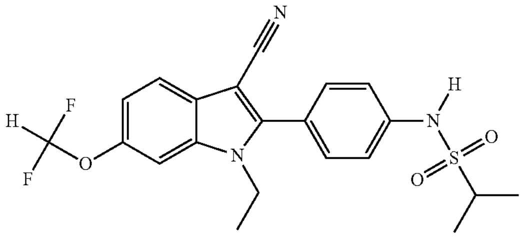
932
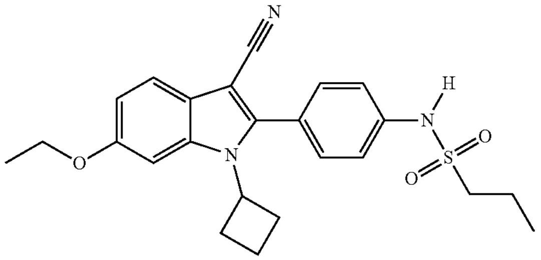
933
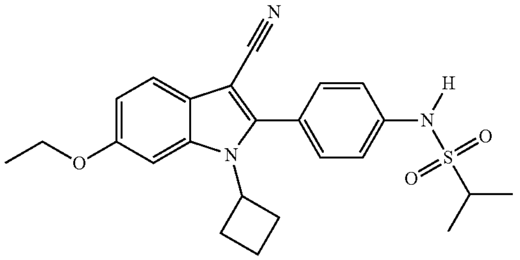
934
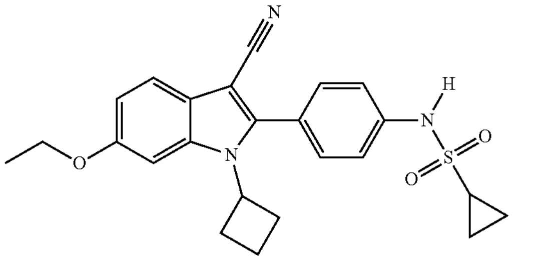
935
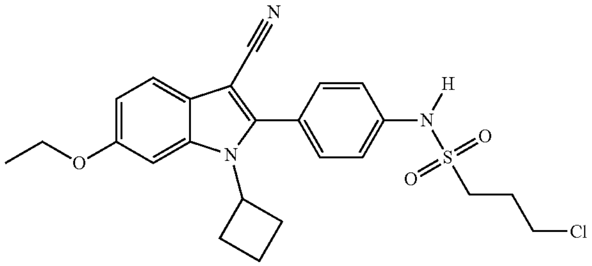
936
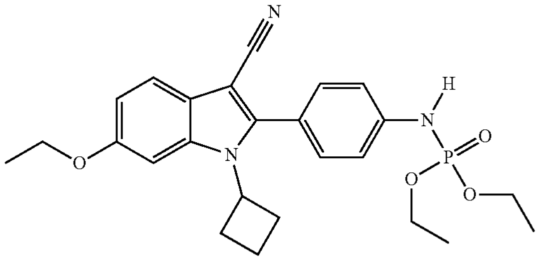
937
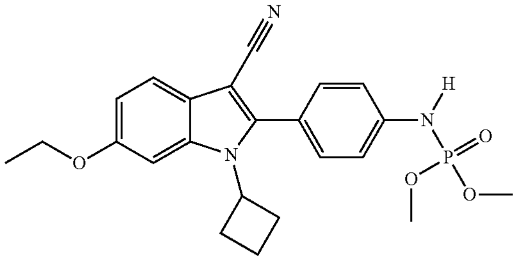
938
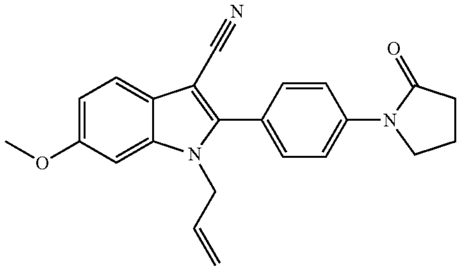
939
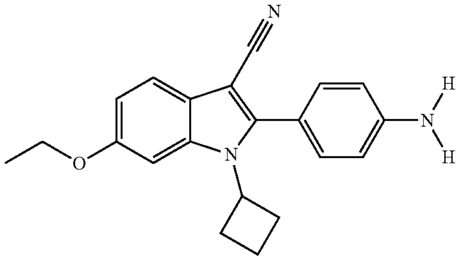

-continued
941
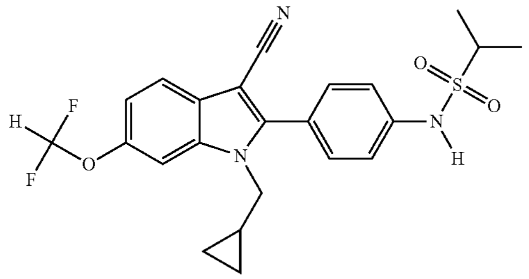
942
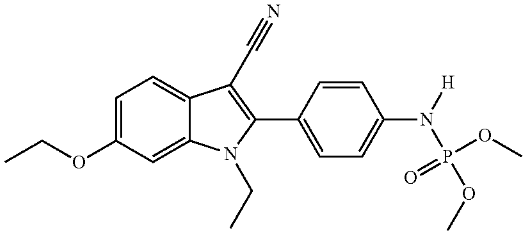
943
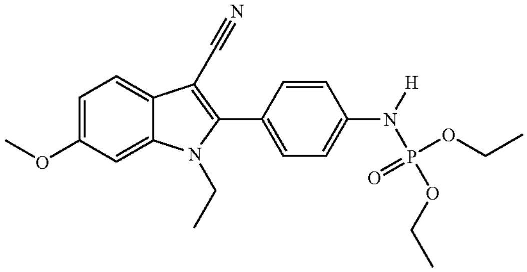
944
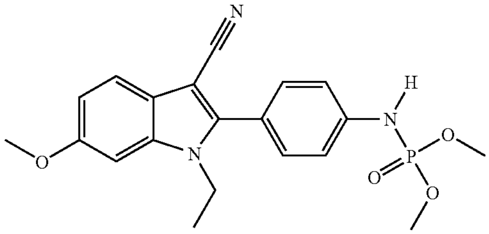
945
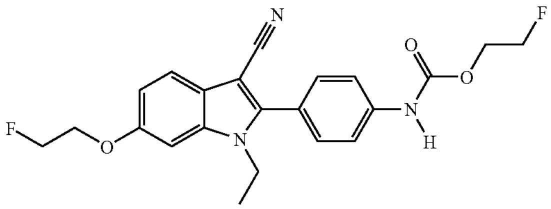
946
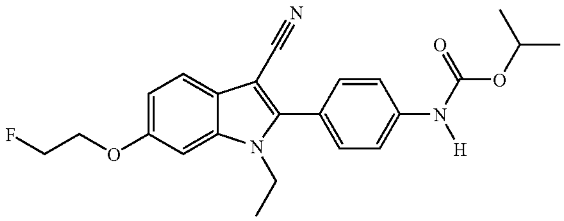
947
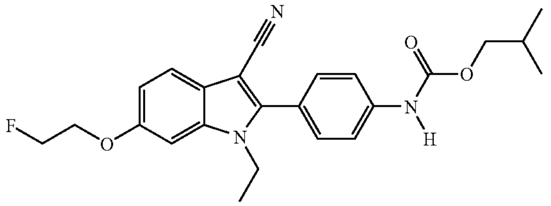
948
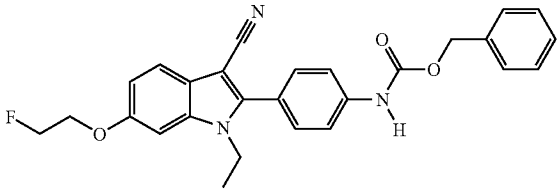
949
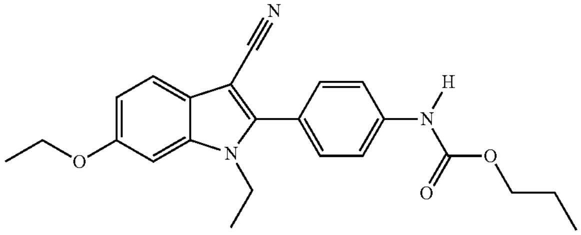
950
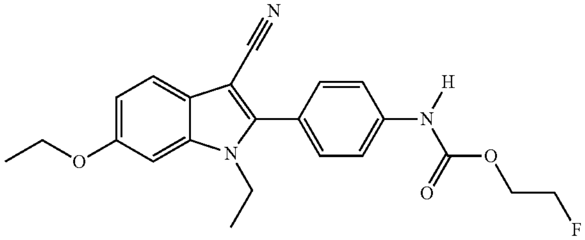
951
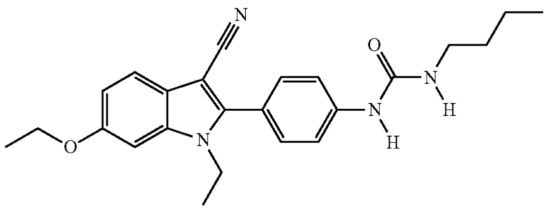
952
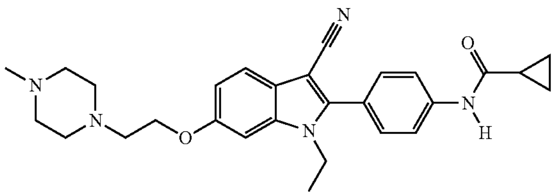

-continued
953
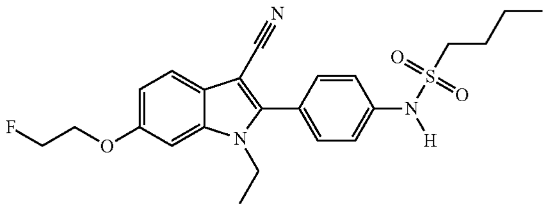
954
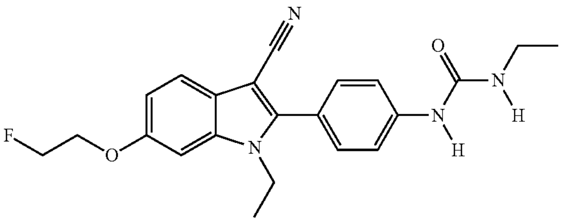
955
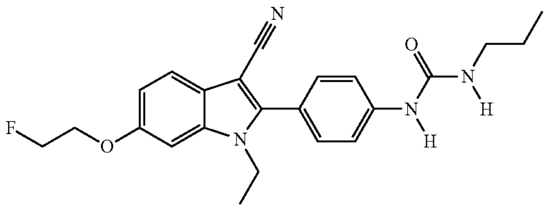
956
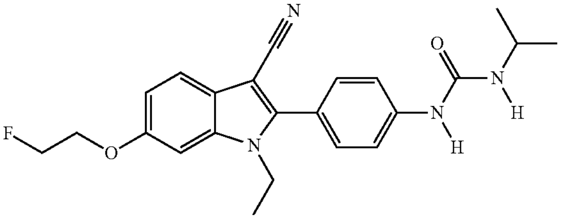
957
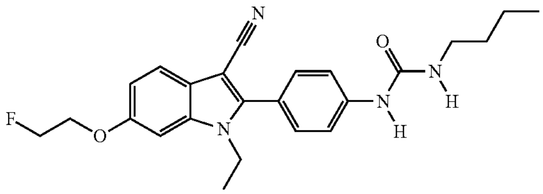
958
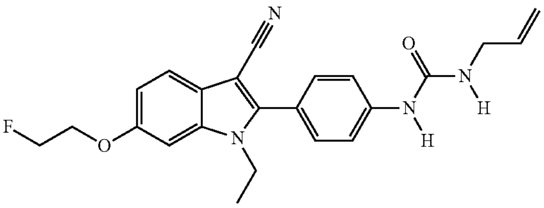
959
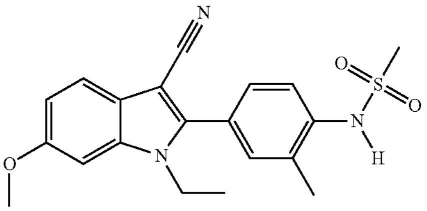
960
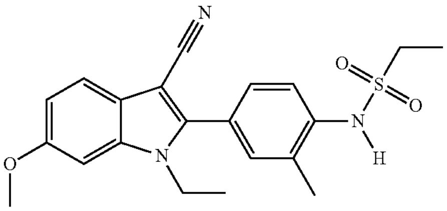
961
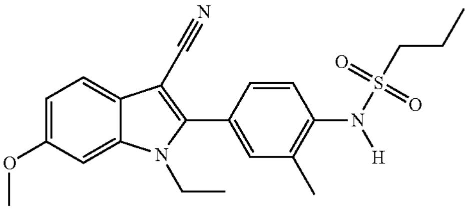
962
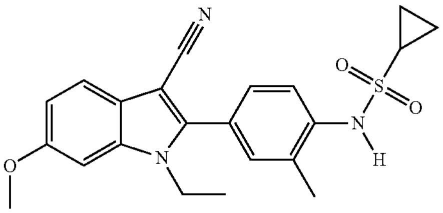
963
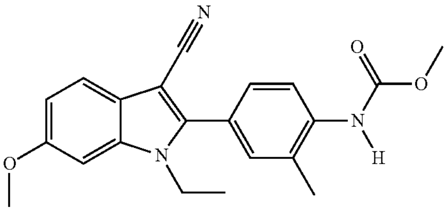
964
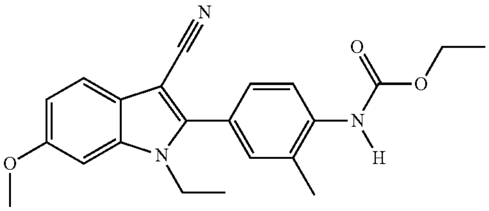
965
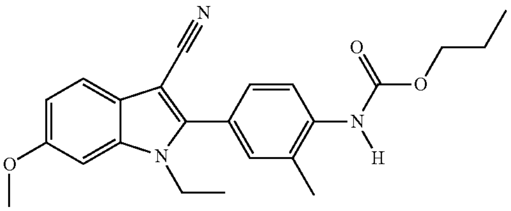
966
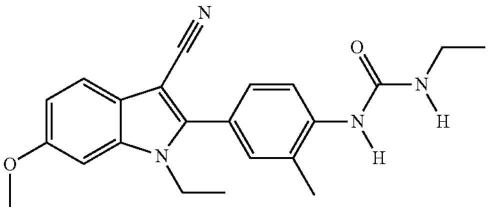

-continued
967
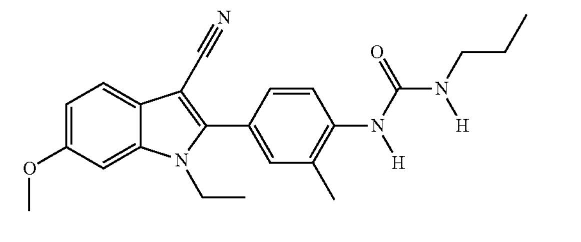
968
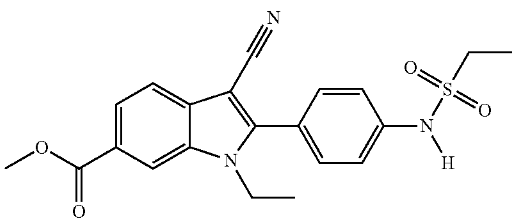
969
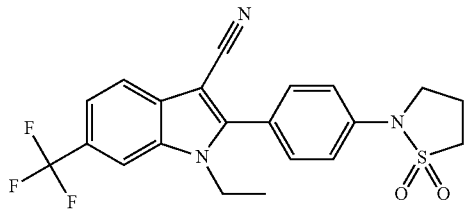
970
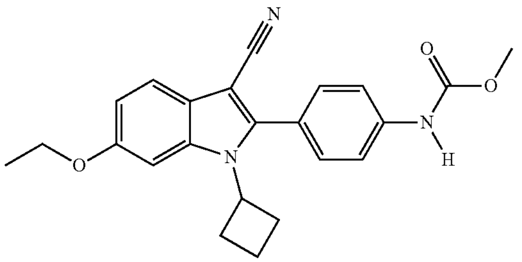
971
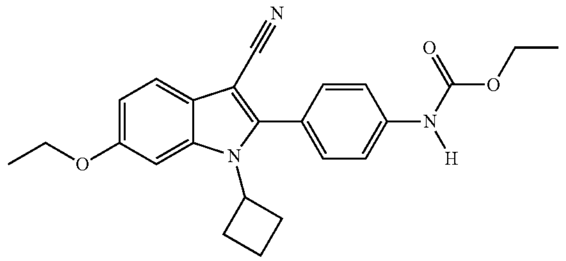
972
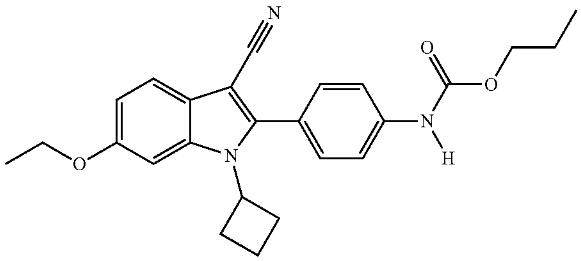
973
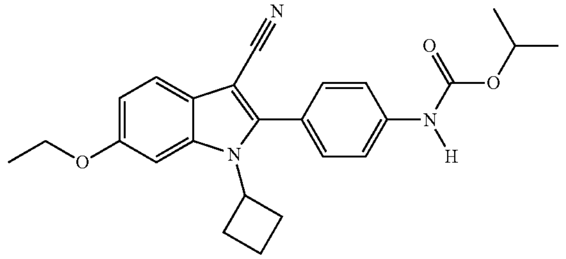
974
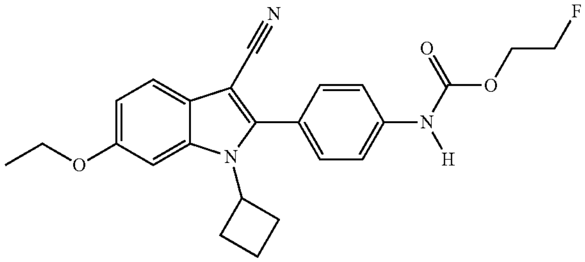
975
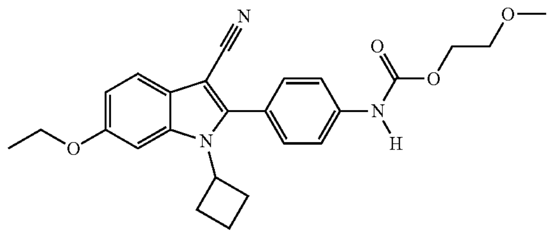
976
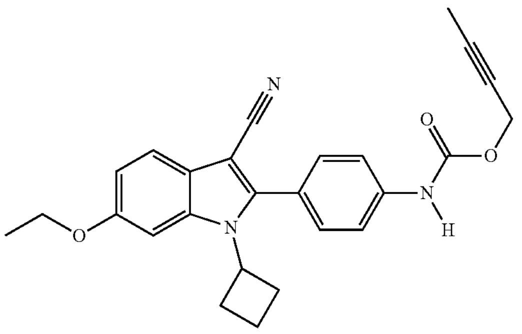

-continued
977
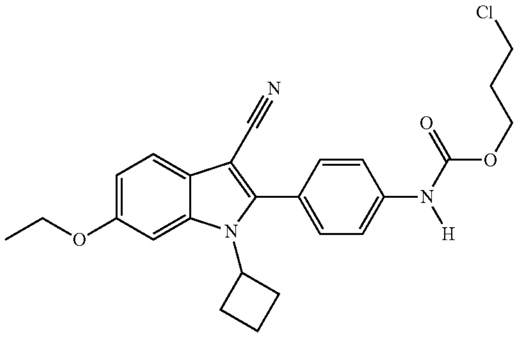
978
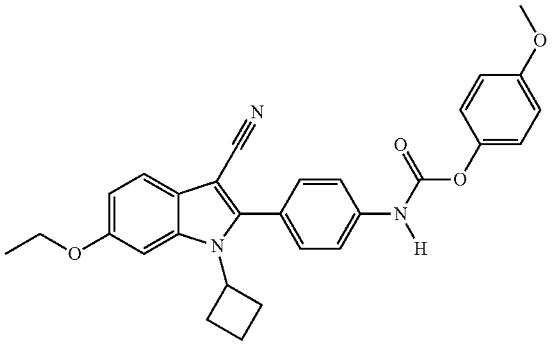
979
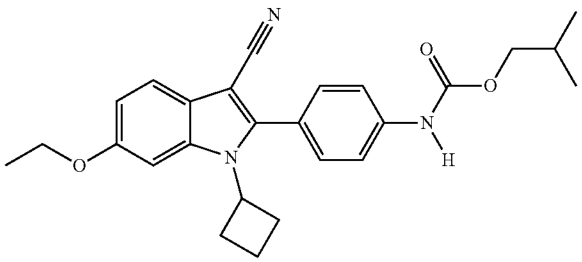
980
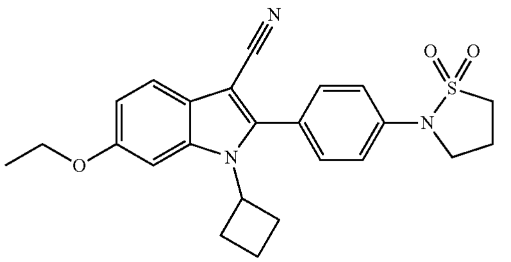
981
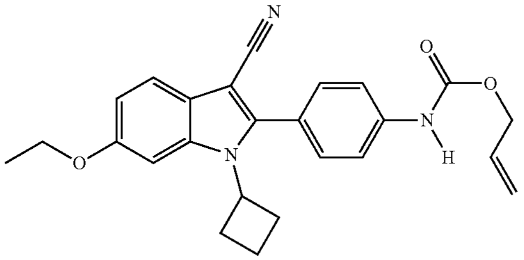
982
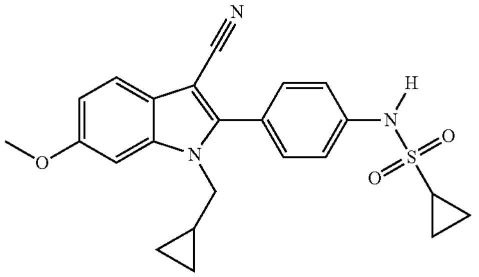
983
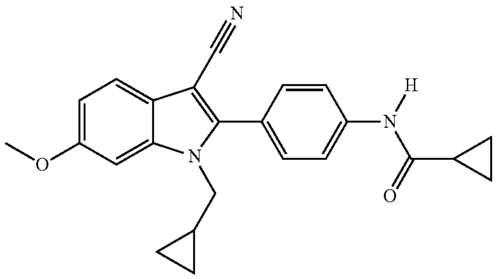
984
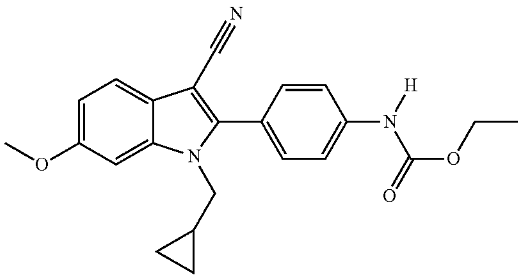
985
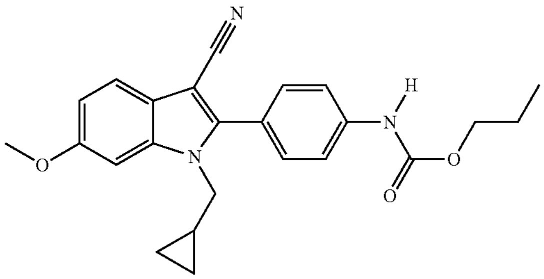
986
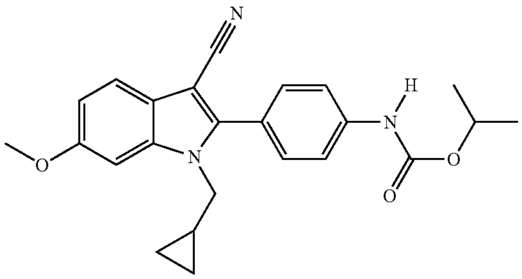

-continued
987
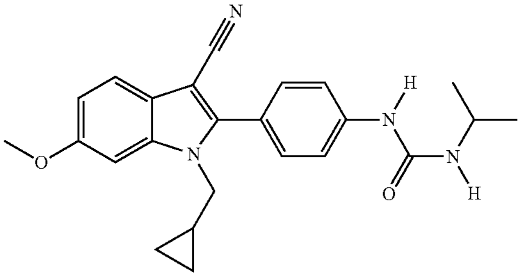
988
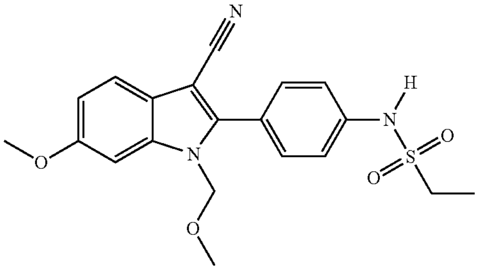
989
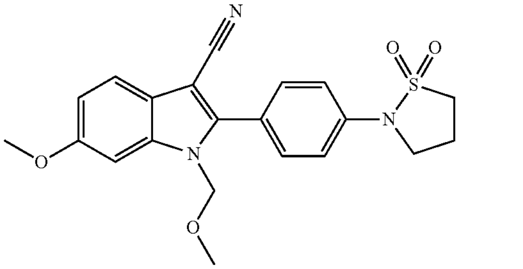
990
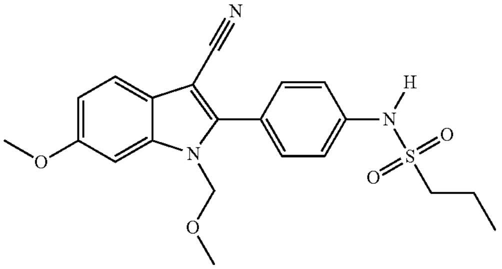
991
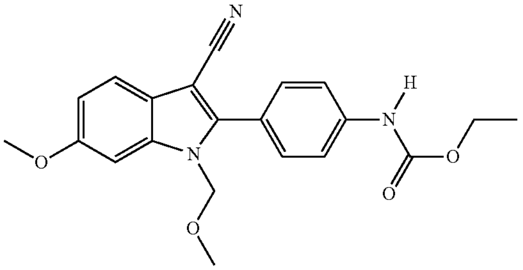
992
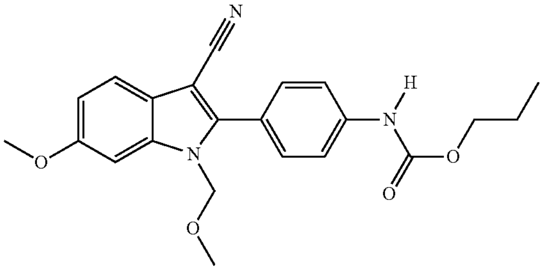
993
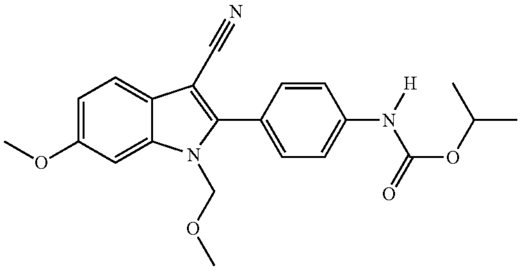
994
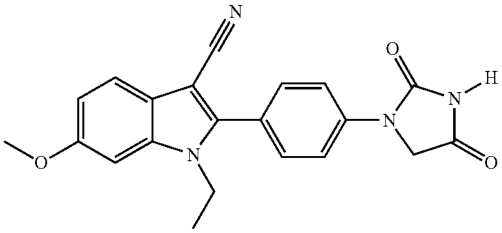
995
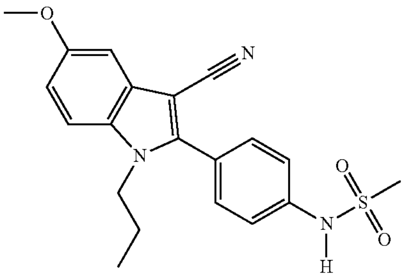
996
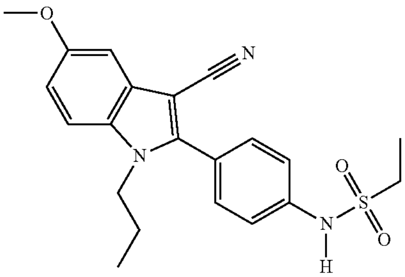

-continued
997
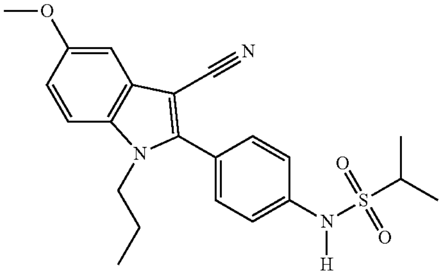
998
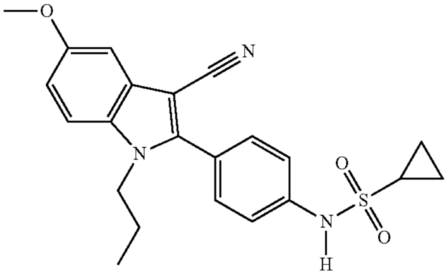
999
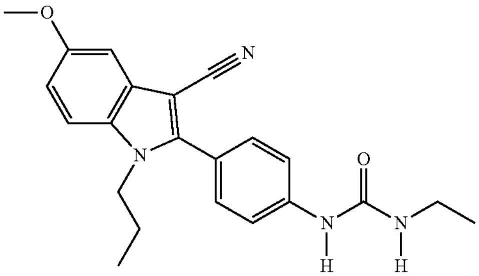
1000
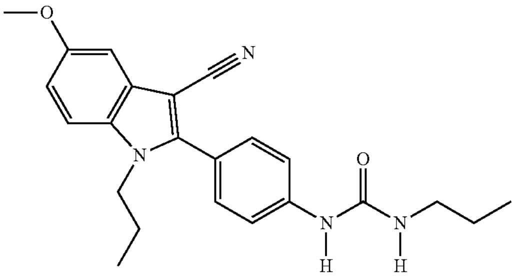
1001
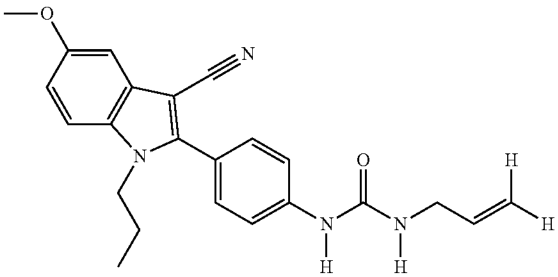
1002
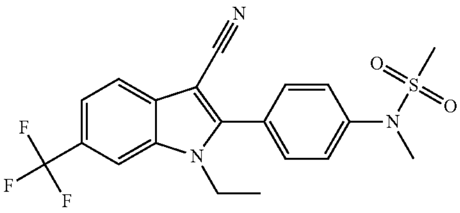
1003
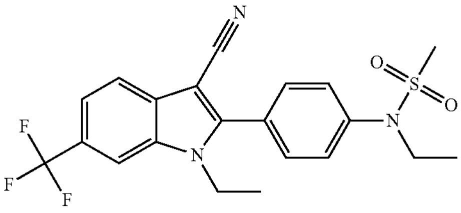
1004
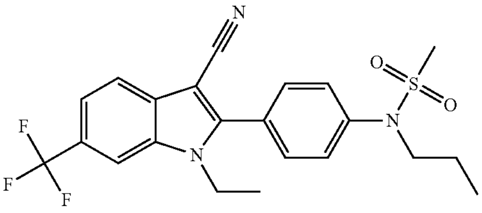
1005
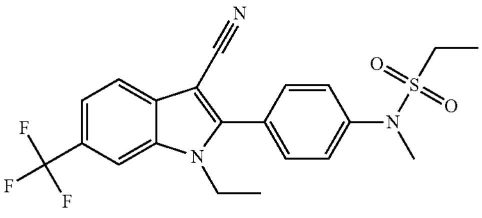
1006
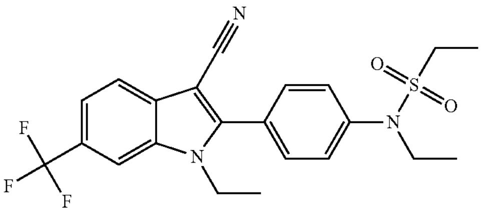
1007
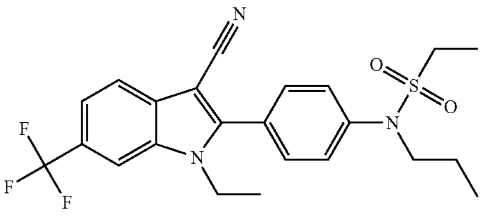
1008
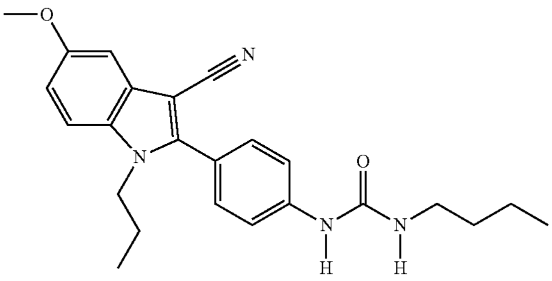

-continued
1009
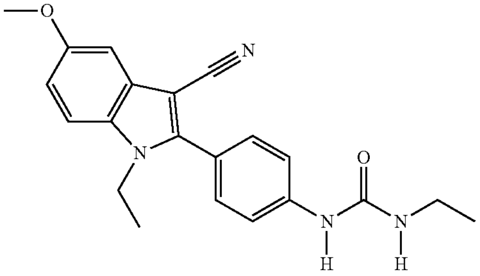
1010
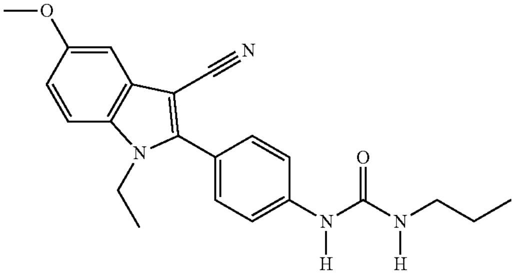
1011
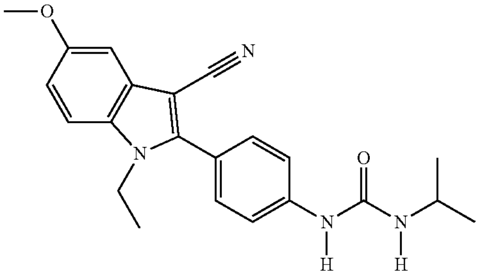
1012
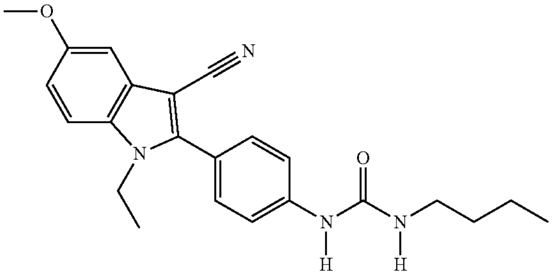
1013
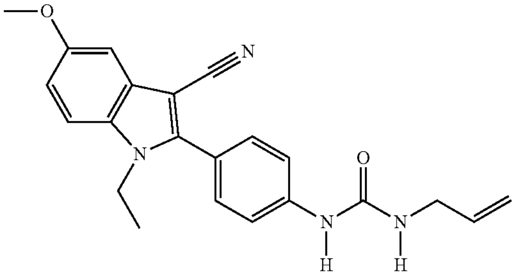
1014
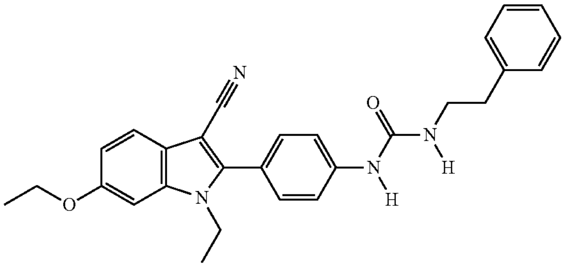
1015
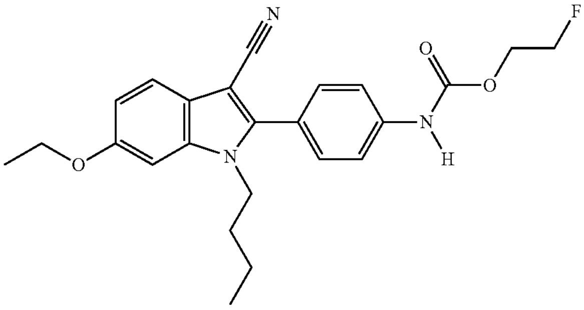
1016
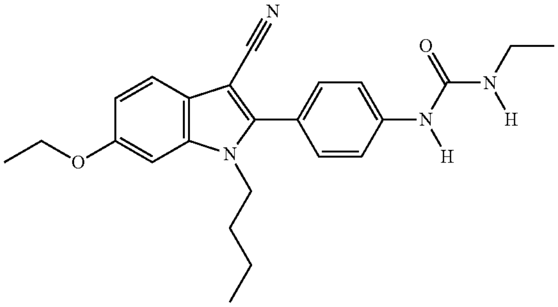
1017
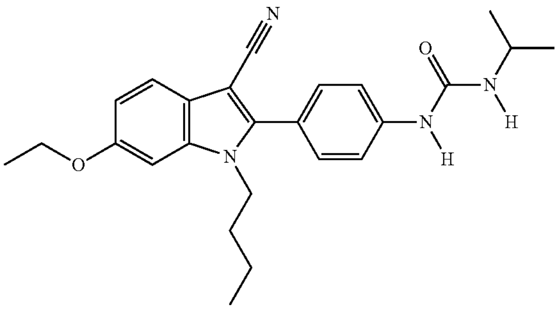
1018
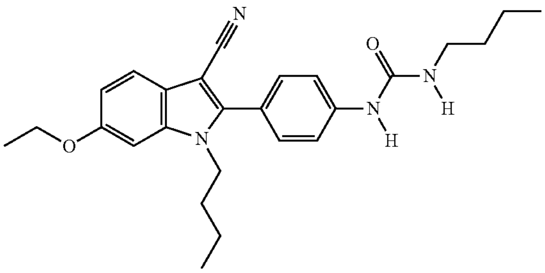

-continued
1019
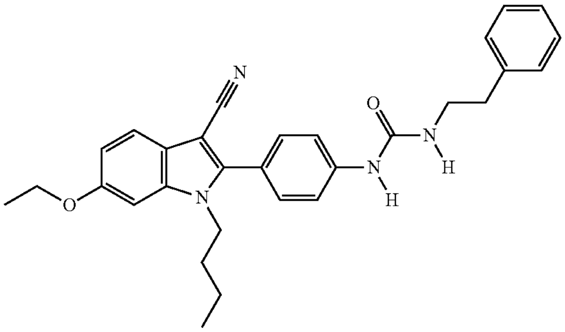
1020
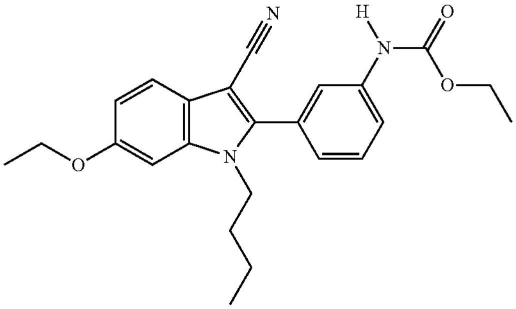
1021
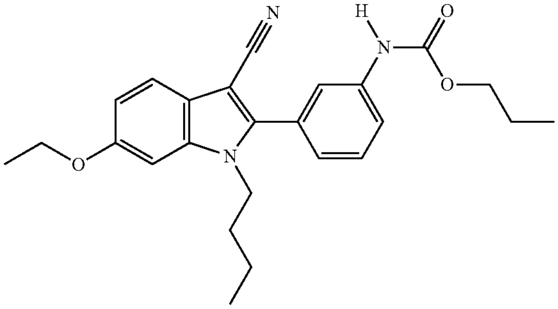
1022
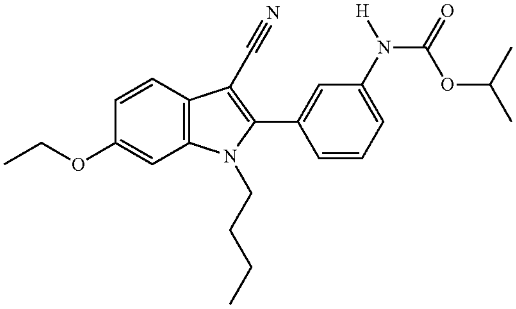
1023
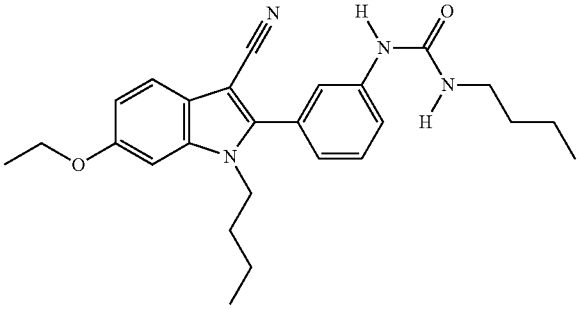
1024
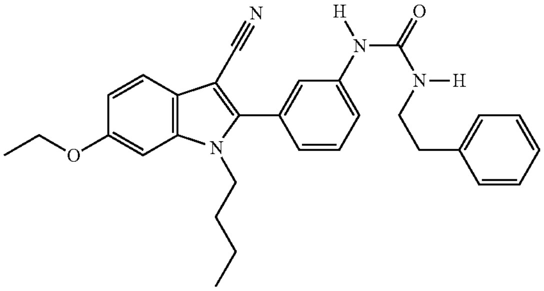
1025
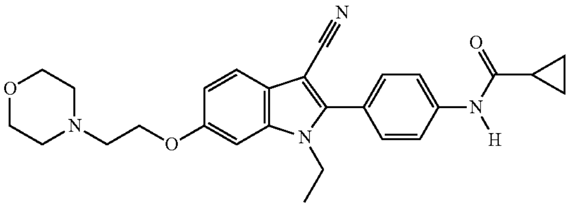
1026
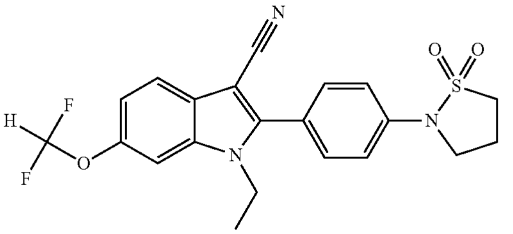
1027
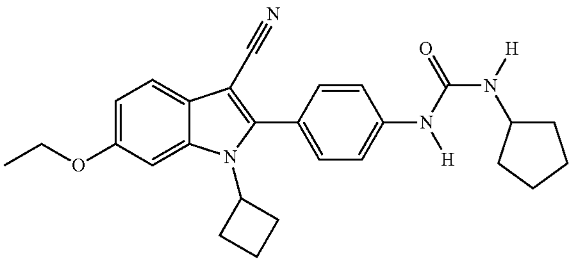
1028
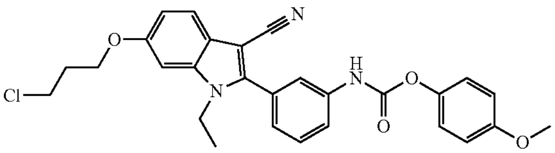

-continued
1029
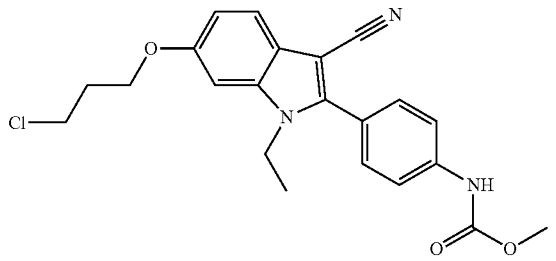
1030
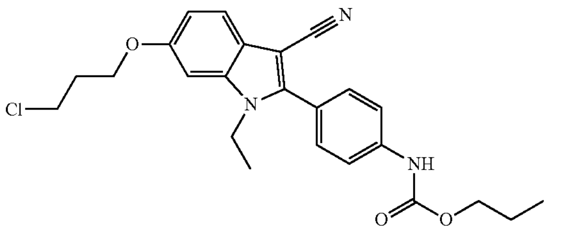
1031
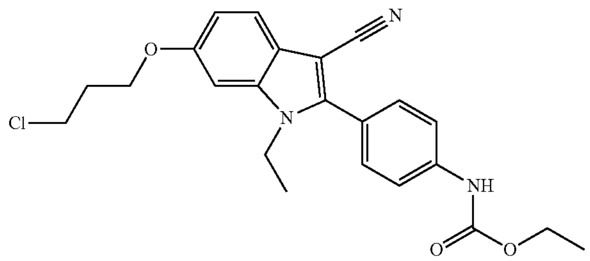
1032
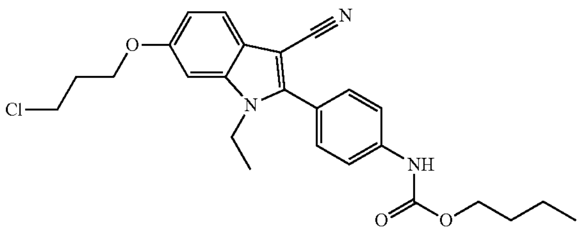
1033
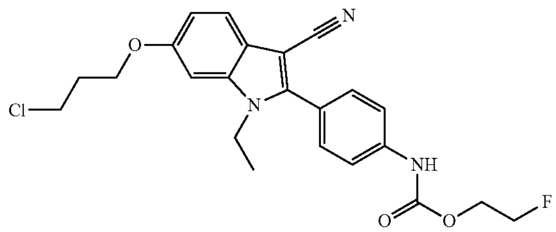
1034
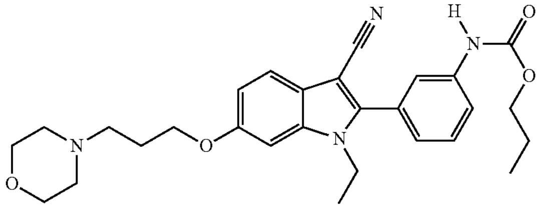
1035
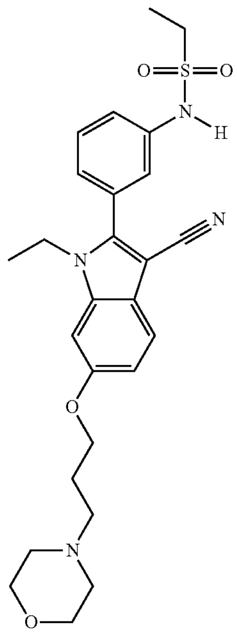
1036
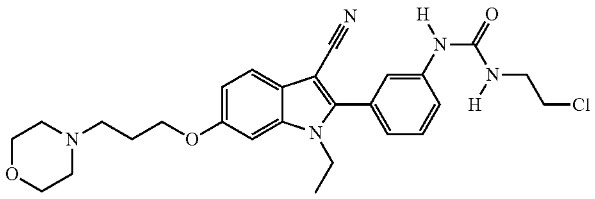

-continued
1037
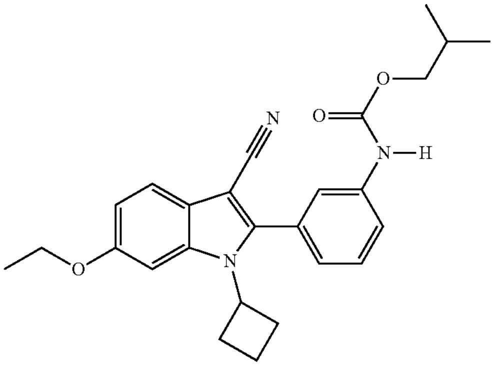
1038
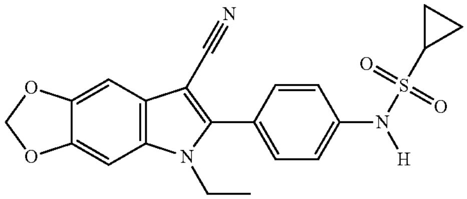
1039
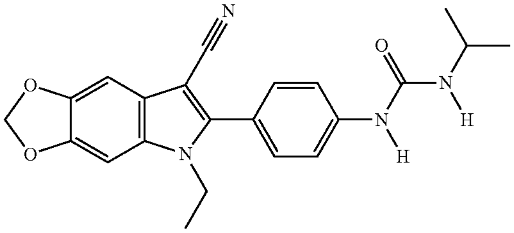
1040
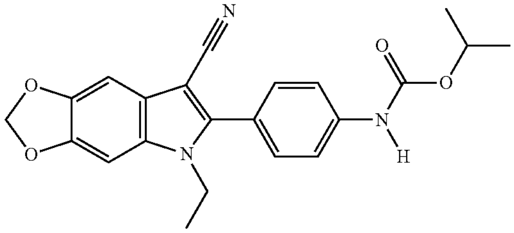
1041
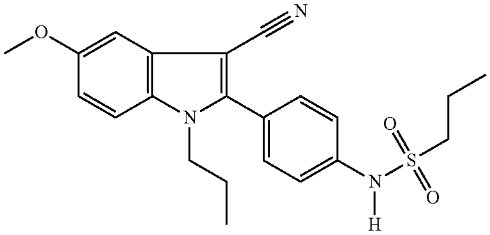
1042
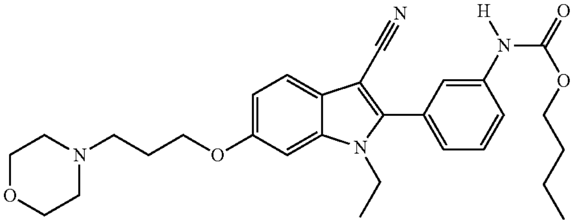
1043
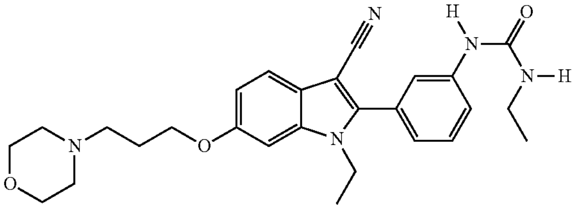
1044
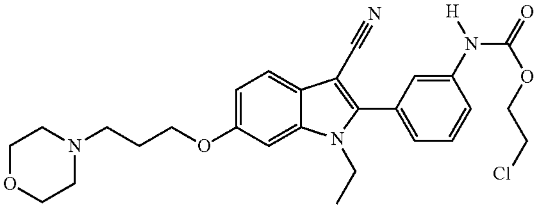
1045
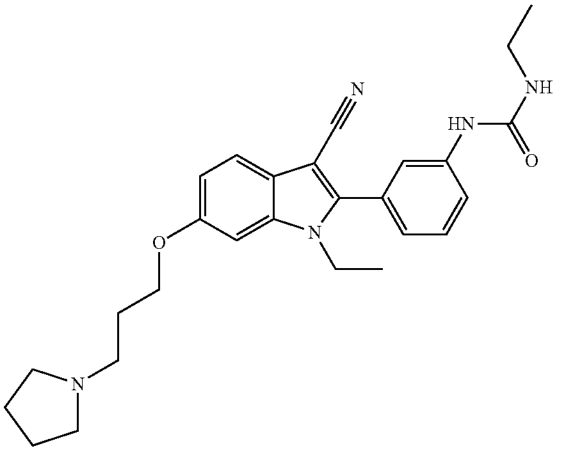
1046
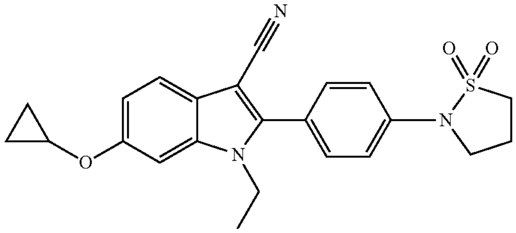

-continued
1047
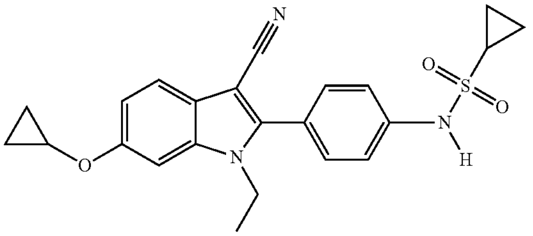
1048
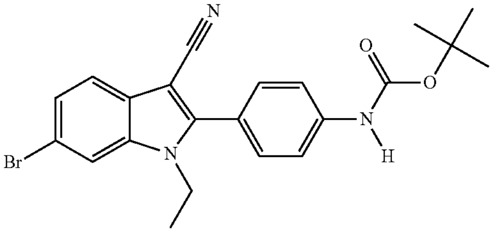
1049
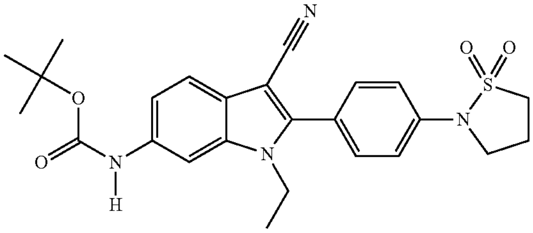
1050
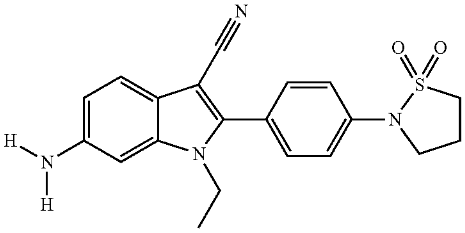
1051
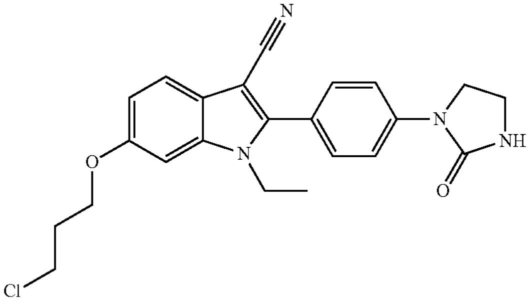
1052
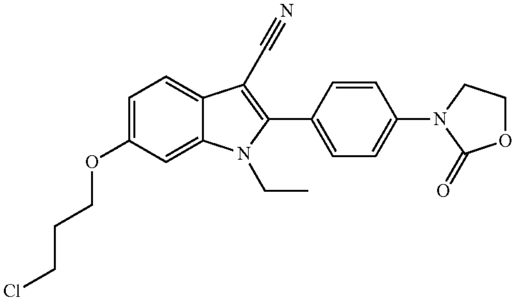
1053
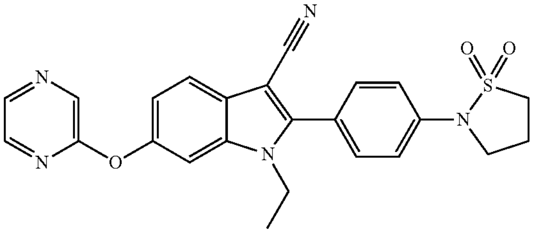
1054
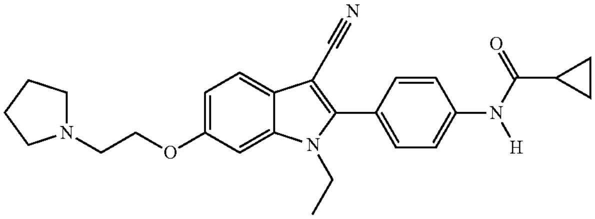
1055
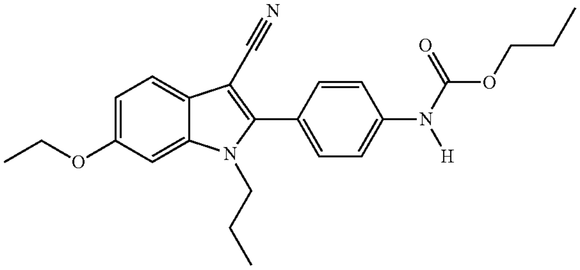
1056
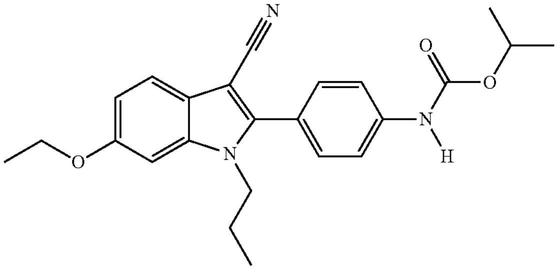
1057
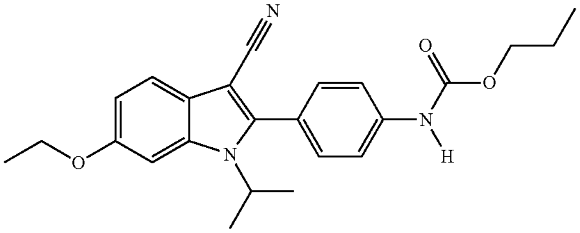
1058
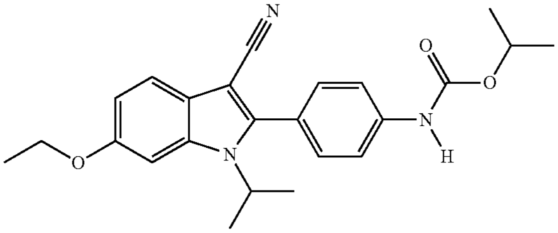

-continued
1059
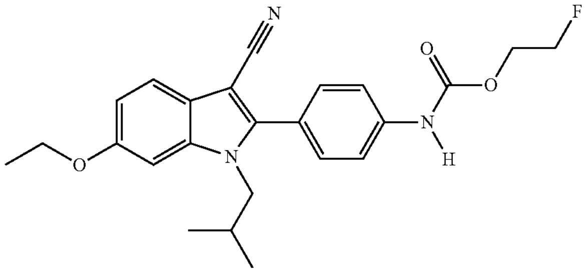
1060
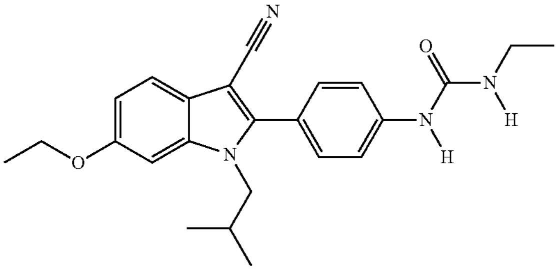
1061
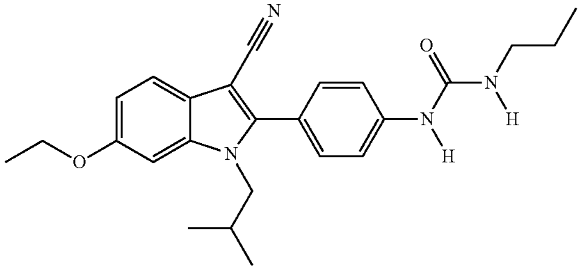
1062
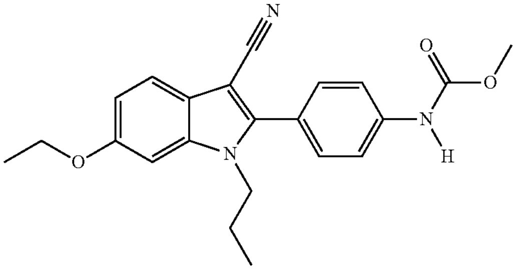
1063
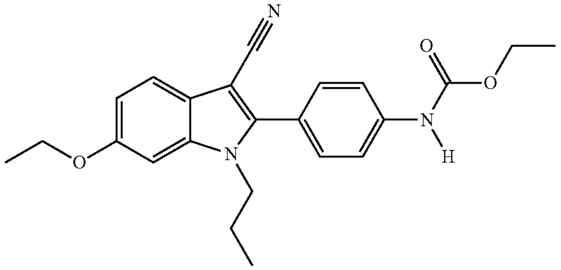
1064
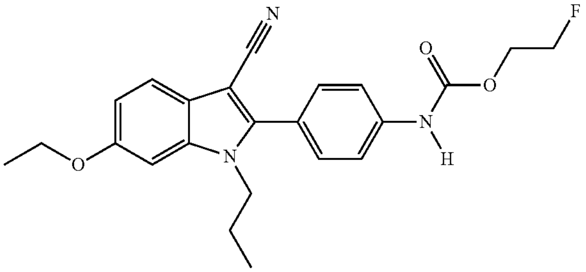
1065
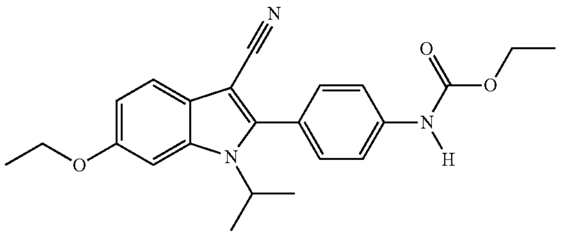
1066
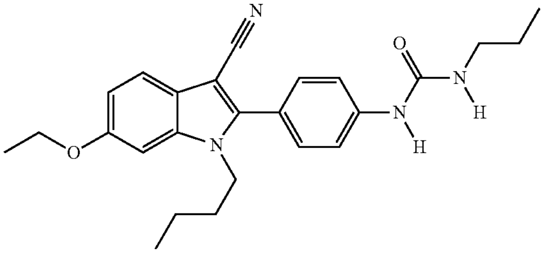
1067
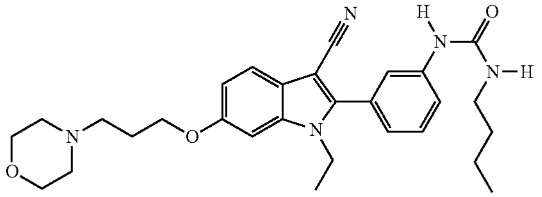
1068
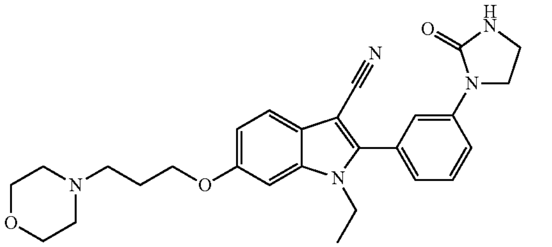

-continued
1069
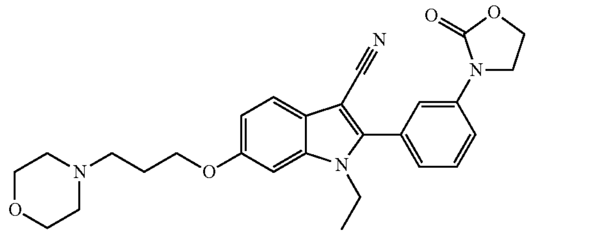
1070
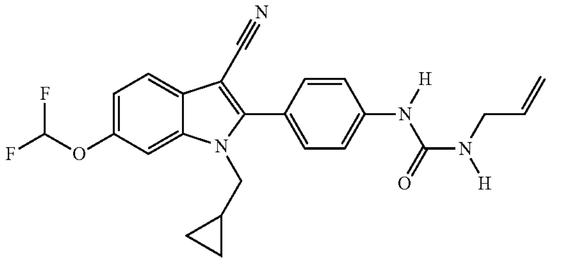
1071
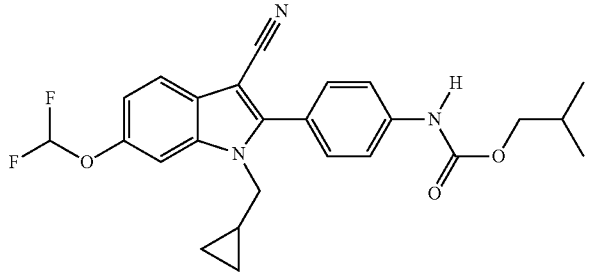
1072
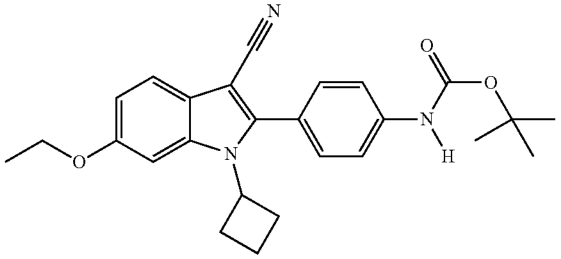
1073
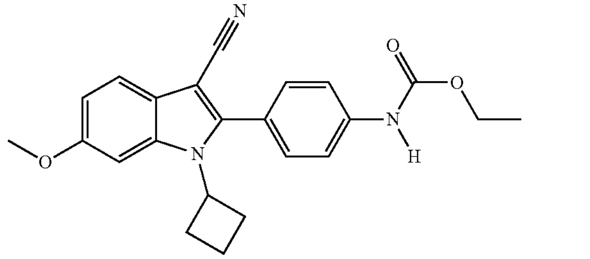
1074
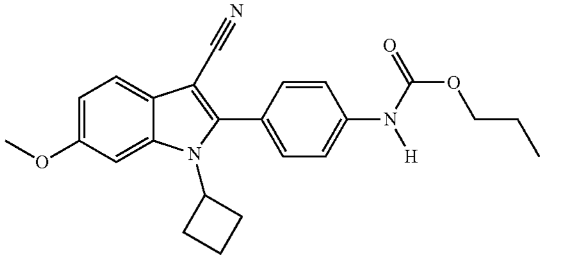
1075
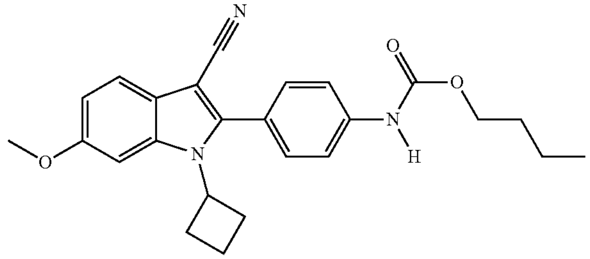
1076
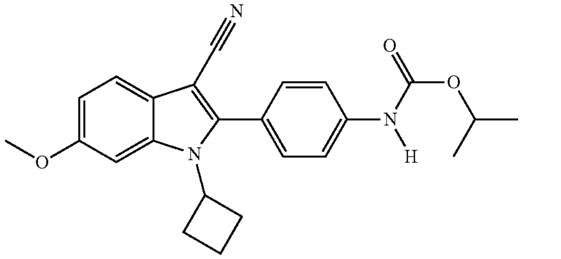
1077
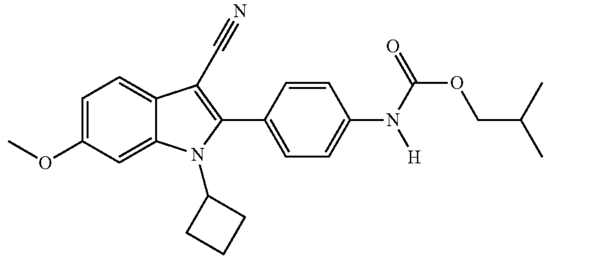
1078
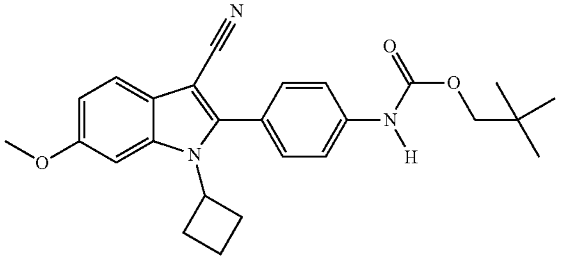

-continued
1079
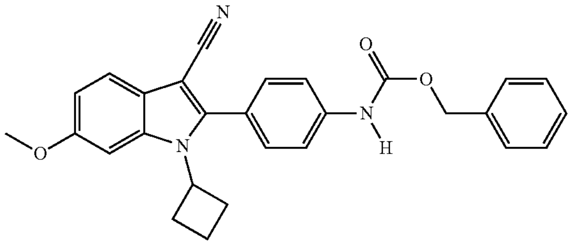
1080
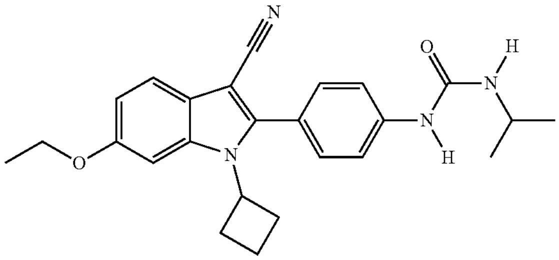
1081
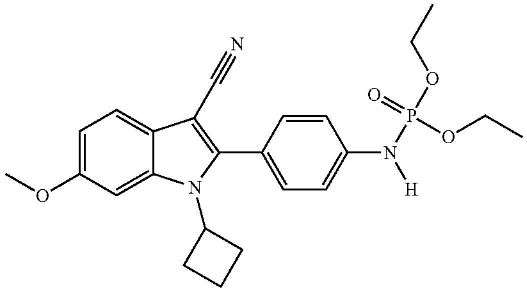
1082
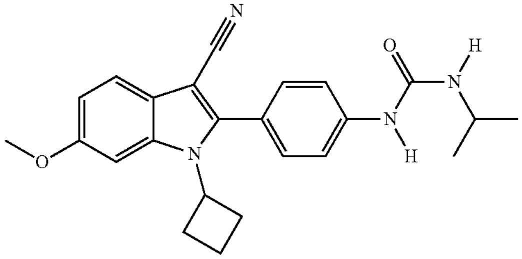
1083
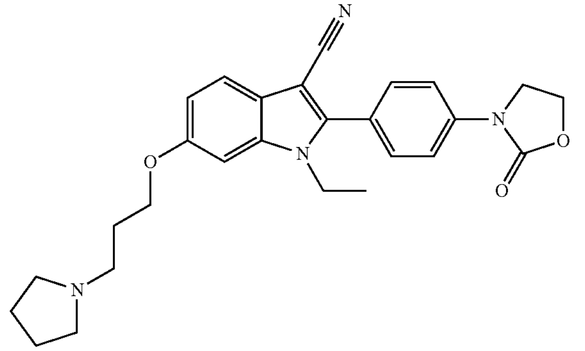
1084
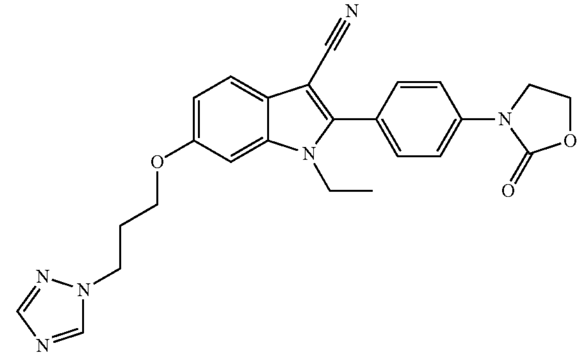
1085
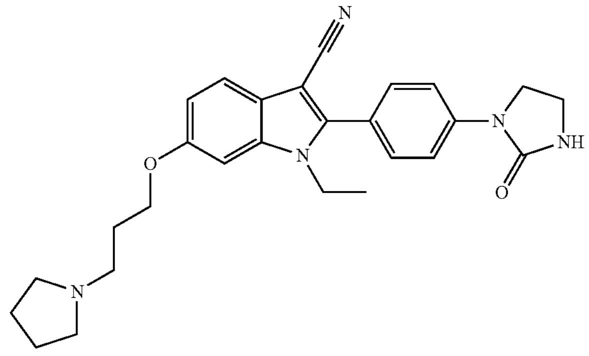
1086
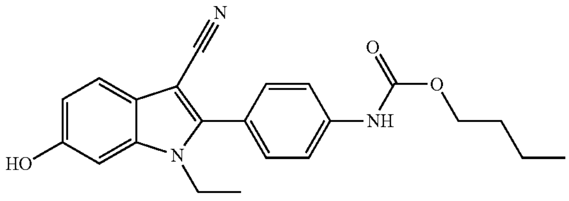
1087
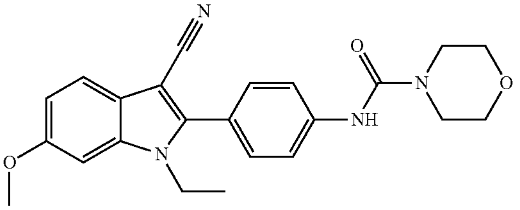
1088
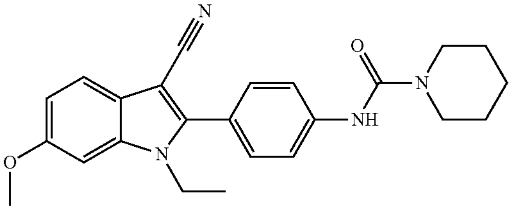

-continued
1089
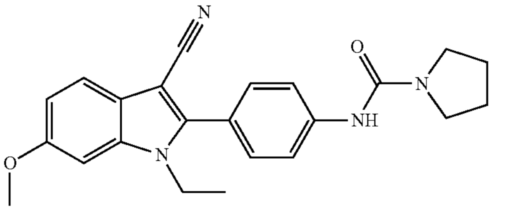
1090
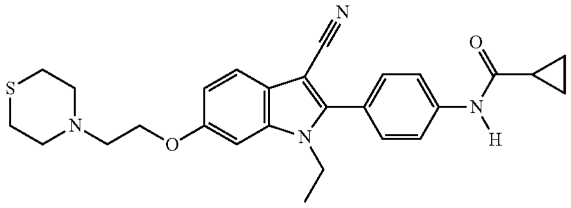
1091
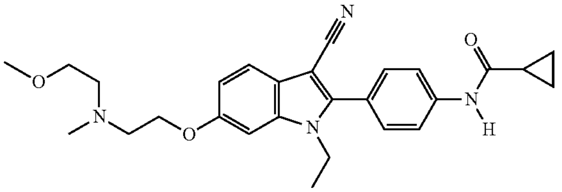
1092
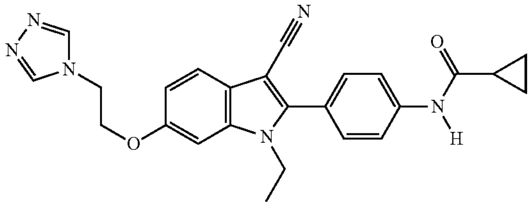
1093
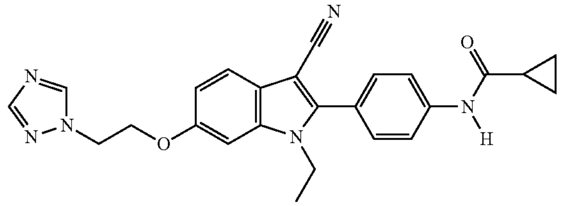
1094
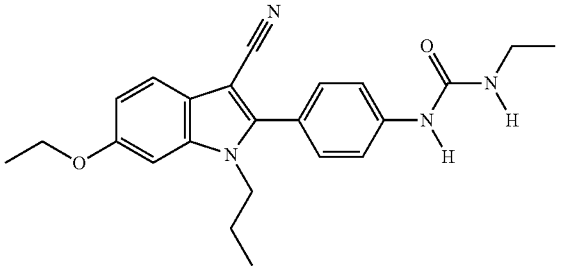
1095
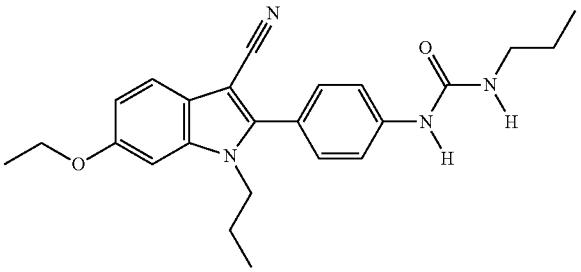
1096
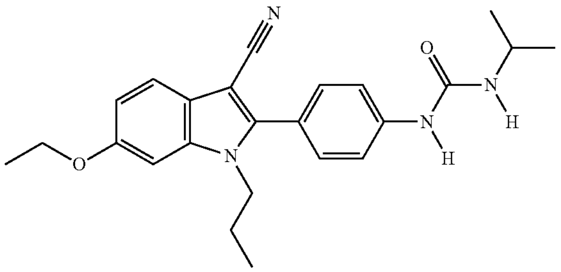
1097
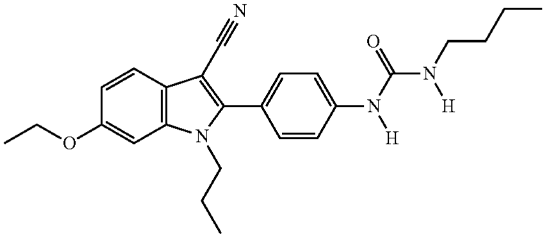
1098
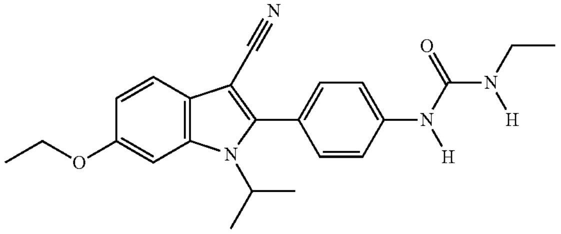
1099
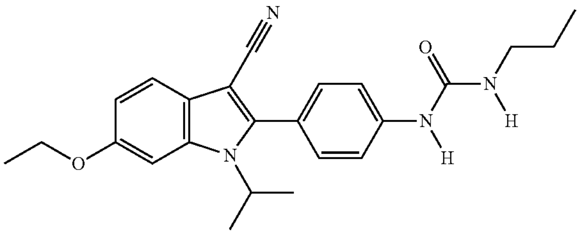
1100
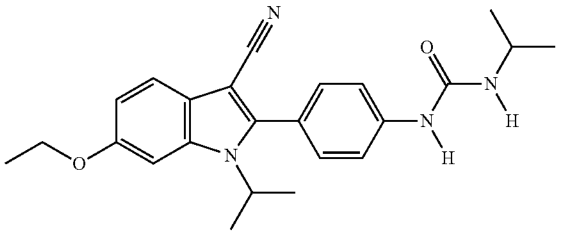

-continued
1101
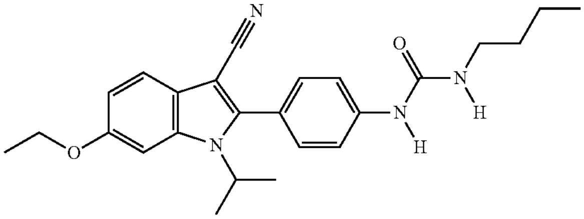
1102
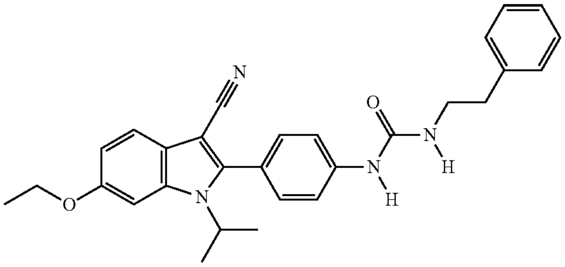
1103
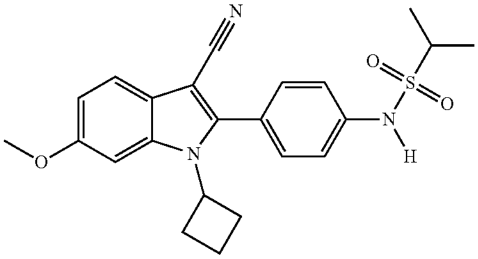
1104
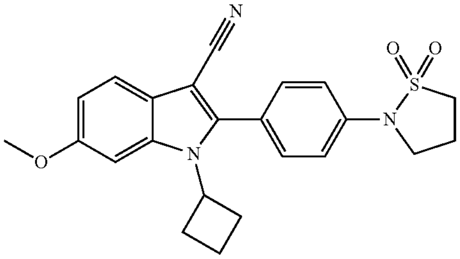
1105
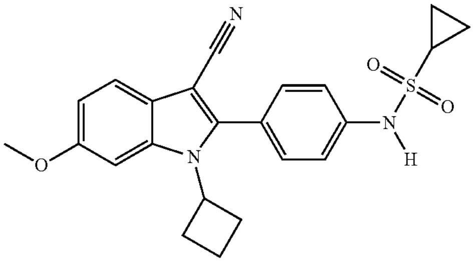
1106
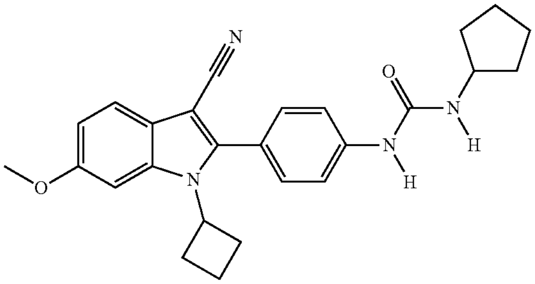
1107
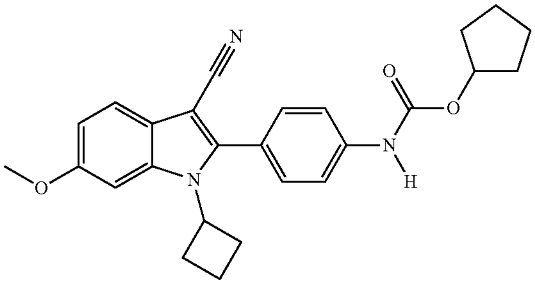
1108
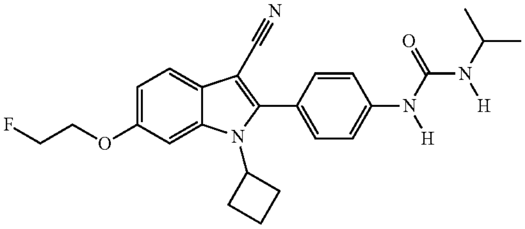
1109
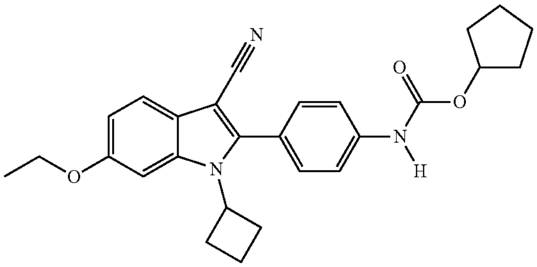
1110
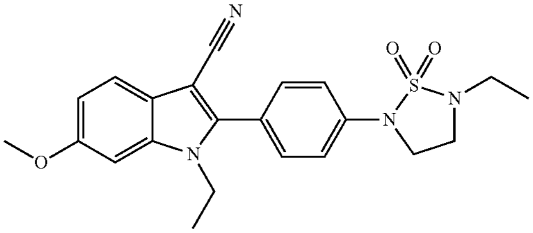

-continued
1111
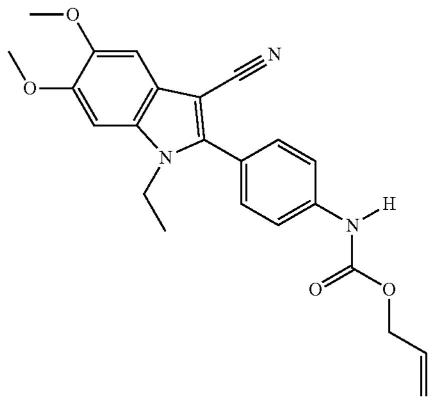
1112
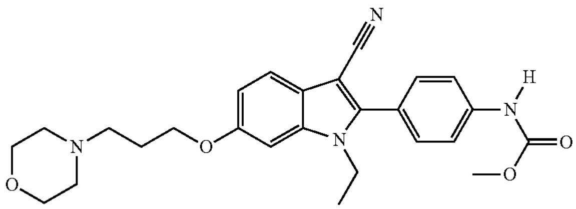
1113
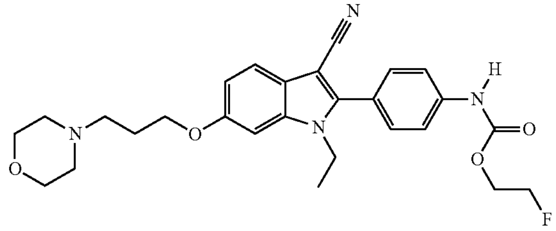
1114
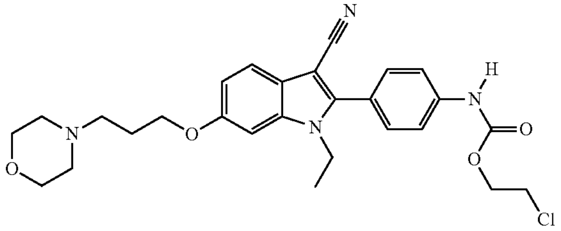
1115
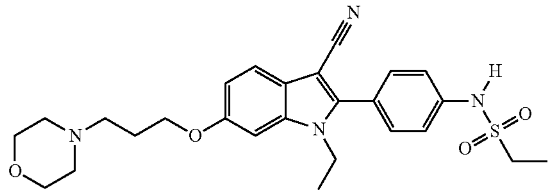
1116
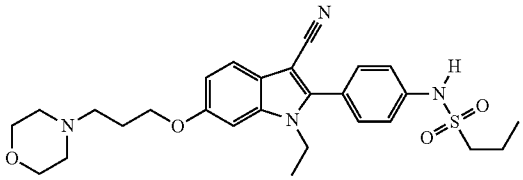
1117
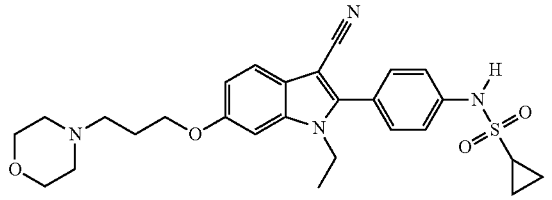
1118
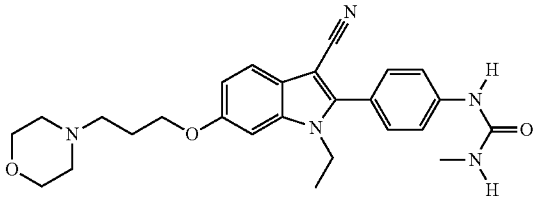
1119
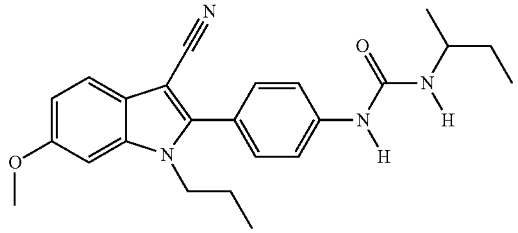
1120
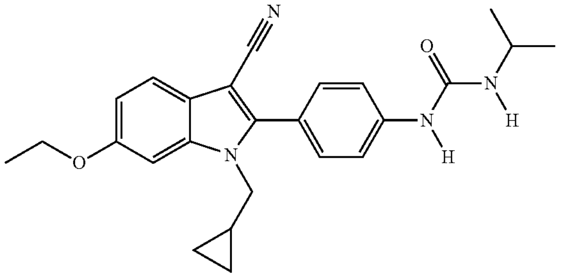

-continued
1121
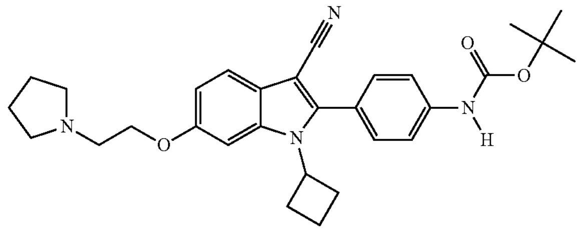
1122
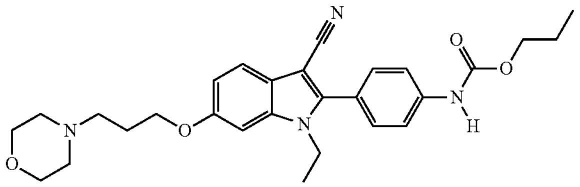
1123
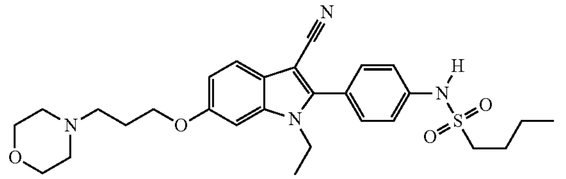
1124
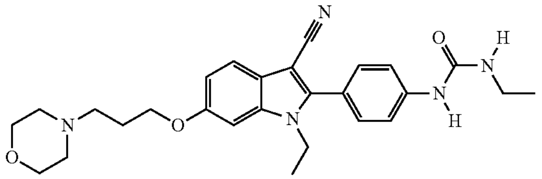
1125
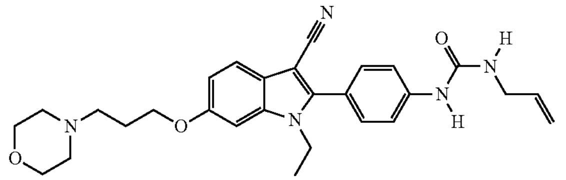
1126
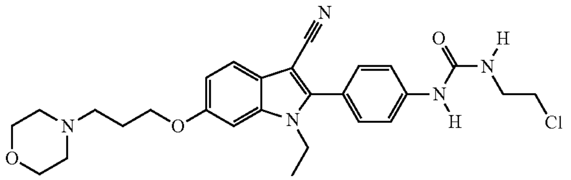
1127
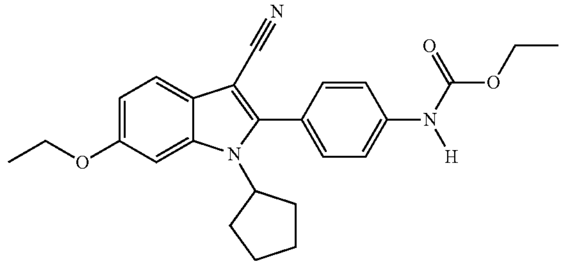
1128
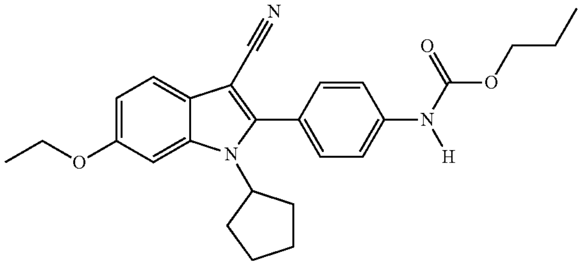
1129
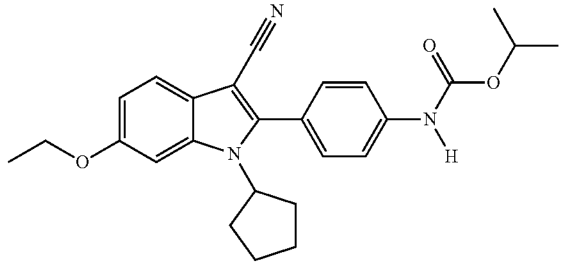
1130
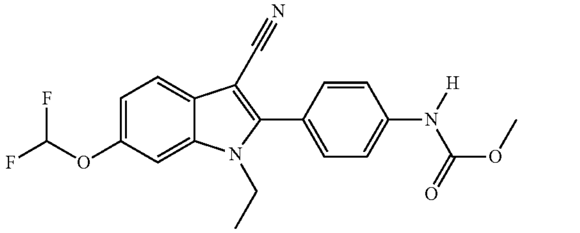
1131
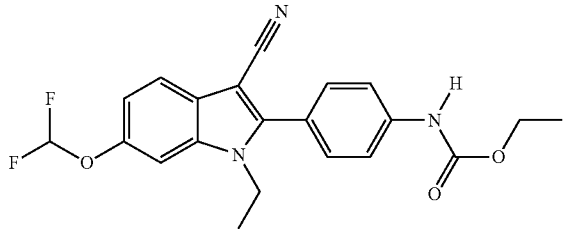
1132
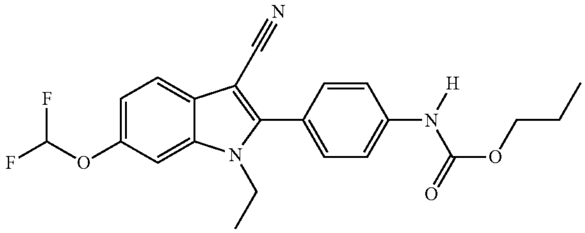

-continued
1133
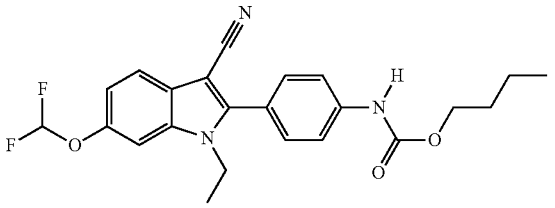
1134
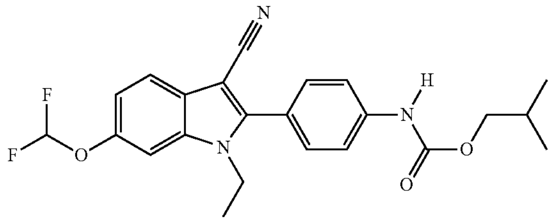
1135
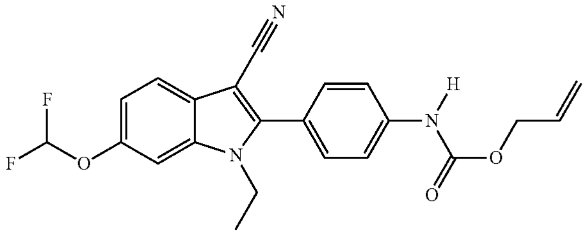
1136
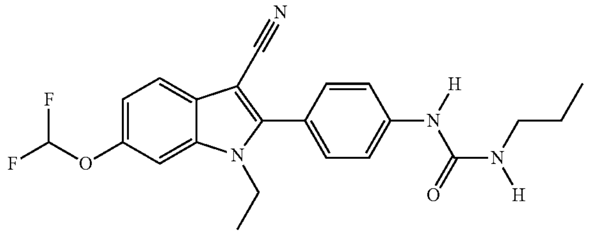
1137
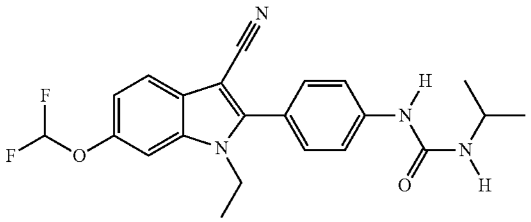
1138
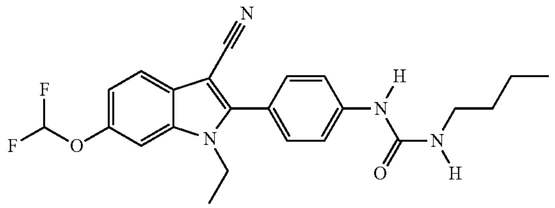
1139
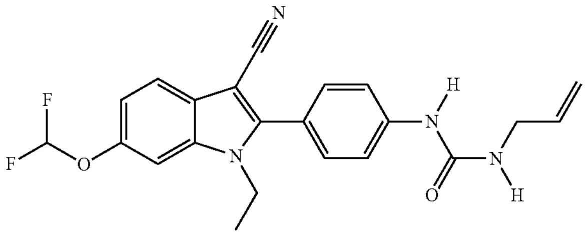
1140
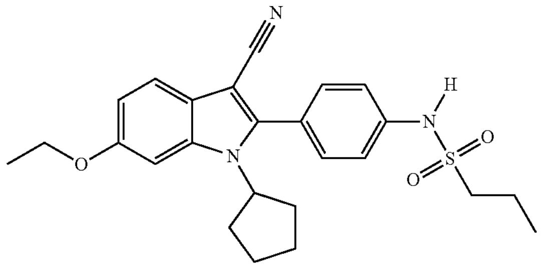
1141
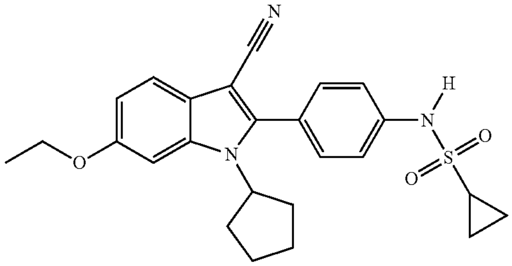
1142
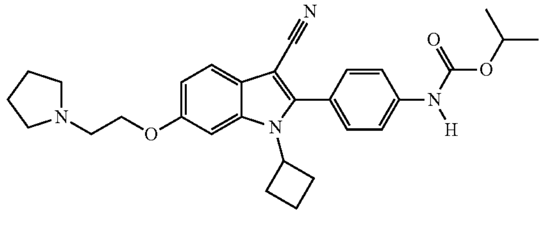
1143
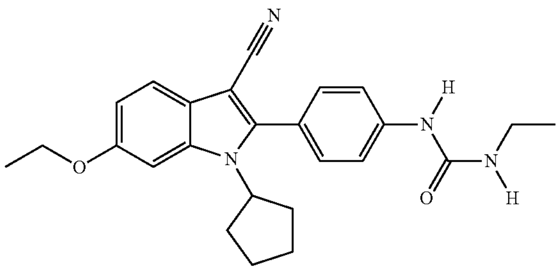
1144
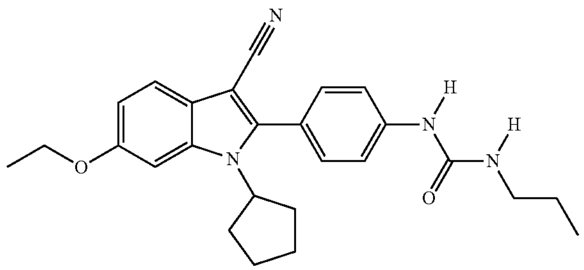

-continued
1146
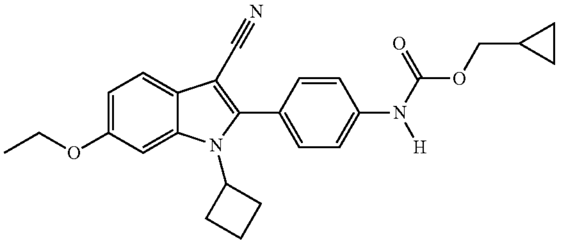
1147
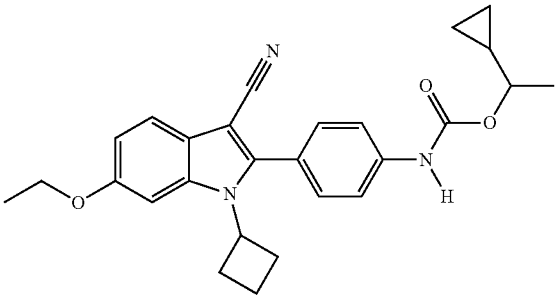
1148
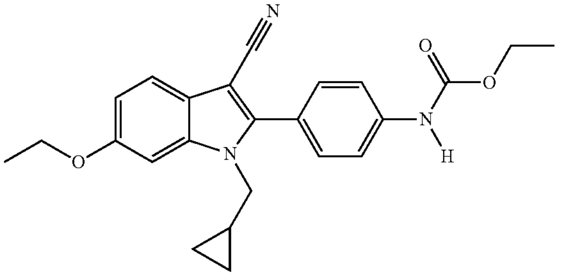
1149
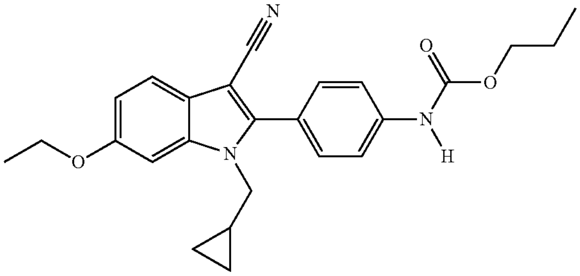
1150
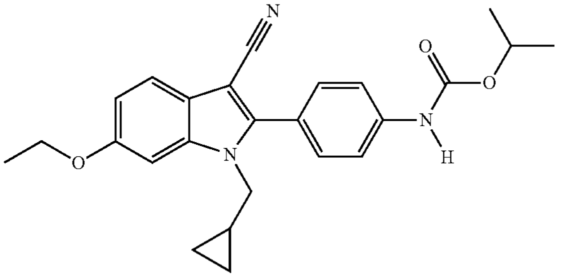
1151
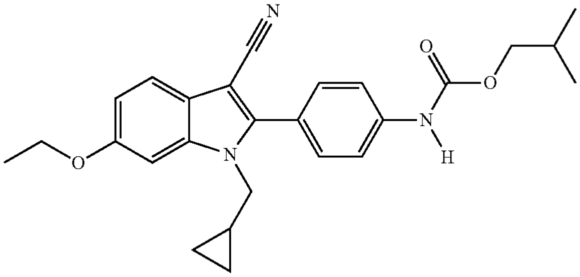
1152
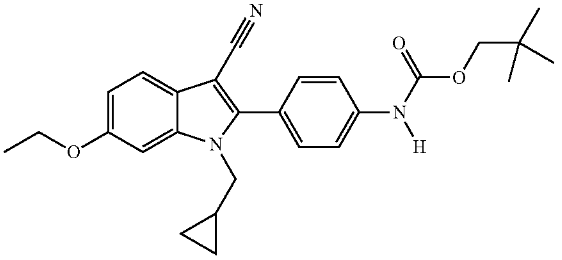
1153
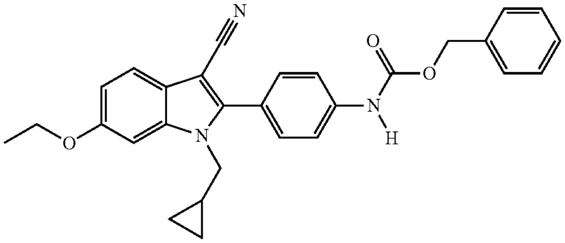
1154
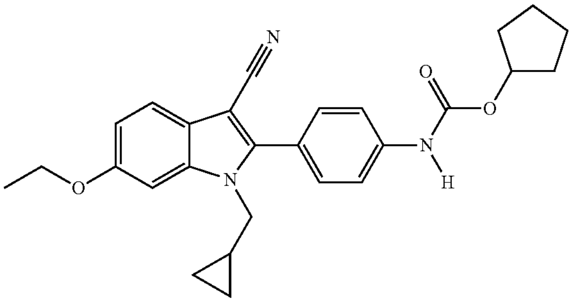
1155
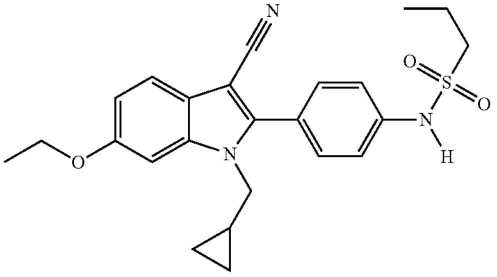

-continued
1156
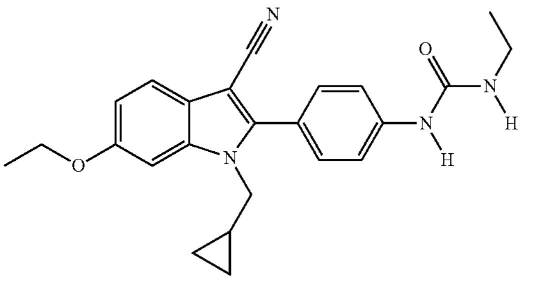
1157
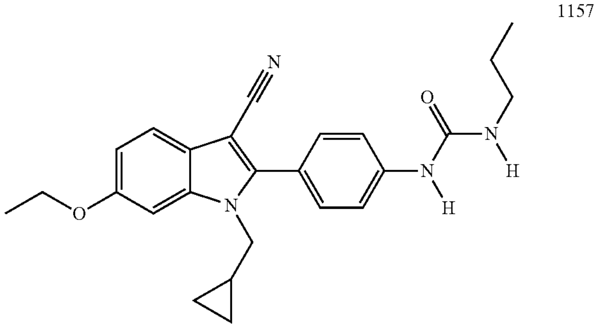
1158
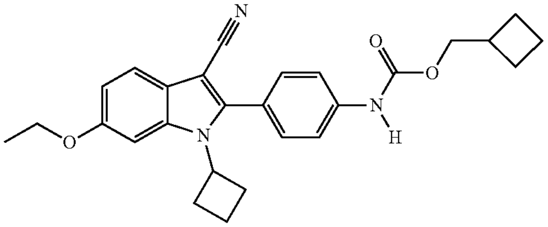
1159
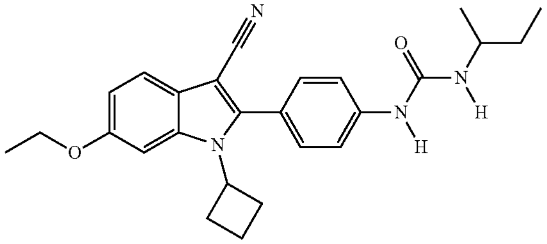
1160
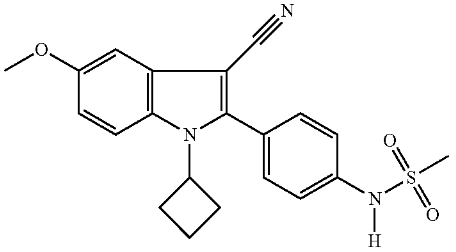
1161
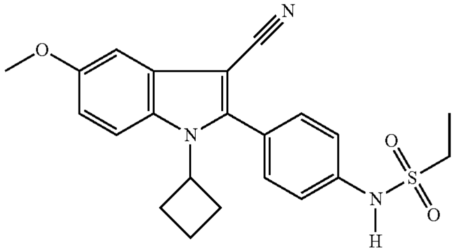
1162
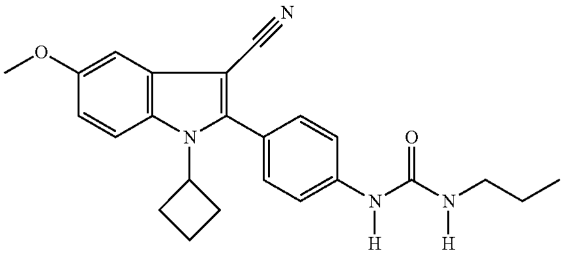
1163
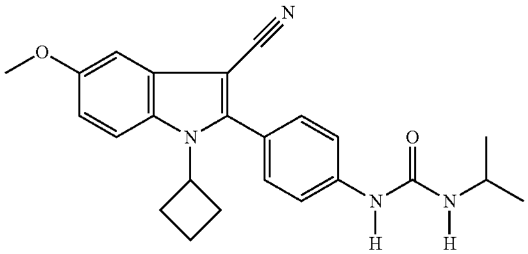
1164
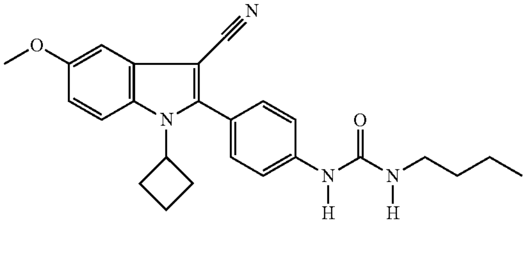
1165
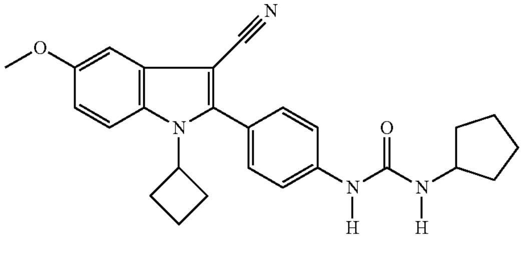

-continued
1166
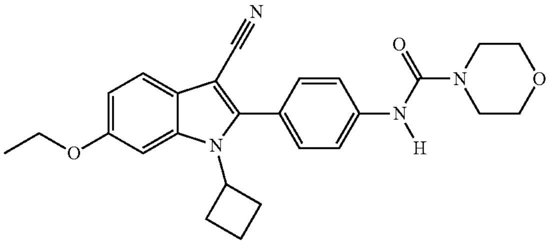
1167
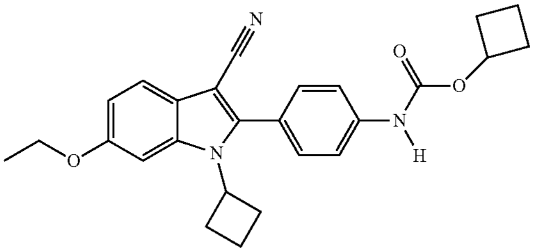
1168
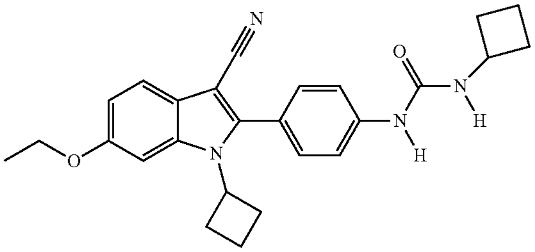
1169
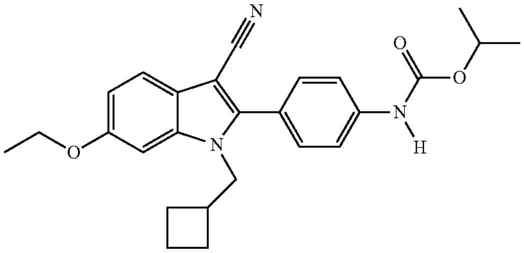
1170
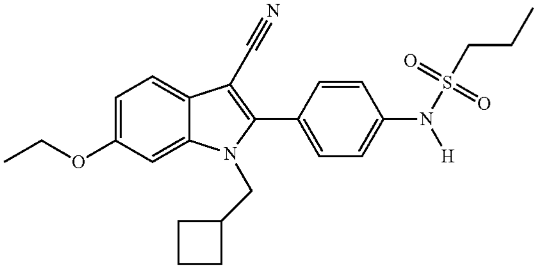
1171
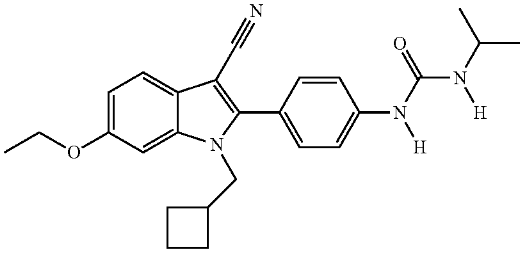
1172
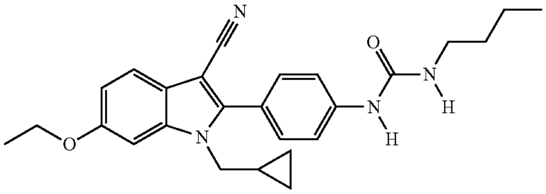
1173
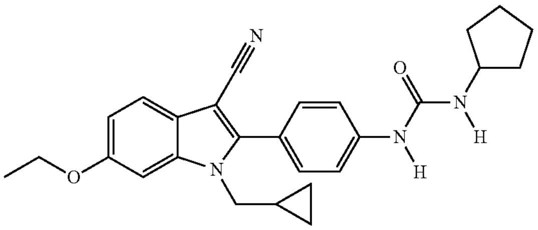
1174
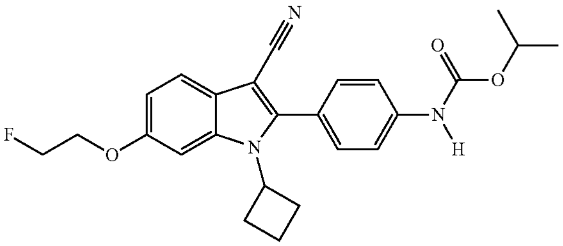
1175
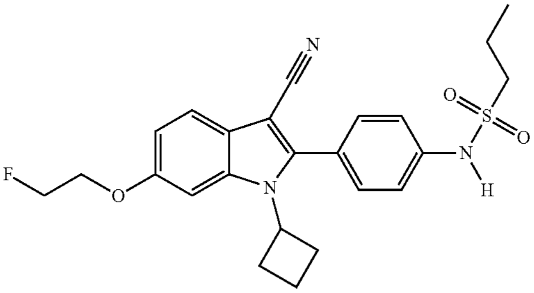

-continued
1176
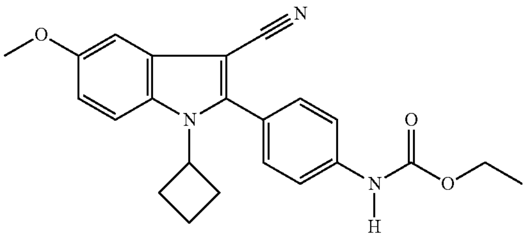
1177
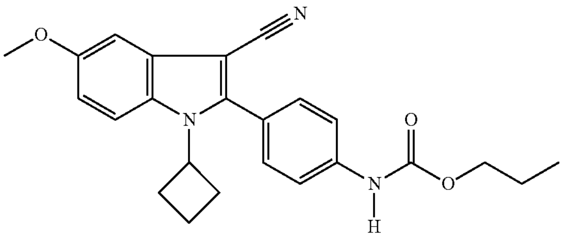
1178
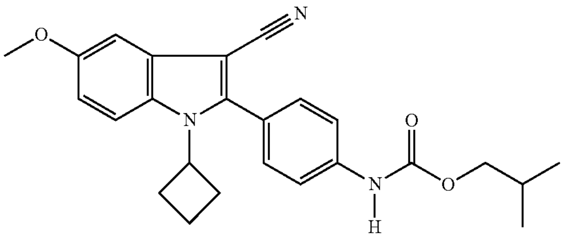
1179
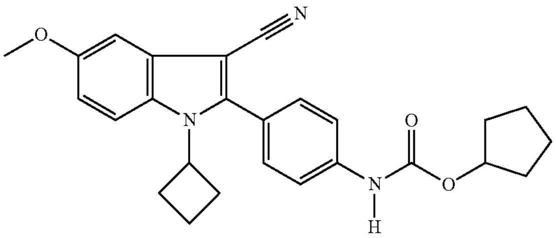
1180
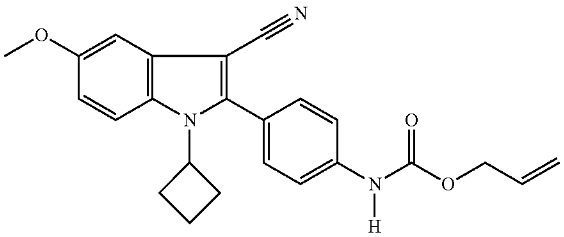
1181
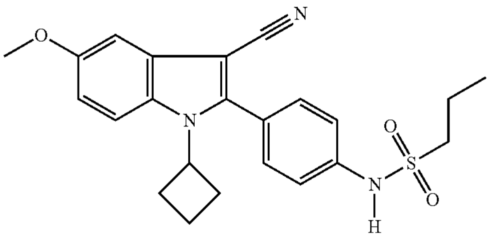
1182
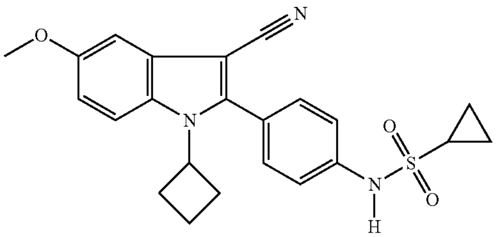
1183
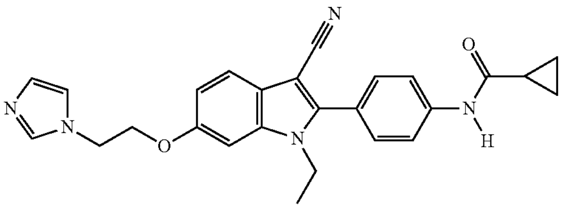
1184
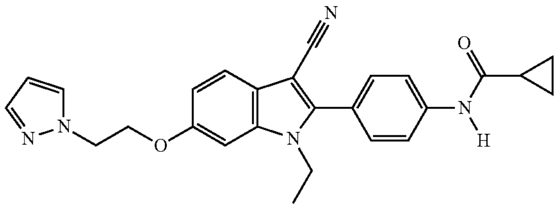
1185
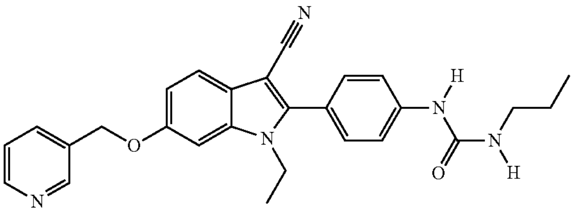
1186
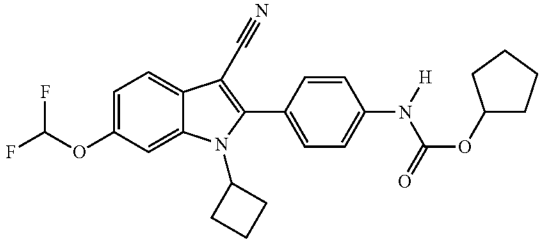
1187
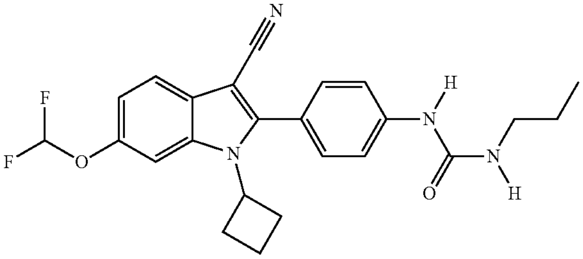

-continued
1188
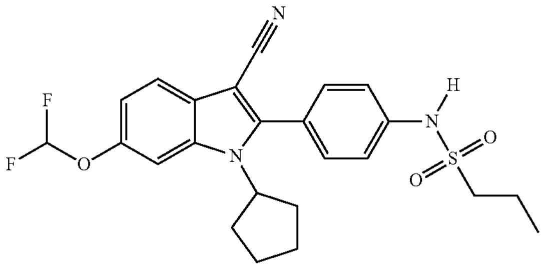
1189
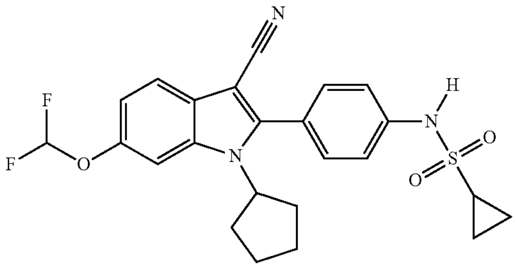
1190
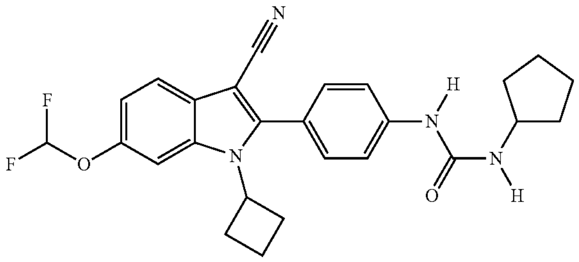
1191
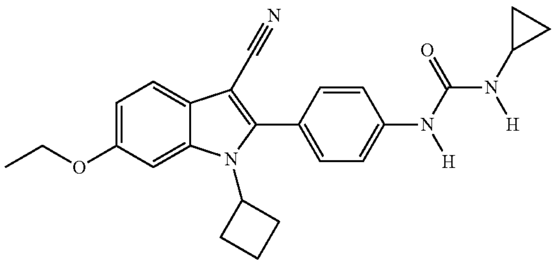
1192
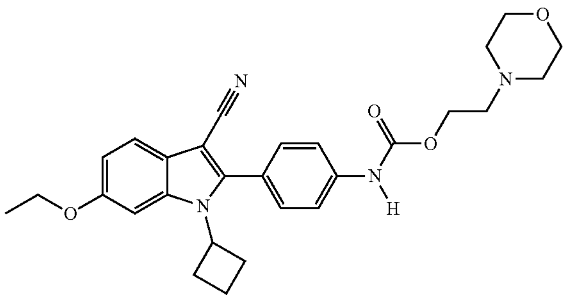
1193
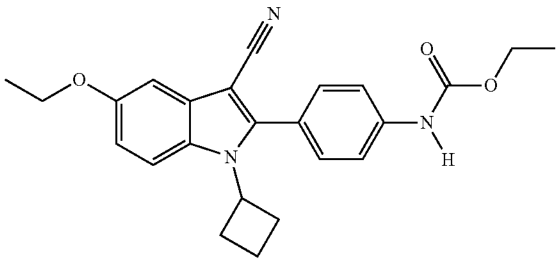
1194
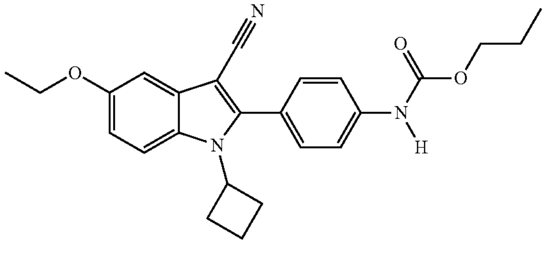
1195
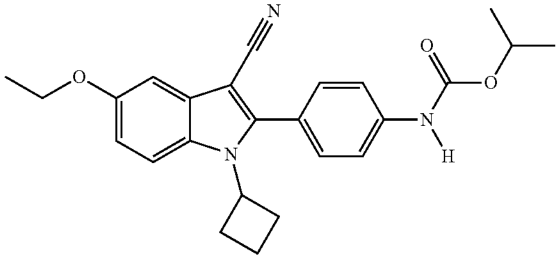
1196
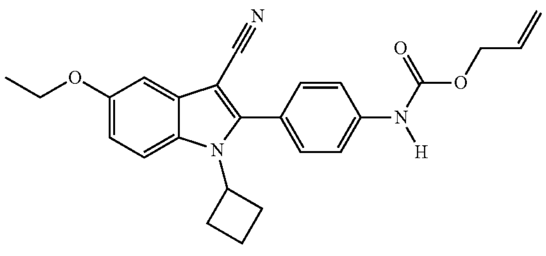
1197
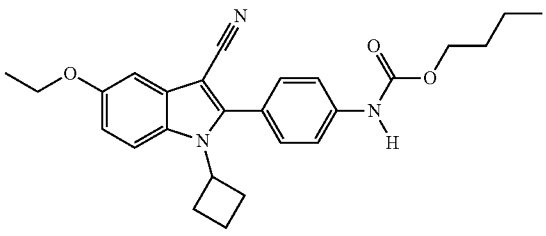

-continued
1198
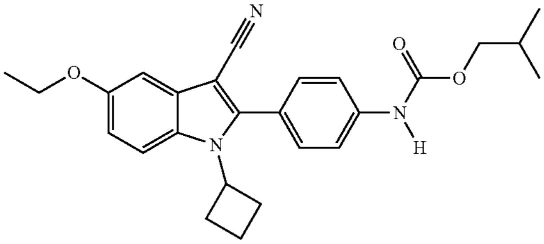
1199
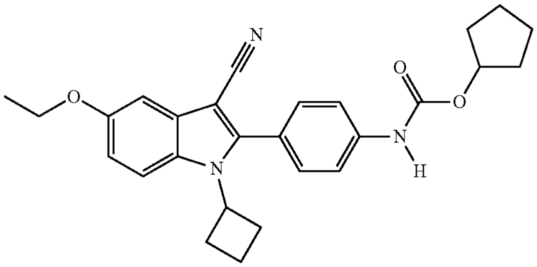
1200
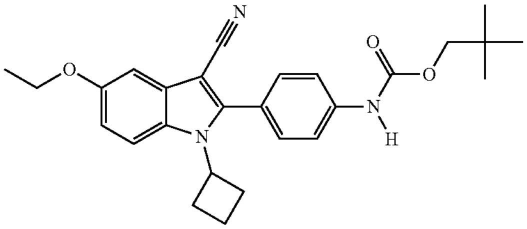
1201
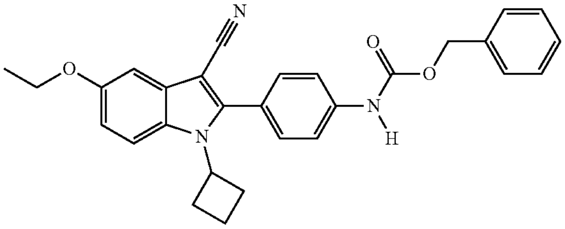
1202
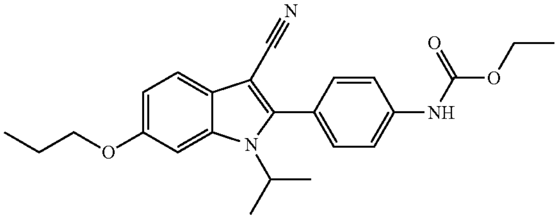
1203
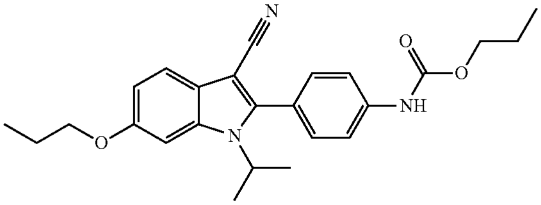
1204
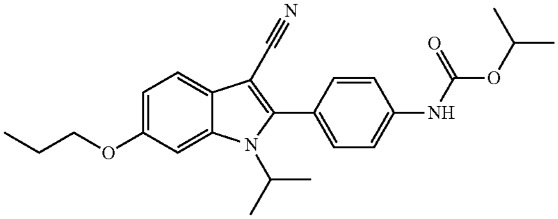
1205
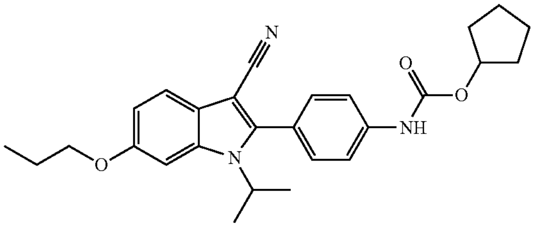
1206
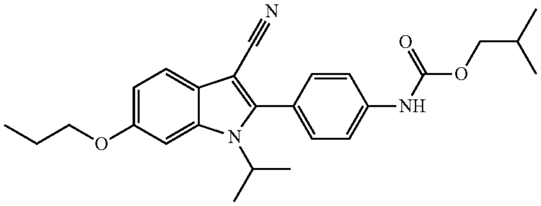
1207
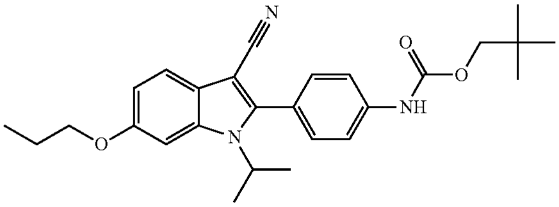
1208
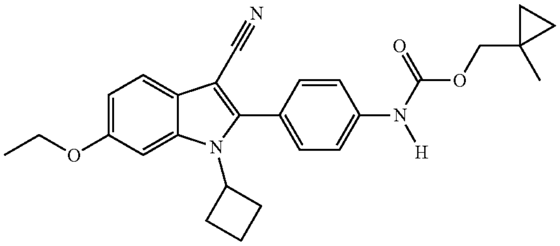
1209
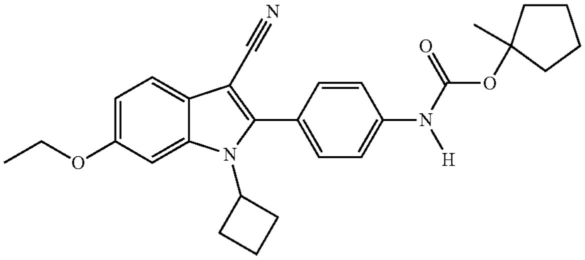

-continued
1210
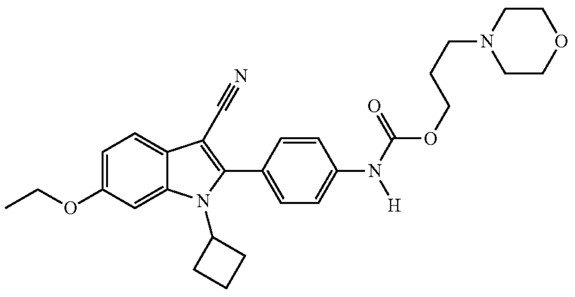
1211
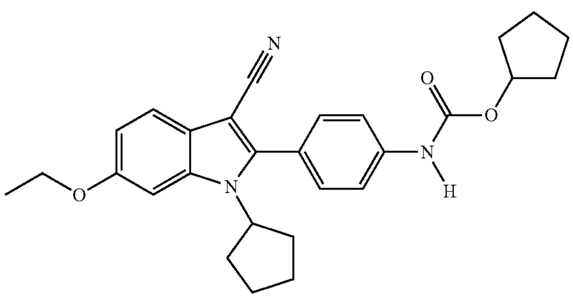
1212
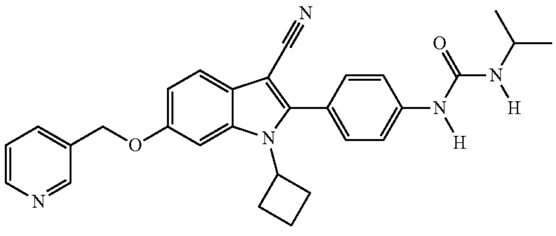
1213
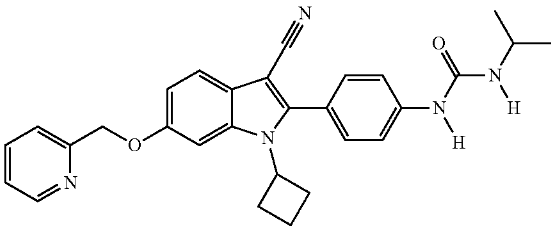
1214
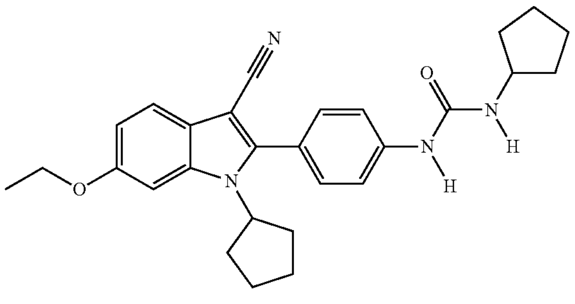
1215
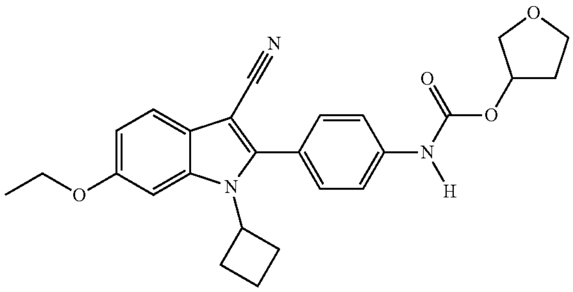
1216
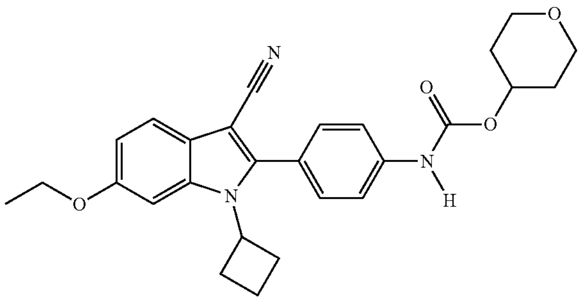
1217
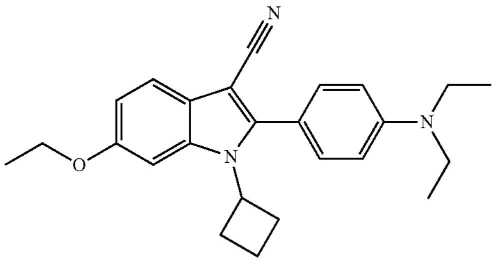
1218
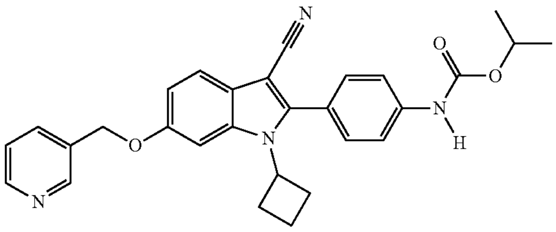
1219
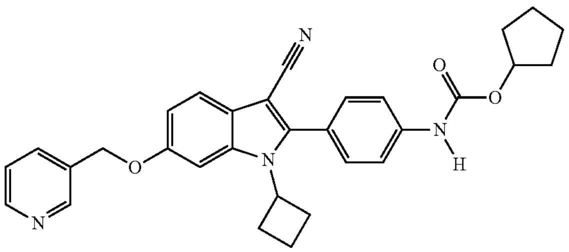

-continued
1220
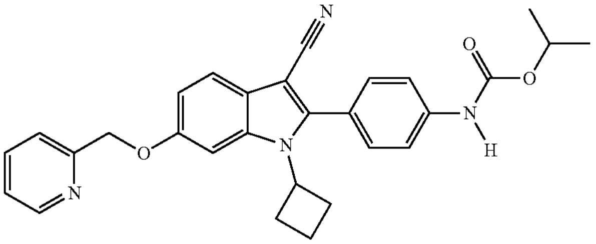
1221
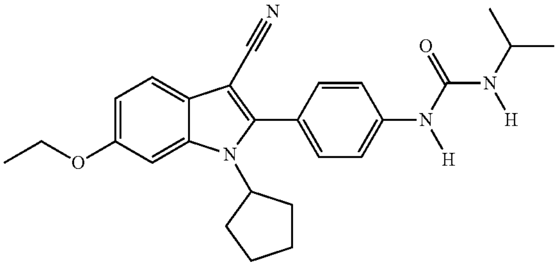
1222
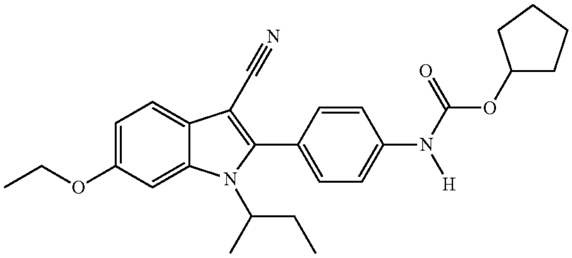
1223
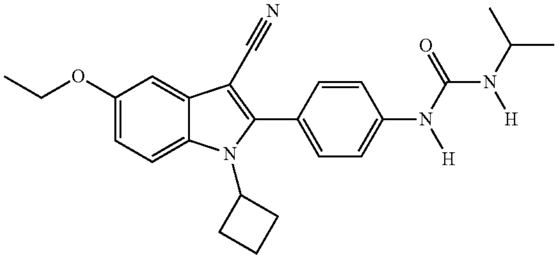
1224
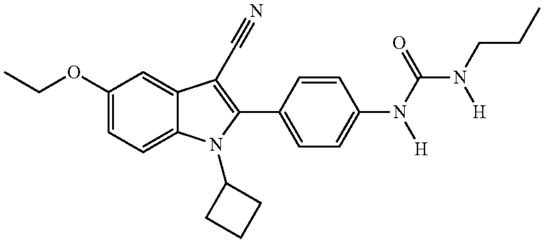
1225
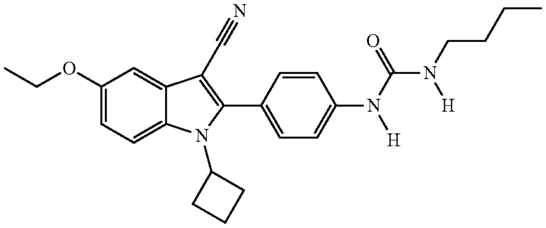
1226
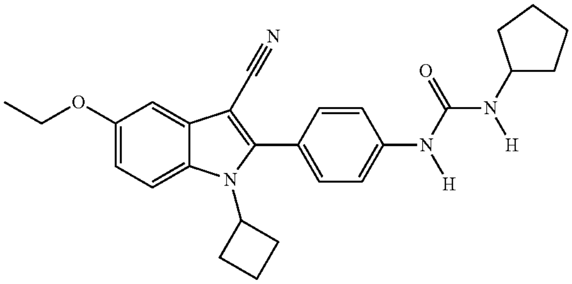
1227
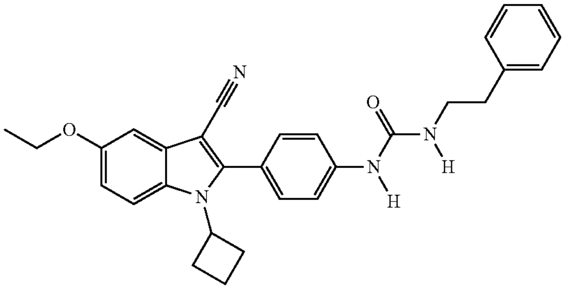
1228
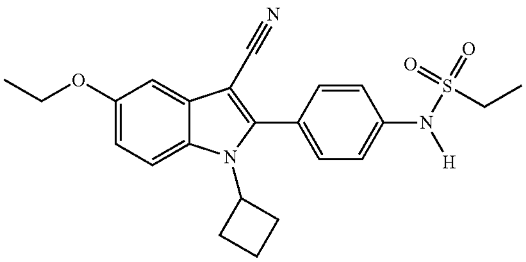
1229
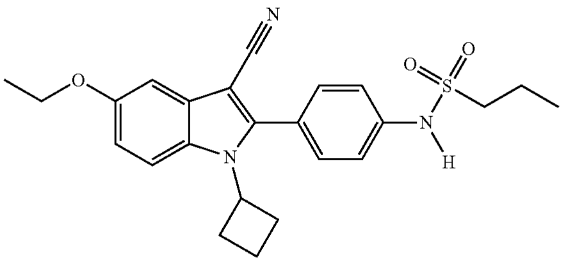

-continued
1230
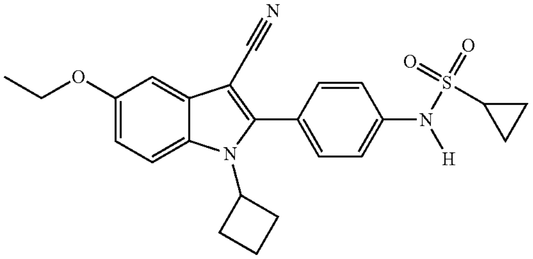
1231
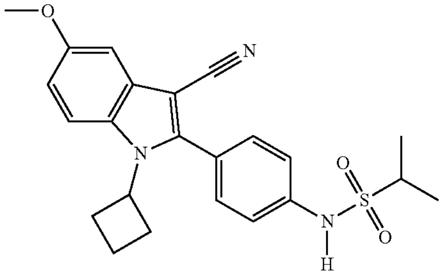
1232
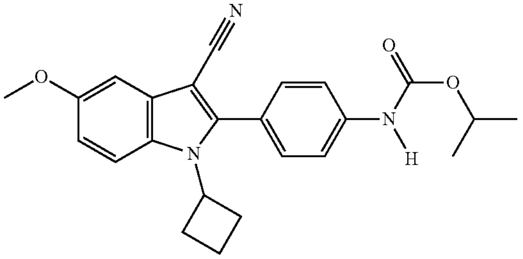
1233
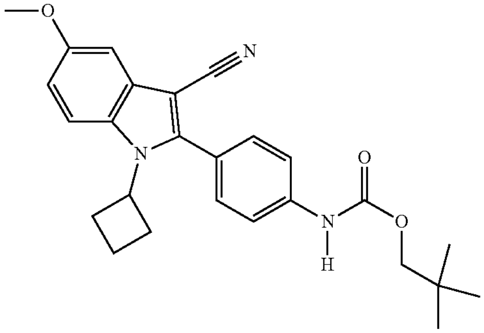
1234
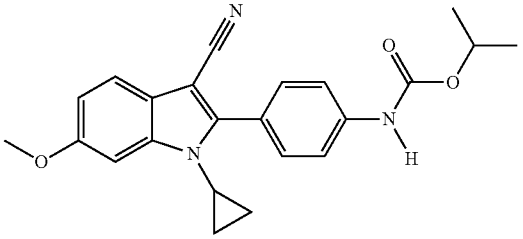
1235
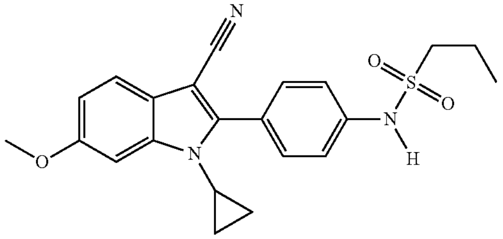
1236
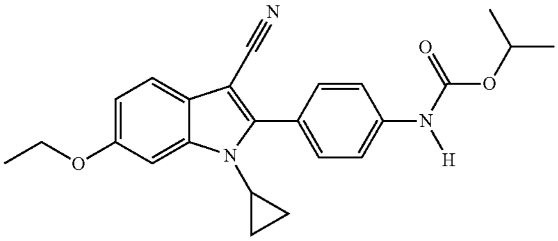
1237
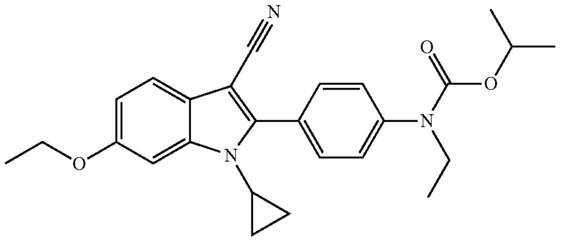
1238
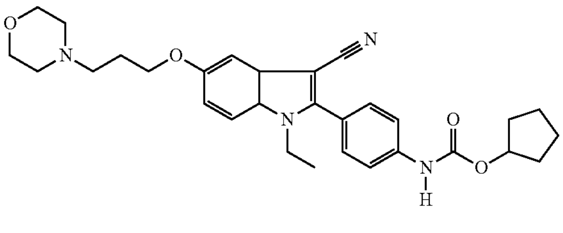
1239
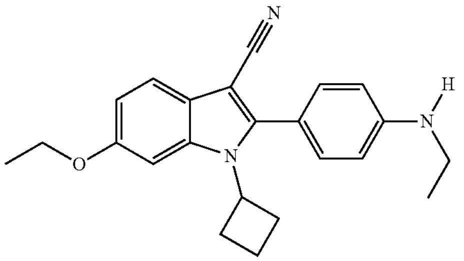

-continued
1240
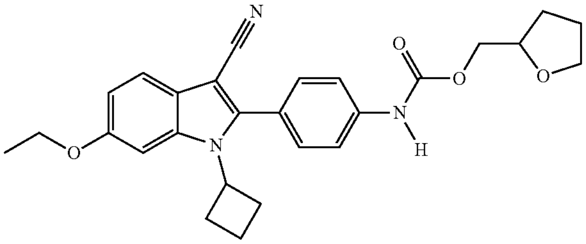
1241
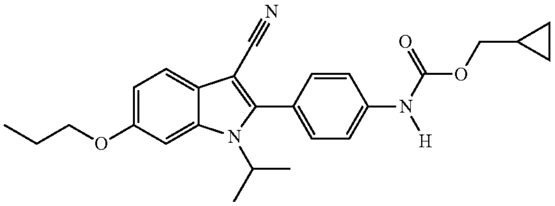
1242
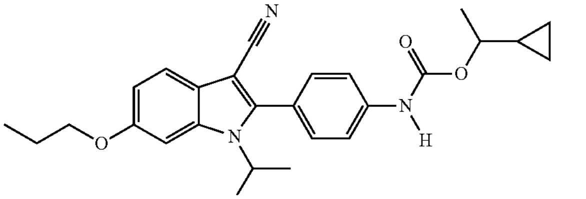
1243
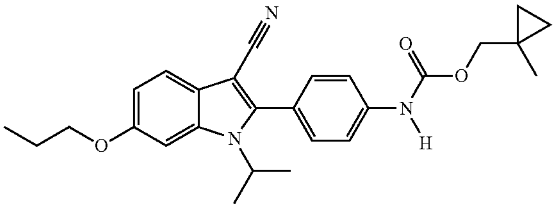
1244
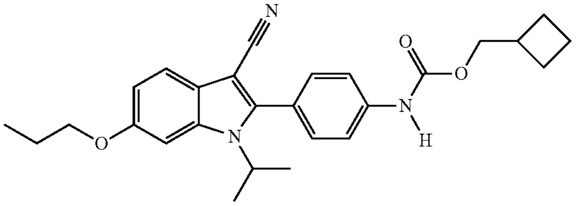
1245
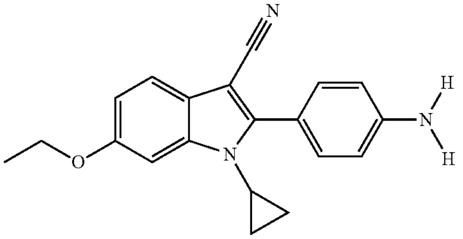
1246
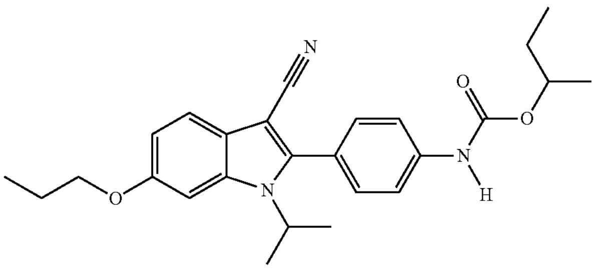
1247
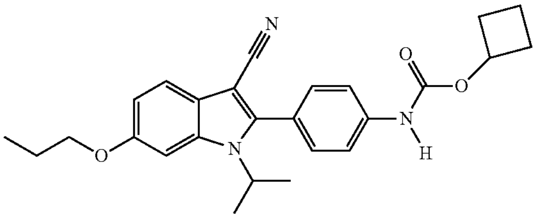
1248
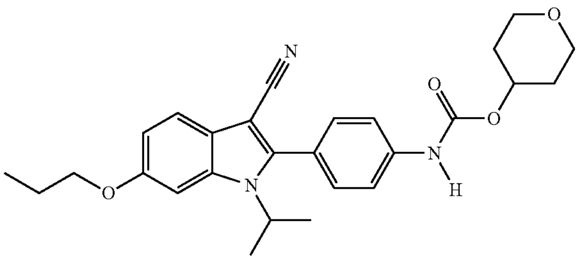
1249
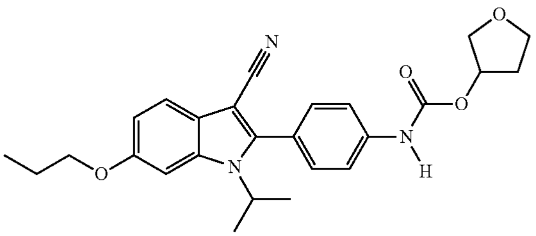

-continued
1250
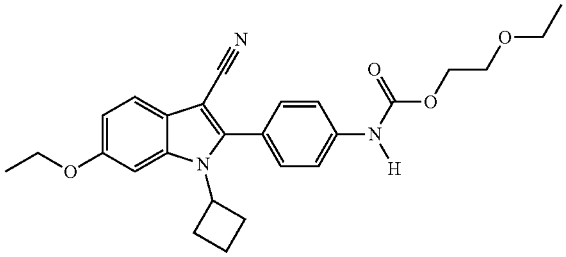
1251
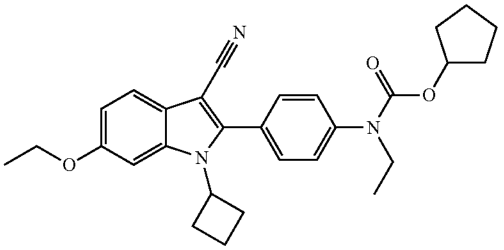
1252
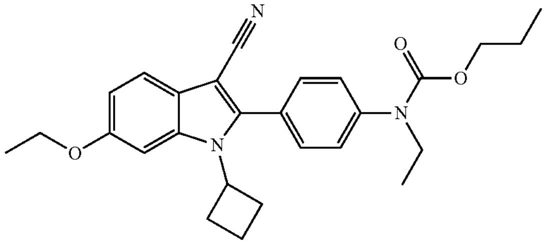
1253
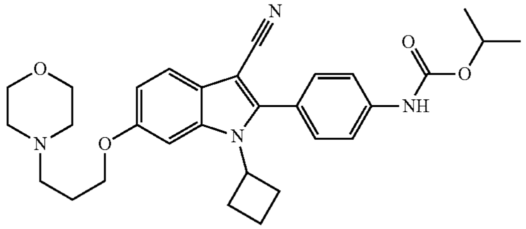
1254
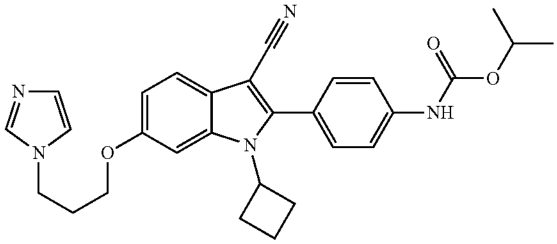
1255
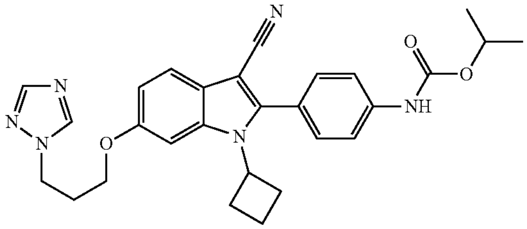
1256
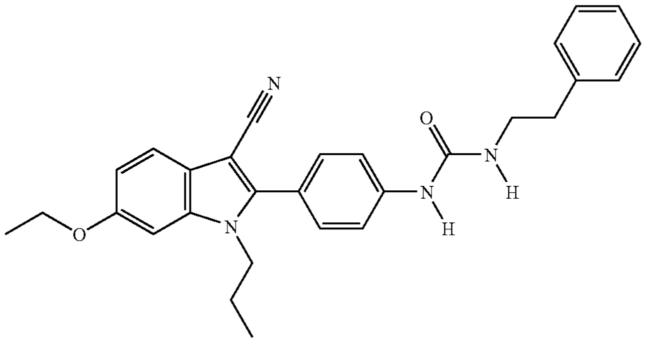
1257
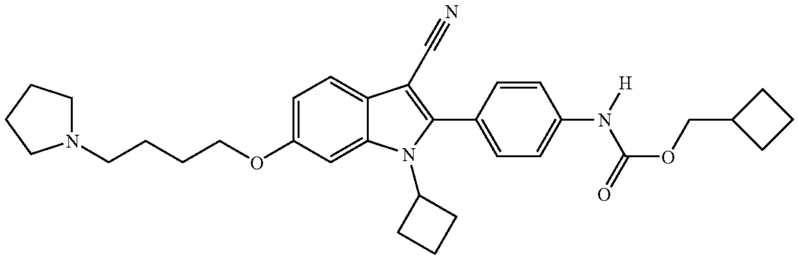

-continued
1258
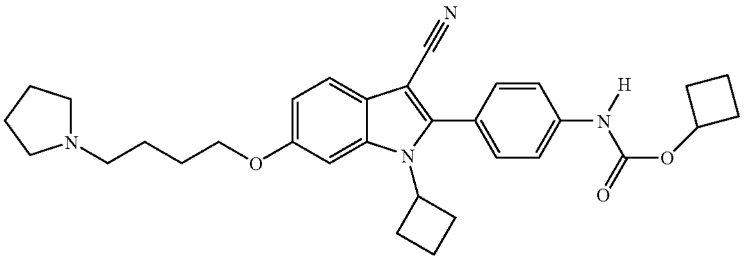
1259
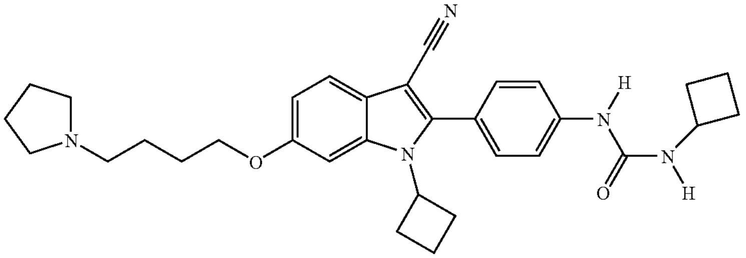
1260
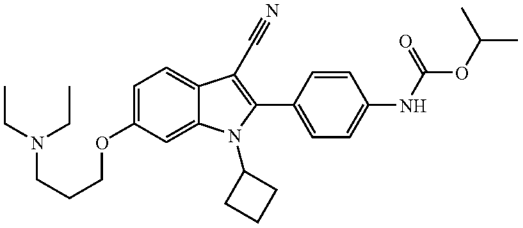
1261
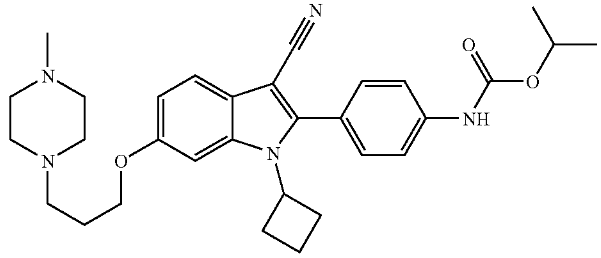
1262
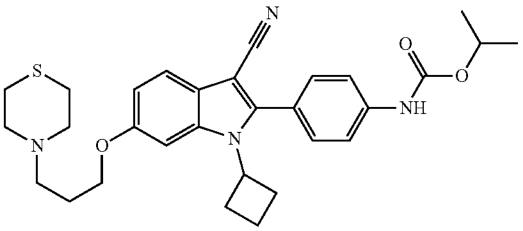
1263
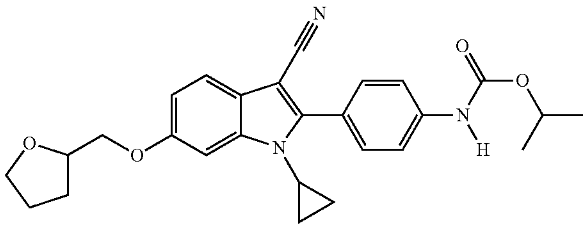
1264
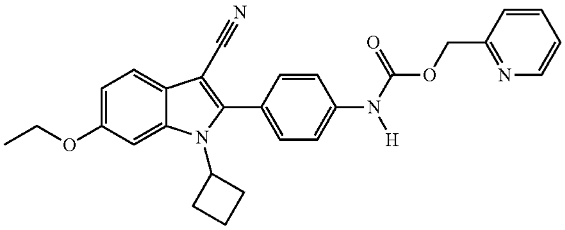
1265
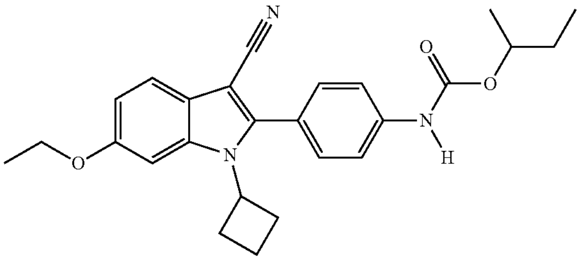

-continued
1266
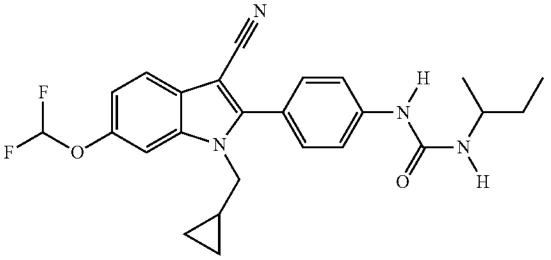
1267
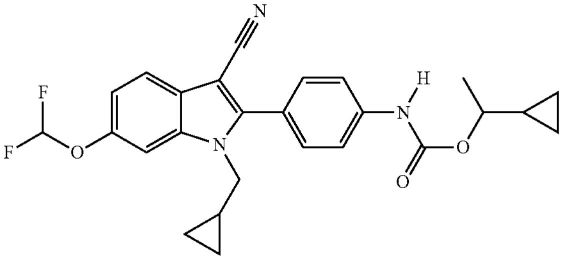
1268
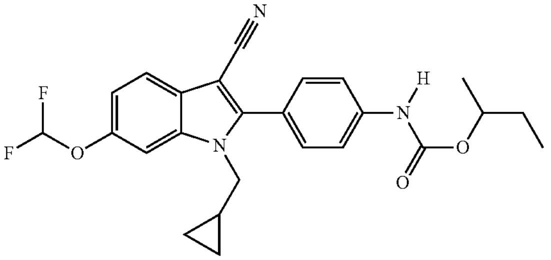
1269
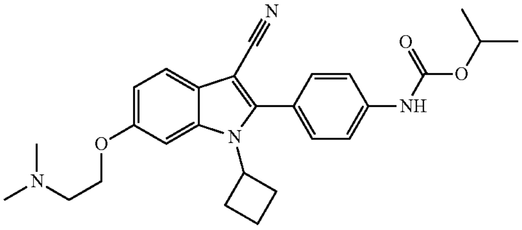
1270
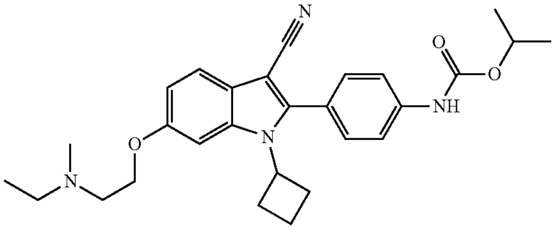
1271
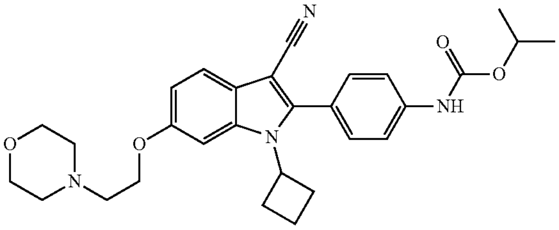
1272
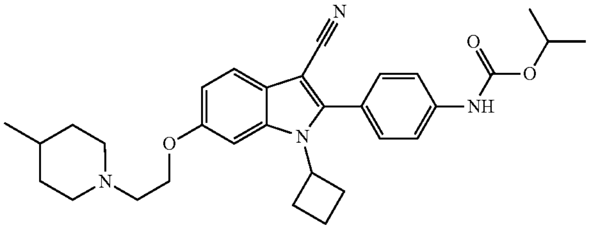
1273
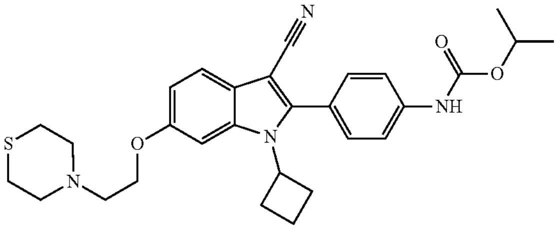
1274
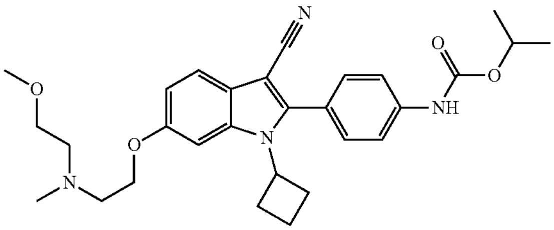
1275
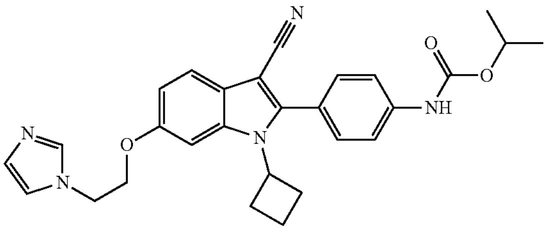
1276
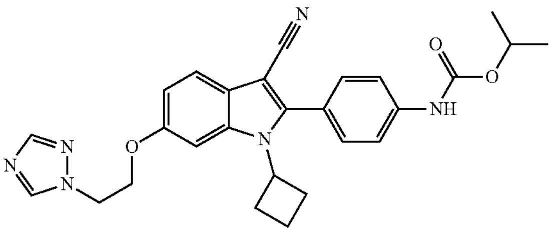
1277
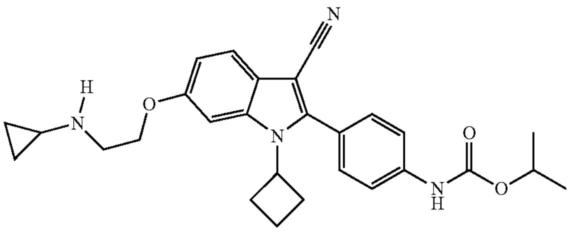

-continued
1278
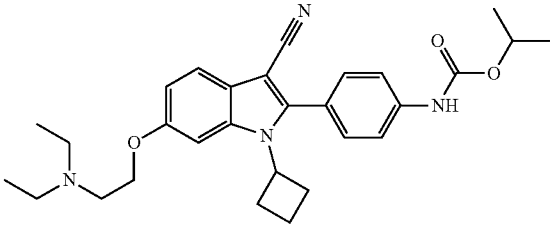
1279
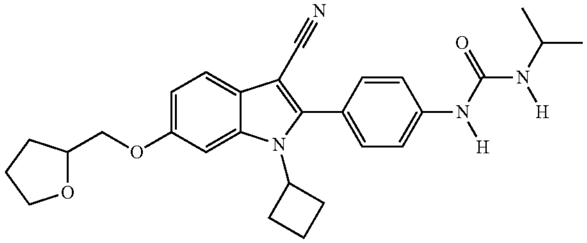
1280
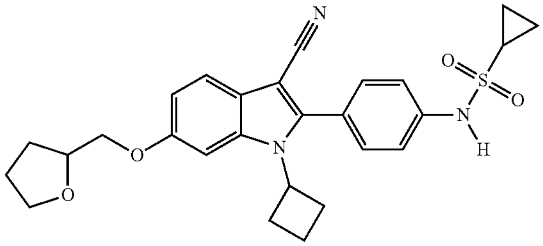
1281
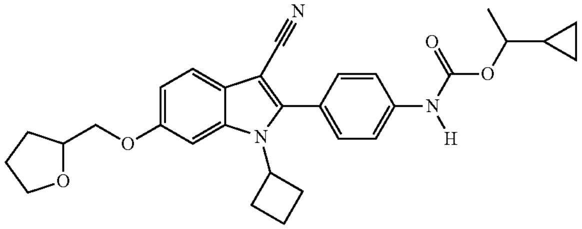
1282
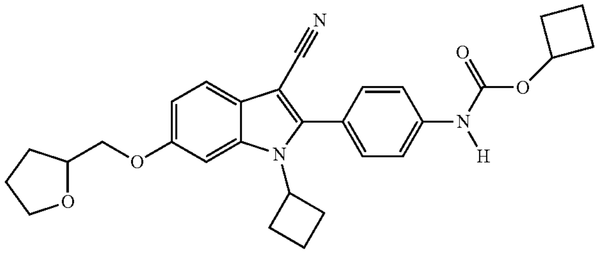
1283
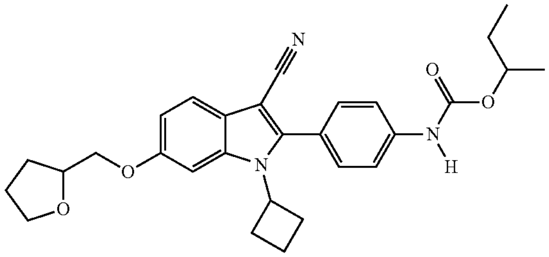
1284
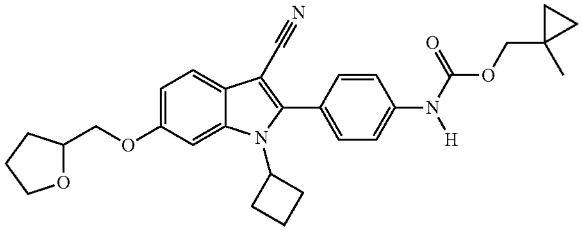
1285
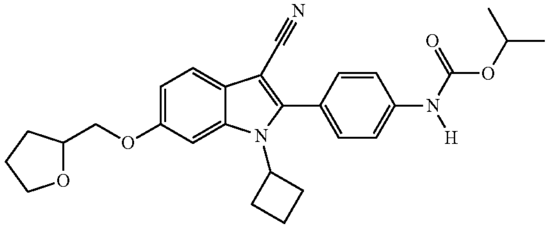
1286
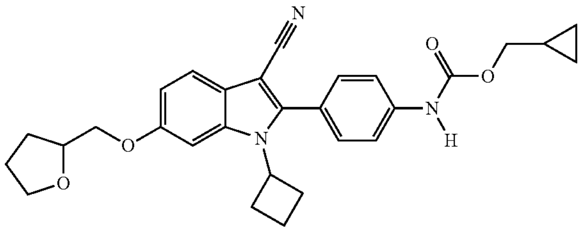
1287
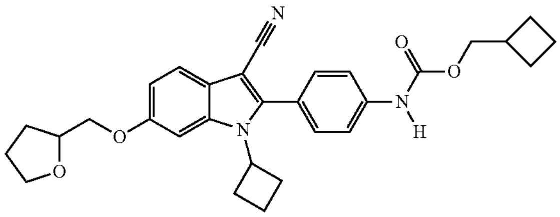
1288
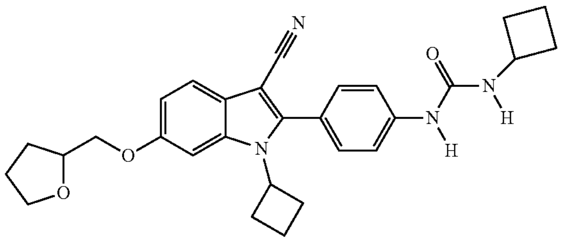
1289
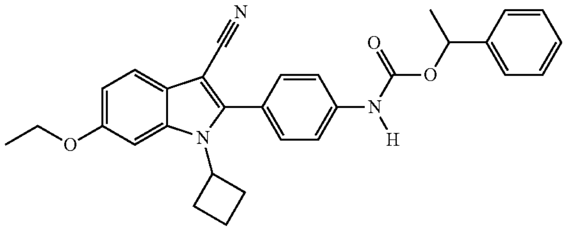

-continued
1290
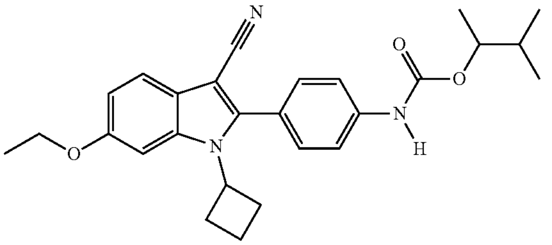
1291
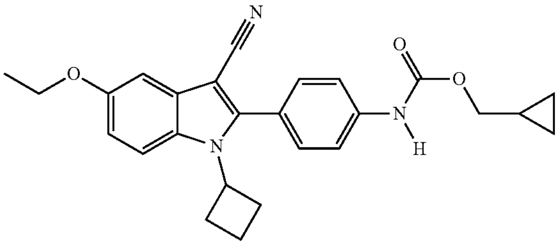
1292
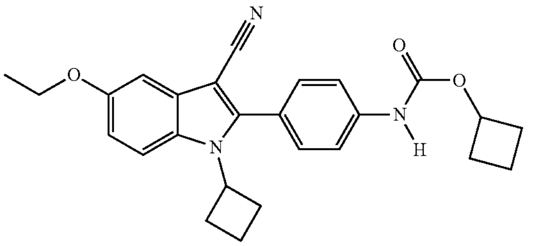
1293
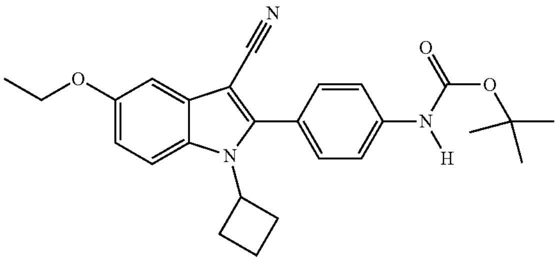
1294
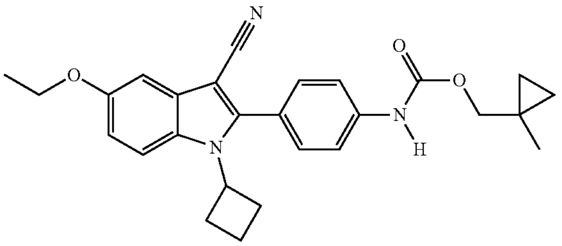
1295
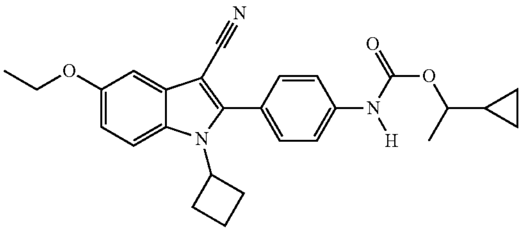
1296
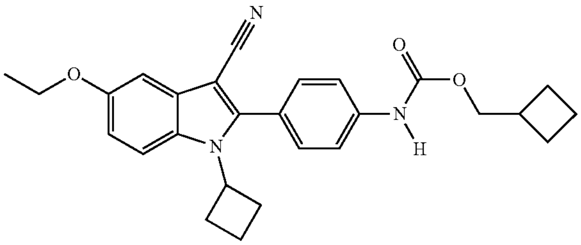
1297
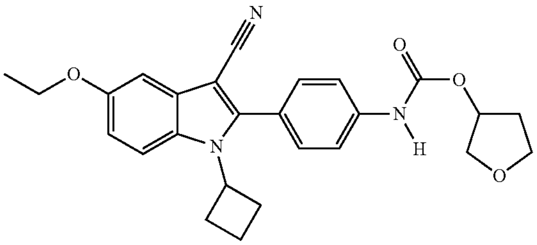
1298
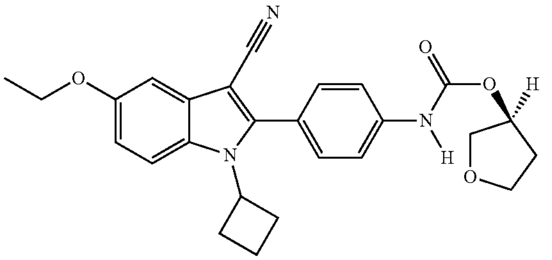
1299
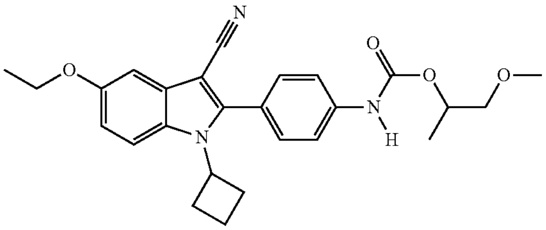

-continued
1300
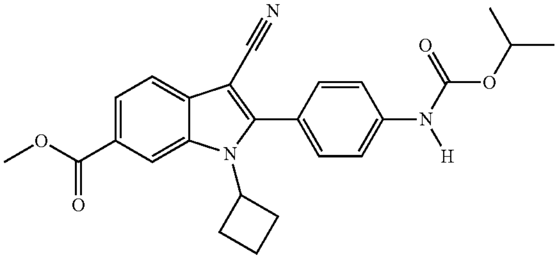
1301
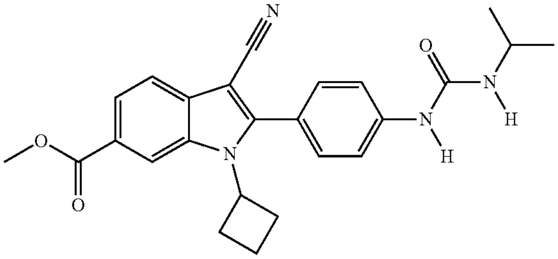
1302
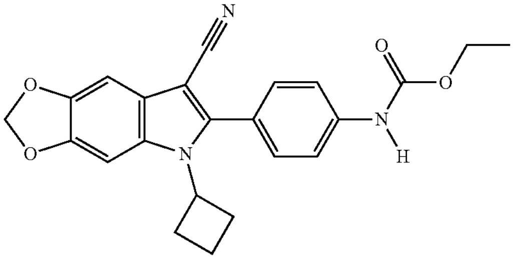
1303
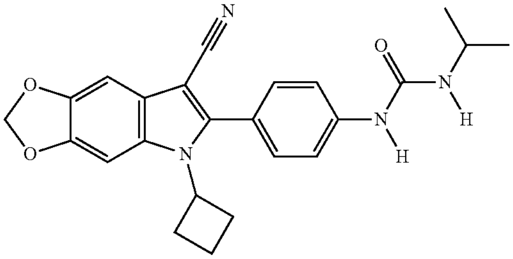
1304
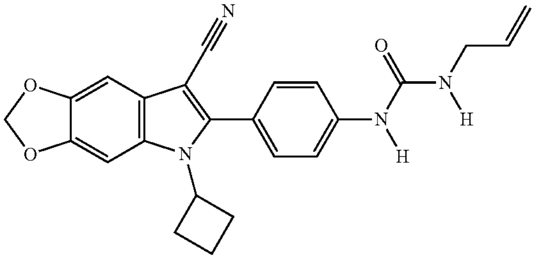
1305
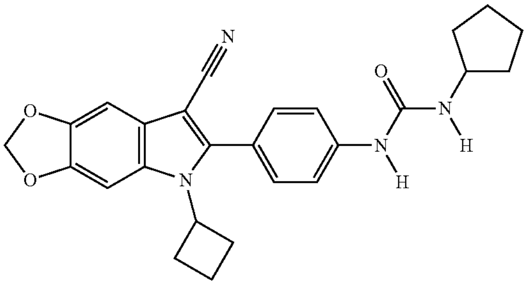
1306
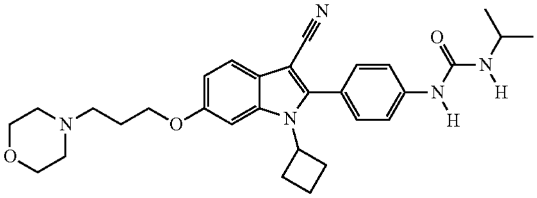
1307
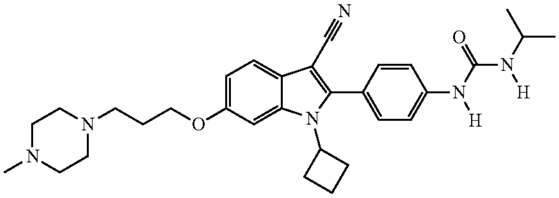
1308
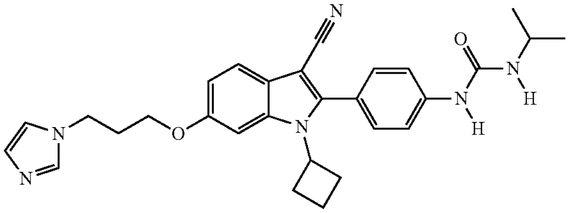
1309
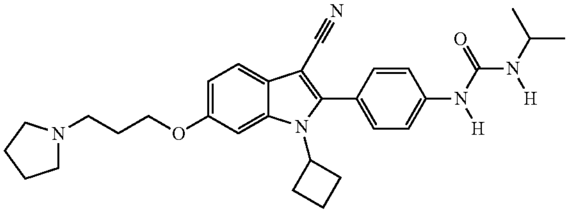
1310
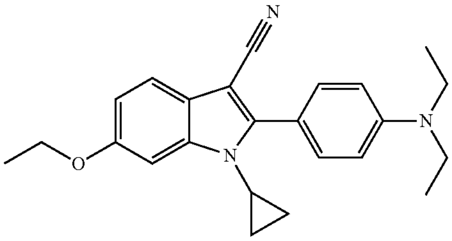
1311
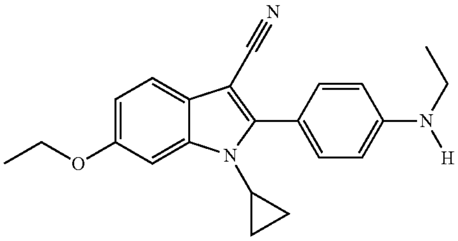

-continued
1312
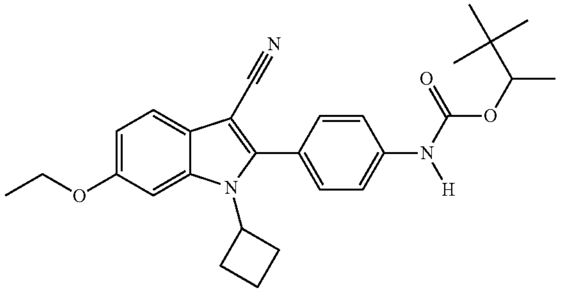
1313
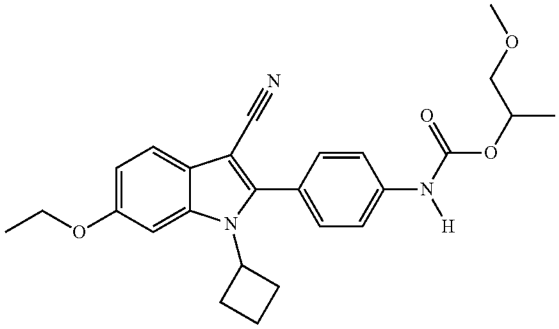
1314
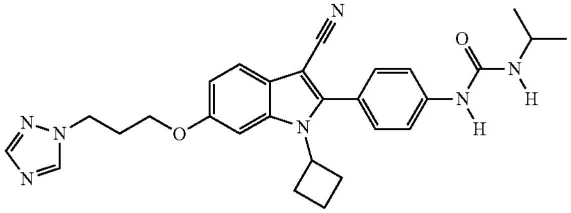
1315
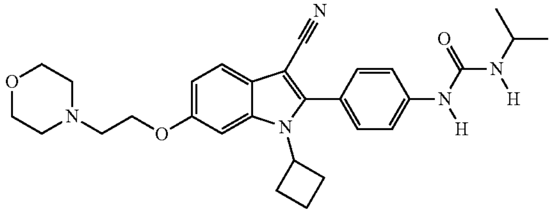
1316
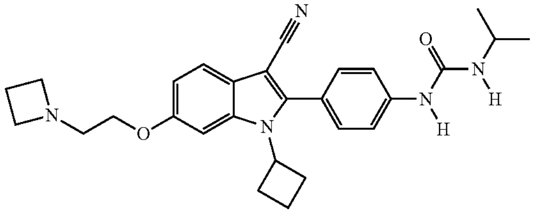
1317
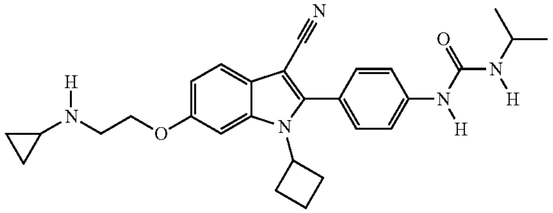
1318
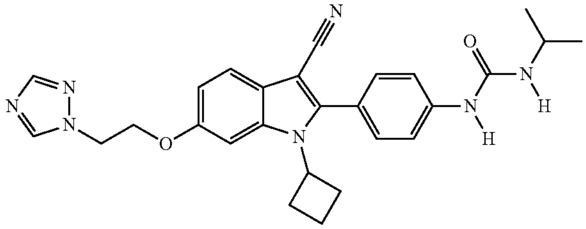
1319
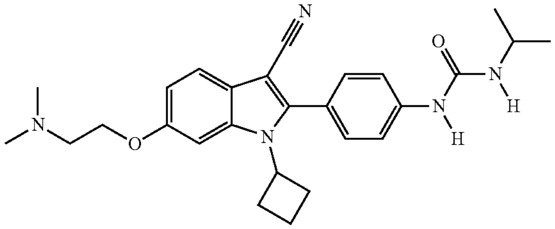
1320
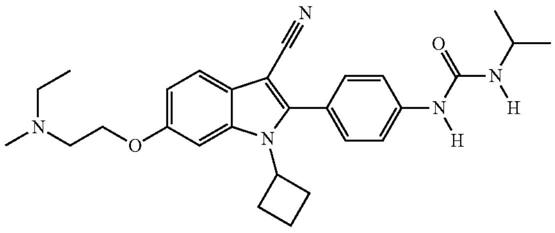
1321
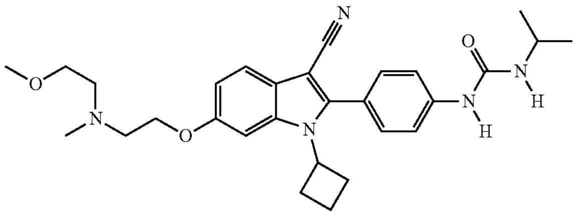
1322
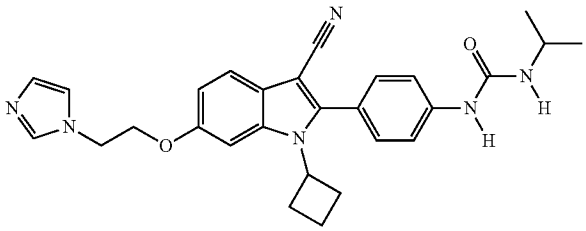
1323
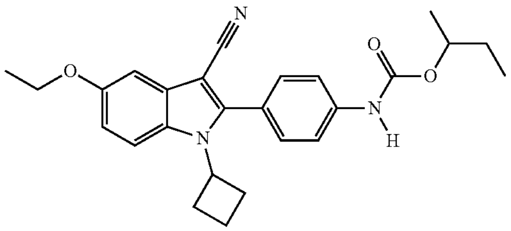

-continued
1324
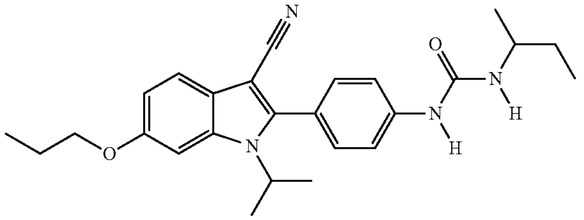
1325
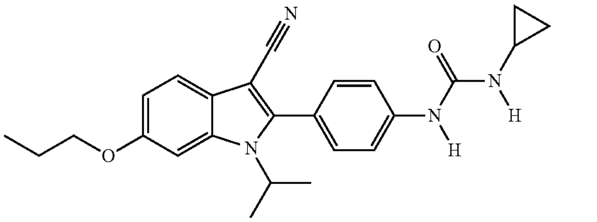
1326
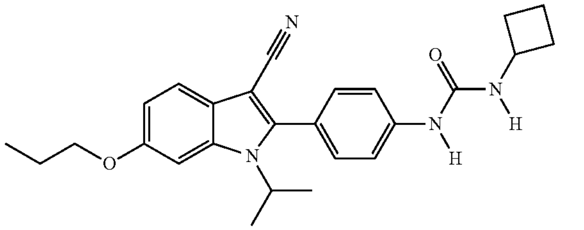
1327
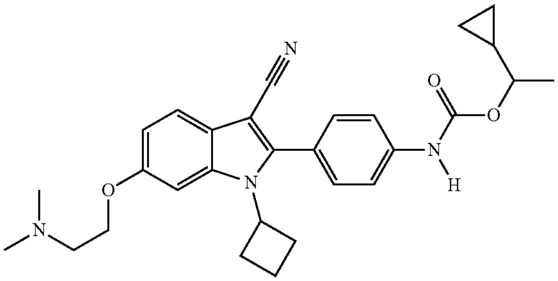
1328
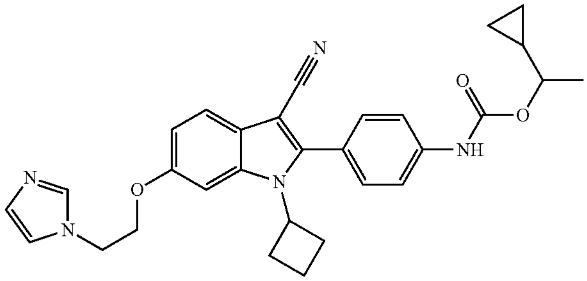
1329
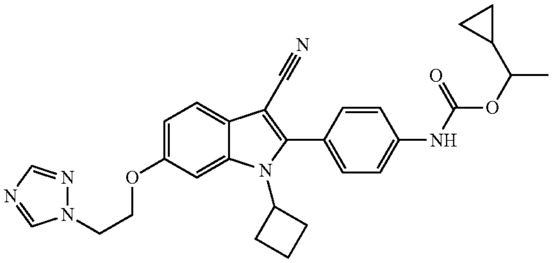
1484
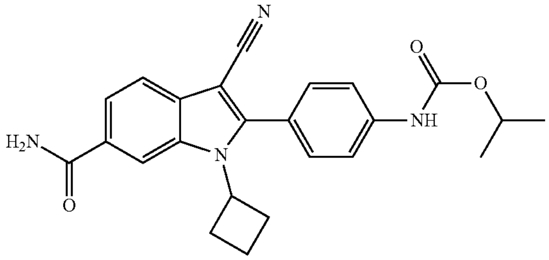
1491
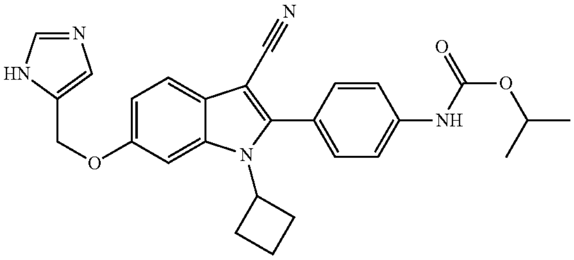
1492
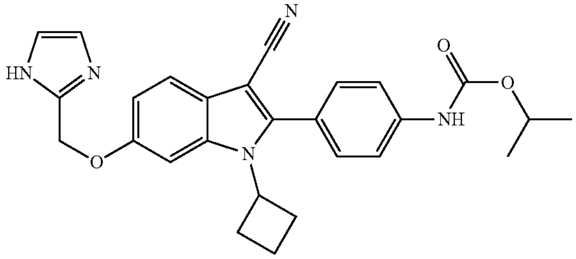
1493
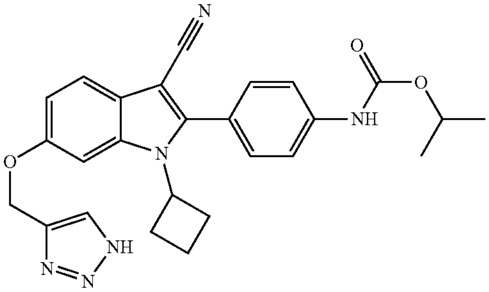

-continued
1494
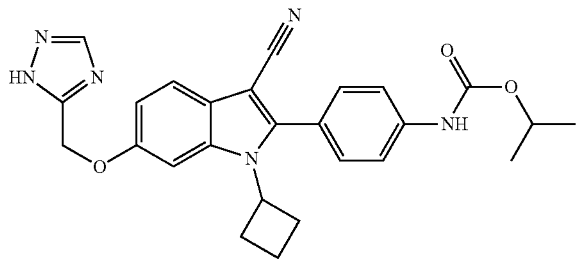
1495
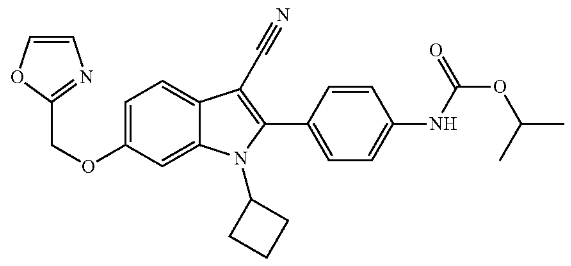
1496
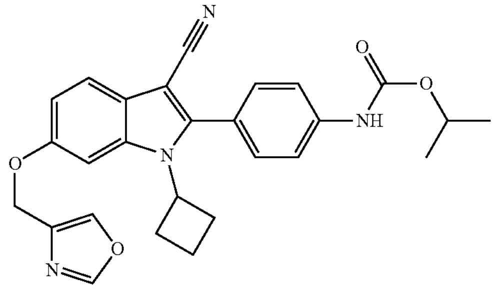
1497
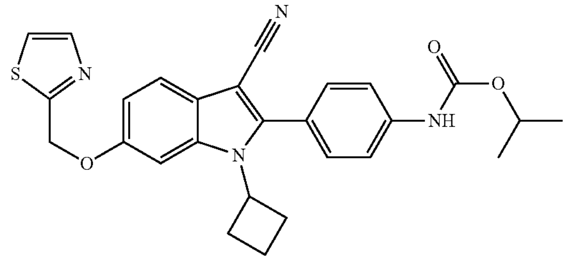
1506
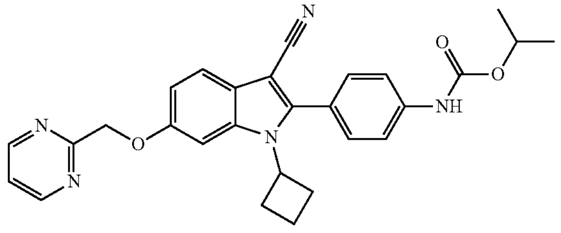
1507
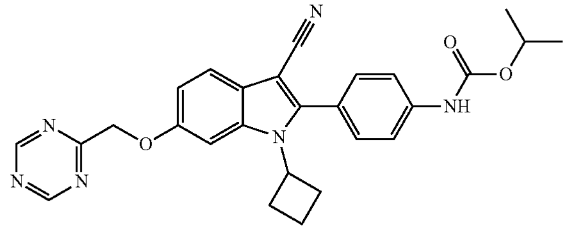
1510
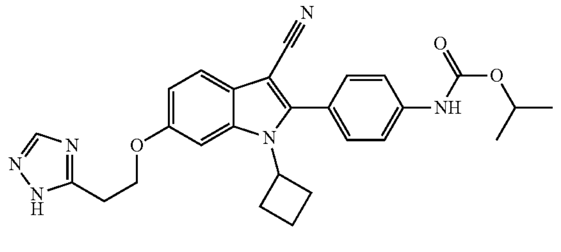
1511
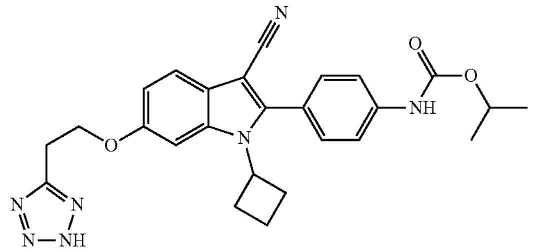
1512
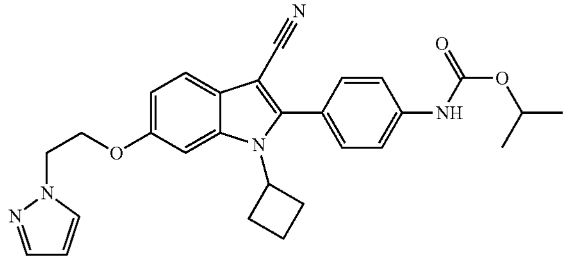
1513
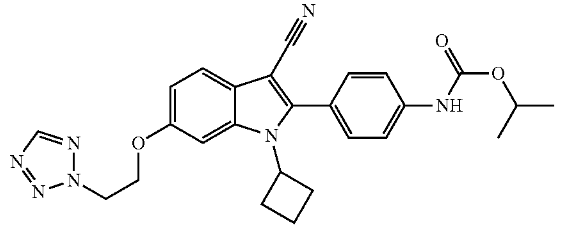

-continued
1514
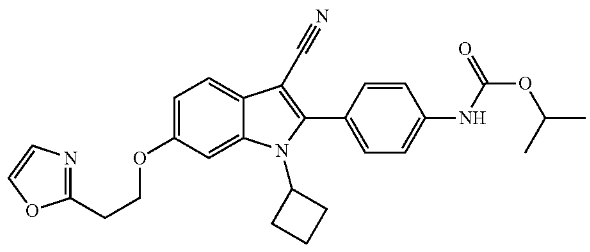
1517
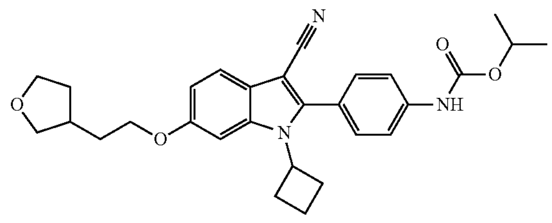
1518
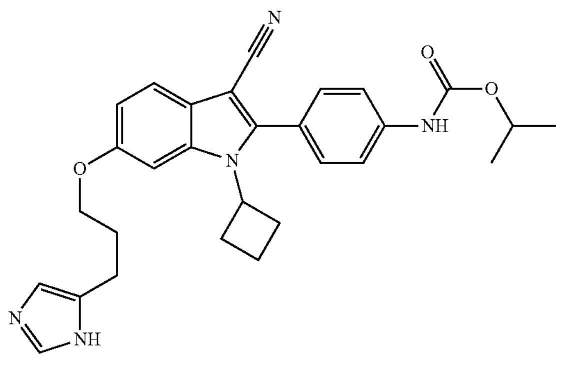
1519
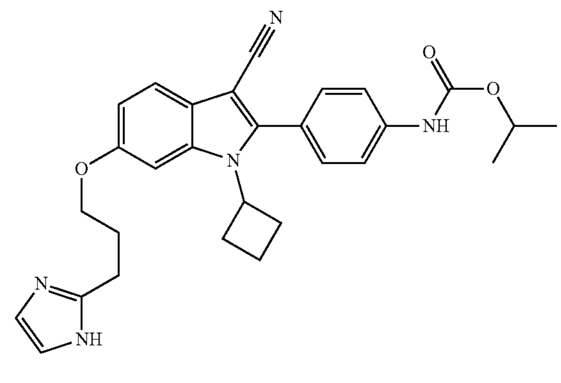
1520
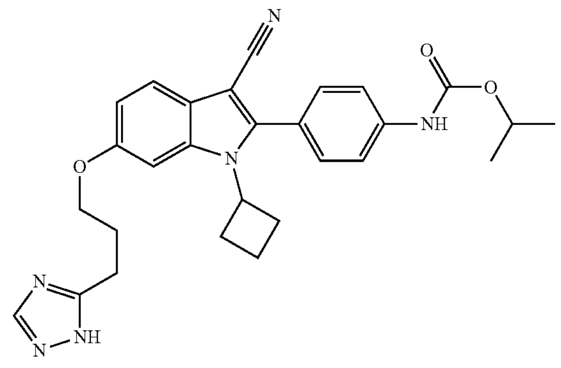
1521
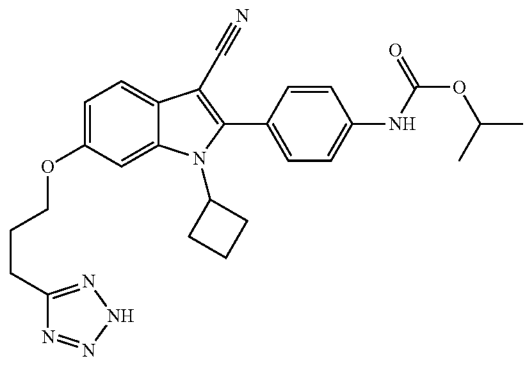
1522
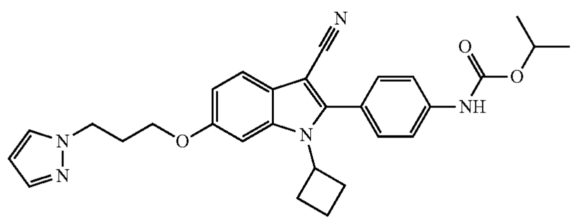
1523
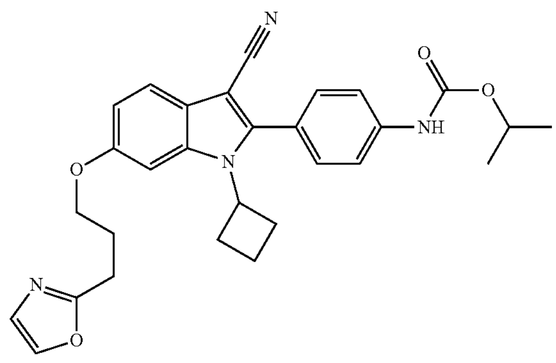

-continued
1540
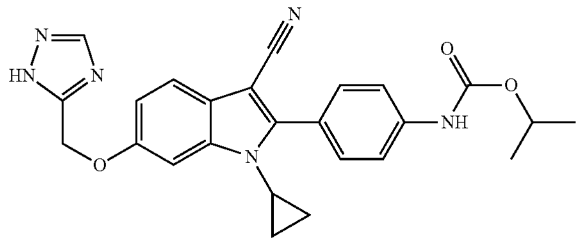
1541
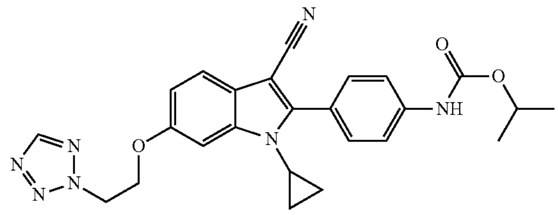
1542
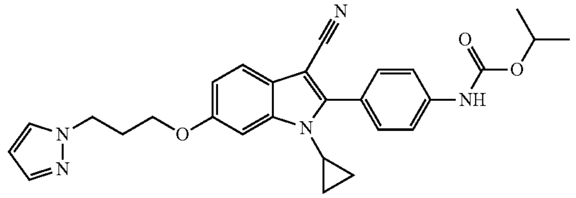
1574
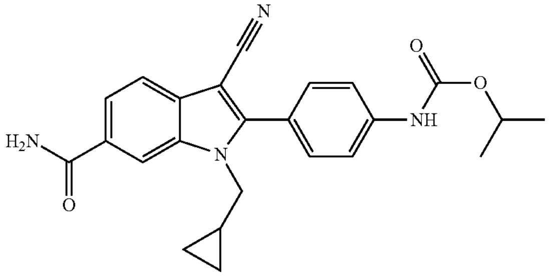
1581
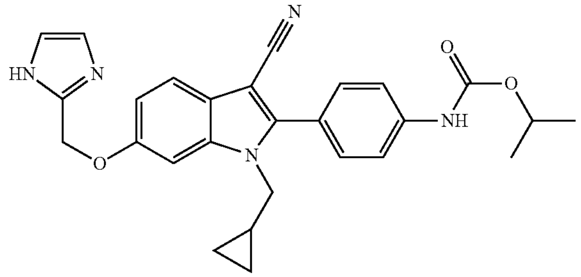
1582
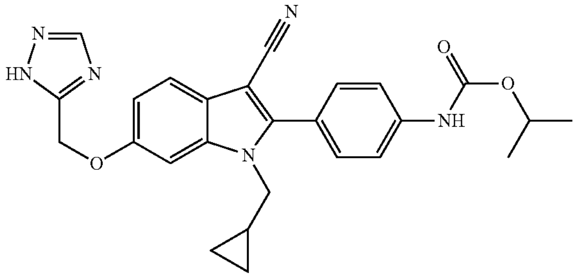
1583
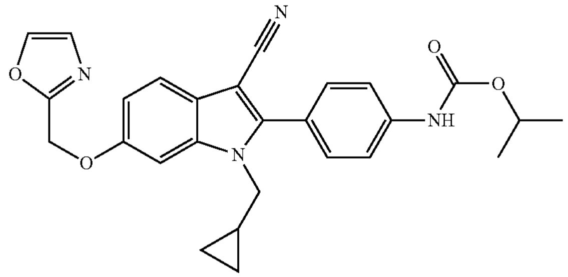
1584
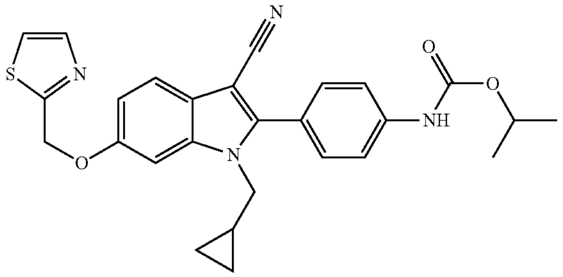
1590
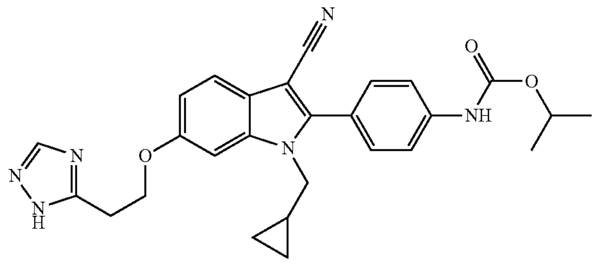
1591
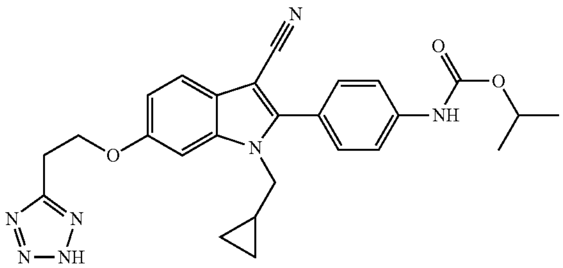

-continued
1592
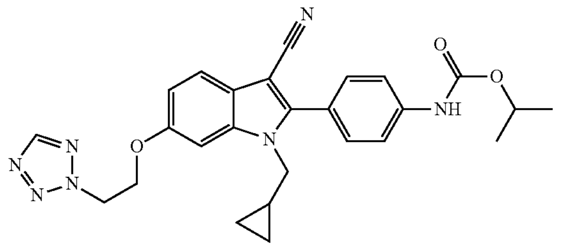
1593
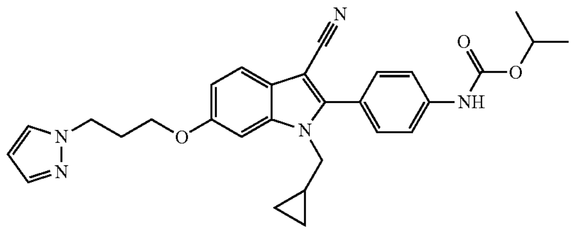
1610
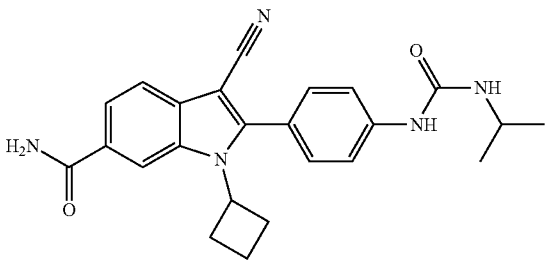
1617
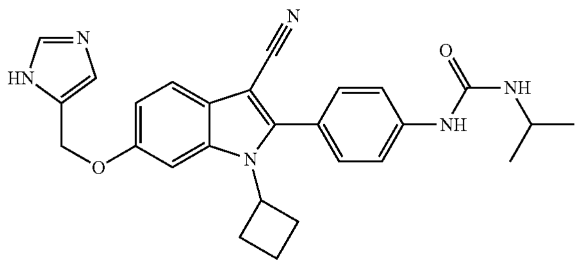
1618
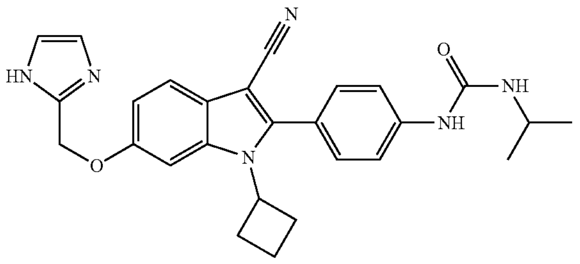
1619
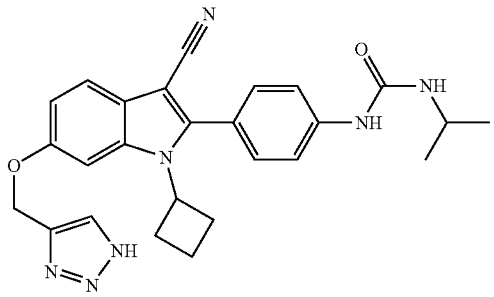
1620
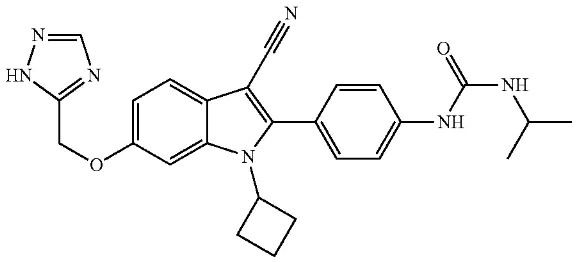
1621
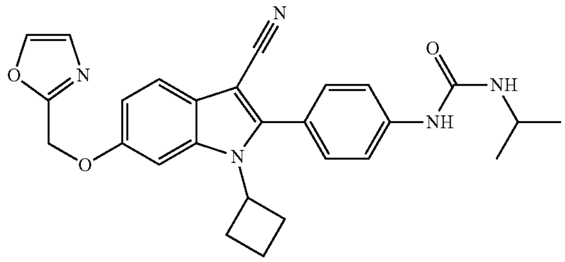
1622
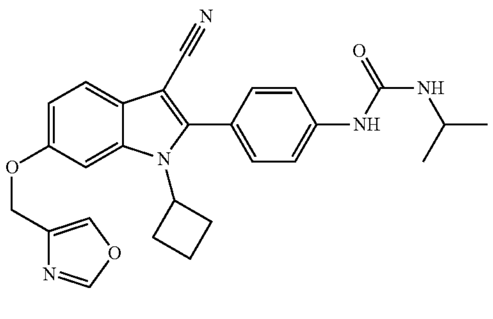
1623
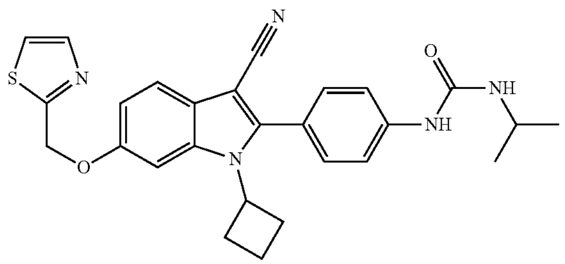

-continued
1632
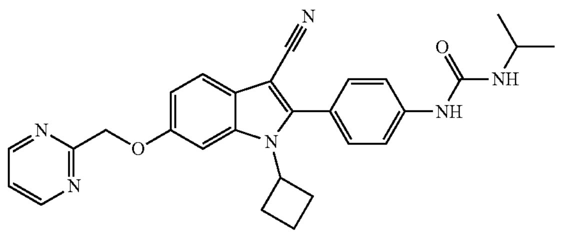
1633
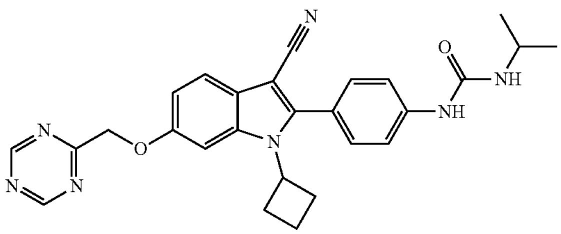
1636
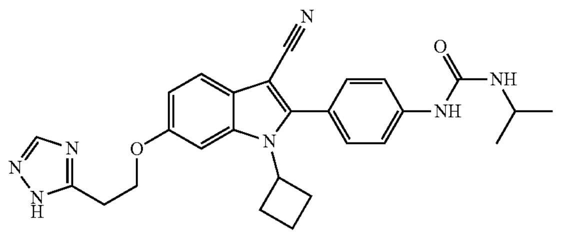
1637
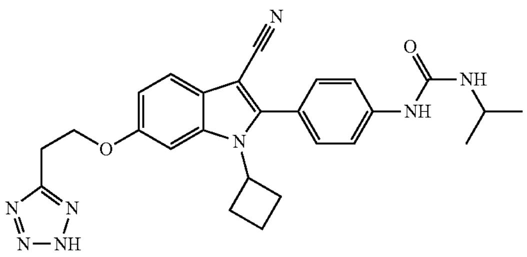
1638
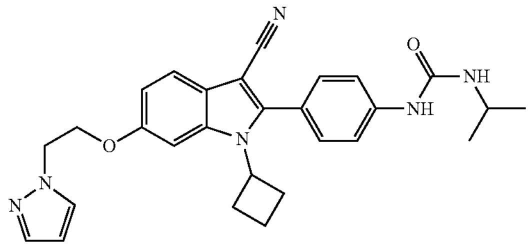
1639
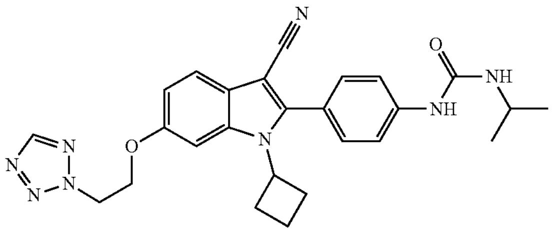
1640
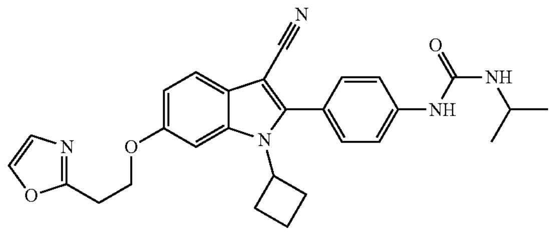
1643
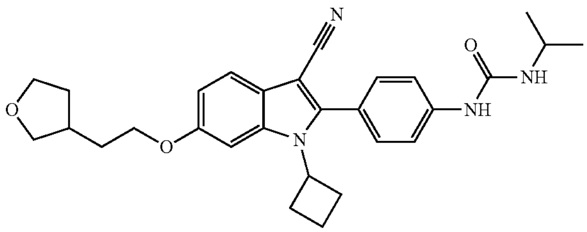
1644
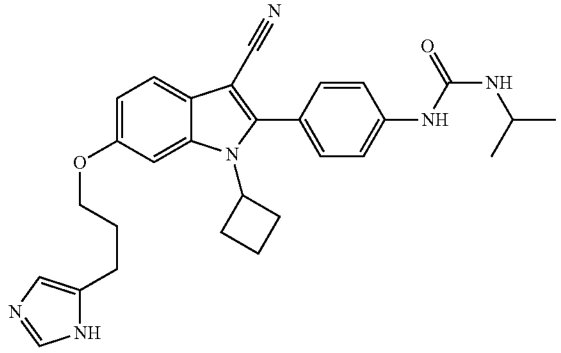
1645
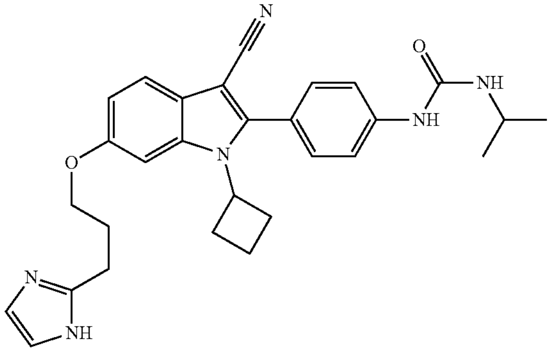

-continued
1646
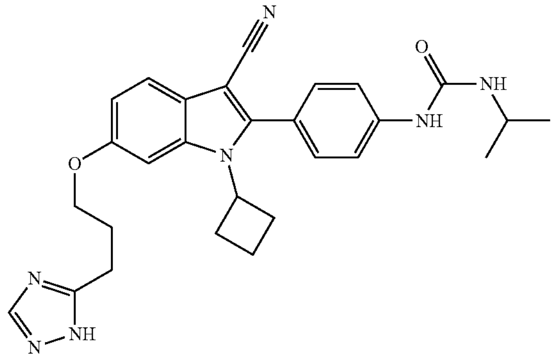
1647
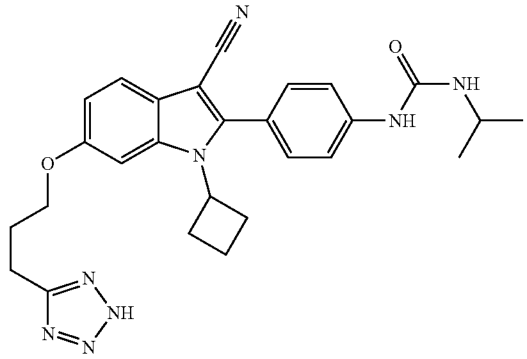
1648
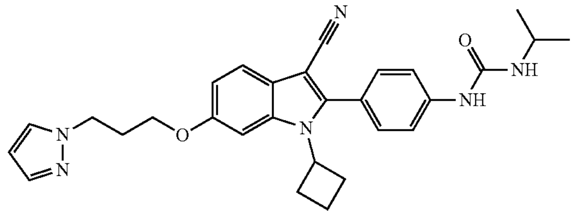
1649
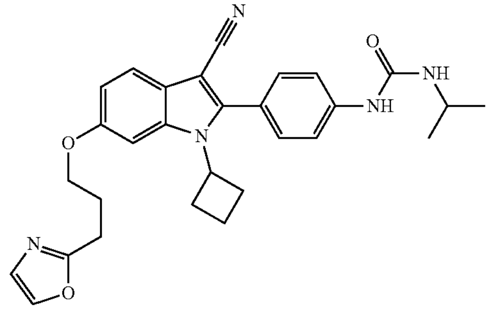
1687
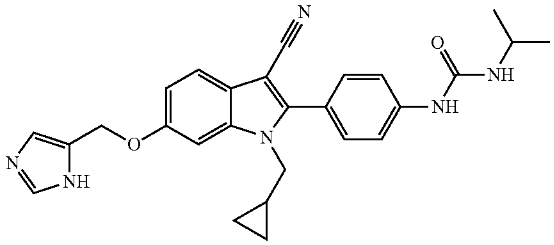
1688
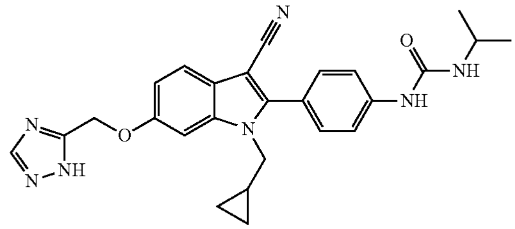
1689
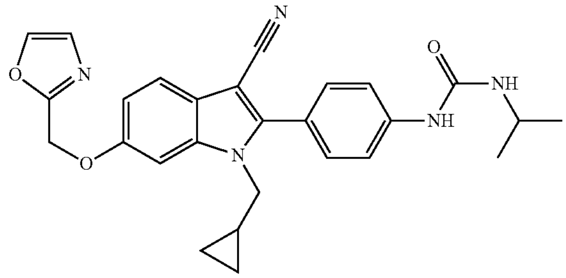
1690
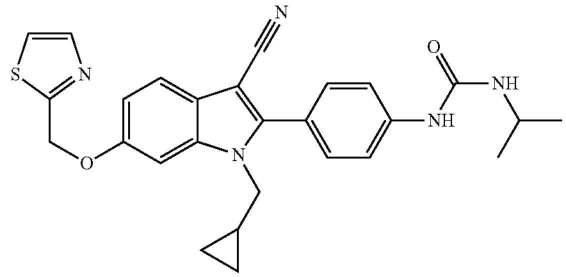
1695
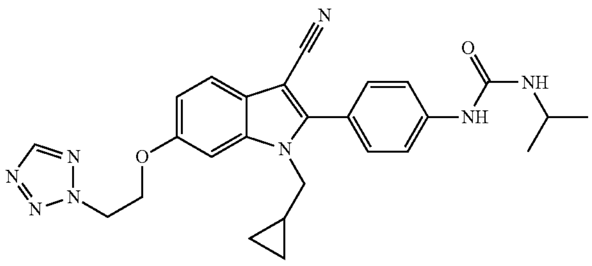
1749
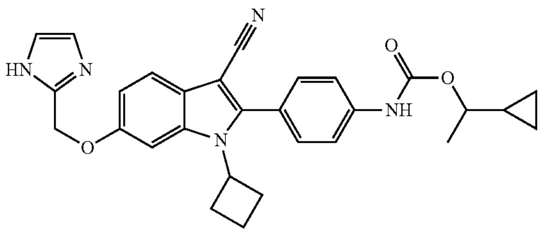

-continued
1750
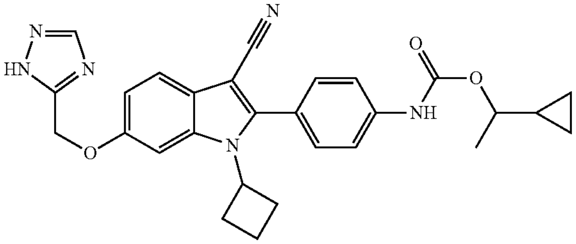
1751
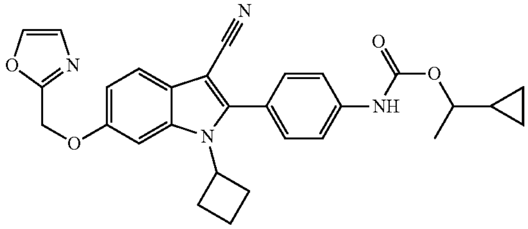
1752
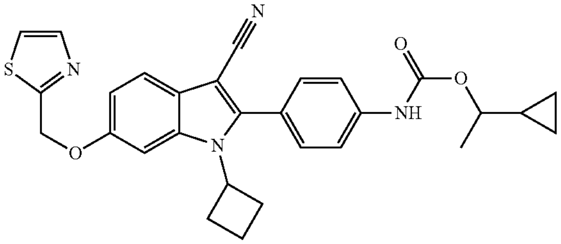
1759
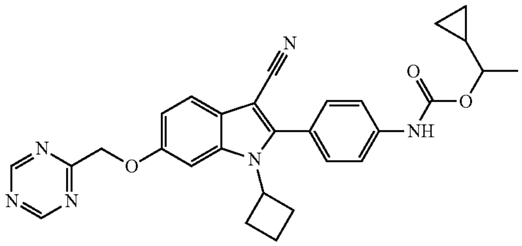
1761
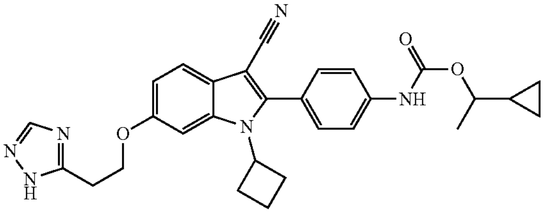
1762
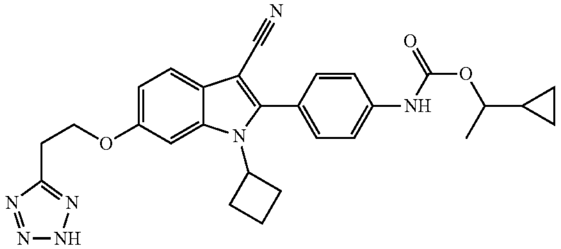
1763
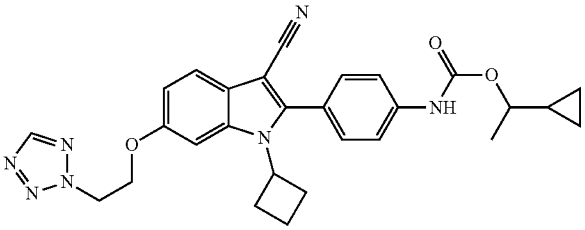
1765
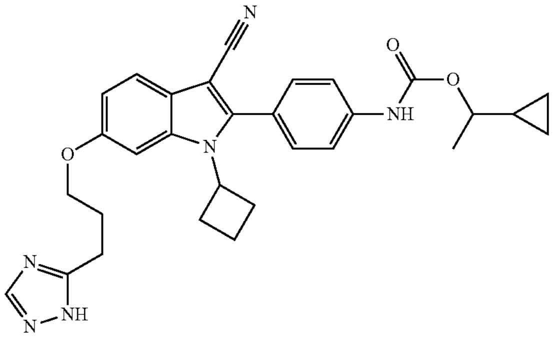
1766
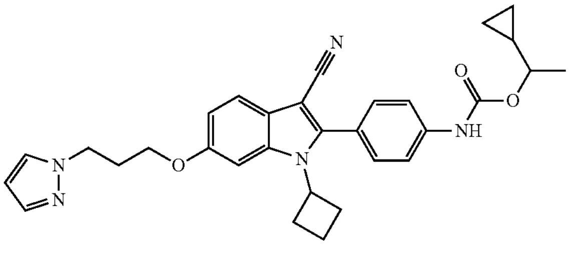
1771
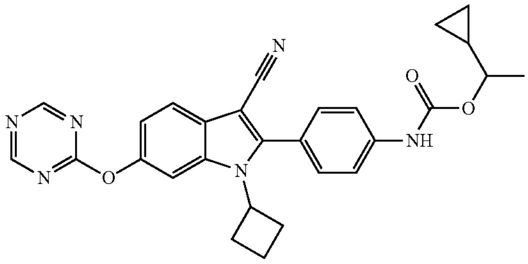

-continued
1778
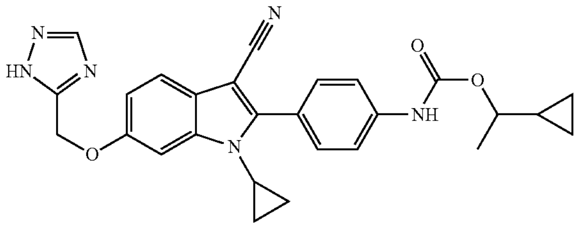
1783
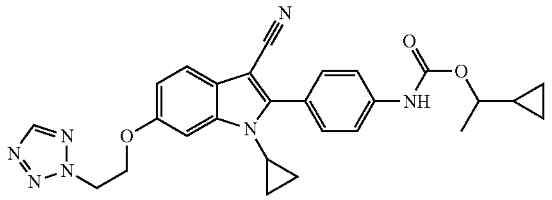
1809
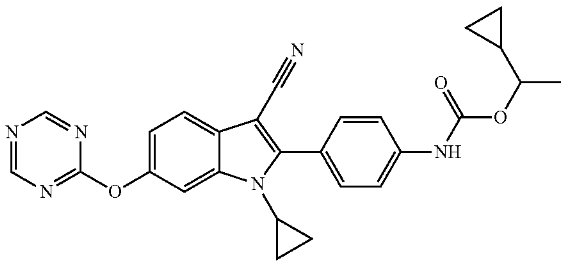
1812
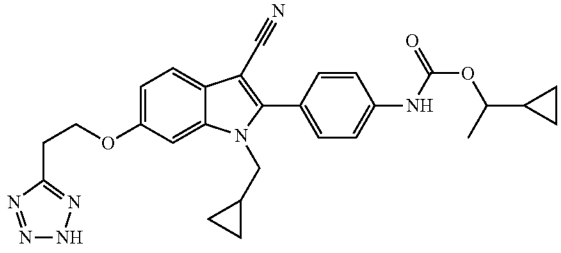
1813
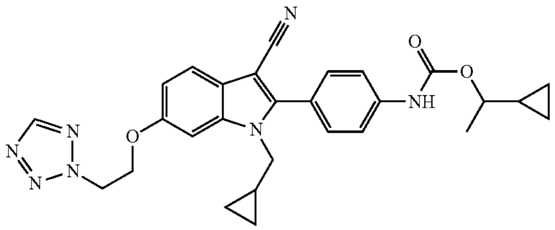
1967
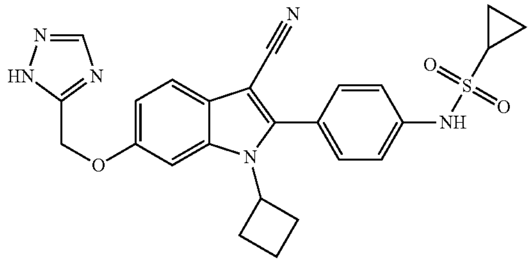
1968
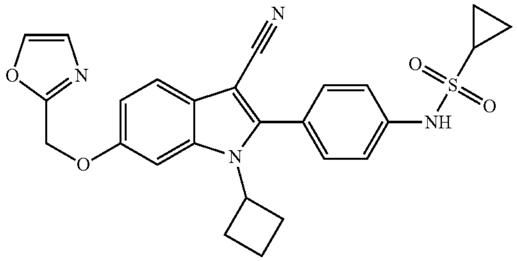
1969
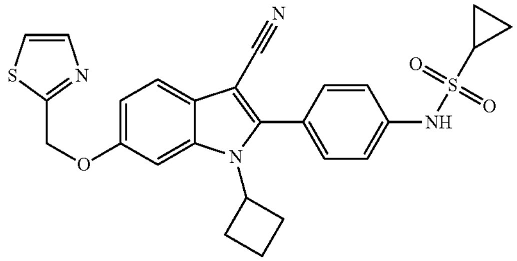
2015
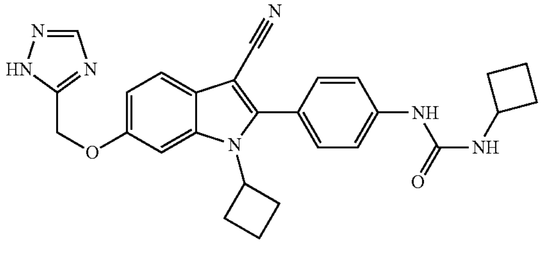
2016
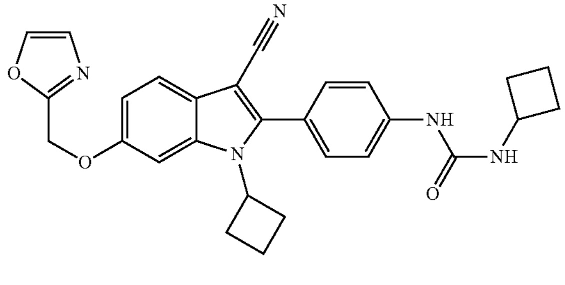

-continued
2017
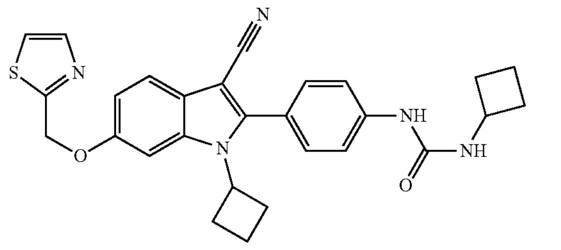
2022
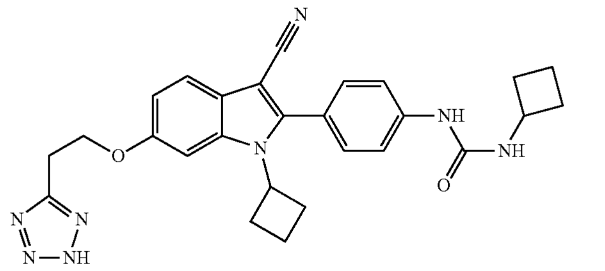
2023
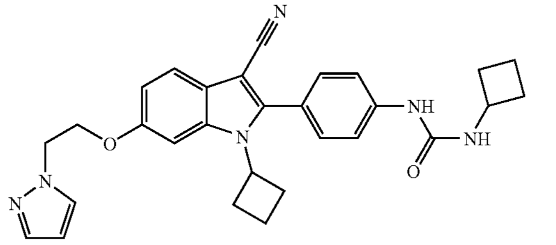
2024
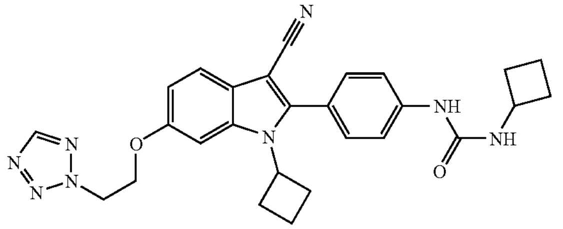
2127
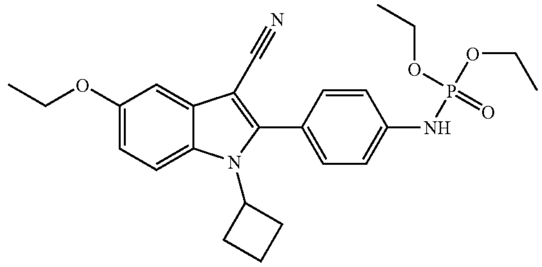
;
or a pharmaceutically acceptable salt thereof.
29. The compound of claim 28 which is selected from:
866
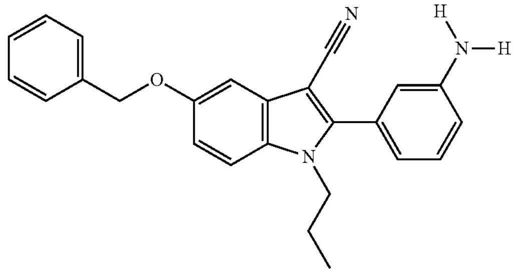
867
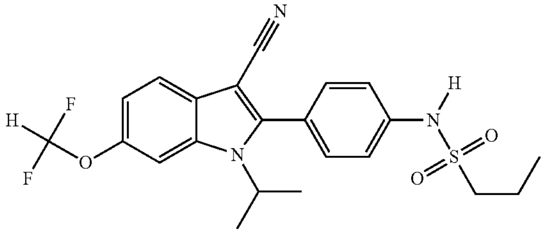
868
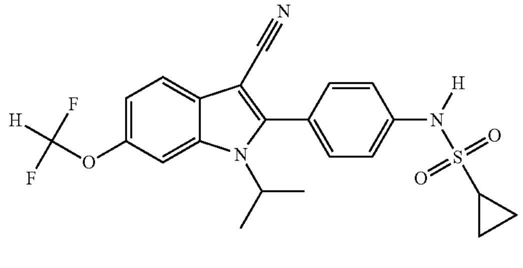
869
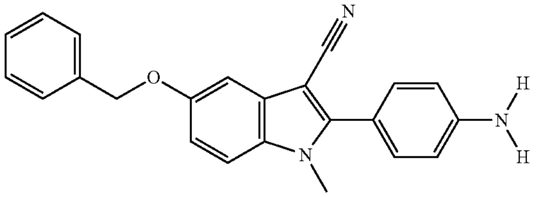

-continued
870
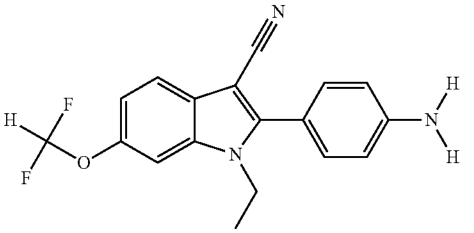
871
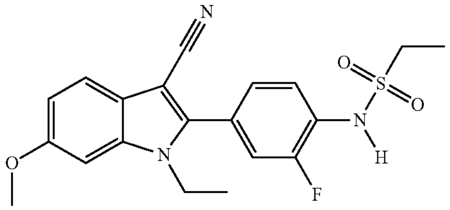
872
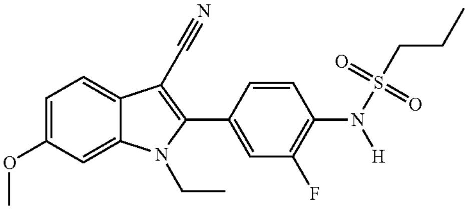
873
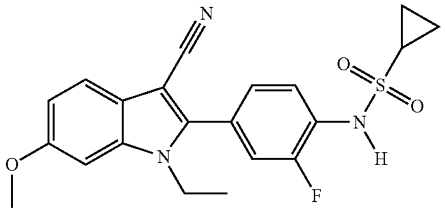
874
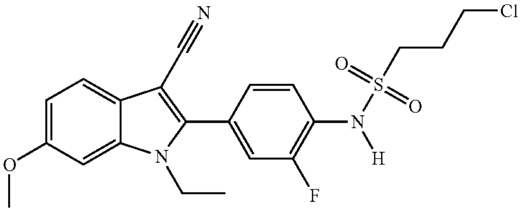
875
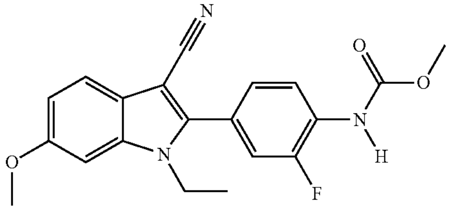
876
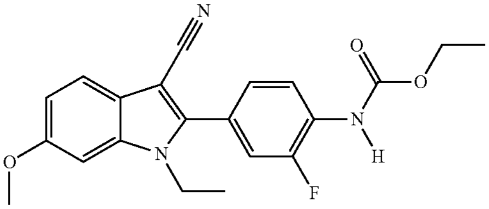
877
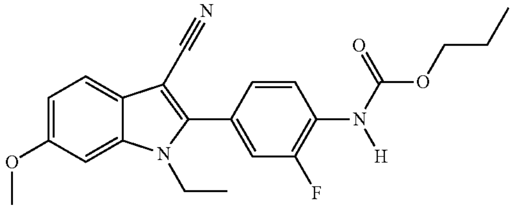
878
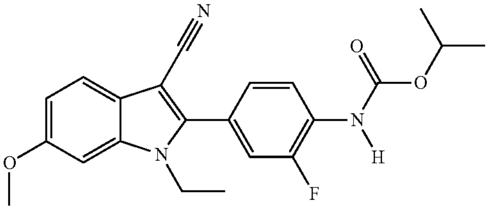
879
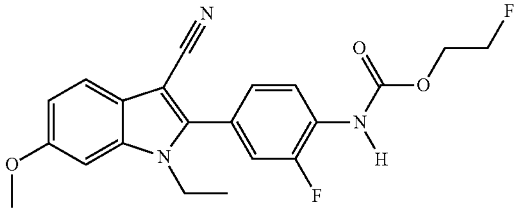
880
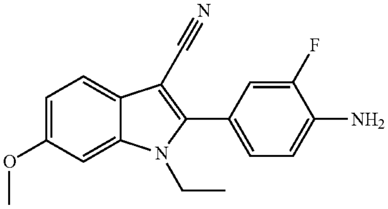
881
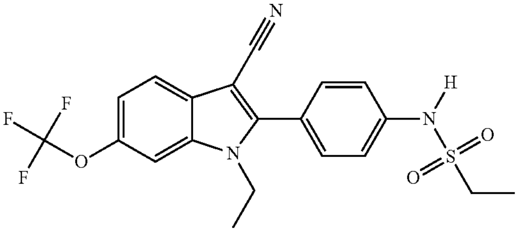
882
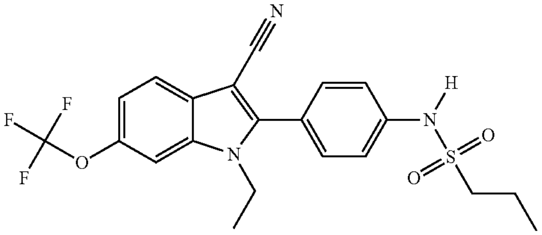
883
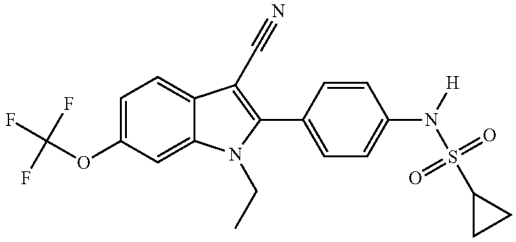

-continued
884
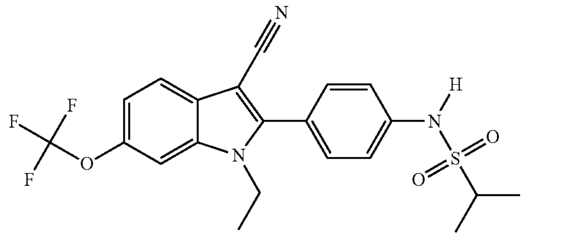
885
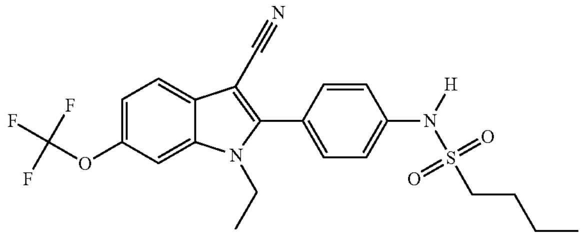
886
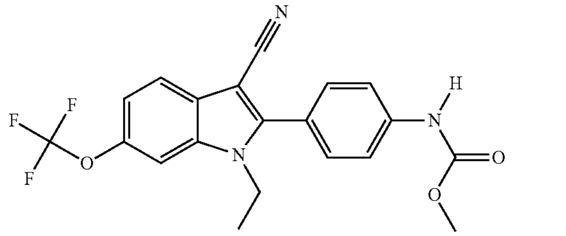
887
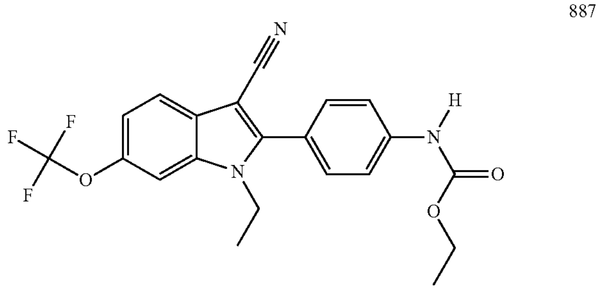
888
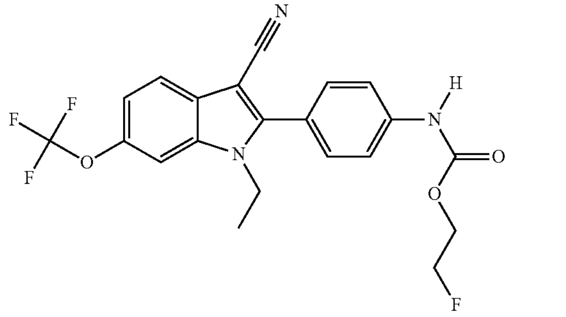
889
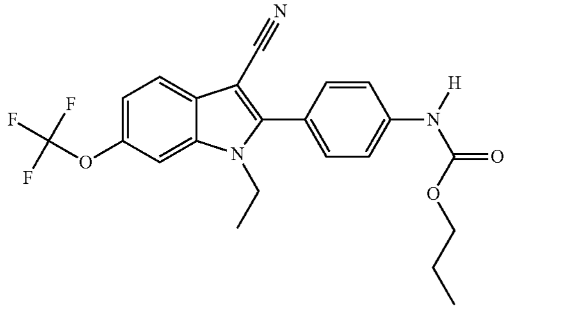
890
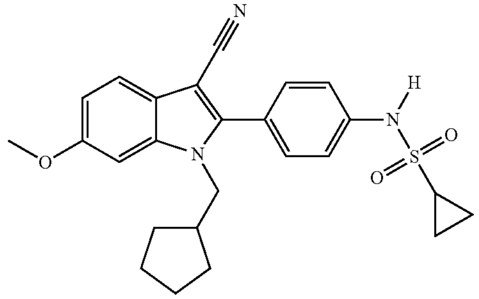
891
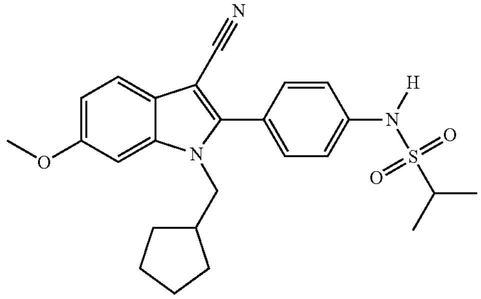
892
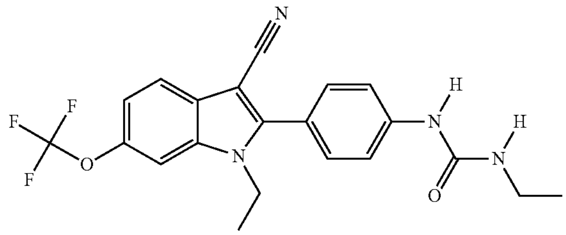
893
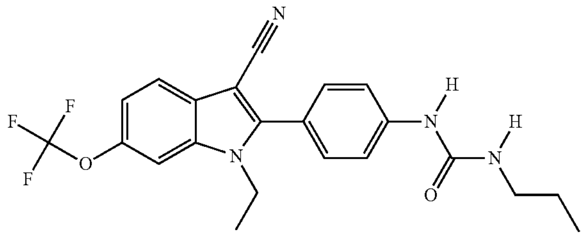

-continued
894
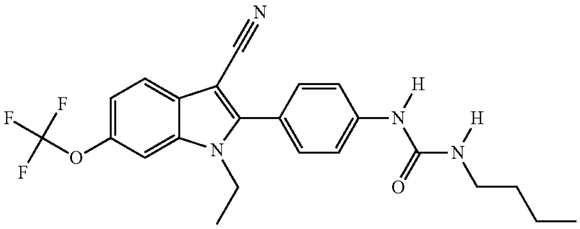
895
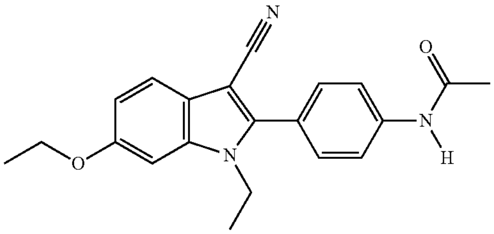
896
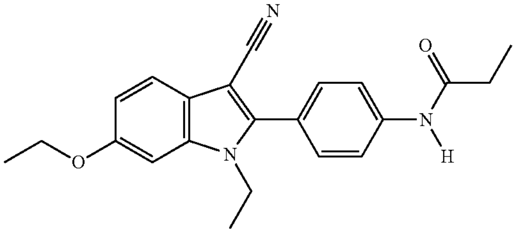
897
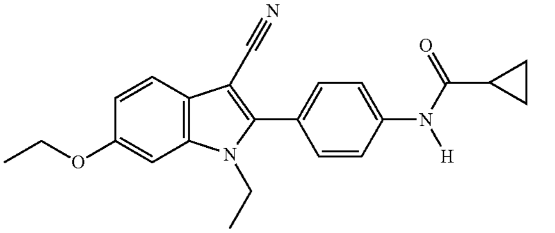
898
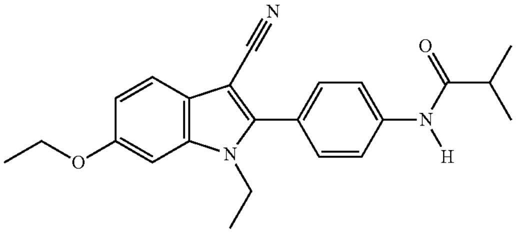
899
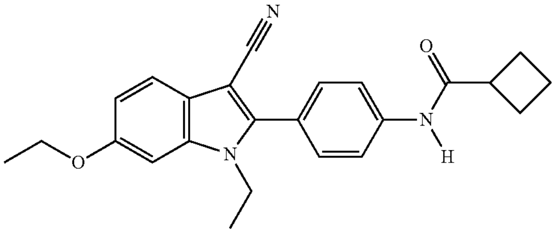
900
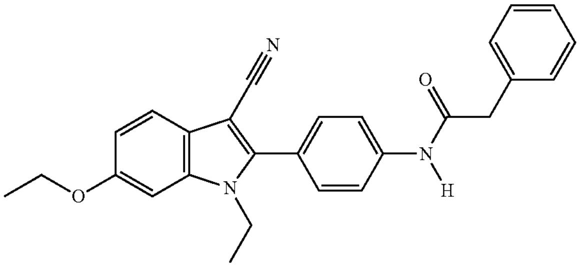
901
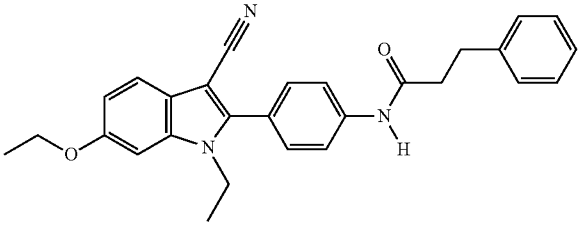
902
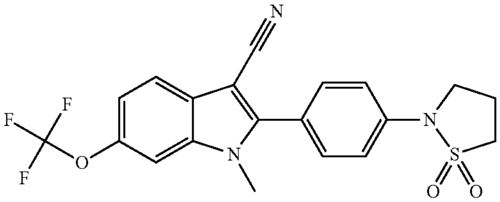
903
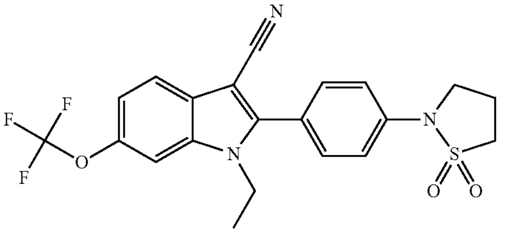
904
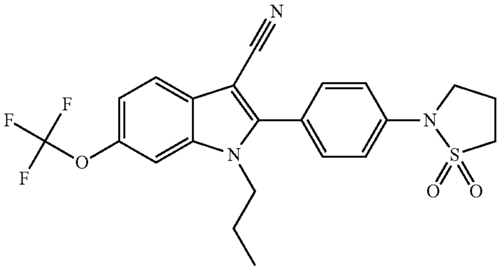
905
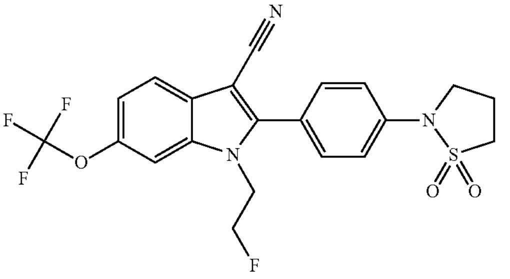

-continued
906
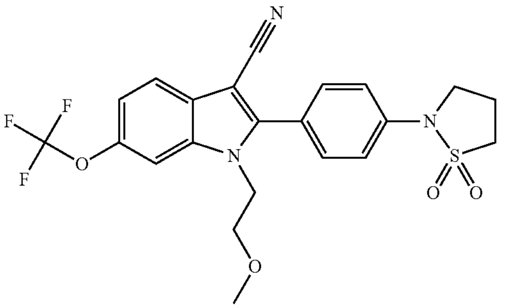
907
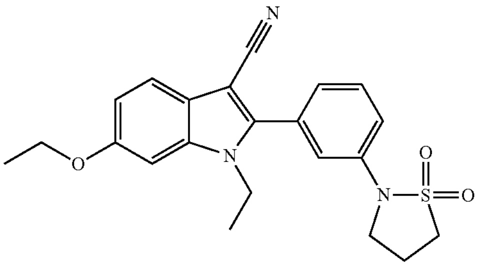
908
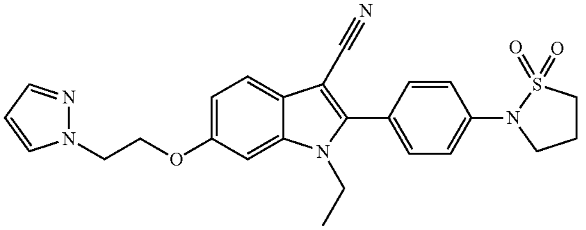
909
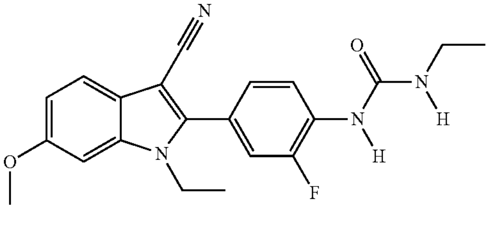
910
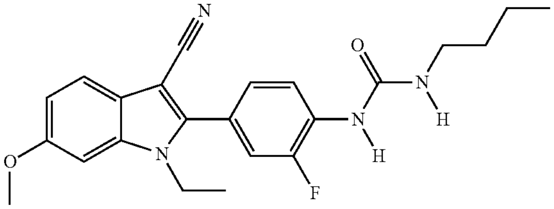
911
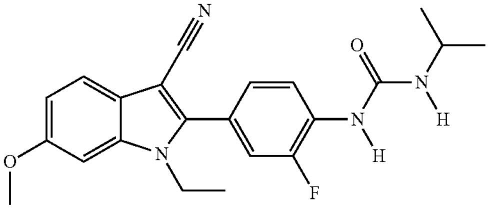
912
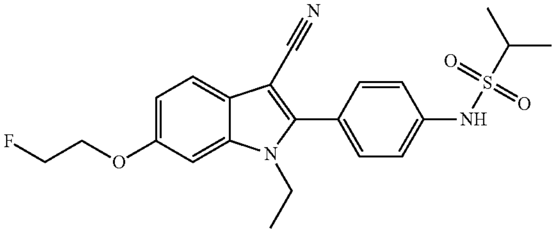
913
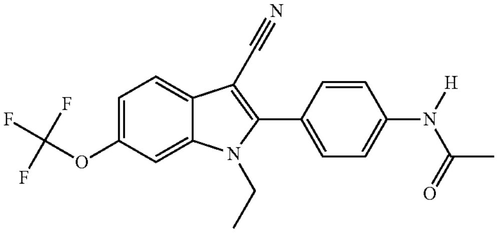
914
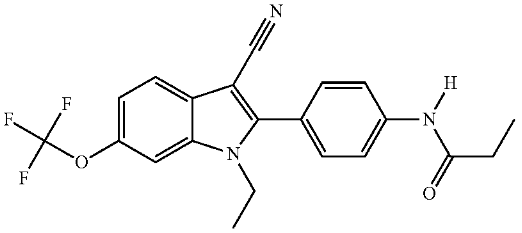
915
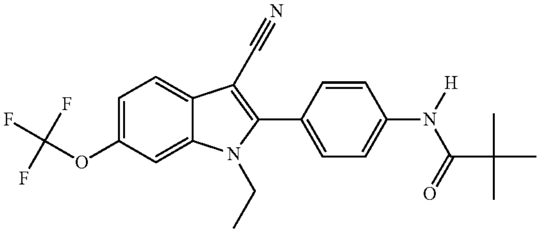
916
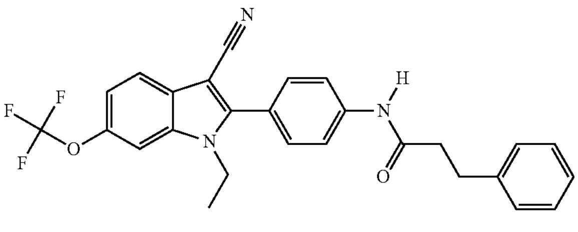
917
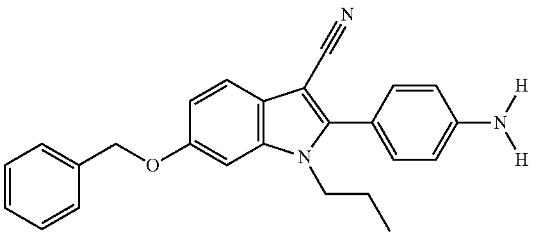

-continued
918
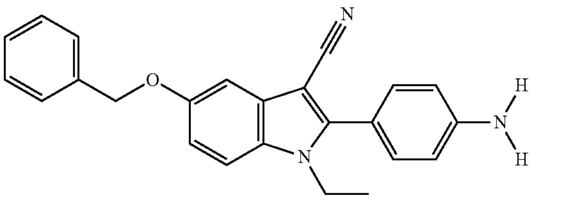
919
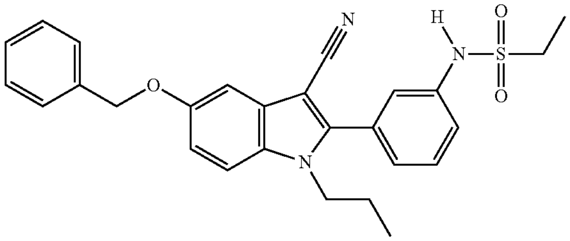
920
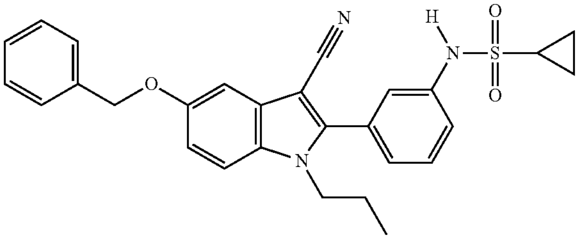
921
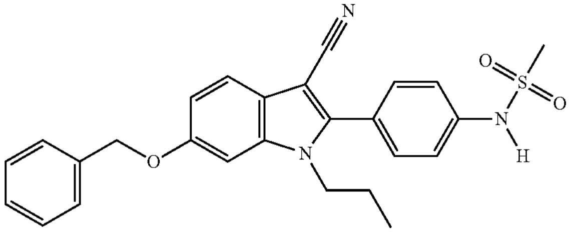
922
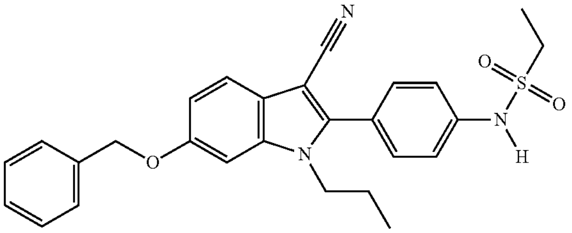
923
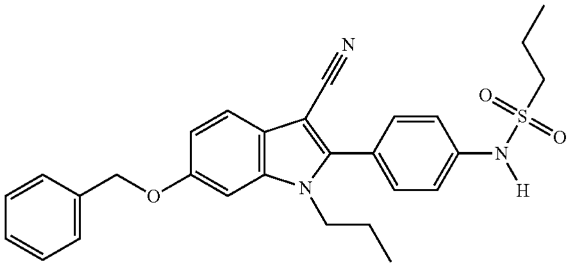
924
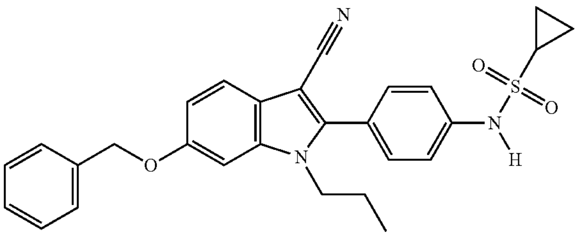
925
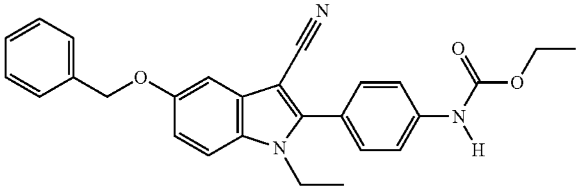
926
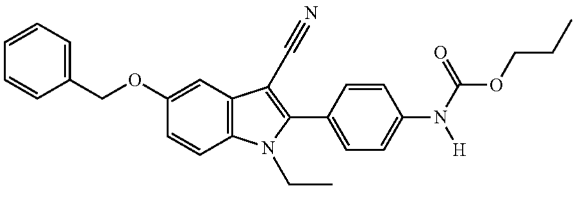
927
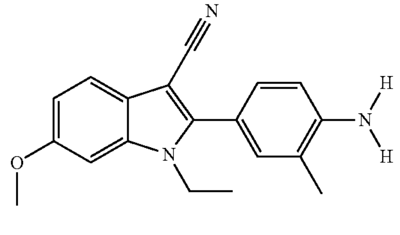
928
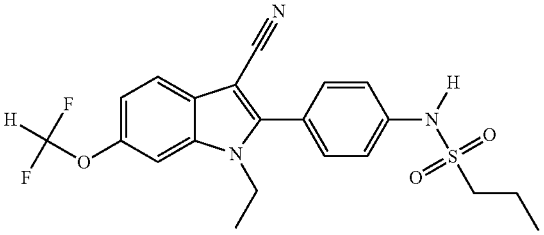
929
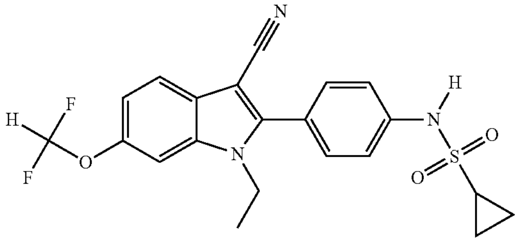

-continued
930
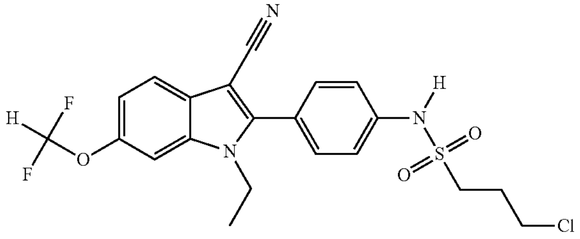
931
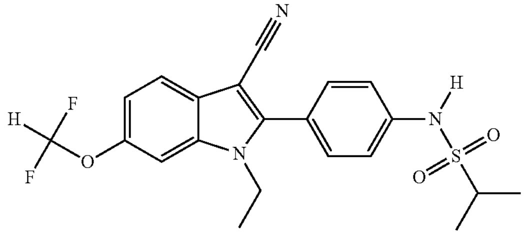
932
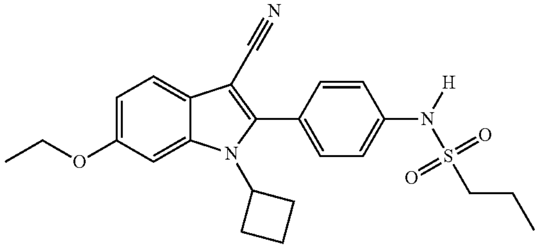
933
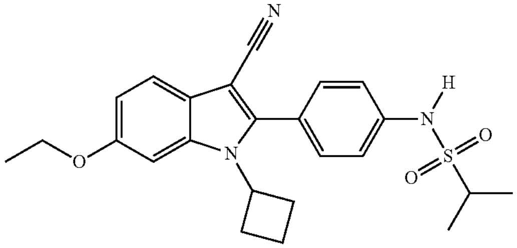
934
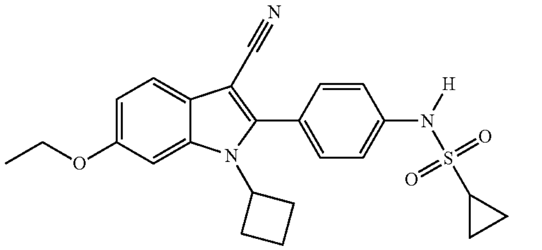
935
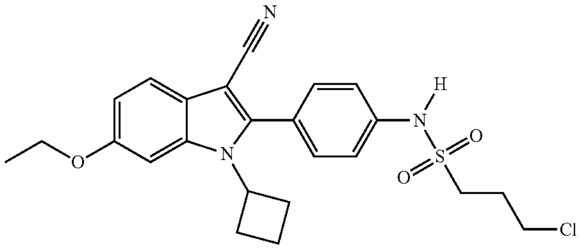
936
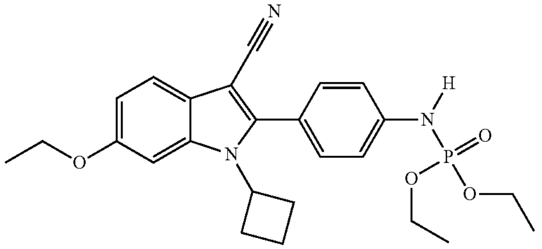
937
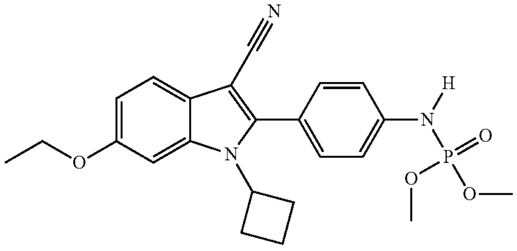
938
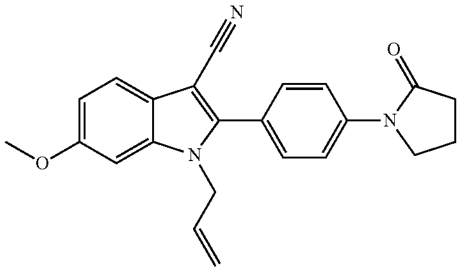
939
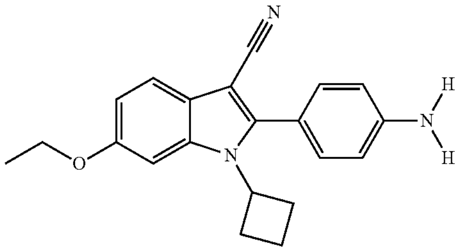
941
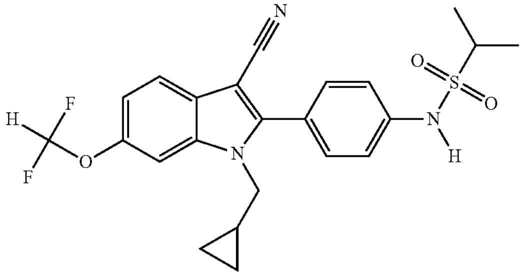
942
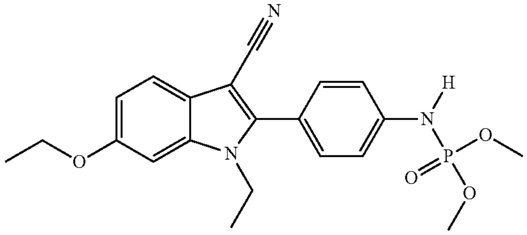

-continued
943
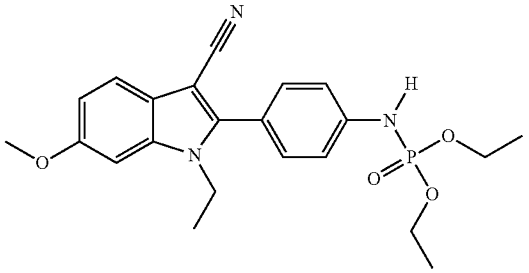
944
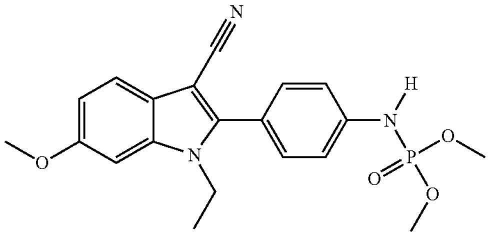
945
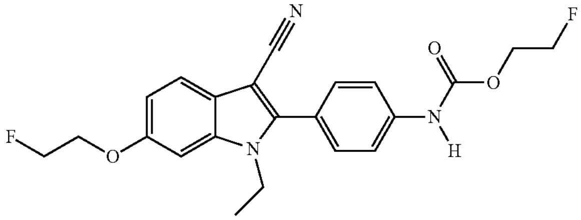
946
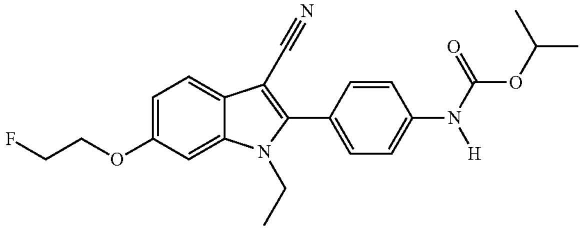
947
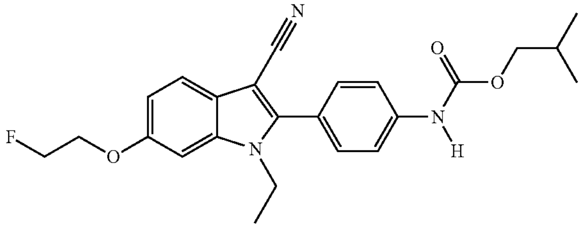
948
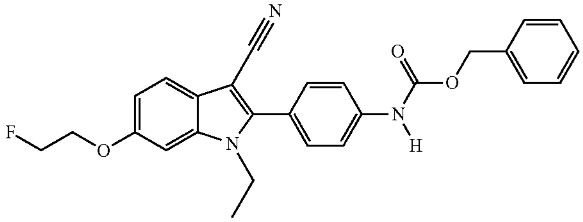
949
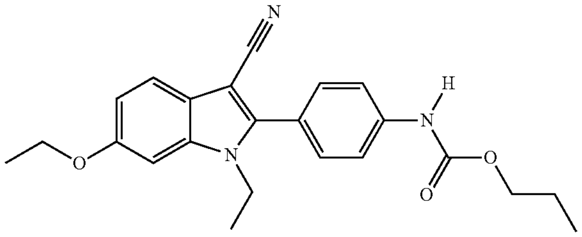
950
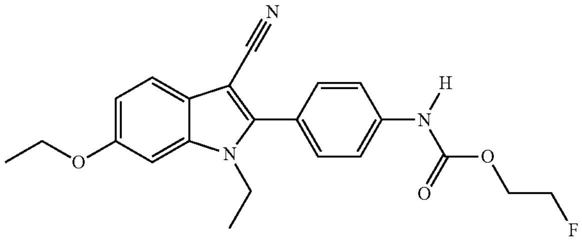
951
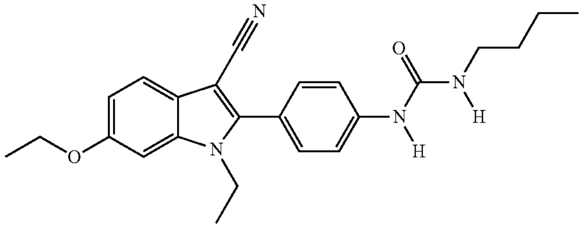
952
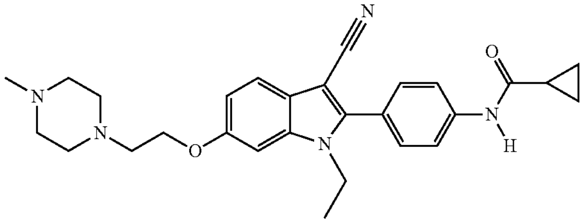
953
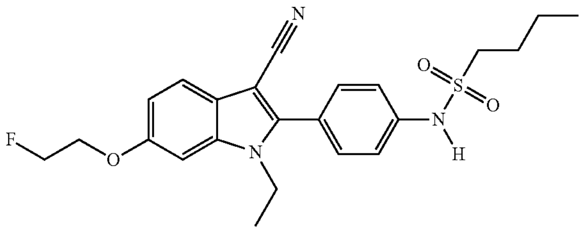
954
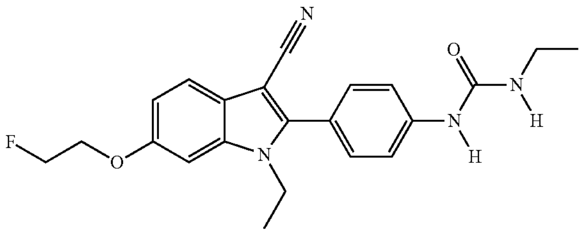

-continued
955
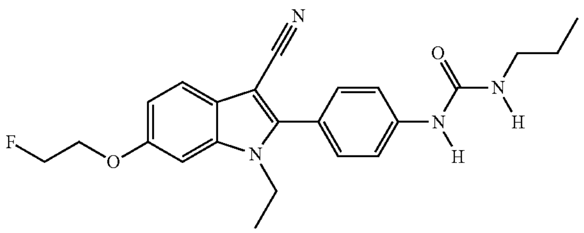
956
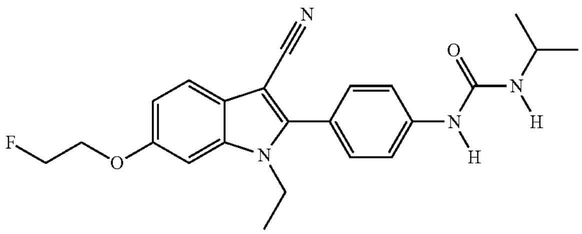
957
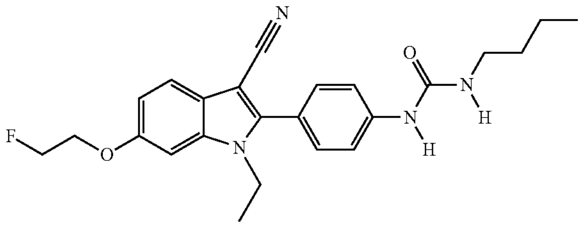
958
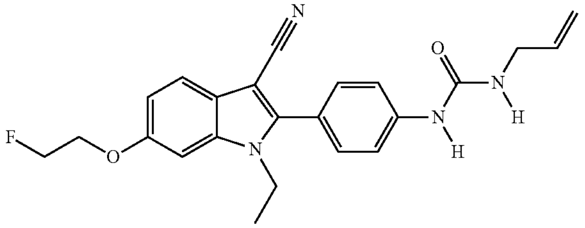
959
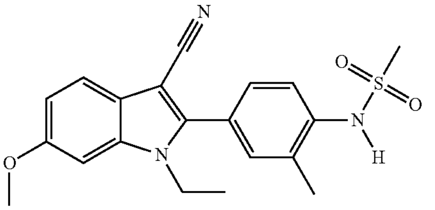
960
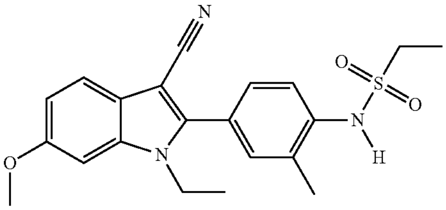
961
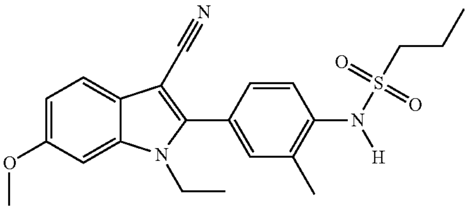
962
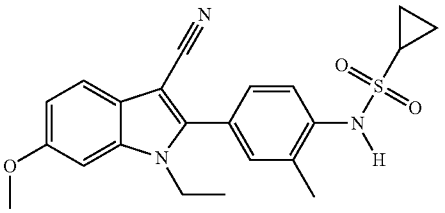
963
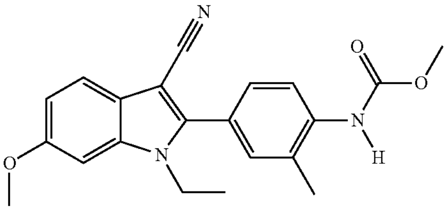
964
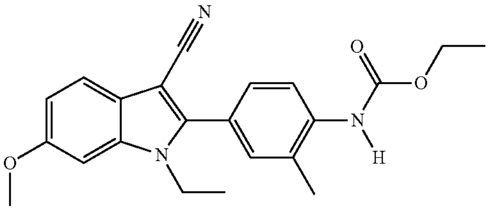
965
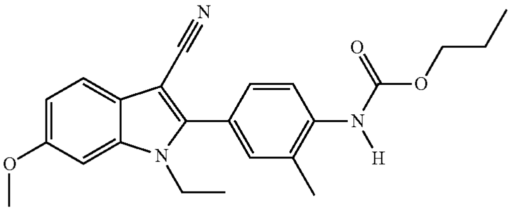
966
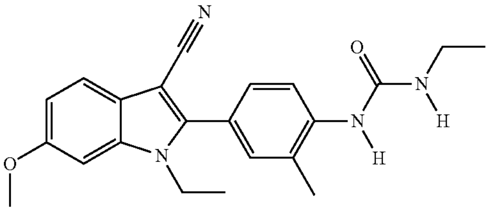
967
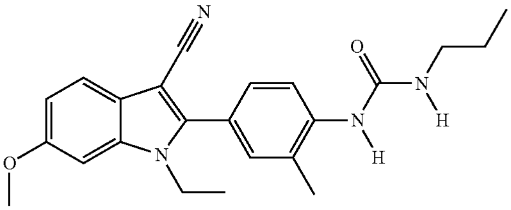
968
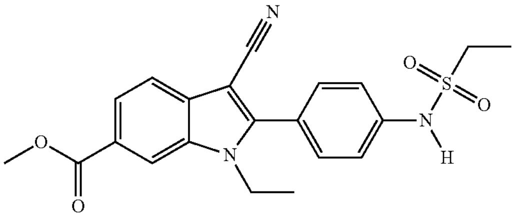

-continued
969
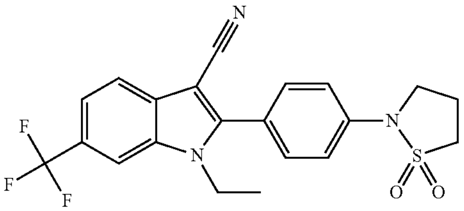
970
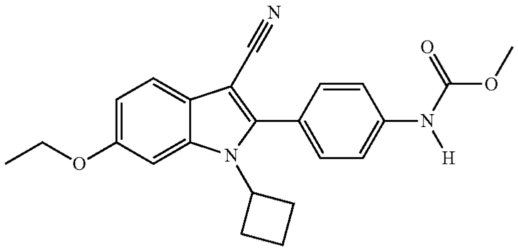
971
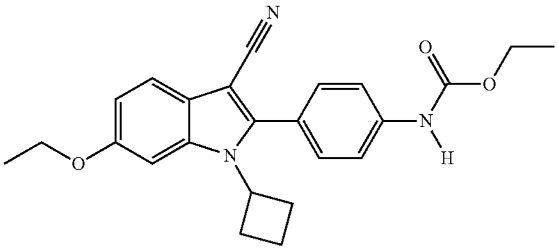
972
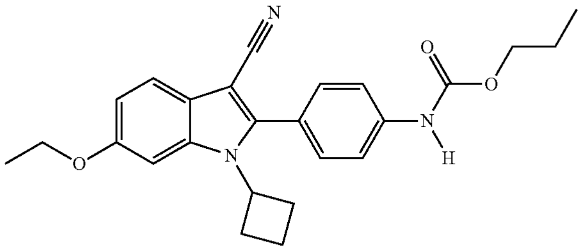
973
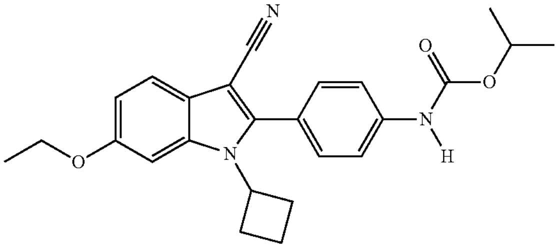
974
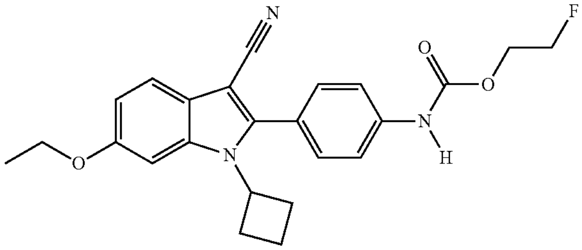
975
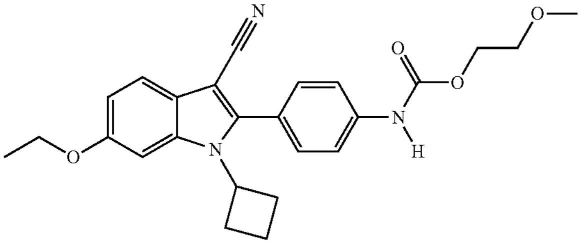
976
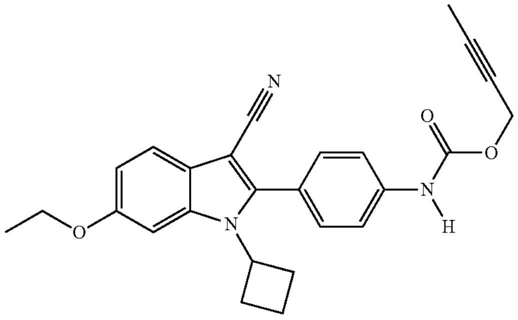
977
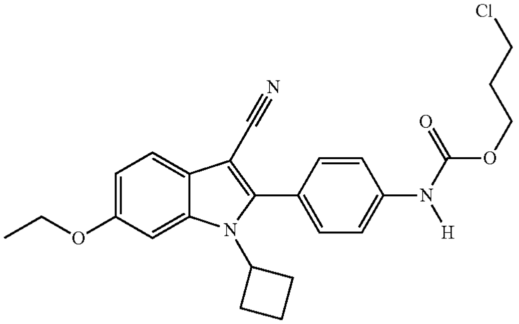
978
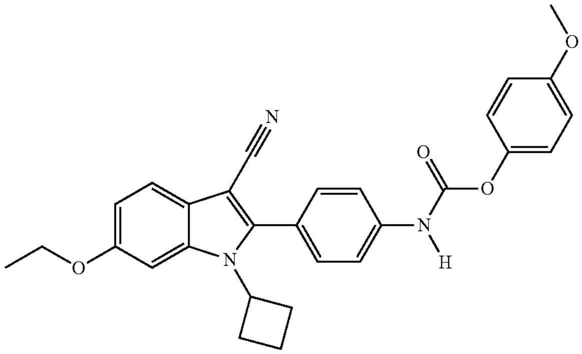

-continued
979
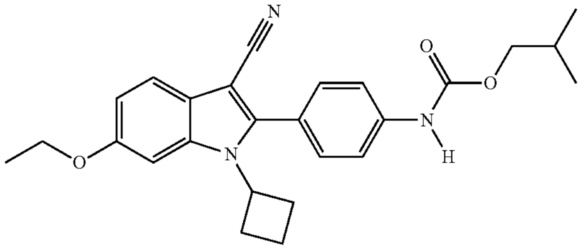
980
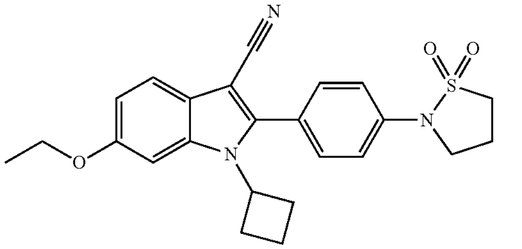
981
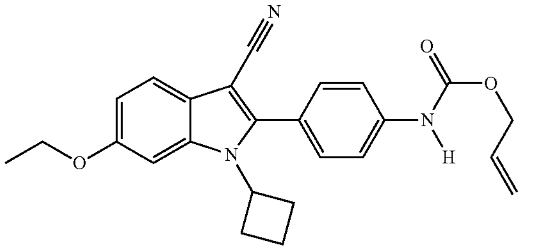
982
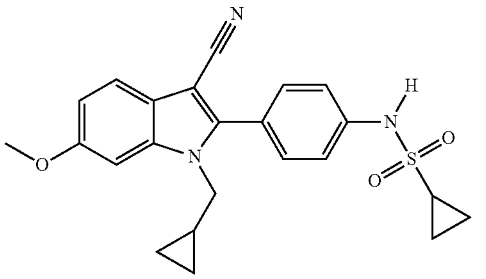
983
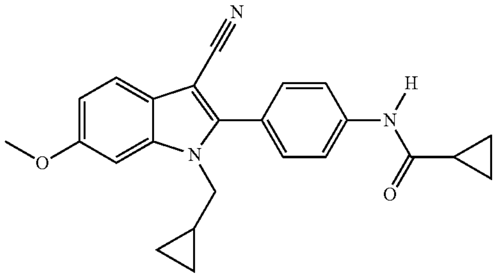
984
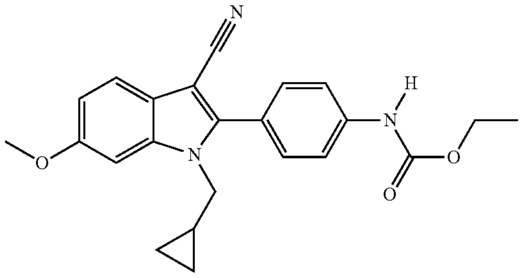
985
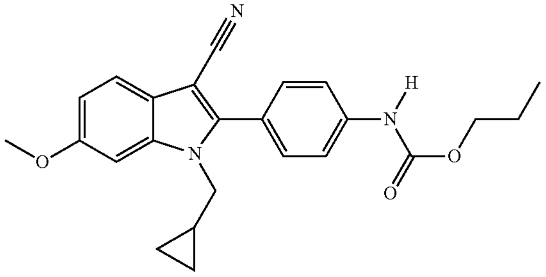
986
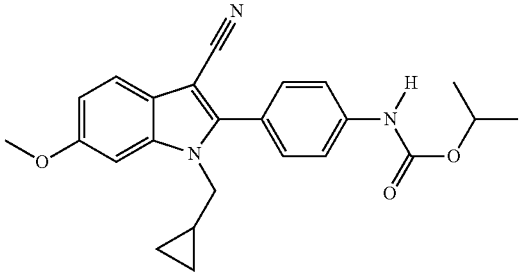
987
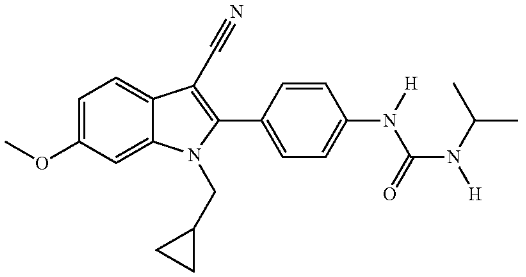
988
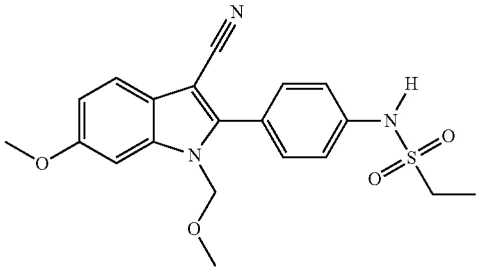

-continued
989
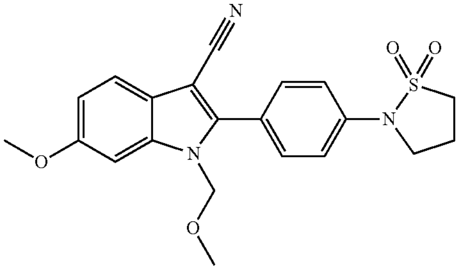
990
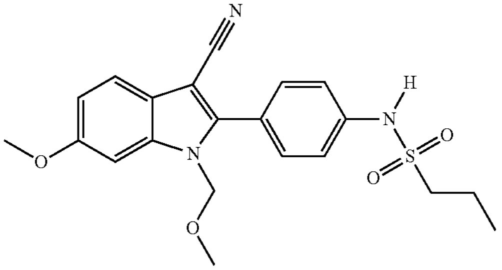
991
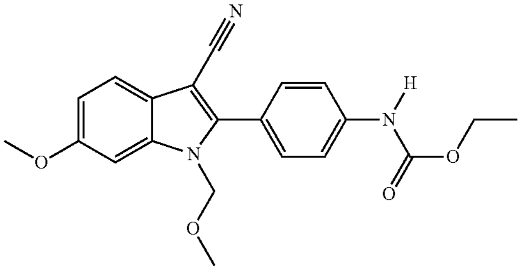
992
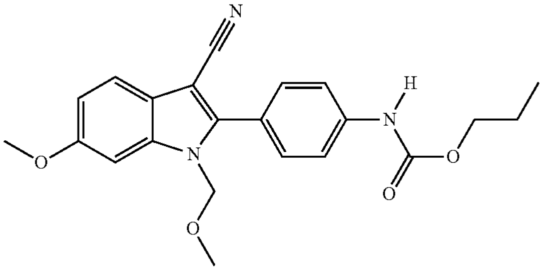
993
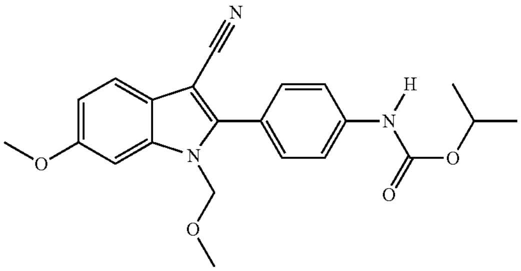
994
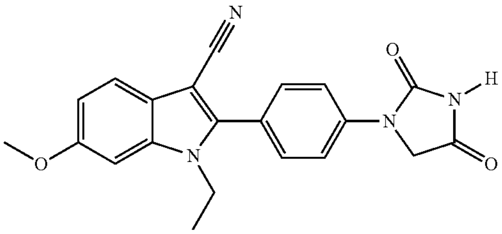
995
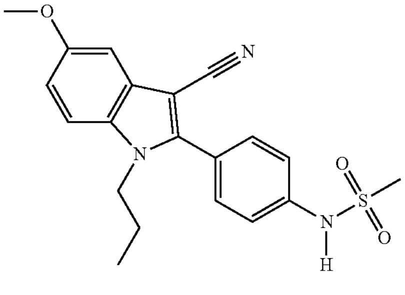
996
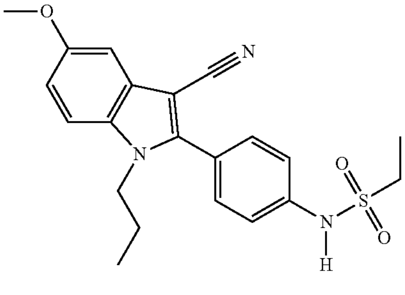
997
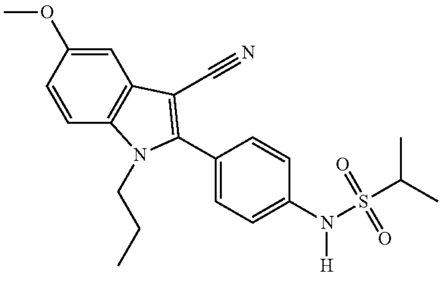
998
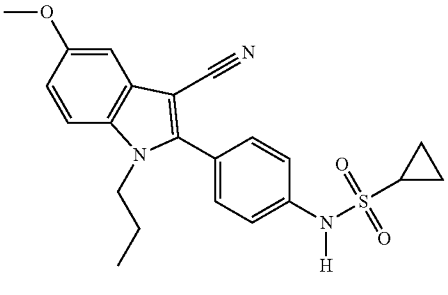

-continued
999
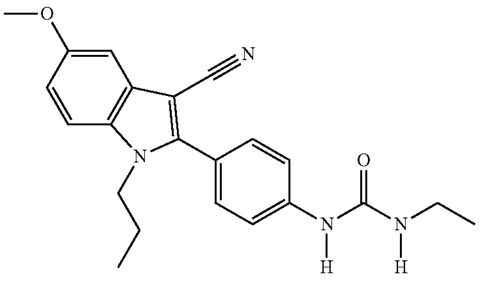
1000
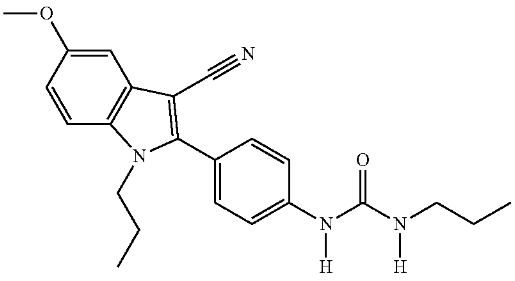
1001
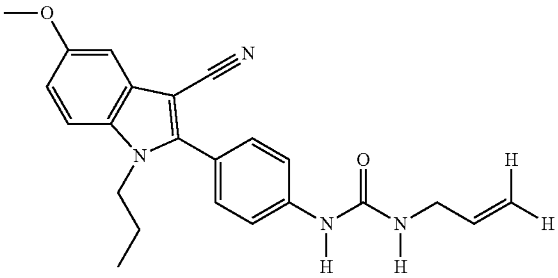
1002
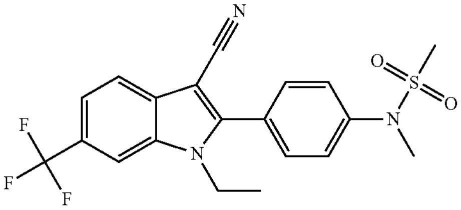
1003
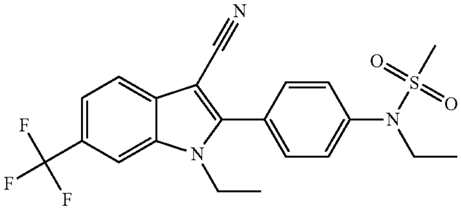
1004
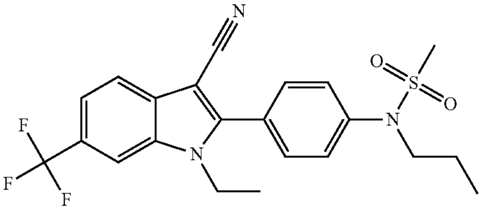
1005
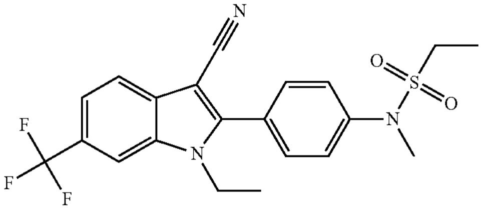
1006
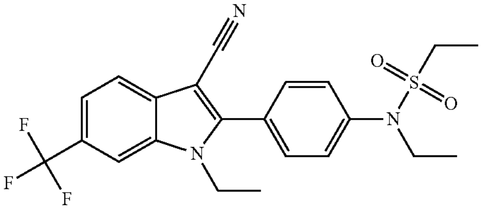
1007
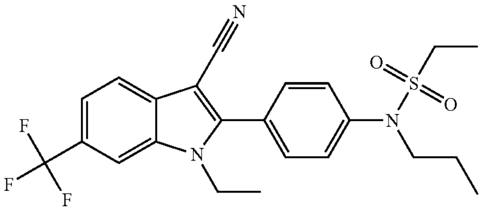
1008
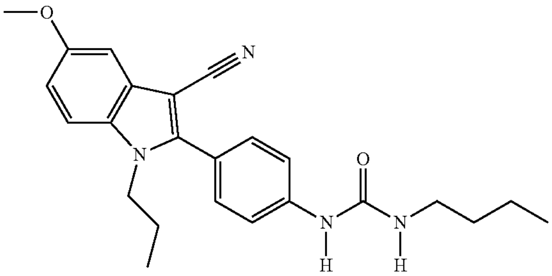
1009
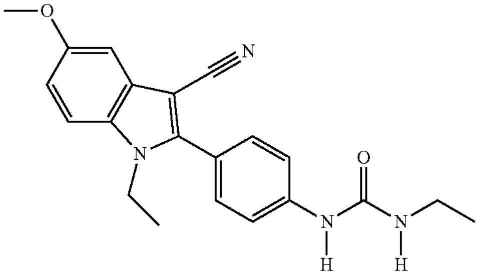
1010
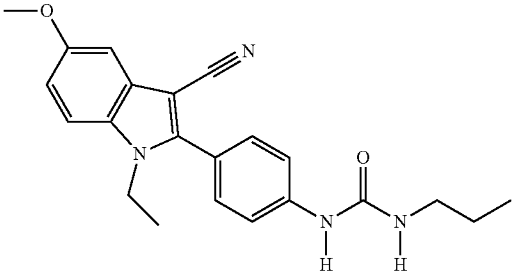

-continued
1011
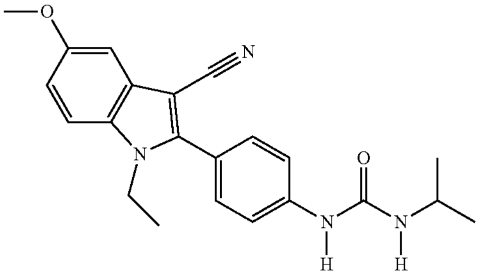
1012
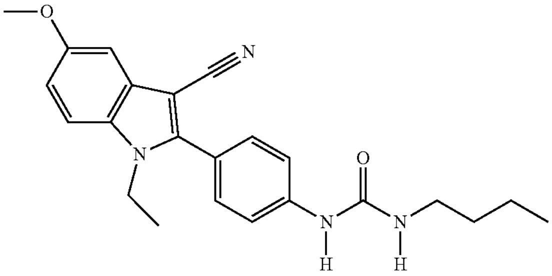
1013
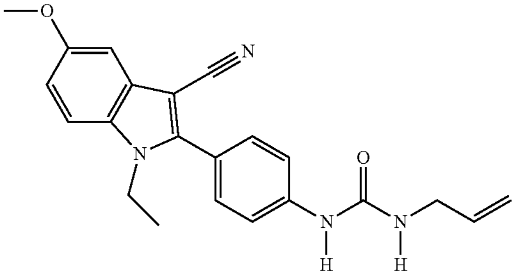
1014
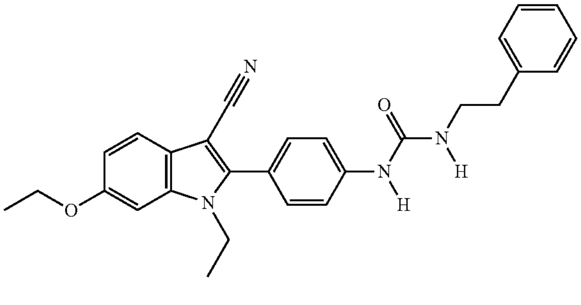
1015
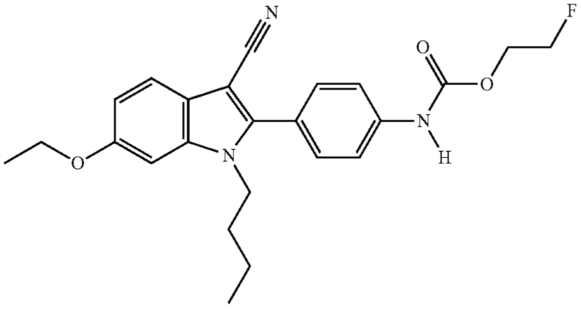
1016
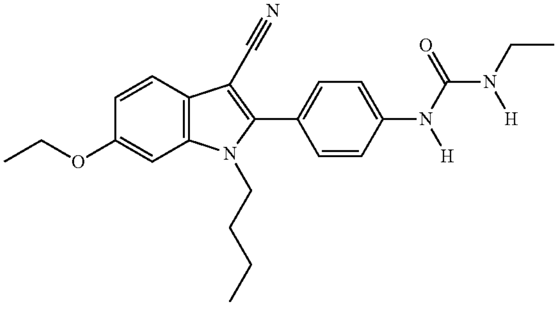
1017
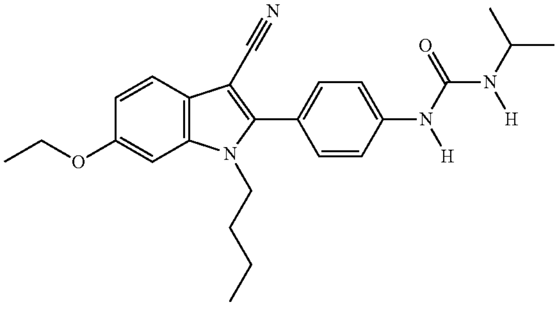
1018
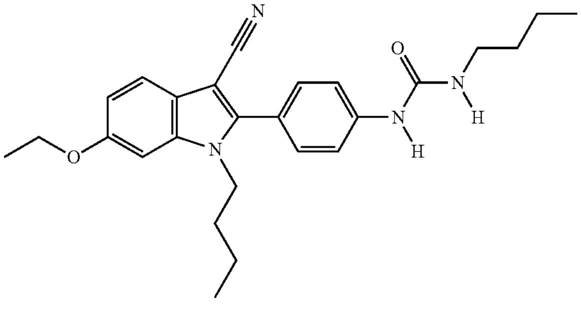

-continued
1019
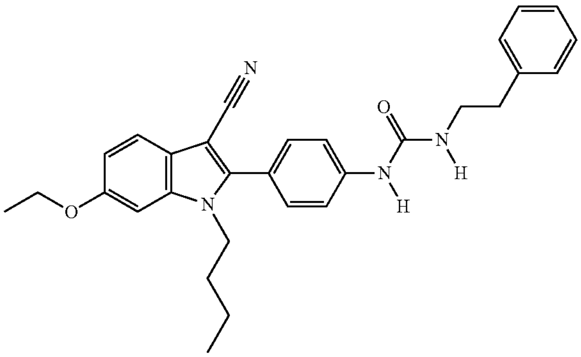
1020
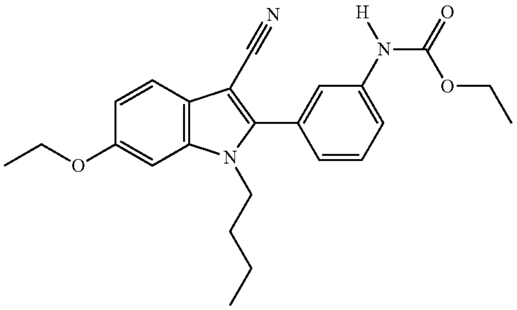
1021
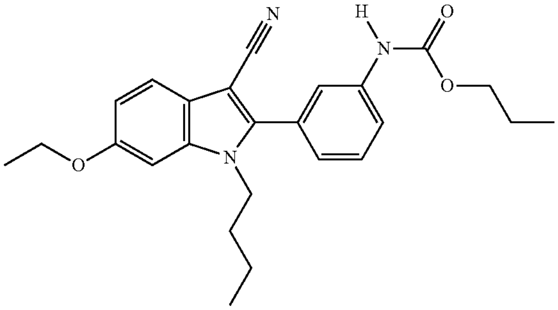
1022
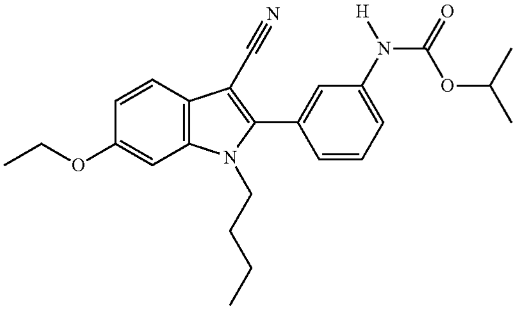
1023
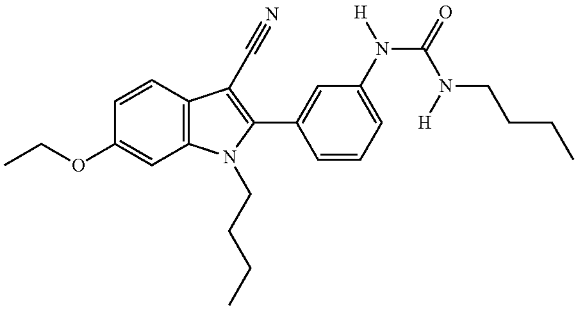
1024
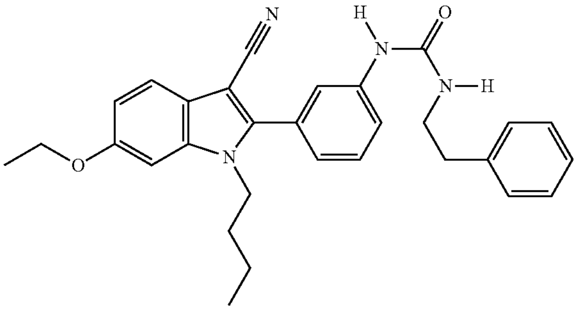
1025
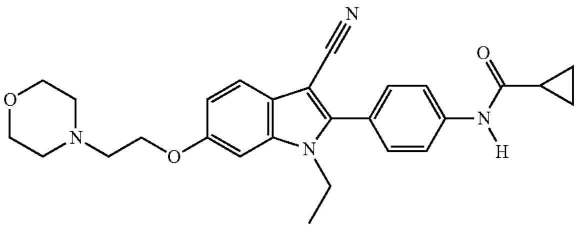
1026
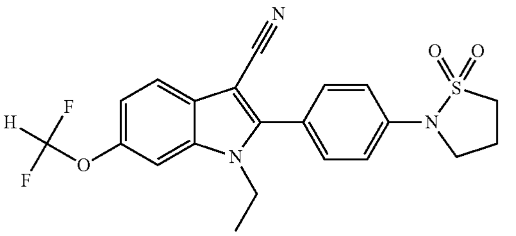
1027
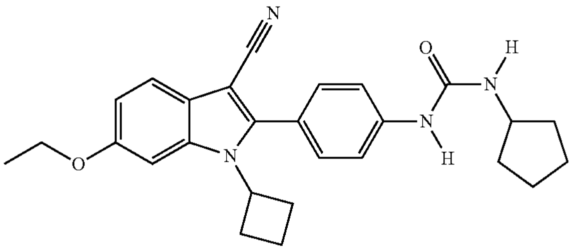
1028
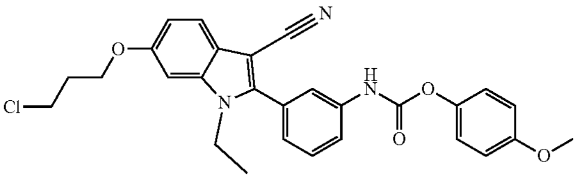

-continued
1029
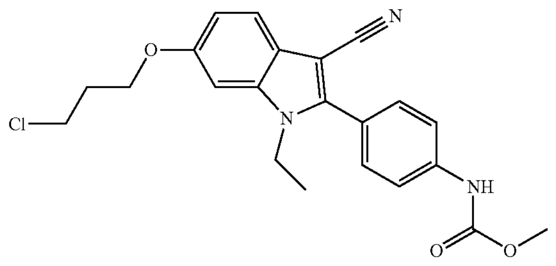
1030
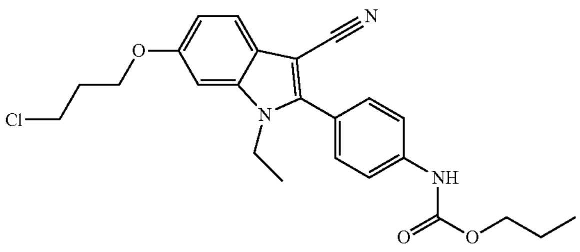
1031
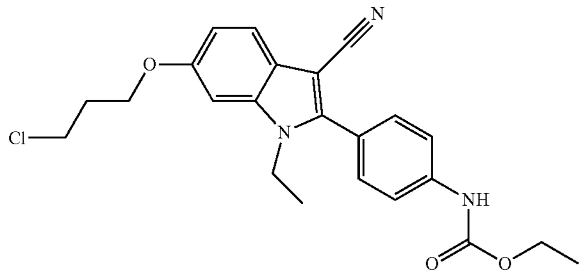
1032
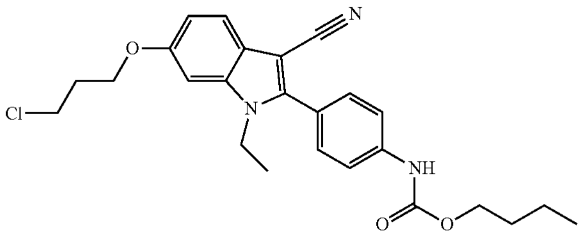
1033
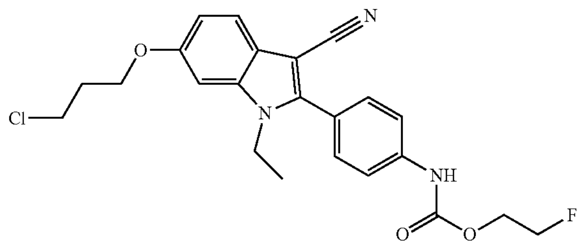
1034
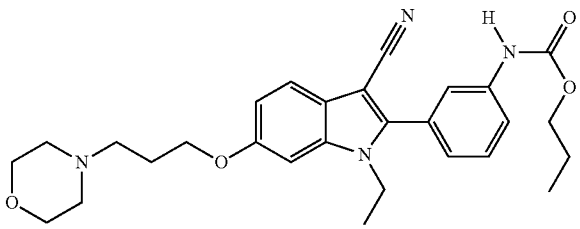
1035
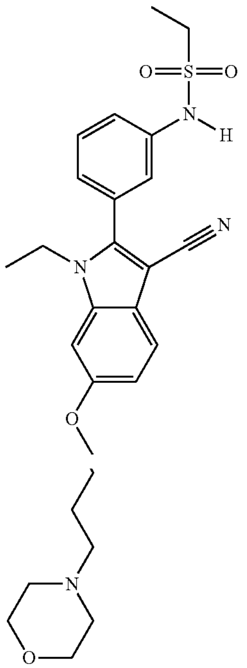

-continued
1036
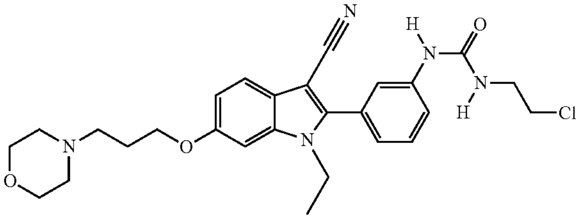
1037
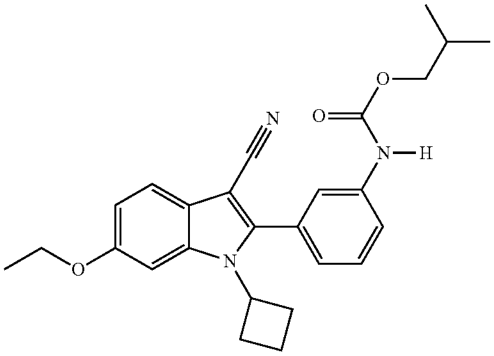
1038
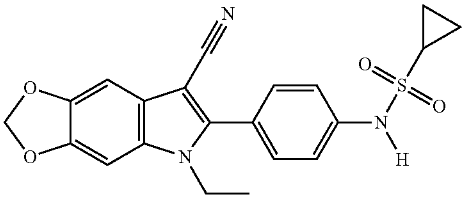
1039
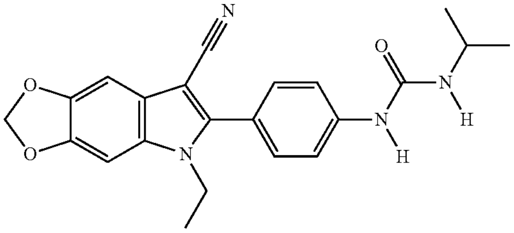
1040
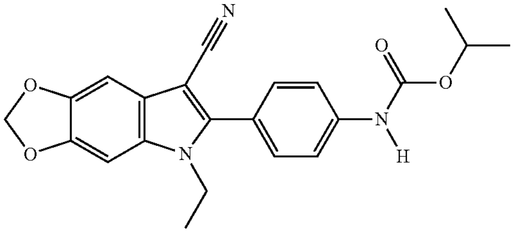
1041
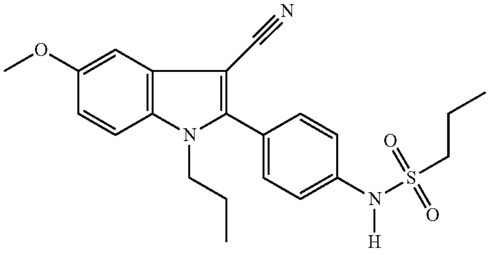
1042
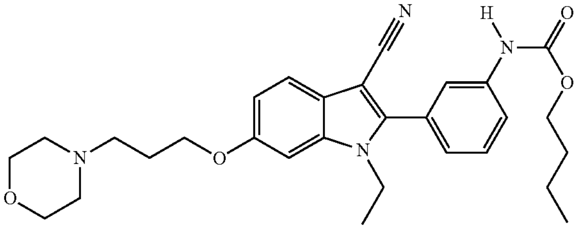
1043
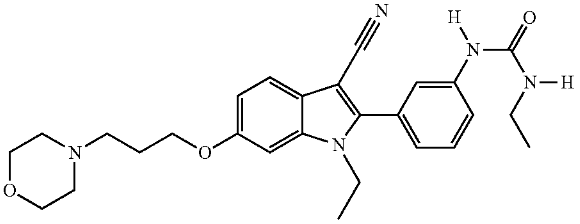
1044
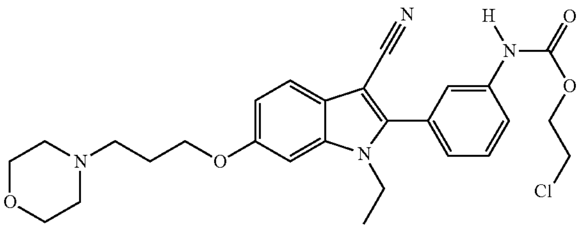
1045
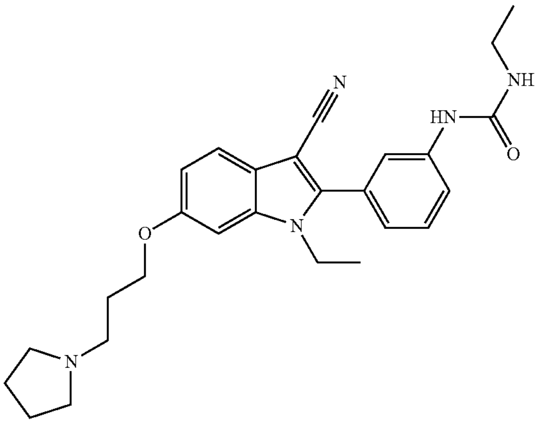

-continued
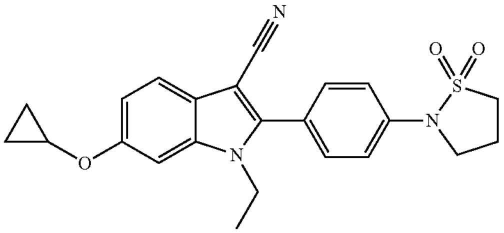
1046
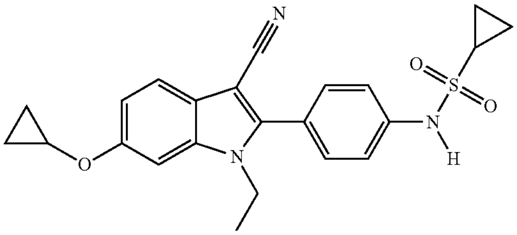
1047
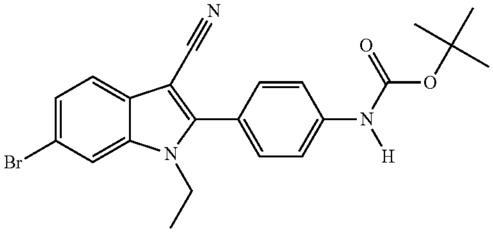
1048
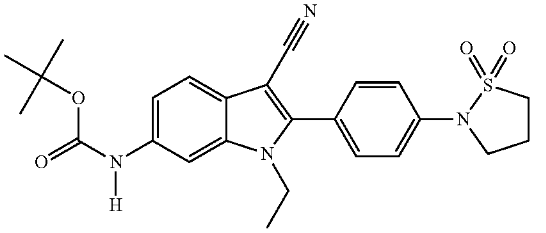
1049
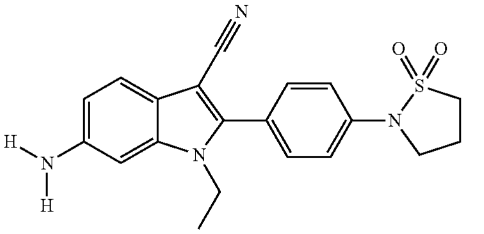
1050
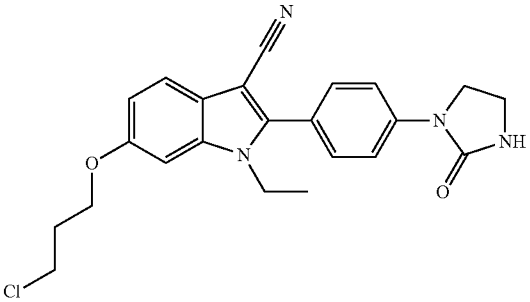
1051
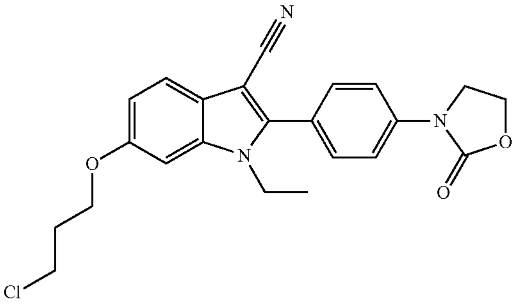
1052
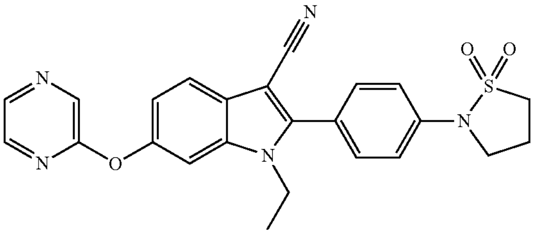
1053
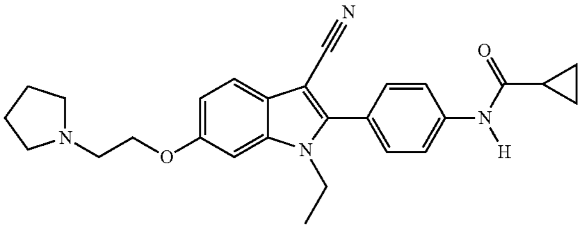
1054
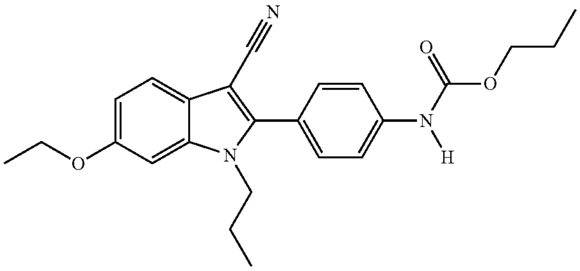
1055

-continued
1056
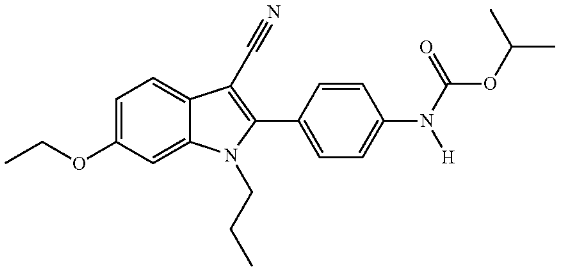
1057
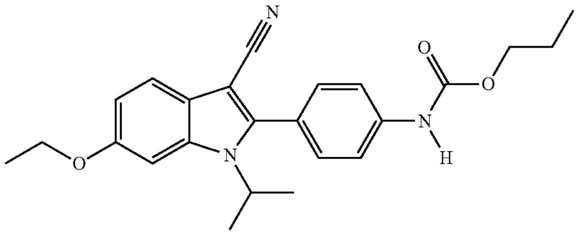
1058
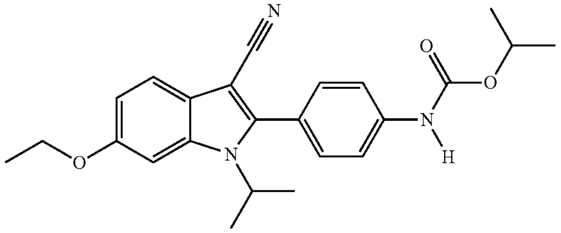
1059
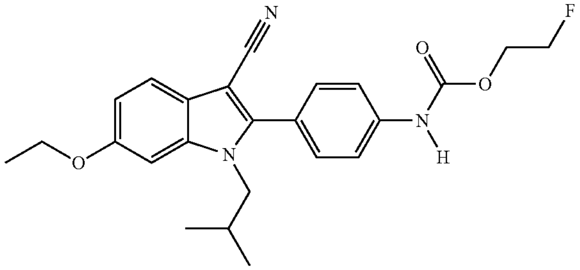
1060
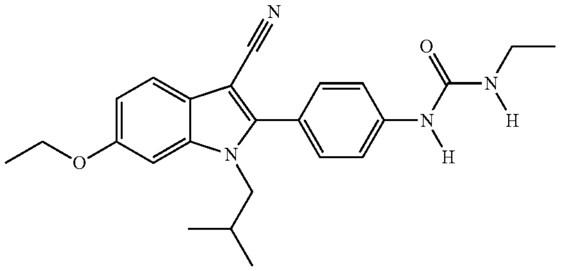
1061
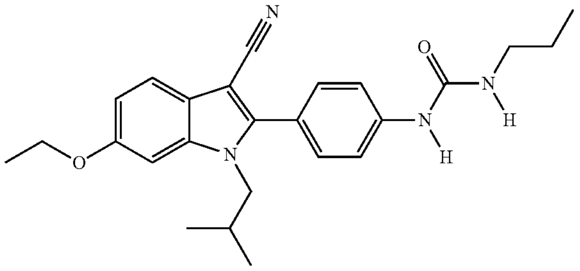
1062
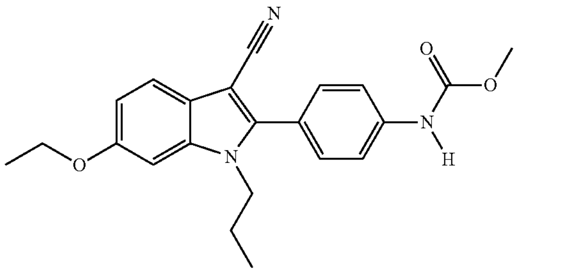
1063
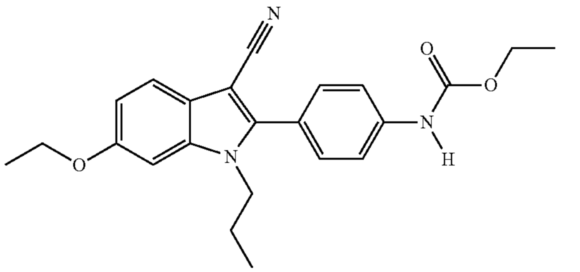
1064
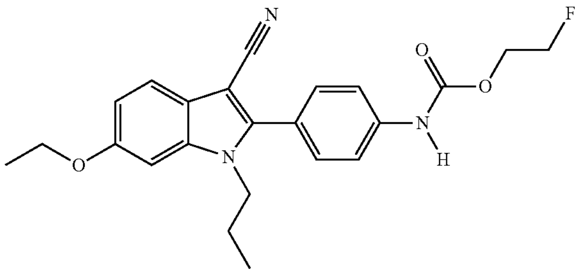
1065
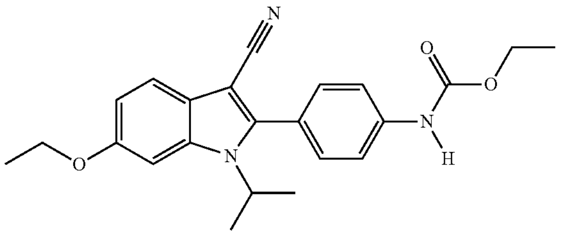

-continued
1066
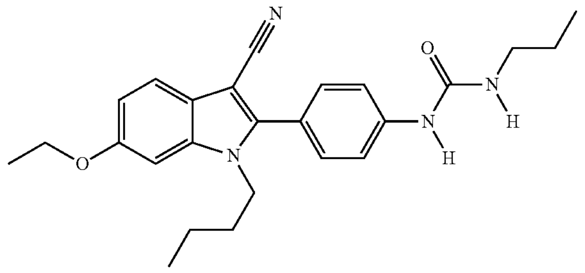
1067
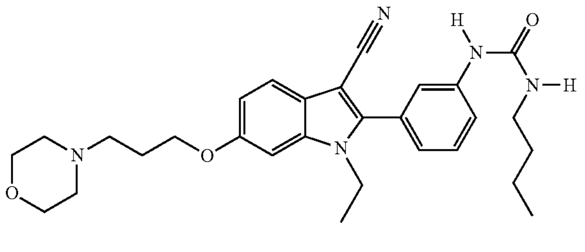
1068
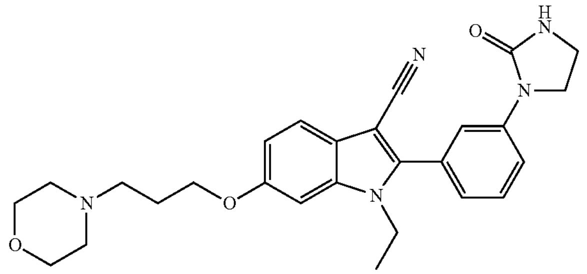
1069
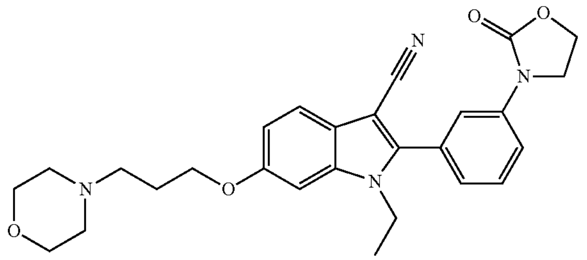
1070
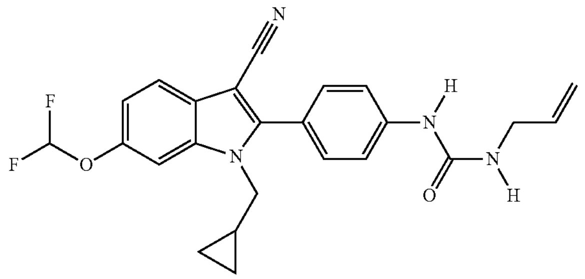
1071
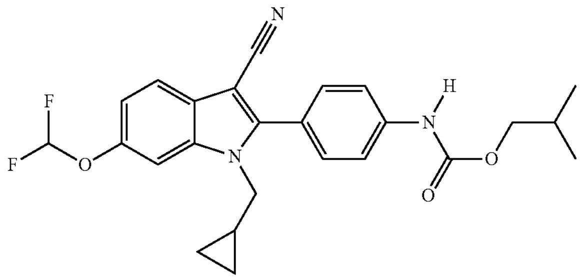
1072
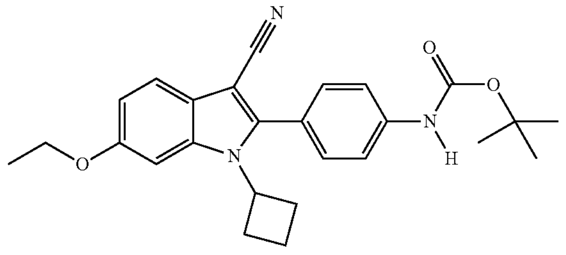
1073
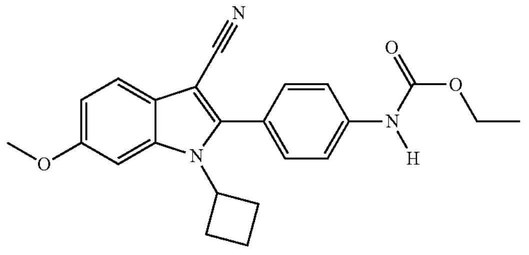
1074
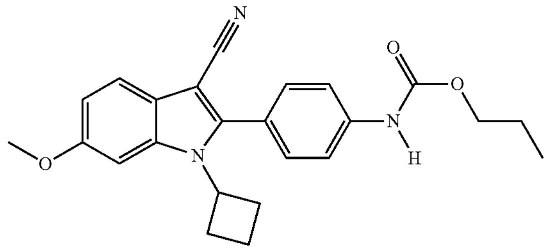
1075
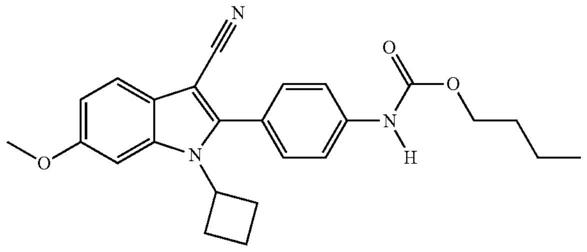

-continued
1076
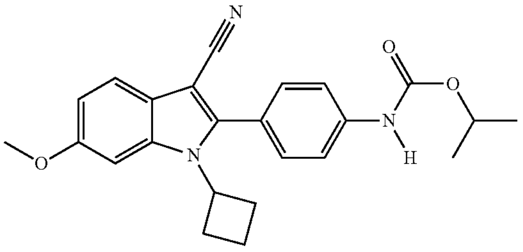
1077
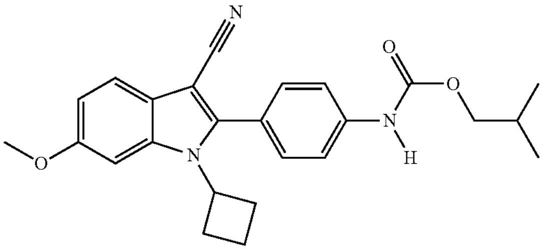
1078
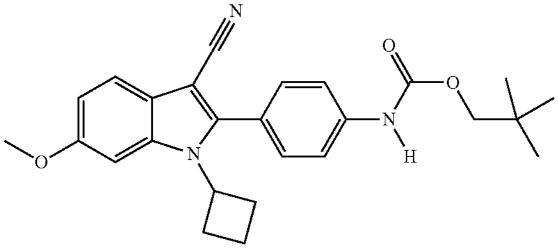
1079
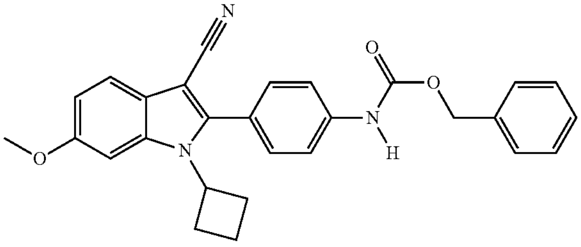
1080
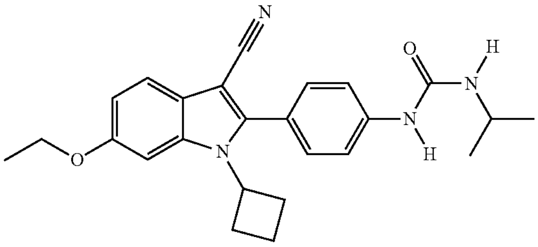
1081
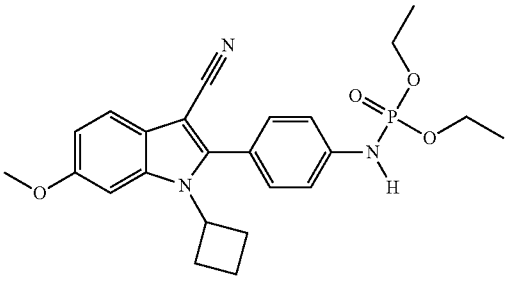
1082
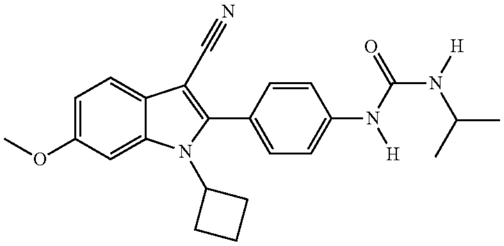
1083
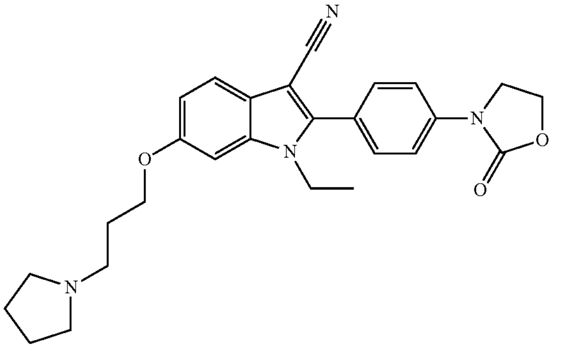
1084
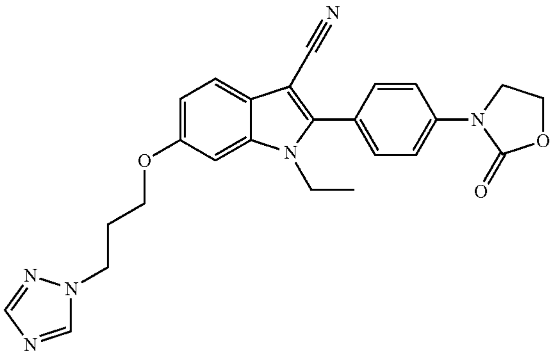
1085
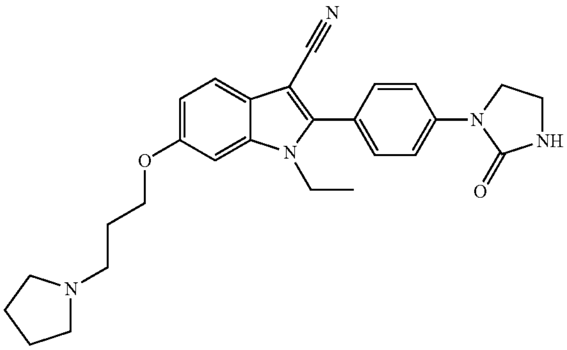

-continued
1086
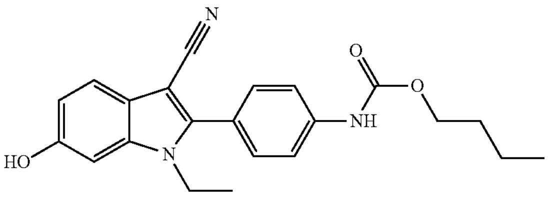
1087
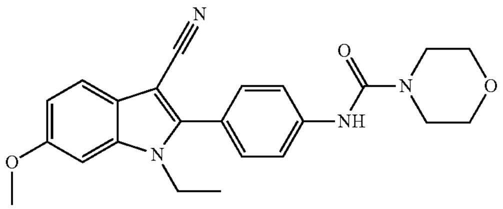
1088
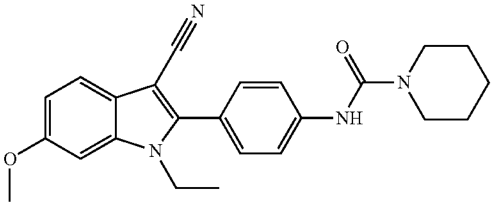
1089
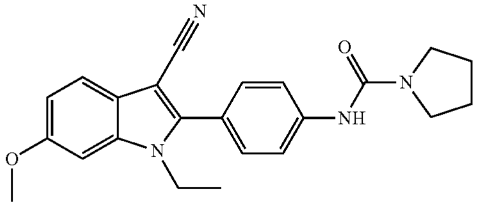
1090
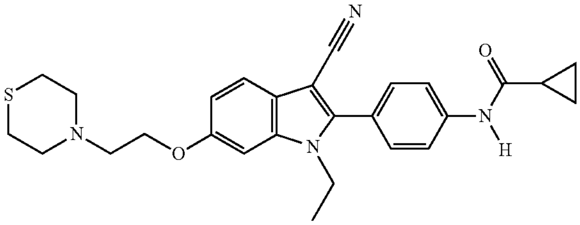
1091
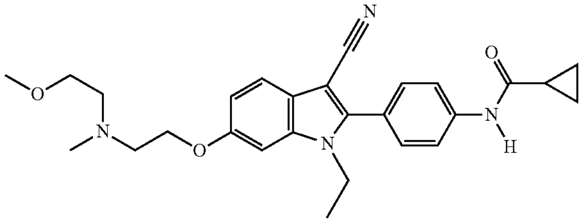
1092
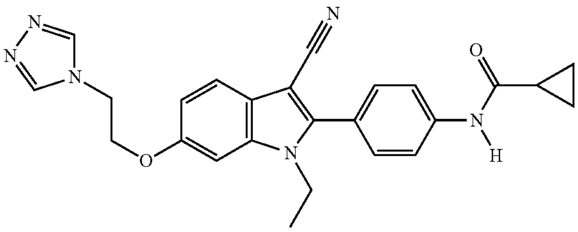
1093
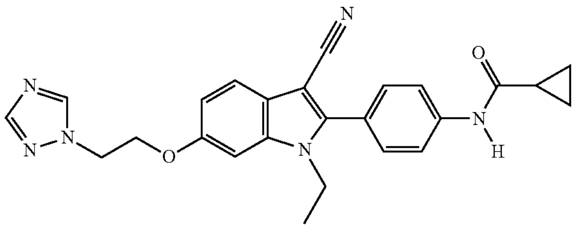
1094
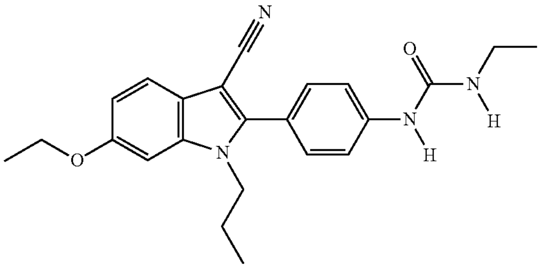
1095
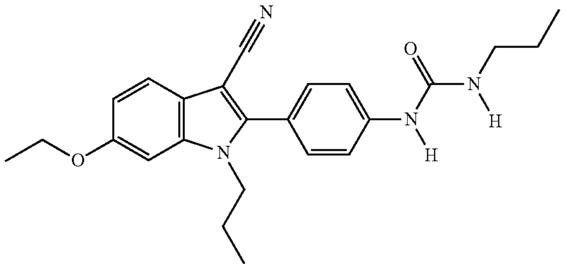
1096
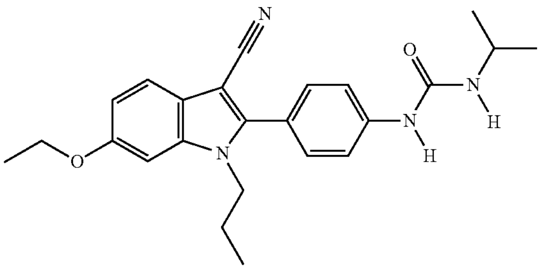
1097
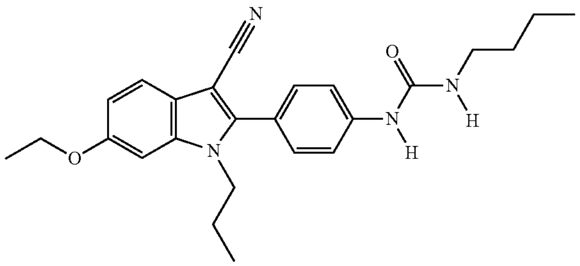

-continued
1098
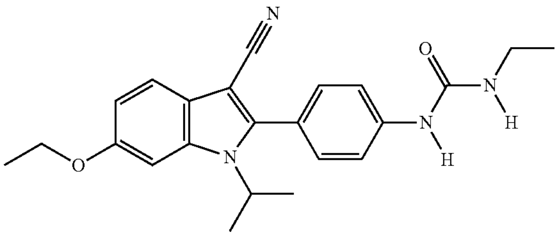
1099
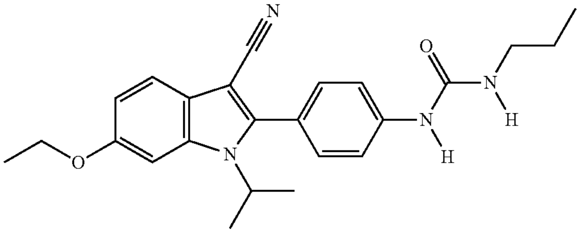
1100
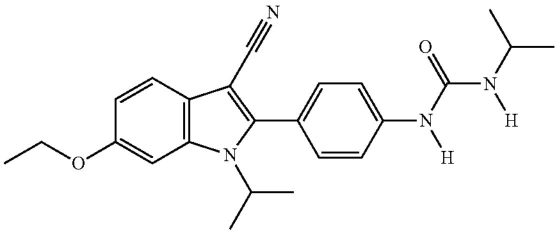
1101
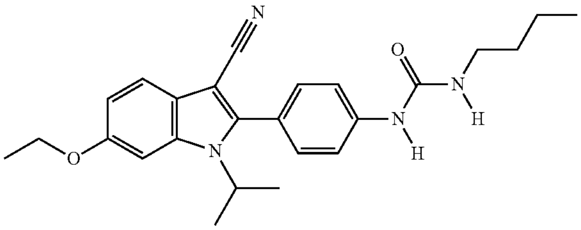
1102
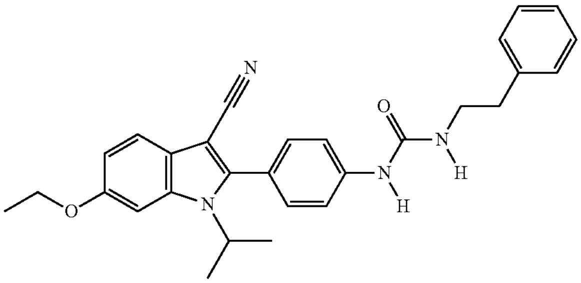
1103
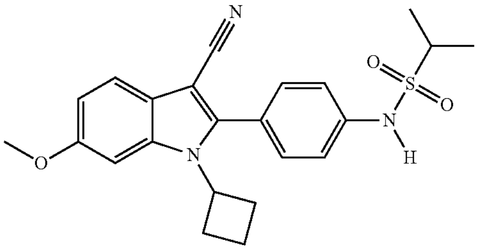
1104
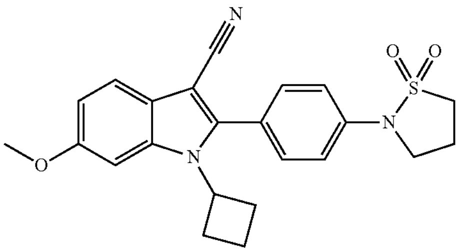
1105
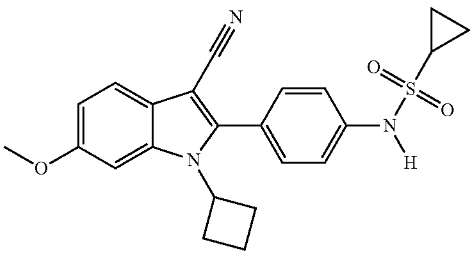
1106
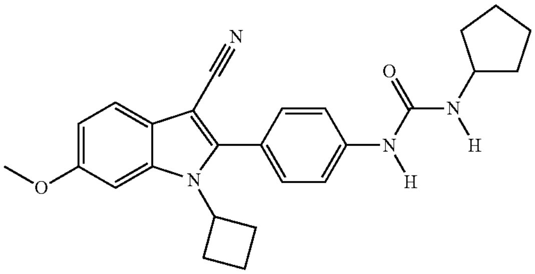
1107
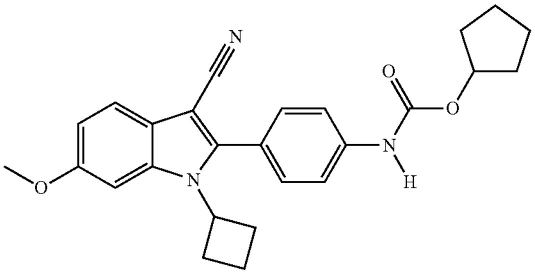

-continued
1108
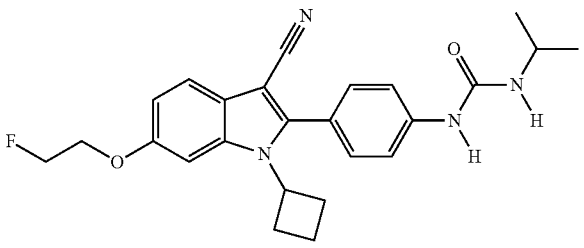
1109
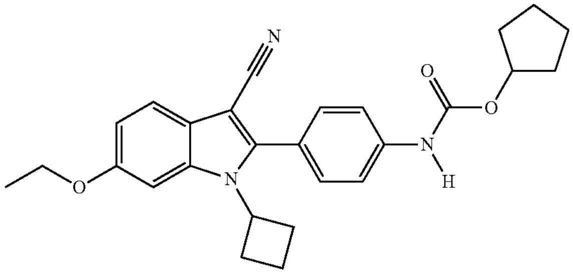
1110
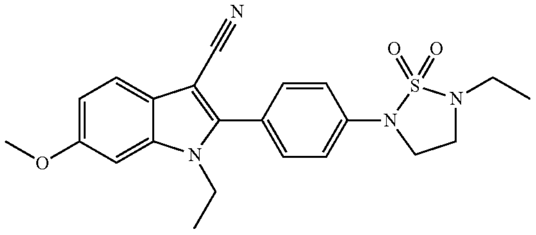
1111
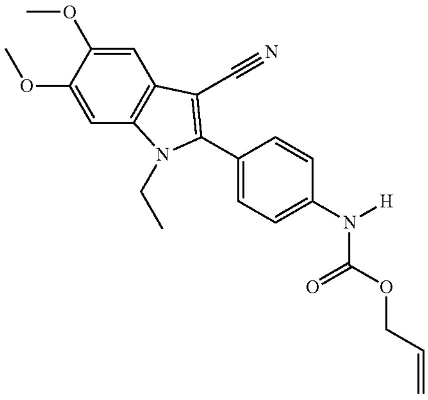
1112
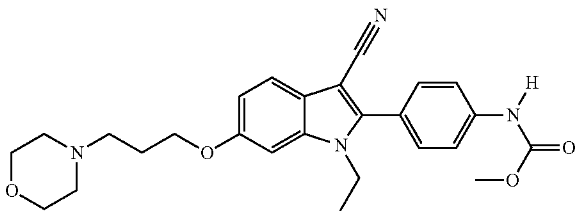
1113
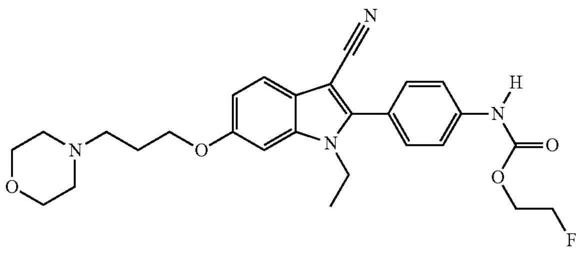
1114
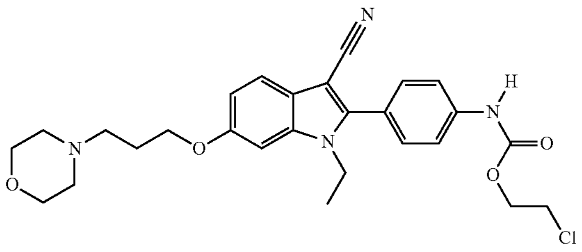
1115
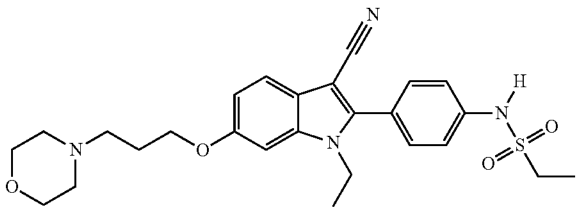
1116
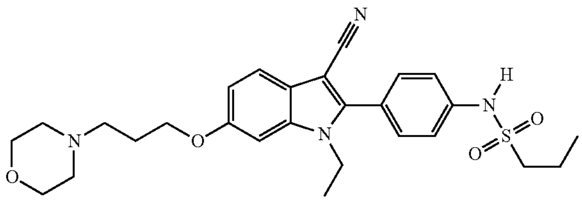
1117
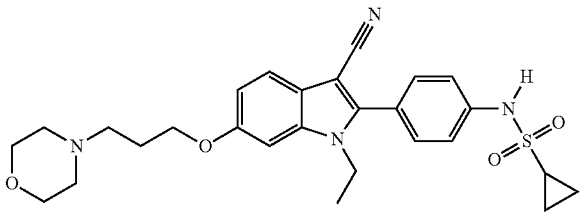

-continued
1118
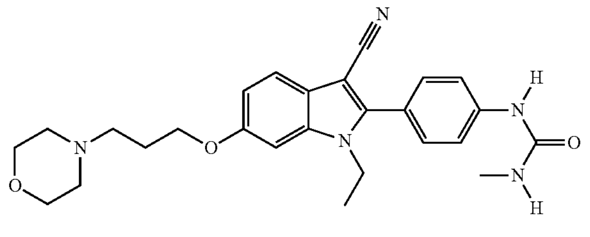
1119
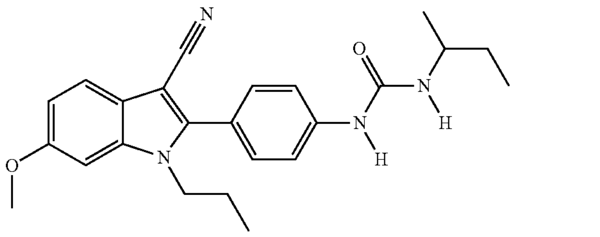
1120
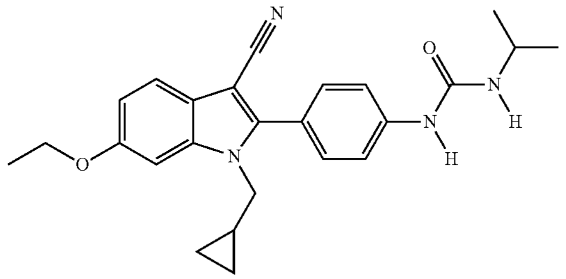
1121
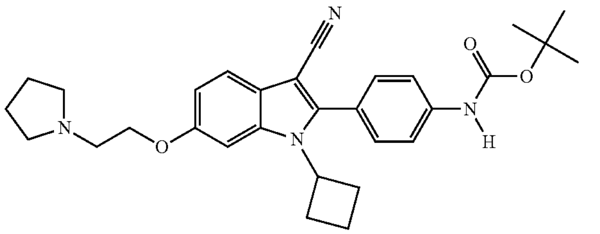
1122
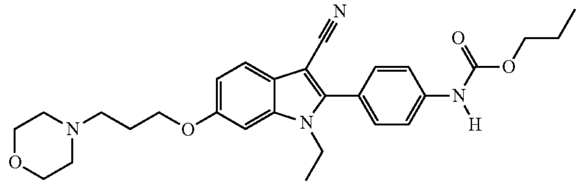
1123
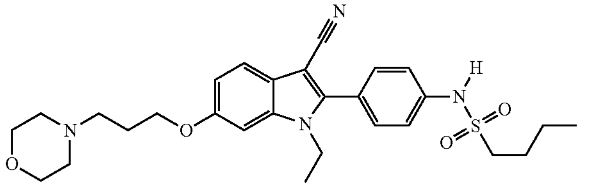
1124
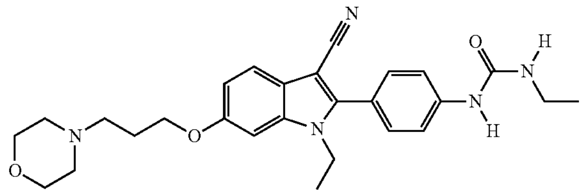
1125
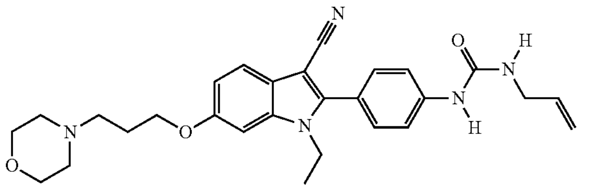
1126
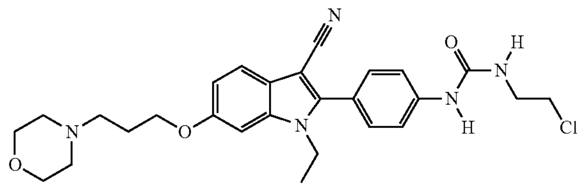
1127
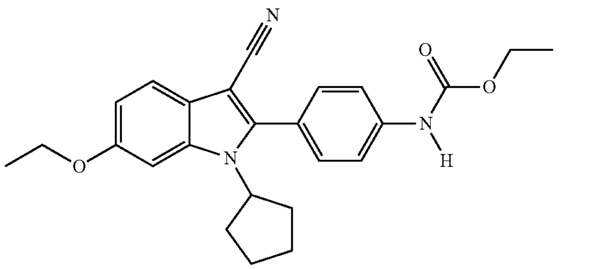
1128
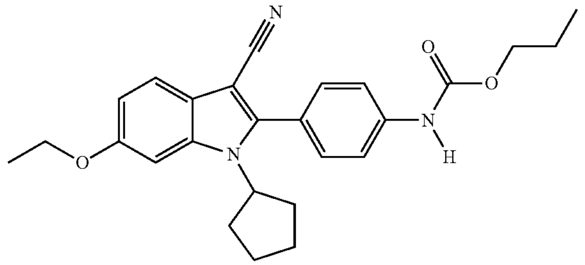
1129
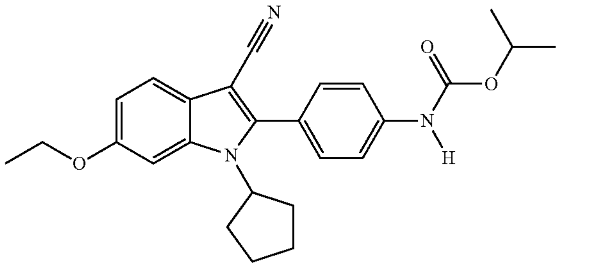

-continued
1130
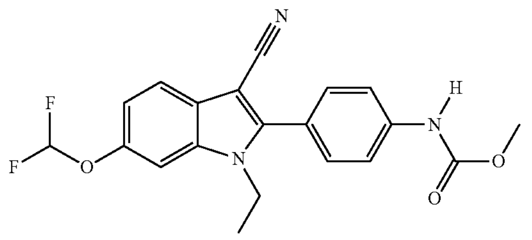
1131
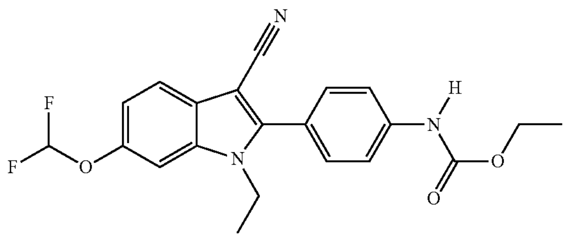
1132
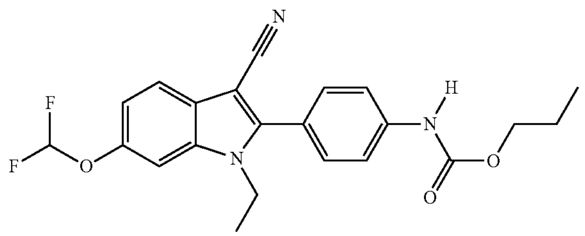
1133
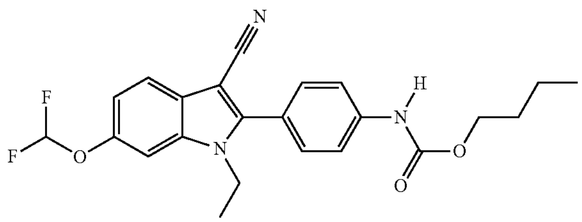
1134
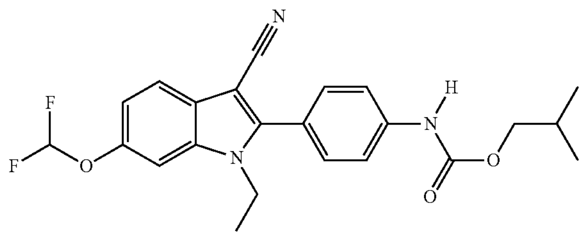
1135
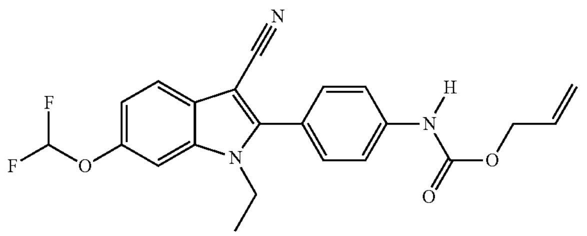
1136
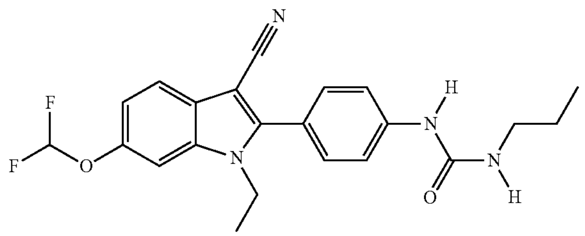
1137
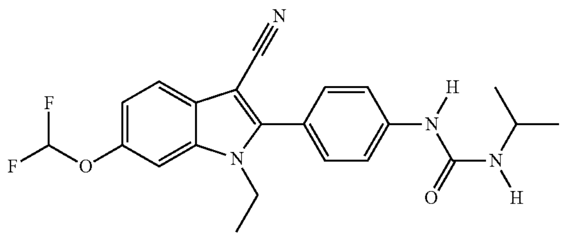
1138
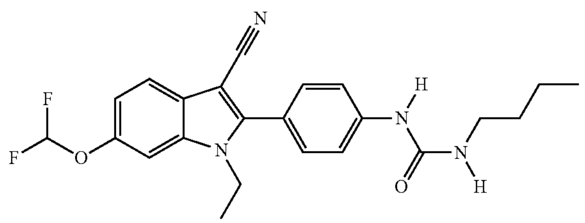
1139
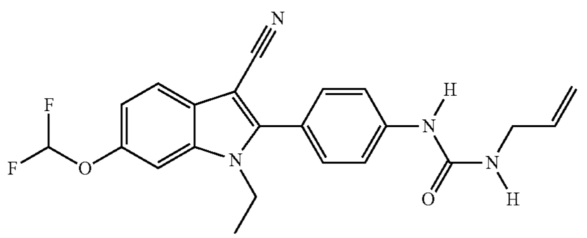
1140
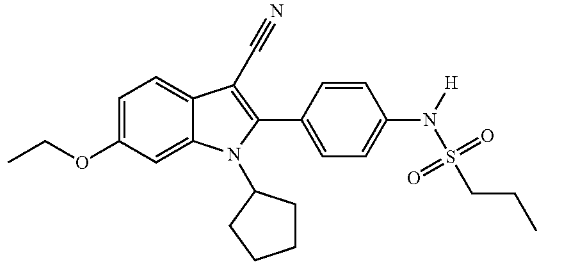
1141
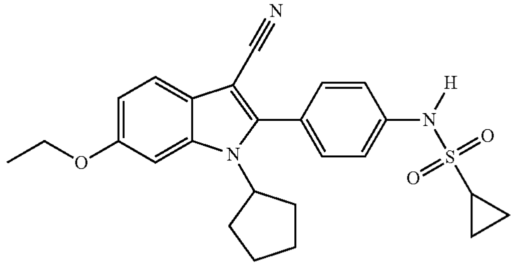

-continued
1142
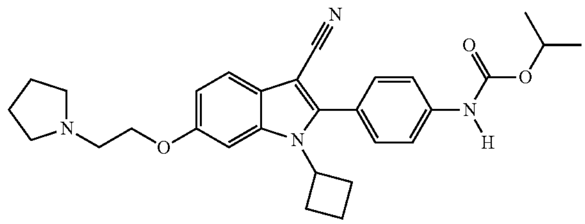
1143
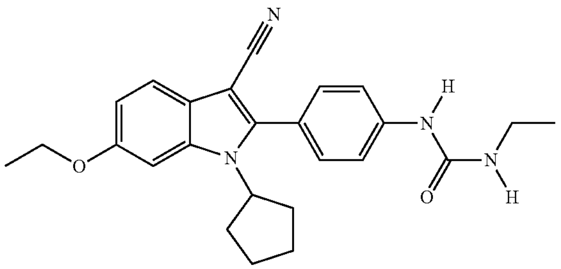
1144
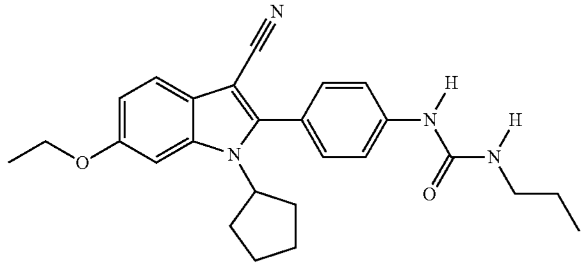
1146
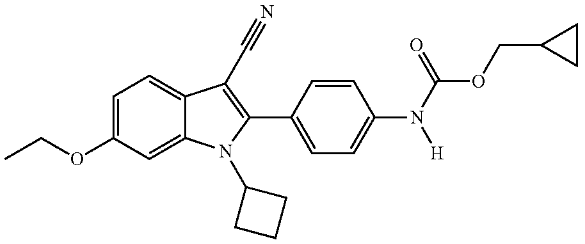
1147
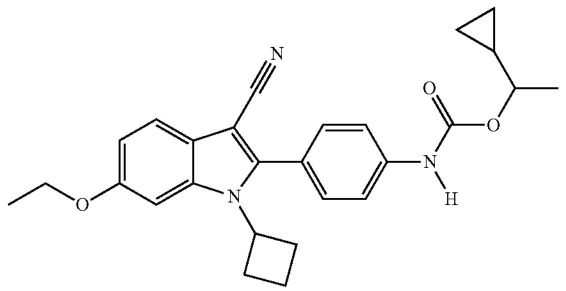
1148
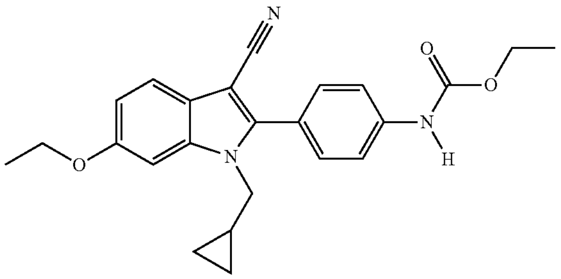
1149
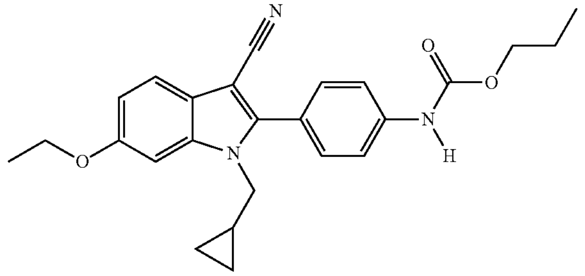
1150
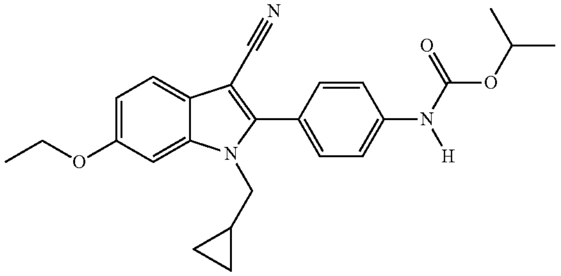
1151
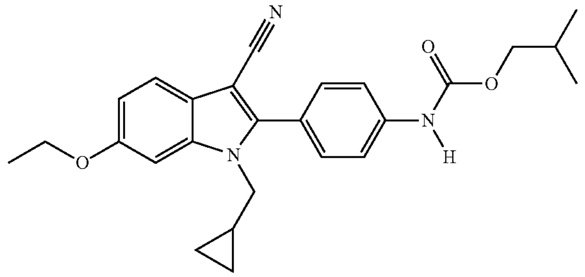
1152
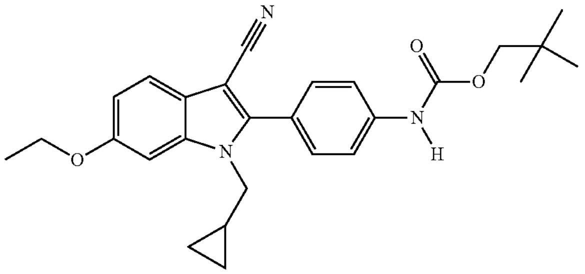

-continued
1153
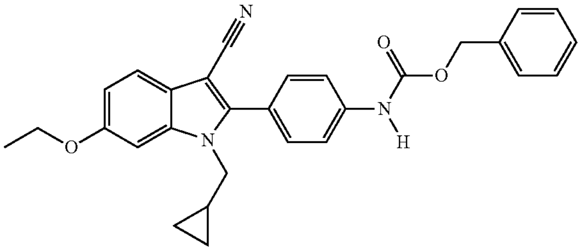
1154
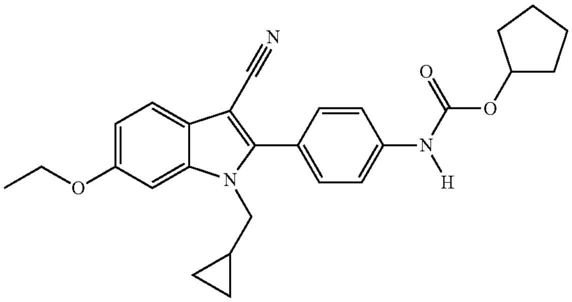
1155
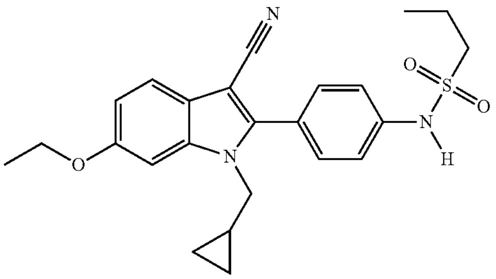
1156
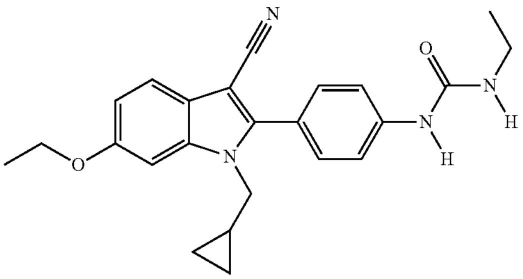
1157
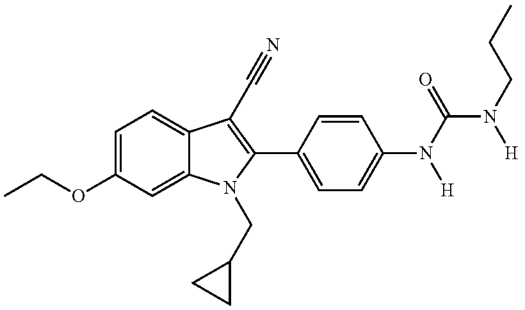
1158
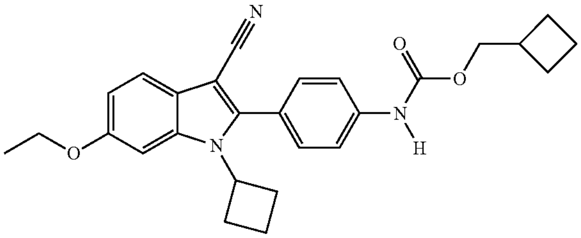
1159
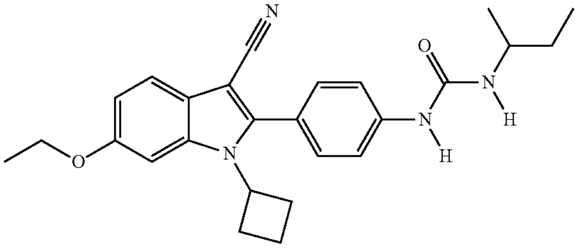
1160
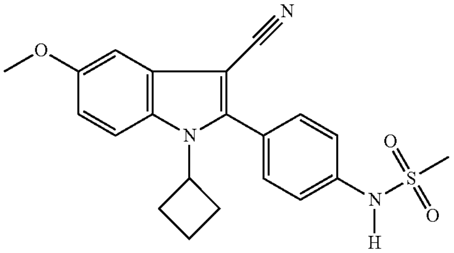
1161
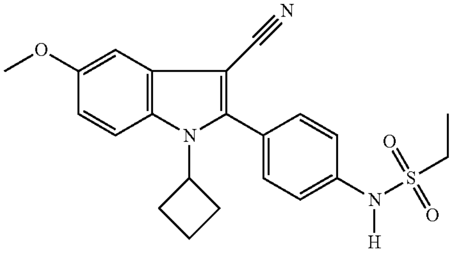
1162
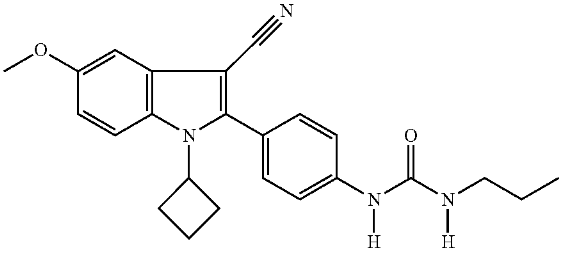

-continued
1163
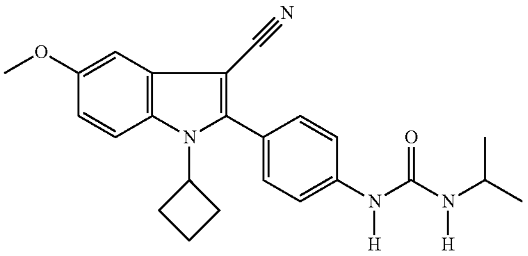
1164
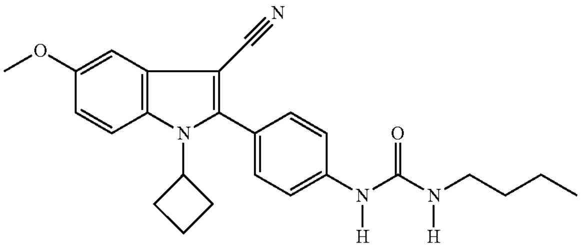
1165
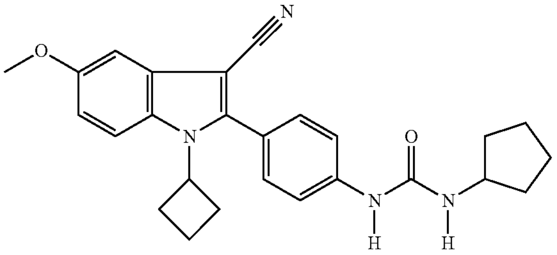
1166
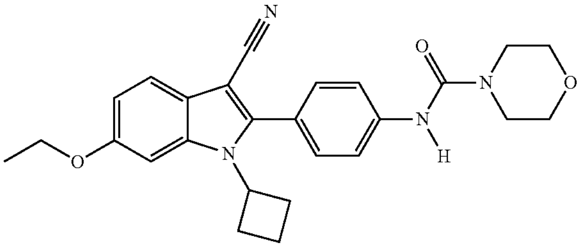
1167
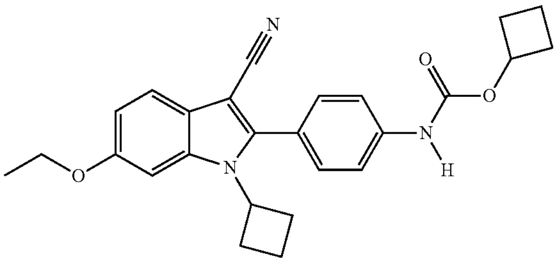
1168
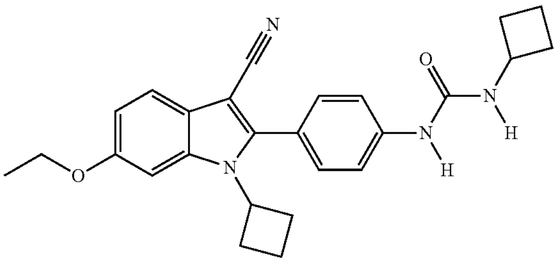
1169
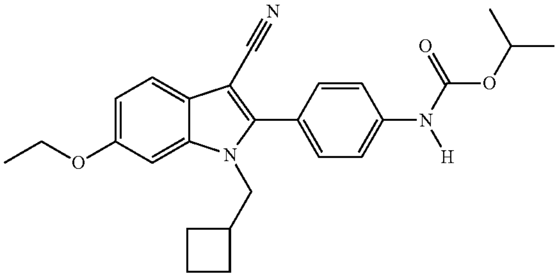
1170
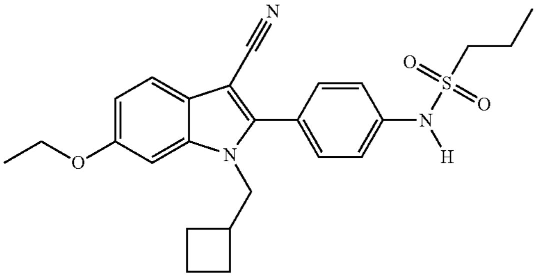
1171
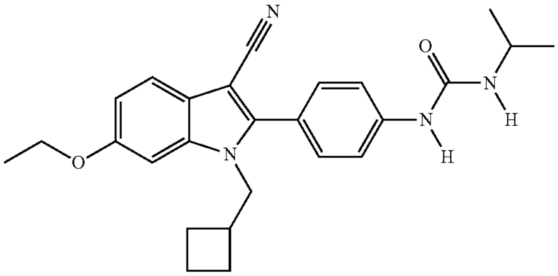
1172
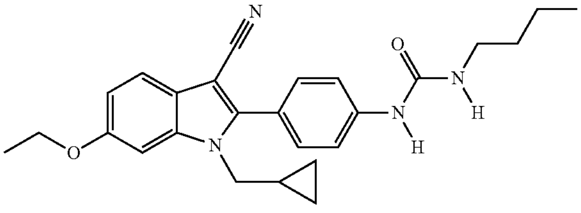

-continued
1173
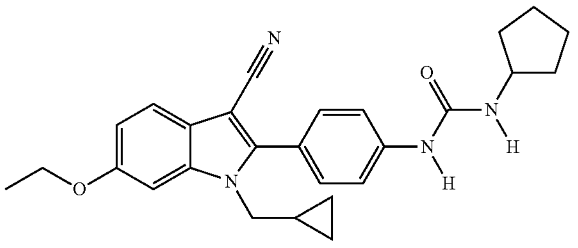
1174
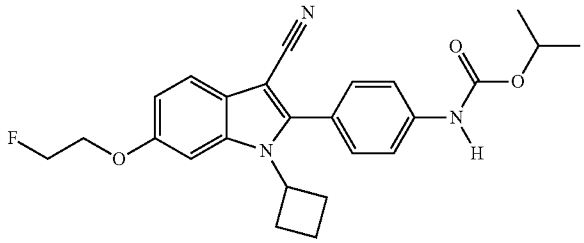
1175
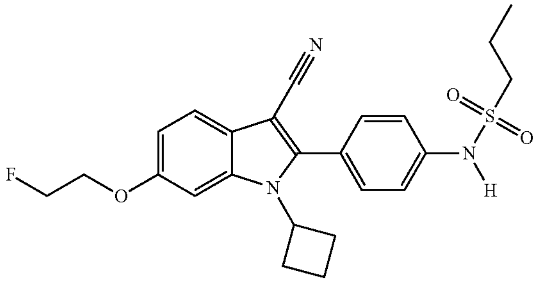
1176
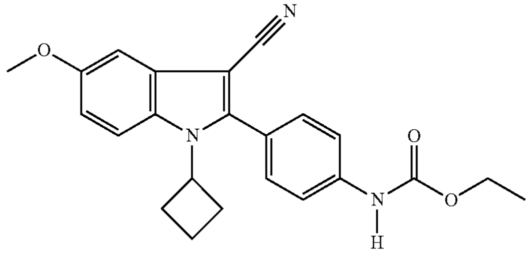
1177
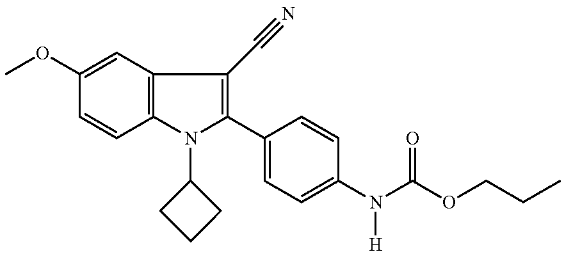
1178
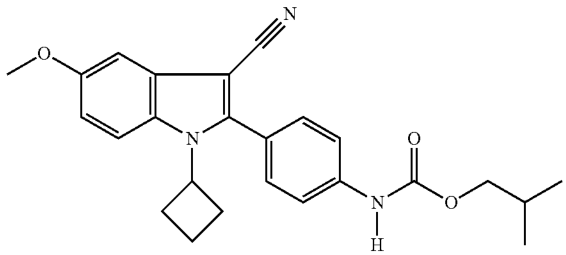
1179
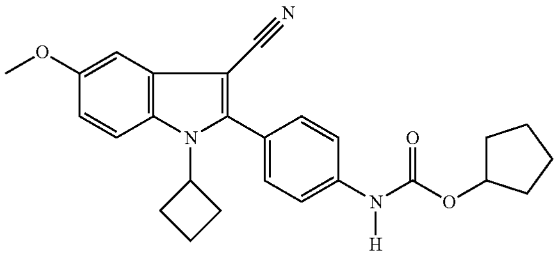
1180
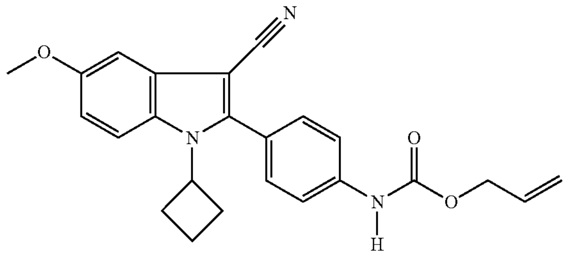
1181
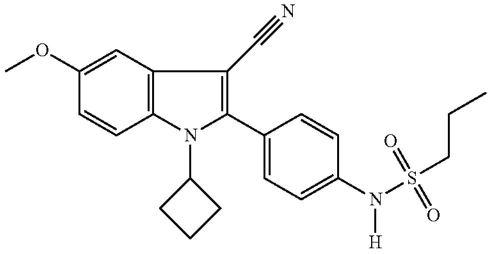
1182
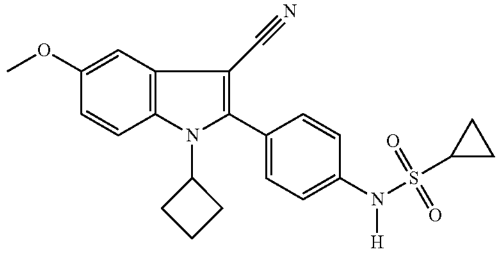
1183
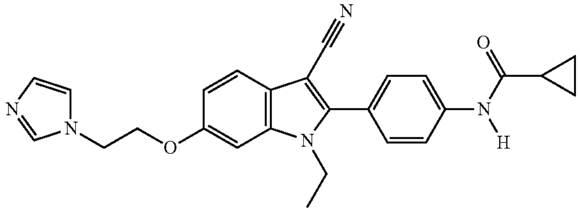
1184
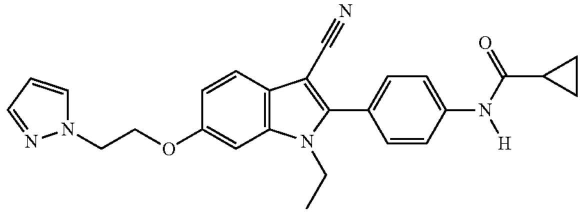

-continued
1185
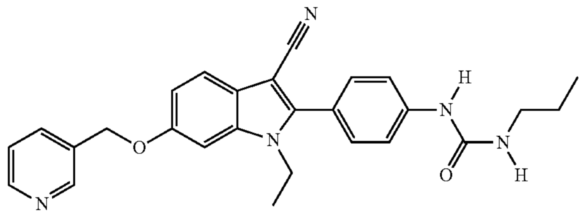
1186
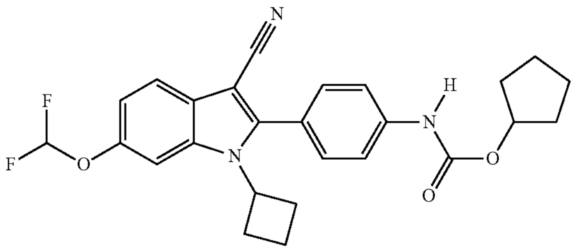
1187
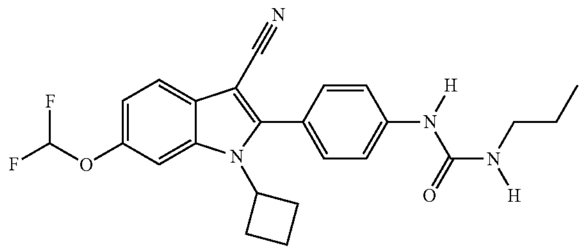
1188
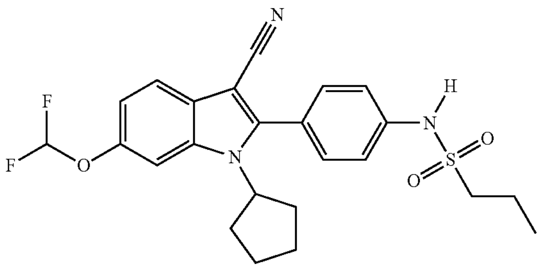
1189
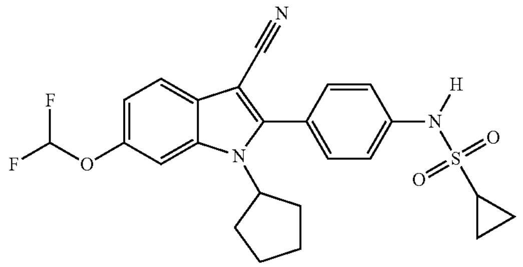
1190
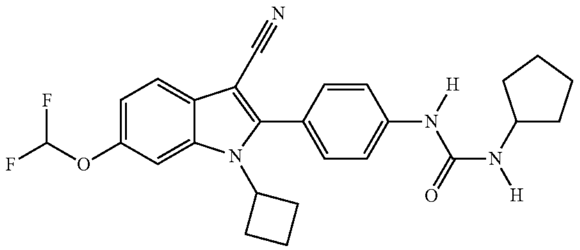
1191
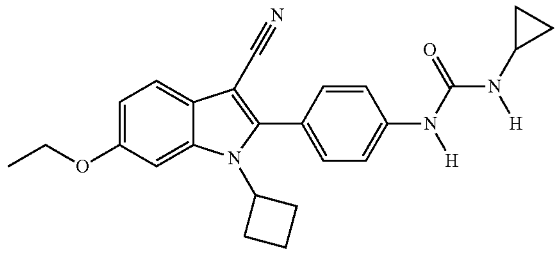
1192
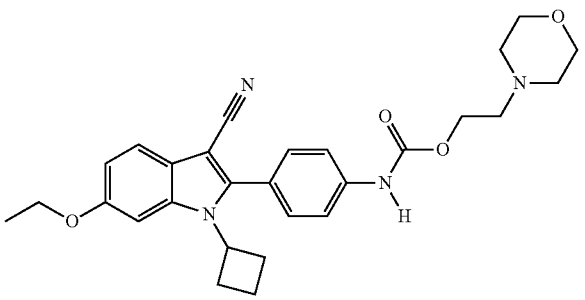
1193
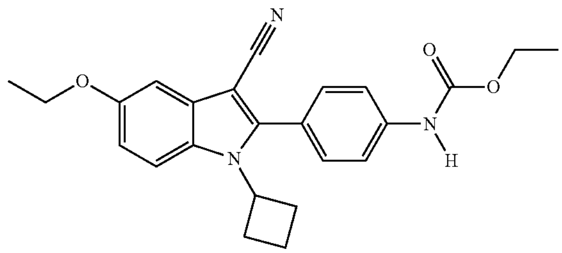
1194
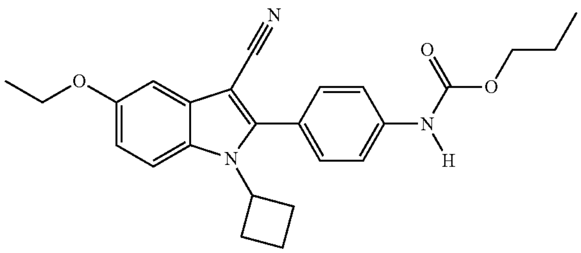

-continued
1195
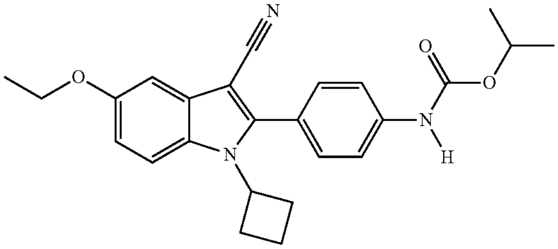
1196
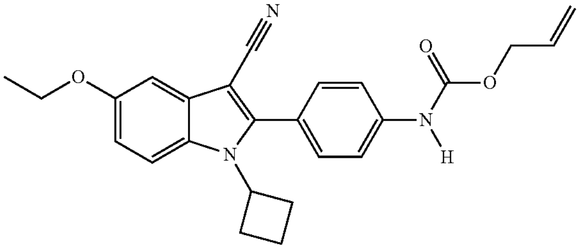
1197
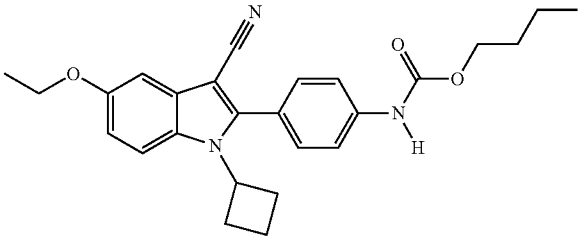
1198
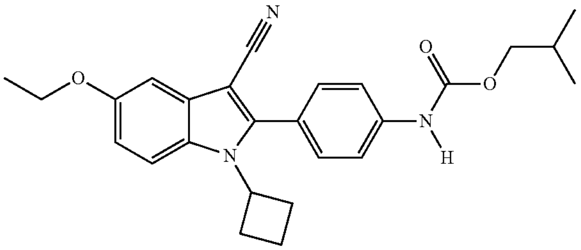
1199
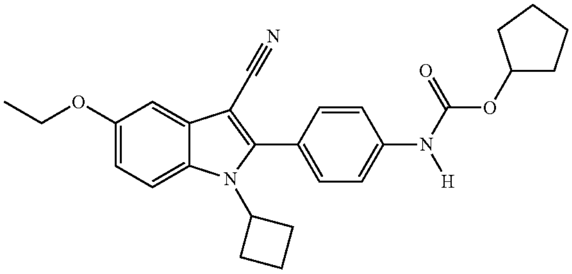
1200
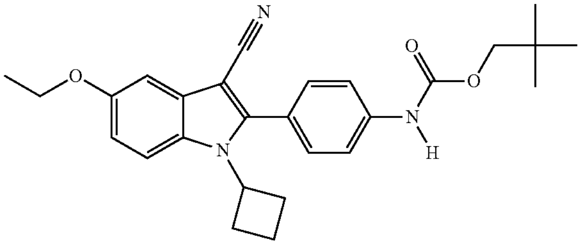
1201
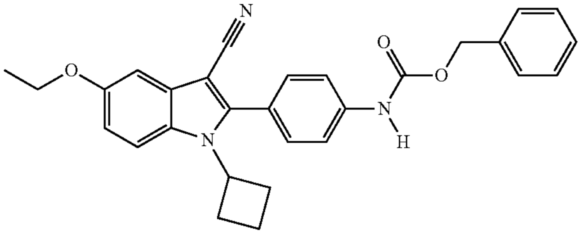
1202
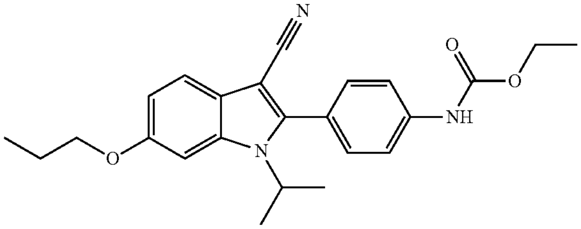
1203
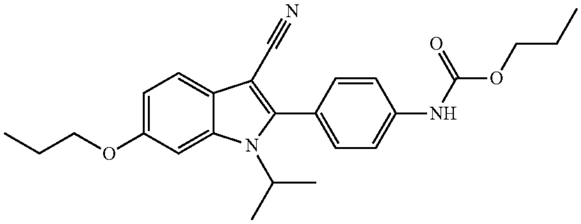
1204
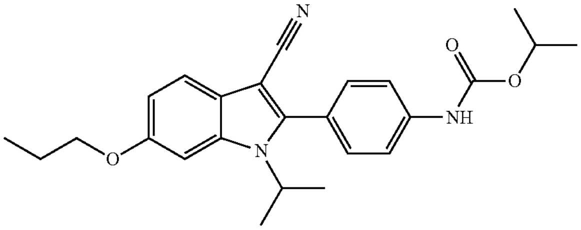

-continued
1205
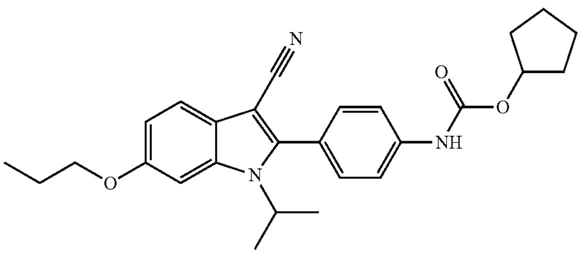
1206
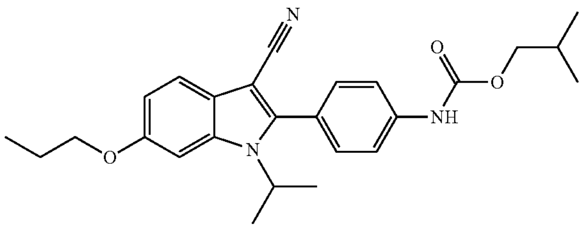
1207
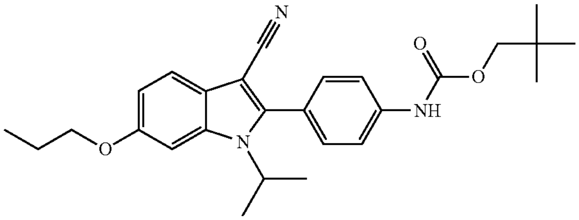
1208
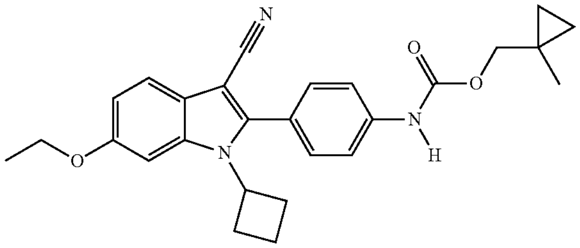
1209
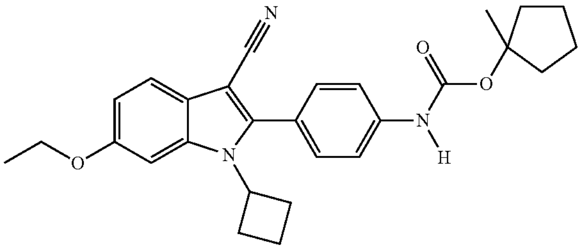
1210
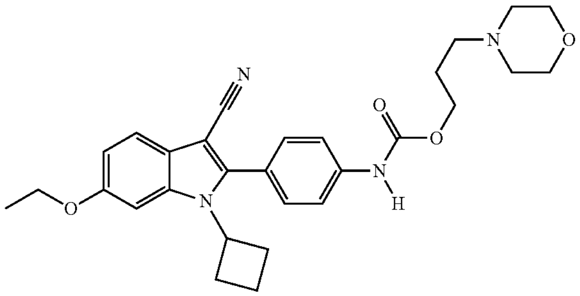
1211
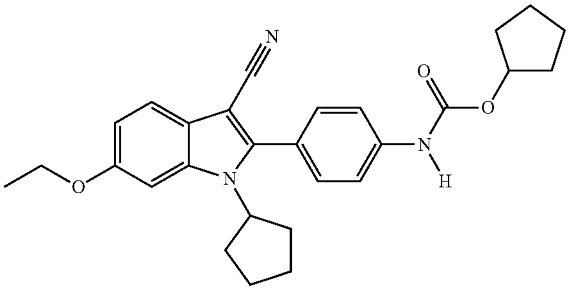
1212
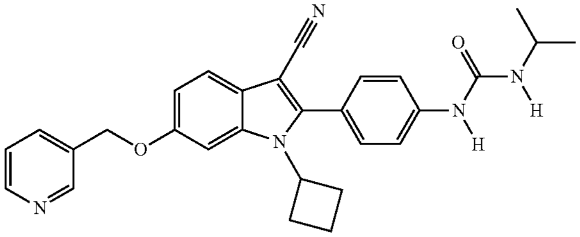
1213
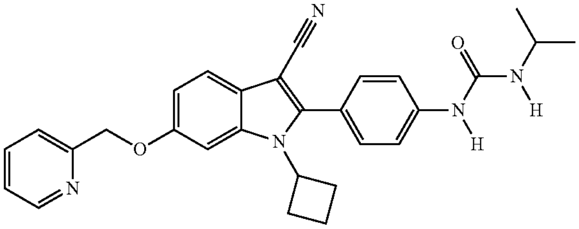
1214
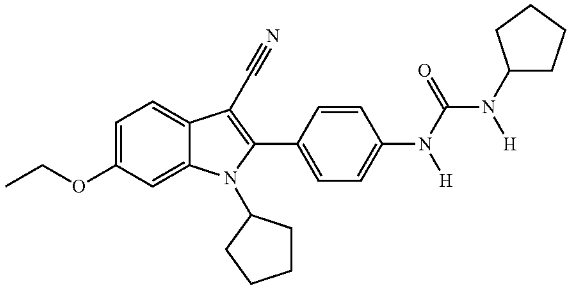

-continued
1215
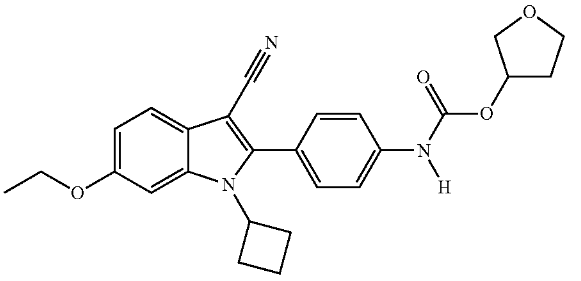
1216
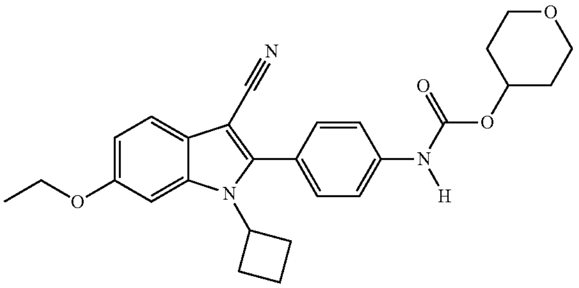
1217
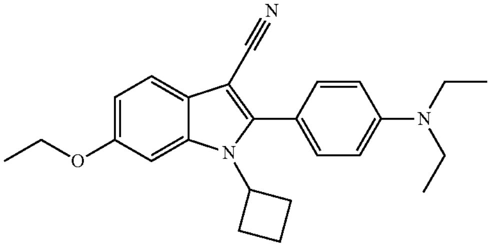
1218
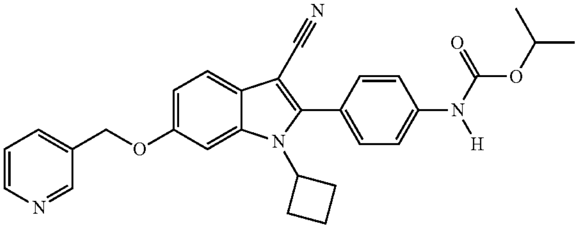
1219
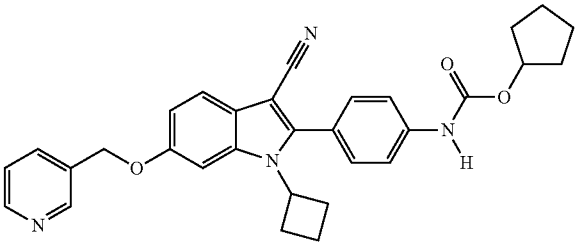
1220
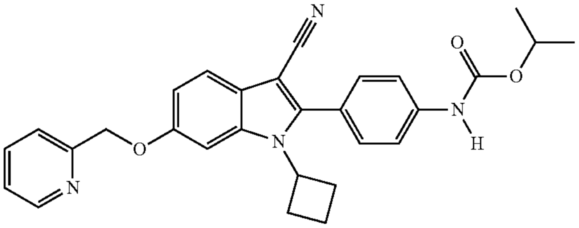
1221
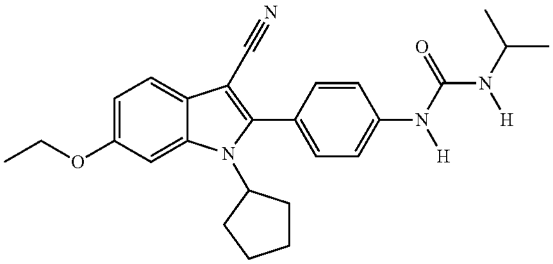
1222
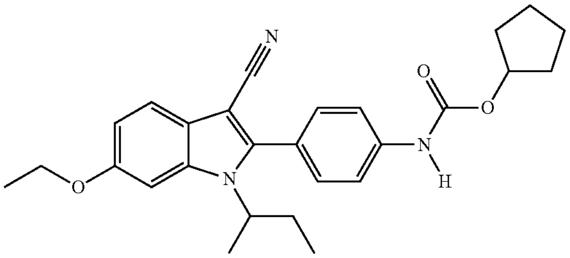
1223
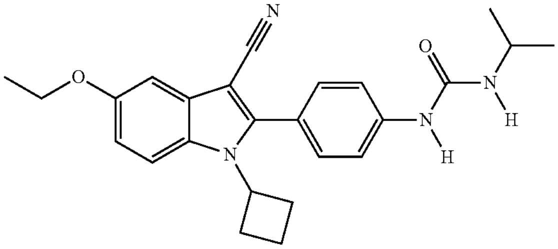
1224
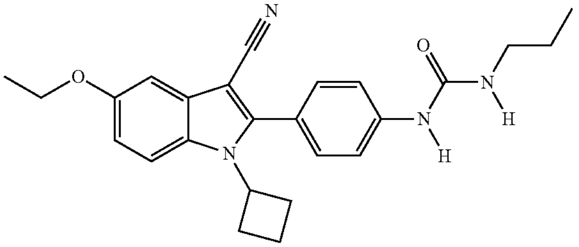

-continued
1225
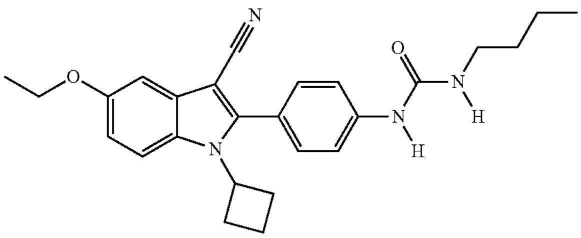
1226
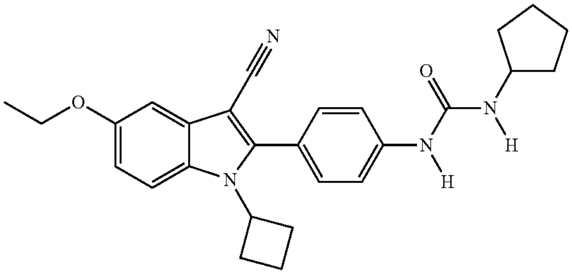
1227
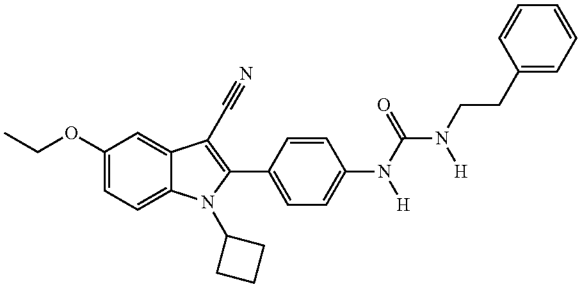
1228
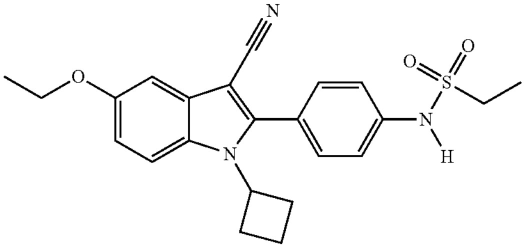
1229
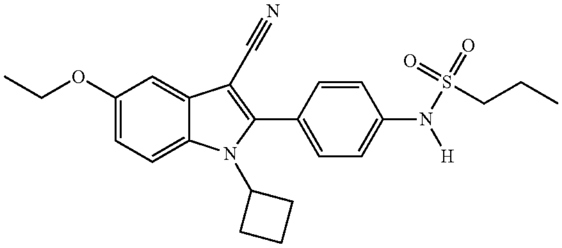
1230
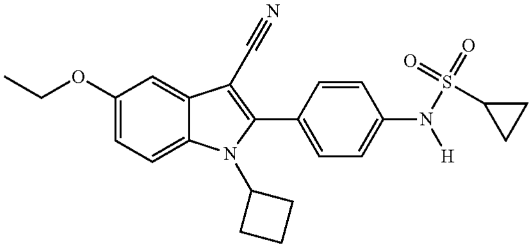
1231
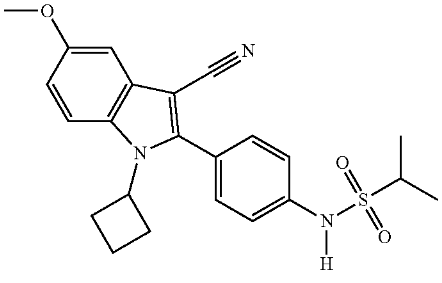
1232
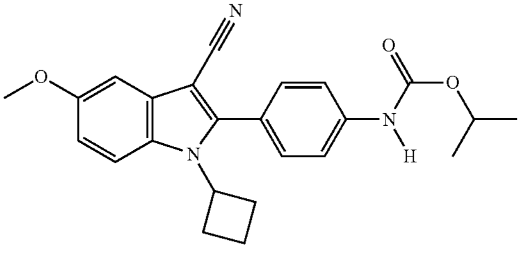
1233
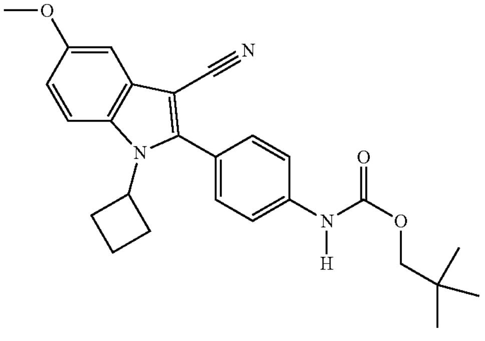
1234
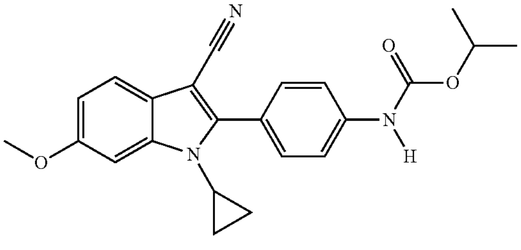

-continued
1235
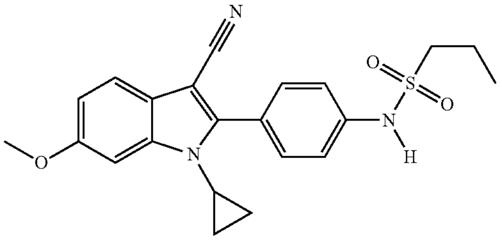
1236
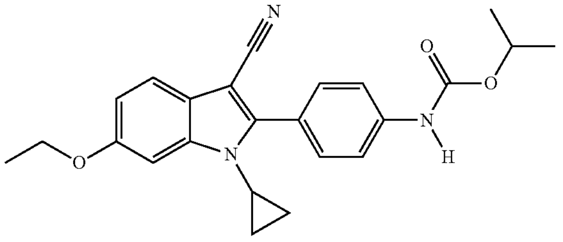
1237
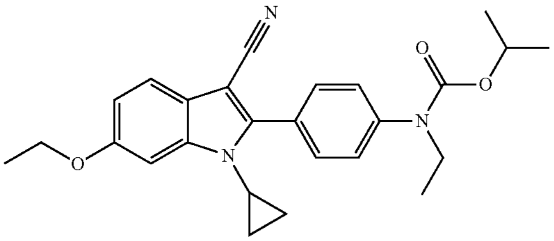
1238
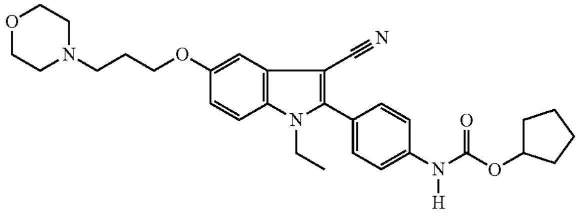
1239
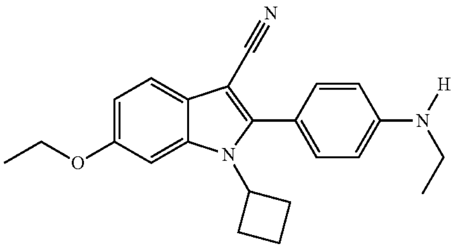
1240
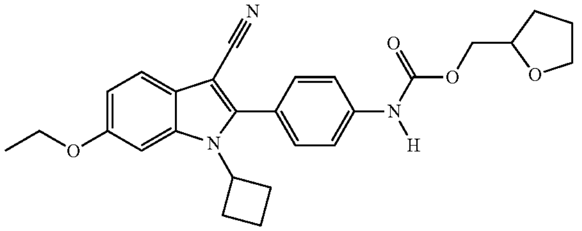
1241
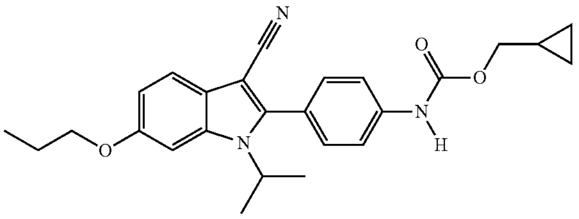
1242
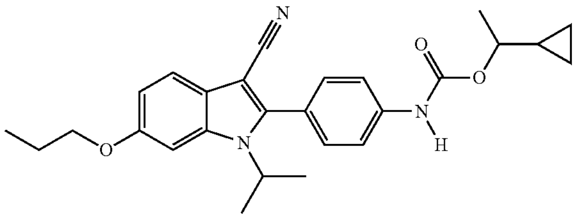
1243
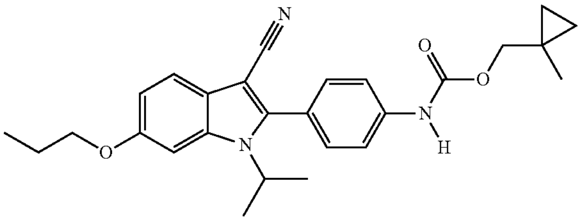
1244
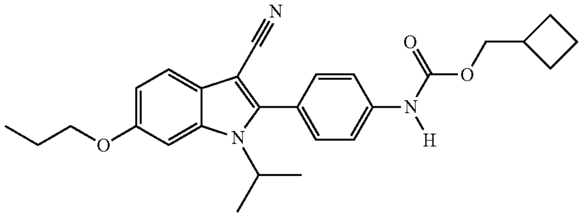
1245
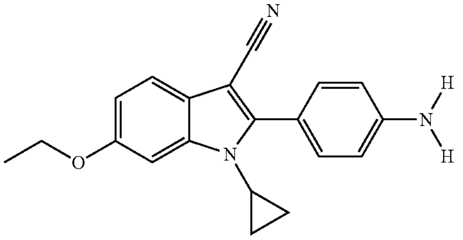
1246
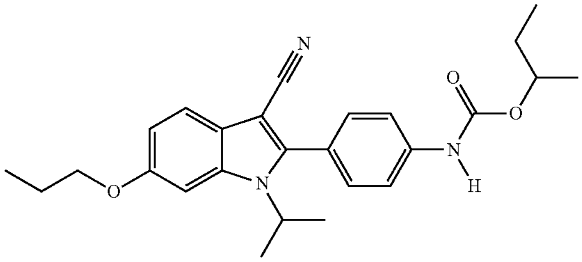

-continued
1247
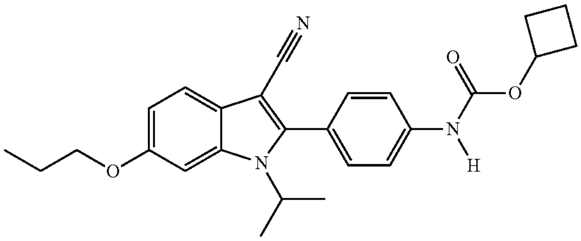
1248
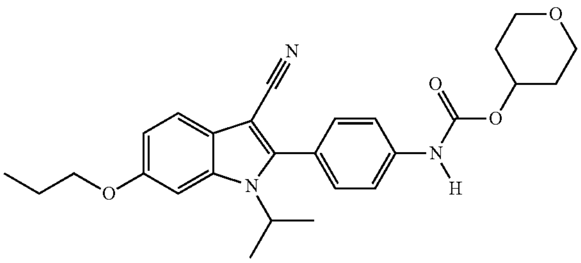
1249
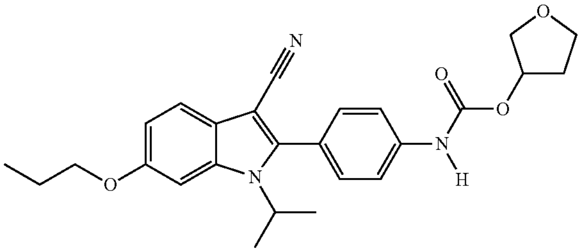
1250
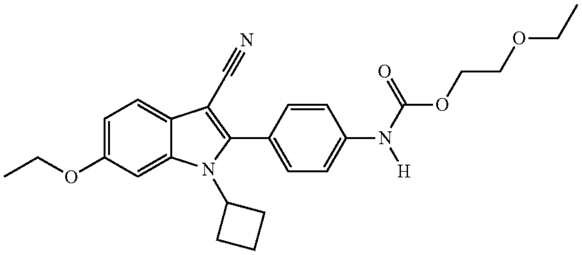
1251
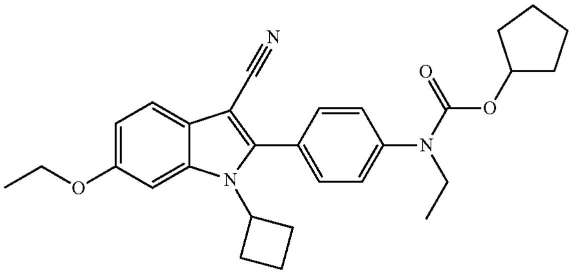
1252
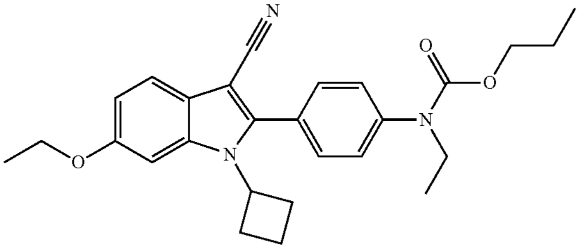
1253
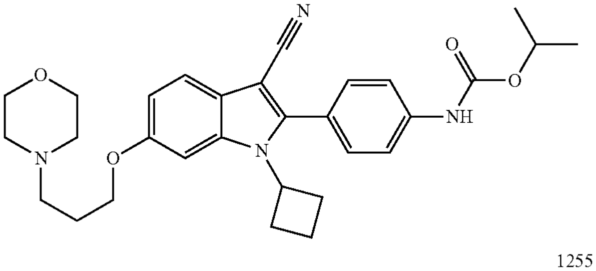
1254
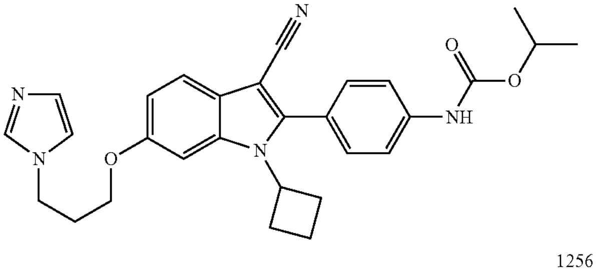
1255
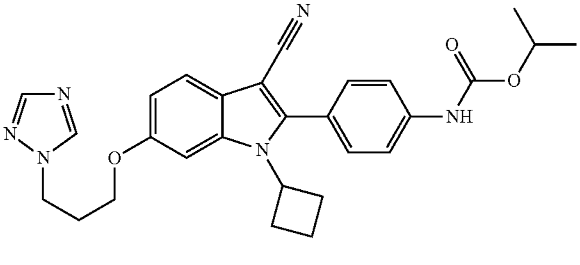
1256
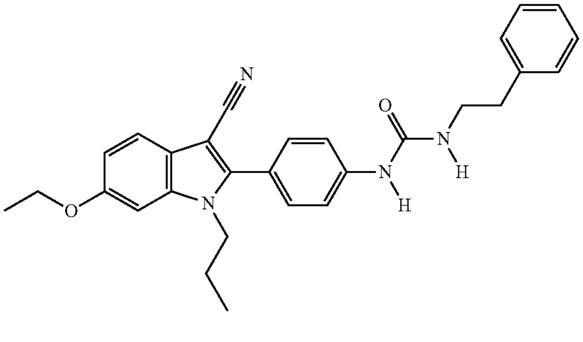

-continued
1257
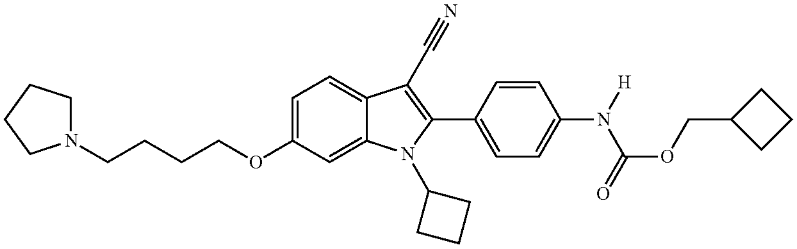
1258
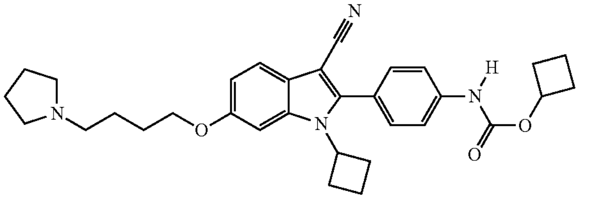
1259
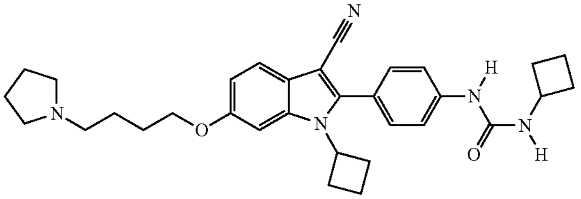
1260
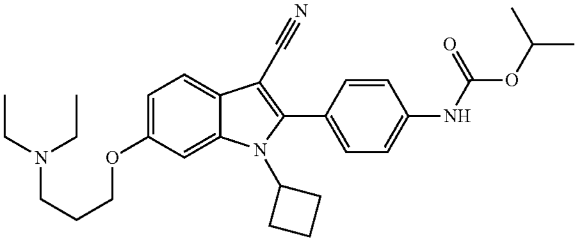
1261
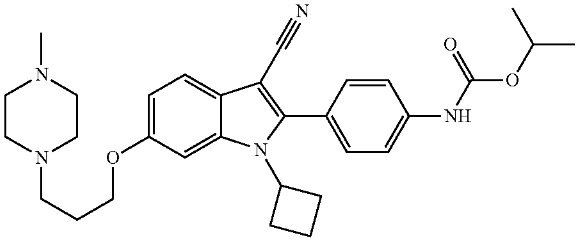
1262
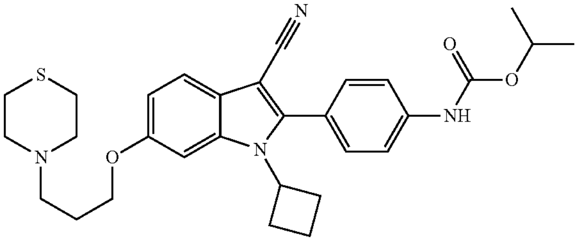
1263
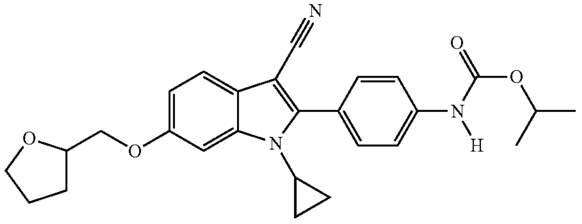
1264
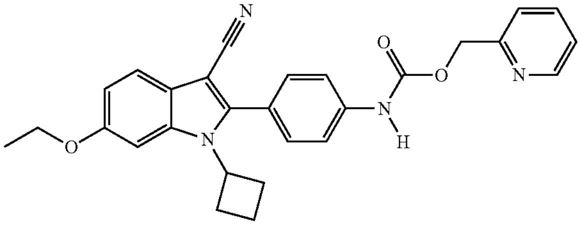
1265
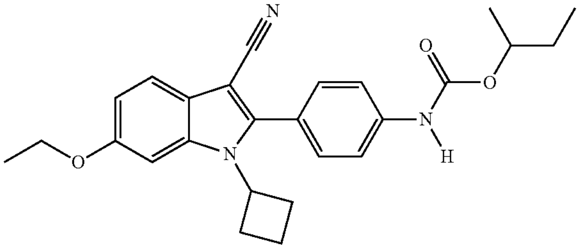
1266
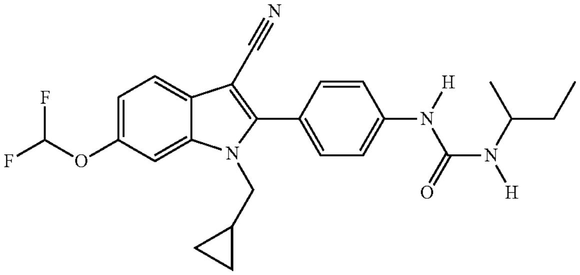
1267
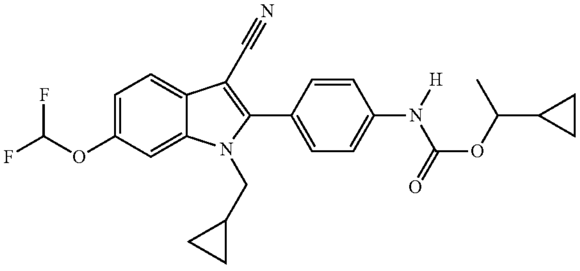

-continued
1268
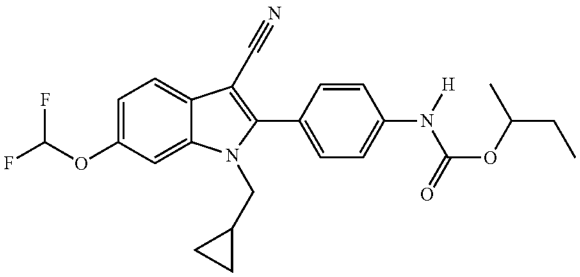
1269
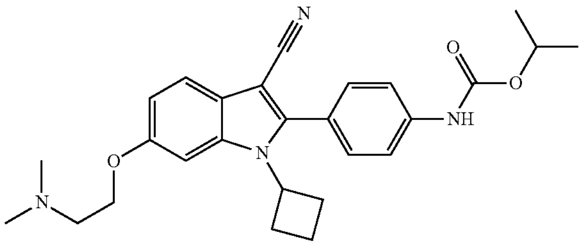
1270
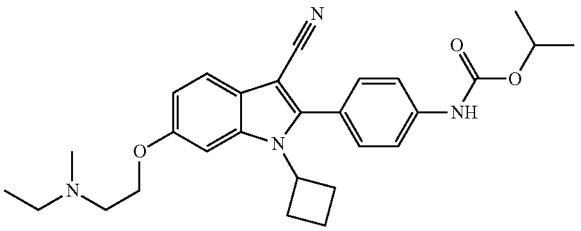
1271
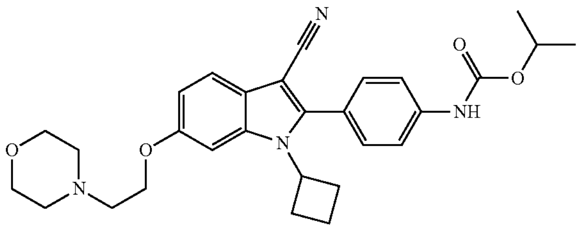
1272
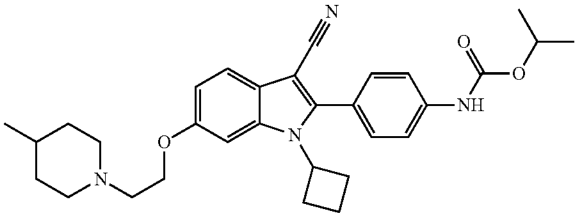
1273
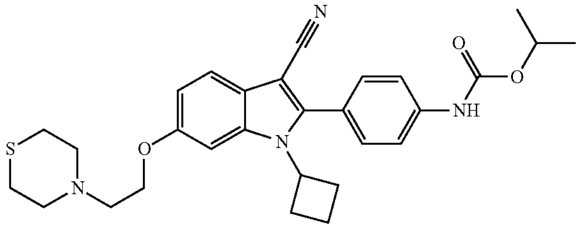
1274
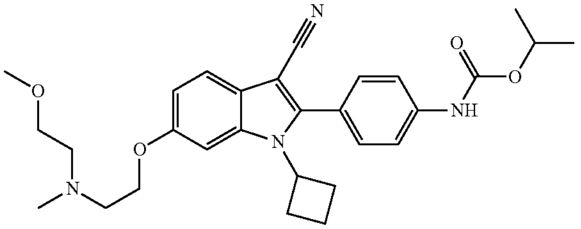
1275
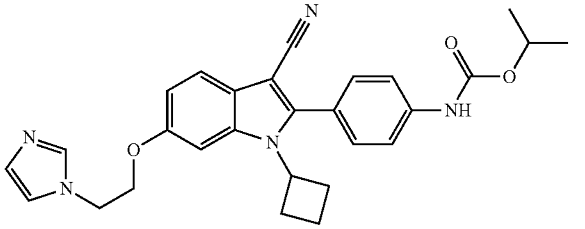
1276
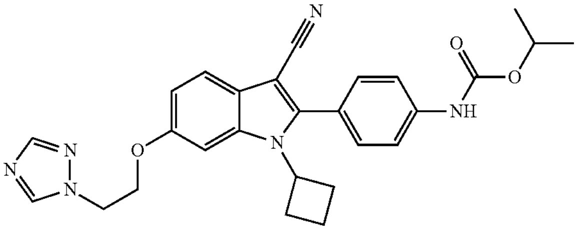
1277
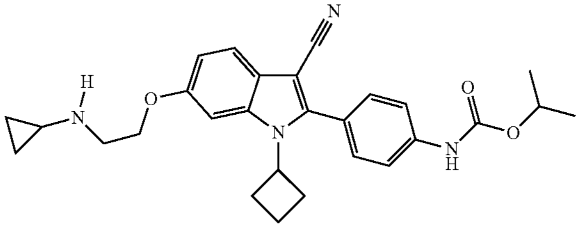
1278
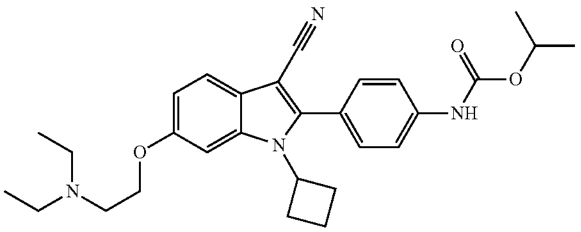
1279
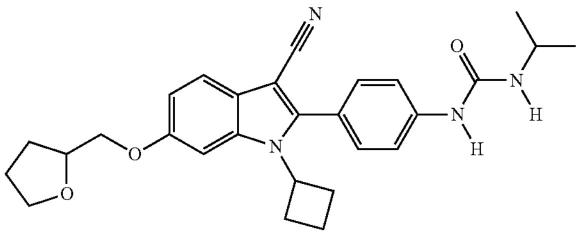

-continued
1280
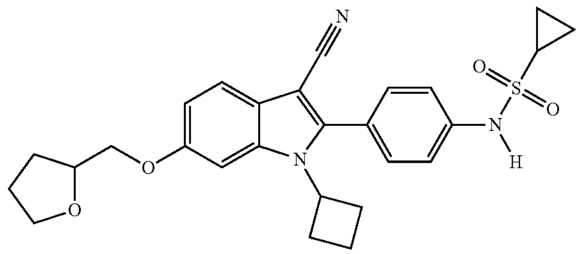
1281
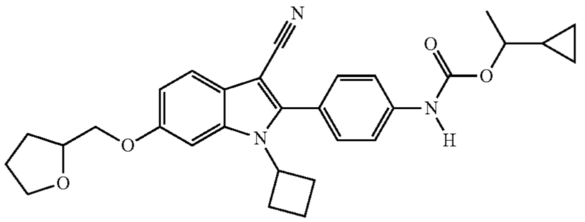
1282
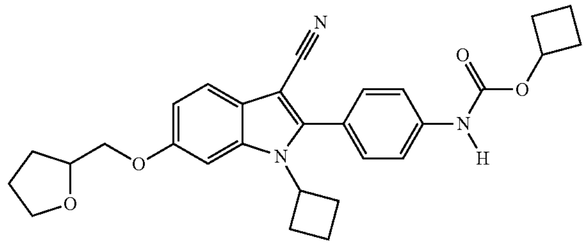
1283
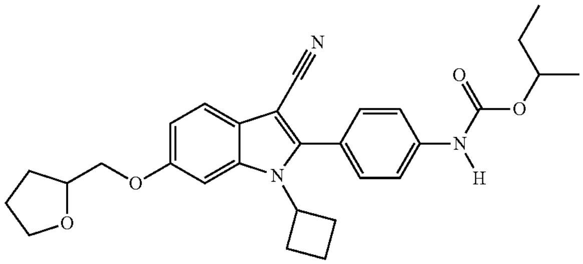
1284
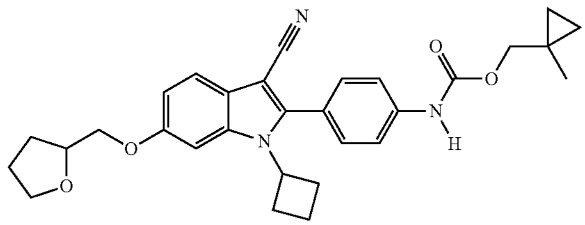
1285
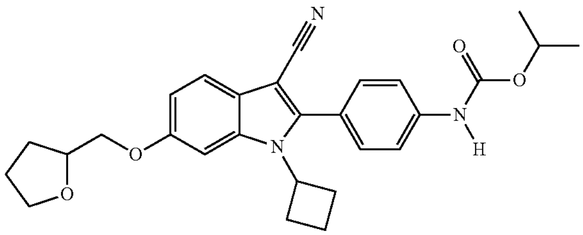
1286
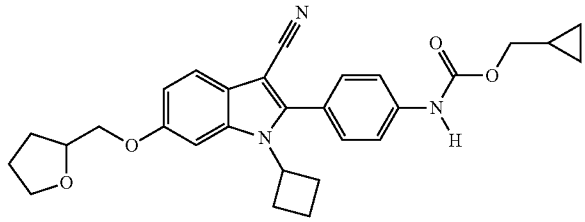
1287
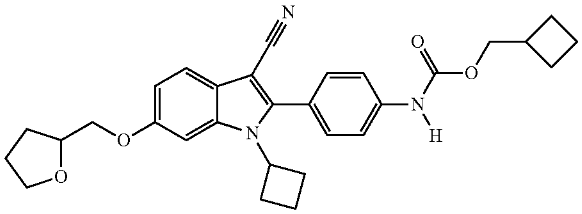
1288
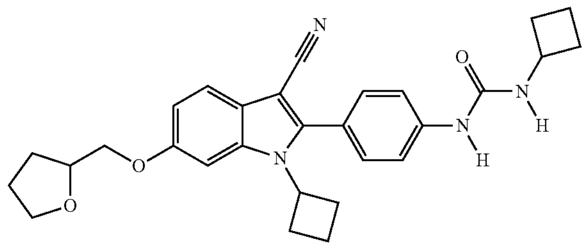
1289
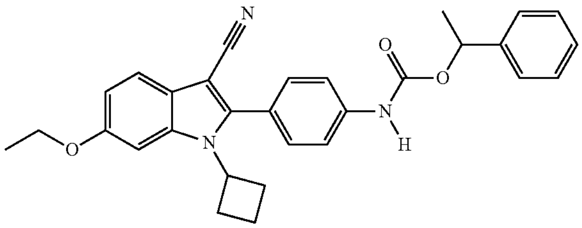
1290
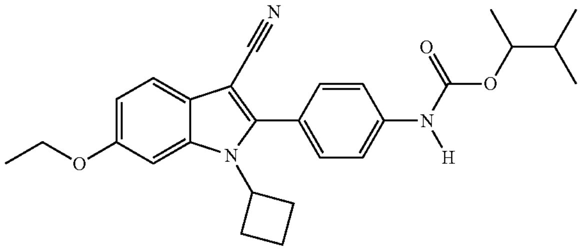
1291
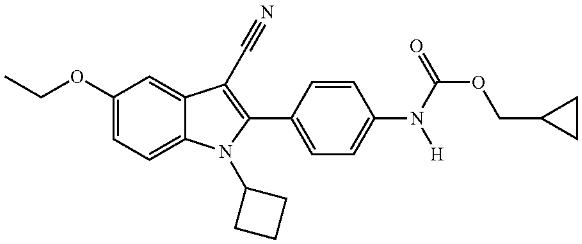

-continued
1292
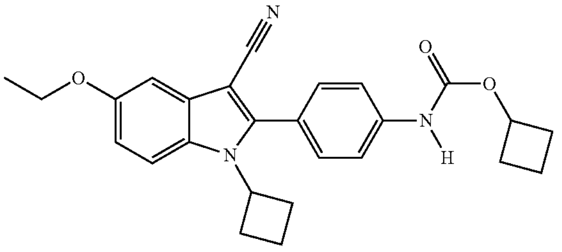
1293
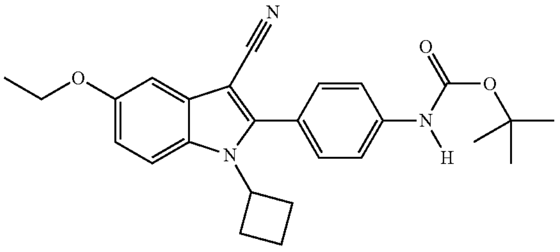
1294
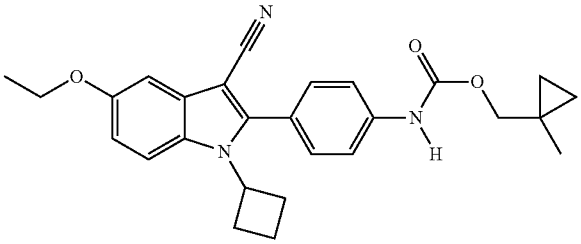
1295
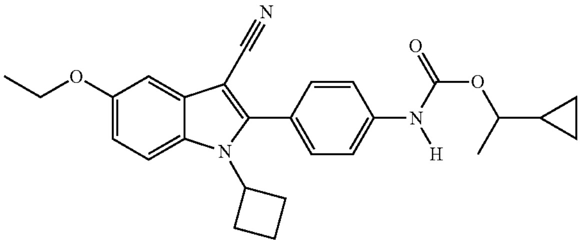
1296
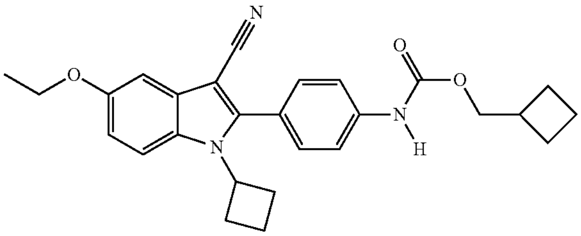
1297
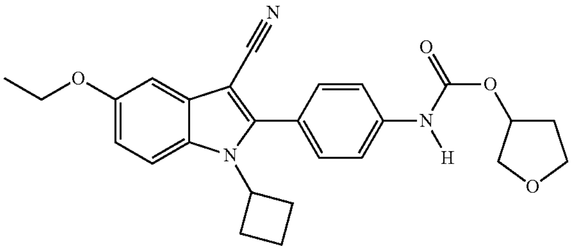
1298
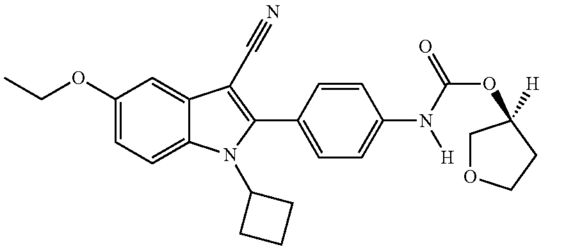
1299
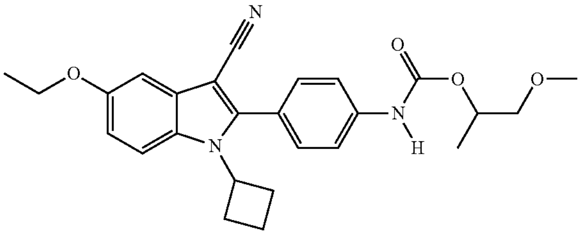
1300
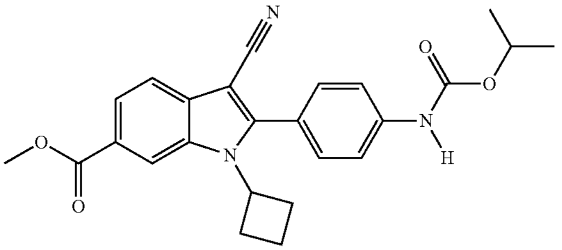
1301
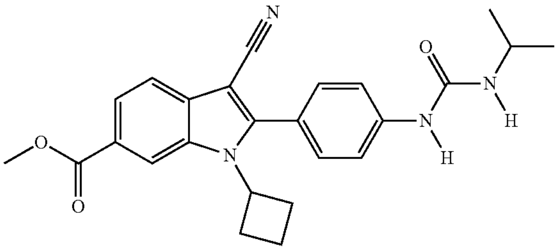

-continued
1302
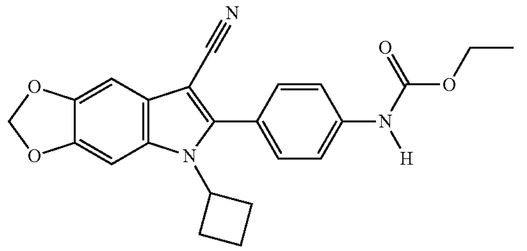
1303
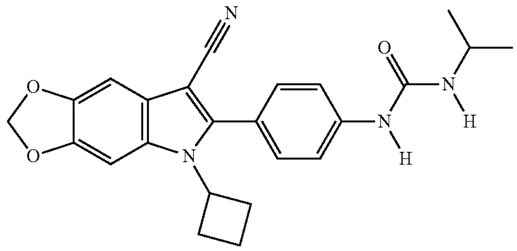
1304
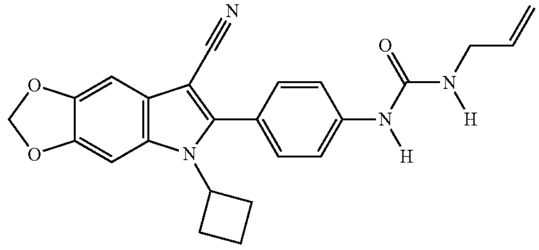
1305
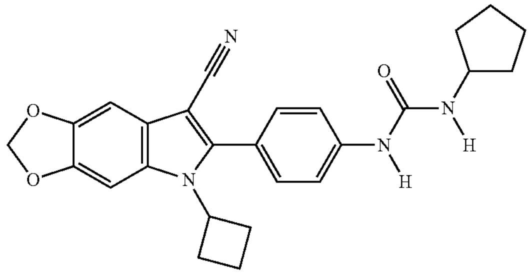
1306
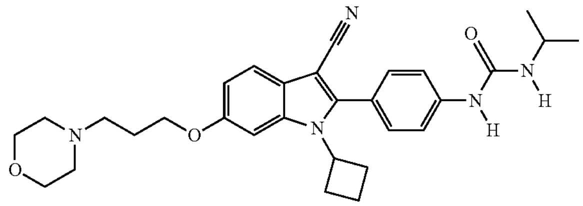
1307
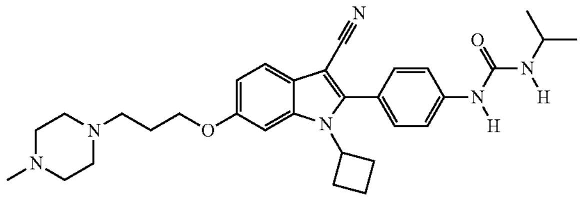
1308
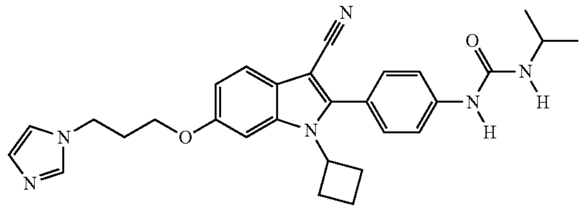
1309
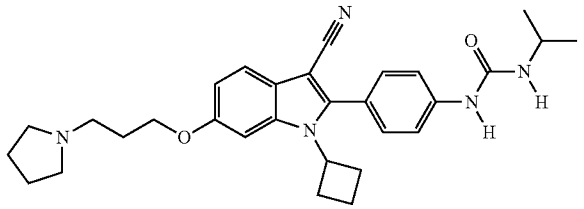
1310
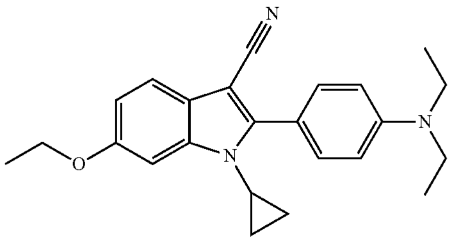
1311
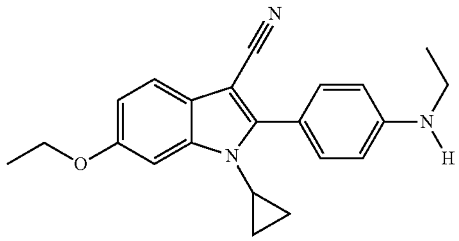
1312
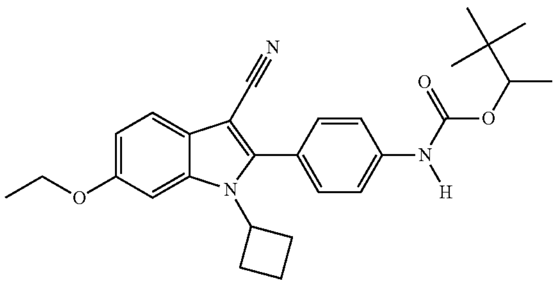
1313
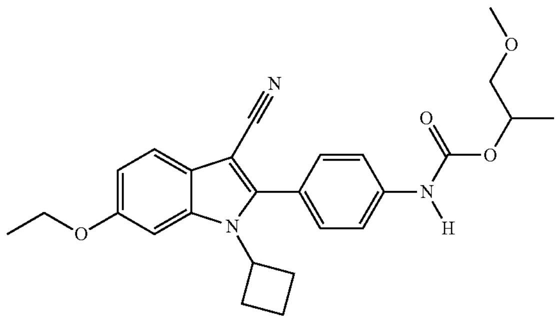

-continued
1314
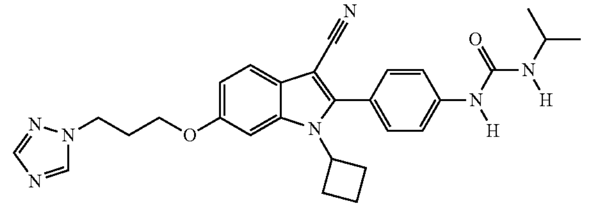
1315
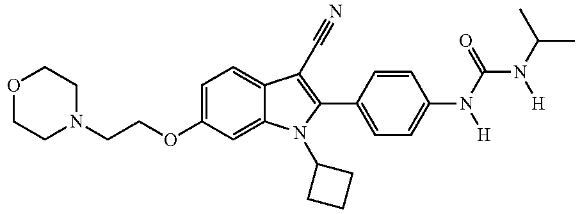
1316
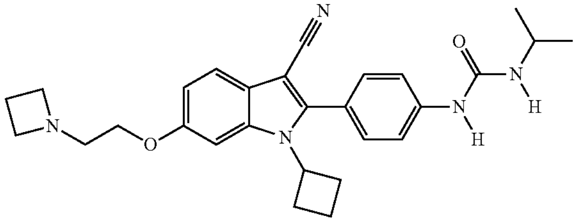
1317
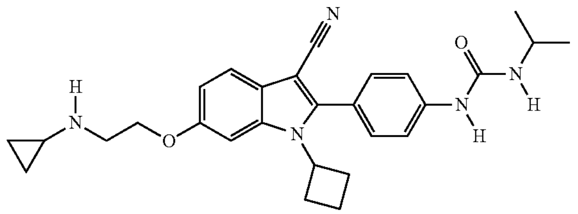
1318
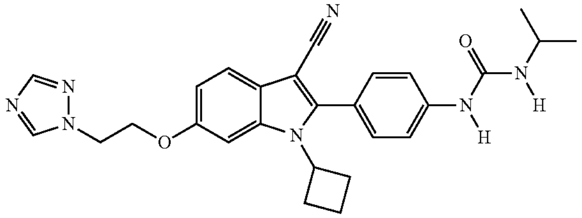
1319
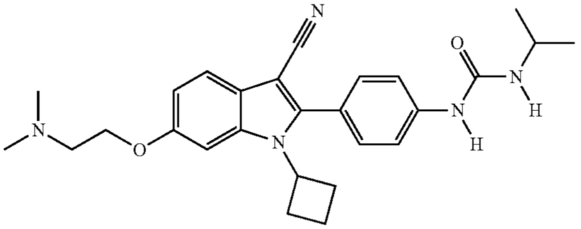
1320
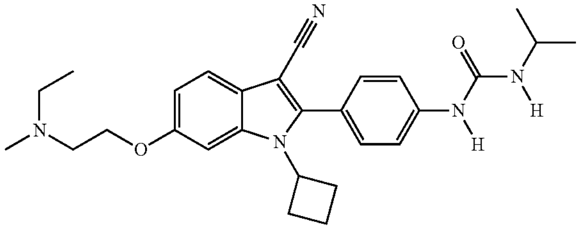
1321
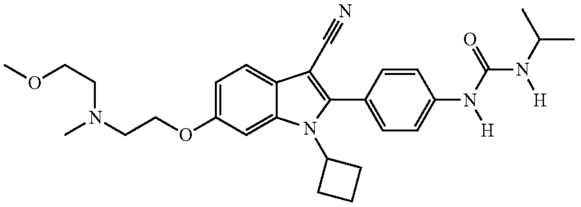
1322
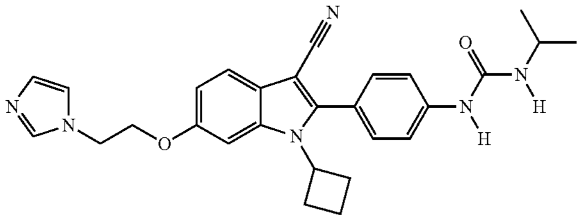
1323
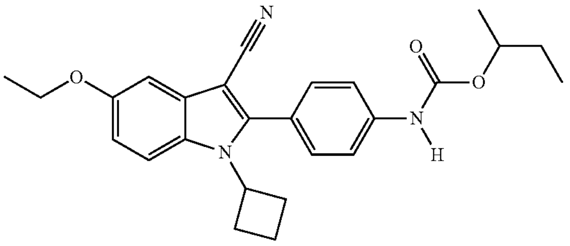
1324
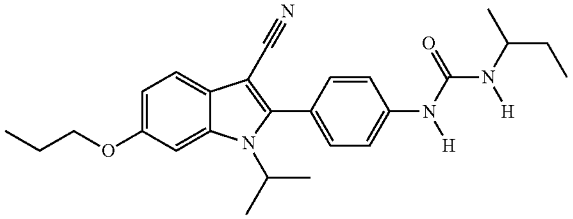
1325
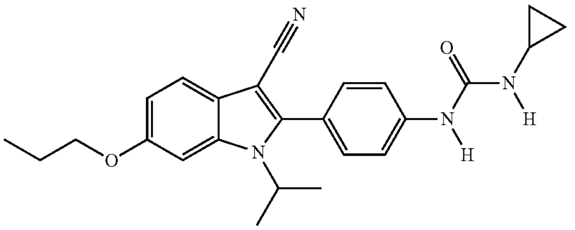

-continued

1326

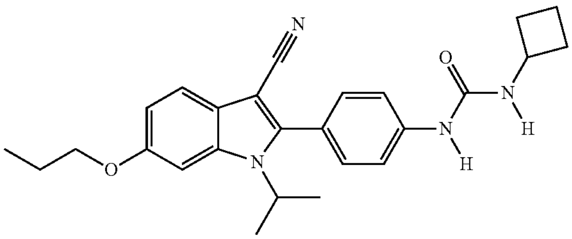

1327

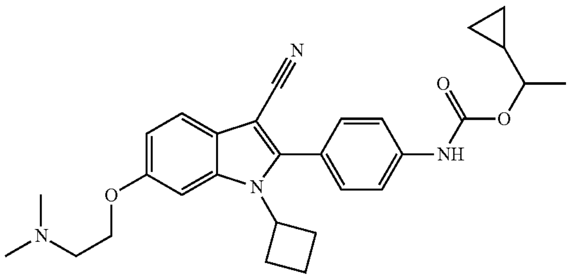

1328

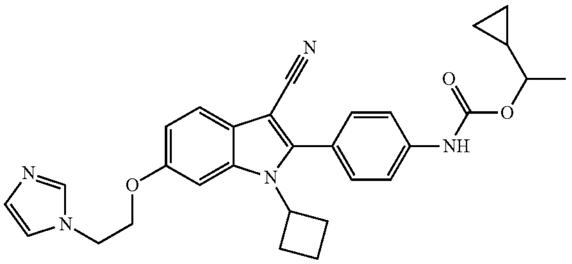

1329

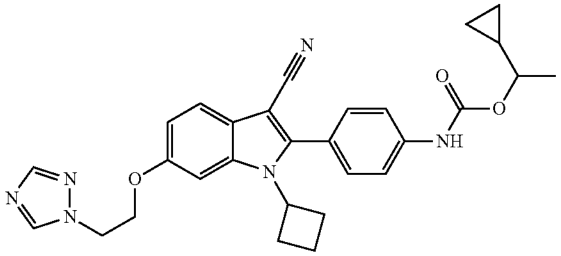

;

or a pharmaceutically acceptable salt thereof.

30. A pharmaceutical composition comprising:

(i) a compound of formula I

I

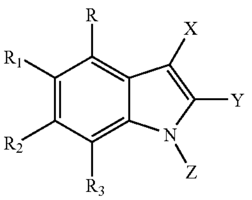

wherein:

X is:

a cyano group;

Y is:

a $C_6$ aryl, substituted with one or more of the following:

an alkoxy, optionally substituted with:

an alkoxy, a hydroxy, one or more halogen(s), a 5 or 6 membered heterocycle, optionally substituted with:

a $C_1$ to $C_6$ alkyl, or a hydroxy, an amino group optionally substituted with one or more $C_1$ to $C_6$ alkyl(s), a —$NR_iSO_2R_x$ group, where $R_x$ is a $C_1$ to $C_6$ alkyl and $R_i$ is:

a hydrogen, a $C_1$ to $C_6$ alkyl, a —$COR_x$ group, where $R_x$ is as defined above, a haloalkyl, or a haloalkoxy, a —$NR_jCOR_k$ group, where $R_k$ is:

a $C_1$ to $C_6$ alkyl, a hydrogen, or an amino optionally substituted with one or more $C_1$ to $C_6$ alkyl(s), and $R_j$ is:

a hydrogen, a $C_1$ to $C_6$ alkyl, a —$COR_x$ group, where $R_x$ is as defined above, a haloalkyl, or a haloalkoxy, a —$N{=}N^+{=}N^-$ group, or a —$COR_1$, where $R_1$ is a 5 or 6 membered heterocycle optionally substituted with a hydroxy, an amino optionally substituted with one or more $C_1$ to $C_6$ alkyl(s), a nitro group, a $C_1$ to $C_6$ alkyl group, optionally substituted with:

a —$NHSO_2R_x$ group, where $R_x$ is as defined above, or a —$NR_xSO_2R_x$ group, where $R_x$ is as defined above, a haloalkoxy, a halogen, a hydroxy, a —$COOR_x$ group, where $R_x$ is as defined above, a —$COR_m$ group, where $R_m$ is:

an amino optionally substituted with one or more $C_1$ to $C_6$ alkyl(s), where the $C_1$ to $C_6$ alkyls are optionally substituted with:

a hydroxy a 5 or 6 membered heterocycle, an amino optionally substituted with one or more $C_1$ to $C_6$ alkyl(s), or an alkoxy, a 3 to 7 membered heterocycle, optionally substituted with a $C_1$ to $C_6$ alkyl, optionally substituted with a dialkyl-amino, or a —$NHR_n$ group, where $R_n$ is:

a —$CH_2CONH_2$, or a $C_6$ to $C_8$ aryl optionally substituted with:

an alkyl, one or more halogen(s), a nitro group, or one or more alkoxy(s), a —$NR_oCOR_p$ group, where $R_p$ is:
a $C_1$ to $C_6$ alkyl optionally substituted with:
a halogen,
an alkoxy, or
a $C_6$ to $C_8$ aryl,
a 5 or 6 membered heterocycle,
a $C_6$ to $C_8$ aryl, optionally substituted with a halogen,
a 5 or 6 membered heteroaryl optionally substituted with one or more $C_1$ to $C_6$ alkyl(s),
a hydrogen,
a cyclopropyl,
a cyclobutyl,
a cyclopentyl,
a cyclohexyl,
a cyclopropylmethyl,

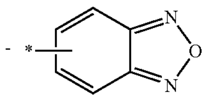
or
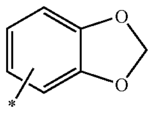
, and where $R_o$ is:
a hydrogen,
a $C_1$ to $C_6$ alkyl,
a —$COR_x$ group, where $R_x$ is as defined above,
a haloalkyl, or
a haloalkoxy,
a —$NR_qCONR_qR_r$ group, where $R_q$ is:
a hydrogen,
a $C_1$ to $C_6$ alkyl,
a haloalkyl,
a haloalkoxy, or
a —$COR_x$ group, where $R_x$ is as defined above, and where $R_r$ is:
a $C_6$ to $C_8$ aryl optionally substituted with:

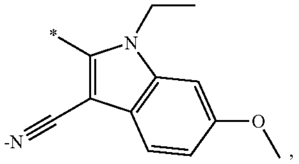

a $C_1$ to $C_6$ alkyl,
a haloalkyl,
a —$OR_s$ group, where $R_s$ is a $C_6$ to $C_8$ aryl, or
a —$COOR_x$ group, where $R_x$ is as defined above,
a $C_1$ to $C_6$ alkyl optionally substituted with one or more of the following:
a halogen,
an alkenyl,
a $C_6$ to $C_8$ aryl, or
a —$COOR_x$ group, where $R_x$ is as defined above,
a —$COOR_x$ group, where $R_x$ is as defined above,
a cyclopropyl,
a cyclobutyl,
a cyclopentyl,
a cyclohexyl, or
a cyclopropylmethyl;
a —$NR_tCOOR_u$ group, where $R_u$ is:
a $C_1$ to $C_{12}$ alkyl, optionally substituted with:
a $C_6$ to $C_8$ aryl optionally substituted with a $C_1$ to $C_6$ alkyl or an alkoxy,
an alkenyl,
an alkoxy,
an alkynyl,
a halogen, or
a 5 or 6 membered heterocycle,
a $C_6$ to $C_8$ aryl, optionally substituted with:
an alkoxy,
a halogen, or
a $C_1$ to $C_6$ alkyl,
a 5 or 6 membered heterocycle,
a cyclopropyl,
a cyclobutyl,
a cyclopentyl,
a cyclohexyl,
a cyclopropylmethyl,
a cyclopropylethyl,
a cyclobutylmethyl,
a (1-methylcyclopropyl)methyl, or
a 1-methylcyclopentyl, and where $R_t$ is:
a hydrogen,
a $C_1$ to $C_6$ alkyl,
a —$COR_x$ group, where $R_x$ is as defined above,
a haloalkyl, or
a haloalkoxy,
a —$NR_vSO_2R_w$ group, where $R_v$ is:
a hydrogen,
a —$COR_x$, where $R_x$ is as defined above, or
a $C_1$ to $C_6$ alkyl, optionally substituted with:
a halogen,
a —$COR_x$ group, where $R_x$ is as defined above,
a —$OCOR_x$ group, where $R_x$ is as defined above,
a hydroxy, or
an alkoxy, and where $R_w$ is:
a $C_1$ to $C_6$ alkyl optionally substituted with:
a halogen,
a haloalkyl,
a $C_6$ to $C_8$ aryl, or
a 5 or 6 membered heterocycle,
a $C_2$ to $C_6$ alkenyl,
a mono-alkyl-amino or dialkyl-amino optionally substituted on alkyl with a halogen,
a 5 or 6 membered heterocycle,
a 5 or 6 membered heteroaryl optionally substituted with:
a $C_1$ to $C_6$ alkyl,
a 5 or 6 membered heterocycle, or

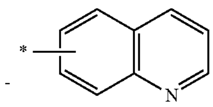
;

a cyclopropyl,
a cyclobutyl,
a cyclopentyl,
a cyclohexyl, or
a cyclopropylmethyl,

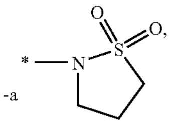

-continued

-a 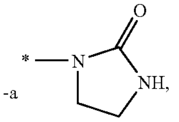

-a 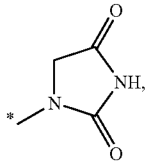

-a 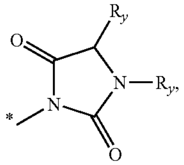

a optionally substituted with a $C_1$ to $C_6$ alkyl, where $R_y$ is a $C_1$ to $C_6$ alkyl or hydrogen, -a 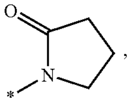

-a 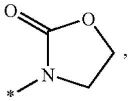

-a 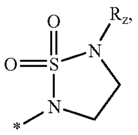

where $R_z$ is hydrogen or a $C_1$ to $C_6$ alkyl, optionally substituted with a $C_6$ to $C_8$ aryl,
a —$SR_x$ group, where $R_x$ is as defined above,
a —$SO_2R_{aa}$ group, where $R_{aa}$ is:
a $C_1$ to $C_6$ alkyl,
an amino group,
a mono-alkyl-amino or dialkyl-amino group optionally substituted with a hydroxy
or a —$COOR_x$ group, where $R_x$ is as defined above,
a 5 or 6 membered heteroaryl,
a $C_6$ to $C_8$ aryl, or
a —$NHR_{bb}$ group, where $R_{bb}$ is:

- 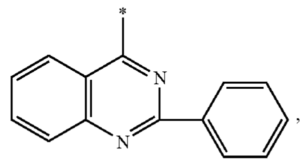

- 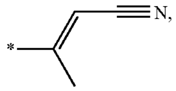

a —C(=S)$NH_2$ group, or
a —$PO(OR_x)_2$ group, where $R_x$ is as defined above;

Z is:
a $C_1$ to $C_6$ alkyl optionally substituted with:
an alkoxy,
one or more halogen(s), or
a $C_6$ to $C_8$ aryl;
a $C_2$ to $C_6$ alkenyl;
a cyclopropyl;
a cyclobutyl;
a cyclopentyl;
a cyclohexyl;
a cyclopropylmethyl;
a cyclobutylmethyl; or
a cyclopentylmethyl;
R is a hydrogen, a halogen or an alkoxy;
$R_1$ is:
a hydrogen;
a hydroxy;
a halogen;
a haloalkyl;
a nitro group;
a 5 or 6 membered heteroaryl;
a 5 or 6 membered heterocycle;
an alkoxy optionally substituted with:
one or more halogen(s),
a $C_6$ to $C_8$ aryl, or
a 5 or 6 membered heterocycle;
a $C_6$ to $C_8$ aryl optionally substituted with an alkoxy;
a —$COR_x$ group, where $R_x$ is as defined above; or
a $C_1$ to $C_6$ alkyl optionally substituted with a dialkyl-amino or a 5 or 6 membered heterocycle;
$R_2$ is:
a nitro group;
a hydrogen;
a halogen;
a hydroxy group;
a $C_1$ to $C_6$ alkyl group, optionally substituted with one or more halogen(s);
an amino group;
an alkoxy group optionally substituted with:
one or more halogen(s),
an —$OCOR_x$ group, where $R_x$ is as defined above,
an amino substituted with:
(i) —a cyclopropyl,
(ii) —a cyclobutyl,
(iii) —a cyclopentyl,
(iv) —a cyclohexyl, or
(v) —a cyclopropylmethyl,
a dialkyl-amino optionally substituted on alkyl with an alkoxy,
a 5 or 6 membered heterocycle group optionally substituted with a $C_1$ to $C_6$ alkyl,
a 5 or 6 membered heteroaryl group, or
a $C_6$ to $C_8$ aryl group;
a —$COOR_x$ group, where $R_x$ is as defined above;
a haloalkyl;
an amide group optionally substituted with:
a hydroxy group, or
a $C_6$ to $C_8$ aryl;
a 5 or 6 membered heteroaryl;
a —$OCOR_x$ group, where $R_x$ is as defined above;
a —$NHCOR_{jj}$ group, where $R_{jj}$ is:
an alkoxy, or
an amino optionally substituted with one or more $C_1$ to $C_6$ alkyl(s);
a —$OR_{kk}$ group, where $R_{kk}$ is a 5 to 6 membered heteroaryl;
a —$NHSO_2R_x$ group, where $R_x$ is as defined above;

—a cyclopropyl; —a cyclobutyl; —a cyclopentyl; —a cyclohexyl; —a cyclopropylmethyl; or
—a cyclopropoxy;
$R_3$ is:
a hydrogen; or
—$CH_2OCOR_x$, and $R_x$ is as defined above;
or one or more pharmaceutically acceptable salt(s) thereof; and
(ii) one or more pharmaceutically acceptable excipient(s).

31. A method for treating a Hepatitis C viral (HCV) infection in a subject in need thereof, comprising administering to the subject one or more compound(s) of formula I or a pharmaceutical composition comprising one or more compound(s) of formula I

I

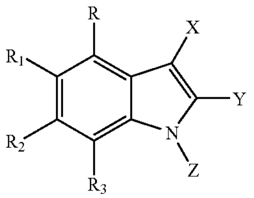

wherein:
X is:
a cyano group;
Y is:
a $C_6$ aryl, substituted with one or more of the following:
an alkoxy, optionally substituted with:
an alkoxy,
a hydroxy,
one or more halogen(s),
a 5 or 6 membered heterocycle, optionally substituted with:
a $C_1$ to $C_6$ alkyl, or
a hydroxy,
an amino group optionally substituted with one or more $C_1$ to $C_6$ alkyl(s),
a —$NR_iSO_2R_x$ group, where $R_x$ is a $C_1$ to $C_6$ alkyl and $R_i$ is:
a hydrogen,
a $C_1$ to $C_6$ alkyl,
a —$COR_x$ group, where $R_x$ is as defined above,
a haloalkyl, or
a haloalkoxy,
a —$NR_jCOR_k$ group, where $R_k$ is:
a $C_1$ to $C_6$ alkyl,
a hydrogen, or
an amino optionally substituted with one or more $C_1$ to $C_6$ alkyl(s), and $R_j$ is:
a hydrogen,
a $C_1$ to $C_6$ alkyl,
a —$COR_x$ group, where $R_x$ is as defined above,
a haloalkyl, or
a haloalkoxy,
a —$N{=}N^+{=}N^-$ group, or
a —$COR_1$, where $R_1$ is a 5 or 6 membered heterocycle optionally substituted with a hydroxy,
an amino optionally substituted with one or more $C_1$ to $C_6$ alkyl(s),
a nitro group,
a $C_1$ to $C_6$ alkyl group, optionally substituted with:
a —$NHSO_2R_x$ group, where $R_x$ is as defined above, or
a —$NR_xSO_2R_x$ group, where $R_x$ is as defined above,
a haloalkoxy,
a halogen,
a hydroxy,
a —$COOR_x$ group, where $R_x$ is as defined above,
a —$COR_m$ group, where $R_m$ is:
an amino optionally substituted with one or more $C_1$ to $C_6$ alkyl(s), where the one or more $C_1$ to $C_6$ alkyl(s) is optionally substituted with:
a hydroxy
a 5 or 6 membered heterocycle,
an amino optionally substituted with one or more $C_1$ to $C_6$ alkyl(s), or
an alkoxy,
a 3 to 7 membered heterocycle, optionally substituted with a $C_1$ to $C_6$ alkyl, optionally substituted with a dialkyl-amino, or
a —$NHR_n$ group, where $R_n$ is:
a —$CH_2CONH_2$, or
a $C_6$ to $C_8$ aryl optionally substituted with:
an alkyl,
one or more halogen(s),
a nitro group, or
one or more alkoxy(s),
a —$NR_oCOR_p$ group, where $R_p$ is:
a $C_1$ to $C_6$ alkyl optionally substituted with:
a halogen,
an alkoxy, or
a $C_6$ to $C_8$ aryl,
a 5 or 6 membered heterocycle,
a $C_6$ to $C_8$ aryl, optionally substituted with a halogen,
a 5 or 6 membered heteroaryl optionally substituted with one or more $C_1$ to $C_6$ alkyl(s),
a hydrogen,
a cyclopropyl,
a cyclobutyl,
a cyclopentyl,
a cyclohexyl,
a cyclopropylmethyl,

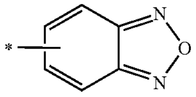
or
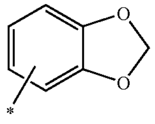
, and where $R_o$ is:
a hydrogen,
a $C_1$ to $C_6$ alkyl,
a —$COR_x$ group, where $R_x$ is as defined above,
a haloalkyl, or
a haloalkoxy,
a —$NR_qCONR_qR_r$ group, where $R_q$ is:
a hydrogen,
a $C_1$ to $C_6$ alkyl,
a haloalkyl,
a haloalkoxy, or
a —$COR_x$ group, where $R_x$ is as defined above, and where $R_r$ is:
a $C_6$ to $C_8$ aryl optionally substituted with:

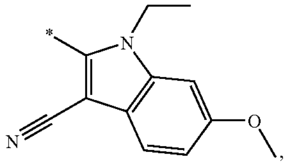

a $C_1$ to $C_6$ alkyl,
a haloalkyl,
a —$OR_s$ group, where $R_s$ is a $C_6$ to $C_8$ aryl, or
a —$COOR_x$ group, where $R_x$ is as defined above,
a $C_1$ to $C_6$ alkyl optionally substituted with one or more of the following:
a halogen,
an alkenyl,
a $C_6$ to $C_8$ aryl, or
a —$COOR_x$ group, where $R_x$ is as defined above,
a —$COOR_x$ group, where $R_x$ is as defined above,
a cyclopropyl,
a cyclobutyl,
a cyclopentyl,
a cyclohexyl, or
a cyclopropylmethyl;
a —$NR_tCOOR_u$ group, where $R_u$ is:
a $C_1$ to $C_{12}$ alkyl, optionally substituted with:
a $C_6$ to $C_8$ aryl optionally substituted with a $C_1$ to $C_6$ alkyl or an alkoxy,
an alkenyl,
an alkoxy,
an alkynyl,
a halogen, or
a 5 or 6 membered heterocycle,
a $C_6$ to $C_8$ aryl, optionally substituted with:
an alkoxy,
a halogen, or
a $C_1$ to $C_6$ alkyl,
a 5 or 6 membered heterocycle,
a cyclopropyl,
a cyclobutyl,
a cyclopentyl,
a cyclohexyl,
a cyclopropylmethyl,
a cyclopropylethyl,
a cyclobutylmethyl,
a (1-methylcyclopropyl)methyl, or
a 1-methylcyclopentyl, and where $R_t$ is:
a hydrogen,
a $C_1$ to $C_6$ alkyl,
a —$COR_x$ group, where $R_x$ is as defined above,
a haloalkyl, or
a haloalkoxy,
a —$NR_vSO_2R_w$ group, where $R_v$ is:
a hydrogen,
a —$COR_x$, where $R_x$ is as defined above, or
a $C_1$ to $C_6$ alkyl, optionally substituted with:
a halogen,
a —$COR_x$ group, where $R_x$ is as defined above,
a —$OCOR_x$ group, where $R_x$ is as defined above,
a hydroxy, or
an alkoxy, and where $R_w$ is:
a $C_1$ to $C_6$ alkyl optionally substituted with:
a halogen,
a haloalkyl,
a $C_6$ to $C_8$ aryl, or
a 5 or 6 membered heterocycle, a $C_2$ to $C_6$ alkenyl,
a mono-alkyl-amino or dialkyl-amino optionally substituted on alkyl with a halogen,
a 5 or 6 membered heterocycle,
a 5 or 6 membered heteroaryl optionally substituted with:
a $C_1$ to $C_6$ alkyl,
a 5 or 6 membered heterocycle, or

-

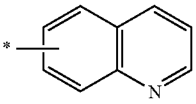

;

a cyclopropyl,
a cyclobutyl,
a cyclopentyl,
a cyclohexyl, or
a cyclopropylmethyl, -a 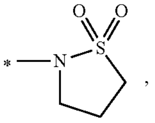 , -a 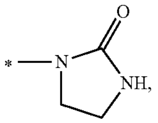

-a 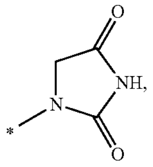

-a 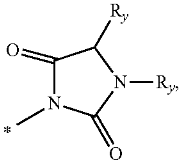

a optionally substituted with a $C_1$ to $C_6$ alkyl, where $R_y$ is a $C_1$ to $C_6$ alkyl or hydrogen, -a 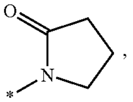 , -a 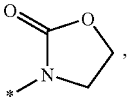 , -a 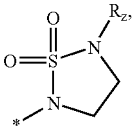

where $R_z$ is hydrogen or a $C_1$ to $C_6$ alkyl, optionally substituted with a $C_6$ to $C_8$ aryl,
a —$SR_x$ group, where $R_x$ is as defined above,
a —$SO_2R_{aa}$ group, where $R_{aa}$ is:
a $C_1$ to $C_6$ alkyl,
an amino group,
a mono-alkyl-amino or dialkyl-amino group optionally substituted with a hydroxy or a —$COOR_x$ group, where $R_x$ is as defined above,
a 5 or 6 membered heteroaryl,
a $C_6$ to $C_8$ aryl, or
a —$NHR_{bb}$ group, where $R_{bb}$ is:

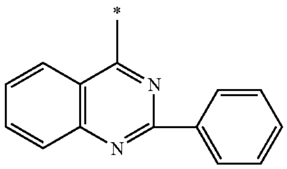

,

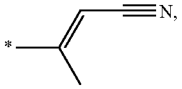

a —C(=S)$NH_2$ group, or a —$PO(OR_x)_2$ group, where $R_x$ is as defined above;

Z is:

a $C_1$ to $C_6$ alkyl optionally substituted with:

an alkoxy, one or more halogen(s), or a $C_6$ to $C_8$ aryl;

a $C_2$ to $C_6$ alkenyl;

a cyclopropyl;

a cyclobutyl;

a cyclopentyl;

a cyclohexyl;

a cyclopropylmethyl;

a cyclobutylmethyl; or a cyclopentylmethyl;

R is a hydrogen, a halogen or an alkoxy;

$R_1$ is:

a hydrogen;

a hydroxy;

a halogen;

a haloalkyl;

a nitro group;

a 5 or 6 membered heteroaryl;

a 5 or 6 membered heterocycle;

an alkoxy optionally substituted with:

one or more halogen(s), a $C_6$ to $C_8$ aryl, or a 5 or 6 membered heterocycle;

a $C_6$ to $C_8$ aryl optionally substituted with an alkoxy;

a —$COR_x$ group, where $R_x$ is as defined above; or a $C_1$ to $C_6$ alkyl optionally substituted with a dialkyl-amino or a 5 or 6 membered heterocycle;

$R_2$ is:

a nitro group;

a hydrogen;

a halogen;

a hydroxy group;

a $C_1$ to $C_6$ alkyl group, optionally substituted with one or more halogen(s);

an amino group;

an alkoxy group optionally substituted with:

one or more halogen(s), an —$OCOR_x$ group, where $R_x$ is as defined above, an amino substituted with:

(i) —a cyclopropyl, (ii) —a cyclobutyl, (iii) —a cyclopentyl, (iv) —a cyclohexyl, or (v) —a cyclopropylmethyl, a dialkyl-amino optionally substituted on alkyl with an alkoxy, a 5 or 6 membered heterocycle group optionally substituted with a $C_1$ to $C_6$ alkyl, a 5 or 6 membered heteroaryl group, or a $C_6$ to $C_8$ aryl group;

a —$COOR_x$ group, where $R_x$ is as defined above;

a haloalkyl;

an amide group optionally substituted with:

a hydroxy group, or a $C_6$ to $C_8$ aryl;

a 5 or 6 membered heteroaryl;

a —$OCOR_x$ group, where $R_x$ is as defined above;

a —$NHCOR_{jj}$ group, where $R_{jj}$ is:

an alkoxy, or an amino optionally substituted with one or more $C_1$ to $C_6$ alkyl(s);

a —$OR_{kk}$ group, where $R_{kk}$ is a 5 to 6 membered heteroaryl; or a —$NHSO_2R_x$ group, where $R_x$ is as defined above;

$R_3$ is:

a hydrogen;

—$CH_2OCOR_x$, and $R_x$ is as defined above;

—a cyclopropyl; —a cyclobutyl; —a cyclopentyl; —a cyclohexyl; —a cyclopropylmethyl; or —a cyclopropoxy; or one or more pharmaceutically acceptable salt(s) thereof.

* * * * *